United States Patent
Cao et al.

(10) Patent No.: US 9,856,279 B2
(45) Date of Patent: Jan. 2, 2018

(54) THERAPEUTICALLY ACTIVE COMPOSITIONS AND THEIR METHODS OF USE

(71) Applicant: AGIOS PHARMACEUTICALS, INC, Cambridge, MA (US)

(72) Inventors: Sheldon Cao, Fuyang (CN); Janeta Popovici-Muller, Windham, NH (US); Francesco G. Salituro, Marlborough, MA (US); Jeffrey O. Saunders, Lincoln, MA (US); Xuefei Tan, Shanghai (CN); Jeremy M. Travins, Southborough, MA (US); Shunqi Yan, Irvine, CA (US); Zhixiong Ye, Beijing (CN)

(73) Assignee: AGIOS PHARMACEUTICALS, INC., Cambridge, MA (US)

( * ) Notice: Subject to any disclaimer, the term of this patent is extended or adjusted under 35 U.S.C. 154(b) by 0 days.

(21) Appl. No.: 15/130,358

(22) Filed: Apr. 15, 2016

(65) Prior Publication Data

US 2016/0229876 A1    Aug. 11, 2016

Related U.S. Application Data

(63) Continuation of application No. 14/126,763, filed as application No. PCT/CN2012/000841 on Jun. 18, 2012, now abandoned.

(Continued)

(30) Foreign Application Priority Data

Jun. 17, 2011    (CN) .......................... 2011 1 0172169

(51) Int. Cl.

| | |
|---|---|
| C07D 401/04 | (2006.01) |
| C07D 401/14 | (2006.01) |
| C07D 407/14 | (2006.01) |
| C07D 413/14 | (2006.01) |
| C07D 471/04 | (2006.01) |
| A61K 31/496 | (2006.01) |
| C07F 9/6509 | (2006.01) |
| C07D 405/14 | (2006.01) |
| C07D 213/85 | (2006.01) |
| C07D 401/12 | (2006.01) |
| C07D 405/12 | (2006.01) |
| C07D 409/14 | (2006.01) |
| C07D 417/14 | (2006.01) |
| C07F 9/6558 | (2006.01) |
| A61K 31/498 | (2006.01) |
| A61K 31/4985 | (2006.01) |
| A61K 31/501 | (2006.01) |
| A61K 31/502 | (2006.01) |
| A61K 31/506 | (2006.01) |
| A61K 31/517 | (2006.01) |
| C07D 487/04 | (2006.01) |

(Continued)

(52) U.S. Cl.
CPC ...... *C07F 9/650952* (2013.01); *A61K 31/496* (2013.01); *A61K 31/498* (2013.01); *A61K 31/4985* (2013.01); *A61K 31/501* (2013.01); *A61K 31/502* (2013.01); *A61K 31/506* (2013.01); *A61K 31/517* (2013.01); *A61K 31/5377* (2013.01); *A61K 31/675* (2013.01); *C07D 213/85* (2013.01); *C07D 401/04* (2013.01); *C07D 401/12* (2013.01); *C07D 401/14* (2013.01); *C07D 405/12* (2013.01); *C07D 405/14* (2013.01); *C07D 409/14* (2013.01); *C07D 413/14* (2013.01); *C07D 417/14* (2013.01); *C07D 471/04* (2013.01); *C07D 487/04* (2013.01); *C07D 498/04* (2013.01); *C07F 9/65583* (2013.01)

(58) Field of Classification Search
None
See application file for complete search history.

(56) References Cited

U.S. PATENT DOCUMENTS

| | | |
|---|---|---|
| 2,390,529 A | 12/1945 | Friedheim |
| 3,755,322 A | 8/1973 | Winter et al. |

(Continued)

FOREIGN PATENT DOCUMENTS

| | | |
|---|---|---|
| CN | 101296909 A | 10/2008 |
| CN | 101575408 A | 11/2009 |

(Continued)

OTHER PUBLICATIONS

Partial Machine Translation for WO 2010007756 (Jan. 2010).*
Pollard et al, "Cancer. Puzzling patterns of predisposition." Science (2009) vol. 324, pp. 192-194.
Popovici-Muller et al. "Discovery of the First Potent Inhibitors of Mutant IDH1 That Lower Tumor2-HG in Vivo" ACS Medicinal Chemistry Letters (2012) vol. 3, No. 10, pp. 850-855.

(Continued)

*Primary Examiner* — Emily A Bernhardt
(74) *Attorney, Agent, or Firm* — Goodwin Procter LLP

(57) ABSTRACT

Provided are piperazine compounds of Formula I useful for treating cancer and methods of treating cancer comprising administering to a subject in need thereof a compound described here.

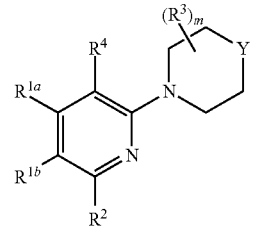

Formula I

26 Claims, No Drawings

Related U.S. Application Data

(60) Provisional application No. 61/584,210, filed on Jan. 6, 2012, provisional application No. 61/509,071, filed on Jul. 18, 2011.

(51) Int. Cl.
    *C07D 498/04*     (2006.01)
    *A61K 31/5377*     (2006.01)
    *A61K 31/675*     (2006.01)

(56) References Cited

U.S. PATENT DOCUMENTS

| | | |
|---|---|---|
| 3,867,383 A | 2/1975 | Winter |
| 4,084,053 A | 4/1978 | Desai et al. |
| 5,021,421 A | 6/1991 | Hino et al. |
| 5,489,591 A | 2/1996 | Kobayashi et al. |
| 5,807,876 A | 9/1998 | Armistead et al. |
| 5,834,485 A | 11/1998 | Dyke et al. |
| 5,965,559 A | 10/1999 | Faull et al. |
| 5,965,569 A | 10/1999 | Camps Garcia et al. |
| 5,984,882 A | 11/1999 | Rosenschein et al. |
| 6,262,113 B1 | 7/2001 | Widdowson et al. |
| 6,274,620 B1 | 8/2001 | Labrecque et al. |
| 6,313,127 B1 | 11/2001 | Waterson et al. |
| 6,399,358 B1 | 6/2002 | Williams et al. |
| 6,576,235 B1 | 6/2003 | Williams et al. |
| 6,723,730 B2 | 4/2004 | Bakthavatchalam et al. |
| 6,783,965 B1 | 8/2004 | Sherman et al. |
| 6,979,675 B2 | 12/2005 | Tidmarsh |
| 7,173,025 B1 | 2/2007 | Stocker et al. |
| 7,858,782 B2 | 12/2010 | Tao et al. |
| 8,133,900 B2 | 3/2012 | Hood et al. |
| 8,465,673 B2 | 6/2013 | Yasuda et al. |
| 9,579,324 B2 | 2/2017 | Konteatis et al. |
| 2002/0049310 A1 | 4/2002 | Tateishi et al. |
| 2002/0188027 A1 | 12/2002 | Robinson et al. |
| 2003/0095958 A1 | 5/2003 | Bhisetti et al. |
| 2003/0109527 A1 | 6/2003 | Jin et al. |
| 2003/0207882 A1 | 11/2003 | Stocker et al. |
| 2003/0213405 A1 | 11/2003 | Harada et al. |
| 2004/0067234 A1 | 4/2004 | Einat et al. |
| 2004/0248221 A1 | 12/2004 | Stockwell |
| 2005/0261268 A1 | 11/2005 | Arnost et al. |
| 2006/0084645 A1 | 4/2006 | Pal et al. |
| 2006/0281122 A1 | 12/2006 | Bryant et al. |
| 2007/0244088 A1 | 10/2007 | Brickmann et al. |
| 2008/0132490 A1 | 6/2008 | Bergman et al. |
| 2008/0300208 A1 | 12/2008 | Einat et al. |
| 2009/0093526 A1 | 4/2009 | Miller et al. |
| 2009/0163508 A1 | 6/2009 | Kori et al. |
| 2009/0163545 A1 | 6/2009 | Goldfarb |
| 2009/0281089 A1 | 11/2009 | Gunzner et al. |
| 2010/0129350 A1 | 5/2010 | Zacharie et al. |
| 2010/0144722 A1 | 6/2010 | Alexander et al. |
| 2010/0273808 A1 | 10/2010 | Armitage et al. |
| 2010/0331307 A1 | 12/2010 | Salituro et al. |
| 2011/0073007 A1 | 3/2011 | Yasuda et al. |
| 2011/0086088 A1 | 4/2011 | Berry |
| 2011/0288065 A1 | 11/2011 | Fujihara et al. |
| 2012/0121515 A1 | 5/2012 | Dang et al. |
| 2012/0129865 A1 | 5/2012 | Wang et al. |
| 2012/0164143 A1 | 6/2012 | Teeling et al. |
| 2012/0202818 A1 | 8/2012 | Tao et al. |
| 2012/0238576 A1 | 9/2012 | Tao et al. |
| 2012/0277233 A1 | 11/2012 | Tao et al. |
| 2013/0035329 A1 | 2/2013 | Saunders et al. |
| 2013/0109643 A1 | 5/2013 | Riggins et al. |
| 2013/0183281 A1 | 7/2013 | Su et al. |
| 2013/0184222 A1 | 7/2013 | Popovici-Muller et al. |
| 2013/0190249 A1 | 7/2013 | Lemieux et al. |
| 2013/0190287 A1 | 7/2013 | Cianchetta et al. |
| 2014/0187435 A1 | 7/2014 | Dang et al. |
| 2015/0018328 A1 | 1/2015 | Konteatis et al. |
| 2015/0031627 A1 | 1/2015 | Lemieux et al. |
| 2015/0044716 A1 | 2/2015 | Balss et al. |

FOREIGN PATENT DOCUMENTS

| | | |
|---|---|---|
| CN | 102659765 A | 9/2012 |
| CN | 2014081957 A2 | 12/2016 |
| DE | 3314663 A1 | 10/1983 |
| DE | 3512630 A1 | 10/1986 |
| EP | 0384228 A1 | 8/1990 |
| EP | 0385237 A2 | 9/1990 |
| EP | 0945446 A1 | 9/1999 |
| EP | 1391487 A2 | 2/2004 |
| FR | 2735127 A1 | 12/1996 |
| GB | 1033266 A | 6/1966 |
| JP | 4099768 | 3/1992 |
| JP | H05140126 A | 6/1993 |
| JP | 9291034 A | 11/1997 |
| JP | 11158073 | 6/1999 |
| JP | 2004107220 A | 4/2004 |
| JP | 2005264016 A | 9/2005 |
| JP | 2009237115 A | 10/2009 |
| JP | 2010079130 A | 4/2010 |
| JP | 2010181540 A | 8/2010 |
| JP | 4753336 B2 | 8/2011 |
| JP | 2013519858 A | 5/2013 |
| MX | 2013/000614 A | 6/2013 |
| WO | 9630343 A1 | 10/1996 |
| WO | 97/28128 A1 | 8/1997 |
| WO | 97/28129 A1 | 8/1997 |
| WO | 9744322 A1 | 11/1997 |
| WO | 9932463 A1 | 7/1999 |
| WO | 0002864 A1 | 1/2000 |
| WO | 0116097 A1 | 3/2001 |
| WO | 0119788 A2 | 3/2001 |
| WO | 0119798 A2 | 3/2001 |
| WO | 0147897 A1 | 7/2001 |
| WO | 0164642 A2 | 9/2001 |
| WO | 0164643 A2 | 9/2001 |
| WO | 02100822 A1 | 12/2002 |
| WO | 02102313 A2 | 12/2002 |
| WO | 030016289 A1 | 2/2003 |
| WO | 2004009562 A1 | 1/2004 |
| WO | 2004046120 A2 | 6/2004 |
| WO | 2004050033 A2 | 6/2004 |
| WO | 2004/073619 A2 | 9/2004 |
| WO | 2004/074438 A2 | 9/2004 |
| WO | 2004089470 A2 | 10/2004 |
| WO | 2005035507 A2 | 4/2005 |
| WO | 2005060956 A1 | 7/2005 |
| WO | 2005065691 A1 | 7/2005 |
| WO | 2005103015 A1 | 11/2005 |
| WO | 2005120474 A2 | 12/2005 |
| WO | 2006034341 A2 | 3/2006 |
| WO | 2006-038594 A1 | 4/2006 |
| WO | 2006070198 A1 | 7/2006 |
| WO | 2006079791 A1 | 8/2006 |
| WO | 2006/110761 A2 | 10/2006 |
| WO | 2007003934 A2 | 1/2007 |
| WO | 2007023186 A1 | 3/2007 |
| WO | 2008036835 A2 | 3/2008 |
| WO | 2008/050168 A1 | 5/2008 |
| WO | 2008052190 A2 | 5/2008 |
| WO | 2008070661 A1 | 6/2008 |
| WO | 2008073670 A2 | 6/2008 |
| WO | 2008076883 A2 | 6/2008 |
| WO | 2008131547 A1 | 11/2008 |
| WO | 2008154026 A1 | 12/2008 |
| WO | 2009013126 A1 | 1/2009 |
| WO | 2009015254 A1 | 1/2009 |
| WO | 2009016410 A2 | 2/2009 |
| WO | 2009118567 A2 | 10/2009 |
| WO | 2009126863 A2 | 10/2009 |
| WO | 2009150248 A1 | 12/2009 |
| WO | 2010007756 A1 | 1/2010 |
| WO | 2010/028099 A1 | 3/2010 |
| WO | 2010105243 A1 | 9/2010 |
| WO | 2010/129596 A1 | 11/2010 |
| WO | 2010130638 A1 | 11/2010 |
| WO | 2010144338 A1 | 12/2010 |
| WO | 2010144404 A1 | 12/2010 |
| WO | 2011002817 A1 | 1/2011 |

(56) References Cited

FOREIGN PATENT DOCUMENTS

| WO | 2011/027249 A2 | 3/2011 |
|---|---|---|
| WO | 2011032169 A2 | 3/2011 |
| WO | 2011047432 A1 | 4/2011 |
| WO | 2011050210 A1 | 4/2011 |
| WO | 2011/072174 A1 | 6/2011 |
| WO | 2012/009678 A1 | 1/2012 |
| WO | 2012006506 A1 | 1/2012 |
| WO | 2012074999 A1 | 6/2012 |
| WO | 2012/092442 A1 | 7/2012 |
| WO | 2012151452 A1 | 11/2012 |
| WO | 2012160034 A1 | 11/2012 |
| WO | 2012/171337 A1 | 12/2012 |
| WO | 2012171506 A1 | 12/2012 |
| WO | 2013/004332 A1 | 1/2013 |
| WO | 2013007708 A1 | 1/2013 |
| WO | 2013102431 A1 | 7/2013 |
| WO | 2013107291 A1 | 7/2013 |
| WO | 2013107405 A1 | 7/2013 |
| WO | 2013133367 A1 | 9/2013 |
| WO | 2014015422 A1 | 1/2014 |
| WO | 2015/003360 A2 | 1/2015 |

OTHER PUBLICATIONS

Pubchem CID 4078245 [online]; Sep. 13, 2005 [retrieved on Feb. 4, 2012]; retrieved from http://pubchem.ncbi.nim.nih.gov/; 2d-structure.
Pubchem CID 4854170 [online]; Sep. 17, 2005 [retrieved on Feb. 4, 2012]; retrieved from http://pubchem.ncbi.nim.nih.gov/; 2d-structure.
Raynaud et al. "Absence of R140Q Mutation of Isocitrate Dehydrogenase 2 in Gliomas and Breast Cancers" Oncology Letters (2010) vol. 1, No. 5, pp. 883-884.
Reitman et al. "Isocitrate Dehydrogenase 1 and 2 Mutations in Cancer: Alterations at a Crossroads of Cellular Metabolism" Journal of the National Cancer Institute (2010) vol. 102, No. 13, pp. 932-941.
Rohle et al. "An Inhibitor of Mutant IDH1 Delays Growth and Promotes Differentiation of Glioma Cells" Science (2013) vol. 340, No. 6132, pp. 626-630.
Scharn et al. "Spatially Addressed Synthesis of Amino- and Amino-Oxy-Substituted 1,3,5-Triazine Arrays on Polymeric Membranes" Journal of Combinatorial Chemistry (2000) vol. 2, No. 4, pp. 361-369.
Shih et al. "The Role of Mutations in Epigenetic Regulators in Myeloid Malignancies" Nature Reviews Cancer (2012) vol. 12, No. 9, pp. 599-612.
Sirkanyan et al "Synthesis of new derivatives of piperazine-substituted pyrano[3,4-c]pyridines" Hayastani Kimiakan Handes—Chemical Journal of Armenia (2009) vol. 62, No. 3-4 pp. 378-385. English Abstract Only.
Sonoda et al. "Analysis of IDH1 and IDH2 mutations in Japanese glioma patients" Cancer Science, vol. 100, No. 10, pp. 1996-1998.
Sosnovik et al. "Emerging concepts in molecular MRI" Current Opinions in Biotechnology (2007) vol. 18, pp. 4-10.
STN File CA, Registry No. 1023444-33-8, entered STN on May 29, 2008, Chemical Abstracts Index Name "Benzenesulfonamide, 3-[[4-(1,3-benzodioxol-5-ylmethyl)-1-piperazinyl]carbonyl]-N-(4-butylphenyl)-4-methyl-".
STN File CA, Registry No. 1090629-29-0, entered STN on Dec. 28, 2008, Chemical Abstracts Index Name "Benzenesulfonamide, 3[[4-(2,5-dimethoxyphenyl)methyl]-1-piperazinyl]carbonyl]-N-(4-methoxypheny1)-4-methyl-".
STN File CA, Registry No. 134538-28-6, entered STN on Jun. 28, 1991, Chemical Abstracts Index Name "1H-Pyrano[3,4-c]pyridine-5-carbonitrile, 3,4-dihydro-3,3-dimethyl-6[4-(1-oxobutyl)-1-piperazinyl]-8-phenyl-", disclosed in Paronikyan et al. Armyanskii Khimicheskii Zhurnal, 1990, vol. 43, No. 8.
STN File CA, Registry No. 134538-29-7, entered STN on Jun. 28, 1991, Chemical Abstracts Index Name "1H-Pyrano[3,4-c]pyridine-5-carbonitrile, 3,4-dihydro-3,3-dimethyl-6[4-(2-methyl-1-oxopropyl)-1-piperazinyl]-8-phenyl-", disclosed in Paronikyan et al. Armyanskii Khimicheskii Zhurnal, 1990, vol. 43, No. 8.
STN File CA, Registry No. 134538-30-0, entered STN on Jun. 28, 1991, Chemical Abstracts Index Name "1H-Pyrano[3,4-c]pyridine-5-carbonitrile,6-(4-benzoyl-1-piperazinyl)-3,4-dihydro-3,3-dimethyl-8-phenyl-", disclosed in Paronikyan et al. Armyanskii Khimicheskii Zhurnal, 1990, vol. 43, No. 8.
STN File CA, Registry No. 134538-31-1, entered STN on Jun. 28, 1991, Chemical Abstracts Index Name "1H-Pyrano[3,4-c]pyridine-5-carbonitrile, 6-[4-(2-furanylcarbonyl)-1-piperazinyl]-3,4-dihydro-3,3-dimethyl-8-phenyl-", disclosed in Paronikyan et al. Armyanskii Khimicheskii Zhurnal, 1990, vol. 43, No. 8.
STN File CA, Registry No. 380466-24-0 entered STN on Jan. 4, 2002, Chemical Abstracts Index Name "Benzenesulfonamide, N-methyl-N-phenyl-3-[[4-(2-pyridinyl)-1-piperazinyl]carbonyl]".
STN File CA, Registry No. 713505-78-3, entered STN on Jul. 21, 2004, Chemical Abstracts Index Name "1-Piperazinecarboxylic acid, 4[4-methyl-3-[(phenylamino)sulfonyl]benzoyl], ethyl ester".
STN File CA, Registry No. 736168-79-9 entered STN on Aug. 31, 2004, Chemical Abstracts Index Name "Benzenesulfonamide, 3,4-difluoro-N-[3-334-(phenylmethyl0-1-piperazinyl]carbonyl]phenyl".
STN File CA, Registry No. 847757-57-7, entered STN on Apr. 1, 2005, Chemical Abstracts Index Name "Benzenesulfonamide, 3-[[4-(1,3-benzodioxol-5-ylmethyl)-1-piperazinyl]carbonyl]-N-(4-ethoxyphenyl)-N,4-dimethyl-" or "Piperazine, 1-(1,3-benzodioxol-5-ylmethyl)-4-[5-[[(4-ethoxyphenyl)methylamino]sulfonyl]-2-methylbenzoyl]-".
STN Registry, L23 Answer 2 of 3 (CAS No. 1032450-21-7), Database: ASINEX Ltd.,Entered STN: Jul. 3, 2008 (Jul. 3, 2008).
STN Registry. L23 Answer 1 of 3 (CAS No. 1038821-72-5),Database: ChemDB (University of California Irvine), Entered STN: Aug. 5, 2008 (Aug. 5, 2008).
STN Tokyo, Registry No. 1001833-18-6, Entered STN on Feb. 6, 2008, Chemical Abstracts Index Name "1,4-Benzodioxin-6-sulfonamide, 2,3-dihydro-N-[4- [(4-methyl-I-piperazinyl)carbonyl]phenyl]-".
STN Tokyo, Registry No. 1030142-35-8, Entered STN on Jun. 24, 2008, Chemical Abstracts Index Name "1,4-Benzodioxin-6-sulfonamide, 2,3-dihydro-N-[4- [[4-[(5-methyl-3-isoxazolyl)methyl]-I-piperazinyl]carbonyl]phenyl]-".
STN Tokyo, Registry No. 1031531-78-8, Entered STN on Jun. 29, 2008 Chemical Abstracts Index Name "1,4-Benzodioxin-6-sulfonamide, N-4[4-[(4-acetyl-1-piperazinyl)carbonyl]phenyl]-2,3-dihydro-".
STN Tokyo, Registry No. 1057928-35-4, Entered STN on Oct. 7, 2008, Chemical Abstracts Index Name "1,4-Benzodioxin-6-sulfonamide, 2,3-dihydro-N-[4- [[4-(2-pyridinyl)-I-piperazinyl]carbonyl]phenyl]-".
STN Tokyo, Registry No. 1240875-006, entered STN on Sep. 14, 2010, Chemical Abstracts Index Name "1,4-Benzodioxin-6-sulfonamide, 2,3-dihydro-N-[4-[[4-(2-thiazolyl)-1-piperazinyl]carbonyl]phenyl]-".
STN Tokyo, Registry No. 748791-86-8, Entered STN on Sep. 21, 2004, Chemical Abstracts Index Name "1,4-Benzodioxin-6-sulfonamide, N-[4- [[4-(2-furanylcarbonyl)-1-piperazinyl]carbonyl]phenyl]-2,3-dihydro-".
STN Tokyo, Registry No. 878469-24-0, Entered STN on Mar. 29, 2006, Chemical Abstracts Index Name "1,4-Benzodioxin-6-sulfonamide, 2,3-dihydro-N-[4-[[4-(2-pyrimidinyl)-1-piperazinyl]carbonyl]phenyl]-".
STN Tokyo, Registry No. 878474-39-6, Entered STN on Mar. 29, 2006, Chemical Abstracts Index Name "1,4-Benzodioxin-6-sulfonamide, 2,3-dihydro-N-[4 [(4-phenyl-1-piperazinyl)carbonyl]phenyl]-".
STN Tokyo, Registry No. 878590-33-1, Entered STN on Mar. 30, 2006, Chemical Abstracts Index Name "1,4-Benzodioxin-6-sulfonamide, 2,3-dihydro-N-[4-{{4-(tetrahydro-2-furanyl)methyl]-1-piperazinyl]carbonyl]phenyl]-".
STN Tokyo, Registry No. 878943-66-9 Entered STN on Apr. 2, 2006, Chemical Abstracts Index Name "1,4-Benzodioxin-6-sulfonamide, 3,4-dihydro-N-[[4-(2-pyrimidinyl)-1-piperazinyl)carbonyl]phenyl]-".

(56) References Cited

OTHER PUBLICATIONS

STN Tokyo, Registry No. 878956-06-0, Entered STN on Apr. 2, 2006, Chemical Abstracts Index Name "1,4-Benzodioxin-6-sulfonamide, N-[4- [[4-(cyclopropylcarbonyl)-1-piperazinyl]carbonyl]phenyl]-2,3-dihydro-".
STN Tokyo, Registry No. 9200679-46-5, Entered STN on Feb. 13, 2007, Chemical Abstracts Index Name "1,4-Benzodioxin-6-sulfonamide, 2,3-dihydro-N-[4- [[4-(4-pyridinyl)-1-piperazinyl]carbonyl]phenyl]-".
STN Tokyo, Registry No. 920822-52-2, Entered STN on Feb. 14, 2007, Chemical Abstracts Index Name "1,4-Benzodioxin-6-sulfonamide, N-[4- [[4-(4-fluoropheyl)-1-piperazinyl]carbonyl]phenyl]-2,3dihydro-".
STN Tokyo, Registry No. 920824-56-2, Entered STN on Feb. 14, 2007, Chemical Abstracts Index Name "1,4-Benzodioxin-6-sulfonamide, 2,3-dihydro-N-[4- [[4-(3-thienylmethyl)-1-piperazinyl]carbonyl]phenyl]-".
STN Tokyo, Registry No. 920847-34-3, Entered STN on Feb. 14, 2007, Chemical Abstracts Index Name "1,4-Benzodioxin-6-sulfonamide, 2,3-dihydro-N-[4- [[4-(2-methylphenyl)-1-piperazinyl]carbonyl]phenyl]-".
STN Tokyo, Registry No. 920875-39-4, Entered STN on Feb. 14, 2007, Chemical Abstracts Index Name "1,4-Benzodioxin-6-sulfonamide, 2,3-dihydro-N-[4- [[4-(2-hydroxyphenyl)-1-piperazinyl]carbonyl]phenyl]-".
STN Tokyo, Registry No. 920902-88-1, Entered STN on Feb. 14, 2007, Chemical Abstracts Index Name "1,4-Benzodioxin-6-sulfonamide, 2,3-dihydro-N-[4- [[4-(2-thienylmethyl)-I-piperazinyl]carbonyl]phenyl]-".
STN Tokyo, Registry No. 920921-09-1 Entered STN on Feb. 14, 2007, Chemical Abstracts Index Name "2H-1, 5-Benzodioxepin-7-sulfonamide, 3,4-dihydro-N-[4- [[4-(2pyridinyl)-1-piperazinyl]carbonyl]phenyl]-".
STN Tokyo, Registry No. 920924-42-1, Entered STN on Feb. 14, 2007, Chemical Abstracts Index Name "1,4-Benzodioxin-6-sulfonamide, 2,3-dihydro-N-[4- [[4-(2-pyridinylmethyl)-1-piperazinyl]carbonyl]phenyl]-".
STN Tokyo, Registry No. 941220-77-5, Entered STN on Jul. 4, 2007, Chemical Abstracts Index Name "2H-1, 5-Benzodioxepin-7-sulfonamide, 3,4-dihydro-N-[4-[(4-methyl-I-piperazinyl)carbonyl]phenyl]-".
Struys et al. "Investigations by mass isotopomer analysis of the formation of D-2-hydroxyglutarate by cultured lymphoblasts from two patients with D-2-hydroxyglutaric aciduria" FEBS Letters (2004) vol. 557, pp. 115-120.
Struys et al. "Mutations in the D-2-hydroxyglutarate dehydrogenase gene cause D-2-hydroxyglutaric aciduria" American Journal of Human Genetics (2005) vol. 76, pp. 358-360.
Takagi et al. "Synthesis of poly(triazinylstyrene) containing nitrogen-bawed ligand and function as metal ion adsorbent and oxidation catalyst" Reactive & Functional Polymers (2006) vol. 31, pp. 1718-1724.
The radiation fact sheet published by the National Cancer Institute, http://www.cancer.gov/about-cancer/treatment/types/radiation-therapy/radiation-fact-sheet, reviewed Jun. 30, 2010.
Thompson, "Metabolic Enzymes as Oncogenes or Tumor Suppressors." The New England Journal of Medicine (2009) vol. 360, No. 8, pp. 813-815.
Van Schaftingen et al. "L-2-Hydroglutaric aciduria, a disorder of metabolite repair" J Inherit. Metab. Dis. (2009) vol. 32, pp. 135-142.
Aghili et al. "Hydroxyglutaric aciduria and malignant brain tumor: a case report and literature review", Journal of Neuroncology (2008) 91 pp. 233-236.
Ansell et al. "The interactions of artificial coenzymes with alcohol dehydrogenase and other NAD(P)(H) dependent enzymes" Journal of Molecular Catalysis B: Enzymatic (1999) vol. 6, No. 1-2, pp. 111-123.
Balss, "Analysis of the IDH1 codon 132 mutation in brain tumors", Acta Neuropathol (2008) vol. 116, pp. 597-602.

Benner et al, "Evolution, language and analogy in functional genomics", Trends in Genetics (2001) vol. 17, pp. 414-418.
Bhushan et al. "Reversed-phase liquid chromatographic resolution of diastereomers of protein and non-protein amino acids prepared with newly synthesized chiral derivatizing reagents based on cyanuric chloride" Amino Acids (2011) vol. 40, pp. 403-409.
Bleeker et al., "IDH1 mutations at residue p.R132 (IDH1 (R132)) occur frequently in high-grade 18-22 gliomas but not in other solid tumors." Hum Muta1., (2009) vol. 30, No. 1, pp. 7-11.
Braun et al. "Triazine-based polymers: 4. MALDI-MS of triazine-based polyamines" Polymer (1996) vol. 37, No. 5, pp. 777-783.
Cairns et al. "Oncogenic Isocitrate Dehydrogenase Mutations: Mechanisms, Models, and Clinical Opportunities" Cancer Discovery (2013) vol. 3, Iss 7, pp. 730-741.
Cecil Text Book of Medicine, edited by Bennet and Plum, (1997) 20th edition, vol. 1, pp. 1004-1010.
Chan et al. "Multi-domain hydrogen-bond forming metal chelates: X-ray crystal structures of dicyclopalladated 2,3-bis[6-(2-amino-4-phenylamino-1 ,3,5-triazinyl)]pyrazine (H2L) [Pd2Br2L] and 2,6-bis[6-(2-amino-4-phenylamino-1,3,5-triazinylium)]-pyridine dichloride" Chemical Communications (1996) No. 1, pp. 81-83.
Chapman et al. "Substituted aminopyrimidine protein kinase B (PknB) inhibitors show activity against Mycobacterium tuberculosis" Bioorganic & Medicinal Chemistry Letters (2012) vol. 22, pp. 3349-3353.
Chen et al. "Cytotoxicity, Hemolysis, and Acute in Vivo Toxicity of Dendrimers Based on Melamine, Candidate Vehicles for Delivery" J. Am. Chem. Soc. (2004) vol. 126, No. 32, pp. 10044-10048.
Cocco et al. "Synthesis of Triflouromethylated Pyridinecarbonitriles" Journal of Heterocyclic Chemistry (1995) vol. 32, pp. 543-545.
Dang et al., "Cancer-associated IDH1 mutations produce 2-hydroxyglutarate." Nature (2009) vol. 462, No. 7274, pp. 739-744.
Dang et al. "IDH Mutations in Glioma and Acute Myeloid Leukemia" Trends in Molecular Medicine (2010) vol. 16, No. 9, pp. 387-397.
Davis et al. "Biochemical, Cellular, and Biophysical Characterization of a Potent Inhibitor of Mutant Isocitrate Dehydrogenase IDH1" The Journal of Biological Chemistry (2014) vol. 289, No. 20, pp. 13717-13725.
Dermer "another Anniversary for the War on Cancer" Bio/Technology (1994) vol. 12, p. 320.
Dohner et al. "Impact of Genetic Features on Treatment Decisions in AML" American Society of Hematology (2011) pp. 36-42.
Duanmu et al. "Dendron-Functionalized Superparamagnetic Nanoparticles with Switchable Solubility in Organic and Aqueous Media: Matriced for Homogeneous Catalysis and Potential MRI Contrast Agents" Chem. Mater. (2006) vol. 18, No. 25, pp. 5973-5981.
European Search Report for European Application No. 12799802.9 dated Sep. 24, 2014.
European Search Report for European Application No. EP 128000015 dated Oct. 10, 2014.
Freshney et al. "Culture of Animal Cells, A Manual of Basic Techniques" Alan R. Liss, Inc. (1983) pp. 1-6.
Genetics Home Reference, "L2HGDH". <http:...ghr.nlm.nih.gove/gene/L2HGDH> accessed on Sep. 4, 2015.
Gewald et al. "Discovery of triazines as potent, selective and orally active PDE4 inhibitors" Bioorganic & medicinal Chemistry Letters (2013) vol. 23, pp. 4308-4314.
Golub et al. "Molecular Classification of Cancer: Class Discovery and Class Prediction by Gene Expression Monitoring" Science (1999) vol. 286, pp. 531-537.
Hartmann et al. "Type and Frequency of IDH1 and IDH2 mutations are related to astrocytic and oligodendroglial differentiation and age: a study of 1010 diffuse gliomas" Acta Neuropathologica (2009) vol. 118, pp. 469-474.
Holmes et al. "750 MHz 1H NMR spectroscopy characterisation of the complex metabolic pattern of urine from patients with inborn errors of metabolism: 2-hydroxyglutaric aciduria and maple syrup urine disease" Journal of Pharmaceutical and Biomedical Analysis (1997) vol. 15, pp. 1647-1659.

(56) References Cited

OTHER PUBLICATIONS

International Preliminary Report on Patentability for International Application No. PCT/CN2012/000841 dated Dec. 17, 2013.
International Preliminary Report on Patentability for International Application No. PCT/CN2012/077096 dated Sep. 17, 2013.
International Search Report for PCT/CN2012/000841 dated Sep. 27, 2012.
International Search Report for PCT/CN2012/077096 dated Oct. 4, 2012.
Irikura et al. "New s-Triazine Derivatives as Depressants for Reticuloendothelial Hyperfunction Induced by Bacterial Endotoxin" Journal of Medicinal Chemistry (2000) vol. 31, pp. 1081-1089.
Jennings et al. "Expression and mutagenesis of mammalian cytosolic NADP+-specific isocitrate dehydrogenase" Biochemistry (1997) vol. 36, pp. 13743-13747.
Kaila et al. "A convenient one-pot synthesis of trisubstituted 1,3,5-triazines through intermediary amidinothioureas" Tetrahedron Letters (2010) vol. 51, pp. 1486-1489.
Kelarev et al. "Synthesis and properties of sym-triazines. 10 Synthesis of 2,4-diamino-sym-triazines containing a sterically hindered phenol substituent" Chemistry of Heterocyclic Compounds (1992) vol. 28, No. 10, pp. 1189-1193.
Kim et al. "Identification and Functional Characterization of a Novel, Tissue-specific NAD+-dependent Isocitrate Dehydrogenase b Subunit Isoform" JBC (1999) vol. 274, No. 52, pp. 36866-36875.
Kim et al. "Ser95, Asn97, and Thr78 are important for the catalytic function of porcine NADP-dependent isocitrate dehydrogenase" Protein Science (2005) vol. 14, pp. 140-147.
Koshelev et al. "Synthesis of 1-3,7 N-substituted 2,4-diamino-1,3,5-triazines containing pyridyl groups" Russian Journal of Organic Chemistry (1995) vol. 31, No. 2, pp. 260-263.
Kranendijk et al. "IDH2 Mutations in Patients with D-2-Hydroxyglutaric Aciduria" Science (2010) vol. 330, p. 336.
Krell et al., "IDH mutations in tumorigenesis and their potential role as novel therapeutic targets" Future Oncology (2013) vol. 9, Iss 12, pp. 1923-1935.
Kusakabe et al. Chemical Abstracts vol. 152, No. 191956, Abstract for WO2010007756 (2010).
Lee et al. "Combinatorial Solid-Phase Synthesis of 6-Aryl-1,3,4-triazines via Suzuki Coupling" Aust. J. Chem. (2011) vol. 64, pp. 540-544.
Liu et al. "Inhibition of Cancer-Associated Mutant Isocitrate Dehydrogenases: Synthesis, Structure—Activity Relationship, and Selective Antitumor Activity" Journal of Medicinal Chemistry (2014) vol. 57, pp. 8307-8318.
Lou, "IDH1: function follows form" SciBX (2009) vol. 2, No. 48, pp. 1-2.
Madsen-Duggan et al. "Lead optimization of 5.6-diarylpyridines as CB1 receptor inverse agonists" Bioorganic & Medicinal Chemistry Letters (2007) vol. 17, pp. 2031-2035.
May et al. "How many species are there on earth" Science (1988) vol. 241, p. 1441.
Moreno et al. "Identification of diamine linkers with differing reactivity and their applicationin the synthesis of melamine dendrimers" Tetrahedron Letters (2008) vol. 49, pp. 1152-1154.
Moreno et al. "Molecular recognition in dendrimers based on melamine" Polymer Preprints (2005) vol. 46, No. 2, pp. 1127.
Parsons et al. "An Integrated Genomic Analysis of Human Glioblastoma Multiforme" Science (2008) vol. 321, pp. 1807-1812 and Supplemental Data.
Registry (STN) [online], Apr. 13, 2007 [Retrieved on Jan. 29, 2016] CAS Registration No. 929819-92-1.
Registry (STN) [online], Apr. 19, 2009 [Retrieved on Jan. 29, 2016] CAS Registration No. 1136498-70-8.
Registry (STN) [online], Aug. 27, 2009 [Retrieved on Jan. 29, 2016] CAS Registration No. 1176756-98-1.
Registry (STN) [online], Aug. 23, 2006 [Retrieved on Jan. 29, 2016] CAS Registration No. 903869-26-1.
Registry (STN) [online], Aug. 23, 2006 [Retrieved on Jan. 29, 2016] CAS Registration No. 903862-76-0.
Registry (STN) [online], Apr. 13, 2007 [Retrieved on Jan. 29, 2016] CAS Registration No. 929971-43-7.
Struys, EA. et al. "Measurement of Urinary D- and L-2-Hydroxyglutarate Enantiomers by Stable-Isotope-Dilution LiquidChromatography—Tandem Mass Spectrometry after Derivatization with Diacetyi-L-Tartaric Anhydride." Clinical Chemistry (2004) 501391-1395.
Lutker et al, "Crystal Polymorphism in a Carbamazepine Derivative: Oxcarbazepine". NIH Public Access. J Pharm Sci. Feb. 2010 ; 99(2): 794-803. doi: 10.1002/jps.21873.
Rao et al., "Polymorphism in Drugs and its Significance in Therapeutics". Journal of Scientific & Industrial Research vol. 46 Oct. 1987 pp. 450-455.
Docoslis et al., "Characterization of the Distribution, Polymorphism, and Stability of Nimodipine in Its Solid Dispersions in Polyethylene Glycol by Micro-Raman Spectroscopy and Powder X-Ray Diffraction". The AAPS Journal 2007; 9 (3) Article 43, E361-E370.
Extended European Search Report for European application No. 16152308.9 dated Jul. 18, 2016.
Wang et al "Facile Synthesis of 2,4-Dianiino-6-alkyi- or 6-Aryl-Pyrimidine Derivatives" Journal of Heterocyclic Chemistry (2010) vol. 47 pp. 1056-1061.
Wang et al. "A novel ligand N,N'-di(2-pyridyl)-2,4-diamino-6-phenyl-1,3,5-triazine (dpdapt) and its complexes: [Cu(dpdapt)Cl2] and [Cu(dpdapt)(NO3)(H2O)] • NO3 • H2O" Polyhedron (2006) vol. 25, No. 1, pp. 195-202.
Ward et al. "The Common Feature of Leukemia-Associated IDH1 and IDH2 Mutations Is a Neomorphic Enzyme Activity Converting [alpha]-Ketoglutarate to 2-Hydroxyglutarate" Cancer Cell (2010) vol. 17, No. 3 pp. 225-234.
Watanabe et al., "IDH1 Mutations Are Early Events in the Development of Astrocytomas and Oligodendrogliomas". American Journal of Pathology (2009) vol. 174, No. 4, pp. 1149-1153.
Yan et al., "IDH1 and IDH2 Mutations in Gliomas." The New England Journal of Medicine, (2009) vol. 360, No. 8, pp. 765-773.
Zhao et al. "Glioma-derived mutations in IDH1 dominantly inhibit IDH1 catalytic activity and induce HIF-1alpha", Science (2009) vol. 324, No. 5924, pp. 261-265.
Zheng et al. "Synthesis and antitumor evaluation of a novel series of triaminotriazine derivatives" Bioorganic & Medicinal Chemistry (2007) vol. 15, pp. 1815-1827.
Mikhaylichenko, Svetlana, et al. "Synthesis and structure of new 1, 2, 3-triazolyl substituted 1, 3, 5-triazines." European Journal of Chemistry 3.1 (2012): 1-9.
Drew, MGB, et al. "Solvent extraction and lanthanide complexation studies with new terdentate ligands containing two 1, 3, 5-triazine moieties." Dalton Transactions 2 (2004): 244-251.
Mikhailichenko, S. N., et al. "sym-triazines. 7. Hydrolysis and cyclization of 1, 3, 5-triazine series mononitriles." Chemistry of Heterocyclic Compounds 42.5 (2006): 642-647.
Enholm, EJ., Jed M. Hastings, and Chris Edwards. "Hydrogen-Bonded Arrays Coupled by Cross-Metathesis." Synlett Feb. 2008 (2008): 203-206.
Database CA [Online] Chemical Abstracts Service. Columbus. Ohio. US; Krimmer. Hans Peter et al: "Reaction of .beta.-mercapto .alpha.-amino acids with nitriles".XP002764690.retrieved from STN Database accession No. 1988:529623* abstract* & Krimmer. Hans Peter et al: "Reaction of .beta.-mercapto .alpha.-amino acids with nitriles".CHEMIKER-Zeitung • 111(12). 357-61 Coden: CMKZAT; ISSN: 0009-2894.1987.
Database CA [Online] Chemical Abstracts Service, Columbus,Ohio, US; Ambartsumyan, E. N. et al: "Synthesis and transformations of chloropyrazolylazines", XP002764692, retrieved from STN Database accession No. 2012:876343 * abstract * & Ambartsumyan, E. N. et al: "Synthesis and transformations of chloropyrazolylazines", Hayastani Kimiakan Handes ( 2011 ), 64(4), 544-550 Coden: KZARF3; ISSN: 561-4190, 2011.
Maison, "Multicomponent synthesis of novel amino acid-nucleobase chimeras: a versatile approach to PNA-monomers," Bioorganic & Medicinal Chemistry (2000) vol. 8, pp. 1343-1360.

(56) References Cited

OTHER PUBLICATIONS

Registry (STN) [online], Apr. 16, 2010, CAS Registration No. 1219379-97-1.
Registry (STN) [online], Jul. 4, 2008, CAS Registration No. 1032747-65-1.
Registry (STN) [online], Jul. 3, 2008, CAS Registration No. 1032470-22-6.
Registry (STN) [online], Jul. 3, 2008, CAS Registration No. 1032461-94-1.
Search Report for SG 11201600185U dated Nov. 16, 2016.
Written Opinion for SG 11201600185U dated Nov. 16, 2016.
Pitts et al., "Rapid Synthesis of Triazine Inhibitors of Inosine Monophosphate Dehydrogenase." Bioorganic & Medicinal Chemistry Letters (2002) vol. 12, pp. 2137-2140.
Shahin et al., "Elaborate ligand-based modeling and subsequent synthetic exploration unveil new nanomora Ca2+/calmodulin-dependent protein kinase II inhibitory leads" Bioorganic & Medicinal Chemistry (2012) vol. 20, pp. 377-400.
Huang et al., "N4-phenyl modifications of N2-(2-hydroxyl)ethyl-6-(pyrrolidin-1-yl)-1,3,5-triazine-2,4-diamines enhance glucocerebrosidase inhibition by small molecules with potential as chemical chaperones for Gaucher disease," Bioorganic & Medicinal Chemistry Letters (2007) vol. 12, pp. 5783-5789.
Yrjola et al., "Discovery of novel cannabinoid receptor ligands by a virtual screening approach: Further development of 2,4,6-trisubstituted 1,3,5-triazines as CB2 agonists." European Journal of Pharmaceutical Sciences (2013) vol. 48, pp. 9-20.
Kumar et al., "Synthesis and bioevaluation of hybrid 4-aminoquinoline triazines as a new class of antimalarial agents." Bioorganic & Medicinal chemistry Letters (2008) vol. 18, pp. 6530-6533.
Ho et al., "Triazine and pyrimidine based ROCK inhibitors with efficacy in spontaneous hypertensive rat model." Bioorganic & Medicinal Chemistry Letters (2009) vol. 19, pp. 6027-6031.
Jana et al., "Synthesis and Antibacterial Activity of Some Novel 4-Benzyl-piperazinyl-s-triazine Derivatives." Asian Journal of Chemistry (2013) vol. 25, No. 1, pp. 186-190.
Kumar et al., "4-Anilinoquinoline triazines: A novel class of hybrid antimalarial agents" European Journal of Medicinal Chemistry (2011) vol. 46, pp. 676-690.
Extended European Search Report for European application No. 14823630.0 dated Oct. 21, 2016.
McRobbie et al. "MRI from Picture to Proton," Cambridge University Press, 2007, pp. 307-308.

\* cited by examiner

THERAPEUTICALLY ACTIVE COMPOSITIONS AND THEIR METHODS OF USE

CLAIM OF PRIORITY

This application is a continuation of U.S. Ser. No. 14/126,763, filed Mar. 10, 2014, which is a national stage application under 35 U.S.C. §371 of International Application No. PCT/CN2012/000841, filed Jun. 18, 2012, published as International Publication No. WO 2012/171337 on Dec. 20, 2012, which claims priority from Chinese Patent Application No. CN 201110172169.1, filed Jun. 17, 2011, U.S. Ser. No. 61/509,071, filed Jul. 18, 2011 and U.S. Ser. No. 61/584,210, filed Jan. 6, 2012, each of which is incorporated by reference in its entirety.

BACKGROUND OF INVENTION

Isocitrate dehydrogenases (IDHs) catalyze the oxidative decarboxylation of isocitrate to 2-oxoglutarate (i.e., α-ketoglutarate). These enzymes belong to two distinct subclasses, one of which utilizes NAD(+) as the electron acceptor and the other NADP(+). Five isocitrate dehydrogenases have been reported: three NAD(+)-dependent isocitrate dehydrogenases, which localize to the mitochondrial matrix, and two NADP(+)-dependent isocitrate dehydrogenases, one of which is mitochondrial and the other predominantly cytosolic. Each NADP(+)-dependent isozyme is a homodimer.

IDH1 (isocitrate dehydrogenase 1 (NADP+), cytosolic) is also known as IDH; IDP; IDCD; IDPC or PICD. The protein encoded by this gene is the NADP(+)-dependent isocitrate dehydrogenase found in the cytoplasm and peroxisomes. It contains the PTS-1 peroxisomal targeting signal sequence. The presence of this enzyme in peroxisomes suggests roles in the regeneration of NADPH for intraperoxisomal reductions, such as the conversion of 2, 4-dienoyl-CoAs to 3-enoyl-CoAs, as well as in peroxisomal reactions that consume 2-oxoglutarate, namely the alpha-hydroxylation of phytanic acid. The cytoplasmic enzyme serves a significant role in cytoplasmic NADPH production.

The human IDH1 gene encodes a protein of 414 amino acids. The nucleotide and amino acid sequences for human IDH1 can be found as GenBank entries NM_005896.2 and NP_005887.2 respectively. The nucleotide and amino acid sequences for IDH1 are also described in, e.g., Nekrutenko et al., Mol. Biol. Evol. 15:1674-1684 (1998); Geisbrecht et al., J. Biol. Chem. 274:30527-30533 (1999); Wiemann et al., Genome Res. 11:422-435 (2001); The MGC Project Team, Genome Res. 14:2121-2127 (2004); Lubec et al., Submitted (December-2008) to UniProtKB; Kullmann et al., Submitted (June-1996) to the EMBL/GenBank/DDBJ databases; and Sjoeblom et al., Science 314:268-274 (2006).

Non-mutant, e.g., wild type, IDH1 catalyzes the oxidative decarboxylation of isocitrate to α-ketoglutarate thereby reducing NAD+ (NADP+) to NADP (NADPH), e.g., in the forward reaction:

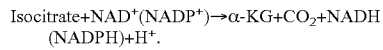
Isocitrate+NAD+(NADP+)→α-KG+CO$_2$+NADH (NADPH)+H+.

It has been discovered that mutations of IDH1 present in certain cancer cells result in a new ability of the enzyme to catalyze the NADPH-dependent reduction of α-ketoglutarate to R(−)-2-hydroxyglutarate (2HG). 2HG is not formed by wild-type IDH1. The production of 2HG is believed to contribute to the formation and progression of cancer (Dang, L et al, Nature 2009, 462:739-44).

The inhibition of mutant IDH1 and its neoactivity is therefore a potential therapeutic treatment for cancer. Accordingly, there is an ongoing need for inhibitors of IDH1 mutants having alpha hydroxyl neoactivity.

SUMMARY OF INVENTION

Described herein are compounds of Structural Formula I:

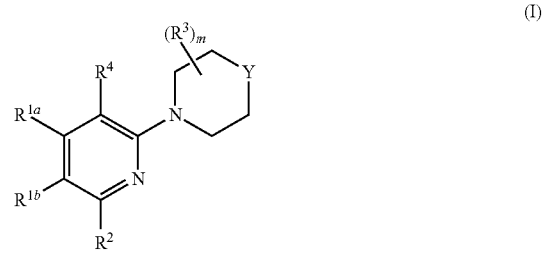

(I)

or a pharmaceutically acceptable salt thereof, wherein:

Y is —N(R$^5$)—, —N(R$_5$)—CH$_2$—, —CH$_2$—N(R$^5$)—, or —CH(R$^5$)—;

each R$^{1a}$ and R$^{1b}$ is independently hydrogen, —C$_1$-C$_4$ alkyl, —N(R$^7$)(C$_1$-C$_4$ alkylene)-N(R$^7$)(C$_1$-C$_4$ alkyl), aryl, heteroaryl, heterocyclyl, —C(O)N(R$^7$)-aryl, —N(R$^7$)C(O)-aryl, —(C$_1$-C$_4$ alkylene)-aryl, —(C$_1$-C$_4$ alkylene)-heteroaryl, —O—(C$_0$-C$_4$ alkylene)-aryl, —O—(C$_0$-C$_4$ alkylene)-heteroaryl, —O—(C$_0$-C$_4$ alkylene)-heterocyclyl, —O—(C$_0$-C$_4$ alkylene)-carbocyclyl, —N(R$^7$)-aryl, —N(R$^7$)-hetero aryl, —N(R$^9$)-aryl, —N(R$^9$)-hetero aryl, —O—(C$_1$-C$_4$ alkeylene)-N(R$^7$)C(O)O—(C$_1$-C$_4$ alkylene)-aryl, or —N(R$^9$)—C(O)—(C$_2$-C$_4$ alkenyl) wherein:

at least one of R$^{1a}$ and R$^{1b}$ is not hydrogen or methyl;

any alkylene moiety present in R$^{1a}$ or R$^{1b}$ is optionally substituted with OH or F;

each R$^7$ is independently selected from hydrogen and C$_1$-C$_4$ alkyl; and any aryl, carbocyclyl, heteroaryl, or heterocyclyl of R$^{1a}$ or R$^{1b}$ is optionally substituted with one or more substituents selected from -G-L-M, halo, —NO$_2$, C$_1$-C$_6$ alkyl, —C≡N, =O, —CF$_3$ and OCF$_3$;

G is a bond or a bivalent C$_1$-C$_6$ saturated or unsaturated, straight or branched hydrocarbon chain wherein optionally one, two or three methylene units of the hydrocarbon chain are independently replaced by —NR$^8$—, —O—, —C(O)—, —OC(O)—, —C(O)O—, —S—, —SO—, —SO$_2$—, —C(=S)—, —C(=NR$^8$)—, —N=N—, or —C(=N$_2$)—;

L is a covalent bond or a bivalent C$_{1-8}$ saturated or unsaturated, straight or branched, hydrocarbon chain, wherein one, two, or three methylene units of L are optionally and independently replaced by cyclopropylene, —NR$^8$—, —N(R$^8$)C(O)—, —C(O)N(R$^8$)—, —N(R$^8$) SO$_2$—, SO$_2$N(R$^8$)—, —O—, —C(O)—, —OC(O)—, —C(O)O—, —S—, —SO—, —SO$_2$—, —C(=S)—, —C(=NR$^8$)—, —N=N—, or —C(=N$_2$)—;

M is E, or a 3-10 membered monocyclic or bicyclic, saturated, partially unsaturated, or aromatic ring having 0-3 heteroatoms independently selected from nitrogen, oxygen, or sulfur, and wherein said ring is substituted with at 1-4 groups independently selected from -D-E, oxo, NO$_2$, halogen, CN, C$_1$-C$_6$ alkyl, C$_2$-C$_6$ alkenyl, or C$_2$-C$_6$ alkynyl;

D is a covalent bond or a bivalent C$_1$-C$_6$ saturated or unsaturated, straight or branched, hydrocarbon chain, wherein one or two methylene units of D are optionally and independently replaced by —$NR^8$—, —S—, —O—, —C(O)—, —SO—, or —$SO_2$—;

E is hydrogen, $C_1$-$C_6$ alkyl, $C_2$-$C_6$ alkenyl, or $C_2$-$C_6$ alkynyl, wherein said alkyl, alkenyl or alkynyl is optionally substituted with oxo, halogen, or CN; and each $R^8$ is independently hydrogen, $C_1$-$C_6$ alkyl, $C_2$-$C_6$ alkenyl, $C_2$-$C_6$ alkynyl, —S(O)$_2$—$C_2$-$C_4$ alkenyl, —$C_1$-$C_6$ alkoxy, or an optionally substituted group selected from phenyl, a 4-7 membered heterocyclyl having 1-2 heteroatoms independently selected from nitrogen, oxygen, or sulfur, or a 5-6 membered monocyclic heteroaryl ring having 1-4 heteroatoms independently selected from nitrogen, oxygen, or sulfur;

$R^2$ is selected from phenyl, a 3-7 membered cycloalkyl, $C_2$-$C_4$ alkyl, or $CF_3$, wherein the phenyl or cycloalkyl is optionally substituted with a substituent selected from methyl or fluoro;

each $R^3$ is independently selected from halo, —($C_1$-$C_4$ alkylene)-O—($C_1$-$C_4$ alkyl), —$C_1$-$C_4$ fluoroalkyl, —C(O)—O—($C_1$-$C_4$ alkyl), -phenyl, -heteroaryl, $C_3$-$C_7$ cycloalkyl, —$CH_2$—N($C_1$-$C_4$ alkyl)$_2$, C(O)—N—($C_1$-$C_4$ alkyl)$_2$, —C(O)—NH—($C_1$-$C_4$ alkyl), —$C_1$-$C_4$ alkyl optionally substituted with one or more halo or —OH, or two $R^3$s are taken together to form a 3-8 saturated ring or a fused phenyl wherein said saturated ring or fused phenyl is optionally substituted with 1 to 2 methyl;

$R^4$ is selected from hydrogen, —CN, halo, $C_1$-$C_4$ alkoxy, —$CH_2NH$($C_1$-$C_4$ alkyl), $C_2$-$C_4$ alkenyl, $C_2$-$C_4$ alkynyl, —($C_1$-$C_4$ alkyl)-O—($C_1$-$C_4$ alkyl), $C_1$-$C_4$ fluoroalkyl, C(O)—N—($C_1$-$C_4$ alkyl)$_2$, —C(O)—NH—($C_1$-$C_4$ alkyl), —C(O)—O—($C_1$-$C_4$ alkyl), —C(O)—OH, —S(O)$_2$—($C_1$-$C_4$ alkyl), and a 5-membered heteroaryl;

$R^5$ is selected from: —C(O)—($C_1$-$C_5$ alkyl), —C(O)—($C_2$-$C_6$ alkenyl), —C(O)—($C_0$-$C_2$ alkylene)-Q, —C(O)—($C_1$-$C_4$ alkenylene)-Q, —C(O)—($C_0$-$C_2$ alkylene)-N($R^6$)—($C_0$-$C_2$ alkylene)-Q, —C(O)—O—($C_0$-$C_2$ alkylene)-Q, —C(O)—($C_1$-$C_2$ alkylene)-O—($C_0$-$C_2$ alkylene)-Q, —C(O)—C(O)-Q, —S(O)$_2$-Q, —C(O)—($C_1$-$C_4$ alkylene)-O—C(O)—($C_1$-$C_4$ alkyl), —C(O)—($C_1$-$C_4$ alkylene)-C(O)—O—($C_1$-$C_4$ alkyl), —C(O)—N($R^6$)—($C_1$-$C_4$ alkylene)-O—C(O)—($C_1$-$C_4$ alkyl), —C(O)—N($R^6$)—($C_1$-$C_4$ alkylene)-C(O)—O—($C_1$-$C_4$ alkyl), —C(O)—($C_0$-$C_2$ alkylene)-N($R^6$)—($C_1$-$C_6$ alkyl), —C(O)—($C_0$-$C_2$ alkylene)N($R^6$)—($C_2$-$C_6$ alkynyl), —C(O)—($C_0$-$C_2$ alkylene)-N($R^6$)—($C_2$-$C_6$ alkenyl), —C(O)—($C_0$-$C_2$ alkylene)-N($R^6$)—($C_0$-$C_2$ alkylene)-O—($C_1$-$C_4$ alkyl), —C(O)—($C_1$-$C_2$ alkylene)-O—($C_1$-$C_4$ alkyl), —C(O)—($C_1$-$C_2$ alkylene)-C(O)C(O)N(R)($C_1$-$C_4$ alkyl), —C(O)—O—($C_1$-$C_4$ alkylene)-O—($C_1$-$C_4$ alkyl), —($C_0$-$C_4$ alkylene)-O—C(O)—($C_1$-$C_4$ alkyl), —($C_0$-$C_4$ alkylene)-C(O)—O—($C_1$-$C_4$ alkyl), —($C_0$-$C_4$ alkylene)-O—($C_1$-$C_4$ alkyl), —C(O)—($C_1$-$C_2$ alkylene)-S(O)$_{0-2}$—($C_1$-$C_4$ alkyl), —S(O)$_2$—($C_1$-$C_4$ alkyl), —C(O)—($C_1$-$C_4$ alkylene)-C(O)C(O)N($R^6$)($C_1$-$C_6$ alkyl), —C(O)—($C_1$-$C_4$ alkylene)-N($R^6$)S(O)$_2$—($C_1$-$C_6$ alkyl), or —C(O)—($C_1$-$C_4$ alkylene)-N($R^6$)S(O)$_2$Q, wherein:

any alkylene moiety present in $R^5$ is optionally substituted with $OCH_3$, OH or F;

any terminal methyl moiety present in $R^5$ is optionally replaced with —$CH_2OH$, $CF_3$, —$CH_2F$, —$CH_2Cl$, $C(O)CH_3$, $C(O)CF_3$, CN, —$OCH_3$, —C(O)H, —OP(O)(OH)$_2$, —OP(O)($C_1$-$C_4$ alkoxy)$_2$ or $CO_2H$;

each $R^6$ is independently selected from hydrogen and methyl;

Q is selected from aryl, heteroaryl, carbocyclyl and heterocyclyl, wherein Q is optionally substituted with up to 3 substituents independently selected from $C_1$-$C_4$ alkyl optionally substituted with —OH, $C_1$-$C_4$ alkoxy, —C(O)O—($C_1$-$C_4$ alkyl), —($C_1$-$C_4$ alkylene)-($C_1$-$C_4$ alkoxy), —CN, —OH, fluoro, chloro, and bromo;

$R^9$ is selected from aryl and heteroaryl, wherein each aryl or heteroaryl is optionally substituted with one or more substituents selected from -G-L-M, halo, $C_1$-$C_6$ alkyl, —C≡N, =O, —$CF_3$ and $OCF_3$; and m is 0, 1, 2 or 3.

The compound of formula I inhibits mutant IDH1, particularly mutant IDH1 having alpha hydroxyl neoactivity. Also described herein are pharmaceutical compositions comprising a compound of formula I or a salt thereof and methods of using such compositions to treat cancers characterized by the presence of a mutant IDH1.

DETAILED DESCRIPTION OF THE INVENTION

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

Definitions

The term "halo" or "halogen" refers to any radical of fluorine, chlorine, bromine or iodine.

The term "alkyl" refers to a hydrocarbon chain that may be a straight chain or branched chain, containing the indicated number of carbon atoms. For example, $C_1$-$C_{12}$ alkyl indicates that the group may have from 1 to 12 (inclusive) carbon atoms in it. The term "haloalkyl" refers to an alkyl in which one or more hydrogen atoms are replaced by halo, and includes alkyl moieties in which all hydrogens have been replaced by halo (e.g., perfluoroalkyl). The terms "arylalkyl" or "aralkyl" refer to an alkyl moiety in which an alkyl hydrogen atom is replaced by an aryl group. Aralkyl includes groups in which more than one hydrogen atom has been replaced by an aryl group. Examples of "arylalkyl" or "aralkyl" include benzyl, 2-phenylethyl, 3-phenylpropyl, 9-fluorenyl, benzhydryl, and trityl groups.

The term "alkylene" refers to a divalent alkyl, e.g., —$CH_2$—, —$CH_2CH_2$—, —$CH_2CH_2CH_2$— and $CH_2CH(CH_3)CH_2$—.

The term "alkenyl" refers to a straight or branched hydrocarbon chain containing 2-12 carbon atoms and having one or more double bonds. Examples of alkenyl groups include, but are not limited to, allyl, propenyl, 2-butenyl, 3-hexenyl and 3-octenyl groups. One of the double bond carbons may optionally be the point of attachment of the alkenyl substituent.

The term "alkynyl" refers to a straight or branched hydrocarbon chain containing 2-12 carbon atoms and characterized in having one or more triple bonds. Examples of alkynyl groups include, but are not limited to, ethynyl, propargyl, and 3-hexynyl. One of the triple bond carbons may optionally be the point of attachment of the alkynyl substituent.

The term "alkoxy" refers to an —O-alkyl radical. The term "haloalkoxy" refers to an alkoxy in which one or more hydrogen atoms are replaced by halo, and includes alkoxy moieties in which all hydrogens have been replaced by halo (e.g., perfluoroalkoxy).

The term "aryl" refers to a fully aromatic monocyclic, bicyclic, or tricyclic hydrocarbon ring system. Examples of aryl moieties are phenyl, naphthyl, and anthracenyl. Unless otherwise specified, any ring atom in an aryl can be substituted by one or more substituents.

The term "carbocyclyl" refers to a non-aromatic, monocyclic, bicyclic, or tricyclic hydrocarbon ring system. Carbocyclyl groups include fully saturated ring systems (e.g., cycloalkyls), and partially saturated ring systems.

The term "cycloalkyl" as employed herein includes saturated cyclic, bicyclic, tricyclic, or polycyclic hydrocarbon groups having 3 to 12 carbons. Any ring atom can be substituted (e.g., by one or more substituents). Examples of cycloalkyl moieties include, but are not limited to, cyclopropyl, cyclohexyl, methylcyclohexyl, adamantyl, and norbornyl.

The term "heteroaryl" refers to a fully aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (or the oxidized forms such as $N^+$—$O^-$, S(O) and S(O)$_2$).

The term "heterocyclyl" refers to a nonaromatic, 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (or the oxidized forms such as $N^+$—$O^-$, S(O) and S(O)$_2$). The heteroatom may optionally be the point of attachment of the heterocyclyl substituent. Examples of heterocyclyl include, but are not limited to, tetrahydrofuranyl, tetrahydropyranyl, piperidinyl, morpholino, pyrrolinyl, pyrimidinyl, and pyrrolidinyl. Heterocyclyl groups include fully saturated ring systems, and partially saturated ring systems.

Bicyclic and tricyclic ring systems containing one or more heteroatoms and both aromatic and non-aromatic rings where the point of attachment from the ring system to the rest of the molecule is through a non-aromatic ring are considered to be heterocyclyl groups. Bicyclic or tricyclic ring systems where an aryl or a heteroaryl is fused to a carbocyclyl or heterocyclyl and the point of attachment from the ring system to the rest of the molecule is through an aromatic ring are considered to be aryl or heteroaryl groups.

Aryl, heteroaryl, carbocyclyl (including cycloalkyl), and heterocyclyl groups, either alone or a part of a group (e.g., the aryl portion of an aralkyl group), are optionally substituted at one or more substitutable atoms with, unless specified otherwise, substituents independently selected from: halo, —C≡N, $C_1$-$C_4$ alkyl, =O, —$OR^b$, —$OR^{b'}$, —$SR^b$, —$SR^{b'}$, —($C_1$-$C_4$ alkyl)-N($R^b$)($R^b$), —($C_1$-$C_4$ alkyl)-N($R^b$)($R^{b'}$), —N($R^b$)($R^b$), —N($R^b$)($R^{b'}$), —O—($C_1$-$C_4$ alkyl)-N($R^b$)($R^b$), —O—($C_1$-$C_4$ alkyl)-N($R^b$)($R^{b'}$), —($C_1$-$C_4$ alkyl)-O—($C_1$-$C_4$ alkyl)-N($R^b$)($R^b$), —($C_1$-$C_4$ alkyl)-O—($C_1$-$C_4$ alkyl)-N($R^b$)($R^b$), —C(O)—N($R^b$)($R^b$), —($C_1$-$C_4$ alkyl)-C(O)—N($R^b$)($R^b$), —($C_1$-$C_4$ alkyl)-C(O)—N($R^b$)($R^{b'}$), —$OR^{b'}$, $R^{b'}$, —C(O)($C_1$-$C_4$ alkyl), —C(O)$R^{b'}$, —C(O)N($R^b$)($R^{b'}$), —N($R^b$)C(O)($R^b$), —N($R^b$)C(O)($R^{b'}$), —N($R^b$)SO$_2$($R^b$), —SO$_2$N($R^b$)($R^b$), —N($R^b$)SO$_2$($R^{b'}$), and —SO$_2$N($R^b$)($R^{b'}$), wherein any alkyl substituent is optionally further substituted with one or more of —OH, —O—($C_1$-$C_4$ alkyl), halo, —NH$_2$, —NH($C_1$-$C_4$ alkyl), or —N($C_1$-$C_4$ alkyl)$_2$;

each $R^b$ is independently selected from hydrogen, and —$C_1$-$C_4$ alkyl; or two $R^b$s are taken together with the nitrogen atom to which they are bound to form a 4- to 8-membered heterocyclyl optionally comprising one additional heteroatom selected from N, S, and O; and each $R^{b'}$ is independently selected from $C_3$-$C_7$ carbocyclyl, phenyl, heteroaryl, and heterocyclyl, wherein one or more substitutable positions on said phenyl, cycloalkyl, heteroaryl or heterocycle substituent is optionally further substituted with one or more of —($C_1$-$C_4$ alkyl), —($C_1$-$C_4$ fluoroalkyl), —OH, —O—($C_1$-$C_4$ alkyl), —O—($C_1$-$C_4$ fluoroalkyl), halo, —NH$_2$, —NH($C_1$-$C_4$ alkyl), or —N($C_1$-$C_4$ alkyl)$_2$.

Heterocyclyl groups, either alone or as part of a group, are optionally substituted on one or more any substitutable nitrogen atom with oxo, —$C_1$-$C_4$ alkyl, or fluoro-substituted $C_1$-$C_4$ alkyl.

The term "substituted" refers to the replacement of a hydrogen atom by another group.

As used herein, the term "elevated levels of 2HG" means 10%, 20% 30%, 50%, 75%, 100%, 200%, 500% or more 2HG then is present in a subject that does not carry a mutant IDH1 allele. The term "elevated levels of 2HG" may refer to the amount of 2HG within a cell, within a tumor, within an organ comprising a tumor, or within a bodily fluid.

The term "bodily fluid" includes one or more of amniotic fluid surrounding a fetus, aqueous humour, blood (e.g., blood plasma), serum, Cerebrospinal fluid, cerumen, chyme, Cowper's fluid, female ejaculate, interstitial fluid, lymph, breast milk, mucus (e.g., nasal drainage or phlegm), pleural fluid, pus, saliva, sebum, semen, serum, sweat, tears, urine, vaginal secretion, or vomit.

As used herein, the terms "inhibit" or "prevent" include both complete and partial inhibition and prevention. An inhibitor may completely or partially inhibit the intended target.

The term "treat" means decrease, suppress, attenuate, diminish, arrest, or stabilize the development or progression of a disease/disorder (e.g., a cancer), lessen the severity of the disease/disorder (e.g., a cancer) or improve the symptoms associated with the disease/disorder (e.g., a cancer).

As used herein, an amount of a compound effective to treat a disorder, or a "therapeutically effective amount" refers to an amount of the compound which is effective, upon single or multiple dose administration to a subject, in treating a cell, or in curing, alleviating, relieving or improving a subject with a disorder beyond that expected in the absence of such treatment.

As used herein, the term "subject" is intended to include human and non-human animals. Exemplary human subjects include a human patient (referred to as a patient) having a disorder, e.g., a disorder described herein or a normal subject. The term "non-human animals" of the invention includes all vertebrates, e.g., non-mammals (such as chickens, amphibians, reptiles) and mammals, such as non-human primates, domesticated and/or agriculturally useful animals, e.g., sheep, dog, cat, cow, pig, etc.

Compounds
Provided is a compound of Structural Formula I:

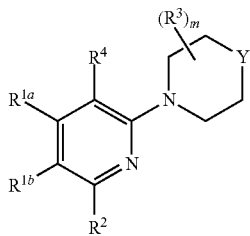

or a pharmaceutically acceptable salt thereof, wherein:
Y is $-N(R^5)-$, $-N(R_5)-CH_2-$, $-CH_2-N(R^5)-$, or $-CH(R^5)-$;

each $R^{1a}$ and $R^{1b}$ is independently hydrogen, $-C_1-C_4$ alkyl, $-N(R^7)(C_1-C_4$ alkylene)-$N(R^7)(C_1-C_4$ alkyl), aryl, heteroaryl, heterocyclyl, $-C(O)N(R^7)$-aryl, $-N(R^7)C(O)$-aryl, $-(C_1-C_4$ alkylene)-aryl, $-(C_1-C_4$ alkylene)-heteroaryl, $-O-(C_0-C_4$ alkylene)-aryl, $-O-(C_0-C_4$ alkylene)-heteroaryl, $-O-(C_0-C_4$ alkylene)-heterocyclyl, $-O-(C_0-C_4$ alkylene)-carbocyclyl, $-N(R^7)$-aryl, $-N(R^7)$-heteroaryl, $-N(R^9)$-aryl, $-N(R^9)$-heteroaryl, $-O-(C_1-C_4$ alkeylene)-$N(R^7)C(O)O-(C_1-C_4$ alkylene)-aryl, or $-N(R^9)-C(O)-(C_2-C_4$ alkenyl) wherein:
at least one of $R^{1a}$ and $R^{1b}$ is not hydrogen or methyl;
any alkylene moiety present in $R^{1a}$ or $R^{1b}$ is optionally substituted with OH or F;
each $R^7$ is independently selected from hydrogen and $C_1-C_4$ alkyl; and
any aryl, carbocyclyl, heteroaryl, or heterocyclyl of $R^{1a}$ or $R^{1b}$ is optionally substituted with one or more substituents selected from -G-L-M, halo, $-NO_2$, $C_1-C_6$ alkyl, $-C\equiv N$, $=O$, $-CF_3$ and $-OCF_3$;
G is a bond or a bivalent $C_1-C_6$ saturated or unsaturated, straight or branched hydrocarbon chain wherein optionally one, two or three methylene units of the hydrocarbon chain are independently replaced by $-NR^8-$, $-O-$, $-C(O)-$, $-OC(O)-$, $-C(O)O-$, $-S-$, $-SO-$, $-SO_2-$, $-C(=S)-$, $-C(=NR^8)-$, $-N=N-$, or $-C(=N_2)-$;
L is a covalent bond or a bivalent $C_{1-8}$ saturated or unsaturated, straight or branched, hydrocarbon chain, wherein one, two, or three methylene units of L are optionally and independently replaced by cyclopropylene, $-NR^8-$, $-N(R^8)C(O)-$, $-C(O)N(R^8)-$, $-N(R^8)SO_2-$, $SO_2N(R^8)-$, $-O-$, $-C(O)-$, $-OC(O)-$, $-C(O)O-$, $-S-$, $-SO-$, $-SO_2-$, $-C(=S)-$, $-C(=NR^8)-$, $-N=N-$, or $-C(=N_2)-$;
M is E, or a 3-10 membered monocyclic or bicyclic, saturated, partially unsaturated, or aromatic ring having 0-3 heteroatoms independently selected from nitrogen, oxygen, or sulfur, and wherein said ring is substituted with at 1-4 groups independently selected from -D-E, oxo, $NO_2$, halogen, CN, $C_1-C_6$ alkyl, $C_2-C_6$ alkenyl, or $C_2-C_6$ alkynyl;
D is a covalent bond or a bivalent $C_1-C_6$ saturated or unsaturated, straight or branched, hydrocarbon chain, wherein one or two methylene units of D are optionally and independently replaced by $-NR^8-$, $-S-$, $-O-$, $-C(O)-$, $-SO-$, or $-SO_2-$;
E is hydrogen, $C_1-C_6$ alkyl, $C_2-C_6$ alkenyl, or $C_2-C_6$ alkynyl, wherein said alkyl, alkenyl or alkynyl is optionally substituted with oxo, halogen, or CN; and
each $R^8$ is independently hydrogen, $C_1-C_6$ alkyl, $C_2-C_6$ alkenyl, $C_2-C_6$ alkynyl, $-C_1-C_6$ alkoxy, $-S(O)_2-C_2-C_4$ alkenyl, or an optionally substituted group selected from phenyl, a 4-7 membered heterocyclyl having 1-2 heteroatoms independently selected from nitrogen, oxygen, or sulfur, or a 5-6 membered monocyclic heteroaryl ring having 1-4 heteroatoms independently selected from nitrogen, oxygen, or sulfur;

$R^2$ is selected from phenyl, a 3-7 membered cycloalkyl, $C_2-C_4$ alkyl, or $CF_3$, wherein the phenyl or cycloalkyl is optionally substituted with a substituent selected from methyl or fluoro;

each $R^3$ is independently selected from halo, $-(C_1-C_4$ alkylene)-$O-(C_1-C_4$ alkyl), $-C_1-C_4$ fluoroalkyl, $-C(O)-O-(C_1-C_4$ alkyl), -phenyl, -heteroaryl, $C_3-C_7$ cycloalkyl, $-CH_2-N(C_1-C_4$ alkyl)$_2$, $C(O)-N-(C_1-C_4$ alkyl)$_2$, $-C(O)-NH-(C_1-C_4$ alkyl), $-C_1-C_4$ alkyl optionally substituted with one or more halo or $-OH$, or two $R^3$s are taken together to form a 3-8 saturated ring or a fused phenyl wherein said saturated ring or fused phenyl is optionally substituted with 1 to 2 methyl;

$R^4$ is selected from hydrogen, $-CN$, halo, $C_1-C_4$ alkoxy, $-CH_2NH(C_1-C_4$ alkyl), $C_2-C_4$ alkenyl, $C_2-C_4$ alkynyl, $-(C_1-C_4$ alkyl)-$O-(C_1-C_4$ alkyl), $C_1-C_4$ fluoroalkyl, $C(O)-N-(C_1-C_4$ alkyl)$_2$, $-C(O)-NH-(C_1-C_4$ alkyl), $-C(O)-O-(C_1-C_4$ alkyl), $-C(O)-OH$, $-S(O)_2-(C_1-C_4$ alkyl), and a 5-membered heteroaryl;

$R^5$ is selected from: $-C(O)-(C_1-C_5$ alkyl), $-C(O)-(C_2-C_6$ alkenyl), $-C(O)-(C_0-C_2$ alkylene)-Q, $-C(O)-(C_1-C_4$ alkenylene)-Q, $-C(O)-(C_0-C_2$ alkylene)-$N(R^6)-(C_0-C_2$ alkylene)-Q, $-C(O)-O-(C_0-C_2$ alkylene)-Q, $-C(O)-(C_1-C_2$ alkylene)-$O-(C_0-C_2$ alkylene)-Q, $-C(O)-C(O)-Q$, $-S(O)_2-Q$, $-C(O)-(C_1-C_4$ alkylene)-$O-C(O)-(C_1-C_4$ alkyl), $-C(O)-(C_1-C_4$ alkylene)-C(O)-O-(C_1-C_4$ alkyl), $-C(O)-N(R^6)-(C_1-C_4$ alkylene)-$O-C(O)-(C_1-C_4$ alkyl), $-C(O)-N(R^6)-(C_1-C_4$ alkylene)-C(O)-O-(C_1-C_4$ alkyl), $-C(O)-(C_0-C_2$ alkylene)-$N(R^6)-(C_1-C_6$ alkyl), $-C(O)-(C_0-C_2$ alkylene)N $(R^6)-(C_2-C_6$ alkynyl), $-C(O)-(C_0-C_2$ alkylene)-$N(R^6)-(C_2-C_6$ alkenyl), $-C(O)-(C_0-C_2$ alkylene)-$N(R^6)-(C_0-C_2$ alkylene)-$O-(C_1-C_4$ alkyl), $-C(O)-(C_1-C_2$ alkylene)-$O-(C_1-C_4$ alkyl), $-C(O)-(C_1-C_2$ alkylene)-C(O)C(O)N(R)(C_1-C_4$ alkyl), $-C(O)-O-(C_1-C_4$ alkylene)-$O-(C_1-C_4$ alkyl), $-(C_0-C_4$ alkylene)-$O-C(O)-(C_1-C_4$ alkyl), $-(C_0-C_4$ alkylene)-$C(O)-O-(C_1-C_4$ alkyl), $-(C_0-C_4$ alkylene)-$O-(C_1-C_4$ alkyl), $-C(O)-(C_1-C_2$ alkylene)-$S(O)_{0-2}-(C_1-C_4$ alkyl), $-S(O)_2-(C_1-C_4$ alkyl), $-C(O)-(C_1-C_4$ alkylene)-$C(O)C(O)N(R^6)(C_1-C_6$ alkyl), $-C(O)-(C_1-C_4$ alkylene)-$N(R^6)S(O)_2-(C_1-C_6$ alkyl), or $-C(O)-(C_1-C_4$ alkylene)-$N(R^6)S(O)_2Q$, wherein:
any alkylene moiety present in $R^5$ is optionally substituted with $OCH_3$, OH or F;
any terminal methyl moiety present in $R^5$ is optionally replaced with $-CH_2OH$, $CF_3$, $-CH_2F$, $-CH_2Cl$, $C(O)CH_3$, $C(O)CF_3$, CN, $-OCH_3$, $-C(O)H$, $-OP(O)(OH)_2$, $-OP(O)(C_1-C_4$ alkoxy)$_2$ or $CO_2H$;
each $R^6$ is independently selected from hydrogen and methyl;

Q is selected from aryl, heteroaryl, carbocyclyl and heterocyclyl, wherein Q is optionally substituted with up to 3 substituents independently selected from $C_1-C_4$ alkyl optionally substituted with $-OH$, $C_1-C_4$ alkoxy, $-C(O)$ $O-(C_1-C_4$ alkyl), $-(C_1-C_4$ alkylene)-$(C_1-C_4$ alkoxy), $-CN$, $-OH$, fluoro, chloro, and bromo;

$R^9$ is selected from aryl, and heteroaryl, wherein each aryl or heteroaryl is optionally substituted with one or more substituents selected from -G-L-M, halo, $C_1-C_6$ alkyl, $-C\equiv N$, $=O$, $-CF_3$ and $OCF_3$; and
m is 0, 1, 2 or 3.

In some embodiments, provided is a compound of Structural Formula I:

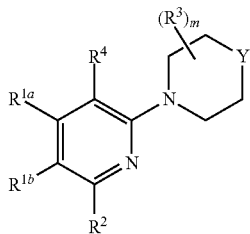

or a pharmaceutically acceptable salt thereof, wherein:

Y is —N($R^5$)— or —CH($R^5$)—;

each $R^{1a}$ and $R^{1b}$ is independently hydrogen, —$C_1$-$C_4$ alkyl, —N($R^7$)($C_1$-$C_4$ alkylene)-N($R^7$)($C_1$-$C_4$ alkyl), aryl, heteroaryl, heterocyclyl, —C(O)N($R^7$)-aryl, —N($R^7$)C(O)-aryl, —($C_1$-$C_4$ alkylene)-aryl, —($C_1$-$C_4$ alkylene)-heteroaryl, —O—($C_1$-$C_4$ alkylene)-aryl, —O—($C_1$-$C_4$ alkylene)-heteroaryl, —O—($C_1$-$C_4$ alkylene)-heterocyclyl, —N($R^7$)-aryl, or —N($R^7$)-heteroaryl, wherein:

at least one of $R^{1a}$ and $R^{1b}$ is not hydrogen or methyl;

any alkylene moiety present in $R^{1a}$ or $R^{1b}$ is optionally substituted with OH or F;

each $R^7$ is independently selected from hydrogen and $C_1$-$C_4$ alkyl; and any aryl, heteroaryl, or heterocyclyl of $R^{1a}$ or $R^{1b}$ is optionally substituted with one or more substituents selected from -G-L-M, halo, $C_1$-$C_6$ alkyl, —C≡N, =O, —$CF_3$ and —$OCF_3$;

G is a bond or a bivalent $C_1$-$C_6$ saturated or unsaturated, straight or branched hydrocarbon chain wherein optionally one, two or three methylene units of the hydrocarbon chain are independently replaced by —$NR^8$—, —O—, —C(O)—, —OC(O)—, —C(O)O—, —S—, —SO—, —$SO_2$—, —C(=S)—, —C(=$NR^8$)—, —N=N—, or —C(=$N_2$)—;

L is a covalent bond or a bivalent $C_{1-8}$ saturated or unsaturated, straight or branched, hydrocarbon chain, wherein one, two, or three methylene units of L are optionally and independently replaced by cyclopropylene, —$NR^8$—, —N($R^8$)C(O)—, —C(O)N($R^8$)—, —N($R^8$)$SO_2$—, $SO_2$N($R^8$)—, —O—, —C(O)—, —OC(O)—, —C(O)O—, —S—, —SO—, —$SO_2$—, —C(=S)—, —C(=$NR^8$)—, —N=N—, or —C(=$N_2$)—; M is E, or a 3-10 membered monocyclic or bicyclic, saturated, partially unsaturated, or aromatic ring having 0-3 heteroatoms independently selected from nitrogen, oxygen, or sulfur, and wherein said ring is substituted with at 1-4 groups independently selected from -D-E, oxo, $NO_2$, halogen, CN, $C_1$-$C_6$ alkyl, $C_2$-$C_6$ alkenyl, or $C_2$-$C_6$ alkynyl;

D is a covalent bond or a bivalent $C_1$-$C_6$ saturated or unsaturated, straight or branched, hydrocarbon chain, wherein one or two methylene units of D are optionally and independently replaced by —$NR^8$—, —S—, —O—, —C(O)—, —SO—, or —$SO_2$—;

E is hydrogen, $C_1$-$C_6$ alkyl, $C_2$-$C_6$ alkenyl, or $C_2$-$C_6$ alkynyl, wherein said alkyl, alkenyl or alkynyl is optionally substituted with oxo, halogen, or CN; and each $R^8$ is independently hydrogen, $C_1$-$C_6$ alkyl, $C_2$-$C_6$ alkenyl, $C_2$-$C_6$ alkynyl, or an optionally substituted group selected from phenyl, a 4-7 membered heterocyclyl having 1-2 heteroatoms independently selected from nitrogen, oxygen, or sulfur, or a 5-6 membered monocyclic heteroaryl ring having 1-4 heteroatoms independently selected from nitrogen, oxygen, or sulfur;

$R^2$ is selected from phenyl, a 3-7 membered cycloalkyl, and $C_2$-$C_4$ alkyl, wherein the phenyl or cycloalkyl is optionally substituted with a substituent selected from methyl or fluoro;

each $R^3$ is independently selected from —$C_1$-$C_4$ alkyl, —($C_1$-$C_4$ alkyl)-O—($C_1$-$C_4$ alkyl), —$C_1$-$C_4$ fluoroalkyl, —C(O)—O—($C_1$-$C_4$ alkyl), -phenyl, -heteroaryl, $C_3$-$C_7$ cycloalkyl, —$CH_2$—N($C_1$-$C_4$ alkyl)$_2$, C(O)—N—($C_1$-$C_4$ alkyl)$_2$, and —C(O)—NH—($C_1$-$C_4$ alkyl), or or two $R^3$s are taken together to form a 3-8 saturated ring or a fused phenyl wherein said saturated ring or fused phenyl is optionally substituted with 1 to 2 methyl groups;

$R^4$ is selected from hydrogen, —CN, halo, $C_1$-$C_4$ alkoxy, —$CH_2$NH($C_1$-$C_4$ alkyl), $C_2$-$C_4$ alkenyl, $C_2$-$C_4$ alkynyl, —($C_1$-$C_4$ alkyl)-O—($C_1$-$C_4$ alkyl), $C_1$-$C_4$ fluoroalkyl, C(O)—N—($C_1$-$C_4$ alkyl)$_2$, —C(O)—NH—($C_1$-$C_4$ alkyl), —C(O)—O—($C_1$-$C_4$ alkyl), —C(O)—OH, —S(O)$_2$—($C_1$-$C_4$ alkyl), and a 5-membered heteroaryl;

$R^5$ is selected from: —C(O)—($C_1$-$C_4$alkyl), —C(O)—($CH_2$)$_{0-2}$-Q, —C(O)—($CH_2$)$_{0-2}$—N($R^6$)—($CH_2$)$_{0-2}$-Q, —C(O)—O—($CH_2$)$_{1-2}$-Q, —C(O)—($CH_2$)$_{1-2}$—O—($CH_2$)$_{0-2}$-Q, —C(O)—C(O)-Q, —S(O)$_2$-Q, —C(O)—($C_1$-$C_4$ alkylene)-O—C(O)—($C_1$-$C_4$ alkyl), —C(O)—($C_1$-$C_4$ alkylene)-C(O)—O—($C_1$-$C_4$ alkyl), —C(O)—N($R^6$)—($C_1$-$C_4$ alkylene)-O—C(O)—($C_1$-$C_4$ alkyl), —C(O)—N($R^6$)—($C_1$-$C_4$ alkylene)-C(O)—O—($C_1$-$C_4$ alkyl), —C(O)—($CH_2$)$_{0-2}$—N($R^6$)—($C_1$-$C_6$ alkyl), —C(O)—($CH_2$)$_{0-2}$—N($R^6$)—($C_2$-$C_6$ alkynyl), —C(O)—($CH_2$)$_{0-2}$—N($R^6$)—($C_2$-$C_6$ alkenyl), —C(O)—($CH_2$)$_{0-2}$—N($R^6$)—($CH_2$)$_{0-2}$—O—($C_1$-$C_4$ alkyl), —C(O)—($CH_2$)$_{1-2}$—O—($C_1$-$C_4$ alkyl), —C(O)—O—($C_1$-$C_4$ alkylene)-O—($C_1$-$C_4$ alkyl), —($CH_2$)$_{0-4}$—O—C(O)—($C_1$-$C_4$ alkyl), —($CH_2$)$_{0-4}$—C(O)—O—($C_1$-$C_4$ alkyl), —($CH_2$)$_{0-4}$—O—($C_1$-$C_4$ alkyl), —C(O)—($CH_2$)$_{1-2}$—S—($C_1$-$C_4$ alkyl), —S(O)$_2$—($C_1$-$C_4$ alkyl), —C(O)—($C_1$-$C_4$ alkylene)-C(O)C(O)N($R^6$)($C_1$-$C_6$ alkyl), —C(O)—($C_1$-$C_4$ alkylene)-N($R^6$)S(O)$_2$—($C_1$-$C_6$ alkyl), and —C(O)—($C_1$-$C_4$ alkylene)-N($R^6$)S(O)$_2$Q, wherein:

any alkylene moiety present in $R^5$ is optionally substituted with OH or F;

any terminal methyl moiety present in $R^5$ is optionally replaced with —$CH_2$OH, $CF_3$, —$CH_2$F, —$CH_2$Cl, C(O)$CH_3$, or C(O)$CF_3$;

each $R^6$ is independently selected from hydrogen and methyl;

Q is selected from aryl, heteroaryl, carbocyclyl and heterocyclyl, wherein Q is optionally substituted with up to 3 substituents independently selected from $C_1$-$C_4$ alkyl, $C_1$-$C_4$ alkoxy, —CN, fluoro, chloro, and bromo; and m is 0, 1, 2 or 3.

In some embodiments, m is 0, 1 or 2; and each $R^3$, if present, is independently selected from methyl, ethyl, $CF_3$, isopropyl, cyclopropyl and phenyl. In some embodiments, $R^3$ is methyl or cyclopropyl. In some embodiments, $R^3$ is methyl. In some embodiments, $R^3$ is cyclopropyl.

In some embodiments, m is 1. In some embodiments, m is 2.

In some embodiments, m is 1 and $R^3$ is $C_{3-7}$ cycloalkyl (e.g., cyclopropyl). In some embodiments, m is 1 and $R^3$ is $C_1$-$C_4$ (alkyl) (e.g., methyl or isopropyl). In some embodiments, m is 1 and $R^3$ is haloalkyl (e.g., $C_1$-$C_4$ fluoroalkyl, e.g., $CF_3$). In some embodiments, m is 2, one $R^3$ is $C_{1-4}$ alkyl (e.g., methyl) and the other $R^3$ is halo (e.g., fluoro).

In some embodiments, $R^4$ is —CN or —C(O)—O—($C_1$-$C_4$ alkyl). In some embodiments, $R^4$ is CN.

In some embodiments, $R^4$ is:

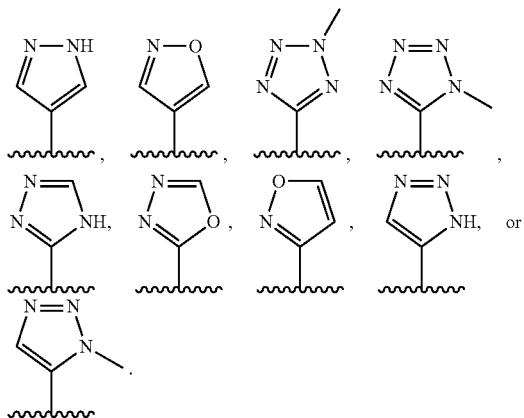

In some embodiments, $R^4$ is

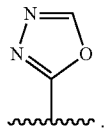

In some embodiments, Y is —N($R_5$)—$CH_2$— or —$CH_2$—N($R^5$)—; $R^5$ is —C(O)-Q and Q is cyclopropyl.

In some embodiments, Y is —N($R^5$)—; $R^5$ is —C(O)$R^{10}$; and $R^{10}$ is selected from heteroaryl, aryl, —$CH_2$-aryl, —$CH_2$-heteroaryl, and —$(CH_2)_2$—O—$CH_3$, wherein any aryl or heteroaryl portion of $R^8$ is optionally substituted with methyl.

In some embodiments, Y is —N($R^5$)—; $R^5$ is selected from selected from: —C(O)—($C_1$-$C_5$ alkyl), —C(O)—($C_2$-$C_6$ alkenyl), —C(O)—($C_0$-$C_2$ alkylene)-Q, —C(O)—($C_1$-$C_4$ alkenylene)-Q, —C(O)—($C_0$-$C_2$ alkylene)-N($R^6$)—($C_0$-$C_2$ alkylene)-Q, —C(O)—($C_1$-$C_2$ alkylene)-O—($C_0$-$C_2$ alkylene)-Q, —C(O)—($C_1$-$C_4$ alkylene)-O—C(O)—($C_1$-$C_4$ alkyl), —C(O)—($C_1$-$C_4$ alkylene)-C(O)—O—($C_1$-$C_4$ alkyl), —C(O)—($C_0$-$C_2$ alkylene)-N($R^6$)—($C_1$-$C_6$ alkyl), —C(O)—($C_0$-$C_2$ alkylene)N($R^6$)—($C_2$-$C_6$ alkynyl), —C(O)—($C_0$-$C_2$ alkylene)-N($R^6$)—($C_2$-$C_6$ alkenyl), —C(O)—($C_0$-$C_2$ alkylene)-N($R^6$)—($C_0$-$C_2$ alkylene)-O—($C_1$-$C_4$ alkyl), —($C_0$ alkylene)-C(O)O—($C_1$-$C_4$ alkyl), —C(O)—($C_1$-$C_2$ alkylene)-O—($C_1$-$C_4$ alkyl), —C(O)—($C_1$-$C_2$ alkylene)-C(O)C(O)N(R)($C_1$-$C_4$ alkyl), or —C(O)—($C_1$-$C_4$ alkylene)-C(O)C(O)N($R^6$)($C_1$-$C_6$ alkyl), wherein:

any alkylene moiety present in $R^5$ is optionally substituted with $OCH_3$, OH or F;
any terminal methyl moiety present in $R^5$ is optionally replaced with —$CH_2$OH, $CF_3$, —$CH_2$F, —$CH_2$Cl, C(O)$CH_3$, C(O)$CF_3$, CN, —$OCH_3$, —C(O)H, —OP(O)(OH)$_2$, —OP(O)($C_1$-$C_4$ alkoxy)$_2$ or $CO_2$H;
each $R^6$ is independently selected from hydrogen and methyl;
Q is cyclopropyl, cyclobutyl, oxetanyl, furanyl, azetidinonyl, pyrrolidinonyl, tetrahydrofuranyl, dihydrofuranonyl, or cyclopentyl, wherein each member of Q is optionally substituted with up to 3 substituents independently selected from $C_1$-$C_4$ alkyl optionally substituted with OH, $C_1$-$C_4$ alkoxy, —C(O)O—($C_1$-$C_4$ alkyl), —($C_1$-$C_4$ alkylene)-($C_1$-$C_4$ alkoxy), —CN, —OH, fluoro, chloro, and bromo.

In some embodiments, Y is —N($R^5$)—; and $R^5$ is C(O)—($C_1$-$C_3$ alkyl)-O—($C_1$-$C_2$ alkyl), —C(O)-Q, —C(O)—($C_1$-$C_5$ alkyl), —C(O)—($C_1$-$C_2$ alkylene)-Q, —C(O)—($C_2$-$C_4$ alkenyl), —C(O)O—($C_1$-$C_4$ alkyl), or —C(O)—($C_1$-$C_4$ alkenylene)-Q; wherein: any alkylene moiety present in $R^5$ is optionally substituted with OH; any terminal methyl moiety present in $R^5$ is optionally replaced with OH, $CF_3$, $OCH_3$, —C(O)H, OP(O)($C_1$-$C_4$ alkoxy)$_2$, or —OP(O)(OH)$_2$ (or a salt thereof, such as a sodium salt); Q is cyclopropyl, cyclobutyl, oxetanyl, furanyl, azetidinonyl, pyrrolidinonyl, tetrahydrofuranyl, dihydrofuranonyl, or cyclopentyl, wherein each member of Q is optionally substituted with one substituent independently selected from $C_1$-$C_4$ alkyl optionally substituted with OH, $C_1$-$C_4$ alkoxy, —($C_1$-$C_4$ alkylene)-($C_1$-$C_4$ alkoxy), and —OH.

In some embodiments, Y is —N($R^5$)—; and $R^5$ is C(O)—($C_1$-$C_3$ alkyl)-O—($C_1$-$C_2$ alkyl). In some embodiments, Y is —N($R^5$)—; and $R^5$ is —C(O)—($CH_2$)$_2$—$OCH_3$. In some embodiments, Y is —N($R^5$)— and $R^5$ is C(O)—($C_1$-$C_3$ alkyl)-$CF_3$. In some embodiments, Y is —N($R^5$)— and $R^5$ is —C(O)—$CH_2$—$CF_3$. In some embodiments, Y is —N($R^5$)—; $R^5$ is —C(O)-Q and Q is cyclopropyl, oxetanyl or furanyl. In some embodiments, Y is —N($R^5$)— and $R^5$ is —C(O)—$CH_2$—$CH_2$OH. In some embodiments, Y is —N($R^5$)—; $R^5$ is —C(O)-Q where Q is substituted with $C_{1-4}$ alkoxy. In some embodiments, Y is —N($R^5$)— and $R^5$ is —C(O)-cyclopropyl substituted with $C_{1-4}$ alkoxy (e.g., ethoxy). In some embodiments, Y is —N($R^5$)— and $R^5$ is —C(O)—$OCH_3$. In some embodiments, Y is —N($R^5$)— and $R^5$—C(O)-Q where Q is substituted with ($C_{1-4}$ alkylene)-$OCH_3$. In some embodiments, Y is —N($R^5$)— and $R^5$—C(O)-cyclopropyl substituted with $CH_2OCH_3$. In some embodiments, Y is —N($R^5$)— and $R^5$—C(O)-Q where Q is substituted with $C_{1-4}$ alkyl wherein alkyl is optionally substituted with —OH. In some embodiments, Y is —N($R^5$)— and $R^5$—C(O)-cyclopropyl substituted with $CH_2OH$. In some embodiments, Y is —N($R^5$)—; $R^5$ is —C(O)-Q where Q is substituted with OH. In some embodiments, Y is —N($R^5$)—; $R^5$ is —C(O)-cyclopropyl substituted with OH. In some embodiments, Y is —N($R^5$)—; $R^5$ is —C(O)—($C_{1-4}$ alkyl)-OH. In some embodiments, Y is —N($R^5$)—; $R^5$ is —C(O)—$CH_2C(OH)(CH_3)_2$. In some embodiments, Y is —N($R^5$)—; $R^5$ is —C(O)—$CH_2CH(OH)CH_3$. In some embodiments, Y is —N($R^5$)—; $R^5$ is —C(O)—$CH_2CH_2CH_2OH$. In some embodiments, Y is —N($R^5$)—; $R^5$ is —C(O)—$CH_2CH_2OH$. In some embodiments, Y is —N($R^5$)—; and $R^5$ is —C(O)—($C_1$-$C_4$ alkyl). In some embodiments, Y is —N($R^5$)—; and $R^5$ is —C(O)—$CH_3$. In some embodiments, Y is —N($R^5$)—; $R^5$ is —C(O)—($C_{1-4}$ alkyl)-($OCH_3$)$_2$. In some embodiments, Y is —N($R^5$)—; $R^5$ is —C(O)—$CH_2CH_2C(H)(OCH_3)_2$. In some embodiments, Y is —N($R^5$)—; $R^5$ is —C(O)—($C_{1-4}$ alkyl)-C(O)H. In some embodiments, Y is —N($R^5$)—; $R^5$ is —C(O)—$CH_2CH_2C(O)H$. In some embodiments, Y is —N($R^5$)—; $R^5$ is —C(O)—C(cyclopropyl)(OH). In some embodiments, Y is —N($R^5$)—; $R^5$ is —C(O)—($C_{1-4}$ alkyl)-C(O)$OCH_3$. In some embodiments, Y is —N($R^5$)—; $R^5$ is —C(O)—$CH_2CH_2C(O)OCH_3$. In some embodiments, Y is —N($R^5$)— and $R^5$ is —C(O)—($C_0$-$C_2$ alkylene)-Q. In some embodiments, Y is —N($R^5$)— and $R^5$ is —C(O)—($C_0$-$C_2$ alkylene)-Q, where Q is cyclopropyl, cyclobutyl, oxetanyl, furanyl, azetidinonyl, pyrrolidinonyl, tetrahydrofuranyl, dihydrofuranonyl, or cyclopentyl. In some embodiments, Y is —N($R^5$)— and $R^5$ is —C(O)—$CH_2$-oxetanyl, —C(O)—

CH₂-azetidinonyl, —C(O)—CH₂-pyrrolidinonyl, —C(O)—CH₂-cyclobutyl, —C(O)—CH₂-cyclopropyl, —C(O)—CH₂CH₂-cyclopropyl, —C(O)—CH₂-tetrahydrofuranyl, —C(O)—CH₂-dihydrofuranone, —C(O)—CH₂-oxetanyl, —C(O)—CH₂CH₂-furanyl, —C(O)—CH₂-tetrahydrofuranyl, —C(O)—CH₂CH₂-tetrahydrofuranyl or —C(O)—CH₂-cyclopentyl. In some embodiments, Y is —N(R⁵)— and R⁵ is —C(O)—(C₂-C₄ alkenyl)-OH. In some embodiments, Y is —N(R⁵)— and R⁵ is —C(O)—CH═CH—CH₂CH₂OH. In some embodiments, Y is —N(R⁵)— and R⁵—(C₀-C₄ alkylene)-C(O)—O—(C₁-C₄ alkyl). In some embodiments, Y is —N(R⁵)— and R⁵—C(O)—O-(t-butyl). In some embodiments, Y is —N(R⁵)— and R⁵—C(O)—(C₁-C₄ alkyl)-OP(O)(C₁-C₄ alkoxy)₂. In some embodiments, Y is —N(R⁵)— and R⁵—C(O)—CH₂CH₂CH₂—OP(O)(t-butoxy)₂. In some embodiments, Y is —N(R⁵)— and R⁵—C(O)—(C₁-C₄ alkyl)-OP(O)(OH)₂ or a salt thereof, such as a sodium salt. In some embodiments, Y is —N(R⁵)— and R⁵—C(O)—CH₂CH₂—OP(O)(t-butoxy)₂. In some embodiments, Y is —N(R⁵)—; and R⁵ is —C(O)—(C₁-C₅ alkyl). In some embodiments, Y is —N(R⁵)—; and R⁵ is —C(O)-pentyl. In some embodiments, Y is —N(R⁵)—; and R⁵—C(O)—(C₁-C₄ alkenylene)-Q. In some embodiments, Y is —N(R⁵)—; and R⁵—C(O)—CH═cyclobutyl.

In some embodiments, one of $R^{1a}$ or $R^{1b}$ is selected from hydrogen and methyl; and the other of $R^{1a}$ or $R^{1b}$ is selected from isopropyl, —N(CH₃)—(CH₂)₂—NH—CH₃, aryl, heteroaryl, —CH₂-aryl, —CH₂-heteroaryl, —O—CH₂-aryl, and —O—CH₂-heteroaryl; wherein any aryl or heteroaryl of $R^{1a}$ or $R^{1b}$ is optionally substituted with one or more substituents independently selected from alkoxy, OH, halo, C₁-C₆ alkyl, —CF₃, CN, —OC(O)CH₃, and —OCF₃.

In some embodiments, one of $R^{1a}$ or $R^{1b}$ is selected from hydrogen and methyl; and the other of $R^{1a}$ or $R^{1b}$ is selected from aryl, heteroaryl, heterocyclyl, —(C₁-C₄ alkylene)-aryl, —(C₁-C₄ alkylene)-heteroaryl, —O—(C₀-C₄ alkylene)-aryl, —O—(C₀-C₄ alkylene)-heteroaryl, —N(R⁷)-aryl, —N(R⁷)heteroaryl, —N(R⁹)-aryl, or —N(R⁹)-heteroaryl, wherein said aryl, heterocyclyl, or heteroaryl is substituted with -G-L-M, CH₃, CN, alkoxy, OH, halo, C₁-C₆ alkyl, —CF₃, —OC(O)CH₃, or —OCF₃.

In some embodiments, one of $R^{1a}$ or $R^{1b}$ is selected from hydrogen and methyl; and the other of $R^{1a}$ or $R^{1b}$ is selected from aryl, heteroaryl, heterocyclyl, —(C₁-C₄ alkylene)-aryl, —(C₁-C₄ alkylene)-heteroaryl, —O—(C₀-C₄ alkylene)-aryl, —O—(C₀-C₄ alkylene)-heteroaryl, —N(R⁷)-aryl, —N(R⁷) heteroaryl, —N(R⁹)-aryl, or —N(R⁹)-heteroaryl, wherein said aryl or heteroaryl is substituted with -G-L-M, CH₃, or CN.

In some embodiments, $R^{1a}$ is H and $R^{1b}$ is aryl, heteroaryl, heterocyclyl, —(C₁-C₄ alkylene)-aryl, —(C₁-C₄ alkylene)-heteroaryl, —O—(C₀-C₄ alkylene)-aryl, or —O—(C₀-C₄ alkylene)-heteroaryl, —N(R⁷)-aryl, —N(R⁷)heteroaryl, —N(R⁹)-aryl, —N(R⁹)-heteroaryl, wherein said aryl or heteroaryl is substituted with -G-L-M, CH₃, or CN. In some aspects of the preceding embodiments, $R^{1a}$ is H and $R^{1b}$ is aryl, heteroaryl, heterocyclyl, —CH₂-aryl, —CH₂-heteroaryl, —O-aryl, —O-heteroaryl, —O—(CH₂)-aryl, —O—CH(CH₃)-aryl, —O(CH)(C(CH₃)₂)-aryl, —O—CH(CH₂CH₃)-aryl, —NH-aryl, —NH-heteroaryl, —N(CH₃)-aryl, —N(CH₃)-heteroaryl, —N(aryl)-aryl, —N(heteroaryl)-heteroaryl, —O—(CH₂)-heteroaryl or —O—CH(CH₃)-heteroaryl, wherein aryl is phenyl, heteroaryl is pyridyl, pyrimidinyl, naphthyridinyl, quinolyl, isoquinolyl, isoxazolyl, benzoxazolyl, imidazopyrazinyl, benzothiazolyl, benzimidazolyl, pyrollopyridinyl, pyrazolopyridinyl, indolyl, indazolyl, imidazopyridinyl, quinoxalinyl, quinazolinyl, pyridazinyl or pyrazolyl, and heterocyclyl is benzodioxole, pyridazinone, benzoxazolone, indolinone, N-methylindolinone, piperazinyl, N-methylisoquinolinone, tetrahydropyridinyl, dihydropyrrolyl and said phenyl, pyridyl, pyrimidinyl, naphthyridinyl, quinolyl, isoquinolyl, isoxazolyl, benzoxazolyl, imidazopyrazinyl, benzothiazolyl, benzimidazolyl, pyrollopyridinyl, pyrazolopyridinyl, indolyl, indazolyl, imidazopyridinyl, quinoxalinyl, quinazolinyl, pyridazinyl, pyrazolyl, benzodioxole, pyridazinone, benzoxazolone, indolinone, N-methylindolinone, piperazinyl, N-methylisoquinolinone, tetrahydropyridinyl, or dihydropyrrolyl is substituted with -G-L-M, —CF₃, —OCF₃, halo (e.g., fluoro, chloro or bromo), CH₃, or CN.

In some embodiments, $R^{1a}$ is methyl and $R^{1b}$ is aryl, heteroaryl, heterocyclyl, —O—(C₀-C₄ alkylene)-aryl, or —O—(C₀-C₄ alkylene)-heteroaryl, wherein said aryl or heteroaryl is substituted with -G-L-M, CH₃, or CN. In some aspects of the preceding embodiments, $R^{1a}$ is methyl or H and $R^{1b}$ is aryl, heteroaryl, heterocyclyl, —O—(CH₂)-aryl, —O—CH(CH₃)-aryl, —O—(CH₂)-heteroaryl or —O—CH(CH₃)-heteroaryl, wherein aryl is phenyl or naphthyl and heteroaryl is quinolinyl, pyrazolyl, isoquinolinyl, pyridyl, pyrimidinyl, indolyl, or pyrazolyl, and heterocyclyl is tetrahydropyridinyl and said phenyl, pyridyl, pyrimidinyl, indolyl, or pyrazolyl is substituted with -G-L-M, halo (e.g., chloro or fluoro), CH₃, or CN.

In some embodiments, -G-L-M is:

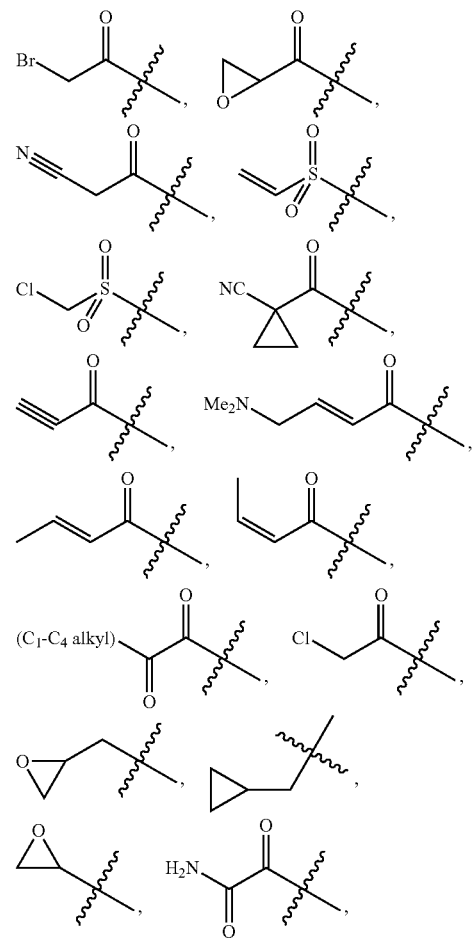

-continued

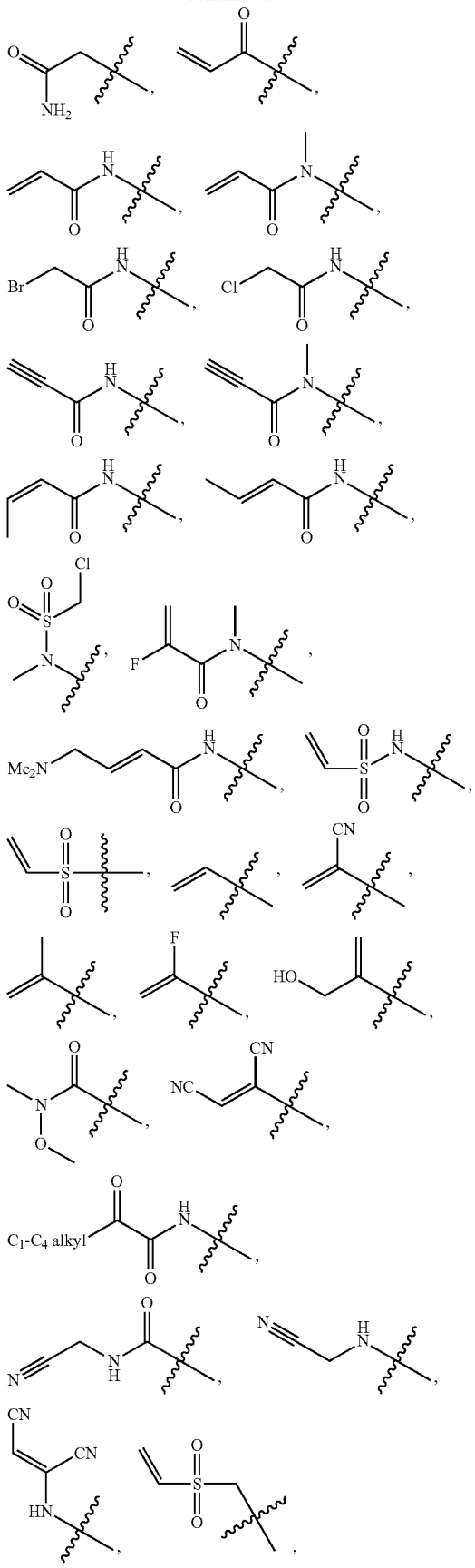

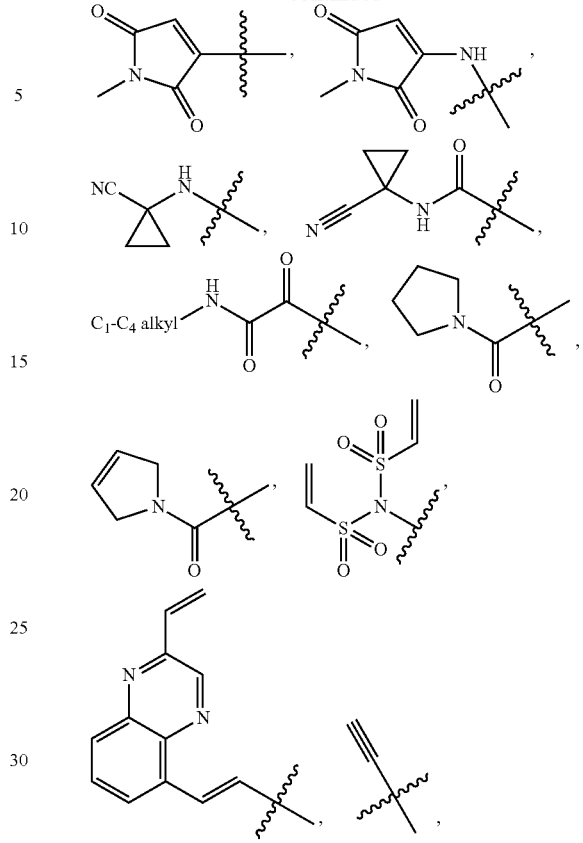

C$_1$-C$_4$ alkyl, C$_2$-C$_4$ alkenyl, C$_1$-C$_4$ alkoxy, hydrogen, tetrazolyl, morpholino, piperazinyl, pyrrolidinone, pyrazolyl, benzyl, —(CH$_2$)$_{1-4}$—SH, —(CH$_2$)$_{1-4}$—NH$_2$, —NH$_2$, (CH$_2$)$_{1-4}$—OH, —N(H)C(O)OCH(CH$_3$)$_3$, —(CH$_2$)$_{1-4}$—OCH$_3$, —NH—(CH$_2$)$_{1-4}$—OH, —C(O)—(C$_1$-C$_4$ alkyl), —C(O)—(C$_1$-C$_4$ alkenyl), —O—(CH$_2$)$_{1-4}$—C(O)—O—(C$_1$-C$_4$ alkyl), —C(O)NH$_2$, —(CH$_2$)$_{1-4}$C(O)CH$_3$, —N(CH$_3$)(CH$_3$), —NHC(O)(C$_2$-C$_4$ alkenyl), —NHC(O)(C$_2$-C$_4$ alkyl), —SO$_2$(CH$_2$)$_{1-4}$, —(CH$_2$)$_{1-4}$—NHSO$_2$Me, —NHSO$_2$(CH$_2$)$_{1-4}$, —O—SO$_2$CF$_3$, —SO$_2$NH—(C$_1$-C$_4$ alkyl), —SO$_2$NH—(C$_2$-C$_4$ alkenyl), SO$_2$—NH$_2$ or NHSO$_2$Me.

In some embodiments, R$^2$ is selected from isopropyl, cyclopropyl, cyclohexyl, and phenyl. In some embodiments, R$^2$ is cyclopropyl. In some embodiments, R$_2$ is isopropyl.

In some embodiments, R$^4$ is CN; Y is —N(R$^5$)—; R$^5$ is —C(O)R$^{10}$; and the compound has Structural Formula II:

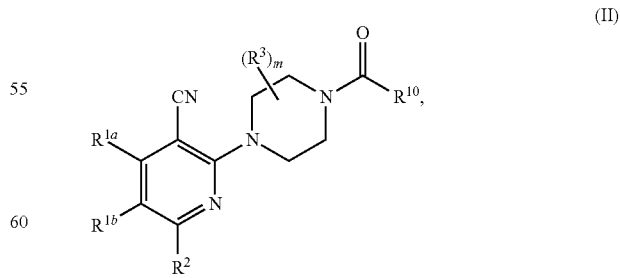

or a pharmaceutically acceptable salt thereof, wherein:
one of R$^{1a}$ or R$^{1b}$ is selected from hydrogen and methyl;
the other of R$^{1a}$ or R$^{1b}$ is selected from aryl, heteroaryl, heterocyclyl, —(C$_1$-C$_4$ alkylene)-aryl, —(C$_1$-C$_4$ alkylene)- heteroaryl, —O—(C₀-C₄ alkylene)-aryl, —O—(C₀-C₄ alkylene)-heteroaryl, —N(R⁷)-aryl, —N(R⁷)heteroaryl, —N(R⁹)-aryl, or —N(R⁹)-heteroaryl, wherein said aryl, heterocyclyl, or heteroaryl is substituted with -G-L-M, CH₃, CN, alkoxy, OH, halo, C₁-C₆ alkyl, —CF₃, —OC(O)CH₃, or —OCF₃;

R² is selected from isopropyl, cyclopropyl, cyclohexyl, and phenyl;

each R³, if present, is selected from methyl, ethyl, isopropyl, CF₃, cyclopropyl and phenyl;

R¹⁰ is selected from —(C₁-C₃ alkyl)-O—(C₁-C₂ alkyl), Q, (C₁-C₅ alkyl), C₁-C₂ alkylene)-Q, (C₂-C₄ alkenyl), —O—(C₁-C₄ alkyl), or —(C₁-C₄ alkenylene)-Q; wherein: any alkylene moiety present in R¹⁰ is optionally substituted with OH; any terminal methyl moiety present in R¹⁰ is optionally replaced with OH, CF₃, OCH₃, —C(O)H, —OP(O)(C₁-C₄ alkoxy)₂, or —OP(O)(OH)₂ (or a salt thereof, such as a sodium salt); Q is cyclopropyl, cyclobutyl, oxetanyl, furanyl, azetidinonyl, pyrrolidinonyl, tetrahydrofuranyl, dihydrofuranonyl, or cyclopentyl, wherein each member of Q is optionally substituted with one substituent independently selected from C₁-C₄ alkyl optionally substituted with OH, C₁-C₄ alkoxy, —(C₁-C₄ alkylene)-(C₁-C₄ alkoxy), and —OH; and m is 0, 1, or 2.

In certain embodiments, m is 1; and the compound has Structural Formula IIa:

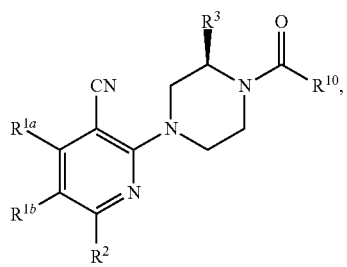

(IIa)

or a pharmaceutically acceptable salt thereof, wherein:
R¹ᵃ is hydrogen or methyl;
R¹ᵇ is selected from aryl, heteroaryl, heterocyclyl, —(C₁-C₄ alkylene)-aryl, —(C₁-C₄ alkylene)-heteroaryl, —O—(C₀-C₄ alkylene)-aryl, —O—(C₀-C₄ alkylene)-heteroaryl, —N(R⁷)-aryl, —N(R⁷)heteroaryl, —N(R⁹)-aryl, or —N(R⁹)-heteroaryl, wherein said aryl, heterocyclyl, or heteroaryl is substituted with -G-L-M, CH₃, CN, alkoxy, OH, halo, C₁-C₆ alkyl, —CF₃, —OC(O)CH₃, or —OCF₃;

R² is selected from isopropyl, cyclopropyl, cyclohexyl, and phenyl;

each R³, if present, is selected from methyl, isopropyl, and cyclopropyl;

R¹⁰ is selected from —(C₁-C₃ alkyl)-O—(C₁-C₂ alkyl), Q, (C₁-C₅ alkyl), C₁-C₂ alkylene)-Q, (C₂-C₄ alkenyl), —O—(C₁-C₄ alkyl), or —(C₁-C₄ alkenylene)-Q; wherein: any alkylene moiety present in R¹⁰ is optionally substituted with OH; any terminal methyl moiety present in R¹⁰ is optionally replaced with —OH, CF₃, OCH₃, —C(O)H, —OP(O)(C₁-C₄ alkoxy)₂, or —OP(O)(OH)₂ (or a salt thereof, such as a sodium salt); Q is cyclopropyl, cyclobutyl, oxetanyl, furanyl, azetidinonyl, pyrrolidinonyl, tetrahydrofuranyl, dihydrofuranonyl, or cyclopentyl, wherein each member of Q is optionally substituted with one substituent independently selected from C₁-C₄ alkyl optionally substituted with OH, C₁-C₄ alkoxy, —(C₁-C₄ alkylene)-(C₁-C₄ alkoxy), and —OH; and m is 0, 1, or 2.

In some embodiments, R⁴ is CN; Y is —N(R⁵)—; R⁵ is —C(O)R¹⁰; and the compound has Structural Formula II:

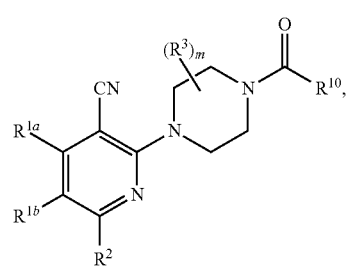

(II)

or a pharmaceutically acceptable salt thereof, wherein:
one of R¹ᵃ or R¹ᵇ is selected from hydrogen and methyl;
the other of R¹ᵃ or R¹ᵇ is selected from isopropyl, —N(CH₃)—(CH₂)₂—NH—CH₃, aryl, heteroaryl, —CH₂-aryl, —CH₂-heteroaryl, —O—CH₂-aryl, and —O—CH₂-heteroaryl; wherein any aryl or heteroaryl portion of R¹ᵃ or R¹ᵇ is optionally substituted with one or more substituents independently selected from alkoxy, hydroxy, halo, C₁-C₆ alkyl, —CF₃, —OC(O)CH₃, and —OCF₃;

R² is selected from isopropyl, cyclopropyl, cyclohexyl, and phenyl;

each R³, if present, is selected from methyl, ethyl, isopropyl, cyclopropyl and phenyl;

R¹⁰ is selected from heteroaryl, aryl, —CH₂-aryl, —CH₂-heteroaryl, and —(CH₂)₂—O—CH₃, wherein any aryl or heteroaryl portion of R¹⁰ is optionally substituted with methyl; and m is 0, 1, or 2.

In certain embodiments, m is 1; and the compound has Structural Formula IIa:

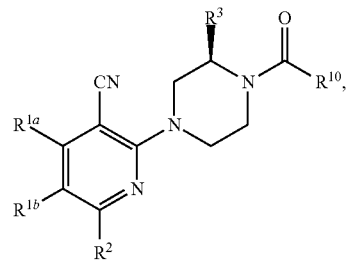

(IIa)

or a pharmaceutically acceptable salt thereof, wherein:
R¹ᵃ is selected from hydrogen and methyl;
R¹ᵇ is selected from aryl, and heteroaryl; wherein the aryl or heteroaryl is optionally substituted with one or more substituents independently selected from methoxy, fluoro, chloro, methyl, —CF₃, —OCF₃;

R² is selected from isopropyl and cyclopropyl;

R³ is selected from methyl, ethyl, isopropyl and cyclopropyl; and

R¹⁰ is selected from —(CH₂)₂—O—CH₃, furan-3-yl, 2-methylfuran-3-yl and thien-2-yl.

In some embodiments, $R^4$ is CN; Y is —N($R^5$)—; $R^5$ is —C(O)$R^{10}$; and the compound has Structural Formula II:

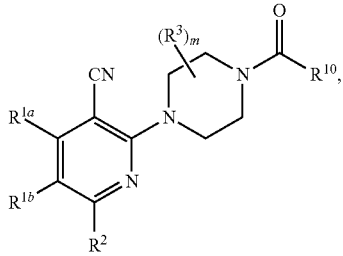

or a pharmaceutically acceptable salt thereof, wherein:

$R^{1a}$ is H;

$R^{1b}$ is aryl, 1 heteroaryl, —O—($C_1$-$C_4$ alkylene)-aryl, or —O—($C_1$-$C_4$ alkylene)-heteroaryl, wherein said aryl or heteroaryl is substituted with -G-L-M, $CH_3$, or CN;

$R^2$ is selected from isopropyl, cyclopropyl, cyclohexyl, and phenyl;

each $R^3$, if present, is selected from methyl, ethyl, isopropyl, cyclopropyl and phenyl;

$R^{10}$ is selected from heteroaryl, aryl, —$CH_2$-aryl, —$CH_2$-heteroaryl, and —($CH_2$)$_2$—O—$CH_3$, wherein any aryl or heteroaryl portion of $R^{10}$ is optionally substituted with methyl; and m is 0, 1, or 2.

In certain embodiments, m is 1; and the compound has Structural Formula IIa:

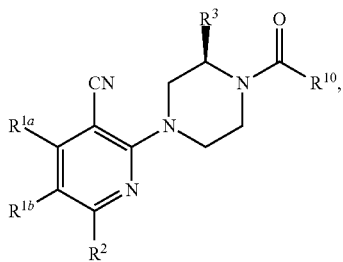

or a pharmaceutically acceptable salt thereof, wherein:

$R^{1a}$ is H;

$R^{1b}$ is aryl, heteroaryl, —O—($CH_2$)-aryl, —O—CH($CH_3$)-aryl, —O—($CH_2$)-heteroaryl or —O—CH($CH_3$)-heteroaryl, wherein aryl is phenyl and heteroaryl is pyridyl, pyrimidinyl, indolyl, or pyrazolyl, and said phenyl, pyridyl, pyrimidinyl, indolyl or pyrazolyl is substituted with -G-L-M, $CH_3$, or CN;

$R^2$ is selected from isopropyl and cyclopropyl;

$R^3$ is selected from methyl, ethyl, isopropyl and cyclopropyl; and $R^{10}$ is selected from —($CH_2$)$_2$—O—$CH_3$, furan-3-yl 2-methylfuran-3-yl and thien-2-yl.

In another embodiment, the compound is selected from any one of the compounds set forth in Table 1, below.

TABLE 1

Exemplary Compounds of Formula I.

| Cmpd No. | Structure |
|---|---|
| 100 | 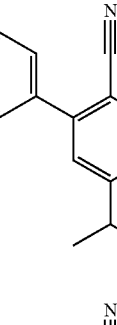 |
| 101 | 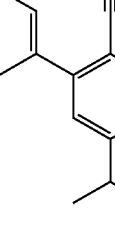 |
| 102 | 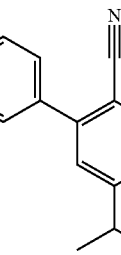 |
| 103 | 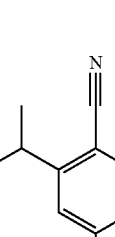 |
| 104 | 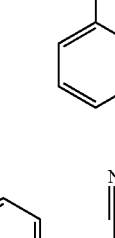 |

TABLE 1-continued

Exemplary Compounds of Formula I.

| Cmpd No. | Structure |
|---|---|
| 105 | 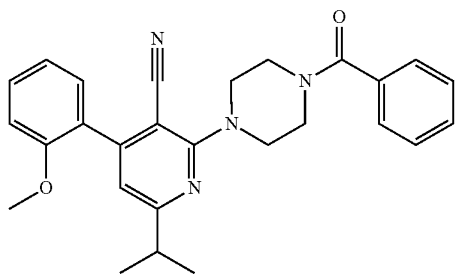 [SMILES: COc1ccccc1-c1cc(C(C)C)nc(N2CCN(C(=O)c3ccccc3)CC2)c1C#N] |
| 106 | 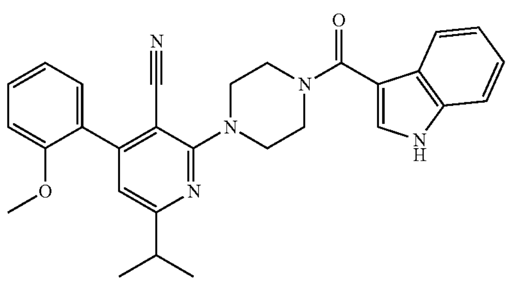 [SMILES: COc1ccccc1-c1cc(C(C)C)nc(N2CCN(C(=O)c3c[nH]c4ccccc34)CC2)c1C#N] |
| 107 | 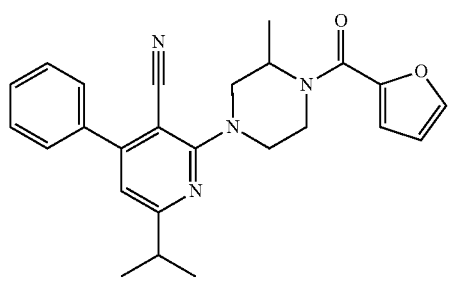 [SMILES: CC(C)c1cc(-c2ccccc2)c(C#N)c(N2CCN(C(=O)c3ccco3)C(C)C2)n1] |
| 108 | 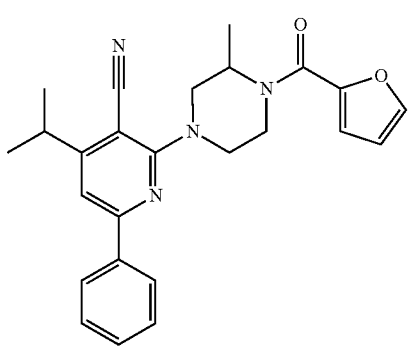 [SMILES: CC(C)c1cc(-c2ccccc2)nc(N2CCN(C(=O)c3ccco3)C(C)C2)c1C#N] |
| 109 | 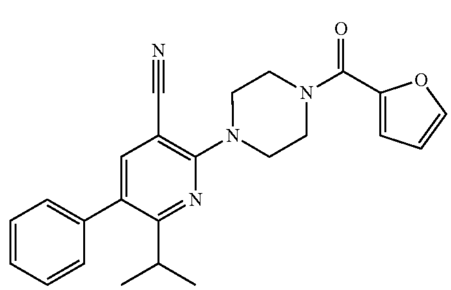 [SMILES: CC(C)c1nc(N2CCN(C(=O)c3ccco3)CC2)c(C#N)cc1-c1ccccc1] |
| 110 | |
| 111 | |
| 113 | |
| 114 | |
| 115 | |

TABLE 1-continued

Exemplary Compounds of Formula I.

| Cmpd No. | Structure |
|---|---|
| 116 | 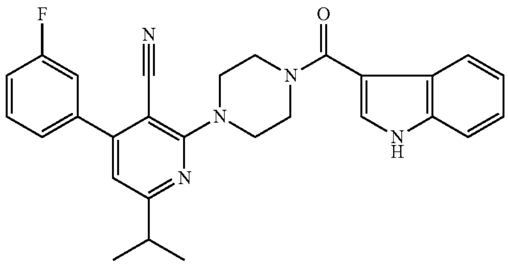 [SMILES: CC(C)c1cc(-c2cccc(F)c2)c(C#N)c(N2CCN(C(=O)c3c[nH]c4ccccc34)CC2)n1] |
| 117 | 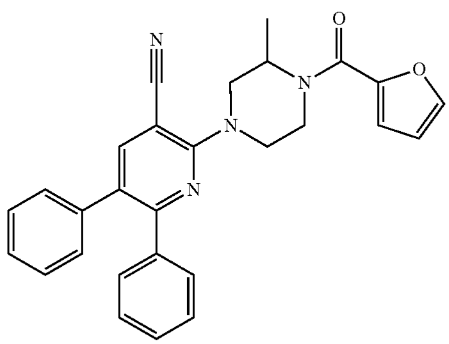 [SMILES: CC1CN(c2nc(-c3ccccc3)c(-c3ccccc3)cc2C#N)CCN1C(=O)c1ccco1] |
| 118 | 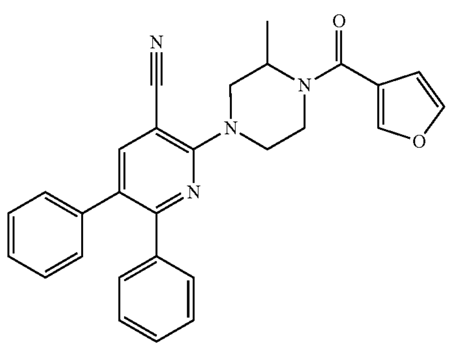 [SMILES: CC1CN(c2nc(-c3ccccc3)c(-c3ccccc3)cc2C#N)CCN1C(=O)c1ccoc1] |
| 119 | 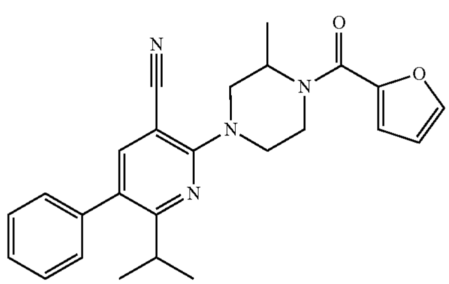 [SMILES: CC(C)c1nc(N2CCN(C(=O)c3ccco3)C(C)C2)c(C#N)cc1-c1ccccc1] |
| 120 | 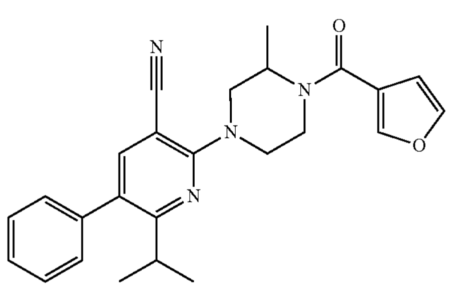 [SMILES: CC(C)c1nc(N2CCN(C(=O)c3ccoc3)C(C)C2)c(C#N)cc1-c1ccccc1] |
| 121 | |
| 122 | |
| 123 | |
| 124 | |

TABLE 1-continued

Exemplary Compounds of Formula I.

| Cmpd No. | Structure |
|---|---|
| 125 | 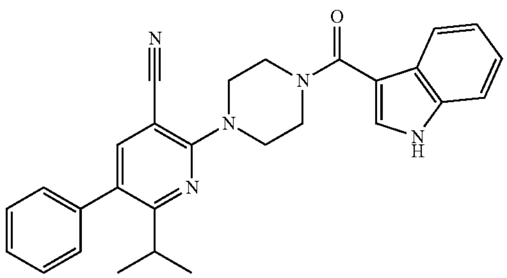 [SMILES: CC(C)c1nc(N2CCN(C(=O)c3c[nH]c4ccccc34)CC2)c(C#N)cc1-c1ccccc1] |
| 126 | 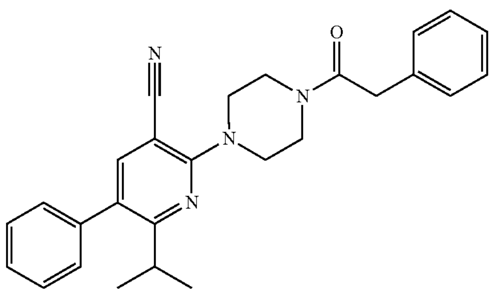 [SMILES: CC(C)c1nc(N2CCN(C(=O)Cc3ccccc3)CC2)c(C#N)cc1-c1ccccc1] |
| 127 | 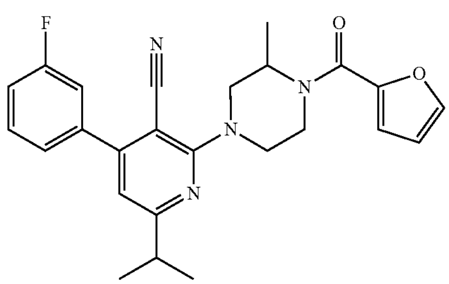 [SMILES: CC(C)c1cc(-c2cccc(F)c2)c(C#N)c(N2CCN(C(=O)c3ccco3)C(C)C2)n1] |
| 128 | 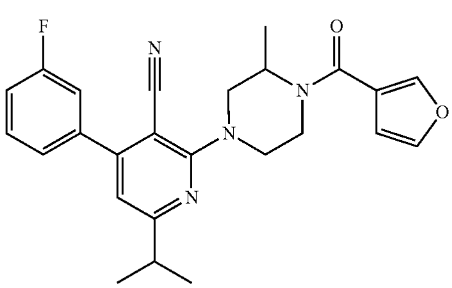 [SMILES: CC(C)c1cc(-c2cccc(F)c2)c(C#N)c(N2CCN(C(=O)c3ccoc3)C(C)C2)n1] |
| 129 | 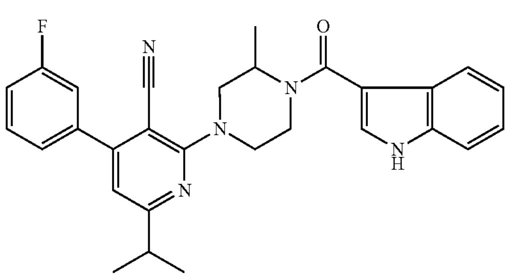 [SMILES: CC(C)c1cc(-c2cccc(F)c2)c(C#N)c(N2CCN(C(=O)c3c[nH]c4ccccc34)C(C)C2)n1] |
| 130 | |
| 131 | |
| 132 | |
| 133 | |
| 134 | |

TABLE 1-continued

Exemplary Compounds of Formula I.

| Cmpd No. | Structure |
|---|---|
| 135 | |
| 136 | |
| 137 | |
| 138 | |
| 139 | 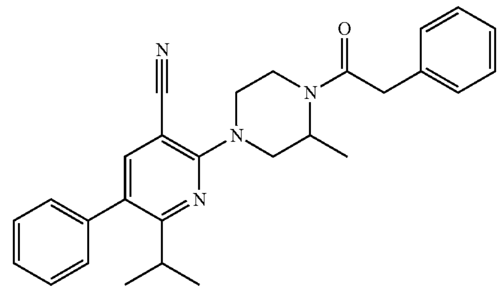 [SMILES: CC(C)c1nc(N2CCN(C(=O)Cc3ccccc3)C(C)C2)c(C#N)cc1-c1ccccc1] |
| 140 | 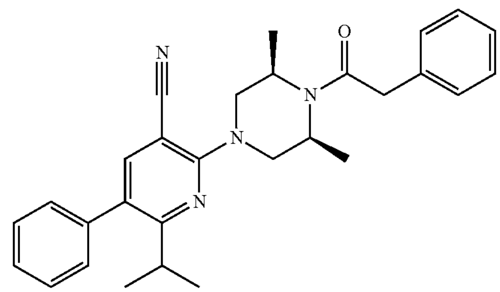 [SMILES: CC(C)c1nc(N2C[C@@H](C)N(C(=O)Cc3ccccc3)[C@@H](C)C2)c(C#N)cc1-c1ccccc1] |
| 141 | 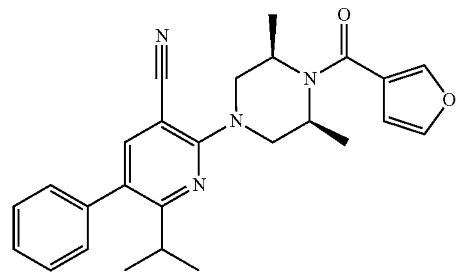 [SMILES: CC(C)c1nc(N2C[C@@H](C)N(C(=O)c3ccoc3)[C@@H](C)C2)c(C#N)cc1-c1ccccc1] |
| 142 | 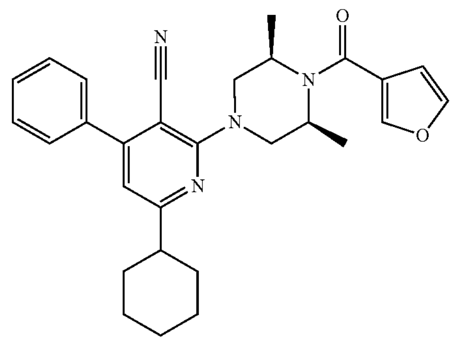 [SMILES: C[C@@H]1CN(c2nc(C3CCCCC3)cc(-c3ccccc3)c2C#N)C[C@H](C)N1C(=O)c1ccoc1] |
| 143 | 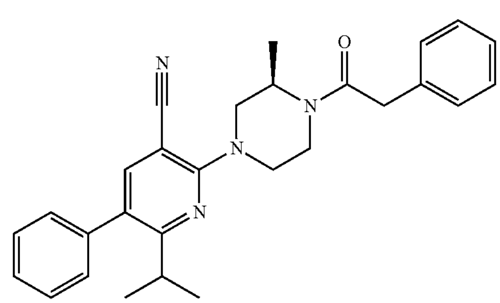 [SMILES: CC(C)c1nc(N2CCN(C(=O)Cc3ccccc3)[C@H](C)C2)c(C#N)cc1-c1ccccc1] |

TABLE 1-continued

Exemplary Compounds of Formula I.

| Cmpd No. | Structure |
|---|---|
| 144 | 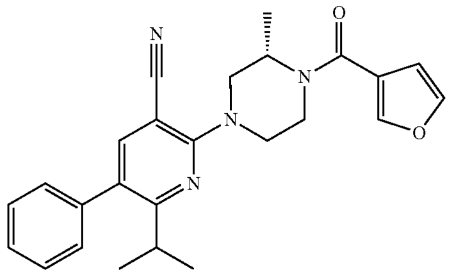 [SMILES: CC(C)c1nc(N2CCN(C(=O)c3ccoc3)[C@@H](C)C2)c(C#N)cc1-c1ccccc1] |
| 145 | 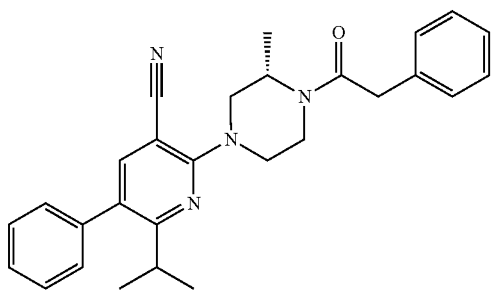 [SMILES: CC(C)c1nc(N2CCN(C(=O)Cc3ccccc3)[C@@H](C)C2)c(C#N)cc1-c1ccccc1] |
| 146 | 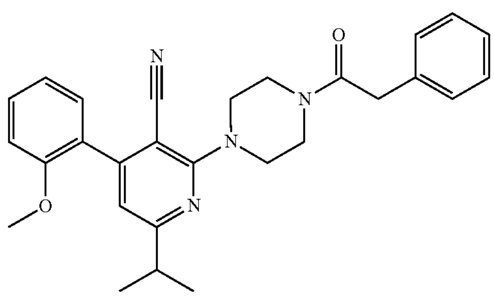 [SMILES: COc1ccccc1-c1cc(C(C)C)nc(N2CCN(C(=O)Cc3ccccc3)CC2)c1C#N] |
| 147 | 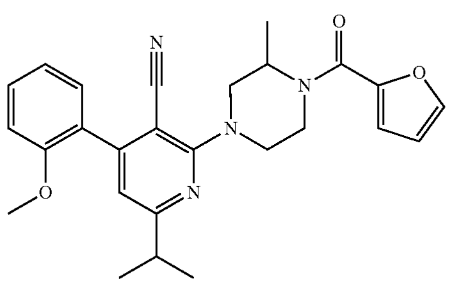 [SMILES: COc1ccccc1-c1cc(C(C)C)nc(N2CCN(C(=O)c3ccco3)C(C)C2)c1C#N] |
| 148 | 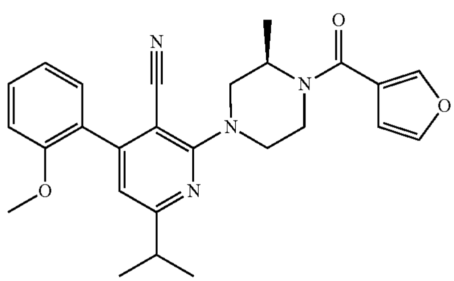 [SMILES: COc1ccccc1-c1cc(C(C)C)nc(N2CCN(C(=O)c3ccoc3)[C@H](C)C2)c1C#N] |
| 149 | |
| 150 | |
| 151 | |
| 152 | |
| 153 | |

TABLE 1-continued

Exemplary Compounds of Formula I.

| Cmpd No. | Structure |
|---|---|
| 154 | 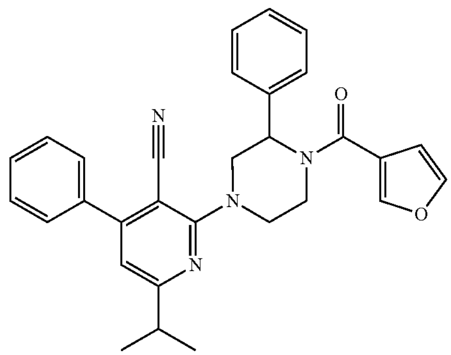 [SMILES: CC(C)c1cc(-c2ccccc2)c(C#N)c(N2CCN(C(=O)c3ccoc3)C(c3ccccc3)C2)n1] |
| 155 | 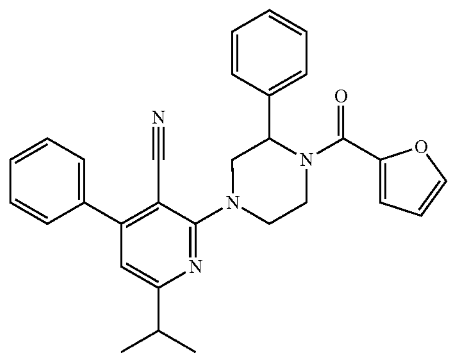 [SMILES: CC(C)c1cc(-c2ccccc2)c(C#N)c(N2CCN(C(=O)c3ccco3)C(c3ccccc3)C2)n1] |
| 156 | 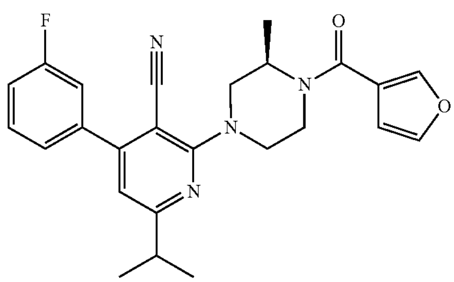 [SMILES: CC(C)c1cc(-c2cccc(F)c2)c(C#N)c(N2CCN(C(=O)c3ccoc3)[C@H](C)C2)n1] |
| 157 | 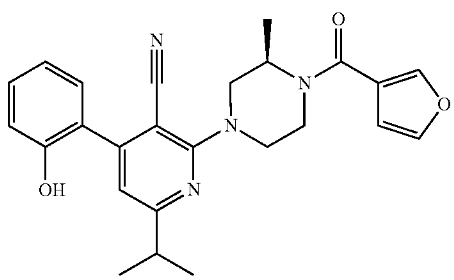 [SMILES: CC(C)c1cc(-c2ccccc2O)c(C#N)c(N2CCN(C(=O)c3ccoc3)[C@H](C)C2)n1] |
| 158 | 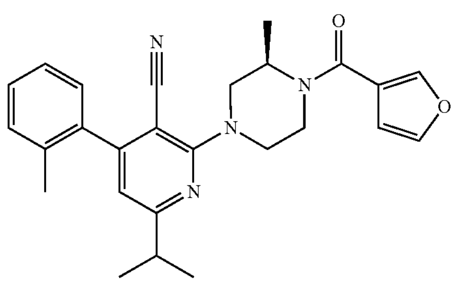 [SMILES: Cc1ccccc1-c1cc(C(C)C)nc(N2CCN(C(=O)c3ccoc3)[C@H](C)C2)c1C#N] |
| 159 | |
| 160 | |
| 161 | |
| 162 | |
| 163 | |

TABLE 1-continued

Exemplary Compounds of Formula I.

| Cmpd No. | Structure |
|---|---|
| 164 | 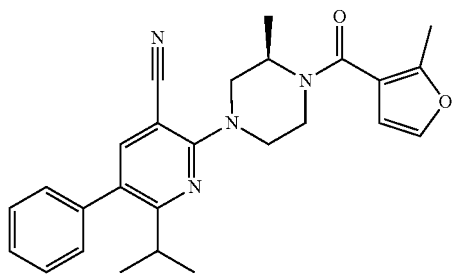 [SMILES: Cc1occc1C(=O)N1CCN(c2nc(C(C)C)c(-c3ccccc3)cc2C#N)C[C@H]1C] |
| 165 | 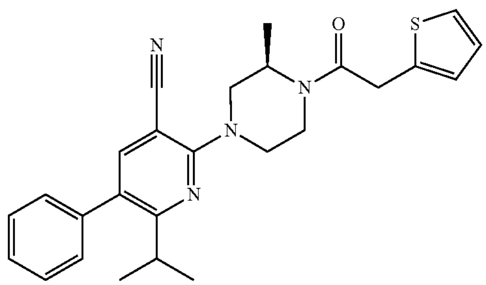 [SMILES: CC(C)c1nc(N2CCN(C(=O)Cc3cccs3)[C@H](C)C2)c(C#N)cc1-c1ccccc1] |
| 166 | 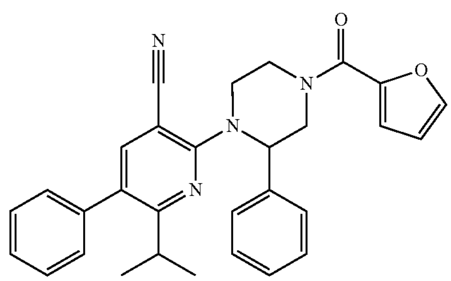 [SMILES: CC(C)c1nc(N2CCN(C(=O)c3ccco3)CC2c2ccccc2)c(C#N)cc1-c1ccccc1] |
| 167 | 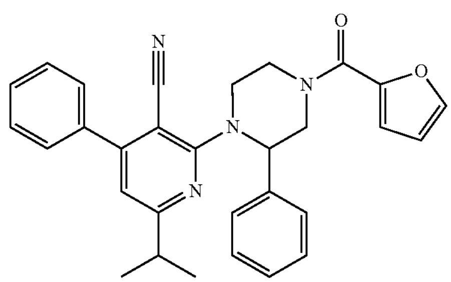 [SMILES: CC(C)c1cc(-c2ccccc2)c(C#N)c(N2CCN(C(=O)c3ccco3)CC2c2ccccc2)n1] |
| 168 | 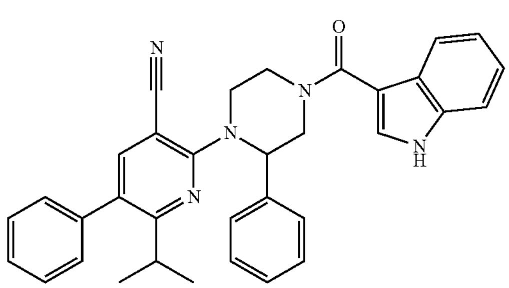 [SMILES: CC(C)c1nc(N2CCN(C(=O)c3c[nH]c4ccccc34)CC2c2ccccc2)c(C#N)cc1-c1ccccc1] |
| 169 | |
| 170 | |
| 171 | |
| 172 | |
| 173 | |

TABLE 1-continued
Exemplary Compounds of Formula I.
| Cmpd No. | Structure |
|---|---|
| 174 | 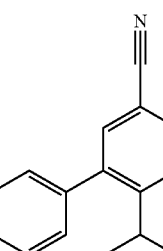 |
| 175 | 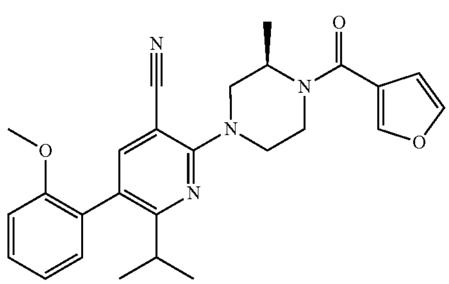 [SMILES: COc1ccccc1-c1cc(C#N)c(N2CCN(C(=O)c3ccoc3)[C@H](C)C2)nc1C(C)C] |
| 176 | 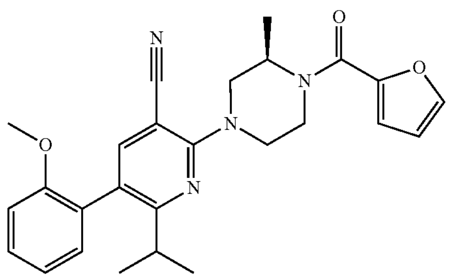 [SMILES: COc1ccccc1-c1cc(C#N)c(N2CCN(C(=O)c3ccco3)[C@H](C)C2)nc1C(C)C] |
| 177 | 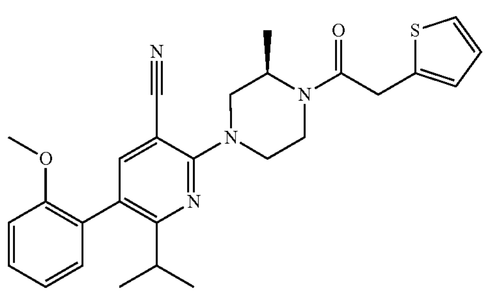 [SMILES: COc1ccccc1-c1cc(C#N)c(N2CCN(C(=O)Cc3cccs3)[C@H](C)C2)nc1C(C)C] |
| 178 | 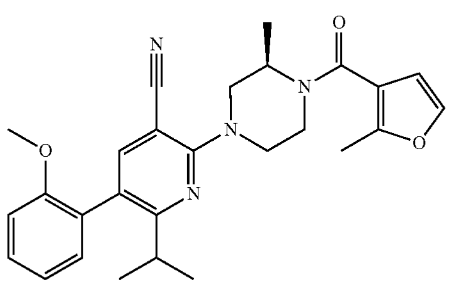 [SMILES: COc1ccccc1-c1cc(C#N)c(N2CCN(C(=O)c3ccoc3C)[C@H](C)C2)nc1C(C)C] |
| 179 | 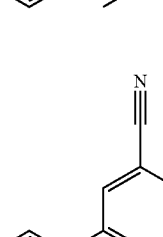 |
| 180 | |
| 181 | |
| 182 | |
| 183 | |

TABLE 1-continued

Exemplary Compounds of Formula I.

| Cmpd No. | Structure |
|---|---|
| 184 | 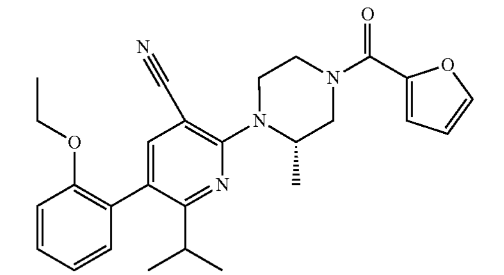 [SMILES: CCOc1ccccc1-c1cc(C#N)c(N2CCN(C(=O)c3ccco3)C[C@@H]2C)nc1C(C)C] |
| 185 | 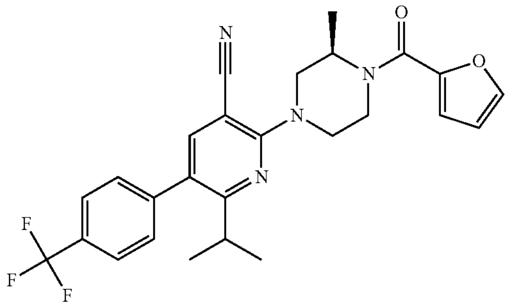 [SMILES: CC(C)c1nc(N2CCN(C(=O)c3ccco3)[C@H](C)C2)c(C#N)cc1-c1ccc(C(F)(F)F)cc1] |
| 187 | 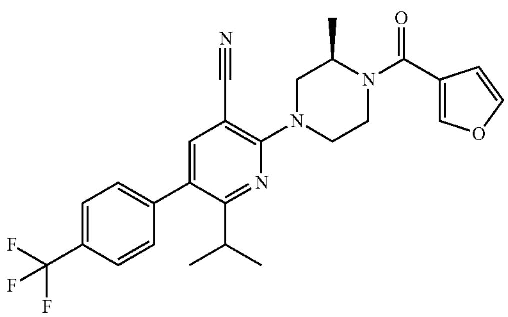 [SMILES: CC(C)c1nc(N2CCN(C(=O)c3ccoc3)[C@H](C)C2)c(C#N)cc1-c1ccc(C(F)(F)F)cc1] |
| 188 | 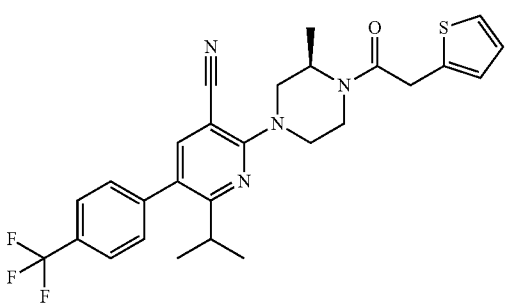 [SMILES: CC(C)c1nc(N2CCN(C(=O)Cc3cccs3)[C@H](C)C2)c(C#N)cc1-c1ccc(C(F)(F)F)cc1] |
| 189 | 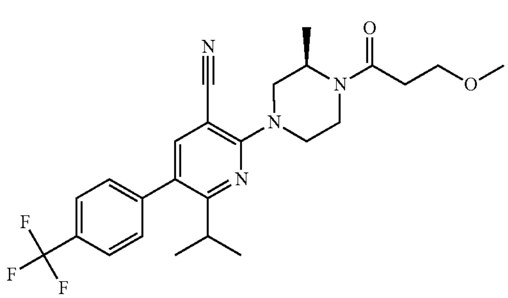 [SMILES: COCCC(=O)N1CCN(c2nc(C(C)C)c(-c3ccc(C(F)(F)F)cc3)cc2C#N)C[C@H]1C] |
| 190 | |
| 191 | |
| 192 | |
| 193 | |
| 195 | |

TABLE 1-continued

Exemplary Compounds of Formula I.

| Cmpd No. | Structure |
|---|---|
| 196 | 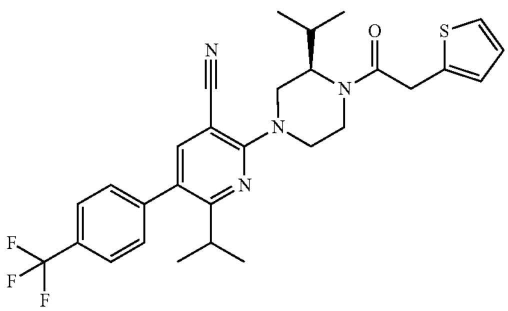 [SMILES: CC(C)c1nc(N2CCN(C(=O)Cc3cccs3)[C@H](C(C)C)C2)c(C#N)cc1-c1ccc(C(F)(F)F)cc1] |
| 197 | 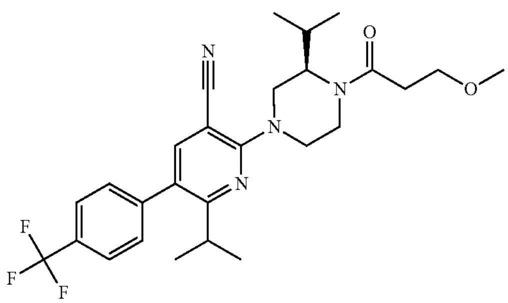 [SMILES: COCCC(=O)N1CCN(c2nc(C(C)C)c(-c3ccc(C(F)(F)F)cc3)cc2C#N)C[C@H]1C(C)C] |
| 198 | 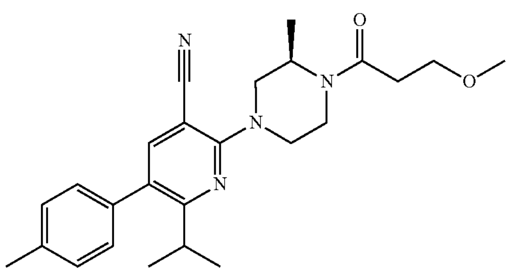 |
| 199 | 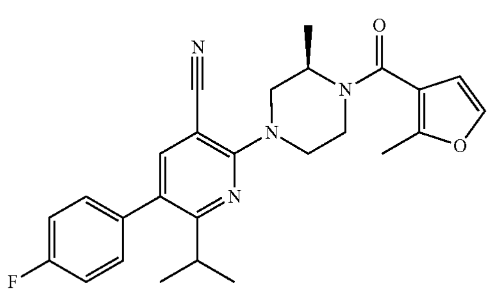 [SMILES: Cc1occc1C(=O)N1CCN(c2nc(C(C)C)c(-c3ccc(F)cc3)cc2C#N)C[C@H]1C] |
| 200 | 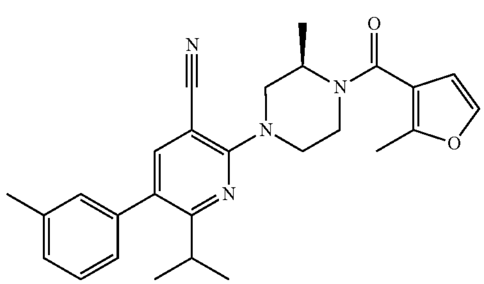 [SMILES: Cc1cccc(-c2cc(C#N)c(N3CCN(C(=O)c4ccoc4C)[C@H](C)C3)nc2C(C)C)c1] |
| 201 | |
| 202 | |
| 203 | |
| 204 | |
| 205 | |

TABLE 1-continued

Exemplary Compounds of Formula I.

| Cmpd No. | Structure |
|---|---|
| 206 | 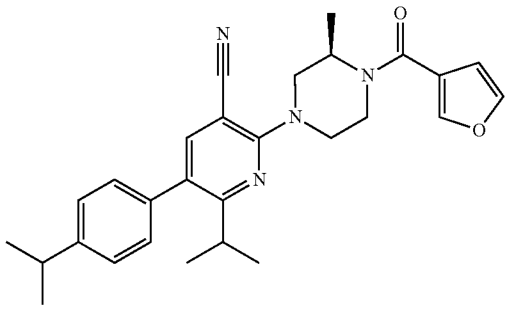 [SMILES: CC(C)c1ccc(-c2cc(C#N)c(N3CCN(C(=O)c4ccoc4)[C@H](C)C3)nc2C(C)C)cc1] |
| 207 | 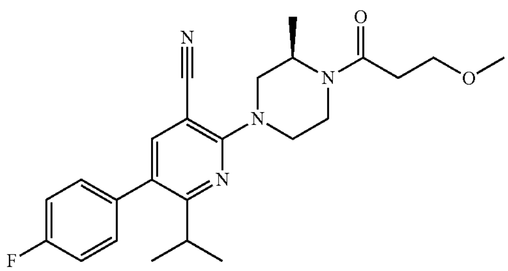 [SMILES: COCCC(=O)N1CCN(c2nc(C(C)C)c(-c3ccc(F)cc3)cc2C#N)C[C@H]1C] |
| 208 | 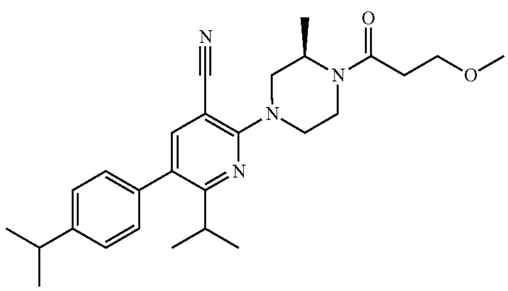 [SMILES: COCCC(=O)N1CCN(c2nc(C(C)C)c(-c3ccc(C(C)C)cc3)cc2C#N)C[C@H]1C] |
| 209 | 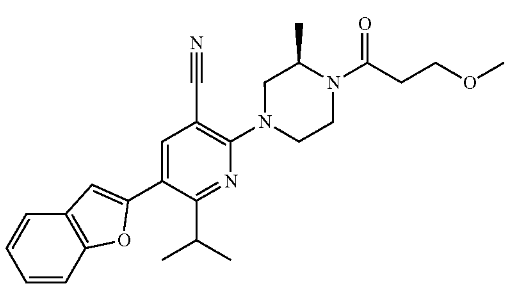 [SMILES: COCCC(=O)N1CCN(c2nc(C(C)C)c(-c3cc4ccccc4o3)cc2C#N)C[C@H]1C] |
| 210 | 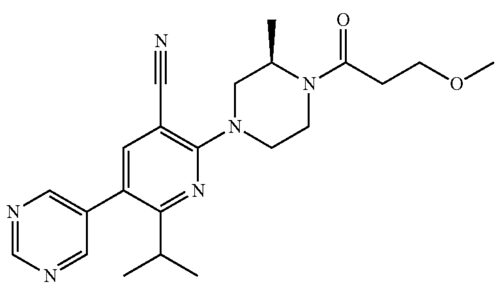 [SMILES: COCCC(=O)N1CCN(c2nc(C(C)C)c(-c3cncnc3)cc2C#N)C[C@H]1C] |
| 211 | |
| 212 | |
| 213 | |
| 214 | |
| 215 | |

TABLE 1-continued
Exemplary Compounds of Formula I.
| Cmpd No. | Structure |
|---|---|
| 216 | 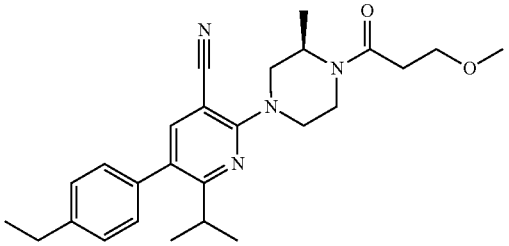 [SMILES: CCc1ccc(-c2cc(C#N)c(N3CCN(C(=O)CCOC)[C@H](C)C3)nc2C(C)C)cc1] |
| 217 | 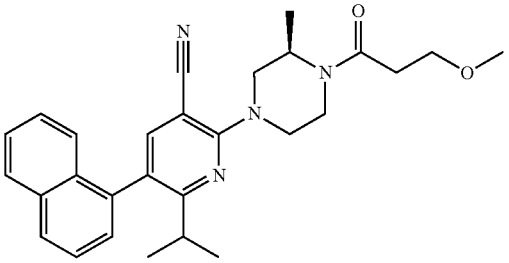 [SMILES: COCCC(=O)N1CCN(c2nc(C(C)C)c(-c3cccc4ccccc34)cc2C#N)C[C@H]1C] |
| 218 | 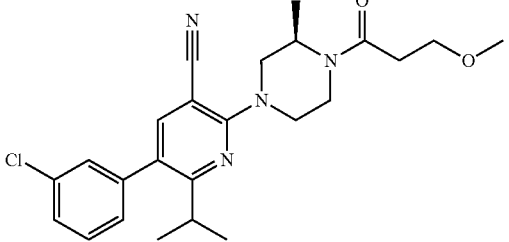 |
| 219 | 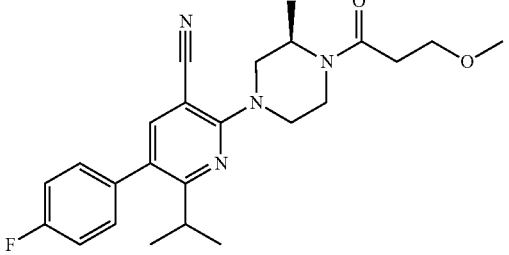 |
| 220 | 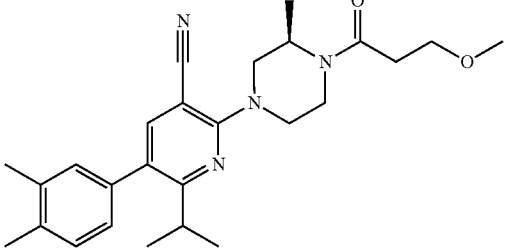 |
| 221 | 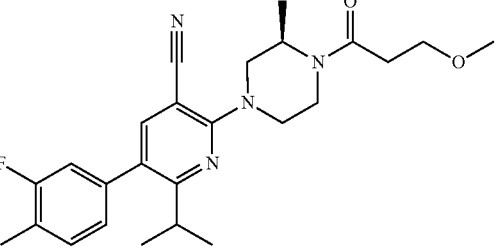 |
| 222 | 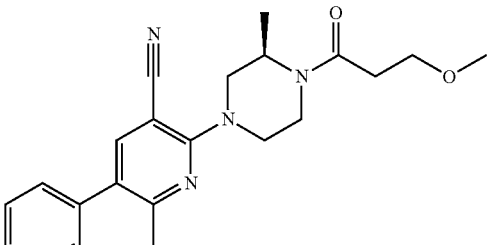 |
| 223 | 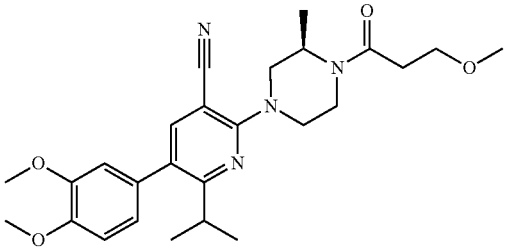 |
| 224 | 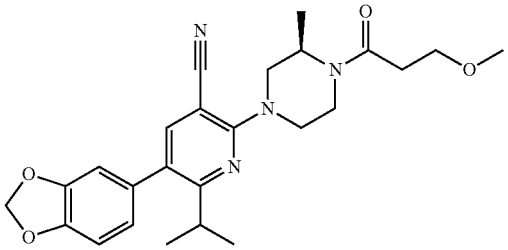 [SMILES: COCCC(=O)N1CCN(c2nc(C(C)C)c(-c3ccc4c(c3)OCO4)cc2C#N)C[C@H]1C] |
| 225 | 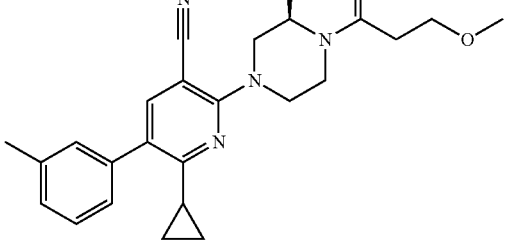 |

TABLE 1-continued

Exemplary Compounds of Formula I.

| Cmpd No. | Structure |
|---|---|
| 226 | 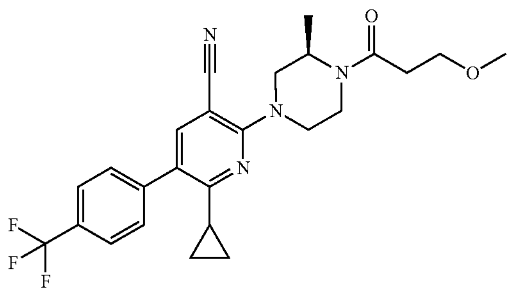 [SMILES: COCCC(=O)N1CCN(c2nc(C3CC3)c(-c3ccc(C(F)(F)F)cc3)cc2C#N)C[C@H]1C] |
| 227 | 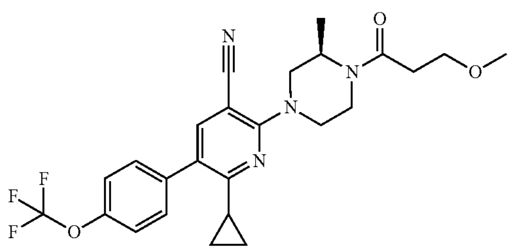 [SMILES: COCCC(=O)N1CCN(c2nc(C3CC3)c(-c3ccc(OC(F)(F)F)cc3)cc2C#N)C[C@H]1C] |
| 228 | 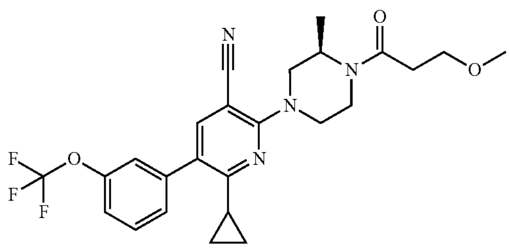 [SMILES: COCCC(=O)N1CCN(c2nc(C3CC3)c(-c3cccc(OC(F)(F)F)c3)cc2C#N)C[C@H]1C] |
| 229 | 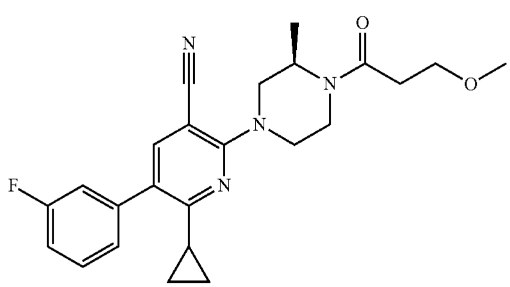 [SMILES: COCCC(=O)N1CCN(c2nc(C3CC3)c(-c3cccc(F)c3)cc2C#N)C[C@H]1C] |
| 230 | 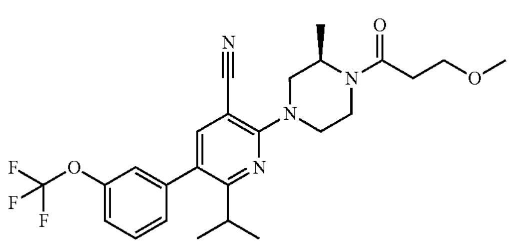 [SMILES: COCCC(=O)N1CCN(c2nc(C(C)C)c(-c3cccc(OC(F)(F)F)c3)cc2C#N)C[C@H]1C] |
| 231 | |
| 232 | |
| 233 | |
| 234 | |
| 235 | |

TABLE 1-continued
Exemplary Compounds of Formula I.
| Cmpd No. | Structure |
|---|---|
| 236 | 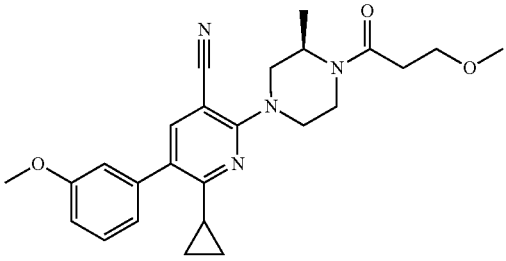 |
| 237 | 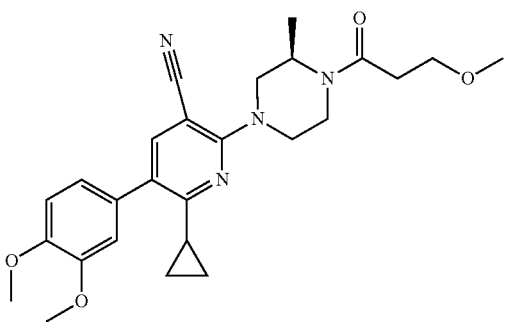 [SMILES: COCCC(=O)N1CCN(c2nc(C3CC3)c(-c3ccc(OC)c(OC)c3)cc2C#N)C[C@H]1C] |
| 238 | 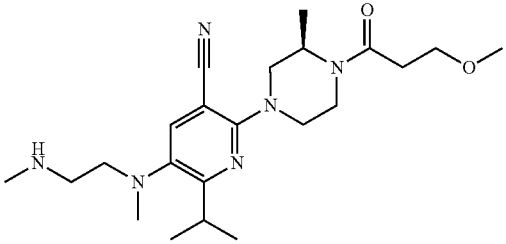 |
| 239 | 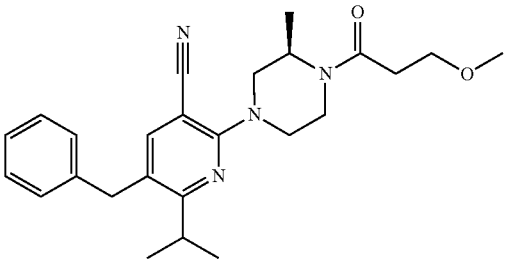 [SMILES: COCCC(=O)N1CCN(c2nc(C(C)C)c(Cc3ccccc3)cc2C#N)C[C@H]1C] |
| 240 | 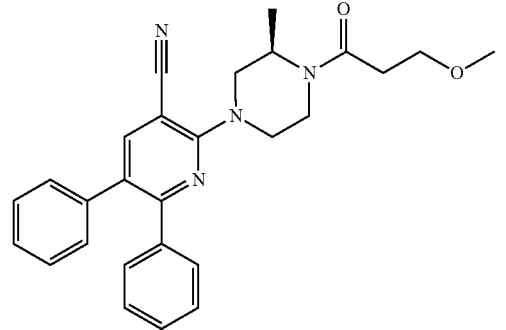 [SMILES: COCCC(=O)N1CCN(c2nc(-c3ccccc3)c(-c3ccccc3)cc2C#N)C[C@H]1C] |
| 241 | 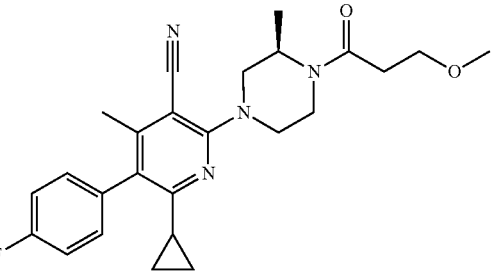 |
| 242 | 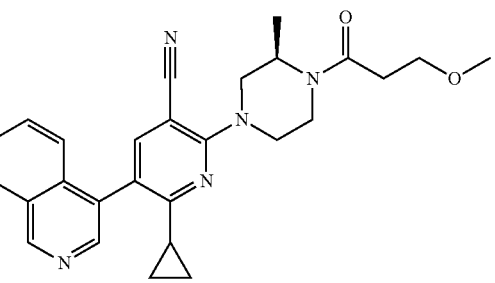 |
| 243 | 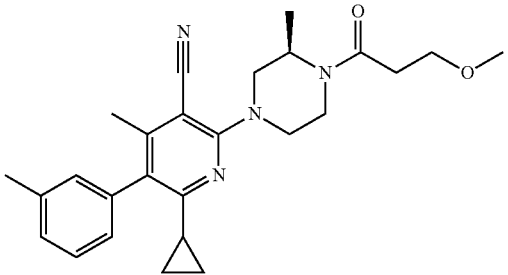 |
| 244 | 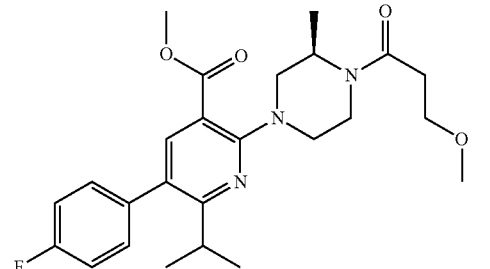 |
| 245 | 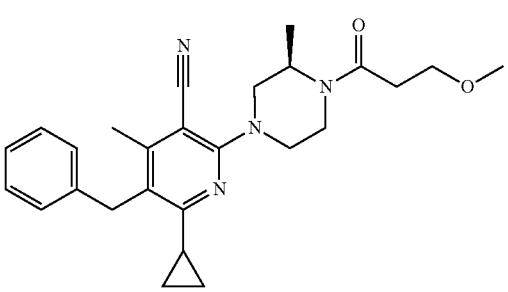 [SMILES: COCCC(=O)N1CCN(c2nc(C3CC3)c(Cc3ccccc3)c(C)c2C#N)C[C@H]1C] |

TABLE 1-continued

Exemplary Compounds of Formula I.

| Cmpd No. | Structure |
|---|---|
| 246 | 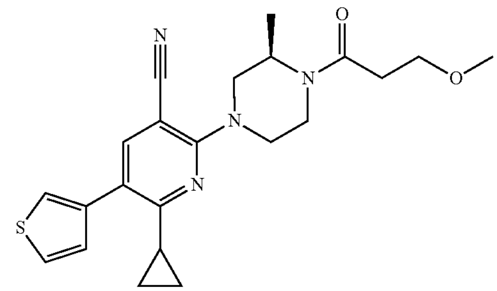 [SMILES: COCCC(=O)N1CCN(c2nc(C3CC3)c(-c3ccsc3)cc2C#N)C[C@H]1C] |
| 247 | 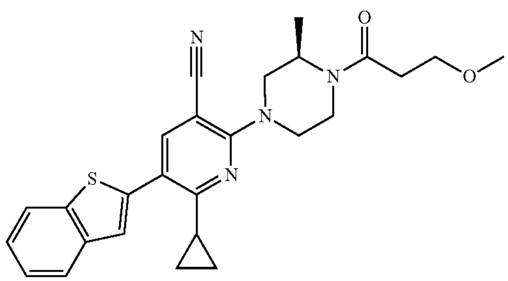 [SMILES: COCCC(=O)N1CCN(c2nc(C3CC3)c(-c3cc4ccccc4s3)cc2C#N)C[C@H]1C] |
| 248 | 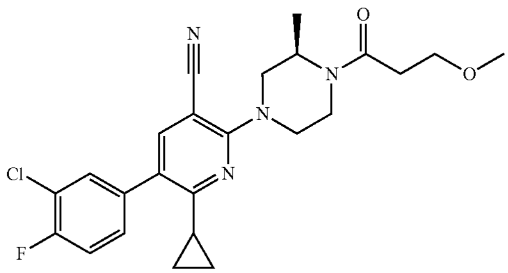 [SMILES: COCCC(=O)N1CCN(c2nc(C3CC3)c(-c3ccc(F)c(Cl)c3)cc2C#N)C[C@H]1C] |
| 249 | 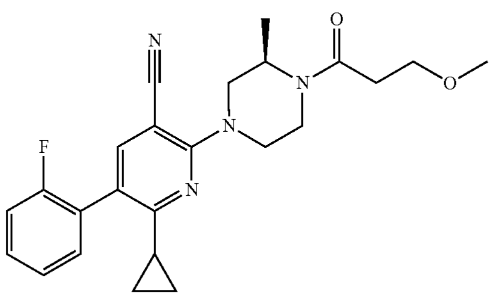 [SMILES: COCCC(=O)N1CCN(c2nc(C3CC3)c(-c3ccccc3F)cc2C#N)C[C@H]1C] |
| 250 | 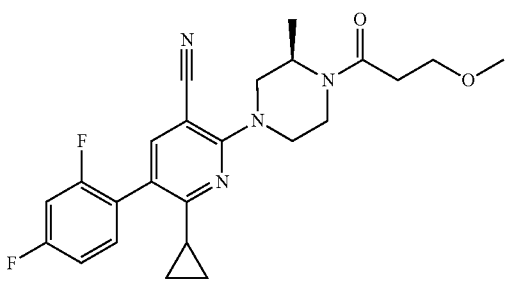 [SMILES: COCCC(=O)N1CCN(c2nc(C3CC3)c(-c3ccc(F)cc3F)cc2C#N)C[C@H]1C] |
| 251 | |
| 252 | |
| 253 | |
| 254 | |
| 255 | |

TABLE 1-continued
Exemplary Compounds of Formula I.
| Cmpd No. | Structure |
|---|---|
| 256 | 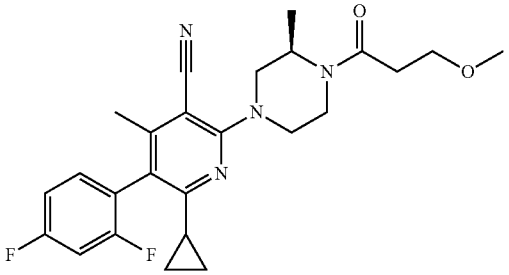 [SMILES: COCCC(=O)N1CCN(c2nc(C3CC3)c(-c3ccc(F)cc3F)c(C)c2C#N)C[C@H]1C] |
| 257 | 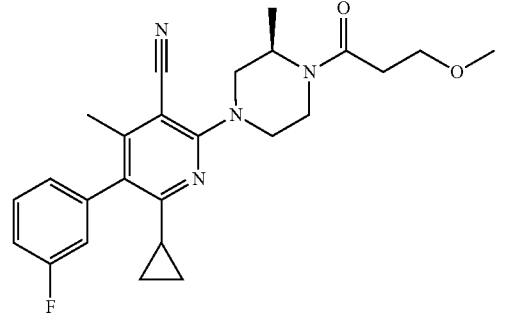 [SMILES: COCCC(=O)N1CCN(c2nc(C3CC3)c(-c3cccc(F)c3)c(C)c2C#N)C[C@H]1C] |
| 258 | 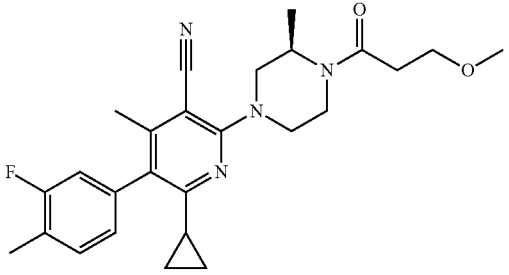 |
| 259 | 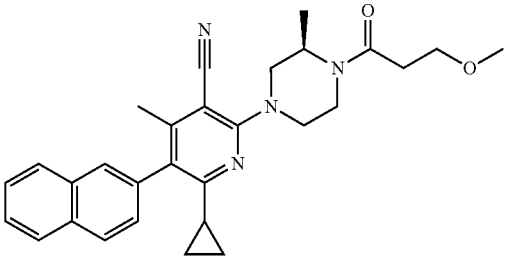 [SMILES: COCCC(=O)N1CCN(c2nc(C3CC3)c(-c3ccc4ccccc4c3)c(C)c2C#N)C[C@H]1C] |
| 260 | 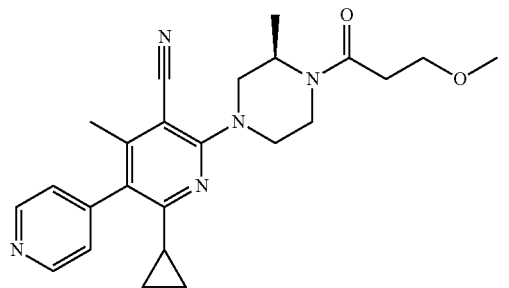 [SMILES: COCCC(=O)N1CCN(c2nc(C3CC3)c(-c3ccncc3)c(C)c2C#N)C[C@H]1C] |
| 261 | 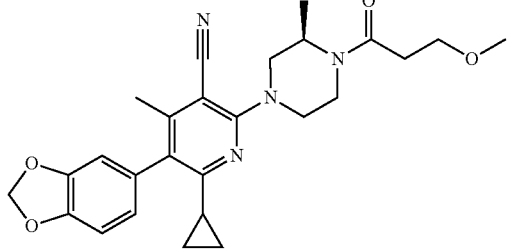 |
| 262 | 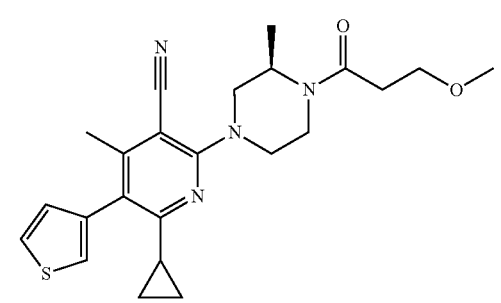 [SMILES: COCCC(=O)N1CCN(c2nc(C3CC3)c(-c3ccsc3)c(C)c2C#N)C[C@H]1C] |
| 59 | 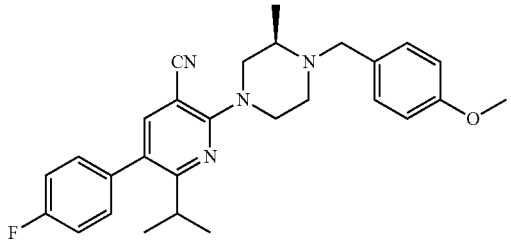 [SMILES: COc1ccc(CN2CCN(c3nc(C(C)C)c(-c4ccc(F)cc4)cc3C#N)C[C@H]2C)cc1] |
| 60 | 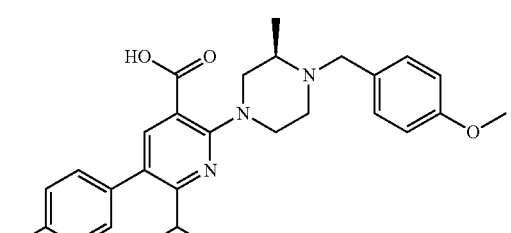 |
| 61 | 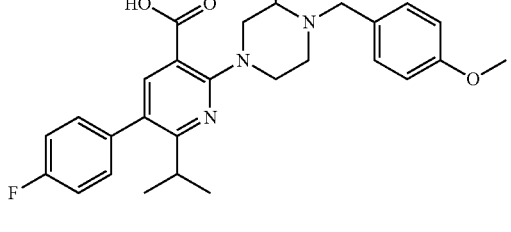 |
In another embodiment, the compound is selected from any one of the compounds set forth in Table 5, below.

TABLE 5

Exemplary Compounds of Formula I.

| Cpd # | Structure |
|---|---|
| 263 | 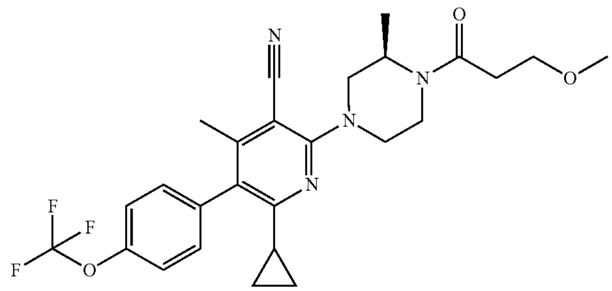 [SMILES: COCCC(=O)N1CCN(c2nc(C3CC3)c(-c3ccc(OC(F)(F)F)cc3)c(C)c2C#N)C[C@H]1C] |
| 264 | 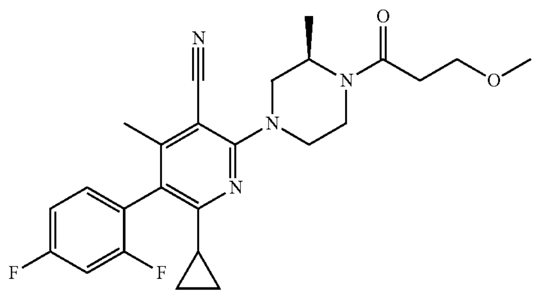 [SMILES: COCCC(=O)N1CCN(c2nc(C3CC3)c(-c3ccc(F)cc3F)c(C)c2C#N)C[C@H]1C] |
| 265 | 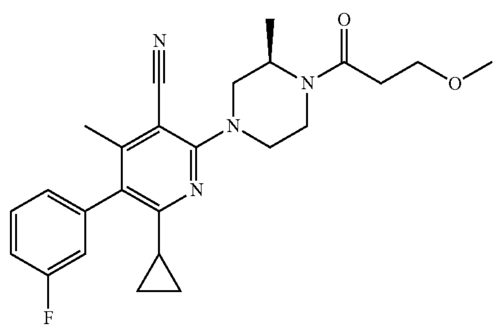 [SMILES: COCCC(=O)N1CCN(c2nc(C3CC3)c(-c3cccc(F)c3)c(C)c2C#N)C[C@H]1C] |
| 266 | 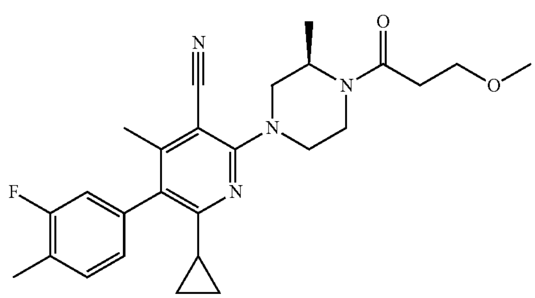 |
| 267 | 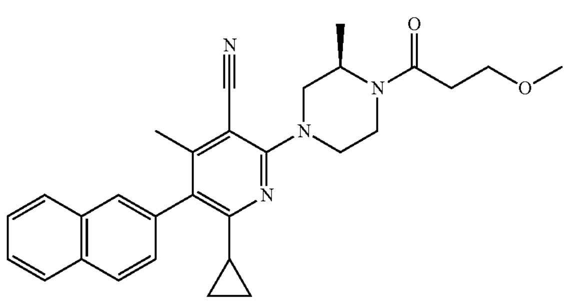 [SMILES: COCCC(=O)N1CCN(c2nc(C3CC3)c(-c3ccc4ccccc4c3)c(C)c2C#N)C[C@H]1C] |

TABLE 5-continued
Exemplary Compounds of Formula I.
| Cpd # | Structure |
|---|---|
| 268 | 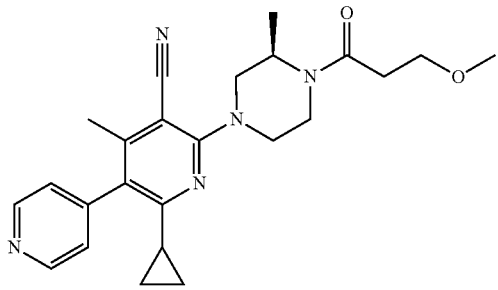 [SMILES: COCCC(=O)N1CCN(c2nc(C3CC3)c(-c3ccncc3)c(C)c2C#N)C[C@H]1C] |
| 269 | 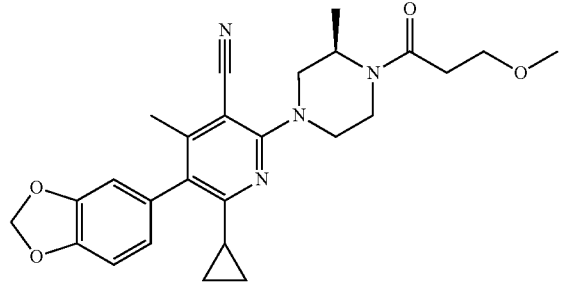 [SMILES: COCCC(=O)N1CCN(c2nc(C3CC3)c(-c3ccc4c(c3)OCO4)c(C)c2C#N)C[C@H]1C] |
| 270 | 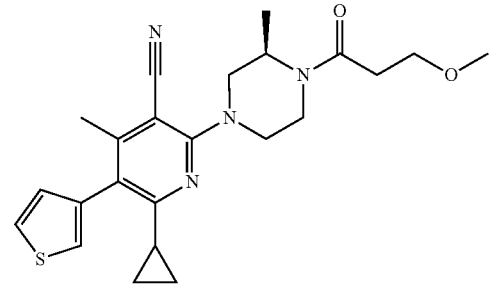 [SMILES: COCCC(=O)N1CCN(c2nc(C3CC3)c(-c3ccsc3)c(C)c2C#N)C[C@H]1C] |
| 271 | 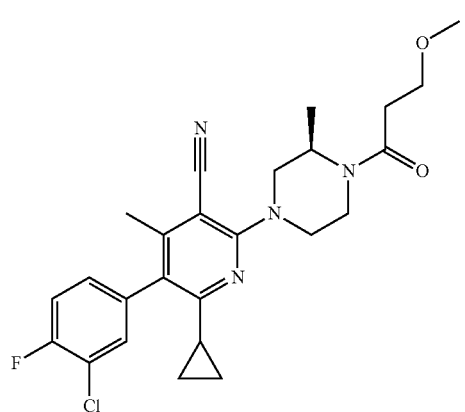 [SMILES: COCCC(=O)N1CCN(c2nc(C3CC3)c(-c3ccc(F)c(Cl)c3)c(C)c2C#N)C[C@H]1C] |

TABLE 5-continued

Exemplary Compounds of Formula I.

| Cpd # | Structure |
|---|---|
| 272 | 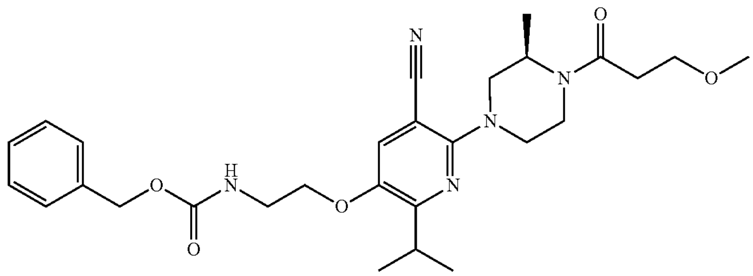 [SMILES: COCCC(=O)N1CCN(c2nc(C(C)C)c(OCCNC(=O)OCc3ccccc3)cc2C#N)C[C@H]1C] |
| 273 | 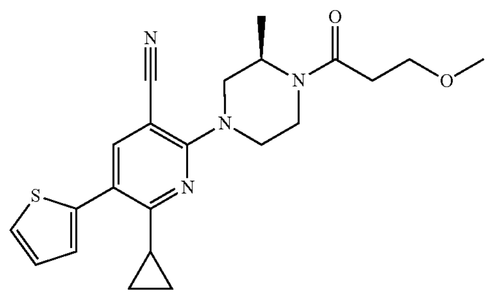 [SMILES: COCCC(=O)N1CCN(c2nc(C3CC3)c(-c3cccs3)cc2C#N)C[C@H]1C] |
| 274 | 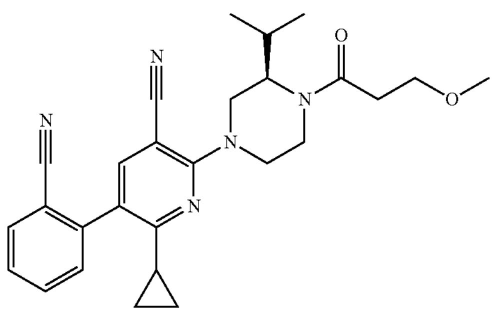 [SMILES: COCCC(=O)N1CCN(c2nc(C3CC3)c(-c3ccccc3C#N)cc2C#N)C[C@H]1C(C)C] |
| 275 | 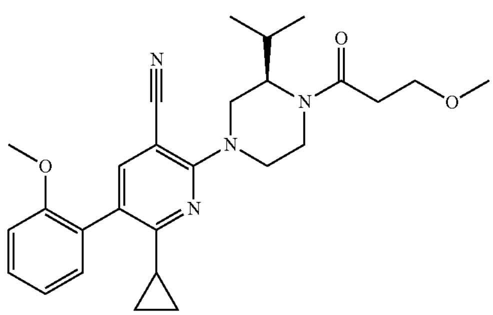 [SMILES: COCCC(=O)N1CCN(c2nc(C3CC3)c(-c3ccccc3OC)cc2C#N)C[C@H]1C(C)C] |
| 276 | 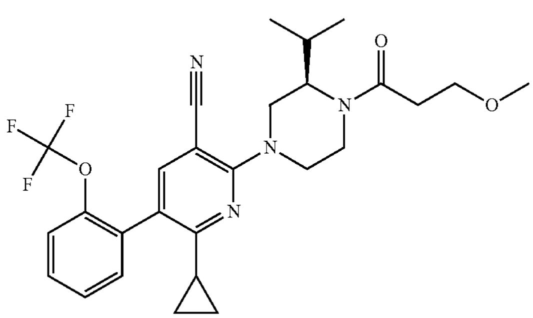 [SMILES: COCCC(=O)N1CCN(c2nc(C3CC3)c(-c3ccccc3OC(F)(F)F)cc2C#N)C[C@H]1C(C)C] |

TABLE 5-continued

Exemplary Compounds of Formula I.

| Cpd # | Structure |
|---|---|
| 277 | 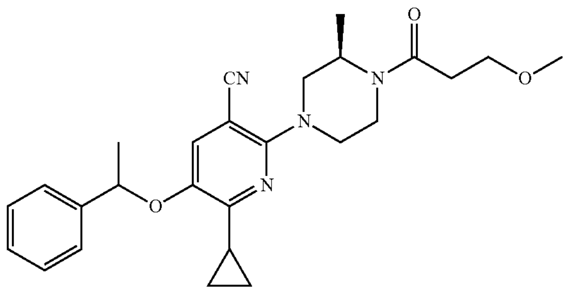 [SMILES: COCCC(=O)N1CCN(c2nc(C3CC3)c(OC(C)c3ccccc3)cc2C#N)C[C@H]1C] |
| 278 | 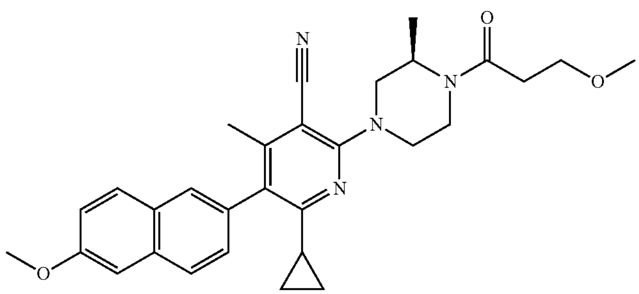 |
| 279 | 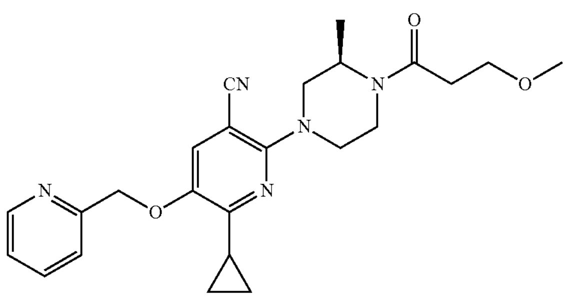 [SMILES: COCCC(=O)N1CCN(c2nc(C3CC3)c(OCc3ccccn3)cc2C#N)C[C@H]1C] |
| 280 | 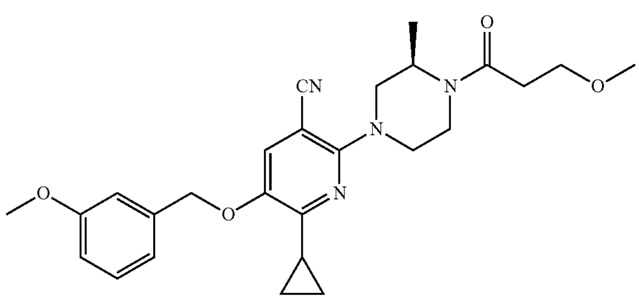 |
| 281 | 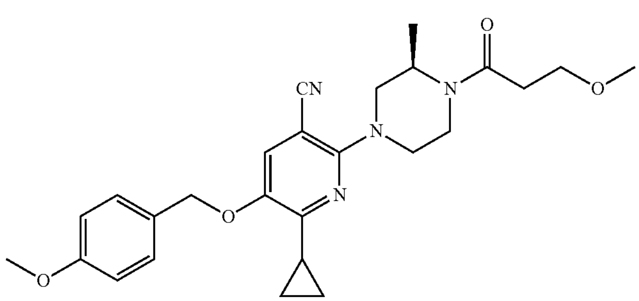 |

TABLE 5-continued

Exemplary Compounds of Formula I.

| Cpd # | Structure |
|---|---|
| 282 | |
| 283 | |
| 284 | |
| 285 | |
| 286 | |

TABLE 5-continued
Exemplary Compounds of Formula I.
| Cpd # | Structure |
|---|---|
| 287 | 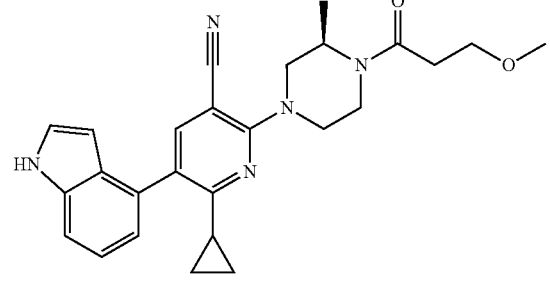 |
| 288 | 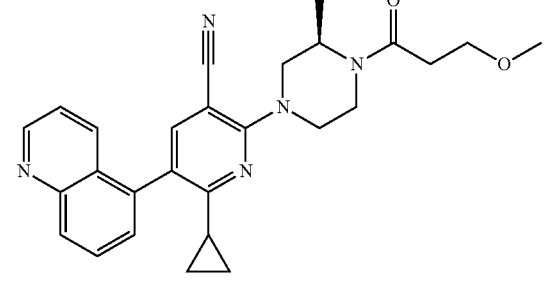 |
| 289 | 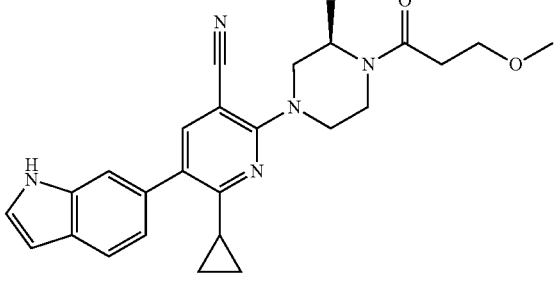 |
| 290 | 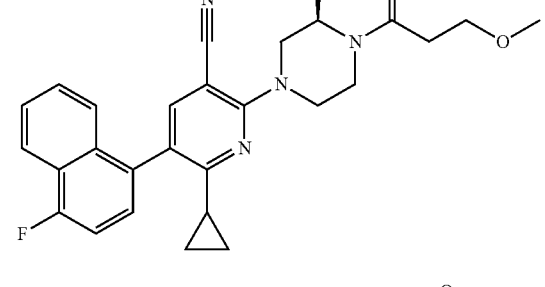 |
| 291 | 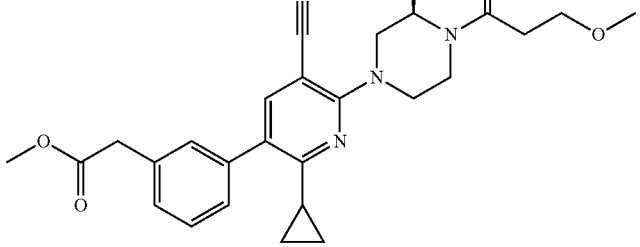 |

TABLE 5-continued
Exemplary Compounds of Formula I.
| Cpd # | Structure |
|---|---|
| 292 | 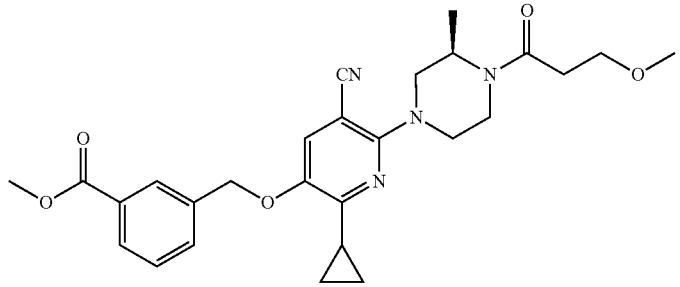 |
| 293 | 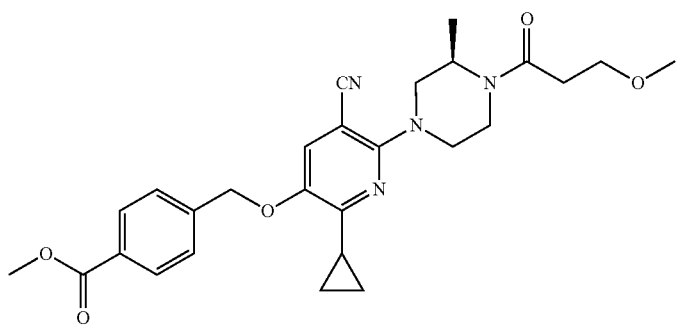 |
| 294 | 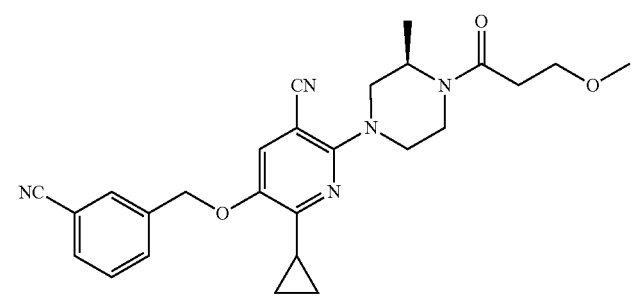 [SMILES: COCCC(=O)N1CCN(c2nc(C3CC3)c(OCc3cccc(C#N)c3)cc2C#N)C[C@H]1C] |
| 295 | 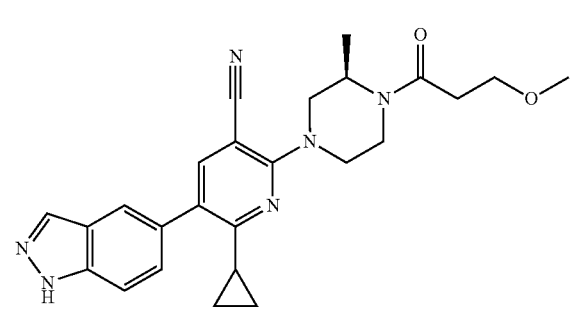 [SMILES: COCCC(=O)N1CCN(c2nc(C3CC3)c(-c3ccc4[nH]ncc4c3)cc2C#N)C[C@H]1C] |
| 296 | 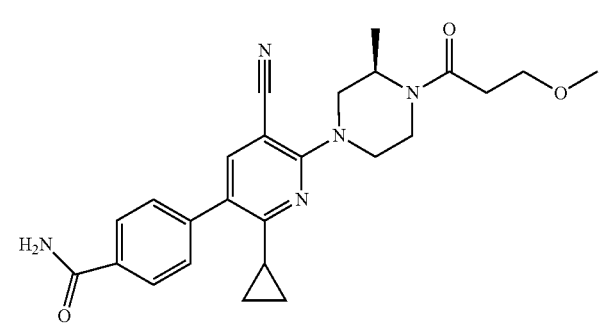 [SMILES: COCCC(=O)N1CCN(c2nc(C3CC3)c(-c3ccc(C(N)=O)cc3)cc2C#N)C[C@H]1C] |

TABLE 5-continued

Exemplary Compounds of Formula I.

| Cpd # | Structure |
|---|---|
| 297 | 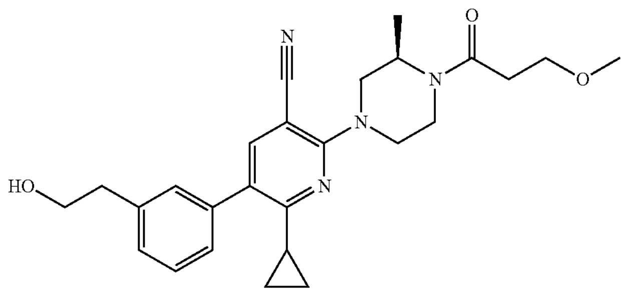 [SMILES: COCCC(=O)N1CCN(c2nc(C3CC3)c(-c3cccc(CCO)c3)cc2C#N)C[C@H]1C] |
| 298 | 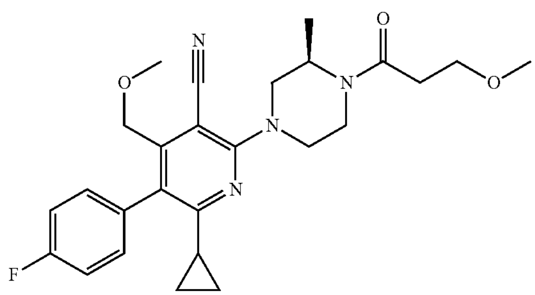 [SMILES: COCCC(=O)N1CCN(c2nc(C3CC3)c(-c3ccc(F)cc3)c(COC)c2C#N)C[C@H]1C] |
| 299 | 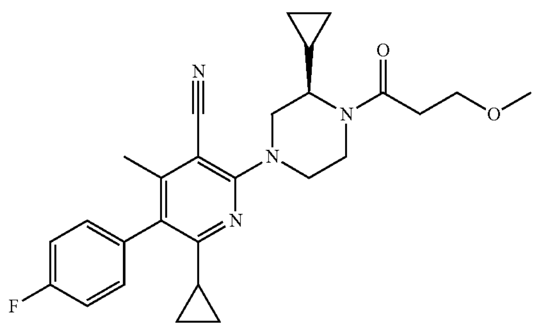 [SMILES: COCCC(=O)N1CCN(c2nc(C3CC3)c(-c3ccc(F)cc3)c(C)c2C#N)C[C@H]1C1CC1] |
| 300 | 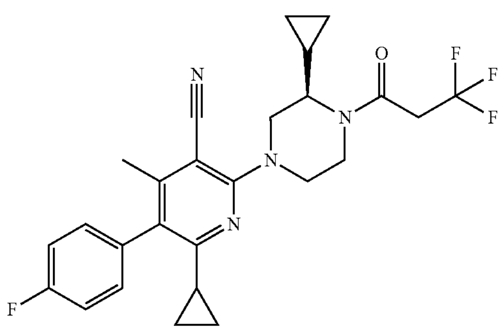 [SMILES: Cc1c(C#N)c(N2CCN(C(=O)CC(F)(F)F)[C@H](C3CC3)C2)nc(C2CC2)c1-c1ccc(F)cc1] |
| 301 | 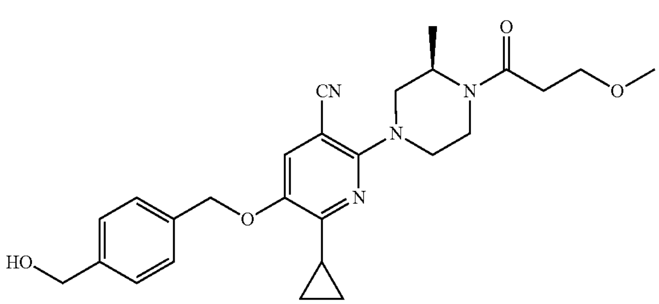 [SMILES: COCCC(=O)N1CCN(c2nc(C3CC3)c(OCc3ccc(CO)cc3)cc2C#N)C[C@H]1C] |

TABLE 5-continued

Exemplary Compounds of Formula I.

| Cpd # | Structure |
|---|---|
| 302 | 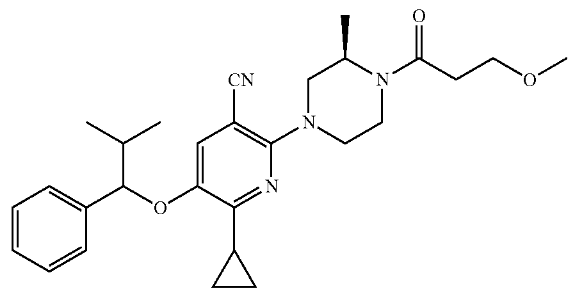 [SMILES: COCCC(=O)N1CCN(c2nc(C3CC3)c(OC(c3ccccc3)C(C)C)cc2C#N)C[C@H]1C] |
| 303 | 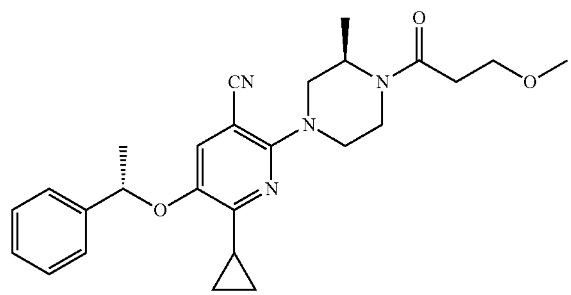 [SMILES: COCCC(=O)N1CCN(c2nc(C3CC3)c(O[C@@H](C)c3ccccc3)cc2C#N)C[C@H]1C] |
| 304 | 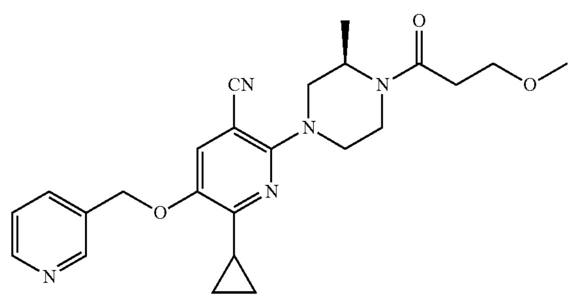 [SMILES: COCCC(=O)N1CCN(c2nc(C3CC3)c(OCc3cccnc3)cc2C#N)C[C@H]1C] |
| 305 | 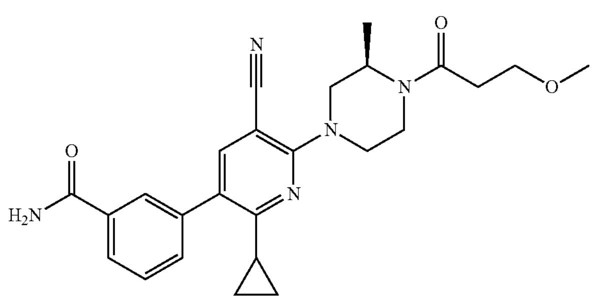 [SMILES: COCCC(=O)N1CCN(c2nc(C3CC3)c(-c3cccc(C(N)=O)c3)cc2C#N)C[C@H]1C] |
| 306 | 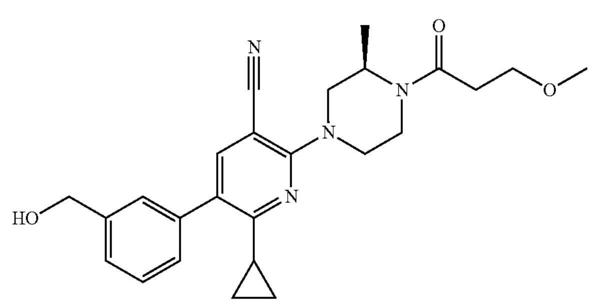 [SMILES: COCCC(=O)N1CCN(c2nc(C3CC3)c(-c3cccc(CO)c3)cc2C#N)C[C@H]1C] |

TABLE 5-continued

Exemplary Compounds of Formula I.

| Cpd # | Structure |
|---|---|
| 307 | 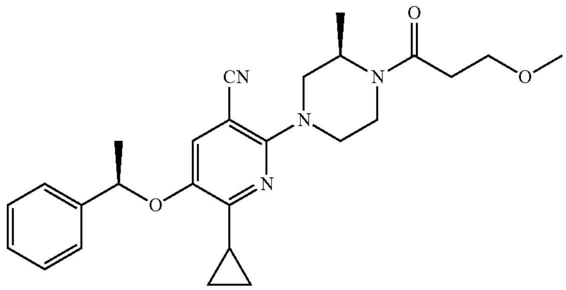 [SMILES: COCCC(=O)N1CCN(c2nc(C3CC3)c(O[C@H](C)c3ccccc3)cc2C#N)C[C@H]1C] |
| 308 | 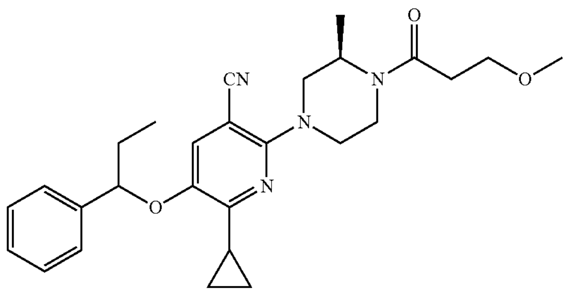 [SMILES: CCC(Oc1cc(C#N)c(N2CCN(C(=O)CCOC)[C@H](C)C2)nc1C1CC1)c1ccccc1] |
| 309 | 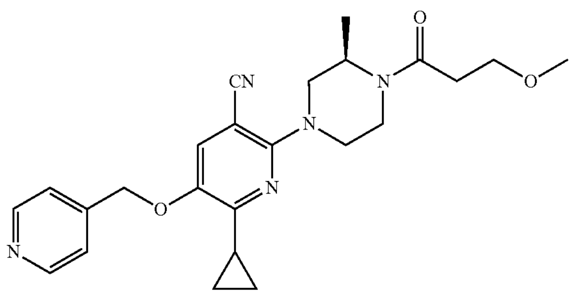 [SMILES: COCCC(=O)N1CCN(c2nc(C3CC3)c(OCc3ccncc3)cc2C#N)C[C@H]1C] |
| 310 | 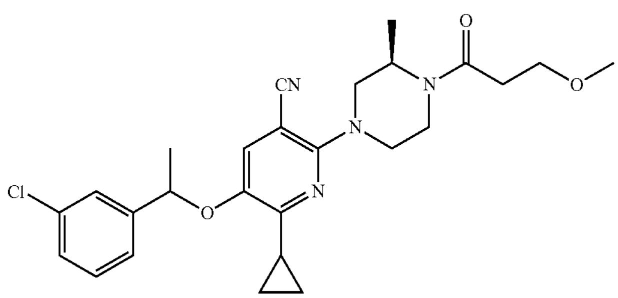 [SMILES: COCCC(=O)N1CCN(c2nc(C3CC3)c(OC(C)c3cccc(Cl)c3)cc2C#N)C[C@H]1C] |
| 311 | 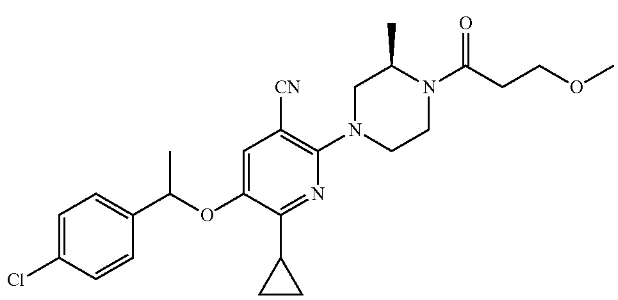 [SMILES: COCCC(=O)N1CCN(c2nc(C3CC3)c(OC(C)c3ccc(Cl)cc3)cc2C#N)C[C@H]1C] |

US 9,856,279 B2
TABLE 5-continued
Exemplary Compounds of Formula I.
| Cpd # | Structure |
|---|---|
| 312 | 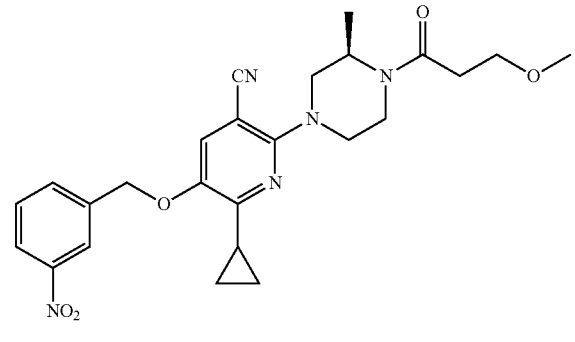 [SMILES: COCCC(=O)N1CCN(c2nc(C3CC3)c(OCc3cccc([N+](=O)[O-])c3)cc2C#N)C[C@H]1C] |
| 313 | 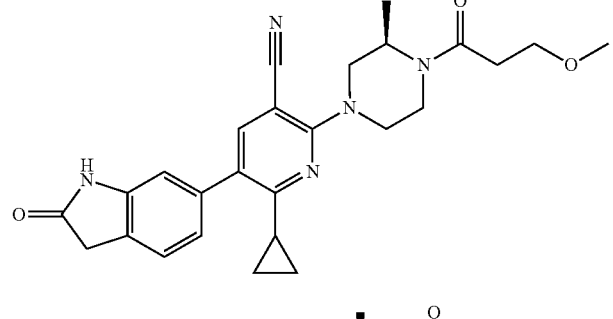 |
| 314 | 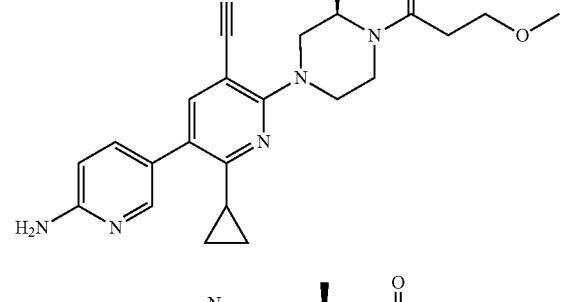 |
| 315 | 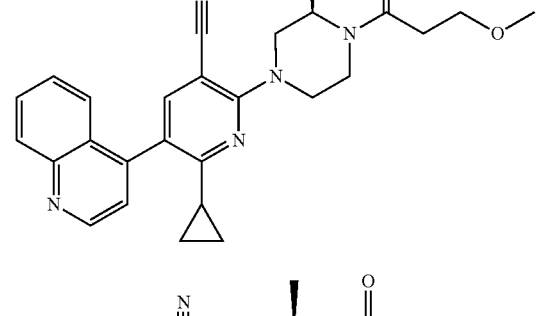 |
| 316 | 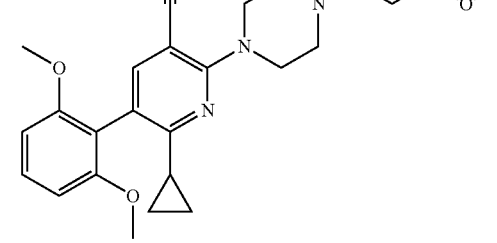 |

TABLE 5-continued
Exemplary Compounds of Formula I.
| Cpd # | Structure |
|---|---|
| 317 | 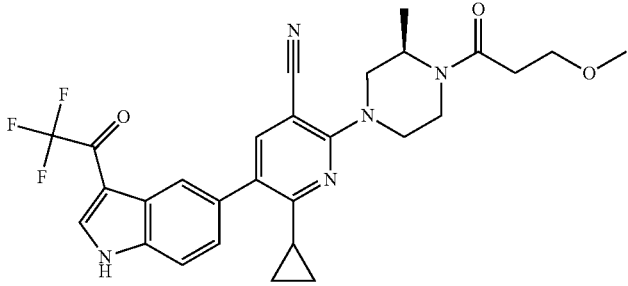 [SMILES: COCCC(=O)N1CCN(c2nc(C3CC3)c(-c3ccc4[nH]cc(C(=O)C(F)(F)F)c4c3)cc2C#N)C[C@H]1C] |
| 318 | 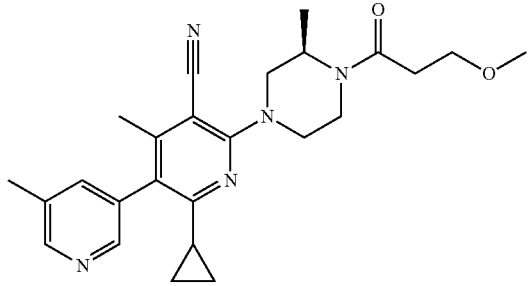 |
| 319 | 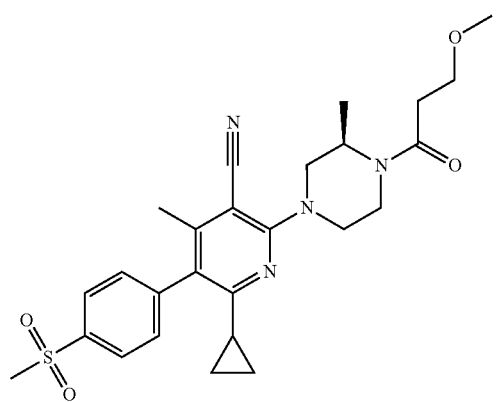 |
| 320 | 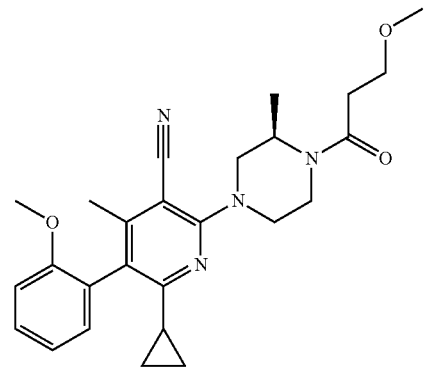 |

TABLE 5-continued
Exemplary Compounds of Formula I.
| Cpd # | Structure |
|---|---|
| 321 | 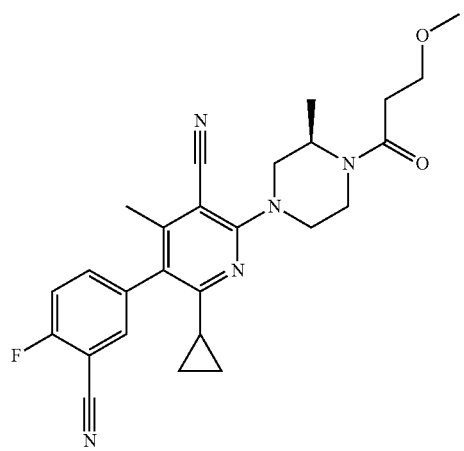 [SMILES: COCCC(=O)N1CCN(c2nc(C3CC3)c(-c3ccc(F)c(C#N)c3)c(C)c2C#N)C[C@H]1C] |
| 322 | 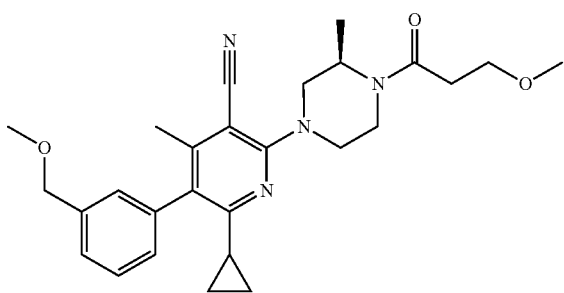 |
| 323 | 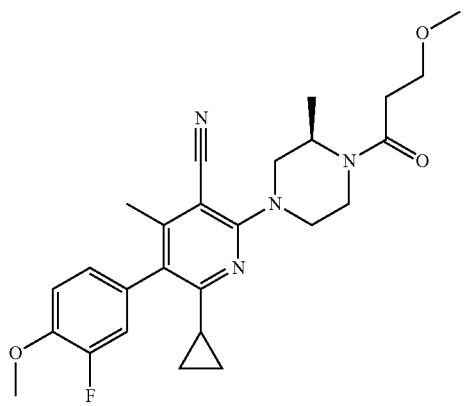 [SMILES: COCCC(=O)N1CCN(c2nc(C3CC3)c(-c3ccc(OC)c(F)c3)c(C)c2C#N)C[C@H]1C] |

TABLE 5-continued
Exemplary Compounds of Formula I.
| Cpd # | Structure |
|---|---|
| 324 | 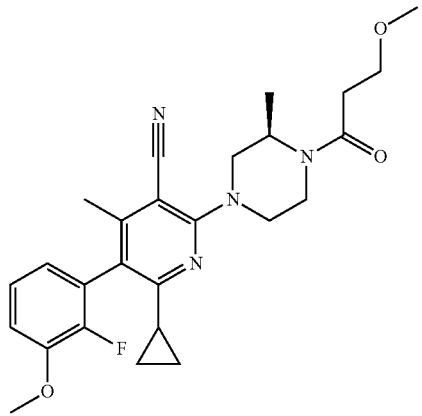 [SMILES: COCCC(=O)N1CCN(c2nc(C3CC3)c(-c3cccc(OC)c3F)c(C)c2C#N)C[C@H]1C] |
| 325 | 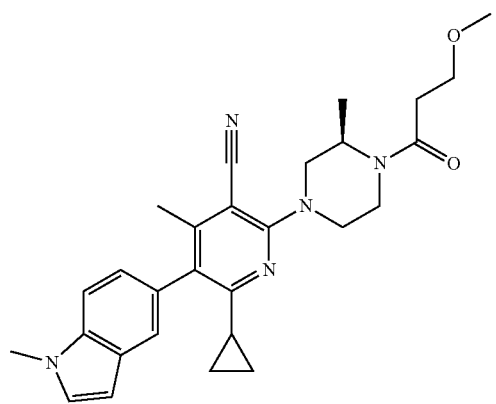 |
| 326 | 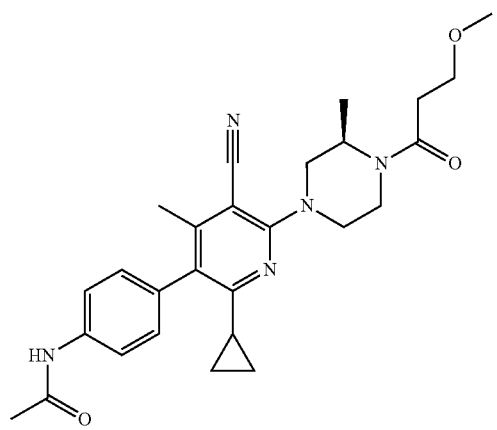 [SMILES: COCCC(=O)N1CCN(c2nc(C3CC3)c(-c3ccc(NC(C)=O)cc3)c(C)c2C#N)C[C@H]1C] |

US 9,856,279 B2
TABLE 5-continued
Exemplary Compounds of Formula I.
| Cpd # | Structure |
|---|---|
| 327 | 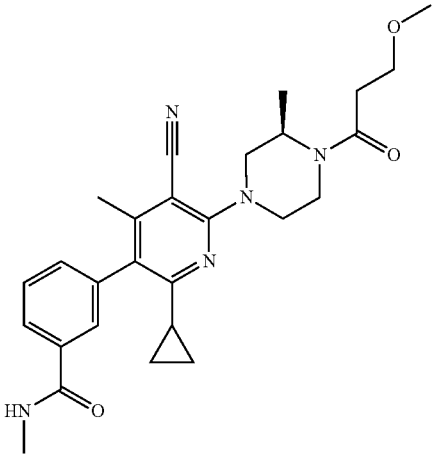 [SMILES: CNC(=O)c1cccc(-c2c(C3CC3)nc(N3CCN(C(=O)CCOC)[C@H](C)C3)c(C#N)c2C)c1] |
| 328 | 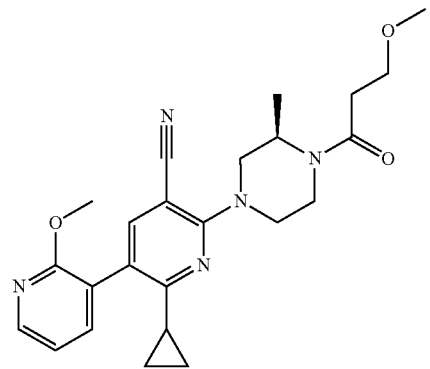 [SMILES: COCCC(=O)N1CCN(c2nc(C3CC3)c(-c3cccnc3OC)cc2C#N)C[C@H]1C] |
| 329 | 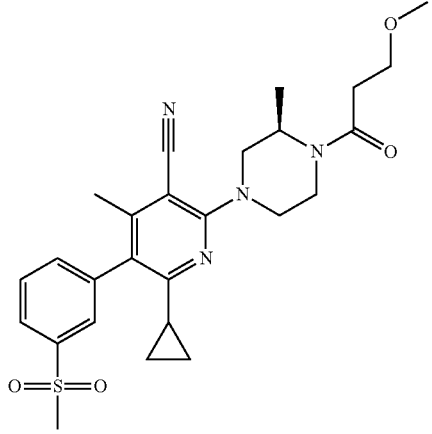 [SMILES: COCCC(=O)N1CCN(c2nc(C3CC3)c(-c3cccc(S(C)(=O)=O)c3)c(C)c2C#N)C[C@H]1C] |

TABLE 5-continued

Exemplary Compounds of Formula I.

| Cpd # | Structure |
| --- | --- |
| 330 | 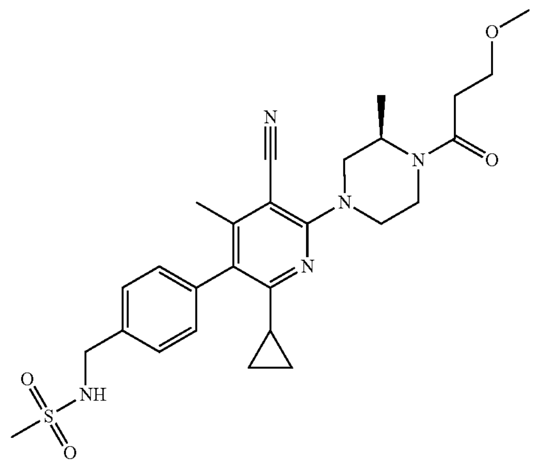 |
| 331 | 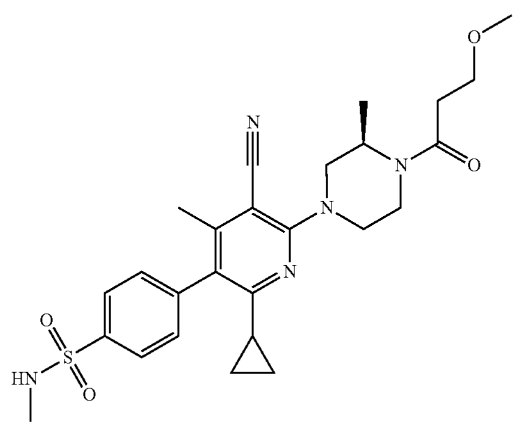 [SMILES: CNS(=O)(=O)c1ccc(-c2c(C3CC3)nc(N3CCN(C(=O)CCOC)[C@H](C)C3)c(C#N)c2C)cc1] |
| 332 | 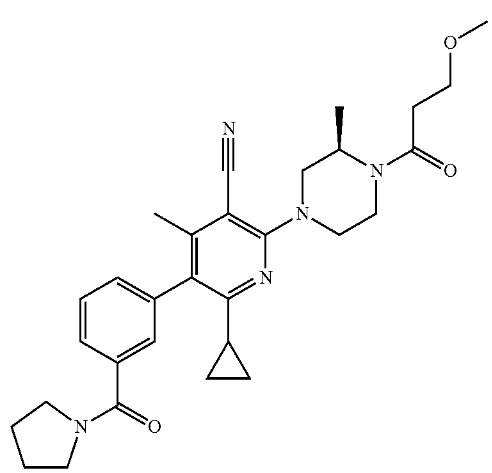 [SMILES: COCCC(=O)N1CCN(c2nc(C3CC3)c(-c3cccc(C(=O)N4CCCC4)c3)c(C)c2C#N)C[C@H]1C] |

TABLE 5-continued
Exemplary Compounds of Formula I.
| Cpd # | Structure |
|---|---|
| 333 | 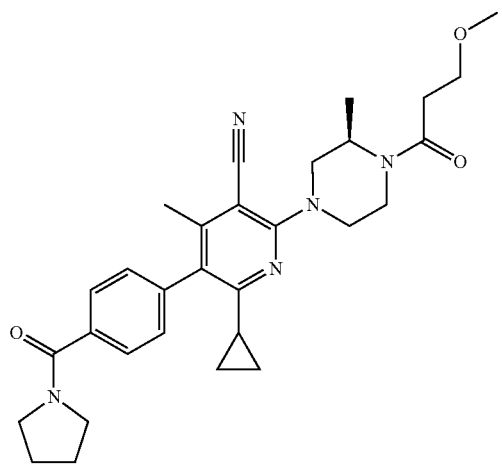 [SMILES: COCCC(=O)N1CCN(c2nc(C3CC3)c(-c3ccc(C(=O)N4CCCC4)cc3)c(C)c2C#N)C[C@H]1C] |
| 334 | 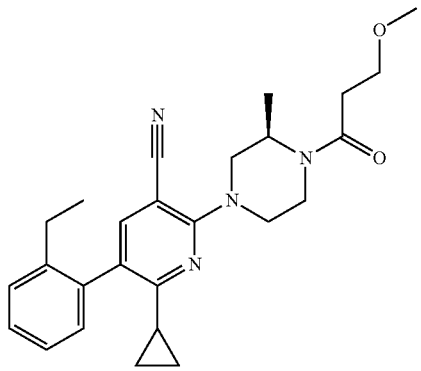 [SMILES: CCc1ccccc1-c1cc(C#N)c(N2CCN(C(=O)CCOC)[C@H](C)C2)nc1C1CC1] |
| 335 | 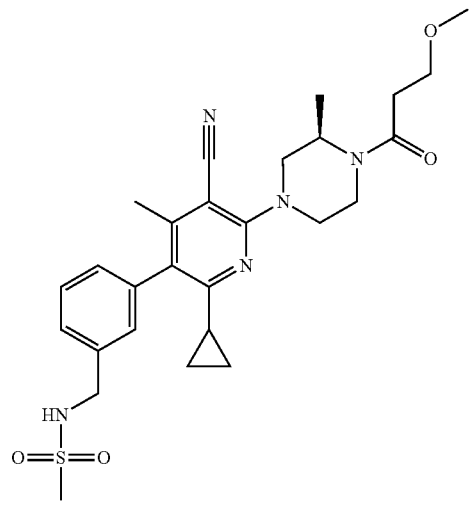 [SMILES: COCCC(=O)N1CCN(c2nc(C3CC3)c(-c3cccc(CNS(C)(=O)=O)c3)c(C)c2C#N)C[C@H]1C] |

TABLE 5-continued
Exemplary Compounds of Formula I.
| Cpd # | Structure |
|---|---|
| 336 | 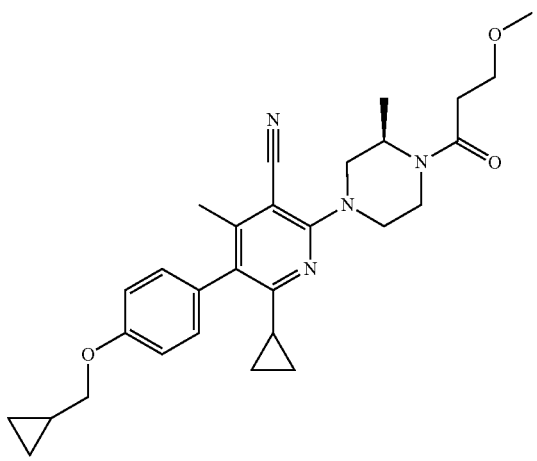 [SMILES: COCCC(=O)N1CCN(c2nc(C3CC3)c(-c3ccc(OCC4CC4)cc3)c(C)c2C#N)C[C@H]1C] |
| 337 | 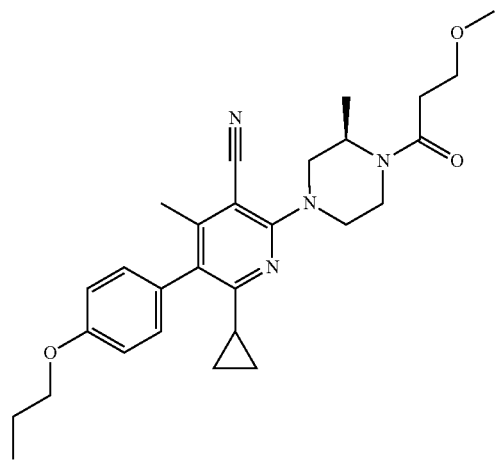 [SMILES: CCCOc1ccc(-c2c(C3CC3)nc(N3CCN(C(=O)CCOC)[C@H](C)C3)c(C#N)c2C)cc1] |
| 338 | 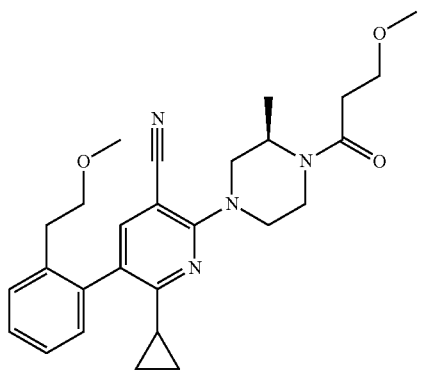 [SMILES: COCCC(=O)N1CCN(c2nc(C3CC3)c(-c3ccccc3CCOC)cc2C#N)C[C@H]1C] |

US 9,856,279 B2
89
90
TABLE 5-continued
Exemplary Compounds of Formula I.
| Cpd # | Structure |
|---|---|
| 339 | 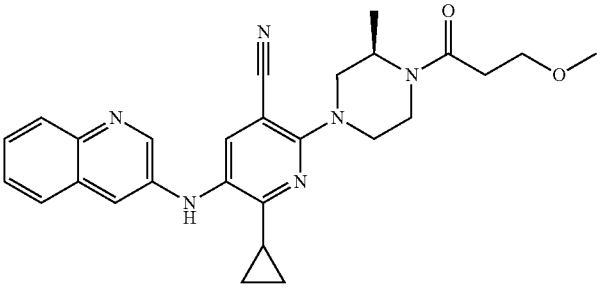 [SMILES: COCCC(=O)N1CCN(c2nc(C3CC3)c(Nc3cnc4ccccc4c3)cc2C#N)C[C@H]1C] |
| 340 | 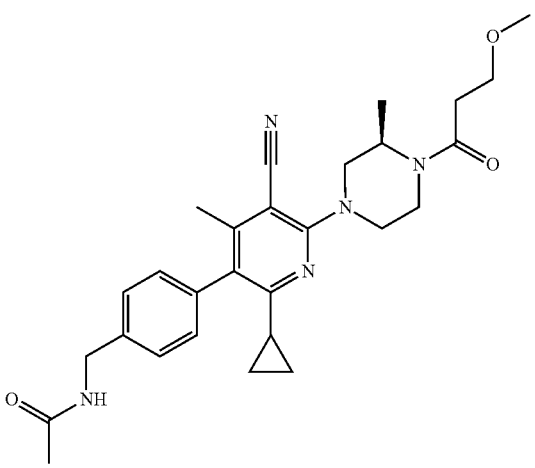 [SMILES: COCCC(=O)N1CCN(c2nc(C3CC3)c(-c3ccc(CNC(C)=O)cc3)c(C)c2C#N)C[C@H]1C] |
| 341 | 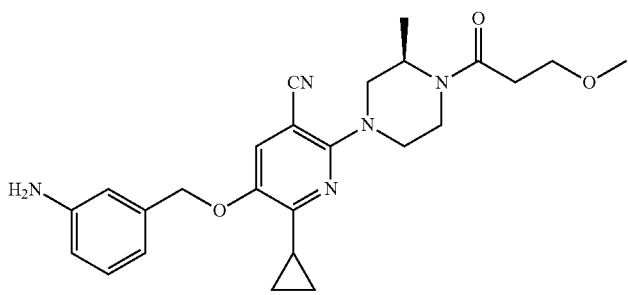 [SMILES: COCCC(=O)N1CCN(c2nc(C3CC3)c(OCc3cccc(N)c3)cc2C#N)C[C@H]1C] |
| 342 | 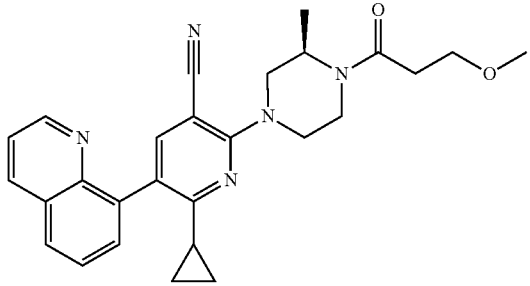 [SMILES: COCCC(=O)N1CCN(c2nc(C3CC3)c(-c3cccc4cccnc34)cc2C#N)C[C@H]1C] |

TABLE 5-continued

Exemplary Compounds of Formula I.

| Cpd # | Structure |
|---|---|
| 343 | (structure) |
| 344 | (structure) |
| 345 | (structure) |
| 346 | (structure) |

TABLE 5-continued
Exemplary Compounds of Formula I.
| Cpd # | Structure |
|---|---|
| 347 | 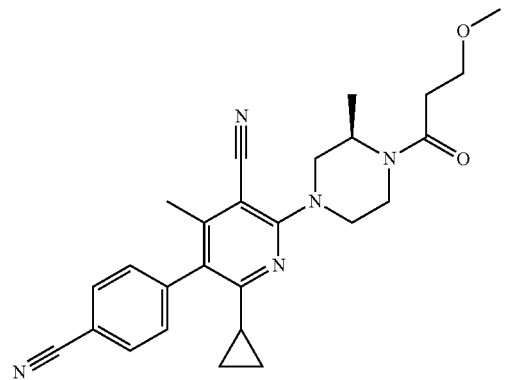 [SMILES: COCCC(=O)N1CCN(c2nc(C3CC3)c(-c3ccc(C#N)cc3)c(C)c2C#N)C[C@H]1C] |
| 348 | 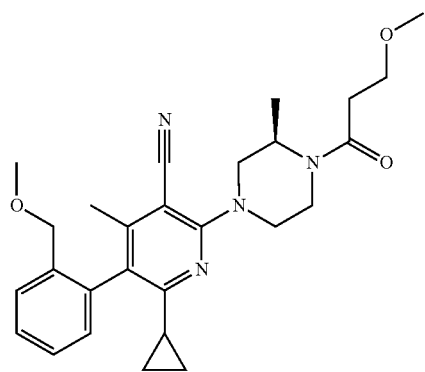 [SMILES: COCCC(=O)N1CCN(c2nc(C3CC3)c(-c3ccccc3COC)c(C)c2C#N)C[C@H]1C] |
| 349 | 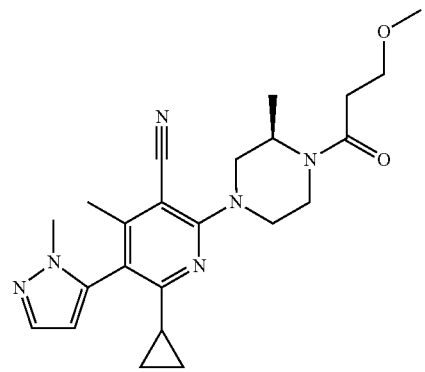 [SMILES: COCCC(=O)N1CCN(c2nc(C3CC3)c(-c3ccnn3C)c(C)c2C#N)C[C@H]1C] |

TABLE 5-continued
Exemplary Compounds of Formula I.
| Cpd # | Structure |
|---|---|
| 350 | 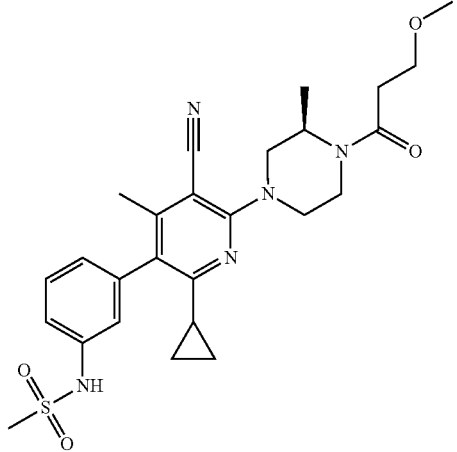 |
| 351 | 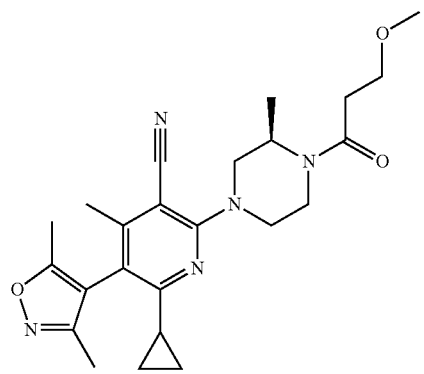 [SMILES: COCCC(=O)N1CCN(c2nc(C3CC3)c(-c3c(C)noc3C)c(C)c2C#N)C[C@H]1C] |
| 352 | 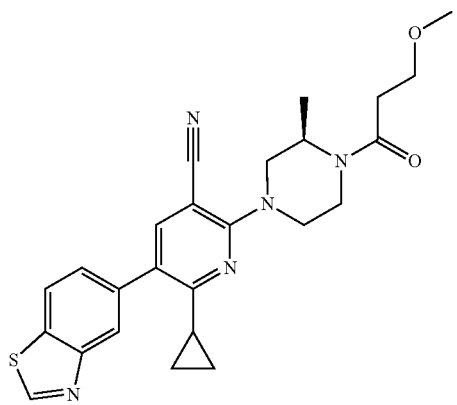 [SMILES: COCCC(=O)N1CCN(c2nc(C3CC3)c(-c3ccc4scnc4c3)cc2C#N)C[C@H]1C] |

TABLE 5-continued

Exemplary Compounds of Formula I.

| Cpd # | Structure |
|---|---|
| 353 | 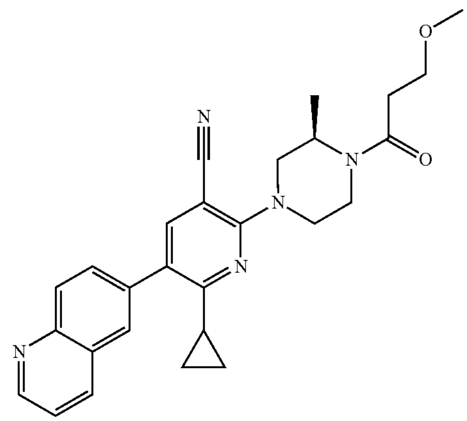 [SMILES: COCCC(=O)N1CCN(c2nc(C3CC3)c(-c3ccc4ncccc4c3)cc2C#N)C[C@H]1C] |
| 354 | 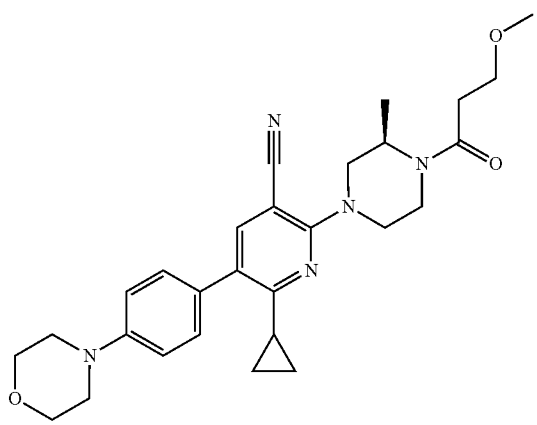 [SMILES: COCCC(=O)N1CCN(c2nc(C3CC3)c(-c3ccc(N4CCOCC4)cc3)cc2C#N)C[C@H]1C] |
| 355 | 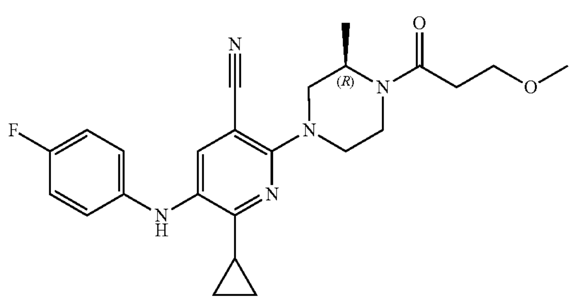 |
| 356 | 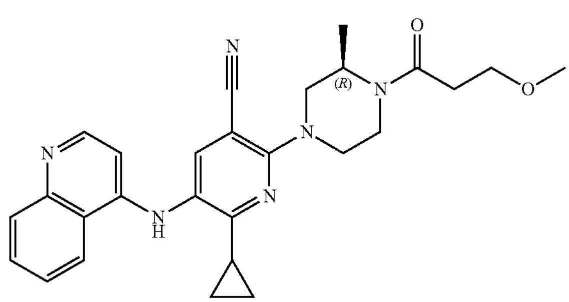 |

TABLE 5-continued
Exemplary Compounds of Formula I.
| Cpd # | Structure |
|---|---|
| 357 | 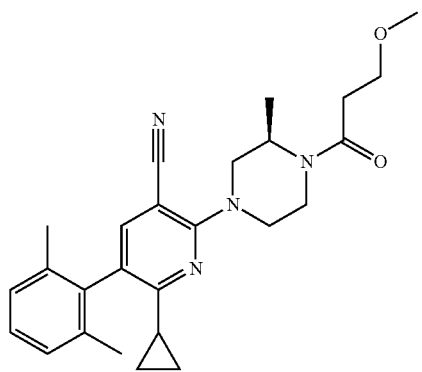 [SMILES: COCCC(=O)N1CCN(c2nc(C3CC3)c(-c3c(C)cccc3C)cc2C#N)C[C@H]1C] |
| 358 | 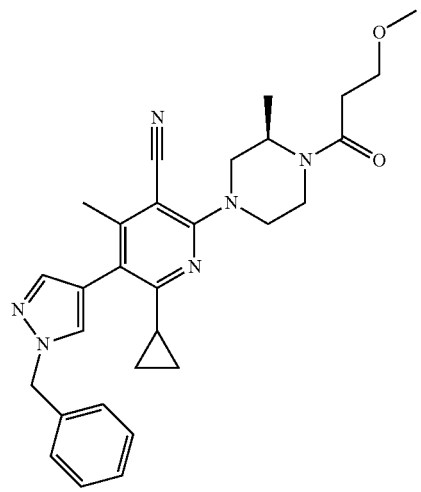 [SMILES: COCCC(=O)N1CCN(c2nc(C3CC3)c(-c3cnn(Cc4ccccc4)c3)c(C)c2C#N)C[C@H]1C] |
| 359 | 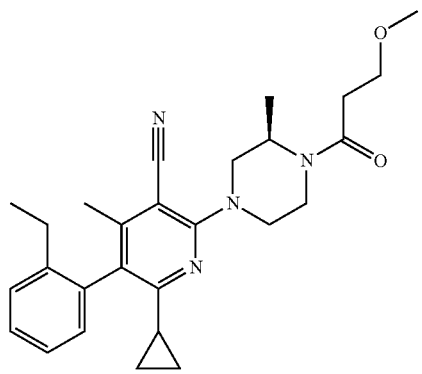 |

TABLE 5-continued
Exemplary Compounds of Formula I.
| Cpd # | Structure |
|---|---|
| 360 | 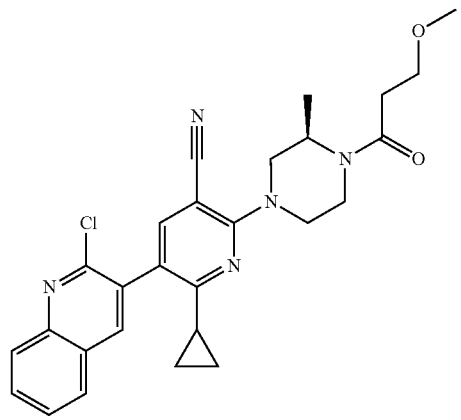 [SMILES: COCCC(=O)N1CCN(c2nc(C3CC3)c(-c3cc4ccccc4nc3Cl)cc2C#N)C[C@H]1C] |
| 361 | 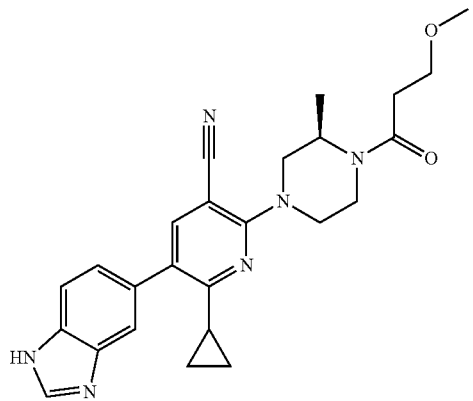 [SMILES: COCCC(=O)N1CCN(c2nc(C3CC3)c(-c3ccc4[nH]cnc4c3)cc2C#N)C[C@H]1C] |
| 362 | 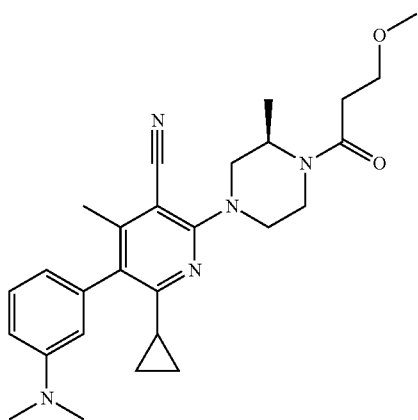 [SMILES: COCCC(=O)N1CCN(c2nc(C3CC3)c(-c3cccc(N(C)C)c3)c(C)c2C#N)C[C@H]1C] |

TABLE 5-continued
Exemplary Compounds of Formula I.
| Cpd # | Structure |
|---|---|
| 363 | 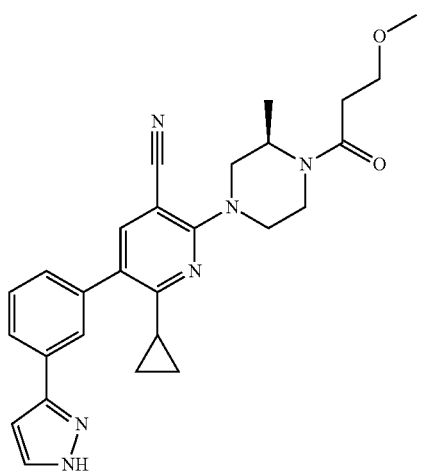 [SMILES: COCCC(=O)N1CCN(c2nc(C3CC3)c(-c3cccc(-c4cc[nH]n4)c3)cc2C#N)C[C@H]1C] |
| 364 | 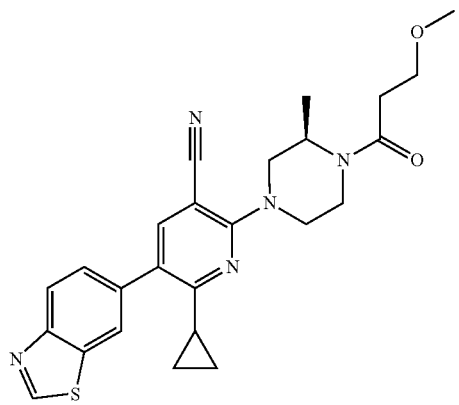 [SMILES: COCCC(=O)N1CCN(c2nc(C3CC3)c(-c3ccc4ncsc4c3)cc2C#N)C[C@H]1C] |
| 365 | 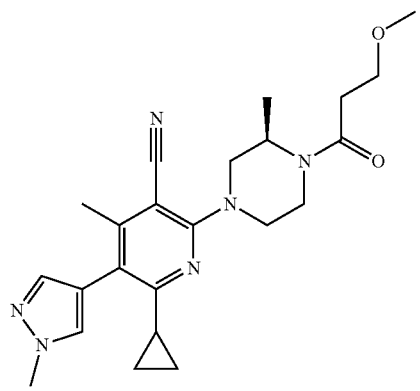 [SMILES: COCCC(=O)N1CCN(c2nc(C3CC3)c(-c3cnn(C)c3)c(C)c2C#N)C[C@H]1C] |

TABLE 5-continued

Exemplary Compounds of Formula I.

| Cpd # | Structure |
|---|---|
| 366 | 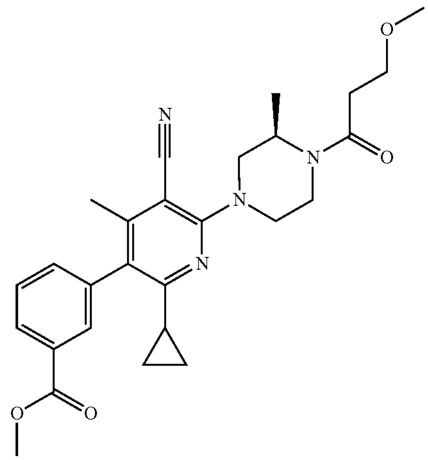 [SMILES: COCCC(=O)N1CCN(c2nc(C3CC3)c(-c3cccc(C(=O)OC)c3)c(C)c2C#N)C[C@H]1C] |
| 367 | 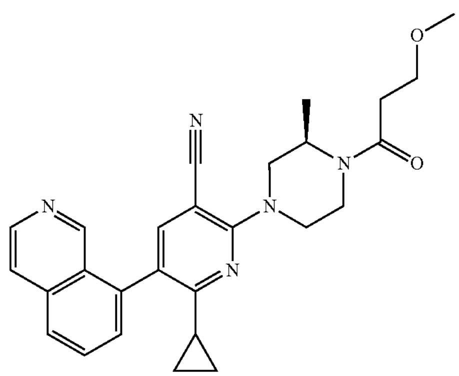 [SMILES: COCCC(=O)N1CCN(c2nc(C3CC3)c(-c3cccc4ccncc34)cc2C#N)C[C@H]1C] |
| 368 | 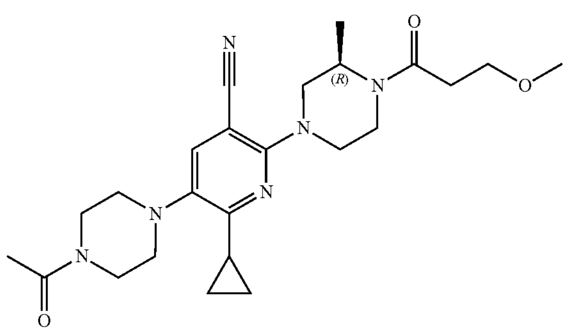 |
| 369 | 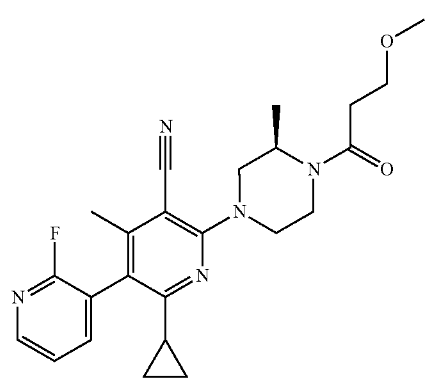 [SMILES: COCCC(=O)N1CCN(c2nc(C3CC3)c(-c3cccnc3F)c(C)c2C#N)C[C@H]1C] |

TABLE 5-continued

Exemplary Compounds of Formula I.

| Cpd # | Structure |
|---|---|
| 370 | 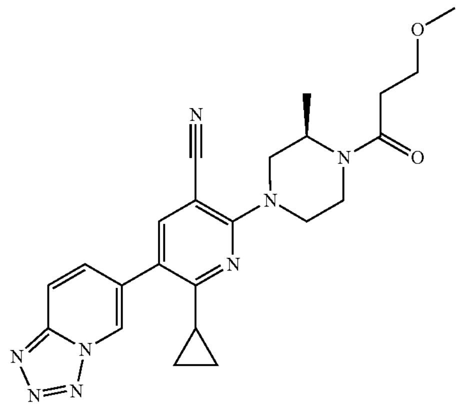 [SMILES: COCCC(=O)N1CCN(c2nc(C3CC3)c(-c3ccc4nnnn4c3)cc2C#N)C[C@H]1C] |
| 371 | 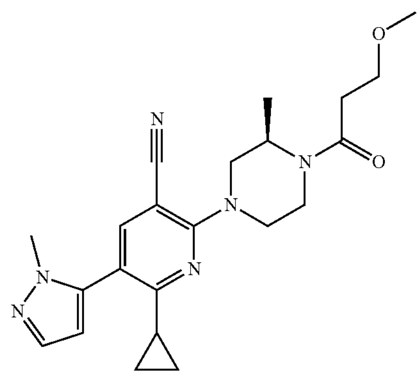 [SMILES: COCCC(=O)N1CCN(c2nc(C3CC3)c(-c3ccnn3C)cc2C#N)C[C@H]1C] |
| 372 | 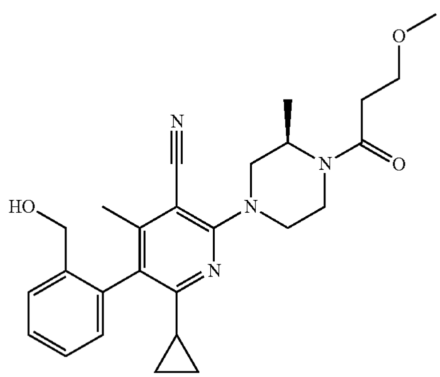 [SMILES: COCCC(=O)N1CCN(c2nc(C3CC3)c(-c3ccccc3CO)c(C)c2C#N)C[C@H]1C] |
| 373 | 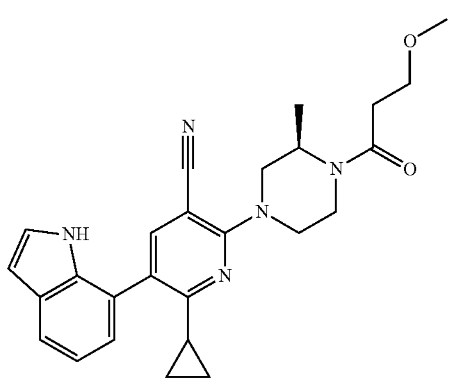 [SMILES: COCCC(=O)N1CCN(c2nc(C3CC3)c(-c3cccc4cc[nH]c34)cc2C#N)C[C@H]1C] |

TABLE 5-continued
Exemplary Compounds of Formula I.
| Cpd # | Structure |
|---|---|
| 374 | 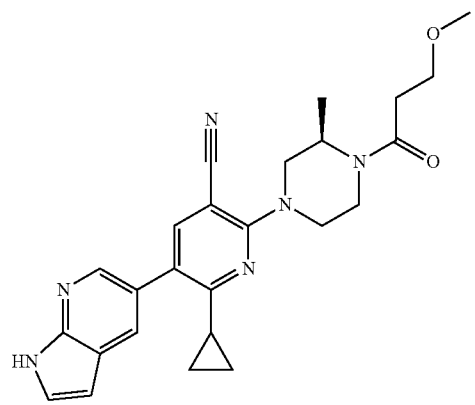 [SMILES: COCCC(=O)N1CCN(c2nc(C3CC3)c(-c3cnc4[nH]ccc4c3)cc2C#N)C[C@H]1C] |
| 375 | 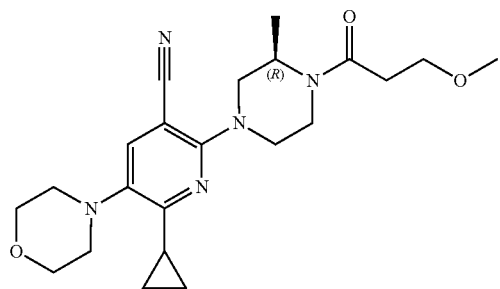 |
| 376 | 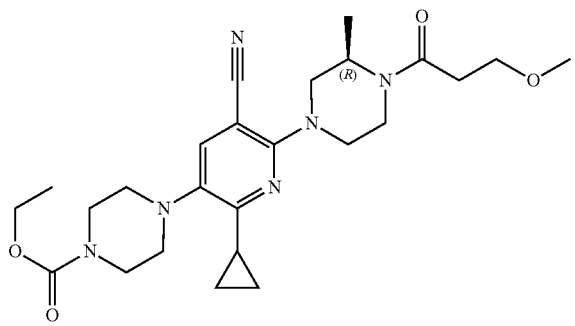 |
| 377 | 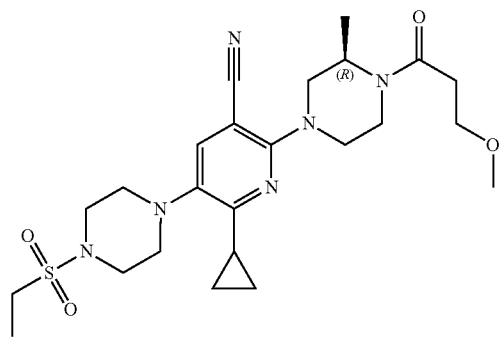 |

TABLE 5-continued

Exemplary Compounds of Formula I.

| Cpd # | Structure |
|---|---|
| 378 | 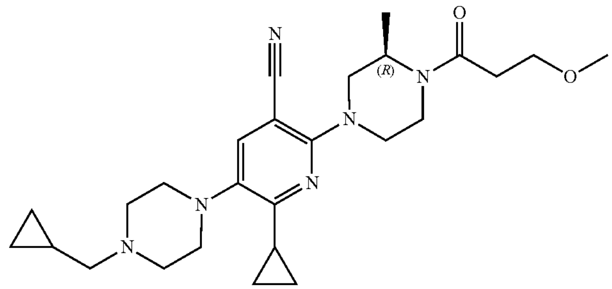 |
| 379 | 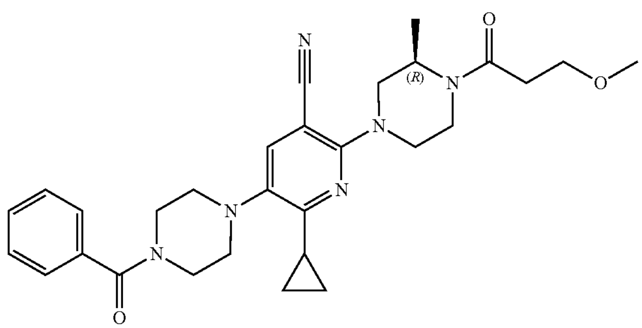 |
| 380 | 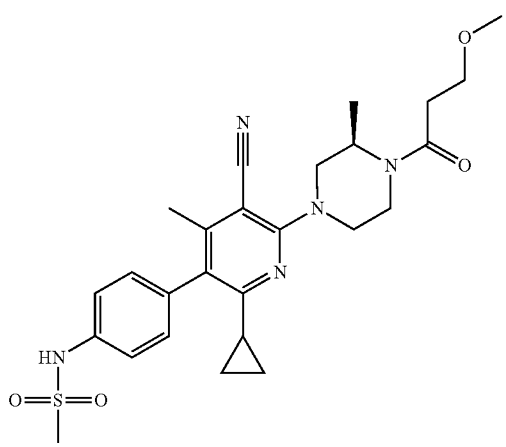 [SMILES: COCCC(=O)N1CCN(c2nc(C3CC3)c(-c3ccc(NS(C)(=O)=O)cc3)c(C)c2C#N)C[C@H]1C] |
| 381 | 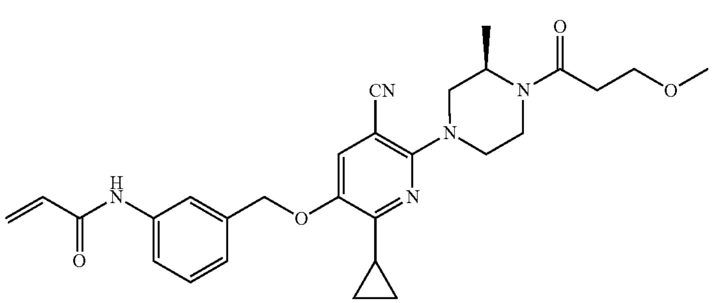 [SMILES: C=CC(=O)Nc1cccc(COc2cc(C#N)c(N3CCN(C(=O)CCOC)[C@H](C)C3)nc2C2CC2)c1] |

TABLE 5-continued

Exemplary Compounds of Formula I.

| Cpd # | Structure |
|---|---|
| 382 | 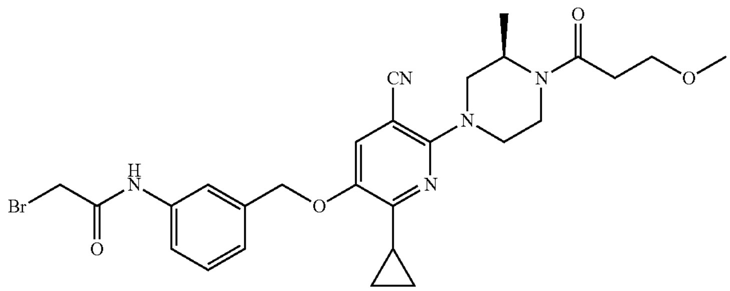 [SMILES: COCCC(=O)N1CCN(c2nc(C3CC3)c(OCc3cccc(NC(=O)CBr)c3)cc2C#N)C[C@H]1C] |
| 383 | 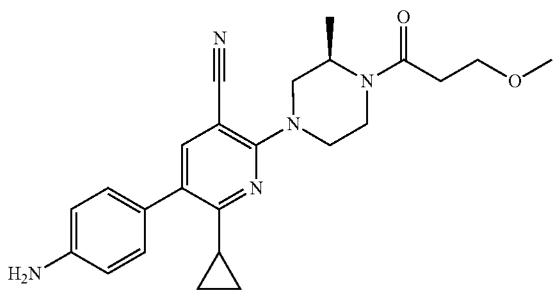 [SMILES: COCCC(=O)N1CCN(c2nc(C3CC3)c(-c3ccc(N)cc3)cc2C#N)C[C@H]1C] |
| 384 | 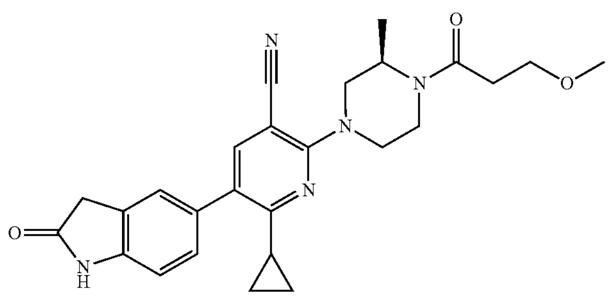 [SMILES: COCCC(=O)N1CCN(c2nc(C3CC3)c(-c3ccc4c(c3)CC(=O)N4)cc2C#N)C[C@H]1C] |
| 385 | 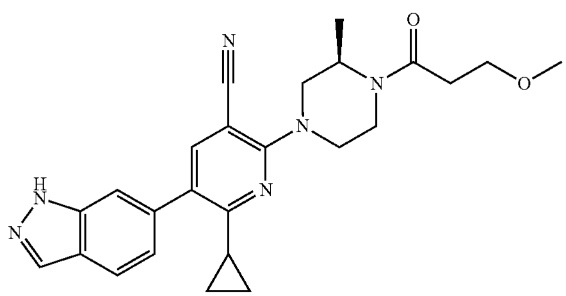 [SMILES: COCCC(=O)N1CCN(c2nc(C3CC3)c(-c3ccc4cn[nH]c4c3)cc2C#N)C[C@H]1C] |
| 386 | 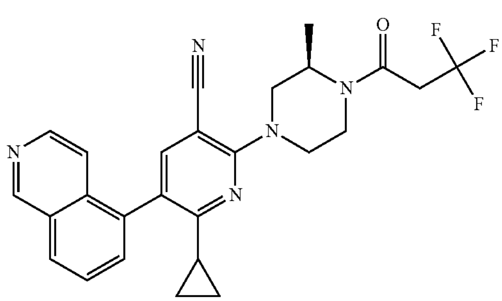 [SMILES: C[C@@H]1CN(c2nc(C3CC3)c(-c3cccc4cnccc34)cc2C#N)CCN1C(=O)CC(F)(F)F] |

TABLE 5-continued
Exemplary Compounds of Formula I.
| Cpd # | Structure |
|---|---|
| 387 | 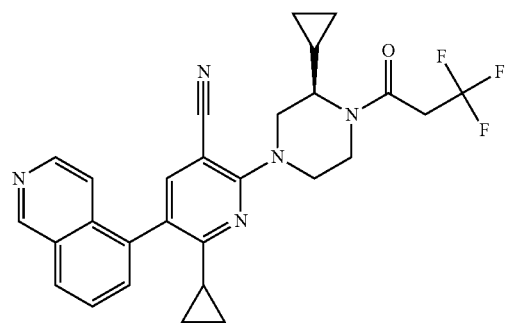 [SMILES: N#Cc1cc(-c2cccc3cnccc23)c(C2CC2)nc1N1CCN(C(=O)CC(F)(F)F)[C@H](C2CC2)C1] |
| 388 | 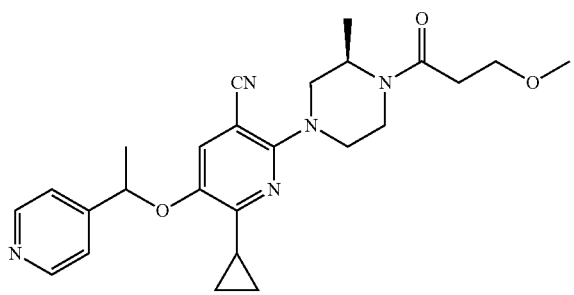 |
| 389 | 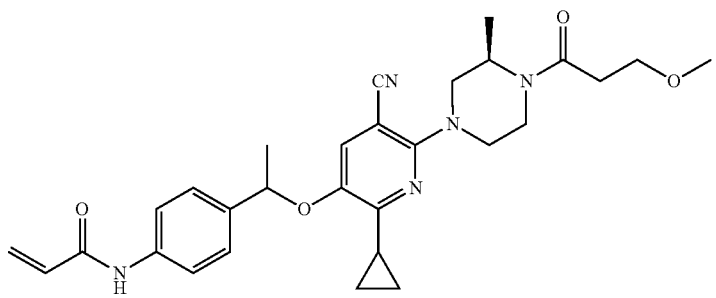 [SMILES: C=CC(=O)Nc1ccc(C(C)Oc2cc(C#N)c(N3CCN(C(=O)CCOC)[C@H](C)C3)nc2C2CC2)cc1] |
| 390 | 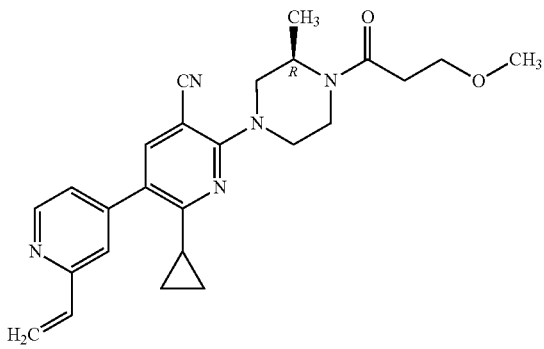 |

TABLE 5-continued
Exemplary Compounds of Formula I.
| Cpd # | Structure |
|---|---|
| 391 | 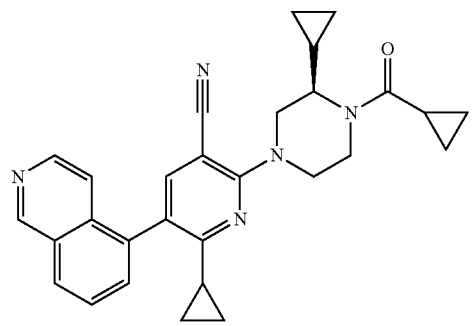 [SMILES: N#Cc1cc(-c2cccc3cnccc23)c(C2CC2)nc1N1CCN(C(=O)C2CC2)[C@H](C2CC2)C1] |
| 392 | 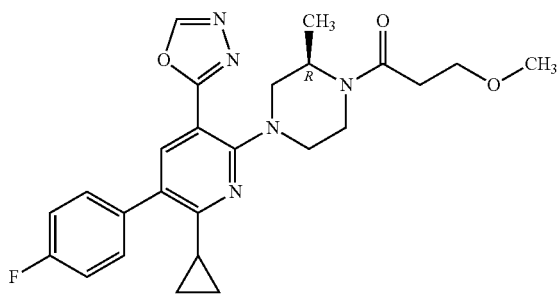 |
| 393 | 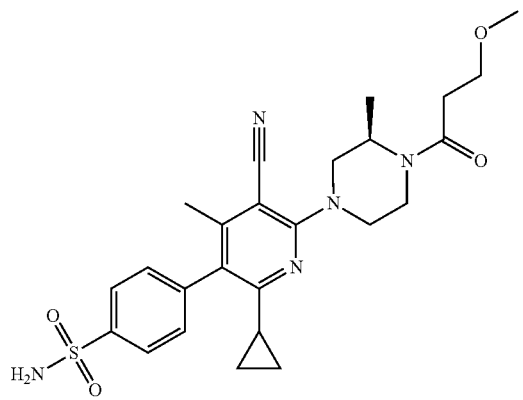 [SMILES: COCCC(=O)N1CCN(c2nc(C3CC3)c(-c3ccc(S(N)(=O)=O)cc3)c(C)c2C#N)C[C@H]1C] |
| 394 | 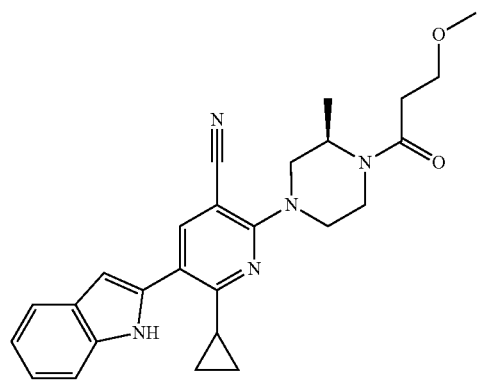 [SMILES: COCCC(=O)N1CCN(c2nc(C3CC3)c(-c3cc4ccccc4[nH]3)cc2C#N)C[C@H]1C] |

TABLE 5-continued

Exemplary Compounds of Formula I.

| Cpd # | Structure |
|---|---|
| 395 | 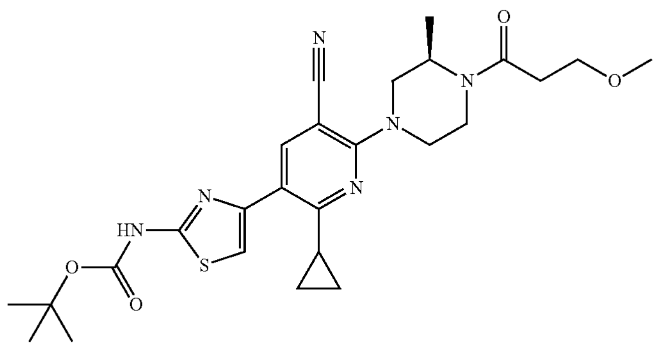 [SMILES: COCCC(=O)N1CCN(c2nc(C3CC3)c(-c3csc(NC(=O)OC(C)(C)C)n3)cc2C#N)C[C@H]1C] |
| 396 | 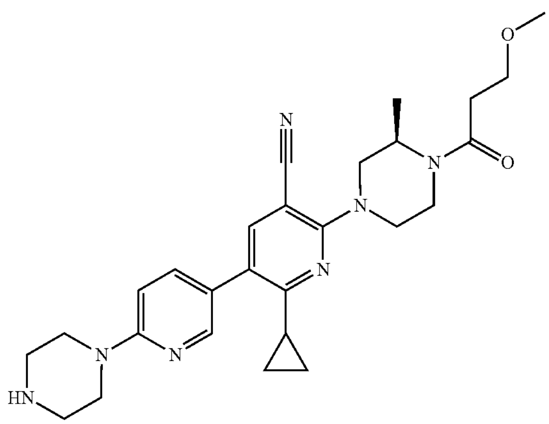 [SMILES: COCCC(=O)N1CCN(c2nc(C3CC3)c(-c3ccc(N4CCNCC4)nc3)cc2C#N)C[C@H]1C] |
| 397 | 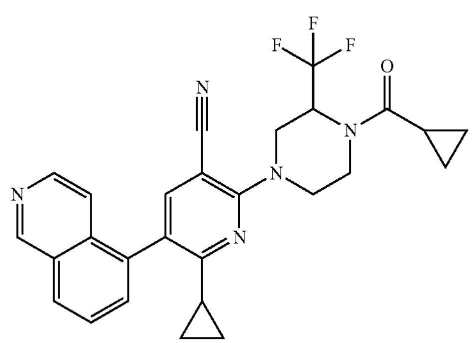 [SMILES: N#Cc1cc(-c2cccc3cnccc23)c(C2CC2)nc1N1CCN(C(=O)C2CC2)C(C(F)(F)F)C1] |
| 398 | 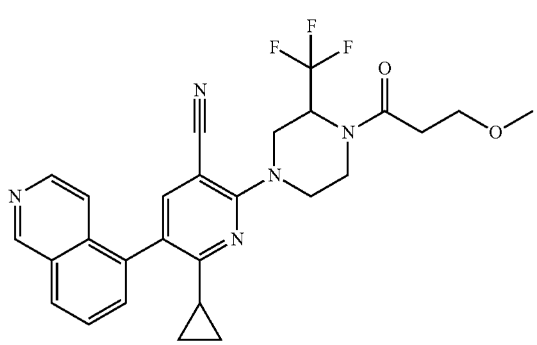 [SMILES: COCCC(=O)N1CCN(c2nc(C3CC3)c(-c3cccc4cnccc34)cc2C#N)CC1C(F)(F)F] |

US 9,856,279 B2
121
122
TABLE 5-continued
Exemplary Compounds of Formula I.
| Cpd # | Structure |
|---|---|
| 399 | 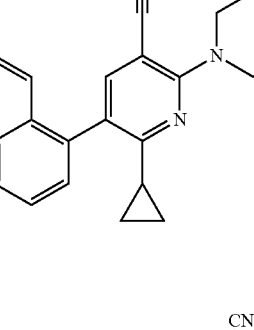 |
| 400 | 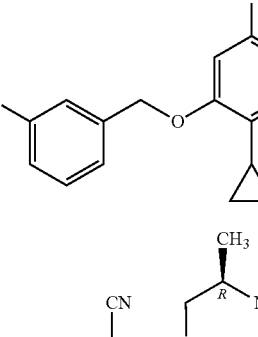 |
| 401 | 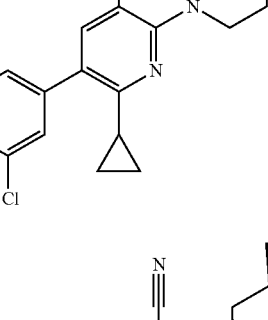 |
| 402 | 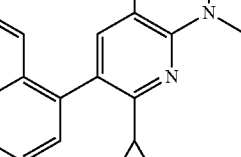 |
| 403 | 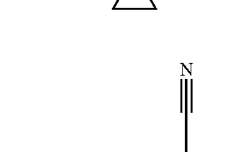 |

TABLE 5-continued
Exemplary Compounds of Formula I.
| Cpd # | Structure |
|---|---|
| 404 | 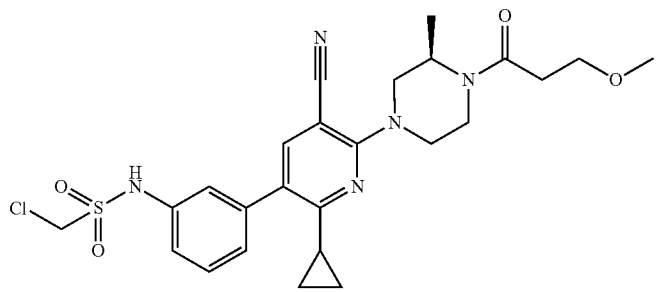 [SMILES: COCCC(=O)N1CCN(c2nc(C3CC3)c(-c3cccc(NS(=O)(=O)CCl)c3)cc2C#N)C[C@H]1C] |
| 405 | 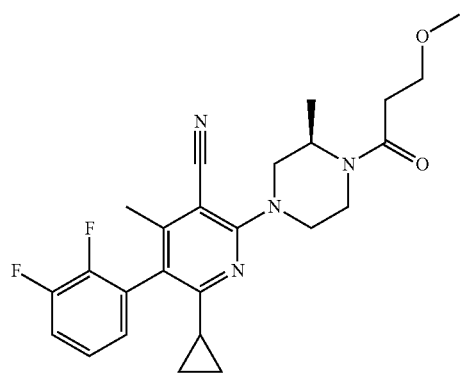 [SMILES: COCCC(=O)N1CCN(c2nc(C3CC3)c(-c3cccc(F)c3F)c(C)c2C#N)C[C@H]1C] |
| 406 | 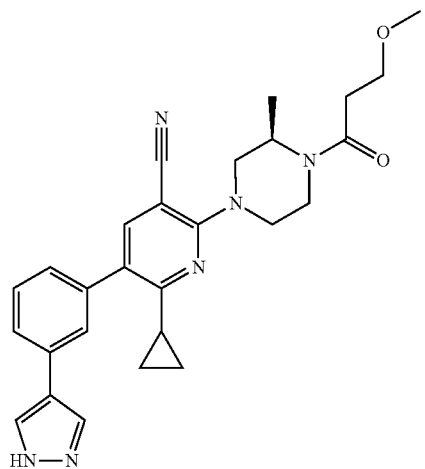 [SMILES: COCCC(=O)N1CCN(c2nc(C3CC3)c(-c3cccc(-c4cn[nH]c4)c3)cc2C#N)C[C@H]1C] |
| 407 | 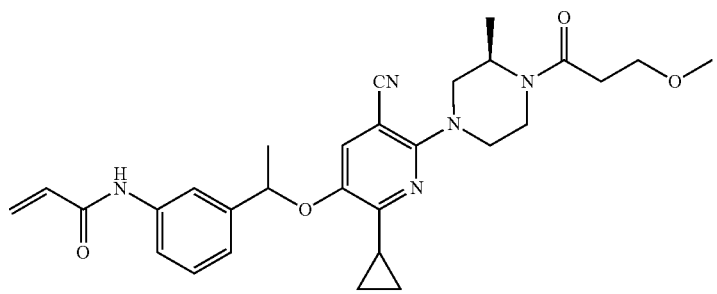 [SMILES: C=CC(=O)Nc1cccc(C(C)Oc2cc(C#N)c(N3CCN(C(=O)CCOC)[C@H](C)C3)nc2C2CC2)c1] |

TABLE 5-continued
Exemplary Compounds of Formula I.
| Cpd # | Structure |
|---|---|
| 408 | 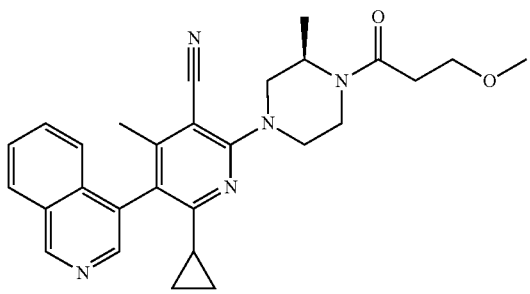 [SMILES: COCCC(=O)N1CCN(c2nc(C3CC3)c(-c3cncc4ccccc34)c(C)c2C#N)C[C@H]1C] |
| 409 | 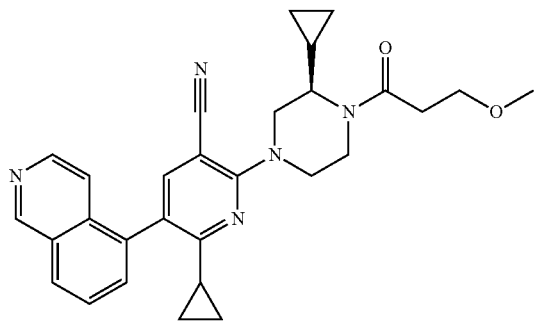 [SMILES: COCCC(=O)N1CCN(c2nc(C3CC3)c(-c3cccc4cnccc34)cc2C#N)C[C@H]1C1CC1] |
| 410 | 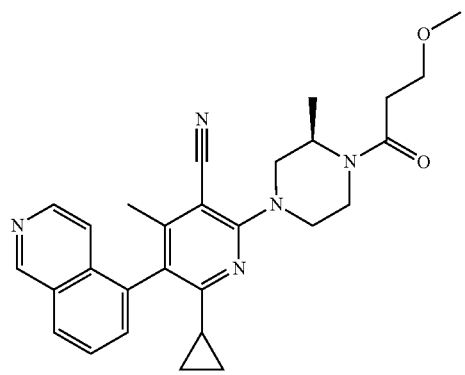 [SMILES: COCCC(=O)N1CCN(c2nc(C3CC3)c(-c3cccc4cnccc34)c(C)c2C#N)C[C@H]1C] |
| 411 | 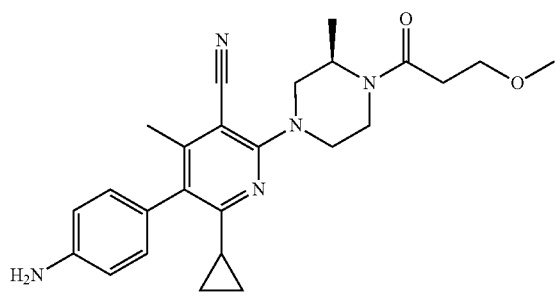 [SMILES: COCCC(=O)N1CCN(c2nc(C3CC3)c(-c3ccc(N)cc3)c(C)c2C#N)C[C@H]1C] |

TABLE 5-continued

Exemplary Compounds of Formula I.

| Cpd # | Structure |
|---|---|
| 412 | 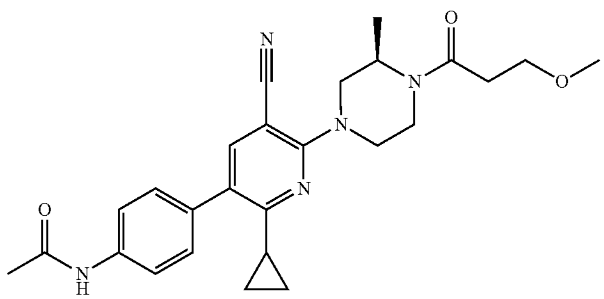 [SMILES: COCCC(=O)N1CCN(c2nc(C3CC3)c(-c3ccc(NC(C)=O)cc3)cc2C#N)C[C@H]1C] |
| 413 | 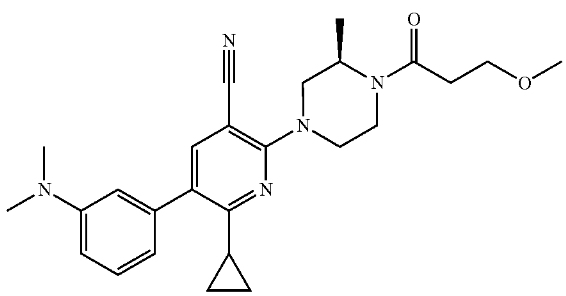 |
| 414 | 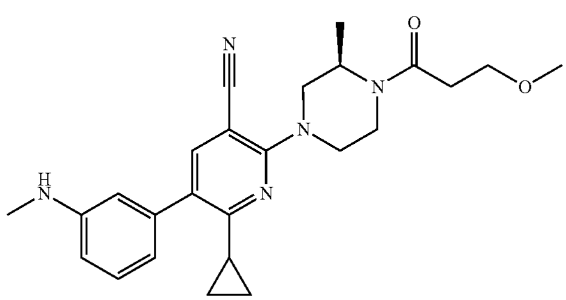 |
| 415 | 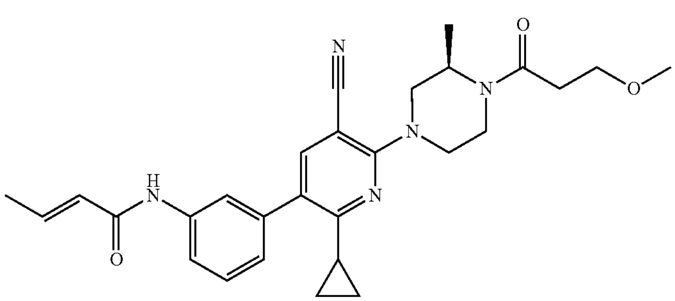 [SMILES: C/C=C/C(=O)Nc1cccc(-c2cc(C#N)c(N3CCN(C(=O)CCOC)[C@H](C)C3)nc2C2CC2)c1] |
| 416 | 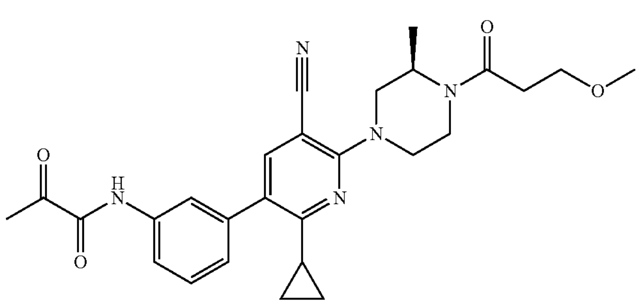 [SMILES: COCCC(=O)N1CCN(c2nc(C3CC3)c(-c3cccc(NC(=O)C(C)=O)c3)cc2C#N)C[C@H]1C] |

TABLE 5-continued
Exemplary Compounds of Formula I.
| Cpd # | Structure |
|---|---|
| 417 | 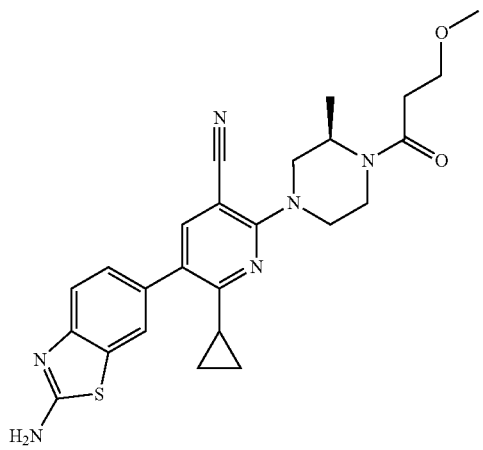 [SMILES: COCCC(=O)N1CCN(c2nc(C3CC3)c(-c3ccc4nc(N)sc4c3)cc2C#N)C[C@H]1C] |
| 418 | 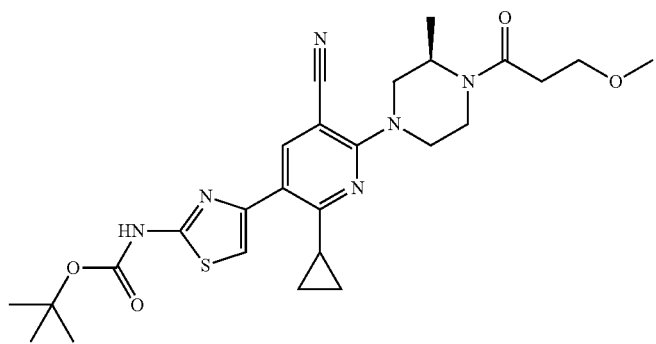 [SMILES: COCCC(=O)N1CCN(c2nc(C3CC3)c(-c3csc(NC(=O)OC(C)(C)C)n3)cc2C#N)C[C@H]1C] |
| 419 | 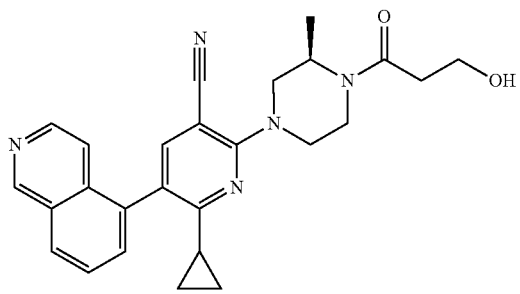 [SMILES: C[C@@H]1CN(c2nc(C3CC3)c(-c3cccc4cnccc34)cc2C#N)CCN1C(=O)CCO] |
| 420 | 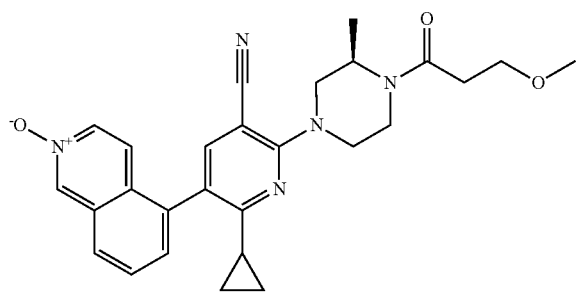 [SMILES: COCCC(=O)N1CCN(c2nc(C3CC3)c(-c3cccc4c[n+]([O-])ccc34)cc2C#N)C[C@H]1C] |

US 9,856,279 B2
131                                                                                        132
TABLE 5-continued
Exemplary Compounds of Formula I.
| Cpd # | Structure |
|---|---|
| 421 | 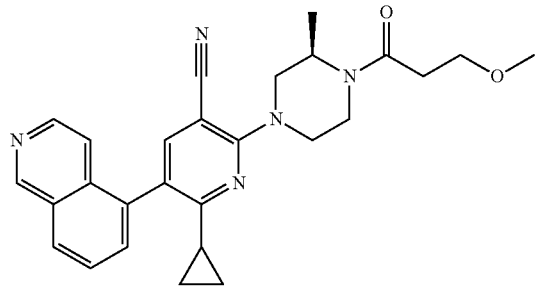 [SMILES: COCCC(=O)N1CCN(c2nc(C3CC3)c(-c3cccc4cnccc34)cc2C#N)C[C@H]1C] |
| 422 | 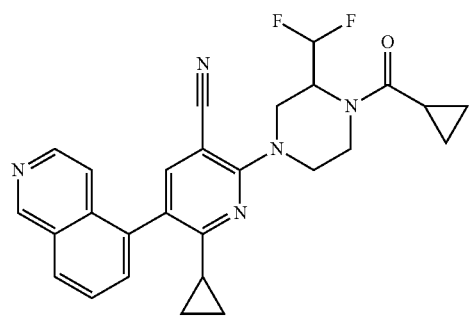 [SMILES: N#Cc1cc(-c2cccc3cnccc23)c(C2CC2)nc1N1CCN(C(=O)C2CC2)C(C(F)F)C1] |
| 423 | 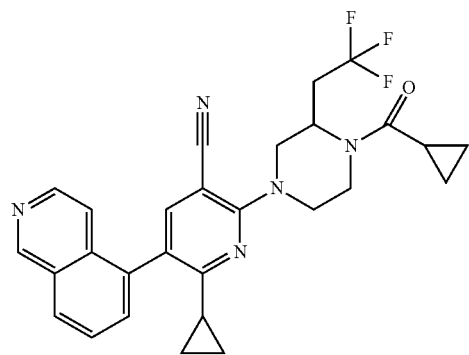 [SMILES: N#Cc1cc(-c2cccc3cnccc23)c(C2CC2)nc1N1CCN(C(=O)C2CC2)C(CC(F)(F)F)C1] |
| 424 | 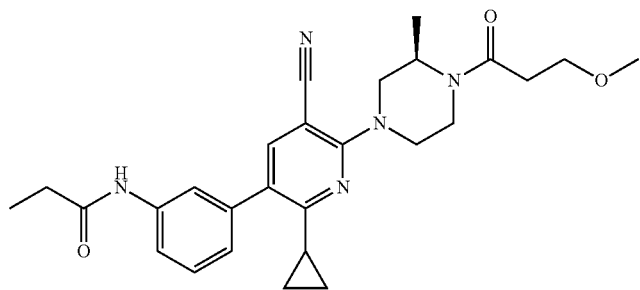 [SMILES: CCC(=O)Nc1cccc(-c2cc(C#N)c(N3CCN(C(=O)CCOC)[C@H](C)C3)nc2C2CC2)c1] |

TABLE 5-continued

Exemplary Compounds of Formula I.

| Cpd # | Structure |
|---|---|
| 425 | 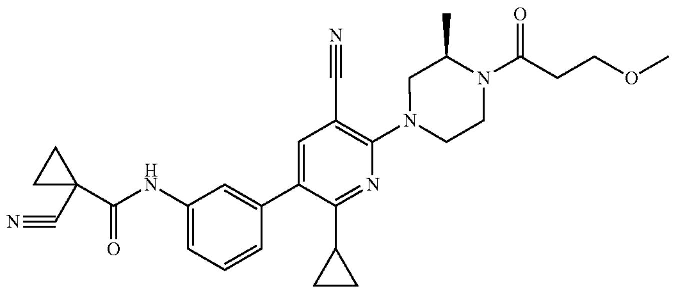 [SMILES: COCCC(=O)N1CCN(c2nc(C3CC3)c(-c3cccc(NC(=O)C4(C#N)CC4)c3)cc2C#N)C[C@H]1C] |
| 426 | 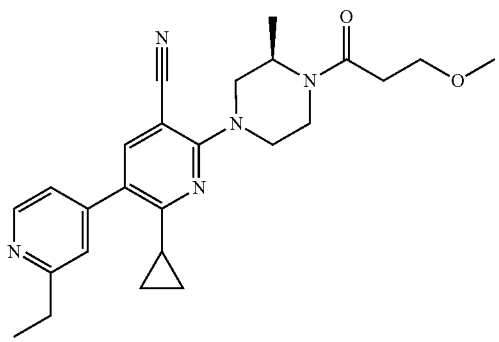 [SMILES: CCc1cc(-c2cc(C#N)c(N3CCN(C(=O)CCOC)[C@H](C)C3)nc2C2CC2)ccn1] |
| 427 | 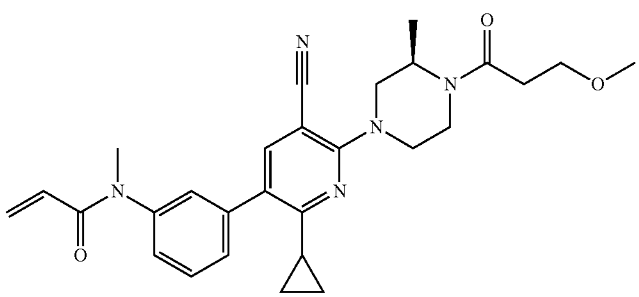 [SMILES: C=CC(=O)N(C)c1cccc(-c2cc(C#N)c(N3CCN(C(=O)CCOC)[C@H](C)C3)nc2C2CC2)c1] |
| 428 | 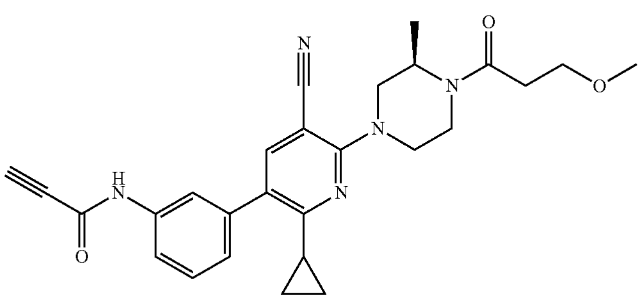 [SMILES: C#CC(=O)Nc1cccc(-c2cc(C#N)c(N3CCN(C(=O)CCOC)[C@H](C)C3)nc2C2CC2)c1] |
| 429 | 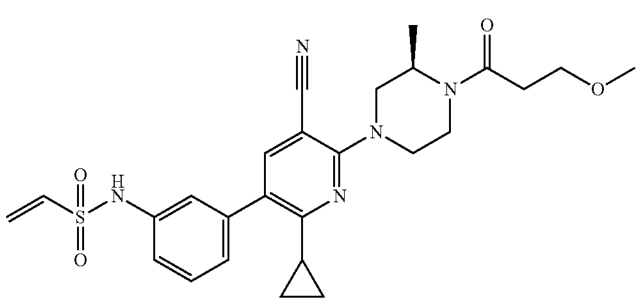 [SMILES: C=CS(=O)(=O)Nc1cccc(-c2cc(C#N)c(N3CCN(C(=O)CCOC)[C@H](C)C3)nc2C2CC2)c1] |

TABLE 5-continued

Exemplary Compounds of Formula I.

| Cpd # | Structure |
|---|---|
| 430 | 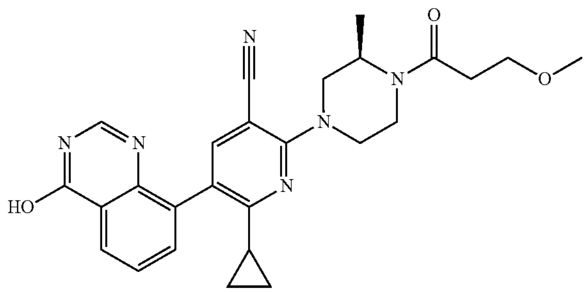 [SMILES: COCCC(=O)N1CCN(c2nc(C3CC3)c(-c3cccc4c(O)ncnc34)cc2C#N)C[C@H]1C] |
| 431 | 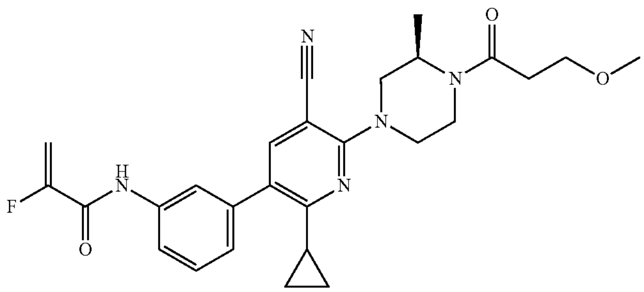 [SMILES: C=C(F)C(=O)Nc1cccc(-c2cc(C#N)c(N3CCN(C(=O)CCOC)[C@H](C)C3)nc2C2CC2)c1] |
| 432 | 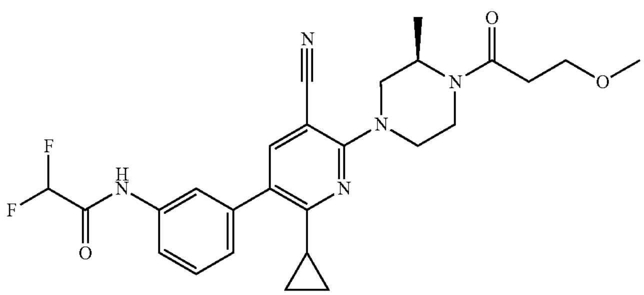 [SMILES: COCCC(=O)N1CCN(c2nc(C3CC3)c(-c3cccc(NC(=O)C(F)F)c3)cc2C#N)C[C@H]1C] |
| 433 | 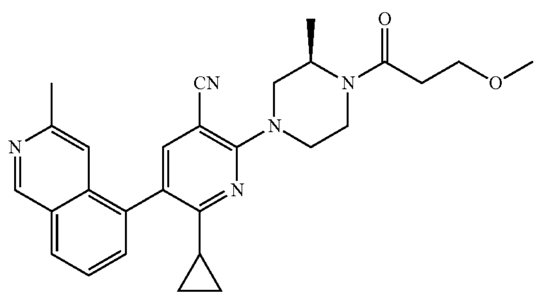 [SMILES: COCCC(=O)N1CCN(c2nc(C3CC3)c(-c3cccc4cnc(C)cc34)cc2C#N)C[C@H]1C] |
| 434 | 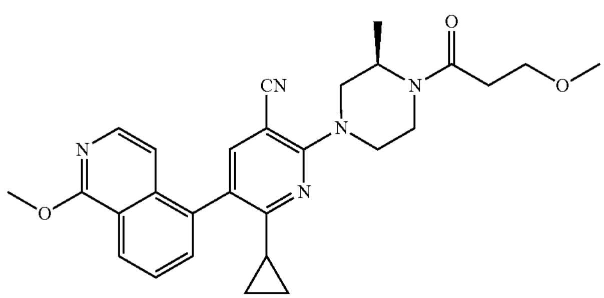 |

TABLE 5-continued
Exemplary Compounds of Formula I.
| Cpd # | Structure |
|---|---|
| 435 | 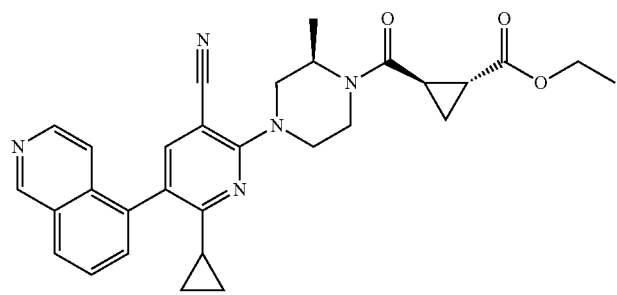 [SMILES: CCOC(=O)[C@@H]1C[C@H]1C(=O)N1CCN(c2nc(C3CC3)c(-c3cccc4cnccc34)cc2C#N)C[C@H]1C] |
| 436 | 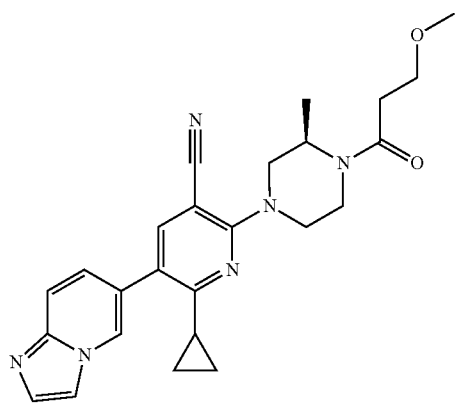 [SMILES: COCCC(=O)N1CCN(c2nc(C3CC3)c(-c3ccc4nccn4c3)cc2C#N)C[C@H]1C] |
| 437 | 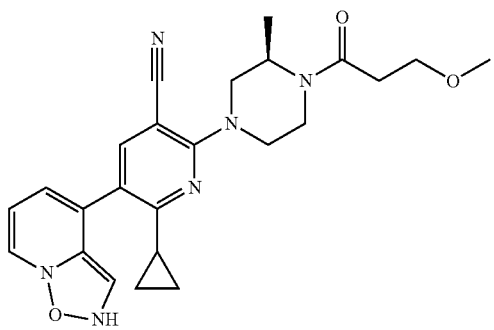 [SMILES: COCCC(=O)N1CCN(c2nc(C3CC3)c(C3=CC=CN4ONC=C34)cc2C#N)C[C@H]1C] |
| 438 | 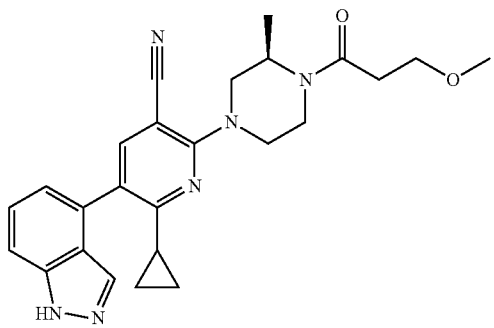 [SMILES: COCCC(=O)N1CCN(c2nc(C3CC3)c(-c3cccc4[nH]ncc34)cc2C#N)C[C@H]1C] |

TABLE 5-continued

Exemplary Compounds of Formula I.

| Cpd # | Structure |
|---|---|
| 439 | 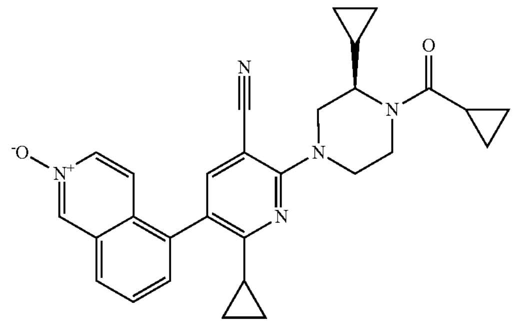 [SMILES: N#Cc1cc(-c2cccc3c[n+]([O-])ccc23)c(C2CC2)nc1N1CCN(C(=O)C2CC2)[C@H](C2CC2)C1] |
| 440 | 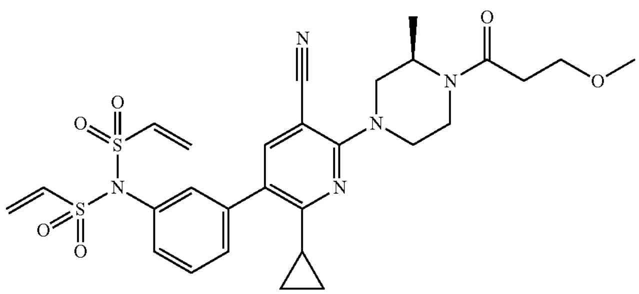 [SMILES: C=CS(=O)(=O)N(c1cccc(-c2cc(C#N)c(N3CCN(C(=O)CCOC)[C@H](C)C3)nc2C2CC2)c1)S(=O)(=O)C=C] |
| 441 | 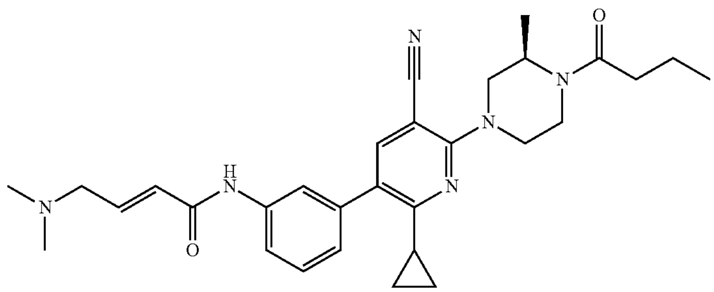 [SMILES: CCCC(=O)N1CCN(c2nc(C3CC3)c(-c3cccc(NC(=O)/C=C/CN(C)C)c3)cc2C#N)C[C@H]1C] |
| 442 | 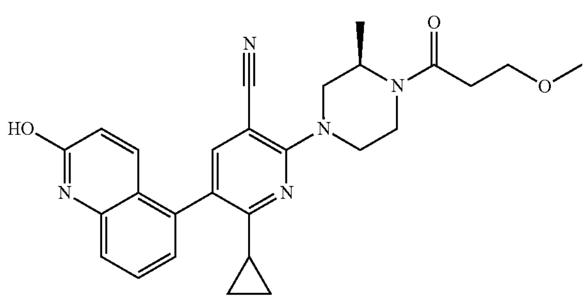 [SMILES: COCCC(=O)N1CCN(c2nc(C3CC3)c(-c3cccc4nc(O)ccc34)cc2C#N)C[C@H]1C] |
| 443 | 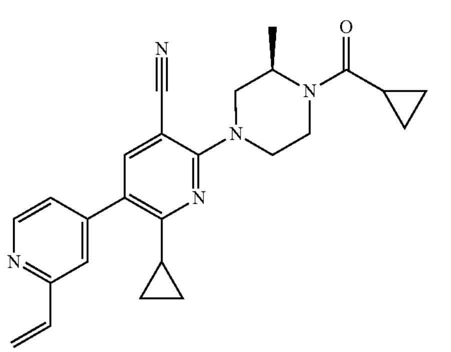 [SMILES: C=Cc1cc(-c2cc(C#N)c(N3CCN(C(=O)C4CC4)[C@H](C)C3)nc2C2CC2)ccn1] |

TABLE 5-continued
Exemplary Compounds of Formula I.
| Cpd # | Structure |
|---|---|
| 444 | 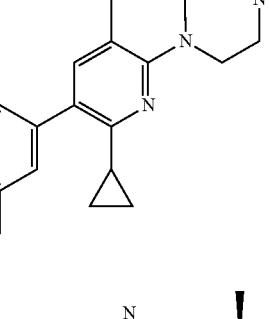 |
| 445 | 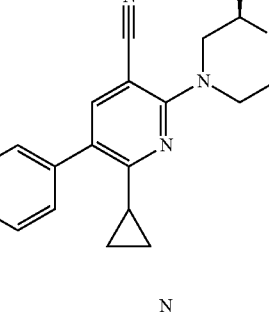 |
| 446 | 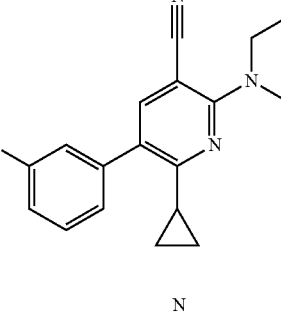 |
| 447 | 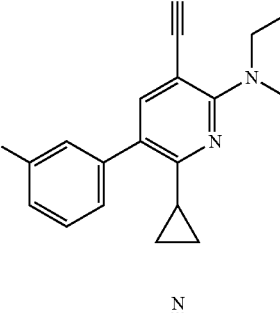 |
| 448 | 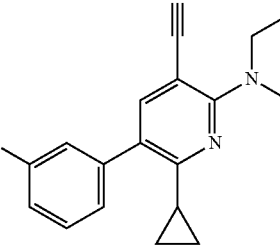 |

US 9,856,279 B2
143
TABLE 5-continued
144
Exemplary Compounds of Formula I.
| Cpd # | Structure |
|---|---|
| 449 | 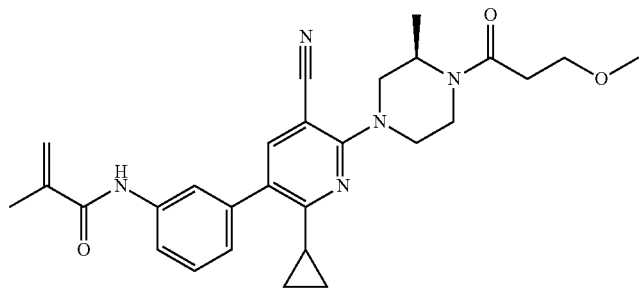 [SMILES: C=C(C)C(=O)Nc1cccc(-c2cc(C#N)c(N3CCN(C(=O)CCOC)[C@H](C)C3)nc2C2CC2)c1] |
| 450 | 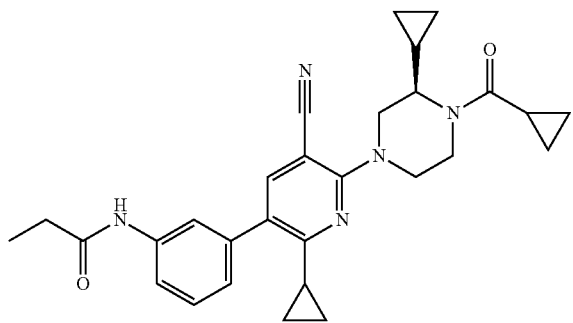 [SMILES: CCC(=O)Nc1cccc(-c2cc(C#N)c(N3CCN(C(=O)C4CC4)[C@H](C4CC4)C3)nc2C2CC2)c1] |
| 451 | 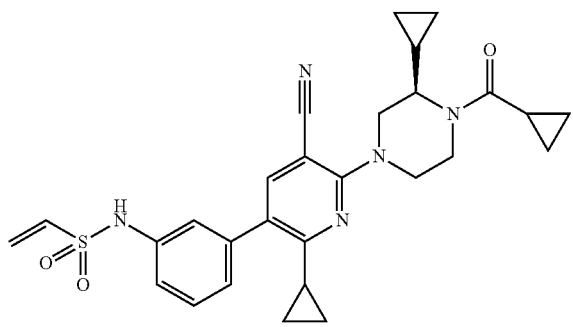 [SMILES: C=CS(=O)(=O)Nc1cccc(-c2cc(C#N)c(N3CCN(C(=O)C4CC4)[C@H](C4CC4)C3)nc2C2CC2)c1] |
| 452 | 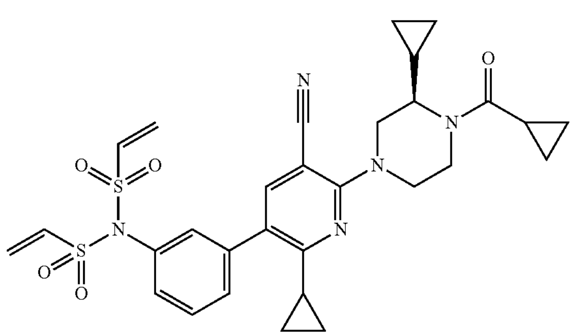 [SMILES: C=CS(=O)(=O)N(c1cccc(-c2cc(C#N)c(N3CCN(C(=O)C4CC4)[C@H](C4CC4)C3)nc2C2CC2)c1)S(=O)(=O)C=C] |

TABLE 5-continued

Exemplary Compounds of Formula I.

| Cpd # | Structure |
|---|---|
| 453 | 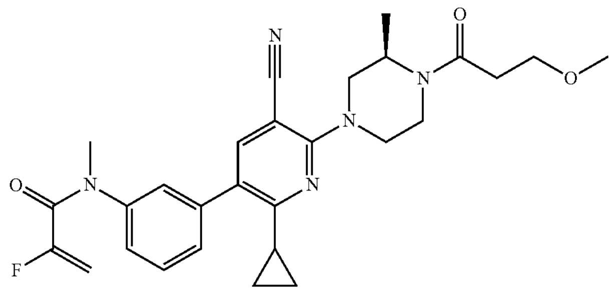 [SMILES: C=C(F)C(=O)N(C)c1cccc(-c2cc(C#N)c(N3CCN(C(=O)CCOC)[C@H](C)C3)nc2C2CC2)c1] |
| 454 | 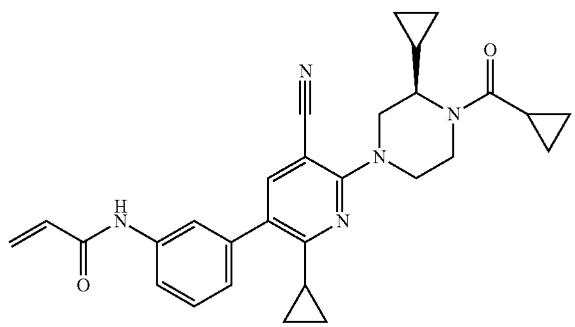 [SMILES: C=CC(=O)Nc1cccc(-c2cc(C#N)c(N3CCN(C(=O)C4CC4)[C@H](C4CC4)C3)nc2C2CC2)c1] |
| 455 | 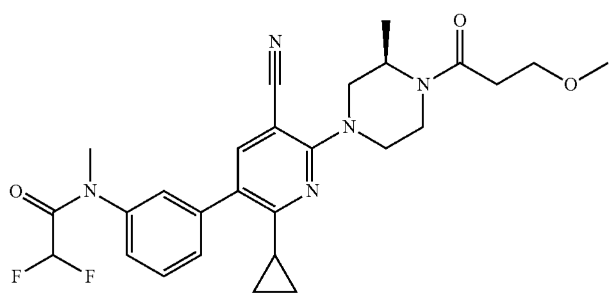 [SMILES: COCCC(=O)N1CCN(c2nc(C3CC3)c(-c3cccc(N(C)C(=O)C(F)F)c3)cc2C#N)C[C@H]1C] |
| 456 | 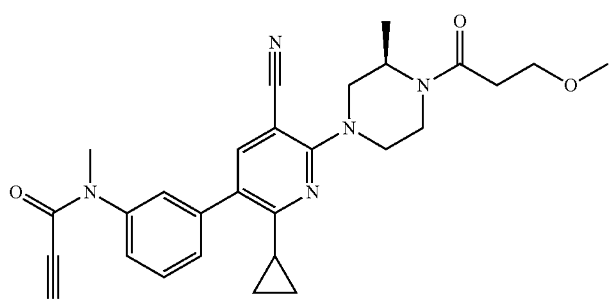 [SMILES: C#CC(=O)N(C)c1cccc(-c2cc(C#N)c(N3CCN(C(=O)CCOC)[C@H](C)C3)nc2C2CC2)c1] |
| 457 | 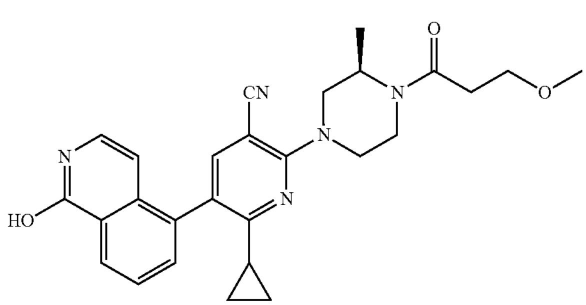 [SMILES: COCCC(=O)N1CCN(c2nc(C3CC3)c(-c3cccc4c(O)nccc34)cc2C#N)C[C@H]1C] |

TABLE 5-continued

Exemplary Compounds of Formula I.

| Cpd # | Structure |
|---|---|
| 458 | 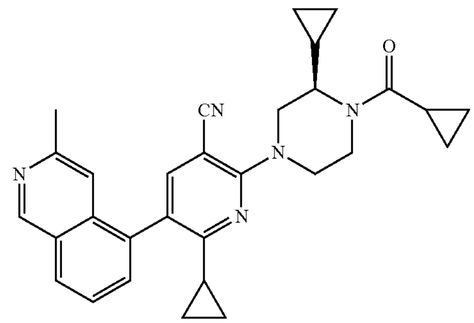 [SMILES: Cc1cc2c(-c3cc(C#N)c(N4CCN(C(=O)C5CC5)[C@H](C5CC5)C4)nc3C3CC3)cccc2cn1] |
| 459 | 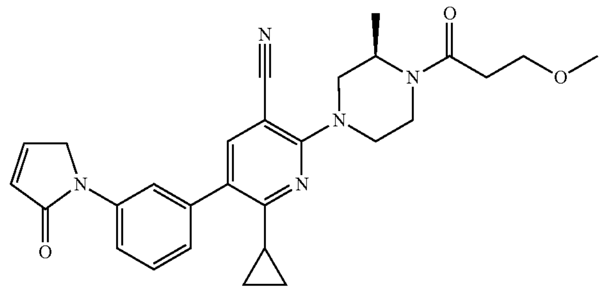 [SMILES: COCCC(=O)N1CCN(c2nc(C3CC3)c(-c3cccc(N4CC=CC4=O)c3)cc2C#N)C[C@H]1C] |
| 460 | 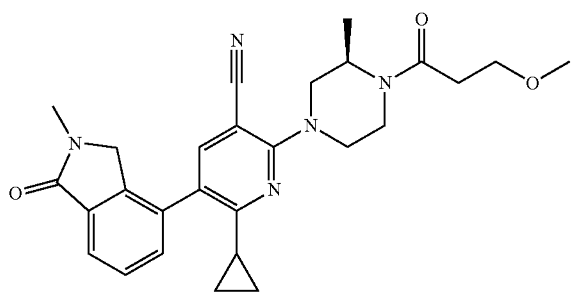 [SMILES: COCCC(=O)N1CCN(c2nc(C3CC3)c(-c3cccc4c3CN(C)C4=O)cc2C#N)C[C@H]1C] |
| 461 | 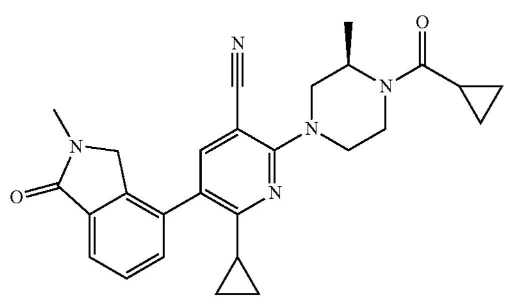 [SMILES: C[C@@H]1CN(c2nc(C3CC3)c(-c3cccc4c3CN(C)C4=O)cc2C#N)CCN1C(=O)C1CC1] |
| 462 | 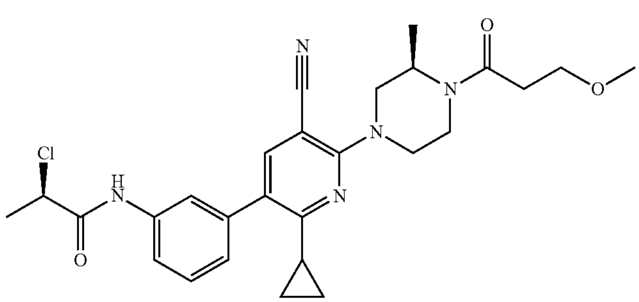 [SMILES: COCCC(=O)N1CCN(c2nc(C3CC3)c(-c3cccc(NC(=O)[C@@H](C)Cl)c3)cc2C#N)C[C@H]1C] |

TABLE 5-continued
Exemplary Compounds of Formula I.
| Cpd # | Structure |
|---|---|
| 463 | 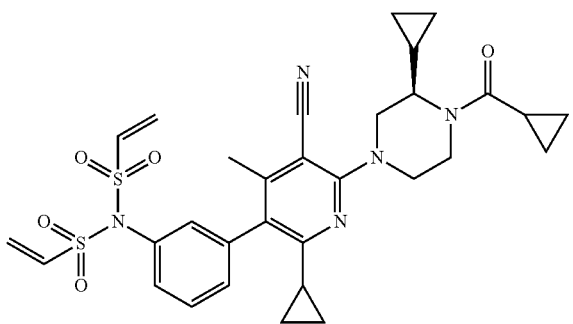 [SMILES: C=CS(=O)(=O)N(c1cccc(-c2c(C3CC3)nc(N3CCN(C(=O)C4CC4)[C@H](C4CC4)C3)c(C#N)c2C)c1)S(=O)(=O)C=C] |
| 464 | 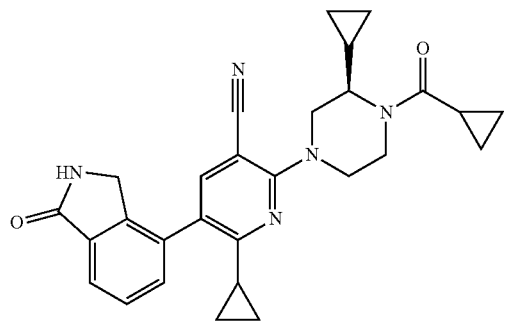 [SMILES: N#Cc1cc(-c2cccc3c2CNC3=O)c(C2CC2)nc1N1CCN(C(=O)C2CC2)[C@H](C2CC2)C1] |
| 465 | 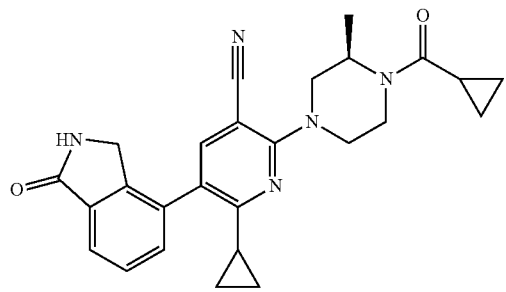 [SMILES: C[C@@H]1CN(c2nc(C3CC3)c(-c3cccc4c3CNC4=O)cc2C#N)CCN1C(=O)C1CC1] |
| 466 | 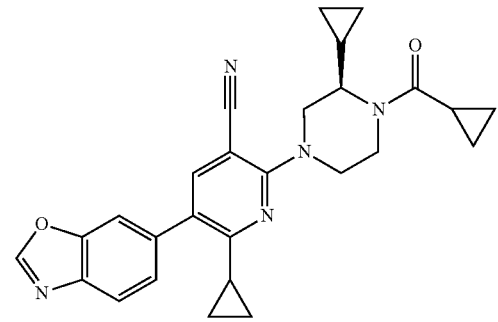 |

TABLE 5-continued
Exemplary Compounds of Formula I.
| Cpd # | Structure |
|---|---|
| 467 | 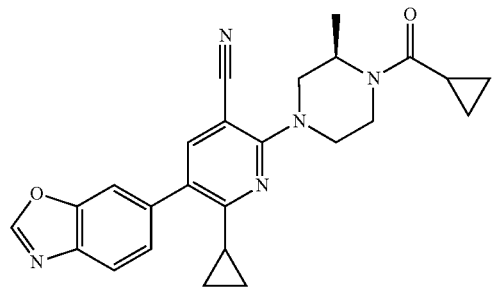 [SMILES: C[C@@H]1CN(c2nc(C3CC3)c(-c3ccc4ncoc4c3)cc2C#N)CCN1C(=O)C1CC1] |
| 470 | 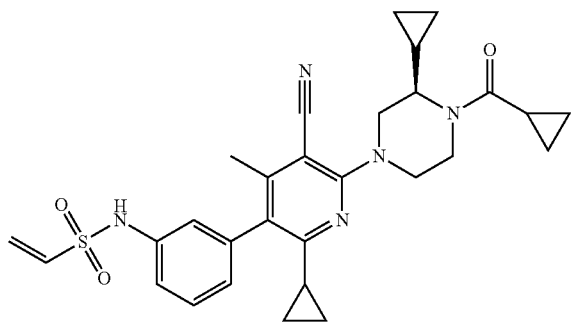 [SMILES: C=CS(=O)(=O)Nc1cccc(-c2c(C3CC3)nc(N3CCN(C(=O)C4CC4)[C@H](C4CC4)C3)c(C#N)c2C)c1] |
| 471 | 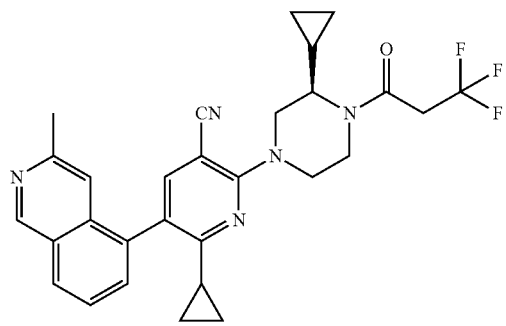 [SMILES: Cc1cc2c(-c3cc(C#N)c(N4CCN(C(=O)CC(F)(F)F)[C@H](C5CC5)C4)nc3C3CC3)cccc2cn1] |
| 472 | 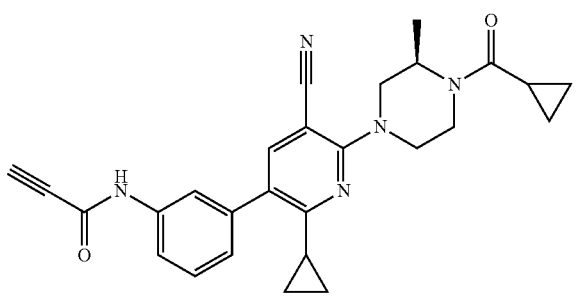 [SMILES: C#CC(=O)Nc1cccc(-c2cc(C#N)c(N3CCN(C(=O)C4CC4)[C@H](C)C3)nc2C2CC2)c1] |

TABLE 5-continued
Exemplary Compounds of Formula I.
| Cpd # | Structure |
|---|---|
| 473 | 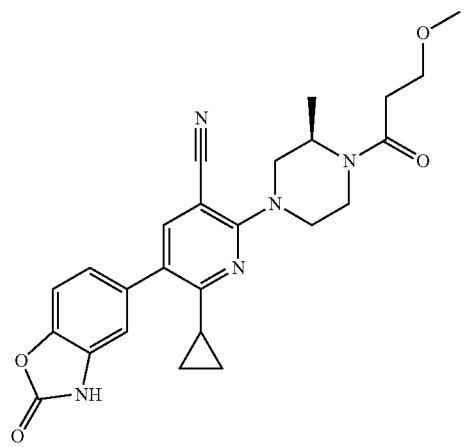 [SMILES: COCCC(=O)N1CCN(c2nc(C3CC3)c(-c3ccc4oc(=O)[nH]c4c3)cc2C#N)C[C@H]1C] |
| 474 | 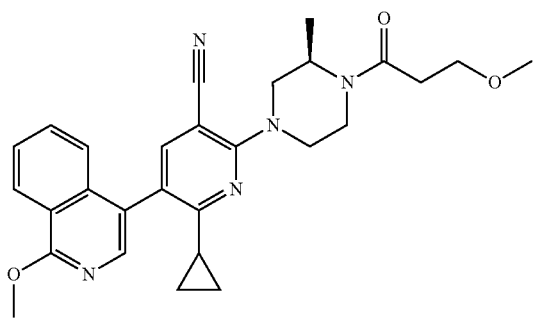 [SMILES: COCCC(=O)N1CCN(c2nc(C3CC3)c(-c3cnc(OC)c4ccccc34)cc2C#N)C[C@H]1C] |
| 475 | 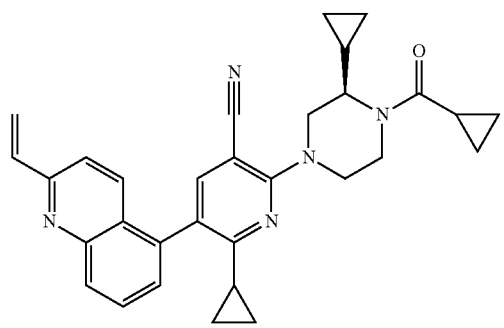 [SMILES: C=Cc1ccc2c(-c3cc(C#N)c(N4CCN(C(=O)C5CC5)[C@H](C5CC5)C4)nc3C3CC3)cccc2n1] |
| 476 | 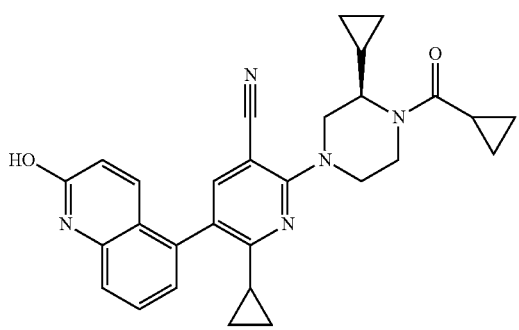 [SMILES: N#Cc1cc(-c2cccc3nc(O)ccc23)c(C2CC2)nc1N1CCN(C(=O)C2CC2)[C@H](C2CC2)C1] |

TABLE 5-continued
Exemplary Compounds of Formula I.
| Cpd # | Structure |
|---|---|
| 477 | 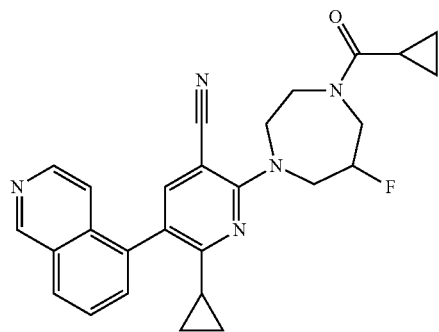 [SMILES: N#Cc1cc(-c2cccc3cnccc23)c(C2CC2)nc1N1CCN(C(=O)C2CC2)CC(F)C1] |
| 478 | 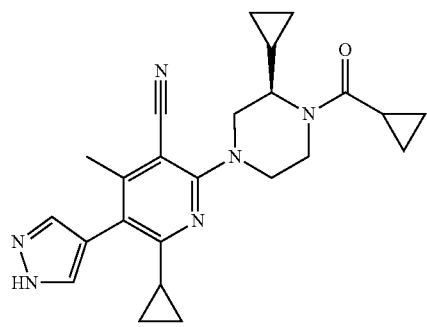 [SMILES: Cc1c(C#N)c(N2CCN(C(=O)C3CC3)[C@H](C3CC3)C2)nc(C2CC2)c1-c1cn[nH]c1] |
| 479 | 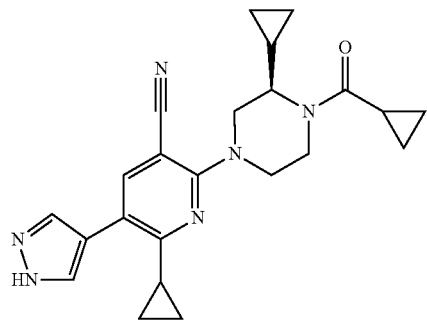 [SMILES: N#Cc1cc(-c2cn[nH]c2)c(C2CC2)nc1N1CCN(C(=O)C2CC2)[C@H](C2CC2)C1] |
| 480 | 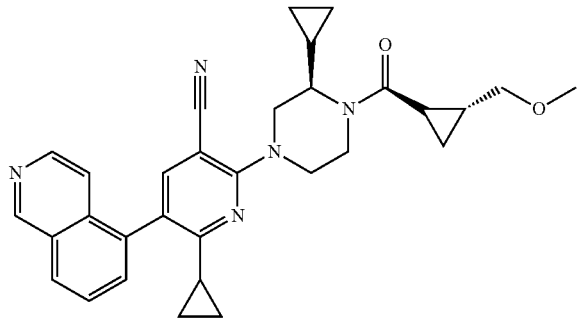 |

TABLE 5-continued
Exemplary Compounds of Formula I.
| Cpd # | Structure |
|---|---|
| 481 | 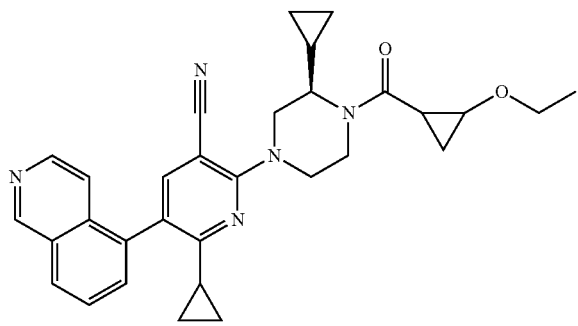 [SMILES: CCOC1CC1C(=O)N1CCN(c2nc(C3CC3)c(-c3cccc4cnccc34)cc2C#N)C[C@H]1C1CC1] |
| 482 | 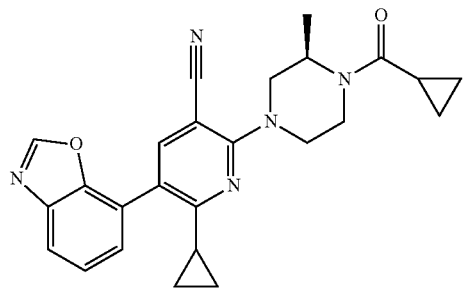 [SMILES: C[C@@H]1CN(c2nc(C3CC3)c(-c3cccc4ncoc34)cc2C#N)CCN1C(=O)C1CC1] |
| 483 | 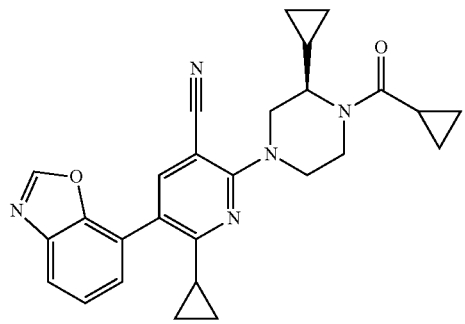 [SMILES: N#Cc1cc(-c2cccc3ncoc23)c(C2CC2)nc1N1CCN(C(=O)C2CC2)[C@H](C2CC2)C1] |
| 484 | 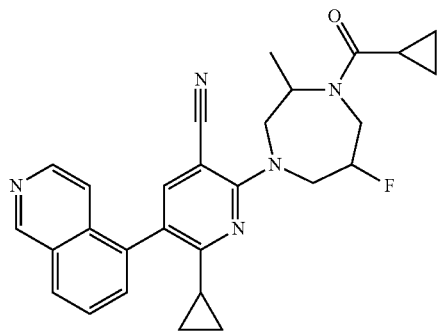 [SMILES: CC1CN(c2nc(C3CC3)c(-c3cccc4cnccc34)cc2C#N)CC(F)CN1C(=O)C1CC1] |

TABLE 5-continued

Exemplary Compounds of Formula I.

| Cpd # | Structure |
|---|---|
| 485 | 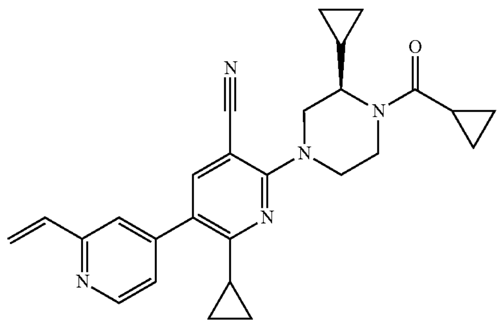 [SMILES: C=Cc1cc(-c2cc(C#N)c(N3CCN(C(=O)C4CC4)[C@H](C4CC4)C3)nc2C2CC2)ccn1] |
| 486 | 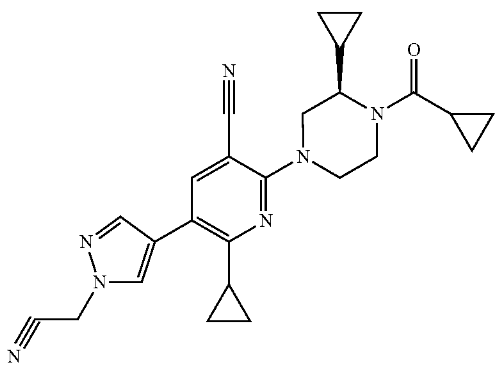 [SMILES: N#CCn1cc(-c2cc(C#N)c(N3CCN(C(=O)C4CC4)[C@H](C4CC4)C3)nc2C2CC2)cn1] |
| 487 | 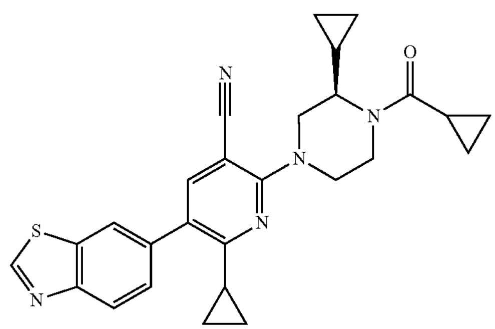 |
| 488 | 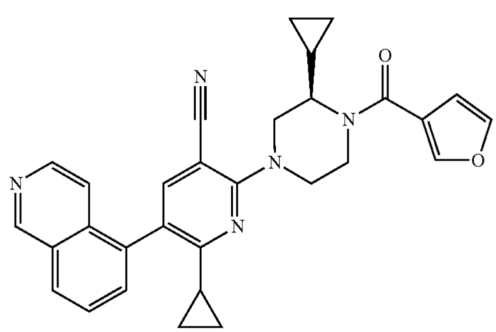 [SMILES: N#Cc1cc(-c2cccc3cnccc23)c(C2CC2)nc1N1CCN(C(=O)c2ccoc2)[C@H](C2CC2)C1] |

TABLE 5-continued

Exemplary Compounds of Formula I.

| Cpd # | Structure |
|---|---|
| 489 | 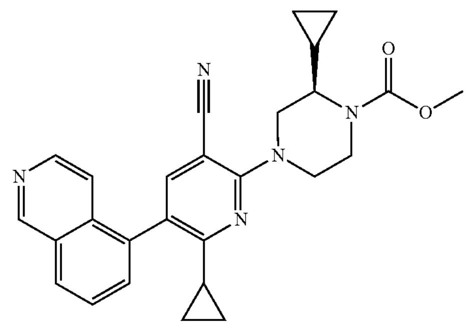 [SMILES: COC(=O)N1CCN(c2nc(C3CC3)c(-c3cccc4cnccc34)cc2C#N)C[C@H]1C1CC1] |
| 490 | 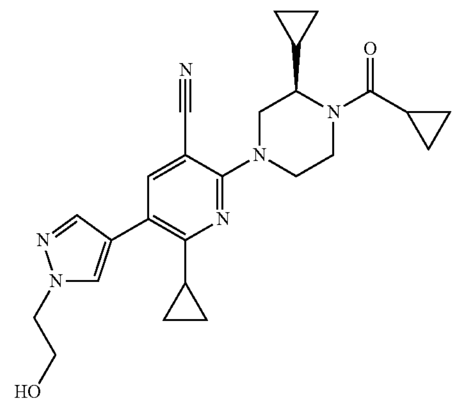 [SMILES: N#Cc1cc(-c2cnn(CCO)c2)c(C2CC2)nc1N1CCN(C(=O)C2CC2)[C@H](C2CC2)C1] |
| 493 | 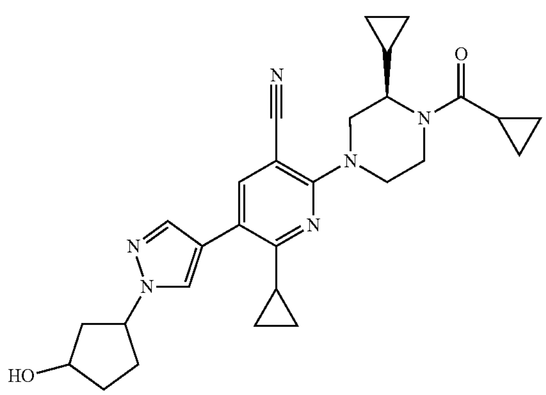 [SMILES: N#Cc1cc(-c2cnn(C3CCC(O)C3)c2)c(C2CC2)nc1N1CCN(C(=O)C2CC2)[C@H](C2CC2)C1] |
| 494 | 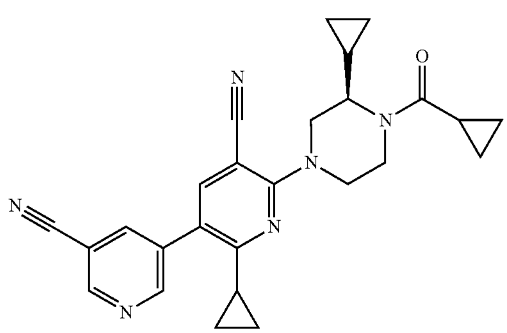 [SMILES: N#Cc1cncc(-c2cc(C#N)c(N3CCN(C(=O)C4CC4)[C@H](C4CC4)C3)nc2C2CC2)c1] |

TABLE 5-continued
Exemplary Compounds of Formula I.
| Cpd # | Structure |
|---|---|
| 495 | 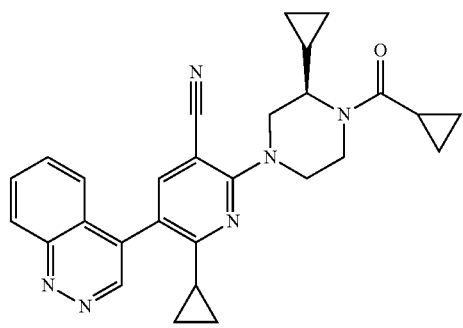 [SMILES: N#Cc1cc(-c2cnnc3ccccc23)c(C2CC2)nc1N1CCN(C(=O)C2CC2)[C@H](C2CC2)C1] |
| 496 | 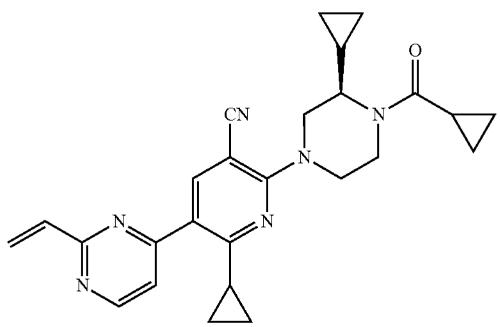 [SMILES: C=Cc1nccc(-c2cc(C#N)c(N3CCN(C(=O)C4CC4)[C@H](C4CC4)C3)nc2C2CC2)n1] |
| 497 | 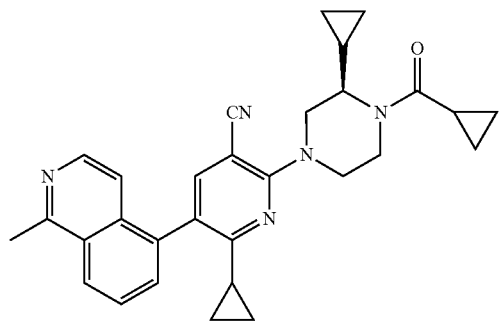 [SMILES: Cc1nccc2c(-c3cc(C#N)c(N4CCN(C(=O)C5CC5)[C@H](C5CC5)C4)nc3C3CC3)cccc12] |
| 498 | 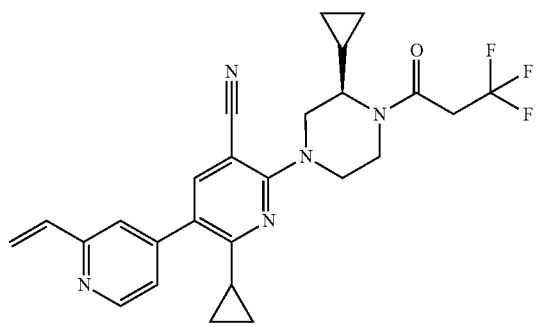 [SMILES: C=Cc1cc(-c2cc(C#N)c(N3CCN(C(=O)CC(F)(F)F)[C@H](C4CC4)C3)nc2C2CC2)ccn1] |

TABLE 5-continued
Exemplary Compounds of Formula I.
| Cpd # | Structure |
|---|---|
| 499 | 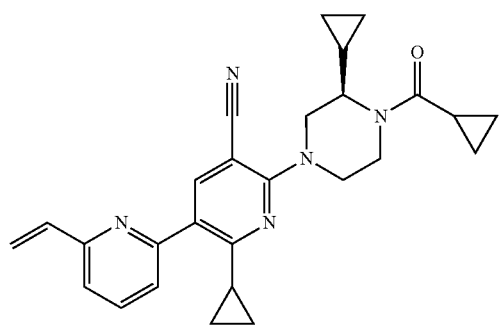 [SMILES: C=Cc1cccc(-c2cc(C#N)c(N3CCN(C(=O)C4CC4)[C@H](C4CC4)C3)nc2C2CC2)n1] |
| 500 | 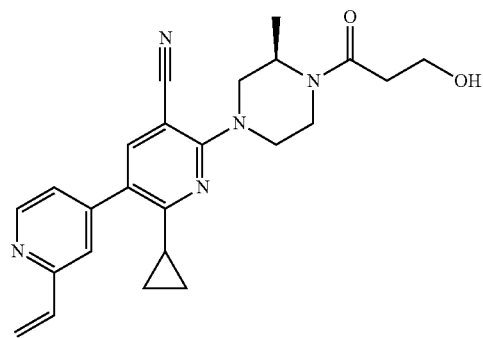 [SMILES: C=Cc1cc(-c2cc(C#N)c(N3CCN(C(=O)CCO)[C@H](C)C3)nc2C2CC2)ccn1] |
| 501 | 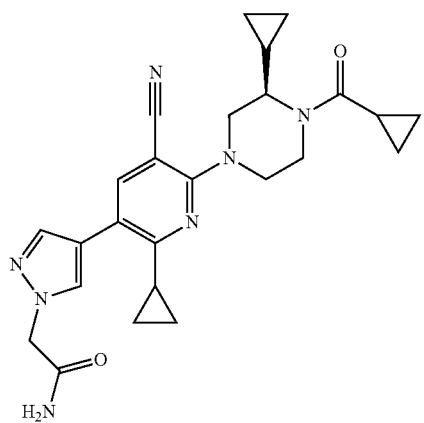 [SMILES: N#Cc1cc(-c2cnn(CC(N)=O)c2)c(C2CC2)nc1N1CCN(C(=O)C2CC2)[C@H](C2CC2)C1] |
| 502 | 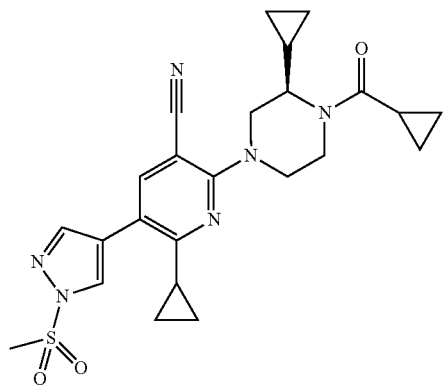 [SMILES: CS(=O)(=O)n1cc(-c2cc(C#N)c(N3CCN(C(=O)C4CC4)[C@H](C4CC4)C3)nc2C2CC2)cn1] |

TABLE 5-continued
Exemplary Compounds of Formula I.
| Cpd # | Structure |
|---|---|
| 503 | 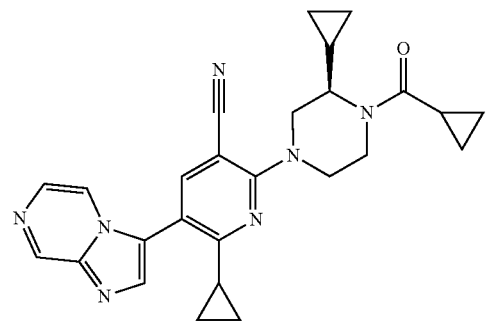 [SMILES: N#Cc1cc(-c2cnc3cnccn23)c(C2CC2)nc1N1CCN(C(=O)C2CC2)[C@H](C2CC2)C1] |
| 504 | 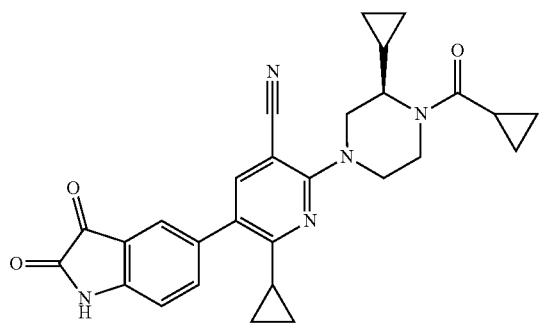 [SMILES: N#Cc1cc(-c2ccc3c(c2)C(=O)C(=O)N3)c(C2CC2)nc1N1CCN(C(=O)C2CC2)[C@H](C2CC2)C1] |
| 505 | 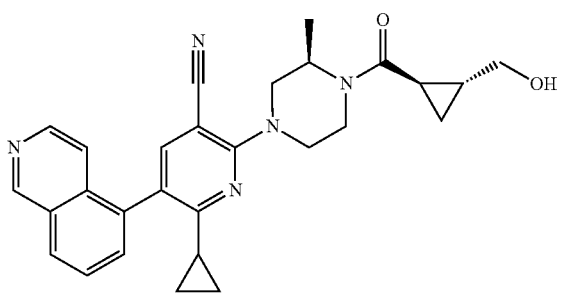 [SMILES: C[C@@H]1CN(c2nc(C3CC3)c(-c3cccc4cnccc34)cc2C#N)CCN1C(=O)[C@@H]1C[C@H]1CO] |
| 506 | 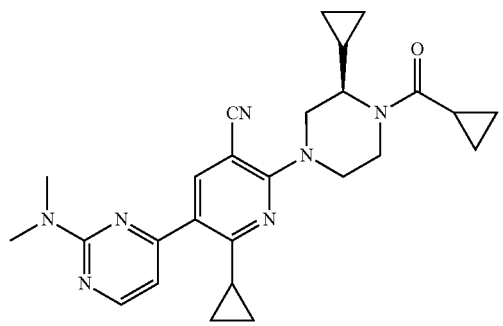 [SMILES: CN(C)c1nccc(-c2cc(C#N)c(N3CCN(C(=O)C4CC4)[C@H](C4CC4)C3)nc2C2CC2)n1] |

TABLE 5-continued

Exemplary Compounds of Formula I.

| Cpd # | Structure |
|---|---|
| 507 | 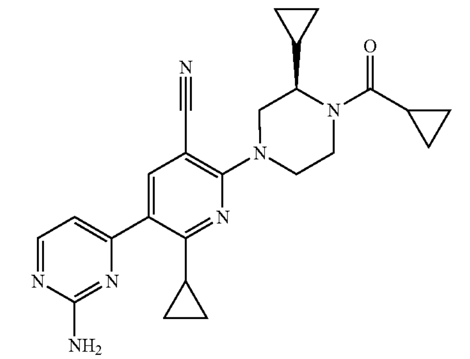 [SMILES: N#Cc1cc(-c2ccnc(N)n2)c(C2CC2)nc1N1CCN(C(=O)C2CC2)[C@H](C2CC2)C1] |
| 508 | 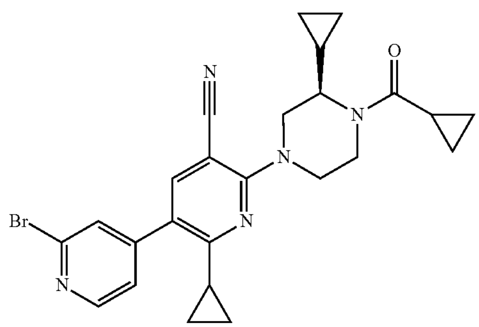 |
| 509 | 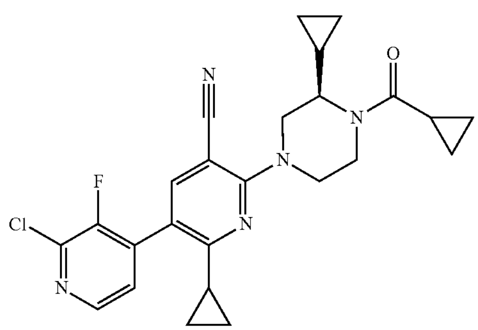 [SMILES: N#Cc1cc(-c2ccnc(Cl)c2F)c(C2CC2)nc1N1CCN(C(=O)C2CC2)[C@H](C2CC2)C1] |
| 510 | 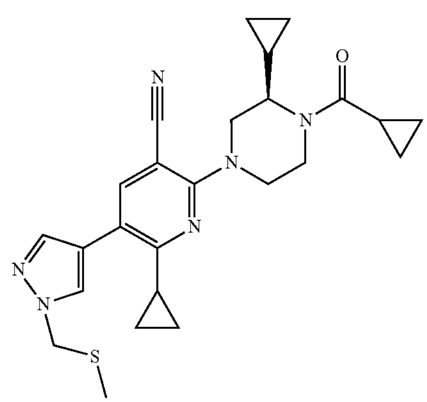 [SMILES: CSCn1cc(-c2cc(C#N)c(N3CCN(C(=O)C4CC4)[C@H](C4CC4)C3)nc2C2CC2)cn1] |

TABLE 5-continued
Exemplary Compounds of Formula I.
| Cpd # | Structure |
|---|---|
| 511 | 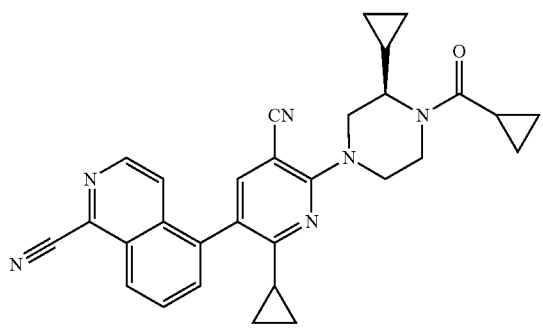 [SMILES: N#Cc1cc(-c2cccc3c(C#N)nccc23)c(C2CC2)nc1N1CCN(C(=O)C2CC2)[C@H](C2CC2)C1] |
| 512 | 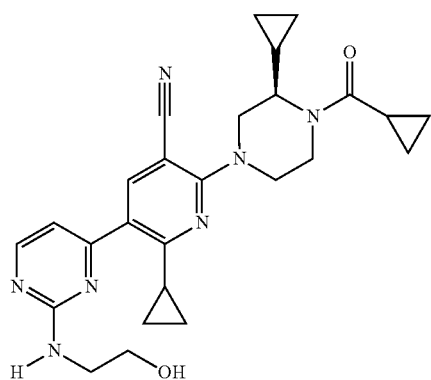 [SMILES: N#Cc1cc(-c2ccnc(NCCO)n2)c(C2CC2)nc1N1CCN(C(=O)C2CC2)[C@H](C2CC2)C1] |
| 513 | 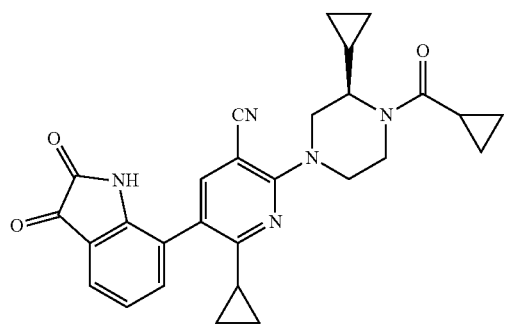 [SMILES: N#Cc1cc(-c2cccc3c2NC(=O)C3=O)c(C2CC2)nc1N1CCN(C(=O)C2CC2)[C@H](C2CC2)C1] |
| 514 | 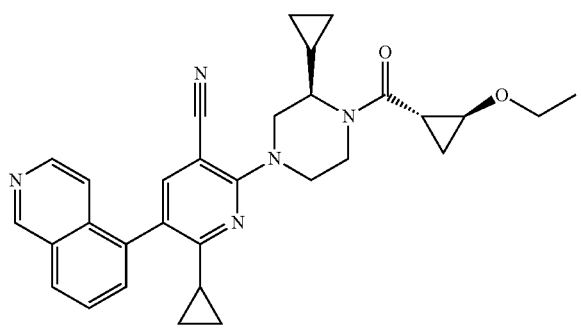 [SMILES: CCO[C@H]1C[C@@H]1C(=O)N1CCN(c2nc(C3CC3)c(-c3cccc4cnccc34)cc2C#N)C[C@H]1C1CC1] |

TABLE 5-continued
Exemplary Compounds of Formula I.
| Cpd # | Structure |
|---|---|
| 515 | 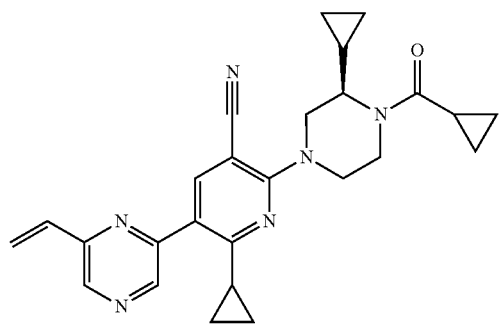 [SMILES: C=Cc1cncc(-c2cc(C#N)c(N3CCN(C(=O)C4CC4)[C@H](C4CC4)C3)nc2C2CC2)n1] |
| 516 | 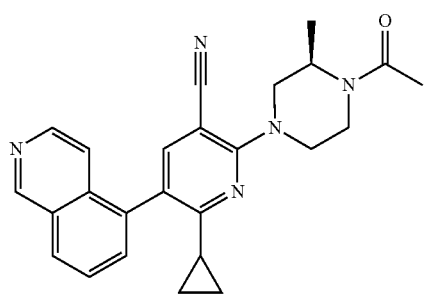 [SMILES: CC(=O)N1CCN(c2nc(C3CC3)c(-c3cccc4cnccc34)cc2C#N)C[C@H]1C] |
| 517 | 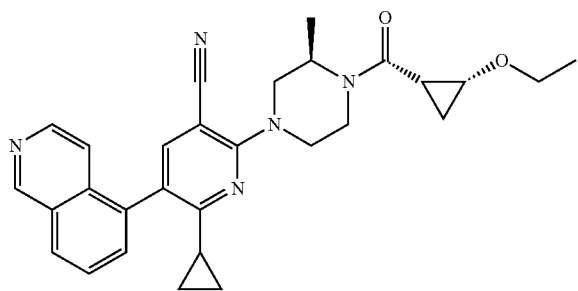 |
| 518 | 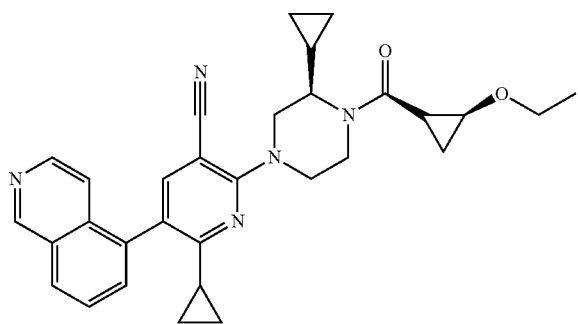 |

TABLE 5-continued
Exemplary Compounds of Formula I.
| Cpd # | Structure |
|---|---|
| 519 | 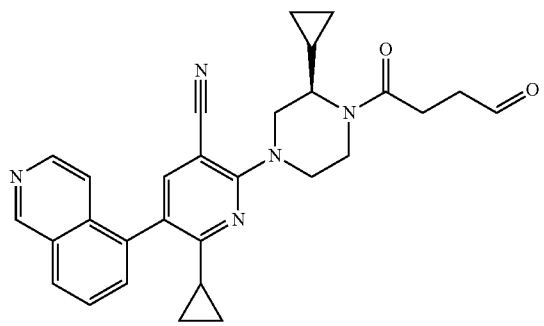 [SMILES: N#Cc1cc(-c2cccc3cnccc23)c(C2CC2)nc1N1CCN(C(=O)CCC=O)[C@H](C2CC2)C1] |
| 520 | 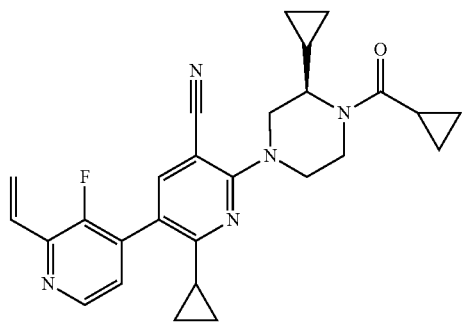 [SMILES: C=Cc1nccc(-c2cc(C#N)c(N3CCN(C(=O)C4CC4)[C@H](C4CC4)C3)nc2C2CC2)c1F] |
| 521 | 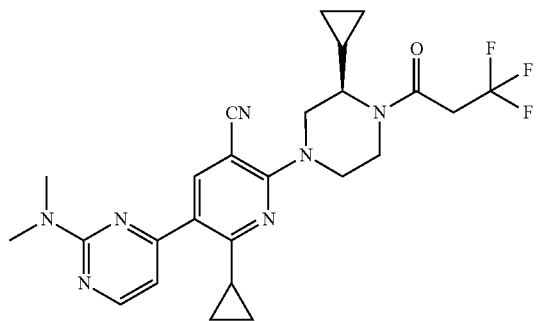 [SMILES: CN(C)c1nccc(-c2cc(C#N)c(N3CCN(C(=O)CC(F)(F)F)[C@H](C4CC4)C3)nc2C2CC2)n1] |
| 522 | 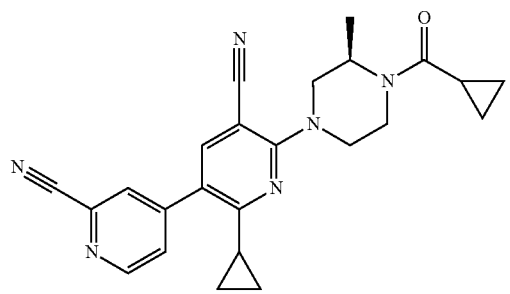 [SMILES: C[C@@H]1CN(c2nc(C3CC3)c(-c3ccnc(C#N)c3)cc2C#N)CCN1C(=O)C1CC1] |

TABLE 5-continued
Exemplary Compounds of Formula I.
| Cpd # | Structure |
|---|---|
| 523 | 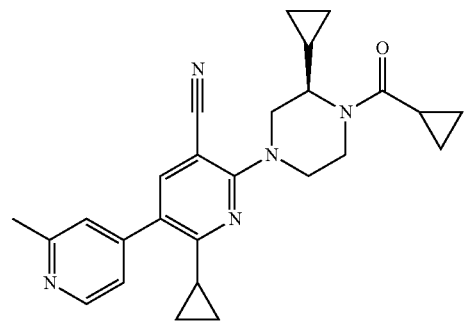 [SMILES: Cc1cc(-c2cc(C#N)c(N3CCN(C(=O)C4CC4)[C@H](C4CC4)C3)nc2C2CC2)ccn1] |
| 524 | 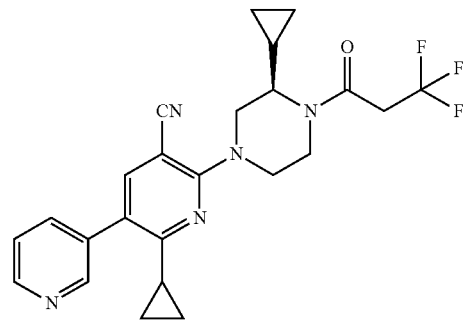 [SMILES: N#Cc1cc(-c2cccnc2)c(C2CC2)nc1N1CCN(C(=O)CC(F)(F)F)[C@H](C2CC2)C1] |
| 525 | 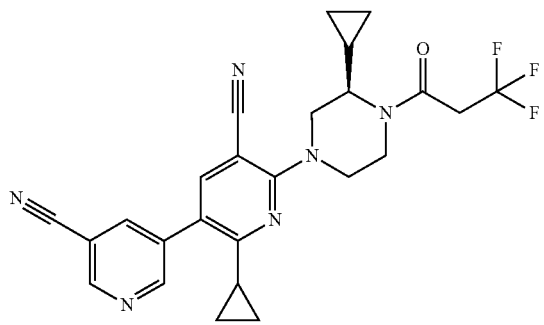 [SMILES: N#Cc1cncc(-c2cc(C#N)c(N3CCN(C(=O)CC(F)(F)F)[C@H](C4CC4)C3)nc2C2CC2)c1] |
| 526 | 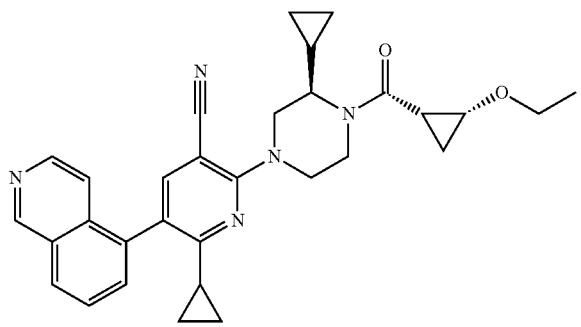 |

TABLE 5-continued
Exemplary Compounds of Formula I.
| Cpd # | Structure |
|---|---|
| 527 | 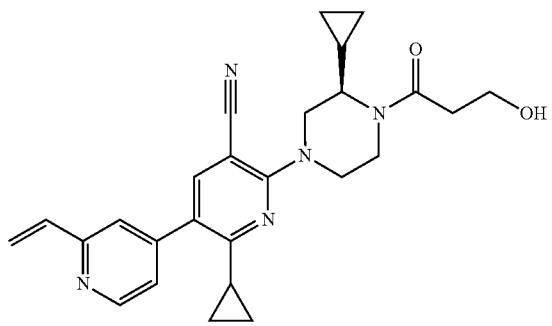 [SMILES: C=Cc1cc(-c2cc(C#N)c(N3CCN(C(=O)CCO)[C@H](C4CC4)C3)nc2C2CC2)ccn1] |
| 528 | 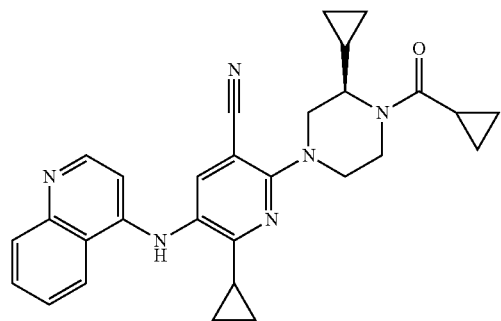 [SMILES: N#Cc1cc(Nc2ccnc3ccccc23)c(C2CC2)nc1N1CCN(C(=O)C2CC2)[C@H](C2CC2)C1] |
| 529 | 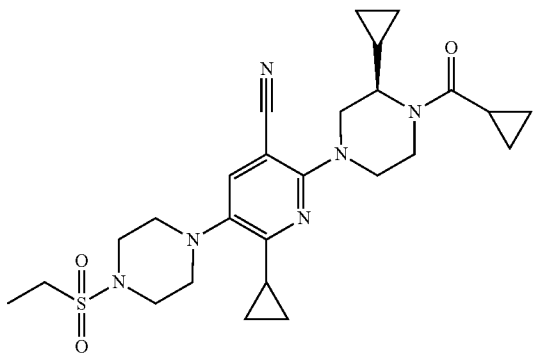 [SMILES: CCS(=O)(=O)N1CCN(c2cc(C#N)c(N3CCN(C(=O)C4CC4)[C@H](C4CC4)C3)nc2C2CC2)CC1] |
| 530 | 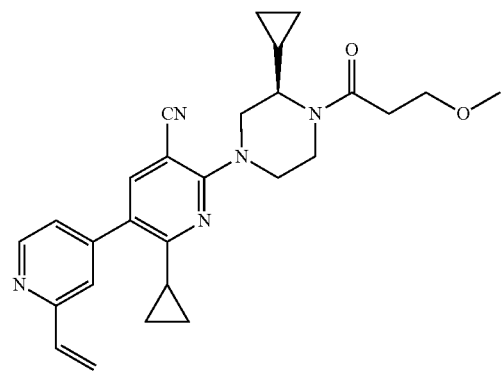 [SMILES: C=Cc1cc(-c2cc(C#N)c(N3CCN(C(=O)CCOC)[C@H](C4CC4)C3)nc2C2CC2)ccn1] |

TABLE 5-continued
Exemplary Compounds of Formula I.
| Cpd # | Structure |
|---|---|
| 531 | 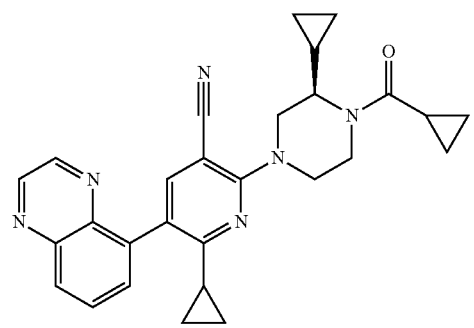 [SMILES: N#Cc1cc(-c2cccc3nccnc23)c(C2CC2)nc1N1CCN(C(=O)C2CC2)[C@H](C2CC2)C1] |
| 532 | 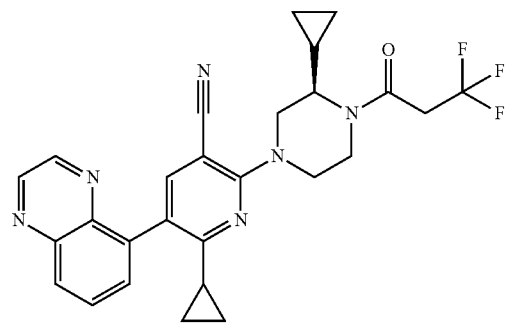 [SMILES: N#Cc1cc(-c2cccc3nccnc23)c(C2CC2)nc1N1CCN(C(=O)CC(F)(F)F)[C@H](C2CC2)C1] |
| 533 | 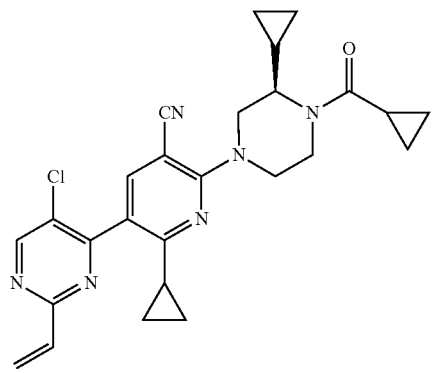 [SMILES: C=Cc1ncc(Cl)c(-c2cc(C#N)c(N3CCN(C(=O)C4CC4)[C@H](C4CC4)C3)nc2C2CC2)n1] |
| 534 | 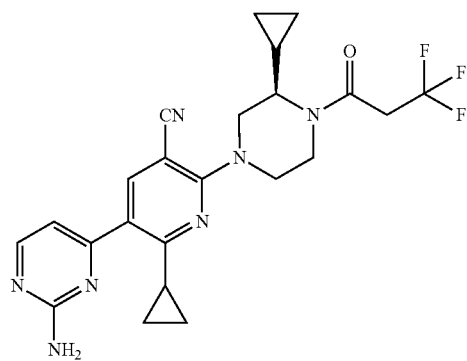 [SMILES: N#Cc1cc(-c2ccnc(N)n2)c(C2CC2)nc1N1CCN(C(=O)CC(F)(F)F)[C@H](C2CC2)C1] |

TABLE 5-continued
Exemplary Compounds of Formula I.
| Cpd # | Structure |
|---|---|
| 535 | 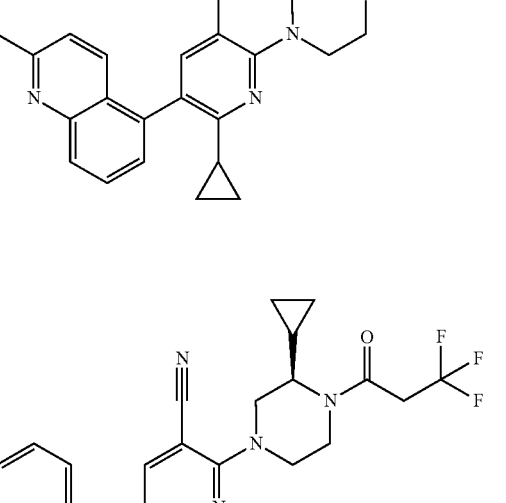 |
| 536 | 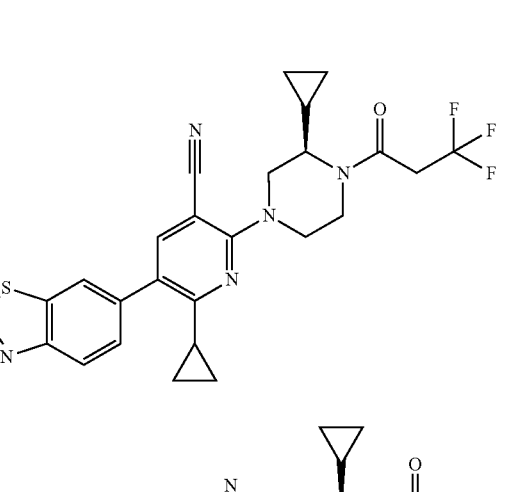 |
| 537 | 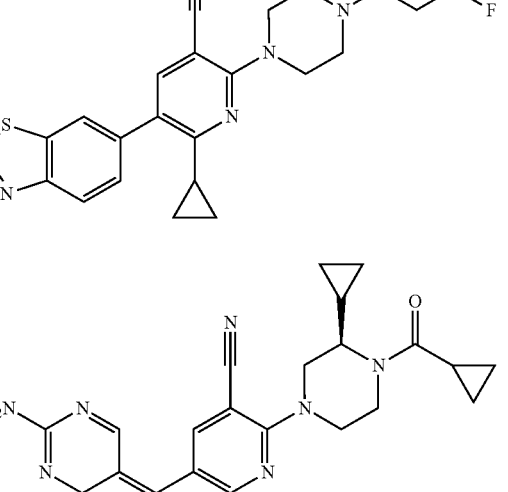 |
| 538 | 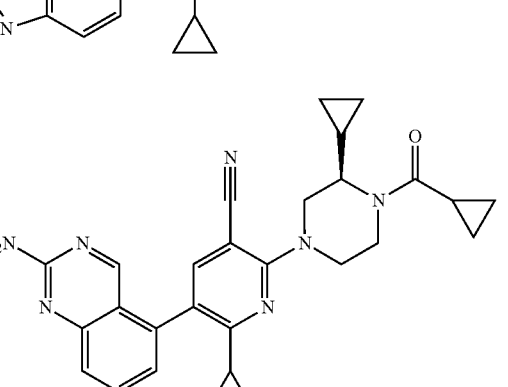 |

US 9,856,279 B2
185 186
TABLE 5-continued
Exemplary Compounds of Formula I.
| Cpd # | Structure |
|---|---|
| 539 | 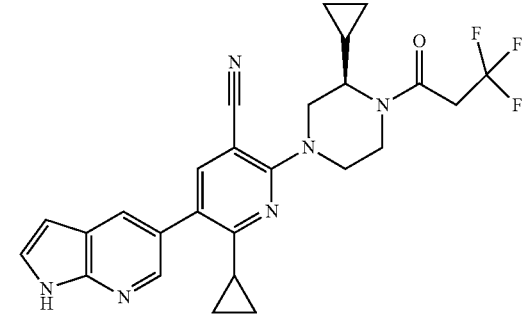 [SMILES: N#Cc1cc(-c2cnc3[nH]ccc3c2)c(C2CC2)nc1N1CCN(C(=O)CC(F)(F)F)[C@H](C2CC2)C1] |
| 540 | 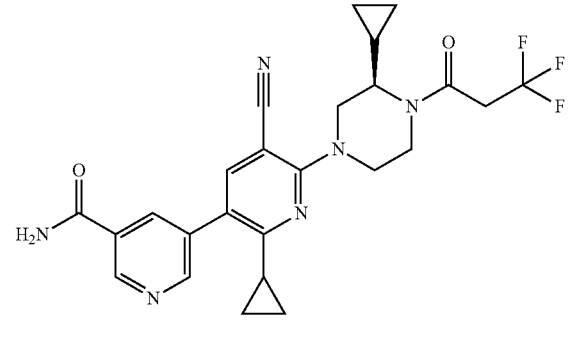 [SMILES: N#Cc1cc(-c2cncc(C(N)=O)c2)c(C2CC2)nc1N1CCN(C(=O)CC(F)(F)F)[C@H](C2CC2)C1] |
| 541 | 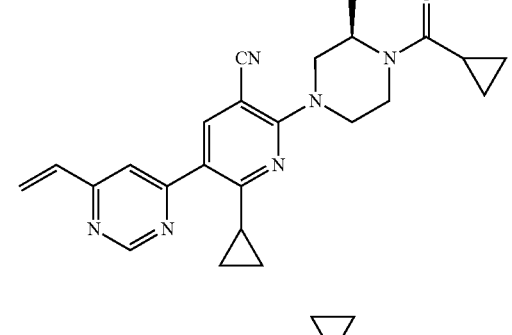 |
| 542 | 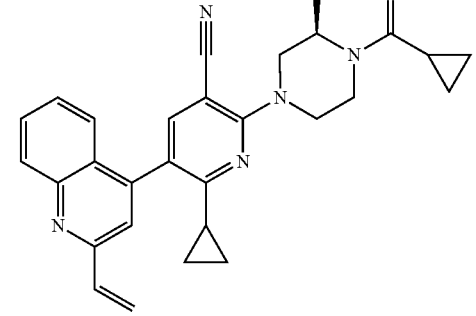 |

TABLE 5-continued
Exemplary Compounds of Formula I.
| Cpd # | Structure |
|---|---|
| 543 | 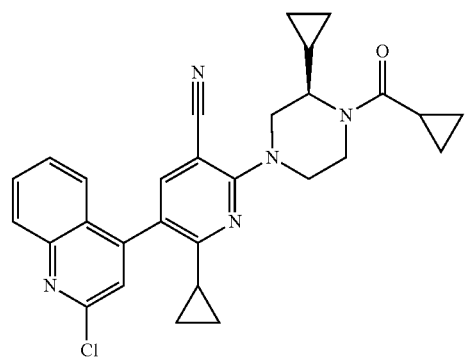 [SMILES: N#Cc1cc(-c2cc(Cl)nc3ccccc23)c(C2CC2)nc1N1CCN(C(=O)C2CC2)[C@H](C2CC2)C1] |
| 544 | 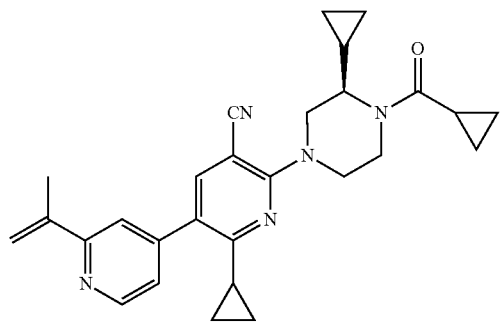 [SMILES: C=C(C)c1cc(-c2cc(C#N)c(N3CCN(C(=O)C4CC4)[C@H](C4CC4)C3)nc2C2CC2)ccn1] |
| 546 | 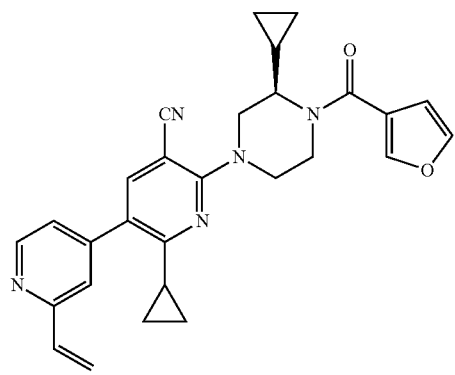 [SMILES: C=Cc1cc(-c2cc(C#N)c(N3CCN(C(=O)c4ccoc4)[C@H](C4CC4)C3)nc2C2CC2)ccn1] |
| 547 | 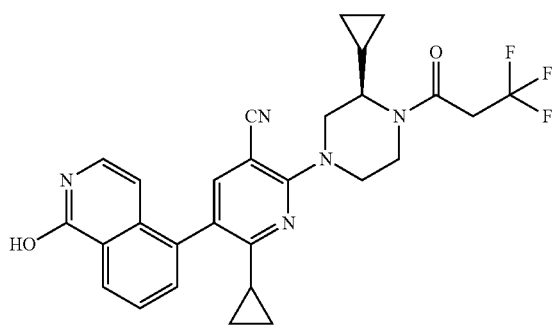 [SMILES: N#Cc1cc(-c2cccc3c(O)nccc23)c(C2CC2)nc1N1CCN(C(=O)CC(F)(F)F)[C@H](C2CC2)C1] |

TABLE 5-continued

Exemplary Compounds of Formula I.

| Cpd # | Structure |
|---|---|
| 548 | 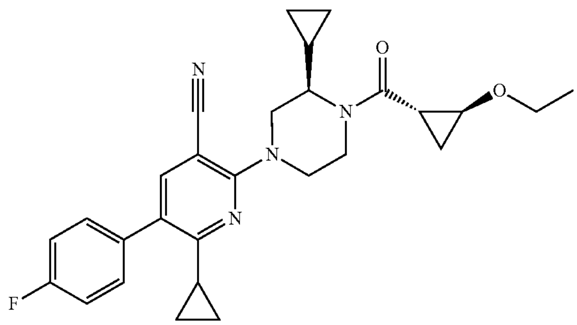 [SMILES: CCO[C@H]1C[C@@H]1C(=O)N1CCN(c2nc(C3CC3)c(-c3ccc(F)cc3)cc2C#N)C[C@H]1C1CC1] |
| 549 | 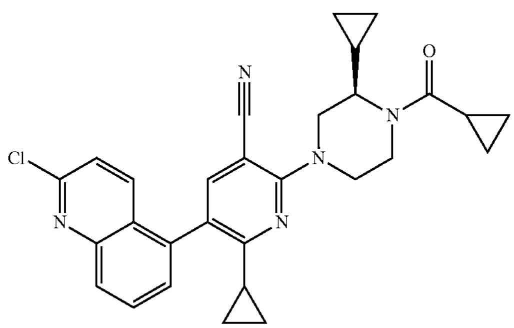 [SMILES: N#Cc1cc(-c2cccc3nc(Cl)ccc23)c(C2CC2)nc1N1CCN(C(=O)C2CC2)[C@H](C2CC2)C1] |
| 550 | 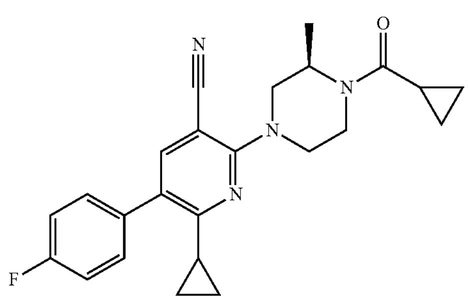 [SMILES: C[C@@H]1CN(c2nc(C3CC3)c(-c3ccc(F)cc3)cc2C#N)CCN1C(=O)C1CC1] |
| 551 | 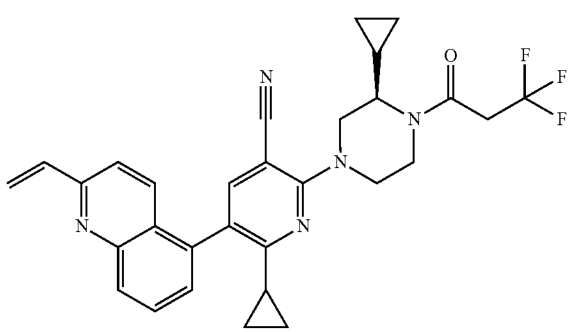 [SMILES: C=Cc1ccc2c(-c3cc(C#N)c(N4CCN(C(=O)CC(F)(F)F)[C@H](C5CC5)C4)nc3C3CC3)cccc2n1] |

TABLE 5-continued
Exemplary Compounds of Formula I.
| Cpd # | Structure |
|---|---|
| 552 | 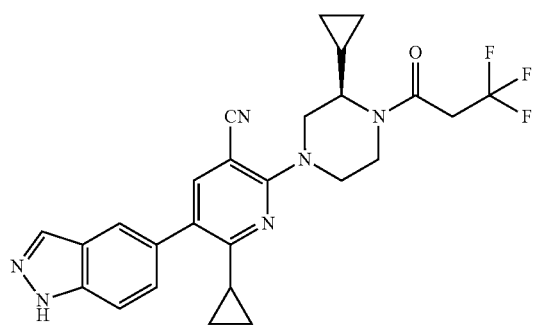 [SMILES: N#Cc1cc(-c2ccc3[nH]ncc3c2)c(C2CC2)nc1N1CCN(C(=O)CC(F)(F)F)[C@H](C2CC2)C1] |
| 553 | 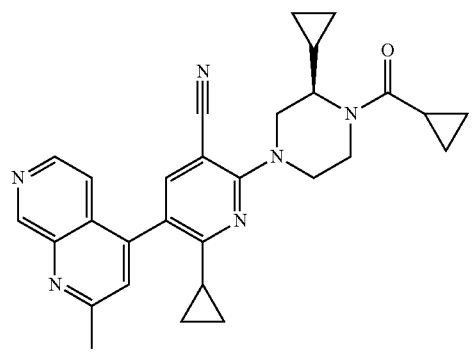 [SMILES: Cc1cc(-c2cc(C#N)c(N3CCN(C(=O)C4CC4)[C@H](C4CC4)C3)nc2C2CC2)c2ccncc2n1] |
| 554 | 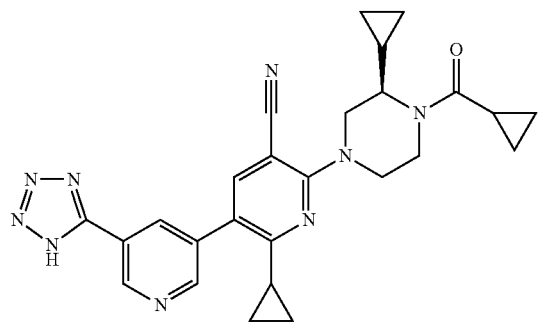 [SMILES: N#Cc1cc(-c2cncc(-c3nnn[nH]3)c2)c(C2CC2)nc1N1CCN(C(=O)C2CC2)[C@H](C2CC2)C1] |
| 555 | 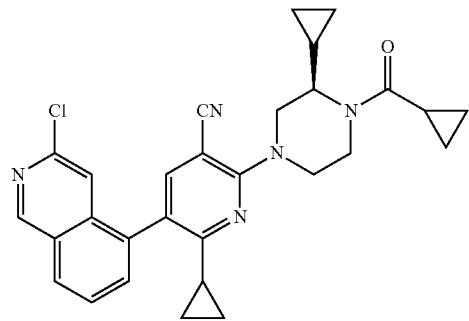 [SMILES: N#Cc1cc(-c2cccc3cnc(Cl)cc23)c(C2CC2)nc1N1CCN(C(=O)C2CC2)[C@H](C2CC2)C1] |

TABLE 5-continued
Exemplary Compounds of Formula I.
| Cpd # | Structure |
|---|---|
| 556 | 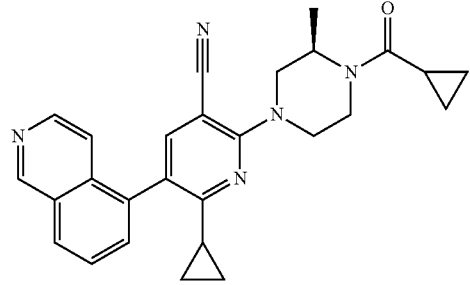 [SMILES: C[C@@H]1CN(c2nc(C3CC3)c(-c3cccc4cnccc34)cc2C#N)CCN1C(=O)C1CC1] |
| 557 | 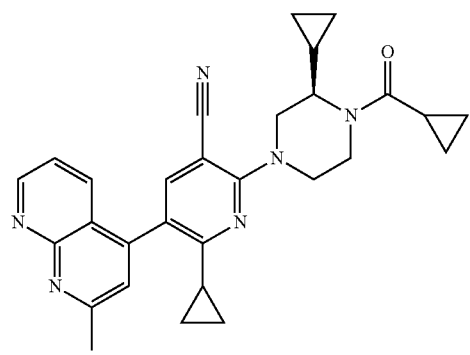 [SMILES: Cc1cc(-c2cc(C#N)c(N3CCN(C(=O)C4CC4)[C@H](C4CC4)C3)nc2C2CC2)c2cccnc2n1] |
| 558 | 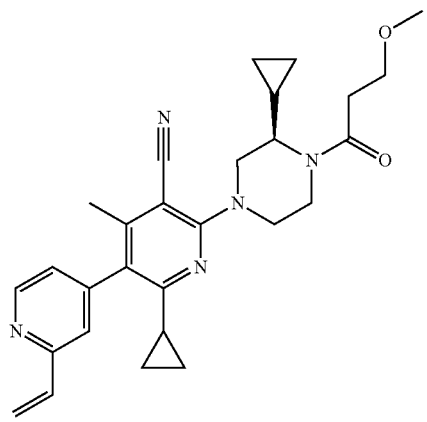 [SMILES: C=Cc1cc(-c2c(C3CC3)nc(N3CCN(C(=O)CCOC)[C@H](C4CC4)C3)c(C#N)c2C)ccn1] |
| 559 | 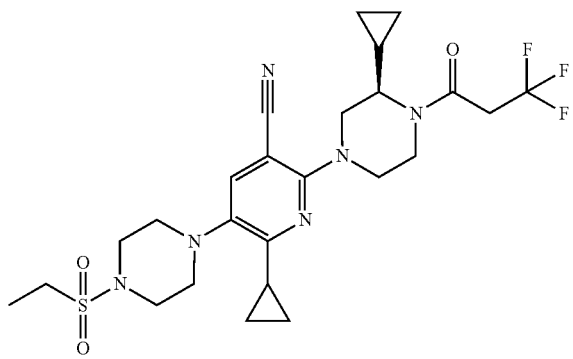 [SMILES: CCS(=O)(=O)N1CCN(c2cc(C#N)c(N3CCN(C(=O)CC(F)(F)F)[C@H](C4CC4)C3)nc2C2CC2)CC1] |

TABLE 5-continued
Exemplary Compounds of Formula I.
| Cpd # | Structure |
|---|---|
| 560 | 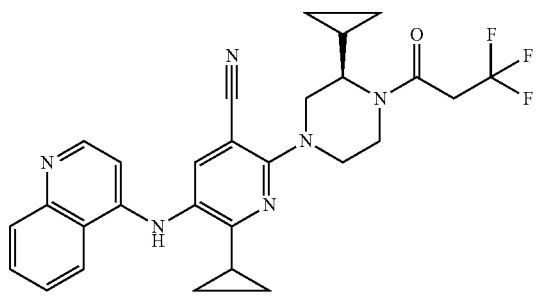 [SMILES: N#Cc1cc(Nc2ccnc3ccccc23)c(C2CC2)nc1N1CCN(C(=O)CC(F)(F)F)[C@H](C2CC2)C1] |
| 561 | 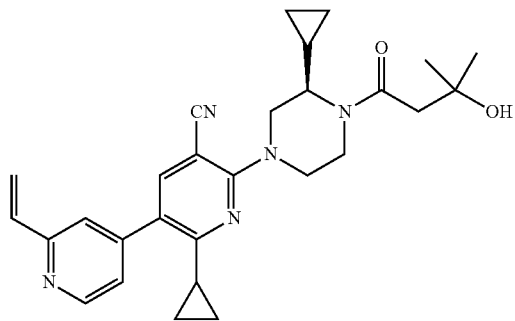 [SMILES: C=Cc1cc(-c2cc(C#N)c(N3CCN(C(=O)CC(C)(C)O)[C@H](C4CC4)C3)nc2C2CC2)ccn1] |
| 562 | 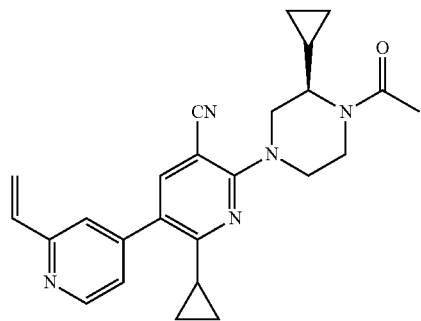 [SMILES: C=Cc1cc(-c2cc(C#N)c(N3CCN(C(C)=O)[C@H](C4CC4)C3)nc2C2CC2)ccn1] |
| 563 | 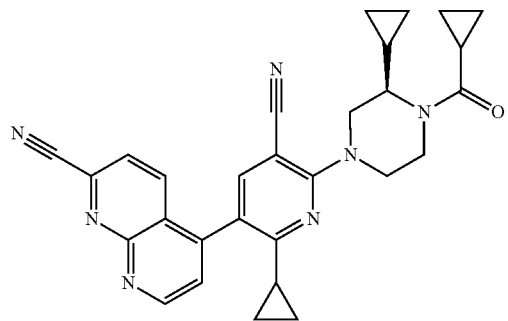 [SMILES: N#Cc1ccc2c(-c3cc(C#N)c(N4CCN(C(=O)C5CC5)[C@H](C5CC5)C4)nc3C3CC3)ccnc2n1] |

TABLE 5-continued
Exemplary Compounds of Formula I.
| Cpd # | Structure |
|---|---|
| 564 | 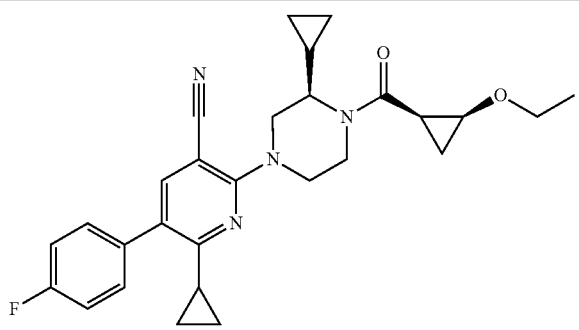 [SMILES: CCO[C@H]1C[C@H]1C(=O)N1CCN(c2nc(C3CC3)c(-c3ccc(F)cc3)cc2C#N)C[C@H]1C1CC1] |
| 565 | 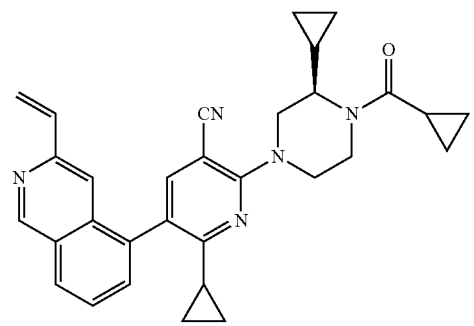 [SMILES: C=Cc1cc2c(-c3cc(C#N)c(N4CCN(C(=O)C5CC5)[C@H](C5CC5)C4)nc3C3CC3)cccc2cn1] |
| 566 | 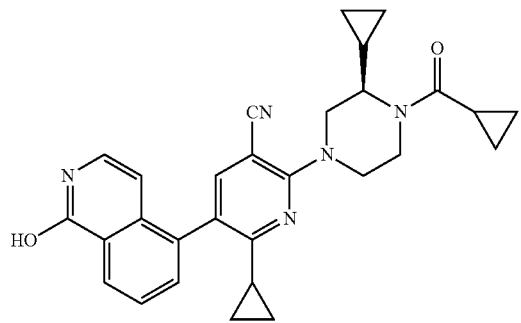 [SMILES: N#Cc1cc(-c2cccc3c(O)nccc23)c(C2CC2)nc1N1CCN(C(=O)C2CC2)[C@H](C2CC2)C1] |
| 567 | 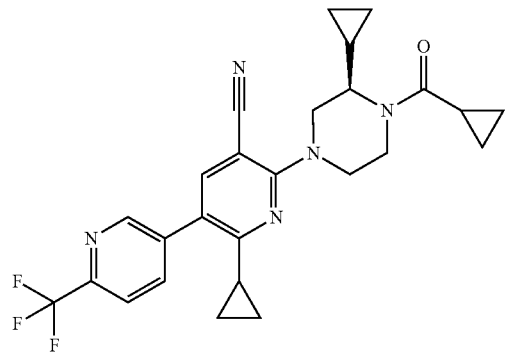 [SMILES: N#Cc1cc(-c2ccc(C(F)(F)F)nc2)c(C2CC2)nc1N1CCN(C(=O)C2CC2)[C@H](C2CC2)C1] |

TABLE 5-continued

Exemplary Compounds of Formula I.

| Cpd # | Structure |
|---|---|
| 568 | 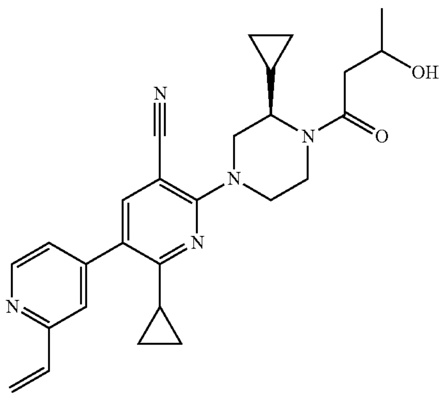 [SMILES: C=Cc1cc(-c2cc(C#N)c(N3CCN(C(=O)CC(C)O)[C@H](C4CC4)C3)nc2C2CC2)ccn1] |
| 569 | 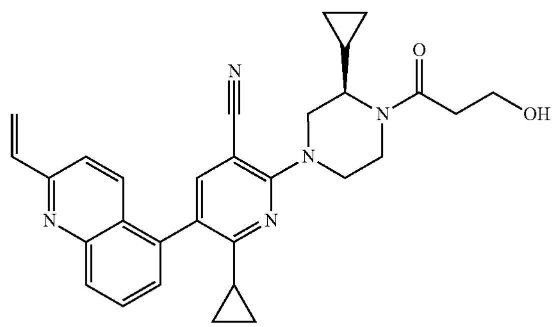 [SMILES: C=Cc1ccc2c(-c3cc(C#N)c(N4CCN(C(=O)CCO)[C@H](C5CC5)C4)nc3C3CC3)cccc2n1] |
| 570 | 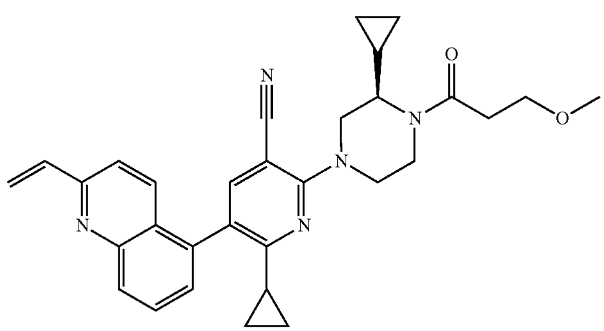 [SMILES: C=Cc1ccc2c(-c3cc(C#N)c(N4CCN(C(=O)CCOC)[C@H](C5CC5)C4)nc3C3CC3)cccc2n1] |
| 571 | 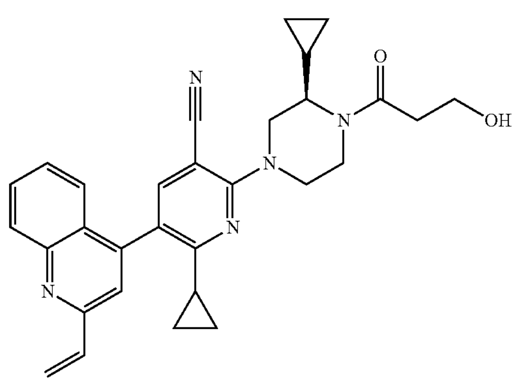 [SMILES: C=Cc1cc(-c2cc(C#N)c(N3CCN(C(=O)CCO)[C@H](C4CC4)C3)nc2C2CC2)c2ccccc2n1] |

TABLE 5-continued

Exemplary Compounds of Formula I.

| Cpd # | Structure |
|---|---|
| 572 | 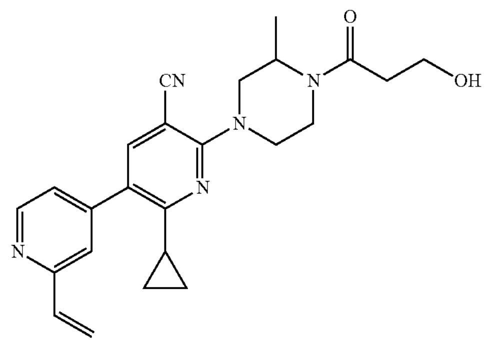 [SMILES: C=Cc1cc(-c2cc(C#N)c(N3CCN(C(=O)CCO)C(C)C3)nc2C2CC2)ccn1] |
| 573 | 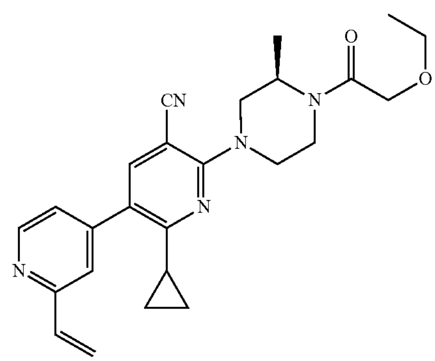 [SMILES: C=Cc1cc(-c2cc(C#N)c(N3CCN(C(=O)COCC)[C@H](C)C3)nc2C2CC2)ccn1] |
| 574 | 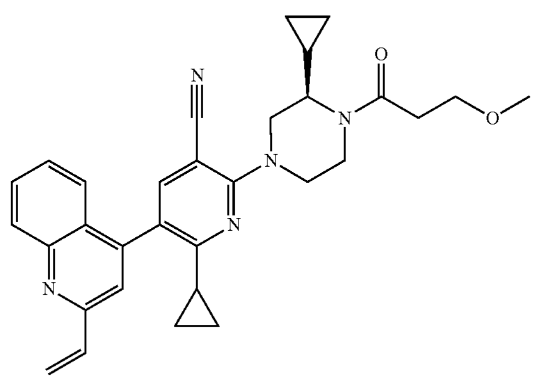 [SMILES: C=Cc1cc(-c2cc(C#N)c(N3CCN(C(=O)CCOC)[C@H](C4CC4)C3)nc2C2CC2)c2ccccc2n1] |
| 575 | 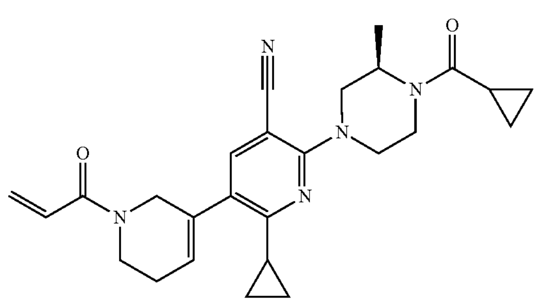 [SMILES: C=CC(=O)N1CCC=C(c2cc(C#N)c(N3CCN(C(=O)C4CC4)[C@H](C)C3)nc2C2CC2)C1] |

TABLE 5-continued
Exemplary Compounds of Formula I.
| Cpd # | Structure |
|---|---|
| 576 | 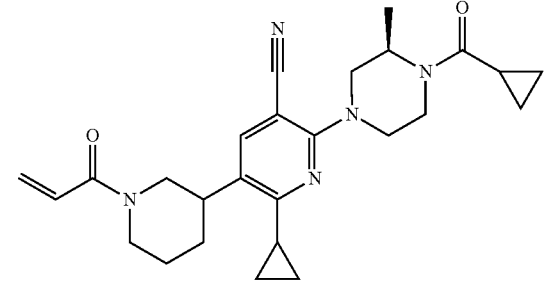 [SMILES: C=CC(=O)N1CCCC(c2cc(C#N)c(N3CCN(C(=O)C4CC4)[C@H](C)C3)nc2C2CC2)C1] |
| 577 | 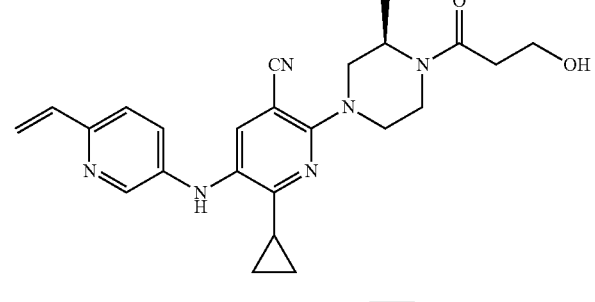 |
| 578 | 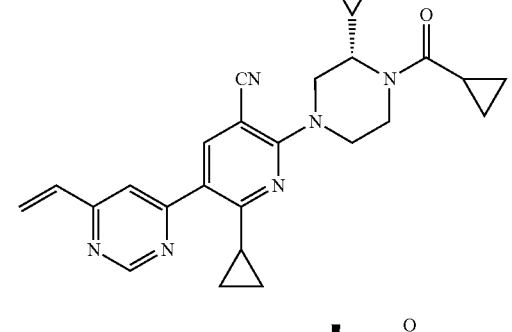 |
| 579 | 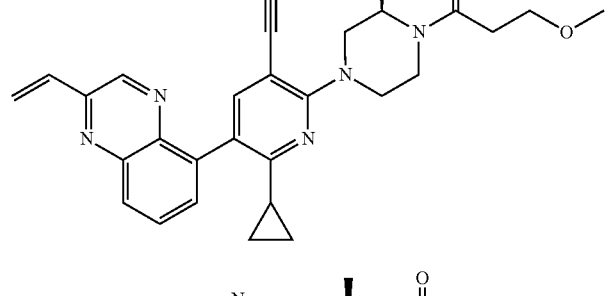 |
| 580 | 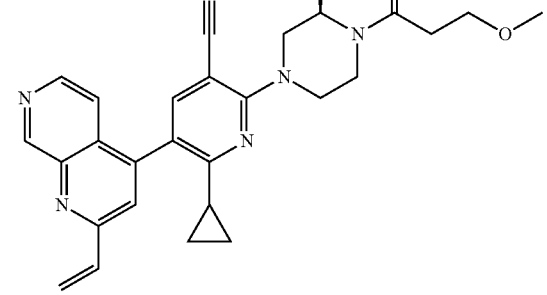 |

TABLE 5-continued
Exemplary Compounds of Formula I.
| Cpd # | Structure |
|---|---|
| 581 | 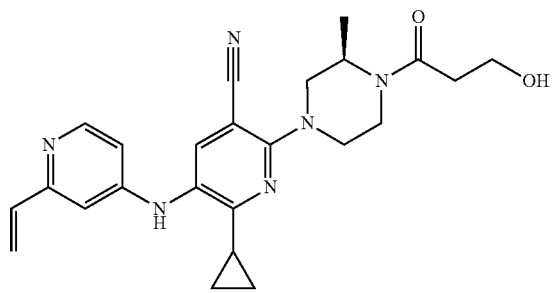 [SMILES: C=Cc1cc(Nc2cc(C#N)c(N3CCN(C(=O)CCO)[C@H](C)C3)nc2C2CC2)ccn1] |
| 582 | 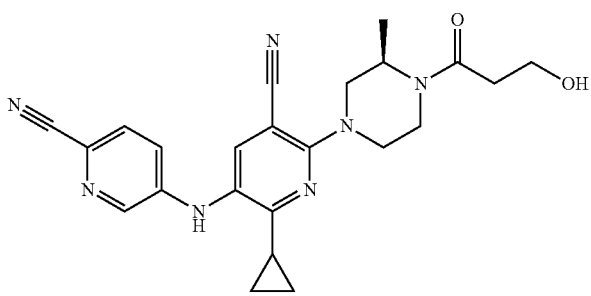 [SMILES: C[C@@H]1CN(c2nc(C3CC3)c(Nc3ccc(C#N)nc3)cc2C#N)CCN1C(=O)CCO] |
| 583 | 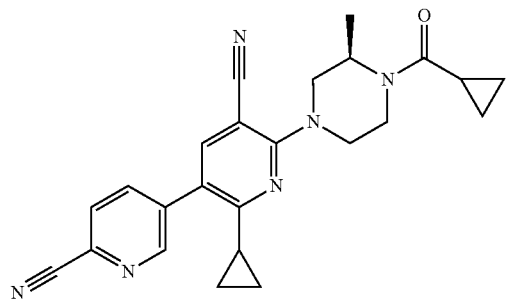 [SMILES: C[C@@H]1CN(c2nc(C3CC3)c(-c3ccc(C#N)nc3)cc2C#N)CCN1C(=O)C1CC1] |
| 584 | 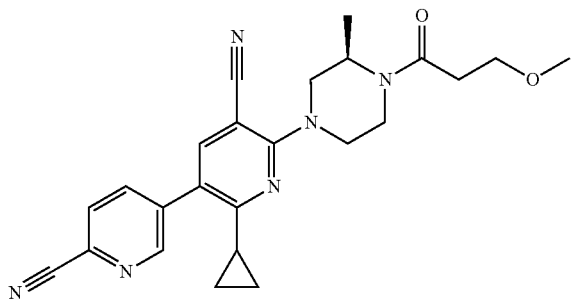 [SMILES: COCCC(=O)N1CCN(c2nc(C3CC3)c(-c3ccc(C#N)nc3)cc2C#N)C[C@H]1C] |

TABLE 5-continued
Exemplary Compounds of Formula I.
| Cpd # | Structure |
|---|---|
| 585 | 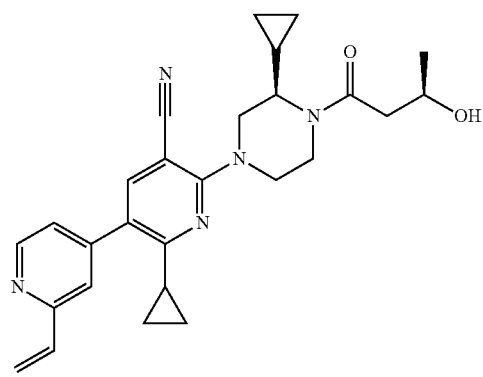 [SMILES: C=Cc1cc(-c2cc(C#N)c(N3CCN(C(=O)C[C@@H](C)O)[C@H](C4CC4)C3)nc2C2CC2)ccn1] |
| 586 | 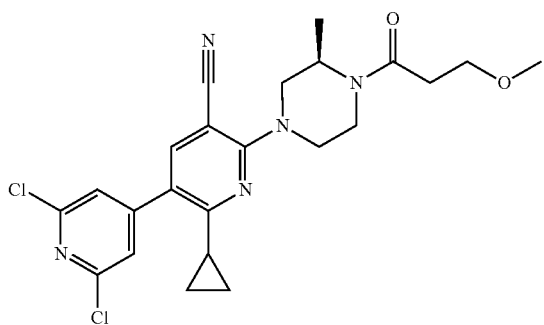 [SMILES: COCCC(=O)N1CCN(c2nc(C3CC3)c(-c3cc(Cl)nc(Cl)c3)cc2C#N)C[C@H]1C] |
| 587 | 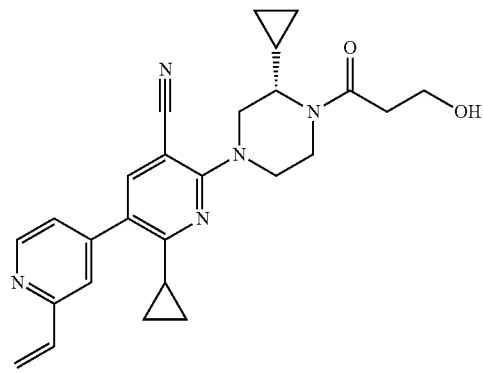 [SMILES: C=Cc1cc(-c2cc(C#N)c(N3CCN(C(=O)CCO)[C@@H](C4CC4)C3)nc2C2CC2)ccn1] |
| 588 | 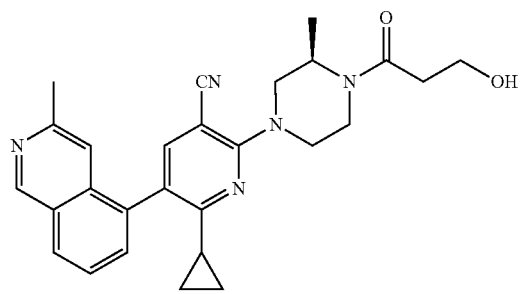 [SMILES: Cc1cc2c(-c3cc(C#N)c(N4CCN(C(=O)CCO)[C@H](C)C4)nc3C3CC3)cccc2cn1] |

TABLE 5-continued
Exemplary Compounds of Formula I.
| Cpd # | Structure |
|---|---|
| 589 | 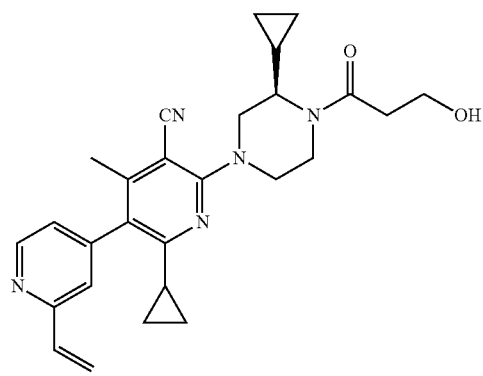 [SMILES: C=Cc1cc(-c2c(C3CC3)nc(N3CCN(C(=O)CCO)[C@H](C4CC4)C3)c(C#N)c2C)ccn1] |
| 590 | 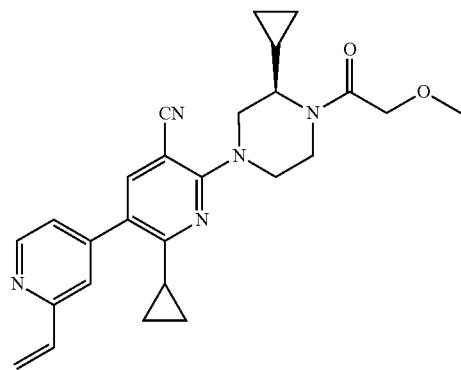 [SMILES: C=Cc1cc(-c2cc(C#N)c(N3CCN(C(=O)COC)[C@H](C4CC4)C3)nc2C2CC2)ccn1] |
| 591 | 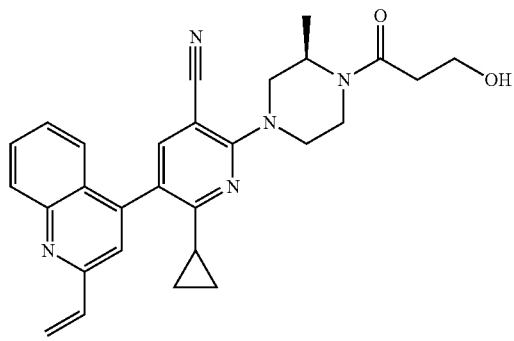 [SMILES: C=Cc1cc(-c2cc(C#N)c(N3CCN(C(=O)CCO)[C@H](C)C3)nc2C2CC2)c2ccccc2n1] |
| 592 | 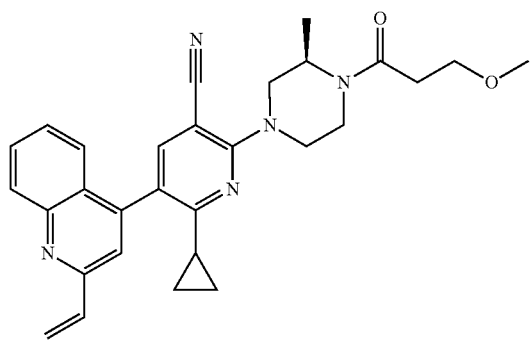 [SMILES: C=Cc1cc(-c2cc(C#N)c(N3CCN(C(=O)CCOC)[C@H](C)C3)nc2C2CC2)c2ccccc2n1] |

TABLE 5-continued

Exemplary Compounds of Formula I.

| Cpd # | Structure |
|---|---|
| 593 | 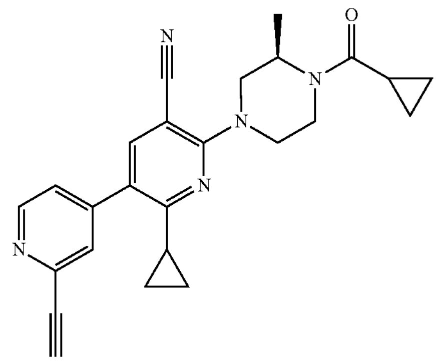 [SMILES: C#Cc1cc(-c2cc(C#N)c(N3CCN(C(=O)C4CC4)[C@H](C)C3)nc2C2CC2)ccn1] |
| 594 | 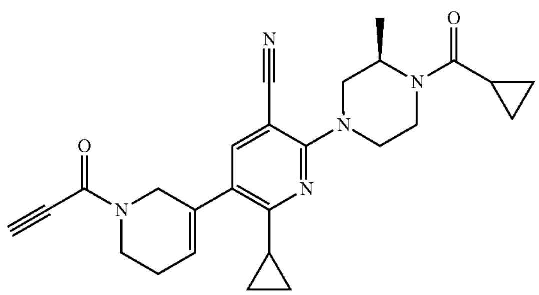 [SMILES: C#CC(=O)N1CCC=C(c2cc(C#N)c(N3CCN(C(=O)C4CC4)[C@H](C)C3)nc2C2CC2)C1] |
| 595 | 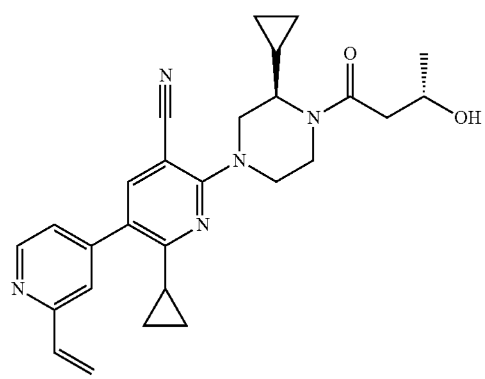 [SMILES: C=Cc1cc(-c2cc(C#N)c(N3CCN(C(=O)C[C@H](C)O)[C@H](C4CC4)C3)nc2C2CC2)ccn1] |
| 596 | 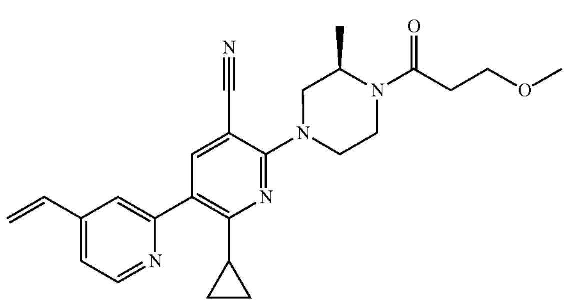 [SMILES: C=Cc1ccnc(-c2cc(C#N)c(N3CCN(C(=O)CCOC)[C@H](C)C3)nc2C2CC2)c1] |

TABLE 5-continued

Exemplary Compounds of Formula I.

| Cpd # | Structure |
|---|---|
| 597 | 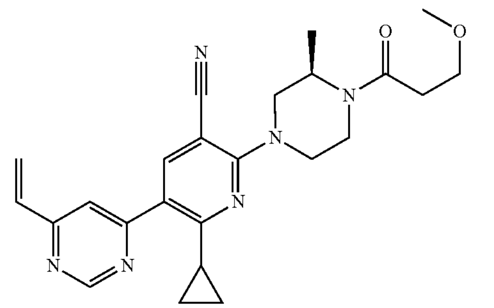 [SMILES: C=Cc1cc(-c2cc(C#N)c(N3CCN(C(=O)CCOC)[C@H](C)C3)nc2C2CC2)ncn1] |
| 598 | 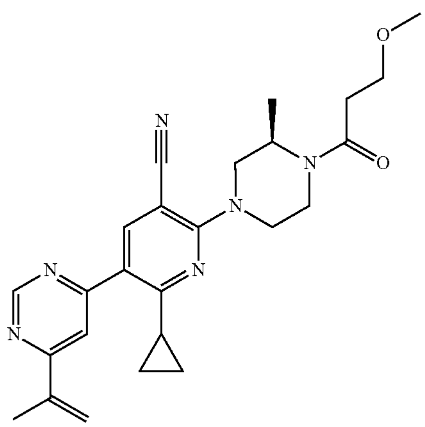 [SMILES: C=C(C)c1cc(-c2cc(C#N)c(N3CCN(C(=O)CCOC)[C@H](C)C3)nc2C2CC2)ncn1] |
| 599 | 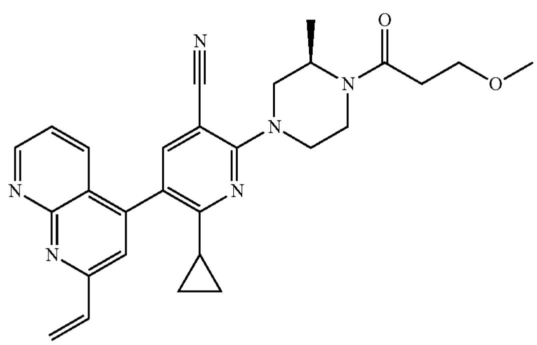 [SMILES: C=Cc1cc(-c2cc(C#N)c(N3CCN(C(=O)CCOC)[C@H](C)C3)nc2C2CC2)c2cccnc2n1] |
| 600 | 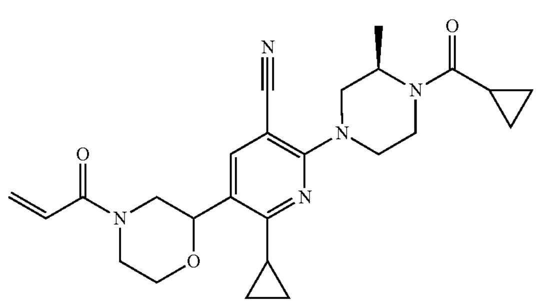 [SMILES: C=CC(=O)N1CCOC(c2cc(C#N)c(N3CCN(C(=O)C4CC4)[C@H](C)C3)nc2C2CC2)C1] |

TABLE 5-continued
Exemplary Compounds of Formula I.
| Cpd # | Structure |
|---|---|
| 601 | 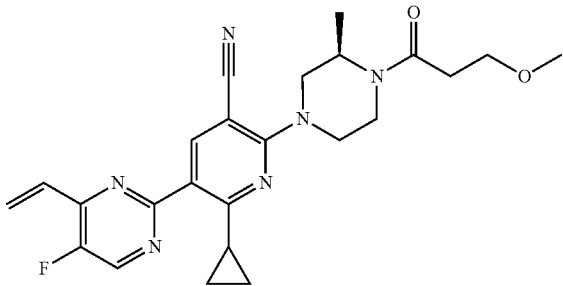 [SMILES: C=Cc1nc(-c2cc(C#N)c(N3CCN(C(=O)CCOC)[C@H](C)C3)nc2C2CC2)ncc1F] |
| 602 | 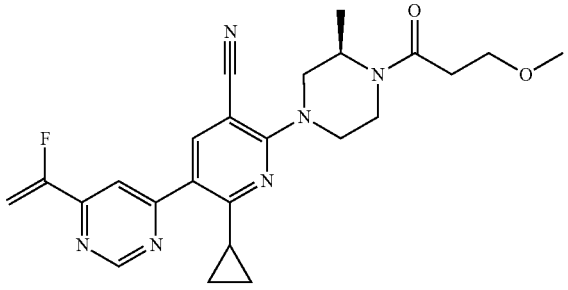 [SMILES: C=C(F)c1cc(-c2cc(C#N)c(N3CCN(C(=O)CCOC)[C@H](C)C3)nc2C2CC2)ncn1] |
| 603 | 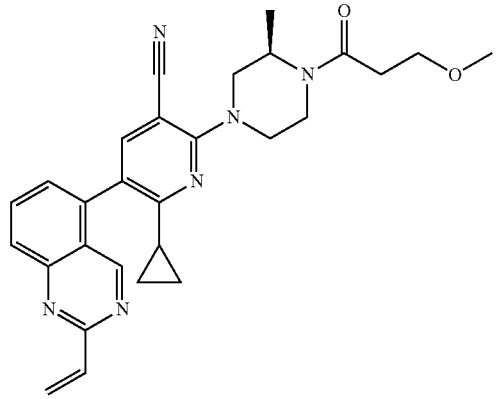 [SMILES: C=Cc1ncc2c(-c3cc(C#N)c(N4CCN(C(=O)CCOC)[C@H](C)C4)nc3C3CC3)cccc2n1] |
| 604 | 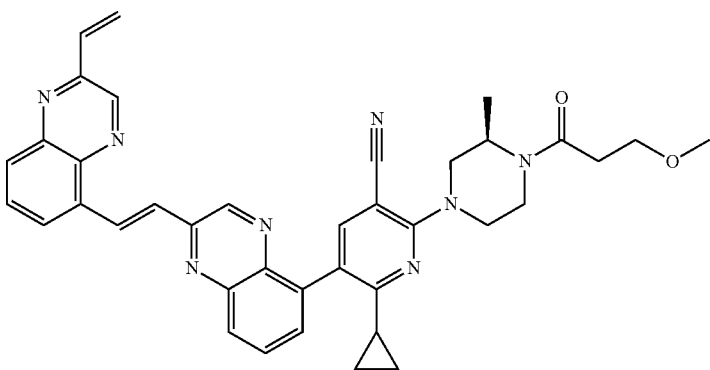 [SMILES: C=Cc1cnc2c(/C=C/c3cnc4c(-c5cc(C#N)c(N6CCN(C(=O)CCOC)[C@H](C)C6)nc5C5CC5)cccc4n3)cccc2n1] |

TABLE 5-continued

Exemplary Compounds of Formula I.

| Cpd # | Structure |
|---|---|
| 605 | 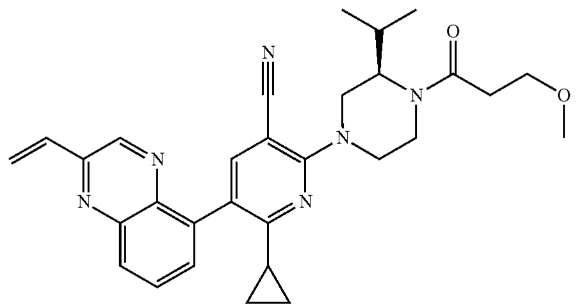 [SMILES: C=Cc1cnc2c(-c3cc(C#N)c(N4CCN(C(=O)CCOC)[C@H](C(C)C)C4)nc3C3CC3)cccc2n1] |
| 606 | 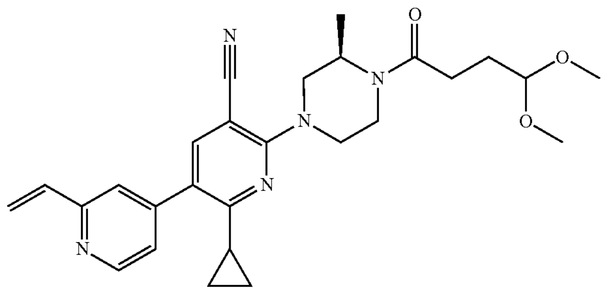 [SMILES: C=Cc1cc(-c2cc(C#N)c(N3CCN(C(=O)CCC(OC)OC)[C@H](C)C3)nc2C2CC2)ccn1] |
| 607 | 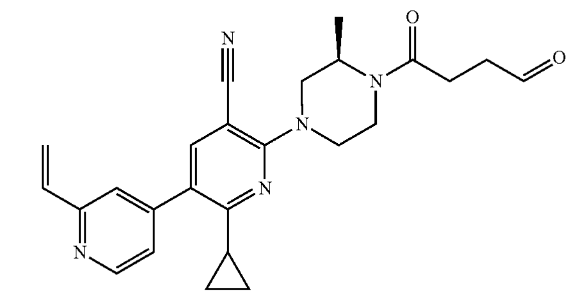 [SMILES: C=Cc1cc(-c2cc(C#N)c(N3CCN(C(=O)CCC=O)[C@H](C)C3)nc2C2CC2)ccn1] |
| 608 | 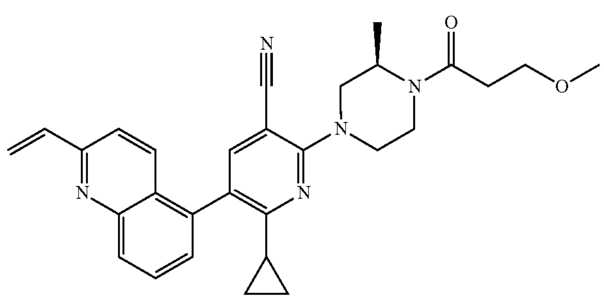 [SMILES: C=Cc1ccc2c(-c3cc(C#N)c(N4CCN(C(=O)CCOC)[C@H](C)C4)nc3C3CC3)cccc2n1] |
| 609 | 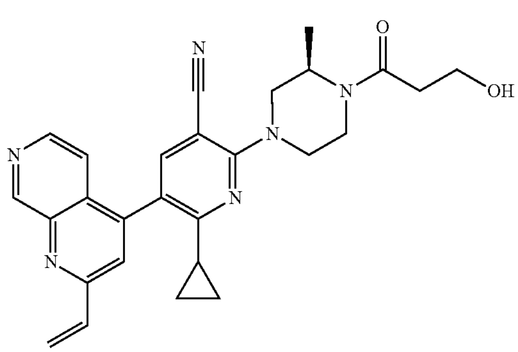 [SMILES: C=Cc1cc(-c2cc(C#N)c(N3CCN(C(=O)CCO)[C@H](C)C3)nc2C2CC2)c2ccncc2n1] |

TABLE 5-continued
Exemplary Compounds of Formula I.
| Cpd # | Structure |
|---|---|
| 610 | 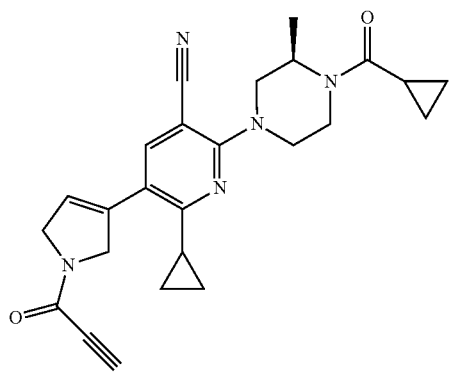 [SMILES: C#CC(=O)N1CC=C(c2cc(C#N)c(N3CCN(C(=O)C4CC4)[C@H](C)C3)nc2C2CC2)C1] |
| 611 | 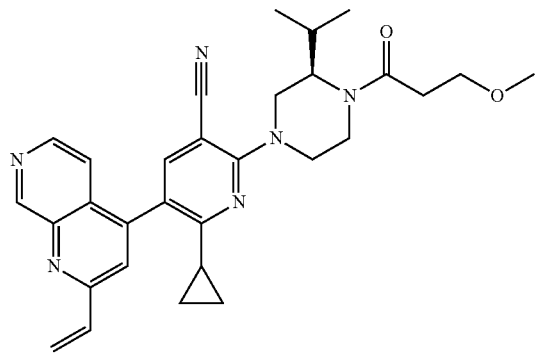 [SMILES: C=Cc1cc(-c2cc(C#N)c(N3CCN(C(=O)CCOC)[C@H](C(C)C)C3)nc2C2CC2)c2ccncc2n1] |
| 612 | 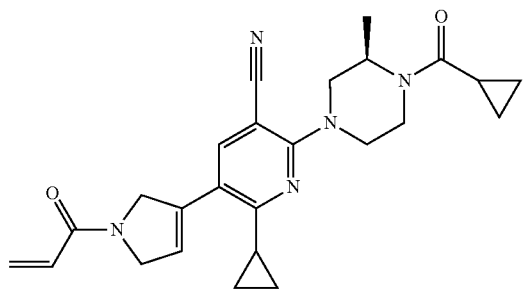 [SMILES: C=CC(=O)N1CC=C(c2cc(C#N)c(N3CCN(C(=O)C4CC4)[C@H](C)C3)nc2C2CC2)C1] |
| 613 | 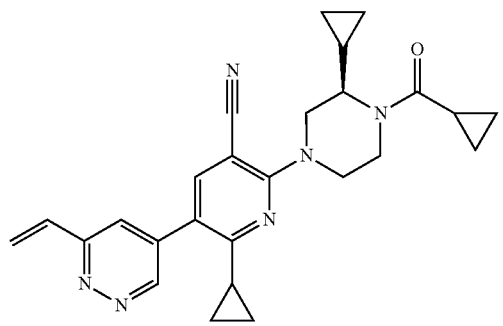 [SMILES: C=Cc1cc(-c2cc(C#N)c(N3CCN(C(=O)C4CC4)[C@H](C4CC4)C3)nc2C2CC2)cnn1] |

TABLE 5-continued

Exemplary Compounds of Formula I.

| Cpd # | Structure |
|---|---|
| 614 | 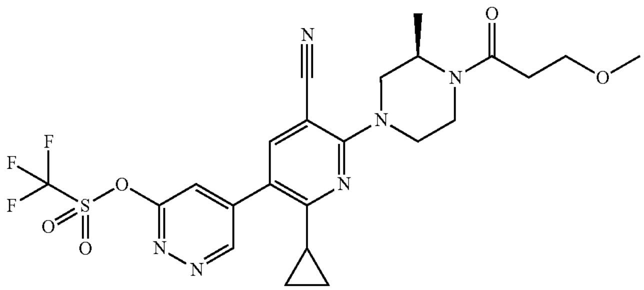 [SMILES: COCCC(=O)N1CCN(c2nc(C3CC3)c(-c3cnnc(OS(=O)(=O)C(F)(F)F)c3)cc2C#N)C[C@H]1C] |
| 615 | 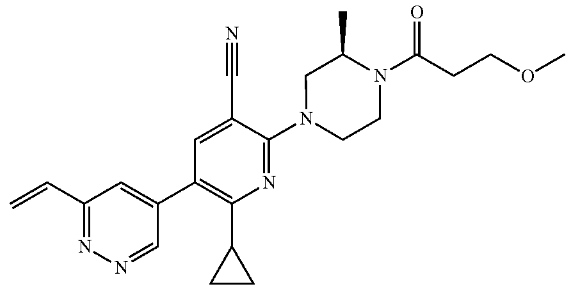 [SMILES: C=Cc1cc(-c2cc(C#N)c(N3CCN(C(=O)CCOC)[C@H](C)C3)nc2C2CC2)cnn1] |
| 616 | 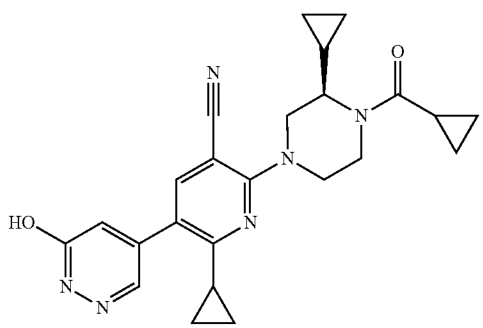 [SMILES: N#Cc1cc(-c2cnnc(O)c2)c(C2CC2)nc1N1CCN(C(=O)C2CC2)[C@H](C2CC2)C1] |
| 617 | 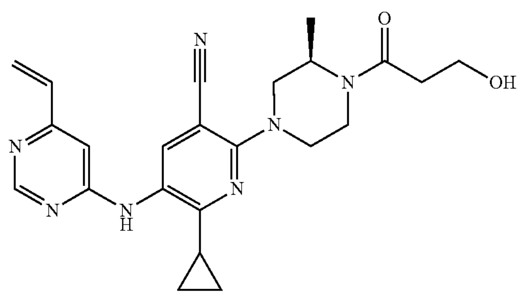 [SMILES: C=Cc1cc(Nc2cc(C#N)c(N3CCN(C(=O)CCO)[C@H](C)C3)nc2C2CC2)ncn1] |
| 618 | 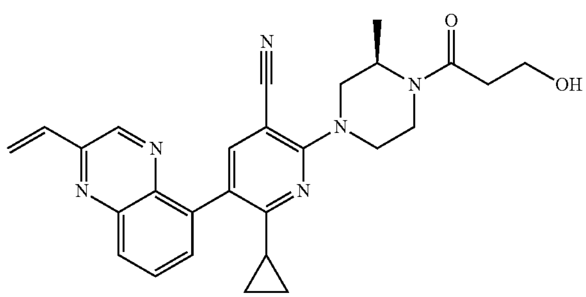 [SMILES: C=Cc1cnc2c(-c3cc(C#N)c(N4CCN(C(=O)CCO)[C@H](C)C4)nc3C3CC3)cccc2n1] |

TABLE 5-continued
Exemplary Compounds of Formula I.
| Cpd # | Structure |
|---|---|
| 619 | 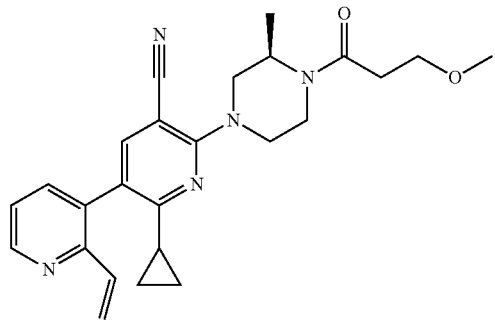 [SMILES: C=Cc1ncccc1-c1cc(C#N)c(N2CCN(C(=O)CCOC)[C@H](C)C2)nc1C1CC1] |
| 620 | 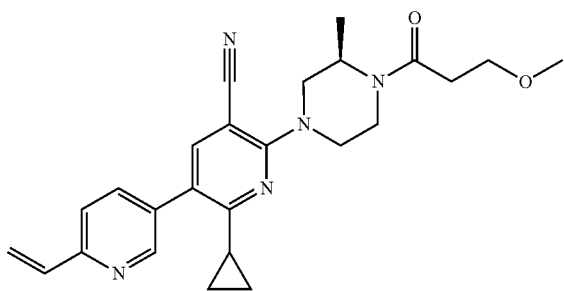 [SMILES: C=Cc1ccc(-c2cc(C#N)c(N3CCN(C(=O)CCOC)[C@H](C)C3)nc2C2CC2)cn1] |
| 621 | 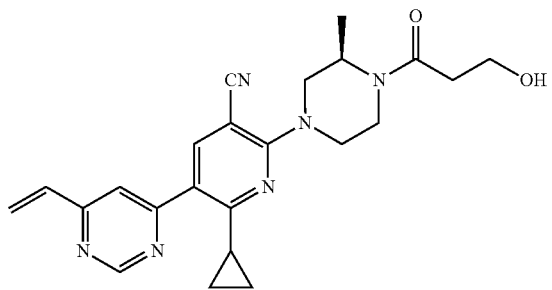 [SMILES: C=Cc1cc(-c2cc(C#N)c(N3CCN(C(=O)CCO)[C@H](C)C3)nc2C2CC2)ncn1] |
| 622 | 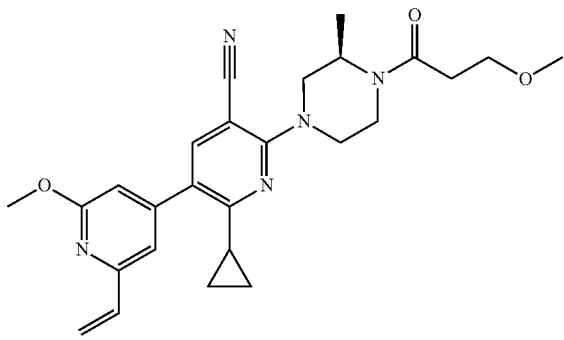 |

TABLE 5-continued

Exemplary Compounds of Formula I.

| Cpd # | Structure |
|---|---|
| 623 | 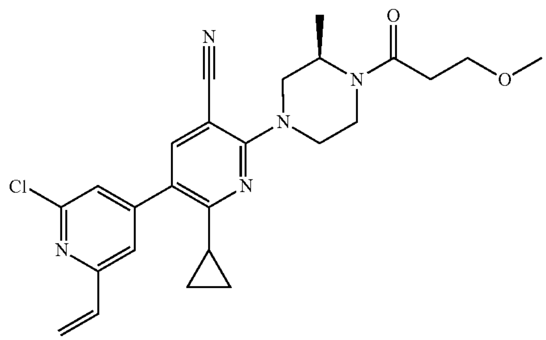 [SMILES: C=Cc1cc(-c2cc(C#N)c(N3CCN(C(=O)CCOC)[C@H](C)C3)nc2C2CC2)cc(Cl)n1] |
| 624 | 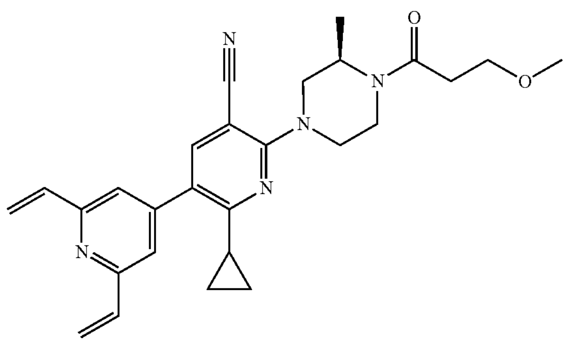 [SMILES: C=Cc1cc(-c2cc(C#N)c(N3CCN(C(=O)CCOC)[C@H](C)C3)nc2C2CC2)cc(C=C)n1] |
| 625 | 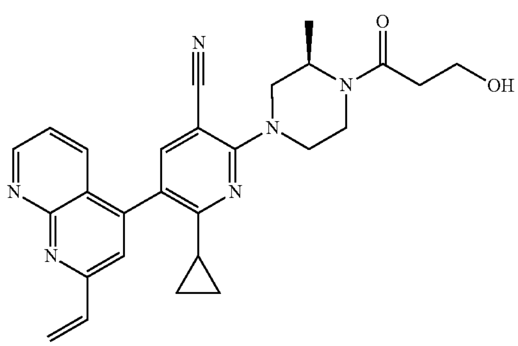 [SMILES: C=Cc1cc(-c2cc(C#N)c(N3CCN(C(=O)CCO)[C@H](C)C3)nc2C2CC2)c2cccnc2n1] |
| 626 | 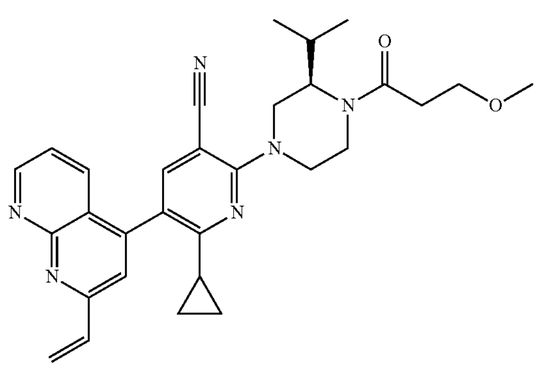 [SMILES: C=Cc1cc(-c2cc(C#N)c(N3CCN(C(=O)CCOC)[C@H](C(C)C)C3)nc2C2CC2)c2cccnc2n1] |

TABLE 5-continued
Exemplary Compounds of Formula I.
| Cpd # | Structure |
|---|---|
| 627 | 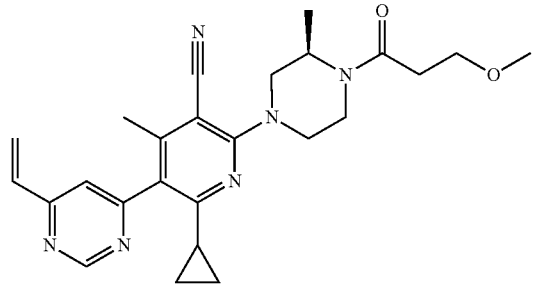 [SMILES: C=Cc1cc(-c2c(C3CC3)nc(N3CCN(C(=O)CCOC)[C@H](C)C3)c(C#N)c2C)ncn1] |
| 628 | 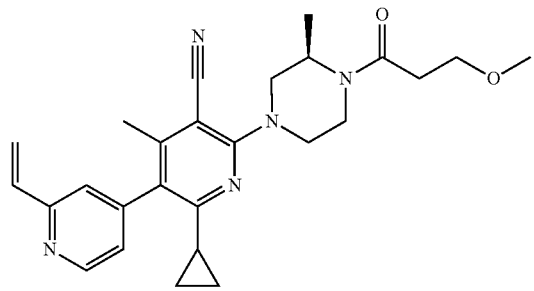 |
| 629 | 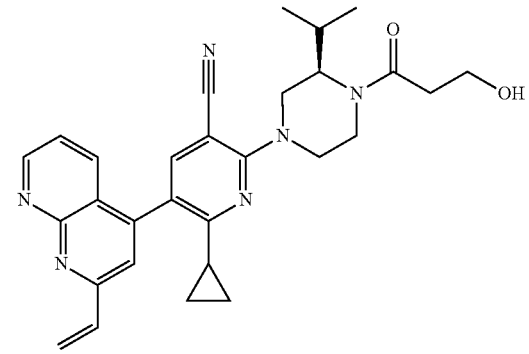 [SMILES: C=Cc1cc(-c2cc(C#N)c(N3CCN(C(=O)CCO)[C@H](C(C)C)C3)nc2C2CC2)c2cccnc2n1] |
| 630 | 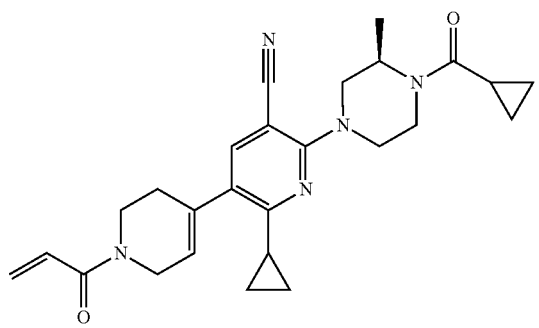 [SMILES: C=CC(=O)N1CC=C(c2cc(C#N)c(N3CCN(C(=O)C4CC4)[C@H](C)C3)nc2C2CC2)CC1] |

TABLE 5-continued
Exemplary Compounds of Formula I.
| Cpd # | Structure |
|---|---|
| 631 | 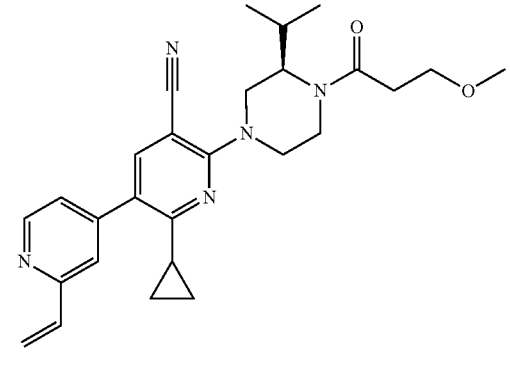 [SMILES: C=Cc1cc(-c2cc(C#N)c(N3CCN(C(=O)CCOC)[C@H](C(C)C)C3)nc2C2CC2)ccn1] |
| 632 | 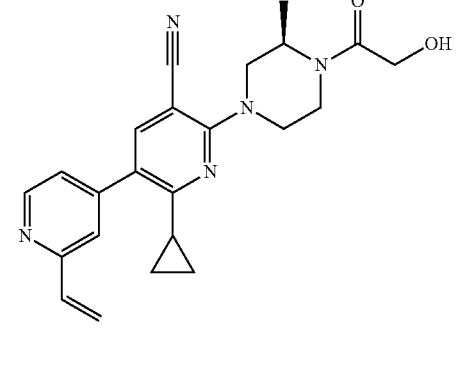 |
| 633 | 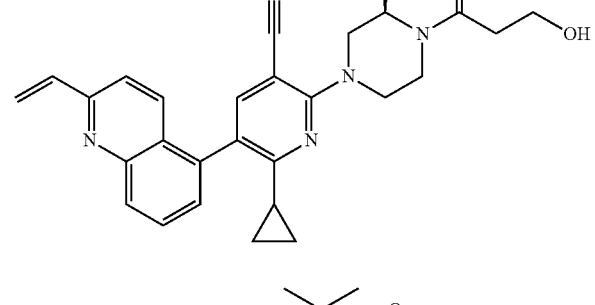 |
| 634 | 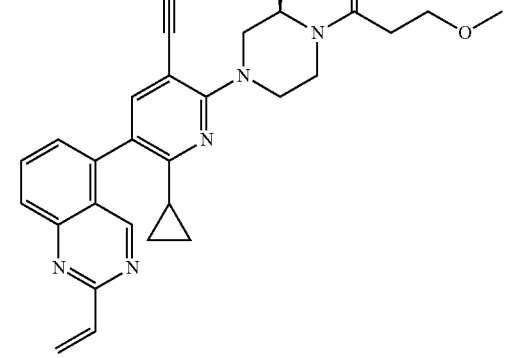 |

TABLE 5-continued

Exemplary Compounds of Formula I.

| Cpd # | Structure |
|---|---|
| 635 | 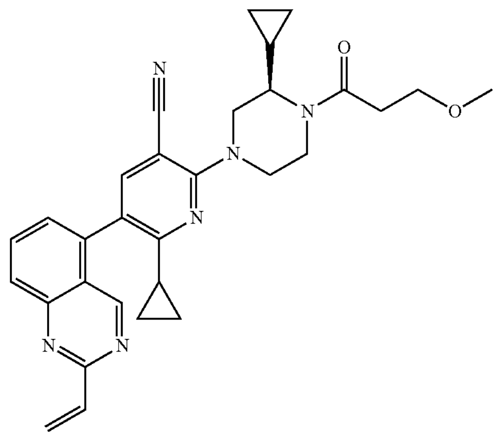 [SMILES: C=Cc1ncc2c(-c3cc(C#N)c(N4CCN(C(=O)CCOC)[C@H](C5CC5)C4)nc3C3CC3)cccc2n1] |
| 636 | 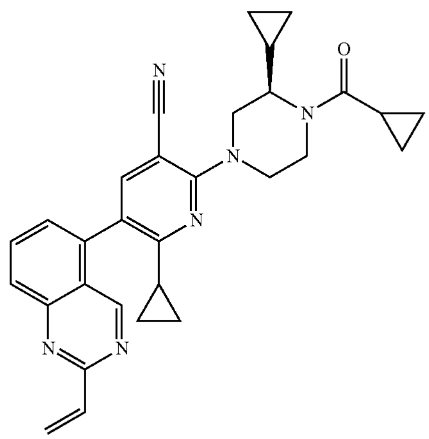 [SMILES: C=Cc1ncc2c(-c3cc(C#N)c(N4CCN(C(=O)C5CC5)[C@H](C5CC5)C4)nc3C3CC3)cccc2n1] |
| 637 | 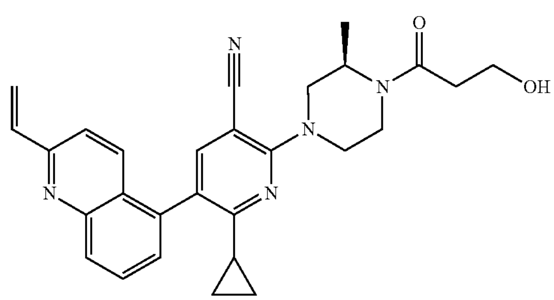 [SMILES: C=Cc1ccc2c(-c3cc(C#N)c(N4CCN(C(=O)CCO)[C@H](C)C4)nc3C3CC3)cccc2n1] |
| 638 | 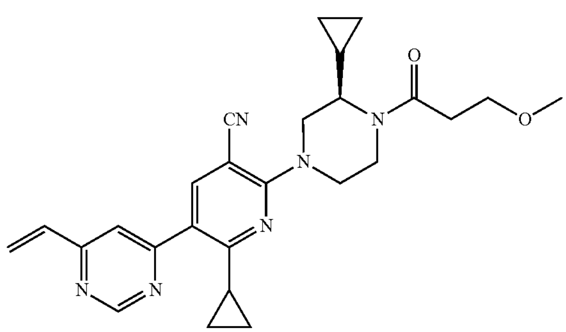 [SMILES: C=Cc1cc(-c2cc(C#N)c(N3CCN(C(=O)CCOC)[C@H](C4CC4)C3)nc2C2CC2)ncn1] |

TABLE 5-continued

Exemplary Compounds of Formula I.

| Cpd # | Structure |
|---|---|
| 639 | 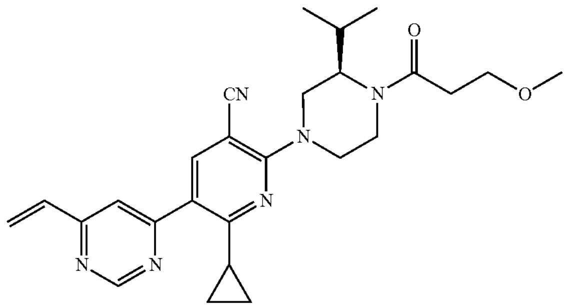 [SMILES: C=Cc1cc(-c2cc(C#N)c(N3CCN(C(=O)CCOC)[C@H](C(C)C)C3)nc2C2CC2)ncn1] |
| 640 | 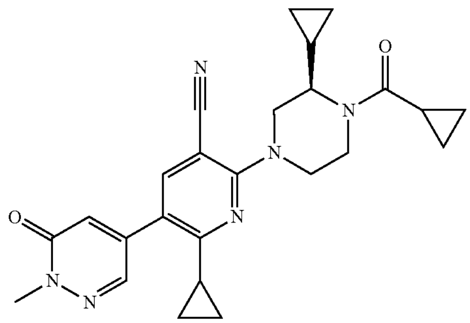 [SMILES: Cn1ncc(-c2cc(C#N)c(N3CCN(C(=O)C4CC4)[C@H](C4CC4)C3)nc2C2CC2)cc1=O] |
| 641 | 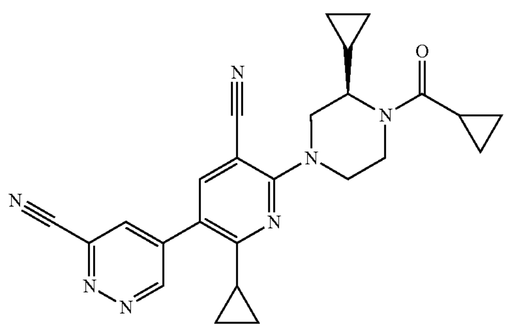 [SMILES: N#Cc1cc(-c2cc(C#N)c(N3CCN(C(=O)C4CC4)[C@H](C4CC4)C3)nc2C2CC2)cnn1] |
| 642 | 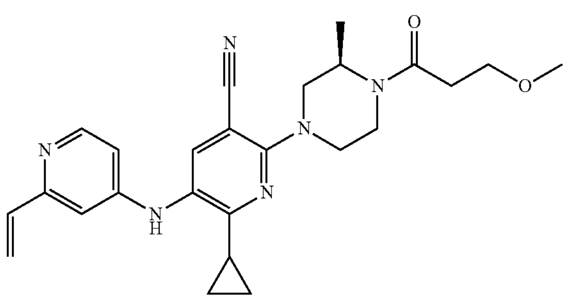 [SMILES: C=Cc1cc(Nc2cc(C#N)c(N3CCN(C(=O)CCOC)[C@H](C)C3)nc2C2CC2)ccn1] |
| 643 | 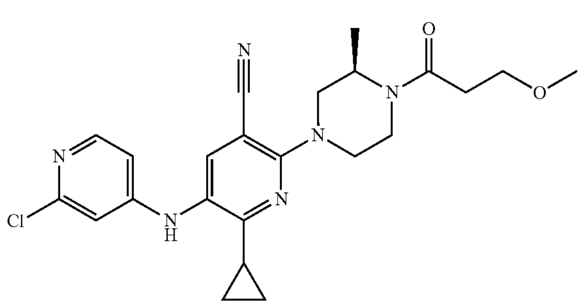 [SMILES: COCCC(=O)N1CCN(c2nc(C3CC3)c(Nc3ccnc(Cl)c3)cc2C#N)C[C@H]1C] |

US 9,856,279 B2
TABLE 5-continued
Exemplary Compounds of Formula I.
| Cpd # | Structure |
|---|---|
| 644 | 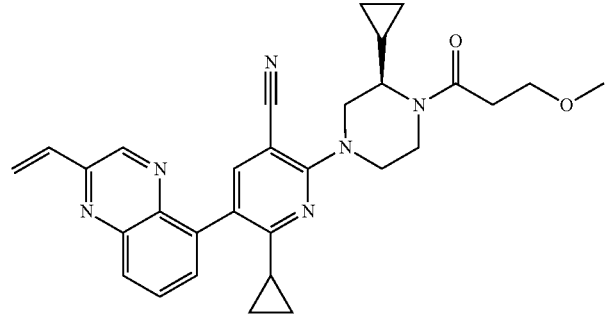 [SMILES: C=Cc1cnc2c(-c3cc(C#N)c(N4CCN(C(=O)CCOC)[C@H](C5CC5)C4)nc3C3CC3)cccc2n1] |
| 645 | 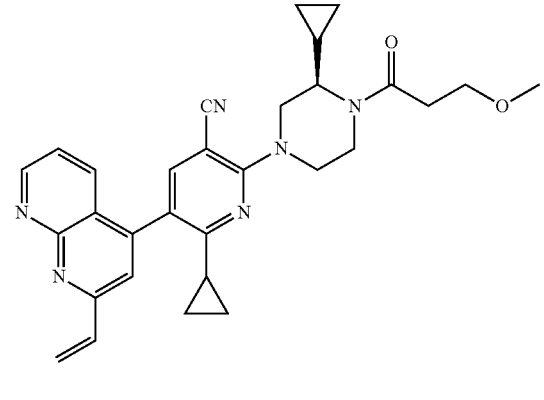 [SMILES: C=Cc1cc(-c2cc(C#N)c(N3CCN(C(=O)CCOC)[C@H](C4CC4)C3)nc2C2CC2)c2cccnc2n1] |
| 646 | 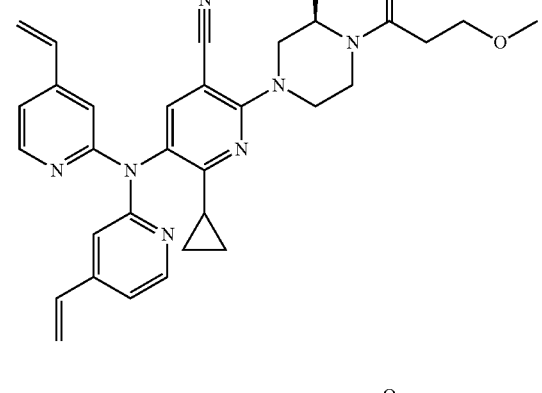 |
| 647 | 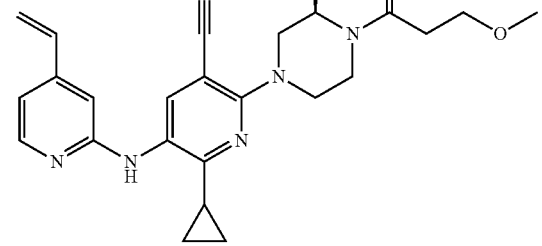 |

TABLE 5-continued

Exemplary Compounds of Formula I.

| Cpd # | Structure |
|---|---|
| 648 | 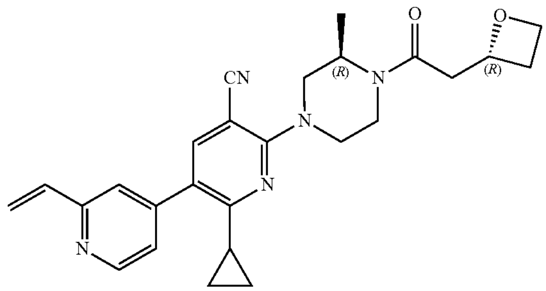 |
| 649 | 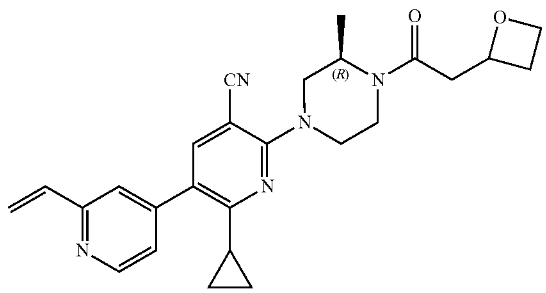 |
| 650 | 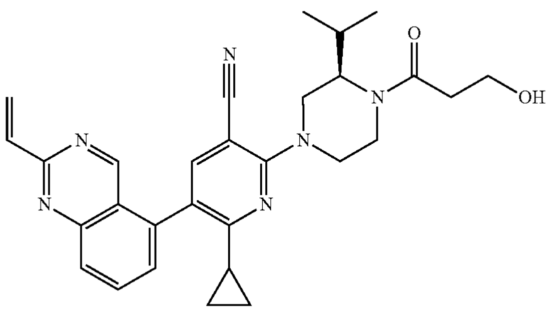 [SMILES: C=Cc1ncc2c(-c3cc(C#N)c(N4CCN(C(=O)CCO)[C@H](C(C)C)C4)nc3C3CC3)cccc2n1] |
| 651 | 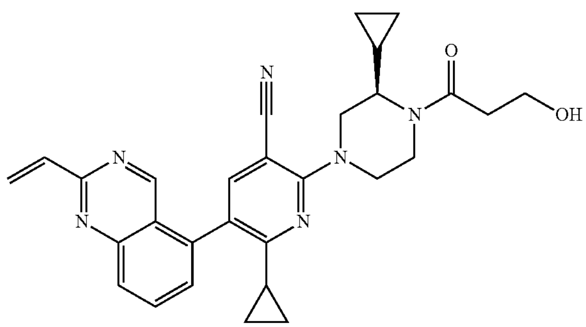 [SMILES: C=Cc1ncc2c(-c3cc(C#N)c(N4CCN(C(=O)CCO)[C@H](C5CC5)C4)nc3C3CC3)cccc2n1] |
| 652 | 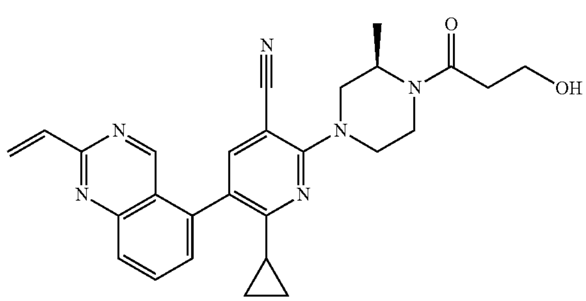 [SMILES: C=Cc1ncc2c(-c3cc(C#N)c(N4CCN(C(=O)CCO)[C@H](C)C4)nc3C3CC3)cccc2n1] |

TABLE 5-continued

Exemplary Compounds of Formula I.

| Cpd # | Structure |
|---|---|
| 653 | 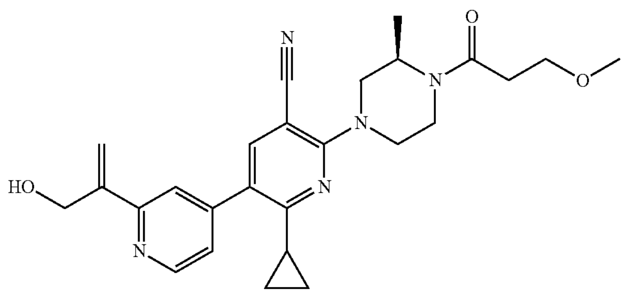 [SMILES: C=C(CO)c1cc(-c2cc(C#N)c(N3CCN(C(=O)CCOC)[C@H](C)C3)nc2C2CC2)ccn1] |
| 654 | 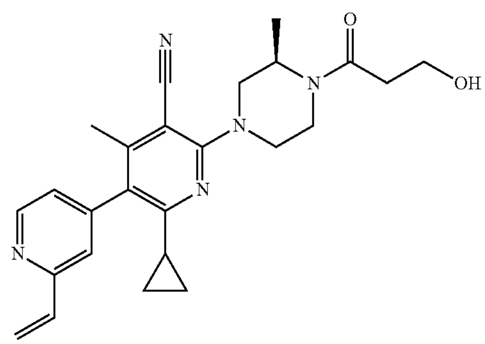 [SMILES: C=Cc1cc(-c2c(C3CC3)nc(N3CCN(C(=O)CCO)[C@H](C)C3)c(C#N)c2C)ccn1] |
| 655 | 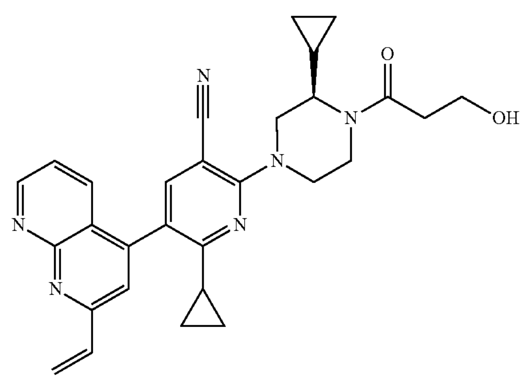 [SMILES: C=Cc1cc(-c2cc(C#N)c(N3CCN(C(=O)CCO)[C@H](C4CC4)C3)nc2C2CC2)c2cccnc2n1] |
| 656 | 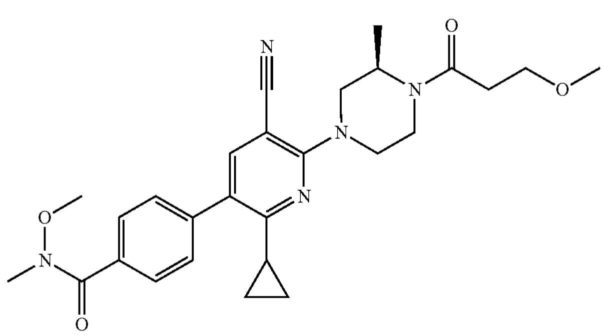 |

US 9,856,279 B2
241
242
TABLE 5-continued
Exemplary Compounds of Formula I.
| Cpd # | Structure |
|---|---|
| 657 | 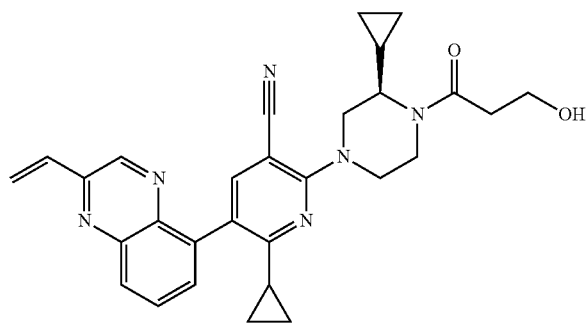 [SMILES: C=Cc1cnc2c(-c3cc(C#N)c(N4CCN(C(=O)CCO)[C@H](C5CC5)C4)nc3C3CC3)cccc2n1] |
| 658 | 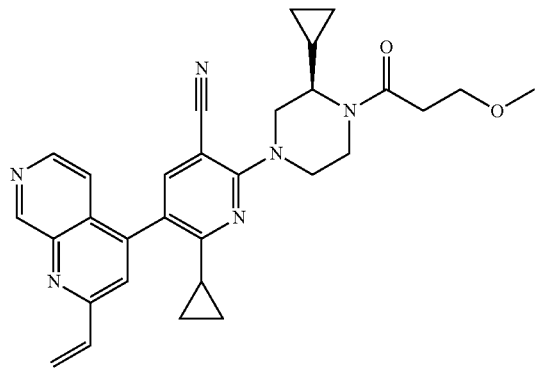 [SMILES: C=Cc1cc(-c2cc(C#N)c(N3CCN(C(=O)CCOC)[C@H](C4CC4)C3)nc2C2CC2)c2ccncc2n1] |
| 659 | 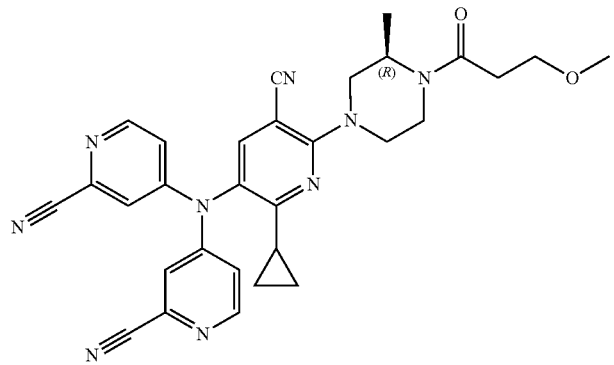 |
| 660 | 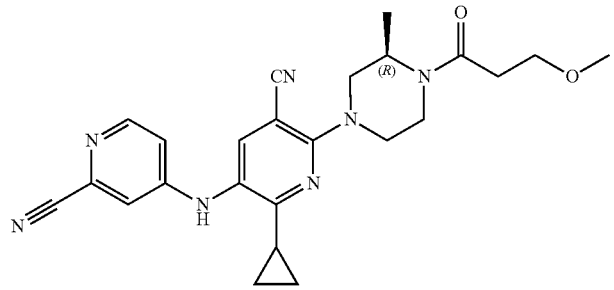 |

TABLE 5-continued
Exemplary Compounds of Formula I.
| Cpd # | Structure |
|---|---|
| 661 | 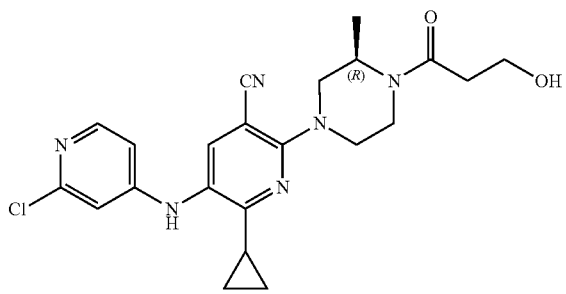 |
| 662 | 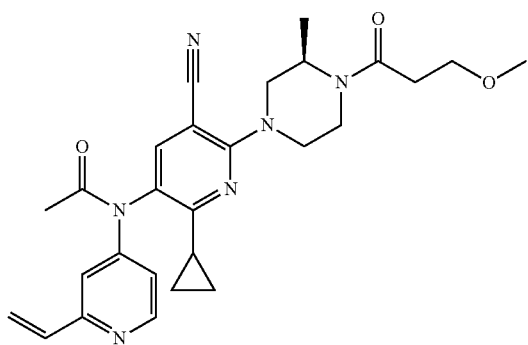 [SMILES: C=Cc1cc(N(C(C)=O)c2cc(C#N)c(N3CCN(C(=O)CCOC)[C@H](C)C3)nc2C2CC2)ccn1] |
| 663 | 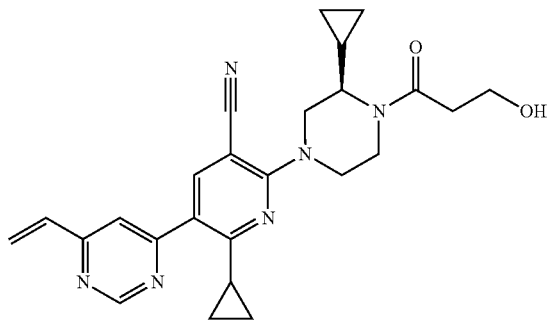 |
| 664 | 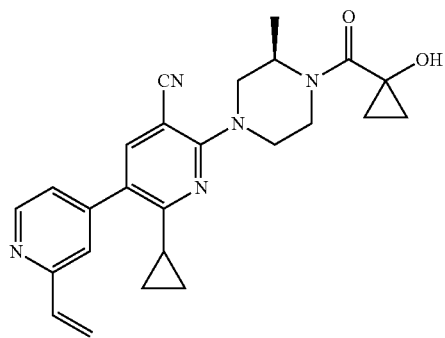 [SMILES: C=Cc1cc(-c2cc(C#N)c(N3CCN(C(=O)C4(O)CC4)[C@H](C)C3)nc2C2CC2)ccn1] |

TABLE 5-continued
Exemplary Compounds of Formula I.
| Cpd # | Structure |
|---|---|
| 665 | 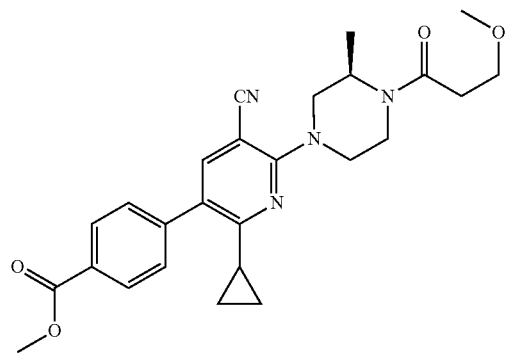 [SMILES: COCCC(=O)N1CCN(c2nc(C3CC3)c(-c3ccc(C(=O)OC)cc3)cc2C#N)C[C@H]1C] |
| 666 | 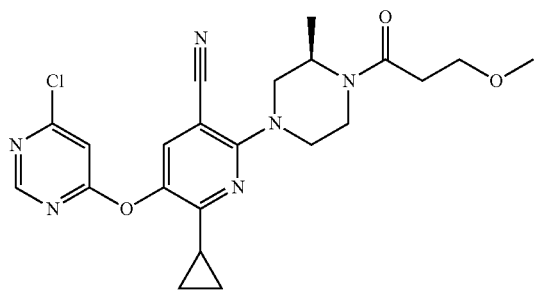 [SMILES: COCCC(=O)N1CCN(c2nc(C3CC3)c(Oc3cc(Cl)ncn3)cc2C#N)C[C@H]1C] |
| 667 | 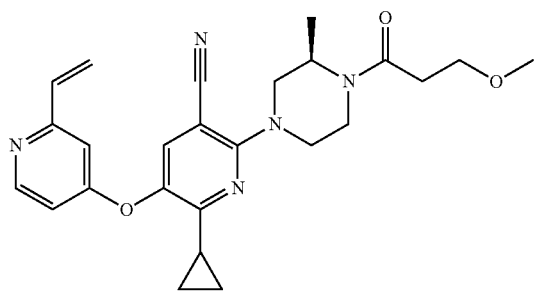 [SMILES: C=Cc1cc(Oc2cc(C#N)c(N3CCN(C(=O)CCOC)[C@H](C)C3)nc2C2CC2)ccn1] |
| 668 | 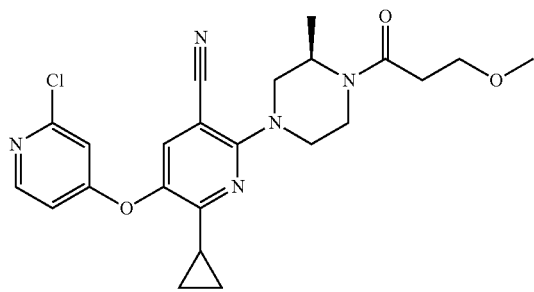 [SMILES: COCCC(=O)N1CCN(c2nc(C3CC3)c(Oc3ccnc(Cl)c3)cc2C#N)C[C@H]1C] |

TABLE 5-continued
Exemplary Compounds of Formula I.
| Cpd # | Structure |
|---|---|
| 669 | 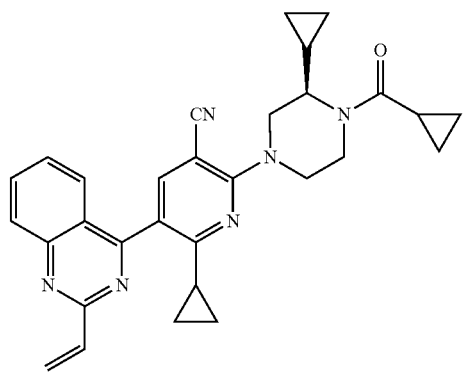 [SMILES: C=Cc1nc(-c2cc(C#N)c(N3CCN(C(=O)C4CC4)[C@H](C4CC4)C3)nc2C2CC2)c2ccccc2n1] |
| 670 | 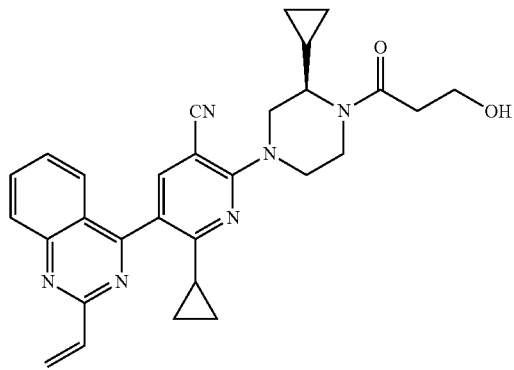 [SMILES: C=Cc1nc(-c2cc(C#N)c(N3CCN(C(=O)CCO)[C@H](C4CC4)C3)nc2C2CC2)c2ccccc2n1] |
| 671 | 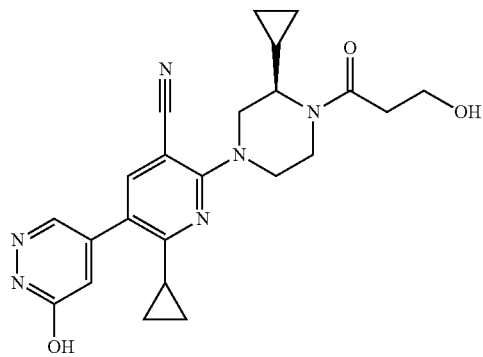 [SMILES: N#Cc1cc(-c2cnnc(O)c2)c(C2CC2)nc1N1CCN(C(=O)CCO)[C@H](C2CC2)C1] |
| 672 | 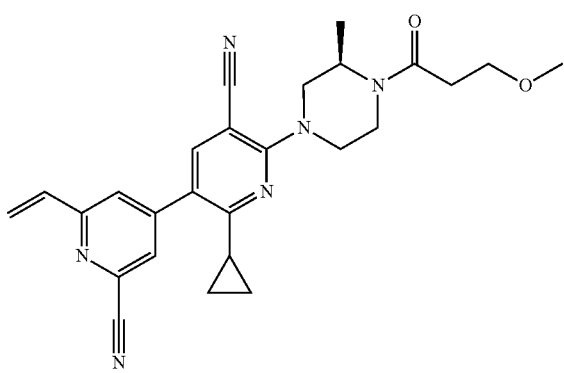 [SMILES: C=Cc1cc(-c2cc(C#N)c(N3CCN(C(=O)CCOC)[C@H](C)C3)nc2C2CC2)cc(C#N)n1] |

TABLE 5-continued
Exemplary Compounds of Formula I.
| Cpd # | Structure |
|---|---|
| 673 | 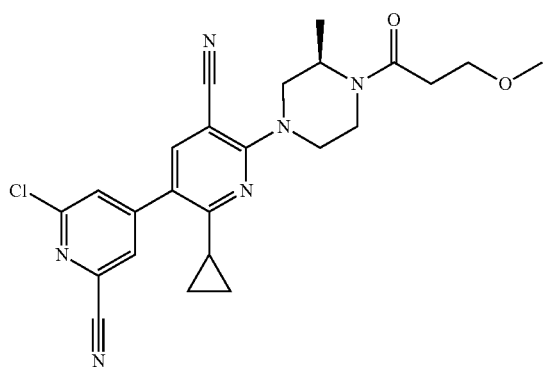 [SMILES: COCCC(=O)N1CCN(c2nc(C3CC3)c(-c3cc(Cl)nc(C#N)c3)cc2C#N)C[C@H]1C] |
| 674 | 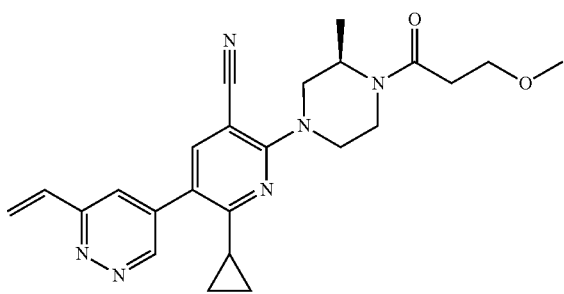 [SMILES: C=Cc1cc(-c2cc(C#N)c(N3CCN(C(=O)CCOC)[C@H](C)C3)nc2C2CC2)cnn1] |
| 675 | 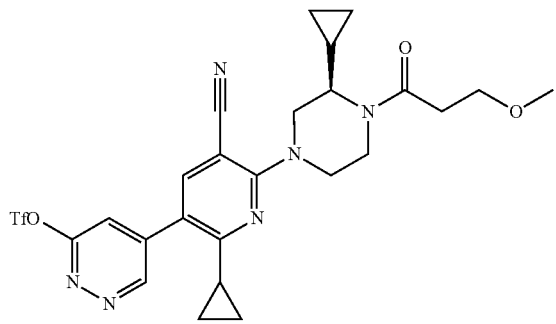 [SMILES: COCCC(=O)N1CCN(c2nc(C3CC3)c(-c3cnnc(OS(=O)(=O)C(F)(F)F)c3)cc2C#N)C[C@H]1C1CC1] |
| 676 | 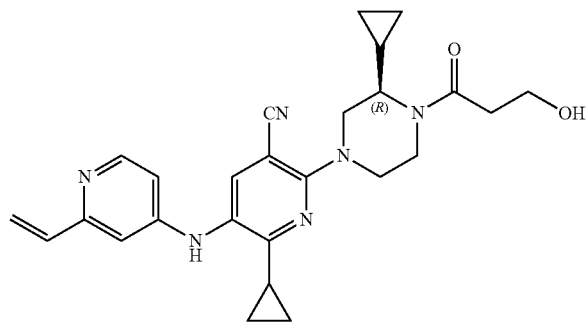 |

TABLE 5-continued
Exemplary Compounds of Formula I.
| Cpd # | Structure |
|---|---|
| 677 | 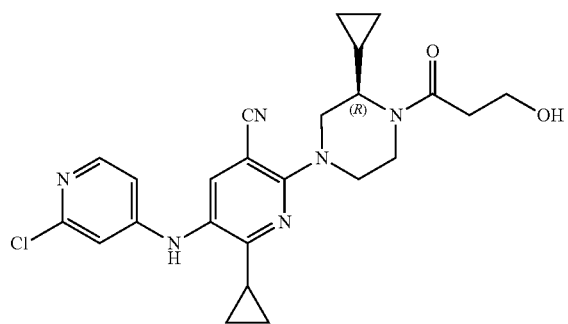 |
| 678 | 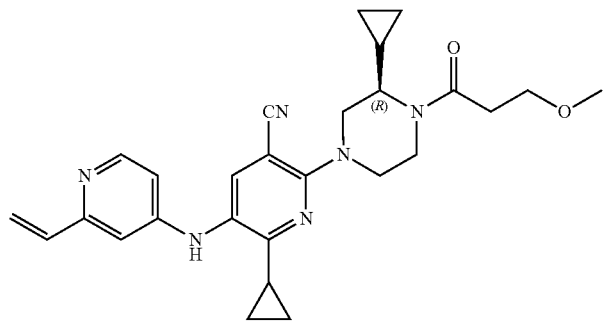 |
| 679 | 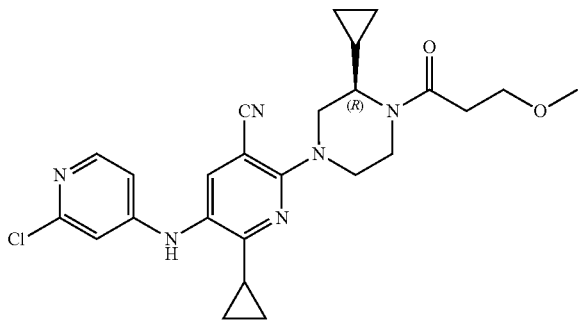 |
| 680 | 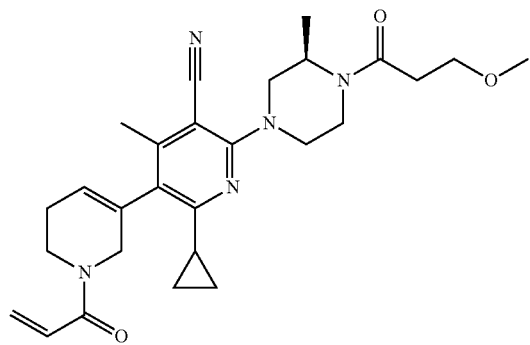 [SMILES: C=CC(=O)N1CCC=C(c2c(C3CC3)nc(N3CCN(C(=O)CCOC)[C@H](C)C3)c(C#N)c2C)C1] |

US 9,856,279 B2
253
254
TABLE 5-continued
Exemplary Compounds of Formula I.
| Cpd # | Structure |
|---|---|
| 681 | 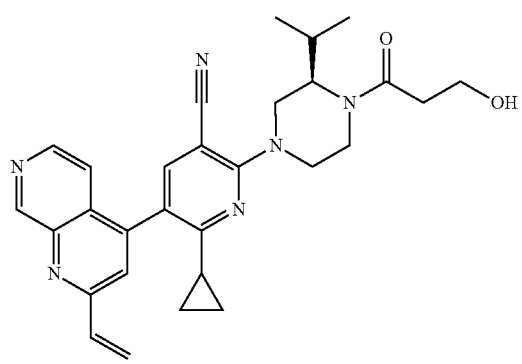 [SMILES: C=Cc1cc(-c2cc(C#N)c(N3CCN(C(=O)CCO)[C@H](C(C)C)C3)nc2C2CC2)c2ccncc2n1] |
| 682 | 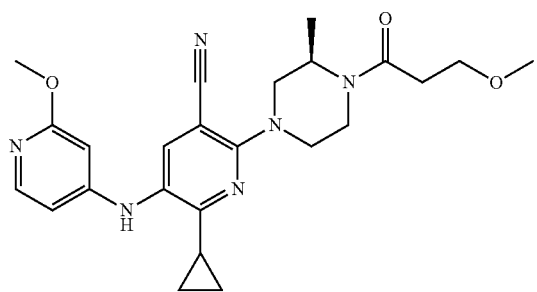 [SMILES: COCCC(=O)N1CCN(c2nc(C3CC3)c(Nc3ccnc(OC)c3)cc2C#N)C[C@H]1C] |
| 683 | 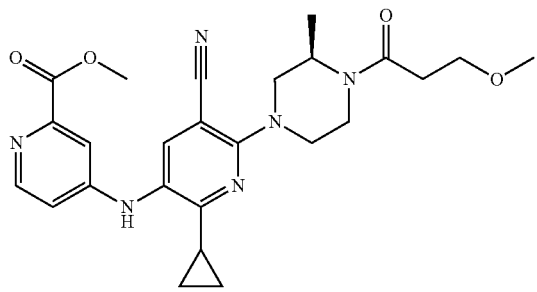 [SMILES: COCCC(=O)N1CCN(c2nc(C3CC3)c(Nc3ccnc(C(=O)OC)c3)cc2C#N)C[C@H]1C] |
| 684 | 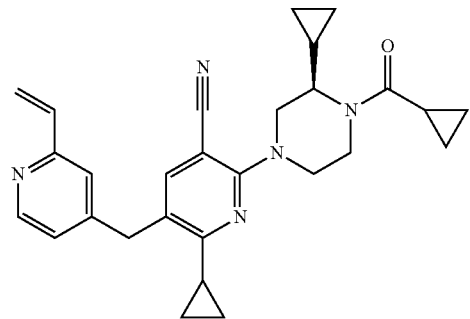 [SMILES: C=Cc1cc(Cc2cc(C#N)c(N3CCN(C(=O)C4CC4)[C@H](C4CC4)C3)nc2C2CC2)ccn1] |

TABLE 5-continued
Exemplary Compounds of Formula I.
| Cpd # | Structure |
|---|---|
| 685 | 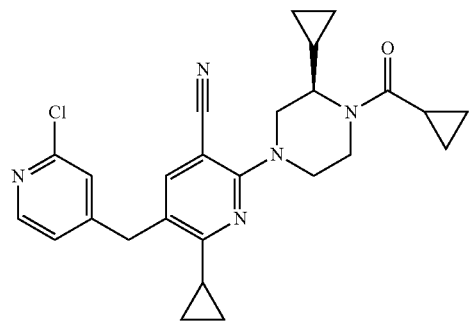 [SMILES: N#Cc1cc(Cc2ccnc(Cl)c2)c(C2CC2)nc1N1CCN(C(=O)C2CC2)[C@H](C2CC2)C1] |
| 686 | 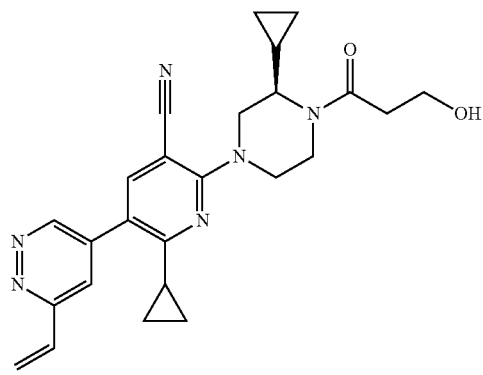 [SMILES: C=Cc1cc(-c2cc(C#N)c(N3CCN(C(=O)CCO)[C@H](C4CC4)C3)nc2C2CC2)cnn1] |
| 687 | 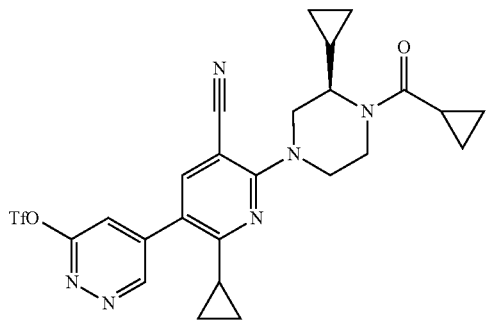 [SMILES: N#Cc1cc(-c2cnnc(OS(=O)(=O)C(F)(F)F)c2)c(C2CC2)nc1N1CCN(C(=O)C2CC2)[C@H](C2CC2)C1] |
| 688 | 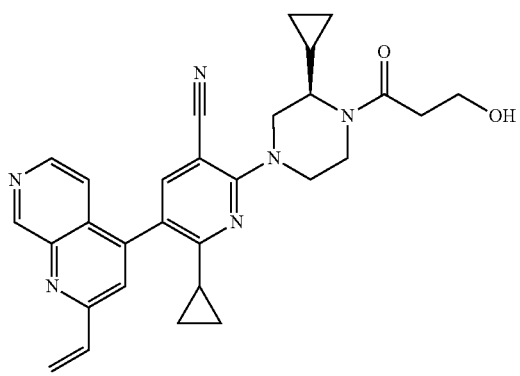 [SMILES: C=Cc1cc(-c2cc(C#N)c(N3CCN(C(=O)CCO)[C@H](C4CC4)C3)nc2C2CC2)c2ccncc2n1] |

TABLE 5-continued
Exemplary Compounds of Formula I.
| Cpd # | Structure |
|---|---|
| 689 | 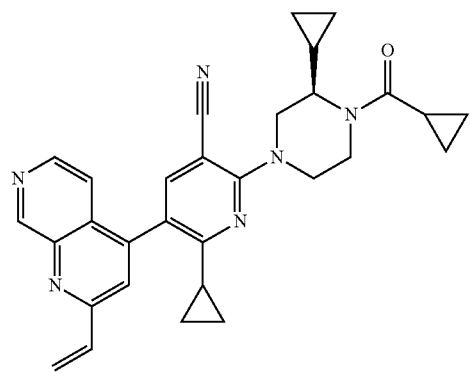 [SMILES: C=Cc1cc(-c2cc(C#N)c(N3CCN(C(=O)C4CC4)[C@H](C4CC4)C3)nc2C2CC2)c2ccncc2n1] |
| 690 | 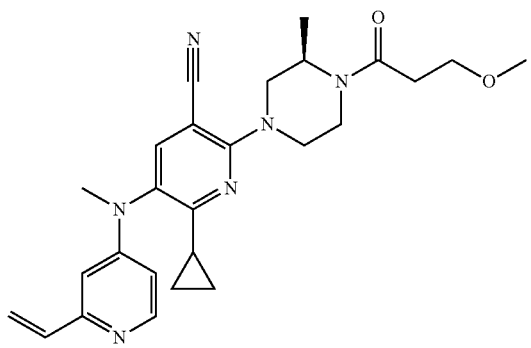 [SMILES: C=Cc1cc(N(C)c2cc(C#N)c(N3CCN(C(=O)CCOC)[C@H](C)C3)nc2C2CC2)ccn1] |
| 691 | 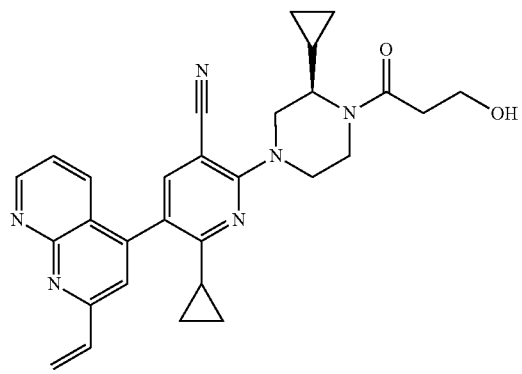 [SMILES: C=Cc1cc(-c2cc(C#N)c(N3CCN(C(=O)CCO)[C@H](C4CC4)C3)nc2C2CC2)c2cccnc2n1] |
| 692 | 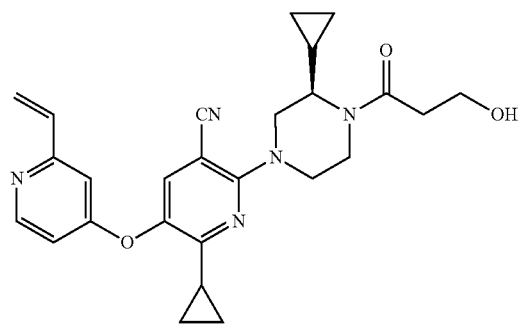 [SMILES: C=Cc1cc(Oc2cc(C#N)c(N3CCN(C(=O)CCO)[C@H](C4CC4)C3)nc2C2CC2)ccn1] |

TABLE 5-continued
Exemplary Compounds of Formula I.
| Cpd # | Structure |
|---|---|
| 693 | 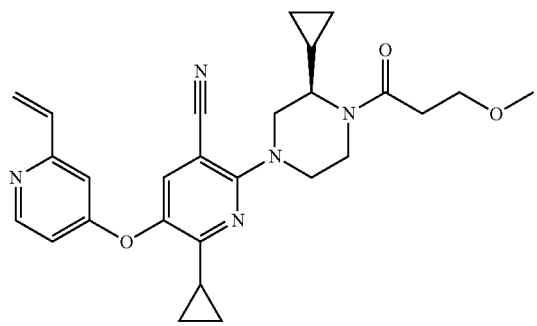 [SMILES: C=Cc1cc(Oc2cc(C#N)c(N3CCN(C(=O)CCOC)[C@H](C4CC4)C3)nc2C2CC2)ccn1] |
| 694 | 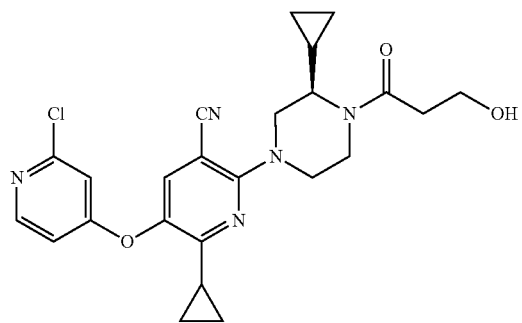 [SMILES: N#Cc1cc(Oc2ccnc(Cl)c2)c(C2CC2)nc1N1CCN(C(=O)CCO)[C@H](C2CC2)C1] |
| 695 | 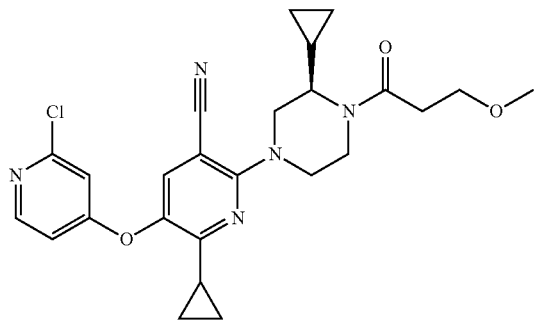 [SMILES: COCCC(=O)N1CCN(c2nc(C3CC3)c(Oc3ccnc(Cl)c3)cc2C#N)C[C@H]1C1CC1] |
| 696 | 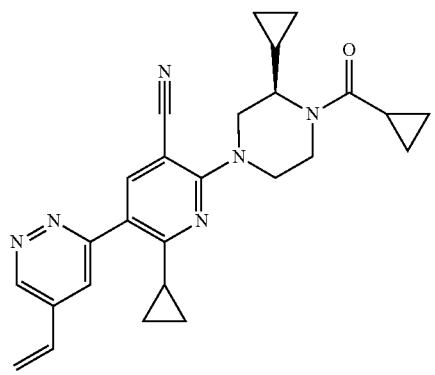 [SMILES: C=Cc1cnnc(-c2cc(C#N)c(N3CCN(C(=O)C4CC4)[C@H](C4CC4)C3)nc2C2CC2)c1] |

TABLE 5-continued
Exemplary Compounds of Formula I.
| Cpd # | Structure |
|---|---|
| 697 | 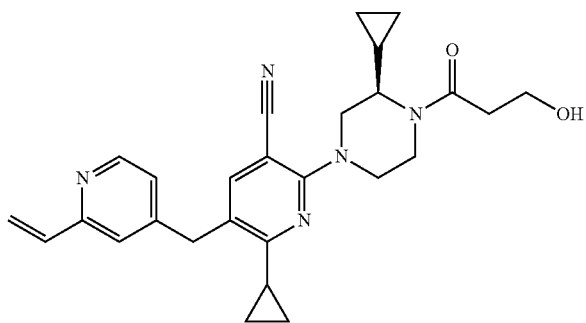 [SMILES: C=Cc1cc(Cc2cc(C#N)c(N3CCN(C(=O)CCO)[C@H](C4CC4)C3)nc2C2CC2)ccn1] |
| 698 | 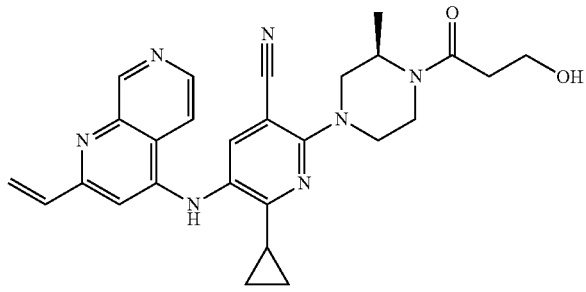 [SMILES: C=Cc1cc(Nc2cc(C#N)c(N3CCN(C(=O)CCO)[C@H](C)C3)nc2C2CC2)c2ccncc2n1] |
| 699 | 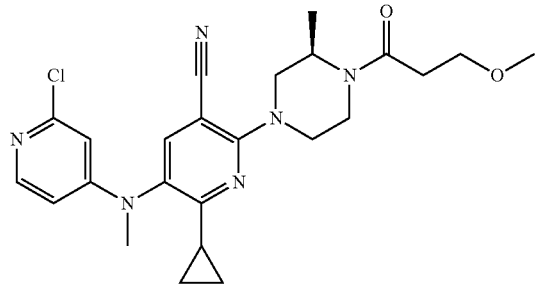 [SMILES: COCCC(=O)N1CCN(c2nc(C3CC3)c(N(C)c3ccnc(Cl)c3)cc2C#N)C[C@H]1C] |
| 700 | 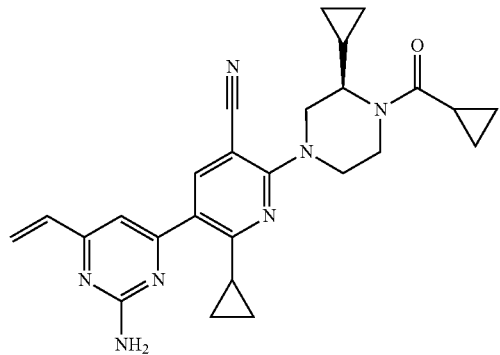 [SMILES: C=Cc1cc(-c2cc(C#N)c(N3CCN(C(=O)C4CC4)[C@H](C4CC4)C3)nc2C2CC2)nc(N)n1] |

TABLE 5-continued
Exemplary Compounds of Formula I.
| Cpd # | Structure |
|---|---|
| 701 | 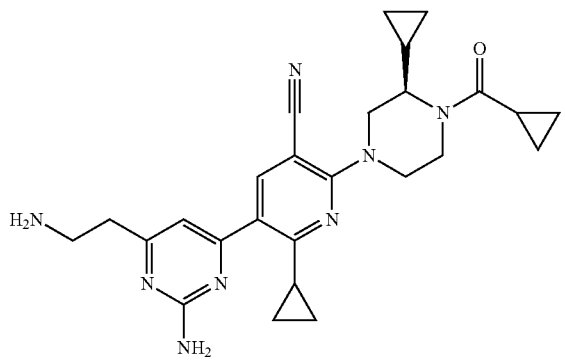 [SMILES: N#Cc1cc(-c2cc(CCN)nc(N)n2)c(C2CC2)nc1N1CCN(C(=O)C2CC2)[C@H](C2CC2)C1] |
| 702 | 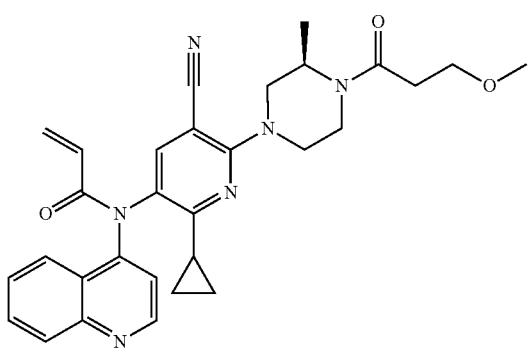 [SMILES: C=CC(=O)N(c1cc(C#N)c(N2CCN(C(=O)CCOC)[C@H](C)C2)nc1C1CC1)c1ccnc2ccccc12] |
| 703 | 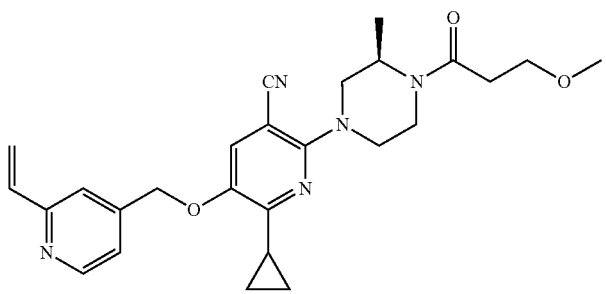 [SMILES: C=Cc1cc(COc2cc(C#N)c(N3CCN(C(=O)CCOC)[C@H](C)C3)nc2C2CC2)ccn1] |
| 704 | 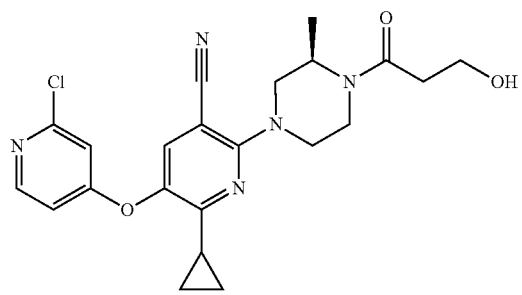 [SMILES: C[C@@H]1CN(c2nc(C3CC3)c(Oc3ccnc(Cl)c3)cc2C#N)CCN1C(=O)CCO] |

TABLE 5-continued
Exemplary Compounds of Formula I.
| Cpd # | Structure |
|---|---|
| 705 | 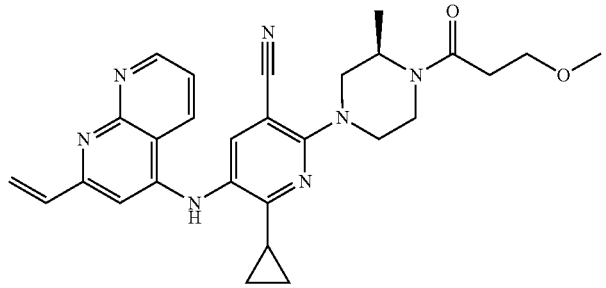 [SMILES: C=Cc1cc(Nc2cc(C#N)c(N3CCN(C(=O)CCOC)[C@H](C)C3)nc2C2CC2)c2cccnc2n1] |
| 706 | 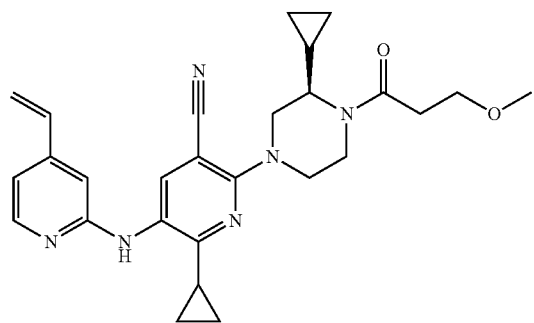 [SMILES: C=Cc1ccnc(Nc2cc(C#N)c(N3CCN(C(=O)CCOC)[C@H](C4CC4)C3)nc2C2CC2)c1] |
| 707 | 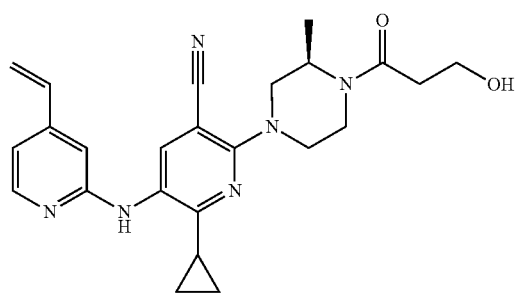 [SMILES: C=Cc1ccnc(Nc2cc(C#N)c(N3CCN(C(=O)CCO)[C@H](C)C3)nc2C2CC2)c1] |
| 708 | 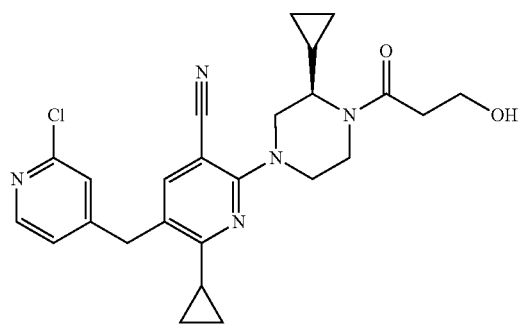 [SMILES: N#Cc1cc(Cc2ccnc(Cl)c2)c(C2CC2)nc1N1CCN(C(=O)CCO)[C@H](C2CC2)C1] |

TABLE 5-continued
Exemplary Compounds of Formula I.
| Cpd # | Structure |
|---|---|
| 709 | 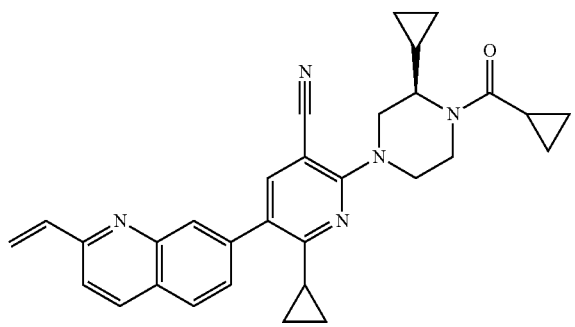 [SMILES: C=Cc1ccc2ccc(-c3cc(C#N)c(N4CCN(C(=O)C5CC5)[C@H](C5CC5)C4)nc3C3CC3)cc2n1] |
| 710 | 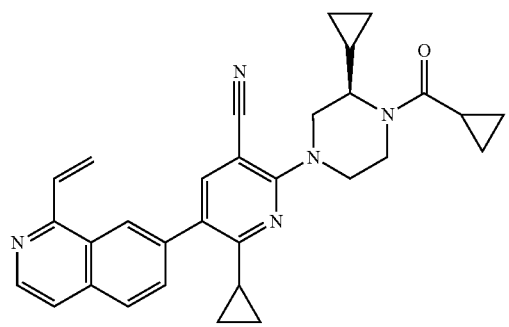 [SMILES: C=Cc1nccc2ccc(-c3cc(C#N)c(N4CCN(C(=O)C5CC5)[C@H](C5CC5)C4)nc3C3CC3)cc12] |
| 711 | 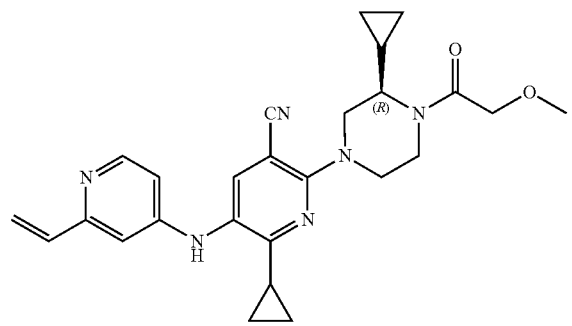 |
| 712 | 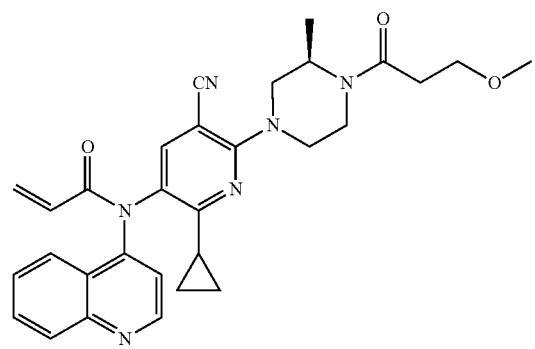 [SMILES: C=CC(=O)N(c1cc(C#N)c(N2CCN(C(=O)CCOC)[C@H](C)C2)nc1C1CC1)c1ccnc2ccccc12] |

TABLE 5-continued
Exemplary Compounds of Formula I.
| Cpd # | Structure |
|---|---|
| 713 | 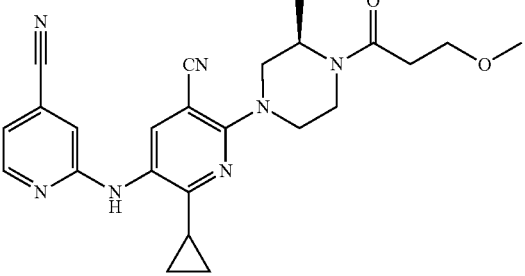 |
| 714 | 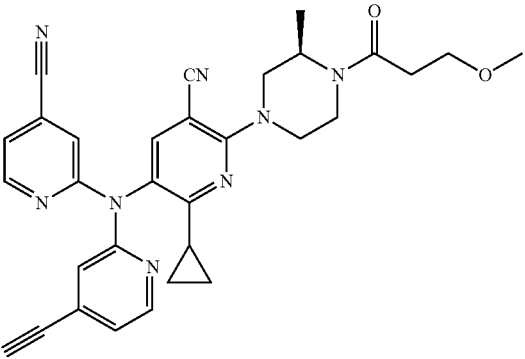 [SMILES: C#Cc1ccnc(N(c2cc(C#N)ccn2)c2cc(C#N)c(N3CCN(C(=O)CCOC)[C@H](C)C3)nc2C2CC2)c1] |
| 715 | 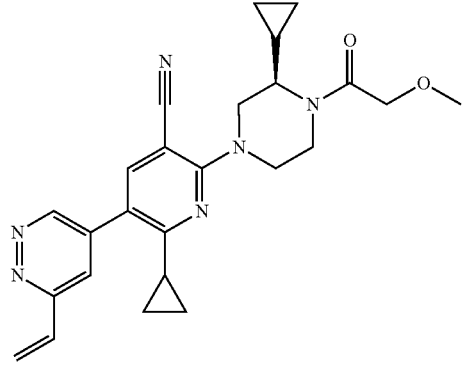 [SMILES: C=Cc1cc(-c2cc(C#N)c(N3CCN(C(=O)COC)[C@H](C4CC4)C3)nc2C2CC2)cnn1] |
| 716 | 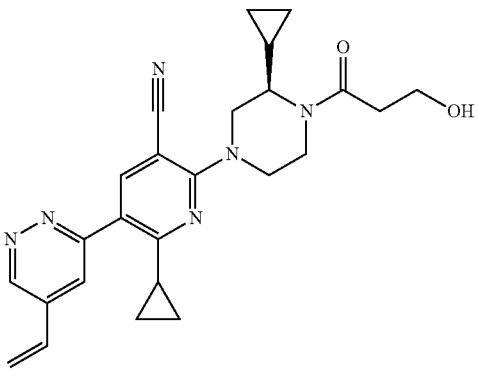 [SMILES: C=Cc1cnnc(-c2cc(C#N)c(N3CCN(C(=O)CCO)[C@H](C4CC4)C3)nc2C2CC2)c1] |

US 9,856,279 B2
TABLE 5-continued
Exemplary Compounds of Formula I.
| Cpd # | Structure |
|---|---|
| 717 | 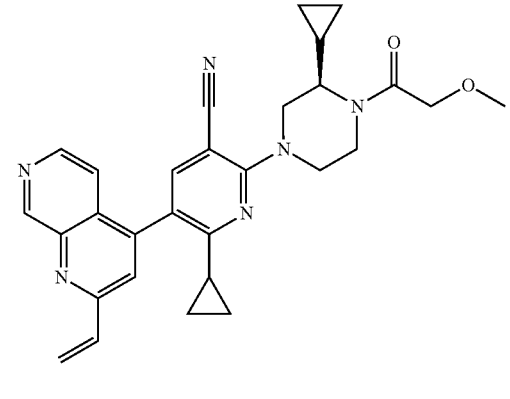 [SMILES: C=Cc1cc(-c2cc(C#N)c(N3CCN(C(=O)COC)[C@H](C4CC4)C3)nc2C2CC2)c2ccncc2n1] |
| 718 | 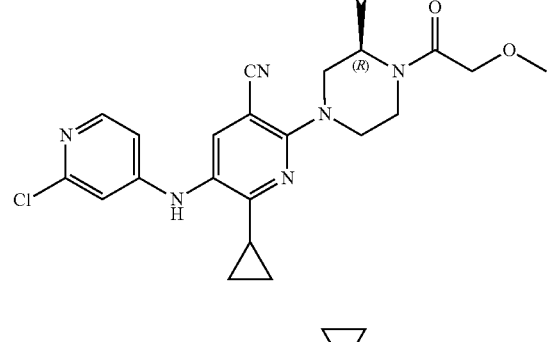 |
| 719 | 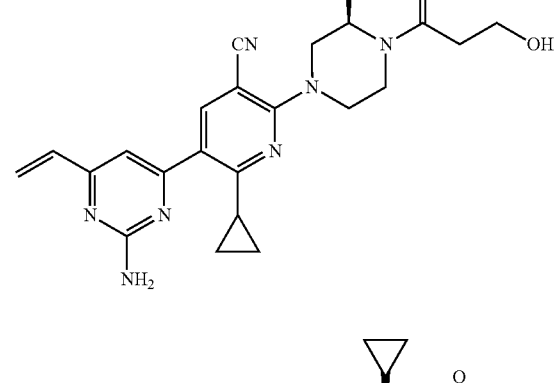 |
| 720 | 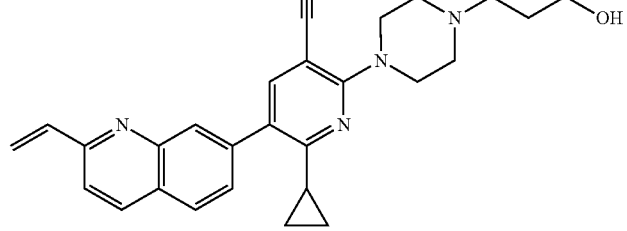 |

US 9,856,279 B2
273
274
TABLE 5-continued
Exemplary Compounds of Formula I.
| Cpd # | Structure |
|---|---|
| 721 | 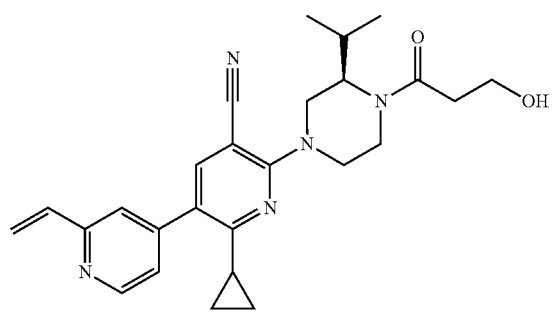 [SMILES: C=Cc1cc(-c2cc(C#N)c(N3CCN(C(=O)CCO)[C@H](C(C)C)C3)nc2C2CC2)ccn1] |
| 722 | 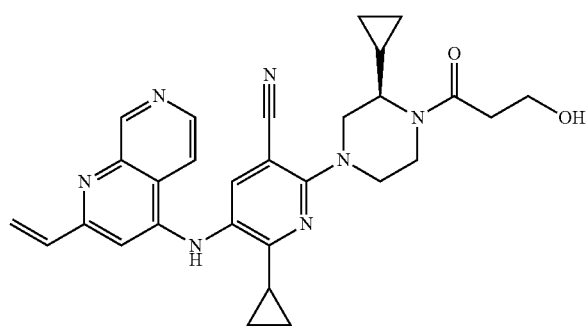 [SMILES: C=Cc1cc(Nc2cc(C#N)c(N3CCN(C(=O)CCO)[C@H](C4CC4)C3)nc2C2CC2)c2ccncc2n1] |
| 723 | 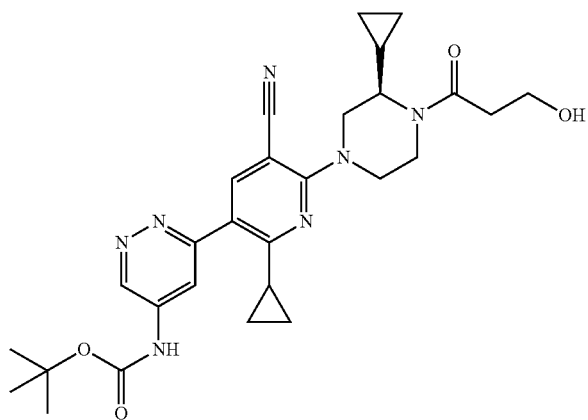 [SMILES: CC(C)(C)OC(=O)Nc1cnnc(-c2cc(C#N)c(N3CCN(C(=O)CCO)[C@H](C4CC4)C3)nc2C2CC2)c1] |
| 724 | 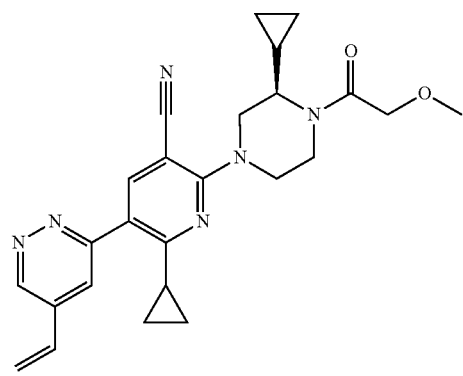 [SMILES: C=Cc1cnnc(-c2cc(C#N)c(N3CCN(C(=O)COC)[C@H](C4CC4)C3)nc2C2CC2)c1] |

TABLE 5-continued
Exemplary Compounds of Formula I.
| Cpd # | Structure |
|---|---|
| 725 | 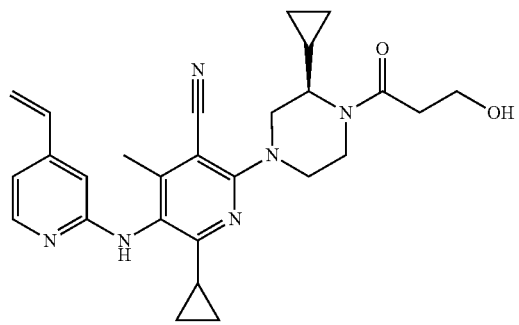 [SMILES: C=Cc1ccnc(Nc2c(C3CC3)nc(N3CCN(C(=O)CCO)[C@H](C4CC4)C3)c(C#N)c2C)c1] |
| 726 | 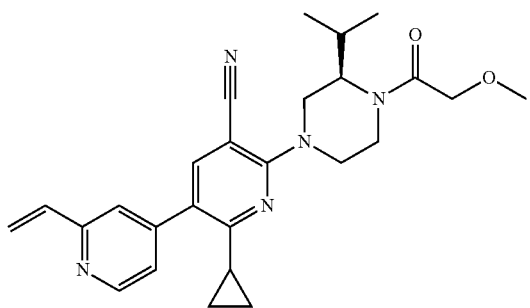 [SMILES: C=Cc1cc(-c2cc(C#N)c(N3CCN(C(=O)COC)[C@H](C(C)C)C3)nc2C2CC2)ccn1] |
| 727 | 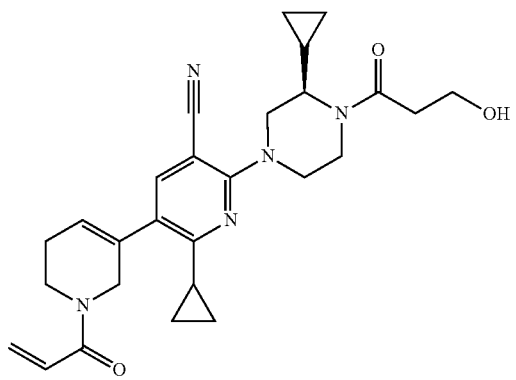 [SMILES: C=CC(=O)N1CCC=C(c2cc(C#N)c(N3CCN(C(=O)CCO)[C@H](C4CC4)C3)nc2C2CC2)C1] |
| 728 | 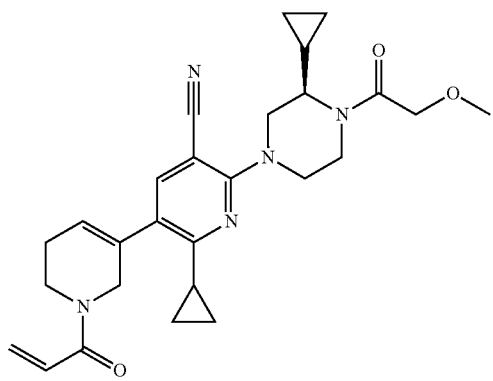 [SMILES: C=CC(=O)N1CCC=C(c2cc(C#N)c(N3CCN(C(=O)COC)[C@H](C4CC4)C3)nc2C2CC2)C1] |

TABLE 5-continued
Exemplary Compounds of Formula I.
| Cpd # | Structure |
|---|---|
| 729 | 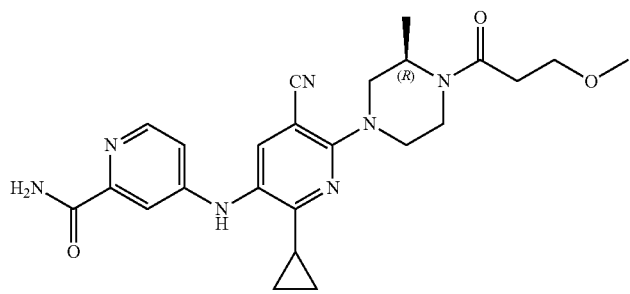 |
| 730 | 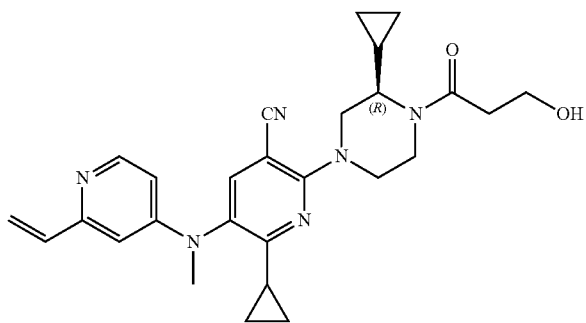 |
| 731 | 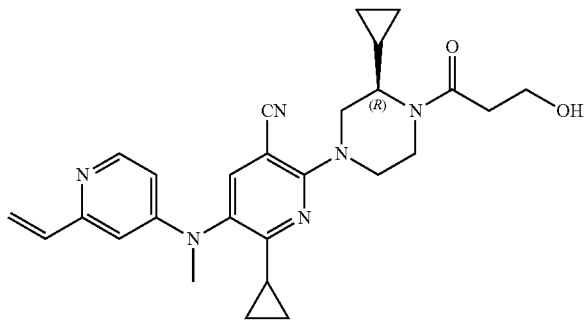 |
| 732 | 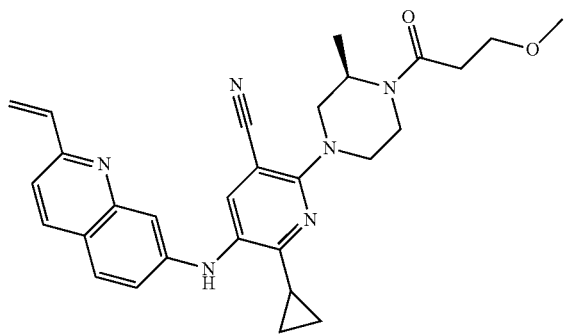 [SMILES: C=Cc1ccc2ccc(Nc3cc(C#N)c(N4CCN(C(=O)CCOC)[C@H](C)C4)nc3C3CC3)cc2n1] |

TABLE 5-continued
Exemplary Compounds of Formula I.
| Cpd # | Structure |
|---|---|
| 733 | 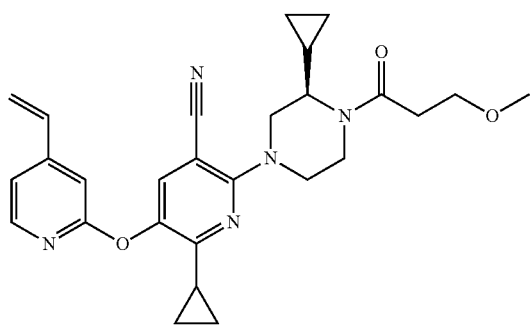 [SMILES: C=Cc1ccnc(Oc2cc(C#N)c(N3CCN(C(=O)CCOC)[C@H](C4CC4)C3)nc2C2CC2)c1] |
| 734 | 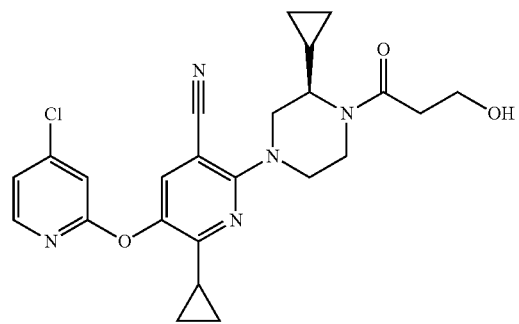 [SMILES: N#Cc1cc(Oc2cc(Cl)ccn2)c(C2CC2)nc1N1CCN(C(=O)CCO)[C@H](C2CC2)C1] |
| 735 | 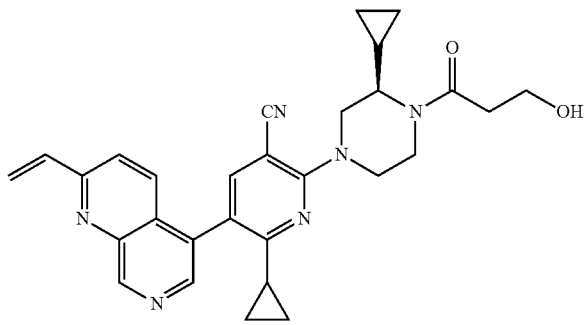 [SMILES: C=Cc1ccc2c(-c3cc(C#N)c(N4CCN(C(=O)CCO)[C@H](C5CC5)C4)nc3C3CC3)cncc2n1] |
| 736 | 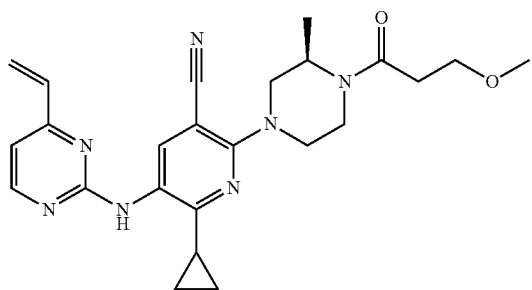 [SMILES: C=Cc1ccnc(Nc2cc(C#N)c(N3CCN(C(=O)CCOC)[C@H](C)C3)nc2C2CC2)n1] |

TABLE 5-continued

Exemplary Compounds of Formula I.

| Cpd # | Structure |
|---|---|
| 737 | 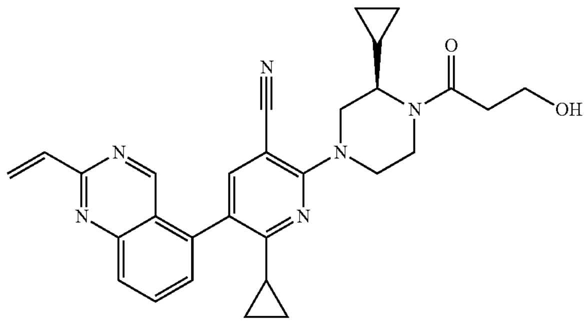 [SMILES: C=Cc1ncc2c(-c3cc(C#N)c(N4CCN(C(=O)CCO)[C@H](C5CC5)C4)nc3C3CC3)cccc2n1] |
| 738 | 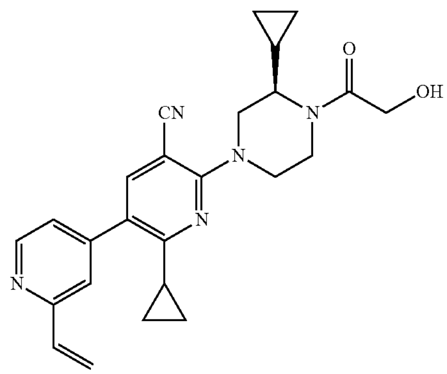 [SMILES: C=Cc1cc(-c2cc(C#N)c(N3CCN(C(=O)CO)[C@H](C4CC4)C3)nc2C2CC2)ccn1] |
| 739 | 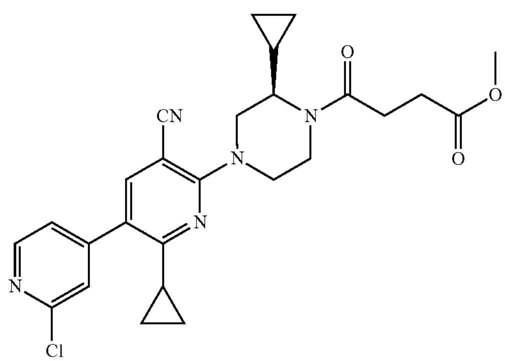 [SMILES: COC(=O)CCC(=O)N1CCN(c2nc(C3CC3)c(-c3ccnc(Cl)c3)cc2C#N)C[C@H]1C1CC1] |
| 740 | 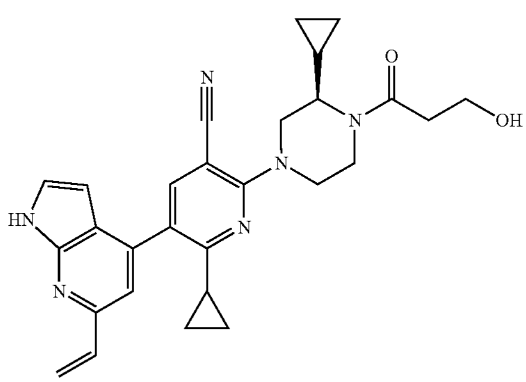 [SMILES: C=Cc1cc(-c2cc(C#N)c(N3CCN(C(=O)CCO)[C@H](C4CC4)C3)nc2C2CC2)c2cc[nH]c2n1] |

TABLE 5-continued
Exemplary Compounds of Formula I.
| Cpd # | Structure |
|---|---|
| 741 | 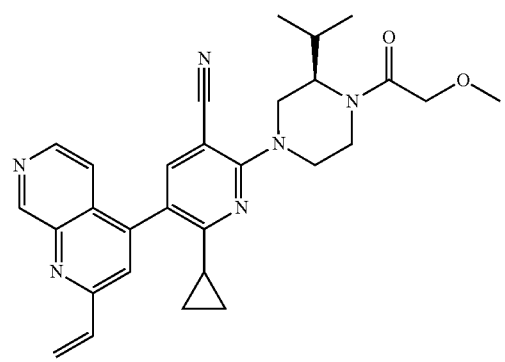 [SMILES: C=Cc1cc(-c2cc(C#N)c(N3CCN(C(=O)COC)[C@H](C(C)C)C3)nc2C2CC2)c2ccncc2n1] |
| 742 | 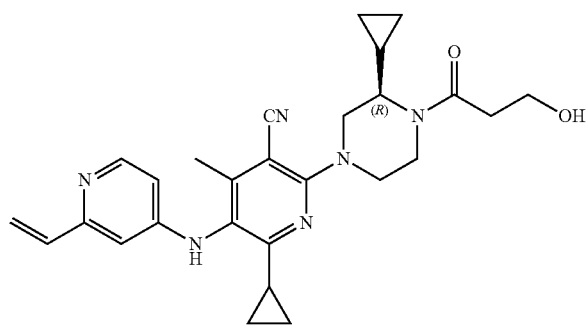 |
| 743 | 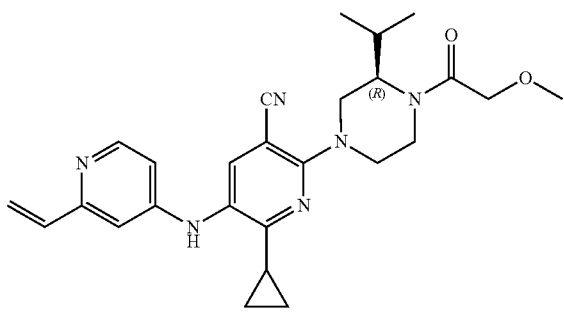 |
| 744 | 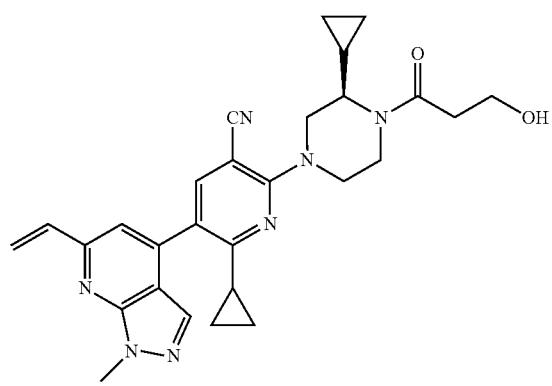 [SMILES: C=Cc1cc(-c2cc(C#N)c(N3CCN(C(=O)CCO)[C@H](C4CC4)C3)nc2C2CC2)c2cnn(C)c2n1] |

TABLE 5-continued
Exemplary Compounds of Formula I.
| Cpd # | Structure |
|---|---|
| 745 | 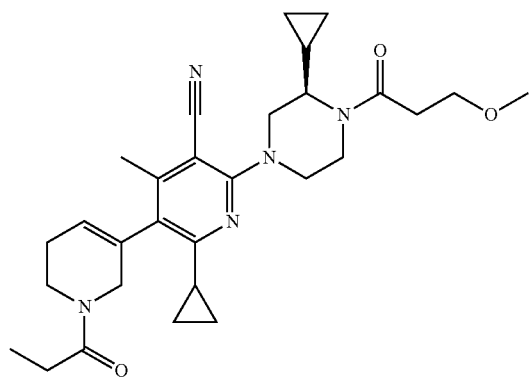 [SMILES: CCC(=O)N1CCC=C(c2c(C3CC3)nc(N3CCN(C(=O)CCOC)[C@H](C4CC4)C3)c(C#N)c2C)C1] |
| 746 | 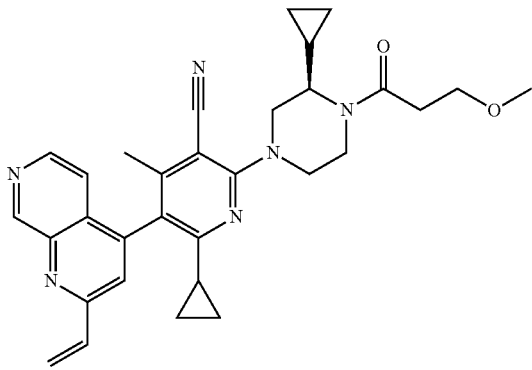 [SMILES: C=Cc1cc(-c2c(C3CC3)nc(N3CCN(C(=O)CCOC)[C@H](C4CC4)C3)c(C#N)c2C)c2ccncc2n1] |
| 747 | 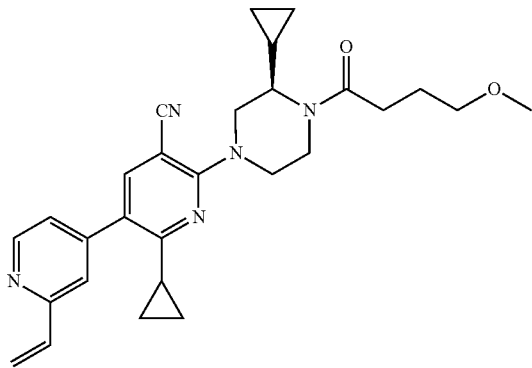 [SMILES: C=Cc1cc(-c2cc(C#N)c(N3CCN(C(=O)CCCOC)[C@H](C4CC4)C3)nc2C2CC2)ccn1] |
| 748 | 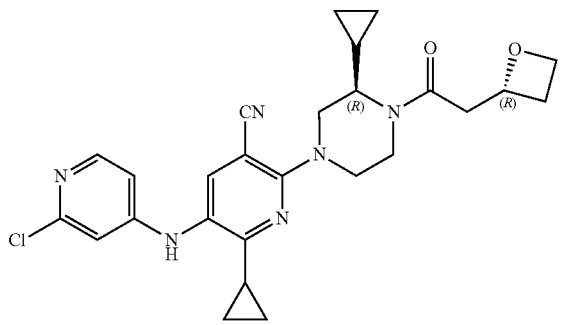 |

TABLE 5-continued
Exemplary Compounds of Formula I.
| Cpd # | Structure |
|---|---|
| 749 | 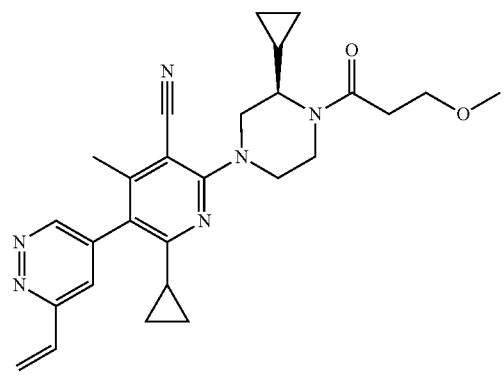 [SMILES: C=Cc1cc(-c2c(C3CC3)nc(N3CCN(C(=O)CCOC)[C@H](C4CC4)C3)c(C#N)c2C)cnn1] |
| 750 | 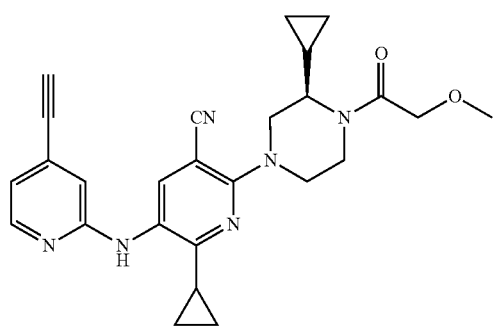 [SMILES: C#Cc1ccnc(Nc2cc(C#N)c(N3CCN(C(=O)COC)[C@H](C4CC4)C3)nc2C2CC2)c1] |
| 751 | 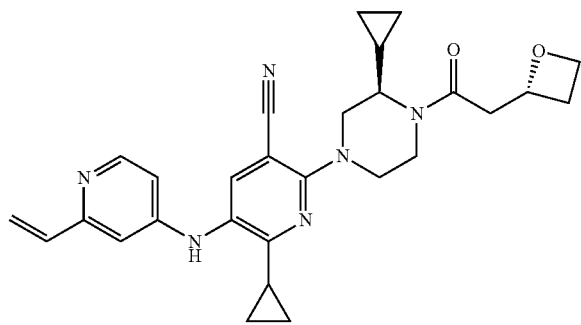 [SMILES: C=Cc1cc(Nc2cc(C#N)c(N3CCN(C(=O)C[C@H]4CCO4)[C@H](C4CC4)C3)nc2C2CC2)ccn1] |
| 752 | 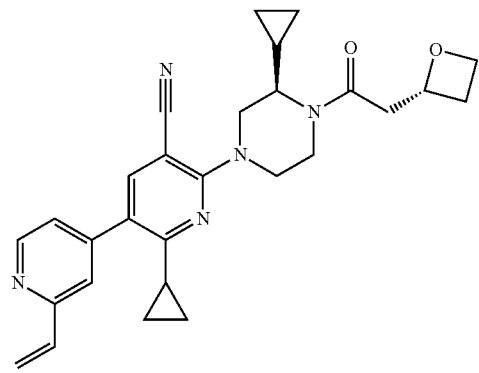 [SMILES: C=Cc1cc(-c2cc(C#N)c(N3CCN(C(=O)C[C@H]4CCO4)[C@H](C4CC4)C3)nc2C2CC2)ccn1] |

US 9,856,279 B2
TABLE 5-continued
Exemplary Compounds of Formula I.
| Cpd # | Structure |
|---|---|
| 753 | 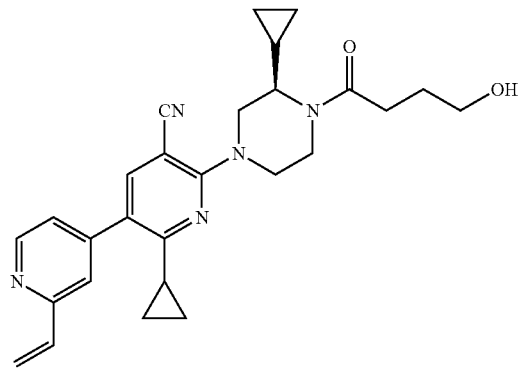 [SMILES: C=Cc1cc(-c2cc(C#N)c(N3CCN(C(=O)CCCO)[C@H](C4CC4)C3)nc2C2CC2)ccn1] |
| 754 | 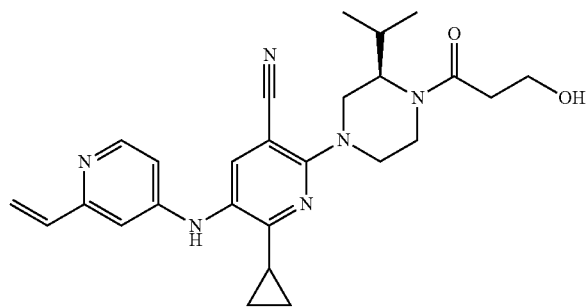 [SMILES: C=Cc1cc(Nc2cc(C#N)c(N3CCN(C(=O)CCO)[C@H](C(C)C)C3)nc2C2CC2)ccn1] |
| 755 | 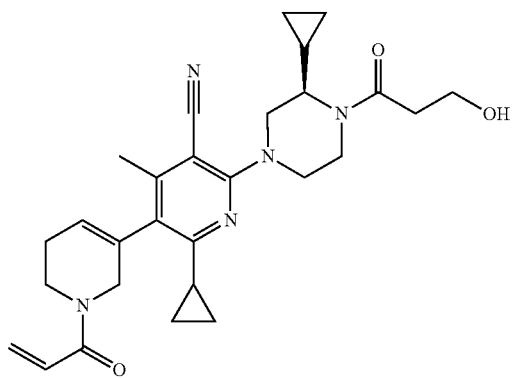 [SMILES: C=CC(=O)N1CCC=C(c2c(C3CC3)nc(N3CCN(C(=O)CCO)[C@H](C4CC4)C3)c(C#N)c2C)C1] |
| 756 | 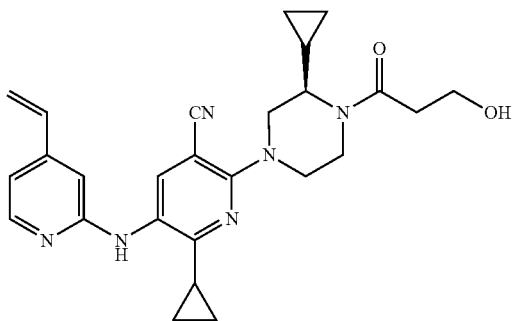 [SMILES: C=Cc1ccnc(Nc2cc(C#N)c(N3CCN(C(=O)CCO)[C@H](C4CC4)C3)nc2C2CC2)c1] |

TABLE 5-continued
Exemplary Compounds of Formula I.
| Cpd # | Structure |
|---|---|
| 757 | 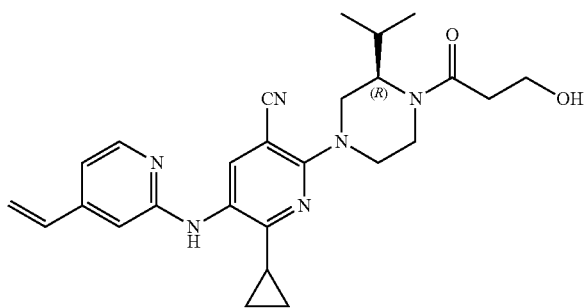 |
| 758 | 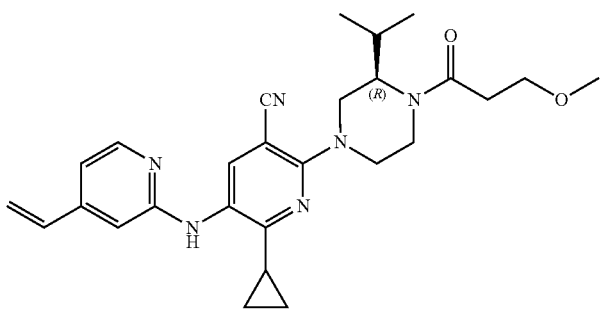 |
| 759 | 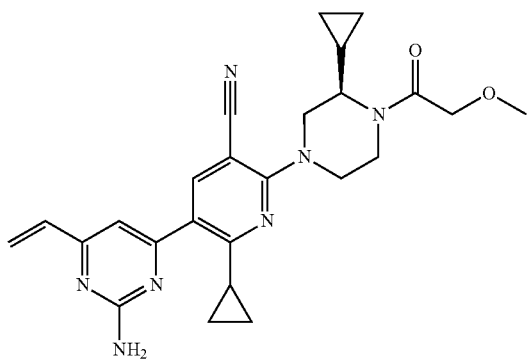 [SMILES: C=Cc1cc(-c2cc(C#N)c(N3CCN(C(=O)COC)[C@H](C4CC4)C3)nc2C2CC2)nc(N)n1] |
| 760 | 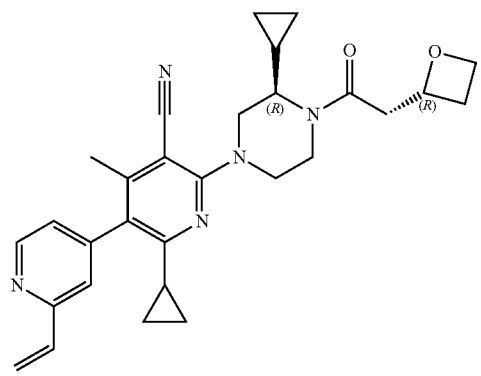 |

TABLE 5-continued

Exemplary Compounds of Formula I.

| Cpd # | Structure |
|---|---|
| 761 | 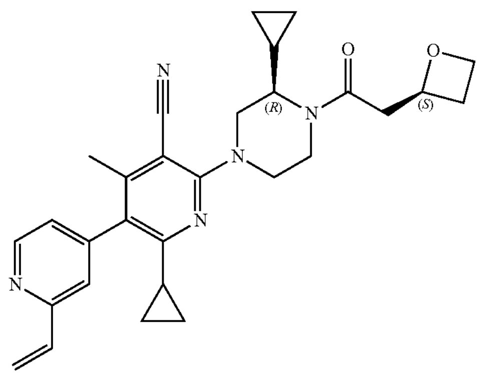 |
| 762 | 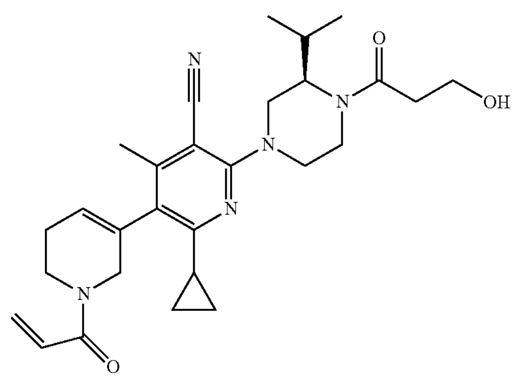 [SMILES: C=CC(=O)N1CCC=C(c2c(C3CC3)nc(N3CCN(C(=O)CCO)[C@H](C(C)C)C3)c(C#N)c2C)C1] |
| 763 | 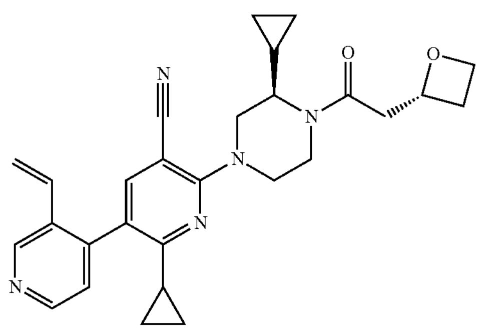 [SMILES: C=Cc1cnccc1-c1cc(C#N)c(N2CCN(C(=O)C[C@H]3CCO3)[C@H](C3CC3)C2)nc1C1CC1] |
| 764 | 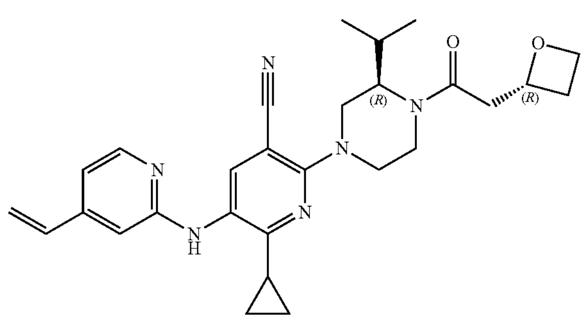 |

TABLE 5-continued
Exemplary Compounds of Formula I.
| Cpd # | Structure |
|---|---|
| 765 | 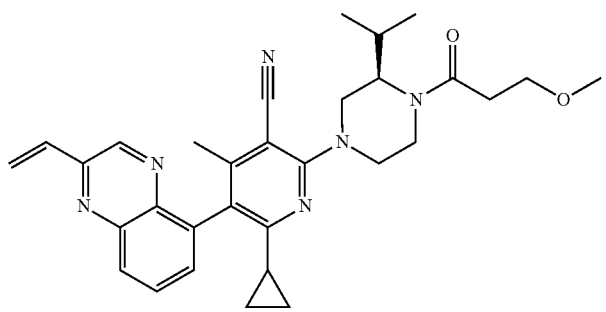 [SMILES: C=Cc1cnc2c(-c3c(C4CC4)nc(N4CCN(C(=O)CCOC)[C@H](C(C)C)C4)c(C#N)c3C)cccc2n1] |
| 766 | 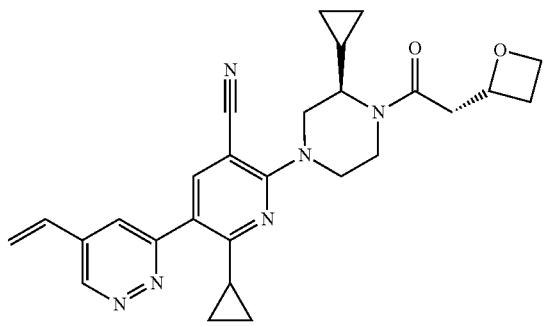 |
| 767 | 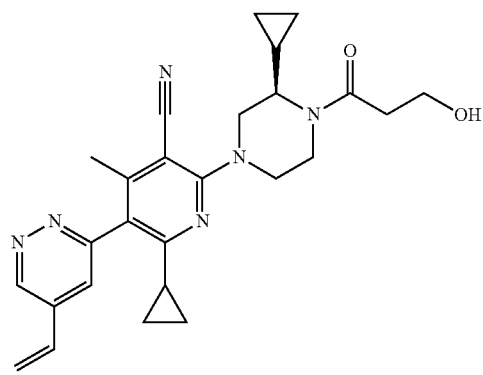 [SMILES: C=Cc1cnnc(-c2c(C3CC3)nc(N3CCN(C(=O)CCO)[C@H](C4CC4)C3)c(C#N)c2C)c1] |
| 768 | 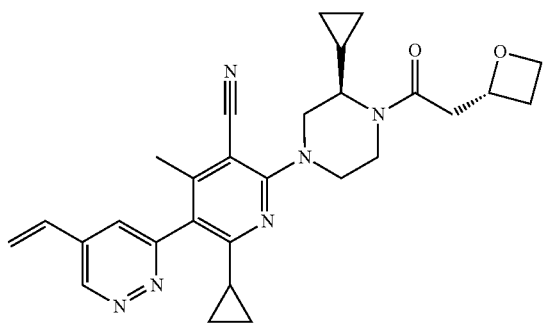 [SMILES: C=Cc1cnnc(-c2c(C3CC3)nc(N3CCN(C(=O)C[C@H]4CCO4)[C@H](C4CC4)C3)c(C#N)c2C)c1] |

TABLE 5-continued

Exemplary Compounds of Formula I.

| Cpd # | Structure |
|---|---|
| 769 | 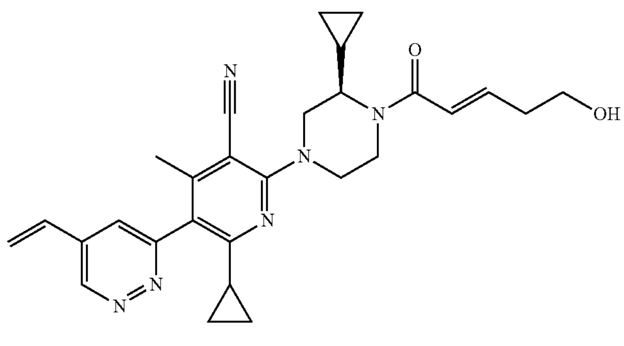 [SMILES: C=Cc1cnnc(-c2c(C3CC3)nc(N3CCN(C(=O)/C=C/CCO)[C@H](C4CC4)C3)c(C#N)c2C)c1] |
| 770 | 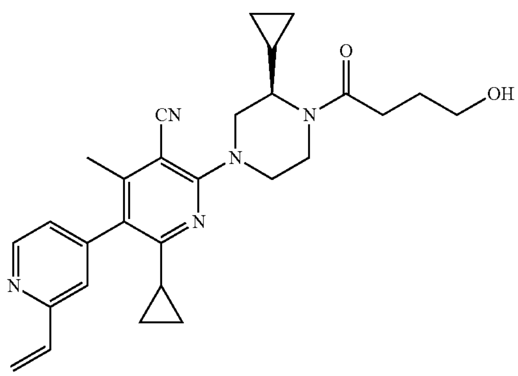 [SMILES: C=Cc1cc(-c2c(C3CC3)nc(N3CCN(C(=O)CCCO)[C@H](C4CC4)C3)c(C#N)c2C)ccn1] |
| 771 | 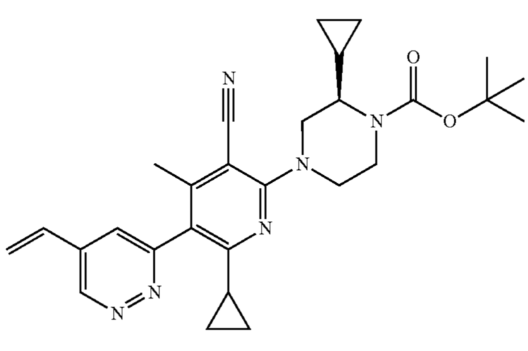 [SMILES: C=Cc1cnnc(-c2c(C3CC3)nc(N3CCN(C(=O)OC(C)(C)C)[C@H](C4CC4)C3)c(C#N)c2C)c1] |
| 772 | 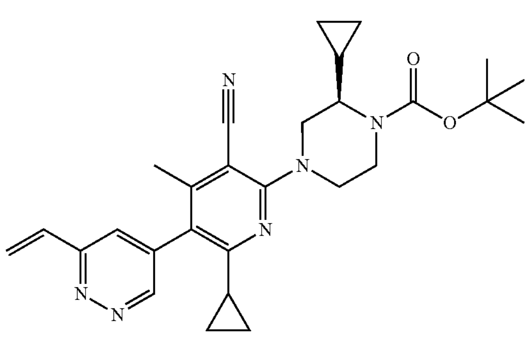 [SMILES: C=Cc1cc(-c2c(C3CC3)nc(N3CCN(C(=O)OC(C)(C)C)[C@H](C4CC4)C3)c(C#N)c2C)cnn1] |

TABLE 5-continued
Exemplary Compounds of Formula I.
| Cpd # | Structure |
|---|---|
| 773 | 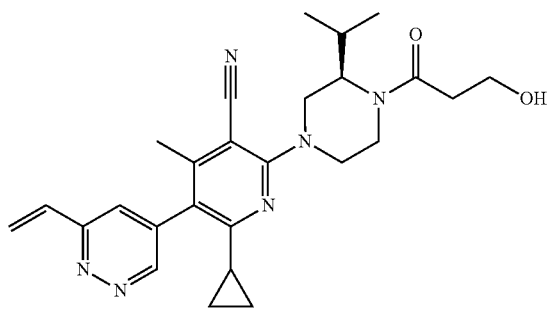 [SMILES: C=Cc1cc(-c2c(C3CC3)nc(N3CCN(C(=O)CCO)[C@H](C(C)C)C3)c(C#N)c2C)cnn1] |
| 774 | 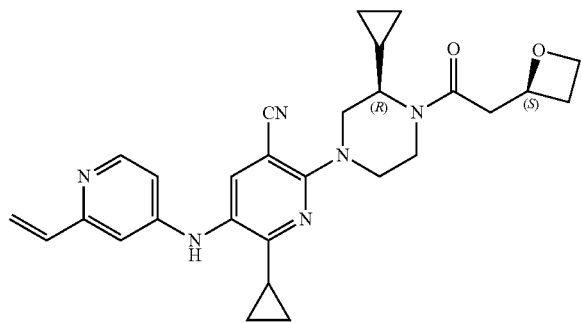 |
| 775 | 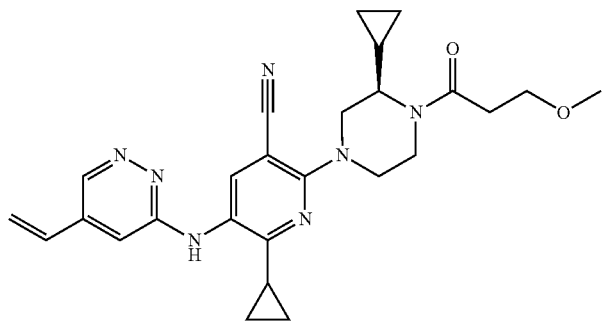 [SMILES: C=Cc1cnnc(Nc2cc(C#N)c(N3CCN(C(=O)CCOC)[C@H](C4CC4)C3)nc2C2CC2)c1] |
| 776 | 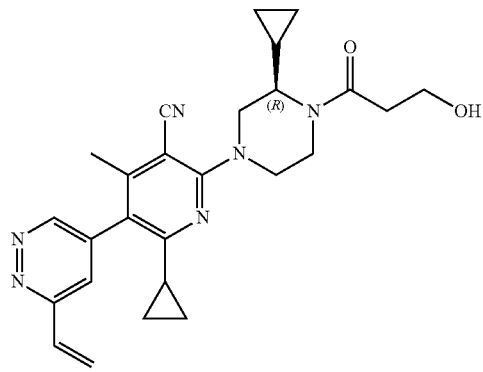 |

TABLE 5-continued
Exemplary Compounds of Formula I.
| Cpd # | Structure |
|---|---|
| 777 | 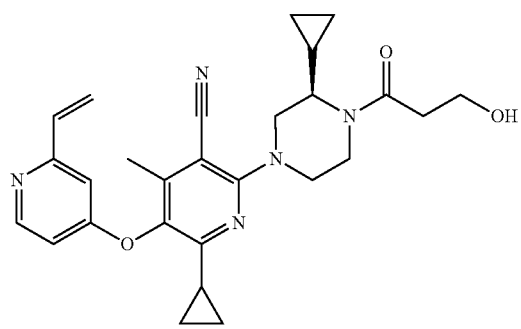 [SMILES: C=Cc1cc(Oc2c(C3CC3)nc(N3CCN(C(=O)CCO)[C@H](C4CC4)C3)c(C#N)c2C)ccn1] |
| 778 | 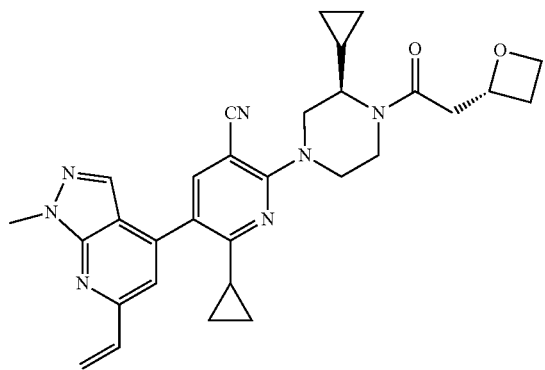 [SMILES: C=Cc1cc(-c2cc(C#N)c(N3CCN(C(=O)C[C@H]4CCO4)[C@H](C4CC4)C3)nc2C2CC2)c2cnn(C)c2n1] |
| 779 | 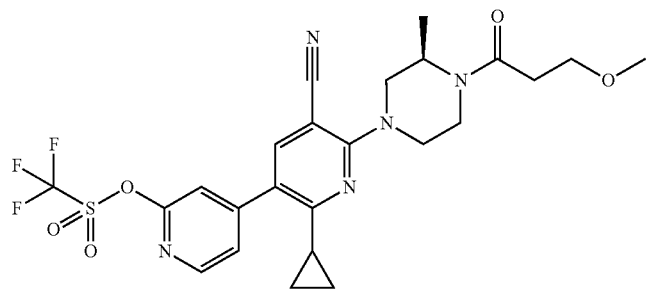 [SMILES: COCCC(=O)N1CCN(c2nc(C3CC3)c(-c3ccnc(OS(=O)(=O)C(F)(F)F)c3)cc2C#N)C[C@H]1C] |
| 780 | 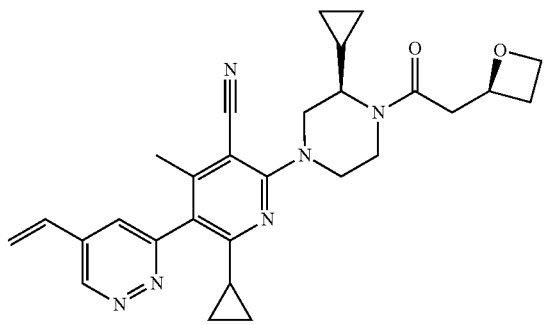 [SMILES: C=Cc1cnnc(-c2c(C3CC3)nc(N3CCN(C(=O)C[C@@H]4CCO4)[C@H](C4CC4)C3)c(C#N)c2C)c1] |

TABLE 5-continued
Exemplary Compounds of Formula I.
| Cpd # | Structure |
|---|---|
| 781 | 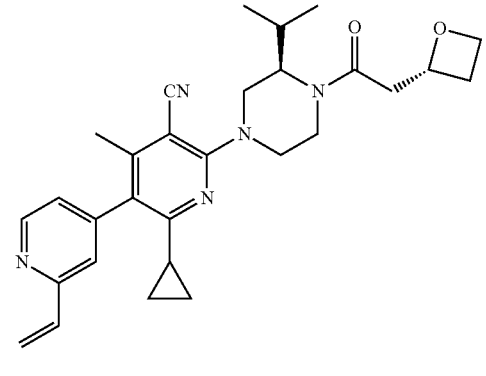 [SMILES: C=Cc1cc(-c2c(C3CC3)nc(N3CCN(C(=O)C[C@H]4CCO4)[C@H](C(C)C)C3)c(C#N)c2C)ccn1] |
| 782 | 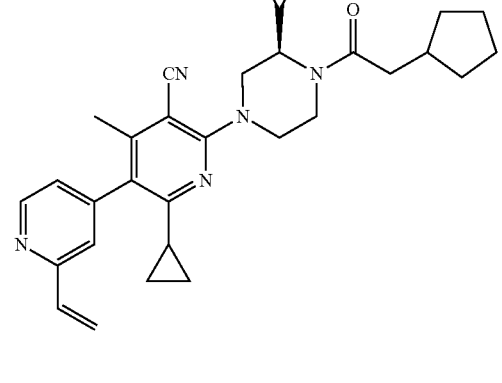 |
| 783 | 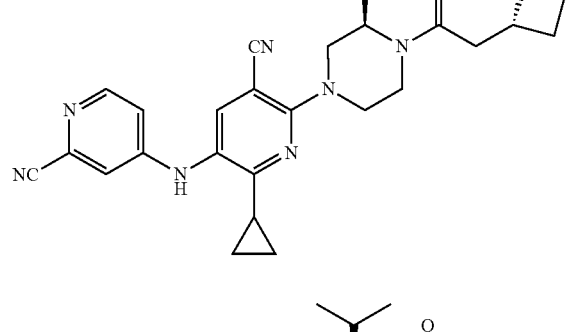 |
| 784 | 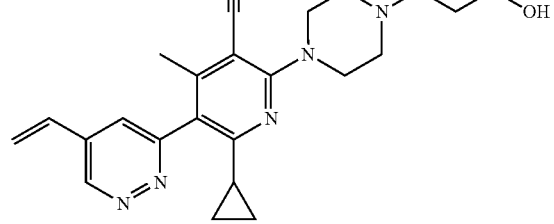 |

US 9,856,279 B2
TABLE 5-continued
Exemplary Compounds of Formula I.
| Cpd # | Structure |
|---|---|
| 785 | 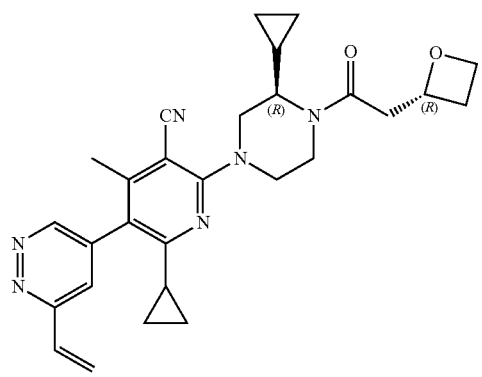 |
| 786 | 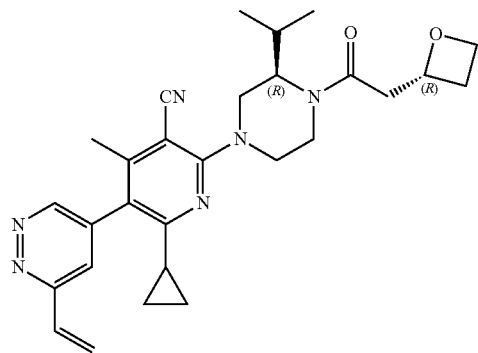 |
| 787 | 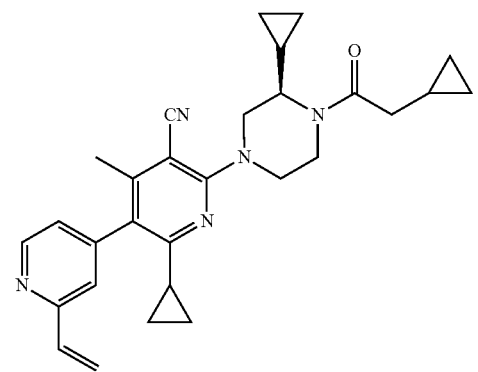 [SMILES: C=Cc1cc(-c2c(C3CC3)nc(N3CCN(C(=O)CC4CC4)[C@H](C4CC4)C3)c(C#N)c2C)ccn1] |
| 788 | 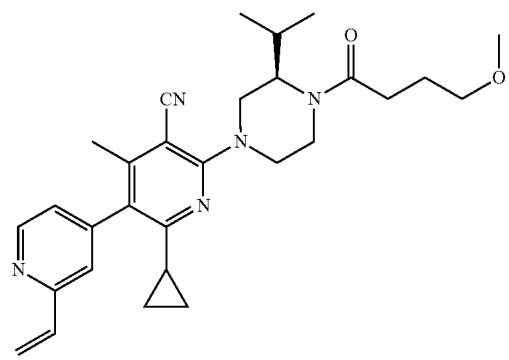 [SMILES: C=Cc1cc(-c2c(C3CC3)nc(N3CCN(C(=O)CCCOC)[C@H](C(C)C)C3)c(C#N)c2C)ccn1] |

TABLE 5-continued
Exemplary Compounds of Formula I.
| Cpd # | Structure |
|---|---|
| 789 | 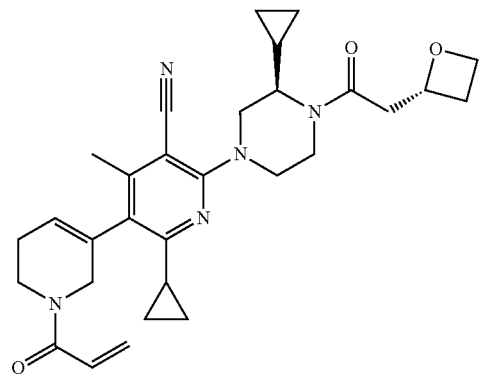 [SMILES: C=CC(=O)N1CCC=C(c2c(C3CC3)nc(N3CCN(C(=O)C[C@H]4CCO4)[C@H](C4CC4)C3)c(C#N)c2C)C1] |
| 790 | 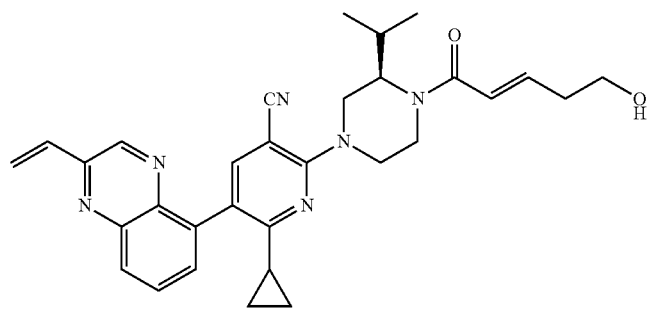 [SMILES: C=Cc1cnc2c(-c3cc(C#N)c(N4CCN(C(=O)/C=C/CCO)[C@H](C(C)C)C4)nc3C3CC3)cccc2n1] |
| 791 | 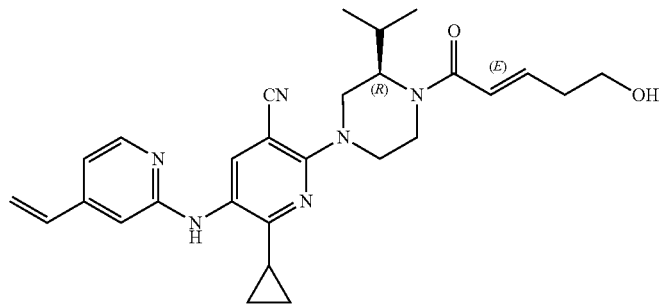 |
| 792 | 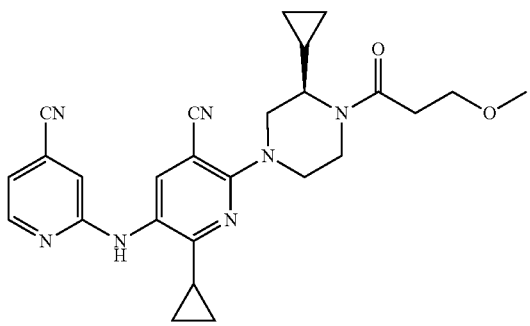 [SMILES: COCCC(=O)N1CCN(c2nc(C3CC3)c(Nc3cc(C#N)ccn3)cc2C#N)C[C@H]1C1CC1] |

TABLE 5-continued
Exemplary Compounds of Formula I.
| Cpd # | Structure |
|---|---|
| 793 | 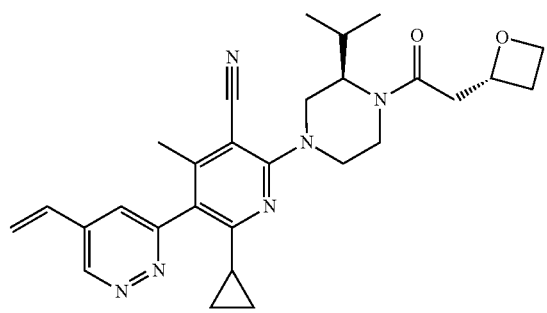 [SMILES: C=Cc1cnnc(-c2c(C3CC3)nc(N3CCN(C(=O)C[C@H]4CCO4)[C@H](C(C)C)C3)c(C#N)c2C)c1] |
| 794 | 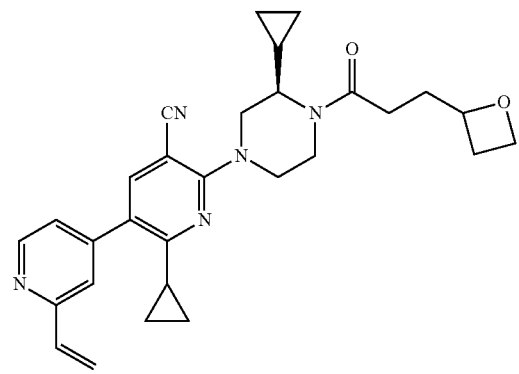 [SMILES: C=Cc1cc(-c2cc(C#N)c(N3CCN(C(=O)CCC4CCO4)[C@H](C4CC4)C3)nc2C2CC2)ccn1] |
| 795 | 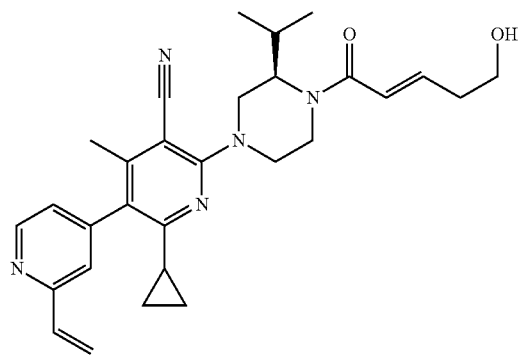 [SMILES: C=Cc1cc(-c2c(C3CC3)nc(N3CCN(C(=O)/C=C/CCO)[C@H](C(C)C)C3)c(C#N)c2C)ccn1] |
| 796 | 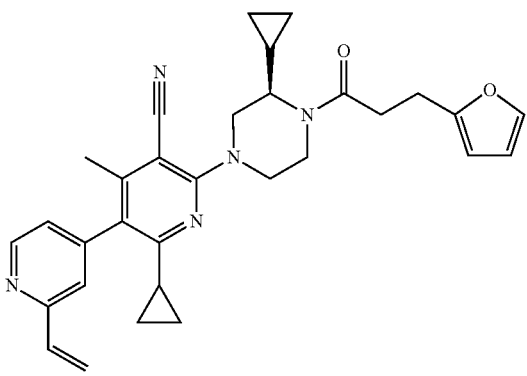 [SMILES: C=Cc1cc(-c2c(C3CC3)nc(N3CCN(C(=O)CCc4ccco4)[C@H](C4CC4)C3)c(C#N)c2C)ccn1] |

TABLE 5-continued
Exemplary Compounds of Formula I.
| Cpd # | Structure |
|---|---|
| 797 | 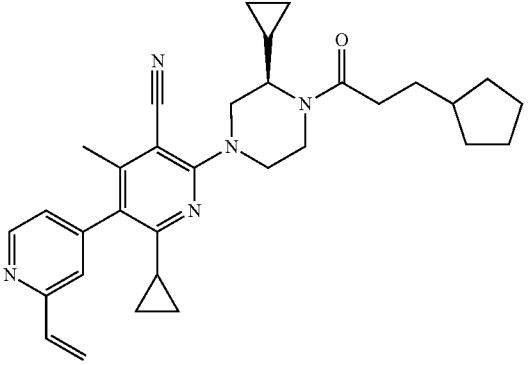 [SMILES: C=Cc1cc(-c2c(C3CC3)nc(N3CCN(C(=O)CCC4CCCC4)[C@H](C4CC4)C3)c(C#N)c2C)ccn1] |
| 798 | 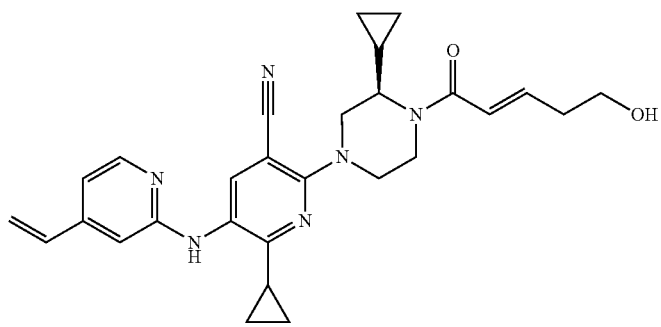 [SMILES: C=Cc1ccnc(Nc2cc(C#N)c(N3CCN(C(=O)/C=C/CCO)[C@H](C4CC4)C3)nc2C2CC2)c1] |
| 799 | 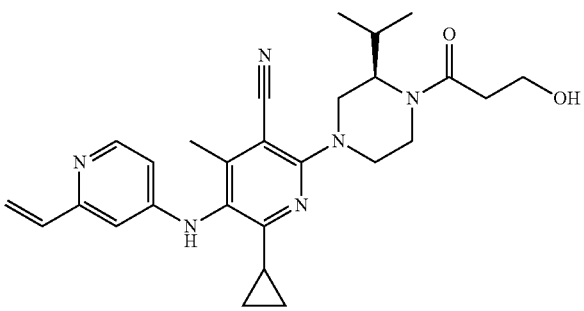 [SMILES: C=Cc1cc(Nc2c(C3CC3)nc(N3CCN(C(=O)CCO)[C@H](C(C)C)C3)c(C#N)c2C)ccn1] |
| 800 | 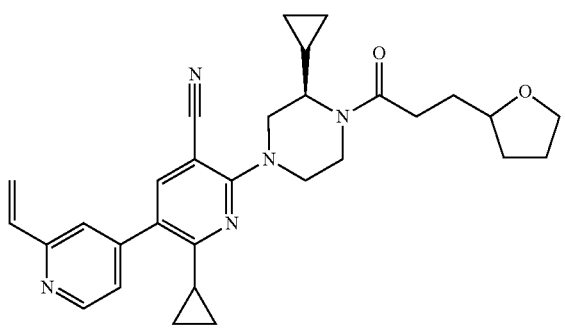 [SMILES: C=Cc1cc(-c2cc(C#N)c(N3CCN(C(=O)CCC4CCCO4)[C@H](C4CC4)C3)nc2C2CC2)ccn1] |

TABLE 5-continued

Exemplary Compounds of Formula I.

| Cpd # | Structure |
|---|---|
| 801 | 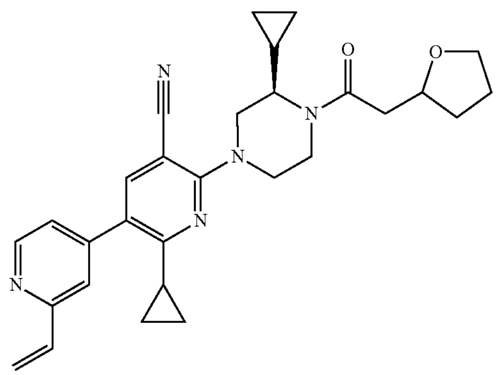 [SMILES: C=Cc1cc(-c2cc(C#N)c(N3CCN(C(=O)CC4CCCO4)[C@H](C4CC4)C3)nc2C2CC2)ccn1] |
| 802 | 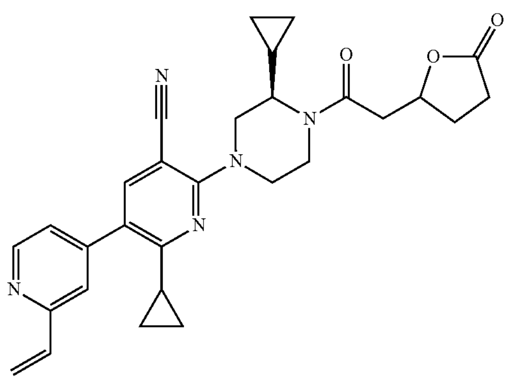 |
| 803 | 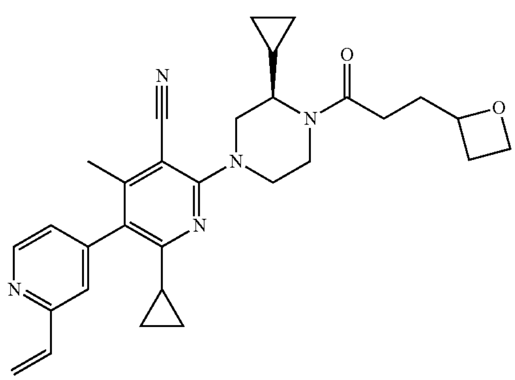 [SMILES: C=Cc1cc(-c2c(C3CC3)nc(N3CCN(C(=O)CCC4CCO4)[C@H](C4CC4)C3)c(C#N)c2C)ccn1] |
| 804 | 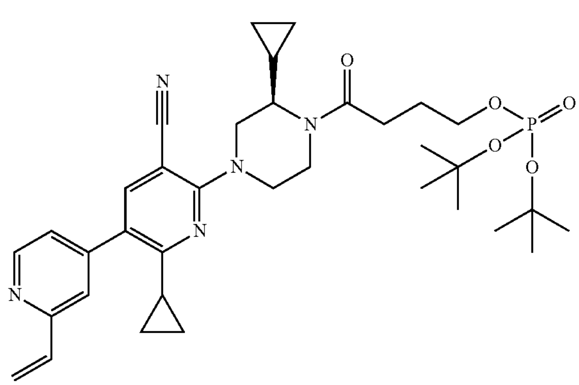 [SMILES: C=Cc1cc(-c2cc(C#N)c(N3CCN(C(=O)CCCOP(=O)(OC(C)(C)C)OC(C)(C)C)[C@H](C4CC4)C3)nc2C2CC2)ccn1] |

TABLE 5-continued
Exemplary Compounds of Formula I.
| Cpd # | Structure |
|---|---|
| 805 | 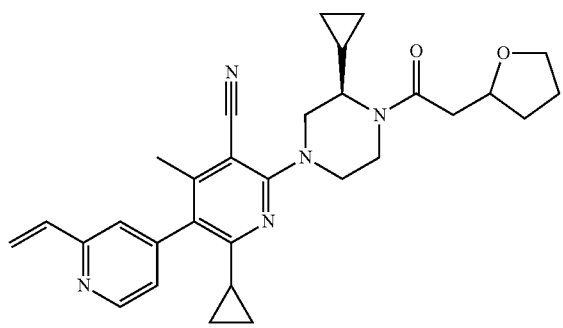 [SMILES: C=Cc1cc(-c2c(C3CC3)nc(N3CCN(C(=O)CC4CCCO4)[C@H](C4CC4)C3)c(C#N)c2C)ccn1] |
| 806 | 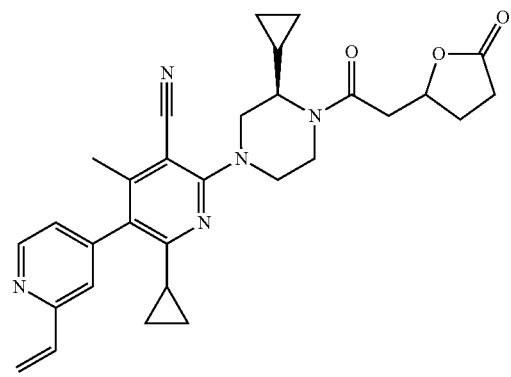 |
| 807 | 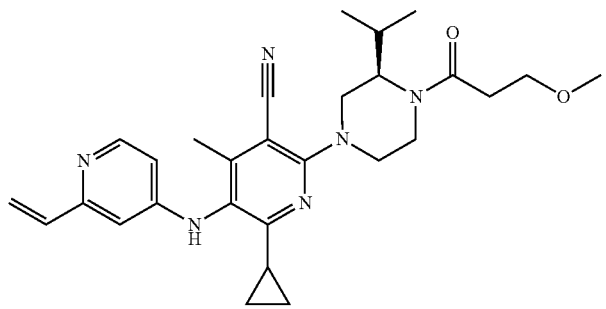 [SMILES: C=Cc1cc(Nc2c(C3CC3)nc(N3CCN(C(=O)CCOC)[C@H](C(C)C)C3)c(C#N)c2C)ccn1] |
| 808 | 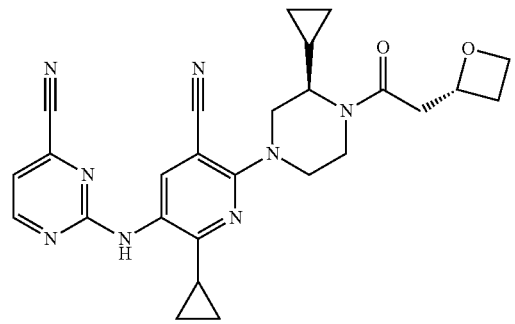 [SMILES: N#Cc1ccnc(Nc2cc(C#N)c(N3CCN(C(=O)C[C@H]4CCO4)[C@H](C4CC4)C3)nc2C2CC2)n1] |

TABLE 5-continued
Exemplary Compounds of Formula I.
| Cpd # | Structure |
|---|---|
| 809 | 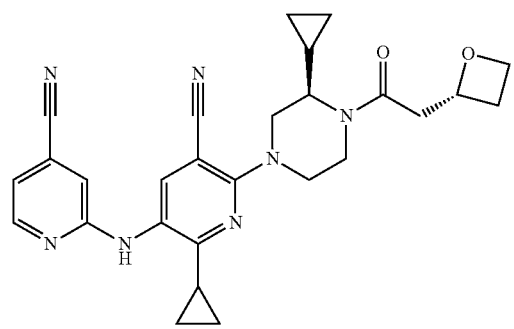 [SMILES: N#Cc1ccnc(Nc2cc(C#N)c(N3CCN(C(=O)C[C@H]4CCO4)[C@H](C4CC4)C3)nc2C2CC2)c1] |
| 810 | 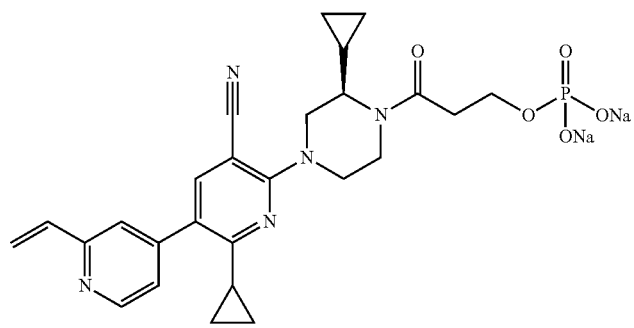 |
| 811 | 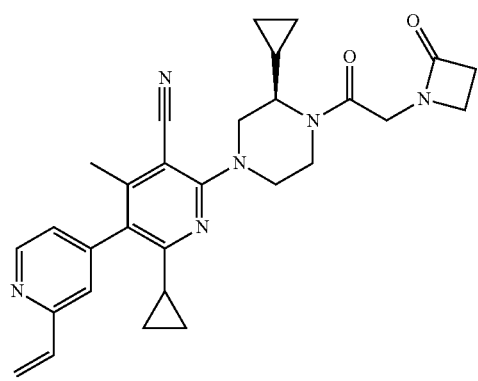 [SMILES: C=Cc1cc(-c2c(C3CC3)nc(N3CCN(C(=O)CN4CCC4=O)[C@H](C4CC4)C3)c(C#N)c2C)ccn1] |
| 812 | 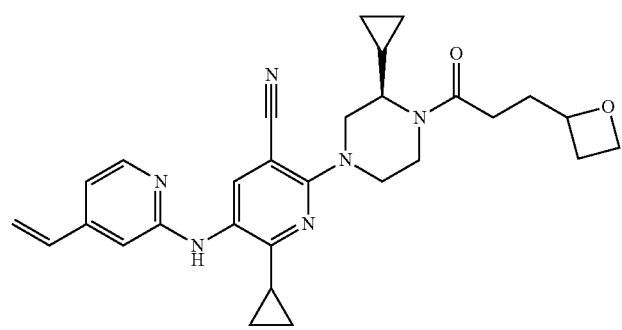 [SMILES: C=Cc1ccnc(Nc2cc(C#N)c(N3CCN(C(=O)CCC4CCO4)[C@H](C4CC4)C3)nc2C2CC2)c1] |

TABLE 5-continued
Exemplary Compounds of Formula I.
| Cpd # | Structure |
|---|---|
| 813 | 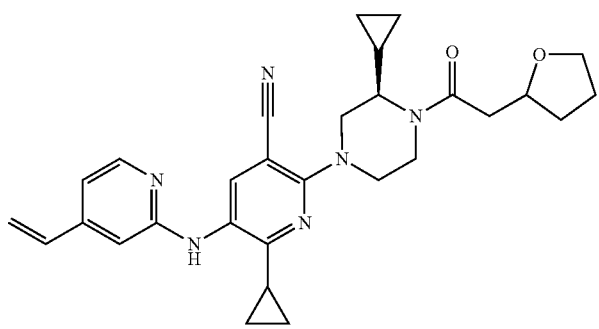 [SMILES: C=Cc1ccnc(Nc2cc(C#N)c(N3CCN(C(=O)CC4CCCO4)[C@H](C4CC4)C3)nc2C2CC2)c1] |
| 814 | 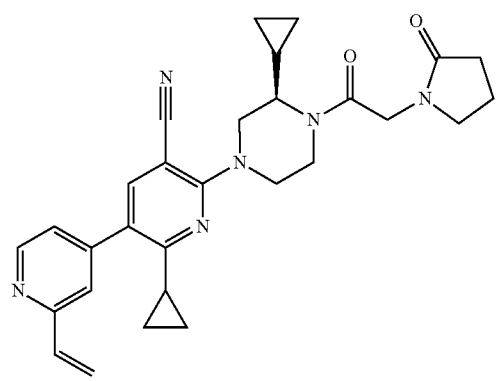 [SMILES: C=Cc1cc(-c2cc(C#N)c(N3CCN(C(=O)CN4CCCC4=O)[C@H](C4CC4)C3)nc2C2CC2)ccn1] |
| 815 | 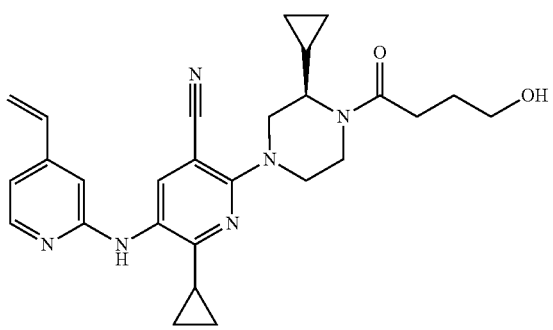 [SMILES: C=Cc1ccnc(Nc2cc(C#N)c(N3CCN(C(=O)CCCO)[C@H](C4CC4)C3)nc2C2CC2)c1] |
| 816 | 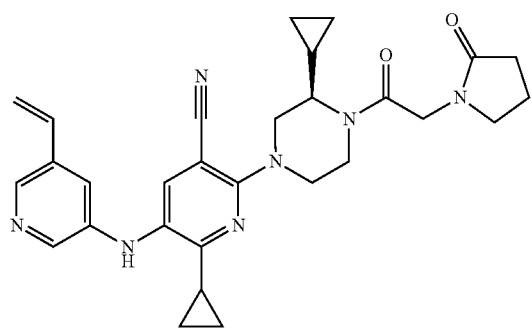 [SMILES: C=Cc1cncc(Nc2cc(C#N)c(N3CCN(C(=O)CN4CCCC4=O)[C@H](C4CC4)C3)nc2C2CC2)c1] |

TABLE 5-continued
Exemplary Compounds of Formula I.
| Cpd # | Structure |
|---|---|
| 817 | 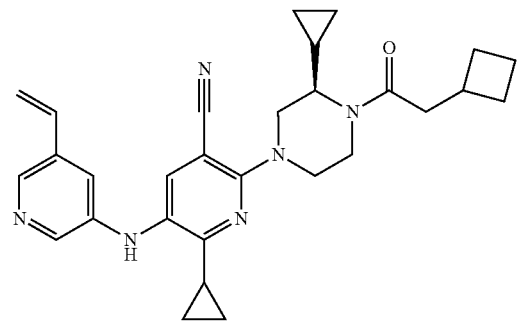 [SMILES: C=Cc1cncc(Nc2cc(C#N)c(N3CCN(C(=O)CC4CCC4)[C@H](C4CC4)C3)nc2C2CC2)c1] |
| 818 | 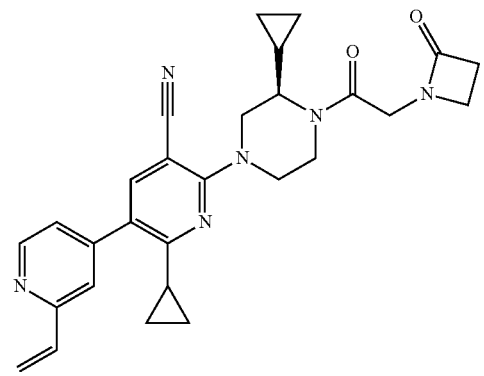 [SMILES: C=Cc1cc(-c2cc(C#N)c(N3CCN(C(=O)CN4CCC4=O)[C@H](C4CC4)C3)nc2C2CC2)ccn1] |
| 819 | 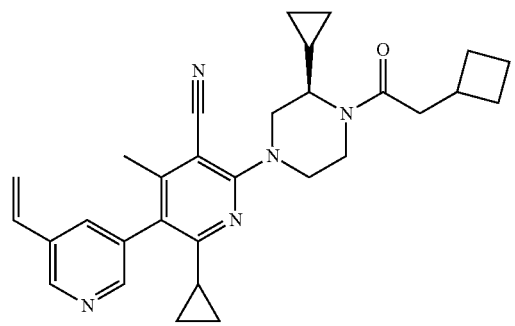 [SMILES: C=Cc1cncc(-c2c(C3CC3)nc(N3CCN(C(=O)CC4CCC4)[C@H](C4CC4)C3)c(C#N)c2C)c1] |
| 820 | 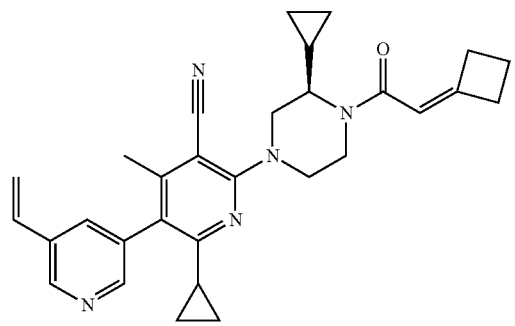 [SMILES: C=Cc1cncc(-c2c(C3CC3)nc(N3CCN(C(=O)C=C4CCC4)[C@H](C4CC4)C3)c(C#N)c2C)c1] |

TABLE 5-continued
Exemplary Compounds of Formula I.
| Cpd # | Structure |
|---|---|
| 821 | 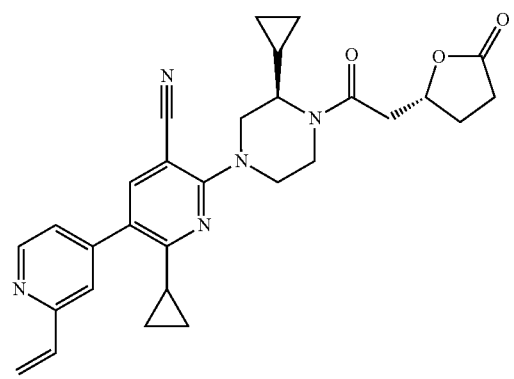 [SMILES: C=Cc1cc(-c2cc(C#N)c(N3CCN(C(=O)C[C@H]4CCC(=O)O4)[C@H](C4CC4)C3)nc2C2CC2)ccn1] |
| 822 | 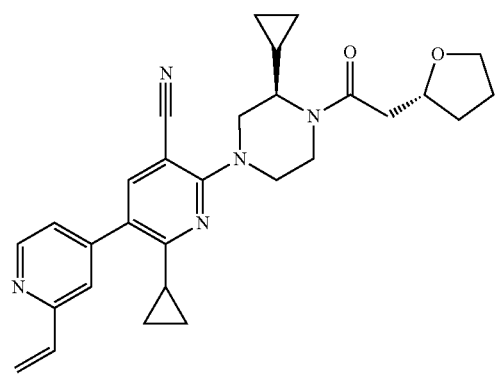 |
| 823 | 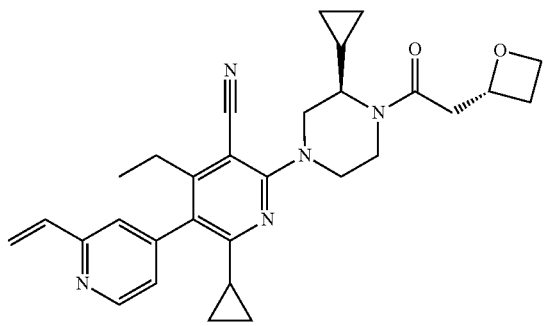 [SMILES: C=Cc1cc(-c2c(C3CC3)nc(N3CCN(C(=O)C[C@H]4CCO4)[C@H](C4CC4)C3)c(C#N)c2CC)ccn1] |
| 824 | 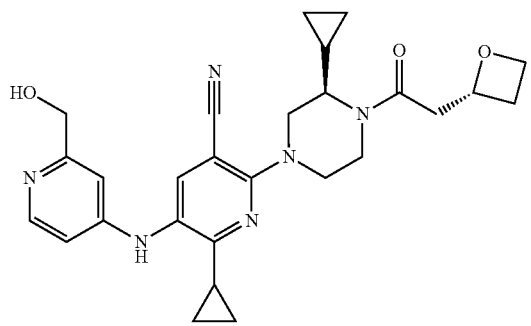 [SMILES: N#Cc1cc(Nc2ccnc(CO)c2)c(C2CC2)nc1N1CCN(C(=O)C[C@H]2CCO2)[C@H](C2CC2)C1] |

325 326
TABLE 5-continued
Exemplary Compounds of Formula I.
| Cpd # | Structure |
|---|---|
| 825 | 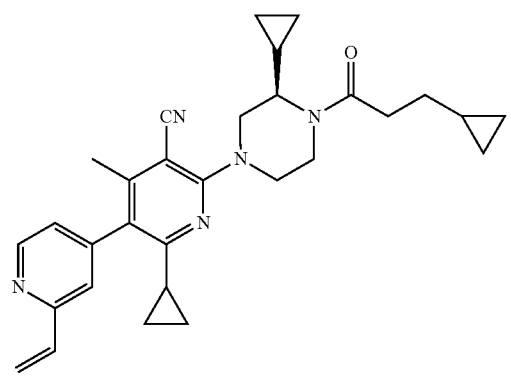 [SMILES: C=Cc1cc(-c2c(C3CC3)nc(N3CCN(C(=O)CCC4CC4)[C@H](C4CC4)C3)c(C#N)c2C)ccn1] |
| 826 | 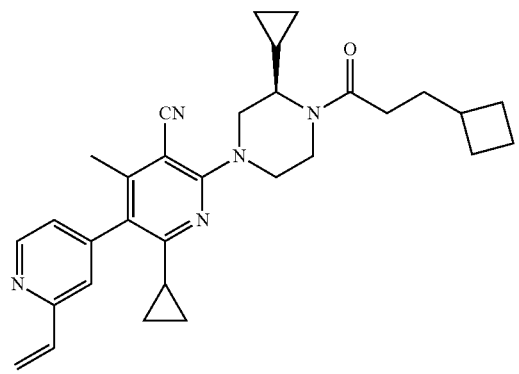 [SMILES: C=Cc1cc(-c2c(C3CC3)nc(N3CCN(C(=O)CCC4CCC4)[C@H](C4CC4)C3)c(C#N)c2C)ccn1] |
| 827 | 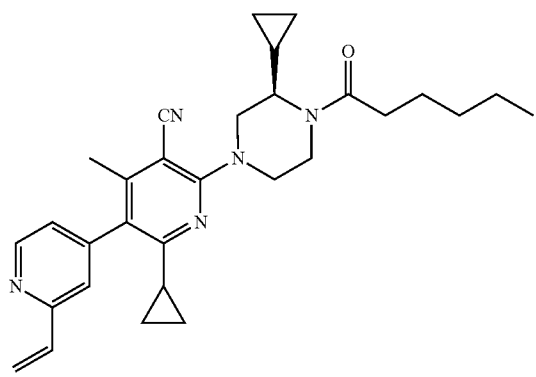 [SMILES: C=Cc1cc(-c2c(C3CC3)nc(N3CCN(C(=O)CCCCC)[C@H](C4CC4)C3)c(C#N)c2C)ccn1] |
| 828 | 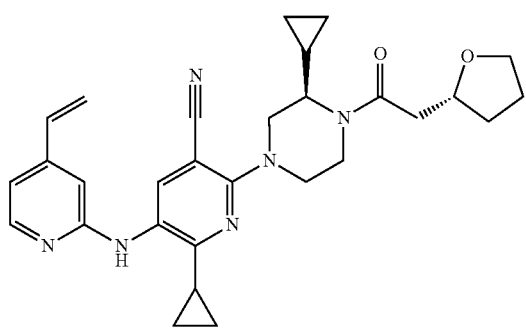 [SMILES: C=Cc1ccnc(Nc2cc(C#N)c(N3CCN(C(=O)C[C@H]4CCCO4)[C@H](C4CC4)C3)nc2C2CC2)c1] |

TABLE 5-continued

Exemplary Compounds of Formula I.

| Cpd # | Structure |
|---|---|
| 829 | 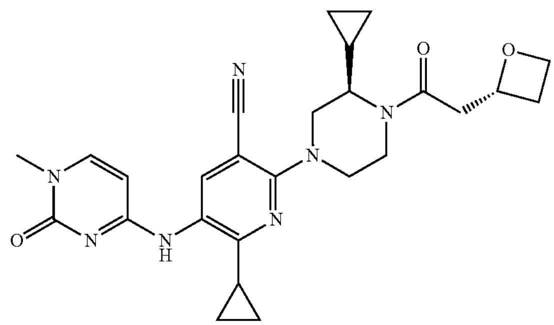 [SMILES: Cn1ccc(Nc2cc(C#N)c(N3CCN(C(=O)C[C@H]4CCO4)[C@H](C4CC4)C3)nc2C2CC2)nc1=O] |
| 830 | 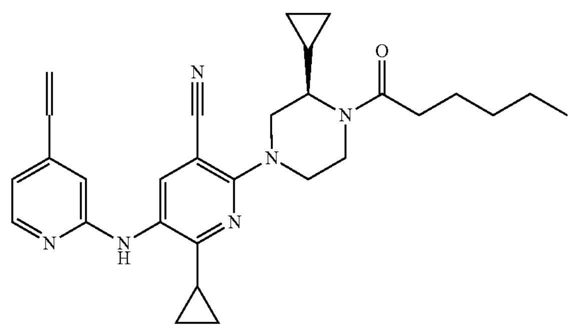 [SMILES: C=Cc1ccnc(Nc2cc(C#N)c(N3CCN(C(=O)CCCCC)[C@H](C4CC4)C3)nc2C2CC2)c1] |

The compounds of this invention may contain one or more asymmetric centers and thus occur as racemates, racemic mixtures, scalemic mixtures, and diastereomeric mixtures, as well as single enantiomers or individual stereoisomers that are substantially free from another possible enantiomer or stereoisomer. The term "substantially free of other stereoisomers" as used herein means a preparation enriched in a compound having a selected stereochemistry at one or more selected stereocenters by at least about 60%, 65%, 70%, 75%, 80%, 85%, 90%, 95%, 96%, 97%, 98%, or 99%. The term "enriched" means that at least the designated percentage of a preparation is the compound having a selected stereochemistry at one or more selected stereocenters. Methods of obtaining or synthesizing an individual enantiomer or stereoisomer for a given compound are known in the art and may be applied as practicable to final compounds or to starting material or intermediates.

The compounds of Formula I, II and IIa may also comprise one or more isotopic substitutions. For example, H may be in any isotopic form, including $^1H$, $^2H$ (D or deuterium), and $^3H$ (T or tritium); C may be in any isotopic form, including $^{12}C$, $^{13}C$, $^{14}C$; O may be in any isotopic form, including $^{16}O$ and $^{18}O$; and the like.

Unless otherwise indicated when a disclosed compound is named or depicted by a structure without specifying the stereochemistry and has one or more chiral centers, it is understood to represent all possible stereoisomers of the compound.

The compounds of this invention may also be represented in multiple tautomeric forms, in such instances, the invention expressly includes all tautomeric forms of the compounds described herein, even though only a single tautomeric form may be represented (e.g., alkylation of a ring system may result in alkylation at multiple sites, the invention expressly includes all such reaction products). All such isomeric forms of such compounds are expressly included in the present invention. All crystal forms of the compounds described herein are expressly included in the present invention.

It may be convenient or desirable to prepare, purify, and/or handle a corresponding salt of the active compound, for example, a pharmaceutically-acceptable salt. Examples of pharmaceutically acceptable salts are discussed in Berge et al., 1977, "Pharmaceutically Acceptable Salts." J. Pharm. Sci. Vol. 66, pp. 1-19.

For example, if the compound is anionic, or has a functional group which may be anionic (e.g., —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{3+}$. Examples of suitable organic cations include, but are not limited to, ammonium ion (i.e., NH$_4^+$) and substituted ammonium ions (e.g., NH$_3$R$^+$, NH$_2$R$^{2+}$, NHR$^{3+}$, NR$^{4+}$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group that may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucoheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

Compositions and Routes of Administration

The compounds utilized in the methods described herein may be formulated together with a pharmaceutically acceptable carrier or adjuvant into pharmaceutically acceptable compositions prior to be administered to a subject. In another embodiment, such pharmaceutically acceptable compositions further comprise additional therapeutic agents in amounts effective for achieving a modulation of disease or disease symptoms, including those described herein.

The term "pharmaceutically acceptable carrier or adjuvant" refers to a carrier or adjuvant that may be administered to a subject, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

The pharmaceutical compositions of this invention may be administered orally, parenterally, by inhalation spray, topically, rectally, nasally, buccally, vCompound AGInally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions may be in the form of a sterile injectable preparation, for example, as a sterile injectable aqueous or oleCompound AGInous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The compounds described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular subject will depend upon a variety of factors, including the activity of the specific compound employed, the age, body weight, general health status, sex, diet, time of administration, rate of excretion, drug combination, the severity and course of the disease, condition or symptoms, the subject's disposition to the disease, condition or symptoms, and the judgment of the treating physician.

Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Subjects may, however, require intermittent treatment on a long-term basis upon any recurrence of disease symptoms.

The pharmaceutical compositions described above comprising a compound of Structural Formula I, II or IIa or a compound described in any one of the embodiments herein, may further comprise another therapeutic agent useful for treating cancer.

Methods of Use

Provided is a method for inhibiting a mutant IDH1 activity comprising contacting a subject in need thereof a compound of Structural Formula I, II or IIa, a compound described in any one of the embodiments herein, or a pharmaceutically acceptable salt thereof. In one embodiment, the cancer to be treated is characterized by a mutant allele of IDH1 wherein the IDH1 mutation result in a new ability of the enzyme to catalyze the NADPH-dependent reduction of α-ketoglutarate to R(−)-2-hydroxyglutarate in a subject. In one aspect of this embodiment, the mutant IDH1 has an R132X mutation. In one aspect of this embodiment, the R132X mutation is selected from R132H, R132C, R132L, R132V, R132S and R132G. In another aspect, the R132X mutation is R132H or R132C. In yet another aspect, the R132X mutation is R132H.

Also provided are methods of treating a cancer characterized by the presence of a mutant allele of IDH1 comprising the step of administering to subject in need thereof (a) a compound of Structural Formula I, II or IIa, a compound described in any one of the embodiments herein, or a pharmaceutically acceptable salt thereof, or (b) a pharmaceutical composition comprising (a) and a pharmaceutically acceptable carrier.

In one embodiment, the cancer to be treated is characterized by a mutant allele of IDH1 wherein the IDH1 mutation result in a new ability of the enzyme to catalyze the NADPH-dependent reduction of α-ketoglutarate to R(−)-2-hydroxyglutarate in a patient. In one aspect of this embodiment, the IDH1 mutation is an R132X mutation. In another aspect of this embodiment, the R132X mutation is selected from R132H, R132C, R132L, R132V, R132S and R132G. In another aspect, the R132X mutation is R132 H or R132C. A cancer can be analyzed by sequencing cell samples to determine the presence and specific nature of (e.g., the changed amino acid present at) a mutation at amino acid 132 of IDH1.

Without being bound by theory, applicants believe that mutant alleles of IDH1 wherein the IDH1 mutation result in a new ability of the enzyme to catalyze the NADPH-dependent reduction of α-ketoglutarate to R(−)-2-hydroxyglutarate, and in particular R132H mutations of IDH1, characterize a subset of all types of cancers, without regard to their cellular nature or location in the body. Thus, the compounds and methods of this invention are useful to treat any type of cancer that is characterized by the presence of a mutant allele of IDH1 imparting such activity and in particular an IDH1 R132H or R132C mutation.

In one aspect of this embodiment, the efficacy of cancer treatment is monitored by measuring the levels of 2HG in the subject. Typically levels of 2HG are measured prior to treatment, wherein an elevated level is indicative of the use of the compound of Formula I to treat the cancer. Once the elevated levels are established, the level of 2HG is determined during the course of and/or following termination of treatment to establish efficacy. In certain embodiments, the level of 2HG is only determined during the course of and/or following termination of treatment. A reduction of 2HG levels during the course of treatment and following treatment is indicative of efficacy. Similarly, a determination that 2HG levels are not elevated during the course of or following treatment is also indicative of efficacy. Typically, the these 2HG measurements will be utilized together with other well-known determinations of efficacy of cancer treatment, such as reduction in number and size of tumors and/or other cancer-associated lesions, improvement in the general health of the subject, and alterations in other biomarkers that are associated with cancer treatment efficacy.

2HG can be detected in a sample by LC/MS. The sample is mixed 80:20 with methanol, and centrifuged at 3,000 rpm for 20 minutes at 4 degrees Celsius. The resulting supernatant can be collected and stored at −80 degrees Celsius prior to LC-MS/MS to assess 2-hydroxyglutarate levels. A variety of different liquid chromatography (LC) separation methods can be used. Each method can be coupled by negative electrospray ionization (ESI, −3.0 kV) to triple-quadrupole mass spectrometers operating in multiple reaction monitoring (MRM) mode, with MS parameters optimized on infused metabolite standard solutions. Metabolites can be separated by reversed phase chromatography using 10 mM tributyl-amine as an ion pairing agent in the aqueous mobile phase, according to a variant of a previously reported method (Luo et al. *J Chromatogr A* 1147, 153-64, 2007). One method allows resolution of TCA metabolites: t=0, 50% B; t=5, 95% B; t=7, 95% B; t=8, 0% B, where B refers to an organic mobile phase of 100% methanol. Another method is specific for 2-hydroxyglutarate, running a fast linear gradient from 50%-95% B (buffers as defined above) over 5 minutes. A Synergi Hydro-RP, 100 mm×2 mm, 2.1 μm particle size (Phenomenex) can be used as the column, as described above. Metabolites can be quantified by comparison of peak areas with pure metabolite standards at known concentration. Metabolite flux studies from $^{13}$C-glutamine can be performed as described, e.g., in Munger et al. Nat Biotechnol 26, 1179-86, 2008.

In one embodiment 2HG is directly evaluated.

In another embodiment a derivative of 2HG formed in process of performing the analytic method is evaluated. By way of example such a derivative can be a derivative formed in MS analysis. Derivatives can include a salt adduct, e.g., a Na adduct, a hydration variant, or a hydration variant which is also a salt adduct, e.g., a Na adduct, e.g., as formed in MS analysis.

In another embodiment a metabolic derivative of 2HG is evaluated. Examples include species that build up or are elevated, or reduced, as a result of the presence of 2HG, such as glutarate or glutamate that will be correlated to 2HG, e.g., R-2HG.

Exemplary 2HG derivatives include dehydrated derivatives such as the compounds provided below or a salt adduct thereof:

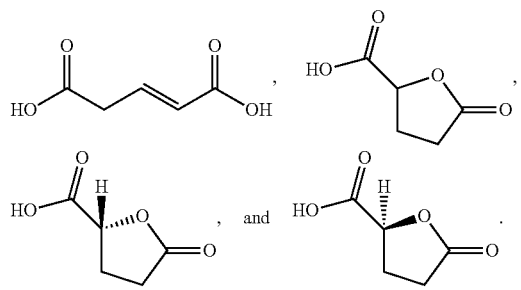

In one embodiment the cancer is a tumor wherein at least 30, 40, 50, 60, 70, 80 or 90% of the tumor cells carry an IDH1 mutation, and in particular an IDH1 R132H or R132C mutation, at the time of diagnosis or treatment.

IDH1 R132X mutations are known to occur in certain types of cancers as indicated in Table 2, below.

TABLE 2

IDH mutations associated with certain cancers

| Cancer Type | IDH1 R132X Mutation | Tumor Type |
|---|---|---|
| brain tumors | R132H | primary tumor |
| | R132C | primary tumor |
| | R132S | primary tumor |
| | R132G | primary tumor |
| | R132L | primary tumor |
| | R132V | primary tumor |
| fibrosarcoma | R132C | HT1080 fibrosarcoma cell line |
| Acute Myeloid Leukemia (AML) | R132H | primary tumor |
| | R132G | primary tumor |
| | R132C | primary tumor |
| Prostate cancer | R132H | primary tumor |
| | R132C | primary tumor |
| Acute lymphoblastic leukemia (ALL) | R132C | primary tumor |
| paragangliomas | R132C | primary tumor |

IDH1 R132H mutations have been identified in glioblastoma, acute myelogenous leukemia, sarcoma, melanoma, non-small cell lung cancer, cholangiocarcinomas, chondrosarcoma, myelodysplastic syndromes (MDS), myeloproliferative neoplasm (MPN), colon cancer, and angio-immunoblastic non-Hodgkin's lymphoma (NHL). Accordingly, in one embodiment, the methods described herein are used to treat glioma (glioblastoma), acute myelogenous leukemia, sarcoma, melanoma, non-small cell lung cancer (NSCLC) or cholangiocarcinomas, chondrosarcoma, myelodysplastic syndromes (MDS), myeloproliferative neoplasm (MPN) or colon cancer in a patient.

Accordingly in one embodiment, the cancer is a cancer selected from any one of the cancer types listed in Table 2, and the IDH R132X mutation is one or more of the IDH1 R132X mutations listed in Table 2 for that particular cancer type.

Treatment methods described herein can additionally comprise various evaluation steps prior to and/or following treatment with a compound of Structural Formula I, II or IIa or a compound described in any one of the embodiments described herein.

In one embodiment, prior to and/or after treatment with a compound of Structural Formula I, II or IIa or a compound described in any one of the embodiments described herein, the method further comprises the step of evaluating the growth, size, weight, invasiveness, stage and/or other phenotype of the cancer.

In one embodiment, prior to and/or after treatment with a compound of formula I or I-a or a compound described in any one of the embodiments described herein, the method further comprises the step of evaluating the IDH1 genotype of the cancer. This may be achieved by ordinary methods in the art, such as DNA sequencing, immuno analysis, and/or evaluation of the presence, distribution or level of 2HG.

In one embodiment, prior to and/or after treatment with a compound of formula I or I-a or a compound described in any one of the embodiments described herein, the method further comprises the step of determining the 2HG level in the subject. This may be achieved by spectroscopic analysis, e.g., magnetic resonance-based analysis, e.g., MRI and/or MRS measurement, sample analysis of bodily fluid, such as serum or spinal cord fluid analysis, or by analysis of surgical material, e.g., by mass-spectroscopy.

Combination Therapies

In some embodiments, the methods described herein comprise the additional step of co-administering to a subject in need thereof a second therapy e.g., an additional cancer therapeutic agent or an additional cancer treatment. Exemplary additional cancer therapeutic agents include for example, chemotherapy, targeted therapy, antibody therapies, immunotherapy, and hormonal therapy. Additional cancer treatments include, for example: surgery, and radiation therapy. Examples of each of these treatments are provided below.

The term "co-administering" as used herein with respect to an additional cancer therapeutic agents means that the additional cancer therapeutic agent may be administered together with a compound of this invention as part of a single dosage form (such as a composition of this invention comprising a compound of the invention and an second therapeutic agent as described above) or as separate, multiple dosage forms. Alternatively, the additional cancer therapeutic agent may be administered prior to, consecutively with, or following the administration of a compound of this invention. In such combination therapy treatment, both the compounds of this invention and the second therapeutic agent(s) are administered by conventional methods. The administration of a composition of this invention, comprising both a compound of the invention and a second therapeutic agent, to a subject does not preclude the separate administration of that same therapeutic agent, any other second therapeutic agent or any compound of this invention to said subject at another time during a course of treatment. The term "co-administering" as used herein with respect to an additional cancer treatment means that the additional cancer treatment may occur prior to, consecutively with, concurrently with or following the administration of a compound of this invention.

In some embodiments, the additional cancer therapeutic agent is a chemotherapy agent. Examples of chemotherapeutic agents used in cancer therapy include, for example, antimetabolites (e.g., folic acid, purine, and pyrimidine derivatives), alkylating agents (e.g., nitrogen mustards, nitrosoureas, platinum, alkyl sulfonates, hydrazines, triazenes, aziridines, spindle poison, cytotoxic agents, topoisomerase inhibitors and others) and hypomethylating agents (e.g., decitabine (5-aza-deoxycytidine), zebularine, isothiocyanates, azacitidine (5-azacytidine), 5-flouro-2'-deoxycytidine, 5,6-dihydro-5-azacytidine and others). Exemplary agents include Aclarubicin, Actinomycin, Alitretinoin, Altretamine, Aminopterin, Aminolevulinic acid, Amrubicin, Amsacrine, Anagrelide, Arsenic trioxide, AsparCompound AGInase, Atrasentan, Belotecan, Bexarotene, bendamustine, Bleomycin, Bortezomib, Busulfan, Camptothecin, Capecitabine, Carboplatin, Carboquone, Carmofur, Carmustine, Celecoxib, Chlorambucil, Chlormethine, Cisplatin, Cladribine, Clofarabine, Crisantaspase, Cyclophosphamide, Cytarabine, Dacarbazine, Dactinomycin, Daunorubicin, Decitabine, Demecolcine, Docetaxel, Doxorubicin, Efaproxiral, Elesclomol, Elsamitrucin, Enocitabine, Epirubicin, Estramustine, Etoglucid, Etoposide, Floxuridine, Fludarabine, Fluorouracil (5FU), Fotemustine, Gemcitabine, Gliadel implants, Hydroxycarbamide, Hydroxyurea, Idarubicin, Ifosfamide, Irinotecan, Irofulven, Ixabepilone, Larotaxel, Leucovorin, Liposomal doxorubicin, Liposomal daunorubicin, Lonidamine, Lomustine, Lucanthone, Mannosulfan, Masoprocol, Melphalan, Mercaptopurine, Mesna, Methotrexate, Methyl aminolevulinate, Mitobronitol, Mitoguazone, Mitotane, Mitomycin, Mitoxantrone, Nedaplatin, Nimustine, Oblimersen, Omacetaxine, Ortataxel, Oxaliplatin, Paclitaxel, Pegaspargase, Pemetrexed, Pentostatin, Pirarubicin, Pixantrone, Plicamycin, Porfimer sodium, Prednimustine, Procarbazine, Raltitrexed, Ranimustine, Rubitecan, Sapacitabine, Semustine, Sitimagene ceradenovec, Strataplatin, Streptozocin, Talaporfin, Tegafur-uracil, Temoporfin, Temozolomide, Teniposide, Tesetaxel, Testolactone, Tetranitrate, Thiotepa, Tiazofurine, Tioguanine, Tipifarnib, Topotecan, Trabectedin, Triaziquone, Triethylenemelamine, Triplatin, Tretinoin, Treosulfan, Trofosfamide, Uramustine, Valrubicin, Verteporfin, Vinblastine, Vincristine, Vindesine, Vinflunine, Vinorelbine, Vorinostat, Zorubicin, and other cytostatic or cytotoxic agents described herein.

Because some drugs work better together than alone, two or more drugs are often given at the same time. Often, two or more chemotherapy agents are used as combination chemotherapy.

In some embodiments, the additional cancer therapeutic agent is a differentiation agent. Such differentiation agent includes retinoids (such as all-trans-retinoic acid (ATRA), 9-cis retinoic acid, 13-cis-retinoic acid (13-cRA) and 4-hydroxy-phenretinamide (4-HPR)); arsenic trioxide; histone deacetylase inhibitors HDACs (such as azacytidine (Vidaza) and butyrates (e.g., sodium phenylbutyrate)); hybrid polar compounds (such as hexamethylene bisacetamide ((HMBA)); vitamin D; and cytokines (such as colony-stimulating factors including G-CSF and GM-CSF, and interferons).

In some embodiments the additional cancer therapeutic agent is a targeted therapy agent. Targeted therapy constitutes the use of agents specific for the deregulated proteins of cancer cells. Small molecule targeted therapy drugs are generally inhibitors of enzymatic domains on mutated, overexpressed, or otherwise critical proteins within the cancer cell. Prominent examples are the tyrosine kinase inhibitors such as Axitinib, Bosutinib, Cediranib, dasatinib, erlotinib, imatinib, gefitinib, lapatinib, Lestaurtinib, Nilotinib, Semaxanib, Sorafenib, Sunitinib, and Vandetanib, and also cyclin-dependent kinase inhibitors such as Alvocidib and Seliciclib. Monoclonal antibody therapy is another strategy in which the therapeutic agent is an antibody which specifically binds to a protein on the surface of the cancer cells. Examples include the anti-HER2/neu antibody trastuzumab (HERCEPTIN®) typically used in breast cancer, and the anti-CD20 antibody rituximab and Tositumomab typically used in a variety of B-cell malignancies. Other exemplary antibodies include Cetuximab, Panitumumab, Trastuzumab, Alemtuzumab, Bevacizumab, Edrecolomab, and Gemtuzumab. Exemplary fusion proteins include Aflibercept and Denileukin diftitox. In some embodiments, the targeted therapy can be used in combination with a compound described herein, e.g., a biguanide such as metformin or phenformin, preferably phenformin.

Targeted therapy can also involve small peptides as "homing devices" which can bind to cell surface receptors or affected extracellular matrix surrounding the tumor. Radionuclides which are attached to these peptides (e.g., RGDs) eventually kill the cancer cell if the nuclide decays in the vicinity of the cell. An example of such therapy includes BEXXAR®.

In some embodiments, the additional cancer therapeutic agent is an immunotherapy agent. Cancer immunotherapy refers to a diverse set of therapeutic strategies designed to induce the subject's own immune system to fight the tumor. Contemporary methods for generating an immune response against tumors include intravesicular BCG immunotherapy for superficial bladder cancer, and use of interferons and other cytokines to induce an immune response in renal cell carcinoma and melanoma subjects.

Allogeneic hematopoietic stem cell transplantation can be considered a form of immunotherapy, since the donor's immune cells will often attack the tumor in a graft-versus-tumor effect. In some embodiments, the immunotherapy agents can be used in combination with a compound or composition described herein.

In some embodiments, the additional cancer therapeutic agent is a hormonal therapy agent. The growth of some cancers can be inhibited by providing or blocking certain hormones. Common examples of hormone-sensitive tumors include certain types of breast and prostate cancers. Removing or blocking estrogen or testosterone is often an important additional treatment. In certain cancers, administration of hormone agonists, such as progestogens may be therapeutically beneficial. In some embodiments, the hormonal therapy agents can be used in combination with a compound or a composition described herein.

Other possible additional therapeutic modalities include imatinib, gene therapy, peptide and dendritic cell vaccines, synthetic chlorotoxins, and radiolabeled drugs and antibodies.

EXAMPLES

Abbreviations anhy.—anhydrous chromatography
aq.—aqueous Hz—hertz
min—minute(s) δ—chemical shift
mL—milliliter J—coupling constant
mmol—millimole(s) s—singlet
mol—mole(s) d—doublet
MS—mass spectrometry t—triplet
NMR—nuclear magnetic resonance q—quartet
TLC—thin layer chromatography m—multiplet
HPLC—high-performance liquid br—broad
qd—quartet of doublets Na$_2$CO$_3$—sodium carbonate
dquin—doublet of quintets TFA—trifluoroacetic acid
dd—doublet of doublets Na$_2$SO$_4$—sodium sulfate
dt—doublet of triplets NaBH$_4$—sodium borohydride
CHCl$_3$—chloroform NaHCO$_3$—sodium bicarbonate
DCM—dichloromethane LiHMDS—lithium hexamethyldisilylamide
DMF—dimethylformamide NaHMDS—sodium hexamethyldisilylamide
Et$_2$O—diethyl ether LAH—lithium aluminum hydride
EtOH—ethyl alcohol NaBH$_4$—sodium borohydride
EtOAc—ethyl acetate LDA—lithium diisopropylamide
MeOH—methyl alcohol Et$_3$N—triethylamine
MeCN—acetonitrile DMAP—4-(dimethylamino)pyridine
PE—petroleum ether DIPEA—N,N-diisopropylethylamine
THF—tetrahydrofuran NH$_4$OH—ammonium hydroxide
AcOH—acetic acid EDCI—1-ethyl-3-(3-dimethylaminopropyl)carbodiimide
HCl—hydrochloric acid
H$_2$SO$_4$—sulfuric acid HOBt—1-hydroxybenzotriazole
NH$_4$Cl—ammonium chloride HATU—O-(7-azabenzotriazol-1-yl)-N,N,N',N'-tetra-methyluronium
KOH—potassium hydroxide
NaOH—sodium hydroxide BINAP—2,2'-bis(diphenylphosphanyl)-1,1'-binaphthyl
K$_2$CO$_3$—potassium carbonate In the following examples, reagents were purchased from commercial sources (including Alfa, Acros, Sigma Aldrich, TCI and Shanghai Chemical Reagent Company), and used without further purification. Flash chromatography was performed on an Ez Purifier III using a column with silica gel particles of 200-300 mesh. Analytical and preparative thin layer chromatography plates (TLC) were HSGF 254 (0.15-0.2 mm thickness, Shanghai Anbang Company, China). Nuclear magnetic resonance (NMR) spectra were obtained on a Brucker AMX-400 NMR (Brucker, Switzerland). Chemical shifts were reported in parts per million (ppm, δ) downfield from tetramethylsilane. Mass spectra were run with electrospray ionization (ESI) from a Waters LCT TOF Mass Spectrometer (Waters, USA). HPLC chromatographs were recorded on an Compound AGIlent 1200 Liquid Chromatography (Compound AGIlent, USA, column: Ultimate 4.6 mm×50 mm, 5 µm, mobile phase A: 0.1% formic acid in water; mobile phase B: acetonitrile). Microwave reactions were run on an Initiator 2.5 Microwave Synthesizer (Biotage, Sweden).

For exemplary compounds disclosed in this section, the specification of a stereoisomer (e.g., an (R) or (S) stereoisomer) indicates a preparation of that compound such that the compound is enriched at the specified stereocenter by at least about 90%, 95%, 96%, 97%, 98%, or 99%.

Example 1. Preparation of (R)-5-bromo-6-isopropyl-2-(4-(3-methoxypropanoyl)-3-methylpiperazin-1-yl)nicotinonitrile (R)-5-bromo-6-isopropyl-2-(4-(3-methoxypropanoyl)-3-methylpiperazin-1-yl)nicotinonitrile (7, wherein $R^{1a}$ is hydrogen; m is 1; $R^3$ is 3-methyl; and $R^8$ is methoxyethyl) was prepared according to general Scheme 1, below.

Scheme 1:

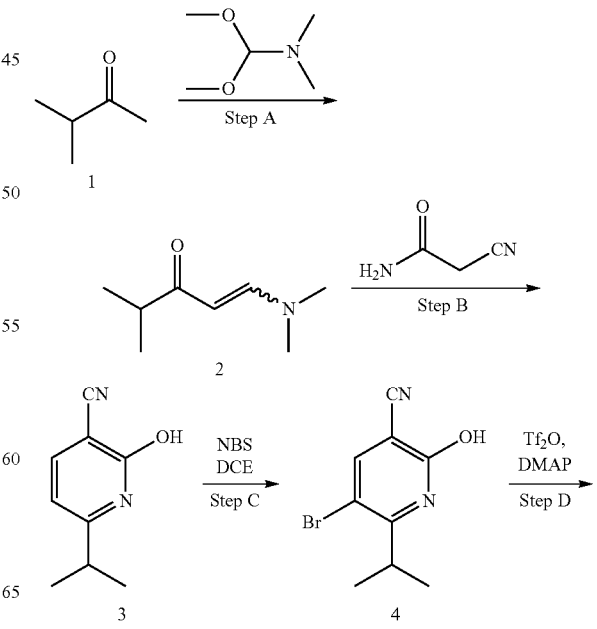

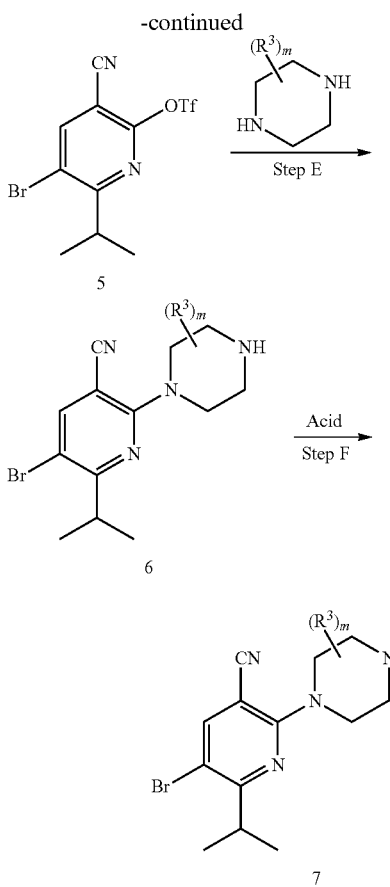

1H), 7.96-8.18 (m, 1H), 6.24 (d, J=7.5 Hz, 1H), 2.83 (spt, J=6.9 Hz, 1H), 1.19 (s, 29H), 1.17 (s, 3H).

Step C: 5-bromo-6-isopropyl-2-oxo-1,2-dihydropyridine-3-carbonitrile (4)

To a solution of 2-hydroxy-6-isopropylnicotinonitrile (3; 3.0 g, 19 mmol) in 50 mL of DCE was added NBS (5 g, 28 mmol) at room temperature. The reaction mixture was then heated at reflux for 3 hours. After LC-MS showed the completion of reaction, the mixture was cooled to room temperature and poured into water and extracted with methylene chloride. The combined organic layer was dried over anhy. $Na_2SO_4$ and concentrated in vacuo. Column chromatography (4% MeOH/DCM) afforded 3.9 g of title compound as a brown solid. MS (ES) M+H expected 241.0. found 240.9. $^1$H NMR (DMSO-$d_6$) δ 12.58 (br. s., 1H), 8.38 (s, 1H), 3.25-3.32 (m, 1H), 1.23 (s, 3H), 1.21 (s, 3H).

Step D: 5-bromo-3-cyano-6-isopropylpyridin-2-yl trifluoromethanesulfonate (5)

To a solution of 5-bromo-2-hydroxy-6-isopropylnicotinonitrile (4; 2.0 g, 8 mmol) in 20 mL of methylene chloride was added DMAP (100 mg, 0.8 mmol), and triethylamine (1.01 g, 10 mmol). The mixture was cooled to 0° C. in an ice-water bath, and trifluoromethanesulfonic anhydride (2.82 g, 10 mmol) was added dropwise by syringe. The resulting reaction mixture was stirred at 0° C. for 30 min before it was allowed to warm to room temperature and stirred for additional 2 hours. After TLC showed the complete conversion of starting material to product, the reaction mixture was concentrated and purified by column chromatography (20% EtOAc/petroleum ether) to afford 2.8 g of title compound. $^1$H NMR (CHLOROFORM-d) δ 8.22 (s, 1H), 3.57 (spt, J=6.7 Hz, 1H), 1.28 (d, J=6.8 Hz, 6H).

Step E: (R)-5-bromo-6-isopropyl-2-(3-methylpiperazin-1-yl)nicotinonitrile (6)

A mixture of the above triflate 5 (1.68 g, 4.5 mmol), (R)-2-methylpiperazine (770 mg, 6.77 mmol), and triethylamine (1.9 mL, 13.5 mmol) suspended in 5 mL of MeCN was subjected to microwave reaction at 175° C. for 45 min. After the mixture was concentrated in vacuo, the residue was purified by column chromatography (10% DCM/MeOH) to afford 0.91 g of title compound as a light yellowish solid. MS (ES) M+H expected 323.1. found 323.0. $^1$H NMR (CHLOROFORM-d) δ 7.79 (s, 1H), 4.35-4.40 (m, 0.5H), 4.32-4.35 (m, 1H), 4.30 (t, J=2.4 Hz, 0.5H), 3.37-3.45 (m, 1H), 3.08-3.13 (m, 0.5H), 3.05-3.08 (m, 1H), 3.04 (d, J=2.5 Hz, 0.5H), 2.96-3.01 (m, 1H), 2.89-2.96 (m, 1H), 2.65-2.74 (m, 1H), 1.21 (dd, J=6.8, 0.8 Hz, 6H), 1.13 (d, J=6.3 Hz, 3H).

Step F: (R)-5-bromo-6-isopropyl-2-(4-(3-methoxypropanoyl)-3-methylpiperazin-1-yl)nicotinonitrile (7)

To a 25 mL of round-bottom flask was added (R)-5-bromo-6-isopropyl-2-(3-methylpiperazin-1-yl)nicotinonitrile (6; 680 mg, 2.1 mmol), 3-methoxypropanoic acid (438 mg, 4.2 mmol), HATU (1.6 g, 4.2 mmol), DIPEA (1.1 mL, 6.31 mmol) and 5 mL of methylene chloride. The resulting reaction mixture was stirred at room temperature for 4 hours until TLC showed the completion of the reaction. After washing with Satd. $NaHCO_3$, brine, the combined organic Step A: 1-(dimethylamino)-4-methylpent-1-en-3-one (2)

To a solution of commerically available 3-methylbutan-2-one (1; 8.613 g, 100 mmol) in 150 mL of anhydrous DMF was added commercially available 1,1-dimethoxy-N,N-dimethylmethanamine (29.80 g, 250 mmol). The resulting mixture was stirred at 100° C. overnight. After removal of DMF and excess of acetal, 14 g of title compound was obtained as a crude product and used in subsequent reaction without further purification. $^1$H NMR (CHLOROFORM-d) δ 7.57 (d, J=12.8 Hz, 1H), 5.05 (d, J=12.5 Hz, 1H), 2.80-3.10 (m, 6H), 2.56 (dt, J=13.7, 6.8 Hz, 1H), 1.06-1.14 (m, 6H).

Step B: 6-isopropyl-2-oxo-1,2-dihydropyridine-3-carbonitrile (3)

8.8 g of 1-(dimethylamino)-4-methylpent-1-en-3-one (2; 62 mmol) and 5.3 g of commercially available cyanoacetamide (62 mmol) in 24 mL of $H_2O$ was treated with a premixed buffer solution of 0.7 mL of acetic acid, 1.8 mL of $H_2O$, and enough piperidine to make the buffer solution basic. The resulting solution was refluxed for 2 hrs and LC-MS showed the formation of desired product. After cooling to room temperature, the mixture was acidified with glacial acetic acid, and a brown yellowish precipitate was formed. The filter cake was washed with $H_2O$ and air-dried to give 6.5 g of title compound. MS (ES) M+H expected 163.1. found 163.0. $^1$H NMR (DMSO-$d_6$) δ 12.51 (br. s., layer was dried over anhy. Na₂SO₄ and concentrated in vacuo. Column chromatography purification (20% EtOAc/petroleum ether) afforded 550 mg of title compound as a light yellowish solid. MS (ES) M+H expected 409.1. found 409.0. ¹H NMR (CHLOROFORM-d) δ 7.83 (s, 1H), 4.90 (br. s., 0.5H), 4.52 (d, J=12.3 Hz, 0.5H), 4.19-4.39 (m, 3H), 3.76-3.85 (m, 0.5H), 3.73 (t, J=6.4 Hz, 2H), 3.50-3.61 (m, 0.5H), 3.37 (s, 3H), 3.25-3.35 (m, 1H), 3.02-3.20 (m, 1H), 2.63-2.80 (m, 1H), 2.51-2.61 (m, 1H), 1.35 (d, J=7.0 Hz, 1.5H), 1.25 (d, J=6.3 Hz, 1.5H), 1.21-1.23 (m, 3H), 1.19-1.21 (m, 3H)

Other intermediates 7 were prepared by similar steps according to Scheme 1 and either: (1) replacing (R)-2-methylpiperazine in Step E with an alternately substituted or unsubstituted piperazine; and/or (2) replacing 3-methoxypropanoic acid in Step F with an alternate acid.

Example 2. Preparation of (R)-5-bromo-6-cyclopropyl-2-(4-(3-methoxypropanoyl)-3-methylpiperazin-1-yl)nicotinonitrile (R)-5-bromo-6-cyclopropyl-2-(4-(3-methoxypropanoyl)-3-methylpiperazin-1-yl)nicotinonitrile (17; wherein R¹ᵃ is hydrogen; R² is cyclopropyl; m is 1; R³ is 3-methyl; and R⁸ is methoxyethyl) was prepared according to general Scheme 2, below.

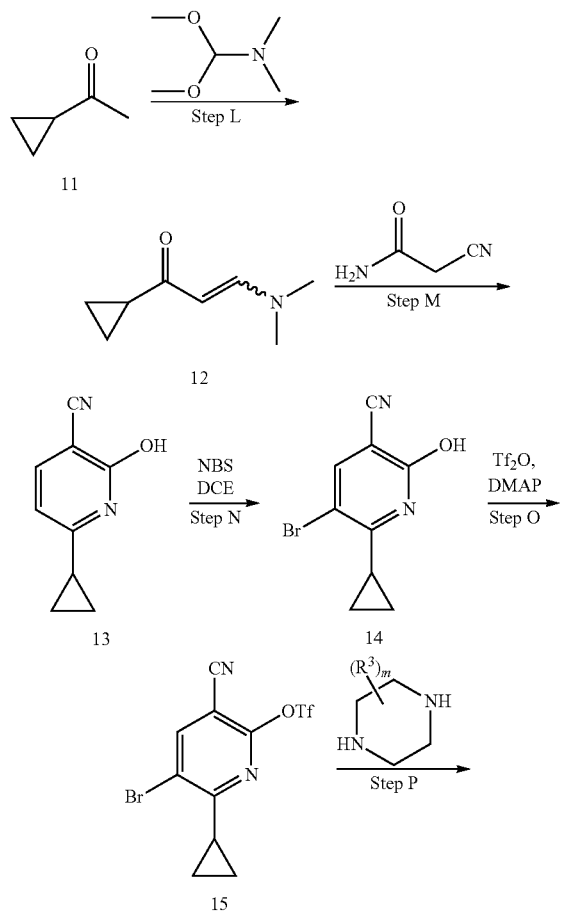

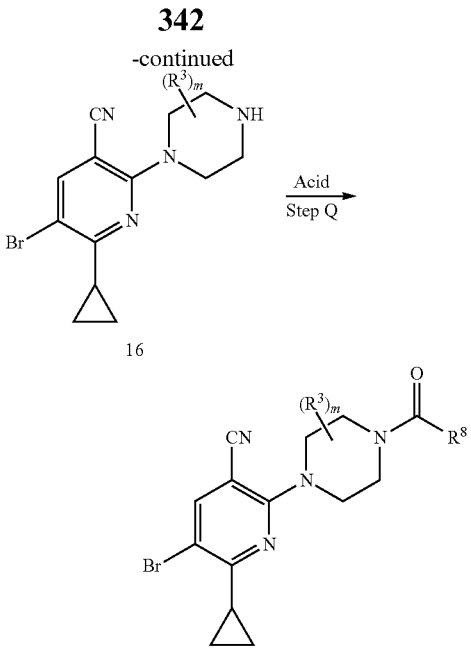

Step L: 1-cyclopropyl-3-(dimethylamino)prop-2-en-1-one (12)

To a solution of commercially available 1-cyclopropylethanone (11; 8.584 g, 100 mmol) in 200 mL of anhydrous DMF was added 1,1-dimethoxy-N,N-dimethylmethanamine (29.80 g, 250 mmol). The resulting mixture was stirred at 100° C. overnight. After removal of DMF and excess of acetal, 13.9 g of title compound was obtained as a crude product and used in subsequent reaction without further purification. ¹H NMR (CHLOROFORM-d) δ 7.56 (d, J=12.8 Hz, 1H), 5.20 (d, J=12.5 Hz, 1H), 2.78-3.08 (m, 6H), 1.79 (tt, J=7.9, 4.5 Hz, 1H), 0.94-1.04 (m, 2H), 0.67-0.80 (m, 2H).

Step M: 6-cyclopropyl-2-hydroxynicotinonitrile (13)

3.532 g of 1-cyclopropyl-3-(dimethylamino)prop-2-en-1-one 12 and 2.032 g of cyanoacetamide in 10 mL of H₂O was treated with a premixed buffer solution of 0.33 mL of acetic acid, 0.82 mL of H₂O, and enough amount of piperidine to make solution basic. The resulting solution was refluxed for 2 hrs and LC-MS showed the formation of desired product 13. After cooling to room temperature, the mixture was acidified with glacial acetic acid, and a brown yellowish precipitated was formed. The thick brown slurry was filtered and filter cake was washed with H₂O and air-dried to give 1.30 g of title compound. MS (ES) M+H expected 161.1. found 161.0. 1H NMR (CHLOROFORM-d) δ 13.60 (br. s., 1H), 7.77 (d, J=7.8 Hz, 1H), 5.91 (d, J=7.8 Hz, 1H), 1.96-2.12 (m, 1H), 1.29-1.36 (m, 2H), 1.04-1.11 (m, 2H).

Step N: 5-bromo-6-cyclopropyl-2-hydroxynicotinonitrile (14)

To a solution of 6-cyclopropyl-2-hydroxynicotinonitrile (13; 0.32 g, 2.0 mmol) in 5 mL of DCE was added NBS (0.534 g, 3.0 mmol) at room temperature. The reaction mixture was heated at reflux for 3 hours. After LC-MS showed completion of reaction, the reaction mixture was cooled to room temperature and poured into water. After extraction with methylene chloride (3×5 mL), the combined organic layer was dried over anhy. $Na_2SO_4$ and concentrated in vacuo. Column chromatography (4% MeOH/DCM) afforded 0.45 g of 14. MS (ES) M+H expected 239.0. found 238.9. $^1$H NMR (CHLOROFORM-d) δ 8.49-8.72 (br. s., 1H), 7.93 (s, 1H), 2.23-2.34 (m, 1H), 1.36-1.42 (m, 2H), 1.29-1.36 (m, 2H).

Step O: 5-bromo-3-cyano-6-cyclopropylpyridin-2-yl trifluoromethanesulfonate (15)

To a 5-bromo-6-cyclopropyl-2-hydroxynicotinonitrile (14; 0.45 g, 1.882 mmol) in 10 mL of methylene chloride was added DMAP (23.2 mg, 0.19 mmol), and triethylamine (0.247 g, 2.45 mmol). The mixture was cooled to 0° C. in an ice-water bath, and trifluoromethanesulfonic anhydride (0.69 g, 2.45 mmol) was added dropwise via syringe. The resulting reaction mixture was stirred at 0° C. for 30 min before it was allowed to warm to room temperature and stirred for additional 2 hours. After TLC showed the complete conversion of starting material to product, the reaction mixture was concentrated and purified by column chromatography (20% ethyl acetate/petroleum ether) to afford 537 mg of 15. $^1$H NMR (CHLOROFORM-d) δ 8.14-8.19 (m, 1H), 2.55-2.66 (m, 1H), 1.30 (dt, J=7.8, 3.1 Hz, 2H), 1.21-1.27 (m, 2H).

Step P: (R)-5-bromo-6-cyclopropyl-2-(3-methylpiperazin-1-yl)nicotinonitrile (16)

A mixture of above triflate 15 (1.68 g, 4.6 mmol), (R)-2-methylpiperazine (790 mg, 6.9 mmol), and triethylamine (1.9 mL, 13.8 mmol) suspended in 5 mL of MeCN was subjected to microwave reaction at 175° C. for 60 min. After the mixture was concentrated under reduced pressure, the residue was extracted between ethyl acetate and water. The combined organic layer was then washed with aq. $NaHCO_3$, brine, dried —$Na_2SO_4$ and concentrated in vacuo to give 1.26 g of crude 16. MS (ES) M+H expected 321.1. found 321.2. $^1$H NMR (CHLOROFORM-d) δ 7.78 (s, 1H), 4.14-4.24 (m, 2H), 3.09-3.14 (m, 1H), 3.02-3.07 (m, 1H), 2.96-3.00 (m, 2H), 2.71 (dd, J=12.9, 10.2 Hz, 1H), 2.42-2.52 (m, 1H), 1.16 (d, J=6.3 Hz, 3H), 1.08 (s, 2H), 1.07 (d, J=3.8 Hz, 2H).

Step Q: (R)-5-bromo-6-cyclopropyl-2-(4-(3-methoxypropanoyl)-3-methylpiperazin-1-yl)nicotinonitrile (17)

To a 25 mL of round-bottom flask was added (R)-5-bromo-6-cyclopropyl-2-(3-methylpiperazin-1-yl)nicotinonitrile (16; 1.26 g, 3.9 mmol), 3-methoxypropanoic acid (0.74 mL, 7.8 mmol), HATU (2.98 g, 7.8 mmol), DIPEA (2 mL, 11.76 mmol) and 10 mL of methylene chloride. The resulting reaction mixture was stirred at room temperature overnight until TLC showed the completion of the reaction. Reaction mixture was with Satd. $NaHCO_3$ and brine. The combined organic layer was then dried over anhy. $Na_2SO_4$ and concentrated in vacuo. Column chromatography purification (30% EtOAc/petroleum ether) afforded 1.28 g of title compound as a white solid. MS (ES) M+H expected 407.1. found 407.0. $^1$H NMR (CHLOROFORM-d) δ 7.78-7.85 (m, 1H), 4.82-4.92 (m, 0.5H), 4.50 (d, J=13.6 Hz, 0.5H), 4.18-4.21 (m, 2H), 4.07-4.16 (m, 1H), 3.75-3.82 (m, 0.5H), 3.70-3.75 (m, 2H), 3.45-3.55 (m, 0.5H), 3.36 (s, 3H), 3.15-3.27 (m, 1H), 2.92-3.14 (m, 1H), 2.67-2.78 (m, 1H), 2.51-2.61 (m, 1H), 2.40-2.51 (m, 1H), 1.34 (d, J=6.8 Hz, 1.5H), 1.25 (d, J=2.5 Hz, 1.5H), 1.09 (d, J=3.5 Hz, 2H), 1.08 (s, 2H).

Other intermediates 17 were similarly prepared according to Scheme 2 by either: (1) replacing (R)-2-methylpiperazine in Step P with an alternately substituted or unsubstituted piperazine; and/or (2) replacing 3-methoxypropanoic acid in Step Q with an alternate acid.

Example 3. Preparation of (R)-5-bromo-6-cyclopropyl-2-(4-(3-methoxypropanoyl)-3-methylpiperazin-1-yl)-4-methylnicotinonitrile (R)-5-bromo-6-cyclopropyl-2-(4-(3-methoxypropanoyl)-3-methylpiperazin-1-yl)-4-methylnicotinonitrile (28; wherein $R^{1a}$ is methyl; $R^2$ is cyclopropyl; m is 1; $R^3$ is 3-methyl; and $R^8$ is methoxyethyl) was prepared according to general Scheme 3, below.

Scheme 3:

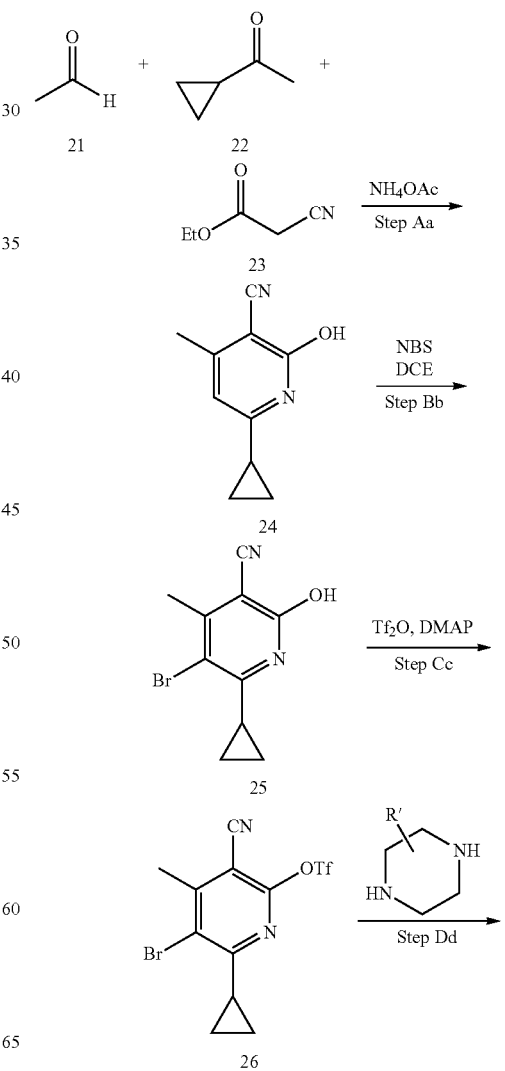

-continued

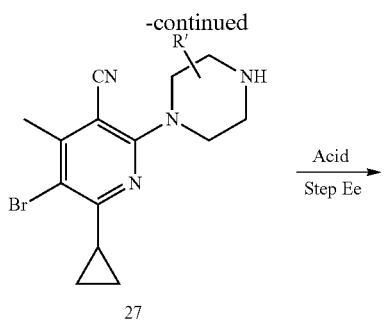

27

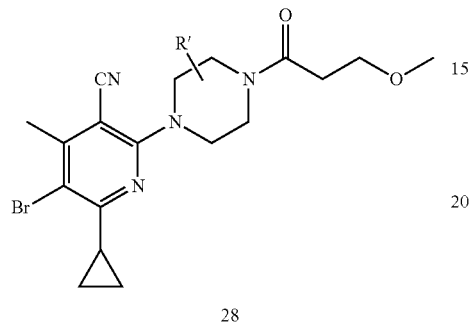

28

Step Aa:
6-cyclopropyl-2-hydroxy-4-methylnicotinonitrile
(24)

To a suspension of ammonium acetate (140 g, 1.82 mol) in 400 mL of EtOH was added successively commercially available 1-cyclopropylethanone (22; 22.5 mL, 22.7 mmol), acetaldehyde (21; 10 g, 22.7 mmol), and ethyl cyanoacetate (23; 24.2 mL, 22.7 mmol). The resulting mixture was stirred at reflux temperature for 2 hrs and subsequently at room temperature overnight. After the LC-MS showed the formation of the desired product, the solvent was removed under reduced pressure. Flash column chromatography (10% MeOH/DCM) afforded 1.3 g of 24 as a white solid. MS (ES) M+H expected 175.1. found 175.1. $^1$H NMR (DMSO-d6) δ 12.36 (br. s., 1H), 5.93 (s, 1H), 2.26 (s, 3H), 1.81-1.91 (m, 1H), 1.06-1.14 (m, 2H), 0.91-0.95 (m, 2H).

Step Bb: 5-bromo-6-cyclopropyl-2-hydroxy-4-methylnicotinonitrile (25)

To a solution of 6-cyclopropyl-2-hydroxy-4-methylnicotinonitrile (24; 2.6 g, 15 mmol) in 10 mL of DCE was added NBS (4 g, 22.5 mmol) at room temperature. The reaction mixture was then heated at reflux for 3 hours. After LC-MS showed the completion of reaction, the mixture was cooled to room temperature and poured into water and extracted with methylene chloride. The combined organic layer was dried over anhy. Na$_2$SO$_4$ and concentrated in vacuo. Column chromatography (4% MeOH/DCM) afforded 4 g of 25 as a brown solid. MS (ES) M+H expected 253.0. found 253.0. $^1$H NMR (CHLOROFORM-d) δ 2.68 (s, 3H), 1.79-1.88 (m, 1H), 1.03-1.09 (m, 2H), 0.93-1.01 (m, 2H).

Step Cc: 5-bromo-3-cyano-6-cyclopropyl-4-methyl-pyridin-2-yl trifluoromethanesulfonate (26)

To a solution of 5-bromo-2-hydroxy-6-isopropylnicotinonitrile (25; 4.0 g, 14.6 mmol) in 20 mL of methylene chloride was added DMAP (178 mg, 1.46 mmol), and triethylamine (2.5 mL, 17.5 mmol). The mixture was cooled to 0° C. in an ice-water bath, and trifluoromethanesulfonic anhydride (3.7 mL, 21.9 mmol) was added dropwise by syringe. The resulting reaction mixture was stirred at 0° C. for 30 min then allowed to warm to room temperature and stirred overnight. After TLC showed the complete conversion of starting material to product, the reaction mixture was concentrated and purified by column chromatography (20% EtOAc/petroleum ether) to afford 1.66 g of 26. $^1$H NMR (CHLOROFORM-d) δ 2.70 (s, 3H), 2.16-2.20 (m, 1H), 1.23-1.25 (m, 2H), 1.19-1.22 (m, 2H).

Step Dd: (R)-5-bromo-6-cyclopropyl-4-methyl-2-(3-methylpiperazin-1-yl)nicotinonitrile (27)

A mixture of above triflate 26 (1.66 g, 4.3 mmol), (R)-2-methylpiperazine (738 mg, 6.46 mmol), and triethylamine (1.8 mL, 12.9 mmol) suspended in 5 mL of MeCN was subjected to microwave reaction at 150° C. for 1 hour. After removal of solvent under reduced pressure, the residue was extracted between EtOAc and water. The organic layer was then washed with satd. aq. NaHCO$_3$ and brine, dried over anhy. Na$_2$SO$_4$ and concentrated in vacuo. Flash column chromatography (10% DCM/MeOH) afforded 330 mg of 27 as a light yellowish solid. MS (ES) M+H expected 335.1. found 335.2. $^1$H NMR (CHLOROFORM-d) δ 4.08-4.16 (m, 0.5H), 4.05-4.08 (m, 1H), 4.01-4.04 (m, 0.5H), 2.99-3.08 (m, 1H), 2.97 (d, J=8.8 Hz, 2H), 2.88-2.95 (m, 1H), 2.58-2.65 (m, 1H), 2.55-2.57 (m, 3H), 1.77 (br. s., 1H), 1.12 (s, 1.5H), 1.10 (s, 1.5H), 1.05-1.09 (m, 2H), 1.00-1.05 (m, 2H).

Step Ee: (R)-5-bromo-6-cyclopropyl-2-(4-(3-methoxypropanoyl)-3-methylpiperazin-1-yl)-4-methylnicotinonitrile (28)

To a 50 mL of round-bottom flask was added (R)-5-bromo-6-cyclopropyl-4-methyl-2-(3-methylpiperazin-1-yl) nicotinonitrile (27; 1.12 g, 3.34 mmol), 3-methoxypropanoic acid (0.63 mL, 6.68 mmol), HATU (2.54 g, 6.68 mmol), DIPEA (3.8 g, 10 mmol) and 10 mL of methylene chloride. The resulting reaction mixture was stirred at room temperature overnight until TLC showed the completion of the reaction. After washing the reaction mixture with Satd. NaHCO$_3$, brine, the organic layer was dried over anhy. Na$_2$SO$_4$ and concentrated in vacuo. Flash column chromatography (20% EtOAc/petroleum ether) afforded 1.7 g of 28 as a yellowish solid. MS (ES) M+H expected 421.1. found 421.3. $^1$H NMR (CHLOROFORM-d) δ 4.90 (br. s., 0.5H), 4.52 (d, J=13.6 Hz, 0.5H), 4.22 (br. s., 0.5H), 3.95-4.13 (m, 2H), 3.78 (br. s., 0.5H), 3.74 (t, J=5.9 Hz, 2H), 3.50-3.61 (m, 0.5H), 3.38 (s, 3H), 3.07-3.24 (m, 1.5H), 2.90-3.06 (m, 1H), 2.65-2.79 (m, 1H), 2.60 (s, 3H), 2.52-2.63 (m, 1H), 2.17-2.21 (m, 1H), 1.37 (d, J=6.5 Hz, 1.5H), 1.27 (d, J=6.3 Hz, 1.5H), 1.09 (s, 2H), 1.05-1.08 (m, 2H).

Other intermediates 28 were similarly prepared according to Scheme 3 by either: (1) replacing (R)-2-methylpiperazine in Step Dd with an alternately substituted or unsubstituted piperazine; and/or (2) replacing 3-methoxypropanoic acid in Step Ee with an alternate acid.

Example 4. Preparation of (R)-6-isopropyl-2-(4-(3-methoxypropanoyl)-3-methylpiperazin-1-yl)-5-(4-(trifluoromethyl)phenyl)-nicotinonitrile (Compound 189)

A mixture of bromide 7 from Example 1 (26 mg, 0.06 mmol), 4-(trifluoromethyl)phenylboronic acid (17 mg, 0.089 mmol), Pd(PPh₃)₄ (3 mg, 0.003 mmol), and K₂CO₃ (16 mg, 0.119 mmol) suspended in 1 mL of DMF was subjected to microwave reaction at 150° C. for 45 min. After the reaction, the reaction mixture was concentrated in vacuo, and the residue was purified by column chromatography to afford 19 mg of Compound 189 as yellowish oil. MS (ES) M+H expected 475.2. found 475.1. 1H NMR (CHLOROFORM-d) δ 7.70 (d, J=8.0 Hz, 2H), 7.60 (s, 1H), 7.38 (d, J=8.0 Hz, 2H), 4.93 (br. s., 0.5H), 4.56 (d, J=11.0 Hz, 0.5H), 4.44 (d, J=12.3 Hz, 1H), 4.32-4.39 (m, 1H), 4.28 (br. s., 0.5H), 3.83 (d, J=13.3 Hz, 0.5H), 3.68-3.79 (m, 2H), 3.53-3.64 (m, 0.5H), 3.38 (s, 3H), 3.36 (br. s., 0.5H), 3.33 (br. s., 0.5H), 3.10-3.28 (m, 1.5H), 3.07 (dt, J=13.3, 1 Hz, 1H), 2.65-2.80 (m, 1H), 2.52-2.65 (m, 1H), 1.40 (d, J=6.5 Hz, 1.5H), 1.30 (d, J=6.3 Hz, 1.5H), 1.16 (d, J=6.5 Hz, 6H).

Other Compounds of Formula II listed below, wherein R$^{1b}$ is aryl or heteroaryl; and R$^2$ is isopropyl or cyclopropyl were similarly prepared using any of intermediates 7 (Scheme 1), 17 (Scheme 2), or 28 (Scheme 3) as starting material.

(R)-2-(4-(furan-2-carbonyl)-3-methylpiperazin-1-yl)-6-isopropyl-5-(4-(trifluoromethyl)phenyl) nicotinonitrile (Compound 185)

¹H NMR (CHLOROFORM-d) δ 7.70 (d, J=8.0 Hz, 2H), 7.61 (s, 1H), 7.47-7.56 (m, 1H), 7.38 (d, J=7.8 Hz, 1H), 7.07 (d, J=3.5 Hz, 1H), 6.48-6.55 (m, 1H), 4.86-4.96 (m, 1H), 4.43-4.59 (m, 2H), 4.38 (dt, J=13.3, 2.0 Hz, 1H), 3.56 (br. s., 1H), 3.46 (dd, J=13.3, 3.8 Hz, 1H), 3.28 (td, J=12.4, 3.4 Hz, 1H), 3.07 (quin, J=6.7 Hz, 1H), 1.47 (d, J=6.8 Hz, 3H), 1.16 (dd, J=6.7, 1.6 Hz, 6H). LC-MS: m/z 483.1 (M+H)⁺.

(R)-2-(4-(furan-3-carbonyl)-3-methylpiperazin-1-yl)-6-isopropyl-5-(4-(trifluoromethyl)phenyl)nicotinonitrile (Compound 187)

¹H NMR (CHLOROFORM-d) δ 7.76 (s, 1H), 7.70 (d, J=8.0 Hz, 2H), 7.61 (s, 1H), 7.44-7.49 (m, 1H), 7.38 (d, J=8.0 Hz, 2H), 6.56-6.63 (m, 1H), 4.75 (br. s., 1H), 4.45 (d, J=13.1 Hz, 1H), 4.35-4.42 (m, 2H), 3.42-3.64 (m, 1H), 3.31-3.41 (m, 1H), 3.18 (td, J=12.5, 3.5 Hz, 1H), 3.07 (dt, J=13.2, 6.6 Hz, 1H), 1.44 (d, J=6.8 Hz, 3H), 1.16 (dd, J=6.7, 1.9 Hz, 6H). LC-MS: m/z 483.2 (M+H)⁺.

(R)-6-isopropyl-2-(3-methyl-4-(2-(thiophen-2-yl)acetyl)piperazin-1-yl)-5-(4-(trifluoromethyl)phenyl)nicotinonitrile (Compound 188)

¹H NMR (CHLOROFORM-d) δ 7.69 (d, J=8.3 Hz, 2H), 7.59 (s, 1H), 7.37 (d, J=8.0 Hz, 2H), 7.22 (dd, J=5.1, 1.1 Hz, 1H), 6.95-7.00 (m, 1H), 6.89-6.95 (m, 1H), 4.95 (br. s., 0.5H), 4.59 (d, J=12.8 Hz, 0.5H), 4.19-4.48 (m, 3H), 3.89-4.06 (m, 2H), 3.82 (d, J=13.6 Hz, 0.5H), 3.57 (t, J=11.3 Hz, 0.5H), 3.20-3.38 (m, 1H), 3.08-3.20 (m, 1H), 3.00-3.08 (m, 1H), 1.35 (d, J=6.5 Hz, 1.5H), 1.31 (d, J=6.5 Hz, 1.5H), 1.15 (d, J=6.5 Hz, 6H). LC-MS: m/z 513.1 (M+H)⁺.

(R)-2-(4-(furan-2-carbonyl)-3-methylpiperazin-1-yl)-6-isopropyl-5-m-tolylnicotinonitrile (Compound 190)

¹H NMR (CHLOROFORM-d) δ 7.60 (s, 1H), 7.51 (d, J=1.0 Hz, 1H), 7.31 (t, J=7.8 Hz, 1H), 7.19 (d, J=7.8 Hz, 1H), 7.01-7.09 (m, 3H), 6.51 (dd, J=3.3, 1.8 Hz, 1H), 4.90 (br. s., 1H), 4.52 (d, J=13.3 Hz, 1H), 4.42 (d, J=13.8 Hz, 1H), 4.30-4.37 (m, 1H), 3.56 (br. s., 1H), 3.41 (dd, J=13.2, 3.6 Hz, 1H), 3.24 (td, J=12.4, 3.3 Hz, 1H), 3.15 (dt, J=13.3, 6.7 Hz, 1H), 2.40 (s, 3H), 1.48 (d, J=6.5 Hz, 3H), 1.15 (dd, J=6.8, 2.3 Hz, 6H). LC-MS: m/z 429.1 (M+H)⁺.

(R)-2-(4-furan-3-carbonyl)-3-methylpiperazin-1-yl)-6-isopropyl-5-m-tolylnicotinonitrile (Compound 191)

¹H NMR (CHLOROFORM-d) δ 7.75 (s, 1H), 7.61 (s, 1H), 7.46 (t, J=1.6 Hz, 1H), 7.31 (t, J=7.8 Hz, 1H), 7.20 (d, J=7.8 Hz, 1H), 7.00-7.08 (m, 2H), 6.59 (d, J=1.0 Hz, 1H), 4.74 (br. s., 1H), 4.20-4.50 (m, 3H), 3.41-3.61 (m, 1H), 3.32 (dd, J=13.1, 3.0 Hz, 1H), 3.08-3.19 (m, 2H), 2.40 (s, 3H), 1.45 (d, J=6.8 Hz, 3H), 1.08-1.19 (m, 6H). LC-MS: m/z 429.1 (M+H)⁺.

(R)-6-isopropyl-2-(3-methyl-4-(2-(thiophen-2-yl)acetyl)piperazin-1-yl)-5-m-tolylnicotinonitrile (Compound 192)

¹H NMR (CHLOROFORM-d) δ 7.59 (s, 1H), 7.28-7.35 (m, 1H), 7.16-7.25 (m, 2H), 7.00-7.07 (m, 2H), 6.89-6.99 (m, 2H), 4.94 (br. s., 0.5H), 4.58 (d, J=13.3 Hz, 0.5H), 4.33-4.43 (m, 1H), 4.19-4.33 (m, 2H), 3.90-4.05 (m, 2H), 3.80 (d, J=13.3 Hz, 0.5H), 3.51-3.63 (m, 0.5H), 3.17-3.33 (m, 1H), 3.10-3.17 (m, 1H), 2.99-3.10 (m, 1H), 2.40 (s, 3H), 1.36 (d, J=6.3 Hz, 1.5H), 1.32 (d, J=6.8 Hz, 1.5H), 1.14 (d, J=6.8 Hz, 6H). LC-MS: m/z 459.1 (M+H)⁺.

(R)-6-isopropyl-2-(4-(3-methoxypropanoyl)-3-methylpiperazin-1-yl)-5-m-tolylnicotinonitrile (Compound 193)

¹H NMR (CHLOROFORM-d) δ 7.60 (s, 1H), 7.31 (t, J=7.9 Hz, 1H), 7.19 (d, J=7.8 Hz, 1H), 7.01-7.08 (m, 2H), 4.93 (br. s., 0.5H), 4.56 (d, J=13.1 Hz, 0.5H), 4.30-4.44 (m, 2H), 4.19-4.30 (m, 2H), 3.81 (d, J=13.6 Hz, 0.5H), 3.71-3.78 (m, 2H), 3.52-3.65 (m, 0.5H), 3.38 (s, 3H), 3.24-3.36 (m, 1H), 3.10-3.23 (m, 2H), 2.65-2.80 (m, 1H), 2.54-2.64 (m, 1H), 2.40 (s, 3H), 1.41 (d, J=6.5 Hz, 1.5H), 1.31 (d, J=6.8 Hz, 1.5H), 1.15 (d, J=6.5 Hz, 6H). LC-MS: m/z 421.1 (M+H)⁺.

(R)-2-(4-furan-3-carbonyl)-3-isopropylpiperazin-1-yl)-6-isopropyl-5-(4-(trifluoromethyl)phenyl)nicotinonitrile (Compound 195)

¹H NMR (CHLOROFORM-d) δ 7.67-7.84 (m, 3H), 7.57-7.64 (m, 1H), 7.45-7.53 (m, 1H), 7.38 (d, J=8.0 Hz, 2H), 6.58 (s, 1H), 4.84 (d, J=13.6 Hz, 1H), 4.49-4.69 (m, 2H), 3.81-4.22 (m, 1H), 3.22-3.57 (br. s., 3H), 3.07 (dt, J=13.3, 6.7 Hz, 1H), 2.19-2.38 (m, 1H), 1.18 (d, J=6.8 Hz, 3H), 1.14 (d, J=6.8 Hz, 3H), 0.88-1.05 (m, 6H). LC-MS: m/z 511.1 (M+H)⁺.

(R)-6-isopropyl-2-(3-isopropyl-4-(2-(thiophen-2-yl)acetyl)piperazin-1-yl)-5-(4-(trifluoromethyl)phenyl)-nicotinonitrile (Compound 196)

¹H NMR (CHLOROFORM-d) δ 7.64-7.75 (m, 2H), 7.55-7.62 (m, 1H), 7.37-7.46 (d, J=8.5 Hz, 2H), 7.22 (ddd, J=4.8, 3.2, 1.3 Hz, 1H), 6.87-7.02 (m, 2H), 4.68-4.82 (m, 1.5H), 4.35-4.54 (m, 1.5H), 3.81-4.11 (m, 3H), 3.63 (d, J=10.3 Hz, 0.5H), 3.37-3.53 (m, 0.5H), 3.08-3.20 (m, 1H), 2.96-3.08 (m, 2H), 2.18-2.32 (m, 0.5H), 2.04-2.17 (m, 0.5H), 1.17 (dd, J=6.7, 3.6 Hz, 3H), 1.13 (d, J=6.5 Hz, 3H), 1.08 (dd, J=11.0, 6.5 Hz, 3H), 0.87-0.93 (m, 1.5H), 0.85 (d, J=6.8 Hz, 1.5H). LC-MS: m/z 541.1 (M+H)+.

(R)-6-isopropyl-2-(3-isopropyl-4-(3-methoxypropanoyl)piperazin-1-yl)-5-(4-(trifluoromethyl)phenyl)nicotinonitrile (Compound 197)

¹H NMR (CHLOROFORM-d) δ 7.66-7.76 (m, 2H), 7.59 (d, J=2.3 Hz, 1H), 7.38 (d, J=8.0 Hz, 2H), 4.68-4.84 (m, 1.5H), 4.47-4.5 (s, 1.5H), 3.88 (d, J=13.6 Hz, 0.5H), 3.69-3.82 (m, 2H), 3.61 (d, J=10.3 Hz, 0.5H), 3.42-3.52 (m, 0.5H), 3.38 (d, J=2.8 Hz, 3H), 3.12-3.27 (m, 2H), 3.02-3.12 (m, 1H), 2.90-3.02 (m, 0.5H), 2.53-2.83 (m, 2H), 2.17-2.30 (m, 0.5H), 1.98-2.16 (m, 0.5H), 1.18 (d, J=6.5 Hz, 3H), 1.14 (d, J=6.8 Hz, 3H), 1.08 (dd, J=6.5, 2.8 Hz, 3H), 0.91 (d, J=6.8 Hz, 1.5H), 0.85 (d, J=6.8 Hz, 1.5H). LC-MS: m/z 407.4 (M+H)+.

(R)-5-(4-fluorophenyl)-6-isopropyl-2-(3-methyl-4-(2-methylfuran-3-carbonyl)piperazin-1-yl)nicotinonitrile (Compound 199)

¹H NMR (CHLOROFORM-d) δ 7.58 (s, 1H), 7.29 (d, J=2.0 Hz, 1H), 7.17-7.24 (m, 2H), 7.08-7.16 (m, 2H), 6.38 (d, J=1.8 Hz, 1H), 4.68 (br. s., 1H), 4.41 (d, J=13.1 Hz, 1H), 4.36 (d, J=13.1 Hz, 1H), 4.20-4.28 (d, J=13.6 Hz, 1H), 3.39-3.59 (m, 1H), 3.25-3.37 (m, 1H), 3.03-3.18 (m, 2H), 2.41 (s, 3H), 1.41 (d, J=6.5 Hz, 3H), 1.14 (dd, J=6.8, 2.3 Hz, 6H). LC-MS: m/z 447.2 (M+H)+.

(R)-6-isopropyl-2-(3-methyl-4-(2-methylfuran-3-carbonyl)piperazin-1-yl)-5-m-tolylnicotinonitrile (Compound 200)

¹H NMR (CHLOROFORM-d) δ 7.58 (s, 1H), 7.29 (d, J=2.0 Hz, 2H), 7.17-7.24 (m, 1H), 7.08-7.16 (m, 2H), 6.38 (d, J=1.8 Hz, 1H), 4.68 (br. s., 1H), 4.41 (d, J=13.1 Hz, 1H), 4.36 (d, J=13.1 Hz, 1H), 4.20-4.28 (d, J=13.6 Hz, 1H), 3.39-3.59 (m, 4H), 3.25-3.37 (m, 4H), 3.03-3.18 (m, 8H), 2.41 (s, 11H), 1.41 (d, J=6.5 Hz, 11H), 1.14 (dd, J=6.8, 2.3 Hz, 6H). LC-MS: m/z 443.3 (M+H)+.

(R)-6-isopropyl-2-(3-methyl-4-(2-methylfuran-3-carbonyl)piperazin-1-yl)-5-(4-(trifluoromethyl)phenyl)-nicotinonitrile (Compound 201)

¹H NMR (CHLOROFORM-d) δ 7.70 (d, J=8.0 Hz, 2H), 7.57-7.64 (m, 1H), 7.37 (d, J=8.0 Hz, 2H), 7.27-7.32 (m, 1H), 6.35-6.42 (m, 1H), 4.68 (br. s., 1H), 4.34-4.53 (m, 2H), 4.20-4.34 (m, 1H), 3.48 (d, J=4.8 Hz, 1H), 3.28-3.40 (m, 1H), 3.16 (td, J=12.6, 3.4 Hz, 1H), 3.00-3.11 (m, 1H), 2.41 (s, 3H), 1.38-1.48 (m, 3H), 1.16 (dd, J=6.8, 2.3 Hz, 6H). LC-MS: m/z 497.2 (M+H)+.

(R)-6-isopropyl-5-(4-isopropylphenyl)-2-(3-methyl-4-(2-methylfuran-3-carbonyl)piperazin-1-yl)nicotinonitrile (Compound 202)

¹H NMR (CHLOROFORM-d) δ 7.58-7.65 (m, 1H), 7.28 (d, J=8.3 Hz, 3H), 7.11-7.20 (m, 2H), 6.37 (d, J=2.0 Hz, 1H), 4.59-4.68 (br. s., 1H), 4.30-4.43 (m, 2H), 4.19 (br. s., 1H), 3.40-3.54 (m, 1H), 3.30 (dd, J=12.8, 3.0 Hz, 1H), 3.14-3.22 (m, 1H), 3.06-3.14 (m, 1H), 2.96 (spt, J=6.9 Hz, 1H), 2.41 (s, 3H), 1.39-1.45 (m, 3H), 1.30 (d, J=7.0 Hz, 6H), 1.15 (dd, J=6.8, 3.0 Hz, 6H). LC-MS: m/z 471.3 (M+H)+.

(R)-5-(furan-3-yl)-6-isopropyl-2-(3-methyl-4-(2-methylfuran-3-carbonyl)piperazin-1-yl)nicotinonitrile (Compound 203)

¹H NMR (CHLOROFORM-d) δ 7.64 (s, 1H), 7.49-7.53 (m, 1H), 7.43-7.47 (m, 1H), 7.29 (d, J=1.8 Hz, 1H), 6.45 (d, J=0.8 Hz, 1H), 6.36 (d, J=1.8 Hz, 1H), 4.68 (br. s., 1H), 4.39 (d, J=13.1 Hz, 1H), 4.34 (d, J=13.1 Hz, 1H), 4.18-4.26 (br. s., 1H), 3.38-3.56 (m, 1H), 3.22-3.35 (m, 2H), 3.11 (td, J=12.6, 3.4 Hz, 1H), 2.36-2.47 (m, 3H), 1.39 (d, J=6.5 Hz, 3H), 1.18 (dd, J=6.7, 1.6 Hz, 6H). LC-MS: m/z 419.2 (M+H)+.

(R)-2-(4-(furan-3-carbonyl)-3-methylpiperazin-1-yl)-5-(furan-3-yl)-6-isopropylnicotinonitrile (Compound 204)

¹H NMR (CHLOROFORM-d) δ 7.72-7.77 (m, 1H), 7.64 (s, 1H), 7.50 (t, J=1.8 Hz, 1H), 7.44-7.47 (m, 2H), 6.58 (dd, J=1.8, 0.8 Hz, 1H), 6.45 (dd, J=1.8, 0.8 Hz, 1H), 5.30 (s, 1H), 4.73 (br. s., 1H), 4.38 (s, 1H), 4.41 (s, 1H), 4.31 (t, J=2.1 Hz, 1H), 4.35 (t, J=2.0 Hz, 1H), 3.48 (br. s., 1H), 3.32 (dd, J=9.9, 3.1 Hz, 1H), 3.24-3.30 (m, 1H), 3.14 (td, J=12.5, 3.5 Hz, 1H), 1.42 (d, J=7.0 Hz, 3H), 1.19 (dd, J=6.8, 1.0 Hz, 6H). LC-MS: m/z 405.2 (M+H)+.

(R)-5-(furan-3-yl)-6-isopropyl-2-(4-(3-methoxypropanoyl)-3-methylpiperazin-1-yl)nicotinonitrile (Compound 205)

¹H NMR (CHLOROFORM-d) δ 7.63 (s, 1H), 7.50 (t, J=1.8 Hz, 1H), 7.42-7.47 (m, 1H), 6.44 (dd, J=1.8, 0.8 Hz, 1H), 4.92 (br. s., 0.5H), 4.54 (d, J=13.1 Hz, 0.5H), 4.38 (dd, J=12.2, 2.1 Hz, 1H), 4.17-4.35 (m, 2H), 3.80 (d, J=13.1 Hz, 0.5H), 3.74 (t, J=6.5 Hz, 2H), 3.51-3.62 (m, 0.5H), 3.36-3.39 (m, 3H), 3.23-3.35 (m, 2H), 3.06-3.17 (m, 1H), 2.64-2.80 (m, 1H), 2.51-2.63 (m, 1H), 1.38 (d, J=6.3 Hz, 1.5H), 1.28 (d, J=6.0 Hz, 1.5H), 1.19 (d, J=6.8 Hz, 6H).
LC-MS: m/z 397.2 (M+H)+.

(R)-2-(4-(furan-3-carbonyl)-3-methylpiperazin-1-yl)-6-isopropyl-5-(4-isopropylphenyl)nicotinonitrile (Compound 206)

¹H NMR (CHLOROFORM-d) δ 7.72-7.77 (m, 1H), 7.61 (s, 1H), 7.46 (t, J=1.6 Hz, 1H), 7.28 (d, J=8.0 Hz, 2H), 7.12-7.19 (m, 2H), 6.59 (dd, J=1.8, 0.8 Hz, 1H), 4.74 (br. s., 1H), 4.39 (d, J=13.3 Hz, 1H), 4.33 (dt, J=13.2, 1.9 Hz, 2H), 3.49 (br. s., 1H), 3.32 (dd, J=13.2, 3.4 Hz, 1H), 3.08-3.23 (m, 2H), 2.96 (dt, J=13.8, 6.9 Hz, 1H), 1.45 (d, J=6.8 Hz, 3H), 1.30 (d, J=7.0 Hz, 6H), 1.15 (dd, J=6.5, 2.3 Hz, 6H). LC-MS: m/z 457.2 (M+H)+.

(R)-5-(4-fluorophenyl)-6-isopropyl-2-(4-(3-methoxypropanoyl)-3-methylpiperazin-1-yl)nicotinonitrile (Compound 207)

¹H NMR (CHLOROFORM-d) δ 7.58 (s, 1H), 7.17-7.24 (m, 2H), 7.08-7.16 (m, 2H), 4.92 (br. s., 0.5H), 4.55 (d, J=12.0 Hz, 0.5H), 4.40 (dd, J=12.2, 1.9 Hz, 1H), 4.19-4.35 (m, 2H), 3.82 (d, J=12.5 Hz, 0.5H), 3.69-3.78 (m, 2H), 3.53-3.63 (m, 0.5H), 3.38 (s, 3H), 3.26-3.35 (m, 1H), 3.13-3.22 (m, 1H), 3.03-3.12 (m, 1H), 2.65-2.81 (m, 1H), 2.53-2.64 (m, 1H), 1.40 (d, J=6.3 Hz, 1.5H), 1.30 (d, J=6.5 Hz, 1.5H), 1.14 (d, J=6.8 Hz, 6H). LC-MS: m/z 425.2 (M+H)+.

(R)-6-isopropyl-5-(4-isopropylphenyl)-2-(4-(3-methoxypropanoyl)-3-methylpiperazin-1-yl)nicotinonitrile (Compound 208)

$^1$H NMR (CHLOROFORM-d) δ 7.59-7.65 (m, 1H), 7.29-7.33 (m, 2H), 7.14-7.22 (m, 2H), 4.95 (br. s., 0.5H), 4.58 (d, J=13.1 Hz, 0.5H), 4.37-4.44 (m, 1H), 4.22-4.37 (m, 2H), 3.83 (d, J=13.3 Hz, 0.5H), 3.70-3.80 (m, 2H), 3.55-3.67 (m, 0.5H), 3.40 (s, 3H), 3.33 (t, J=12.3 Hz, 1H), 3.15-3.25 (m, 2H), 2.98 (quin, J=6.9 Hz, 1H), 2.67-2.83 (m, 1H), 2.55-2.67 (m, 1H), 1.43 (d, J=5.8 Hz, 1.5H), 1.34 (m, 1.5H), 1.32 (d, J=7.0 Hz, 6H), 1.17 (d, J=6.8 Hz, 6H). LC-MS: m/z 449.2 (M+H)$^+$.

(R)-5-(benzofuran-2-yl)-6-isopropyl-2-(4-(3-methoxypropanoyl)-3-methylpiperazin-1-yl)nicotinonitrile (Compound 209)

$^1$H NMR (CHLOROFORM-d) δ 8.12 (s, 1H), 7.61 (dd, J=7.7, 0.9 Hz, 1H), 7.48-7.56 (m, 1H), 7.32 (td, J=7.7, 1.5 Hz, 1H), 7.24-7.29 (m, 1H), 6.78-6.88 (m, 1H), 4.93 (br. s., 0.5H), 4.38-4.64 (m, 2H), 4.27 (br. s., 0.5H), 3.83 (d, J=12.8 Hz, 1H), 3.75 (br. s., 2H), 3.55 (quin, J=6.7 Hz, 2H), 3.38 (s, 3H), 3.08-3.29 (m, 2H), 2.66-2.83 (m, 1H), 2.60 (br. s., 1H), 1.38 (d, J=6.0 Hz, 1.5H), 1.33 (br. s., 1.5H), 1.28 (d, J=6.5 Hz, 6H). LC-MS: m/z 447.1 (M+H)$^+$.

(R)-6-isopropyl-2-(4-(3-methoxypropanoyl)-3-methylpiperazin-1-yl)-5-0γ(pyrimidin-5-yl)nicotinonitrile (Compound 210)

$^1$H NMR (CHLOROFORM-d) δ 9.23-9.28 (m, 1H), 8.69 (s, 2H), 7.62 (s, 1H), 4.94 (br. s., 0.5H), 4.56 (d, J=9.5 Hz, 0.5H), 4.37-4.53 (m, 2H), 4.29 (br. s., 0.5H), 3.84 (d, J=13.3 Hz, 0.5H), 3.68-3.79 (m, 2H), 3.52-3.64 (m, 0.5H), 3.40-3.46 (m, 0.5H), 3.38 (s, 3H), 3.20-3.32 (m, 1H), 3.16 (d, J=9.5 Hz, 1H), 2.93-3.04 (m, 1H), 2.65-2.78 (m, 1H), 2.52-2.64 (m, 1H), 1.39 (d, J=6.5 Hz, 1.5H), 1.29 (d, J=6.8 Hz, 1.5H), 1.19 (dd, J=6.7, 1.1 Hz, 6H). LC-MS: m/z 409.2 (M+H)$^+$.

(R)-6-isopropyl-2-(4-(3-methoxypropanoyl)-3-methylpiperazin-1-yl)-5-(naphthalen-2-yl)nicotinonitrile (Compound 211)

$^1$H NMR (CHLOROFORM-d) δ 7.83-7.97 (m, 3H), 7.66-7.77 (m, 2H), 7.49-7.60 (m, 2H), 7.36 (dd, J=8.4, 1.6 Hz, 1H), 4.94 (br. s., 0.5H), 4.57 (d, J=12.8 Hz, 0.5H), 4.42 (d, J=12.8 Hz, 1H), 4.30-4.38 (m, 1H), 4.27 (br. s., 1H), 3.83 (d, J=13.3 Hz, 0.5H), 3.69-3.79 (m, 2H), 3.54-3.65 (m, 0.5H), 3.39 (s, 3H), 3.29-3.38 (m, 1H), 3.18-3.24 (m, 1H), 3.06-3.17 (m, 1H), 2.66-2.83 (m, 1H), 2.52-2.65 (m, 1H), 1.42 (d, J=7.3 Hz, 1.5H), 1.32 (d, J=6.5 Hz, 1.5H), 1.17 (d, J=6.8 Hz, 6H). LC-MS: m/z 457.1 (M+H)$^+$.

(R)-6-isopropyl-5-(3-methoxyphenyl)-2-(4-(3-methoxypropanoyl)-3-methylpiperazin-1-yl)nicotinonitrile (Compound 212)

$^1$H NMR (CHLOROFORM-d) δ 7.61 (s, 1H), 7.34 (t, J=7.9 Hz, 1H), 6.92 (dd, J=8.3, 1.8 Hz, 1H), 6.82 (d, J=7.5 Hz, 1H), 6.74-6.79 (m, 1H), 4.93 (br. s., 0.5H), 4.56 (d, J=12.8 Hz, 0.5H), 4.39 (d, J=13.6 Hz, 1H), 4.21-4.34 (m, 2H), 3.84 (s, 3H), 3.79 (d, J=8.0 Hz, 0.5H), 3.70-3.77 (m, 2H), 3.53-3.64 (m, 0.5H), 3.38 (s, 3H), 3.26-3.36 (m, 1H), 3.12-3.22 (m, 2H), 2.65-2.80 (m, 1H), 2.52-2.64 (m, 1H), 1.41 (d, J=1.5 Hz, 4H), 1.31 (d, J=6.5 Hz, 1.5H), 1.10-1.19 (m, 6H). LC-MS: m/z 437.1 (M+H)$^+$.

(R)-2-isopropyl-6-(4-(3-methoxypropanoyl)-3-methylpiperazin-1-yl)-3,4'-bipyridine-5-carbonitrile (Compound 213)

$^1$H NMR (CHLOROFORM-d) δ 8.69 (d, J=5.3 Hz, 2H), 7.61 (s, 1H), 7.22 (d, J=5.5 Hz, 2H), 4.93 (br. s., 0.5H), 4.56 (d, J=9.8 Hz, 0.5H), 4.34-4.51 (m, 2H), 4.28 (br. s., 1H), 3.83 (d, J=13.3 Hz, 0.5H), 3.68-3.79 (m, 2H), 3.58 (t, J=11.0 Hz, 0.5H), 3.38 (s, 3H), 3.14-3.28 (m, 2H), 3.03-3.14 (m, 1H), 2.65-2.83 (m, 1H), 2.52-2.65 (m, 1H), 1.39 (d, J=6.3 Hz, 1.5H), 1.29 (d, J=6.5 Hz, 1.5H), 1.18 (d, J=6.5 Hz, 6H). LC-MS: m/z 408.1 (M+H)$^+$.

(R)-6-isopropyl-5-(4-methoxyphenyl)-2-(4-(3-methoxypropanoyl)-3-methylpiperazin-1-yl)nicotinonitrile (Compound 214)

$^1$H NMR (CHLOROFORM-d) δ 7.59 (s, 1H), 7.11-7.20 (m, 2H), 6.92-7.01 (m, 2H), 4.92 (br. s., 0.5H), 4.56 (d, J=12.8 Hz, 0.5H), 4.37 (d, J=12.5 Hz, 1H), 4.29 (d, J=13.1 Hz, 2H), 3.86 (s, 3H), 3.81 (d, J=13.6 Hz, 0.5H), 3.75 (br. s., 2H), 3.53-3.64 (m, 0.5H), 3.38 (s, 3H), 3.31 (t, J=13.2 Hz, 1H), 3.11-3.20 (m, 2H), 2.66-2.82 (m, 1H), 2.52-2.64 (m, 1H), 1.41 (d, J=6.0 Hz, 1.5H), 1.31 (d, J=5.8 Hz, 1.5H), 1.14 (d, J=6.8 Hz, 6H). LC-MS: m/z 437.3 (M+H)$^+$.

(R)-5-(4-chlorophenyl)-6-isopropyl-2-(4-(3-methoxypropanoyl)-3-methylpiperazin-1-yl)nicotinonitrile (Compound 215)

$^1$H NMR (CHLOROFORM-d) δ 7.58 (s, 1H), 7.38-7.43 (m, 2H), 7.14-7.20 (m, 2H), 4.93 (br. s., 0.5H), 4.55 (d, J=12.5 Hz, 0.5H), 4.40 (d, J=12.8 Hz, 1H), 4.21-4.36 (m, 2H), 3.82 (d, J=13.6 Hz, 0.5H), 3.69-3.78 (m, 2H), 3.53-3.63 (m, 0.5H), 3.38 (s, 3H), 3.27-3.37 (m, 1H), 3.11-3.23 (m, 1H), 3.02-3.11 (m, 1H), 2.65-2.81 (m, 1H), 2.53-2.64 (m, 1H), 1.40 (d, J=6.5 Hz, 1.5H), 1.30 (d, J=6.8 Hz, 1.5H), 1.14 (d, J=6.5 Hz, 6H). LC-MS: m/z 441.1 (M+H)$^+$.

5-(4-ethylphenyl)-6-isopropyl-2-(4-(3-methoxypropanoyl)-3-methylpiperazin-1-yl)nicotinonitrile (Compound 216)

$^1$H NMR (CHLOROFORM-d) δ 7.60 (s, 1H), 7.27 (s, 1H), 7.25 (s, 1H), 7.15 (d, J=8.0 Hz, 2H), 4.93 (br. s., 0.5H), 4.56 (d, J=12.5 Hz, 0.5H), 4.38 (d, J=12.3 Hz, 1H), 4.30 (d, J=12.3 Hz, 2H), 3.81 (d, J=13.3 Hz, 0.5H), 3.75 (br. s., 2H), 3.51-3.64 (m, 0.5H), 3.38 (s, 3H), 3.31 (t, J=13.6 Hz, 1H), 3.12-3.22 (m, 2H), 3.10 (d, J=14.3 Hz, 0.5H), 2.77 (br. s., 0.5H), 2.71 (q, J=7.5 Hz, 2H), 2.61 (br. s., 1H), 1.41 (d, J=6.0 Hz, 1.5H), 1.32 (br. s., 1.5H), 1.29 (t, J=7.5 Hz, 3H), 1.15 (d, J=6.8 Hz, 6H). LC-MS: m/z 435.3 (M+H)$^+$.

(R)-6-isopropyl-2-(4-(3-methoxypropanoyl)-3-methylpiperazin-1-yl)-5-(naphthalen-1-yl)nicotinonitrile (Compound 217)

$^1$H NMR (CHLOROFORM-d) δ 7.92 (t, J=7.4 Hz, 2H), 7.63 (s, 1H), 7.49-7.57 (m, 2H), 7.39-7.47 (m, 2H), 7.27-7.34 (m, 1H), 4.96 (br. s., 0.5H), 4.59 (d, J=12.5 Hz, 0.5H), 4.45 (d, J=13.3 Hz, 1H), 4.32-4.41 (m, 1H), 4.30 (br. s., 1H), 3.85 (d, J=13.6 Hz, 0.5H), 3.70-3.81 (m, 2H), 3.55-3.67 (m, 0.5H), 3.39 (s, 3H), 3.07-3.27 (m, 2H), 2.67-2.76 (m, 2H), 2.53-2.66 (m, 1H), 1.45 (d, J=5.5 Hz, 1.5H), 1.36 (d, J=6.5 Hz, 1.5H), 1.06 (d, J=6.5 Hz, 6H). LC-MS: m/z 457.3 (M+H)$^+$.

(R)-5-(3-chlorophenyl)-6-isopropyl-2-(4-(3-methoxypropanoyl)-3-methylpiperazin-1-yl)nicotinonitrile (Compound 218)

$^1$H NMR (CHLOROFORM-d) δ 7.56-7.61 (m, 1H), 7.35-7.39 (m, 2H), 7.21-7.25 (m, 1H), 7.11-7.14 (m, 1H), 4.93 (br. s., 0.5H), 4.55 (d, J=11.8 Hz, 0.5H), 4.42 (d, J=12.5 Hz, 1H), 4.29-4.37 (m, 1H), 4.26 (br. s., 1H), 3.82 (d, J=13.6 Hz, 0.5H), 3.68-3.78 (m, 2H), 3.53-3.65 (m, 0.5H), 3.38 (s, 3H), 3.28-3.37 (m, 1H), 3.12-3.24 (m, 1H), 3.04-3.12 (m, 1H), 2.65-2.80 (m, 1H), 2.50-2.64 (m, 1H), 1.40 (d, J=6.5 Hz, 1.5H), 1.30 (d, J=6.5 Hz, 1.5H), 1.15 (d, J=6.5 Hz, 6H). LC-MS: m/z 441.2 (M+H)$^+$.

(R)-5-(3,4-dimethylphenyl)-6-isopropyl-2-(4-(3-methoxypropanoyl)-3-methylpiperazin-1-yl)nicotinonitrile (Compound 220)

$^1$H NMR (CHLOROFORM-d) δ 7.58 (s, 1H), 7.18 (d, J=7.5 Hz, 1H), 7.00 (s, 1H), 6.97 (dd, J=7.7, 1.6 Hz, 1H), 4.93 (br. s., 0.5H), 4.55 (d, J=13.1 Hz, 0.5H), 4.32-4.42 (m, 1H), 4.29 (d, J=12.8 Hz, 1H), 3.78-3.85 (m, 0.5H), 3.71-3.77 (m, 2H), 3.53-3.64 (m, 0.5H), 3.38 (s, 3H), 3.24-3.35 (m, 1H), 3.17 (dt, J=13.3, 6.7 Hz, 2H), 3.01-3.12 (m, 1H), 2.65-2.80 (m, 1H), 2.53-2.63 (m, 1H), 2.31 (d, J=3.0 Hz, 6H), 1.40 (d, J=6.5 Hz, 1.5H), 1.31 (d, J=6.8 Hz, 1.5H), 1.14 (d, J=6.5 Hz, 6H). LC-MS: m/z 435.4 (M+H)$^+$.

(R)-5-(3-fluoro-4-methylphenyl)-6-isopropyl-2-(4-(3-methoxypropanoyl)-3-methylpiperazin-1-yl)nicotinonitrile (Compound 221)

$^1$H NMR (CHLOROFORM-d) δ 7.58 (s, 1H), 7.23 (t, J=8.0 Hz, 1H), 6.90-6.95 (m, 1H), 6.89 (dd, J=5.8, 1.3 Hz, 1H), 4.93 (br. s., 0.5H), 4.55 (d, J=12.8 Hz, 0.5H), 4.21-4.45 (m, 3H), 3.81 (d, J=13.3 Hz, 0.5H), 3.70-3.77 (m, 2H), 3.52-3.63 (m, 0.5H), 3.38 (s, 3H), 3.26-3.37 (m, 1H), 3.10-3.18 (m, 2H), 2.65-2.80 (m, 1H), 2.53-2.63 (m, 1H), 2.33 (d, J=1.5 Hz, 3H), 1.40 (d, J=6.5 Hz, 1.5H), 1.30 (d, J=6.5 Hz, 1.5H), 1.15 (d, J=6.8 Hz, 6H). LC-MS: m/z 439.4 (M+H)$^+$.

(R)-6-isopropyl-2-(4-(3-methoxypropanoyl)-3-methylpiperazin-1-yl)-5-phenylnicotinonitrile (Compound 222)

$^1$H NMR (CHLOROFORM-d) δ 7.56-7.61 (m, 1H), 7.35-7.39 (m, 3H), 7.21-7.25 (m, 2H), 4.93 (br. s., 0.5H), 4.55 (d, J=11.8 Hz, 0.5H), 4.42 (d, J=12.5 Hz, 1H), 4.29-4.37 (m, 1H), 4.26 (br. s., 1H), 3.82 (d, J=13.6 Hz, 0.5H), 3.68-3.78 (m, 2H), 3.53-3.65 (m, 0.5H), 3.38 (s, 3H), 3.28-3.37 (m, 1H), 3.12-3.24 (m, 1H), 3.04-3.12 (m, 1H), 2.65-2.80 (m, 1H), 2.50-2.64 (m, 1H), 1.40 (d, J=6.5 Hz, 1.5H), 1.30 (d, J=6.5 Hz, 1.5H), 1.15 (d, J=6.5 Hz, 6H). LC-MS: m/z 407.4 (M+H)$^+$.

(R)-5-(3,4-dimethoxyphenyl)-6-isopropyl-2-(4-(3-methoxypropanoyl)-3-methylpiperazin-1-yl)nicotinonitr-ile (Compound 223)

$^1$H NMR (CHLOROFORM-d) δ 7.61 (s, 1H), 6.92 (d, J=8.3 Hz, 1H), 6.78 (dd, J=8.2, 1.9 Hz, 1H), 6.73 (d, J=2.0 Hz, 1H), 4.88-4.96 (m, 0.5H), 4.55 (d, J=13.1 Hz, 0.5H), 4.18-4.46 (m, 3H), 3.93 (s, 3H), 3.89 (s, 3H), 3.78-3.86 (m, 0.5H), 3.71-3.78 (m, 2H), 3.52-3.64 (m, 0.5H), 3.38 (s, 3H), 3.31 (t, J=10.8 Hz, 1H), 3.10-3.22 (m, 2H), 2.65-2.80 (m, 1H), 2.52-2.64 (m, 1H), 1.33 (s, 1.5H), 1.28 (s, 1.5H), 1.16 (d, J=6.8 Hz, 6H). LC-MS: m/z 467.3 (M+H)$^+$.

(R)-5-(benzo[d][1,3]dioxol-5-yl)-6-isopropyl-2-(4-(3-methoxypropanoyl)-3-methylpiperazin-1-yl)nicotinonitrile (Compound 221)

$^1$H NMR (CHLOROFORM-d) δ 7.57 (s, 1H), 6.83-6.90 (m, 1H), 6.64-6.73 (m, 2H), 6.02 (s, 2H), 4.92 (br. s., 0.5H), 4.55 (d, J=12.5 Hz, 0.5H), 4.20-4.43 (m, 3H), 3.81 (d, J=12.8 Hz, 0.5H), 3.74 (t, J=6.3 Hz, 2H), 3.53-3.64 (m, 0.5H), 3.38 (s, 3H), 3.25-3.36 (m, 1H), 3.10-3.22 (m, 2H), 2.64-2.80 (m, 1H), 2.52-2.64 (m, 1H), 1.40 (d, J=6.0 Hz, 1.5H), 1.30 (d, J=6.5 Hz, 1.5H), 1.14 (d, J=6.8 Hz, 6H). LC-MS: m/z 451.3 (M+H)$^+$.

(R)-6-isopropyl-2-(4-(3-methoxypropanoyl)-3-methylpiperazin-1-yl)-5-(3-(trifluoromethoxy)phenyl)nicotinonitrile (Compound 230)

1H NMR (CHLOROFORM-d) δ 7.58-7.63 (m, 1H), 7.42-7.51 (m, 1H), 7.22-7.26 (m, 1H), 7.18 (dd, J=7.8, 1.3 Hz, 1H), 7.11 (s, 1H), 4.93 (br. s., 0.5H), 4.55 (d, J=11.8 Hz, 0.5H), 4.27-4.46 (m, 3H), 3.78-3.88 (m, 0.5H), 3.75 (t, J=6.4 Hz, 2H), 3.50-3.64 (m, 0.5H), 3.38 (s, 3H), 3.29-3.36 (m, 1H), 3.13-3.24 (m, 1H), 3.07 (dt, J=13.3, 6.7 Hz, 1H), 2.65-2.81 (m, 1H), 2.52-2.64 (m, 1H), 1.40 (d, J=6.3 Hz, 1.5H), 1.30 (d, J=6.3 Hz, 1.5H), 1.16 (d, J=6.5 Hz, 6H). LC-MS: m/z 491.3 (M+H)$^+$.

(R)-5-(3-fluorophenyl)-6-isopropyl-2-(4-(3-methoxypropanoyl)-3-methylpiperazin-1-yl)nicotinonitrile (Compound 231)

$^1$H NMR (CHLOROFORM-d) δ 7.59 (s, 1H), 7.39 (td, J=8.0, 6.1 Hz, 1H), 7.05-7.13 (m, 1H), 7.02 (d, J=7.8 Hz, 1H), 6.95 (dt, J=9.4, 2.1 Hz, 1H), 4.93 (br. s., 0.5H), 4.55 (d, J=11.8 Hz, 0.5H), 4.26-4.45 (m, 3H), 3.82 (d, J=13.1 Hz, 0.5H), 3.75 (t, J=6.1 Hz, 2H), 3.51-3.64 (m, 0.5H), 3.38 (s, 3H), 3.27-3.35 (m, 1H), 3.16-3.23 (m, 1H), 3.09-3.14 (m, 1H), 2.65-2.81 (m, 1H), 2.60 (t, J=5.9 Hz, 1H), 1.40 (d, J=6.3 Hz, 1.5H), 1.30 (d, J=6.5 Hz, 1.5H), 1.15 (d, J=6.8 Hz, 6H). LC-MS: m/z 443.3 (M+H)$^+$.

(R)-6-isopropyl-2-(4-(3-methoxypropanoyl)-3-methylpiperazin-1-yl)-5-(4-(trifluoromethoxy)phenyl)nicotinonitrile (Compound 232)

$^1$H NMR (CHLOROFORM-d) δ 7.59 (s, 1H), 7.27 (s, 4H), 4.93 (br. s., 0.5H), 4.49-4.61 (m, 0.5H), 4.26-4.47 (m, 3H), 3.82 (d, J=13.6 Hz, 0.5H), 3.72-3.77 (m, 2H), 3.51-3.65 (m, 0.5H), 3.38 (s, 3H), 3.28-3.36 (m, 1H), 3.13-3.23 (m, 1H), 3.08 (dt, J=13.3, 6.7 Hz, 1H), 2.65-2.80 (m, 1H), 2.60 (t, J=5.9 Hz, 1H), 1.40 (d, J=6.0 Hz, 1.5H), 1.30 (d, J=6.5 Hz, 1.5H), 1.16 (d, J=6.5 Hz, 6H). LC-MS: m/z 491.3 (M+H)$^+$.

(R)-5-(2,3-dihydrobenzo[b][1,4]dioxin-6-yl)-6-isopropyl-2-(4-(3-methoxypropanoyl)-3-methylpiperazin-1-yl)nicotinonitrile (Compound 233)

$^1$H NMR (CHLOROFORM-d) δ 7.59 (s, 1H), 7.27 (s, 4H), 4.93 (br. s., 0.5H), 4.49-4.61 (m, 0.5H), 4.26-4.47 (m, 3H), 3.82 (d, J=13.6 Hz, 0.5H), 3.72-3.77 (m, 2H), 3.51-3.65

(m, 0.5H), 3.38 (s, 3H), 3.28-3.36 (m, 1H), 3.13-3.23 (m, 1H), 3.08 (dt, J=13.3, 6.7 Hz, 1H), 2.65-2.80 (m, 1H), 2.60 (t, J=5.9 Hz, 1H), 1.40 (d, J=6.0 Hz, 1.5H), 1.30 (d, J=6.5 Hz, 1.5H), 1.16 (d, J=6.5 Hz, 6H). LC-MS: m/z 465.3 (M+H)$^+$.

(R)-6-isopropyl-5-(isoquinolin-4-yl)-2-(4-(3-methoxypropanoyl)-3-methylpiperazin-1-yl)nicotinonitrile (Compound 231)

$^1$H NMR (CHLOROFORM-d) δ 9.33 (s, 1H), 8.37 (s, 1H), 8.06-8.16 (m, 1H), 7.64-7.69 (m, 2H), 7.45-7.50 (m, 2H), 4.96 (br. s., 0.5H), 4.58 (br. s., 0.5H), 4.31-4.54 (m, 3H), 3.86 (d, J=12.5 Hz, 0.5H), 3.76 (t, J=6.4 Hz, 2H), 3.56-3.67 (m, 0.5H), 3.42 (d, J=3.8 Hz, 1H), 3.36-3.40 (m, 3H), 3.08-3.33 (m, 1H), 2.65-2.78 (m, 2H), 2.54-2.64 (m, 1H), 1.44 (d, J=4.5 Hz, 1.5H), 1.35 (d, J=6.0 Hz, 1.5H), 1.05-1.11 (m, 6H). LC-MS: m/z 458.2 (M+H)$^+$.

(R)-6-cyclopropyl-5-(4-fluorophenyl)-2-(4-(3-methoxypropanoyl)-3-methylpiperazin-1-yl)nicotinonitrile (Compound 219)

$^1$H NMR (CHLOROFORM-d) δ 7.57 (s, 1H), 7.31-7.39 (m, 2H), 7.27 (s, 1H), 7.10-7.18 (m, 2H), 4.90 (br. s., 0.5H), 4.53 (d, J=13.6 Hz, 0.5H), 4.07-4.33 (m, 3H), 3.77-3.84 (m, 0.5H), 3.71-3.76 (m, 2H), 3.48-3.60 (m, 0.5H), 3.36-3.41 (m, 3H), 3.25 (t, J=10.4 Hz, 1H), 3.06-3.18 (m, 1H), 2.63-2.79 (m, 1H), 2.51-2.62 (m, 1H), 1.95-2.07 (m, 1H), 1.38 (d, J=6.5 Hz, 1.5H), 1.28 (d, J=6.8 Hz, 1.5H), 1.12-1.18 (m, 2H), 0.91-0.97 (m, 2H). LC-MS: m/z 423.3 (M+H)$^+$.

(R)-6-cyclopropyl-2-(4-(3-methoxypropanoyl)-3-methylpiperazin-1-yl)-5-m-tolylnicotinonitrile (Compound 225)

$^1$H NMR (CHLOROFORM-d) δ 7.59 (s, 1H), 7.30-7.36 (m, 1H), 7.14-7.22 (m, 3H), 4.90 (br. s., 0.5H), 4.52 (d, J=13.1 Hz, 0.5H), 3.80-4.36 (m, 3H), 3.80 (br. s., 0.5H), 3.74 (t, J=6.3 Hz, 2H), 3.50-3.61 (m, 0.5H), 3.37 (s, 3H), 3.19-3.29 (m, 1H), 3.07-3.17 (m, 1H), 2.63-2.80 (m, 1H), 2.53-2.62 (m, 1H), 2.41 (s, 3H), 2.03-2.13 (m, 1H), 1.39 (d, J=5.8 Hz, 1.5H), 1.29 (d, J=6.5 Hz, 1.5H), 1.11-1.17 (m, 2H), 0.89-0.97 (m, 2H). LC-MS: m/z 419.3 (M+H)$^+$.

(R)-6-cyclopropyl-2-(4-(3-methoxypropanoyl)-3-methylpiperazin-1-yl)-5-(4-(trifluoromethyl)phenyl)nicotinonitrile (Compound 226)

$^1$H NMR (CHLOROFORM-d) δ 7.71 (d, J=8.0 Hz, 2H), 7.60 (s, 1H), 7.52 (d, J=8.0 Hz, 2H), 4.82-4.95 (m, 0.5H), 4.53 (d, J=12.8 Hz, 0.5H), 4.17-4.39 (m, 3H), 3.80 (d, J=13.6 Hz, 0.5H), 3.74 (t, J=6.3 Hz, 2H), 3.49-3.62 (m, 0.5H), 3.37 (s, 3H), 3.24-3.33 (m, 1H), 3.03-3.15 (m, 1H), 2.63-2.80 (m, 1H), 2.51-2.62 (m, 1H), 1.93-2.02 (m, 1H), 1.38 (d, J=6.5 Hz, 1.5H), 1.28 (d, J=3.5 Hz, 1.5H), 1.14-1.20 (m, 2H), 0.93-0.99 (m, 2H). LC-MS: m/z 473.3 (M+H)$^+$.

(R)-6-cyclopropyl-2-(4-(3-methoxypropanoyl)-3-methylpiperazin-1-yl)-5-(4-(trifluoromethoxy)phenyl)nicotinonitrile (Compound 227)

$^1$H NMR (CHLOROFORM-d) δ 7.58 (s, 1H), 7.41-7.44 (m, 1H), 7.38-7.41 (m, 1H), 7.30 (s, 1H), 7.28 (s, 1H), 4.90 (br. s., 0.5H), 4.53 (d, J=11.5 Hz, 0.5H), 4.12-4.34 (m, 3H), 3.81 (br. s., 0.5H), 3.74 (t, J=6.3 Hz, 2H), 3.55 (t, J=11.4 Hz, 0.5H), 3.37 (s, 3H), 3.26 (br. s., 1H), 3.11 (br. s., 1H), 2.63-2.78 (m, 1H), 2.58 (d, J=5.8 Hz, 1H), 1.95-2.05 (m, 1H), 1.38 (d, J=5.8 Hz, 1.5H), 1.28 (d, J=5.8 Hz, 1.5H), 1.13-1.18 (m, 2H), 0.93-0.99 (m, 2H). LC-MS: m/z 489.2 (M+H)$^+$.

(R)-6-cyclopropyl-2-(4-(3-methoxypropanoyl)-3-methylpiperazin-1-yl)-5-(3-(trifluoromethoxy)phenyl)-nicotinonitrile (Compound 228)

$^1$H NMR (CHLOROFORM-d) δ 7.60 (s, 1H), 7.48 (t, J=7.9 Hz, 1H), 7.33 (d, J=7.8 Hz, 1H), 7.27 (br. s., 1H), 7.21-7.26 (m, 1H), 4.90 (br. s., 0.5H), 4.53 (d, J=12.8 Hz, 0.5H), 4.17-4.36 (m, 3H), 3.77-3.86 (m, 0.5H), 3.74 (t, J=6.1 Hz, 2H), 3.51-3.62 (m, 0.5H), 3.37 (s, 3H), 3.28 (t, J=8.9 Hz, 1H), 3.12 (d, J=10.8 Hz, 1H), 2.64-2.80 (m, 1H), 2.52-2.63 (m, 1H), 1.96-2.04 (m, 1H), 1.35-1.42 (m, 1.5H), 1.28 (d, J=5.5 Hz, 1.5H), 1.14-1.20 (m, 2H), 0.93-1.01 (m, 2H). LC-MS: m/z 489.2 (M+H)$^+$.

(R)-6-cyclopropyl-5-(3-fluorophenyl)-2-(4-(3-methoxypropanoyl)-3-methylpiperazin-1-yl)nicotinonitrile (Compound 22)

$^1$H NMR (CHLOROFORM-d) δ 7.59 (s, 1H), 7.41 (td, J=7.8, 6.1 Hz, 1H), 7.14-7.19 (m, 1H), 7.04-7.13 (m, 2H), 4.90 (br. s., 0.5H), 4.52 (d, J=13.1 Hz, 0.5H), 4.12-4.34 (m, 3H), 3.77-3.85 (m, 0.5H), 3.74 (t, J=6.1 Hz, 2H), 3.48-3.61 (m, 0.5H), 3.37 (s, 3H), 3.26 (t, J=9.4 Hz, 1H), 3.06-3.16 (m, 1H), 2.64-2.79 (m, 1H), 2.51-2.62 (m, 1H), 1.99-2.08 (m, 1H), 1.38 (d, J=6.0 Hz, 1.5H), 1.28 (d, J=6.5 Hz, 1.5H), 1.12-1.19 (m, 2H), 0.93-0.99 (m, 2H). LC-MS: m/z 423.3 (M+H)$^+$.

(R)-6-cyclopropyl-5-(3-fluoro-4-methylphenyl)-2-(4-(3-methoxypropanoyl)-3-methylpiperazin-1-yl)nicotinonitrile (Compound 235)

$^1$H NMR (CHLOROFORM-d) δ 7.57 (s, 1H), 7.21-7.26 (m, 1H), 7.06 (s, 1H), 7.01-7.05 (m, 1H), 4.89 (br. s., 0.5H), 4.52 (d, J=12.8 Hz, 0.5H), 4.11-4.33 (m, 3H), 3.80 (br. s., 0.5H), 3.74 (t, J=6.3 Hz, 2H), 3.49-3.60 (m, 0.5H), 3.36-3.41 (m, 3H), 3.25 (t, J=9.8 Hz, 1H), 3.03-3.15 (m, 1H), 2.63-2.79 (m, 1H), 2.51-2.61 (m, 1H), 2.32 (d, J=1.5 Hz, 3H), 2.01-2.09 (m, 1H), 1.38 (d, J=6.0 Hz, 1.5H), 1.26-1.30 (m, 1.5H), 1.12-1.17 (m, 2H), 0.92-0.97 (m, 2H).
LC-MS: m/z 437.3 (M+H)$^+$.

(R)-6-cyclopropyl-5-(3-methoxyphenyl)-2-(4-(3-methoxypropanoyl)-3-methylpiperazin-1-yl)nicotinonitrile (Compound 236)

$^1$H NMR (CHLOROFORM-d) δ 7.60 (s, 1H), 7.32-7.38 (m, 1H), 6.94-6.99 (m, 1H), 6.87-6.94 (m, 2H), 4.90 (br. s., 0.5H), 4.53 (d, J=13.1 Hz, 0.5H), 4.18-4.26 (m, J=12.7 Hz, 3H), 3.84 (s, 3H), 3.81 (d, J=5.5 Hz, 0.5H), 3.74 (t, J=6.1 Hz, 2H), 3.55 (t, J=11.0 Hz, 0.5H), 3.37 (s, 3H), 3.25 (t, J=10.2 Hz, 1H), 3.03-3.15 (m, 1H), 2.63-2.79 (m, 1H), 2.51-2.62 (m, 1H), 2.05-2.15 (m, 1H), 1.39 (d, J=6.0 Hz, 1.5H), 1.29 (d, J=6.3 Hz, 1.5H), 1.11-1.18 (m, 2H), 0.91-0.96 (m, 2H). LC-MS: m/z 435.3 (M+H)$^+$.

(R)-6-cyclopropyl-5-(3,4-dimethoxyphenyl)-2-(4-(3-methoxypropanoyl)-3-methylpiperazin-1-yl)nicotinonitrile (Compound 237)

$^1$H NMR (CHLOROFORM-d) δ 7.60 (s, 1H), 6.92-6.95 (m, 2H), 6.88 (s, 1H), 4.89 (br. s., 0.5H), 4.53 (d, J=14.1 Hz, 0.5H), 4.16-4.30 (m, 3H), 3.93 (s, 3H), 3.90 (s, 3H), 3.78-3.84 (m, 0.5H), 3.71-3.77 (m, 2H), 3.55 (br. s., 0.5H), 3.37 (s, 1H), 3.24 (br. s., 1H), 3.03-3.09 (m., 1H), 2.66-2.79 (m, 1H), 2.59 (br. s., 1H), 2.08-2.15 (m, 1.5H), 1.38 (br. s., 1.5H), 1.13-1.17 (m, 2H), 0.93 (dd, J=8.0, 3.3 Hz, 2H). LC-MS: m/z 465.1 (M+H)+.

(R)-6-cyclopropyl-5-(isoquinolin-4-yl)-2-(4-(3-methoxypropanoyl)-3-methylpiperazin-1-yl)nicotinonitrile (Compound 242)

$^1$H NMR (DMSO-d$_6$) δ 7.47 (dd, J=5.0, 3.0 Hz, 1H), 7.17 (dd, J=2.8, 1.3 Hz, 1H), 7.00 (dd, J=5.0, 1.3 Hz, 1H), 4.91 (br. s., 0.5H), 4.55 (d, J=10.8 Hz, 0.5H), 3.98-4.27 (m, 3H), 3.75 (q, J=6.0 Hz, 2.5H), 3.53-3.63 (m, 0.5H), 3.40 (s, 3H), 3.11-3.25 (m, 1H), 2.94-3.06 (m, 1H), 2.69-2.81 (m, 1H), 2.67 (d, J=7.3 Hz, 1H), 2.25 (s, 3H), 1.71-1.78 (m, 1H), 1.42 (d, J=6.5 Hz, 1.5H), 1.32 (d, J=6.8 Hz, 1.5H), 1.06-1.08 (m, 2H), 0.83-0.88 (m, 2H). LC-MS: m/z 456.2 (M+H)+.

(R)-6-cyclopropyl-2-(4-(3-methoxypropanoyl)-3-methylpiperazin-1-yl)-5-(thiophen-3-yl)nicotinonitrile (Compound 246)

$^1$H NMR (CHLOROFORM-d) δ 7.64 (s, 1H), 7.41 (dd, J=4.8, 3.0 Hz, 1H), 7.29 (dd, J=3.0, 1.3 Hz, 1H), 7.18 (dd, J=5.0, 1.3 Hz, 1H), 4.90 (br. s., 0.5H), 4.52 (d, J=13.6 Hz, 0.5H), 4.14-4.32 (m, 2.5H), 3.67-3.84 (m, 2.5H), 3.55 (br. s., 0.5H), 3.18-3.34 (m, 1H), 2.96-3.18 (m, 1.5H), 2.50-2.71 (m, 2H), 2.12-2.23 (m, 1H), 1.34-1.41 (m, 1.5H), 1.24-1.30 (m, 1.5H), 1.12-1.18 (m, 2H), 0.92-1.02 (m, 2H). LC-MS: m/z 411.3 (M+H)+.

(R)-5-(benzo[b]thiophen-2-yl)-6-cyclopropyl-2-(4-(3-methoxypropanoyl)-3-methylpiperazin-1-yl)nicotinonitrile (Compound 247)

$^1$H NMR (CHLOROFORM-d) δ 7.82-7.87 (m, 1H), 7.78-7.82 (m, 1H), 7.77 (s, 1H), 7.33-7.42 (m, 2H), 7.32 (s, 1H), 4.90 (br. s., 0.5H), 4.52 (d, J=12.8 Hz, 0.5H), 4.24-4.39 (m, 3H), 3.70-3.80 (m, 2.5H), 3.35-3.41 (m, 3H), 3.29 (t, J=9.8 Hz, 1H), 3.03-3.20 (m, 1.5H), 2.63-2.78 (m, 1H), 2.52-2.63 (m, 1H), 2.34-2.44 (m, 1H), 1.37 (d, J=6.0 Hz, 1.5H), 1.23-1.29 (m, 1.5H), 1.15-1.21 (m, 2H), 0.95-1.06 (m, 2H). LC-MS: m/z 461.3 (M+H)+.

(R)-5-(3-chloro-4-fluorophenyl)-6-cyclopropyl-2-(4-(3-methoxypropanoyl)-3-methylpiperazin-1-yl)nicotinonitrile (Compound 218)

$^1$H NMR (CHLOROFORM-d) δ 7.58 (s, 1H), 7.45 (dd, J=6.9, 1.9 Hz, 1H), 7.22-7.28 (m, 2H), 4.92 (br. s., 0.5H), 4.54 (d, J=12.8 Hz, 0.5H), 4.16-4.37 (m, 3H), 3.70-3.81 (m, 2.5H), 3.50-3.64 (m, 0.5H), 3.37-3.42 (m, 3H), 3.28 (t, J=10.2 Hz, 1H), 3.12 (d, J=11.0 Hz, 1H), 2.65-2.87 (m, 1H), 2.55-2.65 (m, 1H), 1.94-2.05 (m, 1H), 1.39 (d, J=6.5 Hz, 1.5H), 1.28 (d, J=4.0 Hz, 1.5H), 1.14-1.21 (m, 2H), 0.94-1.03 (m, 2H). LC-MS: m/z 457.3 (M+H)+.

(R)-6-cyclopropyl-5-(2-fluorophenyl)-2-(4-(3-methoxypropanoyl)-3-methylpiperazin-1-yl)nicotinonitrile (Compound 219)

$^1$H NMR (CHLOROFORM-d) δ7.62 (s, 1H), 7.37-7.45 (m, 1H), 7.30-7.36 (m, 1H), 7.22-7.27 (m, 1H), 7.19 (t, J=9.0 Hz, 1H), 4.92 (br. s., 0.5H), 4.54 (d, J=13.3 Hz, 0.5H), 4.19-4.37 (m, 3H), 3.78-3.86 (m, 0.5H), 3.70-3.78 (m, 2H), 3.51-3.61 (m, 0.5H), 3.39 (s, 3H), 3.27 (t, J=12.5 Hz, 1H), 3.02-3.16 (m, 1H), 2.65-2.82 (m, 1H), 2.54-2.64 (m, 1H), 1.83-1.90 (m, 1H), 1.41 (d, J=6.3 Hz, 1.5H), 1.30 (d, J=6.8 Hz, 1.5H), 1.12-1.19 (m, 2H), 0.92-0.98 (m, 2H). LC-MS: m/z 423.3 (M+H)+.

(R)-6-cyclopropyl-5-(2,4-difluorophenyl)-2-(4-(3-methoxypropanoyl)-3-methylpiperazin-1-yl)nicotinonitrile (Compound 250)

$^1$H NMR (CHLOROFORM-d) δ 7.58 (s, 1H), 7.26-7.35 (m, 1H), 6.91-7.04 (m, 2H), 4.92 (br. s., 0.5H), 4.54 (d, J=13.3 Hz, 0.5H), 4.18-4.37 (m, 3H), 3.78-3.85 (m, 0.5H), 3.71-3.78 (m, 2H), 3.51-3.62 (m, 0.5H), 3.39 (s, 3H), 3.23-3.33 (m, 1H), 3.14 (d, J=10.5 Hz, 1H), 2.65-2.80 (m, 1H), 2.53-2.63 (m, 1H), 1.77-1.85 (m, 1H), 1.40 (d, J=6.3 Hz, 1.5H), 1.30 (d, J=6.5 Hz, 1.5H), 1.11-1.19 (m, 2H), 0.96 (dd, J=7.8, 3.0 Hz, 2H). LC-MS: m/z 441.3 (M+H)+.

(R)-2-cyclopropyl-6'-methoxy-6-(4-(3-methoxypropanoyl)-3-methylpiperazin-1-yl)-3,3'-bipyridine-5-carbonitrile (Compound 252)

$^1$H NMR (CHLOROFORM-d) δ 8.18 (d, J=2.3 Hz, 1H), 7.60 (dd, J=8.5, 2.5 Hz, 1H), 7.56 (s, 1H), 6.83 (d, J=8.5 Hz, 1H), 4.90 (br. s., 0.5H), 4.52 (d, J=13.1 Hz, 0.5H), 4.15-4.36 (m, 3H), 3.96-4.02 (m, 3H), 3.76-3.86 (m, 0.5H), 3.74 (t, J=6.3 Hz, 2H), 3.53-3.61 (m, 0.5H), 3.37 (s, 3H), 3.21-3.31 (m, 1H), 3.12 (d, J=11.3 Hz, 1H), 2.63-2.80 (m, 1H), 2.51-2.62 (m, 1H), 1.93-2.04 (m, 1H), 1.38 (d, J=6.0 Hz, 1.5H), 1.28 (d, J=6.3 Hz, 1.5H), 1.12-1.19 (m, 2H), 0.92-1.00 (m, 2H). LC-MS: m/z 436.2 (M+H)+.

(R)-6-cyclopropyl-5-(1H-indol-5-yl)-2-(4-(3-methoxypropanoyl)-3-methylpiperazin-1-yl)nicotinonitrile (Compound 253)

$^1$H NMR (CHLOROFORM-d) δ 8.28 (br. s., 1H), 7.66 (s, 1H), 7.63 (s, 1H), 7.46 (d, J=8.3 Hz, 1H), 7.29 (t, J=2.8 Hz, 1H), 7.20 (dd, J=8.3, 1.8 Hz, 1H), 6.60 (t, J=2.1 Hz, 1H), 4.91 (br. s., 0.5H), 4.54 (d, J=13.3 Hz, 0.5H), 4.12-4.33 (m, 3H), 3.81 (br. s., 0.5H), 3.75 (t, J=6.4 Hz, 2H), 3.51-3.63 (m, 0.5H), 3.38 (s, 3H), 3.22 (d, J=14.1 Hz, 1H), 3.01-3.17 (m, 1H), 2.66-2.81 (m, 1H), 2.62 (t, J=5.8 Hz, 1H), 2.11-2.21 (m, 1H), 1.41 (d, J=5.5 Hz, 1.5H), 1.31 (d, J=6.3 Hz, 1.5H), 1.11-1.17 (m, 2H), 0.87-0.94 (m, 2H). LC-MS: m/z 444.3 (M+H)+.

(R)-6-cyclopropyl-5-(4-fluorophenyl)-2-(4-(3-methoxypropanoyl)-3-methylpiperazin-1-yl)-4-methylnicotinonitrile (Compound 241)

$^1$H NMR (CHLOROFORM-d) δ 7.17 (s, 2H), 7.16 (d, J=1.8 Hz, 2H), 4.90 (br. s., 0.5H), 4.53 (d, J=13.3 Hz, 0.5H), 4.03-4.22 (m, 3H), 3.79 (br. s., 0.5H), 3.74 (t, J=6.3 Hz, 2H), 3.52-3.63 (m, 0.5H), 3.38 (s, 3H), 3.16-3.25 (m, 1H), 2.92-3.08 (m, 1H), 2.64-2.79 (m, 1H), 2.51-2.63 (m, 1H), 2.18 (s, 3H), 1.56-1.63 (m, 1H), 1.41 (d, J=6.5 Hz, 1.5H), 1.31 (d, J=6.5 Hz, 1.5H), 1.03-1.09 (m, 2H), 0.79-0.84 (m, 2H). LC-MS: m/z 437.2 (M+H)+.

(R)-6-cyclopropyl-2-(4-(3-methoxypropanoyl)-3-methylpiperazin-1-yl)-4-methyl-5-m-tolylnicotinonitrile (Compound 243)

$^1$H NMR (DMSO-d$_6$) δ 7.36 (t, J=7.5 Hz, 1H), 7.22 (d, J=7.5 Hz, 1H), 6.97-7.04 (m, 2H), 4.92 (br. s., 0.5H), 4.55

(d, J=12.3 Hz, 0.5H), 4.24 (br. s., 0.5H), 4.03-4.19 (m, 2H), 3.76 (s, 0.5H), 3.75 (s, 2H), 3.55-3.64 (m, 0.5H), 3.40 (s, 3H), 3.11-3.26 (m, 1H), 2.93-3.08 (m, 1H), 2.68-2.80 (m, 1H), 2.61 (d, J=11.0 Hz, 1H), 2.42 (s, 3H), 2.20 (s, 3H), 1.62-1.71 (m, 1H), 1.43 (d, J=6.5 Hz, 1.5H), 1.34 (d, J=6.0 Hz, 1.5H), 1.01-1.11 (m, 2H), 0.80-0.85 (m, 2H). LC-MS: m/z 433.3 (M+H)$^+$.

(R)-6-cyclopropyl-5-(3-methoxyphenyl)-2-(4-(3-methoxypropanoyl)-3-methylpiperazin-1-yl)-4-methylnicotinonitrile (Compound 251)

$^1$H NMR (CHLOROFORM-d) δ 7.37 (t, J=7.8 Hz, 1H), 6.93 (dd, J=8.3, 2.5 Hz, 1H), 6.78 (d, J=7.5 Hz, 1H), 6.74 (s, 1H), 4.90 (br. s., 0.5H), 4.53 (d, J=12.8 Hz, 0.5H), 3.96-4.21 (m, 3H), 3.83 (s, 3H), 3.71-3.77 (m, 2H), 3.52-3.63 (m, 1H), 3.37 (s, 3H), 3.09-3.25 (m, 1H), 2.89-3.04 (m, 1H), 2.63-2.79 (m, 1H), 2.59 (br. s., 1H), 2.16-2.29 (m, 3H), 1.63-1.72 (m, 1H), 1.41 (d, J=6.3 Hz, 1.5H), 1.29-1.33 (m, 1.5H), 1.06 (d, J=7.3 Hz, 2H), 0.78-0.84 (m, 2H). LC-MS: m/z 449.3 (M+H)$^+$.

(R)-6-cyclopropyl-2-(4-(3-methoxypropanoyl)-3-methylpiperazin-1-yl)-4-methyl-5-(4-(trifluoromethoxy)-phenyl)nicotinonitrile (Compound 255)

$^1$H NMR (CHLOROFORM-d) δ 7.31-7.36 (m, J=8.0 Hz, 2H), 7.23-7.28 (m, J=8.3 Hz, 2H), 4.92 (br. s., 0.5H), 4.55 (d, J=13.8 Hz, 0.5H), 4.01-4.22 (m, 2.5H), 3.69-3.85 (m, 2.5H), 3.53-3.67 (m, 0.5H), 3.36-3.43 (m, 3H), 3.12-3.28 (m, 1.5H), 2.94-3.12 (m, 1H), 2.66-2.83 (m, 1H), 2.61 (br. s., 1H), 2.16-2.22 (m, 3H), 1.54-1.65 (m, 1H), 1.39-1.46 (m, 1.5H), 1.32 (d, J=6.3 Hz, 1.5H), 1.03-1.12 (m, 2H), 0.80-0.89 (m, 2H). LC-MS: m/z 503.3 (M+H)$^+$.

6-cyclopropyl-5-(2,4-difluorophenyl)-2-((R)-4-(3-methoxypropanoyl)-3-methylpiperazin-1-yl)-4-methyl-nicotinonitrile (Compound 256)

$^1$H NMR (CHLOROFORM-d) δ 7.16-7.25 (m, 1H), 6.93-7.07 (m, 2H), 4.92 (br. s., 0.5H), 4.55 (d, J=13.3 Hz, 0.5H), 4.03-4.30 (m, 2.5H), 3.71-3.86 (m, 2.5H), 3.51-3.67 (m, 0.5H), 3.40 (s, 3H), 3.12-3.30 (m, 1.5H), 2.95-3.11 (m, 1H), 2.73 (td, J=15.3, 7.3 Hz, 1H), 2.54-2.64 (m, 1H), 2.18-2.25 (m, 3H), 1.53-1.61 (m, 1H), 1.39-1.47 (m, 1.5H), 1.32 (t, J=5.8 Hz, 1.5H), 1.03-1.17 (m, 2H), 0.82-0.93 (m, 2H). LC-MS: m/z 455.4 (M+H)$^+$.

(R)-6-cyclopropyl-5-(3-fluorophenyl)-2-(4-(3-methoxypropanoyl)-3-methylpiperazin-1-yl)-4-methylnicotinonitrile (Compound 257)

$^1$H NMR (CHLOROFORM-d) δ 7.41-7.51 (m, 1H), 7.12 (td, J=8.5, 2.5 Hz, 1H), 7.01 (d, J=7.5 Hz, 1H), 6.95 (d, J=9.0 Hz, 1H), 4.92 (br. s., 0.5H), 4.55 (d, J=12.8 Hz, 0.5H), 4.04-4.22 (m, 2.5H), 3.72-3.84 (m, 2.5H), 3.53-3.67 (m, 0.5H), 3.40 (s, 3H), 3.12-3.29 (m, 1.5H), 2.93-3.11 (m, 1H), 2.66-2.83 (m, 1H), 2.61 (d, J=6.3 Hz, 1H), 2.16-2.25 (m, 3H), 1.57-1.64 (m, 1H), 1.43 (d, J=6.5 Hz, 1.5H), 1.33 (d, J=6.8 Hz, 1.5H), 1.08 (t, J=4.6 Hz, 2H), 0.80-0.91 (m, 2H). LC-MS: m/z 437.4 (M+H)$^+$.

(R)-6-cyclopropyl-5-(3-fluoro-4-methylphenyl)-2-(4-(3-methoxypropanoyl)-3-methylpiperazin-1-yl)-4-methylnicotinonitrile (Compound 258)

$^1$H NMR (CHLOROFORM-d) δ 7.23-7.33 (m, 2H), 6.89 (s, 1H), 6.87 (d, J=3.5 Hz, 1H), 4.91 (br. s., 0.5H), 4.54 (d, J=13.3 Hz, 0.5H), 4.23 (br. s., 1H), 4.01-4.21 (m, 1.5H), 3.70-3.84 (m, 2.5H), 3.50-3.66 (m, 0.5H), 3.39 (s, 3H), 3.10-3.28 (m, 1.5H), 2.92-3.09 (m, 1H), 2.65-2.81 (m, 1H), 2.53-2.64 (m, 1H), 2.32-2.39 (m, 3H), 2.20 (s, 3H), 1.60-1.70 (m, 1H), 1.39-1.47 (m, 1.5H), 1.30-1.35 (m, 1.5H), 1.07 (t, J=4.6 Hz, 2H), 0.83 (dt, J=7.5, 3.5 Hz, 2H). LC-MS: m/z 451.4 (M+H)$^+$.

(R)-6-cyclopropyl-2-(4-(3-methoxypropanoyl)-3-methylpiperazin-1-yl)-4-methyl-5-(naphthalen-2-yl) nicotinonitrile (Compound 259)

$^1$H NMR (DMSO-d$_6$) δ 7.96 (d, J=8.5 Hz, 1H), 7.91-7.95 (m, 1H), 7.88 (dd, J=6.1, 3.4 Hz, 1H), 7.71 (s, 1H), 7.53-7.59 (m, 2H), 7.34 (dd, J=8.4, 1.4 Hz, 1H), 4.94 (br. s., 0.5H), 4.57 (d, J=13.3 Hz, 0.5H), 4.05-4.32 (m, 3H), 3.83 (br. s., 0.5H), 3.77 (t, J=6.3 Hz, 2H), 3.56-3.67 (m, 0.5H), 3.41 (s, 3H), 3.17-3.29 (m, 1H), 2.96-3.12 (m, 1H), 2.67-2.83 (m, 1H), 2.55-2.65 (m, 1H), 2.23 (s, 3H), 1.63-1.71 (m, 1H), 1.45 (d, J=5.8 Hz, 1.5H), 1.35 (d, J=5.5 Hz, 1.5H), 1.05-1.14 (m, 2H), 0.77-0.83 (m, 2H). LC-MS: m/z 469.4 (M+H)$^+$.

(R)-2-cyclopropyl-6-(4-(3-methoxypropanoyl)-3-methylpiperazin-1-yl)-4-methyl-3,4'-bipyridine-5-carbonitrile (Compound 260)

$^1$H NMR (DMSO-d$_6$) δ 8.87 (br. s., 2H), 7.86 (br. s., 2H), 4.94 (br. s., 0.5H), 4.71 (s, 0.5H), 4.31-4.35 (s, 3H), 3.82 (br. s., 0.5H), 3.71-3.79 (m, 2H), 3.58 (br. s., 0.5H), 3.40 (s, 3H), 3.21 (br. s., 1H), 3.14 (br. s., 1H), 2.68 (br. s., 1H), 2.61 (br. s., 1H), 2.04 (br. s., 1H), 1.45 (d, J=5.8 Hz, 1.5H), 1.35 (d, J=5.5 Hz, 1.5H), 1.05-1.14 (m, 2H), 0.77-0.83 (m, 2H). LC-MS: m/z 420.5 (M+H)$^+$.

(R)-5-(benzo[d][1,3]dioxol-5-yl)-6-cyclopropyl-2-(4-(3-methoxypropanoyl)-3-methylpiperazin-1-yl)-4-methylnicotinonitrile (Compound 261)

$^1$H NMR (DMSO-d$_6$) δ 6.91 (d, J=8.0 Hz, 1H), 6.62-6.71 (m, 2H), 6.03-6.10 (m, 2H), 4.92 (br. s., 0.5H), 4.55 (d, J=13.6 Hz, 0.5H), 4.03-4.24 (m, 3H), 3.80 (br. s., 0.5H), 3.76 (t, J=6.1 Hz, 2H), 3.59 (t, J=11.7 Hz, 0.5H), 3.39 (s, 3H), 3.18-3.25 (m, 1H), 2.92-3.08 (m, 1H), 2.65-2.80 (m, 1H), 2.54-2.65 (m, 1H), 2.22 (s, 3H), 1.68-1.77 (m, 1H), 1.42 (d, J=6.5 Hz, 1.5H), 1.33 (d, J=6.5 Hz, 1.5H), 1.06 (t, J=5.3 Hz, 2H), 0.84 (t, J=6.1 Hz, 2H)
LC-MS: m/z 463.3 (M+H)$^+$.

(R)-6-cyclopropyl-2-(4-(3-methoxypropanoyl)-3-methylpiperazin-1-yl)-4-methyl-5-(thiophen-3-yl) nicotinonitrile (Compound 262)

$^1$H NMR (DMSO-d$_6$) δ 7.47 (dd, J=5.0, 3.0 Hz, 1H), 7.17 (dd, J=2.8, 1.3 Hz, 1H), 7.00 (dd, J=5.0, 1.3 Hz, 1H), 4.91 (br. s., 0.5H), 4.55 (d, J=10.8 Hz, 0.5H), 3.98-4.27 (m, 3H), 3.75 (q, J=6.0 Hz, 2.5H), 3.53-3.63 (m, 0.5H), 3.40 (s, 3H), 3.11-3.25 (m, 1H), 2.94-3.06 (m, 1H), 2.69-2.81 (m, 1H), 2.67 (d, J=7.3 Hz, 1H), 2.25 (s, 3H), 1.71-1.78 (m, 1H), 1.42 (d, J=6.5 Hz, 1.5H), 1.32 (d, J=6.8 Hz, 1.5H), 1.06-1.08 (m, 2H), 0.83-0.88 (m, 2H). LC-MS: m/z 425.3 (M+H)$^+$.

Example 5. Preparation of (R)-5-benzyl-6-isopropyl-2-(4-(3-methoxypropanoyl)-3-methylpiperazin-1-yl)nicotinonitrile (Compound 239)

A mixture of the bromide 7 from Example 1 (20 mg, 0.049 mmol) and PdCl$_2$(dppf).CH$_2$Cl$_2$ (4 mg, 0.005 mmol) in 1 mL of dry THF was stirred at room temperature for 5 min under nitrogen atmosphere. Benzyl zinc bromide (2 mL of 0.5M solution in THF, 0.098 mmol) was then added via a transfer needle, and the resulting reaction mixture was then refluxed for 4 h before the volatile was evaporated under reduced pressure. The black solid was applied to the top of a flash silica gel column, which was eluted with $CH_2Cl_2$ and then 8:1 $CH_2Cl_2$-EtOAc to obtain 5.1 mg of Compound 239 as a reddish solid. MS (ES) M+H expected 421.3. found 421.2. $^1$H NMR (CHLOROFORM-d) δ 7.43 (s, 1H), 7.28-7.36 (m, 2H), 7.19-7.25 (m, 1H), 7.08 (d, J=7.0 Hz, 2H), 4.90 (br. s., 0.5H), 4.53 (d, J=13.6 Hz, 0.5H), 4.16-4.36 (m, 3H), 3.91 (s, 2H), 3.79 (br. s., 0.5H), 3.73 (t, J=6.5 Hz, 2H), 3.51-3.61 (m, 0.5H), 3.37 (s, 3H), 3.22-3.30 (m, 1H), 3.12-3.21 (m, 1H), 2.63-2.78 (m, 1H), 2.51-2.61 (m, 1H), 1.38 (d, J=5.8 Hz, 1.5H), 1.28-1.32 (m, 1.5H), 1.12 (d, J=6.5 Hz, 6H). Other Compounds of Formula II listed below, wherein $R^{1b}$ is alkyl, —$CH_2$-aryl or —$CH_2$-heteroaryl; and $R^2$ is isopropyl or cyclopropyl were similarly prepared using any of intermediates 7 (Scheme 1), 17 (Scheme 2), or 28 (Scheme 3) as starting material.

(R)-5-benzyl-6-cyclopropyl-2-(4-(3-methoxypropanoyl)-3-methylpiperazin-1-yl)-4-methylnicotinonitrile (Compound 245)

$^1$H NMR (CHLOROFORM-d) δ 7.29-7.35 (m, 2H), 7.24 (d, J=7.5 Hz, 1H), 7.09 (d, J=7.3 Hz, 2H), 4.91 (br. s., 0.5H), 4.54 (d, J=14.1 Hz, 0.5H), 4.22 (br. s., 0.5H), 4.16 (s, 2H), 4.09 (d, J=15.6 Hz, 1.5H), 3.97-4.05 (m, 1H), 3.69-3.82 (m, 2H), 3.53-3.63 (m, 1H), 3.36-3.42 (m, 3H), 3.15 (t, J=13.9 Hz, 1H), 2.90-3.05 (m, 1H), 2.66-2.81 (m, 1H), 2.54-2.63 (m, 1H), 2.40 (s, 3H), 2.04 (dd, J=8.0, 4.8 Hz, 1H), 1.42 (d, J=6.8 Hz, 1.5H), 1.35 (br. s., 1.5H), 1.07-1.15 (m, 2H), 0.90-0.92 (m, 2H). LC-MS: m/z 433.3 (M+H)$^+$.

Example 6. Preparation of (R)-6-cyclopropyl-2-(4-(3-methoxypropanoyl)-3-methylpiperazin-1-yl)-5-(methyl(2-(methyl amino)ethyl)amino)nicotinonitrile (Compound 238)

(R)-6-cyclopropyl-2-(4-(3-methoxypropanoyl)-3-methylpiperazin-1-yl)-5-(methyl(2-(methyl amino)ethyl)amino)nicotinonitrile (Compound 238) was prepared by mixing bromide 7 (30 mg, 0.074 mmol), CuI (0.7 mg, 0.004 mmol), $K_2CO_3$ (20 mg, 0.147 mmol), and N1,N2-dimethylethane-1,2-diamine (3.25 mg, 0.035 mmol) in a 5 mL microwave tube capped with a rubber septum. The tube was placed under vacuum and refilled with nitrogen three times. Piperidine (19 mg, 0.22 mmol) and DMSO (1 mL) were added to the tube and the rubber septum was quickly replaced with microwave tube cap. The reaction was heated in an oil bath at 120° C. overnight before it was cooled, diluted with EtOAc, and filtered through a pad of Celite. The EtOAc was removed on a rotary evaporator. Compound 238 was obtained in 10 mg of quantity via preparative TLC (DCM:MeOH/10:1) separation. MS (ES) M+H expected 417.3. found 417.5. $^1$H NMR (CHLOROFORM-d) δ 7.56 (s, 1H), 4.91 (br. s., 0.5H), 4.53 (d, J=12.3 Hz, 0.5H), 4.02-4.31 (m, 3H), 3.67-3.83 (m, 3H), 3.47-3.64 (m, 2H), 3.34-3.41 (m, 3H), 3.16-3.30 (m, 1H), 2.93-3.13 (m, 4H), 2.74-2.84 (m, 2H), 2.61 (s, 3H), 2.53 (s, 3H), 1.39 (d, J=5.8 Hz, 1.5H), 1.30-1.34 (m, 1.5H), 1.17 (d, J=6.5 Hz, 6H).

Example 7. Preparation of (R)-5-amino-6-isopropyl-2-(4-(3-methoxypropanoyl)-3-methylpiperazin-1-yl)nicotinonitrile (R)-5-amino-6-isopropyl-2-(4-(3-methoxypropanoyl)-3-methylpiperazin-1-yl)nicotinonitrile was prepared according to Scheme 4.

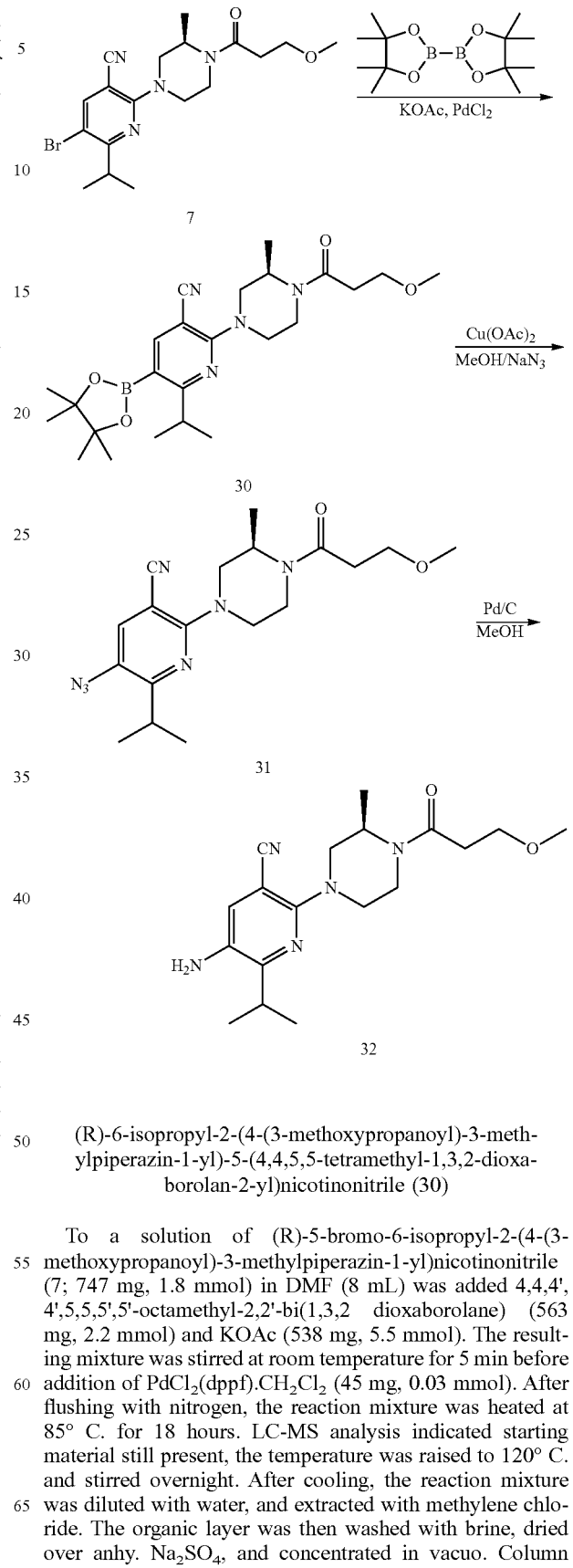

Scheme 4:

(R)-6-isopropyl-2-(4-(3-methoxypropanoyl)-3-methylpiperazin-1-yl)-5-(4,4,5,5-tetramethyl-1,3,2-dioxaborolan-2-yl)nicotinonitrile (30)

To a solution of (R)-5-bromo-6-isopropyl-2-(4-(3-methoxypropanoyl)-3-methylpiperazin-1-yl)nicotinonitrile (7; 747 mg, 1.8 mmol) in DMF (8 mL) was added 4,4,4',4',5,5,5',5'-octamethyl-2,2'-bi(1,3,2 dioxaborolane) (563 mg, 2.2 mmol) and KOAc (538 mg, 5.5 mmol). The resulting mixture was stirred at room temperature for 5 min before addition of $PdCl_2$(dppf).$CH_2Cl_2$ (45 mg, 0.03 mmol). After flushing with nitrogen, the reaction mixture was heated at 85° C. for 18 hours. LC-MS analysis indicated starting material still present, the temperature was raised to 120° C. and stirred overnight. After cooling, the reaction mixture was diluted with water, and extracted with methylene chloride. The organic layer was then washed with brine, dried over anhy. $Na_2SO_4$, and concentrated in vacuo. Column chromatography (25% EtOAc/petroleum ether) afforded 334 mg of 30 as a white solid. MS (ES) M+H expected 457.3. found 457.4. ¹H NMR (CHLOROFORM-d) δ 8.16 (s, 1H), 4.90 (br. s., 0.5H), 4.52 (d, J=12.3 Hz, 0.5H), 4.19-4.39 (m, 3H), 3.76-3.85 (m, 0.5H), 3.73 (t, J=6.4 Hz, 2H), 3.50-3.61 (m, 0.5H), 3.37 (s, 3H), 3.25-3.35 (m, 1H), 3.02-3.20 (m, 1H), 2.63-2.80 (m, 1H), 2.51-2.61 (m, 1H), 1.45 (d, J=7.0 Hz, 1.5H), 1.35 (d, J=6.3 Hz, 1.5H), 1.34 (s, 12H), 1.19-1.21 (dd, J=6.8, 2.0 Hz, 3H), 1.23-1.25 (d, J=6.8 Hz, 3H).

(R)-5-azido-6-isopropyl-2-(4-(3-methoxypropanoyl)-3-methylpiperazin-1-yl)nicotinonitrile (31)

To a solution of above boronate 30 (10 mg, 0.022 mmol) and Cu(OAc)₂.H₂O (0.5 mg, 0.0025 mmol) in MeOH (0.2 mL) was added slowly NaN₃ (2.4 mg, 0.037 mmol) with stirring. After the addition, the reaction mixture was heated to 50° C. and stirred overnight. After cooling and dilution with water, the reaction mixture was extracted with methylene chloride. The organic layer was then washed with brine, dried over anhy. Na₂SO₄, and concentrated in vacuo. Column chromatography (25% ethyl acetate/petroleum ether) afforded 3.7 mg of 31 as a yellowish solid. MS (ES) M+H expected 372.2. found 372.3.

(R)-5-amino-6-isopropyl-2-(4-(3-methoxypropanoyl)-3-methylpiperazin-1-yl)nicotinonitrile (32)

To a solution of above azide 31 (10 mg, 0.027 mmol) in 1 mL of MeOH was added 10% Pd/C (0.5 mg). The resulting mixture was purged with hydrogen and stirred at room temperature for 1 h under hydrogen atmosphere. After LC-MS analysis showed the formation of desired product, the reaction mixture was filtered, the filtrate was concentrated in vacuo. Column chromatography (25% EtOAc/petroleum ether) afforded 9 mg of 32 as a pink solid. MS (ES) M+H expected 346.2. found 346.1. ¹H NMR (CHLOROFORM-d) δ 7.25 (s, 1H), 4.90 (br. s., 0.5H), 4.53 (d, J=13.1 Hz, 0.5H), 4.20 (br. s., 1H), 3.95-4.07 (m, 1H), 3.93 (br. s., 1H), 3.75 (br. s., 0.5H) 3.73 (t, J=6.4 Hz, 2H), 3.52-3.63 (m, 0.5H), 3.37 (s, 3H), 3.02-3.21 (m, 2H), 2.88-3.02 (m, 1H), 2.62-2.78 (m, 1H), 2.59 (t, J=5.8 Hz, 1H), 1.41 (d, J=5.8 Hz, 1.5H), 1.31-1.32 (m, 1.5H), 1.26 (s, 6H).

Example 8. Preparation of (R)-5-(benzyloxy)-6-isopropyl-2-(4-(3-methoxypropanoyl)-3-methylpiperazin-1-yl)nicotinonitrile (Compound 254)

Compound 254 was prepared according to general Scheme 5, below:

Scheme 5:

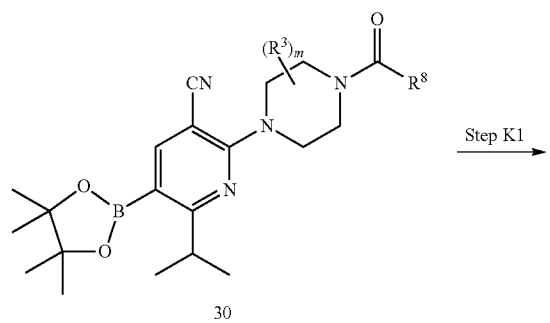

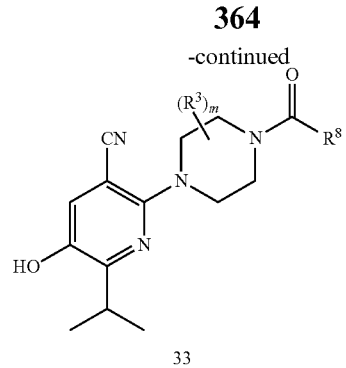

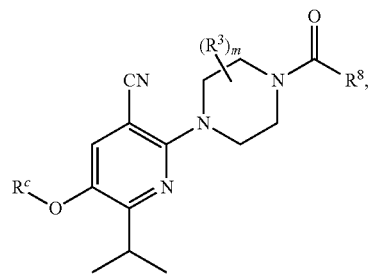

Formula II wherein R^c is —CH₂-aryl or —CH₂-heteroaryl.

Step K-1: (R)-5-hydroxy-6-isopropyl-2-(3-isopropyl-4-(3-methoxypropanoyl)piperazin-1-yl)nicotinonitrile To a solution of boronate 30 from Example 7 (30 mg, 0.066 mmol) in 15 mL of THF, at room temperature, was added aq. NaOH solution (2.86 g, 0.07 mmol). After stirring for 5 min, a solution of 30% of H₂O₂ (2.43 mg, 0.07 mmol) was added. The reaction mixture was allowed to stir at room temperature for additional 30 min before it was adjusted to neutral pH and concentrated in vacuo. Column chromatography (50% EtOAc/petroleum ether) afforded 21 mg of 33. MS (ES) M+H expected 347.2. found 347.3. ¹H NMR (METHANOL-d₄) δ 7.26 (s, 1H), 4.82 (br. s., 0.5H), 4.47 (d, J=13.1 Hz, 0.5H), 4.39 (br. s., 0.5H), 3.95 (d, J=13.1 Hz, 0.5H), 3.79-3.92 (m, 2H), 3.55-3.74 (m, 3H), 3.36 (s, 3H), 3.10-3.23 (m, 1H), 2.95-3.10 (m, 1H), 2.81-2.93 (m, 1H), 2.71-2.81 (m, 1H), 2.59-2.69 (m, 1H), 1.45 (d, J=6.8 Hz, 1.5H), 1.36 (br. s., 1.5H), 1.23 (d, J=6.8 Hz, 6H).

Step K-2: (R)-5-(benzyloxy)-6-isopropyl-2-(4-(3-methoxypropanoyl)-3-methylpiperazin-1-yl)nicotinonitrile (Compound 254)

To a solution of (R)-5-hydroxy-6-isopropyl-2-(3-isopropyl-4-(3-methoxypropanoyl)piperazin-1-yl)nicotinonitrile (33; 15 mg, 0.043 mmol) in 1 mL of THF was added 60% NaH (2.1 mg, 0.052 mmol) at 0° C. After stirring at room temperature for 30 min, benzyl bromide (8.9 mg, 0.052 mmol) was then added. The reaction mixture was stirred at 0° C. for 30 min and then at room temperature overnight. After the reaction mixture was concentrated, preparative TLC separation of the crude (50% ethyl acetate/petroleum ether) afforded 6.5 mg of Compound 254 as a yellowish solid. MS (ES) M+H expected 437.3. found 437.4. 1H NMR (CHLOROFORM-d) δ 7.33-7.43 (m, 5H), 7.23 (s, 1H), 5.02 (s, 2H), 4.90 (br. s., 0.5H), 4.53 (d, J=13.3 Hz, 0.5H), 4.21 (br. s., 0.5H), 4.02-4.09 (m, 1H), 3.90-4.02 (m, 1H), 3.65-3.85 (m, 3H), 3.51-3.61 (m, 0.5H), 3.42-3.51 (m, 1H), 3.37

(s, 3H), 3.09-3.23 (m, 1H), 2.91-3.07 (m, 1H), 2.63-2.78 (m, 1H), 2.51-2.62 (m, 1H), 1.40 (d, J=6.5 Hz, 1.5H), 1.31 (d, J=6.5 Hz, 1.5H), 1.20 (d, J=6.8 Hz, 6H).

Other Compounds of Formula II listed below, wherein $R^{1b}$ is —O—$CH_2$-aryl or —O—$CH_2$-heteroaryl; and $R^2$ is isopropyl or cyclopropyl were similarly prepared according to Scheme 5 by replacing (R)-6-isopropyl-2-(4-(3-methoxypropanoyl)-3-methylpiperazin-1-yl)-5-(4,4,5,5-tetramethyl-1,3,2-dioxaborolan-2-yl)nicotinonitrile 30 with alternate boronates prepared from any of intermediates 7 (Scheme 1), 17 (Scheme 2), or 28 (Scheme 3) using similar procedures set forth in Example 7 to prepare 30.

(R)-5-(benzyloxy)-6-cyclopropyl-2-(4-(3-methoxypropanoyl)-3-methylpiperazin-1-yl)nicotinonitrile (Compound 254)

1H NMR (CHLOROFORM-d) δ 7.33-7.43 (m, 5H), 7.23 (s, 1H), 5.02 (s, 2H), 4.90 (br. s., 0.5H), 4.53 (d, J=13.3 Hz, 0.5H), 4.21 (br. s., 0.5H), 4.02-4.09 (m, 1H), 3.90-4.02 (m, 1H), 3.65-3.85 (m, 3H), 3.51-3.61 (m, 0.5H), 3.42-3.51 (m, 1H), 3.37 (s, 3H), 3.09-3.23 (m, 1H), 2.91-3.07 (m, 1H), 2.63-2.78 (m, 1H), 2.51-2.62 (m, 1H), 1.40 (d, J=6.5 Hz, 1.5H), 1.31 (d, J=6.5 Hz, 1.5H), 1.20 (d, J=6.8 Hz, 6H). LC-MS: m/z 437.4 (M+H)+.

Example 9. Preparation of (R)-6-isopropyl-2-(3-methyl-4-(2-methylfuran-3-carbonyl)piperazin-1-yl)-5-phenylnicotinonitrile (Compound 164)

Compound 164 (45, wherein m is 1; $R^3$ is 3-methyl; and $R^8$ is 2-methylfuran-3yl) was prepared according to the general scheme set forth below in general Scheme 6.

Scheme 6:

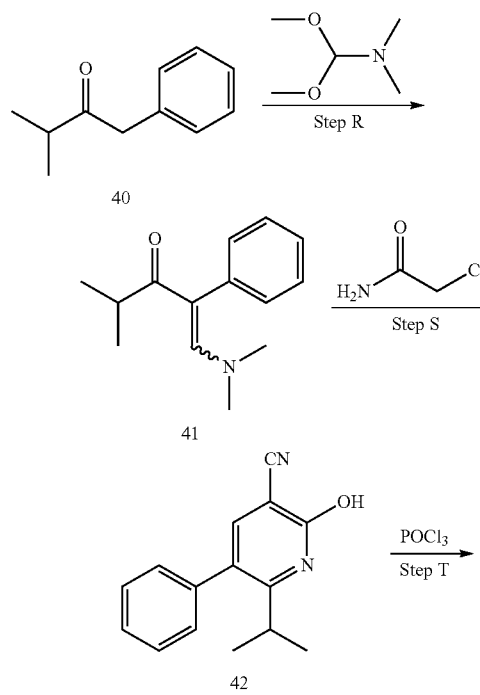

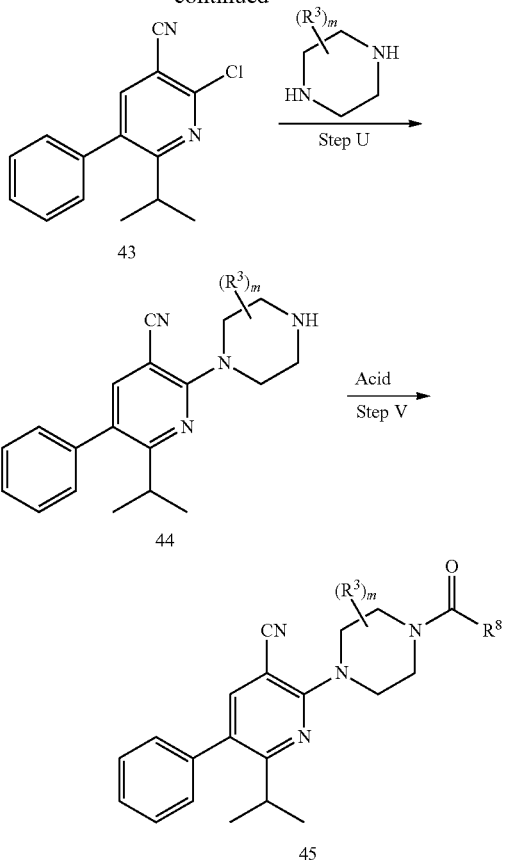

Step R: 1-(dimethylamino)-4-methyl-2-phenylpent-1-en-3-one (41)

To a solution of 3-methyl-1-phenylbutan-2-one (40; 3.38 g, 20 mmol) in 40 mL of anhydrous DMF was added 1,1-dimethoxy-N,N-dimethylmethanamine (5.958 g, 50 mmol). The resulting mixture was stirred at 100° C. overnight. After removal of DMF and excess of acetal, 4.3 g of 41 was obtained as a crude product and used in subsequent reaction without further purification. MS (ES) M+H expected 218.2. found 218.0.

Step S:
2-hydroxy-6-isopropyl-5-phenylnicotinonitrile (42)

To a 20 mL of anhydrous DMF solution containing 960 mg of sodium hydride (22 mmol, 60% dispersion in mineral oil) was added dropwise a solution of crude 1-(dimethylamino)-4-methyl-2-phenylpent-1-en-3-one (41; 4.3 g, 20 mmol DMF solution), cyano acetamide (1.72 g, 20 mmol), and 2 mL of MeOH in 35 mL of DMF. After the addition was completed, the resulting mixture was stirred at 80° C. overnight. After removal of DMF under reduced pressure, the residue was re-dissolved in methylene chloride and washed with water, and brine. The organic layer was then dried over anhy. $Na_2SO_4$ and concentrated in vacuo. Flash column chromatography (1:10 ethyl acetate/petroleum ether) afforded 3.84 g of 42 as a white solid. MS (ES) M+H expected 239.1. found 239.0. $^1$H NMR (DMSO-$d_6$) δ 8.03 (s, 1H), 7.43-7.50 (m, 2H), 7.37-7.43 (m, 1H), 7.30-7.33 (m, 1H), 7.29 (s, 1H), 2.85-2.97 (m, 1H), 1.21 (s, 3H), 1.20 (s, 3H).

Step T: 2-chloro-6-isopropyl-5-phenylnicotinonitrile (43)

A mixture of 2-hydroxy-6-isopropyl-5-phenylnicotinonitrile (42; 2.3 g, 10 mmol), 5 mL of phosphoryl trichloride and one drop of DMF were heated to reflux overnight until LC-MS indicated the complete conversion to the product. After evaporation of excess of phosphoryl trichloride under reduced pressure, the residue was re-dissolved in methylene chloride and neutralized carefully with satd. aq. NaHCO$_3$ and washed subsequently with 1N HCl and brine. The combined organic layer was dried over anhy. Na$_2$SO$_4$ and concentrated in vacuo. Flash column chromatography (1:5 ethyl acetate/petroleum ether) afforded 2.4 g of 43 as a yellowish solid. MS (ES) M+H expected 257.1. found 257.0. $^1$H NMR (CHLOROFORM-d) δ 7.76-7.82 (m, 1H), 7.43-7.54 (m, 3H), 7.28 (br. s., 1H), 7.22-7.26 (m, 1H), 3.20 (spt, J=6.7 Hz, 1H), 1.22 (s, 3H), 1.20 (s, 3H).

Step U: (R)-6-isopropyl-2-(3-methylpiperazin-1-yl)-5-phenylnicotinonitrile (44)

A mixture of above chloride 43 (192.5 mg, 0.75 mmol), (R)-2-methylpiperazine (187.8 mg, 1.875 mmol), and triethylamine (0.261 mL, 1.875 mmol) suspended in 2 mL of acetonitrile was subjected to microwave reaction at 175° C. for 45 min. After the reaction mixture was concentrated in vacuo, the residue was purified by flash column chromatography to give 184 mg of 44 as yellowish oil. MS (ES) M+H expected 321.2. found 321.1. $^1$H NMR (CHLOROFORM-d) δ 7.56-7.66 (m, 1H), 7.34-7.51 (m, 3H), 7.19-7.28 (m, 2H), 4.31-4.59 (m, 2H), 3.11-3.27 (m, 3H), 3.01-3.11 (m, 2H), 2.84 (dd, J=12.8, 10.3 Hz, 1H), 1.22 (d, J=6.3 Hz, 3H), 1.15 (dd, J=6.7, 1.1 Hz, 6H).

Step V: (R)-6-isopropyl-2-(3-methyl-4-(2-methylfuran-3-carbonyl)piperazin-1-yl)-5-phenylnicotinonitrile (Compound 164)

In a 5-mL of amber glass vial was placed (R)-6-isopropyl-2-(3-methylpiperazin-1-yl)-5-phenyl-nicotinonitrile (50 mg, 0.156 mmol), 2-methylfuran-3-carboxylic acid (39 mg, 0.312 mmol), EDCI (60 mg, 0.312 mmol), HOBt (42 mg, 0.312 mmol), triethylamine (40 mg, 0.312 mmol) and 2 mL of methylene chloride. The resulting reaction mixture was stirred at room temperature overnight. The mixture was quenched with 1 N HCl aqueous solution, extracted with EtOAc three times. The combined organic layer was washed with satd. NaHCO$_3$ and brine, dried over anhy. Na$_2$SO$_4$, and concentrated in vacuo. The crude product was purified by preparative TLC (EtOAc: petroleum ether/100:20) to afford 28 mg of the title compound as a white solid. MS (ES) M+H expected 429.2. found 429.1. $^1$H NMR (METHANOL-d$_4$) δ 7.59-7.67 (m, 1H), 7.37-7.50 (m, 3H), 7.31 (d, J=2.0 Hz, 1H), 7.21-7.28 (m, 2H), 6.39 (d, J=2.0 Hz, 1H), 4.70 (br. s., 1H), 4.29-4.50 (m, 2H), 4.23 (br. s., 1H), 3.49 (br. s., 1H), 3.33 (dd, J=12.9, 3.1 Hz, 1H), 3.08-3.23 (m, 2H), 2.40-2.47 (m, 3H), 1.43 (d, J=6.8 Hz, 3H), 1.16 (dd, J=6.8, 2.8 Hz, 6H).

Other Compounds of Formula II listed below, wherein R$^{1a}$ is hydrogen; R$^{1b}$ is optionally substituted phenyl; were similarly prepared according to Scheme 6 by replacing one or more of: (1) methyl-1-phenylbutan-2-one (40) with an alternate phenyl ketone as starting material; (2) (R)-2-methylpiperazine with an alternate piperazine in Step U; and (3) 2-methylfuran-3-carboxylic acid with an alternate acid in Step V.

2-(4-(furan-2-carbonyl)piperazin-1-yl)-6-isopropyl-5-phenylnicotinonitrile (Compound 109)

$^1$H NMR (CHLOROFORM-d) δ 7.65 (s, 1H), 7.53-7.58 (m, 1H), 7.38-7.49 (m, 3H), 7.24-7.28 (m, 2H), 7.10 (d, J=3.3 Hz, 1H), 6.54 (dd, J=3.3, 1.8 Hz, 1H), 4.03 (br. s., 4H), 3.89 (dd, J=6.4, 3.6 Hz, 4H), 3.17 (dt, J=13.4, 6.7 Hz, 1H), 1.18 (d, J=6.5 Hz, 6H). LC-MS: m/z 401.1 (M+H)$^+$.

2-(4-(furan-2-carbonyl)-3-methylpiperazin-1-yl)-6-isopropyl-5-phenylnicotinonitrile (Compound 119)

$^1$H NMR (CHLOROFORM-d) δ 7.62-7.69 (m, 1H), 7.54 (d, J=0.8 Hz, 1H), 7.40-7.47 (m, 3H), 7.23-7.28 (m, 2H), 7.08 (d, J=3.5 Hz, 1H), 6.53 (dd, J=3.5, 1.8 Hz, 1H), 4.93 (br. s., 1H), 4.54 (d, J=12.8 Hz, 1H), 4.45 (d, J=12.3 Hz, 1H), 4.37 (d, J=13.3 Hz, 1H), 3.58 (br. s., 1H), 3.44 (dd, J=13.3, 3.8 Hz, 1H), 3.27 (td, J=12.4, 3.4 Hz, 1H), 3.16 (dt, J=13.3, 6.7 Hz, 1H), 1.50 (d, J=6.8 Hz, 3H), 1.17 (dd, J=6.7, 1.9 Hz, 6H). LC-MS: m/z 414.9 (M+H)$^+$.

2-(4-(furan-3-carbonyl)-3-methylpiperazin-1-yl)-6-isopropyl-5-phenylnicotinonitrile (Compound 120)

$^1$H NMR (CHLOROFORM-d) δ 7.77 (s, 1H), 7.64 (s, 1H), 7.40-7.51 (m, 4H), 7.24-7.28 (m, 2H), 6.61 (d, J=1.3 Hz, 1H), 4.76 (br. s., 1H), 4.33-4.52 (m, 3H), 3.51 (s, 1H), 3.35 (dd, J=13.2, 3.1 Hz, 1H), 3.12-3.22 (m, 2H), 1.47 (d, J=6.8 Hz, 3H), 1.17 (dd, J=6.5, 2.0 Hz, 6H).
LC-MS: m/z 414.9 (M+H)$^+$.

2-(4-(furan-3-carbonyl)piperazin-1-yl)-6-isopropyl-5-phenylnicotinonitrile (Compound 124)

$^1$H NMR (CHLOROFORM-d) δ 7.76-7.81 (m, 1H), 7.65 (s, 1H), 7.36-7.51 (m, 4H), 7.23-7.28 (m, 2H), 6.62 (dd, J=1.9, 0.9 Hz, 1H), 3.91 (br. s., 4H), 3.84 (br. s., 4H), 3.17 (dt, J=13.4, 6.6 Hz, 1H), 1.17 (d, J=6.8 Hz, 6H). LC-MS: m/z 401.1 (M+H)$^+$.

2-(4-(1H-indole-3-carbonyl)piperazin-1-yl)-6-isopropyl-5-phenylnicotinonitrile (Compound 125)

$^1$H NMR (CHLOROFORM-d) δ 8.97 (br. s., 1H), 7.74-7.81 (m, 1H), 7.64 (s, 1H), 7.53 (br. s., 1H), 7.38-7.50 (m, 4H), 7.28-7.31 (m, 1H), 7.24-7.28 (m, 3H), 3.94 (br. s., 4H), 3.85 (br. s., 4H), 3.16 (dt, J=13.2, 6.6 Hz, 1H), 1.17 (d, J=6.5 Hz, 6H). LC-MS: m/z 450.2 (M+H)$^+$.

6-isopropyl-5-phenyl-2-(4-(2-phenylacetyl)piperazin-1-yl)nicotinonitrile (Compound 126)

$^1$H NMR (CHLOROFORM-d) δ 7.62 (s, 1H), 7.41-7.47 (m, 3H), 7.38-7.41 (m, 1H), 7.37 (s, 1H), 7.34-7.36 (m, 1H), 7.32 (s, 1H), 7.30 (s, 1H), 7.25 (d, J=1.5 Hz, 1H), 7.24 (s, 1H), 3.84-3.89 (m, 2H), 3.83 (s, 2H), 3.73-3.78 (m, 2H), 3.64-3.68 (m, 2H), 3.58-3.63 (m, 2H), 3.15 (dt, J=13.3, 6.7 Hz, 1H), 1.15 (d, J=6.5 Hz, 6H). LC-MS: m/z 425.1 (M+H)$^+$.

6-isopropyl-2-(3-methyl-4-(2-phenylacetyl)piperazin-1-yl)-5-phenylnicotinonitrile (Compound 139)

$^1$H NMR (CHLOROFORM-d) δ 7.61 (s, 1H), 7.37-7.51 (m, 4H), 7.33-7.37 (m, 2H), 7.29-7.33 (m, 2H), 7.22-7.27 (m, 2H), 4.62 (d, J=13.6 Hz, 0.5H), 4.42 (d, J=12.5 Hz, 0.5H), 4.19-4.35 (m, 2H), 3.81 (br. s., 1H), 3.76 (d, J=13.1

Hz, 0.5H), 3.49 (t, J=12.0 Hz, 0.5H), 2.91-3.29 (m, 3H), 1.31 (br. s., 3H), 1.15 (d, J=6.8 Hz, 6H). LC-MS: m/z 439.2 (M+H)⁺.

2-((3S,5R)-3,5-dimethyl-4-(2-phenylacetyl)piperazin-1-yl)-6-isopropyl-5-phenylnicotinonitrile (Compound 140)

¹H NMR (CHLOROFORM-d) δ 7.61-7.64 (m, 1H), 7.41-7.48 (m, 3H), 7.38-7.41 (m, 1H), 7.37 (s, 1H), 7.34-7.36 (m, 1H), 7.32 (s, 1H), 7.30 (s, 1H), 7.27 (d, J=1.8 Hz, 1H), 7.23-7.26 (m, 1H), 4.90 (br. s., 1H), 4.46 (br. s., 2H), 4.20 (br. s., 1H), 3.82 (s, 2H), 3.12-3.22 (m, 2H), 3.11 (br. s., 1H), 1.43 (d, J=7.0 Hz, 6H), 1.16 (d, J=6.8 Hz, 6H). LC-MS: m/z 453.1 (M+H)⁺.

2-((3S,5R)-4-(furan-3-carbonyl)-3,5-dimethylpiperazin-1-yl)-6-isopropyl-5-phenylnicotinonitrile (Compound 141)

¹H NMR (CHLOROFORM-d) δ 7.77 (dd, J=1.5, 0.8 Hz, 1H), 7.65 (s, 1H), 7.47-7.49 (m, 1H), 7.45-7.47 (m, 1H), 7.44 (s, 1H), 7.40-7.43 (m, 1H), 7.24-7.28 (m, 2H), 6.65 (dd, J=1.9, 0.9 Hz, 1H), 4.71 (br. s., 2H), 4.47 (s, 1H), 4.50 (s, 1H), 3.27 (dd, J=12.9, 4.1 Hz, 2H), 3.18 (dt, J=13.3, 6.7 Hz, 1H), 1.55 (d, J=7.0 Hz, 6H), 1.18 (d, J=6.5 Hz, 6H). LC-MS: m/z 429.2 (M+H)⁺.

(R)-6-isopropyl-2-(3-methyl-4-(2-phenylacetyl)piperazin-1-yl)-5-phenylnicotinonitrile (Compound 143)

¹H NMR (CHLOROFORM-d) δ 7.61 (s, 1H), 7.39-7.47 (m, 3H), 7.34-7.39 (m, 2H), 7.29-7.33 (m, 2H), 7.22-7.28 (m, 3H), 4.98 (br. s., 0.5H), 4.62 (d, J=13.8 Hz, 0.5H), 4.42 (d, J=12.0 Hz, 0.5H), 4.15-4.35 (m, 2H), 3.81 (br. s., 2H), 3.72-3.79 (m, 0.5H), 3.49 (t, J=11.3 Hz, 0.5H), 3.29 (d, J=10.0 Hz, 0.5H), 3.04-3.21 (m, 2.5H), 2.88-3.01 (m, 0.5H), 1.27-1.34 (m, 3H), 1.15 (d, J=6.5 Hz, 6H). LC-MS: m/z 439.2 (M+H)⁺.

(S)-2-(4-(furan-3-carbonyl)-3-methylpiperazin-1-yl)-6-isopropyl-5-phenylnicotinonitrile (Compound 144)

¹H NMR (CHLOROFORM-d) δ 7.74-7.80 (m, 1H), 7.64 (s, 1H), 7.36-7.52 (m, 4H), 7.27 (dd, J=7.9, 6.4 Hz, 2H), 6.59-6.64 (m, 1H), 4.76 (br. s., 1H), 4.20-4.50 (m, 3H), 3.51 (br. s., 1H), 3.35 (dd, J=13.3, 3.3 Hz, 1H), 3.06-3.24 (m, 2H), 1.47 (d, J=6.8 Hz, 3H), 1.17 (dd, J=6.5, 2.0 Hz, 6H). LC-MS: m/z 415.2 (M+H)⁺.

(R)-6-isopropyl-2-(3-methyl-4-(2-phenylacetyl)piperazin-1-yl)-5-phenylnicotinonitrile (Compound 145)

¹H NMR (CHLOROFORM-d) δ 7.61 (s, 1H), 7.29-7.47 (m, 7H), 7.22-7.28 (m, 3H), 4.98 (br. s., 0.5H), 4.62 (d, J=13.6 Hz, 0.5H), 4.42 (d, J=12.8 Hz, 0.5H), 4.15-4.37 (m, 2H), 3.80-3.85 (m, 2H), 3.76 (d, J=12.8 Hz, 0.5H), 3.49 (t, J=11.2 Hz, 0.5H), 3.25-3.37 (m, 0.5H), 3.02-3.23 (m, 2.5H), 2.88-3.01 (m, 0.5H), 1.26-1.35 (m, 3H), 1.15 (d, J=6.8 Hz, 6H). LC-MS: m/z 439.2 (M+H)⁺.

(R)-2-(4-(furan-3-carbonyl)-3-methylpiperazin-1-yl)-6-isopropyl-5-phenylnicotinonitrile (Compound 150)

¹H NMR (CHLOROFORM-d) δ 7.77 (dd, J=1.5, 1.0 Hz, 1H), 7.63-7.66 (m, 1H), 7.38-7.50 (m, 4H), 7.23-7.28 (m, 2H), 6.61 (dd, J=1.8, 0.8 Hz, 1H), 4.76 (br. s., 1H), 4.30-4.51 (m, 3H), 3.52 (br. s., 1H), 3.35 (dd, J=13.2, 3.6 Hz, 1H), 3.06-3.24 (m, 2H), 1.47 (d, J=6.8 Hz, 3H), 1.17 (dd, J=6.8, 2.0 Hz, 6H). LC-MS: m/z 415.1 (M+H)⁺.

2-(4-(furan-3-carbonyl)-3-phenylpiperazin-1-yl)-6-isopropyl-5-phenylnicotinonitrile (Compound 153)

¹H NMR (CHLOROFORM-d) δ 7.59-7.74 (m, 1H), 7.56 (s, 1H), 7.33-7.50 (m, 8H), 7.29 (d, J=7.3 Hz, 1H), 7.17-7.25 (m, 2H), 6.54 (br. s., 1H), 5.74 (br. s., 1H), 4.79 (br. s., 1H), 4.51 (br. s., 1H), 4.33 (d, J=9.5 Hz, 1H), 3.95 (d, J=11.5 Hz, 1H), 3.58 (br. s., 2H), 3.12 (spt, J=6.6 Hz, 1H), 1.08-1.18 (m, 6H). LC-MS: m/z 477.1 (M+H)⁺.

2-(4-(furan-3-carbonyl)-2-phenylpiperazin-1-yl)-6-isopropyl-5-phenylnicotinonitrile (Compound 159)

¹H NMR (CHLOROFORM-d) δ 7.72 (br. s., 1H), 7.48-7.60 (m, 5H), 7.46 (br. s., 3H), 7.40 (br. s., 2H), 7.27 (br. s., 1H), 7.20 (d, J=6.8 Hz, 1H), 6.77 (s, 1H), 6.59 (s, 1H), 5.14-5.37 (m, 1H), 4.25 (br. s., 2H), 3.87 (br. s., 3H), 3.64 (br. s., 1H), 2.81-2.95 (m, 1H), 1.16 (d, J=6.5 Hz, 3H), 1.06 (d, J=6.3 Hz, 3H). LC-MS: m/z 477.2 (M+H)⁺.

(R)-6-isopropyl-2-(3-methyl-4-(2-(thiophen-2-yl)acetyl)piperazin-1-yl)-5-phenylnicotinonitrile (Compound 165)

¹H NMR (METHANOL-d₄) δ 7.62 (s, 1H), 7.35-7.57 (m, 3H), 7.21-7.28 (m, 3H), 6.87-7.11 (m, 2H), 4.60 (d, J=13.3 Hz, 1H), 4.29-4.37 (m, 2H), 3.98 (s, 2H), 3.59 (t, J=11.4 Hz, 1H), 3.04-3.27 (m, 4H), 1.36 (dd, J=15.2, 5.9 Hz, 3H), 1.16 (d, J=6.5 Hz, 6H). LC-MS: m/z 445.0 (M+H)⁺.

2-(4-(furan-2-carbonyl)-2-phenylpiperazin-1-yl)-6-isopropyl-5-phenylnicotinonitrile (Compound 166)

¹H NMR (CHLOROFORM-d) δ 7.54-7.56 (m, 2H), 7.52 (br. s., 3H), 7.43 (br. s., 2H), 7.24-7.30 (m, 3H), 7.20 (d, J=7.3 Hz, 1H), 7.08 (d, J=3.3 Hz, 1H), 6.77 (s, 1H), 6.52 (br. s., 1H), 5.31-5.37 (br. s., 1H), 4.40 (br. s., 1H), 4.32 (br. s., 1H), 3.85-4.03 (m, 2H), 3.79 (d, J=13.1 Hz, 1H), 3.68 (d, J=4.8 Hz, 1H), 2.87 (dt, J=13.4, 6.8 Hz, 1H), 1.15 (d, J=6.8 Hz, 3H), 1.06 (d, J=6.5 Hz, 3H). LC-MS: m/z 477.2 (M+H)⁺.

2-(4-(1H-indole-3-carbonyl)-2-phenylpiperazin-1-yl)-6-isopropyl-5-phenylnicotinonitrile (Compound 168)

¹H NMR (CHLOROFORM-d) δ 9.09 (br. s., 1H), 7.76 (br. s., 1H), 7.51 (s, 2H), 7.55 (s, 3H), 7.39 (br. s., 3H), 7.29 (s, 2H), 7.33 (s, 3H), 7.24 (br. s., 3H), 6.77 (br. s., 1H), 5.29 (br. s., 1H), 4.30 (d, J=11.5 Hz, 1H), 4.18 (br. s., 1H), 3.93 (br. s., 3H), 3.64 (br. s., 1H), 2.89 (br. s., 1H), 1.16 (d, J=5.8 Hz, 3H), 1.07 (d, J=5.8 Hz, 3H). LC-MS: m/z 526.1 (M+H)⁺.

(R)-2-(4-(furan-3-carbonyl)-3-isopropylpiperazin-1-yl)-6-isopropyl-5-phenylnicotinonitrile (Compound 170)

¹H NMR (CHLOROFORM-d) δ 7.74 (br. s., 1H), 7.61 (s, 1H), 7.47 (t, J=1.6 Hz, 1H), 7.35-7.46 (m, 3H), 7.20-7.26 (m, 2H), 6.58 (s, 1H), 4.79 (d, J=12.8 Hz, 1H), 4.54-4.68 (br. s., 1H), 4.45 (br. s., 1H), 3.8-4.07 (m, 1H), 3.56-3.74 (m,

1H), 3.19 (br. s., 1H), 3.06-3.18 (m, 3H), 1.52-1.59 (m, 3H), 1.40-1.48 (m, 3H), 1.17 (d, J=6.8 Hz, 3H), 1.13 (d, J=6.8 Hz, 3H). LC-MS: m/z 443.1 (M+H)+.

(R)-2-(3-ethyl-4-(furan-3-carbonyl)piperazin-1-yl)-6-isopropyl-5-phenylnicotinonitrile (Compound 171)

$^1$H NMR (CHLOROFORM-d) δ 7.74 (s, 1H), 7.58-7.65 (m, 1H), 7.35-7.50 (m, 4H), 7.20-7.26 (m, 2H), 6.58 (dd, J=1.8, 0.8 Hz, 1H), 5.02 (s, 1H), 4.69 (br. s., 1H), 4.50 (d, J=13.1 Hz, 1H), 4.41 (d, J=12.3 Hz, 1H), 4.23-4.31 (br. s., 1H), 3.46-3.86 (m, 2H), 3.27 (dd, J=13.3, 3.3 Hz, 1H), 3.10-3.21 (m, 2H), 1.79-1.96 (m, 2H), 1.54 (d, J=6.5 Hz, 1.5H), 1.45 (d, J=6.5 Hz, 1.5H), 1.15 (dd, J=6.8, 3.5 Hz, 6H). LC-MS: m/z 429.1 (M+H)+.

(R)-2-(3-ethyl-4-(furan-2-carbonyl)piperazin-1-yl)-6-isopropyl-5-phenylnicotinonitrile (Compound 172)

$^1$H NMR (CHLOROFORM-d) δ 7.59-7.64 (m, 1H), 7.51 (dd, J=1.8, 0.8 Hz, 1H), 7.36-7.46 (m, 3H), 7.21-7.26 (m, 2H), 7.02-7.10 (m, 1H), 6.51 (dd, J=3.5, 1.8 Hz, 1H), 4.71 (br. s., 1H), 4.38-4.60 (m, 3H), 3.50 (br. s., 1H), 3.35 (dd, J=13.3, 3.5 Hz, 1H), 3.22 (td, J=12.5, 3.4 Hz, 1H), 3.08-3.18 (m, 1H), 1.90-2.06 (m, 1H), 1.83 (dquin, J=14.2, 7.2 Hz, 1H), 1.15 (dd, J=6.7, 3.1 Hz, 6H), 0.97 (t, J=7.4 Hz, 3H). LC-MS: m/z 429.1 (M+H)+.

(R)-2-(3-ethyl-4-(2-methylfuran-3-carbonyl)piperazin-1-yl)-6-isopropyl-5-phenylnicotinonitrile (Compound 173)

$^1$H NMR (CHLOROFORM-d) δ 7.58-7.66 (m, 1H), 7.35-7.47 (m, 3H), 7.29 (d, J=2.0 Hz, 1H), 7.21-7.26 (m, 2H), 6.32-6.41 (m, 1H), 4.59-4.80 (m, 1H), 4.50 (d, J=13.1 Hz, 1H), 4.42 (br. s., 1H), 3.91-3.97 (br. s., 1H), 3.45-3.65 (m, 1H), 3.27 (dd, J=13.1, 3.3 Hz, 1H), 3.05-3.19 (m, 2H), 2.41 (s, 3H), 1.86-1.95 (m, 1H), 1.79 (dt, J=14.1, 7.0 Hz, 1H), 1.15 (dd, J=6.8, 2.0 Hz, 6H), 0.87-0.99 (m, 3H). LC-MS: m/z 443.1 (M+H)+.

(R)-2-(3-ethyl-4-(2-(thiophen-2-yl)acetyl)piperazin-1-yl)-6-isopropyl-5-phenylnicotinonitrile (Compound 174)

$^1$H NMR (CHLOROFORM-d) δ 7.59 (s, 1H), 7.35-7.49 (m, 3H), 7.17-7.25 (m, 3H), 6.92-6.99 (m, 2H), 4.75 (br. s., 0.5H), 4.59-4.71 (m, 0.5H), 4.30-4.50 (m, 2H), 3.79-4.07 (m, 3H), 3.46-3.56 (m, 0.5H), 3.17-3.30 (m, 0.5H), 2.97-3.17 (m, 3H), 1.78-1.89 (m, 1H), 1.69-1.78 (m, 1H), 1.10-1.16 (m, 6H), 0.90-0.97 (m, 3H). LC-MS: m/z 459.1 (M+H)+.

2-(4-(furan-2-carbonyl)-3-methylpiperazin-1-yl)-5,6-diphenylnicotinonitrile (Compound 117)

Compound 117 was synthesized was synthesized was synthesized using 1,2-diphenylethanone as starting material.
1H NMR (CHLOROFORM-d) δ 7.87 (s, 1H), 7.53 (dd, J=1.5, 0.8 Hz, 1H), 7.37-7.44 (m, 2H), 7.27-7.35 (m, 6H), 7.12-7.19 (m, 2H), 7.06-7.12 (m, 1H), 6.53 (dd, J=3.4, 1.9 Hz, 1H), 4.94 (br. s., 1H), 4.53 (t, J=11.7 Hz, 2H), 4.36-4.46 (m, 1H), 3.62 (br. s., 1H), 3.44-3.54 (m, 1H), 3.26-3.37 (m, 1H), 1.52 (d, J=6.5 Hz, 3H). LC-MS: m/z 448.9 (M+H)+.

2-(4-(furan-3-carbonyl)-3-methylpiperazin-1-yl)-5,6-diphenylnicotinonitrile (Compound 118)

Compound 118 was synthesized using 1,2-diphenylethanone as starting material.
1H NMR (CHLOROFORM-d) δ 7.88 (s, 1H), 7.77 (s, 1H), 7.48 (s, 1H), 7.38 (d, J=8.0 Hz, 2H), 7.27-7.33 (m, 6H), 7.13-7.16 (m, 2H), 6.61 (s, 1H), 4.71-4.79 (br. s., 1H), 4.47-4.50 (s, 1H), 4.38 (s, 1H), 4.41 (s, 1H), 3.48-3.64 (m, 1H), 3.38-3.42 (m, 1H), 3.21 (td, J=12.4, 3.0 Hz, 1H), 1.49 (d, J=6.5 Hz, 3H). LC-MS: m/z 448.9 (M+H)+.

2-(4-(furan-3-carbonyl)piperazin-1-yl)-5,6-diphenylnicotinonitrile (Compound 122)

Compound 122 was synthesized using 1,2-diphenylethanone as starting material.
$^1$H NMR (CHLOROFORM-d) δ 7.88 (s, 1H), 7.78 (s, 1H), 7.47-7.51 (m, 1H), 7.37-7.42 (m, 2H), 7.27-7.35 (m, 6H), 7.15 (dd, J=6.5, 3.0 Hz, 2H), 6.62 (s, 1H), 3.92 (br. s., 4H), 3.89 (br. s., 4H). LC-MS: m/z 435.1 (M+H)+.

5,6-diphenyl-2-(4-(2-phenylacetyl)piperazin-1-yl)nicotinonitrile (Compound 123)

Compound 123 was synthesized using 1,2-diphenylethanone as starting material.
$^1$H NMR (CHLOROFORM-d) δ 7.85 (s, 1H), 7.34-7.39 (m, 4H), 7.28-7.33 (m, 8H), 7.22-7.26 (m, 1H), 7.13 (dd, J=6.5, 3.0 Hz, 2H), 3.85-3.91 (m, 2H), 3.79-3.84 (m, 4H), 3.66 (s, 4H). LC-MS: m/z 459.1 (M+H)+.

(R)-5-(3-fluorophenyl)-2-(4-(furan-3-carbonyl)-3-methylpiperazin-1-yl)-6-isopropylnicotinonitrile (Compound 161)

Compound 161 was synthesized using 1-(3-fluorophenyl)-3-methylbutan-2-one as starting material.
$^1$H NMR (CHLOROFORM-d) δ 7.73-7.79 (m, 1H), 7.61 (s, 1H), 7.47 (t, J=1.6 Hz, 1H), 7.35-7.44 (m, 1H), 7.06-7.13 (m, 1H), 7.00-7.04 (m, 1H), 6.96 (dt, J=9.3, 2.1 Hz, 1H), 6.54-6.63 (m, 1H), 4.61-4.90 (m, 1H), 4.41 (s, 0.5H), 4.44 (s, 0.5H), 4.19-4.39 (m, 2H), 3.42-3.49 (br. s., 1H), 3.34 (dd, J=13.2, 3.1 Hz, 1H), 3.14-3.23 (m, 1H), 3.06-3.14 (m, 1H), 1.44 (d, J=6.8 Hz, 3H), 1.15 (dd, J=6.8, 1.8 Hz, 6H). LC-MS: m/z 433.1 (M+H)+.

(R)-2-(4-(furan-3-carbonyl)-3-methylpiperazin-1-yl)-6-isopropyl-5-(2-methoxyphenyl)nicotinonitrile (Compound 175)

Compound 175 was synthesized using 1-(2-methoxyphenyl)-3-methylbutan-2-one as starting material.
$^1$H NMR (CHLOROFORM-d) δ 7.75 (s, 1H), 7.56 (s, 1H), 7.46 (t, J=1.5 Hz, 1H), 7.34-7.41 (m, 1H), 7.06-7.12 (m, 1H), 7.01 (t, J=7.3 Hz, 1H), 6.96 (d, J=8.3 Hz, 1H), 6.55-6.62 (m, 1H), 4.74 (br. s., 1H), 4.18-4.46 (m, 3H), 3.77 (s, 3H), 3.49 (br. s., 1H), 3.31 (dd, J=13.2, 3.1 Hz, 1H), 3.14 (td, J=12.5, 3.0 Hz, 1H), 2.86 (quin, J=6.7 Hz, 1H), 1.46 (d, J=6.8 Hz, 3H), 1.15 (br. s., 3H), 1.04 (br. s., 3H). LC-MS: m/z 445.2 (M+H)+.

(R)-2-(4-(furan-2-carbonyl)-3-methylpiperazin-1-yl)-6-isopropyl-5-(2-methoxyphenyl)nicotinonitrile (Compound 176)

Compound 176 was synthesized using 1-(2-methoxyphenyl)-3-methylbutan-2-one as starting material.

¹H NMR (CHLOROFORM-d) δ 7.56 (s, 1H), 7.50-7.53 (m, 1H), 7.34-7.41 (m, 1H), 7.07-7.13 (m, 1H), 7.03-7.06 (m, 1H), 6.99-7.02 (m, 1H), 6.96 (d, J=8.3 Hz, 1H), 6.51 (dd, J=3.3, 1.8 Hz, 1H), 4.90 (br. s., 1H), 4.51 (d, J=13.6 Hz, 1H), 4.41 (d, J=13.8 Hz, 1H), 4.34 (d, J=13.3 Hz, 1H), 3.77 (s, 3H), 3.57 (d, J=10.5 Hz, 1H), 3.39 (dd, J=13.1, 3.5 Hz, 1H), 3.23 (td, J=12.4, 3.1 Hz, 1H), 2.86 (dt, J=13.3, 6.7 Hz, 1H), 1.49 (d, J=6.5 Hz, 3H), 1.16 (br. s., 3H), 1.05 (br. s., 3H). LC-MS: m/z 445.2 (M+H)+.

(R)-6-isopropyl-5-(2-methoxyphenyl)-2-(3-methyl-4-(2-(thiophen-2-yl)acetyl)piperazin-1-yl)nicotinonitril-e (Compound 177)

Compound 177 was synthesized using 1-(2-methoxyphenyl)-3-methylbutan-2-one as starting material.
¹H NMR (CHLOROFORM-d) δ 7.54 (s, 1H), 7.33-7.41 (m, 1H), 7.20-7.24 (m, 1H), 7.05-7.11 (m, 1H), 6.98-7.04 (m, 1H), 6.89-6.98 (m, 3H), 4.94 (br. s., 0.5H), 4.58 (d, J=12.8 Hz, 0.2H), 4.17-4.46 (m, 3H), 3.91-4.04 (m, 2H), 3.76 (s, 3H), 3.56 (t, J=11.2 Hz, 0.5H), 3.27 (d, J=12.8 Hz, 0.5H), 3.13-3.23 (m, 1H), 2.98-3.11 (m, 1H), 2.85 (dt, J=13.3, 6.7 Hz, 1H), 1.33-1.39 (m, 3H), 1.15 (br. s., 3H), 1.04 (br. s., 3H). LC-MS: m/z 475.2 (M+H)+.

(R)-6-isopropyl-5-(2-methoxyphenyl)-2-(3-methyl-4-(2-methylfuran-3-carbonyl)piperazin-1-yl)nico-tino-nitrile (Compound 778)

Compound 178 was synthesized using 1-(2-methoxyphenyl)-3-methylbutan-2-one as starting material.
¹H NMR (CHLOROFORM-d) δ 7.52-7.59 (m, 1H), 7.34-7.41 (m, 1H), 7.29 (d, J=1.8 Hz, 1H), 7.08 (dd, J=7.3, 1.8 Hz, 1H), 7.01 (t, J=7.2 Hz, 1H), 6.96 (d, J=8.3 Hz, 1H), 6.38 (d, J=1.8 Hz, 1H), 4.69 (br. s., 1H), 4.29-4.43 (m, 2H), 4.00-4.29 (m, 1H), 3.77 (s, 3H), 3.46 (br. s., 1H), 3.24-3.39 (m, 1H), 3.11 (td, J=12.5, 3.0 Hz, 1H), 2.86 (spt, J=6.6 Hz, 1H), 2.41 (s, 3H), 1.43 (d, J=6.8 Hz, 3H), 1.12-1.19 (m, 3H), 1.04 (br. s., 3H). LC-MS: m/z 459.1 (M+H)+.

(R)-2-(4-(furan-3-carbonyl)-3-methylpiperazin-1-yl)-6-isopropyl-5-p-tolylnicotinonitrile (Compound 179)

Compound 179 was synthesized using 3-methyl-1-p-tolylbutan-2-one as starting material.
¹H NMR (CHLOROFORM-d) δ 7.75 (s, 1H), 7.60 (s, 1H), 7.44-7.49 (m, 1H), 7.24 (d, J=7.8 Hz, 2H), 7.13 (d, J=8.0 Hz, 2H), 6.55-6.62 (m, 1H), 4.74 (br. s., 1H), 4.20-4.49 (m, 3H), 3.38-3.57 (m, 3H), 3.31 (dd, J=13.1, 3.0 Hz, 1H), 3.07-3.22 (m, 2H), 2.37-2.46 (m, 3H), 1.45 (d, J=6.8 Hz, 3H), 1.07-1.20 (m, 6H). LC-MS: m/z 429.1 (M+H)+.

(R)-2-(4-(furan-2-carbonyl)-3-methylpiperazin-1-yl)-6-isopropyl-5-p-tolylnicotinonitrile (Compound 180)

Compound 180 was synthesized using 3-methyl-1-p-tolylbutan-2-one as starting material.
¹H NMR (CHLOROFORM-d) δ 7.60 (s, 1H), 7.50-7.53 (m, 1H), 7.24 (d, J=7.8 Hz, 2H), 7.13 (d, J=8.0 Hz, 2H), 7.05 (d, J=3.5 Hz, 1H), 6.46-6.55 (m, 1H), 4.90 (br. s., 1H), 4.51 (d, J=13.6 Hz, 1H), 4.42 (d, J=14.1 Hz, 1H), 4.33 (dt, J=13.3, 2.0 Hz, 1H), 3.57 (d, J=10.3 Hz, 1H), 3.40 (dd, J=13.2, 3.6 Hz, 1H), 3.18-3.30 (m, 1H), 3.09-3.18 (m, 1H), 2.41 (s, 3H), 1.48 (d, J=6.8 Hz, 3H), 1.07-1.20 (m, 6H). LC-MS: m/z 429.2 (M+H)+.

(R)-6-isopropyl-2-(3-methyl-4-(2-(thiophen-2-yl)acetyl)piperazin-1-yl)-5-p-tolylnicotinonitrile (Compound 181)

Compound 181 was synthesized using 3-methyl-1-p-tolylbutan-2-one as starting material.
¹H NMR (CHLOROFORM-d) δ 7.58 (s, 1H), 7.20-7.25 (m, 3H), 7.12 (d, J=7.8 Hz, 2H), 6.88-7.00 (m, 2H), 4.94 (br. s., 0.5H), 4.58 (d, J=13.1 Hz, 0.5H), 4.32-4.43 (m, 1H), 4.27 (s, 1H), 4.30 (s, 1H), 3.91-4.05 (m, 2H), 3.80 (d, J=13.6 Hz, 0.5H), 3.51-3.63 (m, 0.5H), 3.20-3.33 (m, 1H), 3.11-3.20 (m, 1H), 2.98-3.10 (m, 1H), 2.41 (s, 3H), 1.36 (d, J=6.3 Hz, 1.5H), 1.32 (d, J=6.8 Hz, 1.5H), 1.13 (d, J=6.5 Hz, 6H). LC-MS: m/z 459.1 (M+H)+.

(R)-6-isopropyl-2-(3-methyl-4-(2-methylfuran-3-carbonyl)piperazin-1-yl)-5-p-tolylnicotinonitrile (Compound 182)

Compound 182 was synthesized using 3-methyl-1-p-tolylbutan-2-one as starting material.
¹H NMR (CHLOROFORM-d) δ 7.60 (s, 1H), 7.28-7.32 (m, 1H), 7.24 (d, J=8.0 Hz, 2H), 7.12 (d, J=8.0 Hz, 2H), 6.36-6.41 (m, 1H), 4.69 (br. s., 1H), 4.38 (d, J=13.3 Hz, 1H), 4.33 (d, J=13.1 Hz, 1H), 4.23 (d, J=12.0 Hz, 1H), 3.46 (br. s., 1H), 3.26-3.34 (m, 1H), 3.13-3.21 (m, 1H), 3.05-3.13 (m, 1H), 2.41 (s, 6H), 1.41 (d, J=6.8 Hz, 3H), 1.14 (dd, J=6.7, 3.4 Hz, 6H).
LC-MS: m/z 443.2 (M+H)+.

(R)-6-isopropyl-5-(2-methoxyphenyl)-2-(4-(3-methoxypropanoyl)-3-methylpiperazin-1-yl)nicotinonitrile (Compound 183)

Compound 183 was synthesized using 1-(2-methoxyphenyl)-3-methylbutan-2-one as starting material.
¹H NMR (CHLOROFORM-d) δ 7.55 (s, 1H), 7.34-7.42 (m, 1H), 7.05-7.12 (m, 1H), 6.99-7.05 (m, 1H), 6.96 (d, J=8.3 Hz, 1H), 4.93 (br. s., 0.5H), 4.55 (d, J=13.1 Hz, 0.5H), 4.19-4.43 (m, 3H), 3.82 (d, J=7.5 Hz, 0.5H), 3.76 (s, 3H), 3.70-3.76 (m, 2H), 3.54-3.64 (m, 0.5H), 3.38 (s, 3H), 3.30 (t, J=13.3 Hz, 1H), 3.02-3.22 (m, 1H), 2.82-2.92 (m, 1H), 2.66-2.80 (m, 1H), 2.53-2.65 (m, 1H), 1.42 (d, J=6.5 Hz, 1.5H), 1.32 (d, J=6.5 Hz, 1.5H), 1.16 (br. s., 3H), 1.05 (br. s., 3H). LC-MS: m/z 437.1 (M+H)+.

(S)-5-(2-ethoxyphenyl)-2-(4-(furan-2-carbonyl)-2-methylpiperazin-1-yl)-6-isopropylnicotinonitrile (Compound 184)

Compound 184 was synthesized using 1-(2-ethoxyphenyl)-3-methylbutan-2-one as starting material.
¹H NMR (CHLOROFORM-d) δ 7.55 (s, 1H), 7.48-7.53 (m, 1H), 7.31-7.38 (m, 1H), 7.05-7.11 (m, 2H), 6.96-7.02 (m, 1H), 6.94 (d, J=8.3 Hz, 1H), 6.45-6.56 (m, 1H), 4.77 (br. s., 1H), 4.53 (d, J=11.3 Hz, 1H), 4.36 (d, J=13.3 Hz, 1H), 4.23-4.33 (m, 1H), 4.02 (q, J=6.8 Hz, 2H), 3.38-3.67 (m, 3H), 2.84-2.97 (m, 1H), 1.36 (d, J=6.8 Hz, 3H), 1.27-1.30 (m, 3H), 1.24-1.27 (m, 6H). LC-MS: m/z 459.1 (M+H)+.

(R)-6-isopropyl-2-(4-(3-methoxypropanoyl)-3-methylpiperazin-1-yl)-5-p-tolylnicotinonitrile (Compound 198)

Compound 198 was synthesized using 3-methyl-1-p-tolylbutan-2-one as starting material.

¹H NMR (CHLOROFORM-d) δ 7.59 (s, 1H), 7.23 (d, J=7.8 Hz, 2H), 7.12 (d, J=8.0 Hz, 2H), 4.92 (br. s., 0.5H), 4.55 (d, J=12.8 Hz, 0.5H), 4.21-4.42 (m, 3H), 3.81 (d, J=13.8 Hz, 0.5H), 3.69-3.77 (m, 62H), 3.53-3.64 (m, 0.5H), 3.38 (s, 3H), 3.31 (t, J=12.3 Hz, 1H), 3.11-3.19 (m, 2H), 2.65-2.81 (m, 1H), 2.54-2.63 (m, 1H), 2.41 (s, 3H), 1.40 (d, J=6.3 Hz, 1.5H), 1.31 (d, J=6.5 Hz, 1.5H), 1.14 (d, J=6.8 Hz, 6H). LC-MS: m/z 421.1 (M+H)⁺.

(R)-2-(4-(3-methoxypropanoyl)-3-methylpiperazin-1-yl)-5,6-diphenylnicotinonitrile (Compound 210)

Compound 240 was synthesized using 1,2-diphenylethanone as starting material.

¹H NMR (CHLOROFORM-d) δ 7.84 (s, 1H), 7.33-7.40 (m, 2H), 7.26-7.33 (m, 4H), 7.20-7.25 (m, 2H), 7.08-7.16 (m, 2H), 4.94 (br. s., 0.5H), 4.56 (d, J=12.8 Hz, 0.5H), 4.38-4.49 (m, 1H), 4.23-4.38 (m, 2H), 3.77-3.90 (m, 1H), 3.74 (t, J=6.0 Hz, 2H), 3.54-3.64 (m, 0.5H), 3.37 (s, 3H), 3.34 (d, J=6.3 Hz, 0.5H), 3.19-3.26 (m, 1H), 3.06-3.19 (m, 1H), 2.66-2.78 (m, 1H), 2.55-2.63 (m, 1H), 1.39-1.46 (m, 1.5H), 1.33 (d, J=6.0 Hz, 1.5H). LC-MS: m/z 441.3 (M+H)⁺.

Example 10. Preparation of (R)-2-(4-(furan-3-carbonyl)-3-methylpiperazin-1-yl)-6-isopropyl-4-phenylnicotinonitrile (Compound 130)

Compound 130 (55, wherein m is 1, R³ is methyl; and R⁸ is furan-3-yl) was synthesized according to general Scheme 7.

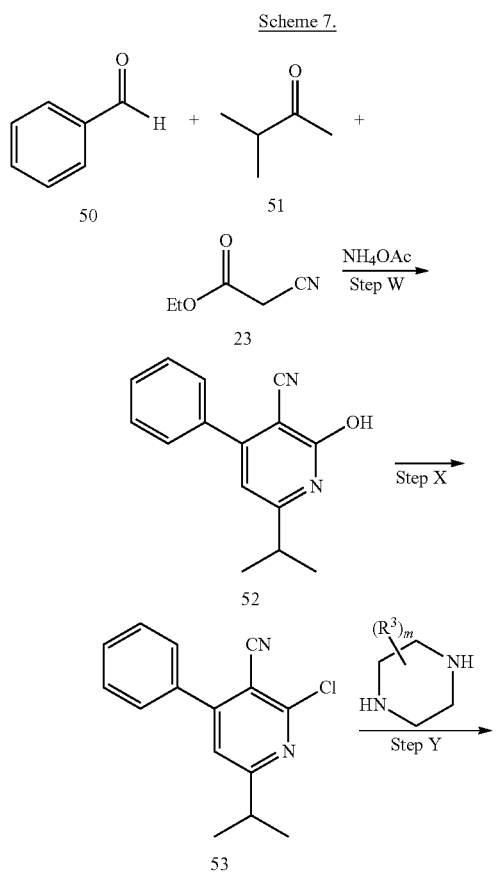

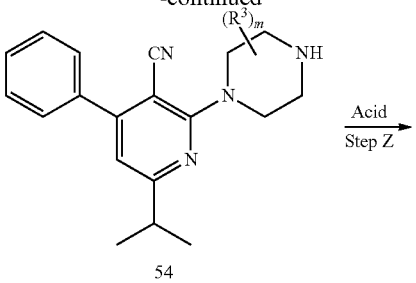

54

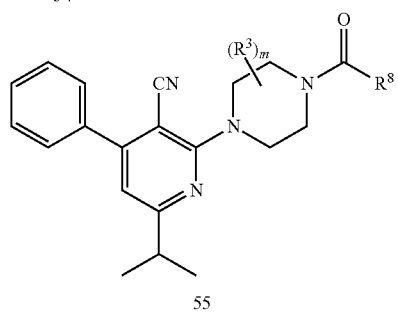

55

Step W:
2-hydroxy-6-isopropyl-4-phenylnicotinonitrile (52)

To a suspension of ammonium acetate (31.46 g, 0.4 mol) in 200 mL of EtOH was added successively the 3-methyl-2-butanone (51; 5.38 mL, 50 mmol), benzaldehyde (50; 5.21 g, 50 mmol), and ethyl cyanoacetate (23; 5.6 mL, 50 mmol). The resulting mixture was stirred at reflux temperature for 3 hrs and subsequently at room temperature overnight. After the LC-MS showed the formation of the desired product, the precipitate formed was filtered and washed with EtOH (10 mL×3 times) and hexane (10 mL×3 times). After air-drying, 2.18 g of 52 was obtained as a white solid. MS (ES) M+H expected 239.1. found 239.0. ¹H NMR (CHLOROFORM-d) δ 7.61-7.70 (m, 2H), 7.51-7.58 (m, 3H), 6.33 (s, 1H), 3.06 (dt, J=13.8, 6.9 Hz, 1H), 1.42 (d, J=7.0 Hz, 6H).

Step X: 2-chloro-6-isopropyl-4-phenylnicotinonitrile (53)

A mixture of 2-hydroxy-6-isopropyl-4-phenylnicotinonitrile 52; (0.702 g, 2.94 mmol), 7 mL of phosphoryl trichloride and one drop of DMF were heated to reflux overnight until LC-MS indicated the complete conversion to the product. After evaporation of excess of phosphoryl trichloride under reduced pressure, the residue was re-dissolved in methylene chloride and neutralized carefully with satd. aq. NaHCO₃ and washed subsequently with 1N HCl and brine. The combined organic layer was dried over anhy. Na₂SO₄ and concentrated in vacuo. Flash column chromatography (1:5 ethyl acetate/petroleum ether) afforded 717 mg of 53 as a yellowish solid. MS (ES) M+H expected 257.1. found 257.0. ¹H NMR (CHLOROFORM-d) δ 7.52-7.64 (m, 5H), 7.26 (s, 1H), 3.09-3.21 (m, 1H), 1.37 (d, J=7.0 Hz, 6H).

Step Y: (R)-6-isopropyl-2-(3-methylpiperazin-1-yl)-4-phenylnicotinonitrile (54)

A mixture of above chloride 53 (192.6 mg, 0.75 mmol), (R)-2-methylpiperazine (150 mg, 1.5 mmol), and triethylamine (0.21 mL, 1.5 mmol) suspended in 1.5 mL of acetonitrile was subjected to microwave reaction at 175° C. for 45 min. After the reaction mixture was concentrated in vacuo, the residue was purified by flash column chromatography to give 197 mg of 54 as yellowish oil. MS (ES) M+H expected 321.2. found 321.1. $^1$H NMR (CHLOROFORM-d) δ 7.54-7.60 (m, 2H), 7.47-7.53 (m, 3H), 6.71 (s, 1H), 4.21-4.35 (m, 2H), 3.03-3.18 (m, 4H), 2.99 (dt, J=13.8, 6.9 Hz, 1H), 2.78 (dd, J=12.7, 10.2 Hz, 1H), 1.30 (d, J=7.0 Hz, 6H), 1.15-1.20 (m, 3H).

Step Z: (R)-2-(4-(furan-3-carbonyl)-3-methylpiperazin-1-yl)-6-isopropyl-4-phenylnicotinonitrile (Compound 130)

In a 5-mL of amber glass vial was placed (R)-6-isopropyl-2-(3-methylpiperazin-1-yl)-4-phenyl-nicotinonitrile (54; 32 mg, 0.1 mmol), furan-3-carboxylic acid (22.4 mg, 0.312 mmol), EDCI (38.2 mg, 0.2 mmol), HOBt (27 mg, 0.2 mmol), triethylamine (35 μL, 0.2 mmol) and 1.5 mL of methylene chloride. The resulting reaction mixture was stirred at room temperature overnight. The mixture was quenched with 1 N HCl aqueous solution, extracted with EtOAc three times. The combined organic layer was washed with satd. NaHCO$_3$ and brine, dried over anhy. Na$_2$SO$_4$, and concentrated in vacuo. The crude product was purified by preparative TLC (EtOAc: petroleum ether/20:100) to afford 23 mg of Compound 130 as a light yellowish solid. MS (ES) M+H expected 415.2. found 415.1. $^1$H NMR (CHLOROFORM-d) δ 7.77 (s, 1H), 7.55-7.58 (m, 2H), 7.50-7.53 (m, 3H), 7.48 (t, J=1.6 Hz, 1H), 6.79 (s, 1H), 6.60-6.62 (m, 1H), 4.76 (br. s., 1H), 4.28 (s, 1H), 4.31 (s, 1H), 4.22 (d, J=13.1 Hz, 1H), 3.56 (br. s., 1H), 3.34 (dd, J=12.9, 3.6 Hz, 1H), 3.17 (td, J=12.5, 3.5 Hz, 1H), 3.01 (spt, J=6.9 Hz, 1H), 1.47 (d, J=6.8 Hz, 3H), 1.31 (d, J=6.8 Hz, 6H).

Other Compounds of Formula II listed below, wherein $R^{1a}$ is optionally substituted phenyl; and $R^{1b}$ is hydrogen; were similarly prepared by general Scheme 7 replacing one or more of: (1) 3-methyl-2-butanone (51) with an alternate ketone as starting material; (2) benzaldehyde (50) with an alternate aldehyde as starting material; (3) (R)-2-methylpiperazine with an alternate piperazine in Step Y; and (4) 2-methylfuran-3-carboxylic acid with an alternate acid in Step Z. In addition, a compound wherein $R^{1a}$ is isopropyl; $R^{1b}$ is hydrogen and $R^2$ is phenyl was also prepared by the same method of general Scheme 7.

2-(4-benzoylpiperazin-1-yl)-6-isopropyl-4-phenylnicotinonitrile (Compound 100)

$^1$H NMR (DMSO-d$_6$) δ 7.54-7.59 (m, 2H), 7.50-7.54 (m, 3H), 7.47 (s, 5H), 6.80 (s, 1H), 4.01 (br. s., 2H), 3.74-3.89 (m, 3H), 3.66 (br. s., 3H), 3.01 (quin, J=6.8 Hz, 1H), 1.32 (s, 3H), 1.30 (s, 3H). LC-MS: m/z 411.1 (M+H)$^+$.

2-((3S,5R)-4-benzoyl-3,5-dimethylpiperazin-1-yl)-6-isopropyl-4-phenylnicotinonitrile (Compound 101)

$^1$H NMR (DMSO-d$_6$) δ 7.53-7.58 (m, 2H), 7.49-7.53 (m, 3H), 7.40-7.47 (m, 5H), 6.79 (s, 1H), 4.54 (br. s., 2H), 4.24 (s, 1H), 4.27 (s, 1H), 3.28 (dd, J=13.1, 4.3 Hz, 2H), 3.01 (dt, J=13.6, 6.9 Hz, 1H), 1.52 (d, J=6.8 Hz, 6H), 1.31 (d, J=7.0 Hz, 6H). LC-MS: m/z 439.1 (M+H)$^+$.

2-((3S,5R)-4-(furan-2-carbonyl)-3,5-dimethylpiperazin-4-yl)-6-isopropyl-4-phenylnicotinonitrile (Compound 102)

$^1$H NMR (CHLOROFORM-d) δ 7.54-7.61 (m, 2H), 7.45-7.54 (m, 4H), 7.08 (d, J=3.5 Hz, 1H), 6.78 (s, 1H), 6.52 (dd, J=3.5, 1.8 Hz, 1H), 4.90 (br. s., 2H), 4.30 (s, 1H), 4.34 (s, 1H), 3.32 (dd, J=12.9, 4.4 Hz, 2H), 3.01 (quin, J=6.9 Hz, 1H), 1.60 (d, J=7.0 Hz, 6H), 1.31 (d, J=7.0 Hz, 6H). LC-MS: m/z 429.1 (M+H)$^+$.

2-(4-(furan-2-carbonyl)piperazin-1-yl)-4-isopropyl-6-phenylnicotinonitrile (Compound 103)

Compound 103 was synthesized using isobutyraldehyde and acetophenone as starting materials.

$^1$H NMR (DMSO-d$_6$) δ 8.02-8.08 (m, 2H), 7.50-7.56 (m, 2H), 7.46-7.50 (m, 2H), 7.30 (s, 1H), 7.08 (dd, J=3.4, 0.6 Hz, 1H), 6.53 (dd, J=3.3, 1.8 Hz, 1H), 4.05 (br. s., 4H), 3.79-3.85 (m, 4H), 3.40 (dt, J=13.7, 6.8 Hz, 1H), 1.38 (d, J=6.8 Hz, 6H). LC-MS: m/z 400.8 (M+H)$^+$.

2-(4-(furan-2-carbonyl)piperazin-1-yl)-6-isopropyl-4-(2-methoxyphenyl)nicotinonitrile (Compound 101)

Compound 104 was synthesized using 2-methoxybenzaldehyde and 3-methylbutan-2-one as starting materials.

$^1$H NMR (CHLOROFORM-d) δ 7.51-7.57 (m, 1H), 7.43-7.51 (m, 1H), 7.23-7.28 (m, 1H), 7.03-7.11 (m, 3H), 6.75 (s, 1H), 6.53 (dd, J=3.0, 1.5 Hz, 1H), 4.02 (br. s., 4H), 3.89 (s, 3H), 3.74-3.82 (m, 4H), 3.00 (dt, J=13.8, 6.9 Hz, 1H), 1.31 (d, J=6.8 Hz, 6H). LC-MS: m/z 430.9 (M+H)$^+$.

2-(4-benzoylpiperazin-1-yl)-6-isopropyl-4-(2-methoxyphenyl)nicotinonitrile (Compound 105)

Compound 105 was synthesized using 2-methoxybenzaldehyde and 3-methylbutan-2-one as starting materials.

$^1$H NMR (DMSO-d$_6$) δ 7.43-7.50 (m, 6H), 7.25 (dd, J=7.4, 1.6 Hz, 1H), 7.07-7.10 (m, 1H), 7.02-7.06 (m, 1H), 6.75 (s, 1H), 3.99 (br. s., 2H), 3.87 (s, 3H), 3.78 (br. s., 2H), 3.64 (br. s., 4H), 2.99 (dt, J=13.8, 6.9 Hz, 1H), 1.31 (s, 3H), 1.29 (s, 3H). LC-MS: m/z 440.8 (M+H)$^+$.

2-(4-(1H-indole-3-carbonyl)piperazin-1-yl)-6-isopropyl-1-(2-methoxyphenyl)nicotinonitrile (Compound 106)

Compound 106 was synthesized using 2-methoxybenzaldehyde and 3-methylbutan-2-one as starting materials.

$^1$H NMR (CHLOROFORM-d) δ 9.02 (br. s., 1H), 7.73-7.80 (m, 1H), 7.41-7.51 (m, 3H), 7.21-7.28 (m, 3H), 7.01-7.11 (m, 2H), 6.75 (s, 1H), 3.94 (br. s., 4H), 3.87 (s, 3H), 3.75 (br. s., 4H), 3.02 (dt, J=13.7, 6.8 Hz, 1H), 1.31 (d, J=6.8 Hz, 6H). LC-MS: m/z 480 (M+H)$^+$.

2-(4-(furan-2-carbonyl)-3-methylpiperazin-1-yl)-6-isopropyl-4-phenylnicotinonitrile (Compound 107)

$^1$H NMR (CHLOROFORM-d) δ 7.55-7.60 (m, 2H), 7.48-7.54 (m, 4H), 7.06 (dd, J=3.5, 0.8 Hz, 1H), 6.77 (s, 1H), 6.52 (dd, J=3.5, 1.8 Hz, 1H), 4.91 (br. s., 1H), 4.52 (d, J=13.6 Hz, 1H), 4.29-4.36 (m, 1H), 4.23 (dt, J=13.1, 2.1 Hz, 1H), 3.62 (br. s., 1H), 3.43 (dd, J=13.1, 3.8 Hz, 1H), 3.26 (td, J=12.4, 3.5 Hz, 1H), 3.00 (quin, J=6.9 Hz, 1H), 1.50 (d, J=6.8 Hz, 3H), 1.31 (d, J=6.8 Hz, 6H). LC-MS: m/z 415.1 (M+H)$^+$.

2-(4-(furan-2-carbonyl)-3-methylpiperazin-1-yl)-4-isopropyl-6-phenylnicotinonitrile (Compound 108)

Compound 108 was synthesized using benzaldehyde and 3-methylbutan-2-one as starting materials.

¹H NMR (CHLOROFORM-d) δ 8.00-8.08 (m, 2H), 7.50-7.57 (m, 2H), 7.45-7.50 (m, 2H), 7.29 (s, 1H), 7.07 (dd, J=3.5, 0.5 Hz, 1H), 6.52 (dd, J=3.5, 1.8 Hz, 1H), 4.94 (br. s., 1H), 4.54 (d, J=13.3 Hz, 1H), 4.34 (dd, J=12.5, 2.3 Hz, 1H), 4.24 (dt, J=13.1, 2.1 Hz, 1H), 3.65 (br. s., 1H), 3.41-3.46 (m, 1H), 3.38-3.41 (m, 1H), 3.25 (td, J=12.4, 3.3 Hz, 1H), 1.53 (d, J=6.8 Hz, 3H), 1.38 (d, J=6.8 Hz, 6H). LC-MS: m/z 415.1 (M+H)⁺.

2-(4-(furan-3-carbonyl)-3-methylpiperazin-1-yl)-6-isopropyl-4-phenylnicotinonitrile (Compound 110)

¹H NMR (CHLOROFORM-d) δ 8.00-8.06 (m, 2H), 7.77 (s, 1H), 7.50 (br. s., 1H), 7.48 (d, J=4.3 Hz, 3H), 7.30 (s, 1H), 6.61 (s, 1H), 4.78 (br. s., 1H), 4.28 (s, 1H), 4.31 (s, 1H), 4.22 (d, J=13.1 Hz, 1H), 3.58 (br. s., 1H), 3.40 (quin, J=6.9 Hz, 1H), 3.33 (dd, J=12.9, 3.1 Hz, 1H), 3.17 (td, J=12.4, 3.3 Hz, 1H), 1.50 (d, J=6.8 Hz, 3H), 1.38 (d, J=6.8 Hz, 6H). LC-MS: m/z 415.0 (M+H)⁺.

2-(4-(furan-3-carbonyl)-3-methylpiperazin-1-yl)-1-isopropyl-6-phenylnicotinonitrile (Compound 111)

Compound 111 was synthesized using benzaldehyde and 3-methylbutan-2-one as starting materials.
¹H NMR (CHLOROFORM-d) δ 7.77 (s, 1H), 7.53-7.61 (m, 2H), 7.49-7.53 (m, 3H), 7.47 (s, 1H), 6.79 (s, 4H), 6.61 (s, 1H), 4.71-4.76 (br. s., 1H), 4.28 (s, 1H), 4.31 (s, 1H), 4.22 (d, J=13.1 Hz, 1H), 3.56 (br. s., 1H), 3.34 (dd, J=13.1, 3.3 Hz, 1H), 3.17 (td, J=12.5, 3.4 Hz, 1H), 3.00 (dt, J=13.7, 6.8 Hz, 1H), 1.47 (d, J=6.8 Hz, 3H), 1.29 (d, J=7.3 Hz, 6H). LC-MS: m/z 414.9 (M+H)⁺.

2-(4-(furan-3-carbonyl)piperazin-1-yl)-6-isopropyl-4-(2-methoxyphenyl)nicotinonitrile (Compound 113)

Compound 113 was synthesized using 2-methoxybenzaldehyde and 3-methylbutan-2-one as starting materials.
¹H NMR (CHLOROFORM-d) δ 7.77 (s, 1H), 7.42-7.53 (m, 2H), 7.25 (dd, J=7.5, 1.5 Hz, 1H), 7.02-7.13 (m, 2H), 6.76 (s, 1H), 6.59-6.66 (m, 1H), 3.90 (br. s., 4H), 3.88 (s, 3H), 3.73 (br. s., 4H), 3.00 (dt, J=13.7, 6.8 Hz, 1H), 1.30 (d, J=6.8 Hz, 6H). LC-MS: m/z 431.0 (M+H)⁺.

4-(3-fluorophenyl)-2-(4-(furan-2-carbonyl)piperazin-1-yl)-6-isopropylnicotinonitrile (Compound 114)

Compound 114 was synthesized using 3-fluorobenzaldehyde and 3-methylbutan-2-one as starting materials.
¹H NMR (CHLOROFORM-d) δ 7.42-7.56 (m, 2H), 7.36 (dq, J=7.7, 0.9 Hz, 1H), 7.17-7.27 (m, 2H), 7.09 (dd, J=3.4, 0.9 Hz, 1H), 6.76 (s, 1H), 6.53 (dd, J=3.5, 1.8 Hz, 1H), 4.03 (br. s., 4H), 3.83 (dd, J=6.3, 4.0 Hz, 4H), 2.95-3.10 (m, 1H), 1.31 (d, J=6.8 Hz, 6H). LC-MS: m/z 419.1 (M+H)⁺.

4-(3-fluorophenyl)-2-(4-(furan-3-carbonyl)piperazin-1-yl)-6-isopropylnicotinonitrile (Compound 115)

Compound 115 was synthesized using 3-fluorobenzaldehyde and 3-methylbutan-2-one as starting materials.
¹H NMR (CHLOROFORM-d) δ 7.77-7.80 (m, 1H), 7.45-7.53 (m, 2H), 7.36 (dt, J=7.7, 1.2 Hz, 1H), 7.17-7.28 (m, 2H), 6.77 (s, 1H), 6.62 (dd, J=1.9, 0.6 Hz, 1H), 3.92 (br. s., 4H), 3.77 (br. s., 4H), 2.92-3.10 (m, 1H), 1.31 (d, J=6.8 Hz, 6H). LC-MS: m/z 419.0 (M+H)⁺.

2-(4-(1H-indole-3-carbonyl)piperazin-1-yl)-4-(3-fluorophenyl)-6-isopropylnicotinonitrile (Compound 116)

Compound 116 was synthesized using 3-fluorobenzaldehyde and 3-methylbutan-2-one as starting materials.
¹H NMR (CHLOROFORM-d) δ 7.75 (d, J=7.0 Hz, 1H), 7.40-7.63 (m, 3H), 7.36 (d, J=7.8 Hz, 1H), 7.17-7.28 (m, 3H), 6.77 (s, 1H), 3.94 (br. s., 4H), 3.79 (br. s., 4H), 3.67 (s, 1H), 3.02-3.13 (m, 1H), 1.32 (d, J=6.8 Hz, 6H). LC-MS: m/z 468.1 (M+H)⁺.

6-isopropyl-2-(3-methyl-4-(2-phenylacetyl)piperazin-1-yl)-4-phenylnicotinonitrile (Compound 121)

¹H NMR (CHLOROFORM-d) δ 7.48-7.58 (m, 5H), 7.33-7.39 (m, 3H), 7.30 (d, J=1.5 Hz, 1H), 7.25-7.28 (m, 1H), 6.75 (s, 1H), 4.71 (s, 1H), 4.27 (br. s., 1H), 4.09-4.20 (m, 2H), 3.80 (br. s., 2H), 3.52 (s, 1H), 3.19-3.26 (s, 1H), 3.06-3.15 (m, 1H), 2.98 (dt, J=13.7, 6.8 Hz, 1H), 1.40 (s, 3H), 1.30 (d, J=4.5 Hz, 19H). LC-MS: m/z 439.2 (M+H)⁺.

4-(3-fluorophenyl)-2-(4-(furan-2-carbonyl)-3-methylpiperazin-1-yl)-6-isopropylnicotinonitrile (Compound 127)

Compound 127 was synthesized using 3-fluorobenzaldehyde and 3-methylbutan-2-one as starting materials.
¹H NMR (CHLOROFORM-d) δ 7.44-7.58 (m, 2H), 7.31-7.40 (m, 1H), 7.14-7.27 (m, 2H), 7.07 (d, J=3.5 Hz, 1H), 6.74 (s, 1H), 6.53 (dd, J=3.5, 1.8 Hz, 1H), 4.92 (br. s., 1H), 4.52 (d, J=13.6 Hz, 1H), 4.34 (d, J=10.5 Hz, 1H), 4.24 (dt, J=13.1, 2.1 Hz, 1H), 3.62 (br. s., 1H), 3.45 (dd, J=13.3, 3.8 Hz, 1H), 3.28 (td, J=12.4, 3.4 Hz, 1H), 3.01 (dt, J=13.6, 6.9 Hz, 1H), 1.44-1.54 (m, 3H), 1.31 (d, J=6.8 Hz, 6H). LC-MS: m/z 433.0 (M+H)⁺.

4-(3-fluorophenyl)-2-(4-(furan-3-carbonyl)-3-methylpiperazin-1-yl)-6-isopropylnicotinonitrile (Compound 128)

Compound 128 was synthesized using 3-fluorobenzaldehyde and 3-methylbutan-2-one as starting materials.
¹H NMR (CHLOROFORM-d) δ 7.73-7.81 (m, 1H), 7.44-7.56 (m, 2H), 7.35 (dt, J=8.0, 1.1 Hz, 1H), 7.12-7.27 (m, 2H), 6.75 (s, 1H), 6.61 (dd, J=1.8, 0.8 Hz, 1H), 4.77 (br. s., 1H), 4.31 (d, J=12.0 Hz, 2H), 4.23 (d, J=13.1 Hz, 1H), 3.57 (br. s., 1H), 3.36 (d, J=10.0 Hz, 1H), 3.19 (td, J=12.4, 3.5 Hz, 1H), 3.01 (dt, J=13.5, 6.9 Hz, 1H), 1.46 (d, J=6.8 Hz, 3H), 1.31 (d, J=6.8 Hz, 6H). LC-MS: m/z 433.1 (M+H)⁺.

2-(4-(1H-indole-3-carbonyl)-3-methylpiperazin-1-yl)-4-(3-fluorophenyl)-6-isopropylnicotinonitrile (Compound 129)

Compound 129 was synthesized using 3-fluorobenzaldehyde and 3-methylbutan-2-one as starting materials.
¹H NMR (CHLOROFORM-d) δ 8.85 (s, 1H), 7.75 (d, J=7.8 Hz, 1H), 7.40-7.54 (m, 3H), 7.35 (d, J=7.8 Hz, 1H), 7.15-7.28 (m, 4H), 6.74 (s, 1H), 4.84 (br. s., 1H), 4.28 (t, J=15.3 Hz, 3H), 3.59 (d, J=11.8 Hz, 1H), 3.41 (d, J=11.0 Hz, 1H), 3.21 (t, J=10.8 Hz, 1H), 3.00 (dt, J=13.8, 6.9 Hz, 1H), 1.45 (d, J=6.5 Hz, 3H), 1.30 (d, J=6.8 Hz, 6H). LC-MS: m/z 482.2 (M+H)⁺.

(R)-2-(4-(furan-3-carbonyl)-3-methylpiperazin-1-yl)-6-isopropyl-4-phenylnicotinonitrile (Compound 130)

$^1$H NMR (CHLOROFORM-d) δ 7.77 (s, 1H), 7.55-7.58 (m, 2H), 7.50-7.53 (m, 3H), 7.48 (t, J=1.6 Hz, 1H), 6.79 (s, 1H), 6.60-6.62 (m, 1H), 4.76 (br. s., 1H), 4.28 (s, 1H), 4.31 (s, 1H), 4.22 (d, J=13.1 Hz, 1H), 3.56 (br. s., 1H), 3.34 (dd, J=12.9, 3.6 Hz, 1H), 3.17 (td, J=12.5, 3.5 Hz, 1H), 3.01 (spt, J=6.9 Hz, 1H), 1.47 (d, J=6.8 Hz, 3H), 1.31 (d, J=6.8 Hz, 6H). LC-MS: m/z 415.1 (M+H)$^+$.

(R)-6-isopropyl-2-(3-methyl-4-(2-phenylacetyl)piperazin-1-yl)-4-phenylnicotinonitrile (Compound 131)

$^1$H NMR (CHLOROFORM-d) δ 7.52-7.57 (m, 2H), 7.47-7.52 (m, 3H), 7.29-7.41 (m, 4H), 7.24-7.28 (m, 1H), 6.75 (s, 1H), 4.98 (br. s., 0.5H), 4.62 (d, J=13.3 Hz, 0.5H), 4.28 (d, J=13.1 Hz, 1H), 4.06-4.20 (m, 2H), 3.81 (br. s., 2H), 3.70-3.79 (m, 0.5H), 3.54 (t, J=11.3 Hz, 0.5H), 3.18-3.33 (m, 1H), 3.03-3.17 (m, 1H), 2.99 (dt, J=13.8, 6.9 Hz, 1H), 1.33 (br. s., 3H), 1.29 (d, J=7.0 Hz, 6H). LC-MS: m/z 439.1 (M+H)$^+$.

(S)-2-(4-(furan-3-carbonyl)-3-methylpiperazin-1-yl)-6-isopropyl-4-phenylnicotinonitrile (Compound 132)

$^1$H NMR (CHLOROFORM-d) δ 7.77 (s, 1H), 7.54-7.59 (m, 2H), 7.49-7.54 (m, 3H), 7.48 (t, J=1.6 Hz, 1H), 6.79 (s, 1H), 6.59-6.63 (m, 1H), 4.76 (br. s., 1H), 4.28 (s, 1H), 4.31 (s, 1H), 4.22 (d, J=13.3 Hz, 1H), 3.57 (br. s., 1H), 3.34 (dd, J=13.2, 3.6 Hz, 1H), 3.17 (td, J=12.5, 3.4 Hz, 1H), 3.01 (spt, J=6.9 Hz, 1H), 1.47 (d, J=6.8 Hz, 3H), 1.31 (d, J=6.8 Hz, 6H). LC-MS: m/z 415.1 (M+H)$^+$.

(S)-6-isopropyl-2-(3-methyl-4-(2-phenylacetyl)piperazin-1-yl)-4-phenylnicotinonitrile (Compound 133)

$^1$H NMR (CHLOROFORM-d) δ 7.53-7.56 (m, 2H), 7.47-7.53 (m, 3H), 7.33-7.39 (m, 2H), 7.29-7.33 (m, 2H), 7.24-7.28 (m, 1H), 6.75 (s, 1H), 4.98 (br. s., 0.5H), 4.62 (d, J=13.3 Hz, 0.5H), 4.28 (d, J=12.8 Hz, 1H), 4.08-4.20 (m, 2H), 3.81 (br. s., 2H), 3.70-3.79 (m, 0.5H), 3.54 (t, J=11.3 Hz, 0.5H), 3.17-3.32 (m, 1H), 3.10 (t, J=12.7 Hz, 1H), 2.98 (dt, J=13.7, 6.8 Hz, 1H), 1.31-1.35 (m, 3H), 1.29 (d, J=7.0 Hz, 6H). LC-MS: m/z 439.1 (M+H)$^+$.

4-(3-fluorophenyl)-2-(4-(furan-3-carbonyl)-3,5-dimethylpiperazin-1-yl)-6-isopropylnicotinonitrile (Compound 134)

Compound 134 was synthesized using 3-fluorobenzaldehyde and 3-methylbutan-2-one as starting materials.

$^1$H NMR (DMSO-d$_6$) δ 7.77 (s, 1H), 7.45-7.53 (m, 2H), 7.35 (d, J=8.3 Hz, 1H), 7.17-7.25 (m, 2H), 6.76 (s, 1H), 6.65 (d, J=1.0 Hz, 1H), 4.71 (br. s., 1H), 4.31 (d, J=12.8 Hz, 2H), 3.50-3.69 (m, 1H), 3.27 (dd, J=13.2, 4.4 Hz, 2H), 3.01 (quin, J=7.0 Hz, 1H), 1.56 (d, J=7.0 Hz, 6H), 1.32 (s, 3H), 1.30 (s, 3H). LC-MS: m/z 447.1 (M+H)$^+$.

2-(3,5-dimethyl-1-(2-phenylacetyl)piperazin-1-yl)-4-(3-fluorophenyl)-6-isopropylnicotinonitrile (Compound 135)

Compound 135 was synthesized using 3-fluorobenzaldehyde and 3-methylbutan-2-one as starting materials.

$^1$H NMR (CHLOROFORM-d) δ 7.43-7.55 (m, 1H), 7.12-7.40 (m, 8H), 6.74 (s, 1H), 4.90 (br. s., 1H), 4.26 (br. s., 3H), 3.82 (s, 2H), 3.14 (br. s., 2H), 3.00 (dt, J=13.8, 6.9 Hz, 1H), 1.44 (d, J=6.8 Hz, 6H), 1.30 (d, J=6.8 Hz, 6H). LC-MS: m/z 471.1 (M+H)$^+$.

4-(3-fluorophenyl)-2-(4-(furan-2-carbonyl)-3,5-dimethylpiperazin-1-yl)-6-isopropylnicotinonitrile (Compound 136)

Compound 136 was synthesized using 3-fluorobenzaldehyde and 3-methylbutan-2-one as starting materials.

$^1$H NMR (CHLOROFORM-d) δ 7.45-7.55 (m, 2H), 7.32-7.38 (m, 1H), 7.15-7.28 (m, 2H), 7.08 (d, J=3.5 Hz, 1H), 6.74 (s, 1H), 6.52 (dd, J=3.5, 1.8 Hz, 1H), 4.90 (br. s., 2H), 4.34 (d, J=13.1 Hz, 2H), 3.33 (dd, J=13.1, 4.5 Hz, 2H), 2.93-3.08 (m, 1H), 1.59 (d, J=7.0 Hz, 6H), 1.31 (d, J=6.8 Hz, 6H). LC-MS: m/z 447.0 (M+H)$^+$.

6-cyclohexyl-2-(4-(furan-2-carbonyl)piperazin-1-yl)-4-phenylnicotinonitrile (Compound 137)

Compound 137 was synthesized using benzaldehyde and 1-cyclohexylethanone as starting materials.

$^1$H NMR (CHLOROFORM-d) δ 7.46-7.61 (m, 6H), 7.08 (dd, J=3.4, 0.9 Hz, 1H), 6.78 (s, 1H), 6.53 (dd, J=3.4, 1.9 Hz, 1H), 4.03 (br. s., 4H), 3.76-3.86 (m, 4H), 2.66 (tt, J=11.6, 3.3 Hz, 1H), 1.92-2.00 (m, 2H), 1.83-1.91 (m, 2H), 1.74-1.82 (m, 1H), 1.55 (qd, J=12.3, 2.8 Hz, 2H), 1.41 (qt, J=12.6, 3.1 Hz, 2H), 1.25-1.35 (m, 1H). LC-MS: m/z 441.0 (M+H)$^+$.

6-cyclohexyl-2-(4-(furan-3-carbonyl)-3-methylpiperazin-1-yl)-4-phenylnicotinonitrile (Compound 138)

Compound 138 was synthesized using benzaldehyde and 1-cyclohexylethanone as starting materials.

$^1$H NMR (CHLOROFORM-d) δ 7.77 (s, 1H), 7.43-7.61 (m, 6H), 6.77 (s, 1H), 6.61 (s, 1H), 4.76 (br. s., 1H), 4.29 (d, J=12.3 Hz, 2H), 4.20 (d, J=13.1 Hz, 1H), 3.56 (br. s., 1H), 3.33 (dd, J=13.2, 3.1 Hz, 1H), 3.16 (td, J=12.5, 3.1 Hz, 1H), 2.56-2.72 (m, 1H), 1.95 (d, J=12.5 Hz, 2H), 1.87 (d, J=12.8 Hz, 2H), 1.78 (d, J=12.8 Hz, 1H), 1.49-1.60 (m, 2H), 1.46 (d, J=6.5 Hz, 3H), 1.35-1.44 (m, 2H), 1.25-1.34 (m, 1H). LC-MS: m/z 455.1 (M+H)$^+$.

6-cyclohexyl-2-((3S,5R)-4-(furan-3-carbonyl)-3,5-dimethylpiperazin-1-yl)-4-phenylnicotinonitrile (Compound 142)

Compound 142 was synthesized using benzaldehyde and 1-cyclohexylethanone as starting materials.

$^1$H NMR (CHLOROFORM-d) δ 7.77 (s, 1H), 7.54-7.58 (m, 2H), 7.49-7.53 (m, 3H), 7.48 (t, J=1.6 Hz, 1H), 6.79 (s, 1H), 6.65 (d, J=2.0 Hz, 1H), 4.73 (br. s., 2H), 4.27 (d, J=13.1 Hz, 2H), 3.25 (dd, J=13.1, 4.5 Hz, 2H), 2.66 (tt, J=11.6, 3.4 Hz, 1H), 1.95 (d, J=12.5 Hz, 2H), 1.84-1.92 (m, 2H), 1.78 (d, J=12.5 Hz, 1H), 1.57 (d, J=7.0 Hz, 6H), 1.49-1.54 (m, 2H), 1.38-1.47 (m, 2H), 1.31-1.37 (m, 1H). LC-MS: m/z 469.1 (M+H)$^+$.

6-isopropyl-4-(2-methoxyphenyl)-2-(4-(2-phenylacetyl)piperazin-1-yl)nicotinonitrile (Compound 146)

Compound 146 was synthesized using 2-methoxybenzaldehyde and 3-methylbutan-2-one as starting materials.

¹H NMR (CHLOROFORM-d) δ 7.42-7.48 (m, 1H), 7.28-7.40 (m, 5H), 7.23 (dd, J=7.5, 1.8 Hz, 1H), 7.01-7.10 (m, 2H), 6.73 (s, 1H), 3.83-3.90 (m, 5H), 3.82 (s, 2H), 3.62-3.70 (m, 4H), 3.49-3.56 (m, 2H), 2.91-3.03 (m, 1H), 1.29 (d, J=6.8 Hz, 6H). LC-MS: m/z 455.2 (M+H)⁺.

2-(4-(furan-2-carbonyl)-3-methylpiperazin-1-yl)-6-isopropyl-4-(2-methoxyphenyl)nicotinonitrile (Compound 147)

Compound 147 was synthesized using 2-methoxybenzaldehyde and 3-methylbutan-2-one as starting materials.
¹H NMR (CHLOROFORM-d) δ 7.52 (dd, J=1.8, 0.8 Hz, 1H), 7.41-7.48 (m, 1H), 7.25 (dd, J=7.5, 1.8 Hz, 1H), 7.00-7.16 (m, 3H), 6.73 (s, 1H), 6.52 (dd, J=3.5, 1.8 Hz, 1H), 4.91 (br. s., 1H), 4.51 (d, J=12.3 Hz, 1H), 4.32 (d, J=12.5 Hz, 1H), 4.22 (dt, J=13.2, 2.0 Hz, 1H), 3.88 (s, 3H), 3.62 (br. s., 1H), 3.39 (dd, J=13.2, 3.6 Hz, 1H), 3.22 (td, J=12.4, 3.5 Hz, 1H), 3.00 (dt, J=13.7, 6.8 Hz, 1H), 1.49 (d, J=6.8 Hz, 3H), 1.30 (d, J=6.8 Hz, 6H). LC-MS: m/z 455.1 (M+H)⁺.

(R)-2-(4-(furan-3-carbonyl)-3-methylpiperazin-1-yl)-6-isopropyl-4-(2-methoxyphenyl)nicotinonitrile (Compound 118)

Compound 148 was synthesized using 2-methoxybenzaldehyde and 3-methylbutan-2-one as starting materials.
¹H NMR (CHLOROFORM-d) δ 7.76 (dd, J=1.5, 0.8 Hz, 1H), 7.40-7.51 (m, 2H), 7.22-7.28 (m, 1H), 7.01-7.11 (m, 2H), 6.70-6.76 (m, 1H), 6.61 (dd, J=1.8, 0.8 Hz, 1H), 4.75 (br. s., 1H), 4.16-4.45 (m, 3H), 3.88 (s, 3H), 3.55 (br. s., 1H), 3.31 (dd, J=12.9, 3.4 Hz, 1H), 3.14 (td, J=12.5, 3.4 Hz, 1H), 3.00 (dt, J=13.7, 6.8 Hz, 1H), 1.46 (d, J=7.0 Hz, 3H), 1.30 (d, J=6.8 Hz, 6H). LC-MS: m/z 445.2 (M+H)⁺.

6-isopropyl-1-(2-methoxyphenyl)-2-(3-methyl-4-(2-phenylacetyl)piperazin-1-yl)nicotinonitrile (Compound 149)

Compound 149 was synthesized using 3-methoxybenzaldehyde and 3-methylbutan-2-one as starting materials.
¹H NMR (CHLOROFORM-d) δ 7.41-7.49 (m, 1H), 7.29-7.40 (m, 4H), 7.20-7.28 (m, 2H), 7.01-7.09 (m, 2H), 6.71 (s, 1H), 4.97 (br. s., 1H), 4.60 (d, J=13.3 Hz, 1H), 4.25 (br. s., 1H), 4.16 (d, J=13.3 Hz, 1H), 3.87 (s, 3H), 3.64-3.81 (m, 2H), 3.53 (t, J=11.4 Hz, 1H), 3.14-3.29 (m, 1H), 2.85-3.14 (m, 2H), 1.62 (s, 3H), 1.29 (s, 6H). LC-MS: m/z 469.1 (M+H)⁺.

(R)-2-(4-(furan-3-carbonyl)-3-methylpiperazin-1-yl)-6-isopropyl-4-(3-methoxyphenyl)nicotinonitrile (Compound 151)

Compound 151 was synthesized using 3-methoxybenzaldehyde and 3-methylbutan-2-one as starting materials.
¹H NMR (CHLOROFORM-d) δ 7.76 (dd, J=1.5, 0.8 Hz, 1H), 7.38-7.50 (m, 2H), 7.00-7.17 (m, 3H), 6.76-6.81 (m, 1H), 6.61 (dd, J=1.9, 0.9 Hz, 1H), 4.76 (br. s., 1H), 4.29 (d, J=12.8 Hz, 2H), 4.21 (d, J=13.1 Hz, 1H), 3.84-3.92 (m, 3H), 3.56 (br. s., 1H), 3.33 (dd, J=13.2, 3.6 Hz, 1H), 3.17 (td, J=12.5, 3.4 Hz, 1H), 3.00 (dt, J=13.7, 6.8 Hz, 1H), 1.47 (d, J=6.8 Hz, 3H), 1.30 (d, J=7.0 Hz, 6H). LC-MS: m/z 445.1 (M+H)⁺.

(R)-2-(4-(furan-3-carbonyl)-3-methylpiperazin-1-yl)-4-(3-hydroxyphenyl)-6-isopropylnicotinonitrile (Compound 152)

Compound 152 was synthesized using 3-hydroxybenzaldehyde and 3-methylbutan-2-one as starting materials.

¹H NMR (CHLOROFORM-d) δ 7.74-7.81 (m, 1H), 7.41-7.51 (m, 1H), 7.34 (t, J=7.9 Hz, 1H), 7.11 (s, 1H), 7.05 (d, J=7.5 Hz, 1H), 6.97 (dd, J=8.2, 2.4 Hz, 1H), 6.79 (s, 1H), 6.57-6.64 (m, 1H), 4.79 (br. s., 1H), 4.15-4.44 (m, 3H), 3.59 (br. s., 1H), 3.34 (d, J=10.5 Hz, 1H), 3.17 (td, J=12.5, 3.1 Hz, 1H), 2.93-3.04 (m, 1H), 1.47 (d, J=6.8 Hz, 3H), 1.27-1.31 (m, 6H).
LC-MS: m/z 431.2 (M+H)⁺.

2-(4-(furan-3-carbonyl)-3-phenylpiperazin-1-yl)-6-isopropyl-4-phenylnicotinonitrile (Compound 151)

¹H NMR (CHLOROFORM-d) δ 7.61 (br. s., 1H), 7.50-7.54 (m, 2H), 7.46-7.50 (m, 3H), 7.37-7.43 (m, 3H), 7.34 (t, J=7.7 Hz, 2H), 7.22-7.27 (m, 1H), 6.67 (s, 1H), 6.52 (br. s., 1H), 5.75 (br. s., 1H), 4.57 (br. s., 2H), 4.29 (d, J=11.5 Hz, 1H), 4.00 (d, J=11.0 Hz, 1H), 3.60-3.74 (m, 1H), 3.55 (d, J=10.5 Hz, 1H), 2.94 (dt, J=13.6, 6.8 Hz, 1H), 1.25-1.27 (m, 3H), 1.23 (d, J=7.0 Hz, 3H). LC-MS: m/z 477.1 (M+H)⁺.

2-(4-(furan-2-carbonyl)-3-phenylpiperazin-1-yl)-6-isopropyl-4-phenylnicotinonitrile (Compound 155)

¹H NMR (CHLOROFORM-d) δ 7.51-7.55 (m, 2H), 7.46-7.50 (m, 4H), 7.45 (d, J=7.5 Hz, 2H), 7.33 (t, J=7.5 Hz, 2H), 7.20-7.25 (m, 1H), 6.92-7.07 (m, 1H), 6.68 (s, 1H), 6.45 (br. s., 1H), 5.95 (t, J=4.5 Hz, 1H), 4.63 (s, 1H), 4.66 (s, 1H), 4.33 (d, J=11.0 Hz, 1H), 4.06 (dd, J=13.6, 4.0 Hz, 1H), 3.69 (br. s., 1H), 3.56-3.65 (m, 1H), 2.97 (dt, J=13.7, 6.8 Hz, 1H), 1.24-1.28 (m, 6H). LC-MS: m/z 477.1 (M+H)⁺.

(R)-1-(3-fluorophenyl)-2-(4-(furan-3-carbonyl)-3-methylpiperazin-1-yl)-6-isopropylnicotinonitrile (Compound 156)

Compound 156 was synthesized using 3-fluorobenzaldehyde and 3-methylbutan-2-one as starting materials.
¹H NMR (CHLOROFORM-d) δ 7.77 (dd, J=1.5, 1.0 Hz, 1H), 7.43-7.53 (m, 2H), 7.35 (dq, J=7.7, 0.9 Hz, 1H), 7.12-7.28 (m, 2H), 6.67-6.80 (m, 1H), 6.61 (dd, J=1.9, 0.9 Hz, 1H), 4.76 (br. s., 1H), 4.17-4.45 (m, 3H), 3.56 (br. s., 1H), 3.36 (dd, J=13.1, 3.5 Hz, 1H), 3.18 (td, J=12.5, 3.5 Hz, 1H), 2.95-3.07 (m, 1H), 1.46 (d, J=6.8 Hz, 3H), 1.29-1.32 (m, 6H). LC-MS: m/z 433.1 (M+H)⁺.

(R)-2-(4-(furan-3-carbonyl)-3-methylpiperazin-1-yl)-4-(2-hydroxyphenyl)-6-isopropylnicotinonitrile (Compound 157)

Compound 157 was synthesized using 2-hydroxybenzaldehyde and 3-methylbutan-2-one as starting materials.
¹H NMR (CHLOROFORM-d) δ 8.01 (dd, J=8.2, 1.4 Hz, 1H), 7.73-7.77 (m, 1H), 7.50-7.60 (m, 1H), 7.46 (t, J=1.6 Hz, 1H), 7.31-7.37 (m, 2H), 7.21 (s, 1H), 6.60 (dd, J=1.6, 0.6 Hz, 1H), 4.71 (br. s., 1H), 4.25 (br. s., 1H), 4.07 (d, J=13.3 Hz, 1H), 3.98 (d, J=13.8 Hz, 1H), 3.71 (br. s., 1H), 3.45-3.56 (m, 1H), 3.15-3.26 (m, 1H), 3.06 (dt, J=13.7, 6.8 Hz, 1H), 1.32-1.37 (m, 9H). LC-MS: m/z 432.2 (M+H)⁺.

(R)-2-(4-(furan-3-carbonyl)-3-methylpiperazin-1-yl)-6-isopropyl-1-o-tolylnicotinonitrile (Compound 158)

Compound 158 was synthesized using 2-methylbenzaldehyde and 3-methylbutan-2-one as starting materials.
¹H NMR (CHLOROFORM-d) δ 7.72-7.79 (m, 1H), 7.47 (t, J=1.6 Hz, 1H), 7.29-7.40 (m, 3H), 7.19 (d, J=6.8 Hz, 1H), 6.65 (s, 1H), 6.60 (dd, J=1.9, 0.9 Hz, 1H), 4.75 (br. s., 1H), 4.17-4.46 (m, 3H), 3.42-3.67 (m, 1H), 3.34 (dd, J=13.1, 3.5 Hz, 1H), 3.16 (td, J=12.5, 3.5 Hz, 1H), 2.92-3.03 (m, 1H), 2.24 (s, 3H), 1.45 (d, J=6.3 Hz, 3H), 1.30 (d, J=6.8 Hz, 6H). LC-MS: m/z 429.1 (M+H)+.

2-(4-(furan-3-carbonyl)-2-phenylpiperazin-1-yl)-6-isopropyl-4-phenylnicotinonitrile (Compound 160)

¹H NMR (CHLOROFORM-d) δ 7.69 (br. s., 1H), 7.64 (s, 1H), 7.45 (br. s., 2H), 7.36-7.44 (m, 4H), 7.31 (br. s., 2H), 7.16-7.26 (m, 3H), 6.57 (br. s., 1H), 5.37 (br. s., 1H), 4.15 (d, J=9.8 Hz, 2H), 3.96 (d, J=8.8 Hz, 4H), 2.98-3.12 (m, 1H), 1.13 (d, J=6.8 Hz, 6H). LC-MS: m/z 477.2 (M+H)+.

(R)-2-(3-cyano-2-(4-(furan-3-carbonyl)-3-methyl-piperazin-1-yl)-6-isopropylpyridin-4-yl)phenylacetate (Compound 162)

Compound 162 was synthesized from (R)-2-(4-(furan-3-carbonyl)-3-methylpiperazin-1-yl)-4-(2-hydroxyphenyl)-6-isopropylnicotinonitrile (Compound 157) by reaction with acetyl chloride.

¹H NMR (METHANOL-d₄) δ 7.76 (s, 1H), 7.39-7.58 (m, 3H), 7.31 (t, J=1.9 Hz, 1H), 7.24 (dd, J=7.7, 1.9 Hz, 1H), 6.78 (s, 1H), 6.61 (d, J=1.3 Hz, 1H), 4.76 (br. s., 1H), 4.17-4.44 (m, 3H), 3.56 (br. s., 1H), 3.34 (dd, J=12.9, 3.4 Hz, 1H), 3.17 (td, J=12.5, 3.5 Hz, 1H), 2.93-3.06 (m, 1H), 2.27-2.43 (m, 3H), 1.46 (d, J=6.8 Hz, 3H), 1.30 (d, J=7.0 Hz, 6H). LC-MS: m/z 473.1 (M+H)+.

(R)-4-(2-ethoxyphenyl)-2-(4-(furan-3-carbonyl)-3-methylpiperazin-1-yl)-6-isopropylnicotinonitrile (Compound 163)

Compound 163 was synthesized from (R)-2-(4-(furan-3-carbonyl)-3-methylpiperazin-1-yl)-4-(2-hydroxyphenyl)-6-isopropylnicotinonitrile (Compound 157) by treatment with NaH/DMF followed by ethyl bromide quench.

¹H NMR (METHANOL-d₄) δ 7.76 (s, 1H), 7.37-7.51 (m, 2H), 6.98-7.16 (m, 3H), 6.79 (s, 1H), 6.57-6.64 (m, 1H), 4.76 (br. s., 1H), 4.17-4.45 (m, 3H), 4.12 (q, J=7.0 Hz, 2H), 3.56 (br. s., 1H), 3.34 (dd, J=12.9, 3.6 Hz, 1H), 3.17 (td, J=12.4, 3.3 Hz, 1H), 3.00 (quin, J=6.9 Hz, 1H), 1.47 (dt, J=6.8, 3.5 Hz, 6H), 1.30 (d, J=6.8 Hz, 6H). LC-MS: m/z 459.1 (M+H)+.

2-(4-(furan-2-carbonyl)-2-phenylpiperazin-1-yl)-6-isopropyl-4-phenylnicotinonitrile (Compound 167)

¹H NMR (CHLOROFORM-d) δ 7.64 (s, 1H), 7.52 (s, 1H), 7.36-7.48 (m, 5H), 7.31 (br. s., 2H), 7.22 (d, J=6.5 Hz, 3H), 7.07 (d, J=3.0 Hz, 1H), 6.52 (br. s., 1H), 5.37-5.59 (br. s., 1H), 4.17 (br. s., 3H), 3.98 (br. s., 2H), 3.92 (br. s., 1H), 3.00-3.12 (m, 1H), 1.13 (d, J=6.5 Hz, 3H), 0.79 (br. s., 3H). LC-MS: m/z 477.1 (M+H)+.

2-(4-(1H-indole-3-carbonyl)-2-phenylpiperazin-1-yl)-6-isopropyl-4-phenylnicotinonitrile (Compound 169)

¹H NMR (CHLOROFORM-d) δ 9.00 (br. s., 1H), 7.71 (d, J=6.3 Hz, 1H), 7.64 (s, 1H), 7.42 (d, J=7.3 Hz, 6H), 7.24-7.34 (m, 4H), 7.22 (d, J=6.3 Hz, 4H), 5.53 (br. s., 1H), 4.13-4.35 (m, 2H), 4.01 (br. s., 2H), 3.76-3.96 (m, 2H), 3.00-3.13 (m, 1H), 1.14 (d, J=6.5 Hz, 3H), 0.80 (d, J=6.5 Hz, 3H). LC-MS: m/z 526.1 (M+H)+.

Example 11. Preparation of (R)-methyl 5-(4-fluorophenyl)-6-isopropyl-2-(4-(3-methoxypropanoyl)-3-methylpiperazin-1-yl)nicotinate (Compound 244)

Compound 244 was prepared according to Scheme 8.

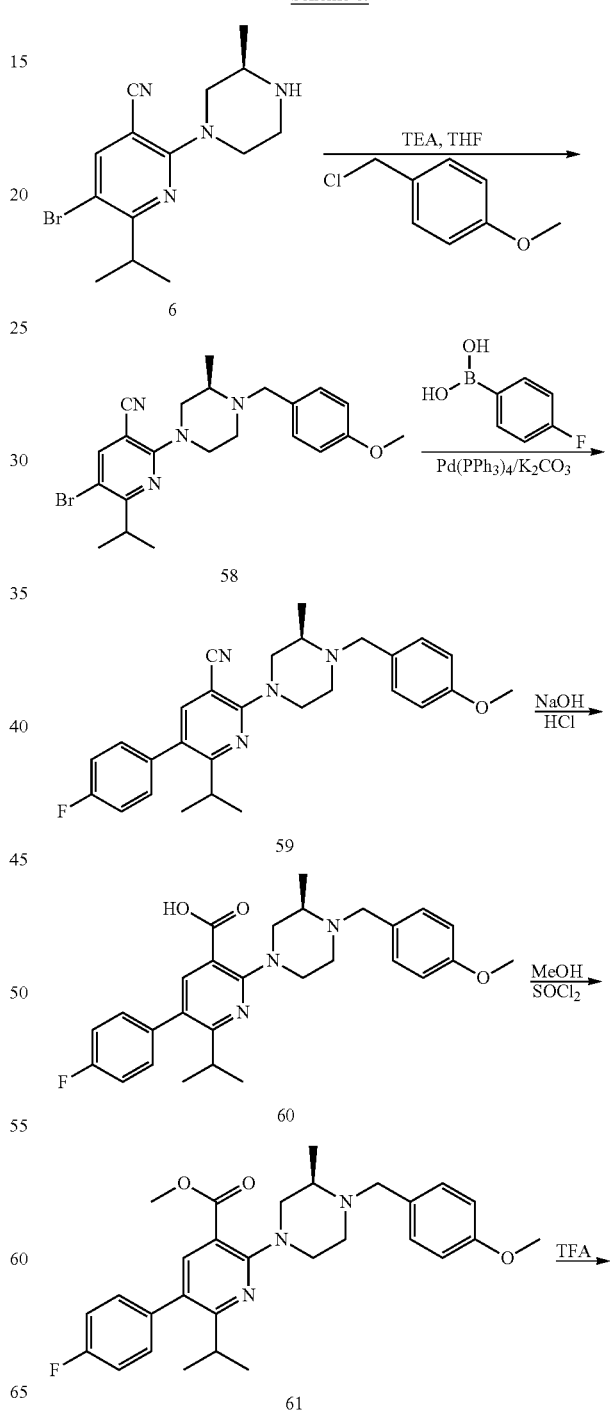

Scheme 8.

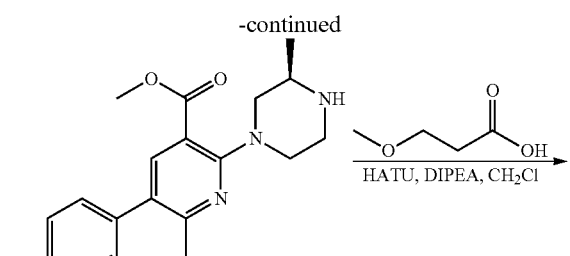

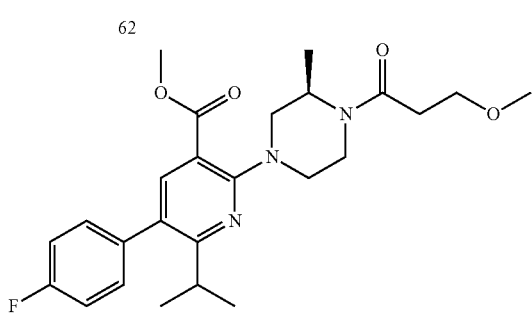

Compound 244

Step 1: (R)-5-bromo-6-isopropyl-2-(4-(4-methoxy-benzyl)-3-methylpiperazin-1-yl)nicotinonitrile (58)

To a solution of (R)-5-bromo-6-isopropyl-2-(3-methyl-piperazin-1-yl)nicotinonitrile (6; Example 1; 1 g, 3.10 mmol) and triethylamine (375 mg, 3.72 mmol) in 20 mL THF was added 1-(chloromethyl)-4-methoxybenzene (485 mg, 3.10 mmol) dropwise at 0° C. The reaction mixture was stirred at 0° C. for 4 hrs before warmed up to room temperature and quenched by adding 20 mL of water. Solvent was removed under reduced pressure and the residue was extracted with EtOAc (3×20 mL). The combined organic layer was then washed with brine, dried over anhy. $Na_2SO_4$ and concentrated in vacuo. Flash column chromatography separation (20% EtOAc/petroleum ether) then afforded 1.3 g of 58 as thick brown oil. MS (ES) M+H expected 443.1. found 443.2

Step 2: (R)-5-(4-fluorophenyl)-6-isopropyl-2-(4-(4-methoxybenzyl)-3-methylpiperazin-1-yl)nicotinonitrile (59)

To a solution of (R)-5-bromo-6-isopropyl-2-(4-(4-methoxybenzyl)-3-methylpiperazin-1-yl)-nicotinonitrile (58; 1 g, 2.18 mmol) and 4-fluorophenylboronic acid (610 mg, 4.36 mmol) in 5 mL of DMF was added $Pd(PPh_3)_4$ (340 mg 0.218 mmol) and $K_2CO_3$ (360 mg, 2.62 mmol) under nitrogen protection. The reaction was subjected to microwave reaction at 150° C. for 1 hour. After dilution with 20 mL of water, the mixture was extracted with EtOAc (3×20 mL). The combined organic layer was washed with brine, dried over anhy. $Na_2SO_4$ and concentrated in vacuo. Flash column chromatography separation (20% EtOAc/petroleum ether) then afforded 600 mg of 59 as thick brown oil. MS (ES) M+H expected 459.3. found 459.2.

Step 3: (R)-5-(4-fluorophenyl)-6-isopropyl-2-(4-(4-methoxybenzyl)-3-methylpiperazin-1-yl)nicotinic acid (60)

To a solution of (R)-5-(4-fluorophenyl)-6-isopropyl-2-(4-(4-methoxybenzyl)-3-methyl-piperazin-1-yl)nicotinonitrile (600 mg, 1.31 mmol) in 20 mL of ethanol was added 20 mL 50% aq. NaOH solution. The reaction mixture was heated to 120° C. overnight, and then acidified with 2N aq. HCl to pH<6. Ethanol was removed under reduced pressure and the residue was washed with water several times and filtered. After air-drying, 500 mg of crude title compound was obtained as a yellowish solid. MS (ES) M+H expected 478.2. found 478.2.

Step 4: (R)-methyl-5-(4-fluorophenyl)-6-isopropyl-2-(4-(4-methoxybenzyl)-3-methylpiperazin-1-yl) nicotinate (61)

To a 25 mL of round-bottom flask was charged with 10 mL of methanol. After cooling at 0° C., 1 mL of thionyl chloride was added dropwise and the solution was stirred at room temperature for 30 min, before adding (R)-5-(4-fluorophenyl)-6-isopropyl-2-(4-(4-methoxybenzyl)-3-methyl-piperazin-1-yl)nicotinic acid (500 mg, 1.05 mmol) slowly. The resulting mixture was then heated to reflux temperature for 2 hrs. After removing the volatile under reduced pressure, 500 mg of crude title compound was obtained and used without further purification. MS (ES) M+H expected 492.3. found 492.2.

Step 5: (R)-methyl 5-(4-fluorophenyl)-6-isopropyl-2-(3-methylpiperazin-1-yl)nicotinate (62)

(R)-methyl-5-(4-fluorophenyl)-6-isopropyl-2-(4-(4-methoxybenzyl)-3-methylpiperazin-1-yl)nicotinate (61; 500 mg, 1.02 mmol) was dissolved in 15 mL of 2,2,2-trifluoroacetic acid. The mixture was heated to reflux overnight. After removal of excess of TFA under reduced pressure, the residue was re-dissolved in methylene chloride and washed with satd. $NaHCO_3$, brine. The organic layer was then dried over anhy. $Na_2SO_4$, and concentrated in vacuo. 300 mg of title compound was obtained as yellowish oil and used subsequently without further purification. MS (ES) M+H expected 372.2. found 372.2.

Step 6 (R)-methyl 5-(4-fluorophenyl)-6-isopropyl-2-(4-(3-methoxypropanoyl)-3-methylpiperazin-1-yl) nicotinate (Compound 244)

1H NMR (CHLOROFORM-d) δ 7.84 (s, 1H), 7.20-7.25 (m, 2H), 7.06-7.15 (m, 2H), 4.86 (br. s., 0.5H), 4.43 (d, J=12.5 Hz, 0.5H), 4.21 (d, J=6.0 Hz, 0.5H), 3.92 (d, J=13.1 Hz, 0.5H), 3.87 (s, 3H), 3.81 (d, J=16.3 Hz, 1H), 3.74 (t, J=6.7 Hz, 3H), 3.64 (br. s., 1H), 3.37 (s, 3H), 3.18-3.34 (m, 1H), 2.96-3.15 (m, 2H), 2.64-2.80 (m, 1H), 2.60 (br. s., 1H), 1.34-1.40 (m, 1.5H), 1.29-1.32 (m, 1.5H), 1.17 (d, J=6.8 Hz, 3H), 1.12 (d, J=6.5 Hz, 3H). LC-MS: m/z 458.2 (M+H)$^+$.

Example 12. Assays for IDH1 R132H Inhibitors

Assays were conducted in a volume of 76 μl assay buffer (150 mM NaCl, 10 mM $MgCl_2$, 20 mM Tris pH 7.5, 0.03% bovine serum albumin) as follows in a standard 384-well plate: To 25 ul of substrate mix (8 uM NADPH, 2 mM aKG), 1 μl of test compound was added in DMSO. The plate was centrifuged briefly, and then 25 μl of enzyme mix was added (0.2 μg/ml IDH1 R132H) followed by a brief centrifugation and shake at 100 RPM. The reaction was incubated for 50 minutes at room temperature, then 25 μl of detection mix (30 μM resazurin, 36 μg/ml) was added and the mixture further incubated for 5 minutes at room temperature. The conversion of resazurin to resorufin was detected by fluorescent spectroscopy at Ex544 Em590 c/o 590.

Certain of the compounds of Formula I set forth in Tables 1 and 5 were tested in this assay and the results set forth below in Table 3. As used in Table 3, "A" refers to an inhibitory activity against IDH1 R132H with an $IC_{50} \leq 1.0$ μM; "B" refers to an inhibitory activity against IDH1 R132H with an $IC_{50}$ greater than 1 μM and $\leq 5$ μM; "C" refers to an inhibitory activity against IDH1 R132H with an $IC_{50}$ greater than 5 μM and $\leq 15$ μM.

TABLE 3

IDH1 R132H Inhibition by Compounds of Formula I.

| Cmpd No. | $IC_{50}$ |
|---|---|
| 100 | C |
| 101 | B |
| 102 | B |
| 103 | C |
| 104 | C |
| 105 | B |
| 106 | C |
| 107 | B |
| 108 | C |
| 109 | C |
| 110 | B |
| 111 | C |
| 113 | C |
| 114 | B |
| 115 | B |
| 116 | C |
| 117 | C |
| 118 | C |
| 119 | C |
| 120 | B |
| 121 | C |
| 122 | C |
| 123 | C |
| 124 | C |
| 125 | C |
| 126 | B |
| 127 | C |
| 128 | B |
| 129 | C |
| 130 | B |
| 131 | B |
| 132 | B |
| 133 | B |
| 134 | B |
| 135 | B |
| 136 | C |
| 137 | C |
| 138 | B |
| 139 | B |
| 140 | B |
| 141 | C |
| 142 | B |
| 143 | B |
| 144 | B |
| 145 | B |
| 146 | C |
| 147 | C |
| 148 | B |
| 149 | B |
| 150 | B |
| 151 | B |
| 152 | B |
| 153 | C |
| 154 | C |
| 155 | C |
| 156 | B |
| 157 | C |
| 158 | B |
| 159 | C |
| 160 | C |
| 161 | B |
| 162 | B |
| 163 | B |
| 164 | B |
| 165 | B |
| 166 | C |
| 167 | B |

TABLE 3-continued

IDH1 R132H Inhibition by Compounds of Formula I.

| Cmpd No. | $IC_{50}$ |
|---|---|
| 168 | B |
| 169 | B |
| 170 | B |
| 171 | B |
| 172 | C |
| 173 | B |
| 174 | B |
| 175 | B |
| 176 | B |
| 177 | B |
| 178 | B |
| 179 | B |
| 180 | B |
| 181 | B |
| 182 | A |
| 183 | B |
| 184 | B |
| 185 | B |
| 187 | A |
| 188 | B |
| 189 | B |
| 190 | C |
| 191 | A |
| 192 | B |
| 193 | B |
| 195 | B |
| 196 | B |
| 197 | B |
| 198 | B |
| 199 | B |
| 200 | B |
| 201 | B |
| 202 | B |
| 203 | B |
| 204 | B |
| 205 | B |
| 206 | B |
| 207 | A |
| 208 | B |
| 209 | B |
| 210 | C |
| 211 | B |
| 212 | A |
| 213 | B |
| 214 | B |
| 215 | B |
| 216 | B |
| 217 | B |
| 218 | B |
| 219 | A |
| 220 | B |
| 221 | B |
| 222 | A |
| 223 | A |
| 224 | A |
| 225 | A |
| 226 | A |
| 227 | A |
| 228 | B |
| 229 | A |
| 230 | B |
| 231 | B |
| 232 | B |
| 233 | B |
| 234 | A |
| 235 | A |
| 236 | A |
| 237 | B |
| 238 | B |
| 239 | B |
| 240 | B |
| 241 | A |
| 242 | A |
| 243 | A |
| 244 | B |
| 245 | B |

TABLE 3-continued

IDH1 R132H Inhibition by Compounds of Formula I.

| Cmpd No. | $IC_{50}$ |
|---|---|
| 246 | A |
| 247 | B |
| 248 | A |
| 249 | A |
| 250 | A |
| 251 | A |
| 252 | A |
| 253 | A |
| 254 | B |
| 255 | A |
| 256 | A |
| 257 | A |
| 258 | A |
| 259 | A |
| 260 | A |
| 261 | A |
| 262 | A |

Certain of the compounds of Formula I set forth in Table 5 were tested in this assay and the assay in Example 13 and the results set forth below in Table 4. As used in Table 4, "A1" refers to an inhibitory activity against IDH1 R132H with an $IC_{50} \leq 0.5$ μM or an $IC_{50}$ for inhibition of 2-HG production $\leq 0.5$ μM; "B1" refers to an inhibitory activity against IDH1 R132H with an $IC_{50}$ greater than 0.5 μM and $\leq 1$ μM or an $IC_{50}$ for inhibition of 2-HG production greater than 0.5 μM and $\leq 1$ μM; "C1" refers to an inhibitory activity against IDH1 R132H with an $IC_{50}$ greater than 1 μM and $\leq 10$ μM or an $IC_{50}$ for inhibition of 2-HG production greater than 1 μM and $\leq 10$ μM; and "D1" refers to an inhibitory activity against IDH1 R132H with an $IC_{50}$ greater than 10 μM or an $IC_{50}$ for inhibition of 2-HG production greater than 10 μM.

TABLE 4

| Cmpd No. | IDH1R132H IC50 (μM) | HT1080 IC50 (μM) | U87R132H IC50 (μM) |
|---|---|---|---|
| 263 | A1 | B1 | C1 |
| 264 | B1 | C1 | C1 |
| 265 | A1 | C1 | C1 |
| 266 | A1 | C1 | C1 |
| 267 | B1 | C1 | C1 |
| 268 | B1 | C1 | C1 |
| 269 | A1 | C1 | C1 |
| 270 | B1 | C1 | C1 |
| 271 | A1 | C1 | C1 |
| 272 | B1 | C1 | C1 |
| 273 | B1 | | |
| 274 | B1 | C1 | C1 |
| 275 | A1 | C1 | C1 |
| 276 | A1 | C1 | C1 |
| 277 | A1 | C1 | C1 |
| 278 | B1 | C1 | C1 |
| 279 | B1 | C1 | C1 |
| 280 | A1 | C1 | C1 |
| 281 | B1 | | |
| 282 | B1 | | |
| 283 | A1 | B1 | C1 |
| 284 | B1 | | |
| 285 | A1 | B1 | C1 |
| 286 | A1 | A1 | A1 |
| 287 | A1 | C1 | C1 |
| 288 | A1 | A1 | A1 |
| 289 | A1 | | |
| 290 | A1 | | |
| 291 | B1 | | |
| 292 | A1 | B1 | C1 |
| 293 | A1 | C1 | C1 |
| 294 | A1 | B1 | B1 |
| 295 | A1 | B1 | B1 |
| 296 | A1 | B1 | B1 |
| 297 | A1 | B1 | C1 |
| 298 | B1 | | |
| 299 | A1 | B1 | B1 |
| 300 | B1 | | |
| 301 | A1 | C1 | C1 |
| 302 | A1 | C1 | C1 |
| 303 | A1 | C1 | C1 |
| 304 | A1 | C1 | B1 |
| 305 | B1 | | |
| 306 | B1 | | |
| 307 | A1 | C1 | C1 |
| 308 | A1 | C1 | C1 |
| 309 | A1 | B1 | B1 |
| 310 | B1 | | |
| 311 | B1 | | |
| 312 | A1 | B1 | C1 |
| 313 | A1 | C1 | B1 |
| 314 | B1 | | |
| 315 | A1 | A1 | B1 |
| 316 | B1 | | |
| 317 | B1 | | |
| 318 | A1 | | |
| 319 | A1 | | |
| 320 | A1 | B1 | A1 |
| 321 | A1 | B1 | A1 |
| 322 | A1 | | |
| 323 | A1 | B1 | B1 |
| 324 | B1 | | |
| 325 | A1 | A1 | A1 |
| 326 | A1 | B1 | A1 |
| 327 | B1 | | |
| 328 | A1 | | |
| 329 | B1 | | |
| 330 | A1 | A1 | A1 |
| 331 | A1 | | |
| 332 | B1 | | |
| 333 | A1 | | |
| 334 | B1 | | |
| 335 | A1 | B1 | A1 |
| 336 | B1 | | |
| 337 | B1 | | |
| 338 | A1 | | |
| 339 | B1 | | |
| 340 | A1 | B1 | B1 |
| 341 | A1 | | |
| 342 | A1 | A1 | A1 |
| 343 | A1 | A1 | A1 |
| 344 | B1 | | |
| 345 | A1 | C1 | B1 |
| 346 | A1 | C1 | B1 |
| 347 | A1 | A1 | A1 |
| 348 | A1 | | |
| 349 | B1 | | |
| 350 | A1 | C1 | B1 |
| 351 | A1 | C1 | B1 |
| 352 | A1 | C1 | B1 |
| 353 | A1 | B1 | B1 |
| 354 | B1 | | |
| 355 | B1 | | |
| 356 | A1 | C1 | C1 |
| 357 | B1 | | |
| 358 | A1 | | |
| 359 | A1 | | |
| 360 | A1 | C1 | C1 |
| 361 | A1 | C1 | B1 |
| 362 | A1 | | |
| 363 | A1 | C1 | B1 |
| 364 | A1 | B1 | A1 |
| 365 | | | |
| 366 | | | |
| 367 | | | |
| 368 | B1 | | |
| 369 | B1 | | |
| 370 | B1 | | |
| 371 | B1 | | |

TABLE 4-continued

| Cmpd No. | IDH1R132H IC50 (μM) | HT1080 IC50 (μM) | U87R132H IC50 (μM) |
|---|---|---|---|
| 372 | A1 | | |
| 373 | A1 | C1 | B1 |
| 374 | A1 | C1 | B1 |
| 375 | B1 | | |
| 376 | A1 | C1 | B1 |
| 377 | A1 | B1 | A1 |
| 378 | A1 | | |
| 379 | B1 | | |
| 380 | A1 | B1 | B1 |
| 381 | A1 | A1 | A1 |
| 382 | A1 | A1 | B1 |
| 383 | A1 | C1 | C1 |
| 384 | A1 | B1 | B1 |
| 385 | B1 | | |
| 386 | A1 | C1 | B1 |
| 387 | A1 | A1 | A1 |
| 388 | A1 | C1 | B1 |
| 389 | A1 | A1 | A1 |
| 390 | A1 | A1 | A1 |
| 391 | A1 | B1 | B1 |
| 392 | A1 | | |
| 393 | A1 | C1 | B1 |
| 394 | B1 | | |
| 395 | B1 | | |
| 396 | A1 | | |
| 397 | A1 | | |
| 398 | A1 | C1 | B1 |
| 399 | B1 | | |
| 400 | B1 | C1 | C1 |
| 401 | B1 | C1 | C1 |
| 402 | A1 | | |
| 403 | A1 | B1 | B1 |
| 404 | B1 | | |
| 405 | A1 | | |
| 406 | A1 | C1 | C1 |
| 407 | A1 | A1 | A1 |
| 408 | A1 | B1 | A1 |
| 409 | A1 | A1 | A1 |
| 410 | A1 | A1 | A1 |
| 411 | A1 | B1 | B1 |
| 412 | A1 | C1 | B1 |
| 413 | B1 | | |
| 414 | B1 | | |
| 415 | A1 | C1 | C1 |
| 416 | B1 | C1 | B1 |
| 417 | A1 | A1 | A1 |
| 418 | A1 | A1 | A1 |
| 419 | A1 | A1 | A1 |
| 420 | A1 | C1 | C1 |
| 421 | B1 | | |
| 422 | B1 | | |
| 423 | B1 | | |
| 424 | A1 | B1 | B1 |
| 425 | B1 | C1 | C1 |
| 426 | B1 | C1 | C1 |
| 427 | A1 | A1 | A1 |
| 428 | A1 | A1 | B1 |
| 429 | A1 | C1 | C1 |
| 430 | C1 | | |
| 431 | B1 | B1 | B1 |
| 432 | B1 | C1 | C1 |
| 433 | A1 | A1 | A1 |
| 434 | A1 | C1 | C1 |
| 435 | B1 | | |
| 436 | A1 | B1 | B1 |
| 437 | B1 | | |
| 438 | A1 | C1 | B1 |
| 439 | A1 | A1 | |
| 440 | A1 | | |
| 441 | B1 | | |
| 442 | A1 | A1 | A1 |
| 443 | A1 | A1 | A1 |
| 444 | A1 | A1 | A1 |
| 445 | A1 | C1 | |
| 446 | A1 | A1 | C1 |
| 447 | B1 | C1 | C1 |
| 448 | A1 | C1 | C1 |
| 449 | B1 | C1 | C1 |
| 450 | B1 | | |
| 451 | A1 | C1 | C1 |
| 452 | A1 | C1 | C1 |
| 453 | A1 | B1 | A1 |
| 454 | A1 | A1 | A1 |
| 455 | B1 | | |
| 456 | A1 | A1 | A1 |
| 457 | A1 | B1 | B1 |
| 458 | A1 | B1 | B1 |
| 459 | A1 | A1 | A1 |
| 460 | A1 | | |
| 461 | B1 | | |
| 462 | B1 | C1 | C1 |
| 463 | A1 | C1 | C1 |
| 464 | B1 | | |
| 465 | B1 | | |
| 466 | A1 | C1 | B1 |
| 467 | B1 | | |
| 468 | A1 | C1 | C1 |
| 469 | A1 | C1 | C1 |
| 470 | A1 | C1 | C1 |
| 471 | A1 | | |
| 472 | A1 | A1 | A1 |
| 473 | A1 | C1 | B1 |
| 474 | A1 | | |
| 475 | A1 | B1 | A1 |
| 476 | A1 | B1 | A1 |
| 477 | B1 | | |
| 478 | B1 | | |
| 479 | B1 | | |
| 480 | A1 | A1 | A1 |
| 481 | A1 | A1 | A1 |
| 482 | A1 | | |
| 483 | A1 | C1 | B1 |
| 484 | B1 | | |
| 485 | A1 | A1 | A1 |
| 486 | B1 | | |
| 487 | A1 | | |
| 488 | A1 | A1 | B1 |
| 489 | B1 | | |
| 490 | B1 | | |
| 491 | A1 | B1 | |
| 492 | B1 | B1 | |
| 493 | B1 | | |
| 494 | A1 | | |
| 495 | B1 | | |
| 496 | B1 | B1 | A1 |
| 497 | A1 | | |
| 498 | A1 | A1 | A1 |
| 499 | B1 | C1 | C1 |
| 500 | A1 | A1 | A1 |
| 501 | B1 | | |
| 502 | B1 | | |
| 503 | A1 | | |
| 504 | B1 | | |
| 505 | A1 | | |
| 506 | B1 | | |
| 507 | B1 | | |
| 508 | A1 | A1 | A1 |
| 509 | B1 | | |
| 510 | B1 | | |
| 511 | A1 | B1 | |
| 512 | A1 | | |
| 513 | B1 | | |
| 514 | A1 | A1 | |
| 515 | B1 | C1 | |
| 516 | A1 | B1 | |
| 517 | A1 | B1 | |
| 518 | A1 | A1 | A1 |
| 519 | B1 | | |
| 520 | B1 | A1 | |
| 521 | A1 | | |
| 522 | B1 | C1 | |
| 523 | B1 | | |

TABLE 4-continued

| Cmpd No. | IDH1R132H IC50 (μM) | HT1080 IC50 (μM) | U87R132H IC50 (μM) |
|---|---|---|---|
| 524 | A1 | | |
| 525 | A1 | | |
| 526 | B1 | A1 | A1 |
| 527 | A1 | A1 | A1 |
| 528 | A1 | B1 | A1 |
| 529 | A1 | B1 | |
| 530 | A1 | A1 | A1 |
| 531 | A1 | | |
| 532 | A1 | | |
| 533 | B1 | C1 | |
| 534 | A1 | | |
| 535 | A1 | A1 | |
| 536 | A1 | A1 | |
| 537 | A1 | B1 | |
| 538 | A1 | | |
| 539 | A1 | C1 | |
| 540 | A1 | | |
| 541 | A1 | A1 | A1 |
| 542 | A1 | A1 | A1 |
| 543 | B1 | | |
| 544 | A1 | B1 | |
| 545 | B1 | | |
| 546 | A1 | A1 | A1 |
| 547 | A1 | A1 | A1 |
| 548 | B1 | | |
| 549 | A1 | | |
| 550 | B1 | A1 | A1 |
| 551 | A1 | A1 | A1 |
| 552 | A1 | | |
| 553 | A1 | A1 | |
| 554 | A1 | | |
| 555 | A1 | B1 | |
| 556 | A1 | | |
| 557 | A1 | B1 | |
| 558 | A1 | A1 | A1 |
| 559 | A1 | C1 | |
| 560 | A1 | C1 | |
| 561 | A1 | A1 | A1 |
| 562 | A1 | A1 | A1 |
| 563 | A1 | A1 | |
| 564 | A1 | | |
| 565 | A1 | B1 | B1 |
| 566 | A1 | B1 | |
| 567 | B1 | | |
| 568 | A1 | A1 | A1 |
| 569 | A1 | A1 | |
| 570 | A1 | A1 | |
| 571 | A1 | A1 | |
| 572 | A1 | A1 | |
| 573 | A1 | A1 | A1 |
| 574 | A1 | A1 | |
| 575 | A1 | A1 | |
| 576 | B1 | A1 | |
| 577 | A1 | A1 | |
| 578 | A1 | A1 | |
| 579 | A1 | A1 | A1 |
| 580 | A1 | A1 | A1 |
| 581 | A1 | A1 | A1 |
| 582 | A1 | C1 | |
| 583 | B1 | | |
| 584 | B1 | | |
| 585 | A1 | A1 | A1 |
| 586 | A1 | | |
| 587 | A1 | A1 | A1 |
| 588 | A1 | A1 | |
| 589 | A1 | A1 | A1 |
| 590 | A1 | A1 | A1 |
| 591 | A1 | A1 | A1 |
| 592 | A1 | A1 | A1 |
| 593 | B1 | | |
| 594 | A1 | A1 | |
| 595 | A1 | A1 | A1 |
| 596 | A1 | A1 | |
| 597 | A1 | A1 | A1 |
| 598 | A1 | B1 | |
| 599 | A1 | A1 | A1 |
| 600 | B1 | B1 | |
| 601 | A1 | | |
| 602 | A1 | A1 | |
| 603 | A1 | A1 | A1 |
| 604 | A1 | A1 | |
| 605 | A1 | A1 | A1 |
| 606 | A1 | A1 | |
| 607 | A1 | A1 | |
| 608 | A1 | A1 | A1 |
| 609 | A1 | A1 | A1 |
| 610 | A1 | A1 | A1 |
| 611 | A1 | A1 | A1 |
| 612 | A1 | A1 | A1 |
| 613 | A1 | A1 | A1 |
| 614 | A1 | | |
| 615 | A1 | A1 | A1 |
| 616 | A1 | | |
| 617 | A1 | A1 | A1 |
| 618 | A1 | A1 | A1 |
| 619 | A1 | A1 | |
| 620 | A1 | A1 | |
| 621 | A1 | A1 | B1 |
| 622 | B1 | C1 | |
| 623 | B1 | | |
| 624 | A1 | A1 | |
| 625 | A1 | A1 | A1 |
| 626 | A1 | A1 | A1 |
| 627 | A1 | A1 | A1 |
| 628 | A1 | A1 | A1 |
| 629 | A1 | A1 | A1 |
| 630 | B1 | | |
| 631 | A1 | A1 | A1 |
| 632 | A1 | | |
| 633 | A1 | A1 | A1 |
| 634 | A1 | A1 | A1 |
| 635 | A1 | A1 | A1 |
| 636 | A1 | A1 | A1 |
| 637 | A1 | A1 | A1 |
| 638 | A1 | A1 | A1 |
| 639 | A1 | A1 | A1 |
| 640 | A1 | | |
| 641 | A1 | | |
| 642 | A1 | A1 | A1 |
| 643 | A1 | A1 | B1 |
| 644 | A1 | A1 | A1 |
| 645 | A1 | A1 | A1 |
| 646 | A1 | | |
| 647 | A1 | A1 | A1 |
| 648 | A1 | A1 | A1 |
| 649 | A1 | A1 | A1 |
| 650 | A1 | | A1 |
| 651 | A1 | | A1 |
| 652 | A1 | A1 | A1 |
| 653 | A1 | A1 | |
| 654 | A1 | A1 | A1 |
| 655 | A1 | A1 | |
| 656 | B1 | | |
| 657 | A1 | A1 | A1 |
| 658 | A1 | | A1 |
| 659 | A1 | | |
| 660 | A1 | A1 | A1 |
| 661 | A1 | | |
| 662 | A1 | A1 | |
| 663 | A1 | A1 | A1 |
| 664 | A1 | A1 | |
| 665 | A1 | | |
| 666 | A1 | A1 | A1 |
| 667 | A1 | A1 | A1 |
| 668 | A1 | B1 | |
| 669 | A1 | A1 | |
| 670 | A1 | A1 | A1 |
| 671 | A1 | | |
| 672 | B1 | C1 | |
| 673 | B1 | | |
| 674 | A1 | A1 | A1 |
| 675 | A1 | C1 | B1 |

TABLE 4-continued

| Cmpd No. | IDH1R132H IC50 (μM) | HT1080 IC50 (μM) | U87R132H IC50 (μM) |
|---|---|---|---|
| 676 | A1 | A1 | A1 |
| 677 | A1 | A1 | |
| 678 | A1 | A1 | A1 |
| 679 | A1 | A1 | |
| 680 | A1 | A1 | |
| 681 | A1 | A1 | A1 |
| 682 | A1 | | |
| 683 | A1 | | |
| 684 | A1 | A1 | |
| 685 | C1 | | |
| 686 | A1 | A1 | A1 |
| 687 | A1 | | B1 |
| 688 | A1 | A1 | A1 |
| 689 | A1 | A1 | A1 |
| 690 | A1 | A1 | A1 |
| 691 | A1 | A1 | A1 |
| 692 | A1 | A1 | A1 |
| 693 | A1 | A1 | A1 |
| 694 | A1 | B1 | A1 |
| 695 | A1 | A1 | A1 |
| 696 | A1 | A1 | A1 |
| 697 | A1 | A1 | A1 |
| 698 | A1 | A1 | A1 |
| 699 | A1 | | |
| 700 | | A1 | A1 |
| 701 | A1 | | |
| 702 | A1 | C1 | C1 |
| 703 | A1 | A1 | A1 |
| 704 | A1 | | |
| 705 | A1 | A1 | A1 |
| 706 | A1 | A1 | A1 |
| 707 | A1 | A1 | A1 |
| 708 | A1 | | C1 |
| 709 | A1 | A1 | A1 |
| 710 | A1 | A1 | A1 |
| 711 | A1 | A1 | A1 |
| 712 | A1 | C1 | |
| 713 | A1 | A1 | A1 |
| 714 | A1 | A1 | A1 |
| 715 | A1 | A1 | A1 |
| 716 | A1 | A1 | A1 |
| 717 | A1 | A1 | A1 |
| 718 | A1 | B1 | A1 |
| 719 | A1 | A1 | A1 |
| 720 | A1 | A1 | A1 |
| 721 | A1 | A1 | A1 |
| 722 | A1 | A1 | A1 |
| 723 | A1 | | |
| 724 | A1 | A1 | A1 |
| 725 | A1 | A1 | A1 |
| 726 | A1 | A1 | A1 |
| 727 | A1 | A1 | A1 |
| 728 | A1 | A1 | A1 |
| 729 | A1 | | |
| 730 | A1 | A1 | A1 |
| 731 | A1 | | |
| 732 | A1 | A1 | A1 |
| 733 | A1 | B1 | A1 |
| 734 | A1 | | |
| 735 | A1 | A1 | A1 |
| 736 | A1 | A1 | A1 |
| 737 | A1 | B1 | B1 |
| 738 | A1 | A1 | A1 |
| 739 | A1 | | |
| 740 | A1 | A1 | A1 |
| 741 | A1 | A1 | A1 |
| 742 | A1 | A1 | A1 |
| 743 | A1 | A1 | A1 |
| 744 | A1 | A1 | A1 |
| 745 | A1 | A1 | A1 |
| 746 | A1 | A1 | A1 |
| 747 | A1 | A1 | A1 |
| 748 | A1 | A1 | A1 |
| 749 | A1 | A1 | A1 |
| 750 | A1 | A1 | A1 |
| 751 | A1 | A1 | A1 |
| 752 | A1 | A1 | A1 |
| 753 | A1 | A1 | A1 |
| 754 | A1 | A1 | A1 |
| 755 | A1 | A1 | A1 |
| 756 | A1 | A1 | |
| 757 | A1 | | A1 |
| 758 | A1 | | A1 |
| 759 | A1 | | A1 |
| 760 | A1 | A1 | A1 |
| 761 | A1 | A1 | A1 |
| 762 | A1 | A1 | A1 |
| 763 | A1 | A1 | A1 |
| 764 | A1 | A1 | A1 |
| 765 | A1 | A1 | A1 |
| 766 | A1 | A1 | A1 |
| 767 | A1 | A1 | A1 |
| 768 | A1 | A1 | A1 |
| 769 | A1 | A1 | A1 |
| 770 | A1 | A1 | A1 |
| 771 | A1 | A1 | A1 |
| 772 | B1 | | |
| 773 | A1 | | A1 |
| 774 | A1 | A1 | A1 |
| 775 | A1 | A1 | A1 |
| 776 | A1 | A1 | A1 |
| 777 | A1 | A1 | A1 |
| 778 | A1 | A1 | A1 |
| 779 | C1 | | |
| 780 | A1 | | |
| 781 | A1 | A1 | A1 |
| 782 | A1 | A1 | A1 |
| 783 | | A1 | A1 |
| 784 | A1 | A1 | A1 |
| 785 | A1 | A1 | A1 |
| 786 | A1 | A1 | A1 |
| 787 | A1 | A1 | A1 |
| 788 | A1 | A1 | A1 |
| 789 | A1 | A1 | A1 |
| 790 | A1 | | |
| 791 | A1 | | |
| 792 | A1 | C1 | C1 |
| 793 | A1 | A1 | A1 |
| 794 | A1 | A1 | A1 |
| 795 | A1 | | |
| 796 | A1 | A1 | A1 |
| 797 | A1 | A1 | A1 |
| 798 | A1 | | |
| 799 | A1 | A1 | A1 |
| 800 | A1 | A1 | A1 |
| 801 | A1 | A1 | A1 |
| 802 | A1 | | |
| 803 | A1 | A1 | A1 |
| 804 | A1 | A1 | B1 |
| 805 | A1 | A1 | A1 |
| 806 | A1 | A1 | A1 |
| 807 | A1 | A1 | |
| 808 | A1 | A1 | |
| 809 | A1 | A1 | |
| 810 | B1 | A1 | A1 |
| 811 | A1 | A1 | A1 |
| 812 | A1 | A1 | A1 |
| 813 | A1 | A1 | A1 |
| 814 | B1 | | |
| 815 | A1 | A1 | |
| 816 | B1 | | |
| 817 | A1 | A1 | |
| 818 | A1 | A1 | |
| 819 | A1 | A1 | |
| 820 | A1 | | |
| 821 | A1 | | |
| 822 | A1 | | A1 |
| 823 | A1 | A1 | |
| 824 | A1 | | |
| 825 | A1 | | |
| 826 | A1 | | |
| 827 | A1 | | |

TABLE 4-continued

| Cmpd No. | IDH1R132H IC50 (μM) | HT1080 IC50 (μM) | U87R132H IC50 (μM) |
|---|---|---|---|
| 828 | A1 | | |
| 829 | A1 | | |
| 830 | A1 | | |

In some embodiments, the invention provides a compound selected from any one of compound numbers 182, 187, 191, 207, 212, 219, 222, 223, 224, 225, 226, 227, 229, 234, 235, 236, 241, 242, 243, 246, 248, 249, 250, 251, 252, 253, 255, 256, 257, 258, 259, 260, 261, and 262.

In some embodiments, the invention provides a compound selected from any one of compound numbers 263, 265, 266, 269, 271, 275, 276, 277, 280, 283, 285, 286, 287, 288, 289, 290, 292, 293, 294, 295, 296, 297, 299, 301, 302, 303, 304, 307, 308, 309, 312, 313, 315, 318, 319, 320, 321, 322, 323, 325, 326, 328, 330, 331, 333, 335, 338, 340, 341, 342, 343, 345, 346, 347, 348, 350, 351, 352, 353, 356, 358, 359, 360, 361, 362, 363, 364, 372, 373, 374, 376, 377, 378, 380, 381, 382, 383, 384, 386, 387, 388, 389, 390, 391, 392, 393, 396, 397, 398, 402, 403, 405, 406, 407, 408, 409, 410, 411, 412, 415, 417, 418, 419, 420, 424, 427, 428, 429, 433, 434, 436, 438, 439, 440, 442, 443, 444, 445, 446, 448, 451, 452, 453, 454, 456, 457, 458, 459, 460, 463, 466, 468, 469, 470, 471, 472, 473, 474, 475, 476, 480, 481, 482, 483, 485, 487, 488, 491, 494, 497, 498, 500, 503, 505, 508, 511, 512, 514, 516, 517, 518, 521, 524, 525, 527, 528, 529, 530, 531, 532, 534, 535, 536, 537, 538, 539, 540, 541, 542, 544, 546, 547, 549, 551, 552, 553, 554, 555, 556, 557, 558, 559, 560, 561, 562, 563, 564, 565, 566, 568, 569, 570, 571, 572, 573, 574, 575, 577, 578, 579, 580, 581, 582, 585, 586, 587, 588, 589, 590, 591, 592, 594, 595, 596, 597, 598, 599, 601, 602, 603, 604, 605, 606, 607, 608, 609, 610, 611, 612, 613, 614, 615, 616, 617, 618, 619, 620, 621, 624, 625, 626, 627, 628, 629, 631, 632, 633, 634, 635, 636, 637, 638, 639, 640, 641, 642, 643, 644, 645, 646, 647, 648, 649, 650, 651, 652, 653, 654, 655, 657, 658, 659, 660, 661, 662, 663, 664, 665, 666, 667, 668, 669, 670, 671, 674, 675, 676, 677, 678, 679, 680, 681, 682, 683, 684, 686, 687, 688, 689, 690, 691, 692, 693, 694, 695, 696, 697, 698, 699, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 773, 774, 775, 776, 777, 778, 780, 781, 782, 784, 785, 786, 787, 788, 789, 790, 791, 792, 793, 794, 795, 796, 797, 798, 799, 800, 801, 802, 803, 804, 805, 806, 807, 808, 809, 811, 812, 813, 815, 817, 818, 819, 820, 821, 822, 823, 824, 825, 826, 827, 828, 829, and 830.

Example 13. Cellular Assays for IDH1m (R132H or R132C) Inhibitors

Cells (e.g., HT1080 or U87MG) and are grown in T125 flasks in DMEM containing 10% FBS, 1× penicillin/streptomycin and 500 ug/mL G418. They are harvested by trypsin and seeded into 96 well white bottom plates at a density of 5000 cell/well in 100 ul/well in DMEM with 10% FBS. No cells are plates in columns 1 and 12. Cells are incubated overnight at 37° C. in 5% CO2. The next day compounds are made up at 2× concentration and 100 ul are added to each cell well. The final concentration of DMSO is 0.2% and the DMSO control wells are plated in row G. The plates are then placed in the incubator for 48 hours. At 48 hours, 100 μl of media is removed from each well and analyzed by LC-MS for 2-HG concentrations. The cell plate is placed back in the incubator for another 24 hours. At 72 hours post compound addition, 10 mL/plate of Promega Cell Titer Glo reagent is thawed and mixed. The cell plate is removed from the incubator and allowed to equilibrate to room temperature. Then 100 ul of reagent is added to each well of media. The cell plate is then placed on an orbital shaker for 10 minutes and then allowed to sit at room temperature for 20 minutes. The plate is then read for luminescence with an integration time of 500 ms.

The $IC_{50}$ for inhibition of 2-HG production (concentration of test compound to reduce 2HG production by 50% compared to control) in these two cell lines for various compounds of formula I is set forth in Table 4 above.

Example 14. Preparation of 2,3,5,6-Tetrasubstituted Pyridines

General Procedure 1:

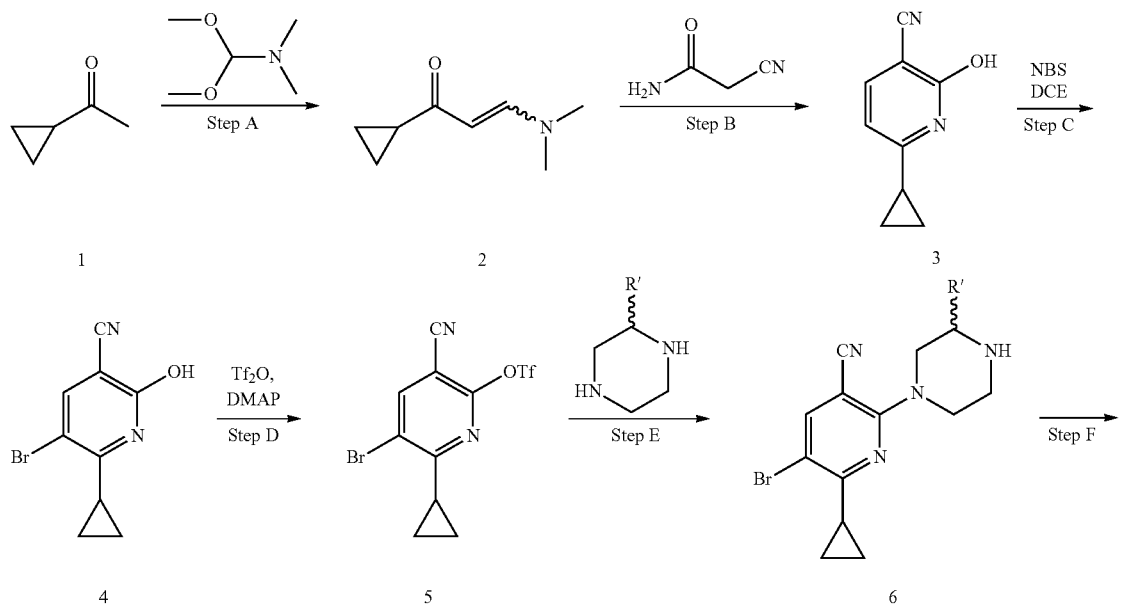

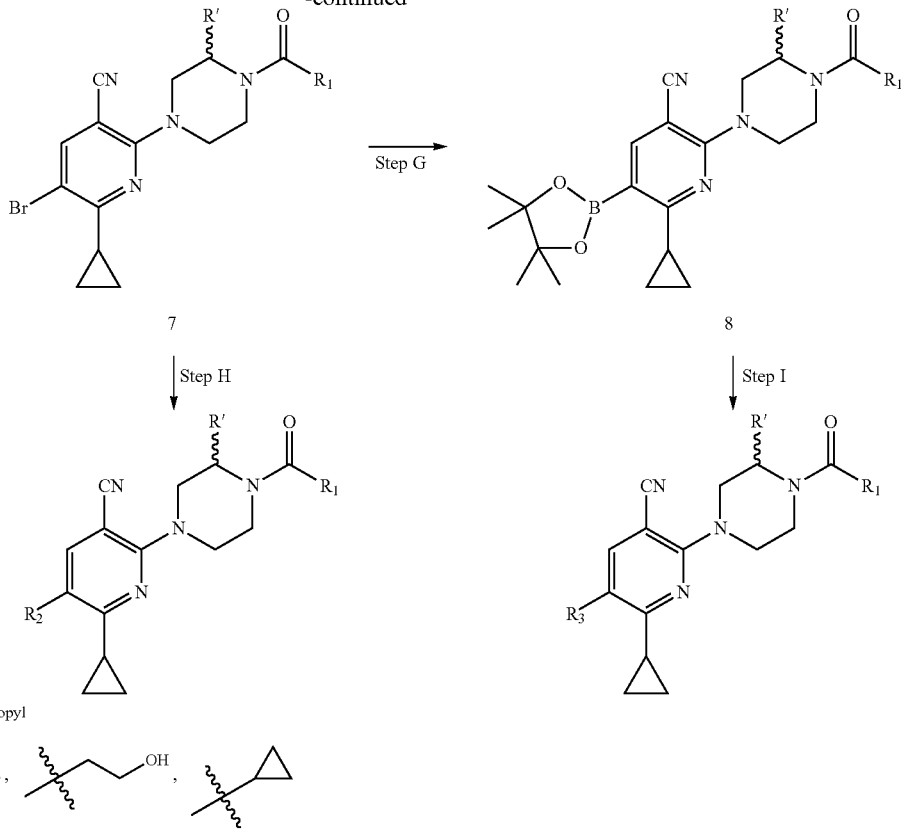

R' = methyl, isopropyl, cyclopropyl

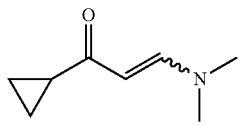

Step A: 1-cyclopropyl-3-(dimethylamino)prop-2-en-1-one (2)

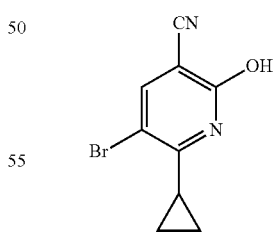

To a solution of 1-cyclopropylethanone (100 g, 1.2 mol) in anhydrous DMF (1300 mL) was added DMFDMA (300 g, 2.5 mol). The resulting mixture was stirred at 100° C. overnight. The solvent was removed in vacuum to give crude 2 (110 g) as yellow solid. $^1$H NMR (CHLOROFORM-d) δ 7.56 (d, J=12.8 Hz, 1H), 5.20 (d, J=12.5 Hz, 1H), 2.78-3.08 (m, 6H), 1.79 (tt, J=7.9, 4.5 Hz, 1H), 0.94-1.04 (m, 2H), 0.67-0.80 (m, 2H).

Step B: 6-cyclopropyl-2-hydroxynicotinonitrile (3)

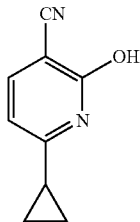 [SMILES: N#Cc1ccc(C2CC2)nc1O]

To a mixture of 1-cyclopropyl-3-dimethylamino-propenone (315 g, 2.3 mol) and cyanoacetamide (270 g, 2.3 mol) in a buffer solution of 47.4 mL of acetic acid and 1485 mL of water was added piperidine to adjust to pH 9. The mixture was then heated at reflux for 2 hours, cooled and acidified by 6N HCl to pH 5 below 25 degree. The yellow precipitate was filtered, washed with water and dried to give 3 as a white solid (561 g). MS (ES) M+H expected 161.1. found 161.0. 1H NMR (CHLOROFORM-d) δ 13.60 (br. s., 1H), 7.77 (d, J=7.8 Hz, 1H), 5.91 (d, J=7.8 Hz, 1H), 1.96-2.12 (m, 1H), 1.29-1.36 (m, 2H), 1.04-1.11 (m, 2H).

Step C: 5-bromo-6-cyclopropyl-2-hydroxynicotinonitrile (4)

A mixture of 6-cyclopropyl-2-hydroxynicotinonitrile (561 g, 3.6 mol) and NBS (624 g, 5.4 mol) in DCE (4500 mL) was heated at reflux for 3 hrs. The mixture was cooled to room temperature and the precipitate was filtered, washed with water and dried to give crude 4 (473 g) as a white solid. MS (ES) M+H expected 239.0. found 238.9. $^1$H NMR (CHLOROFORM-d) δ 8.49-8.72 (br. s., 1H), 7.93 (s, 1H), 2.23-2.34 (m, 1H), 1.36-1.42 (m, 2H), 1.29-1.36 (m, 2H).

Step D: 5-bromo-3-cyano-6-cyclopropylpyridin-2-yl trifluoromethanesulfonate (5)

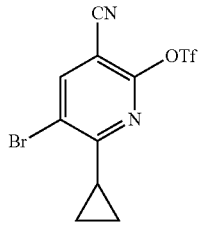 [SMILES: N#Cc1cc(Br)c(C2CC2)nc1OS(=O)(=O)C(F)(F)F]

To a 1 L flask were added 5-bromo-4-cyclopropyl-2-hydroxybenzonitrile (47.6 g, 0.2 mol), pyridine (32 g, 0.4 mol) and Cat. DMAP (500 mg) in DCM (300 mL), and the mixture was cooled to 0° C., and trifluoromethanesulfonic anhydride (59 g, 0.21 mol) in DCM (100 mL) was added dropwise. After addition, the mixture was stirred for another 1 h. TLC (PE:EtOAc=10:1) showed conversion of starting material to product. After reaction, diluted with DCM (300 mL), and washed with 1N HCl. The organic layer was dried over $Na_2SO_4$ and concentrated in vacuo afforded the title compound (70 g) as a yellow solid. $^1$H NMR (CHLOROFORM-d) δ 8.14-8.19 (m, 1H), 2.55-2.66 (m, 1H), 1.30 (dt, J=7.8, 3.1 Hz, 2H), 1.21-1.27 (m, 2H).

Step E: Exemplified by (R)-5-bromo-6-cyclopropyl-2-(3-methylpiperazin-1-yl)nicotinonitrile (6-1) (R'=methyl)

6-1

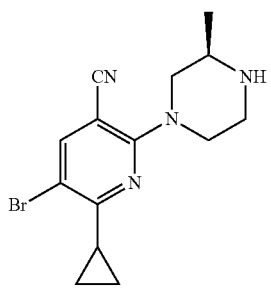

A mixture of above triflate 5 (1.68 g, 4.6 mmol), (R)-2-methylpiperazine (790 mg, 6.9 mmol), and triethylamine (1.9 mL, 13.8 mmol) suspended in 5 mL of MeCN was heated at 70° C. for 2 h. After the mixture was concentrated under reduced pressure, the residue was extracted between ethyl acetate and water. The combined organic layer was then washed with aq. $NaHCO_3$, brine, dried over anhy. $Na_2SO_4$ and concentrated in vacuo to give 1.26 g of crude title compound. MS (ES) M+H expected 321.1. found 321.2. $^1$H NMR (CHLOROFORM-d) δ 7.78 (s, 1H), 4.14-4.24 (m, 2H), 3.09-3.14 (m, 1H), 3.02-3.07 (m, 1H), 2.96-3.00 (m, 2H), 2.71 (dd, J=12.9, 10.2 Hz, 1H), 2.42-2.52 (m, 1H), 1.16 (d, J=6.3 Hz, 3H), 1.08 (s, 2H), 1.07 (d, J=3.8 Hz, 2H).

6-2

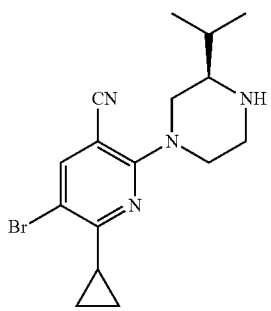

(R)-5-bromo-6-cyclopropyl-2-(3-isopropylpiperazin-1-yl)nicotinonitrile (6-2) (R'=isopropyl) was synthesized by the same procedure described above except using (R)-2-isopropylpiperazine instead of (R)-2-methylpiperazine. MS (ES) M+H expected 349.1. found 349.2. $^1$H NMR (CHLOROFORM-d) δ 7.79 (s, 1H), 4.14-4.24 (m, 2H), 3.09-3.14 (m, 1H), 3.02-3.07 (m, 1H), 2.96-3.00 (m, 2H), 2.71 (dd, 1H), 2.12-2.22 (m, 1H), 1.26 (d, 6H), 1.08 (d, 2H), 1.07 (d, 2H).

6-3

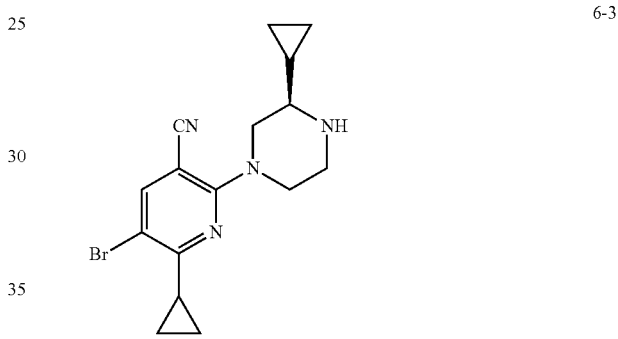

(R)-5-bromo-6-cyclopropyl-2-(3-cyclopropylpiperazin-1-yl)nicotinonitrile (6-3) (R'=cyclopropyl) was synthesized by the same procedure described above except using (R)-2-cyclopropylpiperazine (building block 1) instead of (R)-2-methylpiperazine. MS (ES) M+H expected 347.1. found 349.1. $^1$H NMR (CHLOROFORM-d) δ 7.77 (s, 1H), 4.14-4.24 (m, 2H), 3.09-3.14 (m, 1H), 3.02-3.07 (m, 1H), 2.96-3.00 (m, 2H), 2.71 (dd, 1H), 2.12-2.24 (m, 1H), 1.25 (d, 2H), 1.16 (d, 2H), 1.08 (d, 2H), 1.07 (d, 2H).

Step F, Method 1: Exemplified by (R)-5-bromo-6-cyclopropyl-2-(4-(3-methoxypropanoyl)-3-methylpiperazin-1-yl)nicotinonitrile (7-1) (R'=methyl, R1=c)

7-1

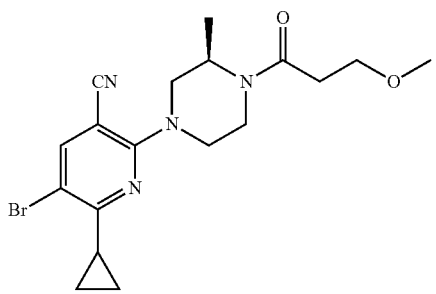

To a 25 mL of round-bottom flask was added (R)-5-bromo-6-cyclopropyl-2-(3-methylpiperazin-1-yl) nicotinonitrile (6-1) (1.26 g, 3.9 mmol), 3-methoxypropanoic acid (0.74 mL, 7.8 mmol), HATU (2.98 g, 7.8 mmol), DIPEA (2 mL, 11.76 mmol) and 10 mL of methylene chloride. The resulting reaction mixture was stirred at room temperature overnight until TLC showed the completion of the reaction. Reaction mixture was with satd. NaHCO$_3$ and brine. The combined organic layer was then dried over anhy. Na$_2$SO$_4$ and concentrated in vacuo. Column chromatography purification (30% EtOAc/petroleum ether) afforded 1.28 g of title compound as a white solid. MS (ES) M+H expected 407.1. found 407.0. $^1$H NMR (CHLOROFORM-d) δ 7.78-7.85 (m, 1H), 4.82-4.92 (m, 0.5H), 4.50 (d, J=13.6 Hz, 0.5H), 4.18-4.21 (m, 2H), 4.07-4.16 (m, 1H), 3.75-3.82 (m, 0.5H), 3.70-3.75 (m, 2H), 3.45-3.55 (m, 0.5H), 3.36 (s, 3H), 3.15-3.27 (m, 1H), 2.92-3.14 (m, 1H), 2.67-2.78 (m, 1H), 2.51-2.61 (m, 1H), 2.40-2.51 (m, 1H), 1.34 (d, J=6.8 Hz, 1.5H), 1.25 (d, J=2.5 Hz, 1.5H), 1.09 (d, J=3.5 Hz, 2H), 1.08 (s, 2H).

Step F, Method 2: Exemplified by (R)-5-bromo-2-(4-(cyclopropanecarbonyl)-3-methylpiperazin-1-yl)-6-cyclopropylnicotinonitrile (7-2)

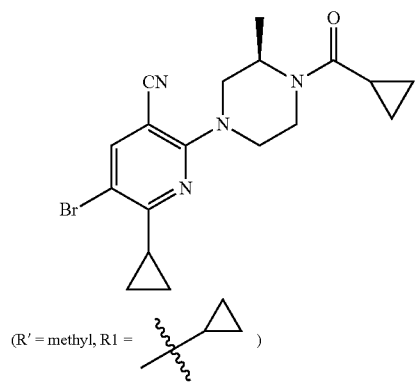

To a 25 mL of round-bottom flask was added (R)-5-bromo-6-cyclopropyl-2-(3-methylpiperazin-1-yl) nicotinonitrile (6-1) (1 g, 3.2 mmol), cyclopropanecarbonyl chloride (0.4 mL, 3.3 mmol), DIPEA (0.4 mL, 3.4 mmol) and 10 mL of methylene chloride. The resulting reaction mixture was stirred at room temperature overnight until TLC showed the completion of the reaction. Reaction mixture was with Satd. NaHCO$_3$ and brine. The combined organic layer was then dried over anhy. Na$_2$SO$_4$ and concentrated in vacuo. Column chromatography purification (10% EtOAc/petroleum ether) afforded 1.1 g of title compound as a white solid. MS (ES) M+H expected 389.1. found 389.0. $^1$H NMR (CHLOROFORM-d) δ 7.85 (s, 1H), 4.18-4.21 (m, 2H), 4.07-4.16 (m, 1H), 3.70-3.75 (m, 2H), 3.15-3.27 (m, 1H), 2.92-3.14 (m, 1H), 2.67-2.78 (m, 1H), 2.51-2.61 (m, 1H), 2.40-2.51 (m, 1H), 1.34 (d, J=6.8 Hz, 1.5H), 1.25 (d, J=2.5 Hz, 1.5H), 1.25-1.36 (m, 4H), 1.09 (d, 2H), 1.08 (d, 2H).

Step F, Method 3: Exemplified by (R)-5-bromo-6-cyclopropyl-2-(4-(3-hydroxypropanoyl)-3-methylpiperazin-1-yl)nicotinonitrile (7-3)

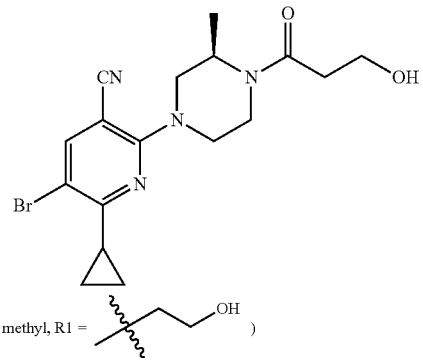

To a 25 mL of round-bottom flask was added (R)-5-bromo-6-cyclopropyl-2-(3-methylpiperazin-1-yl) nicotinonitrile (6-1) (2 g, 6.2 mmol), sodium 2-carboxyethanolate (0.70 g, 6.4 mmol), DIPEA (2 mL, 11.5 mmol) and 10 mL of DMF. The resulting reaction mixture was stirred at room temperature for 5 h until TLC showed the completion of the reaction. Reaction mixture was washed with water and brine. The combined organic layer was then dried over anhy. Na$_2$SO$_4$ and concentrated in vacuo. Column chromatography purification (50% EtOAc/petroleum ether) afforded 1.2 g of title compound as a white solid. MS (ES) M+H expected 393.1. found 393.1. $^1$H NMR (CHLOROFORM-d) δ 7.85 (m, 1H), 4.88-4.97 (m, 0.5H), 4.75 (d, J=13.6 Hz, 0.5H), 4.29-4.48 (m, 2H), 4.11-4.20 (m, 1H), 3.70-3.75 (m, 2H), 3.45-3.55 (m, 2H), 3.15-3.27 (m, 1H), 2.92-3.14 (m, 1H), 2.67-2.78 (m, 1H), 2.51-2.61 (m, 1H), 2.40-2.51 (m, 1H), 1.34 (d, J=6.8 Hz, 1.5H), 1.25 (d, J=2.5 Hz, 1.5H), 1.09 (d, J=3.5 Hz, 2H), 1.08 (s, 2H).

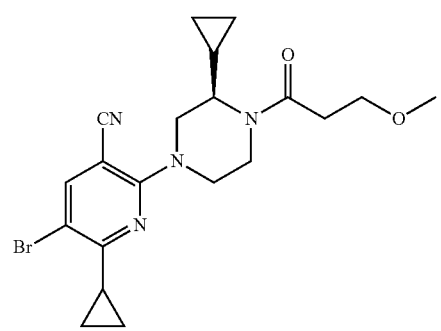

(R)-5-bromo-6-cyclopropyl-2-(3-cyclopropyl-4-(3-methoxypropanoyl)piperazin-1-yl)nicotinonitrile (7-4) was synthesized by method 1 in step F except using 6-3 as the starting material instead of 6-1. MS (ES) M+H expected 433.1. found 433.3.

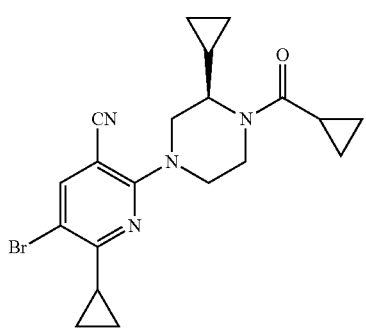

7-5

(R)-5-bromo-2-(4-(cyclopropanecarbonyl)-3-cyclopropylpiperazin-1-yl)-6-cyclopropylnicotinonitrile (7-5) was synthesized by method 2 in step F except using 6-3 as the starting material instead of 6-1. MS (ES) M+H expected 415.1. found 415.1.

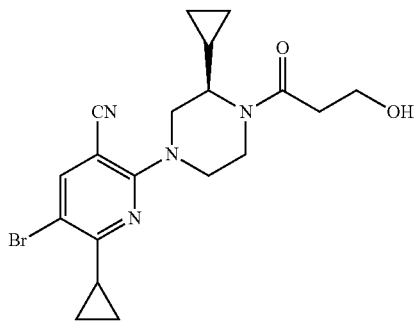

7-6

(R)-5-bromo-6-cyclopropyl-2-(3-cyclopropyl-4-(3-hydroxypropanoyl)piperazin-1-yl)nicotinonitrile (7-6) was synthesized by method 3 in step F except using 6-3 as the starting material instead of 6-1. MS (ES) M+H expected 419.1. found 419.1. $^1$H NMR (CHLOROFORM-d) δ 7.85 (m, 1H), 4.87-4.97 (m, 0.5H), 4.77 (d, J=13.6 Hz, 0.5H), 4.29-4.48 (m, 2H), 4.11-4.20 (m, 1H), 3.70-3.75 (m, 2H), 3.45-3.55 (m, 2H), 3.15-3.27 (m, 1H), 2.92-3.14 (m, 1H), 2.67-2.78 (m, 1H), 2.51-2.61 (m, 1H), 2.40-2.51 (m, 1H), 1.34 (d, J=6.8 Hz, 2H), 1.25 (d, 2H), 1.09 (d, J=3.5 Hz, 2H), 1.08 (s, 2H).

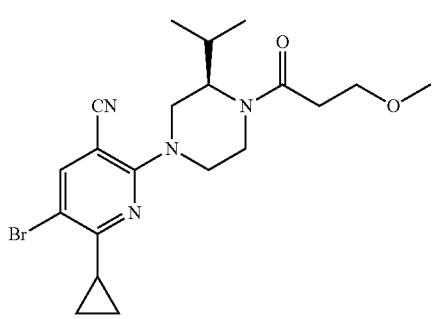

7-7

(R)-5-bromo-6-cyclopropyl-2-(3-isopropyl-4-(3-methoxypropanoyl)piperazin-1-yl)nicotinonitrile (7-7) was synthesized by method 1 in step F except using 6-2 as the starting material instead of 6-1. MS (ES) M+H expected 434.1. found 435.1.

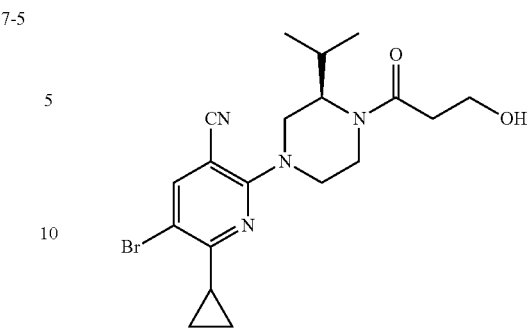

7-8

(R)-5-bromo-6-cyclopropyl-2-(4-(3-hydroxypropanoyl)-3-isopropylpiperazin-1-yl)nicotinonitrile (7-8) was synthesized by method 1 in step F except using 6-2 as the starting material instead of 6-1. MS (ES) M+H expected 421.1. found 421.6.

Step G, Method 1: Exemplified by (R)-6-cyclopropyl-2-(4-(3-methoxypropanoyl)-3-methylpiperazin-1-yl)-5-(4,4,5,5-tetramethyl-1,3,2-dioxaborolan-2-yl)nicotinonitrile (8-1) (R'=methyl, R1=c)

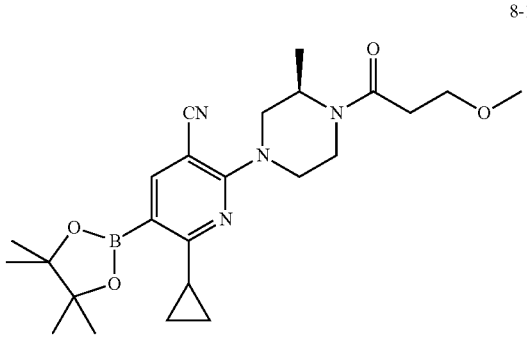

8-1

To a solution of (R)-5-bromo-6-cyclopropyl-2-(4-(3-methoxypropanoyl)-3-methylpiperazin-1-yl) nicotinonitrile (7-1) (747 mg, 1.8 mmol) in DMF (8 mL) was added 4,4,4',4',5,5,5',5'-octamethyl-2,2'-bi(1,3,2 dioxaborolane) (563 mg, 2.2 mmol) and KOAc (538 mg, 5.5 mmol). The resulting mixture was stirred at room temperature for 5 min before addition of PdCl$_2$(dppf).CH$_2$Cl$_2$ (45 mg, 0.03 mmol). After flushing with nitrogen, the reaction mixture was heated at 85° C. for 18 hours. After cooling, the reaction mixture was diluted with water, and extracted with methylene chloride. The organic layer was then washed with brine, dried over anhy. Na$_2$SO$_4$, and concentrated in vacuo. Column chromatography (25% EtOAc/petroleum ether) afforded 334 mg of title compound as a white solid. MS (ES) M+H expected 455.3. found 455.2.

Step G, Method 2: Exemplified by (R)-6-cyclopropyl-2-(4-(3-hydroxypropanoyl)-3-methylpiperazin-1-yl)-5-(4,4,5,5-tetramethyl-1,3,2-dioxaborolan-2-yl) nicotinonitrile

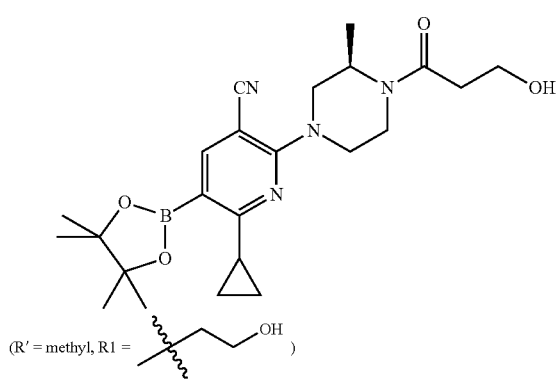

8-2

(R' = methyl, R1 = ~~~OH )

1.4 g of (R)-5-bromo-6-cyclopropyl-2-(4-(3-hydroxypropanoyl)-3-methylpiperazin-1-yl) nicotinonitrile (7-3) (3.3 mmol), 2.12 g of 4,4,4',4',5,5,5',5'-octamethyl-2,2'-bi(1,3,2-dioxaborolane) (8.34 mmol), 0.7 g of KOAc (7.4 mmol), 154 mg of Xphos (0.32 mmol) and 308 mg of $Pd_2(dba)_3$ (0.33 mmol) in 20 mL of dioxane in a round bottom flask was stirred under $N_2$ at 75° C. overnight. Then the mixture was cooled to room temperature. Concentrated, purified by column chromatography (petroleum ether: ethyl acetate from 3:1 to 1:1) to give 670 mg of title compound. MS (ES) M+H expected 441.2. found 441.2.

General Procedure 1, Step H: Exemplified by (R)-6-cyclopropyl-2-(4-(3-methoxypropanoyl)-3-methylpiperazin-1-yl)-5-(thiophen-2-yl)nicotinonitrile (Compound 273)

A mixture of 7-1 (26 mg, 0.06 mmol), thiophen-2-ylboronic acid (14 mg, 0.089 mmol), $Pd(PPh_3)_4$ (3 mg, 0.003 mmol), and $K_2CO_3$ (16 mg, 0.119 mmol) suspended in 1 mL of DMF was subjected to microwave reaction at 150° C. for 45 min. After the reaction was complete, the reaction mixture was concentrated in vacuo, and the residue was purified by column chromatography to afford 19 mg of title compound as yellowish oil. $^1$H NMR (CHLOROFORM-d) δ 7.70 (s, 1H), 7.38 (dd, J=3.9, 2.4 Hz, 1H), 7.07-7.14 (m, 2H), 4.90 (br. s., 0.5H), 4.52 (d, J=13.1 Hz, 0.5H), 4.15-4.41 (m, 2.5H), 3.67-3.89 (m, 2.5H), 3.47-3.63 (m, 0.5H), 3.34-3.43 (m, 3H), 3.20-3.33 (m, 1H), 2.99-3.17 (m, 1.5H), 2.63-2.81 (m, 1H), 2.50-2.62 (m, 1H), 2.26-2.36 (m, 1H), 1.37 (d, J=6.3 Hz, 1.5H), 1.27 (d, J=6.8 Hz, 1.5H), 1.10-1.18 (m, 2H), 0.94-1.05 (m, 2H). LC-MS: m/z 411.1 (M+H)$^+$.

Step I: Exemplified by (R)-6-cyclopropyl-2-(4-(3-methoxypropanoyl)-3-methylpiperazin-1-yl)-5-(2-vinylquinazolin-5-yl)nicotinonitrile (Compound 603)

To a solution of 8-1 (95 mg, 0.197 mmol), 5-chloro-2-vinylquinazoline (25 mg, 0.131 mmol), Xphos (7 mg, 0.013 mmol), $Pd_2(dba)_3$ (6 mg, 0.007 mmol) and $K_3PO_4.H_2O$ (105 mg, 0.393 mmol) was stirred at 100° C. for 16 hours, the mixture was partitioned between EtOAc and water, the organic was washed with water, brine and concentrated to give the crude which was purified by column chromatography to give 25 mg of the product. $^1$H NMR (CHLOROFORM-d) δ 9.16 (d, J=3.0 Hz, 1H), 8.05 (d, J=8.5 Hz, 1H), 7.95 (dd, J=8.5, 7.3 Hz, 1H), 7.66 (s, 1H), 7.45-7.58 (m, 1H), 7.06 (dd, J=17.2, 10.4 Hz, 1H), 6.80 (dd, J=17.3, 1.5 Hz, 1H), 5.80-5.96 (m, 1H), 4.87-5.02 (m, 0.5H), 4.56 (d, J=12.0 Hz, 0.5H), 4.35-4.44 (m, 2.5H), 3.84 (d, J=12.8 Hz, 0.5H), 3.69-3.79 (m, 2H), 3.52-3.65 (m, 0.5H), 3.30-3.43 (m, 4H), 3.05-3.24 (m, 1.5H), 2.65-2.81 (m, 1H), 2.48-2.64 (m, 1H), 1.50-1.59 (m, 1H), 1.30-1.44 (m, 3H), 1.13-1.22 (m, 2H), 0.84-0.89 (m, 2H). LC-MS: m/z 483.2 (M+H)$^+$ General Procedure 2:

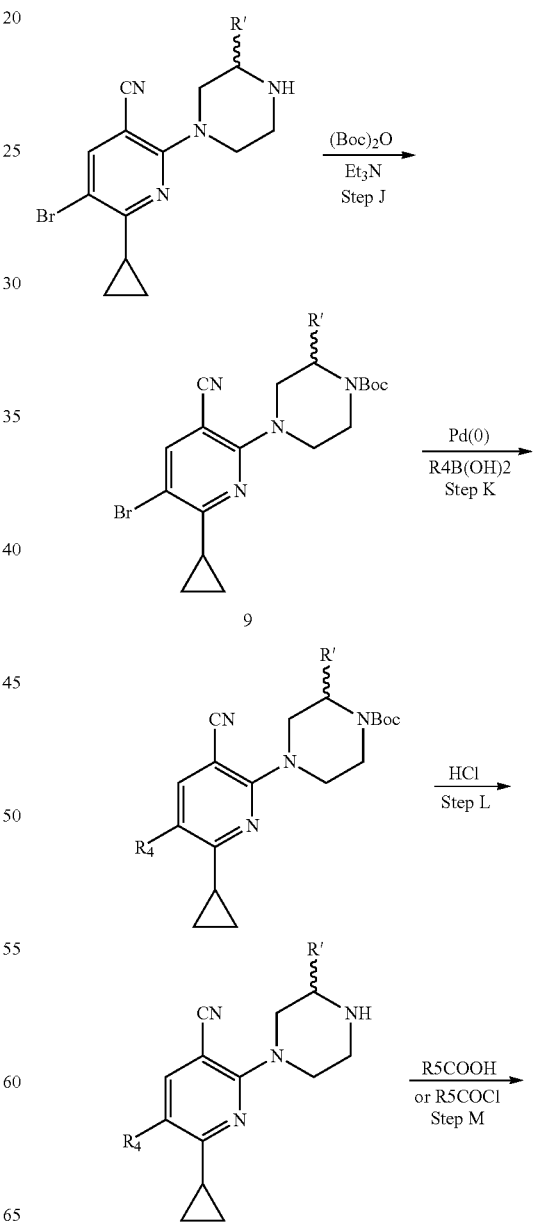

411

-continued

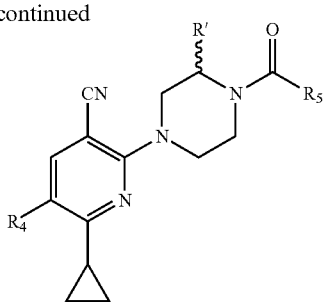

R' = methyl, isopropyl, cyclopropyl

Step J: Exemplified by (R)-tert-butyl 4-(5-bromo-3-cyano-6-cyclopropylpyridin-2-yl)-2-cyclopropy-lpiper-azine-1-carboxylate (9-1, R'=cyclopropyl)

9-1

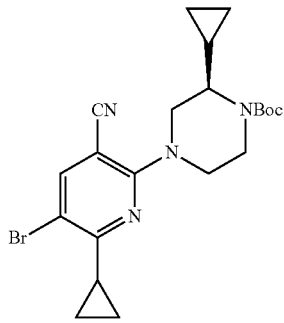

To a solution of 6-3 (1 g, 2.24 mmol) in DCM (8 mL) was added (Boc)$_2$O (0.5 g, 2.26 mmol) and Et$_3$N (0.1 mL). The resultant solution was stirred at room temperature for 2 h. The reaction mixture was diluted with water. The organic layer was then washed with brine, dried over anhy. Na$_2$SO$_4$, and concentrated in vacuo to give the title compound as a white solid (1.5 g), which can be used directly for the next step. $^1$H NMR (CHLOROFORM-d) δ 7.85 (s, 1H), 4.14-4.24 (m, 2H), 3.29-3.34 (m, 1H), 3.12-3.18 (m, 1H), 2.96-3.00 (m, 2H), 2.71 (dd, 1H), 2.12-2.24 (m, 1H), 1.5 (s, 9H), 1.25 (d, 2H), 1.16 (d, 2H), 1.08 (d, 2H), 1.07 (d, 2H).

Step K: Exemplified by (R)-tert-butyl 4-(5-cyano-2-cyclopropyl-[3,3'-bipyridin]-6-yl)-2-cyclopropyl piperazine-1-carboxylate (R'=cyclopropyl, R4=3-pyridinyl)

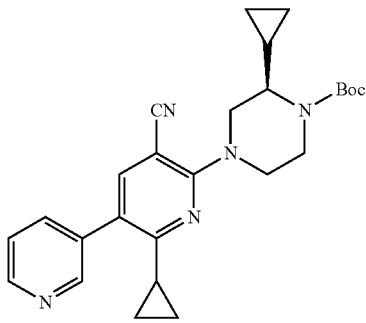 [SMILES: CC(C)(C)OC(=O)N1CCN(c2nc(C3CC3)c(-c3cccnc3)cc2C#N)C[C@H]1C1CC1]

412

To a solution of (R)-tert-butyl 4-(5-bromo-3-cyano-6-cyclopropylpyridin-2-yl)-2-cyclopropylpiperazine-1-carboxylate (150 mg, 0.33 mmol) in 2 mL of dioxane and 0.5 mL water was added pyridin-3-ylboronic acid (45.6 mg, 0.37 mmol), Pd(dppf)Cl2 (24 mg, 0.033 mmol), CsF (100 mg, 0.66 mmol). The resulting mixture was stirred at 100° C. under N2 atmosphere and microwaved for 1 h. After TLC showed the complete conversion of starting material to product, the reaction mixture was concentrated and purified by column chromatography (20% EtOAc/petroleum ether) to afford 100 mg title compound. MS (ES) M+H expected 446.2. found 446.3.

Step L: Exemplified by (R)-2-cyclopropyl-6-(3-cyclopropylpiperazin-1-yl)-[3,3'-bipyridine]-5-carbonitrile (R'=cyclopropyl, R4=3-pyridinyl)

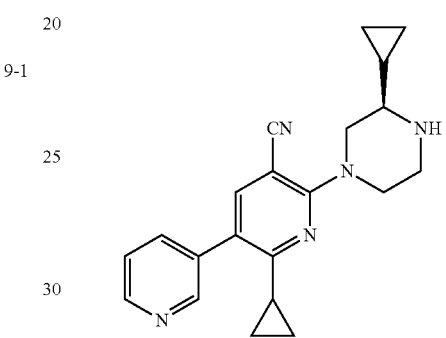

To a solution of (R)-tert-butyl 4-(5-cyano-2-cyclopropyl-[3,3'-bipyridin]-6-yl)-2-cyclopropyl piperazine-1-carboxylate (100 m g, 0.22 mmol) in 3 mL of DCM was added TFA (1 mL). The resulting mixture was stirred at room temperature for 2 h. After TLC showed the complete conversion of starting material to product, the reaction mixture was concentrated and basified with Na$_2$CO$_3$ solution to pH=8. Then the solution was extracted with DCM (10 mL×3). The organic layer was dried and concentrated and purified by Prep-HPLC (5% DCM/MeOH) to get 70 mg title compound. MS (ES) M+H expected 346.2. found 346.2.

General Procedure 2, Step M: Exemplified by (R)-2-cyclopropyl-6-(3-cyclopropyl-4-(3,3,3-trifluoropropanoyl)piperazin-1-yl)-[3,3'-bipyridine]-5-carbonitrile (Compound 524)

To a solution of (R)-2-cyclopropyl-6-(3-cyclopropylpiperazin-1-yl)-[3,3'-bipyridine]-5-carbonitrile (70 mg, 0.2 mmol) in 10 mL DCM was added 3,3,3-trifluoropropanoic acid (31 mg, 0.24 mmol), and triethylamine (1 mL), HOBT (54 mg, 0.4 mmol), EDCI (76.8 mg, 0.4 mmol). The resulting reaction mixture was stirred at r.t. overnight. After TLC showed the complete conversion of starting material to product, the reaction mixture was concentrated and purified by Prep-HPLC (50% EtOAc/petroleum ether) to get 25 mg title compound. $^1$H NMR (CHLOROFORM-d) δ 8.56-8.77 (m, 2H), 7.77 (d, J=7.8 Hz, 1H), 7.65 (s, 1H), 7.44 (dd, J=7.7, 4.9 Hz, 1H), 4.56 (d, J=13.1 Hz, 1H), 4.44 (d, J=13.1 Hz, 1H), 4.12 (br. s., 1H), 3.63-3.86 (m, 2H), 3.32 (d, J=9.3 Hz, 2H), 3.20 (d, J=13.1 Hz, 1H), 3.11 (d, J=11.8 Hz, 1H), 1.99 (td, J=8.0, 3.8 Hz, 1H), 1.11-1.23 (m, 3H), 1.01 (dd, J=7.5, 3.5 Hz, 2H), 0.77-0.95 (m, 2H), 0.66 (br. s., 1H), 0.50 (d, J=5.0 Hz, 2H) LC-MS: m/z 4 456.4 (M+H)$^+$.

General Procedure 3:

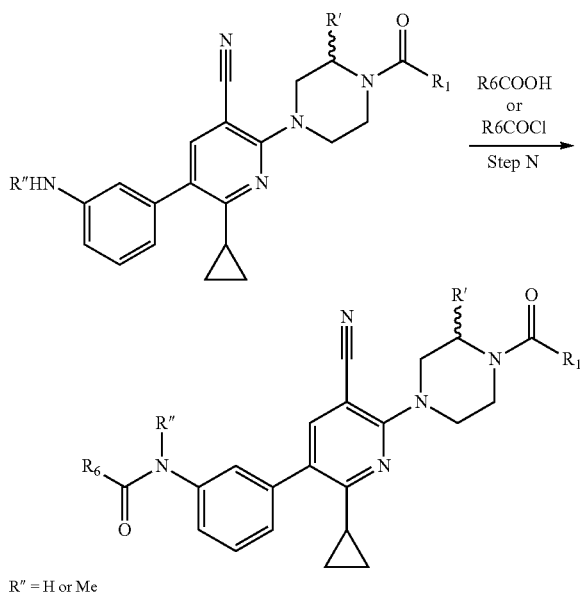

R" = H or Me

Method 1: Exemplified by (R)-2-chloro-N-(3-(5-cyano-2-cyclopropyl-6-(4-(3-methoxypropanoyl)-3-methylpiperazin-1-yl)pyridin-3-yl)phenyl)acetamide (Compound 403)

(R" = H, R1 = )

To a solution of (R)-5-(3-aminophenyl)-6-cyclopropyl-2-(4-(3-methoxypropanoyl)-3-methyl piperazin-1-yl) nicotinonitrile (50 mg, 0.119 mmol) and 2-chloroacetyl chloride (15 mg, 0.131 mmol) in 2 ml of DCM was added dropwise TEA (24 mg, 0.238 mmol) at 0° C., then the mixture was allowed to warm to room temperature and stirred for 2 hours. The mixture was partitioned between EtOAc and water. The organic layer was dried over $Na_2SO_4$ and concentrated to give the crude which was purified by prep-TLC to give 20 mg of the product.

$^1$H NMR (CHLOROFORM-d) □δ 8.34 (s, 1H), 7.66-7.75 (m, 1H), 7.62 (s, 1H), 7.50-7.55 (m, 1H), 7.42-7.48 (m, 1H), 7.22 (d, J=7.8 Hz, 1H), 4.92 (s, 0.5H), 4.50-4.54 (m, 0.5H), 4.29-4.33 (m, 1H), 4.26 (m, 1H), 4.21-4.25 (m, 0.5H), 3.71-3.84 (m, 2.5H), 3.52-3.57 (m, 0.5H), 3.39 (s, 3H), 3.21-3.32 (m, 1H), 3.13 (d, J=11.3 Hz, 1H), 3.05 (d, J=12.3 Hz, 0.5H), 2.66-2.81 (m, 1H), 2.54-2.65 (m, 1H), 2.07-2.12 (m, 1H), 1.40 (d, J=6.3 Hz, 1H), 1.28-1.31 (m, 2H), 1.14-1.19 (m, 2H), 0.94-1.00 (m, 2H). LC-MS: m/z 496.2 $(M+H)^+$.

Method 2: Exemplified by (R)—N-(3-(5-cyano-2-cyclopropyl-6-(4-(3-methoxypropanoyl)-3-methyl-piperazin-1-yl)pyridin-3-yl)phenyl)propionamide (Compound 424)

To a 25 mL of round-bottom flask was added (R)-5-(3-aminophenyl)-6-cyclopropyl-2-(4-(3-methoxypropanoyl)-3-methyl piperazin-1-yl) nicotinonitrile (50 mg, 0.119 mmol), propionic acid (0.1 mL), HATU (20 mg), DIPEA (0.05 mL) and 10 mL of methylene chloride. The resulting reaction mixture was stirred at room temperature overnight until TLC showed the completion of the reaction. Reaction mixture was with satd. $NaHCO_3$ and brine. The combined organic layer was then dried over anhy. $Na_2SO_4$ and concentrated in vacuo. Column chromatography purification (30% EtOAc/petroleum ether) afforded 45 mg of title compound as a white solid. $^1$H NMR (CHLOROFORM-d) □□7.75 (s, 1H), 7.68 (s, 1H), 7.59 (s, 1H), 7.49 (d, J=8.0 Hz, 1H), 7.37 (t, J=7.8 Hz, 1H), 7.11 (d, J=7.5 Hz, 1H), 4.89 (s, 0.5H), 4.52 (d, J=13.3 Hz, 0.5H), 4.14-4.35 (m, 2.5H), 3.67-3.85 (m, 2.5H), 3.49-3.62 (m, 0.5H), 3.37 (s, 3H), 3.17-3.32 (m, 1H), 2.93-3.17 (m, 1.5H), 2.63-2.81 (m, 1H), 2.52-2.63 (m, 1H), 2.37-2.49 (m, 2H), 2.05-2.13 (m, 1H), 1.38 (d, J=6.5 Hz, 1H), 1.22-1.31 (m, 5H), 1.14 (dt, J=7.4, 3.6 Hz, 2H), 0.88-1.01 (m, 2H). LC-MS: m/z 476.3 $(M+H)^+$.

General Procedure 4:

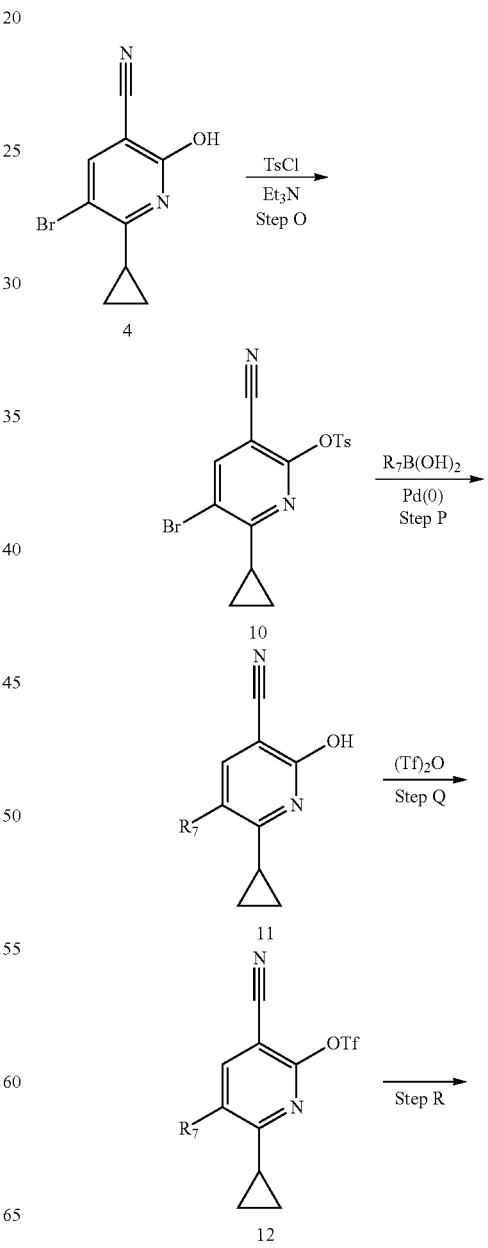

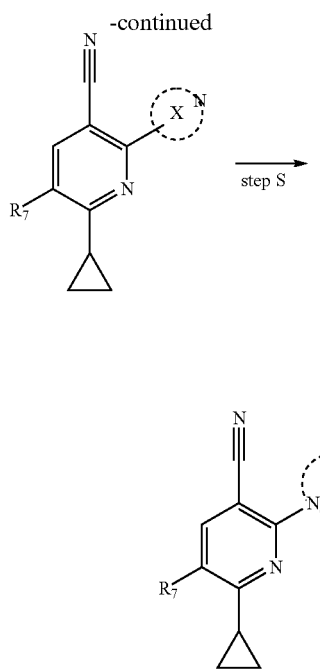

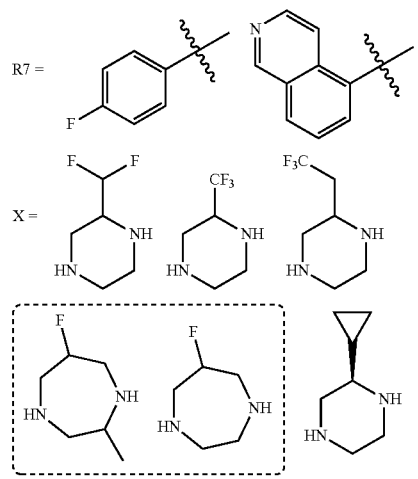

Step O: 5-bromo-3-cyano-6-cyclopropylpyridin-2-yl 4-methylbenzenesulfonate (10)

To a solution of 4 (2.37 g, 10 mmol) in THF (20 mL) was added TsCl (1.9 g, 11 mmol) and Et$_3$N (1 mL). The reaction was stirred at room temperature for 2 h. The resultant solution was partitioned between DCM and water. The organic layer was dried over Na$_2$SO$_4$ and concentrated to give the crude which was purified by column chromatography to give 2.6 g of 10. $^1$H NMR (CHLOROFORM-d) δ 7.86 (s, 1H), 7.35-7.46 (m, 2H), 7.11-7.25 (m, 2H), 1.99-2.17 (m, 1H), 1.21-1.38 (m, 2H), 1.00-1.20 (m, 2H). LC-MS: m/z 393.0 (M+H)$^+$.

Step P: Exemplified by 6-cyclopropyl-5-(4-fluorophenyl)-2-hydroxynicotinonitrile (11-1)

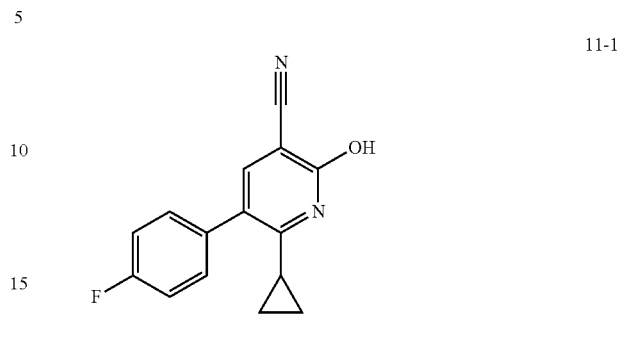

A mixture of 10 (2.6 g, 11 mmol), 4-fluorophenylboronic acid (1.4 g, 10 mmol), Pd(PPh$_3$)$_4$ (30 mg), and K$_2$CO$_3$ (16 mg, 0.119 mmol) suspended in 10 mL of DMF was subjected to microwave reaction at 150° C. for 45 min. After the reaction, the reaction mixture was concentrated in vacuo, and the residue was purified by column chromatography to afford 1.9 g of title compound as a yellow solid. LC-MS: m/z 255.0 (M+H)$^+$ Step Q 12-1

3-cyano-6-cyclopropyl-5-(4-fluorophenyl)pyridin-2-yl trifluoromethanesulfonate. $^1$H NMR (CHLOROFORM-d) δ: 7.87 (s, 1H), 7.32-7.57 (m, 2H), 7.13-7.24 (m, 2H), 1.99-2.17 (m, 1H), 1.21-1.38 (m, 2H), 1.00-1.20 (m, 2H). LC-MS: m/z 387.1 (M+H)$^+$.

Step R

The same procedure as General procedure 1, step E except using 12-1 as the starting material instead of 5 and the suitable building blocks described in the "building block" section.

Step S

The same procedure as General procedure 1, step G except using the suitable building blocks described in the "building block" section.

General Procedure 5:

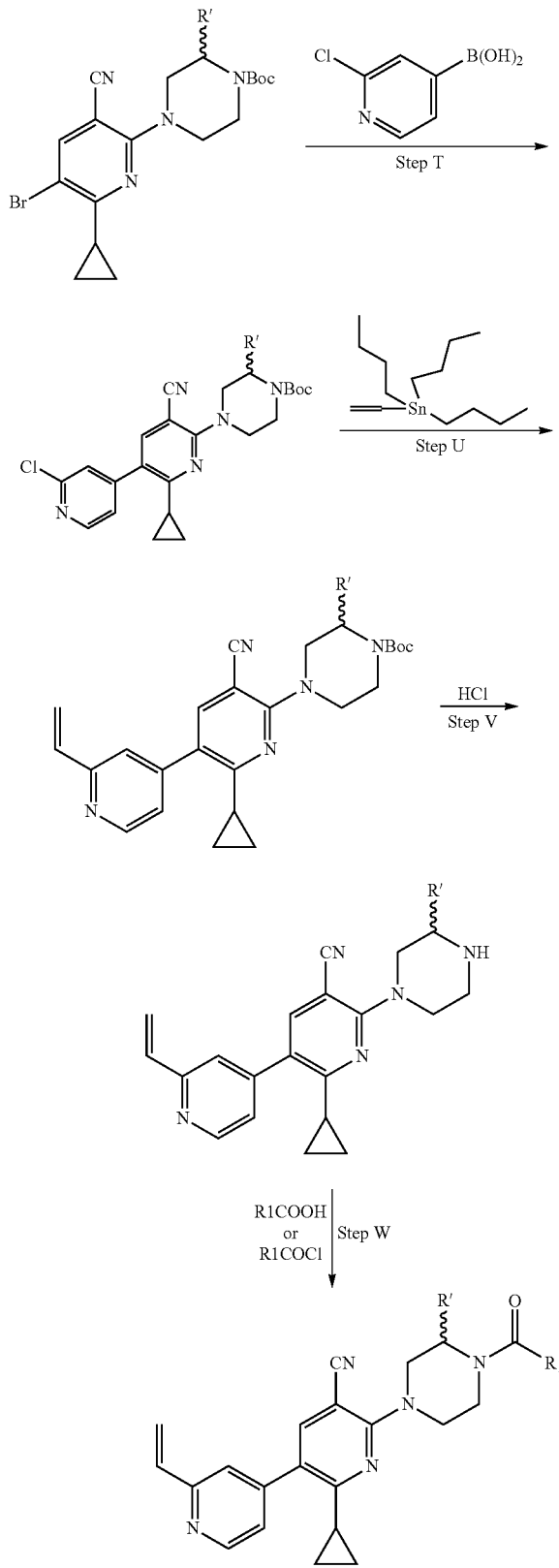

R' = methyl cyclopropyl

Step T: Exemplified by (R)-tert-butyl 4-(2'-chloro-5-cyano-2-cyclopropyl-3,4'-bipyridin-6-yl)-2-cyclopropylpiperazine-1-carboxylate

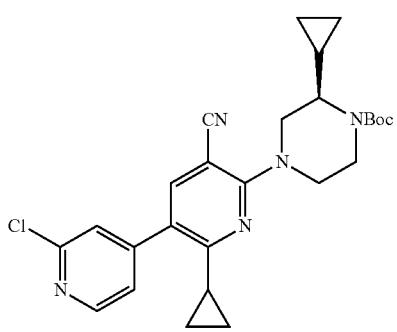 [SMILES: CC(C)(C)OC(=O)N1CCN(c2nc(C3CC3)c(-c3ccnc(Cl)c3)cc2C#N)C[C@H]1C1CC1]

To a 25 mL flask was added with 9-1 (1000 mg 2.235 mmol), 2-chloropyridin-4-ylboronic acid (457 mg, 2.906 mmol), Pd(PPh₃)₄ (120 mg, 0.1 mmol), K₂CO3 (926 mg, 6.705 mmol), and 4 mL DMF. The resultant mixture was stirred at 150° C. for 5 h. After washing with satd. NaHCO₃, brine, the combined organic layer was dried over anhy. Na₂SO₄ and concentrated in vacuo. Column chromatography purification (20% EtOAc/petroleum ether) afforded 640 mg of title compound. ¹H NMR (CHLOROFORM-d) δ 8.48 (d, J=5.0 Hz, 1H), 7.62 (s, 1H), 7.39-7.47 (m, 1H), 7.32 (dd, J=5.1, 1.3 Hz, 1H), 4.59 (d, J=12.9 Hz, 1H), 4.45 (d, J=13.2 Hz, 1H), 4.09 (d, J=13.5 Hz, 1H), 3.50 (d, J=9.1 Hz, 1H), 3.34-3.43 (m, 1H), 3.27 (dd, J=13.2, 3.8 Hz, 1H), 3.11 (td, J=12.5, 3.7 Hz, 1H), 1.94-2.06 (m, 1H), 1.77 (br. s., 2H), 1.50 (s, 9H), 1.34 (br. s., 1H), 1.04 (dd, J=7.9, 3.2 Hz, 2H), 0.56-0.63 (m, 2H), 0.50 (dd, J=8.5, 3.5 Hz, 1H), 0.32-0.42 (m, 1H).

Step U: Exemplified by (R)-tert-butyl-4-(5-cyano-2-cyclopropyl-2'-vinyl-3,4'-bipyridin-6-yl)-2-cyclopropyl piperazine-1-carboxylate

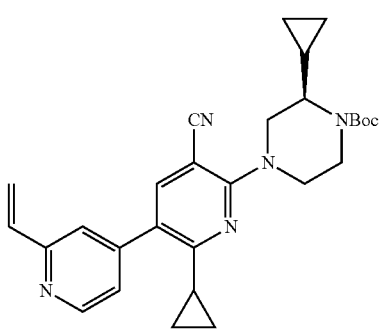 [SMILES: C=Cc1cc(-c2cc(C#N)c(N3CCN(C(=O)OC(C)(C)C)[C@H](C4CC4)C3)nc2C2CC2)ccn1]

To a flask was added with (R)-tert-butyl 4-(2'-chloro-5-cyano-2-cyclopropyl-3,4'-bipyridin-6-yl)-2-cyclopropylpiperazine-1-carboxylate (640 mg 1.33 mmol), tributyl(vinyl) stannane (550 mg, 1.73 mmol), Pd(PPh₃)₄ (120 mg, 0.1 mmol), K2CO3 (460 mg, 3.33 mmol), and 4 mL DMF. The resultant mixture was stirred at 150° C. for 5 h. After washing with satd. NaHCO3, brine, the combined organic layer was dried over anhy. Na₂SO₄ and concentrated in vacuo. Column chromatography purification (20% EtOAc/petroleum ether) afforded the compound. LC-MS: m/z 472.2 (M+H)+.

Step V: (R)-2-cyclopropyl-6-(3-cyclopropylpiperazin-1-yl)-2'-vinyl-3,4'-bipyridine-5-carbonitrile

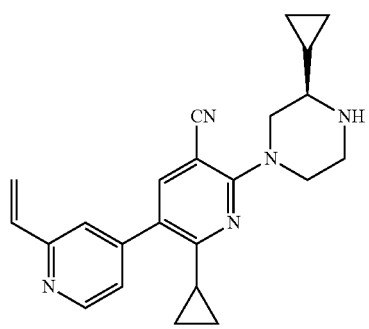 [SMILES: C=Cc1cc(-c2cc(C#N)c(N3CCN[C@H](C4CC4)C3)nc2C2CC2)ccn1]

To a flask was added (R)-tert-butyl 4-(5-cyano-2-cyclopropyl-2'-vinyl-3,4'-bipyridin-6-yl)-2-cyclopropylpiperazine-1-carboxylate and 12 mL EtOH/HCl (1M). The resulting reaction mixture was stirred at 0° C. for 30 minutes until TLC showed the completion of the reaction, which was concentrated in vacuo to afford a product as light yellowish solid. ¹H NMR (CHLOROFORM-d) δ: 8.65 (d, J=5.0 Hz, 1H), 7.62 (s, 1H), 7.38 (s, 1H), 7.23 (dd, J=5.0, 1.8 Hz, 1H), 6.89 (dd, J=17.3, 10.9 Hz, 1H), 6.29 (dd, J=17.6, 1.2 Hz, 1H), 5.57 (dd, J=10.9, 1.2 Hz, 1H), 4.50 (d, J=12.9 Hz, 1H), 4.36 (d, J=13.2 Hz, 1H), 3.28 (br. s., 1H), 3.22 (d, J=12.3 Hz, 1H), 3.10 (br. s., 1H), 2.95 (br. s., 1H), 1.96-2.06 (m, 1H), 1.21 (t, J=4.1 Hz, 1H), 0.95-1.07 (m, 3H), 0.92 (br. s., 1H), 0.62 (d, J=7.9 Hz, 2H), 0.40 (d, J=4.7 Hz, 2H).

Step W

The same procedure as General procedure 1, step G except using the suitable building blocks described in the "building block" section.

General Procedure 6:

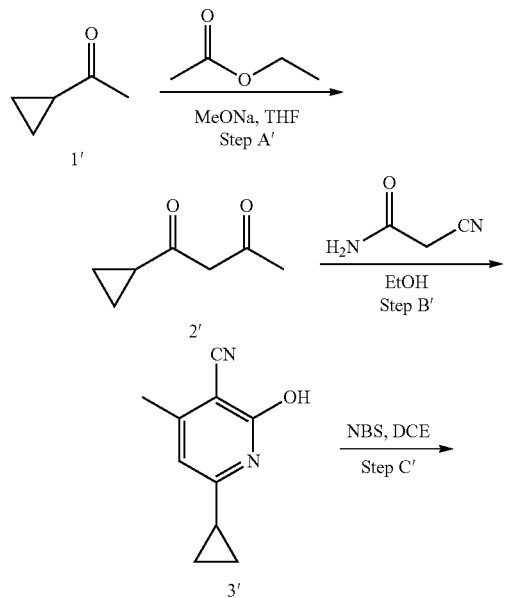

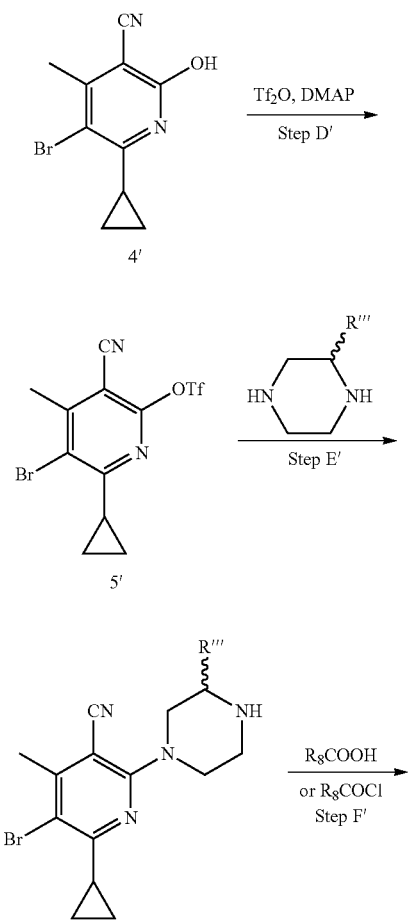

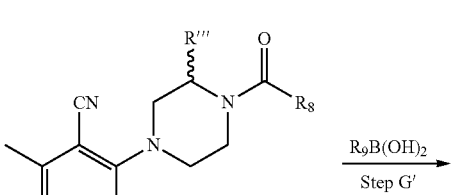

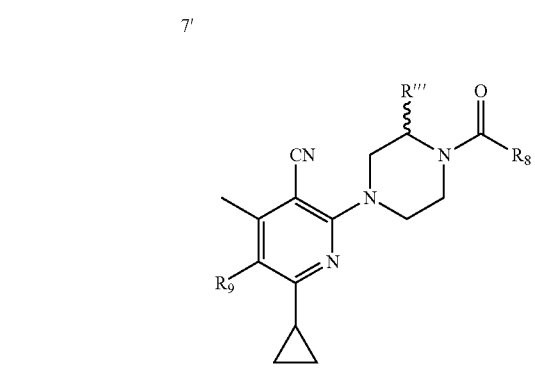

Step A': 1-cyclopropylbutane-1,3-dione

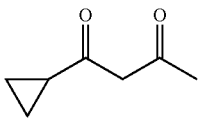

A mixture of CH3ONa (75.65 g, 1.25 mol) and 1-cyclopropylethanone (105.0 g, 1.25 mol) in THF (1000 mL) was stirred at 35° C. for 1 h and followed by addition of ethyl acetate (110.0 g, 1.25 mol) dropwise. After stirring at 50° C. for 4 hrs, the solvent was removed under reduced pressure and the residue was dissolved in H2O 2O (500 mL) and adjusted to pH 3.5 with citric acid. The mixture was extracted by ethyl acetate (500 mL×3). The combined organic layers were concentrated in vacuum to give 1-cyclopropylbutane-1,3-dione (110.0 g, yield 69%) as a yellow oil. $^1$H NMR (CHLOROFORM-d) δ 0.83-0.95 (m, 2H), 1.06-1.10 (m, 2H), 1.54-1.63 (m, 1H), 2.00 (s, 3H).

Step B': 6-cyclopropyl-2-hydroxy-4-methylnicotinonitrile

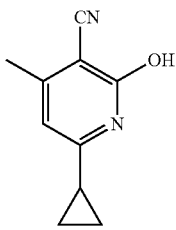

A mixture of 1-cyclopropylbutane-1,3-dione (126.0 g, 1.0 mol) and 2-cyanoacetamide (88.0 g, 1.0 mol) and piperidine (60 mL) in EtOH (1500 mL) was stirred at reflux for 4 hrs. The reaction mixture was filtered, washed with PE (200 mL) and dried in vacuum to give 6-cyclopropyl-2-hydroxy-4-methylnicotinonitrile (90.0 g, 52%) as a white solid. $^1$H NMR (DMSO-d6) δ 12.36 (br. s., 1H), 5.93 (s, 1H), 2.26 (s, 3H), 1.81-1.91 (m, 1H), 1.06-1.14 (m, 2H), 0.91-0.95 (m, 2H).

Step C': 5-bromo-6-cyclopropyl-2-hydroxy-4-methylnicotinonitrile

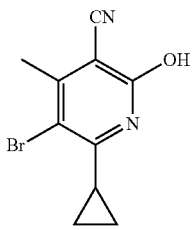

A mixture of 6-cyclopropyl-2-hydroxy-4-methylnicotinonitrile (90.0 g, 0.52 mol) and NBS (100.0 g, 0.57 mol) in DCE (1500 mL) was stirred at reflux temperature for 4 hrs. The reaction mixture was filtered and the residue was washed with DCE (200 mL) and dried in vacuum to give 5-bromo-6-cyclopropyl-2-hydroxy-4-methylnicotinonitrile (100.0 g, 76%) as a white solid. MS (ES) M+H expected 253.0. found 253.0. $^1$H NMR (CHLOROFORM-d) δ 2.68 (s, 3H), 1.79-1.88 (m, 1H), 1.03-1.09 (m, 2H), 0.93-1.01 (m, 2H).

Step D': 5-bromo-3-cyano-6-cyclopropyl-4-methyl-pyridin-2-yl trifluoromethane-sulfonate

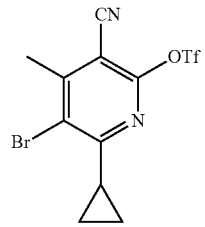 [SMILES: Cc1c(Br)c(C2CC2)nc(OS(=O)(=O)C(F)(F)F)c1C#N]

To a solution of 5-bromo-2-hydroxy-6-isopropylnicotinonitrile (40 g, 0.15 mol) in 200 mL of methylene chloride was added DMAP (1.78 g, 14.6 mmol), and triethylamine (25 mL, 175 mmol). The mixture was cooled to 0° C. in an ice-water bath, and trifluoromethanesulfonic anhydride (37 mL, 0.21 mol) was added dropwise by syringe. The resulting reaction mixture was stirred at 0° C. for 30 min then allowed to warm to room temperature and stirred overnight. After TLC showed the complete conversion of starting material to product, the reaction mixture was concentrated and purified by column chromatography (20% EtOAc/petroleum ether) to afford 55 g of title compound. $^1$H NMR (CHLOROFORM-d) □□2.70 (s, 3H), 2.16-2.20 (m, 1H), 1.23-1.25 (m, 2H), 1.19-1.22 (m, 2H)

Step E': Exemplified by (R)-5-bromo-6-cyclopropyl-4-methyl-2-(3-methylpiperazin-1-yl)nicotinonitrile (R'''=methyl)

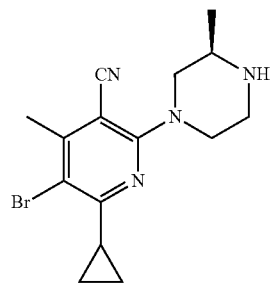 [SMILES: Cc1c(Br)c(C2CC2)nc(N2CCN[C@H](C)C2)c1C#N]

A mixture of 5-bromo-3-cyano-6-cyclopropyl-4-methyl-pyridin-2-yl trifluoromethanesulfonate (50.0 g, 0.13 mol) and (R)-2-methylpiperazine (15.6 g, 0.16 mol) and Et3N (26.0 g, 0.26 mol) in THF (500 mL) was stirred at 80° C. overnight. The resulting mixture concentrated in vacuum to give (R)-5-bromo-6-cyclopropyl-4-methyl-2-(3-methylpiperazin-1-yl) nicotinonitrile (34.8 g, 80%) as a white solid. $^1$H NMR (CHLOROFORM-d) δ 4.08-4.16 (m, 0.5H), 4.05-4.08 (m, 1H), 4.01-4.04 (m, 0.5H), 2.99-3.08 (m, 1H), 2.97 (d, J=8.8 Hz, 2H), 2.88-2.95 (m, 1H), 2.58-2.65 (m, 1H), 2.55-2.57 (m, 3H), 1.77 (br. s., 1H), 1.12 (s, 1.5H), 1.10 (s, 1.5H), 1.05-1.09 (m, 2H), 1.00-1.05 (m, 2H).

Step F': preparation of (R)-5-bromo-6-cyclopropyl-2-(4-(3-methoxypropanoyl)-3-methylpiperazin-1-yl)-4-methylnicotinonitrile

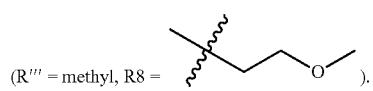

(R''' = methyl, R8 = 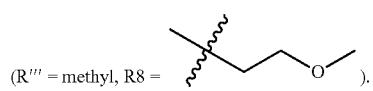).

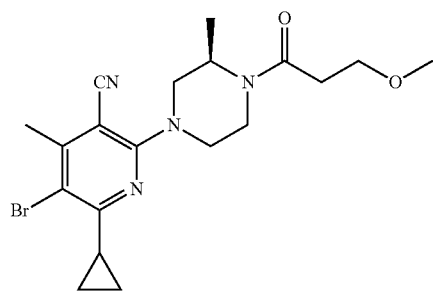

A mixture of (R)-5-bromo-6-cyclopropyl-4-methyl-2-(3-methyl piperazin-1-yl)nicotinonitrile (34.8 g, 0.1 mol) and 3-methoxypropanoic acid (16.0 g, 0.15 mol) in pyridine (500 mL) was stirred at 0° C. for 30 min, and followed by addition of POCl3 (28.7 g, 0.19 mol) dropwise. The resulting mixture was stirred at 20° C. for 2 hrs. The reaction mixture was concentrated and purified by chromatography to give (R)-5-bromo-6-cyclopropyl-2-(4-(3-methoxypropanoyl)-3-methylpiperazin-1-yl)-4-methylnicotinonitrile (25.0 g, 59%) as yellow oil. $^1$H NMR (CHLOROFORM-d) δ 4.90 (br. s., 0.5H), 4.52 (d, J=13.6 Hz, 0.5H), 4.22 (br. s., 0.5H), 3.95-4.13 (m, 2H), 3.78 (br. s., 0.5H), 3.74 (t, J=5.9 Hz, 2H), 3.50-3.61 (m, 0.5H), 3.38 (s, 3H), 3.07-3.24 (m, 1.5H), 2.90-3.06 (m, 1H), 2.65-2.79 (m, 1H), 2.60 (s, 3H), 2.52-2.63 (m, 1H), 2.17-2.21 (m, 1H), 1.37 (d, J=6.5 Hz, 1.5H), 1.27 (d, J=6.3 Hz, 1.5H), 1.09 (s, 2H), 1.05-1.08 (m, 2H).

Step G' was similar to Step H in general procedure 1.

General Procedure 7:

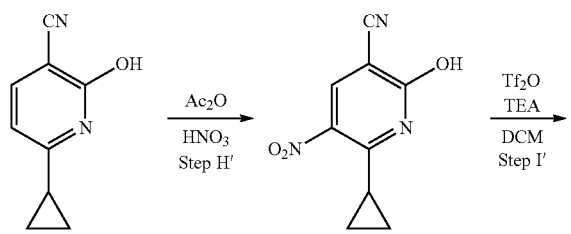

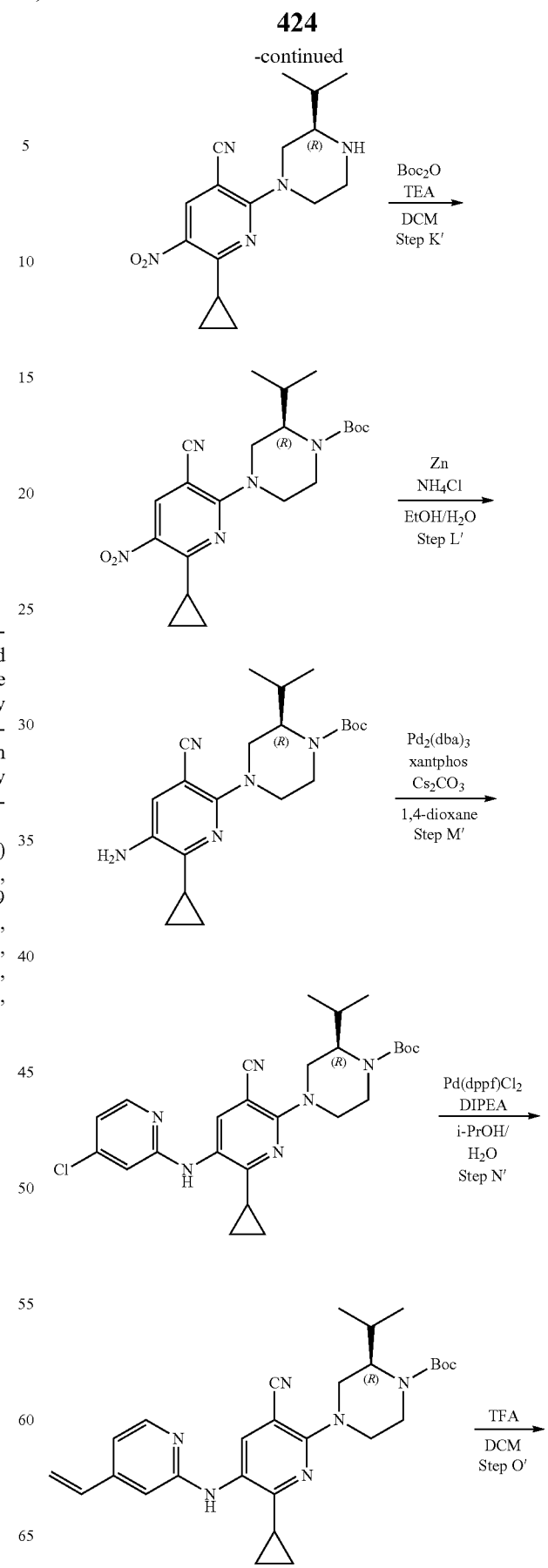

425
-continued

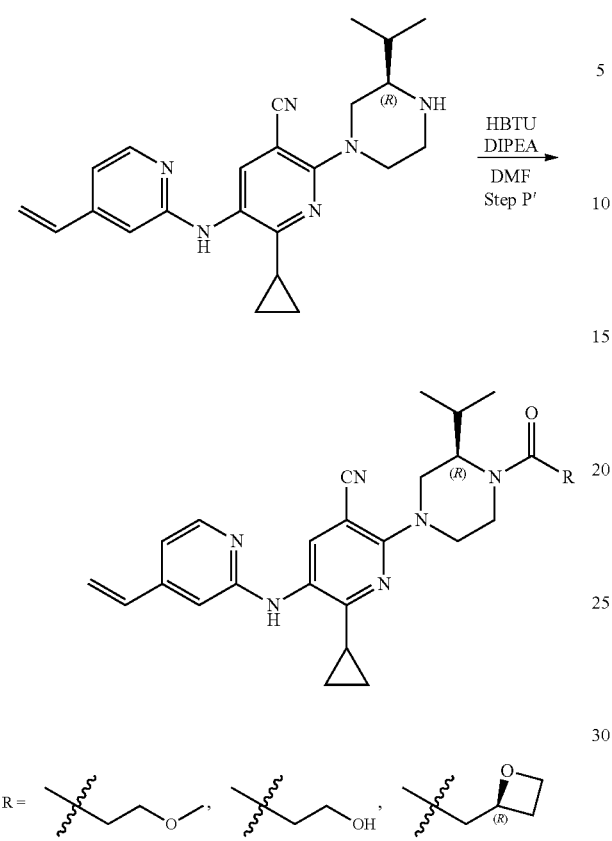

Step H':
6-cyclopropyl-2-hydroxy-5-nitronicotinonitrile

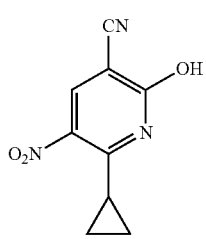 [SMILES: N#Cc1cc([N+](=O)[O-])c(C2CC2)nc1O]

To a solution of 6-cyclopropyl-2-hydroxynicotinonitrile (20 g, 0.125 mmol) in Ac$_2$O (110 mL) was added dropwise HNO$_3$ (15 mL) at 0° C. 40° C. for 30 mins. After the addition, the reaction mixture was stirred at r.t. for 3 hrs. The mixture was cooled to 0° C. and the solid was collected by filtration. The solid was washed with brine dried under vacuum to give the title compound (15.5 g, 60.4%) as a pale yellow solid. $^1$H NMR (CHLOROFORM-d) δ10.71 (s, 1H), 8.68 (s, 1H), 3.13 (tt, J=8.6, 5.6 Hz, 1H), 1.57-1.52 (m, 2H), 1.44-1.37 (m, 2H). LC-MS: m/z 205.9 (M+H)$^+$ 426
Step I': 3-cyano-6-cyclopropyl-5-nitropyridin-2-yl
trifluoromethanesulfonate To a solution of 6-cyclopropyl-2-hydroxy-5-nitronicotinonitrile (7.6 g, 37.7 mmol) in DCM (150 mL) was added DMAP (30.0 mg) and TEA (7.5 g, 74.1 mmol) at r.t. Then Tf$_2$O (15.7 g, 55.6 mmol) was added dropwise to the above solution at −40° C. for 30 min. The reaction mixture was stirred at −40° C. for 2 hs. The mixture was quenched with water at −40° C. The mixture was then extracted with EtOAc (50 mL×2). The combined organic layer was washed with brine, dried over Na$_2$SO$_4$. The organic phase was filtered and the filtrate was concentrated in vacuum to give the title compound (12.5 g, crude) as a pale yellow solid. LC-MS: m/z 337.5 (M+H)$^+$ Step J': (R)-6-cyclopropyl-2-(3-isopropylpiperazin-1-yl)-5-nitronicotinonitrile To a solution of 3-cyano-6-cyclopropyl-5-nitropyridin-2-yl trifluoromethanesulfonate (10.9 g, 32.3 mmol) and (R)-2-isopropylpiperazine (3.45 g, 27.0 mmol) in CH$_3$CN (100 mL) was added TEA (6.5 g, 64.7 mmol) at r.t. The reaction mixture was heated and stirred at 85° C. for 3 hrs. The mixture was concentrated in vacuo and the residue was extracted with EtOAc (50 mL×2). The combined organic layer was washed with brine, dried over Na$_2$SO$_4$. The organic phase was filtered and the filtrate was concentrated in vacuum to give the title compound (8.5 g, crude) as a brown solid. LC-MS: m/z 316.6 (M+H)$^+$

Step K': (R)-tert-butyl 4-(3-cyano-6-cyclopropyl-5-nitropyridin-2-yl)-2-isopropylpiperazine-1-carboxylate

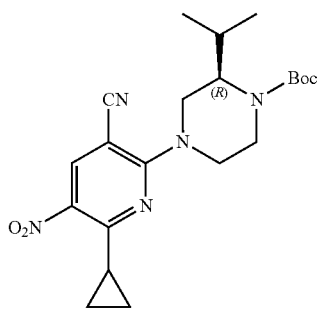

To a solution of (R)-6-cyclopropyl-2-(3-isopropylpiperazin-1-yl)-5-nitronicotinonitrile (8.52 g, 26.2 mmol) and Boc anhydride (8.5 g, 39.3 mmol) in DCM (50 mL) was added TEA (3.9 g, 39.3 mmol) at r.t. The reaction mixture was stirred at 30° C. for 3 hrs. The solvent was removed in vacuum and the residue was purified via silica gel column chromatography (DCM:MeOH) to afford the title compound (10.4 g, 95%) as a yellow liquid. $^1$H NMR (CHLOROFORM-d) δ 8.51 (s, 1H), 4.74 (d, J=13.7 Hz, 1H), 4.55 (d, J=13.1 Hz, 1H), 3.88 (s, 1H), 3.37-3.23 (m, 2H), 3.11 (ddd, J=10.5, 7.7, 5.7 Hz, 2H), 1.86 (tdd, J=13.3, 8.5, 4.9 Hz, 1H), 1.49 (s, 9H), 1.27 (d, J=2.3 Hz, 2H), 1.26-1.17 (m, 4H), 1.01 (d, J=6.6 Hz, 3H), 0.89 (d, J=6.8 Hz, 3H).

Step L': (R)-tert-butyl 4-(5-amino-3-cyano-6-cyclopropylpyridin-2-yl)-2-isopropylpiperazine-1-carboxylate

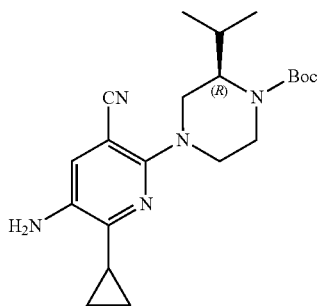

To a solution of (R)-tert-butyl 4-(3-cyano-6-cyclopropyl-5-nitropyridin-2-yl)-2-isopropylpiperazine-1-carboxylate (19 g, 45.8 mmol) in EtOH (200 mL) and H$_2$O (100 mL) was added Zinc (30 g, 458 mmol) and NH$_4$Cl (24.5 g, 458 mmol) at r.t. The reaction mixture was stirred at 40° C. overnight. The mixture was filtered through a pad of silica and the filtrate was extracted with EtOAc (100 mL×2). The combined organic layer was washed with brine, dried over Na$_2$SO$_4$. The organic phase was filtered and the filtrate was concentrated in vacuum to give the title compound (13.1 g, 74.3%) as a yellow solid. $^1$H NMR (CHLOROFORM-d) δ: 7.10 (d, J=2.9 Hz, 1H), 4.02 (t, J=19.0 Hz, 3H), 3.81 (t, J=16.8 Hz, 3H), 3.13 (td, J=12.8, 2.4 Hz, 1H), 2.99-2.86 (m, 2H), 2.25 (tt, J=12.9, 6.5 Hz, 1H), 1.97-1.83 (m, 1H), 1.49 (d, J=2.2 Hz, 9H), 1.13-1.06 (m, 2H), 1.06-1.01 (m, 2H), 0.98 (t, J=9.2 Hz, 3H), 0.87 (t, J=6.6 Hz, 3H).
LC-MS: m/z 386.6 (M+H)$^+$

Step M': (R)-tert-butyl 4-(5-((4-chloropyridin-2-yl)amino)-3-cyano-6-cyclopropylpyridin-2-yl)-2-isopropylpiperazine-1-carboxylate

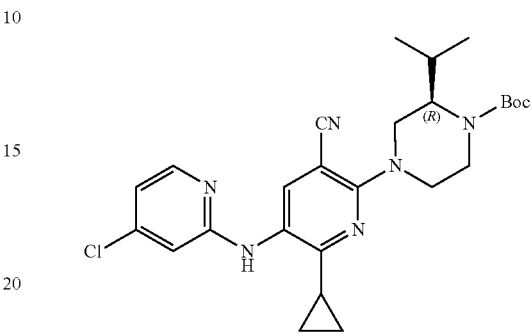

To a solution of (R)-tert-butyl 4-(5-amino-3-cyano-6-cyclopropylpyridin-2-yl)-2-isopropylpiperazine-1-carboxylate (600 mg, 81.6 mmol) and 2-bromo-4-chloropyridine (390.3 mg, 2.03 mmol) in 1,4-dioxane (15 mL) was added Pd$_2$(dba)$_3$ (142.7 mg, 0.156 mmol) and Xantphos (135.3 mg, 0.234 mmol) and Cs$_2$CO$_3$ (1.02 g, 3.12 mmol) at r.t. under N$_2$. The resulting mixture was heated and stirred at 115° C. under N$_2$ in microwave for 1 h. The solvent was removed in vacuum and the residue was purified via reverse phase silica gel column chromatography (MeOH: H$_2$O) to afford the title compound (137 mg, 18%) as a pale yellow solid. $^1$H NMR (CHLOROFORM-d) δ: 8.07 (d, J=5.4 Hz, 1H), 7.72 (d, J=3.3 Hz, 1H), 6.75 (dd, J=5.5, 1.7 Hz, 1H), 6.39 (d, J=1.6 Hz, 1H), 6.25 (s, 1H), 4.45 (d, J=13.2 Hz, 1H), 4.26 (d, J=9.2 Hz, 1H), 4.21-3.61 (m, 2.5H), 3.11 (dt, J=13.5, 6.8 Hz, 2.5H), 2.22-1.98 (m, 2H), 1.52-1.47 (m, 9H), 1.28 (s, 1H), 1.14 (dt, J=8.1, 4.5 Hz, 1H), 1.08 (dd, J=9.7, 4.7 Hz, 1H), 1.01 (dd, J=10.9, 5.2 Hz, 4H), 0.90 (d, J=6.8 Hz, 3H).
LC-MS: m/z 497.6 (M+H)$^+$

Step N': (R)-tert-butyl 4-(3-cyano-6-cyclopropyl-5-((4-vinylpyridin-2-yl)amino)pyridin-2-yl)-2-isopropylpiperazine-1-carboxylate

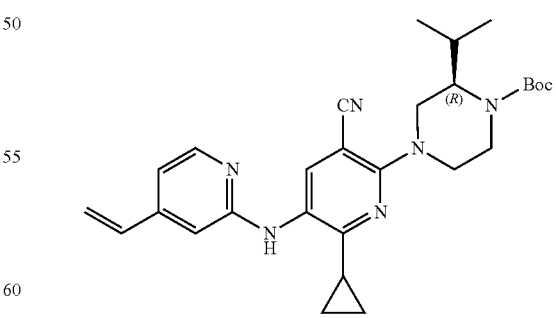

To a solution of (R)-tert-butyl 4-(5-((4-chloropyridin-2-yl)amino)-3-cyano-6-cyclopropylpyridin-2-yl)-2-isopropylpiperazine-1-carboxylate (600 mg, 1.21 mmol) in isopropanol (15 mL) and H$_2$O (3 mL) was added Vinyltrifluoroboric acid potassium salt (324.2 mg, 2.42 mmol), Pd(dppf)Cl₂ (98.7 mg, 0.121 mmol) and DIPEA (312.2 mg, 2.42 mmol) at r.t. under N₂. The reaction mixture was heated and stirred at 125° C. under N₂ in microwave for 1.5 h. The solvent was removed in vacuum and the residue was purified via silica gel column chromatography (DCM: MeOH) to afford the title compound (513 mg, 87%) as a yellow solid.

LC-MS: m/z 489.6 (M+H)⁺

Step O': (R)-6-cyclopropyl-2-(3-isopropylpiperazin-1-yl)-5-((4-vinylpyridin-2-yl)amino)nicotinonitrile

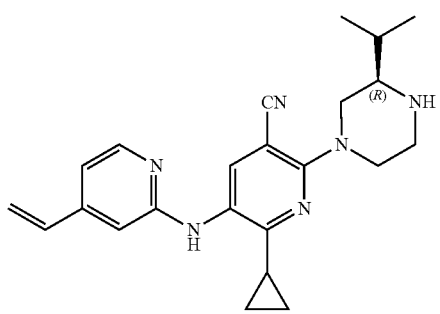

To a solution of (R)-tert-butyl 4-(3-cyano-6-cyclopropyl-5-((4-vinylpyridin-2-yl)amino)pyridin-2-yl)-2-isopropylpiperazine-1-carboxylate (513 mg, 1.05 mmol) in anhydrous DCM (10 mL) was added TFA (5 mL) at r.t. The reaction mixture was stirred at r.t. for 2 hs. The solvent was removed in vacuum and the residue was adjusted to pH>7.0. The residue mixture was extracted with EtOAc (15 mL×2). The combined organic layer was washed with brine, dried over Na₂SO₄. The organic phase was filtered and the filtrate was concentrated in vacuum to give out the title compound (crude, 406 mg) as a yellow liquid. ¹H NMR (CHLOROFORM-d) δ: 7.99 (d, J=6.6 Hz, 1H), 7.72 (s, 1H), 7.04 (dd, J=6.6, 1.3 Hz, 1H), 6.64 (dd, J=17.4, 10.8 Hz, 1H), 6.47 (s, 1H), 6.12 (d, J=17.5 Hz, 1H), 5.81 (d, J=10.8 Hz, 1H), 5.24 (s, 1H), 4.59 (d, J=13.9 Hz, 1H), 4.45 (d, J=14.3 Hz, 1H), 3.63-3.48 (m, 2H), 3.30 (dd, J=14.1, 11.1 Hz, 2H), 3.18 (s, 1H), 2.15-2.01 (m, 2H), 1.28 (d, J=4.8 Hz, 1H), 1.16 (dd, J=10.2, 6.9 Hz, 8H), 1.12-1.09 (m, 1H). LC-MS: m/z 389.5 (M+H)⁺

Step P': (R)-6-cyclopropyl-2-(4-(3-hydroxypropanoyl)-3-isopropylpiperazin-1-yl)-5-((4-vinylpyridin-2-yl)amino)nicotinonitrile (Compound 757)

To a solution of (R)-6-cyclopropyl-2-(3-isopropylpiperazin-1-yl)-5-((4-vinylpyridin-2-yl)amino)nicotinonitrile (300 mg, 0.77 mmol) in DMF (15 mL) was added sodium 3-hydroxypropanoate (208.8 mg, 1.55 mmol), HATU (442.5 mg, 1.2 mmol) and DIPEA (200 mg, 1.55 mmol) at r.t. The reaction mixture was stirred at r.t. for 3 hs. The solvent was removed in vacuum and the residue was purified via silica gel column chromatography (DCM: MeOH) to afford the title compound (138 mg, 38.8%) as a pale yellow solid. ¹H NMR (CHLOROFORM-d) δ: 8.12 (d, J=5.4 Hz, 1H), 7.85 (d, J=5.5 Hz, 1H), 6.84 (d, J=5.4 Hz, 1H), 6.59 (dd, J=17.6, 10.8 Hz, 1H), 6.46 (s, 1H), 6.42 (s, 1H), 5.91 (d, J=17.5 Hz, 1H), 5.48 (d, J=10.9 Hz, 1H), 4.69 (d, J=10.4 Hz, 0.5H), 4.44 (d, J=12.6 Hz, 1.5H), 4.31-4.23 (m, 1H), 3.93 (s, 2H), 3.75 (d, J=13.5 Hz, 0.5H), 3.51-3.38 (m, 2H), 3.14-2.97 (m, 2H), 2.61 (dt, J=5.7, 4.8 Hz, 2H), 2.36-2.25 (m, 0.5H), 2.19 (ddd, J=12.9, 8.1, 4.9 Hz, 1H), 1.29 (t, J=16.6 Hz, 1H), 1.18-0.97 (m, 7H), 0.95-0.88 (m, 1.5H), 0.86 (d, J=6.8 Hz, 1.5H). LC-MS: m/z 461.6 (M+H)⁺

General Procedure 8

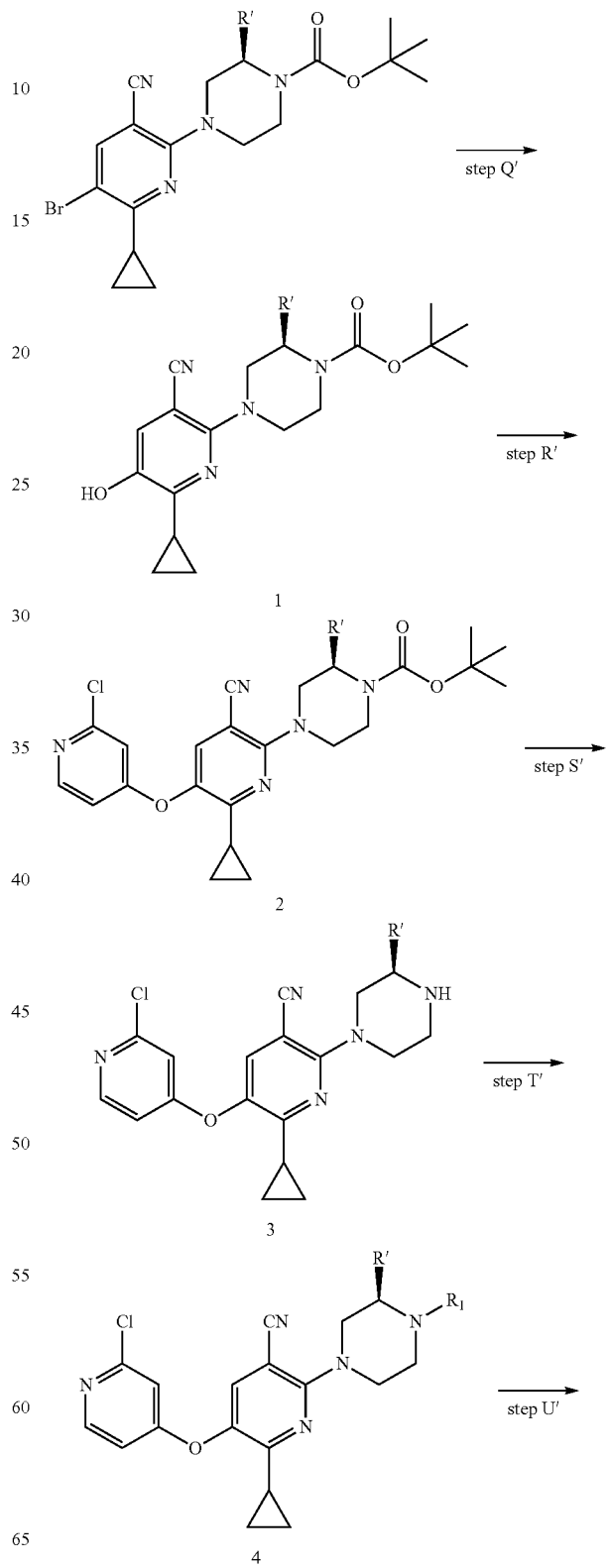

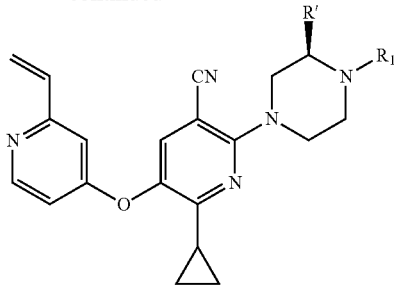

R' = cyclopropyl or methyl

R1 = 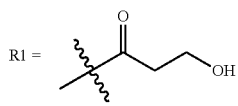

Step Q': ((R)-tert-butyl 4-(3-cyano-6-cyclopropyl-5-hydroxypyridin-2-yl)-2-cyclopropylpiperazine-1-carboxylate

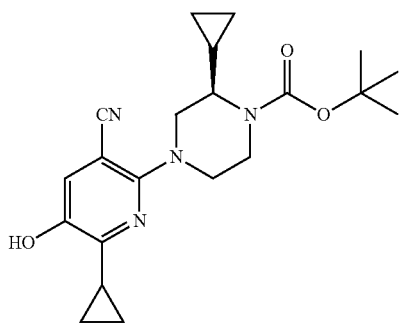 [SMILES: CC(C)(C)OC(=O)N1CCN(c2nc(C3CC3)c(O)cc2C#N)C[C@H]1C1CC1]

To a mixture of (R)-tert-butyl 4-(5-bromo-3-cyano-6-cyclopropylpyridin-2-yl)-2-cyclopropylpiperazine-1-carboxylate (0.35 g, 1.0 mmol), potassium hydroxide (0.22 g, 4 mmol) in a 50 mL flask was added Pd₂(dba)₃ (0.092 g, 0.1 mmol), t-Bu-Xphos (0.082 g, 0.2 mol). Then 10 mL 1,4-dioxane and 1.0 mL water was added, the mixture was stirred at 80° C. for 16 hours, cooled and acidified with 2N HCl to pH 6 (temperature held below 25° C.). Then the mixture was extracted with ethyl acetate (15 mL×2), the organic phase was combined and concentrated to give brown oil, which was further purified by silica gel chromatography (PE:EA=3:1), to give 0.16 g of (1) as a white solid (41% yield). LC-MS: m/z 386.0 (M+H)⁺

Step R': (R)-tert-butyl 4-(5-(2-chloropyridin-4-yloxy)-3-cyano-6-cyclopropylpyridin-2-yl)-2-cyclo propylpiperazine-1-carboxylate

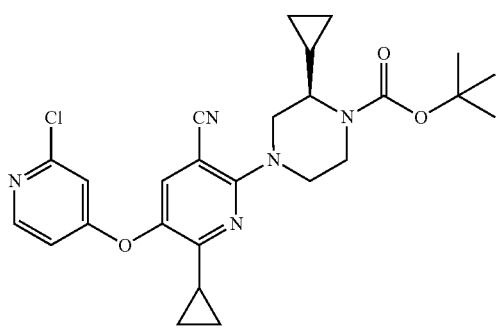 [SMILES: CC(C)(C)OC(=O)N1CCN(c2nc(C3CC3)c(Oc3ccnc(Cl)c3)cc2C#N)C[C@H]1C1CC1]

A mixture of (R)-tert-butyl 4-(5-bromo-3-cyano-6-cyclopropylpyridin-2-yl)-2-cyclopropyl piperazine-1-carboxylate (0.16 g, 0.41 mol), 2-chloro-4-iodopyridine (0.15 g, 0.62 mol), 9 mg Cu(I)Br (0.06 mmol) and 12 mg 2,2,6,6-tetramethylheptane-3,5-dione (0.06 mmol), 0.28 g Cs₂CO₃ was heated under microwave in 4 mL DMSO for 30 min. The mixture was cooled to room temperature and washed with water and purified by silica gel chromatography (DCM:MeOH=20:1) to give 0.10 g of (2) as a yellow solid (52% yield). LC-MS: m/z 486.0 (M+H)⁺

Step S': (R)-5-(2-chloropyridin-4-yloxy)-6-cyclopropyl-2-(3-cyclopropylpiperazin-1-yl)nicotinonitrile

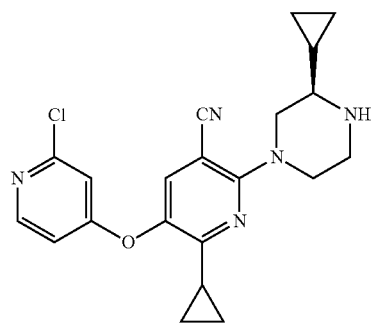 [SMILES: N#Cc1cc(Oc2ccnc(Cl)c2)c(C2CC2)nc1N1CCN[C@H](C2CC2)C1]

A mixture of (R)-tert-butyl 4-(5-(2-chloropyridin-4-yloxy)-3-cyano-6-cyclopropylpyridin-2-yl)-2-cyclo propylpiperazine-1-carboxylate (0.10 g, 0.21 mmol) and TFA (0.35 mL) was stirred in DCM (10 mL) for 2 hrs. The solvent was removed and the residue was basified with NaHCO₃ solution and extracted with DCM (10 mL), the organic phase was separated and concentrated to give a yellow solid (3) (0.075 g, 0.19 mmol, crude yield 90%).
LC-MS: m/z 397.1 (M+H)⁺

Step T': (R)-5-(2-chloropyridin-4-yloxy)-6-cyclopropyl-2-(3-cyclopropyl-4-(3-hydroxypropanoyl)piperazin-1-yl) nicotinonitrile (Compound 694)

A mixture of (R)-5-(2-chloropyridin-4-yloxy)-6-cyclopropyl-2-(3-cyclopropylpiperazin-1-yl) nicotinonitrile (0.35 g, 0.88 mmol), sodium 3-hydroxypropanoate (0.10 g, 0.88 mmol), HATU (0.50 g, 1.32 mmol) and 0.23 g DIEA (1.76 mmol) was stirred in 8 mL DMF for 4 hrs. Then the mixture was quenched by adding 6 mL water and extracted with EA (15 mL×2), the organic phase was combined and concentrated to give a yellow oil, which was further purified by silica gel chromatography (DCM:MeOH=20:1) to give 0.10 g of product as a yellow solid (52% yield). ¹H NMR (CHLOROFORM-d) δ: 8.30 (d, J=5.6 Hz, 1H), 7.48-7.49 (m, 0.5H), 6.81 (dt, J=5.6, 2.0 Hz, 2H), 4.70 (s, 1H), 4.41 (d, J=13.0 Hz, 1H), 4.29 (d, J=13.0 Hz, 1H), 4.12 (dd, J=18.6, 7.4 Hz, 1H), 3.93 (s, 2H), 3.84-3.67 (m, 1H), 3.18 (d, J=12.8 Hz, 1H), 3.13-2.99 (m, 1H), 2.61 (s, 2H), 2.32-2.22 (m, 0.5H), 2.02 (t, J=4.6 Hz, 1H), 1.35 (s, 1H), 1.29 (d, J=9.4 Hz, 3H), 1.14 (dd, J=7.4, 3.0 Hz, 2H), 1.04 (dt, J=7.9, 3.1 Hz, 2H), 0.66-0.67 (m, 2H), 0.46-0.51 (m, 2H). LC-MS: m/z 468.1 (M+H)⁺

Step U': (R)-6-cyclopropyl-2-(3-cyclopropyl-4-(3-hydroxypropanoyl)piperazin-1-yl)-5-(2-vinylpyridin-4-yloxy)nicotinonitrile (Compound 692)

A mixture of (R)-5-(2-chloropyridin-4-yloxy)-6-cyclopropyl-2-(3-cyclopropyl-4-(3-hydroxy propanoyl) piperazin-1-yl)nicotinonitrile (4) 0.35 g, (0.75 mmol), potassium trifluoro(vinyl)borate (0.15 g, 1.1 mmol), PdCl$_2$dppf (80 mg, 0.075 mmol) and DIEA (0.24 mL, 1.5 mmol) was heated in isopropanol at reflux at 85° C. under nitrogen for 5 hrs. Then mixture was then concentrated under reduced pressure to give a yellow solid which was further purified by silica chromatography (PE/EA/MeOH=150/120/8) to give 0.19 g of product as a white solid (55% yield). $^1$H NMR (CHLOROFORM-d) δ: 8.47 (d, J=5.6 Hz, 1H), 7.48-7.49 (m, 0.5H), 6.86 (d, J=2.3 Hz, 1H), 6.77 (dd, J=17.4, 10.8 Hz, 1H), 6.66 (dd, J=5.6, 2.4 Hz, 1H), 6.22 (dd, J=17.4, 0.9 Hz, 1H), 5.53 (dd, J=10.8, 0.8 Hz, 1H), 4.68 (d, J=11.7 Hz, 1H), 4.38 (d, J=12.9 Hz, 1H), 4.30-4.22 (m, 1H), 4.15-4.04 (m, 1H), 3.92 (s, 2H), 3.75 (d, J=20.7 Hz, 1H), 3.47 (d, J=21.7 Hz, 1H), 3.25-3.12 (m, 1H), 3.09-2.95 (m, 1H), 2.60 (s, 2H), 2.32-2.22 (m, 0.5H), 2.11-2.05 (m, 1H), 1.37 (d, J=20.5 Hz, 1H), 1.27 (d, J=2.0 Hz, 1H), 1.16-1.10 (m, 2H), 1.01 (ddd, J=10.1, 6.7, 3.3 Hz, 2H), 0.65 (t, J=33.7 Hz, 2H), 0.45-0.48 (m, 2H). LC-MS: m/z 460.1 (M+H)$^+$ General Procedure 9:

Core 7-1 (120 mg, 0.295 mmol) and amine (0.295 mmol) were dissolved in toluene (2 mL). K3PO4 (125.0 mg, 0.590 mmol), Xantphos (cat.) and Pd2(dba)3(cat.) were added to above mixture under N2. The mixture was shaken at 120□ for 16 hrs. The crude product was purified by prep-HPLC.

Example 15. Building Blocks Syntheses

Building Block 1: (R)-2-cyclopropylpiperazine

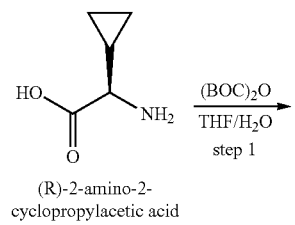

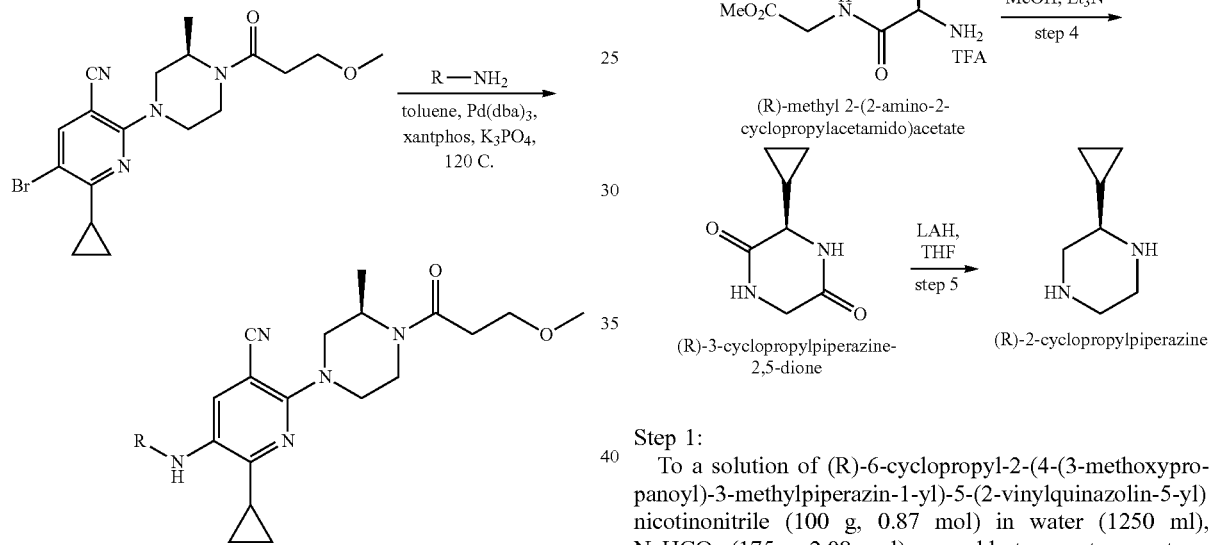

Step 1:
To a solution of (R)-6-cyclopropyl-2-(4-(3-methoxypropanoyl)-3-methylpiperazin-1-yl)-5-(2-vinylquinazolin-5-yl) nicotinonitrile (100 g, 0.87 mol) in water (1250 ml), NaHCO$_3$ (175 g, 2.08 mol) was add at room temperature, then a solution of (Boc)$_2$O in THF (1250 mL) was added and the reaction mixture was heated to reflux overnight. Then the resulting mixture was concentrated to remove THF under reduced pressure. EtOAc (1250 mL) was added to the residue and the resulting mixture was cooled to 5° C. and then adjusted to pH 3 with saturated aqueous NaHSO$_4$. The layers were separated and the aqueous was extracted with EtOAc (1000 mL×3). The combined EtOAc layers were washed with water and brine, dried over Na$_2$SO$_4$ and concentrated under reduced pressure to give (R)-2-(tert-butoxycarbonylamino)-2-cyclopropylacetic acid (165 g, yield 88%). $^1$H NMR (MeOD 400 MHz) □□ 3.16-3.14 (d, J=8.8, 1H), 1.11 (s, 9H), 0.73-0.78 (m, 1H), 0.28-0.2 (m, 3H), 0.18-0.15 (m, 1H) 100 ee %.

Step 2:
Isobutyl chloroformate (81.6 g, 0.6 moL) was added over 1 hr to a stirred mixture of (R)-2-(tert-butoxycarbonylamino)-2-cyclopropylacetic acid (129 g, 0.6 moL) and Et$_3$N (67 g, 0.66 moL) in DCM (1000 mL) at 0° C.-5° C. and the reaction mixture was stirred 1 hr at 0° C.-5° C. In a separate flask, a mixture of glycine methyl ester hydrochloride (82.8 g, 0.66 moL), Et$_3$N (73 g, 0.72 moL) and DCM (1000 mL) was stirred for 1 hr and the mixture was then added to the flask over 2 hrs. After the addition was complete, the mixture was stirred overnight at room temperature for 40 hrs and then washed with water and brine, dried with Na₂SO₄, concentrated under reduced pressure and the residue was purified by column chromatography to give (R)-methyl 2-(2-(tert-butoxycarbonylamino)-2-cyclopropyl acetamido)acetate (100 g, yield 58%) as white solid. 100 ee %. $^1$H NMR (DMSO 400 MHz) □δ 8.2-8.16 (t, J=5.6, 1H), 6.66-6.86 (d, J=8.8, 9H), 3.71-3.92 (m, 2H), 3.62 (s, 3H), 3.46-3.51 (t, J=8.4, 1H), 1.36 (s, 9H), 0.97-1.01 (m, 1H), 0.38-0.44 (m, 3H), 0.25-0.28 (m, 1H).

Step 3:

To a solution of (R)-methyl 2-(2-(tert-butoxycarbonylamino)-2-cyclopropylacetamido) acetate (290 g, 1.014 mol) in DCM (1740 mL), TFA (870 mL) was added dropwise at 0° C. The reaction solution was stirred overnight at room temperature. The resulting solution was concentrated under reduced pressure to give (R)-methyl 2-(2-amino-2-cyclopropylacetamido) acetate (511 g crude).

Step 4:

To a solution (R)-methyl 2-(2-amino-2-cyclopropylacetamido)acetate (255.5 g crude, 0.507 mol) in MeOH (1250 ml), Et₃N (750 ml, 10.78 mol) was added was added dropwise at 0° C. Then the reaction solution was stirred two days at room temperature. The resulting mixture was filtered and the precipitate was washed with MTBE and dried by high vacuum to give (R)-3-cyclopropylpiperazine-2,5-dione (60 g, yield 76.9%). $^1$H NMR (DMSO 400 MHz) δ 7.98 (s, 1H), 7.74 (s, 1H), 3.68-6.64 (d, J=17.6, 1H), 3.30-3.36 (m, 1H), 2.9-2.93 (dd, J=3.2, 1H), 0.87-0.92 (m, 1H), 0.21-0.27 (m, 3H), 0.18-0.21 (m, 1H).

Step 5:

To a suspension mixture of (R)-3-cyclopropylpiperazine-2,5-dione (30 g, 0.195 mmol) in THF (1000 mL), AlLiH₄ (45 g, 1.184 mol) was added in portions over 1.5 hrs at 0° C. Then the reaction mixture was heated to 70° C. overnight. After cooling, water (45 mL) was added dropwise at 0° C. and then a solution of KOH (45 mL, 1%) was added dropwise at 0° C. The resulting mixture was filtered and the residue was washed with EtOAc and MeOH (3:1) and the filtrate was concentrated under reduced pressure to give crude product. Then the crude product was washed with DCM and the filtrate was concentrated under reduced pressure to give (R)-2-cyclopropylpiperazine (18.5 g, yield 75.5%). 99.5 ee %. $^1$H NMR (MeOD 400 MHz) δ 2.9-2.96 (m, 1H), 2.8-2.88 (m, 1H), 2.7-2.8 (m, 1H), 2.55-2.68 (m, 2H), 2.4-2.5 (q, J=10.4, 1H), 1.65-1.73 (m, 1H), 0.55-0.67 (m, 1H), 0.35-0.45 (m, 2H), 0.05-0.25 (m, 2H).

Building Block 2: 2-(2,2,2-trifluoroethyl)piperazine

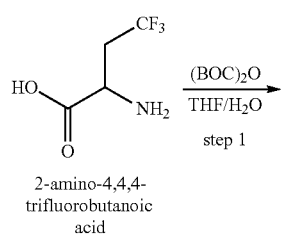

2-amino-4,4,4-trifluorobutanoic acid

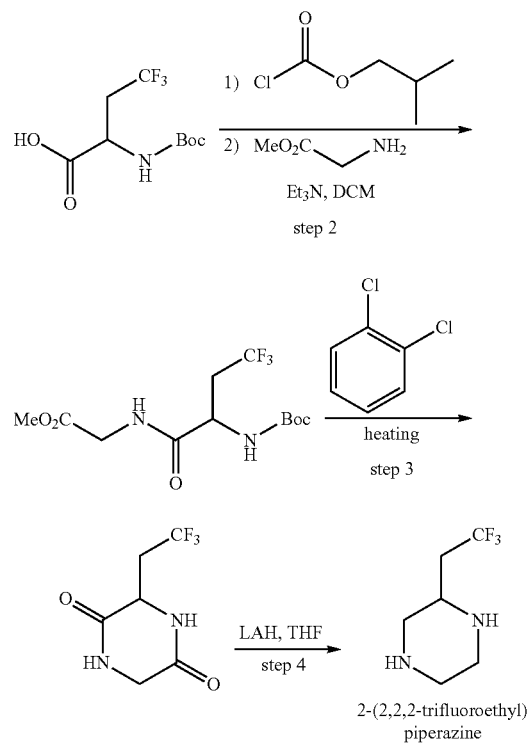

2-(2,2,2-trifluoroethyl) piperazine

Step 1:

To a solution of 2-amino-4,4,4-trifluorobutanoic acid (450 m g, 3 mmol) in 5 mL H₂O and 5 mL THF was added NaHCO₃ (504 mg, 6 mmol), followed by a solution of di-tert-butyl dicarbonate (650 mg, 3 mmol) in THF (3 mL). The resulting mixture was stirred at 80° C. overnight. After removal of THF, poured into water and extracted with methylene chloride. The combined organic layer was dried over anhy. Na₂SO₄ and concentrated in vacuo. 723 mg of 2-(tert-butoxycarbonylamino)-4,4,4-trifluorobutanoic acid was obtained as a crude product and used in subsequent reaction without further purification. MS (ES) M+H expected 258. found 258. 1H NMR (CHLOROFORM-d) δ □ 5.25 (d, J=7.8 Hz, 1H), 4.40-4.67 (m, 1H), 2.60-2.90 (m, 2H), 1.46 (s, 9H).

Step 2:

To a 25 mL of round-bottom flask was added 2-(tert-butoxycarbonylamino)-4,4,4-trifluorobutanoic acid (723 mg, 2.8 mmol), Et₃N (560 mg, 5.6 mmol), isobutyl carbonochloridate (380 g, 2.8 mmol) in 5 mL methylene chloride. The resulting reaction mixture was stirred at 0° C. for 0.5 hours. And methyl 2-aminoacetate (352 mg, 2.8 mmol) was added. The resulting mixture was stirred at room temperature overnight. After washing with Satd. NaHCO₃, brine, the combined organic layer was dried over anhy. Na₂SO₄ and concentrated in vacuo. 900 mg of methyl 2-(2-(tert-butoxycarbonylamino)-4,4,4-trifluorobutanamido)acetate was obtained as a crude product and used in subsequent reaction without further purification. MS (ES) M+H expected 329.1. found 329.0. 1H NMR (CHLOROFORM-d) δ 7.11 (br. s., 1H), 5.28 (br. s., 1H), 4.44-4.67 (m, 1H), 3.84-4.07 (m, 2H), 3.69-3.83 (s, 3H), 2.72-2.95 (m, 1H), 2.42-2.64 (m, 1H), 1.38-1.50 (m, 9H).

Step 3:

A mixture of methyl 2-(2-(tert-butoxycarbonylamino)-4,4,4-trifluorobutanamido)acetate (900 mg, 2.7 mmol) in 5 mL 1,2-dichlorobenzene was heated to 180° C. overnight. The mixture was cooled down and was added MTBE (5 mL). A brown yellowish precipitate was formed. The filter cake was washed with MTBE and air-dried to give 200 mg of 3-(2,2,2-trifluoroethyl)piperazine-2,5-dione. 1H NMR (DMSO-d6) δ 8.28 (d, J=9.3 Hz, 2H), 4.00-4.26 (m, 1H), 3.68-3.87 (m, 2H), 2.66-2.88 (m, 2H).

Step 4:

To a flask was added 3-(2,2,2-trifluoroethyl)piperazine-2,5-dione (200 mg, 1 mmol) in THF (5 mL), and LAH (2.5 mL, 6 mmol) was added dropwise under $N_2$ at 0° C. And the mixture was heated to 65° C. overnight. After reaction, the mixture was cooled down. And 0.23 mL $H_2O$ was added followed by 0.2×3 mL 10% NaOH and 0.46 mL $H_2O$, and the mixture was filtered. The cake was washed with EtOAc. The organic phase was concentrated to give 2-(2,2,2-trifluoroethyl)piperazine 140 mg, which was used without further purification. 1H NMR (CHLOROFORM-d) δ 2.75-3.02 (m, 7H), 2.52 (dd, J=11.7, 9.9 Hz, 1H), 2.10-2.17 (m, 2H).

Building Block 3: 2-(difluoromethyl)piperazine

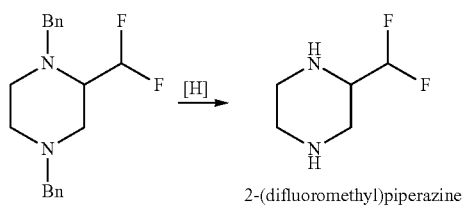

2-(difluoromethyl)piperazine

To a solution of 1,4-dibenzyl-2-(difluoromethyl)piperazine (synthesized according to *Synthetic Communications*, 2011, vol. 41, #14, 2031-2035)(80 mg, 0.253 mmol) in 40 mL of EtOH was added Pd(OH)$_2$/C (15 mg). The resulting mixture was hydrogenated under 50 Psi at r.t. for two days. The reaction mixture was filtered, and the filtrate was concentrated to afford 2-(difluoromethyl)piperazine, which was used directly without further purification. LC-MS: m/z 137.1 (M+H)$^+$ Building Block 4: 6-fluoro-1,4-diazepane

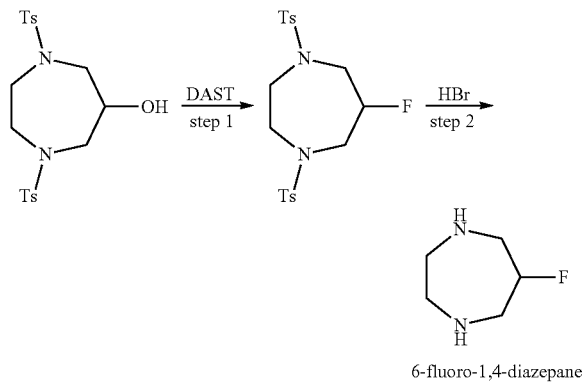

6-fluoro-1,4-diazepane

Step 1:

To a solution of 1,4-ditosyl-1,4-diazepan-6-ol (synthesized according to *Synthesis*, 2003, 2, 223-226) (200 mg, 0.47 mmol) in 5 mL of DCM was added DAST (190 mg, 1.18 mmol). The resulting mixture was stirred at r.t. overnight. The reaction mixture was quenched with aq NaHCO$_3$. The aqueous layer was extracted with DCM and the combined organic phases were dried and concentrated. The residue was purified by prep-TLC to afford 6-fluoro-1,4-ditosyl-1,4-diazepane (120 mg). $^1$H NMR (CHLOROFORM-d) δ 7.66-7.71 (m, 4H), 7.34 (d, J=8.0 Hz, 4H), 5.02-4.92 (m, 1H), 3.60 (dd, J=18.1, 5.3 Hz, 4H), 3.34-3.53 (m, 4H), 2.46 (s, 6H).

Step 2:

A suspension of 6-fluoro-1,4-ditosyl-1,4-diazepane (82 mg, 0.19 mmol) in HOAc—HBr (3 mL, 30 wt %) was heated to 100° C. for 3 mins in a pressure tube using microwave irradiation. The solvent was removed in vacuum and the residue triturated with Et$_2$O, washed with Et$_2$O to give 6-fluoro-1,4-diazepane, which was used directly without further purification. LC-MS: m/z 119.1 (M+H)$^+$ Building Block 5: 6-fluoro-2-methyl-1,4-diazepane

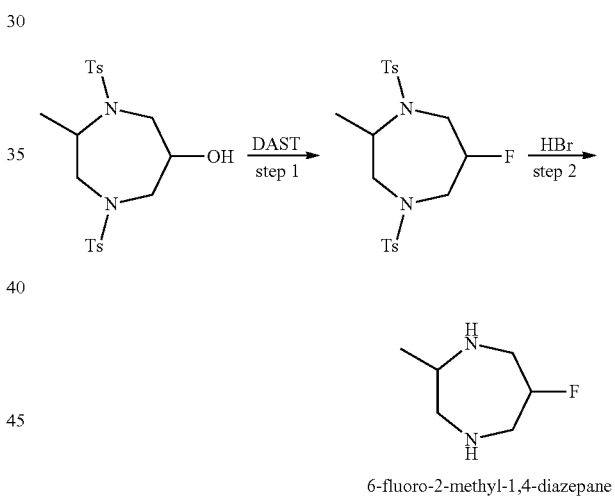

6-fluoro-2-methyl-1,4-diazepane

Step 1:

6-fluoro-2-methyl-1,4-ditosyl-1,4-diazepane (120 mg) was obtained from 2-methyl-1,4-ditosyl-1,4-diazepan-6-ol (synthesized according to *Synthesis*, 2003, 2, 223-226) (200 mg, 0.47 mmol) (200 mg) by the method similar to 6-fluoro-1,4-ditosyl-1,4-diazepane. $^1$H NMR (CHLOROFORM-d) δ 7.62-7.75 (m, 4H), 7.30-7.37 (m, 4H), 5.00-4.84 (m, 1H), 4.09-4.37 (m, 2H), 3.73-3.95 (m, 1H), 3.37-3.62 (m, 2H), 3.12-3.32 (m, 1H), 3.05 (ddd, J=13.6, 7.2, 4.0 Hz, 1H), 2.43-2.46 (m, 6H), 1.05-1.14 (m, 3H).

Step 2:

6-fluoro-2-methyl-1,4-diazepane was obtained from 6-fluoro-2-methyl-1,4-ditosyl-1,4-diazepane by the method similar to 6-fluoro-1,4-ditosyl-1,4-diazepane. LC-MS: m/z 133.1 (M+H)$^+$ Building Block 6: 2-(oxetan-2-yl)acetic acid

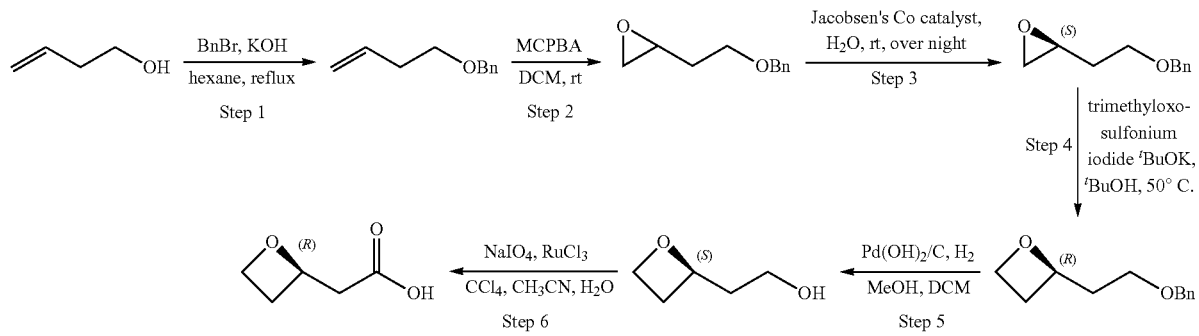

Step 1:
A mixture of 3-buten-1-ol (18.03 g, 0.25 mol), TEA (2.4 mL, 0.02 mol) and sodium hydroxide (15 g, 0.38 mol) in hexane (200 mL) was stirred at 50° C. for 0.5 h. Benzyl bromide (32.7 mL, 0.27 mol) in hexane (50 mL) was added dropwise over a period of 0.5 h. Afterwards, the resulting mixture was heated to reflux overnight (oil temperature: 85° C.). The precipitate was removed via filtration and washed with ethyl acetate twice. The combined organic phase was washed with brine and dried over sodium sulfate. Such obtained product was pure enough for the next reaction step. Yield: 38.21 g, 94.2%, colorless oil. $^1$H NMR (400 MHz, CDCl$_3$) δ 7.46-7.29 (m, 6H), 5.89 (ddt, J=17.0, 10.1, 6.7 Hz, 1H), 5.21-5.03 (m, 2H), 4.56 (s, 2H), 3.57 (t, J=6.8 Hz, 2H), 2.43 (qd, J=6.7, 1.1 Hz, 2H).

Step 2:
To solution of ((but-3-en-1-yloxy)methyl)benzene (38.21 g, 0.24 mol) in dichloromethane (400 mL) was added mCPBA (77.15 g, 0.38 mol) at −20° C. as solid in portions. Afterwards, the resulting suspension was allowed to warm to rt and stirred overnight. The precipitate was filtered off and washed with dichloromethane. Afterwards, the combined organic phase was washed with saturated NaHCO3 and Na2SO3 and brine. The white precipitate was occurred while removing solvents under reduced pressure. More n-hexane was added and the most appeared white solid was filtered off. This procedure was repeated third times. The crude product was subjected to column chromatography on silica gel using a mixture of ethyl acetate with petroleum ether as eluent (EtOAc:PE=1/50 to 1/5) to afford the title compound. Yield: 35.26 g, 84.0%, pale yellow oil. $^1$H NMR (400 MHz, CDCl$_3$) δ 7.41-7.29 (m, 5H), 4.56 (s, 2H), 3.73-3.59 (m, 2H), 3.15-3.06 (m, 1H), 2.85-2.77 (m, 1H), 2.55 (dd, J=5.0, 2.7 Hz, 1H), 1.95 (dddd, J=13.4, 7.2, 6.2, 4.7 Hz, 1H), 1.81 (dq, J=14.3, 5.9 Hz, 1H). LC-MS: m/z 220.0 (M+CH$_3$CN)$^+$.

Step 3:
To a round bottom flask charged with HOAc (60.1 mg, 1.0 mol %) in toluene (20 mL) was added Jacobsen salen Co(II) catalyst (0.30 g, 0.5 mol %) at rt and the resulting solution was stirred at rt for 0.5 h while the flask is open to air in order to absorb oxygen. The volatiles were removed under reduced pressure to give rise to a dark solid. Racemic epoxide (17.82 g, 100 mmol) was added neat, followed by the addition of distilled water (1.0 mL, 56 mmol) dropwise at 0° C. The resulting reaction mixture was allowed to warm to rt slowly and stirred at rt overnight. The reaction mixture was diluted with n-hexane and then passed through a pad of celite. Epoxide was obtained by using petroleum ether and diol was obtained by using a mixture of methanol with dichloromethane (1/30). The obtained epoxide (red oil) was distilled and the desired product was obtained at 145-165° C. (oil temperature); similarly, the diol was obtained at 185-205° C. (oil temperature). Yield of epoxide: 7.83 g, 43.9%, pale yellow oil; Yield of diol: 8.46 g, 43.1%, bright yellow oil. For chiral epoxide: $^1$H NMR (400 MHz, CDCl$_3$) δ 7.41-7.29 (m, 5H), 4.56 (s, 2H), 3.73-3.59 (m, 2H), 3.15-3.06 (m, 1H), 2.85-2.77 (m, 1H), 2.55 (dd, J=5.0, 2.7 Hz, 1H), 1.95 (dddd, J=13.4, 7.2, 6.2, 4.7 Hz, 1H), 1.81 (dq, J=14.3, 5.9 Hz, 1H). LC-MS: m/z 220.0 (M+CH$_3$CN)$^+$. For chiral diol: $^1$H NMR (400 MHz, CDCl$_3$) δ 7.41-7.29 (m, 5H), 4.53 (s, 2H), 3.94 (s, 1H), 3.86-3.41 (m, 5H), 3.18 (s, 1H), 1.91-1.66 (m, 2H). LC-MS: m/z 219.0 (M+Na)$^+$. ee>99%.

Step 4:
A mixture of potassium tert-butoxide (1.68 g, 15 mmol) and trimethyloxosulphonium iodide (3.30 g, 15 mmol) in tert-butoxide (35 mL) was stirred at 50° C. for 1 h. A solution of chiral epoxide (0.89 g, 5 mmol) in tert-butoxide (15 mL) was added dropwise while keeping the temperature around 50° C. Afterwards, the resulting reaction mixture was stirred at 50° C. overnight. The precipitate was removed via filtration and washed with ethyl acetate. The combined organic phase was dried under reduced pressure and diluted with ethyl acetate. The diluted solution was washed with brine and dried over sodium sulfate. The crude product was subjected to column chromatography on silica gel using EtOAc:PE=1/10 as eluent to afford the title compound. Yield: 0.55 g, 57.7%; colorless oil. $^1$H NMR (400 MHz, CDCl$_3$) δ 7.41-7.29 (m, 5H), 5.09-4.94 (m, 1H), 4.70 (dd, J=14.0, 7.8 Hz, 1H), 4.62-4.38 (m, 3H), 3.67-3.51 (m, 2H), 2.72 (dq, J=13.9, 7.8 Hz, 1H), 2.43 (dt, J=10.7, 7.6 Hz, 1H), 2.16 (td, J=13.3, 5.8 Hz, 1H), 2.02 (td, J=13.6, 6.0 Hz, 1H). LC-MS: m/z 234.1 (M+CH3CN)$^+$. ee>99%.

Step 5:
A mixture of (R)-2-(2-(benzyloxy)ethyl)oxetane (4.35 g, 22.63 mmol) and palladium hydroxide on carbon (20%, with 50% of water, 0.80 g, 2.5 mol %) in methanol (50 mL) and dichloromethane (15 mL) was stirred at rt overnight with an input of hydrogen gas. The precipitate was removed via filtration through a pad of celite and washed with dichloromethane. The combined organic phase was dried using water pump at 30° C. and was confirmed pure enough for the next reaction. Yield: 2.28 g, 98.7%; colorless oil. $^1$H NMR (400 MHz, CDCl$_3$) δ 5.09 (qd, J=7.5, 4.6 Hz, 1H), 4.70 (td, J=8.0, 6.0 Hz, 1H), 4.57 (dt, J=9.1, 5.9 Hz, 1H), 3.82 (ddd, J=11.8, 7.3, 4.6 Hz, 1H), 3.74 (ddd, J=11.1, 6.5, 4.9 Hz, 1H), 3.11-2.77 (m, 1H), 2.77-2.62 (m, 1H), 2.45 (ddt, J=11.0, 9.1, 7.4 Hz, 1H), 2.13-1.98 (m, 1H), 1.91 (ddt, J=14.3, 7.3, 4.7 Hz, 1H). ee>99%.

Step 6:

To a mixture of oxetane (3.10 g, 30.48 mmol), sodium periodate (19.56 g, 91.44 mmol), water (30 mL), acetonitrile (60 mL) and carbon tetrachloride (30 mL) was added ruthenium trichloride plus three water (79.7 mg, 1 mol %) at 0-5° C. Afterwards, the resulting mixture was allowed to warm to rt and stirred at this temperature for 2 h. The precipitate was removed via filtration through a pad of celite and washed with diethyl ether (around 100 mL×5). The combined organic phase was washed with brine (50 mL×3) and then dried using water pump at 35° C. and was confirmed pure enough for the next reaction. Yield: 2.26 g, 63.8%; light yellow oil. $^1$H NMR (400 MHz, methanol-d4) δ 5.26-5.15 (m, 1H), 4.69 (ddd, J=8.3, 7.8, 5.9 Hz, 1H), 4.58 (dt, J=9.2, 5.9 Hz, 1H), 2.88-2.70 (m, 3H), 2.51 (ddt, J=11.2, 9.1, 7.3 Hz, 1H). ee>99%.

Building Block 7: 5-bromoisoquinoline 2-oxide

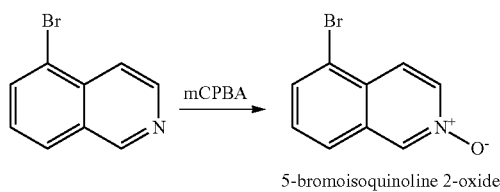 [SMILES: Brc1cccc2cnccc12 ; [O-][n+]1ccc2c(Br)cccc2c1]

5-bromoisoquinoline 2-oxide

To a solution of 5-bromoisoquinoline (1.5 g, 7.2 mmol) in dichloromethane (20 mL) was added mCPBA (1.5 g, 8.6 mmol) at room temperature all at once. The reaction mixture was stirred at room temperature for 2 h. Then the mixture was washed with water (20 mL) and brine (20 mL), dried over Na$_2$SO$_4$. The solvent was removed and the residue was purified by column chromatography over silica gel (EtOAc) to give 0.97 g of title compound as a pale yellow solid.

$^1$H NMR (CHLOROFORM-d) δ 8.71-8.80 (m, 1H), 8.22 (dd, J=7.3, 1.5 Hz, 1H), 8.06 (d, J=7.3 Hz, 1H), 7.81-7.91 (m, 1H), 7.70 (d, J=8.2 Hz, 1H), 7.43-7.54 (m, 1H). LC-MS: m/z 222.9 (M+H)$^+$

Building Block 8: 5-bromo-1-chloroisoquinoline

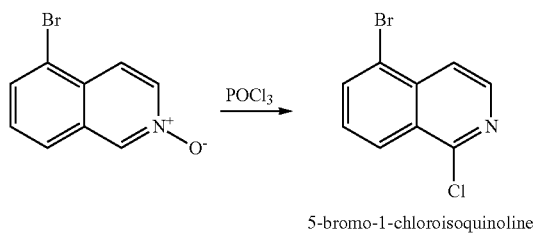

5-bromo-1-chloroisoquinoline

To a solution of 5-bromoisoquinoline 2-oxide (0.4 g, 2.4 mmol) in CHCl$_3$ (10 mL) was added POCl$_3$ (0.7 mL, 3 eq). Then the mixture was refluxed for 2 h. After cooling to room temperature, the reaction mixture was poured into ice-water, neutralized with saturated NaHCO3 (aq), extracted with EtOAc. The solvent was removed and 0.45 g crude product was obtained which was used in next step with further purification. $^1$H NMR (CHLOROFORM-d) δ 8.33-8.44 (m, 2H), 8.02-8.08 (m, 1H), 8.00 (d, J=5.6 Hz, 1H), 7.52-7.61 (m, 1H). LC-MS: m/z 242.9 (M+H)$^+$.

Building Block 9: 5-bromo-1-methoxyisoquinoline

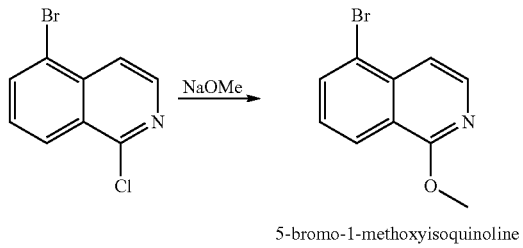

5-bromo-1-methoxyisoquinoline

To a solution of 5-bromo-1-chloroisoquinoline (1.2 g, 5.0 mmol) in methanol (10 mL) was added NaOMe (324 mg, 6.0 mmol). The mixture was refluxed for 2 h. The solvent was removed and the residue was purified by column chromatography over silica gel (10-20% EtOAc/petroleum ether) to obtain 600 mg of title compound as a white solid. $^1$H NMR (DMSO-d$_6$) δ 8.26 (d, J=8.3 Hz, 1H), 8.12 (d, J=6.0 Hz, 1H), 7.95 (dd, J=7.5, 1.0 Hz, 1H), 7.58 (d, J=6.0 Hz, 1H), 7.41 (t, J=7.9 Hz, 1H), 4.17 (s, 3H). LC-MS: m/z 237.0 (M+H)$^+$ Building Block 10: 5-bromo-1-methoxyisoquinoline

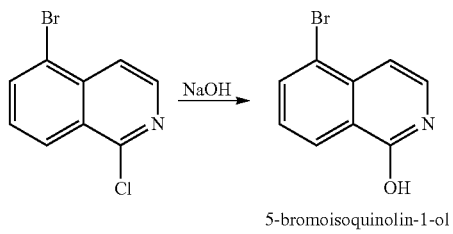

5-bromoisoquinolin-1-ol

To a suspension of 5-bromo-1-chloroisoquinoline (300 mg, 1.2 mmol) in water (10 mL) was added NaOH (240 mg, 6 mmol). The mixture was refluxed for 2 h. After cooling to room temperature, the pH of the mixture was adjusted to 7 with 2N HCl. The precipitate was filtered and dried to get 205 mg crude product as a white solid which was used directly in next step. LC-MS: m/z 222.9 (M+H)$^+$ Building Block 11: 5-bromo-1-methoxyisoquinoline

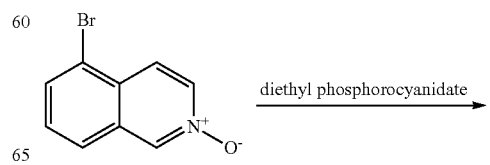

Building Block 13:
4-chloro-2-vinyl-1,7-naphthyridine

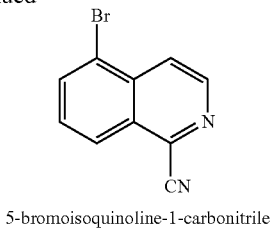

5-bromoisoquinoline-1-carbonitrile

A mixture of 5-bromoisoquinoline 2-oxide (224 mg, 1.0 mmol), diethyl phosphorocyanidate (489 mg, 3.0 mmol) and Et3N (101 mg, 1.0 mmol) in CH3CN (5 mL) was heated at 150° C. for 1.5 h in a microwave oven. After cooling to room temperature, the precipitate was filtered and dried to obtain 110 mg product as a yellow solid. $^1$H NMR (CHLOROFORM-d) δ 8.79 (d, J=5.8 Hz, 1H), 8.38 (d, J=8.5 Hz, 1H), 8.29 (d, J=5.8 Hz, 1H), 8.14 (d, J=7.5 Hz, 1H), 7.70 (t, J=7.9 Hz, 1H). LC-MS: m/z 231.9 (M+H)$^+$

Building Block 12: 5-bromo-3-chloroisoquinoline

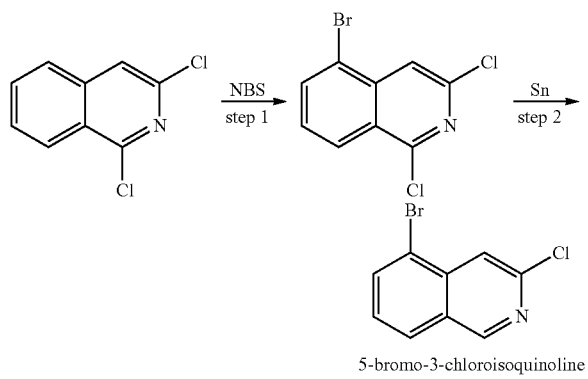

5-bromo-3-chloroisoquinoline

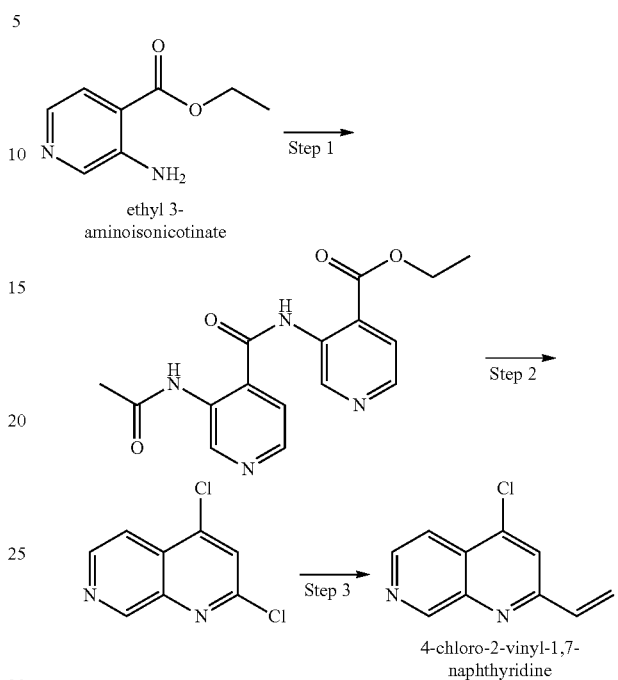

4-chloro-2-vinyl-1,7-naphthyridine

Step 1:

To a solution of 1,3-dichloroisoquinoline (4 g, 20.2 mmol) in CH3CN (100 mL) was added H2SO4 (4 mL), followed by NBS (4.4 g, 24.2 mmol). The mixture was stirred at room temperature for 90 h. Then the precipitate was collected by filtration, washed with water, dried to afford 3.4 g of 5-bromo-1,3-dichloroisoquinoline as a pale yellow solid. $^1$H NMR (CHLOROFORM-d) δ 8.33 (d, J=8.5 Hz, 1H), 8.03-8.10 (m, 2H), 7.56 (dd, J=8.4, 7.7 Hz, 1H). LC-MS: m/z 276.9 (M+H)$^+$ Step 2:

To a suspension of 5-bromo-1,3-dichloroisoquinoline (3 g, 10.8 mmol) in AcOH (30 mL) and conc. HCl (6 mL) was added Sn powder (3.86 g, 32.4 mmol). The mixture was stirred at 60° C. for 20 min. After cooling to room temperature, the mixture was neutralized with NaOH (aq), filtered through celite. The filtrate was extracted with EtOAc (2×30 mL). The solvent was removed and the residue was purified by column chromatography over silica gel (5-10% EtOAc/petroleum ether) to afford 0.8 g of 5-bromo-3-chloroisoquinoline as a white solid. $^1$H NMR (CHLOROFORM-d) δ 9.04 (s, 1H), 8.04 (s, 1H), 7.90-8.02 (m, 2H), 7.47 (t, J=7.9 Hz, 1H).

Step 1:

To a stirred solution of ethyl-2-aminonicotinate (1 g, 6.02 mmol) and ethyl acetate (13 g, 147.7 mmol) in 15 mL of anhydrous THF was added sodium tert-butoxide (1.45 g, 15.1 mmol) portionwise over 1 min. The resulting mixture was stirred at room temperature for 40 mins and at 100° C. for 4 hours. After this time the reaction was cooled to r.t. and evaporated in vacuo. The resulting solid was dissolved in water (20 mL) and neutralized to pH 7 with 1.0M aqueous HCl. The resulting solid was filtered and dried under vacuum overnight to give ethyl 3-(3-acetamidoisonicotinamido)isonicotinate as a tan solid (0.58 g, 59%). LC-MS: m/z 329.1 (M+H)$^+$ $^1$H NMR (CHLOROFORM-d) δ: 11.96 (s, 1H), 10.74 (br. s., 1H), 10.12 (s, 1H), 9.99 (s, 1H), 8.56 (d, J=5.3 Hz, 1H), 8.59 (d, J=5.0 Hz, 1H), 7.89-7.96 (m, 1H), 7.66 (d, J=5.3 Hz, 1H), 4.51 (q, J=7.0 Hz, 2H), 2.24-2.33 (m, 3H), 2.19 (s, 2H), 1.43-1.54 (t, 3H).

Step 2:

A stirred solution of ethyl 3-(3-acetamidoisonicotinamido)isonicotinate (400 mg, 2.47 mmol) in phosphorus oxychloride (2.5 mL) was heated to 120° C. for 3 hours. After this time the reaction was cooled to r.t. and evaporated in vacuo. The resulting residue was carefully basified to pH>10 with an aqueous solution of Na2CO3 and the resulting solid was filtered, washed with water and dried under vacuum to give 2,4-dichloro-1,7-naphthyridine (200 mg, 83%). $^1$H NMR (CHLOROFORM-d) δ: 9.48 (s, 1H), 8.79 (d, J=5.9 Hz, 1H), 8.01 (d, J=5.9 Hz, 1H), 7.74 (s, 1H). LC-MS: m/z 200 (M+H)$^+$ Step 3:

To 5 mg PdCl2(dppf).CH2Cl2 in a reaction tube under nitrogen were added 3 mL isopropanol, 1 mL water, 93.6 mg (0.8 mmol) DIPEA, 52 mg (0.39 mmol) potassium vinyl trifluoroborate and 78 mg (0.39 mmol) 4-chloro-2-vinyl-1, 7-naphthyridine. The reaction solution was heated to 100° C. for half hour under microwave irradiation. The reaction mixture was extracted into ethyl acetate, washed several times with water and purified by prepTLC (petrol:ethyl acetate=1:1) to give 4-chloro-2-vinyl-1,7-naphthyridine 50 mg (66.8%). ¹H NMR (CHLOROFORM-d) δ: 9.51 (d, J=0.6 Hz, 1H), 8.70 (d, J=5.6 Hz, 1H), 7.98-8.04 (m, 1H), 7.89 (s, 1H), 7.02 (dd, J=17.6, 10.9 Hz, 1H), 6.41 (d, J=17.6 Hz, 1H), 5.83 (d, J=11.2 Hz, 1H). LC-MS: m/z 191.6 (M+H)⁺

Building Block 14: 5-chloro-2-vinylquinoxaline

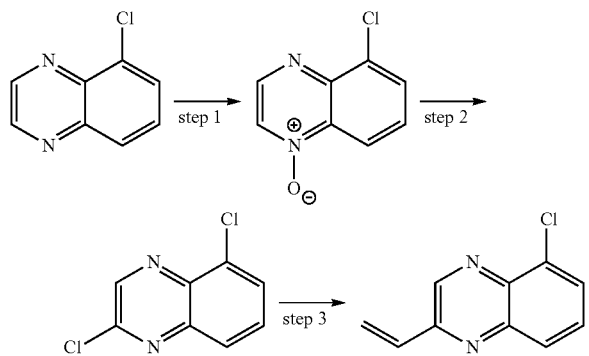

Step 1:

To a solution of 5-chloroquinoxaline (1.4 g, 8.54 mmol) in 50 mL of dichloromethane was added mCPBA (1.62 g, 9.39 mmol). The resulting mixture was stirred at room temperature overnight. After removal of dichloromethane, the crude product obtained was purified by doing column chromatography (100% DCM) to afford 1.5 g of 5-chloroquinoxaline 1-oxide as a white solid.

Step 2:

To a solution of 5-chloroquinoxaline 1-oxide (450 mg, 2.5 mmol) in 5 mL of chloroform was added POCl₃ (1.9 g, 12.5 mmol) slowly. The resulting mixture was heated to 80° C. and held stirring at 80° C. overnight. After removal of chloroform and excess POCl₃, the crude product obtained was purified by doing column chromatography (5% PE/EA) to afford 240 mg of 2,5-dichloroquinoxaline as a white solid. MS (ES) M+H expected 198. found 199. ¹H NMR (CHLOROFORM-d) δ: 8.89 (s, 1H), 7.98 (d, 1H), 7.92 (d, 1H), 7.76 (t, 1H).

Step 3:

To a flask was added 2,5-dichloroquinoxaline (315 mg, 1.59 mmol), potassium trifluoro(vinyl)borate (234 mg, 1.75 mmol), PdCl₂DPPF (130 mg, 0.16 mmol), K₂CO₃ (442 mg, 3.18 mmol), propan-2-ol (4 mL), and H₂O (1 mL), the mixture was degassed with N₂, then heated to 90° C. with stirring for about 3 hrs. TLC (5% PE/EA) showed the consumption of the starting material and new spot appeared. The mixture was then filtered through celite, the cake was washed with ethyl acetate. The filtrate was concentrated in vacuo, the residue was purified by column chromatography (1-5% PE/EA) to afford 256 mg of 5-chloro-2-vinylquinoxaline as a white solid. ¹H NMR (CHLOROFORM-d) δ: 9.10 (s, 1H), 8.02 (d, 1H), 7.85 (d, 1H), 7.71 (t, 1H), 7.09 (q, 1H), 6.57 (d, 1H), 5.89 (d, 1H). MS (ES) M+H expected 190. found 191.

Building Block 15: 2-((R)-4-(cyclopropanecarbonyl)-3-methylpiperazin-1-yl)-6-cyclopropyl-5-(morpholin-2-yl)nicotinonitrile

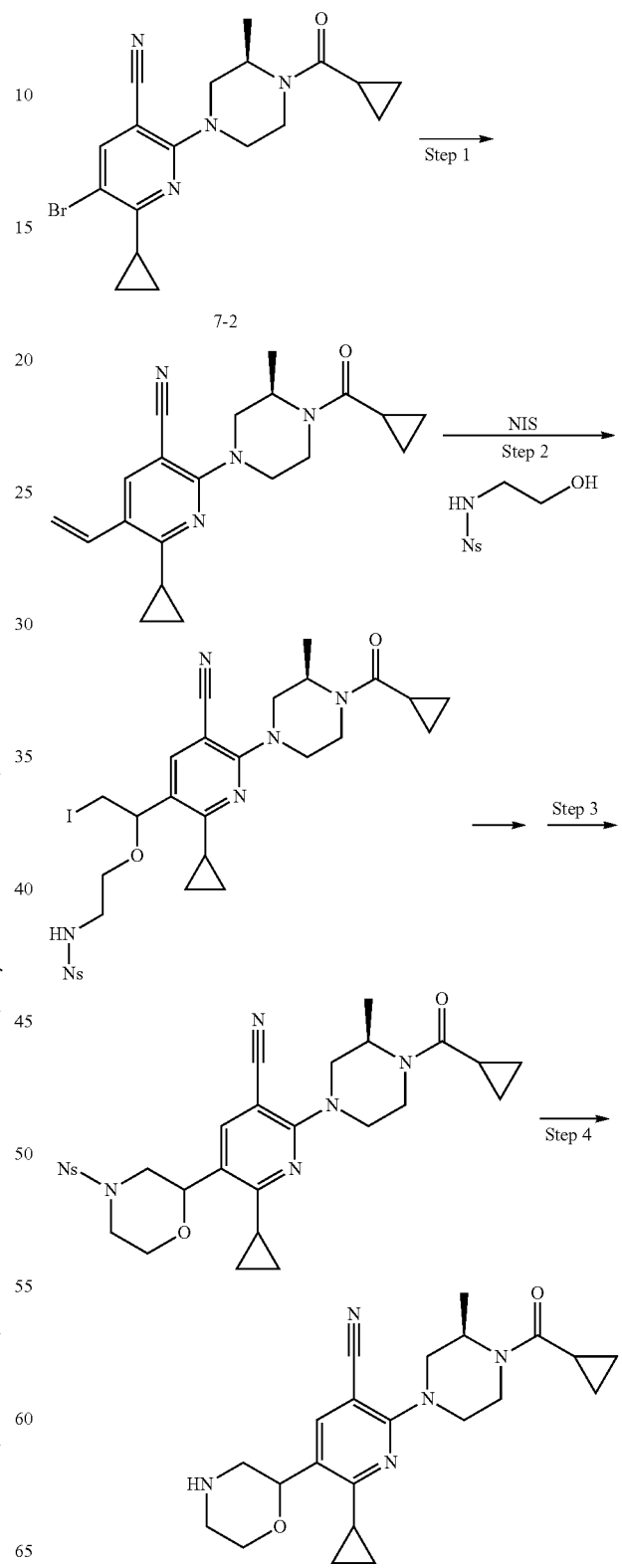

Step 1:

A mixture of 7-2 (500 mg, 1.28 mmol), Potassium vinyltrifluoroborate (258 mg, 1.93 mmol), TEA (650 mg, 6.4 mmol) and Pd(dppf)Cl$_2$ (52 mg, 0.064 mmol) in i-PrOH and water was heated at 100° C. under microwave irradiation for 0.5 hr. The reaction mixture was concentrated and the residue was purified by column chromatography (50% PE/EA) to afford 420 mg of title compound. $^1$H NMR (CHLOROFORM-d) δ 7.80 (s, 1H), 6.99 (dd, J=17.3, 10.8 Hz, 1H), 5.58 (dd, J=17.3, 0.8 Hz, 1H), 5.36 (dd, J=11.0, 0.8 Hz, 1H), 4.86 (br. s., 0.5H), 4.53 (br. s., 0.5H), 4.44 (br. s., 0.5H), 4.09-4.29 (m, 2.5H), 3.65 (br. s., 0.5H), 3.41 (br. s., 0.5H), 3.12-3.24 (m, 2H), 2.14-2.26 (m, 1H), 1.76 (br. s., 1H), 1.25-1.42 (m, 3H), 1.10-1.17 (m, 2H), 0.96-1.10 (m, 4H), 0.82 (dd, J=7.8, 1.8 Hz, 2H).

Step 2:

A mixture of (R)-2-(4-(cyclopropanecarbonyl)-3-methylpiperazin-1-yl)-6-cyclopropyl-5-vinylnicotinonitrile (200 mg, 0.59 mmol), N-(2-hydroxyethyl)-4-nitrobenzenesulfonamide (174 mg, 0.71 mmol, synthesized in accordance with Organic Letters, 2011, 13, #4, p. 728-731), and NIS (159 mg, 0.71 mmol) suspended in 10 mL of MeCN was stirred at r.t. for 2 hrs. After the mixture was concentrated in vacuo, the residue was purified by column chromatography (50% PE/EA) to afford 100 mg of N-(2-(1-(5-cyano-6-((R)-4-(cyclopropanecarbonyl)-3-methylpiperazin-1-yl)-2-cyclopropyl pyridin-3-yl)-2-iodoethoxy)ethyl)-4-nitrobenzenesulfonamide as a light yellowish solid. $^1$H NMR (CHLOROFORM-d) δ 8.36-8.45 (m, J=8.8 Hz, 2H), 8.08-8.17 (m, J=8.8 Hz, 2H), 7.60 (s, 1H), 5.57 (br. s., 1H), 4.83 (br. s., 0.5H), 4.60-4.71 (m, 1H), 4.53 (br. s., 0.5H), 4.40 (br. s., 0.5H), 4.19-4.34 (m, 2.5H), 3.54-3.72 (m, 1H), 3.15-3.48 (m, 8H), 1.88-1.98 (m, 1H), 1.75 (br. s., 1H), 1.34-1.40 (m, 3H), 1.00-1.18 (m, 6H), 0.81 (d, J=7.8 Hz, 2H).

Step 3:

A mixture of N-(2-(1-(5-cyano-6-((R)-4-(cyclopropanecarbonyl)-3-methylpiperazin-1-yl)-2-cyclopropylpyridin-3-yl)-2-iodoethoxy)ethyl)-4-nitrobenzenesulfonamide (100 mg, 0.14 mmol), K$_2$CO$_3$ (97 mg, 0.71 mmol) in 10 mL of MeCN was stirred at r.t. overnight. After the mixture was filtered, the filtrate was concentrated and the residue was purified by column chromatography (50% PE/EA) to afford 66 mg of 2-((R)-4-(cyclopropanecarbonyl)-3-methylpiperazin-1-yl)-6-cyclopropyl-5-(4-((4-nitrophenyl)sulfonyl)morpholin-2-yl)nicotinonitrile as a light yellowish solid. $^1$H NMR (CHLOROFORM-d) δ 8.39-8.49 (m, J=8.5 Hz, 2H), 7.90-8.02 (m, J=8.3 Hz, 2H), 7.70 (s, 1H), 4.91 (dd, J=10.2, 2.1 Hz, 1H), 4.84 (br. s., 0.5H), 4.52 (br. s., 0.5H), 4.42 (br. s., 0.5H), 4.16 (dd, J=11.8, 2.5 Hz, 4H), 3.86-4.00 (m, 2H), 3.76 (d, J=11.5 Hz, 1H), 3.61 (br. s., 0.5H), 3.14-3.38 (m, 3H), 2.52-2.69 (m, 1H), 1.97-2.09 (m, 1H), 1.74 (br. s., 1H), 1.28-1.48 (m, 3H), 1.19-1.25 (m, 2H), 1.11-1.19 (m, 2H), 1.04-1.11 (m, 2H), 0.81 (d, J=7.5 Hz, 2H).

Step 4:

A mixture of 2-((R)-4-(cyclopropanecarbonyl)-3-methylpiperazin-1-yl)-6-cyclopropyl-5-(4-((4-nitrophenyl)sulfonyl)morpholin-2-yl)nicotinonitrile (50 mg, 0.075 mmol), butane-1-thiol (3 d) and LiOH.H$_2$O (20 mg) in 10 mL of MeCN was stirred at r.t. overnight. After the mixture was filtered, the filtrate was concentrated and the residue was purified by column chromatography (10% DCM/MeOH) to afford 21 mg of 2-((R)-4-(cyclopropanecarbonyl)-3-methylpiperazin-1-yl)-6-cyclopropyl-5-(morpholin-2-yl)nicotinonitrile. $^1$H NMR (CHLOROFORM-d) □ δ 7.81 (br. s., 1H), 4.96 (br. s., 1H), 4.34-4.63 (m, 1H), 4.14 (br. s., 3H), 3.97 (br. s., 1H), 3.46 (br. s., 3H), 3.32 (br. s., 2H), 3.09 (br. s., 3H), 2.75 (br. s., 1H), 2.09 (br. s., 1H), 1.74 (br. s., 1H), 1.26 (br. s., 5H), 1.03 (br. s., 4H), 0.80 (br. s., 2H).

Building Block 16: 5-chloro-2-vinylquinazoline

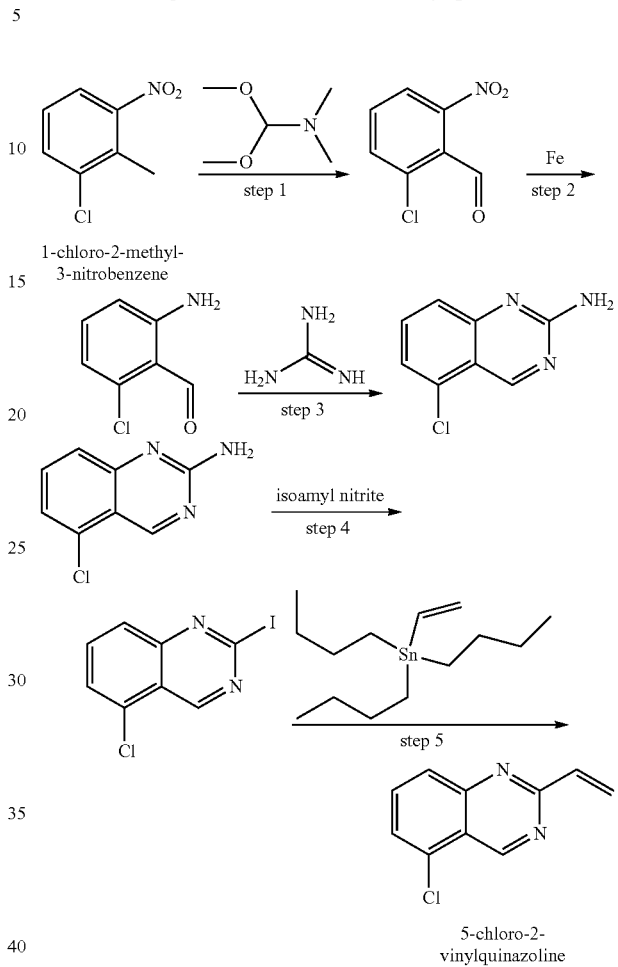

Step 1:

To a solution of 1-chloro-2-methyl-3-nitrobenzene (10.0 g, 58.3 mmol) in 150 mL of anhydrous DMF was added 1,1-dimethoxy-N,N-dimethylmethanamine (21.0 g, 175 mmol). The resulting mixture was stirred at 140° C. for 16 hours. After cooling to 0° C., the mixture was added slowly a solution of NaIO$_4$ (37.4 g, 175 mmol) in H$_2$O and DMF. The mixture was stirred for another 6 hours. The mixture was filtered and partitioned between EtOAc and water. The organic layer was washed with water and dried over Na$_2$SO$_4$ and concentrated to give the crude which was purified by column to afford 6.5 g of 2-chloro-6-nitrobenzaldehyde. 1H NMR (CHLOROFORM-d) δ 10.39 (s, 1H), 7.95-8.04 (m, 1H), 7.74-7.80 (m, 1H), 7.64 (t, J=8.0 Hz, 1H). LC-MS: m/z 186.0 (M+H)$^+$ Step 2:

To a solution of 2-chloro-6-nitrobenzaldehyde (1 g, 0.0054 mmol) in ethanol was added Fe (1.8 g, 0.032 mmol), AcOH (10 ml) and 2N aqueous HCl (5 mL). The resulting mixture was stirred at 25° C. for 2 hours. The mixture was filtered and the filtrate was partitioned between DCM and water, the organic layer was washed with water and brine, concentrated to give 2-amino-6-chlorobenzaldehyde under 25° C. which was without purification for next step. LC-MS: m/z 156.01 (M+H).

Step 3:

The mixture of compound 2-amino-6-chlorobenzaldehyde (2.8 g, 0.018 mol), guanidine (3.43 g, 0.36 mol) and Na$_2$CO$_3$ (3.82 g, 0.36 mol) in naphthalene was stirred at 180° C. for 2 hours. After cooling to room temperature, the mixture was filtered and the solid was washed with water and DCM to give the yellow solid 5-chloroquinazolin-2-amine which was used without purification for next step. 1H NMR (DMSO-d6) δ 9.28 (s, 1H), 7.65 (dd, J=8.5, 7.8 Hz, 1H), 7.39 (d, J=8.5 Hz, 1H), 7.31 (d, J=7.5 Hz, 1H), 7.16 (s, 2H). LC-MS: m/z 180.0 (M+H).

Step 4:

The mixture of 5-chloroquinazolin-2-amine (2.2 g, 12.2 mmol), isoamyl nitrite (4.30 g, 36.7 mmol), CuI (1.17 g, 6.12 mmol) and CH$_2$I$_2$ (16.4 g, 61.2 mmol) in THF was stirred at 60° C. for 72 hours. After cooling to room temperature, the mixture was filtered and the filtrate was partitioned between EtOAc and water, the organic layer was washed with water and brine, dried over Na$_2$SO$_4$. Then the organic layer was concentrate to give the crude which was purified by column to give 5-chloro-2-iodoquinazoline as yellow solid. 1H NMR (CHLOROFORM-d) δ 9.46 (s, 1H), 7.93 (d, J=8.5 Hz, 1H), 7.86 (dd, J=8.5, 7.5 Hz, 1H), 7.72 (dd, J=7.4, 1.1 Hz, 1H). LC-MS: m/z 291.1 (M+H).

Step 5:

The mixture of 5-chloro-2-iodoquinazoline (1.3 g, 4.48 mmol), potassium vinyltrifluoroborate (600 mg, 4.48 mmol), Pd(dppf)Cl$_2$ (165 mg, 0.224 mmol) and CsF (2.04 g, 13.4 mmol) in dioxane/H$_2$O was stirred at 80° C. for 16 hours. After cooling to room temperature, the mixture was partitioned between EtOAc and water. The organic layer was washed with water, brine and dried over Na$_2$SO$_4$, concentrated to give the crude which was purified by column to give 500 mg of 5-chloro-2-vinylquinazoline as yellow solid. 1H NMR (CHLOROFORM-d) δ 9.75 (s, 1H), 7.93 (d, J=8.5 Hz, 1H), 7.80 (t, J=8.0 Hz, 1H), 7.63 (d, J=7.5 Hz, 1H), 7.06 (dd, J=17.2, 10.4 Hz, 1H), 6.85 (dd, J=17.3, 1.8 Hz, 1H), 5.90 (dd, J=10.5, 1.5 Hz, 1H). LC-MS: m/z 191.0 (M+H).

Building Block 17:
4-chloro-2-vinyl-1,8-naphthyridine

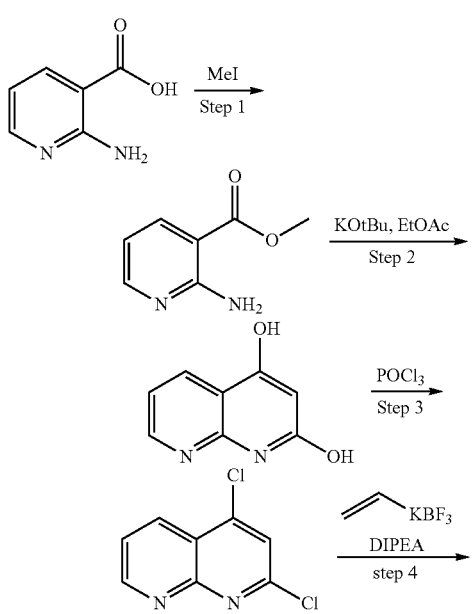

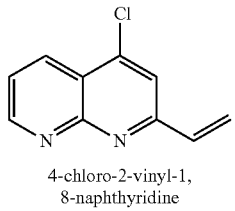

4-chloro-2-vinyl-1,8-naphthyridine

Step 1:

A mixture of 25 g of 2-aminonicotinic acid (0.18 mol), 25 g of K$_2$CO$_3$ (0.18 mol) in 250 mL of DMF was stirred at 140° C. for 30 minutes, then cooled to 10° C. in ice/H$_2$O, 11 mL of MeI (0.18 mol) was added at 10° C. dropwise, the mixture was stirred at room temperature overnight. The mixture was filtered, the filtrate was concentrated, residue was dissolved in EtOAc, and filtered again through a pad of silica gel, the filtrate was concentrated to give 15 g of methyl 2-aminonicotinate. $^1$H NMR (400 MHz, CHLOROFORM-d) δ: 7.67 (d, J=7.0 Hz, 1H), 7.69 (d, J=7.8 Hz, 1H), 7.60-7.44 (m, 1H), 3.54 (br. s., 3H).

Step 2:

To methyl 2-aminonicotinate (7.48 g, 49 mmol) in EtOAc/THF (150 mL/150 mL) was added 13.8 g of KtOBu (123 mmol) in portions slowly at room temperature, and the mixture was stirred at room temperature for 50 minutes before it was refluxed for 4 hours. After cooling to room temperature, the mixture was concentrated, the residue was dissolved in 200 mL of H$_2$O, pH was adjusted to pH=7 with 1N HCl with vigorous stirring, the resulting suspension was filtered, the solid obtained was dried in vacuum to give 7 g of 1,8-naphthyridine-2,4-diol. Step 3: A mixture of 8.0 g of 1,8-naphthyridine-2,4-diol (49 mmol) in 80 mL of POCl$_3$ was refluxed for 1.5 hour, excessive POCl$_3$ was removed under reduced pressure, the residue was poured into satd NaHCO$_3$ slowly with vigorous stirring, the mixture was extracted with EtOAc, and the organic layers were dried over Na$_2$SO$_4$, concentrated to give 2 g of 2,4-dichloro-1,8-naphthyridine, which was used in the subsequent reaction without further purification. $^1$H NMR (400 MHz, CHLOROFORM-d) δ: 9.21-9.12 (m, 1H), 8.59 (dd, J=1.8, 8.3 Hz, 1H), 7.67-7.58 (m, 2H).

Step 4:

100 mg of 2,4-dichloro-1,8-naphthyridine (0.5 mmol), 68 mg of potassium vinyltrifluoroborate (0.5 mmol), 130 mg of DIPEA (1 mmol) in iPrOH/H$_2$O (3 mL/1 mL) was added Pd(dppf)$_2$Cl$_2$, then the mixture was stirred at 105° C. in a sealed tube for 1 hour. When TLC (Petroleum ether: Ethyl acetate=3:1) indicated the completion of the reaction, the mixture was cooled to room temperature, filtered through a pad of celite, the filtrate was concentrated to give 120 mg of crude 4-chloro-2-vinyl-1,8-naphthyridine, and was used in the subsequent reaction without further purification. $^1$H NMR (400 MHz, CHLOROFORM-d) δ: 9.17 (dd, J=1.8, 4.3 Hz, 1H), 8.58 (dd, J=1.9, 8.4 Hz, 1H), 7.62-7.49 (m, 2H), 7.13-6.94 (m, 1H), 6.52 (d, J=17.6 Hz, 1H), 5.81 (d, J=10.8 Hz, 1H).

Building Block 18: 5-chloro-3-vinylpyridazine

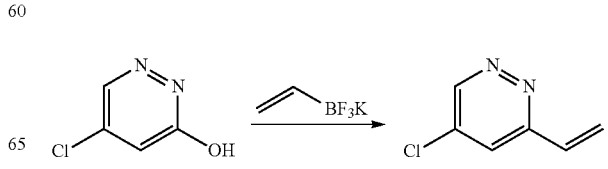

The mixture of 5-chloropyridazin-3-ol (500 mg, 3.36 mmol), potassium vinyltrifluoroborate (450 mg, 3.36 mmol), Pd(dppf)Cl$_2$ (124 mg, 0.168 mmol) and CsF (1.5 g, 10.07 mmol) in dioxane/H$_2$O (8 mL/2 mL) was stirred at 100° C. for 16 hours. The mixture was diluted with EtOAc (50 mL) and filtered. The filtrate was partitioned between EtOAc (50 mL) and water (30 mL), the organic layer was washed with water (30 mL), brine and dried over Na$_2$SO$_4$ and concentrated to give the crude which was purified by prep-TLC to give 200 mg of the product.

$^1$H NMR (CHLOROFORM-d) δ 9.06 (d, J=2.3 Hz, 1H), 7.60 (d, J=2.3 Hz, 1H), 7.02 (dd, J=17.8, 11.0 Hz, 1H), 6.32 (d, J=17.6 Hz, 1H), 5.77 (d, J=10.9 Hz, 1H). LC-MS: m/z 141.0 (M+H)$^+$

Building Block 19 and 20: tert-butyl 6-chloropyridazin-4-ylcarbamate and tert-butyl 5-chloropyridazin-3-ylcarbamate

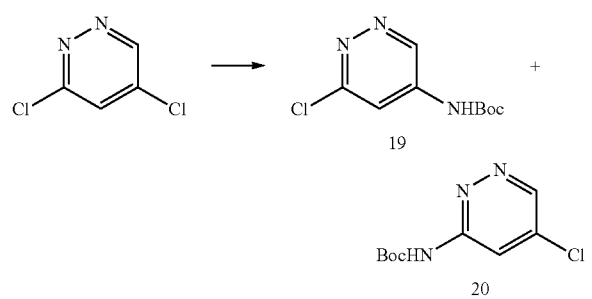

The mixture of 3,5-dichloropyridazine (400 mg, 2.68 mmol), BocNH2 (314 mg, 2.68 mmol), Pd(dppf)Cl2 (99 mg, 0.134 mmol), Xantphos (155 mg, 0.268 mmol) and Cs$_2$CO$_3$ (2.61 g, 8.05 mmol) in toluene was stirred at 80° C. for 16 hours. The mixture was diluted with EtOAc (50 mL) and filtered. The filtrate was partitioned between EtOAc (50 mL) and water (30 mL), the organic layer was washed with water (30 mL), brine and dried over Na$_2$SO$_4$ and concentrated to give the crude which was purified by prep-TLC to give 150 mg of the product 19 and 120 mg of 20. tert-butyl 6-chloropyridazin-4-ylcarbamate $^1$H NMR (CHLOROFORM-d) δ 8.86 (d, J=2.0 Hz, 1H), 8.37 (d, J=2.3 Hz, 1H), 8.12 (br. s., 1H), 1.56 (s, 9H). LC-MS: m/z 230.1 (M+H)$^+$ tert-butyl 5-chloropyridazin-3-ylcarbamate $^1$H NMR (CHLOROFORM-d) δ 8.94 (s, 1H), 8.04 (s, 1H), 7.37 (br. s., 1H), 1.48-1.63 (s, 9H). LC-MS: m/z 230.1 (M+H)$^+$ Building Block 21:
4-chloro-6-vinyl-1H-pyrrolo[2,3-b]pyridine

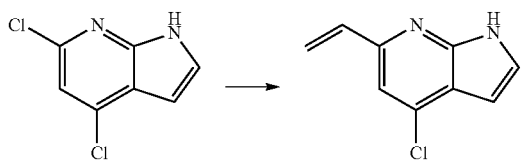

To a solution of 4,6-dichloro-1H-pyrrolo[2,3-b]pyridine (20 mg, 0.1 mmol), potassium vinyl trifluoroborate (13 mg, 0.1 mmol), 5 mg PdCl$_2$(dppf).CH$_2$Cl$_2$ and CsF (45 mg, 0.3 mmol) in dioxane/H2O (5:1) 3 mL was stirred at 100° C. for 1 hours. Then the mixture was partitioned between EtOAc and water, the organic was washed with water, brine and concentrated to give the crude which was purified by column to give 14 mg of the product. $^1$H NMR (CHLOROFORM-d) δ: 11.19 (br. s., 1H), 7.39 (br. s., 1H), 7.28 (s, 2H), 6.91 (dd, J=17.3, 10.9 Hz, 1H), 6.62 (br. s., 1H), 6.21 (d, J=17.3 Hz, 1H), 5.55 (d, J=10.9 Hz, 1H). LC-MS: m/z 179.6 (M+H)$^+$ Building Block 22: 2-vinyl-1,7-naphthyridin-5-yl trifluoromethanesulfonate

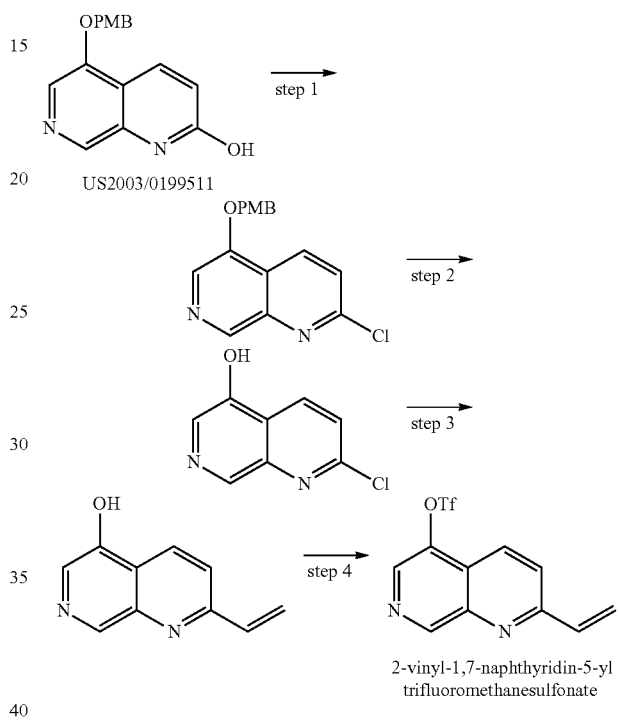

2-vinyl-1,7-naphthyridin-5-yl trifluoromethanesulfonate

Step 1:
To a suspension of 5-(4-methoxybenzyloxy)-1,7-naphthyridin-2-ol (180 mg, 0.64 mmol) in DMF (5 mL) was added POCl3 (293 mg, 1.92 mmol). The mixture was heated at 45° C. for 6 h. After cooling to room temperature, the reaction mixture was poured into ice-water, neutralized with NaHCO3, extracted with EtOAc (3×20 mL). The organic layer washed with water (20 mL) and brine (20 mL). The solvent was removed and 150 mg crude product was obtained which was used in next step without further purification. LC-MS: m/z 300 (M+H)$^+$ Step 2:
To a solution of 2-chloro-5-(4-methoxybenzyloxy)-1,7-naphthyridine (150 mg, 0.5 mmol) in EtOH (10 mL) was added 1N HCl (2.5 mL). Then the mixture was heated at 90° C. for 2 h. After cooling to room temperature, 190 mg of K2CO3 was added and followed 10 mL of methanol. The mixture was stirred vigorously for 1 h at which time silica gel was added. The solvent was removed and the residue was purified by column chromatography (5% methanol/dichloromethane) to give 70 mg of title compound (83%). LC-MS: m/z 180 (M+H)$^+$ Step 3:
A mixture of 2-chloro-1,7-naphthyridin-5-ol (70 mg, 0.39 mmol), Potassium vinyltrifluorobrate (104 mg, 0.78 mmol), Pd(dppf)Cl2 (32 mg, 0.039 mmol) and CsF (119 mg, 0.78 mmol) in dioxane:H₂O=5:1 (5 ml+1 ml) was purged with N2 for three times. Then the mixture was heated at 100° C. for 2 h. The solvent was removed and the residue was purified by column chromatography (5% methanol/dichloromethane) to give 30 mg of title compound (45%).

LC-MS: m/z 173 (M+H)⁺

Step 4:

To a solution of 2-vinyl-1,7-naphthyridin-5-ol (30 mg, 0.17 mmol) and Et3N (35 mg, 0.34 mmol) in dichloromethane (3 mL) was added Tf2O (59 mg, 0.21 mmol) at 0° C. Then the temperature was raised to room temperature and stirred for 2 h. The solvent was removed and the residue was purified by prep. TLC (EtOAc/petroleum ether=3/7) to give 10 mg of title compound (20%). LC-MS: m/z 305 (M+H)⁺

Building Block 23: 4-chloro-1-methyl-6-vinyl-1H-pyrazolo[3,4-b]pyridine

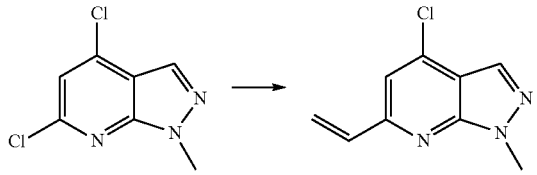

WO2010/59788

A mixture of 4,6-dichloro-1-methyl-1H-pyrazolo[3,4-b]pyridine (0.8 g, 4.0 mmol), Potassium vinyltrifluorobrate (540 mg, 4.0 mmol), Pd(dppf)Cl2 (98 mg, 0.12 mmol) and CsF (1.22 g, 8 mmol) in dioxane:H2O=5:1 (10 mL+2 mL) was purged with N2 three times. Then the mixture was heated at 100° C. for 2 h. The solvent was removed and the residue was purified by column chromatography (30% EtOAc/petroleum ether) to give 500 mg of title compound (65%). ¹H NMR (CHLOROFORM-d) δ 8.03 (s, 1H), 7.24 (s, 1H), 6.89 (dd, J=17.5, 10.7 Hz, 1H), 6.36 (d, J=17.3 Hz, 1H), 5.64 (d, J=10.9 Hz, 1H), 4.16 (s, 3H). LC-MS: m/z 193 (M+H)⁺

Building Block 24: 7-bromo-2-vinylquinoline

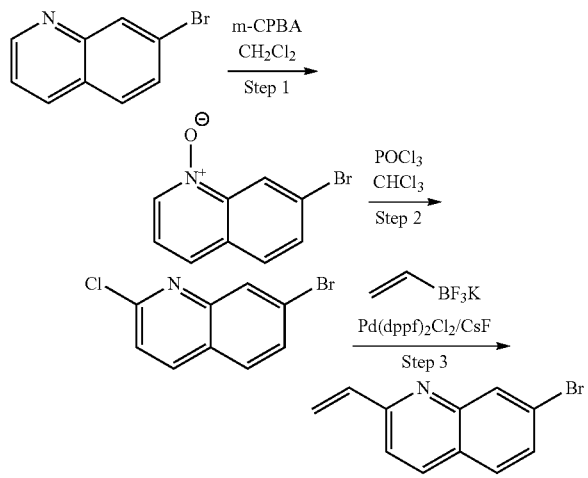

Step 1:

7-bromoquinoline 1-oxide: to a solution of 7-bromoquinoline (1.04 g, 5 mmol) in 20 mL of DCM was added m-Chloroperbenzoic acid (1.01 g, 5 mmol) at room temperature. The reaction mixture was then stirred at room temperature overnight. After LC-MS showed the completion of reaction, the mixture was poured into water and extracted with methylene chloride. The combined organic layer was dried over anhy. Na2SO4 and concentrated in vacuo. Column chromatography (hexane/ethyl acetate=3/1) afforded 1.0 g of title compound as a white solid.

LC-MS: m/z 225.1 (M+H)⁺

Step 2:

7-bromo-2-chloroquinoline: to a solution of 7-bromoquinoline 1-oxide (1.0 g, 4.5 mmol) in 20 mL of chloroform was added Phosphorus oxychloride (3.42 g, 22 mmol) at room temperature. The reaction mixture was then heated at reflux for 3 hours. After LC-MS showed the completion of reaction, the mixture was poured into water and extracted with methylene chloride. The combined organic layer was dried over anhy. Na2SO4 and concentrated in vacuo. Column chromatography (hexane/ethyl acetate=3/1) afforded 0.75 g of title compound as a white solid. LC-MS: m/z 244.1 (M+H)⁺

Step 3:

7-bromo-2-vinylquinoline: to a solution of 7-bromo-2-chloroquinoline (0.75 g, 3 mmol) in 1,4-dioxane (10 mL) was added Potassium vinyltrifluoroborate (0.42 g, 3 mmol), dichlorobis (triphenylphosphine) palladium (II) (143 mg) and Cesium fluoride (1.40 g, 9 mmol), and the mixture was stirred at 100° C. for 10 hours under nitrogen. The mixture was diluted with ethyl acetate and water. The organic layer was separated, washed with brine, dried over magnesium sulfate and evaporated. The residue was purified by column chromatography on silica gel (hexane/ethyl acetate=4/1) afforded 0.42 g of title compound as a white solid. LC-MS: m/z 234.9 (M+H)⁺

Building Block 25:
(R)-2-(tetrahydrofuran-2-yl)acetic acid

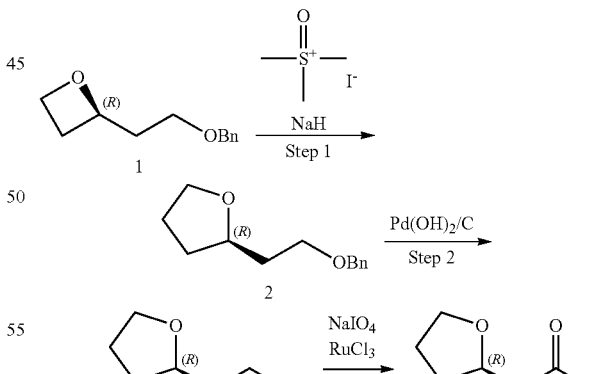

Step 1:

(R)-2-(2-(benzyloxy)ethyl)tetrahydrofuran: to a well stirred suspension of 1.28 g (52 mmol) of NaH in dry diglyme (15 mL) was added 6.86 g (31.2 mmol) of trimethylsulfoxonium iodide at room temperature. The mixture was gently heated to 120° C., and compound 1 (Step 4 product in building block 6 scheme) (1 g, 5.2 mmol) in diglyme (3 mL) was added in one portion. The reaction mixture was stirred at 120° for 4 hours, cooled, carefully quenched with water, and extracted three times with n-hexane. The combined extracts were washed with water and brine and dried over Na2SO4. Removal of solvent and purification by chromatography on silica gel gave the compound 2 (0.5 g, 46%). $^1$H NMR (CHLOROFORM-d) δ 7.34-7.42 (m, 4H), 7.26-7.34 (m, 1H), 4.43-4.63 (m, 2H), 3.91-4.05 (m, 1H), 3.83-3.91 (m, 1H), 3.74 (td, J=7.9, 6.5 Hz, 1H), 3.62 (t, J=6.6 Hz, 2H), 1.96-2.05 (m, 1H), 1.73-1.95 (m, 4H), 1.52 (dd, J=11.9, 8.7 Hz, 1H).

Step 2:

(R)-2-(tetrahydrofuran-2-yl)ethanol: to a solution of compound 2 (0.3 g, 1.45 mmol) in MeOH (15 mL) was added 10% Pd(OH)2/C (20 mg). The reaction mixture was purged with hydrogen and stirred under an atmosphere of hydrogen for 2 d. The black suspension was passed through a plug of celite eluting with MeOH, then the solution was concentrated to yield the desired product as colorless oil (0.15 g, 89%). $^1$H NMR (CHLOROFORM-d, 400 MHz): δ 4.00-4.08 (m, 1H), 3.86-4.00 (m, 1H), 3.66-3.86 (m, 3H), 2.87 (br. s., 1H), 1.98-2.10 (m, 1H), 1.84-1.98 (m, 2H), 1.70-1.84 (m, 2H), 1.46-1.63 ppm (m, 1H).

Step 3:

(R)-2-(tetrahydrofuran-2-yl)acetic acid: to a mixture of compound 3 (0.15 g, 1.3 mmol), sodium periodate (0.72 G, 2.6 mmol), water (10 mL), acetonitrile (20 mL) and carbon tetrachloride (20 mL) was added ruthenium trichloride (29 mg, 10 mol %) at 0-5° C. Afterwards, the resulting mixture was allowed to warm to rt and stirred at this temperature for 2 h. The precipitate was removed via filtration through a pad of celite and washed with diethylether (around 100 mL×5). The combined organic phase was washed with brine (50 mL×3) and then dried under reduced pressure to get the compound 4 (60 mg, contain about 8% of the byproduct).

$^1$H NMR (CHLOROFORM-d, 400 MHz): δ 4.19-4.33 (m, 1H), 3.89-4.06 (m, 1H), 3.83 (td, J=7.8, 6.5 Hz, 1H), 2.62 (dd, J=6.5, 1.5 Hz, 2H), 2.07-2.23 (m, 1H), 1.89-2.06 (m, 2H), 1.54-1.72 (m, 1H).

Example 16: The Following Compounds were Made Following Methods Analogous to Those for Compound 273

(R)-5-(2-cyanophenyl)-6-cyclopropyl-2-(3-isopropyl-4-(3-methoxypropanoyl)piperazin-1-yl)nicotinonitrile (Compound 274; General Procedure 1, Step H)

$^1$H NMR (CHLOROFORM-d) δ 7.76-7.82 (m, 1H), 7.69 (td, J=7.7, 1.4 Hz, 1H), 7.58-7.63 (m, 1H), 7.52 (td, J=7.7, 1.1 Hz, 1H), 7.46 (d, J=7.8 Hz, 1H), 4.56-4.79 (m, 1.5H), 4.44 (t, J=10.3 Hz, 1.5H), 3.86 (d, J=13.8 Hz, 0.5H), 3.70-3.79 (m, 2H), 3.51-3.65 (m, 0.5H), 3.34-3.49 (m, 3.5H), 3.03-3.24 (m, 2H), 2.87-3.00 (m, 0.5H), 2.53-2.82 (m, 2H), 2.05-2.29 (m, 1H), 1.63-1.77 (m, 1H), 1.26 (br. s., 1H), 0.93-1.23 (m, 7H), 0.87-0.92 (m, 1.5H), 0.84 (d, J=6.8 Hz, 1.5H). LC-MS: m/z 458.2 (M+H)$^+$ (R)-6-cyclopropyl-2-(3-isopropyl-4-(3-methoxypropanoyl)piperazin-1-yl)-5-(2-methoxyphenyl)nicotinonitrile (Compound 275; General Procedure 1, Step H)

$^1$H NMR (CHLOROFORM-d) δ 7.58 (d, J=2.5 Hz, 1H), 7.39 (td, J=7.9, 1.8 Hz, 1H), 7.18-7.25 (m, 1H), 7.04 (td, J=7.4, 1.0 Hz, 1H), 6.99 (d, J=8.0 Hz, 1H), 4.69 (d, J=12.8 Hz, 0.5H), 4.49-4.60 (m, 1H), 4.44 (d, J=10.5 Hz, 0.5H), 4.25-4.38 (m, 1H), 3.79-3.89 (m, 4H), 3.68-3.78 (m, 2H), 3.51-3.63 (m, 0.5H), 3.34-3.42 (m, 3H), 2.90-3.16 (m, 2.5H), 2.53-2.82 (m, 2H), 2.09-2.36 (m, 1H), 1.75-1.88 (m, 1H), 1.02-1.18 (m, 5H), 0.79-0.96 (m, 5H). LC-MS: m/z 463.2 (M+H)$^+$

Compound AGI-0007758/NB162-086 (General Procedure 1, Step H)

(R)-6-cyclopropyl-2-(3-isopropyl-4-(3-methoxypropanoyl)piperazin-1-yl)-5-(2-(trifluoromethoxy)phenyl)nicotinonitrile (Compound 276; General Procedure 1, Step H)

$^1$H NMR (CHLOROFORM-d) δ 7.54 (d, J=2.0 Hz, 1H), 7.43-7.48 (m, 1H), 7.33-7.41 (m, 3H), 4.69 (d, J=13.3 Hz, 0.5H), 4.60 (t, J=13.3 Hz, 1H), 4.41 (dd, J=16.8, 13.3 Hz, 1.5H), 3.85 (d, J=13.3 Hz, 0.5H), 3.70-3.79 (m, 2H), 3.52-3.62 (m, 0.5H), 3.35-3.49 (m, 3.5H), 3.03-3.23 (m, 2H), 2.89-3.02 (m, 0.5H), 2.53-2.82 (m, 2H), 1.67-1.78 (m, 1H), 1.04-1.12 (m, 5H), 0.77-0.98 (m, 6H). LC-MS: m/z 517.2 (M+H)$^+$ (R)-1-(4-(6-cyclopropyl-5-(4-fluorophenyl)-3-(3-methyl-1,2,4-oxadiazol-5-yl)pyridin-2-yl)-2-methyl-piperazin-1-yl)-3-methoxypropan-1-one (Compound 831)

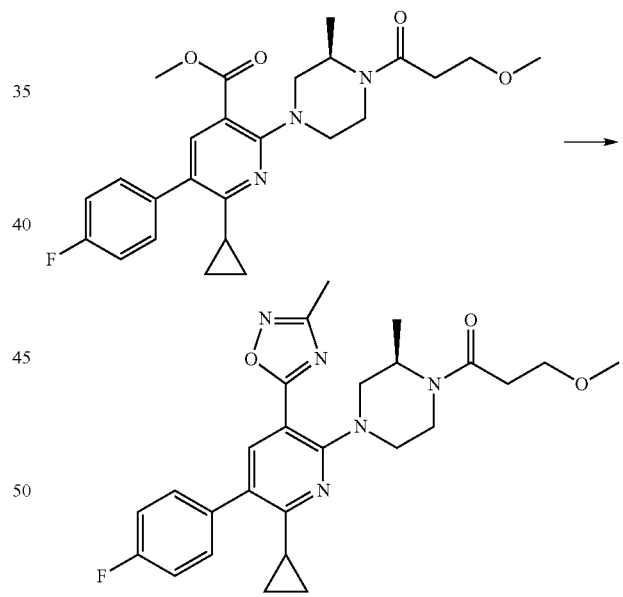

To a solution of N'-hydroxyacetimidamide (221 mg, 2 mmol) hydrochloride in 10 mL anhydrous THF was added NaH (48 mg, 2 mmol). The reaction mixture was heated reflux for 0.5 h and (R)-methyl 6-cyclopropyl-5-(4-fluorophenyl)-2-(4-(3-methoxypropanoyl)-3-methylpiperazin-1-yl)nicotinate (455 mg, 1 mmol) was added to this solution. The reaction was continued reflux for 2 h. The reaction was cooled down to RT and filtered. The filtrate was concentrated to dryness and 120 mg product was obtained by prep-TLC. 1H NMR (CHLOROFORM-d) δ 7.99 (s, 1H), 7.33-7.49 (m, 2H), 7.05-7.23 (m, 2H), 4.85 (br. s., 0.5H), 4.42 (d, J=13.1 Hz, 0.5H), 4.17 (br. s., 0.5H), 3.77-3.93 (m, 2H), 3.47-3.77

(m, 6H), 3.37 (s, 4H), 3.06-3.26 (m, 2H), 2.81-3.06 (m, 1H), 2.51-2.80 (m, 3H), 2.31-2.49 (m, 3H), 1.87-2.11 (m, 1H), 1.28-1.43 (m, 1.5H), 1.15-1.28 (m, 3.5H), 1.12 (br. s., 1H), 0.80-1.06 (m, 2H).

(R)-5-(3-cyanophenyl)-6-cyclopropyl-2-(4-(3-methoxypropanoyl)-3-methylpiperazin-1-yl)nicotinonitrile (Compound 283; General Procedure 1, Step H)

$^1$H NMR (CHLOROFORM-d) δ 7.66-7.71 (m, 2H), 7.62-7.65 (m, 1H), 7.55-7.60 (m, 2H), 4.90 (br. s., 0.5H), 4.53 (d, J=12.8 Hz, 0.5H), 4.18-4.40 (m, 2.5H), 3.67-3.88 (m, 2.5H), 3.46-3.62 (m, 0.5H), 3.38 (s, 3H), 3.24-3.35 (m, 1H), 2.99-3.20 (m, 1.5H), 2.64-2.81 (m, 1H), 2.49-2.63 (m, 1H), 1.85-1.97 (m, 1H), 1.38 (d, J=6.5 Hz, 1.5H), 1.27 (d, J=6.5 Hz, 1.5H), 1.14-1.21 (m, 2H), 0.94-1.04 (m, 2H). LC-MS: m/z 430.2 (M+H)$^+$ (R)-5-(3-aminophenyl)-6-cyclopropyl-2-(4-(3-methoxypropanoyl)-3-methylpiperazin-1-yl)nicotinonitrile (Compound 285; General Procedure 1, Step H)

$^1$H NMR (CHLOROFORM-d) δ 7.57-7.60 (m, 1H), 7.22 (t, J=7.8 Hz, 1H), 6.77 (d, J=7.8 Hz, 1H), 6.68-6.74 (m, 2H), 4.89 (br. s., 0.5H), 4.52 (d, J=13.3 Hz, 0.5H), 4.09-4.31 (m, 2.5H), 3.67-3.81 (m, 2.5H), 3.47-3.60 (m, 0.5H), 3.37 (s, 3H), 3.18-3.29 (m, 1H), 2.95-3.16 (m, 1.5H), 2.63-2.78 (m, 1H), 2.52-2.61 (m, 1H), 2.09-2.17 (m, 1H), 1.38 (d, J=6.5 Hz, 1.5H), 1.28 (d, J=6.8 Hz, 1.5H), 1.06-1.16 (m, 2H), 0.88-0.99 (m, 2H). LC-MS: m/z 420.1 (M+H)$^+$ (R)-6-cyclopropyl-5-(isoquinolin-5-yl)-2-(4-(3-methoxypropanoyl)-3-methylpiperazin-1-yl)nicotinonitrile (Compound 286; General Procedure 1, Step H)

$^1$H NMR (CHLOROFORM-d) δ 9.34 (s, 1H), 8.53 (d, J=6.0 Hz, 1H), 8.06 (d, J=8.0 Hz, 1H), 7.68-7.75 (m, 1H), 7.61-7.68 (m, 2H), 7.43 (t, J=5.6 Hz, 1H), 4.94 (br. s., 0.5H), 4.57 (d, J=13.1 Hz, 0.5H), 4.18-4.47 (m, 2.5H), 3.69-3.86 (m, 2.5H), 3.54-3.67 (m, 0.5H), 3.37-3.44 (m, 3H), 3.34 (dd, J=13.1, 6.3 Hz, 1H), 3.04-3.25 (m, 1.5H), 2.67-2.78 (m, 1H), 2.54-2.67 (m, 1H), 1.48-1.58 (m, 1H), 1.39-1.47 (m, 1.5H), 1.29-1.39 (m, 1.5H), 1.09-1.21 (m, 2H), 0.75-0.89 (m, 2H). LC-MS: m/z 456.1 (M+H)$^+$ (R)-6-cyclopropyl-5-(1H-indol-4-yl)-2-(4-(3-methoxypropanoyl)-3-methylpiperazin-1-yl)nicotinonitrile (Compound 287; General Procedure 1, Step I)

$^1$H NMR (CHLOROFORM-d) δ 8.40 (br. s., 1H), 7.74 (s, 1H), 7.44 (d, J=8.3 Hz, 1H), 7.24-7.29 (m, 1H), 7.02-7.10 (m, 1H), 6.37-6.45 (m, 1H), 4.92 (br. s., 0.5H), 4.55 (d, J=13.6 Hz, 0.5H), 4.17-4.39 (m, 2.5H), 3.71-3.86 (m, 2.5H), 3.51-3.65 (m, 0.5H), 3.35-3.44 (m, 3H), 3.20-3.32 (m, 1H), 2.98-3.17 (m, 1.5H), 2.66-2.81 (m, 1H), 2.54-2.64 (m, 1H), 1.94-2.04 (m, 1H), 1.40-1.46 (m, 1.5H), 1.32 (d, J=6.5 Hz, 1.5H), 1.08-1.17 (m, 2H), 0.80-0.91 (m, 2H). LC-MS: m/z 444.2 (M+H)$^+$ (R)-6-cyclopropyl-2-(4-(3-methoxypropanoyl)-3-methylpiperazin-1-yl)-5-(quinolin-5-yl)nicotinonitrile (Compound 288; General Procedure 1, Step H)

$^1$H NMR (CHLOROFORM-d) δ 8.97 (dd, J=4.1, 1.6 Hz, 1H), 8.23 (d, J=8.5 Hz, 1H), 7.94-8.05 (m, 1H), 7.82 (dd, J=8.5, 7.0 Hz, 1H), 7.61-7.66 (m, 1H), 7.48-7.55 (m, 1H), 7.40-7.48 (m, 1H), 4.83-5.06 (m, 0.5H), 4.56 (d, J=13.1 Hz, 0.5H), 4.15-4.43 (m, 2.5H), 3.69-3.91 (m, 2.5H), 3.57 (d, J=10.5 Hz, 0.5H), 3.36-3.45 (m, 3H), 3.33 (dd, J=13.1, 3.5 Hz, 1H), 3.01-3.26 (m, 1.5H), 2.65-2.82 (m, 1H), 2.52-2.64 (m, 1H), 1.48-1.56 (m, 1H), 1.39-1.47 (m, 1.5H), 1.29-1.38 (m, 1.5H), 1.07-1.18 (m, 2H), 0.74-0.91 (m, 2H). LC-MS: m/z 456.1 (M+H)$^+$ (R)-6-cyclopropyl-5-(1H-indol-6-yl)-2-(4-(3-methoxypropanoyl)-3-methylpiperazin-1-yl)nicotinonitrile (Compound 289; General Procedure 1, Step I)

$^1$H NMR (CHLOROFORM-d) δ 8.41 (br. s., 1H), 7.69 (d, J=8.0 Hz, 1H), 7.66 (s, 1H), 7.39 (s, 1H), 7.27-7.30 (m, 1H), 7.13 (dd, J=8.0, 1.5 Hz, 1H), 6.60 (t, J=2.1 Hz, 1H), 4.91 (br. s., 0.5H), 4.53 (d, J=13.6 Hz, 0.5H), 4.13-4.32 (m, 2.5H), 3.68-3.84 (m, 2.5H), 3.49-3.65 (m, 0.5H), 3.38 (s, 3H), 3.17-3.31 (m, 1H), 2.93-3.16 (m, 1.5H), 2.64-2.82 (m, 1H), 2.53-2.63 (m, 1H), 2.13-2.23 (m, 1H), 1.40 (d, J=6.5 Hz, 1.5H), 1.30 (d, J=6.8 Hz, 1.5H), 1.09-1.17 (m, 2H), 0.84-0.98 (m, 2H). LC-MS: m/z 444.2 (M+H)$^+$ (R)-6-cyclopropyl-5-(4-fluoronaphthalen-1-yl)-2-(4-(3-methoxypropanoyl)-3-methylpiperazin-1-yl)nicotinonitrile (Compound 290; General Procedure 1, Step H)

$^1$H NMR (CHLOROFORM-d) δ 8.19 (d, J=8.0 Hz, 1H), 7.50-7.65 (m, 4H), 7.30-7.37 (m, 1H), 7.22 (dd, J=10.2, 7.9 Hz, 1H), 4.93 (br. s., 0.5H), 4.56 (d, J=13.3 Hz, 0.5H), 4.15-4.42 (m, 2.5H), 3.69-3.90 (m, 2.5H), 3.50-3.68 (m, 0.5H), 3.36-3.43 (m, 3H), 3.24-3.34 (m, 1H), 3.00-3.23 (m, 1.5H), 2.65-2.85 (m, 1H), 2.55-2.64 (m, 1H), 1.54-1.61 (m, 1H), 1.40-1.48 (m, 1.5H), 1.33 (dd, J=6.3, 3.5 Hz, 1.5H), 1.07-1.18 (m, 2H), 0.72-0.85 (m, 2H). LC-MS: m/z 473.1 (M+H)$^+$ (R)-methyl 2-(3-(5-cyano-2-cyclopropyl-6-(4-(3-methoxypropanoyl)-3-methylpiperazin-1-yl)pyridin-3-yl)phenyl)acetate (Compound 291; General Procedure 1, Step H)

$^1$H NMR (CHLOROFORM-d) δ 7.60 (s, 1H), 7.36-7.45 (m, 1H), 7.25-7.34 (m, 3H), 4.90 (br. s., 0.5H), 4.53 (d, J=13.1 Hz, 0.5H), 4.26 (t, J=12.5 Hz, 2.5H), 3.64-3.85 (m, 7H), 3.50-3.61 (m, 0.5H), 3.38 (s, 3H), 3.19-3.30 (m, 1H), 2.93-3.18 (m, 2H), 2.63-2.81 (m, 1H), 2.49-2.63 (m, 1H), 2.02-2.12 (m, 1H), 1.39 (d, J=6.3 Hz, 1.5H), 1.28 (d, J=6.5 Hz, 1.5H), 1.10-1.20 (m, 2H), 0.89-1.00 (m, 2H). LC-MS: m/z 477.1 (M+H)$^+$ (R)-6-cyclopropyl-5-(1H-indazol-5-yl)-2-(4-(3-methoxypropanoyl)-3-methylpiperazin-1-yl)nicotinonitrile (Compound 295; General Procedure 2, Step M)

$^1$H NMR (CHLOROFORM-d) δ 8.14 (br. s., 1H), 7.75 (s, 1H), 7.65 (s, 1H), 7.59 (d, J=8.5 Hz, 1H), 7.42 (dd, J=8.7, 1.4 Hz, 1H), 4.91 (br. s., 0.5H), 4.54 (d, J=13.3 Hz, 0.5H), 4.12-4.39 (m, 2.5H), 3.69-3.89 (m, 2.5H), 3.50-3.64 (m, 0.5H), 3.38 (s, 3H), 3.20-3.33 (m, 1H), 2.97-3.20 (m, 1.5H), 2.66-2.82 (m, 1H), 2.52-2.64 (m, 1H), 1.99-2.14 (m, 1H), 1.36-1.46 (m, 1.5H), 1.30 (d, J=6.8 Hz, 1.5H), 1.13-1.21 (m, 2H), 0.90-0.99 (m, 2H). LC-MS: m/z 445.4 (M+H)$^+$

(R)-4-(5-cyano-2-cyclopropyl-6-(4-(3-methoxypropanoyl)-3-methylpiperazin-1-yl)pyridin-3-yl)benzamide (Compound 296; General Procedure 1, Step H)

$^1$H NMR (CHLOROFORM-d) δ 7.84-7.96 (m, J=8.5 Hz, 2H), 7.57-7.66 (m, 1H), 7.45-7.56 (m, 2H), 6.27 (br. s., 1H), 5.99 (br. s., 1H), 4.90 (br. s., 0.5H), 4.52 (d, J=13.3 Hz, 0.5H), 4.14-4.38 (m, 2.5H), 3.70-3.87 (m, 2.5H), 3.47-3.62 (m, 0.5H), 3.33-3.43 (m, 3H), 3.27 (t, J=10.3 Hz, 1H), 2.99-3.21 (m, 1.5H), 2.64-2.83 (m, 1H), 2.50-2.64 (m, 1H), 1.95-2.09 (m, 1H), 1.38 (d, J=6.3 Hz, 1.5H), 1.25-1.31 (m, 1.5H), 1.13-1.21 (m, 2H), 0.92-1.02 (m, 2H). LC-MS: m/z 448.5 (M+H)$^+$

(R)-6-cyclopropyl-5-(3-(2-hydroxyethyl)phenyl)-2-(4-(3-methoxypropanoyl)-3-methylpiperazin-1-yl)nicotinonitrile (Compound 297; General Procedure 1, Step H)

$^1$H NMR (CHLOROFORM-d) δ 7.60 (s, 1H), 7.35-7.42 (m, 1H), 7.23-7.27 (m, 3H), 4.89 (br. s., 0.5H), 4.52 (d, J=13.1 Hz, 0.5H), 4.14-4.31 (m, 2.5H), 3.91 (t, J=6.7 Hz, 2H), 3.68-3.83 (m, 2.5H), 3.49-3.61 (m, 0.5H), 3.37 (s, 3H), 3.19-3.29 (m, 1H), 2.97-3.18 (m, 1.5H), 2.91-2.97 (m, 2H), 2.64-2.81 (m, 1H), 2.52-2.62 (m, 1H), 2.02-2.14 (m, 1H), 1.39 (d, J=6.3 Hz, 1.5H), 1.27-1.32 (m, 1.5H), 1.08-1.19 (m, 2H), 0.89-1.02 (m, 2H). LC-MS: m/z 449.6 (M+H)$^+$

(R)-3-(5-cyano-2-cyclopropyl-6-(4-(3-methoxypropanoyl)-3-methylpiperazin-1-yl)pyridin-3-yl)benzamide (Compound 305; General Procedure 1, Step H)

$^1$H NMR (METHANOL-d$_4$) δ 7.96 (t, J=1.5 Hz, 1H), 7.91 (dt, J=7.7, 1.6 Hz, 1H), 7.81 (s, 1H), 7.62-7.67 (m, 1H), 7.56-7.62 (m, 1H), 4.82 (br. s., 0.5H), 4.38-4.48 (m, 1H), 4.16-4.29 (m, 2H), 3.97 (d, J=13.6 Hz, 0.5H), 3.68-3.76 (m, 2H), 3.54-3.67 (m, 0.5H), 3.36 (s, 4H), 3.05-3.26 (m, 1.5H), 2.72-2.89 (m, 1H), 2.57-2.70 (m, 1H), 1.99-2.10 (m, 1H), 1.40 (d, J=6.5 Hz, 1.5H), 1.29 (d, J=6.8 Hz, 1.5H), 1.20 (dq, J=4.4, 3.1 Hz, 2H), 0.93-1.04 (m, 2H). LC-MS: m/z 448.3 (M+H)$^+$

(R)-6-cyclopropyl-5-(3-(hydroxymethyl)phenyl)-2-(4-(3-methoxypropanoyl)-3-methylpiperazin-1-yl)nicotinonitrile (Compound 306; General Procedure 1, Step H)

$^1$H NMR (METHANOL-d$_4$) δ 7.71 (br. s., 1H), 7.37-7.48 (m, 3H), 7.32 (d, J=7.5 Hz, 1H), 4.80 (br. s., 1H), 4.68 (s, 3H), 4.36-4.51 (m, 1H), 4.13-4.30 (m, 2H), 3.95 (d, J=13.6 Hz, 0.5H), 3.67-3.78 (m, 2H), 3.50-3.65 (m, 0.5H), 3.27-3.35 (m, 2.5H), 2.99-3.20 (m, 1.5H), 2.70-2.84 (m, 1H), 2.61-2.67 (m, 1H), 2.06-2.13 (m, 1H), 1.40 (d, J=6.5 Hz, 1.5H), 1.28 (d, J=6.8 Hz, 1.5H), 1.12-1.24 (m, 2H), 0.96 (dd, J=7.3, 3.5 Hz, 2H). LC-MS: m/z 435.3 (M+H)$^+$

(R)-6-cyclopropyl-2-(4-(3-methoxypropanoyl)-3-methylpiperazin-1-yl)-5-(2-oxoindolin-6-yl)nicotinonitrile (Compound 313; General Procedure 1, Step H)

$^1$H NMR (CHLOROFORM-d) δ 8.40 (s, 1H), 7.53-7.64 (m, 1H), 7.29 (d, J=7.8 Hz, 1H), 6.98-7.07 (m, 1H), 6.87-6.93 (m, 1H), 4.90 (br. s., 0.5H), 4.53 (d, J=13.4 Hz, 0.5H), 4.13-4.37 (m, 2.5H), 3.68-3.88 (m, 2.5H), 3.49-3.65 (m, 2.5H), 3.34-3.43 (m, 3H), 3.20-3.31 (m, 1H), 2.95-3.18 (m, 1.5H), 2.51-2.81 (m, 2H), 2.02-2.15 (m, 1H), 1.38-1.40 (m, 1.5H), 1.26-1.31 (m, 1.5H), 1.07-1.20 (m, 2H), 0.90-1.04 (m, 2H). LC-MS: m/z 460.2 (M+H)$^+$

(R)-6'-amino-2-cyclopropyl-6-(4-(3-methoxypropanoyl)-3-methylpiperazin-1-yl)-3,3'-bipyridine-5-carbonitrile (Compound 314; General Procedure 1, Step H)

$^1$H NMR (CHLOROFORM-d) δ 8.10 (d, J=2.0 Hz, 1H), 7.54 (s, 1H), 7.44-7.50 (m, 1H), 6.55-6.64 (m, 1H), 4.89 (br. s., 0.5H), 4.72 (br. s., 2H), 4.52 (d, J=13.3 Hz, 0.5H), 4.15-4.31 (m, 2.5H), 3.69-3.85 (m, 2.5H), 3.49-3.63 (m, 0.5H), 3.34-3.43 (m, 3H), 3.19-3.31 (m, 1H), 2.96-3.17 (m, 1.5H), 2.51-2.81 (m, 2H), 1.99-2.08 (m, 1H), 1.23-1.41 (m, 3H), 1.11-1.18 (m, 2H), 0.90-0.99 (m, 2H). LC-MS: m/z 421.4 (M+H)$^+$

(R)-6-cyclopropyl-2-(4-(3-methoxypropanoyl)-3-methylpiperazin-1-yl)-5-(quinolin-4-yl)nicotinonitrile (Compound 315; General Procedure 1, Step H)

$^1$H NMR (CHLOROFORM-d) δ 8.99 (d, J=4.5 Hz, 1H), 8.23 (d, J=8.5 Hz, 1H), 7.78 (t, J=7.5 Hz, 1H), 7.61-7.71 (m, 2H), 7.53-7.61 (m, 1H), 7.36 (d, J=4.0 Hz, 1H), 4.93 (br. s., 0.5H), 4.56 (d, J=12.5 Hz, 0.5H), 4.25-4.45 (m, 2.5H), 3.68-3.91 (m, 2.5H), 3.57 (d, J=9.3 Hz, 0.5H), 3.29-3.45 (m, 4H), 3.01-3.27 (m, 1.5H), 2.65-2.84 (m, 1H), 2.51-2.65 (m, 1H), 1.54 (td, J=8.2, 4.1 Hz, 1H), 1.42 (d, J=5.5 Hz, 1.5H), 1.32 (t, J=5.0 Hz, 1.5H), 1.05-1.21 (m, 2H), 0.74-0.92 (m, 2H). LC-MS: m/z 456.0 (M+H)$^+$

(R)-6-cyclopropyl-5-(2,6-dimethoxyphenyl)-2-(4-(3-methoxypropanoyl)-3-methylpiperazin-1-yl)nicotinonitrile (Compound 316; General Procedure 1, Step H)

$^1$H NMR (CHLOROFORM-d) δ 7.51-7.57 (m, 1H), 7.30-7.38 (m, 1H), 6.65 (d, J=8.3 Hz, 2H), 4.90 (br. s., 0.5H), 4.52 (d, J=13.6 Hz, 0.5H), 4.11-4.34 (m, 2.5H), 3.67-3.84 (m, 8.5H), 3.47-3.62 (m, 0.5H), 3.32-3.43 (m, 3H), 2.95-3.24 (m, 2.5H), 2.63-2.84 (m, 1H), 2.51-2.63 (m, 1H), 1.65-1.72 (m, 1H), 1.41 (d, J=6.5 Hz, 1.5H), 1.31 (d, J=6.8 Hz, 1.5H), 1.00-1.12 (m, 2H), 0.75-0.86 (m, 2H). LC-MS: m/z 465.2 (M+H)$^+$

(R)-6-cyclopropyl-2-(4-(3-methoxypropanoyl)-3-methylpiperazin-1-yl)-5-(3-(2,2,2-trifluoroacetyl)-1H-indol-5-yl)nicotinonitrile (Compound 317; General Procedure 1, Step H)

$^1$H NMR (CHLOROFORM-d) δ 8.44 (s, 1H), 8.10-8.18 (m, 1H), 7.67 (s, 1H), 7.56 (d, J=8.5 Hz, 1H), 7.37 (d, J=8.3 Hz, 1H), 4.92 (br. s., 0.5H), 4.55 (d, J=12.8 Hz, 0.5H), 4.17-4.39 (m, 2.5H), 3.69-3.88 (m, 2.5H), 3.52-3.69 (m, 0.5H), 3.35-3.45 (m, 3H), 3.22-3.35 (m, 1H), 2.98-3.20 (m, 1.5H), 2.54-2.82 (m, 2H), 2.04-2.13 (m, 1H), 1.38-1.47 (m, 1.5H), 1.31 (d, J=6.5 Hz, 1.5H), 1.14-1.19 (m, 2H), 0.90-0.97 (m, 2H). LC-MS: m/z 540.2 (M+H)$^+$

(R)-6-cyclopropyl-2-(4-(3-methoxypropanoyl)-3-methylpiperazin-1-yl)-5-(quinolin-8-yl)nicotinonitrile (Compound 342; General Procedure 1, Step H)

$^1$H NMR (CHLOROFORM-d) δ 8.94 (dd, J=4.1, 1.6 Hz, 1H), 8.23 (dd, J=8.3, 1.8 Hz, 1H), 7.90 (dd, J=8.2, 1.4 Hz,

1H), 7.73 (s, 1H), 7.66-7.71 (m, 1H), 7.59-7.66 (m, 1H), 7.45 (dd, J=8.3, 4.3 Hz, 1H), 4.92 (br. s., 0.5H), 4.54 (d, J=13.3 Hz, 0.5H), 4.13-4.38 (m, 2.5H), 3.68-3.87 (m, 2.5H), 3.50-3.64 (m, 0.5H), 3.38 (s, 3H), 3.24 (t, J=12.8 Hz, 1H), 2.96-3.17 (m, 1.5H), 2.52-2.82 (m, 2H), 1.59-1.68 (m, 1H), 1.43 (d, J=6.5 Hz, 1.5H), 1.33 (d, J=6.5 Hz, 1.5H), 1.07 (br. s., 2H), 0.78 (br. s., 2H)

(R)—N-(3-(5-cyano-2-cyclopropyl-6-(4-(3-methoxypropanoyl)-3-methylpiperazin-1-yl)pyridin-3-yl)phenyl)acetamide (Compound 284; General Procedure 3, Step N, Method 1)

$^1$H NMR (CHLOROFORM-d) δ 7.64 (s, 1H), 7.58 (s, 2H), 7.46 (d, J=8.0 Hz, 1H), 7.38 (t, J=7.8 Hz, 1H), 7.12 (d, J=7.8 Hz, 1H), 4.89 (br. s., 0.5H), 4.52 (d, J=13.3 Hz, 0.5H), 4.11-4.36 (m, 2.5H), 3.67-3.86 (m, 2.5H), 3.54 (t, J=10.9 Hz, 0.5H), 3.33-3.43 (m, 3H), 3.18-3.31 (m, 1H), 2.94-3.17 (m, 1.5H), 2.63-2.79 (m, 1H), 2.51-2.63 (m, 1H), 2.17-2.28 (m, 3H), 2.06-2.14 (m, 1H), 1.38 (d, J=6.5 Hz, 1.5H), 1.27 (d, J=7.0 Hz, 1.5H), 1.08-1.17 (m, 2H), 0.91-1.00 (m, 2H). LC-MS: m/z 462.2 (M+H)$^+$ (R)—N-(3-(5-cyano-2-cyclopropyl-6-(4-(3-methoxypropanoyl)-3-methylpiperazin-1-yl)pyridin-3-yl)phenyl)acrylamide (Compound 343; General Procedure 3, Step N, method 1)

$^1$H NMR (CHLOROFORM-d) δ 7.70-7.79 (m, 2H), 7.54-7.63 (m, 2H), 7.41 (t, J=7.9 Hz, 1H), 7.16 (d, J=7.5 Hz, 1H), 6.48 (dd, J=16.8, 1.0 Hz, 1H), 6.31 (dd, J=16.8, 10.0 Hz, 1H), 5.81 (dd, J=10.2, 1.1 Hz, 1H), 4.91 (br. s., 1H), 4.54 (d, J=13.1 Hz, 0.5H), 4.12-4.36 (m, 2.5H), 3.69-3.88 (m, 2.5H), 3.49-3.65 (m, 0.5H), 3.38 (s, 3H), 3.20-3.33 (m, 1H), 2.96-3.17 (m, 1.5H), 2.54-2.81 (m, 2H), 2.07-2.16 (m, 1H), 1.39 (d, J=6.5 Hz, 1.5H), 1.25-1.35 (m, 1.5H), 1.15 (quin, J=3.6 Hz, 2H), 0.89-1.02 (m, 2H). LC-MS: m/z 474.6 (M+H)$^+$ (R,E)-N-(3-(5-cyano-2-cyclopropyl-6-(4-(3-methoxypropanoyl)-3-methylpiperazin-1-yl)pyridin-3-yl)phenyl)but-2-enamide (Compound 415; General Procedure 3, Step N, Method 2)

$^1$H NMR (CHLOROFORM-d) δ 7.64-7.76 (m, 2H), 7.60-7.63 (m, 1H), 7.49-7.53 (m, 1H), 7.37-7.44 (m, 1H), 7.30-7.35 (m, 1H), 7.14 (d, J=7.8 Hz, 1H), 6.95-7.10 (m, 1H), 5.99 (dd, J=15.1, 1.8 Hz, 1H), 4.92 (s, 0.5H), 4.54 (d, J=12.8 Hz, 0.5H), 4.20-4.32 (m, 2.5H), 3.76 (t, J=6.3 Hz, 2H), 3.50-3.62 (m, 0.5H), 3.39 (s, 3H), 3.18-3.34 (m, 1.5H), 2.97-3.16 (m, 1.5H), 2.65-2.80 (m, 1H), 2.53-2.65 (m, 1H), 2.09-2.16 (m, 1H), 1.95 (dd, J=6.8, 1.5 Hz, 3H), 1.40 (d, J=6.3 Hz, 1H), 1.29-1.31 (m, 2H), 1.12-1.19 (m, 2H), 0.92-1.01 (m, 2H)
LC-MS: m/z 487.3 (M+H)$^+$ (R)—N-(3-(5-cyano-2-cyclopropyl-6-(4-(3-methoxypropanoyl)-3-methylpiperazin-1-yl)pyridin-3-yl)phenyl)-2-oxopropanamide (Compound 416; General Procedure 3, Step N, Method 2)

$^1$H NMR (CHLOROFORM-d) δ 7.38-7.66 (m, 4H), 7.32 (dd, J=3.9, 1.9 Hz, 1H), 7.12-7.25 (m, 1H), 4.89 (s, 0.5H), 4.52 (d, J=10.8 Hz, 0.5H), 4.22-4.34 (m, 2H), 4.10-4.22 (m, 0.5H), 3.66-3.85 (m, 2.5H), 3.55 (d, J=3.5 Hz, 0.5H), 3.39 (d, J=1.5 Hz, 3H), 3.20-3.31 (m, 1H), 3.10-3.14 (m, 1.5H), 2.97-3.09 (m, 1H), 2.66-2.80 (m, 1H), 2.53-2.64 (m, 1H), 1.97-2.07 (m, 1H), 1.55-1.58 (m, 3H), 1.35-1.42 (m, 2H), 1.10-1.17 (m, 1H), 1.05-1.10 (m, 1H), 0.73-0.96 (m, 4H). LC-MS: m/z 490.2 (M+H)$^+$ (R)-2-chloro-N-(3-(5-cyano-2-cyclopropyl-6-(4-(3-methoxypropanoyl)-3-methylpiperazin-1-yl)pyridin-3-yl)phenyl)acetamide (Compound 403; General Procedure 3, Step N, Method 1)

1H NMR (CHLOROFORM-d) δ 8.34 (s, 1H), 7.66-7.75 (m, 1H), 7.62 (s, 1H), 7.50-7.55 (m, 1H), 7.42-7.48 (m, 1H), 7.22 (d, J=7.8 Hz, 1H), 4.92 (s, 0.5H), 4.50-4.54 (m, 0.5H), 4.29-4.33 (m, 1H), 4.26 (m, 1H), 4.21-4.25 (m, 0.5H), 3.71-3.84 (m, 2.5H), 3.52-3.57 (m, 0.5H), 3.39 (s, 3H), 3.21-3.32 (m, 1H), 3.13 (d, J=11.3 Hz, 1H), 3.05 (d, J=12.3 Hz, 0.5H), 2.66-2.81 (m, 1H), 2.54-2.65 (m, 1H), 2.07-2.12 (m, 1H), 1.40 (d, J=6.3 Hz, 1H), 1.28-1.31 (m, 2H), 1.14-1.19 (m, 2H), 0.94-1.00 (m, 2H). LC-MS: m/z 495.2 (M+H)$^+$ (R)-1-chloro-N-(3-(5-cyano-2-cyclopropyl-6-(4-(3-methoxypropanoyl)-3-methylpiperazin-1-yl)pyridin-3-yl)phenyl)methanesulfonamide (Compound 404; General Procedure 3, Step N, Method 1)

$^1$H NMR (CHLOROFORM-d) δ 7.61 (s, 1H), 7.44-7.52 (m, 1H), 7.36-7.41 (m, 1H), 7.29-7.36 (m, 2H), 7.11 (br. s., 1H), 4.92 (s, 1H), 4.45-4.63 (m, 2.5H), 4.18-4.40 (m, 2.5H), 3.66-3.89 (m, 2.5H), 3.50-3.57 (m, 0.5H), 3.39 (s, 3H), 3.29 (t, J=10.2 Hz, 1H), 2.99-3.20 (m, 1.5H), 2.65-2.83 (m, 1H), 2.52-2.64 (m, 1H), 1.99-2.06 (m, 1H), 1.40 (d, J=6.3 Hz, 1H), 1.30 (s, 2H), 1.15-1.22 (m, 2H), 0.96-1.03 (m, 2H). LC-MS: m/z 531.2 (M+H)$^+$ (R)-2-chloro-N-(3-(5-cyano-2-cyclopropyl-6-((R)-4-(3-methoxypropanoyl)-3-methylpiperazin-1-yl)pyridin-3-yl)phenyl)propanamide (Compound 462; General Procedure 3, Step N, Method 2)

$^1$H NMR (CHLOROFORM-d) δ 8.54 (s, 1H), 7.67-7.73 (m, 1H), 7.60 (s, 1H), 7.49-7.57 (m, 1H), 7.38-7.45 (m, 1H), 7.14-7.22 (m, 1H), 4.90 (br. s., 0.5H), 4.44-4.64 (m, 1.5H), 4.16-4.37 (m, 2.5H), 3.68-3.86 (m, 2.5H), 3.50-3.63 (m, 0.5H), 3.37 (s, 3H), 3.19-3.32 (m, 1H), 2.96-3.17 (m, 1.5H), 2.53-2.78 (m, 2H), 2.05-2.12 (m, 1H), 1.83 (d, J=7.0 Hz, 3H), 1.39 (d, J=6.5 Hz, 1.5H), 1.28 (dd, J=6.9, 2.6 Hz, 1.5H), 1.10-1.19 (m, 2H), 0.90-1.02 (m, 2H). LC-MS: m/z 510.2 (M+H)$^+$ (R)—N-(4-(5-cyano-2-cyclopropyl-6-(4-(3-methoxypropanoyl)-3-methylpiperazin-1-yl)pyridin-3-yl)phenyl)acetamide (Compound 412; General Procedure 1, Step H)

1H NMR (CHLOROFORM-d) δ 7.55-7.67 (m, 3H), 7.31-7.44 (m, 3H), 4.91 (s, 0.5H), 4.54 (d, J=13.6 Hz, 0.5H), 4.14-4.33 (m, 2.5H), 3.65-3.93 (m, 2.5H), 3.46-3.65 (m, 0.5H), 3.39 (s, 3H), 3.20-3.30 (m, 1H), 2.98-3.19 (m, 1.5H), 2.51-2.81 (m, 1H), 2.16-2.31 (m, 3H), 1.98-2.13 (m, 1H), 1.24-1.44 (m, 4H), 1.08-1.18 (m, 2H), 0.84-0.99 (m, 2H). LC-MS: m/z 462.6 (M+H)$^+$ (R)—N-(3-(5-cyano-2-cyclopropyl-6-(4-(3-methoxypropanoyl)-3-methylpiperazin-1-yl)pyridin-3-yl)phenyl)propionamide (Compound 424; General Procedure 3, Step N, Method 2)

$^1$H NMR (CHLOROFORM-d) δ 7.75 (s, 1H), 7.68 (s, 1H), 7.59 (s, 1H), 7.49 (d, J=8.0 Hz, 1H), 7.37 (t, J=7.8 Hz,

1H), 7.11 (d, J=7.5 Hz, 1H), 4.89 (s, 0.5H), 4.52 (d, J=13.3 Hz, 0.5H), 4.14-4.35 (m, 2.5H), 3.67-3.85 (m, 2.5H), 3.49-3.62 (m, 0.5H), 3.37 (s, 3H), 3.17-3.32 (m, 1H), 2.93-3.17 (m, 1.5H), 2.63-2.81 (m, 1H), 2.52-2.63 (m, 1H), 2.37-2.49 (m, 2H), 2.05-2.13 (m, 1H), 1.38 (d, J=6.5 Hz, 1H), 1.22-1.31 (m, 5H), 1.14 (dt, J=7.4, 3.6 Hz, 2H), 0.88-1.01 (m, 2H). LC-MS: m/z 476.3 (M+H)$^+$ (R)-1-cyano-N-(3-(5-cyano-2-cyclopropyl-6-(4-(3-methoxypropanoyl)-3-methylpiperazin-1-yl)pyridin-3-yl)phenyl)cyclopropanecarboxamide (Compound 425; General Procedure 3, Step N, Method 2)

$^1$H NMR (CHLOROFORM-d) δ 8.11 (s, 1H), 7.65 (s, 1H), 7.61 (s, 1H), 7.42-7.50 (m, 2H), 7.19-7.25 (m, 1H), 4.92 (s, 0.5H), 4.55 (d, J=12.3 Hz, 0.5H), 4.17-4.39 (m, 2.5H), 3.71-3.76 (m, 2.5H), 3.55-3.58 (m, 0.5H), 3.36-3.46 (m, 3H), 3.21-3.33 (m, 1H), 3.14 (d, J=13.3 Hz, 1.5H), 3.05 (d, J=12.0 Hz, 1H), 2.63-3.75 (s, 1H), 2.61-3.63 (m, 1H), 2.02-2.12 (m, 1H), 1.81-1.91 (m, 2H), 1.66 (q, J=4.5 Hz, 2H), 1.40 (d, J=5.5 Hz, 1H), 1.25-1.33 (m, 2H), 1.12-1.20 (m, 2H), 0.92-1.01 (m, 2H). LC-MS: m/z 513.2 (M+H)$^+$

Compound 427 (General Procedure 3, Step N, Method 1)

$^1$H NMR (CHLOROFORM-d) δ □7.62 (s, 1H), 7.47-7.56 (m, 1H), 7.35-7.44 (m, 1H), 7.18-7.25 (m, 2H), 6.42 (dd, J=16.8, 2.0 Hz, 1H), 6.16 (dd, J=16.6, 10.3 Hz, 1H), 5.57 (dd, J=10.2, 1.6 Hz, 1H), 4.92 (d, J=12.8 Hz, 0.5H), 4.55 (d, J=12.8 Hz, 0.5H), 4.13-4.41 (m, 3H), 3.69-3.90 (m, 3H), 3.58 (d, J=9.3 Hz, 1H), 3.39 (s, 3H), 3.42 (s, 3H), 3.29 (t, J=9.5 Hz, 1H), 3.01-3.21 (m, 2H), 2.65-2.80 (m, 1H), 2.47-2.65 (m, 1H), 1.88-2.07 (m, 1H), 1.65 (br. s., 3H), 1.35-1.44 (m, 2H), 1.25-1.35 (m, 2H), 1.09-1.25 (m, 2H), 0.92-1.09 (m, 2H). LC-MS: m/z 488.2 (M+H)$^+$ (R)—N-(3-(5-cyano-2-cyclopropyl-6-(4-(3-methoxypropanoyl)-3-methylpiperazin-1-yl)pyridin-3-yl)phenyl)propiolamide (Compound 428; General Procedure 3, Step N, Method 2)

$^1$H NMR (CHLOROFORM-d) δ 7.63-7.69 (m, 2H), 7.61 (s, 1H), 7.41-7.50 (m, 2H), 7.20 (d, J=7.3 Hz, 1H), 4.92 (s, 0.5H), 4.54 (d, J=11.8 Hz, 0.5H), 4.12-4.40 (m, 2.5H), 3.72-3.79 (m, 2.5H), 3.51-3.57 (m, 0.5H), 3.40 (s, 3H), 3.23-3.32 (m, 1H), 3.14 (d, J=13.1 Hz, 1H), 3.05 (d, J=11.0 Hz, 1H), 2.99 (s, 1H), 2.65-2.81 (m, 1H), 2.54-2.65 (m, 1H), 2.05-2.13 (m, 1H), 1.40 (d, J=6.5 Hz, 1H), 1.14-1.19 (m, 2H), 0.95-1.01 (m, 2H), 0.88-0.93 (m, 2H).
LC-MS: m/z 472.2 (M+H)$^+$ (R)—N-(3-(5-cyano-2-cyclopropyl-6-(4-(3-methoxypropanoyl)-3-methylpiperazin-1-yl)pyridin-3-yl)phenyl)ethenesulfonamide (Compound 429; General Procedure 3, Step N, Method 1)

To a solution of (R)-5-(3-aminophenyl)-6-cyclopropyl-2-(4-(3-methoxypropanoyl)-3-methylpiperazin-1-yl)nicotinonitrile (20 mg, 0.048 mmol) and 2-chloroethanesulfonyl chloride (8.6 mg, 0.052 mmol) in 5 ml of DCM was added dropwised TEA (15 mg, 0.143 mmol) at 0° C., then the resulting mixture was allowed to warm to room temperature and stirred for 2 hours. The mixture was partitioned between EtOAc and water. The organic layer was dried over Na$_2$SO$_4$ and concentrated to give the crude which was purified by prep-TLC to give 15 mg of the product.

$^1$H NMR (CHLOROFORM-d) δ 7.55-7.61 (m, 1H), 7.37-7.46 (m, 1H), 7.15-7.26 (m, 3H), 6.70 (d, J=12.8 Hz, 1H), 6.62 (dd, J=16.4, 9.9 Hz, 1H), 6.34 (d, J=16.3 Hz, 1H), 6.02 (d, J=9.8 Hz, 1H), 4.92 (s, 0.5H), 4.54 (d, J=13.3 Hz, 0.5H), 4.19-4.37 (m, 2.5H), 3.73-3.79 (m, 3H), 3.52-3.61 (m, 0.5H), 3.39 (s, 3H), 3.28 (t, J=10.4 Hz, 1H), 3.02-3.14 (m, 1H), 2.65-2.80 (m, 1H), 2.55-2.64 (m, 1H), 1.98-2.07 (m, 1H), 1.27 (s, 3H), 1.14-1.19 (m, 2H), 0.95-1.01 (m, 2H).

(R)—N-(3-(5-cyano-2-cyclopropyl-6-(4-(3-methoxypropanoyl)-3-methylpiperazin-1-yl)pyridin-3-yl)phenyl)-2-fluoroacrylamide (Compound 431; General Procedure 3, Step N, Method 2)

$^1$H NMR (CHLOROFORM-d) δ 8.19 (d, J=4.5 Hz, 1H), 7.75 (s, 1H), 7.61 (s, 1H), 7.57 (dd, J=8.0, 1.3 Hz, 1H), 7.43 (t, J=7.9 Hz, 1H), 7.16-7.23 (m, 1H), 5.84 (dd, J=18.0 Hz, J=3.3 Hz, 0.5H), 5.21-5.35 (m, 1H), 4.90 (br. s., 0.5H), 4.52 (d, J=13.1 Hz, 0.5H), 4.10-4.38 (m, 2.5H), 3.66-3.86 (m, 2.5H), 3.50-3.64 (m, 0.5H), 3.38 (s, 3H), 3.19-3.33 (m, 1H), 2.95-3.18 (m, 1.5H), 2.56-2.78 (m, 2H), 2.04-2.16 (m, 1H), 1.39 (d, J=6.3 Hz, 1.5H), 1.28 (d, J=6.8 Hz, 1.5H), 1.11-1.22 (m, 2H), 0.91-1.03 (m, 2H). LC-MS: m/z 492.7 (M+H)$^+$ (R)—N-(3-(5-cyano-2-cyclopropyl-6-(4-(3-methoxypropanoyl)-3-methylpiperazin-1-yl)pyridin-3-yl)phenyl)-2,2-difluoroacetamide (Compound 432; General Procedure 3, Step N, Method 2)

$^1$H NMR (CHLOROFORM-d) δ 8.79 (br. s., 1H), 7.77 (s, 1H), 7.55-7.65 (m, 2H), 7.44 (t, J=7.9 Hz, 1H), 7.22 (d, J=7.8 Hz, 1H), 6.05 (t, J=56.0 Hz, 1H), 4.89 (br. s., 0.5H), 4.51 (d, J=13.3 Hz, 0.5H), 4.08-4.37 (m, 2.5H), 3.66-3.88 (m, 2.5H), 3.49-3.63 (m, 0.5H), 3.36 (s, 3H), 2.96-3.25 (m, 2.5H), 2.81 (s, 6H), 2.50-2.79 (m, 2H), 2.03-2.13 (m, 1H), 1.32-1.45 (m, 1.5H), 1.27 (d, J=6.8 Hz, 1.5H), 1.10-1.17 (m, 2H), 0.91-1.02 (m, 2H)
LC-MS: m/z 498.8 (M+H)$^+$ (R)-5-(4-aminophenyl)-6-cyclopropyl-2-(4-(3-methoxypropanoyl)-3-methylpiperazin-1-yl)nicotinonitrile (Compound 383; General Procedure 1, Step H)

$^1$H NMR (CHLOROFORM-d) δ 7.53-7.62 (m, 1H), 7.11-7.21 (m, 2H), 6.70-6.83 (m, 2H), 4.89 (br. s., 0.5H), 4.52 (d, J=13.6 Hz, 0.5H), 4.04-4.28 (m, 2.5H), 3.64-3.88 (m, 4.5H), 3.47-3.64 (m, 0.5H), 3.30-3.43 (m, 3H), 3.14-3.27 (m, 1H), 2.92-3.14 (m, 1.5H), 2.50-2.79 (m, 2H), 2.08-2.15 (m, 1H), 1.34-1.43 (m, 1.5H), 1.28-1.30 (m, 1.5H), 1.06-1.15 (m, 2H), 0.84-0.95 (m, 2H). LC-MS: m/z 420.1 (M+H)$^+$ (R)-6-cyclopropyl-2-(4-(3-methoxypropanoyl)-3-methylpiperazin-1-yl)-5-(2-oxoindolin-5-yl)nicotinonitrile (Compound 384; General Procedure 1, Step H)

$^1$H NMR (CHLOROFORM-d) δ 8.22 (s, 1H), 7.50-7.64 (m, 1H), 7.21-7.26 (m, 2H), 6.85-7.03 (m, 1H), 4.90 (br. s., 0.5H), 4.53 (d, J=13.6 Hz, 0.5H), 4.10-4.37 (m, 2.5H), 3.68-3.86 (m, 2.5H), 3.48-3.64 (m, 2.5H), 3.35-3.44 (m, 3H), 3.19-3.31 (m, 1H), 2.94-3.17 (m, 1.5H), 2.52-2.82 (m, 2H), 1.99-2.09 (m, 1H), 1.39 (d, J=6.5 Hz, 1.5H), 1.28 (d, J=6.8 Hz, 1.5H), 1.09-1.20 (m, 2H), 0.91-0.99 (m, 2H). LC-MS: m/z 460.5 (M+H)$^+$

(R)-6-cyclopropyl-5-(1H-indazol-6-yl)-2-(4-(3-methoxypropanoyl)-3-methylpiperazin-1-yl)nicotinonitrile (Compound 385; General Procedure 1, Step H)

¹H NMR (CHLOROFORM-d) δ 8.14 (br. s., 1H), 7.82 (d, J=8.3 Hz, 1H), 7.66 (s, 1H), 7.50 (s, 1H), 7.16-7.24 (m, 1H), 4.91 (br. s., 0.5H), 4.54 (d, J=12.5 Hz, 0.5H), 4.16-4.39 (m, 2.5H), 3.69-3.85 (m, 2.5H), 3.50-3.65 (m, 0.5H), 3.38 (s, 3H), 3.20-3.32 (m, 1H), 2.98-3.14 (m, 1.5H), 2.52-2.82 (m, 2H), 2.04-2.13 (m, 1H), 1.28-1.43 (m, 3H), 0.91-0.98 (m, 2H), 0.81-0.89 (m, 2H).
LC-MS: m/z 445.5 (M+H)⁺

(R)-6-cyclopropyl-5-(isoquinolin-5-yl)-2-(3-methyl-4-(3,3,3-trifluoropropanoyl)piperazin-1-yl)nicotinonitrile (Compound 386; General Procedure 2, Step M)

¹H NMR (CHLOROFORM-d) δ 9.30-9.40 (m, 1H), 8.49-8.58 (m, 1H), 8.06 (d, J=8.3 Hz, 1H), 7.67-7.75 (m, 1H), 7.62-7.67 (m, 2H), 7.36-7.45 (m, 1H), 4.95 (br. s., 0.5H), 4.58-4.61 (m, 0.5H), 4.27-4.49 (m, 2H), 4.14 (br. s., 0.5H), 3.59-3.73 (m, 1H), 3.11-3.39 (m, 4.5H), 1.45-1.55 (m, 2.5H), 1.37 (dd, J=6.4, 4.4 Hz, 1.5H), 1.07-1.19 (m, 2H), 0.77-0.87 (m, 2H). LC-MS: m/z 480.1 (M+H)⁺

(R)-6-cyclopropyl-2-(3-cyclopropyl-4-(3,3,3-trifluoropropanoyl)piperazin-1-yl)-5-(isoquinolin-5-yl)nicotinonitrile (Compound 387; General Procedure 2, Step M)

¹H NMR (CHLOROFORM-d) δ 9.40 (br. s., 1H), 8.56 (d, J=4.5 Hz, 1H), 8.10 (d, J=8.0 Hz, 1H), 7.72-7.78 (m, 1H), 7.64-7.71 (m, 2H), 7.46 (dd, J=12.5, 5.8 Hz, 1H), 4.58 (dt, J=13.1, 2.1 Hz, 1H), 4.47 (d, J=12.0 Hz, 1H), 4.09-4.26 (m, 0.5H), 3.80-3.86 (m, 1.5H), 3.08-3.44 (m, 5H), 1.49-1.57 (m, 1H), 1.33 (br. s., 1H), 1.08-1.22 (m, 2H), 0.82-0.91 (m, 2H), 0.41-0.72 (m, 4H).
LC-MS: m/z 506.7 (M+H)⁺

(R)-2-cyclopropyl-6-(4-(3-methoxypropanoyl)-3-methylpiperazin-1-yl)-2'-vinyl-3,4'-bipyridine-5-carbonitrile (Compound 390)

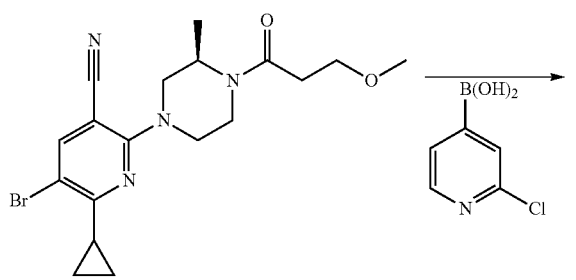

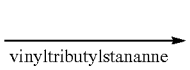

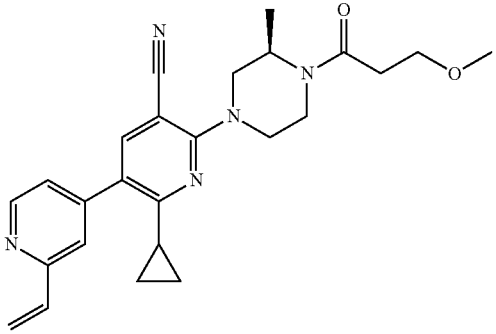

A mixture of 7-1 (410 mg, 1.01 mmol), 2-chloropyridin-4-ylboronic acid (237 mg, 0.95 mmol), K₂CO₃ (414 mg, 3.03 mmol) and Pd(PPh₃)₄ (40 mg, 0.035 mmol) in DMF (2 mL) was stirred at 150° C. in the microwave reactor for 1 h. The resultant mixture was partitioned between EtOAc and water, the organic phase was washed with water, brine and concentrated and purified by prepTLC (PE:EA=1:1) to give 375 mg of (R)-2'-chloro-2-cyclopropyl-6-(4-(3-methoxypropanoyl)-3-methylpiperazin-1-yl)-3,4'-bipyridine-5-carbonitrile. ¹H NMR (CHLOROFORM-d) □ δ 8.34-8.61 (m, 1H), 7.60 (s, 1H), 7.39 (d, J=1.0 Hz, 1H), 4.90 (br. s., 0.5H), 4.52 (d, J=11.8 Hz, 0.5H), 4.21-4.41 (m, 2.5H), 3.68-3.91 (m, 2.5H), 3.54 (d, J=4.0 Hz, 1H), 3.25-3.45 (m, 4H), 2.95-3.25 (m, 1H), 2.63-2.92 (m, 1H), 2.42-2.63 (m, 1H), 1.87-2.07 (m, 1H), 1.36 (d, J=6.5 Hz, 1.5H), 1.11-1.31 (m, 3.5H), 0.81-1.11 (m, 2H). LC-MS: m/z 440.1 (M+H)⁺

A mixture of (R)-2'-chloro-2-cyclopropyl-6-(4-(3-methoxypropanoyl)-3-methylpiperazin-1-yl)-3,4'-bipyridine-5-carbonitrile (40 mg, 0.09 mmol), vinyl tributyl stananne (30 mg, 0.09 mmol), KOAc (10 mg) and Pd(PPh₃)₄ (5 mg) in DMF (2 mL) was stirred at 120° C. in the microwave reactor for 20 min. The resulting mixture was concentrated and purified by prepTLC (PE:EA=1:1) to give 25 mg of the title product. 1H NMR (CHLOROFORM-d) δ 8.64 (d, J=5.0 Hz, 1H), 7.63 (s, 1H), 7.31-7.45 (m, 1H), 7.22 (dd, J=5.0, 1.8 Hz, 1H), 6.87 (dd, J=17.6, 10.8 Hz, 1H), 6.27 (dd, J=17.6, 1.0 Hz, 1H), 5.41-5.71 (m, 1H), 4.90 (m, 0.5H), 5.51 (m, 0.5H), 4.16-4.44 (m, 3H), 3.74 (t, J=6.1 Hz, 3H), 3.38 (s, 4H), 3.31 (d, J=4.0 Hz, 1H), 3.14 (br. s., 2H), 2.59 (t, J=6.0 Hz, 2H), 1.86-2.06 (m, 1H), 1.38 (d, J=6.3 Hz, 1.5H), 1.24-1.33 (m, 1.5H), 1.10-1.24 (m, 2H), 0.83-1.10 (m, 2H). LC-MS: m/z 432.6 (M+H)⁺

(R)-2'-chloro-2-cyclopropyl-6-(4-(3-methoxypropanoyl)-3-methylpiperazin-1-yl)-3,4'-bipyridine-5-carbonitrile (Compound 401)

¹H NMR (CHLOROFORM-d) δ 8.34-8.61 (m, 1H), 7.60 (s, 1H), 7.39 (d, J=1.0 Hz, 1H), 4.90 (br. s., 0.5H), 4.52 (d, J=11.8 Hz, 0.5H), 4.21-4.41 (m, 2.5H), 3.68-3.91 (m, 2.5H), 3.54 (d, J=4.0 Hz, 1H), 3.25-3.45 (m, 4H), 2.95-3.25 (m, 1H), 2.63-2.92 (m, 1H), 2.42-2.63 (m, 1H), 1.87-2.07 (m, 1H), 1.36 (d, J=6.5 Hz, 1.5H), 1.11-1.31 (m, 3.5H), 0.81-1.11 (m, 2H). LC-MS: m/z 440.1 (M+H)⁺

(R)-2-(4-(cyclopropanecarbonyl)-3-cyclopropylpiperazin-1-yl)-6-cyclopropyl-5-(isoquinolin-5-yl)nicotinonitrile (Compound 391; General Procedure 1, Step H)

¹H NMR (CHLOROFORM-d) δ 9.41 (s, 1H), 8.54 (d, J=5.3 Hz, 1H), 8.11 (d, J=8.0 Hz, 1H), 7.68-7.81 (m, 2H), 7.61-7.67 (m, 1H), 7.45-7.56 (m, 1H), 4.58 (d, J=11.5 Hz, 1H), 4.46 (d, J=13.1 Hz, 1H), 3.49-4.23 (m, 2.5H), 3.16-3.33 (m, 2.5H), 1.58-1.69 (m, 1H), 1.42-1.54 (m, 1H), 1.17 (t, J=4.9 Hz, 2H), 1.00-1.10 (m, 3H), 0.76-0.87 (m, 4H), 0.69 (br. s., 1H), 0.41-0.62 (m, 3H); LC-MS: m/z 464.2 (M+H)

(R)-1-(4-(6-cyclopropyl-5-(4-fluorophenyl)-3-(1,3,4-oxadiazol-2-yl)pyridin-2-yl)-2-methylpiperazin-1-yl)-3-methoxypropan-1-one (Compound 392)

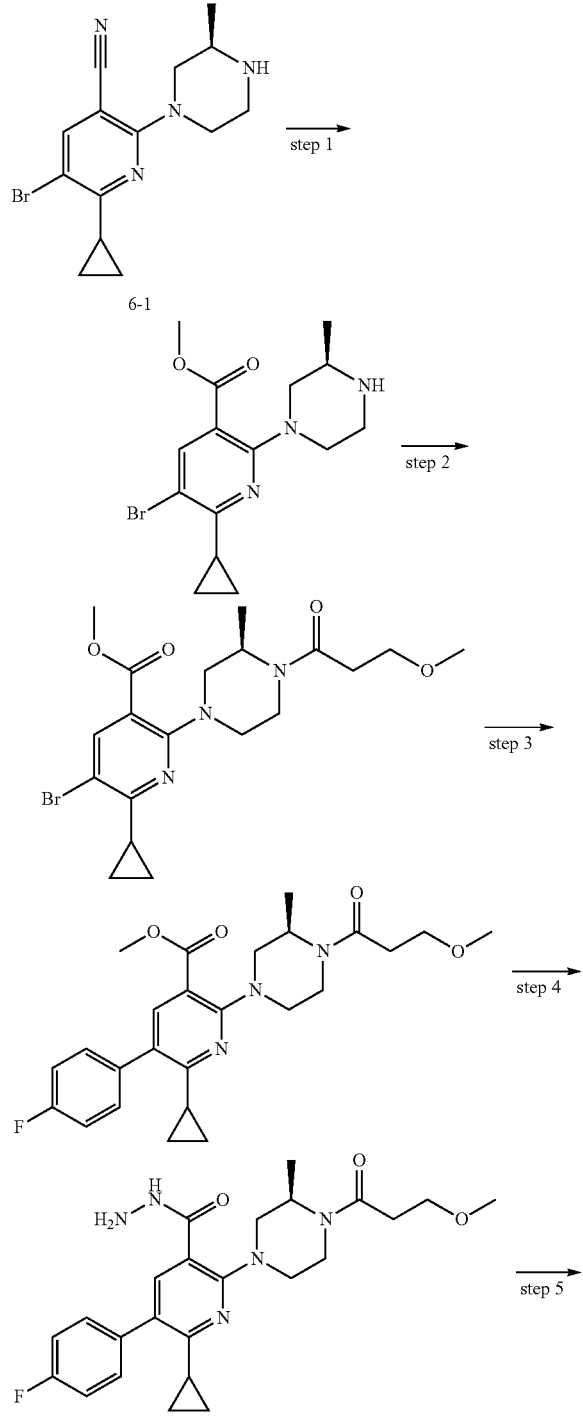

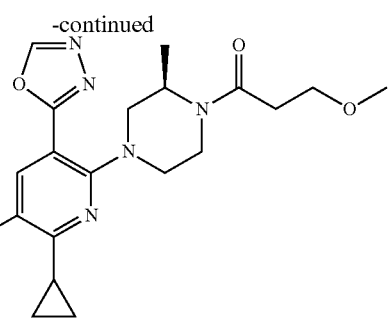

Step 1:
(R)-5-bromo-6-cyclopropyl-2-(3-methylpiperazin-1-yl)nicotinonitrile (2 g, 6.3 mmol) was dissolved in MeOH (5 mL) and NaOH (20% wt aq, 10 mL) and the reaction solution was heated to reflux overnight. The resultant solution was concentrated and then dissolved in MeOH (10 mL), treated with SOCl$_2$ (0.1 ml) and then heated to reflux for 2 h. The resulting solution was concentrated, washed with brine and exacted with EA (50 mL). The organic phase was dried, concentrated and purified with flash column (EA: PE=1:3) to give (R)-methyl 5-bromo-6-cyclopropyl-2-(3-methylpiperazin-1-yl)nicotinate as a white solid (804 mg, 50% yield).

Step 2:
Following the same procedure as General procedure 1, step F, method 1.

Step 3:
Following the same procedure as General procedure 1, step H.

Step 4:
(R)-methyl6-cyclopropyl-5-(4-fluorophenyl)-2-(4-(3-methoxypropanoyl)-3-methylpiperazin-1-yl) nicotinate (500 mg, 1.1 mmol) and 2 mL hydrazine hydrate was dissolved in 10 mL ethanol. The reaction mixture was heated reflux overnight and cooled down to rt. The mixture was filtered and the residue was washed with cold ethanol. 200 mg title compound was obtained without further purification.

Step 5:
(R)-6-cyclopropyl-5-(4-fluorophenyl)-2-(4-(3-methoxypropanoyl)-3-methylpiperazin-1-yl) nicotine-hydrazide (200 mg, 0.44 mmol) was dissolved in trimethoxymethane (25 mL). The reaction mixture was heated to reflux overnight. The rest of trimethoxymethane was removed under reduced pressure and purified by prep-TLC to give 50 mg of title compound. 1H NMR (CHLOROFORM-d) δ 9.33 (s, 1H), 8.51 (d, J=6.0 Hz, 1H), 8.10 (s, 1H), 8.02 (d, J=7.8 Hz, 1H), 7.62-7.89 (m, 2H), 7.27 (s, 1H), 4.63-4.78 (m, 2H), 4.47-4.63 (m, 1H), 3.55-3.84 (m, 3H), 3.39 (s, 4H), 3.19 (dd, J=13.3, 3.5 Hz, 1H), 2.91-3.12 (m, 2H), 2.66-2.88 (m, 3H), 2.44-2.66 (m, 2H), 1.28-1.43 (m, 1.5H), 1.15-1.28 (m, 3.5H), 1.12 (br. s., 1H), 0.80-1.06 (m, 2H); LC-MS: m/z 466.2 (M+H).

2-(4-(cyclopropanecarbonyl)-3-(trifluoromethyl)piperazin-1-yl)-6-cyclopropyl-5-(isoquinolin-5-yl)nicotinonitrile (Compound 397; General Procedure 4, Step R and S)

1H NMR (CHLOROFORM-d) δ 9.35 (s, 1H), 8.54 (t, J=6.4 Hz, 1H), 8.07 (d, J=8.0 Hz, 1H), 7.60-7.76 (m, 3H), 7.35-7.49 (m, 1H), 5.39 (br. s., 0.5H), 4.28-4.86 (m, 3.5H), 3.70-3.97 (m, 1H), 3.44 (d, J=14.3 Hz, 1H), 3.23-3.39 (m,

1H), 1.68-1.91 (m, 1H), 1.53 (td, J=7.8, 3.5 Hz, 1H), 1.08-1.23 (m, 3H), 0.77-1.07 (m, 5H). LC-MS: m/z 492.2 (M+H)$^+$

6-cyclopropyl-5-(isoquinolin-5-yl)-2-(4-(3-methoxypropanoyl)-3-(trifluoromethyl)piperazin-1-yl)nicotinonitrile (Compound 398; General Procedure 4, Step R and S)

1H NMR (CHLOROFORM-d) δ 9.35 (br. s., 1H), 8.55 (t, J=6.0 Hz, 1H), 8.07 (d, J=8.0 Hz, 1H), 7.60-7.80 (m, 3H), 7.42 (dd, J=19.3, 5.5 Hz, 1H), 5.29-5.48 (m, 0.5H), 4.71-4.92 (m, 1.5H), 4.44-4.62 (m, 1H), 4.02 (d, J=13.3 Hz, 0.5H), 3.63-3.86 (m, 2.5H), 3.33-3.51 (m, 3.5H), 3.19-3.32 (m, 2H), 2.75-2.94 (m, 1H), 2.52-2.75 (m, 1H), 2.06 (br. s., 1H), 1.52 (tq, J=8.0, 4.1 Hz, 1H), 1.10-1.22 (m, 2H), 0.76-0.93 (m, 2H). LC-MS: m/z 510.4 (M+H)$^+$

6-cyclopropyl-5-(isoquinolin-5-yl)-2-(3-(trifluoromethyl)-4-(3,3,3-trifluoropropanoyl)piperazin-1-yl)nicotinonitrile (Compound 399; General Procedure 4, Step R and S)

1H NMR (CHLOROFORM-d) δ 9.35 (s, 1H), 8.54 (t, J=6.5 Hz, 1H), 8.07 (d, J=8.0 Hz, 1H), 7.55-7.80 (m, 3H), 7.32-7.45 (m, 1H), 5.26-5.49 (m, 0.5H), 4.45-5.03 (m, 2.5H), 3.72-3.95 (m, 2H), 3.22-3.52 (m, 5H), 1.54 (tq, J=8.0, 4.2 Hz, 1H), 1.10-1.22 (m, 2H), 0.78-0.94 (m, 3H). LC-MS: m/z 534.2 (M+H)$^+$

(R)-6-cyclopropyl-2-(4-(3-hydroxypropanoyl)-3-methylpiperazin-1-yl)-5-(isoquinolin-5-yl)nicotinonitrile (Compound 402; General Procedure 1, Step H)

$^1$H NMR (CHLOROFORM-d) δ 9.36 (br. s., 1H), 8.55 (d, J=5.8 Hz, 1H), 8.08 (d, J=8.0 Hz, 1H), 7.52-7.77 (m, 3H), 7.44 (t, J=6.0 Hz, 1H), 4.93 (br. s., 0.5H), 4.25-4.48 (m, 2.5H), 4.21 (br. s., 0.5H), 3.95 (br. s., 2H), 3.66-3.86 (m, 1.5H), 3.56-3.66 (m, 1H), 3.28-3.47 (m, 1H), 2.99-3.28 (m, 2H), 2.49-2.77 (m, 1H), 1.40-1.57 (m, 3H), 1.11-1.40 (m, 2H), 0.75-1.04 (m, 2H); LC-MS: m/z 442.2 (M+H).

(R)-6-cyclopropyl-5-(3-(dimethylamino)phenyl)-2-(4-(3-methoxypropanoyl)-3-methylpiperazin-1-yl)nicotinonitrile (Compound 413; General Procedure 1, Step H)

$^1$H NMR (CHLOROFORM-d) δ 7.61-7.69 (m, 1H), 7.29-7.34 (m, 1H), 6.65-6.83 (m, 3H), 4.91 (br. s., 0.5H), 4.54 (d, J=13.3 Hz, 0.5H), 4.14-4.34 (m, 2.5H), 3.70-3.87 (m, 2.5H), 3.56 (t, J=11.2 Hz, 0.5H), 3.34-3.46 (m, 3H), 3.00-3.28 (m, 8.5H), 2.54-2.83 (m, 2H), 2.14-2.23 (m, 1H), 1.29-1.43 (m, 3H), 1.07-1.20 (m, 2H), 0.84-1.01 (m, 2H). LC-MS: m/z 448.4 (M+H)$^+$

(R)-6-cyclopropyl-2-(4-(3-methoxypropanoyl)-3-methylpiperazin-1-yl)-5-(3-(methylamino)phenyl)nicotinonitrile (Compound 414; General Procedure 1, Step H)

$^1$H NMR (CHLOROFORM-d) δ 7.63 (s, 1H), 7.23-7.27 (m, 1H), 6.72 (d, J=7.8 Hz, 1H), 6.62-6.68 (m, 1H), 6.56-6.62 (m, 1H), 4.91 (br. s., 0.5H), 4.54 (d, J=13.6 Hz, 0.5H), 4.15-4.33 (m, 2.5H), 3.70-3.88 (m, 2.5H), 3.52-3.62 (m, 0.5H), 3.39 (s, 3H), 3.00-3.28 (m, 2.5H), 2.89 (s, 3H), 2.65-2.83 (m, 1H), 2.51-2.65 (m, 1H), 2.14-2.21 (m, 1H), 1.30-1.47 (m, 3H), 1.10-1.19 (m, 2H), 0.89-0.98 (m, 2H). LC-MS: m/z 434.5 (M+H)$^+$

(R)-6-cyclopropyl-2-(3-cyclopropyl-4-(3-methoxypropanoyl)piperazin-1-yl)-5-(isoquinolin-5-yl)nicotinonitrile (Compound 409; General Procedure 1, Step H)

$^1$H NMR (CHLOROFORM-d) δ 9.36 (br. s., 1H), 8.54 (d, J=4.5 Hz, 1H), 8.07 (d, J=8.0 Hz, 1H), 7.60-7.84 (m, 3H), 7.44 (dd, J=12.3, 6.0 Hz, 1H), 4.71-4.73 (m, 0.5H), 4.56 (d, J=11.8 Hz, 1H), 4.38-4.50 (m, 1H), 4.07-4.19 (m, 0.5H), 3.91 (d, J=11.0 Hz, 0.5H), 3.69-3.83 (m, 3H), 3.51 (s, 3H), 3.20-3.29 (m, 1.5H), 3.13 (br. s., 1H), 2.61-2.70 (m, 2H), 1.52 (ddd, J=12.0, 7.9, 4.6 Hz, 1H), 1.40 (br. s., 1H), 1.12-1.20 (m, 2H), 0.80-0.90 (m, 2H), 0.48-0.77 (m, 4H). LC-MS: m/z 482.6 (M+H)$^+$

(R)-6-cyclopropyl-2-(3-cyclopropyl-4-(3-hydroxypropanoyl)piperazin-1-yl)-5-(isoquinolin-5-yl)nicotinonitrile (Compound 419; General Procedure 1, Step H)

$^1$H NMR (CHLOROFORM-d) δ 9.40 (br. s., 1H), 8.48-8.69 (m, 1H), 8.11 (d, J=8.0 Hz, 1H), 7.63-7.86 (m, 3H), 7.44-7.55 (m, 1H), 4.70-4.73 (m, 0.5H), 4.57 (dd, J=13.1, 2.0 Hz, 1H), 4.41-4.52 (m, 1H), 4.13 (d, J=7.8 Hz, 0.5H), 3.94 (br. s., 2H), 3.69-3.82 (m, 1H), 3.13-3.26 (m, 3H), 2.50-2.71 (m, 2H), 1.48-1.57 (m, 1H), 1.39-1.48 (m, 1H), 1.12-1.21 (m, 2H), 0.86-0.91 (m, 2H), 0.42-0.69 (m, 4H). LC-MS: m/z 468.5 (M+H)$^+$

(R)-5-(5-cyano-2-cyclopropyl-6-(4-(3-methoxypropanoyl)-3-methylpiperazin-1-yl)pyridin-3-yl)isoquinoline 2-oxide (Compound 420)

$^1$H NMR (CHLOROFORM-d) δ 8.88 (br. s., 1H), 8.15 (d, J=6.5 Hz, 1H), 7.81 (d, J=8.3 Hz, 1H), 7.73 (t, J=7.7 Hz, 1H), 7.63 (s, 1H), 7.52-7.58 (m, 1H), 7.44-7.52 (m, 1H), 4.94 (br. s., 0.5H), 4.55-4.59 (m, 0.5H), 4.21-4.44 (m, 2.5H), 3.57-3.86 (m, 3H), 3.34-3.40 (m, 4H), 3.19-3.22 (m, 1.5H), 2.58-2.86 (m, 2H), 1.47-1.55 (m, 1H), 1.30-1.38 (m, 3H), 1.09-1.21 (m, 2H), 0.78-0.95 (m, 2H). LC-MS: m/z 472.4 (M+H)$^+$

6-cyclopropyl-5-(isoquinolin-5-yl)-2-(4-(3-methoxypropanoyl)piperazin-1-yl)nicotinonitrile (Compound 421; General Procedure 1, Step H)

$^1$H NMR (CHLOROFORM-d) δ 9.35 (br. s., 1H), 8.53 (d, J=5.0 Hz, 1H), 8.06 (d, J=8.3 Hz, 1H), 7.68-7.75 (m, 1H), 7.60-7.67 (m, 2H), 7.42 (d, J=5.8 Hz, 1H), 3.39-3.85 (m, 10H), 3.38 (s, 3H), 2.63-2.75 (m, 2H), 1.46-1.55 (m, 1H), 1.08-1.18 (m, 2H), 0.75-0.85 (m, 2H). LC-MS: m/z 442.5 (M+H)$^+$

2-(4-(cyclopropanecarbonyl)-3-(difluoromethyl)piperazin-1-yl)-6-cyclopropyl-5-(isoquinolin-5-yl)nicotinonitrile (Compound 422; General Procedure 4, Step R and S)

1H NMR (CHLOROFORM-d) δ 9.37 (br. s., 1H), 8.56 (br. s., 1H), 8.09 (d, J=8.0 Hz, 1H), 7.60-7.79 (m, 3H), 7.43 (d, J=10.3 Hz, 1H), 6.09 (br. s., 1H), 4.97-5.45 (m, 4H), 3.12-3.89 (m, 3H), 1.98-2.08 (m, 1H), 1.80-1.87 (m, 1H), 1.00-1.21 (m, 4H), 0.83-0.92 (m, 4H). LC-MS: m/z 474.5 (M+H)$^+$ 2-(4-(cyclopropanecarbonyl)-3-(2,2,2-trifluoroethyl) piperazin-1-yl)-6-cyclopropyl-5-(isoquinolin-5-yl) nicotinonitrile (Compound 423; General Procedure 4, Step R and S)

1H NMR (CHLOROFORM-d) δ 9.36 (s, 1H), 8.55 (dd, J=5.8, 3.5 Hz, 1H), 8.08 (d, J=8.0 Hz, 1H), 7.59-7.81 (m, 3H), 7.33-7.50 (m, 1H), 5.24 (br. s., 0.5H), 4.34 (d, J=13.1 Hz, 1H), 4.26-4.50 (m, 2.5H), 3.69 (br. s., 0.5H), 3.20-3.45 (m, 2H), 3.13 (br. s., 0.51H), 2.58-2.75 (m, 2H), 1.77 (br. s., 1H), 1.47-1.61 (m, 1H), 1.09-1.24 (m, 4H), 0.77-0.93 (m, 4H). LC-MS: m/z 506.5 (M+H)$^+$ (R)-2-cyclopropyl-2'-ethyl-6-(4-(3-methoxypropanoyl)-3-methylpiperazin-1-yl)-3,4'-bipyridine-5-carbonitrile (Compound 426)

Compound 390 (18 mg) in EtOH was treated with Pd/C and hydrogenated at room temperature and normal pressure to give the title compound as a white solid. 1H NMR (CHLOROFORM-d) δ 8.63 (d, J=4.8 Hz, 1H), 7.63 (s, 1H), 7.23 (d, J=4.5 Hz, 2H), 4.92 (br. s., 1H), 4.55 (d, J=12.8 Hz, 1H), 4.14-4.43 (m, 3H), 3.64-3.89 (m, 3H), 3.57 (br. s., 1H), 3.40 (s, 3H), 3.32 (d, J=11.8 Hz, 1H), 3.14 (d, J=14.3 Hz, 1H), 2.94 (q, J=7.4 Hz, 2H), 2.65-2.83 (m, 1H), 2.39-2.65 (m, 1H), 2.03 (td, J=8.0, 3.9 Hz, 2H), 1.25-1.42 (m, 8H), 1.11-1.25 (m, 3H), 1.01 (dd, J=7.8, 3.0 Hz, 2H). LC-MS: m/z 434.2 (M+H)$^+$ Compound 430 (General Procedure 1, Step I)

1H NMR (CHLOROFORM-d) δ 8.41 (dd, J=7.9, 1.4 Hz, 1H), 8.14 (s, 1H), 7.72-7.84 (m, 1H), 7.57-7.71 (m, 2H), 4.93 (d, J=13.3 Hz, 0.5H), 4.55 (d, J=13.3 Hz, 0.5H), 4.14-4.43 (m, 3H), 3.69-3.90 (m, 3H), 3.53-3.68 (m, 1H), 3.34-3.46 (m, 3H), 3.27 (t, J=11.2 Hz, 1H), 2.97-3.22 (m, 2H), 2.54-2.84 (m, 2H), 1.55-1.80 (m, 2H), 1.43 (d, J=6.5 Hz, 2H), 1.18-1.38 (m, 3H), 1.09 (br. s., 1H), 0.70-0.99 (m, 2H).
LC-MS: m/z 473.2 (M+H)$^+$ (R)-6-cyclopropyl-2-(4-(3-methoxypropanoyl)-3-methylpiperazin-1-yl)-5-(3-methylisoquinolin-5-yl) nicotinonitrile (Compound 433)

$^1$H NMR (CHLOROFORM-d) δ 9.23 (s, 1H), 7.93-8.03 (m, 1H), 7.50-7.66 (m, 3H), 7.21 (d, J=6.0 Hz, 1H), 4.92 (br. s., 0.5H), 4.55 (d, J=12.8 Hz, 0.5H), 4.19-4.42 (m, 2.5H), 3.83 (d, J=12.3 Hz, 0.5H), 3.65-3.78 (m, 2H), 3.56 (d, J=16.8 Hz, 0.5H), 3.37 (s, 3H), 3.31 (d, J=13.1 Hz, 1H), 2.98-3.25 (m, 1.5H), 2.68-2.84 (m, 1H), 2.53-2.68 (m, 5H), 1.47-1.57 (m, 1H), 1.43 (d, J=6.3 Hz, 1.5H), 1.29-1.36 (m, 1.5H), 1.13 (dd, J=6.5, 4.0 Hz, 2H), 0.76-0.84 (m, 2H). LC-MS: m/z 470.2 (M+H)$^+$ (R)-6-cyclopropyl-5-(4-methoxyisoquinolin-5-yl)-2-(4-(3-methoxypropanoyl)-3-methylpiperazin-1-yl) nicotinonitrile (Compound 434)

$^1$H NMR (CHLOROFORM-d) δ 8.32 (dd, J=7.5, 1.3 Hz, 1H), 7.98 (d, J=6.0 Hz, 1H), 7.52-7.65 (m, 3H), 6.94 (t, J=5.9 Hz, 1H), 4.85 (br. s., 0.5H), 4.55 (d, J=12.8 Hz, 0.5H), 4.20-4.40 (m, 2.5H), 4.15 (s, 3H), 3.66-3.89 (m, 3H), 3.38 (s, 3H), 3.31 (d, J=8.3 Hz, 1H), 3.17 (d, J=13.3 Hz, 1.5H), 2.65-2.84 (m, 1H), 2.51-2.65 (m, 1H), 1.48-1.60 (m, 1H), 1.42 (m, 1.5H), 1.29-1.36 (m, 1.5H), 1.03-1.19 (m, 2H), 0.81 (dd, J=8.0, 3.0 Hz, 2H). LC-MS: m/z 486.2 (M+H)$^+$ (1R,2R)-ethyl 2-((R)-4-(3-cyano-6-cyclopropyl-5-(isoquinolin-5-yl)pyridin-2-yl)-2-methyl piperazine-1-carbonyl)cyclopropanecarboxylate (Compound 435)

1H NMR (CHLOROFORM-d) δ 9.34 (s, 1H), 8.53 (d, J=5.8 Hz, 1H), 8.06 (d, J=8.0 Hz, 1H), 7.62-7.80 (m, 3H), 7.42 (t, J=5.9 Hz, 1H), 4.87 (br. s., 0.5H), 4.38-4.65 (m, 1.5H), 4.33 (d, J=12.0 Hz, 2H), 4.19 (q, J=7.0 Hz, 2H), 3.62-3.85 (m, 0.5H), 3.46 (d, J=13.1 Hz, 0.5H), 3.10-3.40 (m, 2H), 2.36 (br. s., 1H), 2.17-2.31 (m, 1H), 2.09 (br. s., 1H), 1.38-1.45 (m, 2H), 1.22-1.37 (m, 6H), 1.03-1.22 (m, 2H), 0.69-0.94 (m, 2H). LC-MS: m/z 461.2 (M+H)$^+$ (R)-5-(5-cyano-6-(4-(cyclopropanecarbonyl)-3-cyclopropylpiperazin-1-yl)-2-cyclopropylpyridin-3-yl) isoquinoline 2-oxide (Compound 439)

$^1$H NMR (CHLOROFORM-d) δ 8.87 (br. s., 1H), 8.06-8.26 (m, 1H), 7.70-7.83 (m, 2H), 7.61-7.69 (m, 1H), 7.54 (br. s., 2H), 4.59 (d, J=7.0 Hz, 1H), 4.47 (d, J=12.5 Hz, 1H), 3.51-4.30 (m, 3H), 3.32 (br. s., 1H), 3.17 (br. s., 1H), 1.96-2.10 (m, 1H), 1.75 (br. s., 1H), 1.43-1.54 (m, 1H), 1.14-1.23 (m, 2H), 1.00-1.12 (m, 2H), 0.81-0.94 (m, 4H), 0.38-0.73 (m, 4H). LC-MS: m/z 480.2 (M+H)$^+$ (R)—N-(3-(5-cyano-2-cyclopropyl-6-(4-(3-methoxypropanoyl)-3-methylpiperazin-1-yl)pyridin-3-yl)phenyl)-N-(vinylsulfonyl)ethenesulfonamide (Compound 440; General Procedure 3, Step N, Method 1)

$^1$H NMR (CHLOROFORM-d) δ 7.60-7.64 (m, 1H), 7.50-7.56 (m, 2H), 7.29-7.37 (m, 3H), 7.01-7.16 (m, 2H), 6.26-6.40 (m, 2H), 6.11-6.25 (m, 2H), 4.92 (s, 0.5H), 4.54 (d, J=13.3 Hz, 0.5H), 4.19-4.37 (m, 2.5H), 3.73-3.79 (m, 3H), 3.52-3.61 (m, 0.5H), 3.39 (s, 3H), 3.28 (t, J=10.4 Hz, 1H), 3.02-3.14 (m, 1H), 2.65-2.80 (m, 1H), 2.55-2.64 (m, 1H), 1.98-2.07 (m, 1H), 1.27 (s, 3H), 1.14-1.19 (m, 2H), 0.95-1.01 (m, 2H). LC-MS: m/z 600.2 (M+H)$^+$ (R,E)-N-(3-(5-cyano-2-cyclopropyl-6-(4-(3-methoxypropanoyl)-3-methylpiperazin-1-yl)pyridin-3-yl)phenyl)-4-(dimethylamino)but-2-enamide (Compound 441; General Procedure 3, Step N, Method 2)

$^1$H NMR (CHLOROFORM-d) δ 9.22 (s, 1H), 7.68 (s, 1H), 7.53-7.60 (m, 1H), 7.41-7.53 (m, 1H), 7.31 (s, 1H), 7.08 (d, J=7.3 Hz, 1H), 6.86 (s, 1H), 6.61 (d, J=15.3 Hz, 1H), 4.83 (s, 0.5H), 4.46 (d, J=11.0 Hz, 0.5H), 4.22 (d, J=9.8 Hz, 2.5H), 3.90 (s, 1.5H), 3.67-3.81 (m, 2.5H), 3.52 (s, 0.5H), 3.28-3.41 (m, 3H), 3.24 (s, 1H), 3.04-3.15 (m, 1H), 2.94-3.04 (m, 1H), 2.88 (s, 2H), 2.82 (s, 6H), 2.57 (d, J=15.8 Hz, 1H), 1.97-2.08 (m, 1H), 1.33-1.40 (m, 2H), 1.18-1.30 (m, 2H), 1.02-1.15 (m, 2H), 0.89 (s, 2H). LC-MS: m/z 531.3 (M+H)$^+$ (R)-6-cyclopropyl-5-(2-hydroxyquinolin-5-yl)-2-(4-(3-methoxypropanoyl)-3-methylpiperazin-1-yl)nicotinonitrile (Compound 442)

1H NMR (CHLOROFORM-d) δ 7.88 (d, J=9.5 Hz, 1H), 7.63-7.70 (m, 1H), 7.43-7.63 (m, 3H), 6.80 (d, J=9.5 Hz,

1H), 4.92 (br. s., 0.5H), 4.57 (d, J=13.1 Hz, 0.5H), 4.15-4.45 (m, 3H), 3.66-3.87 (m, 2H), 3.40 (s, 2H), 3.29 (t, J=9.7 Hz, 1H), 3.11-3.22 (m, 1H), 2.66-2.88 (m, 1H), 2.48-2.66 (m, 1H), 1.96-2.10 (m, 1H), 1.36-1.56 (m, 1.5H), 1.08-1.36 (m, 3.5H), 0.97 (dd, J=7.8, 3.0 Hz, 2H). LC-MS: m/z 472.3 (M+H)$^+$ (R)-6-(4-(cyclopropanecarbonyl)-3-methylpiperazin-1-yl)-2-cyclopropyl-2'-vinyl-3,4'-bipyridine-5-carbonitrile (Compound 443; General Procedure 5, Step W)

1H NMR (CHLOROFORM-d) δ 8.66 (d, J=4.3 Hz, 1H), 7.59-7.67 (m, 1H), 7.35-7.45 (m, 1H), 7.24 (d, J=4.3 Hz, 1H), 6.89 (dd, J=17.3, 10.8 Hz, 1H), 6.29 (d, J=17.3 Hz, 1H), 5.58 (d, J=10.8 Hz, 1H), 4.87 (br. s., 1H), 4.56 (br. s., 1H), 4.30 (d, J=13.3 Hz, 1H), 4.13 (br. s., 1H), 3.58-3.88 (m, 1H), 3.33 (d, J=10.0 Hz, 1H), 3.20 (br. s., 2H), 1.91-2.09 (m, 1H), 1.38-1.51 (m, 1.5H), 1.11-1.38 (m, 2.5H), 0.87-1.08 (m, 6H), 0.79-0.87 (m, 2H). LC-MS: m/z 414.4 (M+H)$^+$ (R)-2-cyclopropyl-6-(3-methyl-4-(3,3,3-trifluoropropanoyl)piperazin-1-yl)-2'-vinyl-3,4'-bipyridine-5-carbonitrile (Compound 444; General Procedure 5, Step W)

1H NMR (CHLOROFORM-d) δ 7.59-7.69 (m, 1H), 7.34-7.43 (m, 1H), 7.15-7.27 (m, 1H), 6.89 (dd, J=17.6, 10.8 Hz, 1H), 6.23-6.37 (m, 1H), 5.58 (d, J=11.5 Hz, 1H), 4.94 (br. s., 1H), 4.20-4.48 (m, 2H), 3.51-3.79 (m, 1H), 3.37 (d, J=5.5 Hz, 1H), 3.05-3.34 (m, 4H), 1.87-2.07 (m, 1H), 1.42-1.51 (m, 2H), 1.13-1.42 (m, 3H), 0.95-1.08 (m, 2H). LC-MS: m/z 456.8 (M+H)$^+$ (R)-6-(4-(cyclopropanecarbonyl)-3-cyclopropylpiperazin-1-yl)-2-cyclopropyl-2'-vinyl-3,4'-bipyridine-5-carbonitrile (Compound 485; General Procedure 5, Step W)

$^1$H NMR (CHLOROFORM-d) δ 8.77 (br. s., 1H), 7.96 (br. s., 1H), 7.80-7.92 (m, 2H), 7.12-7.27 (m, 1H), 6.82 (d, J=17.6 Hz, 1H), 6.06 (d, J=10.8 Hz, 1H), 4.67 (d, J=12.3 Hz, 1H), 4.54 (d, J=11.5 Hz, 2H), 4.24 (br. s., 1H), 3.67 (br. s., 1H), 3.33 (br. s., 1H), 3.18 (br. s., 1H), 1.93 (br. s., 1H), 1.67 (br. s., 1H), 1.25 (br. s., 2H), 1.04-1.23 (m, 3H), 0.89-1.04 (m, 3H), 0.47 (d, J=4.8 Hz, 2H), 0.39 (br. s., 2H). LC-MS: m/z 440.2 (M+H)$^+$

Compound 527 (General Procedure 5, Step W)

$^1$H NMR (CHLOROFORM-d) δ 8.65 (d, J=4.7 Hz, 1H), 7.65 (s, 1H), 7.38 (s, 1H), 7.23 (d, J=4.1 Hz, 1H), 6.87 (dd, J=17.5, 10.7 Hz, 1H), 6.28 (d, J=17.6 Hz, 1H), 5.56 (d, J=10.9 Hz, 1H), 4.55 (d, J=13.2 Hz, 1H), 4.43 (d, J=12.6 Hz, 1H), 4.03-4.16 (m, 1H), 3.91 (br. s., 2H), 3.65-3.82 (m, 1H), 3.40-3.53 (m, 1H), 3.02-3.32 (m, 3H), 2.49-2.69 (m, 2H), 1.98-2.10 (m, 1H), 1.13-1.38 (m, 3H), 1.01 (dd, J=7.5, 3.4 Hz, 2H), 0.63 (br. s., 1H), 0.55 (br. s., 1H), 0.32-0.51 (m, 2H). LC-MS: m/z 444.3 (M+H)$^+$ (R)-2-cyclopropyl-6-(3-cyclopropyl-4-(3,3,3-trifluoropropanoyl)piperazin-1-yl)-2'-vinyl-3,4'-bipyridine-5-carbonitrile (Compound 498; General Procedure 5, Step W)

$^1$H NMR (CHLOROFORM-d) δ 8.54-8.72 (m, 1H), 7.57-7.74 (m, 1H), 7.38 (d, J=1.0 Hz, 1H), 7.23 (dd, J=5.1, 1.6 Hz, 1H), 6.88 (dd, J=17.3, 10.8 Hz, 1H), 6.28 (dd, J=17.4, 1.1 Hz, 1H), 5.48-5.63 (m, 1H), 4.56 (dd, J=13.2, 1.9 Hz, 1H), 4.45 (d, J=13.1 Hz, 1H), 4.11 (br. s., 1H), 3.65-3.88 (m, 2H), 3.32 (q, J=9.6 Hz, 2H), 3.20 (d, J=12.0 Hz, 1H), 2.98-3.15 (m, 1H), 2.04 (tt, J=8.0, 4.7 Hz, 1H), 1.30-1.39 (m, 1H), 1.14-1.25 (m, 2H), 0.96-1.07 (m, 2H), 0.65 (br. s., 1H), 0.56 (br. s., 1H), 0.41-0.54 (m, 2H). LC-MS: m/z 482.5 (M+H)$^+$ (R)-2-cyclopropyl-6-(4-(3-methoxypropanoyl)-3-methylpiperazin-1-yl)-2'-vinyl-3,4'-bipyridine-5-carbonitrile (Compound 500; General Procedure 5, Step W)

1H NMR (CHLOROFORM-d) δ 8.66 (d, J=5.0 Hz, 1H), 7.60-7.71 (m, 1H), 7.41 (s, 1H), 7.26 (dd, J=5.0, 1.3 Hz, 1H), 6.90 (dd, J=17.4, 10.9 Hz, 1H), 6.31 (d, J=17.1 Hz, 1H), 5.60 (d, J=11.0 Hz, 1H), 4.72-4.99 (m, 0.5H), 4.54 (d, J=13.1 Hz, 0.5H), 4.22-4.49 (m, 2H), 3.74 (d, J=13.6 Hz, 1H), 3.56 (br. s., 1H), 3.40 (br. s., 1H), 3.32 (td, J=8.6, 3.9 Hz, 1H), 2.95-3.25 (m, 2H), 2.68 (br. s., 1H), 2.44-2.65 (m, 2H), 2.00-2.19 (m, 1H), 1.16-1.45 (m, 3H), 0.95-1.12 (m, 3H), 0.90 (t, J=6.8 Hz, 1H). LC-MS: m/z 418.6 (M+H)$^+$ (R)-2-cyclopropyl-6-(4-(4,4-dimethoxybutanoyl)-3-methylpiperazin-1-yl)-2'-vinyl-[3,4'-bipyridine]-5-carbonitrile (Compound 606; General Procedure 5, Step W)

$^1$H NMR (CHLOROFORM-d) δ 8.64 (d, J=5.0 Hz, 1H), 7.63 (s, 1H), 7.38 (s, 1H), 7.23 (dd, J=5.0, 1.5 Hz, 1H), 6.81-6.93 (m, 1H), 6.28 (d, J=11.0 Hz, 1H), 5.56 (d, J=11.0 Hz, 1H), 4.88 (s, 0.5H), 4.24-4.53 (m, 1.5H), 4.24-4.36 (m, 2.5H), 3.78 (d, 0.5H), 3.54 (t, 0.5H), 3.27-3.37 (m, 4H), 3.02-3.18 (m, 1.5H), 2.35-2.56 (m, 2H), 1.92-2.06 (m, 4H), 1.38 (d, 1.5H), 1.28 (d, 1.5H), 1.18-1.21 (m, 2H), 0.99-1.02 (m, 2H). LC-MS: m/z 476.2 (M+H)$^+$ (R)-2-cyclopropyl-6-(3-methyl-4-(4-oxobutanoyl)piperazin-1-yl)-2'-vinyl-[3,4'-bipyridine]-5-carbonitrile (Compound 607), which was Obtained as the by-Product of Compound 606

$^1$H NMR (CHLOROFORM-d) δ 9.90 (s, 1H), 8.65 (d, J=5.0 Hz, 1H), 7.64 (s, 1H), 7.38 (s, 1H), 7.24 (d, J=5.0 Hz, 1H), 6.88 (q, 1H), 6.28 (d, 1H), 5.56 (d, 1H), 4.85 (br. s., 0.5H), 4.48 (d, J=12.8 Hz, 0.5H), 4.25-4.37 (m, 2.5H), 3.80 (br. s., 0.5H), 3.60 (br. s., 0.5H), 3.03-3.38 (m, 3H), 2.62-2.89 (m, 4.5H), 2.03 (m, 1H), 1.42 (d, 1.5H), 1.28 (d, 1.5H), 1.18-1.21 (m, 2H), 0.99-1.10 (m, 2H). LC-MS: m/z 430.2 (M+H)$^+$ (S)-2-cyclopropyl-6-(3-cyclopropyl-4-(3-hydroxypropanoyl)piperazin-1-yl)-2'-vinyl-[3,4'-bipyridine]-5-carbonitrile (Compound 587; General Procedure 5, Step W)

$^1$H NMR (CHLOROFORM-d) δ 8.66 (d, J=5.0 Hz, 1H), 7.62-7.73 (m, 1H), 7.39 (s, 1H), 7.24 (dd, J=5.0, 1.5 Hz, 1H), 6.88 (dd, J=17.6, 10.8 Hz, 1H), 6.29 (d, J=17.3 Hz, 1H), 5.57 (d, J=10.8 Hz, 1H), 4.56 (d, J=13.1 Hz, 1H), 4.43 (d, J=11.3 Hz, 1.5H), 4.09 (d, J=8.8 Hz, 0.5H), 3.93 (d, J=5.0 Hz, 2H), 3.75-3.82 (m, 1.5H), 3.43 (br. s., 1H), 3.16-3.32 (m, 1.5H), 3.02-3.16 (m, 1H), 2.43-2.71 (m, 2H), 2.00-2.09 (m, 1H), 1.67 (s, 1H), 1.16-1.25 (m, 2H), 0.95-1.08 (m, 2H), 0.40-0.80 (m, 4H). LC-MS: m/z 444.2 (M+H)$^+$

(R)-6-cyclopropyl-2-(4-(3-methoxypropanoyl)-3-methylpiperazin-1-yl)-5-(quinoxalin-6-yl)nicotinonitrile (Compound 445; General Procedure 1, Step H)

$^1$H NMR (CHLOROFORM-d) δ 8.90 (d, J=3.0 Hz, 2H), 8.05-8.34 (m, 2H), 7.85 (d, J=8.5 Hz, 1H), 7.74 (s, 1H), 4.92 (br. s., 0.5H), 4.26-4.56 (m, 3H), 3.57-3.84 (m, 3H), 3.31-3.38 (m, 4H), 3.13-3.16 (m, 1.5H), 2.27-2.78 (m, 2H), 2.04-2.16 (m, 1H), 1.41 (d, J=5.8 Hz, 1.5H), 1.30 (d, J=6.0 Hz, 1.5H), 1.22 (br. s., 2H), 0.94-1.06 (m, 2H). LC-MS: m/z 457.2 (M+H)$^+$

Compound 446 (General Procedure 3, Step N, Method 1)

1H NMR (CHLOROFORM-d) δ 7.58-7.67 (m, 1H), 7.38-7.50 (m, 2H), 7.32 (dd, J=7.7, 1.6 Hz, 2H), 6.49 (dd, J=16.6, 10.0 Hz, 1H), 6.25 (d, J=16.6 Hz, 1H), 6.06 (d, J=10.0 Hz, 1H), 4.91 (br. s., 0.5H), 4.54 (d, J=13.1 Hz, 0.5H), 4.13-4.41 (m, 3H), 3.71-3.87 (m, 2H), 3.49-3.63 (m, 1H), 3.39 (s, 3H), 3.21-3.34 (m, 4H), 2.95-3.21 (m, 2H), 2.51-2.81 (m, 2H), 1.91-2.17 (m, 1H), 1.73 (br. s., 2H), 1.23-1.50 (m, 5H), 0.94-1.23 (m, 4H). LC-MS: m/z 524.2 (M+H)$^+$

(S)-2-chloro-N-(3-(5-cyano-2-cyclopropyl-6-((R)-4-(3-methoxypropanoyl)-3-methylpiperazin-1-yl)pyridin-3-yl)phenyl)propanamide (Compound 447; General Procedure 3, Step N, Method 2)

$^1$H NMR (CHLOROFORM-d) δ 8.57 (s, 1H), 7.70 (s, 1H), 7.57-7.64 (m, 1H), 7.47-7.56 (m, 1H), 7.42 (t, J=7.8 Hz, 1H), 7.18 (d, J=7.5 Hz, 1H), 4.90 (br. s., 0.5H), 4.47-4.65 (m, 1.5H), 4.18-4.30 (m, 2.5H), 3.73-3.81 (m, 2.5H), 3.48-3.64 (m, 0.5H), 3.37 (s, 3H), 3.21-3.31 (m, 1H), 2.95-3.18 (m, 1.5H), 2.53-2.79 (m, 2H), 2.04-2.12 (m, 1H), 1.83 (d, J=7.0 Hz, 3H), 1.38 (d, J=6.3 Hz, 1.5H), 1.28 (d, J=6.5 Hz, 1.5H), 1.11-1.18 (m, 2H), 0.89-1.03 (m, 2H). LC-MS: m/z 510.1 (M+H)$^+$

(R)—N-(3-(5-cyano-2-cyclopropyl-6-(4-(3-methoxypropanoyl)-3-methylpiperazin-1-yl)pyridin-3-yl)phenyl)ethanesulfonamide (Compound 448; General Procedure 3, Step N, Method 1)

$^1$H NMR (CHLOROFORM-d) δ 7.60 (s, 1H), 7.38-7.49 (m, 2H), 7.30-7.34 (m, 1H), 7.26 (dd, J=8.0, 1.3 Hz, 1H), 7.18 (d, J=7.8 Hz, 1H), 4.90 (br. s., 0.5H), 4.53 (d, J=13.3 Hz, 0.5H), 4.13-4.40 (m, 2.5H), 3.67-3.93 (m, 2.5H), 3.51-3.66 (m, 0.5H), 3.38 (s, 3H), 3.02-3.32 (m, 4.5H), 2.55-2.84 (m, 2H), 2.00-2.11 (m, 1H), 1.38-1.44 (m, 4H), 1.24-1.31 (m, 2H), 1.12-1.21 (m, 2H), 0.90-1.03 (m, 2H). LC-MS: m/z 512.1 (M+H)$^+$

(R)—N-(3-(5-cyano-2-cyclopropyl-6-(4-(3-methoxypropanoyl)-3-methylpiperazin-1-yl)pyridin-3-yl)phenyl)methacrylamide (Compound 449; General Procedure 3, Step N, Method 1)

$^1$H NMR (CHLOROFORM-d) δ 7.83 (s, 1H), 7.72 (s, 1H), 7.60 (s, 1H), 7.51-7.57 (m, 1H), 7.40 (t, J=7.9 Hz, 1H), 7.15 (d, J=7.8 Hz, 1H), 5.83 (s, 1H), 5.43-5.54 (m, 1H), 4.89 (br. s., 0.5H), 4.52 (d, J=13.3 Hz, 0.5H), 4.13-4.36 (m, 2.5H), 3.68-3.87 (m, 2.5H), 3.55 (t, J=11.3 Hz, 0.5H), 3.35-3.46 (m, 3H), 3.20-3.31 (m, 1H), 2.96-3.17 (m, 1.5H), 2.81 (s, 2H), 2.51-2.77 (m, 2H), 2.03-2.19 (m, 4H), 1.38 (d, J=6.3 Hz, 1.5H), 1.28 (d, J=6.5 Hz, 1.5H), 1.10-1.18 (m, 2H), 0.88-1.02 (m, 2H). LC-MS: m/z 488.1 (M+H)$^+$

(R)—N-(3-(5-cyano-6-(4-(cyclopropanecarbonyl)-3-cyclopropylpiperazin-1-yl)-2-cyclopropylpyridin-3-yl)phenyl)propiolamide (Compound 451; General Procedure 3, Step N, Method 1)

$^1$H NMR (CHLOROFORM-d) δ 7.60 (s, 1H), 7.35-7.47 (m, 1H), 7.28 (s, 1H), 7.23-7.27 (m, 1H), 7.15-7.22 (m, 2H), 6.63 (dd, J=16.6, 9.8 Hz, 1H), 6.26-6.39 (m, 1H), 6.01 (d, J=9.8 Hz, 1H), 4.52 (d, J=12.5 Hz, 1H), 4.40 (d, J=12.3 Hz, 1H), 4.07-4.24 (m, 1H), 3.65-3.90 (m, 1H), 3.22-3.52 (m, 1.5H), 3.10 (s, 1.5H), 2.03-2.10 (m, 1H), 1.29-1.36 (m, 1H), 1.14-1.21 (m, 2H), 0.93-1.12 (m, 4H), 0.85-0.92 (m, 1H), 0.76-0.85 (m, 2H), 0.60-0.71 (m, 1H), 0.38-0.60 (m, 3H). LC-MS: m/z 518.2 (M+H)$^+$

(R)—N-(3-(5-cyano-6-(4-(cyclopropanecarbonyl)-3-cyclopropylpiperazin-1-yl)-2-cyclopropylpyridin-3-yl)phenyl)-N-(vinylsulfonyl)ethenesulfonamide (Compound 452; General Procedure 3, Step N, Method 1)

$^1$H NMR (CHLOROFORM-d) δ 7.63 (s, 1H), 7.49-7.58 (m, 2H), 7.33-7.36 (m, 1H), 7.31 (dt, J=6.7, 2.3 Hz, 1H), 7.07 (d, J=9.8 Hz, 1H), 7.10-7.13 (m, 1H), 6.28-6.38 (m, 2H), 6.14-6.22 (m, 2H), 4.41-4.62 (m, 2.5H), 3.98-4.18 (m, 1H), 3.75-3.90 (m, 1H), 3.09-3.33 (2.5, 1H), 2.00-2.07 (m, 1H), 1.15-1.25 (m, 3H), 0.97-1.11 (m, 4H), 0.86-0.92 (m, 1H), 0.82 (dd, J=7.8, 2.3 Hz, 2H), 0.39-0.67 (m, 4H). LC-MS: m/z 608.2 (M+H)$^+$

(R)—N-(3-(5-cyano-2-cyclopropyl-6-(4-(3-methoxypropanoyl)-3-methylpiperazin-1-yl)pyridin-3-yl)phenyl)-2-fluoro-N-methylacrylamide (Compound 453; General Procedure 3, Step N, Method 2)

$^1$H NMR (CHLOROFORM-d) δ 7.60 (s, 1H), 7.43-7.54 (m, 1H), 7.34 (d, J=7.8 Hz, 1H), 7.17-7.26 (m, 2H), 5.44 (d, J=3.3 Hz, 1H), 5.18-5.38 (m, 1H), 4.82-5.11 (m, 2H), 4.54 (d, J=12.3 Hz, 1H), 4.10-4.40 (m, 3H), 3.75 (br. s., 2H), 3.57 (d, J=7.8 Hz, 1H), 3.35-3.48 (m, 6H), 3.28 (br. s., 1H), 3.14 (d, J=10.5 Hz, 1H), 2.94-3.10 (m, 1H), 2.73 (br. s., 1H), 2.60 (br. s., 1H), 2.19 (s, 1H), 1.90-2.10 (m, 1H), 1.78 (br. s., 1H), 1.23-1.51 (m, 8H), 1.06-1.23 (m, 2H), 0.78-1.06 (m, 3H). LC-MS: m/z 506.2 (M+H)$^+$

(R)—N-(3-(5-cyano-6-(4-(cyclopropanecarbonyl)-3-cyclopropylpiperazin-1-yl)-2-cyclopropylpyridin-3-yl)phenyl)acrylamide (Compound 454; General Procedure 3, Step N, Method 1)

$^1$H NMR (CHLOROFORM-d) δ 7.73-7.80 (m, 2H), 7.63 (s, 1H), 7.51-7.59 (m, 1H), 7.42 (t, J=7.8 Hz, 1H), 7.17 (d, J=7.5 Hz, 1H), 6.40-6.54 (m, 1H), 6.31 (dd, J=16.8, 10.3 Hz, 1H), 5.81 (d, J=10.3 Hz, 1H), 4.51 (d, J=12.3 Hz, 1H), 4.39 (d, J=12.3 Hz, 1H), 3.92-4.27 (m, 1H), 3.51-3.94 (m, 1H), 3.25 (m, 1H), 2.85-3.42 (m, 3H), 2.08-2.15 (m, 1H), 1.29-1.36 (m, 1H), 1.13-1.20 (m, 2H), 0.94-1.11 (m, 4H), 0.86-0.93 (m, 1H), 0.75-0.85 (m, 2H), 0.68 (d, J=12.5 Hz, 1H), 0.40-0.54 (m, 3H). LC-MS: m/z 482.2 (M+H)$^+$

Compound 455 (General Procedure 3, Step N, Method 2)

¹H NMR (CHLOROFORM-d) δ ☐ 7.61 (s, 1H), 7.47 (d, J=7.5 Hz, 1H), 7.31-7.36 (m, 1H), 5.87 (s, 1H), 4.83-5.04 (m, 1H), 4.19-4.42 (m, 3H), 3.76 (br. s., 2H), 3.56 (br. s., 1H), 3.36-3.49 (m, 6H), 3.30 (br. s., 1H), 2.91-3.20 (m, 4H), 2.74 (br. s., 1H), 2.68 (br. s., 1H), 2.61 (br. s., 1H), 1.93-2.02 (m, 1H), 1.15-1.45 (m, 16H), 0.99 (dd, J=7.8, 2.8 Hz, 2H), 0.76-0.94 (m, 2H). LC-MS: m/z 512.2 (M+H)⁺

Compound 456 (General Procedure 3, Step N, Method 2)

¹H NMR (CHLOROFORM-d) δ ☐7.61 (s, 1H), 7.52 (t, J=7.7 Hz, 1H), 7.40 (d, J=7.8 Hz, 1H), 7.29-7.37 (m, 2H), 4.10-4.39 (m, 3H), 3.70-3.90 (m, 2H), 3.66 (s, 1H), 3.49 (s, 1H), 3.38 (s, 5H), 3.30 (d, J=14.8 Hz, 1H), 3.14 (br. s., 2H), 2.71-2.91 (m, 2H), 2.48-2.71 (m, 2H), 2.05 (dt, J=7.8, 4.0 Hz, 2H), 1.13-1.42 (m, 8H), 0.91-1.08 (m, 2H). LC-MS: m/z 486.2 (M+H)⁺

(R)-6-cyclopropyl-5-(4-hydroxyisoquinolin-5-yl)-2-(4-(3-methoxypropanoyl)-3-methylpiperazin-1-yl)nicotinonitrile (Compound 457; General Procedure 1, Step I)

¹H NMR (CHLOROFORM-d) δ 10.93 (s, 1H), 8.51 (dd, J=6.8, 2.3 Hz, 1H), 7.51-7.67 (m, 3H), 6.32 (s, 1H), 4.92 (br. s., 0.5H), 4.55 (d, J=12.8 Hz, 0.5H), 4.18-4.41 (m, 2.5H), 3.53-3.92 (m, 3.5H), 3.40 (s, 1H), 3.16-3.38 (m, 2.5H), 2.51-2.83 (m, 2H), 1.61 (br. s., 1H), 1.39-1.49 (m, 1.5H), 1.31-1.39 (m, 1.5H), 1.14 (dd, J=8.3, 4.8 Hz, 2H), 0.79-0.93 (m, 2H). LC-MS: m/z 472.2 (M+H)⁺

(R)-2-(4-(cyclopropanecarbonyl)-3-cyclopropylpiperazin-1-yl)-6-cyclopropyl-5-(3-methylisoquinolin-5-yl)nicotinonitrile (Compound 458; General Procedure 1, Step I)

¹H NMR (CHLOROFORM-d) δ 9.25 (s, 1H), 8.00 (dd, J=7.2, 1.6 Hz, 1H), 7.54-7.67 (m, 3H), 7.16-7.27 (m, 1H), 4.57 (d, J=12.5 Hz, 1H), 4.46 (d, J=12.5 Hz, 1H), 3.62-4.63 (m, 2H), 3.10-3.40 (m, 2.5H), 2.67 (d, J=4.5 Hz, 3H), 2.25-2.49 (m, 0.5H), 1.74 (br. s., 1H), 1.54 (dtd, J=12.7, 3.9, 1.9 Hz, 2H), 1.13-1.23 (m, 2H), 0.95-1.13 (m, 2H), 0.77-0.91 (m, 4H), 0.70 (br. s., 1H), 0.39-0.60 (m, 3H). LC-MS: m/z 478.2 (M+H)⁺

(R)-6-cyclopropyl-2-(4-(3-methoxypropanoyl)-3-methylpiperazin-1-yl)-5-(3-(2-oxo-2,5-dihydro-1H-pyrrol-1-yl)phenyl)nicotinonitrile (Compound 459)

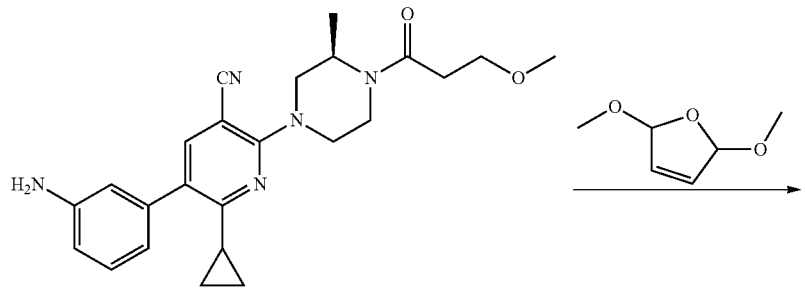

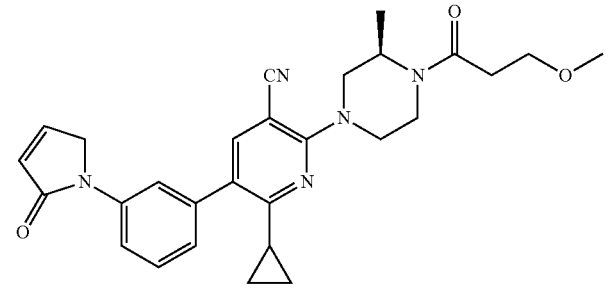

A mixture of (R)-5-(3-aminophenyl)-6-cyclopropyl-2-(4-(3-methoxypropanoyl)-3-methylpiperazin-1-yl)nicotinonitrile (300 mg), pentane-2,4-dione (100 mg) and TFA (1 drop) in cyclohexane was refluxed for 3 h. After evaporation, the residue was dissolved in CH₃CN and some Na₂SO4 was added followed by select-F-TEDA-BF₄ (800 mg). The mixture was refluxed for overnight. After evaporation, the residue was purified by pre-TLC to give the title compound (75 mg). 1H NMR (CHLOROFORM-d) δ 7.86 (s, 1H), 7.58-7.75 (m, 2H), 7.47 (t, J=8.0 Hz, 1H), 7.10-7.26 (m, 2H), 6.33 (dt, J=6.0, 1.8 Hz, 1H), 4.91 (br. s., 0.5H), 4.42-4.63 (m, 2.5H), 4.13-4.40 (m, 2.5H), 3.65-3.95 (m, 2.5H), 3.39 (s, 3H), 3.21-3.32 (m, 1H), 2.99-3.20 (m, 2H), 2.52-2.81 (m, 2H), 2.00-2.29 (m, 1H), 1.35-1.53 (m, 1.5H), 1.23-1.35 (m, 1.5H), 1.07-1.23 (m, 2H), 0.92-1.07 (m, 2H). LC-MS: m/z 486.2 (M+H)⁺

(R)-6-Cyclopropyl-2-(4-(3-methoxypropanoyl)-3-methylpiperazin-1-yl)-5-(2-methyl-1-oxoisoindolin-4-yl)nicotinonitrile (Compound 460; General Procedure 1, Step I)

$^1$H NMR (CHLOROFORM-d) δ 7.93-7.88 (m, 1H), 7.61-7.55 (m, 2H), 7.45 (dd, J=7.5, 0.9 Hz, 1H), 4.97 (ddd, J=13.1, 10.1, 1.5 Hz, 1H), 4.42-4.15 (m, 5H), 3.90-3.49 (m, 3H), 3.39 (d, J=5.2 Hz, 3H), 3.32 (dd, J=13.1, 3.6 Hz, 1H), 3.26-3.09 (m, 4H), 2.85-2.53 (m, 2H), 2.12-1.88 (m, 1H), 1.17 (dd, J=7.5, 3.1 Hz, 3H), 0.96 (dd, J=7.9, 3.2 Hz, 2H), 0.90 (t, J=6.8 Hz, 3H).
LC-MS: m/z 474.6 (M+H)$^+$

(R)-2-(4-(cyclopropanecarbonyl)-3-methylpiperazin-1-yl)-6-cyclopropyl-5-(2-methyl-1-oxoisoindolin-4-yl)nicotinonitrile (Compound 461; General Procedure 1, Step I)

$^1$H NMR (400 MHz, CDCl$_3$) δ=7.93 (d, J=7.5 Hz, 1H), 7.64-7.57 (m, 2H), 7.53-7.47 (m, 1H), 7.44 (s, 1H), 4.93-4.21 (m, 6H), 4.21-2.84 (m, 6H), 1.82-1.65 (m, 2H), 1.55-1.29 (m, 4H), 1.17 (dd, J=7.0, 3.8 Hz, 2H), 1.10-0.97 (m, 2H), 0.95 (dd, J=7.8, 3.2 Hz, 2H), 0.84-0.75 (m, 2H).
LC-MS: m/z 458.6.3 (M+H)$^+$

(R)-2-(4-(Cyclopropanecarbonyl)-3-cyclopropylpiperazin-1-yl)-6-cyclopropyl-5-(1-oxoisoindolin-4-yl)nicotinonitrile (Compound 464; General Procedure 1, Step I)

$^1$H NMR (400 MHz, CDCl$_3$) δ 7.95 (dd, J=7.6, 0.8 Hz, 1H), 7.64-7.59 (m, 2H), 7.51 (dd, J=5.4, 2.1 Hz, 1H), 6.76 (s, 1H), 5.07-4.24 (m, 6H), 3.22 (d, J=59.5 Hz, 2H), 2.05 (dt, J=15.3, 7.7 Hz, 1H), 1.31 (s, 2H), 1.19 (dd, J=4.4, 3.2 Hz, 2H), 0.96 (dd, J=7.9, 3.2 Hz, 2H), 0.90 (t, J=6.8 Hz, 3H), 0.82 (dd, J=7.9, 2.4 Hz, 2H), 0.49 (ddd, J=18.9, 9.9, 4.8 Hz, 3H). LC-MS: m/z 468.6 (M+H)$^+$

(R)-2-(4-(Cyclopropanecarbonyl)-3-methylpiperazin-1-yl)-6-cyclopropyl-5-(2-methyl-1-oxoisoindolin-4-yl)nicotinonitrile (Compound 465; General Procedure 1, Step I)

$^1$H NMR (400 MHz, CDCl$_3$) δ=7.90 (d, J=7.6 Hz, 1H), 7.61-7.54 (m, 2H), 7.45 (d, J=7.5 Hz, 1H), 5.04-3.99 (m, 6H), 3.78-3.06 (m, 6H), 2.13-1.83 (m, 1H), 1.31 (d, J=5.5 Hz, 4H), 1.20-1.14 (m, 2H), 1.09-0.99 (m, 2H), 0.95 (dd, J=7.9, 3.2 Hz, 2H), 0.83 (dd, J=7.9, 1.3 Hz, 2H).
LC-MS: m/z 466.6 (M+H)$^+$

(R)-2-(4-(cyclopropanecarbonyl)-3-cyclopropylpiperazin-1-yl)-6-cyclopropyl-5-(2,3-dioxoindolin-7-yl)nicotinonitrile (Compound 513; General Procedure 1, Step I)

A mixture of (R)-2-(4-(cyclopropanecarbonyl)-3-cyclopropylpiperazin-1-yl)-6-cyclopropyl-5-(4,4,5,5-tetramethyl-1,3,2-dioxaborolan-2-yl)nicotinonitrile (103.9 mg, 0.25 mol), 7-bromoisatin (67.8 mg, 0.30 mmol), Pd(PPh$_3$)$_4$ (29 mg, 0.03 mmol), and K$_2$CO$_3$ (86.3 mg, 0.63 mmol) suspended in 5 mL of 1,4-dioxane was subjected to microwave reaction at 120° C. for 1 h. After the reaction, the reaction mixture was concentrated in vacuo, residue was purified by column chromatography to afford the title compound. Yield: 14.1 mg (11.7%). $^1$H NMR (400 MHz, CDCl$_3$) δ 7.75-7.65 (m, 2H), 7.64 (s, 1H), 7.53 (dd, J=7.8, 1.2 Hz, 1H), 7.25 (d, J=7.7 Hz, 1H), 4.62 (d, J=13.4 Hz, 1H), 4.49 (d, J=12.2 Hz, 1H), 4.24 (m, 1H), 3.77 (m, 1H), 3.26 (m, 2H), 1.88-1.77 (m, 1H), 1.73 (s, 2H), 1.30-1.16 (m, 3H), 1.16-0.96 (m, 4H), 0.83 (dd, J=7.9, 2.5 Hz, 2H), 0.52 (dd, J=17.5, 12.8 Hz, 3H). LC-MS: m/z 482.3 (M+H)$^+$

(R)-5-(benzo[d]oxazol-6-yl)-2-(4-(cyclopropanecarbonyl)-3-cyclopropylpiperazin-1-yl)-6-cyclopropylnicotinonitrile (Compound 466; General Procedure 1, Step I)

1H NMR (CHLOROFORM-d) δ: 8.18 (s, 1H), 7.88 (d, J=8.3 Hz, 1H), 7.68 (s, 1H), 7.65 (d, J=1.0 Hz, 1H), 7.43 (dd, J=8.2, 1.6 Hz, 1H), 4.55 (d, J=12.5 Hz, 1H), 4.43 (d, J=12.5 Hz, 1H), 4.18-4.34 (m, 1H), 3.91-4.18 (m, 1H), 3.73 (br. s., 1H), 3.28 (br. s., 1H), 3.12 (br. s., 1H), 2.00-2.12 (m, 1H), 1.73 (br. s., 1H), 1.44 (br. s., 1H), 1.18-1.24 (m, 2H), 0.94-1.12 (m, 4H), 0.77-0.87 (m, 2H), 0.68 (br. s., 1H), 0.40-0.61 (m, 3H). LC-MS: m/z 454.5 (M+H)$^+$

(R)-5-(benzo[d]oxazol-6-yl)-2-(4-(cyclopropanecarbonyl)-3-methylpiperazin-1-yl)-6-cyclopropylnicotinonitrile (Compound 467; General Procedure 1, Step I)

1H NMR (CHLOROFORM-d) δ: 8.15-8.21 (m, 1H), 7.84-7.90 (m, 1H), 7.67 (s, 1H), 7.61-7.66 (m, 1H), 7.39-7.47 (m, 1H), 4.59 (br. s., 1H), 4.21-4.46 (m, 3H), 3.43-3.61 (m, 1H), 3.39 (br. s., 1H), 3.18 (br. s., 1H), 2.00-2.10 (m, 1H), 1.78 (br. s., 1H), 1.25-1.32 (m, 3H), 1.16-1.24 (m, 2H), 1.00-1.11 (m, 2H), 0.93-1.00 (m, 2H), 0.83 (dd, J=7.8, 1.8 Hz, 2H). LC-MS: m/z 428.5 (M+H)$^+$

(R)-6-cyclopropyl-2-(3-cyclopropyl-4-(3,3,3-trifluoropropanoyl)piperazin-1-yl)-5-(3-methylisoquinolin-5-yl)nicotinonitrile (Compound 471; General Procedure 2, Step M)

$^1$H NMR (CHLOROFORM-d) δ 9.26 (s, 1H), 7.96-8.06 (m, 1H), 7.55-7.69 (m, 3H), 7.21 (d, J=15.1 Hz, 1H), 4.57 (dt, J=13.1, 2.3 Hz, 1H), 4.46 (d, J=12.3 Hz, 1H), 4.15 (br. s., 0.5H), 3.69-3.95 (m, 1.5H), 3.21-3.45 (m, 3H), 3.04-3.21 (m, 2H), 2.67 (d, J=4.5 Hz, 3H), 1.40-1.61 (m, 2H), 1.24-1.31 (m, 1H), 1.07-1.21 (m, 2H), 0.77-0.91 (m, 2H), 0.70 (br. s., 1H), 0.43-0.56 (m, 2H). LC-MS: m/z 520.2 (M+H)$^+$

(R)—N-(3-(5-cyano-6-(4-(cyclopropanecarbonyl)-3-cyclopropylpiperazin-1-yl)-2-cyclopropylpyridin-3-yl)phenyl)ethenesulfonamide (Compound 472; General Procedure 3, Step N, Method 2)

To a solution of (R)-5-(3-aminophenyl)-2-(4-(cyclopropanecarbonyl)-3-cyclopropylpiperazin-1-yl)-6-cyclopropylnicotinonitrile (30 mg, 0.07 mmol) in DCM was added propiolic acid (5 mg, 0.07 mmol) and DCC (18 mg, 0.084 mmol). The mixture was stirred at 25° C. for 16 hours. TLC and LC-MS showed product and the mixture was purified by prep-TLC to give 15 mg of the compound. $^1$H NMR (CHLOROFORM-d) □ δ 8.19 (s, 1H), 7.66-7.77 (m, 1H), 7.62 (s, 1H), 7.47-7.56 (m, 1H), 7.36-7.47 (m, 1H), 7.19 (d, J=7.8 Hz, 1H), 4.51 (d, J=12.0 Hz, 1.5H), 4.29-4.45 (m, 1.5H), 4.08-4.29 (m, 1H), 3.42-3.87 (m, 1H), 3.13-3.42 (m, 1H), 2.99-3.13 (m, 1H), 2.98 (s, 1H), 2.05-2.14 (m, 1H), 1.68-1.77 (m, 1H), 1.11-1.21 (m, 3H), 1.04-1.11 (m, 1H), 0.93-1.04 (m, 3H), 0.76-0.86 (m, 2H), 0.66 (s, 1H), 0.38-0.60 (m, 3H). LC-MS: m/z 480.2 (M+H)$^+$

(R)-2-(4-(cyclopropanecarbonyl)-3-cyclopropylpiperazin-1-yl)-6-cyclopropyl-5-(2-hydroxyquinolin-5-yl)nicotinonitrile (Compound 476; General Procedure, Step I)

1H NMR (CHLOROFORM-d) δ 7.89 (d, J=9.5 Hz, 1H), 7.67 (s, 1H), 7.52-7.64 (m, 3H), 6.81 (d, J=9.5 Hz, 1H), 4.53 (d, J=12.5 Hz, 2H), 4.41 (d, J=12.3 Hz, 2H), 3.28 (br. s., 2H), 3.11 (br. s., 1H), 1.96-2.07 (m, 2H), 1.14-1.32 (m, 2H), 0.93-1.11 (m, 4H), 0.76-0.92 (m, 2H), 0.67 (br. s., 1H), 0.31-0.60 (m, 3H). LC-MS: m/z 490.2 (M+H)

(R)-2-(4-(cyclopropanecarbonyl)-3-cyclopropylpiperazin-1-yl)-6-cyclopropyl-5-(2-vinylquinolin-5-yl)nicotinonitrile (Compound 475)

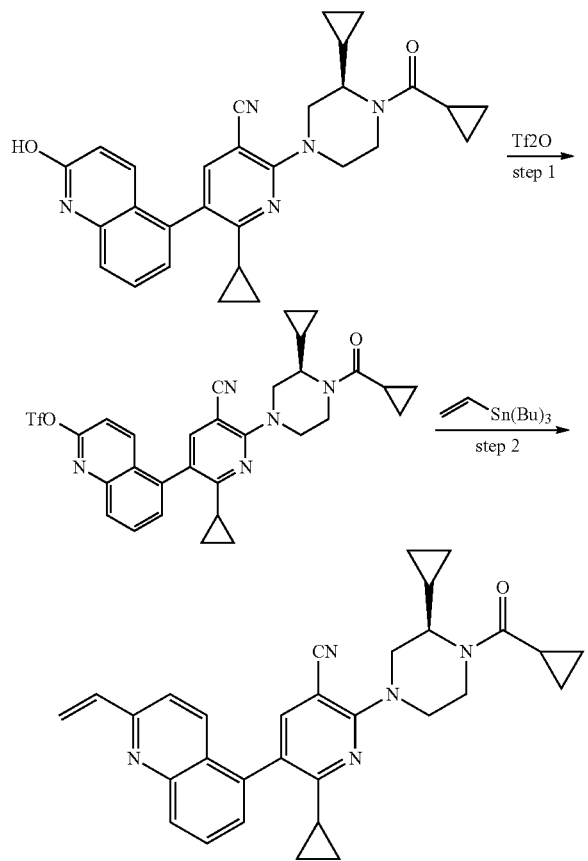

Step 1:
To a solution of (R)-2-(4-(cyclopropanecarbonyl)-3-cyclopropylpiperazin-1-yl)-6-cyclopropyl-5-(2-hydroxyquinolin-5-yl)nicotinonitrile (50 mg, 0.104 mmol), Et3N (12 mg, 0.12 mmol) in DCM (2 mL) was added dropwise Tf2O (30.3 mg, 0.107 mmol) at 0° C. and stirred at r.t. for 3 h. Water was added and the organic layer was combined, dried, concentrated to give 50 mg product after prep-TLC.

Step 2:
To a solution of (R)-5-(5-cyano-6-(4-(cyclopropanecarbonyl)-3-cyclopropylpiperazin-1-yl)-2-cyclopropylpyridin-3-yl)quinolin-2-yl trifluoromethanesulfonate (50 mg, 0.082 mmol), tributyl(vinyl)stannane (27 mg, 0.086 mmol), LiCl (5.2 mg, 0.123 mmol) in THF (2 mL) was added Pd(PPh3)4 (4.7 mg, 0.0041 mmol) under N2 and the reaction mixture was heated to 85° C. for 2 h. The mixture was cooled and the solvent was removed. Product (9 mg) was obtained by prep-TLC. 1H NMR (CHLOROFORM-d) δ 8.16 (t, J=9.3 Hz, 2H), 7.72-7.86 (m, 3H), 7.68 (d, J=8.5 Hz, 1H), 7.04-7.14 (m, 2H), 6.34 (d, J=17.6 Hz, 1H), 5.73 (d, J=11.0 Hz, 1H), 4.53 (d, J=12.5 Hz, 2H), 4.41 (d, J=12.3 Hz, 2H), 3.28 (br. s., 2H), 3.11 (br. s., 1H), 1.67 (br. s., 2H), 0.95-1.16 (m, 6H), 0.77-0.95 (m, 6H). LC-MS: m/z 490.2 (M+H).

2-(4-(cyclopropanecarbonyl)-6-fluoro-1,4-diazepan-1-yl)-6-cyclopropyl-5-(isoquinolin-5-yl)nicotinonitrile (Compound 477; General Procedure 4, Step R and S)

¹H NMR (CHLOROFORM-d) δ 9.36 (s, 1H), 8.48-8.65 (m, 1H), 8.08 (d, J=8.0 Hz, 1H), 7.69-7.77 (m, 1H), 7.62-7.69 (m, 2H), 7.42 (d, J=6.0 Hz, 1H), 4.99 (br. s., 0.5H), 4.84 (br. s., 0.5H), 4.72 (br. s., 1.5H), 4.60 (br. s., 1H), 4.49 (d, J=13.8 Hz, 1H), 4.17-4.39 (m, 2H), 3.76 (br. s., 0.5H), 3.32-3.57 (m, 2H), 3.22 (br. s., 1H), 1.70 (br. s., 1H), 1.54 (br. s., 1H), 1.14-1.20 (m, 2H), 1.04-1.12 (m, 2H), 0.83-0.90 (m, 4H). LC-MS: m/z 456.1 (M+H)

(R)-2-(4-(cyclopropanecarbonyl)-3-cyclopropylpiperazin-1-yl)-6-cyclopropyl-5-(1H-pyrazol-4-yl)nicotinonitrile (Compound 479; General Procedure 1, Step H)

¹H NMR (CHLOROFORM-d) δ 7.70-7.81 (m, 2H), 7.65 (S, 1H), 4.49 (d, J=13.1 Hz, 1H), 4.37 (d, J=12.3 Hz, 1H), 4.13 (d, J=14.8 Hz, 1H), 3.79 (s, 1H), 3.25 (s, 1.5H), 3.08 (s, 1.5H), 2.19-2.28 (m, 1H), 1.64-1.80 (m, 1H), 1.15-1.22 (m, 2H), 0.95-1.11 (m, 4H), 0.86-0.93 (m, 1H), 0.81 (dd, J=7.8, 2.3 Hz, 2H), 0.66 (s, 1H), 0.38-0.59 (m, 3H). LC-MS: m/z 442.2 (M+H)⁺

6-cyclopropyl-2-((R)-3-cyclopropyl-4-((1S,2R)-2-(methoxymethyl)cyclopropanecarbonyl) piperazin-1-yl)-5-(isoquinolin-5-yl)nicotinonitrile (Compound 480)

¹H NMR (CHLOROFORM-d) δ 9.35 (s, 1H), 8.54 (dd, J=6.0, 1.5 Hz, 1H), 8.07 (d, J=8.0 Hz, 1H), 7.65-7.74 (m, 3H), 7.43 (dd, J=6.0 Hz, 1H), 4.58 (br. s., 0.5H), 4.46 (d, J=11.8 Hz, 1H), 4.26 (br. s., 0.5H), 4.09 (br. s., 0.5H), 3.83 (br. s., 0.5H), 3.68 (br. s., 0.5H), 3.52 (dd, J=10.3, 5.3 Hz, 1H), 3.29-3.41 (m, 4H), 3.23 (br. s., 2H), 1.67-1.75 (m, 2H), 1.39-1.59 (m, 2H), 1.26-1.36 (m, 3H), 1.16-1.19 (m, 2H), 0.82-0.85 (m, 3H), 0.55 (br. s., 2H), 0.48 (br. s., 2H). LC-MS: m/z 508.1 (M+H)⁺

Compound 481

¹H NMR (CHLOROFORM-d) δ 9.38 (br. s., 1H), 8.55 (d, J=5.3 Hz, 1H), 8.08 (d, J=8.0 Hz, 1H), 7.66-7.75 (m, 3H), 7.44-7.47 (m, 1H), 4.45-4.59 (m, 2.5H), 4.09-4.19 (m, 1H), 3.86 (s, 0.5H), 3.57-3.68 (m, 3.5H), 3.05-3.45 (m, 2.5H), 1.93 (br. s., 1H), 1.51-1.54 (m, 1H), 1.18-1.25 (m, 6H), 0.83-0.91 (m, 4H), 0.49-0.68 (m, 4H). LC-MS: m/z 508.3 (M+H)⁺

(R)-5-(benzo[d]oxazol-7-yl)-2-(4-(cyclopropanecarbonyl)-3-methylpiperazin-1-yl)-6-cyclopropylnicotinonitrile (Compound 482; General Procedure 1, Step H)

1H NMR (CHLOROFORM-d) δ 8.16 (s, 1H), 7.85 (dd, J=7.8, 1.0 Hz, 1H), 7.49 (t, J=7.7 Hz, 1H), 7.42 (dd, J=7.5, 1.0 Hz, 1H), 4.58 (br. s., 1H), 4.32 (d, J=13.1 Hz, 2H), 3.49-3.62 (m, 1H), 3.46 (br. s., 1H), 3.21 (br. s., 2H), 1.85-1.93 (m, 1H), 1.78 (br. s., 1H), 1.31-1.45 (m, 3H), 1.18-1.25 (m, 2H), 1.00-1.11 (m, 2H), 0.89-0.99 (m, 2H), 0.84 (d, J=6.8 Hz, 2H). LC-MS: m/z 428.5 (M+H)$^+$ (R)-5-(benzo[d]oxazol-7-yl)-2-(4-(cyclopropanecarbonyl)-3-cyclopropylpiperazin-1-yl)-6-cyclopropylnicotinonitrile (Compound 483; General Procedure 1, Step H)

1H NMR (CHLOROFORM-d) δ 8.16 (s, 1H), 7.82-7.87 (m, 1H), 7.79 (s, 1H), 7.49 (t, J=7.8 Hz, 1H), 7.42 (dd, J=7.5, 1.0 Hz, 1H), 4.59 (d, J=12.8 Hz, 1H), 4.47 (d, J=12.0 Hz, 1H), 3.95-4.20 (m, 2H), 3.79 (br. s., 1H), 3.30 (br. s., 1H), 3.15 (br. s., 1H), 1.85-1.97 (m, 1H), 1.61 (br. s., 2H), 1.19-1.25 (m, 2H), 1.06 (d, J=16.8 Hz, 2H), 0.91-0.98 (m, 2H), 0.82 (d, J=6.5 Hz, 2H), 0.68 (br. s., 1H), 0.40-0.61 (m, 3H). LC-MS: m/z 454.5 (M+H)$^+$ 2-(4-(cyclopropanecarbonyl)-6-fluoro-3-methyl-1,4-diazepan-1-yl)-6-cyclopropyl-5-(isoquinolin-5-yl)nicotinonitrile (Compound 484; General Procedure 4, Step R and S)

$^1$H NMR (CHLOROFORM-d) δ 9.40 (br. s., 1H), 8.56 (br. s., 1H), 8.12 (d, J=8.0 Hz, 1H), 7.69-7.81 (m, 2H), 7.68 (d, J=1.0 Hz, 1H), 7.47-7.54 (m, 1H), 4.54-4.98 (m, 6H), 3.25-3.44 (m, 1H), 3.17 (br. s., 1H), 1.77-1.89 (m, 1H), 1.49-1.54 (m, 1H), 1.25-1.30 (m, 3H), 1.19-1.23 (m, 2H), 1.10 (br. s., 2H), 0.84-0.91 (m, 4H). LC-MS: m/z 470.2 (M+H)

(R)-5-(1-(cyanomethyl)-1H-pyrazol-4-yl)-2-(4-(cyclopropanecarbonyl)-3-cyclopropylpiperazin-1-yl)-6-cyclopropylnicotinonitrile (Compound 486)

To a solution of (R)-2-(4-(cyclopropanecarbonyl)-3-cyclopropylpiperazin-1-yl)-6-cyclopropyl-5-(1H-pyrazol-4-yl)nicotinonitrile (60 mg, 0.149 mmol) in DMF was added K$_2$CO$_3$ (42 mg, 0.298 mmol) and 2-bromoacetonitrile (27 mg, 0.224 mmol). The resulting mixture was stirred for 16 hours. Then the mixture was partitioned between EtOAc and water, the organic layer was washed with water, brine and dried over Na$_2$SO$_4$, concentrated to give the crude which was purified by prep-TLC to give 25 mg of the product. $^1$H NMR (CHLOROFORM-d) δ 7.72 (s, 1H), 7.69 (s, 1H), 7.61 (s, 1H), 5.17 (s, 2H), 4.32-4.52 (m, 2.5H), 3.65-3.89 (m, 1H), 4.01-4.22 (m, 1H), 3.55-4.92 (m, 1H), 2.89-3.33 (m, 2.5H), 2.10-2.23 (m, 1H), 1.72 (s, 1H), 1.31-1.47 (m, 1H), 1.14-1.22 (m, 2H), 0.92-1.09 (m, 4H), 0.75-0.86 (m, 2H), 0.39-0.63 (m, 4H). LC-MS: m/z 442.2 (M+H)$^+$ 2-((R)-4-(cyclopropanecarbonyl)-3-cyclopropylpiperazin-1-yl)-6-cyclopropyl-5-(1-(3-hydroxycyclopentyl)-1H-pyrazol-4-yl)nicotinonitrile (Compound 493)

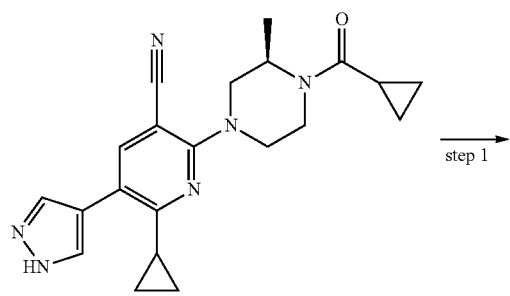

step 1 →

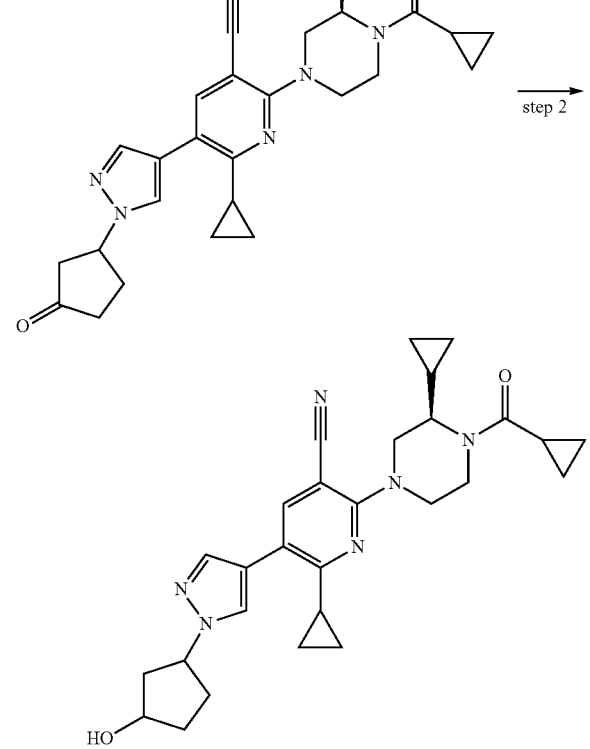

step 2 →

Step 1:
To a solution of (R)-2-(4-(cyclopropanecarbonyl)-3-cyclopropylpiperazin-1-yl)-6-cyclopropyl-5-(1H-pyrazol-4-yl)nicotinonitrile (100 mg, 0.248 mmol) in CH$_2$Cl$_2$ was added cyclopent-2-enone (51 mg, 0.621 mmol) and ScCl$_3$ (338 mg, 2.24 mmol). The mixture was stirred for 16 hours at room temperature. The mixture was partitioned between EtOAc and water. The organic layer was washed with water, brine and dried over Na$_2$SO$_4$, concentrated to give the crude which was purified by prep-TLC to give 50 mg of the product. LC-MS: m/z 485.3 (M+H)$^+$ Step 2:
To a solution of (R)-2-(4-(cyclopropanecarbonyl)-3-cyclopropylpiperazin-1-yl)-6-cyclopropyl-5-(1H-pyrazol-4-yl)nicotinonitrile (40 mg, 0.0825 mmol) in MeOH was added NaBH$_4$, the mixture was stirred for 2 hours at room temperature. The mixture was partitioned between EtOAc and water. The organic layer was washed with water, brine and dried over Na$_2$SO$_4$, concentrated to give the crude which was purified by prep-TLC to give 15 mg of the product. $^1$H NMR (CHLOROFORM-d) δ 7.56-7.70 (m, 3H), 4.85 (br. s., 1H), 4.25-4.70 (m, 4H), 4.00-4.25 (m, 1H), 3.50-3.90 (m, 1H), 2.95-3.41 (m, 3H), 2.12-2.41 (m, 6H), 1.90-2.03 (m, 1H), 1.37-1.54 (m, 1H), 1.23-1.37 (m, 1H), 1.17-1.28 (m, 2H), 0.94-1.09 (m, 4H), 0.76-0.85 (m, 2H), 0.39-0.64 (m, 4H). LC-MS: m/z 487.3 (M+H)$^+$ (R)-2-(4-(cyclopropanecarbonyl)-3-cyclopropylpiperazin-1-yl)-6-cyclopropyl-5-(1-(methylsulfonyl)-1H-pyrazol-4-yl)nicotinonitrile (Compound 502)

To a solution of (R)-2-(4-(cyclopropanecarbonyl)-3-cyclopropylpiperazin-1-yl)-6-cyclopropyl-5-(1H-pyrazol-4- yl)nicotinonitrile (30 mg, 0.074 mmol) in DCM was added TEA (15 mg, 0.149 mmol) and methanesulfonyl chloride (9.4 mg, 0.082 mmol) and the mixture was stirred at r.t. for 2 h. The mixture was partitioned between EtOAc and water. The organic layer was washed with H$_2$O, brine and dried over Na$_2$SO$_4$, concentrated to give the crude which was purified by prep-TLC to give 15 mg of the product. $^1$H NMR (CHLOROFORM-d) δ 8.16 (s, 1H), 7.97 (s, 1H), 7.65 (s, 1H), 4.40-4.60 (m, 2.5H), 4.09-4.25 (m, 1H), 3.53-3.90 (m, 1H), 3.45 (s, 3H), 3.05-3.41 (m, 2.5H), 2.06-2.19 (m, 1H), 1.12-1.26 (m, 3H), 0.95-1.12 (m, 4H), 0.89 (t, J=6.8 Hz, 1H), 0.75-0.85 (m, 2H), 0.36-0.64 (m, 4H). LC-MS: m/z 481.2 (M+H)$^+$ (R)-2-(4-(5-cyano-6-(4-(cyclopropanecarbonyl)-3-cyclopropylpiperazin-1-yl)-2-cyclopropylpyridin-3-yl)-1H-pyrazol-1-yl)acetamide (Compound 501)

To a solution of (R)-2-(4-(cyclopropanecarbonyl)-3-cyclopropylpiperazin-1-yl)-6-cyclopropyl-5-(1H-pyrazol-4-yl)nicotinonitrile (30 mg, 0.0745 mmol) in DMF was added K$_2$CO$_3$ (21 mg, 0.149 mmol) and 2-bromoacetamide (12 mg, 0.082 mmol). The mixture was stirred for 16 hours at room temperature, then the mixture was partitioned between EtOAc and water. The organic layer was partitioned between EtOAc and water, the organic layer was washed with water, brine and dried over Na$_2$SO$_4$ concentrated to give 25 mg of the product. $^1$H NMR (CHLOROFORM-d) δ 7.75 (s, 1H), 7.57-7.69 (m, 2H), 6.43 (br. s., 1H), 6.04 (br. s., 1H), 4.88 (s, 2H), 4.30-4.60 (m, 2.5H), 3.84-4.23 (m, 1H), 3.50-3.80 (m, 1H), 3.00-3.45 (m, 2.5H), 2.13-2.25 (m, 1H), 1.92 (s, 1H), 1.71 (s, 1H), 1.12-1.21 (m, 2H), 0.94-1.10 (m, 4H), 0.72-0.84 (m, 2H), 0.35-0.63 (m, 4H). LC-MS: m/z 460.2 (M+H)$^+$ (R)-2-(4-(cyclopropanecarbonyl)-3-cyclopropylpiperazin-1-yl)-6-cyclopropyl-5-(1-((methylthio)methyl)-1H-pyrazol-4-yl)nicotinonitrile (Compound 510)

To a solution of (R)-2-(4-(cyclopropanecarbonyl)-3-cyclopropylpiperazin-1-yl)-6-cyclopropyl-5-(1H-pyrazol-4-yl)nicotinonitrile (50 mg, 0.124 mmol) in DMF was added NaH (10 mg, 0.248 mmol) and (chloromethyl)(methyl)sulfane (24 mg, 0.248 mmol). The mixture was stirred for 2 hours at room temperature. The mixture was partitioned between EtOAc and water, the organic layer was washed with water, brine and dried over Na$_2$SO$_4$, concentrated to give the crude which was purified by prep-TLC to give 15 mg of the product. $^1$H NMR (CHLOROFORM-d) ☐ δ 7.73 (s, 1H), 7.59-7.68 (m, 2H), 5.20 (s, 2H), 4.28-4.48 (m, 2.5H), 4.26-4.30 (m, 1H), 3.50-3.80 (m, 1H), 2.99-3.40 (m, 2.5H), 2.22-2.28 (m, 1H), 2.21 (s, 3H), 1.73 (s, 1H), 1.30-1.48 (m, 1H), 1.14-1.23 (m, 2H), 0.94-1.10 (m, 4H), 0.75-0.85 (m, 2H), 0.39-0.64 (m, 4H). LC-MS: m/z 463.2 (M+H)$^+$ (R)-2-(4-(cyclopropanecarbonyl)-3-cyclopropylpiperazin-1-yl)-6-cyclopropyl-5-(1-(2-hydroxyethyl)-1H-pyrazol-4-yl)nicotinonitrile (Compound 490)

$^1$H NMR (CHLOROFORM-d) δ 7.66 (s, 1H), 7.58-7.64 (m, 2H), 4.47 (d, J=12.3 Hz, 1H), 4.25-4.41 (m, 3H), 3.97-4.18 (m, 3H), 3.77 (s, 1H), 3.23 (s, 2H), 3.07 (s, 1H), 2.16-2.30 (m, 1H), 1.23-1.35 (m, 2H), 1.12-1.21 (m, 2H), 0.95-1.09 (m, 4H), 0.74-0.87 (m, 2H), 0.38-0.64 (m, 4H). LC-MS: m/z 446.2M+H)$^+$ (R)-5-(benzo[d]thiazol-6-yl)-2-(4-(cyclopropanecarbonyl)-3-cyclopropylpiperazin-1-yl)-6-cyclopropylnicotinonitrile (Compound 487; General Procedure 1, Step I)

$^1$H NMR (CHLOROFORM-d) δ 9.07 (s, 1H), 8.22 (d, J=8.3 Hz, 1H), 8.00 (d, J=1.5 Hz, 1H), 7.68-7.73 (m, 1H), 7.58 (dd, J=8.4, 1.6 Hz, 1H), 4.55 (d, J=12.3 Hz, 1H), 4.43 (d, J=12.3 Hz, 1H), 3.50 (d, J=9.0 Hz, 2H), 3.29 (br. s., 2H), 3.13 (br. s., 1H), 2.04-2.12 (m, 1H), 1.29-1.40 (m, 2H), 1.18-1.25 (m, 2H), 0.94-1.12 (m, 4H), 0.77-0.86 (m, 2H), 0.68 (br. s., 1H), 0.40-0.61 (m, 3H); LC-MS: m/z 470.2 (M+H).

(R)-6-cyclopropyl-2-(3-cyclopropyl-4-(furan-3-carbonyl)piperazin-1-yl)-5-(isoquinolin-5-yl)nicotinonitrile (Compound 488; General Procedure 4, Step R and S)

$^1$H NMR (CHLOROFORM-d) δ 9.36 (s, 1H), 8.55 (dd, J=5.8, 2.0 Hz, 1H), 8.08 (d, J=8.0 Hz, 1H), 7.64-7.79 (m, 4H), 7.41-7.50 (m, 2H), 6.59 (s, 1H), 4.61 (dd, J=13.1, 2.0 Hz, 1H), 4.43 (br. s., 2H), 3.98 (br. s., 1H), 3.73 (br. s., 1H), 3.22-3.36 (m, 1H), 3.07-3.22 (m, 1H), 1.50-1.57 (m, 2H), 1.12-1.21 (m, 2H), 0.81-0.89 (m, 2H), 0.65-0.78 (m, 1H), 0.53-0.62 (m, 1H), 0.47 (br. s., 2H). LC-MS: m/z 490.6 (M+H)$^+$ (R)-methyl 4-(3-cyano-6-cyclopropyl-5-(isoquinolin-5-yl)pyridin-2-yl)-2-cyclopropylpiperazine-1 carboxylate (Compound 489; General Procedure 4, Step R and S)

$^1$H NMR (CHLOROFORM-d) δ 9.37 (br. s., 1H), 8.55 (br. s., 1H), 8.08 (d, J=8.0 Hz, 1H), 7.70-7.77 (m, 1H), 7.60-7.70 (m, 2H), 7.46 (dd, J=12.0, 5.8 Hz, 1H), 4.50-4.60 (m, 1H), 4.37-4.47 (m, 1H), 4.17 (d, J=12.5 Hz, 1H), 3.76 (s, 3H), 3.45-3.59 (m, 2H), 3.29 (ddd, J=12.9, 6.4, 3.8 Hz, 1H), 3.13 (tdd, J=12.5, 7.2, 3.5 Hz, 1H), 1.47-1.57 (m, 1H), 1.34-1.47 (m, 1H), 1.18 (dd, J=7.3, 4.0 Hz, 2H), 0.85-0.93 (m, 2H), 0.60-0.72 (m, 1H), 0.48-0.60 (m, 2H), 0.36-0.48 (m, 1H). LC-MS: m/z 454.5 (M+H)$^+$ (R)-6-(4-(cyclopropanecarbonyl)-3-cyclopropylpiperazin-1-yl)-2-cyclopropyl-[3,3'-bipyridine]-5,5'-dicarbonitrile (Compound 494; General Procedure 1, Step H)

$^1$H NMR (CHLOROFORM-d) δ 8.92 (br. s., 2H), 7.99-8.07 (m, 1H), 7.63 (s, 1H), 4.63 (d, J=12.8 Hz, 1H), 4.50 (d, J=12.3 Hz, 1H), 3.33 (br. s., 1H), 3.17 (m, 2H), 1.80-1.90 (m, 2H), 1.73 (m., 1H), 1.19-1.31 (m, 4H), 0.94-1.12 (m, 4H), 0.76-0.88 (m, 2H), 0.36-0.60 (m, 4H). LC-MS: m/z 439.5 (M+H)$^+$ (R)-5-(cinnolin-4-yl)-2-(4-(cyclopropanecarbonyl)-3-cyclopropylpiperazin-1-yl)-6-cyclopropylnicotinonitrile (Compound 495; General Procedure 1, Step H)

$^1$H NMR (CHLOROFORM-d) δ: 9.28 (d, J=2.0 Hz, 1H), 8.66 (d, J=8.5 Hz, 1H), 7.88-7.97 (m, 1H), 7.72-7.85 (m, 2H), 7.66-7.72 (m, 2H), 4.60-4.74 (m, 1.5H), 4.43-4.60 (m, 1.5H), 3.60-3.89 (m, 1H), 3.35 (br. s., 1H), 3.22 (br. s., 1H), 1.49-1.58 (m, 1H), 1.16-1.36 (m, 4H), 0.99-1.16 (m, 2H), 0.78-0.99 (m, 4H), 0.63-0.78 (m, 1H), 0.42-0.63 (m, 3H). LC-MS: m/z 465.6 (M+H)$^+$

(R)-2-(4-(cyclopropanecarbonyl)-3-cyclopropylpiperazin-1-yl)-6-cyclopropyl-5-(2-vinylpyrimidin-4-yl)nicotinonitrile (Compound 496)

The procedure was similar to the synthesis of Compound 390. $^1$H NMR (CHLOROFORM-d) δ 8.67-8.84 (m, 1H), 8.07 (s, 1H), 7.43 (d, J=5.0 Hz, 1H), 6.87-7.03 (m, 1H), 6.74 (dd, J=17.4, 1.6 Hz, 1H), 5.76-5.88 (m, 1H), 4.68 (d, J=13.1 Hz, 1H), 4.55 (d, J=13.3 Hz, 1H), 4.07 (br. s., 1H), 3.88 (s, 1H), 3.66 (br. s., 1H), 3.33 (br. s., 1H), 3.17 (br. s., 1H), 2.34-2.47 (m, 1H), 1.96-2.08 (m, 2H), 1.30-1.42 (m, 2H), 1.00-1.11 (m, 3H), 0.85-0.93 (m, 1H), 0.82 (dd, J=8.0, 2.5 Hz, 2H), 0.65 (br. s., 1H), 0.39-0.59 (m, 3H). LC-MS: m/z 441.2 (M+H)$^+$

(R)-2-(4-(cyclopropanecarbonyl)-3-cyclopropylpiperazin-1-yl)-6-cyclopropyl-5-(1-methylisoquinolin-5-yl)nicotinonitrile (Compound 497; General Procedure 1, Step I)

$^1$H NMR (CHLOROFORM-d) δ 8.40 (dd, J=6.0, 2.0 Hz, 1H), 8.24 (d, J=8.3 Hz, 1H), 7.68-7.76 (m, 1H), 7.31 (d, J=6.5 Hz, 2H), 4.58 (d, J=10.5 Hz, 1H), 4.46 (d, J=12.5 Hz, 1H), 4.23 (br. s., 1H), 3.82 (br. s., 1H), 3.67 (br. s., 1H), 3.32 (br. s., 1H), 3.17 (br. s., 1H), 2.93-3.12 (m, 3H), 1.74 (br. s., 1H), 1.47-1.57 (m, 2H), 1.14-1.22 (m, 2H), 1.00-1.12 (m, 2H), 0.83 (dd, J=6.7, 4.6 Hz, 4H), 0.70 (br. s., 1H), 0.41-0.63 (m, 3H). LC-MS: m/z 478.3 (M+H)$^+$

(R)-6'-(4-(cyclopropanecarbonyl)-3-cyclopropylpiperazin-1-yl)-2'-cyclopropyl-6-vinyl-2,3'-bipyridine-5'-carbonitrile (Compound 499; General Procedure 1, Step H)

The procedure was similar to the synthesis of Compound 390. $^1$H NMR (CHLOROFORM-d) δ 7.95 (s, 1H), 7.75 (t, J=7.8 Hz, 1H), 7.39-7.45 (m, 1H), 7.32-7.37 (m, 1H), 6.82-6.96 (m, 1H), 6.31 (dd, J=17.6, 1.3 Hz, 1H), 5.49-5.59 (m, 1H), 4.58 (d, J=12.8 Hz, 1H), 4.45 (d, J=12.5 Hz, 1H), 4.19 (br. s., 0.5H), 4.06 (br. s., 0.5H), 3.78 (br. s., 0.5H), 3.60 (br. s., 0.5H), 3.28 (br. s., 2H), 3.11 (br. s., 1H), 2.29-2.39 (m, 1H), 1.67-1.79 (m, 1H), 1.32-1.45 (m, 1H), 1.18-1.25 (m, 2H), 0.96-1.12 (m, 4H), 0.74-0.87 (m, 2H), 0.65 (br. s., 1H), 0.35-0.58 (m, 3H). LC-MS: m/z 440.6 (M+H)$^+$

(R)-2-(4-(cyclopropanecarbonyl)-3-cyclopropylpiperazin-1-yl)-6-cyclopropyl-5-(imidazo[1,2-a]pyrazin-3-yl)nicotinonitrile (Compound 503; General Procedure 1, Step I)

$^1$H NMR (400 MHz, CDCl$_3$) δ=9.20 (s, 1H), 7.89 (dd, J=25.5, 17.4 Hz, 3H), 7.73 (s, 1H), 4.66 (d, J=12.8 Hz, 1H), 4.53 (d, J=12.8 Hz, 1H), 3.49 (s, 4H), 3.36-3.10 (m, 2H), 2.15-1.83 (m, 3H), 1.53 (m, 1H), 1.08-0.95 (m, 4H), 0.84 (m, 3H), 0.61-0.40 (m, 3H). LC-MS: m/z 454.1 (M+H)$^+$

(R)-2-(4-(cyclopropanecarbonyl)-3-cyclopropylpiperazin-1-yl)-6-cyclopropyl-5-(2,3-dioxoindolin-5-yl)nicotinonitrile (Compound 504; General Procedure 1, Step I)

$^1$H NMR (400 MHz, CDCl$_3$) δ=8.38 (s, 1H), 7.68 (d, J=1.8 Hz, 1H), 7.64-7.57 (m, 2H), 7.04 (d, J=8.4 Hz, 1H), 5.48-5.23 (m, 1H), 4.98 (m, 1H), 3.38-3.05 (m, 2H), 2.14-1.88 (m, 4H), 1.01 (dd, J=7.9, 3.4 Hz, 3H), 0.90 (dd, J=9.0, 4.7 Hz, 5H), 0.86-0.77 (m, 3H), 0.57-0.40 (m, 3H). LC-MS: m/z 482.2 (M+H)$^+$

5-(4-acryloylmorpholin-2-yl)-2-((R)-4-(cyclopropanecarbonyl)-3-methylpiperazin-1-yl)-6-cyclopropylnicotinonitrile (Compound 600)

A mixture of 2-((R)-4-(cyclopropanecarbonyl)-3-methylpiperazin-1-yl)-6-cyclopropyl-5-(morpholin-2-yl)nicotinonitrile (13 mg, 0.03 mmol), acryloyl chloride (1 drop) and TEA (1 drop) in 10 mL of DCM was stirred at r.t. for 10 mins. After the mixture was quenched and worked up, the filtrate was concentrated and the residue was purified by column chromatography (50% PE/EA) to afford 11 mg of title compound. $^1$H NMR (CHLOROFORM-d) δ 7.86 (s, 1H), 6.48-6.69 (m, 1H), 6.31-6.48 (m, 1H), 5.80 (d, J=9.3 Hz, 1H), 4.91 (d, J=13.1 Hz, 1H), 4.71 (d, J=8.8 Hz, 1H), 4.44-4.63 (m, 1.5H), 4.05-4.34 (m, 4H), 3.92 (d, J=12.5 Hz, 0.5H), 3.74 (d, J=9.8 Hz, 1.5H), 3.35-3.52 (m, 1.5H), 3.04-3.29 (m, 3H), 2.62 (t, J=11.3 Hz, 0.5H), 2.10 (br. s., 1H), 1.75 (br. s., 1H), 1.40 (br. s., 1.5H), 1.27 (br. s., 1.5H), 1.13 (br. s., 2H), 1.03 (br. s., 4H), 0.81 (d, J=7.0 Hz, 2H). LC-MS: m/z 450.2 (M+H)$^+$

(R)-2-(4-(cyclopropanecarbonyl)-3-cyclopropylpiperazin-1-yl)-6-cyclopropyl-5-(6-vinylpyridazin-4-yl)nicotinonitrile (Compound 613)

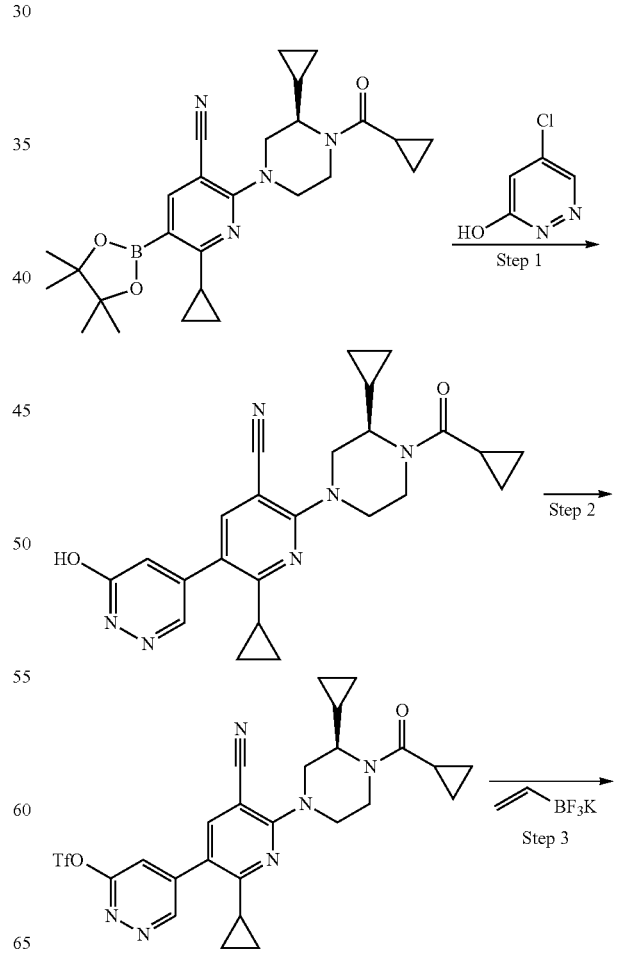

-continued

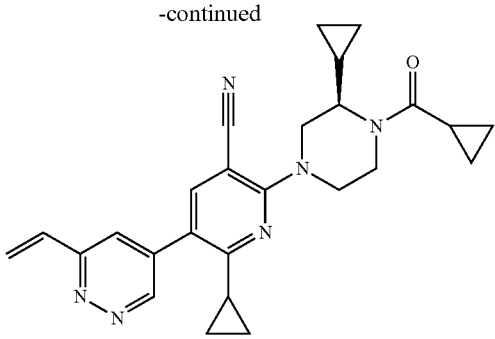

Step 1:

A mixture of 8-4 (50 mg, 0.11 mmol), 5-chloropyridazin-3-ol (21 mg, 0.16 mmol), CsF (33 mg, 0.22 mmol) and Pd(dppf)Cl$_2$ (5 mg) in dioxane and water was heated at 100° C. for 1 hr. The reaction mixture was concentrated and the residue was purified by pre-TLC to afford 35 mg of title compound. $^1$H NMR (CHLOROFORM-d) δ 12.68 (br. s., 1H), 7.97 (s, 1H), 7.65 (s, 1H), 7.02 (br. s., 1H), 4.51-4.64 (m, 2.5H), 4.21 (br. s., 1H), 3.56-3.84 (m, 1H), 3.17-3.32 (m, 2.5H), 1.99 (br. s., 1H), 1.71 (br. s., 1H), 1.24 (br. s., 3H), 1.01-1.08 (m, 4H), 0.72-0.92 (m, 2H), 0.32-0.64 (m, 4H). LC-MS: m/z 431.1 (M+H)$^+$ Step 2:

A solution of (R)-2-(4-(cyclopropanecarbonyl)-3-cyclopropylpiperazin-1-yl)-6-cyclopropyl-5-(6-hydroxypyridazin-4-yl)nicotinonitrile, Tf$_2$O and TEA in DCM was stirred for 1 hr. The reaction mixture was washed with water, dried and concentrated. The residue was purified by pre-TLC to afford 150 mg of title compound. 1H NMR (CHLOROFORM-d, 400 MHz) δ 9.42 (br. s., 1H), 7.72 (s, 1H), 7.52 (s, 1H), 4.58-4.75 (m, 2.5H), 4.32 (br. s., 0.5H), 4.00 (br. s., 0.5H), 3.73 (br. s., 1H), 3.25-3.39 (m, 2.5H), 1.89-1.94 (m, 1H), 1.72 (br. s., 1H), 1.31 (br. s., 3H), 1.00-1.18 (m, 4H), 0.84 (d, J=6.3 Hz, 2H), 0.45-0.66 (m, 4H).

Step 3:

A mixture of (R)-2-(4-(cyclopropanecarbonyl)-3-cyclopropylpiperazin-1-yl)-6-cyclopropyl-5-(6-vinylpyridazin-4-yl)nicotinonitrile (50 mg, 0.09 mmol), potassium vinyltrifluoroborate (24 mg, 0.18 mmol), TEA (27 mg, 0.27 mmol) and Pd(dppf)Cl$_2$ (5 mg) in i-PrOH and water was heated at 100° C. for 1 hr. The reaction mixture was concentrated and the residue was purified by pre-TLC to afford 11 mg of title compound. $^1$H NMR (CHLOROFORM-d) δ □9.20 (br. s., 1H), 7.68 (br. s., 1H), 7.61 (br. s., 1H), 7.04-7.22 (m, 1H), 6.36 (d, J=17.6 Hz, 1H), 5.78 (d, J=10.8 Hz, 1H), 4.53-4.58 (m, 2.5H), 4.17 (br. s., 1H), 3.72 (br. s., 1H), 3.19-3.34 (m, 1H), 1.94 (br. s., 1H), 1.80 (br. s., 1H), 1.26 (br. s., 3H), 1.07 (br. s., 4H), 0.82 (br. s., 2H), 0.46-0.65 (m, 4H). LC-MS: m/z 441.2 (M+H)$^+$ (R)-5-(5-cyano-2-cyclopropyl-6-(4-(3-methoxypropanoyl)-3-methylpiperazin-1-yl)pyridin-3-yl) pyridazin-3-yl trifluoromethanesulfonate (Compound 614)

$^1$H NMR (CHLOROFORM-d) δ 9.41 (s, 1H), 7.71 (s, 1H), 7.50 (d, J=1.3 Hz, 1H), 4.93 (br. s., 0.5H), 4.56 (d, J=7.8 Hz, 0.5H), 4.47 (d, J=7.3 Hz, 1.5H), 4.25-4.40 (m, 1H), 3.86 (d, J=12.5 Hz, 0.5H), 3.76 (br. s., 2H), 3.57 (br. s., 0.5H), 3.36-3.48 (m, 4H), 3.30 (br. s., 0.5H), 3.11-3.24 (m, 1H), 2.71 (br. s., 1H), 2.61 (br. s., 1H), 1.89-1.93 (m, 1H), 1.37 (d, J=5.5 Hz, 1.5H), 1.22-1.32 (m, 3.5H), 1.08-1.22 (m, 2H). LC-MS: m/z 555.1 (M+H)$^+$ (R)-6-cyclopropyl-2-(4-(3-methoxypropanoyl)-3-methylpiperazin-1-yl)-5-(6-vinylpyridazin-4-yl)nicotinonitrile (Compound 615)

The procedure is similar to Compound 613. $^1$H NMR (CHLOROFORM-d) δ 9.20 (br. s., 1H), 7.67 (s, 1H), 7.58-7.65 (m, 1H), 7.13 (dd, J=17.8, 11.0 Hz, 1H), 6.37 (d, J=17.8 Hz, 1H), 5.79 (d, J=11.0 Hz, 1H), 4.92 (br. s., 0.5H), 4.48-4.62 (m, 0.5H), 4.35-4.48 (m, 1.5H), 4.31 (d, J=14.1 Hz, 1H), 3.83 (d, J=13.3 Hz, 0.5H), 3.67-3.80 (m, 2H), 3.51-3.63 (m, 0.5H), 3.30-3.45 (m, 4H), 3.13-3.28 (m, 1.5H), 2.65-2.82 (m, 1H), 2.51-2.65 (m, 1H), 1.92-1.96 (m, 1H), 1.38 (d, J=5.5 Hz, 1.5H), 1.24-1.27 (m, 3.5H), 1.07 (d, J=4.8 Hz, 2H). LC-MS: m/z 433.1 (M+H)$^+$ (R)-2-(4-(cyclopropanecarbonyl)-3-cyclopropylpiperazin-1-yl)-6-cyclopropyl-5-(6-hydroxypyridazin-4-yl)nicotinonitrile (Compound 616)

$^1$H NMR (CHLOROFORM-d) δ 12.68 (br. s., 1H), 7.97 (s, 1H), 7.65 (s, 1H), 7.02 (br. s., 1H), 4.51-4.64 (m, 2.5H), 4.21 (br. s., 1H), 3.56-3.84 (m, 1H), 3.17-3.32 (m, 2.5H), 1.99 (br. s., 1H), 1.71 (br. s., 1H), 1.24 (br. s., 3H), 1.01-1.08 (m, 4H), 0.72-0.92 (m, 2H), 0.32-0.64 (m, 4H). LC-MS: m/z 431.1 (M+H)$^+$ (R)-2-(4-(cyclopropanecarbonyl)-3-cyclopropylpiperazin-1-yl)-6-cyclopropyl-5-(1-methyl-6-oxo-1,6-dihydropyridazin-4-yl)nicotinonitrile (Compound 640)

$^1$H NMR (CHLOROFORM-d) δ 7.85 (br. s., 1H), 7.60 (br. s., 1H), 6.95 (br. s., 1H), 4.50-4.63 (m, 2.5H), 4.21 (br. s., 1H), 3.84 (br. s., 3H), 3.69 (br. s., 1H), 3.17-3.30 (m, 2.5H), 1.99 (br. s., 1H), 1.76 (br. s., 1H), 1.22 (br. s., 3H), 1.07 (br. s., 4H), 0.81 (br. s., 2H), 0.51 (br. s., 4H). LC-MS: m/z 445.2 (M+H)$^+$ (R)-5-(5-cyano-6-(4-(cyclopropanecarbonyl)-3-cyclopropylpiperazin-1-yl)-2-cyclopropylpyridin-3-yl) pyridazine-3-carbonitrile (Compound 641)

$^1$H NMR (CHLOROFORM-d) δ 9.51 (d, J=2.3 Hz, 1H), 7.93 (d, J=2.3 Hz, 1H), 7.70 (s, 1H), 4.59-4.72 (m, 2.5H), 4.09-4.26 (m, 1H), 3.75 (br. s., 1H), 3.23-3.39 (m, 2.5H), 1.82-1.95 (m, 1H), 1.65 (br. s., 1H), 1.26-1.34 (m, 3H), 0.96-1.20 (m, 4H), 0.76-0.91 (m, 2H), 0.38-0.75 (m, 4H). LC-MS: m/z 440.2 (M+H)$^+$ (R)-2-(4-acetyl-3-methylpiperazin-1-yl)-6-cyclopropyl-5-(isoquinolin-5-yl)nicotinonitrile (Compound 516; General Procedure 4, Step R and S)

$^1$H NMR (CHLOROFORM-d) δ 9.35 (s, 1H), 8.54 (d, J=5.8 Hz, 1H), 8.07 (d, J=8.0 Hz, 1H), 7.64-7.74 (m, 3H), 7.43 (t, J=5.9 Hz, 1H), 4.91 (br. s., 0.5H), 4.57-4.53 (d, 0.5H), 4.18-4.39 (m, 2.5H), 3.6-3.77 (m, 1H), 3.34 (br. s., 1H), 3.05-3.25 (m, 1.5H), 1.91 (br. s., 3H), 1.33-1.54 (m, 4H), 1.14-1.17 (m, 2H), 0.82-0.85 (m, 2H). LC-MS: m/z 412.2 (M+H)$^+$

6-cyclopropyl-2-((R)-4-((1S,2R)-2-ethoxycyclopropanecarbonyl)-3-methylpiperazin-1-yl)-5-(isoquinolin-5-yl)nicotinonitrile (Compound 517; General Procedure 4, Step R and S)

¹H NMR (CHLOROFORM-d) δ 9.35 (s, 1H), 8.54 (d, J=5.8 Hz, 1H), 8.06 (d, J=8.0 Hz, 1H), 7.59-7.76 (m, 3H), 7.44 (t, J=6.8 Hz, 1H), 4.87-5.02 (m, 0.5H), 4.61-4.64 (m, 0.5H), 4.12-4.43 (m, 2.5), 3.05-3.70 (m, 5.5H), 2.0 (s, 1H), 1.76-1.86 (m, 1H), 1.40-1.62 (m, 3H), 1.27-1.35 (m, 2H), 1.16-1.21 (m, 4H), 0.92-0.99 (m, 1H), 0.81-0.84 (m, 2H). LC-MS: m/z 482.2 (M+H)⁺

6-cyclopropyl-2-((R)-3-cyclopropyl-4-((1S,2S)-2-ethoxycyclopropanecarbonyl)piperazin-1-yl)-5-(isoquinolin-5-yl)nicotinonitrile (Compound 518; General Procedure 4, Step R and S)

1H NMR (CHLOROFORM-d) δ 9.37 (s, 1H), 8.54 (dd, J=6.0, 2.0 Hz, 1H), 8.08 (d, J=8.0 Hz, 1H), 7.73 (t, 1H), 7.64-7.69 (m, 2H), 7.46 (q, 1H), 4.73 (m, 0.5H), 4.43-4.62 (m, 2.5H), 4.13-4.26 (m, 2H), 3.68-3.87 (m, 1.5H), 3.50-3.60 (m, 3.5H), 3.19-3.30 (s, 2H), 1.97-2.19 (m, 2H), 1.50-1.54 (m, 1H), 1.16-1.23 (m, 6H), 0.82-0.91 (m, 5H), 0.64-0.68 (m, 2H), 0.43-0.51 (m, 2H). LC-MS: m/z 508.2 (M+H)⁺

(R)-6-cyclopropyl-2-(3-cyclopropyl-4-(4-oxobutanoyl)piperazin-1-yl)-5-(isoquinolin-5-yl)nicotinonitrile (Compound 519; General Procedure 4, Step R and S)

¹H NMR (CHLOROFORM-d) δ 9.91 (s, 1H), 9.38 (s, 1H), 8.55 (br. s., 1H), 8.09 (d, J=8.0 Hz, 1H), 7.74 (t, 1H), 7.66-7.70 (m, 2H), 7.47 (q, 1H), 4.55-4.58 (d, 1H), 4.44-4.47 (d, 1H), 4.09 (br. s., 1H), 3.90 (br. s., 1H), 3.07-3.40 (m, 2.5H), 2.69-2.91 (m, 3.5H), 2.05 (m, 2H), 14.53 (m, 1H), 0.83-0.92 (m, 6H), 0.44-0.71 (br. s., 4H). LC-MS: m/z 480.2 (M+H)⁺

6-cyclopropyl-2-((R)-3-cyclopropyl-4-((1S,2R)-2-ethoxycyclopropanecarbonyl)piperazin-1-yl)-5-(isoquinolin-5-yl)nicotinonitrile (Compound 526; General Procedure 4, Step R and S)

¹H NMR (CHLOROFORM-d) δ 9.35 (br. s., 1H), 8.53 (br. s., 1H), 8.07 (d, J=8.0 Hz, 1H), 7.68-7.74 (t, 1H), 7.64-7.67 (m, 2H), 7.45 (dd, J=5.8 Hz, 1H), 4.58 (d, J=12.8 Hz, 1H), 4.49 (d, J=11.3 Hz, 1H), 4.13-4.27 (m, 1.5H), 3.80 (br. s., 0.5H), 3.52-3.59 (m, 3H), 3.22 (br. s., 2H), 1.82 (d, J=7.5 Hz, 1H), 1.47-1.57 (m, 2H), 1.17-1.20 (m, 6H), 0.82-0.99 (m, 5H), 0.45-0.65 (m, 4H). LC-MS: m/z 508.3 (M+H)⁺

6-cyclopropyl-2-((R)-4-((1R,2R)-2-(hydroxymethyl)cyclopropanecarbonyl)-3-methylpiperazin-1-yl)-5-(isoquinolin-5-yl)nicotinonitrile (Compound 505; General Procedure 4, Step R and S)

¹H NMR (CHLOROFORM-d) δ 9.39 (br. s., 1H), 8.56 (br. s., 1H), 8.08 (d, J=8.0 Hz, 1H), 7.71-7.76 (m, 1H), 7.66-7.70 (m, 1H), 7.64 (s, 1H), 7.47 (br. s., 1H), 4.18-4.89 (m, 4H), 3.25-3.80 (m, 5H), 2.01-2.08 (m, 1H), 1.46-1.57 (m, 2H), 1.24-1.39 (m, 4H), 1.10-1.20 (m, 2H), 0.79-0.91 (m, 3H). LC-MS: m/z 468.2 (M+H)⁺

(R)-2-(4-(cyclopropanecarbonyl)-3-cyclopropylpiperazin-1-yl)-6-cyclopropyl-5-(quinoxalin-5-yl)nicotinonitrile (Compound 531; General Procedure 1, Step I)

¹H NMR (CHLOROFORM-d) δ 8.88 (d, J=1.8 Hz, 1H), 8.91 (d, J=1.5 Hz, 1H), 8.21 (dd, J=8.4, 1.4 Hz, 1H), 7.88 (t, J=8.4, 7.2 Hz, 1H), 7.79 (dd, J=7.2, 1.4 Hz, 1H), 7.73 (s, 1H), 4.53 (d, 1H), 4.56 (d, 1H), 4.53-4.27 (m, 2.5H), 3.05-3.45 (m, 2.5H), 1.74 (br. s., 1H), 1.56-1.65 (m, 1H), 0.97-1.26 (m, 6H), 0.42-0.87 (m, 8H). LC-MS: m/z 465.2 (M+H)⁺

(R)-6-cyclopropyl-2-(3-cyclopropyl-4-(3,3,3-trifluoropropanoyl)piperazin-1-yl)-5-(quinoxalin-5-yl)nicotinonitrile (Compound 532; General Procedure 1, Step I)

¹H NMR (CHLOROFORM-d) δ 8.89-8.92 (m, 2H), 8.22 (dd, J=8.4, 1.4 Hz, 1H), 7.89 (t, J=8.3, 7.3 Hz, 1H), 7.79-7.81 (dd, J=8.3, 7.3 Hz, 1H), 7.75 (s, 1H), 4.53 (d, J=13.1 Hz, 1H), 4.44 (d, J=12.0 Hz, 1H), 4.14 (br. s., 0.5H), 3.75-3.89 (m, 1.5H), 3.07-3.37 (m, 5H), 1.62 (m, 1H), 1.19 (br. s., 2H), 0.48-0.84 (m, 6H). LC-MS: m/z 507.3 (M+H)⁺

(R)-6-cyclopropyl-2-(4-(3-methoxypropanoyl)-3-methylpiperazin-1-yl)-5-(2-vinylquinoxalin-5-yl)nicotinonitrile (Compound 579; General Procedure 1, Step I)

¹H NMR (CHLOROFORM-d) δ 9.00 (s, 1H), 8.13 (dd, J=8.5, 1.3 Hz, 1H), 7.84 (dd, J=8.3, 7.3 Hz, 1H), 7.67-7.74 (m, 1H), 7.01-7.12 (m, 1H), 6.50 (d, J=11.3 Hz, 1H), 5.84 (d, J=11.3 Hz, 1H), 4.92 (br. s., 0.5H), 4.57 (br. s., 0.5H), 4.19-4.40 (m, 2.5H), 3.68-3.78 (m, 2.5H), 3.58 (br. s., 0.5H), 3.39 (s, 3H), 3.02-3.31 (m, 2.5H), 2.58-2.75 (m, 2H), 1.86 (br. s., 1H), 1.62 (m, 1H), 1.43 (d, J=6.3 Hz, 1.5H), 1.33 (d, J=6.3 Hz, 1.5H), 1.16 (br. s., 2H), 0.81 (br. s., 2H). LC-MS: m/z 485.2 (M+H)⁺

(R,E)-6-cyclopropyl-2-(4-(3-methoxypropanoyl)-3-methylpiperazin-1-yl)-5-(2-(2-(2-vinylquinoxalin-5-yl)vinyl)quinoxalin-5-yl)nicotinonitrile (Compound 604)

It was obtained as the by-product of Compound 579. ¹H NMR (CHLOROFORM-d) δ 9.23 (s, 1H), 9.09 (s, 1H), 8.17-8.20 (m, 2H), 8.08 (d, J=8.5 Hz, 1H), 7.70-7.87 (m, 5H), 7.04-7.11 (q, 1H), 6.53 (d, J=11.3 Hz, 1H), 5.85 (d, J=11.3 Hz, 1H), 4.94 (br. s., 0.5H), 4.56 (d, J=12.8 Hz, 0.5H), 4.26-4.37 (m, 2.5H), 3.75-3.84 (m, 2.5H), 3.59 (t, 0.5H), 3.40 (s, 3H), 3.06-3.32 (m, 2.5H), 2.59-2.81 (m, 2H), 1.61-1.73 (m, 1H), 1.45 (d, J=6.3 Hz, 1.5H), 1.32 (d, J=6.3 Hz, 1.5H), 1.25-1.29 (m, 2H), 0.83-0.86 (m, 2H). LC-MS: m/z 637.3 (M+H)⁺

(R)-6-cyclopropyl-2-(3-isopropyl-4-(3-methoxypropanoyl)piperazin-1-yl)-5-(2-vinylquinoxalin-5-yl)nicotinonitrile (Compound 605; General Procedure 1, Step I)

¹H NMR (CHLOROFORM-d) δ 9.00 (s, 1H), 8.13 (d, J=8.5 Hz, 1H), 7.83 (t, J=7.8 Hz, 1H), 7.62-7.77 (m, 2H), 6.97-7.13 (q, 1H), 6.50 (d, J=11.0 Hz, 1H), 5.84 (d, J=11.0 Hz, 1H), 4.58-4.73 (m, 1.5H), 4.39-4.48 (m, 1.5H), 3.87 (d, J=13.3 Hz, 0.5H), 3.74 (m, 2H), 3.42-3.60 (m, 1H), 3.39 (d, J=3.3 Hz, 3H), 2.93-3.17 (m, 2.5H), 2.53-2.83 (m, 2H), 2.16-2.33 (m, 1H), 1.62 (br. s., 1H), 1.07-1.10 (m, 4H), 0.82-0.93 (m, 6H). LC-MS: m/z 511.2 (M+H)+

(R)-6-cyclopropyl-2-(4-(3-hydroxypropanoyl)-3-methylpiperazin-1-yl)-5-(2-vinylquinoxalin-5-yl)nicotinonitrile (Compound 618; General Procedure 1, Step I)

¹H NMR (CHLOROFORM-d) δ 9.00 (s, 1H), 8.13 (dd, J=8.5, 1.3 Hz, 1H), 7.84 (dd, J=8.3, 7.3 Hz, 1H), 7.67-7.74 (m, 2H), 7.02-7.07 (m, 1H), 6.50 (d, J=11.3 Hz, 1H), 5.82 (d, J=11.3 Hz, 1H), 4.92 (br. s., 0.5H), 4.57 (br. s., 0.5H), 4.19-4.33 (m, 3H), 3.93 (s, 2.5H), 3.58 (br. s., 0.5H), 3.01-3.48 (m, 4H), 2.48-2.75 (m, 3H), 1.63 (m, 1H), 1.43 (d, J=6.3 Hz, 1.5H), 1.35 (d, J=6.3 Hz, 1.5H), 1.16 (br. s., 2H), 0.82 (br. s., 2H). LC-MS: m/z 469.2 (M+H)+

(R)-6-cyclopropyl-2-(3-cyclopropyl-4-(3-methoxypropanoyl)piperazin-1-yl)-5-(2-vinylquinoxalin-5-yl)nicotinonitrile (Compound 644; General Procedure 1, Step I)

¹H NMR (CHLOROFORM-d) δ 9.00 (s, 1H), 8.13 (dd, J=8.5, 1.3 Hz, 1H), 7.70-7.72 (m, 2H), 7.01-7.12 (q, 1H), 6.50 (d, J=11.3 Hz, 1H), 5.84 (d, J=11.3 Hz, 1H), 4.71 (br. s., 0.5H), 4.52 (d, 1H), 4.41 (d, 1H), 4.12 (br. s., 0.5H), 3.89 (br. s., 0.5H), 3.74 (m, 2H), 3.39 (s, 3H), 3.01-3.31 (m, 3H), 2.59-2.83 (m, 2H), 1.58-1.68 (m, 1H), 0.97-1.32 (m, 4H), 0.46-0.89 (m, 7H).
LC-MS: m/z 509.1 (M+H)+

(R)-2'-bromo-6-(4-(cyclopropanecarbonyl)-3-cyclopropylpiperazin-1-yl)-2-cyclopropyl-3,4'-bipyridine-5-carbonitrile (Compound 508; General Procedure 1, Step H)

¹H NMR (CHLOROFORM-d) δ 8.46 (d, J=5.0 Hz, 1H), 7.63 (s, 1H), 7.57-7.61 (m, 1H), 7.34 (dd, J=5.0, 1.5 Hz, 1H), 4.61 (d, J=12.8 Hz, 1H), 4.49 (d, J=13.6 Hz, 1H), 4.18-4.38 (m, 1H), 3.76 (br. s., 2H), 3.31 (br. s., 1H), 3.15 (br. s., 1H), 1.93-2.08 (m, 1H), 1.72 (br. s., 1H), 1.33 (br. s., 1H), 1.17-1.26 (m, 2H), 0.95-1.12 (m, 4H), 0.76-0.91 (m, 2H), 0.66 (br. s., 1H), 0.35-0.60 (m, 3H). LC-MS: m/z 493.4 (M+H)+

(R)-2'-chloro-6-(4-(cyclopropanecarbonyl)-3-cyclopropylpiperazin-1-yl)-2-cyclopropyl-3'-fluoro-3,4'-bipyridine-5-carbonitrile (Compound 509; General Procedure 1, Step H)

¹H NMR (CHLOROFORM-d) δ 8.29 (d, J=5.0 Hz, 1H), 7.59-7.75 (s, 1H), 7.11-7.41 (d, J=5.0 Hz, 1H), 4.63 (d, J=13.1 Hz, 1H), 4.50 (d, J=12.5 Hz, 1H), 4.06 (br. s., 1H), 3.75 (br. s., 1H), 3.65 (br. s., 1H), 3.31 (br. s., 1H), 3.16 (br. s., 1H), 1.70-1.81 (m, 1H), 1.30-1.42 (m, 1H), 1.13-1.25 (m, 2H), 0.94-1.13 (m, 4H), 0.75-0.87 (m, 2H), 0.66 (br. s., 1H), 0.35-0.60 (m, 3H).
LC-MS: m/z 466.9 (M+H)+

(R)-5-(5-cyano-6-(4-(cyclopropanecarbonyl)-3-cyclopropylpiperazin-1-yl)-2-cyclopropylpyridin-3-yl)isoquinoline-1-carbonitrile (Compound 511)

¹H NMR (CHLOROFORM-d) δ 8.66 (dd, J=5.8, 1.8 Hz, 1H), 8.45 (d, J=8.3 Hz, 1H), 7.87-7.97 (m, 1H), 7.80 (ddd, J=7.2, 2.1, 1.0 Hz, 1H), 7.70 (ddd, J=11.1, 5.8, 0.9 Hz, 1H), 7.64 (d, J=0.8 Hz, 1H), 4.61 (d, J=12.0 Hz, 1H), 4.49 (d, J=12.8 Hz, 1H), 3.42-4.43 (m, 2H), 3.10-3.40 (m, 3H), 1.75 (br. s., 1H), 1.38-1.47 (m, 2H), 0.95-1.12 (m, 2H), 0.75-0.93 (m, 6H), 0.70 (br. s., 1H), 0.38-0.61 (m, 3H). LC-MS: m/z 489.2 (M+H)+

(R)-6-cyclopropyl-2-(3-cyclopropyl-4-(3,3,3-trifluoropropanoyl)piperazin-1-yl)-5-(1-hydroxyisoquinolin-5-yl)nicotinonitrile (Compound 547; General Procedure 2, Step M)

¹H NMR (CHLOROFORM-d) δ 10.95 (s, 1H), 8.53 (dd, J=6.4, 3.1 Hz, 1H), 7.57-7.72 (m, 3H), 7.17 (br. s., 1H), 6.31 (dd, J=12.9, 7.4 Hz, 1H), 4.38-4.61 (m, 2H), 4.15 (br. s., 0.5H), 3.69-3.95 (m, 1.5H), 3.03-3.41 (m, 5H), 1.53-1.77 (m, 3H), 1.16 (dd, J=8.3, 4.5 Hz, 2H), 0.81-0.98 (m, 2H), 0.47-0.64 (m, 3H). LC-MS: m/z 522.2 (M+H)+

(R)-5-(3-chloroisoquinolin-5-yl)-2-(4-(cyclopropanecarbonyl)-3-cyclopropylpiperazin-1-yl)-6-cyclopropylnicotinonitrile (Compound 555; General Procedure 1, Step H)

¹H NMR (CHLOROFORM-d) δ 9.17 (s, 1H), 8.06 (d, J=7.5 Hz, 1H), 7.66-7.73 (m, 2H), 7.64 (d, J=1.0 Hz, 1H), 7.49 (d, J=14.8 Hz, 1H), 4.61 (d, J=12.0 Hz, 1H), 4.49 (d, J=12.8 Hz, 1H), 3.42-4.43 (m, 2H), 3.10-3.40 (m, 3H), 1.69 (br. s., 1H), 1.39-1.57 (m, 2H), 1.15-1.23 (m, 2H), 1.08 (br. s., 2H), 0.79-0.93 (m, 4H), 0.70 (br. s., 1H), 0.38-0.63 (m, 3H). LC-MS: m/z 498.2 (M+H)+

(R)-2-(4-(cyclopropanecarbonyl)-3-cyclopropylpiperazin-1-yl)-6-cyclopropyl-5-(1-hydroxyisoquinolin-5-yl)nicotinonitrile (Compound 566; General Procedure 1, Step H)

¹H NMR (CHLOROFORM-d) δ 11.20 (br. s., 1H), 8.52 (dd, J=7.0, 2.3 Hz, 1H), 7.51-7.76 (m, 3H), 7.12-7.24 (m, 1H), 6.33 (dd, J=12.7, 7.4 Hz, 1H), 4.56 (d, J=12.5 Hz, 1H), 4.44 (d, J=12.3 Hz, 1H), 3.52-4.35 (m, 2H), 3.05-3.45 (m, 3H), 1.63 (td, J=7.8, 4.0 Hz, 1H), 1.27-1.45 (m, 2H), 0.96-1.23 (m, 4H), 0.77-0.96 (m, 4H), 0.70 (br. s., 1H), 0.36-0.62 (m, 3H). LC-MS: m/z 480.2 (M+H)+

(R)-2-(4-(cyclopropanecarbonyl)-3-cyclopropylpiperazin-1-yl)-6-cyclopropyl-5-(3-vinylisoquinolin-5-yl)nicotinonitrile (Compound 565; General Procedure 1, Step H)

¹H NMR (CHLOROFORM-d) δ 9.29 (s, 1H), 8.03 (d, J=7.5 Hz, 1H), 7.55-7.77 (m, 3H), 7.31 (d, J=12.5 Hz, 1H), 6.88 (ddd, J=17.3, 10.6, 6.8 Hz, 1H), 6.38 (ddd, J=17.2, 5.6, 1.3 Hz, 1H), 5.44-5.59 (m, 1H), 4.59 (d, J=11.8 Hz, 1H), 4.47 (d, J=12.5 Hz, 1H), 3.55-4.35 (m, 2H), 3.05-3.45 (m, 3H), 1.68-1.80 (m, 1H), 1.42-1.61 (m, 2H), 1.22-1.34 (m, 2H), 1.00-1.14 (m, 2H), 0.76-0.92 (m, 4H), 0.71 (br. s., 1H), 0.39-0.63 (m, 3H). LC-MS: m/z 490.2 (M+H)+

(R)-6-cyclopropyl-2-(4-(3-hydroxypropanoyl)-3-methylpiperazin-1-yl)-5-(3-methylisoquinolin-5-yl)nicotinonitrile (Compound 588; General Procedure 1, Step H)

¹H NMR (CHLOROFORM-d) δ 9.23 (s, 1H), 7.99 (d, J=7.3 Hz, 1H), 7.53-7.67 (m, 3H), 7.21 (d, J=6.5 Hz, 1H), 4.91 (br. s., 0.5H), 4.54 (d, J=13.1 Hz, 0.5H), 4.15-4.43 (m, 2.5H), 3.86-4.02 (m, 2H), 3.68-3.83 (m, 0.5H), 3.51-3.68 (m, 0.5H), 3.26-3.42 (m, 1H), 2.97-3.24 (m, 1.5H), 2.49-

2.78 (m, 5H), 1.49-1.58 (m, 1H), 1.41-1.49 (m, 1.5H), 1.30-1.40 (m, 1.5H), 1.06-1.20 (m, 2H), 0.72-0.91 (m, 2H). LC-MS: m/z 456.2 (M+H)$^+$ (R)-5-(5-chloro-2-vinylpyrimidin-4-yl)-2-(4-(cyclopropanecarbonyl)-3-cyclopropylpiperazin-1-yl)-6-cyclopropylnicotinonitrile (Compound 533; General Procedure 1, Step H)

1H NMR (CHLOROFORM-d) δ 8.69-8.87 (m, 1H), 7.70-7.91 (m, 1H), 6.91 (dd, J=17.3, 10.5 Hz, 1H), 6.59-6.78 (m, 1H), 5.71-5.98 (m, 1H), 4.66 (d, J=12.8 Hz, 1H), 4.53 (d, J=12.5 Hz, 1H), 3.09-4.42 (m, 5H), 1.76-1.85 (m, 1H), 1.39-1.46 (m, 1H), 1.21-1.25 (m, 2H), 0.99-1.10 (m, 4H), 0.90 (t, J=6.9 Hz, 1H), 0.78-0.85 (m, 2H), 0.66 (br. s., 1H), 0.41-0.60 (m, 3H). LC-MS: m/z 475.2 (M+H)$^+$

Compound 541

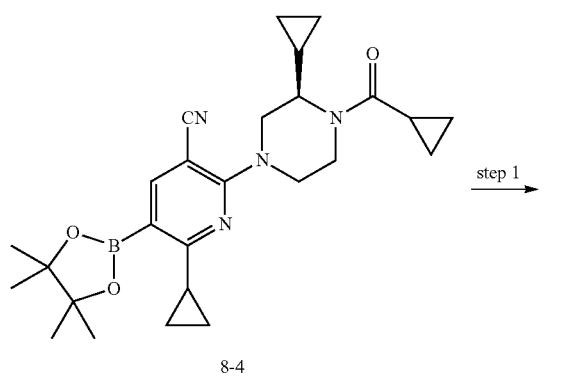

Step 1: (R)-5-(6-chloropyrimidin-4-yl)-2-(4-(cyclopropanecarbonyl)-3-cyclopropylpiperazin-1-yl)-6-cyclopropylnicotinonitrile

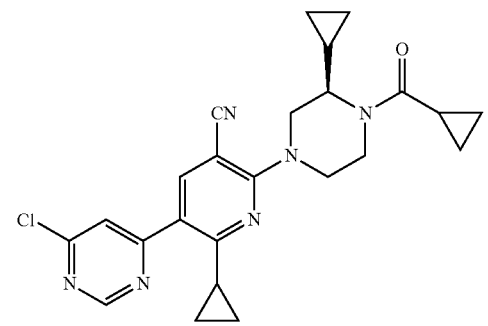 [SMILES: N#Cc1cc(-c2cc(Cl)ncn2)c(C2CC2)nc1N1CCN(C(=O)C2CC2)[C@H](C2CC2)C1]

To a solution of 4,6-dichloropyrimidine (50 mg, 0.32 mmol) in a mixture of dimethoxyethane (3 mL) and a 2M aqueous sodium carbonate solution (0.6 mL) were added 8-4 (100 mg, 0.22 mmol) and tetrakis(triphenylphosphine)palladium(0) (20 mg, 0.1 eq) under nitrogen atmosphere, and the mixture was heated for 2 hours at 100° C. After cooling to ambient temperature, the separated organic layer was evaporated under reduced pressure. The residue was taken up into ethyl acetate, washed in turn with a 10% aqueous potassium carbonate solution and brine, and dried over sodium sulfate. After evaporation, the residue was purified on silica gel eluding with 5%-20% ethyl acetate in petroleum ether to give 4-chloro-6-phenylpyrimidine (75 mg), 69% yield. $^1$H NMR (CHLOROFORM-d) δ 8.67-8.84 (m, 1H), 8.07 (s, 1H), 7.43 (d, J=5.0 Hz, 1H), 4.68 (d, J=13.1 Hz, 1H), 4.53 (d, J=13.3 Hz, 1H), 4.07 (br. s., 1H), 3.88 (s, 1H), 3.68 (br. s., 1H), 3.33 (br. s., 1H), 3.17 (br. s., 1H), 2.34-2.47 (m, 1H), 1.96-2.08 (m, 2H), 1.30-1.42 (m, 2H), 1.00-1.11 (m, 3H), 0.85-0.93 (m, 1H), 0.82 (dd, J=8.0, 2.5 Hz, 2H), 0.65 (br. s., 1H), 0.39-0.59 (m, 3H). LC-MS: m/z 449.2 (M+H)$^+$ Step 2: (R)-2-(4-(cyclopropanecarbonyl)-3-cyclopropylpiperazin-1-yl)-6-cyclopropyl-5-(6-vinylpyrimidin-4-yl)nicotinonitrile (Compound 541)

A mixture of above (R)-5-(6-chloropyrimidin-4-yl)-2-(4-(cyclopropanecarbonyl)-3-cyclopropylpiperazin-1-yl)-6-cyclopropylnicotinonitrile (60 mg, 0.06 mmol) (60 mg, 0.13 mmol), vinyl potassium-trifluoroborate (25 mg, 0.2 mmol), Pd(PPh3)4 (3 mg, 0.1 eq), and CsF (40 mg, 0.26 mmol) were suspended in 5 mL of dioxane and 1 mL of water, the resulting mixture was refluxed for 1 h. After the reaction was complete, the reaction mixture was concentrated in vacuo, and the residue was purified by column chromatography to afford 35 mg of title compound as yellow solid. 75% yield. $^1$H NMR (CHLOROFORM-d) δ 9.16-9.30 (m, 1H), 7.93-8.07 (m, 1H), 7.49-7.56 (m, 1H), 6.82 (dd, J=17.3, 10.5 Hz, 1H), 6.57 (dd, J=17.3, 1.0 Hz, 1H), 5.72-5.83 (m, 1H), 4.68 (d, J=13.1 Hz, 1H), 4.55 (d, J=12.3 Hz, 1H), 4.39-3.11 (br. s., 5H), 2.34-2.43 (m, 1H), 1.70 (br. s., 1H), 1.31-1.40 (m, 2H), 0.99-1.11 (m, 4H), 0.89-0.94 (m, 1H), 0.82 (dd, J=7.9, 2.4 Hz, 2H), 0.64 (br. s., 1H), 0.41-0.58 (m, 3H). LC-MS: m/z 441.2 (M+H)$^+$ (S)-2-(4-(cyclopropanecarbonyl)-3-cyclopropylpiperazin-1-yl)-6-cyclopropyl-5-(6-vinylpyrimidin-4-yl)nicotinonitrile (Compound 578)

$^1$H NMR (CHLOROFORM-d) δ9.24 (d, J=1.3 Hz, 1H), 7.94-8.05 (m, 1H), 7.46-7.58 (m, 1H), 6.82 (dd, J=17.3, 10.8

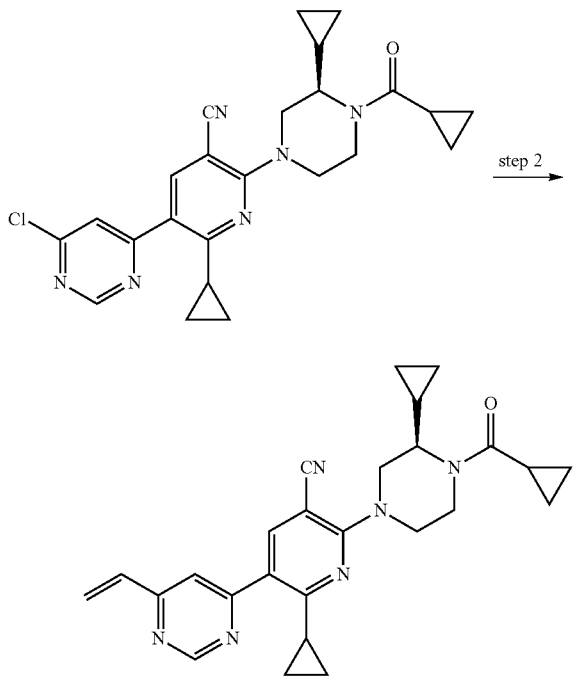

Hz, 1H), 6.57 (dd, J=17.3, 1.0 Hz, 1H), 5.73-5.84 (m, 1H), 4.68 (d, J=12.5 Hz, 1H), 4.55 (d, J=12.3 Hz, 1H), 4.08 (br. s., 1H), 3.76 (s, 1H), 3.66 (t, J=6.7 Hz, 1H), 3.40-3.58 (m, 1H), 3.33 (br. s., 1H), 3.17 (br. s., 1H), 2.34-2.45 (m, 1H), 1.29-1.35 (m, 2H), 1.00-1.11 (m, 4H), 0.89-0.92 (m, 1H), 0.82 (dd, J=7.9, 2.4 Hz, 2H), 0.64 (br. s., 1H), 0.43-0.58 (m, 3H). LC-MS: m/z 441.2 (M+H)⁺

(R)-6-cyclopropyl-2-(4-(3-hydroxypropanoyl)-3-methylpiperazin-1-yl)-5-(6-vinylpyrimidin-4-yl)nicotinonitrile (Compound 621)

¹H NMR (CHLOROFORM-d) δ 9.24 (d, J=1.3 Hz, 1H), 7.82-8.04 (m, 1H), 7.47-7.61 (m, 1H), 6.68-6.93 (m, 1H), 6.42-6.62 (m, 1H), 5.64-5.88 (m, 1H), 4.88 (br. s., 1H), 4.29-4.57 (m, 3H), 4.17 (br. s., 1H), 3.93 (br. s., 2H), 3.74 (d, J=13.3 Hz, 1H), 3.47-3.63 (m, 1H), 3.29-3.41 (m, 1H), 3.05-3.25 (m, 2H), 2.51-2.72 (m, 2H), 2.33-2.42 (m, 1H), 1.32-1.44 (m, 2H), 1.22-1.28 (m, 3H), 1.02-1.11 (m, 2H). LC-MS: m/z 419.2 (M+H)⁺

(R)-6-cyclopropyl-2-(3-cyclopropyl-4-(3-methoxypropanoyl)piperazin-1-yl)-5-(6-vinylpyrimidin-4-yl)nicotinonitrile (Compound 638)

¹H NMR (CHLOROFORM-d) δ 9.24 (s, 1H), 7.95-8.11 (m, 1H), 7.50-7.56 (m, 1H), 6.74-6.87 (m, 1H), 6.48-6.65 (m, 1H), 5.74-5.89 (m, 1H), 4.67 (d, J=12.8 Hz, 1H), 4.53 (d, J=11.0 Hz, 1H), 4.10 (br. s., 0.5H), 3.83-3.93 (m, 0.5H), 3.61-3.81 (m, 3H), 3.39 (s, 3H), 3.21-3.35 (m, 2H), 3.08-3.21 (m, 1H), 2.72 (br. s., 1H), 2.65 (br. s., 1H), 2.33-2.43 (m, 1H), 1.21-1.36 (m, 3H), 1.03-1.13 (m, 2H), 0.60 (br. s., 2H), 0.45 (br. s., 2H). LC-MS: m/z 459.2 (M+H)⁺

(R)-6-cyclopropyl-2-(3-isopropyl-4-(3-methoxypropanoyl)piperazin-1-yl)-5-(6-vinylpyrimidin-4-yl)nicotinonitrile (Compound 639)

1H NMR (CHLOROFORM-d) δ 9.09-9.32 (m, 1H), 7.99 (s, 1H), 7.51 (s, 1H), 6.81 (dd, J=17.3, 10.5 Hz, 1H), 6.56 (d, J=17.3 Hz, 1H), 5.78 (d, J=11.3 Hz, 1H), 4.67-4.76 (m, 1H), 4.50 (d, J=14.6 Hz, 1H), 3.88 (d, J=13.6 Hz, 1H), 3.68-3.79 (m, 2H), 3.60 (d, J=10.5 Hz, 1H), 3.39-3.55 (m, 1H), 3.02-3.24 (m, 2H), 2.85-3.02 (m, 1H), 2.52-2.82 (m, 2H), 2.33-2.43 (m, 1H), 1.92-2.05 (m, 1H), 1.23-1.31 (m, 2H), 1.00-1.10 (m, 5H), 0.83-0.92 (m, 3H). LC-MS: m/z 461.3 (M+H)⁺

(R)-6-cyclopropyl-2-(4-(3-methoxypropanoyl)-3-methylpiperazin-1-yl)-5-(6-vinylpyrimidin-4-yl)nicotinonitrile (Compound 597)

1H NMR (CHLOROFORM-d) δ 9.22 (s, 1H), 7.98 (s, 1H), 7.50 (s, 1H), 6.80 (dd, J=17.3, 10.8 Hz, 1H), 6.44-6.69 (m, 1H), 5.64-5.92 (m, 1H), 4.89 (br. s., 0.5H), 4.52 (d, J=9.5 Hz, 0.5H), 4.28-4.46 (m, 2H), 3.65-3.95 (m, 3H), 3.44-3.65 (m, 1H), 3.27-3.44 (m, 4H), 3.00-3.27 (m, 2H), 2.51-2.81 (m, 2H), 2.25-2.47 (m, 1H), 1.14-1.44 (m, 5H), 0.93-1.14 (m, 2H). LC-MS: m/z 433.2 (M+H)⁺

(R)-6-cyclopropyl-5-(6-(1-fluorovinyl)pyrimidin-4-yl)-2-(4-(3-methoxypropanoyl)-3-methylpiperazin-1-yl)nicotinonitrile (Compound 602)

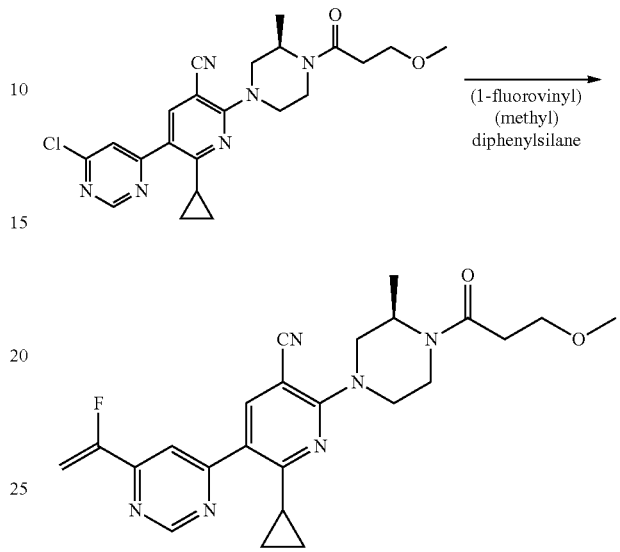

To a solution of (R)-5-(6-chloropyrimidin-4-yl)-6-cyclopropyl-2-(4-(3-methoxypropanoyl)-3-methylpiperazin-1-yl)nicotinonitrile (80 mg 0.21 mmol), CuI (10 mg, 10%), and Pd(PPh3)2Cl2 (15 mg) in 5 ml of DMF was added (1-fluorovinyl)(methyl) diphenylsilane (7.6 mg, 0.41 mmol). The mixture was stirred at room temperature for 2 h under nitrogen atmosphere. After removal of the solvent under reduced pressure, the residue was purified by prep-TLC (20% ethyl acetate in petroleum ether) to afford 20 mg of pure product, 30% yield. ¹H NMR (CHLOROFORM-d) δ □9.25 (s, 1H), 8.04 (s, 1H), 7.76 (s, 1H), 6.11 (d, J=3.0 Hz, 1H), 5.99 (d, J=3.0 Hz, 1H), 5.27 (dd, J=15.8, 3.0 Hz, 1H), 4.91 (br. s., 1H), 4.54 (d, J=10.3 Hz, 1H), 4.31-4.49 (m, 1H), 3.71-3.78 (m, 1H), 3.49-3.63 (m, 1H), 3.31-3.44 (m, 4H), 3.16-3.28 (m, 1H), 3.13 (br. s., 1H), 2.51-2.81 (m, 2H), 2.30-2.44 (m, 1H), 1.35 (d, J=6.5 Hz, 2H), 1.25 (dd, J=4.3, 2.8 Hz, 3H), 1.04-1.13 (m, 2H). LC-MS: m/z 451.2 (M+H)⁺

(R)-6-(4-(cyclopropanecarbonyl)-3-cyclopropylpiperazin-1-yl)-2-cyclopropyl-2'-(prop-1-en-2-yl)-3,4'-bipyridine-5-carbonitrile (Compound 544)

Synthesized according to the procedure described for Compound 602 except using trimethyl(prop-1-en-2-yl)silane instead of (1-fluorovinyl)(methyl) diphenylsilane. ¹H NMR (CHLOROFORM-d) δ8.67 (d, J=5.0 Hz, 1H), 7.65 (s, 1H), 7.53 (s, 1H), 7.16-7.27 (m, 1H), 5.92 (s, 1H), 5.38 (s, 1H), 4.57 (d, J=12.3 Hz, 1H), 4.45 (d, J=12.3 Hz, 1H), 4.07 (br. s., 1H), 3.78 (br. s., 1H), 3.56-3.74 (m, 1H), 3.50 (s, 1H), 3.29 (br. s., 1H), 3.14 (br. s., 1H), 2.26 (s, 3H), 1.98-2.10 (m, 1H), 1.72 (br. s., 1H), 1.17-1.27 (m, 2H), 0.97-1.09 (m, 4H), 0.86-0.95 (m, 1H), 0.76-0.84 (m, 2H), 0.66 (br. s., 1H), 0.40-0.59 (m, 3H). LC-MS: m/z 453.2 (M+H)⁺

(R)-5-(2-aminopyrimidin-4-yl)-2-(4-(cyclopropanecarbonyl)-3-cyclopropylpiperazin-1-yl)-6-cyclopropylnicotinonitrile (Compound 507)

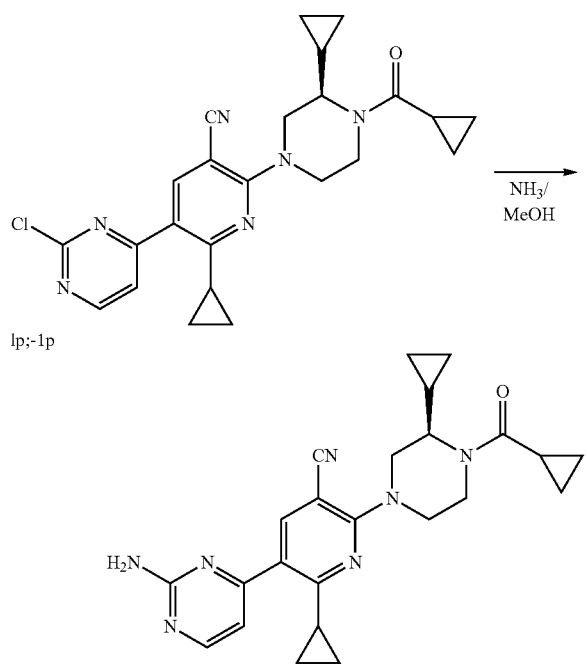

To a solution NH₃/MeOH (10 mL, 7 M) was added (R)-5-(2-chloropyrimidin-4-yl)-2-(4-(cyclopropanecarbonyl)-3-cyclopropylpiperazin-1-yl)-6-cyclopropylnicotinonitrile (40 mg, 0.09 mmol), the mixture was stirred at 50 C overnight. After removal of the solvent under reduced pressure, the residue was purified by prep-TLC (30% ethyl acetate in petroleum ether) to afford 21 mg of pure product, 51% yield. $^1$H NMR (CHLOROFORM-d) δ 8.36 (d, J=5.3 Hz, 1H), 7.97 (s, 1H), 6.90 (d, J=5.0 Hz, 1H), 5.25 (br. s., 2H), 4.64 (d, J=12.5 Hz, 1H), 4.51 (d, J=12.3 Hz, 1H), 3.69 (br. s., 1H), 3.32 (br. s., 1H), 3.26 (br. s., 1H), 3.15 (br. s., 2H), 2.32-2.45 (m, 1H), 2.03-2.08 (m, 1H), 1.02-1.10 (m, 4H), 0.77-0.89 (m, 4H), 0.63 (br. s., 2H), 0.43-0.58 (m, 3H). LC-MS: m/z 430.2 (M+H)$^+$

(R)-2-(4-(cyclopropanecarbonyl)-3-cyclopropylpiperazin-1-yl)-6-cyclopropyl-5-(2-(dimethylamino)pyrimidin-4-yl)nicotinonitrile (Compound 506)

Synthesized according to the procedure described for Compound 507 except using dimethylamine instead of NH₃.EtOH. $^1$H NMR (CHLOROFORM-d) δ 8.38 (d, J=5.0 Hz, 1H), 7.90-8.06 (m, 1H), 6.72 (d, J=5.0 Hz, 1H), 4.61 (d, J=12.8 Hz, 1H), 4.49 (d, J=12.5 Hz, 1H), 4.09-4.26 (m, 1H), 3.30-3.58 (m, 2H), 3.26 (s, 6H), 3.16-3.24 (m, 1H), 3.11 (d, J=18.3 Hz, 1H), 2.48-2.56 (m, 1H), 1.19-1.24 (m, 3H), 0.98-1.08 (m, 4H), 0.86-0.92 (m, 1H), 0.76-0.84 (m, 2H), 0.64 (br. s., 1H), 0.40-0.58 (m, 3H). LC-MS: m/z 458.3 (M+H)$^+$

(R)-6-cyclopropyl-2-(3-cyclopropyl-4-(3,3,3-trifluoropropanoyl)piperazin-1-yl)-5-(2-(dimethylamino)pyrimidin-4-yl)nicotinonitrile (Compound 534)

1H NMR (CHLOROFORM-d) δ8.37 (d, J=5.3 Hz, 1H), 7.97 (s, 1H), 6.89 (d, J=5.0 Hz, 1H), 4.63 (d, J=13.1 Hz, 1H), 4.51 (d, J=12.8 Hz, 1H), 4.00-4.17 (m, 1H), 3.68-3.87 (m, 1H), 3.17-3.38 (m, 3H), 3.12 (d, J=11.8 Hz, 1H), 2.82 (s, 2H), 2.33-2.45 (m, 1H), 1.35 (br. s., 1H), 1.18-1.25 (m, 2H), 0.98-1.10 (m, 2H), 0.64 (br. s., 1H), 0.57 (br. s., 1H), 0.38-0.54 (m, 2H). LC-MS: m/z 472.2 (M+H)$^+$

(R)-2-(4-(cyclopropanecarbonyl)-3-cyclopropylpiperazin-1-yl)-6-cyclopropyl-5-(2-(2-hydroxyethylamino)pyrimidin-4-yl)nicotinonitrile (Compound 512)

Synthesized according to the procedure described in Compound 507 except using 2-(methylamino)ethanol instead of NH₃.EtOH. $^1$H NMR (CHLOROFORM-d) δ 8.32 (d, J=5.0 Hz, 1H), 7.94 (s, 1H), 6.83 (d, J=5.3 Hz, 1H), 5.91 (br. s., 1H), 4.63 (d, J=12.8 Hz, 1H), 4.50 (d, J=12.5 Hz, 1H), 3.96-4.33 (m, 1H), 3.82-3.92 (m, 2H), 3.63-3.72 (m, 2H), 3.29 (br. s., 1H), 3.14 (br. s., 1H), 2.68-2.78 (m, 1H), 2.66 (br. s., 1H), 2.34-2.44 (m, 1H), 1.20-1.35 (m, 4H), 1.04 (dd, J=7.7, 3.4 Hz, 4H), 0.77-0.90 (m, 3H), 0.64 (br. s., 1H), 0.49-0.55 (m, 1H), 0.44 (dt, J=9.3, 4.4 Hz, 1H).
LC-MS: m/z 474.2 (M+H)$^+$

(R)-6-cyclopropyl-2-(3-cyclopropyl-4-(3,3,3-trifluoropropanoyl)piperazin-1-yl)-5-(2-(dimethylamino)pyrimidin-4-yl)nicotinonitrile (Compound 521)

1H NMR (CHLOROFORM-d) δ 8.42 (d, J=5.3 Hz, 1H), 8.00 (s, 1H), 6.75 (d, J=5.3 Hz, 1H), 4.62 (d, J=13.1 Hz, 1H), 4.50 (d, J=12.8 Hz, 1H), 3.96-4.20 (m, 1H), 3.68-3.96 (m, 1H), 3.28-3.42 (m, 2H), 3.09-3.15 (m, 1H), 2.42-2.54 (m, 1H), 1.39-1.56 (m, 1H), 1.14-1.25 (m, 2H), 0.98-1.08 (m, 2H), 0.65 (br. s., 1H), 0.56 (br. s., 1H), 0.43-0.53 (m, 2H). LC-MS: m/z 500.2 (M+H)$^+$

(R)-2-(4-(cyclopropanecarbonyl)-3-cyclopropylpiperazin-1-yl)-6-cyclopropyl-5-(6-vinylpyrazin-2-yl)nicotinonitrile (Compound 515)

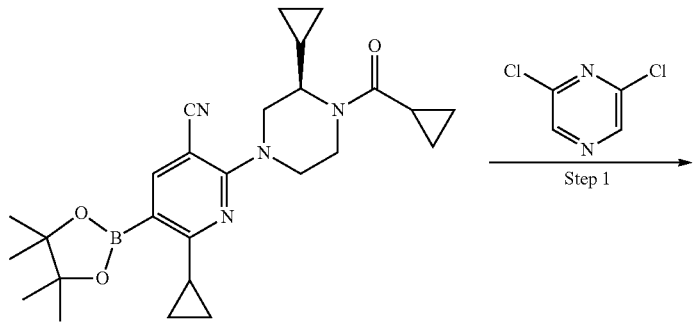

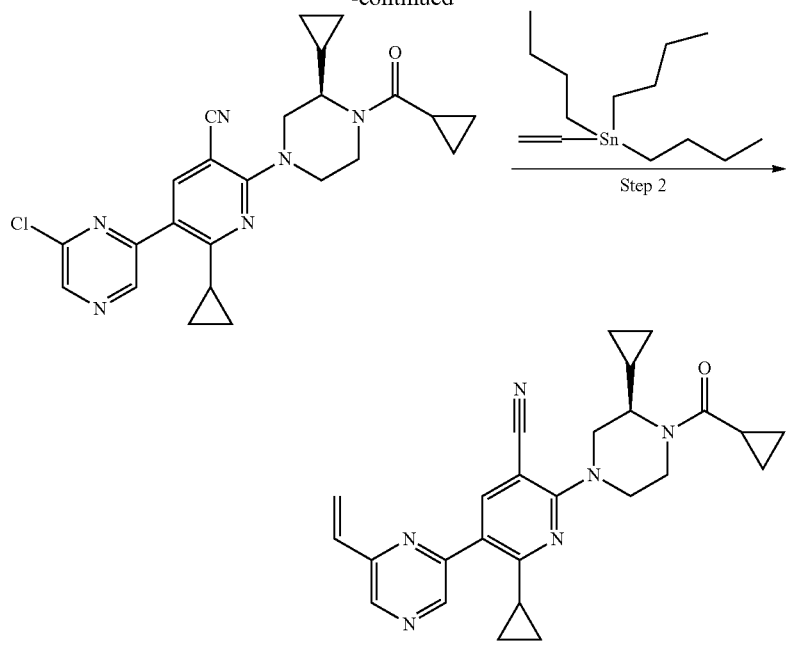

Step 1:

To a flask was added with (R)-2-(4-(cyclopropanecarbonyl)-3-cyclopropylpiperazin-1-yl)-6-cyclopropyl-5-(4,4,5,5-tetramethyl-1,3,2-dioxaborolan-2-yl)nicotinonitrile (70 mg, 0.151 mmol), 2, 6-dichloropyrazine (30 mg, 0.197 mmol), Pd(PPh$_3$)$_4$ (17 mg, 0.015 mmol), K$_2$CO$_3$ (63 mg, 0.453 mmol), and 1.5 mL DMF. The mixture was stirred at 120° C. for 2 h. After washing with Satd. NaHCO3, brine, the combined organic layer was dried over anhy. Na$_2$SO$_4$ and concentrated in vacuo. Prep-TLC purification (20% EtOAc/petroleum ether) afforded 25 mg of (R)-5-(6-chloropyrazin-2-yl)-2-(4-(cyclopropanecarbonyl)-3-cyclopropylpiperazin-1-yl)-6-cyclopropylnicotinonitrile.

Step 2:

To a flask was added with (R)-2-(4-(cyclopropanecarbonyl)-3-cyclopropylpiperazin-1-yl)-6-cyclopropyl-5-(6-vinylpyrazin-2-yl)nicotinonitrile (18 mg 0.04 mmol), tributyl (vinyl) stannane (17 mg, 0.052 mmol), Pd(PPh$_3$)$_4$ (5 mg, 0.004 mmol), K2CO3 (14 mg, 0.052 mmol), and 1.5 mL DMF. The mixture was stirred at 120° C. for 2 h. After washing with NaHCO$_3$, brine, the combined organic layer was dried over anhy. Na$_2$SO$_4$ and concentrated in vacuo. Prep-TLC purification (20% EtOAc/petroleum ether) afforded 10 mg of title compound. $^1$H NMR (CHLOROFORM-d) δ 8.72 (s, 1H), 8.56 (s, 1H), 8.00 (s, 1H), 6.90 (dd, J=17.3, 10.8 Hz, 1H), 6.47 (dd, J=17.6, 1.0 Hz, 1H), 5.70 (dd, J=10.8, 1.0 Hz, 1H), 4.65 (d, J=13.1 Hz, 1H), 4.52 (d, J=12.8 Hz, 1H), 3.99-4.29 (m, 1H), 3.52-3.91 (m, 1H), 3.32 (br. s., 1H), 3.16 (br. s., 1H), 2.22-2.35 (m, 1H), 1.23-1.38 (m, 5H), 0.97-1.14 (m, 4H), 0.81 (dd, J=7.8, 2.3 Hz, 2H), 0.65 (br. s., 1H), 0.48-0.55 (m, 1H), 0.45 (dt, J=9.6, 4.6 Hz, 1H).

LC-MS: m/z 441.2 (M+H)$^+$ (R)-2-cyclopropyl-6-(3-cyclopropyl-4-(3-methoxypropanoyl)piperazin-1-yl)-2'-vinyl-3,4'-bipyridine-5-carbonitrile (Compound 530; General Procedure 5, Step W)

1H NMR (CHLOROFORM-d) δ 8.61 (d, J=5.0 Hz, 1H), 7.55-7.68 (m, 1H), 7.36 (s, 1H), 7.21 (dd, J=5.0, 1.5 Hz, 1H), 6.84 (dd, J=17.6, 10.8 Hz, 1H), 6.17-6.35 (m, 1H), 5.53 (dd, J=10.8, 0.8 Hz, 1H), 4.53 (d, J=12.5 Hz, 1H), 4.32-4.47 (m, 1H), 4.01-4.16 (m, 0.5H), 3.86 (d, J=12.5 Hz, 0.5H), 3.70 (t, J=5.5 Hz, 3H), 3.35 (s, 3H), 3.18 (d, J=11.3 Hz, 2H), 2.94-3.14 (m, 1H), 2.56-2.73 (m, 2H), 1.90-2.10 (m, 1H), 1.22-1.34 (m, 1H), 1.14-1.32 (m, 2H), 0.83-1.06 (m, 2H), 0.58 (br. s., 1H), 0.52 (br. s., 1H), 0.28-0.48 (m, 2H). LC-MS: m/z 458.2 (M+H)$^+$ (R)-6-(4-acetyl-3-cyclopropylpiperazin-1-yl)-2-cyclopropyl-2'-vinyl-3,4'-bipyridine-5-carbonitrile (Compound 562; General Procedure 5, Step W)

1H NMR (CHLOROFORM-d) δ 8.66 (d, J=4.5 Hz, 1H), 7.65 (s, 1H), 7.39 (s, 1H), 7.24 (d, J=4.0 Hz, 1H), 6.88 (dd, J=17.3, 10.8 Hz, 1H), 6.28 (d, J=17.3 Hz, 1H), 5.57 (d, J=10.8 Hz, 1H), 4.65 (br. s., 0.5H), 4.55 (d, J=12.5 Hz, 1H), 4.43 (d, J=12.0 Hz, 1H), 4.08 (br. s., 0.5H), 3.77 (br. s., 1H), 3.21 (br. s., 2H), 3.11 (br. s., 1H), 2.17 (br. s., 2H), 2.11 (br. s., 1H), 2.03 (br. s., 1H), 1.28 (d, J=12.0 Hz, 2H), 1.24-1.50 (br. s., 3H), 0.60 (br. s., 2H), 0.45 (br. s., 2H). LC-MS: m/z 414.3 (M+H)$^+$ (R)-2-cyclopropyl-6-(3-cyclopropyl-4-(3-hydroxy-3-methylbutanoyl)piperazin-1-yl)-2'-vinyl-3,4'-bipyridine-5-carbonitrile (Compound 561; General Procedure 5, Step W)

1H NMR (CHLOROFORM-d) δ 8.66 (d, J=5.0 Hz, 1H), 7.66 (s, 1H), 7.39 (s, 1H), 7.24 (d, J=4.0 Hz, 1H), 6.88 (dd, J=17.6, 10.8 Hz, 1H), 6.28 (d, J=17.6 Hz, 1H), 5.57 (d, J=10.8 Hz, 1H), 5.16 (br. s., 1H), 4.56 (d, J=13.1 Hz, 1H), 4.43 (d, J=12.5 Hz, 1H), 4.14 (d, J=8.8 Hz, 0.5H), 3.65-3.78 (m, 1H), 3.17-3.91 (m, 1.5H), 3.04-3.14 (m, 1H), 2.43-2.57 (m, 2H), 2.02-2.07 (m, 1H), 1.33 (s, 6H), 1.25-1.30 (m, 2H), 1.21 (br. s., 2H), 1.02 (dd, J=7.5, 3.3 Hz, 2H), 0.65 (d, J=6.5 Hz, 1H), 0.42-0.53 (m, 2H). LC-MS: m/z 472.3 (M+H)$^+$

(R)-2-cyclopropyl-6-(4-(2-ethoxyacetyl)-3-methyl-piperazin-1-yl)-2'-vinyl-3,4'-bipyridine-5-carbonitrile (Compound 573; General Procedure 5, Step W)

1H NMR (CHLOROFORM-d) δ 8.65 (d, J=5.0 Hz, 1H), 7.64 (s, 1H), 7.36-7.41 (m, 1H), 7.23 (dd, J=5.0, 1.8 Hz, 1H), 6.88 (dd, J=17.6, 10.8 Hz, 1H), 6.21-6.35 (m, 1H), 5.57 (dd, J=10.9, 0.9 Hz, 1H), 4.84 (br. s., 0.5H), 4.35 (br. s., 2H), 4.27 (br. s., 1H), 4.20 (br. s., 2H), 3.89 (br. s., 0.5H), 3.53-3.65 (m, 2.5H), 3.24-3.35 (m, 1H), 3.17 (br. s., 1.5H), 1.98-2.08 (m, 1H), 1.29-1.41 (m, 3H), 1.23-1.28 (m, 3H), 1.15-1.23 (m, 2H), 0.95-1.07 (m, 2H). LC-MS: m/z 432.2 (M+H)$^+$

(R)-2-cyclopropyl-6-(3-cyclopropyl-4-(2-methoxyacetyl)piperazin-1-yl)-2'-vinyl-3,4'-bipyridine-5-carbonitrile (Compound 590; General Procedure 5, Step W)

1H NMR (CHLOROFORM-d) δ 8.63 (d, J=5.0 Hz, 1H), 7.53-7.75 (m, 2H), 7.37 (s, 1H), 7.22 (dd, J=4.8, 1.5 Hz, 1H), 6.86 (dd, J=17.6, 10.8 Hz, 1H), 6.19-6.37 (m, 1H), 5.54 (d, J=11.5 Hz, 1H), 4.55 (d, J=13.1 Hz, 1H), 4.42 (d, J=12.8 Hz, 1H), 4.11-4.17 (m, 2H), 3.44 (s, 4H), 3.19-3.25 (m, 1H), 3.04-3.11 (m, 1H), 2.80 (s, 1H), 1.89-2.07 (m, 2H), 1.17-1.27 (m, 4H), 0.95-1.02 (m, 2H), 0.41-0.54 (m, 3H). LC-MS: m/z 444.2 (M+H)$^+$

2-cyclopropyl-6-(4-(3-hydroxypropanoyl)-3-methyl-piperazin-1-yl)-2'-vinyl-3,4'-bipyridine-5-carbonitrile (Compound 572; General Procedure 5, Step W)

1H NMR (CHLOROFORM-d) δ 8.66 (d, J=5.0 Hz, 1H), 7.61-7.69 (m, 1H), 7.36-7.44 (m, 1H), 7.24 (dd, J=5.0, 1.8 Hz, 1H), 6.89 (dd, J=17.3, 10.8 Hz, 1H), 6.29 (dd, J=17.6, 1.0 Hz, 1H), 5.58 (dd, J=10.8, 0.8 Hz, 1H), 4.90 (br. s., 0.5H), 4.54 (d, J=13.3 Hz, 0.5H), 4.26-4.40 (m, 2H), 4.12-4.23 (m, 1H), 3.93 (br. s., 2H), 3.74 (d, J=13.1 Hz, 1H), 3.29-3.34 (m, 1H), 3.06-3.18 (m, 1H), 2.50-2.63 (m, 1H), 2.17-2.25 (m, 1H), 2.02-2.07 (m, 1H), 1.41 (d, J=6.8 Hz, 1H), 1.29-1.33 (m, 2H), 1.28 (d, J=2.8 Hz, 1H), 1.19-1.22 (m, 1.5H), 1.02 (dd, J=7.9, 3.1 Hz, 1.5H). LC-MS: m/z 418.2 (M+H)$^+$

(R)-2-cyclopropyl-6-(3-cyclopropyl-4-(furan-3-carbonyl)piperazin-1-yl)-2'-vinyl-3,4'-bipyridine-5-carbonitrile (Compound 546; General Procedure 5, Step W)

1H NMR (CHLOROFORM-d) δ 8.66 (d, J=4.5 Hz, 1H), 7.73 (s, 1H), 7.65 (s, 1H), 7.46 (s, 1H), 7.36-7.44 (m, 1H), 7.25 (d, J=4.3 Hz, 1H), 6.88 (dd, J=17.4, 10.9 Hz, 1H), 6.56 (s, 1H), 6.26 (d, J=17.6 Hz, 1H), 5.56 (d, J=10.8 Hz, 1H), 4.60 (d, J=13.1 Hz, 1H), 4.44 (d, J=12.8 Hz, 1H), 4.27 (br. s., 1H), 3.93 (br. s., 1H), 3.66 (br. s., 1H), 3.19-3.38 (m, 1H), 3.09 (t, J=11.3 Hz, 1H), 2.03 (dd, J=7.4, 3.1 Hz, 1H), 1.35-1.50 (m, 1H), 1.13-1.35 (m, 2H), 0.90-1.08 (m, 2H), 0.59-0.76 (m, 1H), 0.52 (t, J=8.0 Hz, 1H), 0.42 (br. s., 2H). LC-MS: m/z 466.2 (M+H)$^+$

2-cyclopropyl-6-((R)-3-cyclopropyl-4-((S)-3-hydroxybutanoyl)piperazin-1-yl)-2'-vinyl-3,4'-bipyridine-5-carbonitrile (Compound 595; General Procedure 5, Step W)

1H NMR (CHLOROFORM-d) δ 8.65 (d, J=4.8 Hz, 1H), 7.65 (s, 1H), 7.39 (s, 1H), 7.24 (d, J=4.3 Hz, 1H), 6.88 (dd, J=17.4, 10.9 Hz, 1H), 6.28 (d, J=17.3 Hz, 1H), 5.57 (d, J=10.8 Hz, 1H), 4.49-4.79 (m, 2H), 4.43 (d, J=12.5 Hz, 1H), 4.17-4.33 (m, 2H), 3.96-4.17 (m, 1H), 3.79 (br. s., 1H), 3.71 (d, J=11.8 Hz, 1H), 3.02-3.31 (m, 2H), 2.53 (d, J=9.8 Hz, 1H), 2.48 (m, 1H), 2.04 (m, 1H), 1.32 (br. s., 3H), 0.82-1.12 (m, 3H), 0.72 (br. s., 1H), 0.63 (br. s., 1H), 0.55 (br. s., 1H), 0.22-0.51 (m, 2H). LC-MS: m/z 458.2 (M+H)$^+$

(R)-2-cyclopropyl-6-(3-isopropyl-4-(3-methoxypropanoyl)piperazin-1-yl)-2'-vinyl-3,4'-bipyridine-5-carbonitrile (Compound 631; General Procedure 5, Step W)

1H NMR (CHLOROFORM-d) δ $^1$H NMR (CHLOROFORM-d) v 8.61 (d, J=5.0 Hz, 1H), 7.60 (d, J=2.5 Hz, 1H), 7.20 (dd, J=5.0, 1.5 Hz, 1H), 6.84 (dd, J=17.3, 10.8 Hz, 1H), 6.25 (d, J=17.6 Hz, 1H), 5.52 (d, J=11.0 Hz, 1H), 4.50-4.79 (m, 2H), 4.28-4.50 (m, 2H), 3.85 (d, J=13.6 Hz, 1H), 3.63-3.79 (m, 2H), 3.57 (d, J=10.0 Hz, 1H), 3.30-3.49 (m, 3H), 2.99-3.27 (m, 2H), 2.83-2.98 (m, 1H), 2.49-2.79 (m, 1H), 2.17 (dt, J=10.5, 6.7 Hz, 1H), 1.08-1.30 (m, 3H), 0.78-1.08 (m, 7H). LC-MS: m/z 460.1 (M+H)$^+$

(R)-2-cyclopropyl-6-(4-(2-hydroxyacetyl)-3-methyl-piperazin-1-yl)-2'-vinyl-3,4'-bipyridine-5-carbonitrile (Compound 632; General Procedure 5, Step W)

1H NMR (CHLOROFORM-d) δ 8.64 (d, J=5.0 Hz, 1H), 7.64 (s, 1H), 7.31-7.50 (m, 1H), 7.23 (dd, J=5.1, 1.6 Hz, 1H), 6.87 (dd, J=17.4, 10.9 Hz, 1H), 6.27 (dd, J=17.4, 0.9 Hz, 1H), 5.42-5.72 (m, 1H), 4.84 (br. s., 1H), 4.20-4.40 (m, 3H), 4.00-4.20 (m, 1H), 3.36-3.65 (m, 2H), 3.20-3.36 (m, 2H), 2.97-3.20 (m, 1H), 2.70-2.96 (m, 4H), 1.86-2.06 (m, 1H), 1.40 (d, J=6.3 Hz, 1H), 1.09-1.36 (m, 4H), 0.79-1.09 (m, 2H). LC-MS: m/z 404.0 (M+H)$^+$

2-cyclopropyl-6-((R)-3-cyclopropyl-4-((R)-3-hydroxybutanoyl)piperazin-1-yl)-2'-vinyl-3,4'-bipyridine-5-carbonitrile (Compound 585; General Procedure 5, Step W)

1H NMR (CHLOROFORM-d) δ 8.65 (d, J=4.8 Hz, 1H), 7.65 (s, 1H), 7.39 (s, 1H), 7.24 (d, J=4.3 Hz, 1H), 6.88 (dd, J=17.4, 10.9 Hz, 1H), 6.28 (d, J=17.3 Hz, 1H), 5.57 (d, J=10.8 Hz, 1H), 4.49-4.79 (m, 2H), 4.43 (d, J=12.5 Hz, 1H), 4.17-4.33 (m, 2H), 3.96-4.17 (m, 1H), 3.79 (br. s., 1H), 3.71 (d, J=11.8 Hz, 1H), 3.02-3.31 (m, 2H), 2.53 (d, J=9.8 Hz, 1H), 2.48 (m, 1H), 2.04 (m, 1H), 1.32 (br. s., 3H), 0.82-1.12 (m, 3H), 0.72 (br. s., 1H), 0.63 (br. s., 1H), 0.55 (br. s., 1H), 0.22-0.51 (m, 2H). LC-MS: m/z 458.2 (M+H)$^+$

(R)-6-cyclopropyl-2-(3-cyclopropyl-4-(3,3,3-trifluoropropanoyl)piperazin-1-yl)-5-(1H-pyrrolo[2,3-b]pyridin-5-yl)nicotinonitrile (Compound 539; General Procedure 2, Step M)

$^1$H NMR (CHLOROFORM-d) δ 10.76 (br. s., 1H), 8.37 (br. s., 1H), 8.00 (s, 1H), 7.65-7.77 (m, 1H), 7.48 (d, J=3.3 Hz, 1H), 6.59 (d, J=3.3 Hz, 1H), 4.71 (br. s., 0.5H), 4.52 (d, J=13.1 Hz, 1H), 4.41 (d, J=12.5 Hz, 1H), 4.14 (d, J=7.3 Hz, 0.5H), 3.66-3.95 (m, 1.5H), 3.15-3.44 (m, 4.5H), 2.40 (br. s., 1H), 2.05-2.15 (m, 1H), 1.39-1.48 (m, 1H), 1.17-1.25 (m, 2H), 0.94-1.04 (m, 2H), 0.44-0.81 (m, 4H). LC-MS: m/z 495.3 (M+H)$^+$

6-cyclopropyl-2-((R)-3-cyclopropyl-4-((1S,2S)-2-ethoxycyclopropanecarbonyl)piperazin-1-yl)-5-(4-fluorophenyl)nicotinonitrile (Compound 548; General Procedure 3, Step R and S)

¹H NMR (CHLOROFORM-d) δ 7.58-7.63 (m, 1H), 7.33-7.43 (m, 2H), 7.09-7.21 (m, 2H), 4.39-4.50 (m, 2.5H), 4.05-4.13 (m, 1H), 3.82 (br. s., 0.5H), 3.50-3.72 (m, 4H), 2.97-3.29 (m, 3H), 1.99-2.06 (m, 1H), 1.84-1.96 (m, 1H), 1.14-1.27 (m, 7H), 0.93-1.00 (m, 2H), 0.38-0.72 (m, 4H). LC-MS: m/z 475.3 (M+H)⁺

(R)-5-(2-chloroquinolin-5-yl)-2-(4-(cyclopropanecarbonyl)-3-cyclopropylpiperazin-1-yl)-6-cyclopropylnicotinonitrile (Compound 549)

1H NMR (400 MHz, CHLOROFORM-d) δ 8.09 (d, J=8.5 Hz, 1H), 7.91 (dd, J=11.4, 8.9 Hz, 1H), 7.82 (t, J=7.9 Hz, 1H), 7.64 (s, 1H), 7.46-7.57 (m, 1H), 7.39 (d, J=8.8 Hz, 1H), 4.78 (dq, J=13.5, 6.8 Hz, 0.5H), 4.57 (d, J=11.8 Hz, 1.5H), 4.45 (d, J=11.0 Hz, 1H), 3.92-4.07 (m, 0.5H), 3.57-3.76 (m, 0.5H), 3.40 (q, J=7.0 Hz, 1H), 3.18-3.35 (m, 2H), 1.65-1.82 (m, 1H), 1.20-1.31 (m, 4H), 1.07-1.20 (m, 2H), 0.64-0.91 (m, 4H), 0.38-0.60 (m, 4H). LC-MS: m/z 498.2 (M+H)⁺

(R)-2-(4-(cyclopropanecarbonyl)-3-methylpiperazin-1-yl)-6-cyclopropyl-5-(4-fluorophenyl)nicotinonitrile (Compound 550)

1H NMR (CHLOROFORM-d) δ 7.60 (s, 1H), 7.33-7.43 (m, 2H), 7.09-7.20 (m, 2H), 4.55 (br. s., 1H), 4.47 (br. s., 1H), 4.25 (d, J=13.1 Hz, 3H), 3.40 (br. s., 1H), 3.31 (br. s., 1H), 3.15 (br. s., 1H), 1.95-2.10 (m, 1H), 1.77 (br. s., 2H), 1.64 (br. s., 2H), 1.39-1.53 (m, 2H), 1.34 (br. s., 2H), 0.90-1.12 (m, 5H), 0.69-0.90 (m, 2H).
LC-MS: m/z 405.2 (M+H)⁺

6-cyclopropyl-2-((R)-3-cyclopropyl-4-((1R,2S)-2-ethoxycyclopropanecarbonyl)piperazin-1-yl)-5-(4-fluorophenyl)nicotinonitrile (Compound 564)

¹H NMR (CHLOROFORM-d) δ 7.60 (s, 1H), 7.33-7.41 (m, 2H), 7.15 (t, J=8.7 Hz, 2H), 4.69-4.72 (m, 0.5H), 4.31-4.58 (m, 2H), 4.20 (d, J=13.8 Hz, 2H), 3.16-3.82 (m, 7.5H), 1.98-2.09 (m, 1H), 1.77-1.90 (m, 1H), 1.08-1.32 (m, 7H), 0.86-1.08 (m, 2H), 0.31-0.62 (m, 4H). LC-MS: m/z 475.3 (M+H)⁺

(R)-2-(4-(cyclopropanecarbonyl)-3-methylpiperazin-1-yl)-6-cyclopropyl-5-(isoquinolin-5-yl)nicotinonitrile (Compound 556; General Procedure 2, Step M)

¹H NMR (CHLOROFORM-d) δ 9.36 (br. s., 1H), 8.52 (br. s., 1H), 8.07 (d, J=8.0 Hz, 1H), 7.70-7.75 (m, 1H), 7.65-7.69 (m, 1H), 7.63 (s, 1H), 7.47 (t, J=5.6 Hz, 1H), 4.89-5.55 (m, 3H), 4.15-4.58 (m, 4H), 1.56-1.68 (m, 1H), 1.42-1.56 (m, 1H), 1.12-1.21 (m, 2H), 0.97-1.09 (m, 4H), 0.75-0.96 (m, 6H). LC-MS: m/z 438.3 (M+H)⁺

(R)-5-(1-acryloyl-1,2,5,6-tetrahydropyridin-3-yl)-2-(4-(cyclopropanecarbonyl)-3-methylpiperazin-1-yl)-6-cyclopropylnicotinonitrile (Compound 575; General Procedure 1, Step I)

1H NMR (CHLOROFORM-d) δ 7.49 (s, 1H), 6.47-6.77 (m, 1H), 6.22-6.44 (m, 1H), 5.88 (br. s., 1H), 5.76 (d, J=10.0 Hz, 1H), 3.01-4.86 (m, 11H), 2.40 (br. s., 2H), 1.95-2.16 (m, 1H), 1.76 (br. s., 1H), 1.29-1.38 (m, 3H), 1.08-1.19 (m, 2H), 0.92-1.08 (m, 4H), 0.71-0.86 (m, 2H). LC-MS: m/z 448.0 (M+H)⁺

5-(1-acryloylpiperidin-3-yl)-2-((R)-4-(cyclopropanecarbonyl)-3-methylpiperazin-1-yl)-6-cyclopropylnicotinonitrile (Compound 576; General Procedure 1, Step I)

1H NMR (CHLOROFORM-d) δ 7.51-7.57 (m, 1H), 6.53-6.73 (m, 1H), 6.25-6.41 (m, 1H), 5.65-5.80 (m, 1H), 4.02-5.02 (m, 6H), 2.94-4.00 (m, 5H), 2.37-2.49 (m, 1H), 2.28-2.37 (m, 1H), 1.92-2.13 (m, 1H), 1.57-1.80 (m, 6H), 0.96-1.22 (m, 6H), 0.69-0.88 (m, 2H). LC-MS: m/z 448.2 (M+H)⁺

(R)-6-(4-(cyclopropanecarbonyl)-3-methylpiperazin-1-yl)-2-cyclopropyl-3,3'-bipyridine-5,6'-dicarbonitrile (Compound 583; General Procedure 1, Step H)

¹H NMR (CHLOROFORM-d) δ 8.80 (d, J=1.8 Hz, 1H), 7.91 (dd, J=8.0, 2.3 Hz, 1H), 7.81 (d, J=8.0 Hz, 1H), 7.62 (s, 1H), 4.09-4.85 (m, 4H), 3.22-3.64 (m, 3H), 1.82-1.93 (m, 1H), 1.75 (br. s., 1H), 1.19-1.27 (m, 2H), 0.96-1.12 (m, 4H), 0.73-0.92 (m, 2H). LC-MS: m/z 413.2 (M+H)⁺

(R)-2-cyclopropyl-6-(4-(3-methoxypropanoyl)-3-methylpiperazin-1-yl)-3,3'-bipyridine-5,6'-dicarbonitrile (Compound 584; General Procedure 1, Step I)

¹H NMR (CHLOROFORM-d) □ 8.79 (d, J=1.5 Hz, 1H), 7.90 (dd, J=8.0, 2.3 Hz, 1H), 7.81 (d, J=8.0 Hz, 1H), 7.62 (s, 1H), 4.89 (br. s., 0.5H), 4.52 (d, J=9.8 Hz, 0.5H), 4.19-4.44 (m, 2.5H), 3.65-3.78 (m, 2.5H), 3.54 (t, J=11.0 Hz, 0.5H), 3.28-3.43 (m, 4H), 3.03-3.27 (m, 1.5H), 2.50-2.80 (m, 2H), 1.82-1.92 (m, 1H), 1.36 (d, J=6.5 Hz, 1.5H), 1.23-1.28 (m, 1.5H), 1.17-1.23 (m, 2H), 0.94-1.06 (m, 2H); LC-MS: m/z 431.2 (M+H)

(R)-6-(4-(cyclopropanecarbonyl)-3-methylpiperazin-1-yl)-2-cyclopropyl-2'-ethynyl-3,4'-bipyridine-5-carbonitrile (Compound 593; General Procedure 1, Step H)

1H NMR (CHLOROFORM-d) δ 8.67 (d, J=5.3 Hz, 1H), 7.62 (s, 1H), 7.46-7.59 (m, 1H), 7.35 (dd, J=5.1, 1.6 Hz, 1H), 4.15-4.90 (m, 4H), 3.13-3.75 (m, 4H), 1.94-2.04 (m, 1H), 1.76 (br. s., 1H), 1.28-1.39 (m, 3H), 1.21 (dt, J=7.0, 3.5 Hz, 2H), 0.95-1.09 (m, 4H), 0.76-0.88 (m, 2H). LC-MS: m/z 413.9 (M+H)⁺

(R)-2-(4-(cyclopropanecarbonyl)-3-methylpiperazin-1-yl)-6-cyclopropyl-5-(1-propioloyl-1,2,5,6-tetrahydropyridin-3-yl)nicotinonitrile (Compound 594; General Procedure 1, Step H)

1H NMR (CHLOROFORM-d) δ 7.48 (d, J=5.5 Hz, 1H), 5.90 (d, J=11.3 Hz, 1H), 4.01-4.85 (m, 7), 3.96 (t, J=5.9 Hz, 1H), 3.82 (t, J=5.9 Hz, 1H), 3.03-3.80 (m, 4H), 2.82 (s, 1H), 2.44 (d, J=3.5 Hz, 1H), 2.38 (d, J=3.5 Hz, 1H), 2.06-2.12 (m, 1H), 1.31-1.37 (m, 3H), 0.97-1.17 (m, 6H), 0.81 (d, J=7.8 Hz, 2H). LC-MS: m/z 444.1 (M+H)⁺

(R)-6-(4-(cyclopropanecarbonyl)-3-cyclopropylpiperazin-1-yl)-2-cyclopropyl-3'-fluoro-2'-vinyl-3,4'-bipyridine-5-carbonitrile (Compound 520; General Procedure 1, Step I)

¹H NMR (CHLOROFORM-d) δ 8.46 (d, J=4.8 Hz, 1H), 7.64 (s, 1H), 7.19 (t, J=5.1 Hz, 1H), 7.08 (ddd, J=17.4, 11.0, 1.3 Hz, 1H), 6.51 (dd, J=17.3, 1.8 Hz, 1H), 5.66 (dd, J=10.9, 1.6 Hz, 1H), 4.59 (d, J=12.8 Hz, 1H), 4.47 (d, J=12.5 Hz, 1H), 4.22 (br. s., 0.5H), 4.05 (br. s., 0.5H), 3.76 (dt, J=8.2, 4.0 Hz, 1H), 3.47-3.70 (m, 1H), 3.29 (br. s., 1H), 3.14 (br. s., 1H), 1.77-1.85 (m, 1H), 1.57-1.70 (m, 1H), 1.32-1.41 (m, 1H), 1.14-1.24 (m, 2H), 0.88-1.11 (m, 4H), 0.73-0.86 (m, 2H), 0.59-0.73 (m, 1H), 0.36-0.59 (m, 3H). LC-MS: m/z 458.5 (M+H)⁺

6-cyclopropyl-2-((R)-3-cyclopropyl-4 ((1S,2S)-2-ethoxycyclopropanecarbonyl)piperazin-1-yl)-5-(isoquinolin-5-yl)nicotinonitrile (Compound 514; General Procedure 2, Step M)

¹H NMR (CHLOROFORM-d) δ 9.35 (s, 1H), 8.54 (dd, J=5.9, 1.9 Hz, 1H), 8.07 (d, J=8.0 Hz, 1H), 7.69-7.75 (m, 1H), 7.64-7.68 (m, 2H), 7.44 (dd, J=12.5, 6.0 Hz, 1H), 4.46-4.59 (m, 2.5H), 4.08-4.18 (m, 1H), 3.86 (br. s., 0.5H), 3.53-3.74 (m, 3H), 3.21-3.32 (m, 2H), 1.87-2.06 (m, 2H), 1.49-1.58 (m, 1H), 1.33 (d, J=5.8 Hz, 1H), 1.14-1.28 (m, 7H), 0.81-0.90 (m, 2H), 0.65 (br. s., 1H), 0.36-0.59 (m, 3H). LC-MS: m/z 508.2 (M+H)⁺

(R)-6-(4-(cyclopropanecarbonyl)-3-methylpiperazin-1-yl)-2-cyclopropyl-3,4'-bipyridine-2',5-dicarbonitrile (Compound 522; General Procedure 1, Step H)

¹H NMR (CHLOROFORM-d) δ 8.81 (d, J=5.0 Hz, 1H), 7.80 (s, 1H), 7.63 (s, 1H), 7.59 (dd, J=5.1, 1.6 Hz, 1H), 4.86 (br. s., 1H), 4.48 (br. s., 1H), 4.35 (d, J=13.6 Hz, 2H), 3.63 (br. s., 0.5H), 3.53 (br. s., 1H), 3.25 (br. s., 1.5H), 1.85-1.99 (m, 1H), 1.76 (br. s., 1H), 1.60 (br. s., 3H), 1.17-1.34 (m, 4H), 1.07 (dd, J=7.8, 3.0 Hz, 4H). LC-MS: m/z 413.5 (M+H)⁺

(R)-6-(4-(cyclopropanecarbonyl)-3-cyclopropylpiperazin-1-yl)-2-cyclopropyl-2'-methyl-3,4'-bipyridine-5-carbonitrile (Compound 523; General Procedure 1, Step H)

¹H NMR (CHLOROFORM-d) □□8.56 (d, J=5.0 Hz, 1H), 7.62 (s, 1H), 7.21 (s, 1H), 7.17 (d, J=5.3 Hz, 1H), 4.56 (d, J=12.5 Hz, 1H), 4.44 (d, J=12.3 Hz, 1H), 4.04 (br. s., 1H), 3.75 (br. s., 1.5H), 3.28 (br. s., 1.5H), 3.12 (br. s., 1H), 2.58-2.68 (m, 3H), 1.97-2.07 (m, 1H), 1.72 (br. s., 1H), 1.37 (br. s., 1H), 1.14-1.23 (m, 2H), 0.93-1.10 (m, 4H), 0.74-0.85 (m, 2H), 0.65 (br. s., 1H), 0.36-0.58 (m, 3H). LC-MS: m/z 428.5 (M+H)⁺

(R)-2-cyclopropyl-6-(3-cyclopropyl-4-(3,3,3-trifluoropropanoyl)piperazin-1-yl)-[3,3'-bipyridine]-5,5'-dicarbonitrile (Compound 525; General Procedure 2, Step M)

¹H NMR (CHLOROFORM-d) δ8.90 (d, 2H), 8.04 (s, 1H), 7.64 (s, 1H), 4.63 (d, J=13.1 Hz, 1H), 4.51 (d, J=12.3 Hz, 1H), 4.13 (br. s., 1H), 3.78 (br. s., 1H), 3.51 (s, 1H), 3.33 (d, J=9.0 Hz, 2H), 3.24 (d, J=12.5 Hz, 1H), 3.15 (d, J=12.3 Hz, 1H), 2.03 (dt, J=15.3, 7.4 Hz, 1H), 1.01-1.12 (m, 3H), 0.82-0.95 (m, 4H), 0.66 (br. s., 1H), 0.45-0.53 (m, 1H) LC-MS: m/z 481.4 (M+H)⁺

Compound 540 (General Procedure 2, Step M)

(R)-5'-cyano-2'-cyclopropyl-6'-(3-cyclopropyl-4-(3,3,3-trifluoropropanoyl)piperazin-1-yl)-[3,3'-bipyridine]-5-carboxamide ¹H NMR (METHANOL-d) δ9.05 (br. s., 1H), 8.81 (br. s., 1H), 8.26 (t, J=2.1 Hz, 1H), 7.60-7.77 (m, 1H), 6.81 (br. s., 1H), 6.25 (br. s., 1H), 4.57 (d, J=13.1 Hz, 1H), 4.46 (d, J=12.3 Hz, 1H), 4.01-4.25 (m, 1H), 3.65-3.88 (m, 2H), 3.12-3.38 (m, 4H), 2.03-2.24 (m, 1H), 1.86-1.96 (m, 1H), 1.15-1.28 (m, 4H), 0.97-1.06 (m, 2H), 0.28-0.58 (m, 4H) LC-MS: m/z 499.5 (M+H)⁺

Compound 554 (General Procedure, Step I)

(R)-6-(4-(cyclopropanecarbonyl)-3-cyclopropylpiperazin-1-yl)-2-cyclopropyl-5'-(1H-tetrazol-5-yl)-[3,3'-bipyridine]-5-carbonitrile ¹H NMR (CHLOROFORM-d) δ9.47 (br. s., 1H), 8.86 (s, 1H), 8.62 (s, 1H), 7.73 (s, 1H), 4.59-4.47 (m., 7H), 1.19-1.30 (m, 1H), 1.14-1.05 (m, 3H), 0.84-0.98 (m, 10H), 0.42-0.57 (m, 4H) LC-MS: m/z 482.5 (M+H)⁺

Compound 601 (General Procedure, Step I)

(R)-6-cyclopropyl-5-(5-fluoro-4-vinylpyrimidin-2-yl)-2-(4-(3-methoxypropanoyl)-3-methylpiperazin-1-yl)nicotinonitrile ¹H NMR (CHLOROFORM-d) δ8.62 (d, J=1.8 Hz, 1H), 8.35-8.44 (m, 1H), 7.03 (dd, J=17.3, 10.8 Hz, 1H), 6.70-6.82 (m, 1H), 5.81-5.92 (m, 1H), 4.90 (br. s., 0.5H), 4.52 (m, 3.5H), 4.28-4.47 (m, 3H), 3.68-3.86 (m, 3H), 3.54 (br. s., 1H), 3.01-3.21 (m, 3H), 2.63-2.79 (m, 1H), 2.51-2.63 (m, 1H), 1.23-1.26 (m, 4H), 1.18-1.23 (m, 2H), 1.04 (m, 2H) LC-MS: m/z 451.5 (M+H)⁺

Compound 538 (General Procedure 1, Step I)

(R)-5-(2-aminoquinazolin-5-yl)-2-(4-(cyclopropanecarbonyl)-3-cyclopropylpiperazin-1-yl)-6-cyclopropylnicotinonitrile ¹H NMR (CHLOROFORM-d) δ 8.82 (d, J=9.5 Hz, 1H), 7.70-7.84 (m, 1H), 7.55-7.70 (m, 2H), 7.11-7.23 (m, 1H), 5.52 (br. s., 2H), 4.39-4.67 (m, 2.5H), 4.16-4.32 (m, 1H), 3.60-3.85 (m, 1H), 3.10-3.41 (m, 2.5H), 1.73 (s, 1H), 1.53-1.65 (m, 1H), 1.27-1.33 (m, 1H), 1.18-1.24 (m, 1H), 1.11-1.18 (m, 1H), 0.98-1.10 (m, 2H), 0.79-0.90 (m, 4H), 0.61-0.74 (m, 1H), 0.40-0.61 (m, 3H)
LC-MS: m/z 480.2 (M+H)⁺

Compound 567 (General Procedure 1, Step H)

(R)-6-(4-(cyclopropanecarbonyl)-3-cyclopropylpiperazin-1-yl)-2-cyclopropyl-6'-(trifluoromethyl)-[3,3'-bipyridine]-5-carbonitrile ¹H NMR (CHLOROFORM-d) δ 8.83 (d, J=1.8 Hz, 1H), 7.94 (dd, J=8.0, 2.0 Hz, 1H), 7.77-7.87 (m, 1H), 7.65 (s, 1H), 4.40-4.72 (m, 2.5H), 3.97-4.20 (m, 1H), 3.51-3.78 (m, 1H), 3.08-3.62 (m, 2.5H), 1.86-1.98 (m, 1H), 1.72 (s, 1H), 1.34-1.45 (m, 1H), 1.20-1.28 (m, 2H), 0.97-1.10 (m, 4H), 0.76-0.87 (m, 2H), 0.40-0.67 (m, 3H)

LC-MS: m/z 482.2 (M+H)$^+$

Compound 586 (General Procedure 1, Step H)

(R)-2',6'-dichloro-2-cyclopropyl-6-(4-(3-methoxypropanoyl)-3-methylpiperazin-1-yl)-[3,4'-bipyridine]-5-carbonitrile $^1$H NMR (CHLOROFORM-d) δ 7.61 (s, 1H), 7.34 (s, 2H), 4.91 (s, 0.5H), 4.50-4.56 (m, 0.5H), 4.22-4.50 (m, 2.5H), 3.68-3.89 (m, 2.5H), 3.49-3.62 (m, 0.5H), 3.28-3.43 (m, 4H), 3.06-3.27 (m, 1.5H), 2.64-2.83 (m, 1H), 2.55-2.64 (m, 1H), 1.92-2.01 (m, 1H), 1.37 (d, J=6.5 Hz, 2H), 1.21-1.31 (m, 3H), 1.01-1.12 (m, 2H) LC-MS: m/z 474.1 (M+H)$^+$ Compound 622

(R)-2-cyclopropyl-2'-methoxy-6-(4-(3-methoxypropanoyl)-3-methylpiperazin-1-yl)-6'-vinyl-[3,4'-bipyridine]-5-carbonitrile The mixture of (R)-2'-chloro-2-cyclopropyl-6'-methoxy-6-(4-(3-methoxypropanoyl)-3-methylpiperazin-1-yl)-[3,4'-bipyridine]-5-carbonitrile (40 mg, 0.085 mmol), Potassium vinyltrifluoroborate (18 mg, 0.128 mmol), Pd(dppf)Cl$_2$ (4 mg, 0.0043 mmol), CsF (39 mg, 0.255 mmol) in dioxane/H$_2$O was stirred at 100° C. for 16 hours, the mixture was partitioned between EtOAc and water, the organic was washed with water, brine and concentrated to give the crude which was purified by column to give 15 mg of the product.

$^1$H NMR (CHLOROFORM-d) □□7.60 (s, 1H), 6.86 (d, J=1.0 Hz, 1H), 6.75 (dd, J=17.1, 10.5 Hz, 1H), 6.66 (d, J=1.0 Hz, 1H), 6.36 (dd, J=17.2, 1.6 Hz, 1H), 5.49 (dd, J=10.5, 1.8 Hz, 1H), 4.90 (s, 0.5H), 4.53 (d, J=13.3 Hz, 0.5H), 4.22-4.38 (m, 2.5H), 4.02 (s, 3H), 3.78-3.84 (m, 0.5H), 3.75 (t, J=6.1 Hz, 2H), 3.51-3.58 (m, 0.5H), 3.38 (s, 3H), 3.28 (t, J=9.9 Hz, 1H), 3.00-3.19 (m, 1.5H), 2.65-2.79 (m, 1H), 2.54-2.64 (m, 1H) 2.03-2.10 (m, 1H), 1.38 (d, J=6.3 Hz, 1H), 1.28 (d, J=6.8 Hz, 2H), 1.13-1.21 (m, 2H), 0.94-1.03 (m, 2H)

LC-MS: m/z 461.2 (M+H)$^+$

Compound 623

(R)-2'-chloro-2-cyclopropyl-6'-methoxy-6-(4-(3-methoxypropanoyl)-3-methylpiperazin-1-yl)-[3,4'-bipyridine]-5-carbonitrile To a solution of (R)-2',6'-dichloro-2-cyclopropyl-6-(4-(3-methoxypropanoyl)-3-methylpiperazin-1-yl)-[3,4'-bipyridine]-5-carbonitrile (300 mg, 0.623 mmol) MeOH was added NaOMe (69 mg, 1.26 mmol), the mixture was refluxed for 16 hours. After cooling, the mixture was partitioned between EtOAc and water, the organic layer was washed with water, brine and dried over Na$_2$SO$_4$. The organic layer was concentrated to give the crude which was purified by prep-HPLC to obtained 150 mg of the product.

$^1$H NMR (CHLOROFORM-d) □□7.54-7.63 (m, 1H), 6.97 (d, J=1.3 Hz, 1H), 6.70 (d, J=1.0 Hz, 1H), 4.91 (s, 0.5H), 4.54 (d, J=12.8 Hz, 0.5H), 4.23-4.39 (m, 2.5H), 3.96 (s, 3H), 3.79-3.85 (m, 0.5H), 3.68-3.78 (m, 2H), 3.49-3.60 (m, 0.5H), 3.39 (s, 3H), 3.26-3.36 (m, 1H), 3.04-3.20 (m, 1.5H), 2.64-2.82 (m, 1H), 2.50-2.63 (m, 1H), 2.00-2.04 (m, 1), 1.38 (d, J=6.5 Hz, 1H), 1.28 (d, J=5.5 Hz, 2H), 1.13-1.21 (m, 2H), 0.97-1.06 (m, 2H)

LC-MS: m/z 470.2 (M+H)$^+$

Compound 624

(R)-2-cyclopropyl-6-(4-(3-methoxypropanoyl)-3-methylpiperazin-1-yl)-2',6'-divinyl-[3,4'-bipyridine]-5-carbonitrile The mixture of (R)-2',6'-dichloro-2-cyclopropyl-6-(4-(3-methoxypropanoyl)-3-methylpiperazin-1-yl)-[3,4'-bipyridine]-5-carbonitrile (50 mg, 0.105 mmol), Potassium vinyltrifluoroborate (50 mg, 0.316 mmol), Pd(dppf)Cl$_2$ (4 mg, 0.0043 mmol), CsF (50 mg, 0.316 mmol) in dioxane/H$_2$O was stirred at 100° C. for 16 hours, the mixture was partitioned between EtOAc and water, the organic was washed with water, brine and concentrated to give the crude which was purified by column to give 25 mg of the product.

$^1$H NMR (CHLOROFORM-d) □□7.63 (s, 1H), 7.24 (s, 1H), 7.28 (s, 1H), 6.77-6.98 (m, 2H), 6.30 (s, 1H), 6.34 (s, 1H), 5.55 (d, J=10.8 Hz, 2H), 4.09 (s, 0.5H), 4.53 (d, J=12.3 Hz, 0.5H), 4.21-4.36 (m, 2.5H), 3.68-3.85 (m, 3H), 3.50-3.61 (m, 0.5H), 3.38 (s, 4H), 3.03-3.15 (m, 1H), 2.70 (dd, J=15.7, 6.4 Hz, 1H), 2.51-2.59 (m, 1H), 1.90-2.12 (m, 1H), 1.36-1.42 (m, 1H), 1.22-1.30 (m, 2H), 1.18 (s, 2H), 0.94-1.05 (m, 2H)

LC-MS: m/z 458.2 (M+H)$^+$

Compound 634 (General Procedure 1, Step I)

(R)-6-cyclopropyl-2-(3-isopropyl-4-(3-methoxypropanoyl)piperazin-1-yl)-5-(2-vinylquinazolin-5-yl)nicotinonitrile $^1$H NMR (CHLOROFORM-d) δ 9.15 (d, J=11.3 Hz, 1H), 8.03 (d, J=8.3 Hz, 1H), 7.93 (t, J=7.8 Hz, 1H), 7.64 (d, J=3.3 Hz, 1H), 7.50 (dd, J=10.3, 7.3 Hz, 1H), 7.04 (dd, J=17.2, 10.7 Hz, 1H), 6.78 (d, J=17.1 Hz, 1H), 5.85 (d, J=10.5 Hz, 1H), 4.64-4.76 (m, 1H), 4.42-4.49 (m, 1H), 3.88 (d, J=13.6 Hz, 0.5H), 3.73 (d, J=5.8 Hz, 2H), 3.61 (d, J=9.8 Hz, 0.5H), 3.39-3.50 (m, 0.5H), 3.37 (s, 3H), 3.05-3.25 (m, 2H), 2.85-3.10 (m, 0.5H), 2.50-2.85 (m, 2H), 2.18-2.33 (m, 1H), 1.99-2.15 (m, 1H), 0.99-1.22 (m, 6H), 0.82-0.94 (m, 5H)

LC-MS: m/z 511.3 (M+H)$^+$

Compound 635 (General Procedure 1, Step I)

(R)-6-cyclopropyl-2-(3-cyclopropyl-4-(3-methoxypropanoyl)piperazin-1-yl)-5-(2-vinylquinazolin-5-yl)nicotinonitrile $^1$H NMR (CHLOROFORM-d) δ 9.15 (d, J=7.8 Hz, 1H), 8.04 (d, J=8.5 Hz, 1H), 7.94 (t, J=7.8 Hz, 1H), 7.66 (d, J=1.5 Hz, 1H), 7.43-7.56 (m, 1H), 7.04 (dd, J=17.3, 10.5 Hz, 1H), 6.78 (d, J=17.1 Hz, 1H), 5.85 (d, J=10.5 Hz, 1H), 4.33-4.80 (m, 2.5H), 4.07-4.22 (m, 0.5H), 3.85-4.02 (m, 1H), 3.60-3.81 (m, 3H), 3.37 (s, 3H), 2.98-3.26 (m, 2H), 2.37-2.76 (m, 2H), 1.98-2.28 (m, 1H), 1.51-1.61 (m, 1H), 1.11-1.26 (m, 2H), 0.86 (d, J=7.8 Hz, 2H), 0.40-0.55 (m, 4H)

LC-MS: m/z 509.3 (M+H)$^+$

Compound 636 (General Procedure 1, Step I)

(R)-2-(4-(cyclopropanecarbonyl)-3-cyclopropylpiperazin-1-yl)-6-cyclopropyl-5-(2-vinylquinazolin-5-yl)nicotinonitrile $^1$H NMR (CHLOROFORM-d) δ 9.16 (d, J=8.0 Hz, 1H), 8.04 (d, J=8.5 Hz, 1H), 7.94 (t, J=7.8 Hz, 1H), 7.62-7.72 (m, 1H), 7.44-7.56 (m, 1H), 7.05 (dd, J=17.3, 10.5 Hz, 1H), 6.78 (d, J=17.1 Hz, 1H), 5.75-5.95 (m, 1H), 4.49-4.66 (m, 2.5H), 4.05-4.25 (m, 1H), 3.75-3.88 (m, 1H), 3.06-3.32 (m, 2.5H), 2.29 (s, 1H), 1.50-1.57 (m, 1H), 1.34-1.47 (m, 1H), 1.14-1.22 (m, 2H), 0.98-1.09 (m, 2H), 0.77-0.91 (m, 4H), 0.39-0.67 (m, 4H)

LC-MS: m/z 491.2 (M+H)$^+$

Compound 645 (General Procedure 1, Step I)

(R)-6-cyclopropyl-2-(3-cyclopropyl-4-(3-methoxypropanoyl)piperazin-1-yl)-5-(2-vinyl-1,8-naphthyridin-4-yl)nicotinonitrile (Core synthesis method 1 using 4-chloro-2-vinyl-1,8-naphthyridine as starting material)

In a sealed tube was added 120 mg of 4-chloro-2-vinyl-1,8-naphthyridine, 242 mg of 8-3 (0.5 mmol), 230 mg of CsF (1.5 mmol), 41 mg of Pd(dppf)$_2$Cl$_2$ (0.05 mmol) and 10 mL of Dioxane, then the mixture was heated in a microwave reactor (100° C., 30 minutes), when LC-MS indicated the product formation. Then the resulting mixture was filtered, the filtrated was concentrated, purified by Prep-TLC (Petroleum ether: Ethyl acetate=2:1) to give 45 mg of title compound.

$^1$H NMR (CHLOROFORM-d) δ 9.17 (dd, J=4.3, 1.8 Hz, 1H), 8.03 (td, J=8.7, 1.8 Hz, 1H), 7.68 (d, J=1.3 Hz, 1H), 7.61 (d, J=3.5 Hz, 1H), 7.48 (dd, J=8.3, 4.3 Hz, 1H), 7.15 (dd, J=17.7, 10.9 Hz, 1H), 6.57 (dd, J=17.6, 1.8 Hz, 1H), 5.83 (d, J=11.0 Hz, 1H), 4.60 (d, J=12.3 Hz, 2H), 4.49 (d, J=12.8 Hz, 1H), 4.15 (br. s., 0.5H), 3.91 (br. s., 0.5H), 3.65-3.85 (m, 3H), 3.40 (s, 4H), 3.27 (d, J=12.0 Hz, 2H), 2.67 (br. s., 2H), 1.20 (d, J=4.5 Hz, 2H), 0.82-0.98 (m, 2H), 0.66 (br. s., 1H), 0.59 (br. s., 1H), 0.49 (d, J=5.0 Hz, 2H)

LC-MS: m/z 509.1 (M+H)$^+$

Compound 629 (General Procedure 1, Step I)

(R)-6-cyclopropyl-2-(4-(3-hydroxypropanoyl)-3-isopropylpiperazin-1-yl)-5-(2-vinyl-1,8-naphthyridin-4-yl)nicotinonitrile $^1$H NMR (CHLOROFORM-d) δ 8.99-9.21 (m, 1H), 7.99 (dd, J=12.4, 8.4 Hz, 1H), 7.50-7.72 (m, 2H), 7.45 (dt, J=7.8, 3.7 Hz, 1H), 7.11 (dd, J=17.4, 10.9 Hz, 1H), 6.53 (d, J=17.6 Hz, 1H), 5.79 (d, J=10.8 Hz, 1H), 4.56-4.78 (m, 1.5H), 4.35-4.56 (m, 2H), 3.74-3.99 (m, 2.5H), 3.37-3.60 (m, 1H), 3.06-3.28 (m, 2H), 2.92-3.06 (m, 1H), 2.53-2.83 (m, 3H), 2.12 (dt, J=10.0, 6.5 Hz, 1H), 1.43-1.55 (m, 1H), 0.98-1.15 (m, 4H), 0.72-0.97 (m, 5H)

LC-MS: m/z 497.3 (M+H)$^+$

Compound 625 (General Procedure 1, Step I)

(R)-6-cyclopropyl-2-(4-(3-hydroxypropanoyl)-3-methylpiperazin-1-yl)-5-(2-vinyl-1,8-naphthyridin-4-yl)nicotinonitrile $^1$H NMR (CHLOROFORM-d) δ 9.05-9.19 (m, 1H), 7.98 (ddd, J=6.1, 4.3, 2.1 Hz, 1H), 7.63-7.68 (m, 1H), 7.55-7.61 (m, 1H), 7.41-7.47 (m, 1H), 7.03-7.17 (m, 1H), 6.52 (d, J=17.6 Hz, 1H), 5.72-5.84 (m, 1H), 4.89 (br. s., 0.5H), 4.54 (d, J=12.5 Hz, 1H), 4.39 (d, J=13.8 Hz, 1H), 4.29 (d, J=19.8 Hz, 2H), 4.20 (br. s., 1H), 3.82-4.00 (m, 2.5H), 3.01-3.24 (m, 2H), 2.46-2.76 (m, 3H), 1.06-1.19 (m, 2H), 0.75-0.94 (m, 3H)

LC-MS: m/z 469.2 (M+H)$^+$

Compound 626 (General Procedure 1, Step I)

(R)-6-cyclopropyl-2-(3-isopropyl-4-(3-methoxypropanoyl)piperazin-1-yl)-5-(2-vinyl-1,8-naphthyridin-4-yl)nicotinonitrile $^1$H NMR (CHLOROFORM-d) δ 9.12 (S, 1h), 7.99 (br. s., 1H), 7.52-7.69 (m, 2H), 7.36-7.50 (m, 1H), 7.00-7.19 (m, 1H), 6.53 (d, J=17.6 Hz, 1H), 5.78 (d, J=10.8 Hz, 1H), 4.71 (br. s., 1.5H), 4.35-4.52 (m, 2H), 3.58-3.81 (m, 3.5H), 3.37 (d, J=3.0 Hz, 4H), 3.18 (dd, J=13.6, 3.5 Hz, 2H), 2.52-2.82 (m, 2H), 1.08 (dt, J=12.0, 5.7 Hz, 4H), 0.87 (d, J=6.8 Hz, 6H)

LC-MS: m/z 511.2 (M+H)$^+$

Compound 599 (General Procedure 1, Step I)

(R)-6-cyclopropyl-2-(4-(3-methoxypropanoyl)-3-methylpiperazin-1-yl)-5-(2-vinyl-1,8-naphthyridin-4-yl)nicotinonitrile $^1$H NMR (CHLOROFORM-d) δ 9.14 (dd, J=4.1, 1.9 Hz, 1H), 7.98 (br. s., 1H), 7.65 (s, 1H), 7.59 (s, 1H), 7.45 (dd, J=8.3, 4.3 Hz, 1H), 7.11 (d, J=10.8 Hz, 1H), 6.44-6.62 (m, 1H), 5.80 (d, J=10.8 Hz, 1H), 4.94 (br. S., 0.5H), 4.55 (br. s., 0.5H), 4.42 (br. s., 3H), 3.75 (d, J=6.3 Hz, 3H), 3.39 (s, 4H), 3.15 (br. s., 2H), 2.63 (br. s., 2H), 1.10-1.22 (m, 3H), 0.72-0.97 (m, 4H)

LC-MS: m/z 483.1 (M+H)$^+$

Compound 596 (General Procedure 1, Step I)

(R)-2'-cyclopropyl-6'-(4-(3-methoxypropanoyl)-3-methylpiperazin-1-yl)-4-vinyl-2,3'-bipyridine-5'-carbonitrile $^1$H NMR (CHLOROFORM-d) δ: 8.67 (d, J=5.3 Hz, 1H), 7.89 (s, 1H), 7.50 (s, 3H), 6.63-6.82 (m, 1H), 6.04 (d, J=17.6 Hz, 1H), 5.57 (d, J=11.0 Hz, 1H), 4.91 (br. s., 0.5H), 4.51 (br. s., 1H), 4.34 (br. s., 3H), 3.65-3.83 (m, 2.5H), 3.33-3.44 (m, 4H), 3.29 (br. s., 1H), 2.71 (br. s., 1H), 2.62 (br. s., 2H), 1.33-1.43 (m, 3H), 1.15-1.25 (m, 4H)

LC-MS: m/z 431.2 (M+H)$^+$

Compound 612 (General Procedure 1, Step I)

(R)-5-(1-acryloyl-2,5-dihydro-1H-pyrrol-3-yl)-2-(4-(cyclopropanecarbonyl)-3-methylpiperazin-1-yl)-6-cyclopropylnicotinonitrile 1H NMR (CHLOROFORM-d) δ 7.48-7.56 (m, 1H), 6.31-6.57 (m, 2H), 5.97 (d, J=2.0 Hz, 1H), 5.65-5.88 (m, 1H), 4.01-4.90 (m, 8H), 3.02-3.81 (m, 3H), 2.09-2.34 (m, 1H), 1.75 (br. s., 2H), 1.25-1.37 (m, 3H), 1.09-1.22 (m, 2H), 0.95-1.09 (m, 4H), 0.67-0.94 (m, 2H)

LC-MS: m/z 432.2 (M+H)$^+$

Compound 620 (General Procedure 1, Step I)

(R)-2-cyclopropyl-6-(4-(3-methoxypropanoyl)-3-methylpiperazin-1-yl)-6'-vinyl-3,3'-bipyridine-5-carbonitrile ¹H NMR (CHLOROFORM-d) δ 8.63 (d, J=2.0 Hz, 1H), 7.66-7.74 (m, 1H), 7.58-7.65 (m, 1H), 7.40-7.50 (m, 1H), 6.87 (dd, J=17.6, 10.8 Hz, 1H), 6.27 (dd, J=17.6, 1.0 Hz, 1H), 5.54 (dd, J=10.8, 1.0 Hz, 1H), 4.90 (br. s., 0.5H), 4.52 (d, J=13.1 Hz, 0.5H), 4.17-4.41 (m, 2.5H), 3.66-3.88 (m, 2.5H), 3.54 (t, J=11.2 Hz, 0.5H), 3.37 (s, 3H), 3.28 (t, J=9.8 Hz, 1H), 2.99-3.20 (m, 1.5H), 2.52-2.81 (m, 2H), 1.94-2.06 (m, 1H), 1.33-1.41 (m, 1.5H), 1.24-1.29 (m, 1.5H), 1.14-1.23 (m, 2H), 0.91-1.04 (m, 2H)
LC-MS: m/z 432.1 (M+H)⁺

Compound 619 (General Procedure 1, Step I)

(R)-2-cyclopropyl-6-(4-(3-methoxypropanoyl)-3-methylpiperazin-1-yl)-2'-vinyl-3,3'-bipyridine-5-carbonitrile ¹H NMR (CHLOROFORM-d) δ 8.54-8.72 (m, 1H), 7.45-7.58 (m, 2H), 7.18-7.34 (m, 1H), 6.53-6.69 (m, 1H), 6.38-6.47 (m, 1H), 5.43 (d, J=10.8 Hz, 1H), 4.90 (br. s., 0.5H), 4.52 (d, J=13.1 Hz, 0.5H), 4.14-4.39 (m, 2.5H), 3.68-3.88 (m, 2.5H), 3.54 (d, J=4.8 Hz, 0.5H), 3.37 (s, 3H), 3.23-3.33 (m, 1H), 2.99-3.21 (m, 1.5H), 2.51-2.80 (m, 2H), 1.55-1.69 (m, 1H), 1.39 (br. s., 1.5H), 1.29 (br. s., 1.5H), 1.04-1.19 (m, 2H), 0.79-1.00 (m, 2H)
LC-MS: m/z 432.2 (M+H)⁺

Compound 630 (General Procedure 1, Step I)

(R)-5-(1-acryloyl-1,2,3,6-tetrahydropyridin-4-yl)-2-(4-(cyclopropanecarbonyl)-3-methylpiperazin-1-yl)-6-cyclopropylnicotinonitrile 1H NMR (CHLOROFORM-d) δ 7.45 (s, 1H), 6.64 (td, J=16.1, 10.7 Hz, 1H), 6.29-6.42 (m, 1H), 5.67-5.86 (m, 2H), 4.00-5.00 (m, 6H), 3.85-3.93 (m, 1H), 3.79 (t, J=5.3 Hz, 1H), 3.00-3.63 (m, 3H), 2.39-2.52 (m, 2H), 1.96-2.12 (m, 1H), 1.75 (br. s., 1H), 1.28-1.51 (m, 3H), 1.08-1.17 (m, 2H), 0.94-1.08 (m, 4H), 0.76-0.86 (m, 2H)
LC-MS: m/z 446.0 (M+H)⁺

Compound 557 (General Procedure 1, Step I)

(R)-2-(4-(cyclopropanecarbonyl)-3-cyclopropylpiperazin-1-yl)-6-cyclopropyl-5-(2-methyl-1,8-naphthyridin-4-yl)nicotinonitrile ¹H NMR (CHLOROFORM-d) δ 0.39-0.53 (m, 1H) 0.56 (d, J=4.52 Hz, 3H) 0.79-0.94 (m, 4H) 0.94-1.14 (m, 3H) 1.22 (br. s., 2H) 1.27 (br. s., 2H) 1.33 (br. s., 2H) 3.01 (s, 3H) 4.53 (d, J=12.55 Hz, 2.5H) 7.46 (s, 1H) 7.58 (br. s., 1H) 7.67 (s, 1H) 8.14 (br. s., 1H) 9.22 (br. s., 1H)
LC-MS: m/z 479.3 (M+H)⁺

Compound 552 (General Procedure 2, Step M)

(R)-tert-butyl 5-(5-cyano-2-cyclopropyl-6-(3-cyclopropyl-4-(3,3,3-trifluoropropanoyl)piperazin-1-yl)pyridin-3-yl)-1H-indazole-1-carboxylate 70 mg of (R)-6-cyclopropyl-2-(3-cyclopropylpiperazin-1-yl)-5-(1H-indazol-5-yl)nicotinonitrile (NB247-78) (0.18 mmol), 83 mg of HATU (0.22 mmol), 37 mg of TEA in 10 mL of DCM was added 23 mg of 3,3,3-trifluoropropanoic acid (0.18 mmol), then the mixture was stirred at room temperature for 2 hours, concentrated, purified by Prep-TLC (Petroleum ether: Ethyl acetate=1:1) to give 31.5 mg of title compound. ¹H NMR (CHLOROFORM-d) □□7.98 (br. s., 1H), 7.77 (s, 1H), 7.42-7.62 (m, 2H), 7.15 (d, J=7.0 Hz, 1H), 4.56 (d, J=13.1 Hz, 2H), 4.13 (br. s., 0.5H), 3.84 (br. s., 1.5H), 3.35 (d, J=10.0 Hz, 2H), 3.23 (br. s., 2H), 3.12 (br. s., 1H), 1.94 (s, 1H), 1.15-1.32 (m, 5H), 0.94 (dd, J=7.8, 3.3 Hz, 2H), 0.52 (d, J=5.3 Hz, 2H)
LC-MS: m/z 495.2 (M+H)⁺

Compound 537 (General Procedure 2, Step M)

(R)-5-(benzo[d]thiazol-6-yl)-6-cyclopropyl-2-(3-cyclopropyl-4-(3,3,3-trifluoropropanoyl)piperazin-1-yl)nicotinonitrile ¹H NMR (CHLOROFORM-d) δ 9.07 (s, 1H), 8.22 (d, J=8.5 Hz, 1H), 7.99 (d, J=1.5 Hz, 1H), 7.71 (s, 1H), 7.57 (dd, J=8.4, 1.6 Hz, 1H), 4.53 (d, J=13.3 Hz, 1H), 4.42 (d, J=12.8 Hz, 1H), 3.98-4.21 (m, 0.5H), 3.67-3.95 (m, 1.5H), 3.26-3.38 (m, 2H), 3.15-3.26 (m, 2H), 3.09 (t, J=11.3 Hz, 1H), 2.04-2.12 (m, 1H), 1.42 (d, J=14.3 Hz, 1H), 1.17-1.24 (m, 2H), 0.95-1.03 (m, 2H), 0.67 (br. s., 1H), 0.57 (br. s., 1H), 0.45-0.53 (m, 2H)
LC-MS: m/z 512.1 (M+H)⁺

Compound 536 (General Procedure 2, Step M)

(R)-6-cyclopropyl-2-(3-cyclopropyl-4-(3,3,3-trifluoropropanoyl)piperazin-1-yl)-5-(2-methyl-1-oxo-1,2-dihydroisoquinolin-4-yl)nicotinonitrile ¹H NMR (CHLOROFORM-d) δ: 8.45-8.58 (m, 1H), 7.59-7.69 (m, 2H), 7.47-7.59 (m, 1H), 7.23 (d, J=8.0 Hz, 1H), 7.07 (d, J=1.8 Hz, 1H), 4.53 (d, J=13.1 Hz, 1H), 4.43 (d, J=12.0 Hz, 1H), 4.12 (br. s., 0.5H), 3.78 (br. s., 1H), 3.67 (s, 3H), 3.33 (q, J=9.8 Hz, 2H), 3.16-3.26 (m, 1H), 3.03-3.16 (m, 0.5H), 1.92 (br. s., 1H), 1.69-1.80 (m, 1H), 1.20-1.28 (m, 2H), 1.07-1.19 (m, 2H), 0.81-0.95 (m, 2H), 0.67 (br. s., 1H), 0.57 (br. s., 1H), 0.43-0.54 (m, 2H)
LC-MS: m/z 536.2 (M+H)⁺

Compound 580 (General Procedure 1, Step I)

(R)-6-cyclopropyl-2-(4-(3-methoxypropanoyl)-3-methylpiperazin-1-yl)-5-(2-vinyl-1,7-naphthyridin-4-yl)nicotinonitrile 1H NMR (CHLOROFORM-d) δ: 9.56 (s, 1H), 8.59 (d, J=5.8 Hz, 1H), 7.74 (s, 1H), 7.64-7.70 (m, 1H), 7.44-7.52 (m, 1H), 7.11 (dd, J=17.7, 10.9 Hz, 1H), 6.44 (dd, J=17.7, 1.6 Hz, 1H), 5.83 (d, J=11.0 Hz, 1H), 4.95 (br. s., 0.5H), 4.58 (d, J=11.3 Hz, 0.5H), 4.42 (d, J=11.3 Hz, 1.5H), 4.31 (br. s., 1H), 3.86 (d, J=13.1 Hz, 0.5H), 3.72-3.81 (m, 2H), 3.55-3.68 (m, 0.5H), 3.4 (s, 3H) 3.34-3.39 (m, 0.5H), 3.04-3.30 (m, 2H), 2.53-2.83 (m, 2H), 1.47-1.55 (m, 1H), 1.37-1.46 (m, 1.5H), 1.29-1.37 (m, 1.5H), 1.20 (t, J=4.9 Hz, 2H), 0.84-0.96 (m, 2H)
LC-MS: m/z 483.2 (M+H)⁺

Compound 609 (General Procedure 1, Step I)

(R)-6-cyclopropyl-2-(4-(3-hydroxypropanoyl)-3-methylpiperazin-1-yl)-5-(2-vinyl-1,7-naphthyridin-4-yl)nicotinonitrile $^1$H NMR (CHLOROFORM-d) δ 9.50-9.65 (m, 1H), 8.60 (d, J=6.0 Hz, 1H), 7.74-7.82 (m, 1H), 7.62-7.72 (m, 1H), 7.48-7.57 (m, 1H), 7.11 (dd, J=17.7, 10.9 Hz, 1H), 6.45 (dd, J=17.6, 1.8 Hz, 1H), 5.85 (d, J=11.0 Hz, 1H), 4.93 (br. s., 0.5H), 4.50-4.64 (m, 0.5H), 4.40-4.49 (m, 1H), 4.31-4.40 (m, 1H), 4.22 (br. s., 0.5H), 3.91-4.01 (m, 2H), 3.78 (d, J=11.3 Hz, 0.5H), 3.61 (d, J=11.8 Hz, 0.5H), 3.39 (d, J=13.6 Hz, 1H), 3.10-3.31 (m, 1.5H), 2.65-2.80 (m, 1H), 2.52-2.65 (m, 1H), 1.43-1.54 (m, 3H), 1.35 (t, J=5.6 Hz, 2H), 1.21 (dd, J=6.9, 3.6 Hz, 2H), 0.87-0.98 (m, 2H)

LC-MS: m/z 469.2 (M+H)$^+$

Compound 611 (General Procedure 1, Step I)

(R)-6-cyclopropyl-2-(3-isopropyl-4-(3-methoxypropanoyl)piperazin-1-yl)-5-(2-vinyl-1,7-naphthyridin-4-yl)nicotinonitrile 1H NMR (CHLOROFORM-d) δ: 9.57 (s, 1H), 8.60 (dd, J=5.6, 3.1 Hz, 1H), 7.75 (d, J=12.0 Hz, 1H), 7.66 (dd, J=4.8, 3.3 Hz, 1H), 7.45-7.55 (m, 1H), 7.04-7.17 (m, 1H), 6.44 (d, J=17.6 Hz, 1H), 5.84 (d, J=10.8 Hz, 1H), 4.61-4.81 (m, 1.5H), 4.42-4.56 (m, 1.5H), 3.92 (d, J=13.6 Hz, 0.5H), 3.70-3.83 (m, 2H), 3.44-3.56 (m, 0.5H), 3.37-3.43 (m, 3H), 3.08-3.31 (m, 2H), 2.90-3.05 (m, 0.5H), 2.55-2.85 (m, 2H), 1.49 (dd, J=7.4, 4.4 Hz, 1H), 1.14-1.32 (m, 2H), 1.11 (ddd, J=15.2, 6.5, 4.1 Hz, 4H), 0.83-0.98 (m, 5H)

LC-MS: m/z 511.3 (M+H)$^+$

Compound 542

(R)-2-(4-(cyclopropanecarbonyl)-3-cyclopropylpiperazin-1-yl)-6-cyclopropyl-5-(2-vinylquinolin-4-yl)nicotinonitrile

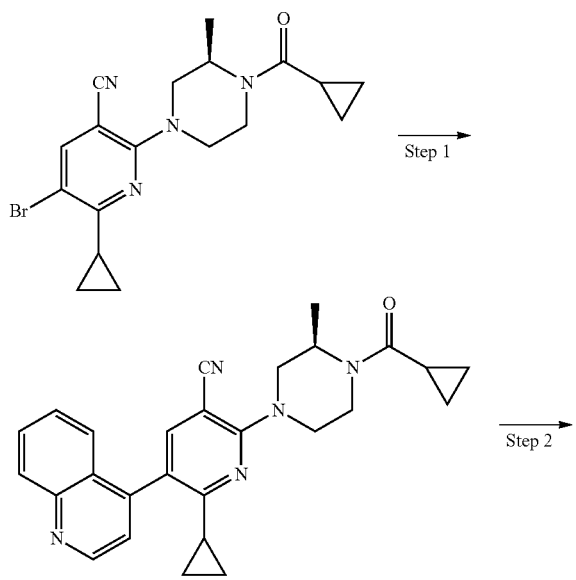

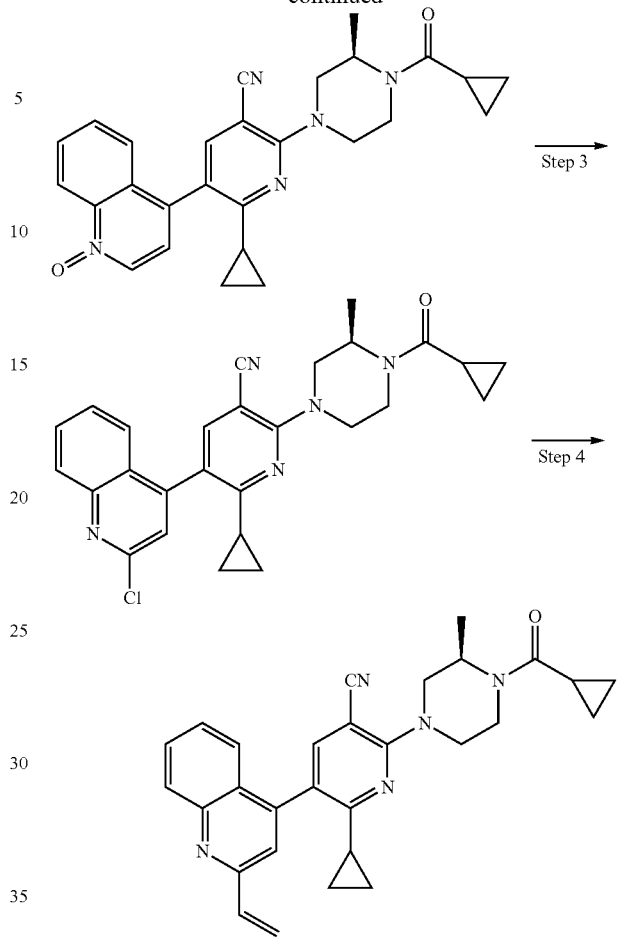

Step 1:

To 10 mg PdCl2(dppf).CH2Cl2 in a reaction tube under nitrogen were added 5 mL dioxane, 3 mL water, 150 mg (0.98 mmol) CsF, 75 mg (0.43 mmol) quinolin-4-ylboronic acid and 150 mg (0.36 mmol) (R)-5-bromo-2-(4-(cyclopropanecarbonyl)-3-cyclopropylpiperazin-1-yl)-6-cyclopropyl-nicotinonitrile. The reaction solution was heated to 100° C. for half hour under microwave irradiation. The reaction was extracted with ethyl acetate, washed several times with water and purified by TLC preparation (petroleum ether:ethyl acetate=1:1) to give desired compound 50 mg (32%, yield). LC-MS: m/z 438.22 (M+H)$^+$ Step 2:

To a stirred solution of (R)-2-(4-(cyclopropanecarbonyl)-3-cyclopropylpiperazin-1-yl)-6-cyclopropyl-5-(quinolin-4-yl)nicotinonitrile (50 mg, 0.108 mmol) in 10 mL of anhydrous CH2Cl2 was added 3-chlorobenzoperoxoic acid (37 mg, 0.216 mmol) portionwise over 1 min. The resulting mixture was stirred at room temperature for 3 hours. Then saturated aqueous Na2SO3 (10 mL) was added to the reaction. The reaction was extracted with ethyl acetate to give desired compound (R)-4-(5-cyano-6-(4-(cyclopropanecarbonyl)-3-methylpiperazin-1-yl)-2-cyclopropylpyridin-3-yl)quinoline 1-oxide 48 mg (93%). LC-MS: m/z 453.22 (M+H)$^+$ Step 3:

To a solution of (R)-4-(5-cyano-6-(4-(cyclopropanecarbonyl)-3-cyclopropylpiperazin-1-yl)-2-cyclopropylpyridin-3-yl)quinoline 1-oxide (35 mg, 0.07 mmol) in 20 mL of CHCl3 was added POCl3 (32 mg, 0.209) dropwise at room temperature. The reaction mixture was then heated at reflux for 3 hours. After LC-MS showed completion of reaction, the mixture was cooled to room temperature and poured into water and extracted with methylene chloride. The combined organic layer was dried over anhy. $Na_2SO_4$ and concentrated in vacuo to give the title compound as a brown solid 30 mg (83.3%). LC-MS: m/z 472.18 $(M+H)^+$ Step 4 is Similar to Compound 390 Step 2: Compound 542

$^1$H NMR (CHLOROFORM-d) δ: 8.21 (d, J=8.3 Hz, 1H), 7.77 (t, J=7.5 Hz, 1H), 7.68 (d, J=1.0 Hz, 1H), 7.48-7.66 (m, 3H), 7.13 (dd, J=17.4, 10.9 Hz, 1H), 6.35 (d, J=17.6 Hz, 1H), 5.76 (d, J=11.0 Hz, 1H), 4.61 (d, J=12.5 Hz, 1.5H), 4.49 (d, J=12.3 Hz, 1.5H), 4.12 (br. s., 1H), 3.67-3.82 (m, 1H), 3.34 (br. s., 1.5H), 3.19 (br. s., 1.5H), 1.58 (ddd, J=12.0, 7.8, 4.5 Hz, 1H), 1.14-1.35 (m, 4H), 1.00-1.13 (m, 2H), 0.76-0.93 (m, 4H), 0.71 (br. s., 1H), 0.38-0.63 (m, 3H)

LC-MS: m/z 490.6 $(M+H)^+$

Compound 543

(R)-5-(2-chloroquinolin-4-yl)-2-(4-(cyclopropanecarbonyl)-3-cyclopropylpiperazin-1-yl)-6-cyclopropylnicotinonitrile The synthesis was similar to Compound 542.

$^1$H NMR (CHLOROFORM-d) δ: 8.12 (d, J=8.3 Hz, 1H), 7.76-7.84 (m, 1H), 7.61-7.68 (m, 2H), 7.53-7.61 (m, 1H), 7.38 (d, J=1.8 Hz, 1H), 4.63 (d, J=12.5 Hz, 1H), 4.51 (d, J=12.5 Hz, 1H), 3.97-4.20 (m, 1H), 3.82 (br. s., 1H), 3.59-3.78 (m, 1H), 3.34 (br. s., 1H), 3.20 (br. s., 1H), 1.74 (br. s., 2H), 1.50-1.59 (m, 1H), 1.14-1.26 (m, 2H), 0.97-1.14 (m, 2H), 0.79-0.97 (m, 4H), 0.70 (br. s., 1H), 0.42-0.63 (m, 3H)

LC-MS: m/z 499.0 $(M+H)^+$

Compound 571

(R)-6-cyclopropyl-2-(3-cyclopropyl-4-(3-hydroxypropanoyl)piperazin-1-yl)-5-(2-vinylquinolin-4-yl)nicotinonitrile The synthesis was similar to Compound 542.

1H NMR (CHLOROFORM-d) δ: 8.18 (d, J=8.5 Hz, 1H), 7.76 (t, J=7.7 Hz, 1H), 7.69 (d, J=1.0 Hz, 1H), 7.46-7.64 (m, 3H), 7.11 (dd, J=17.7, 10.9 Hz, 1H), 6.28-6.39 (m, 1H), 5.75 (d, J=11.0 Hz, 1H), 4.59 (d, J=13.1 Hz, 1H), 4.47 (d, J=13.1 Hz, 1H), 4.13 (d, J=8.3 Hz, 0.5H), 3.94 (br. s., 2H), 3.82 (br. s., 1H), 3.76 (br. s., 1H), 3.43 (br. s., 1H), 3.21-3.37 (m, 1.5H), 3.15 (d, J=11.5 Hz, 1H), 2.55-2.70 (m, 2H), 1.67 (br. s., 1H), 1.59 (tt, J=8.1, 4.3 Hz, 1H), 1.10-1.24 (m, 2H), 0.80-0.94 (m, 2H), 0.69 (br. s., 1H), 0.58 (br. s., 1H), 0.51 (br. s., 2H)

LC-MS: m/z 494.2 $(M+H)^+$

Compound 574

(R)-6-cyclopropyl-2-(3-cyclopropyl-4-(3-methoxypropanoyl)piperazin-1-yl)-5-(2-vinylquinolin-4-yl)nicotinonitrile The synthesis was similar to Compound 542.

$^1$H NMR (CHLOROFORM-d) δ 8.15 (d, J=8.5 Hz, 1H), 7.71-7.78 (m, 1H), 7.67 (d, J=1.0 Hz, 1H), 7.56-7.64 (m, 1H), 7.54 (d, J=4.5 Hz, 1H), 7.46-7.53 (m, 1H), 7.02-7.14 (m, 1H), 6.32 (dd, J=17.6, 1.3 Hz, 1H), 5.73 (d, J=11.3 Hz, 1H), 4.71-4.74 (m, 0.5H), 4.53-4.66 (m, 1H), 4.45 (d, J=13.1 Hz, 1H), 4.06-4.24 (m, 0.5H), 3.91 (d, J=11.5 Hz, 0.5H), 3.68-3.84 (m, 3H), 3.39 (s, 3H), 3.26 (br. s., 1.5H), 3.07-3.21 (m, 1H), 2.61-2.85 (m, 2H), 1.53-1.64 (m, 1H), 1.32-1.44 (m, 1H), 1.11-1.24 (m, 2H), 0.80-0.94 (m, 2H), 0.48-0.78 (m, 1H)

LC-MS: m/z 508.1 $(M+H)^+$

Compound 591

(R)-6-cyclopropyl-2-(4-(3-hydroxypropanoyl)-3-methylpiperazin-1-yl)-5-(2-vinylquinolin-4-yl)nicotinonitrile The synthesis was similar to Compound 542.

$^1$H NMR (CHLOROFORM-d) δ 8.18 (d, J=8.3 Hz, 1H), 7.76 (ddd, J=8.3, 6.8, 1.4 Hz, 1H), 7.68 (s, 1H), 7.57-7.63 (m, 1H), 7.48-7.57 (m, 2H), 7.10 (dd, J=17.7, 10.9 Hz, 1H), 6.34 (dd, J=17.6, 1.8 Hz, 1H), 5.74 (d, J=11.0 Hz, 1H), 4.93 (br. s., 0.5H), 4.48-4.68 (m, 0.5H), 4.26-4.45 (m, 2H), 3.87-3.98 (m, 2H), 3.74-3.87 (m, 0.5H), 3.61 (t, J=12.3 Hz, 0.5H), 3.31-3.48 (m, 2H), 3.05-3.29 (m, 1H), 2.49-2.79 (m, 2H), 1.53-1.63 (m, 1H), 1.46 (dd, J=6.5, 2.5 Hz, 1.5H), 1.32-1.40 (m, 1.5H), 1.15-1.23 (m, 2H), 0.80-0.93 (m, 2H)

LC-MS: m/z 468.2 $(M+H)^+$

Compound 592

(R)-6-cyclopropyl-2-(4-(3-methoxypropanoyl)-3-methylpiperazin-1-yl)-5-(2-vinylquinolin-4-yl)nicotinonitrile The synthesis was similar to Compound 542.

$^1$H NMR (CHLOROFORM-d) δ 8.19 (d, J=8.3 Hz, 1H), 7.76 (t, J=7.5 Hz, 1H), 7.65-7.68 (m, 1H), 7.58-7.64 (m, 1H), 7.48-7.57 (m, 2H), 7.11 (dd, J=17.7, 10.9 Hz, 1H), 6.34 (d, J=17.8 Hz, 1H), 5.75 (d, J=10.8 Hz, 1H), 4.95 (br. s., 0.5H), 4.50-4.70 (m, 0.5H), 4.24-4.47 (m, 2.5H), 3.71-3.89 (m, 2.5H), 3.59 (d, J=9.8 Hz, 0.5H), 3.31-3.45 (m, 4H), 3.07-3.28 (m, 1.5H), 2.67-2.85 (m, 1H), 2.54-2.67 (m, 1H), 1.52-1.62 (m, 1H), 1.33-1.49 (m, 3H), 1.11-1.21 (m, 2H), 0.78-0.93 (m, 2H)

LC-MS: m/z 482.2 $(M+H)^+$

Compound 553 (General Procedure 1, Step I)

(R)-2-(4-(cyclopropanecarbonyl)-3-cyclopropylpiperazin-1-yl)-6-cyclopropyl-5-(2-methyl-1,7-naphthyridin-4-yl)nicotinonitrile 1H NMR (CHLOROFORM-d) δ: 9.53 (s, 1H), 8.59 (d, J=5.5 Hz, 1H), 7.65 (s, 1H), 7.42-7.50 (m, 2H), 4.63 (d, J=9.3 Hz, 1H), 4.51 (d, J=11.0 Hz, 2.5H), 3.08-3.48 (m, 4.5H), 2.87 (s, 3H), 1.59-1.68 (m, 1H), 1.46-1.53 (m, 1H), 1.22 (d, J=3.0 Hz, 1H), 1.05-1.11 (m, 2H), 0.92-0.98 (m, 2H), 0.87-0.92 (m, 2H), 0.84 (dd, J=7.9, 2.6 Hz, 2H), 0.70 (br. s., 1H), 0.42-0.63 (m, 3H)

LC-MS: m/z 479.6 $(M+H)^+$

Compound 551

(R)-6-cyclopropyl-2-(3-cyclopropyl-4-(3,3,3-trifluoropropanoyl)piperazin-1-yl)-5-(2-vinylquinolin-5-yl)nicotinonitrile The synthesis was similar to Compound 542.
$^1$H NMR (400 MHz, CHLOROFORM-d) δ 8.18 (d, J=8.2 Hz, 1H), 7.91 (dd, J=12.5, 8.8 Hz, 1H), 7.79 (t, J=7.8 Hz, 1H), 7.64-7.71 (m, 1H), 7.57-7.64 (m, 1H), 7.46 (dd, J=6.9, 2.3 Hz, 1H), 6.97-7.17 (m, 1H), 6.34 (d, J=17.8 Hz, 1H), 5.75 (d, J=10.7 Hz, 1H), 4.56 (dd, J=13.0, 1.7 Hz, 1H), 4.45 (d, J=11.8 Hz, 1H), 4.15 (m, 0.5H), 3.87 (m, 1.5H), 3.26-3.44 (m, 2.5H), 3.01-3.20 (m, 2.5H), 1.42-1.52 (m, 1H), 1.07-1.21 (m, 2H), 0.79-0.92 (m, 3H), 0.66-0.76 (m, 2H), 0.46-0.56 (m, 2H)
LC-MS: m/z 532.2 (M+H)$^+$

Compound 570

(R)-6-cyclopropyl-2-(3-cyclopropyl-4-(3-methoxypropanoyl)piperazin-1-yl)-5-(2-vinylquinolin-5-yl)nicotinonitrile The synthesis was similar to Compound 542.
$^1$H NMR (400 MHz, CHLOROFORM-d) δ 8.11-8.17 (m, 1H), 7.85-7.95 (m, 1H), 7.78 (t, J=7.3 Hz, 1H), 7.64-7.68 (m, 1H), 7.60 (dd, J=8.8, 1.5 Hz, 1H), 7.42-7.47 (m, 1H), 7.00-7.13 (m, 1H), 6.32 (d, J=17.6 Hz, 1H), 5.72 (d, J=11.0 Hz, 1H), 4.72 (m, 0.5H), 4.54 (d, J=12.5 Hz, 1H), 4.43 (d, J=12.8 Hz, 1H), 4.14 (d, J=7.8 Hz, 0.5H), 3.91 (d, J=11.8 Hz, 0.5H), 3.75 (t, J=5.6 Hz, 2.5H), 3.40 (s, 3H), 3.23 (d, J=8.0 Hz, 1H), 3.01-3.17 (m, 1H), 2.70-2.81 (m, 1H), 2.67 (m, 1H), 2.03 (d, J=5.5 Hz, 1H), 1.56 (td, J=7.8, 4.0 Hz, 1H), 1.11-1.20 (m, 3H), 0.78-0.86 (m, 2H), 0.58-0.66 (m, 2H), 0.42-0.52 (m, 2H)
LC-MS: m/z 508.2 (M+H)$^+$

Compound 569

(R)-6-cyclopropyl-2-(3-cyclopropyl-4-(3-hydroxypropanoyl)piperazin-1-yl)-5-(2-vinylquinolin-5-yl)nicotinonitrile The synthesis was similar to Compound 542.
$^1$H NMR (400 MHz, CHLOROFORM-d) δ8.10-8.19 (m, 1H), 7.90 (dd, J=12.3, 8.8 Hz, 1H), 7.74-7.82 (m, 1H), 7.67 (s, 1H), 7.58-7.63 (m, 1H), 7.45 (ddd, J=7.0, 3.0, 1.0 Hz, 1H), 7.07 (dd, J=17.6, 10.9 Hz, 1H), 6.33 (d, J=17.5 Hz, 1H), 5.73 (d, J=11.0 Hz, 1H), 4.72 (d, J=9.5 Hz, 0.5H), 4.55 (d, J=13.0 Hz, 1H), 4.43 (d, J=12.5 Hz, 1H), 4.12 (d, J=7.2 Hz, 0.5H), 3.87-3.99 (m, 2H), 3.73-3.84 (m, 1H), 3.46 (m, 1H), 3.26 (m, 1.5H), 3.13 (d, J=10.5 Hz, 1H), 2.59-2.68 (m, 1.5H), 2.03 (d, J=6.0 Hz, 1H), 1.54-1.59 (m, 1H), 1.11-1.19 (m, 3H), 0.86-0.94 (m, 2H), 0.80-0.86 (m, 2H), 0.51-0.57 (m, 2H)
LC-MS: m/z 493.3 (M+H)$^+$

Compound 608

(R)-6-cyclopropyl-2-(4-(3-methoxypropanoyl)-3-methylpiperazin-1-yl)-5-(2-vinylquinolin-5-yl)nicotinonitrile The synthesis was similar to Compound 542.
1H NMR (400 MHz, CHLOROFORM-d) δ8.16-8.24 (m, 1H), 7.90-7.97 (m, 1H), 7.76-7.83 (m, 1H), 7.59-7.66 (m, 2H), 7.46 (d, J=7.0 Hz, 1H), 7.12 (dd, J=17.6, 10.9 Hz, 1H), 6.35 (d, J=17.5 Hz, 1H), 5.76 (d, J=11.0 Hz, 1H), 4.95 (m, 0.5H), 4.58 (d, J=12.5 Hz, 0.5H), 4.19-4.44 (m, 2.5H), 3.67-3.91 (m, 1.5H), 3.40 (s, 3H), 3.15-3.26 (m, 1.5H), 2.67-2.82 (m, 1.5H), 2.03 (d, J=5.7 Hz, 1H), 1.55 (td, J=8.0, 4.1 Hz, 1H), 1.31-1.37 (m, 3H), 1.11-1.18 (m, 2H) 0.77-0.86 (m, 2H)
LC-MS: m/z 482.2 (M+H)$^+$

Compound 633 (General Procedure 1, Step I)

(R)-6-cyclopropyl-2-(4-(3-hydroxypropanoyl)-3-methylpiperazin-1-yl)-5-(2-vinylquinolin-5-yl)nicotinonitrile The synthesis was similar to Compound 542.
$^1$H NMR (400 MHz, CHLOROFORM-d) δ 8.21 (d, J=8.2 Hz, 1H), 7.87-7.99 (m, 1H), 7.75-7.85 (m, 1H), 7.58-7.69 (m, 2H), 7.41-7.50 (m, 1H), 7.12 (dd, J=17.0, 11.0 Hz, 1H), 6.35 (d, J=17.5 Hz, 1H), 5.76 (d, J=11.0 Hz, 1H), 4.93 (m, 0.5H), 4.51-4.61 (m, 0.5H), 4.37 (d, J=12.8 Hz, 1H), 4.21-4.29 (m, 1H), 3.88-3.99 (m, 2H), 3.77 (d, J=12.0 Hz, 0.5H), 3.60 (t, J=12.3 Hz, 0.5H), 3.27-3.44 (m, 2H), 3.02-3.26 (m, 1H), 2.49-2.79 (m, 2H), 1.96-2.07 (m, 1H), 1.51-1.60 (m, 1H), 1.27 (s, 3H), 1.08-1.17 (m, 2H), 0.77-0.87 (m, 2H)
LC-MS: m/z 468.2 (M+H)$^+$

Compound 637

(R)-6-cyclopropyl-2-(4-(3-hydroxypropanoyl)-3-methylpiperazin-1-yl)-5-(2-vinylquinazolin-4-yl)nicotinonitrile The synthesis was similar to Compound 542.
$^1$H NMR (CHLOROFORM-d) δ 8.07 (d, J=8.3 Hz, 1H), 7.85-7.96 (m, 2H), 7.81 (d, J=8.0 Hz, 1H), 7.57 (td, J=7.7, 1.0 Hz, 1H), 7.08 (dd, J=17.3, 10.5 Hz, 1H), 6.81 (dd, J=17.3, 1.8 Hz, 1H), 5.79-5.94 (m, 1H), 4.82-4.98 (m, 0.5H), 4.54 (d, J=12 Hz, 0.5H), 4.29-4.48 (m, 2H), 3.93 (br. s., 2H), 3.69-3.82 (m, 0.5H), 3.52-3.66 (m, 0.5H), 3.43-3.52 (m, 1H), 3.31-3.43 (m, 1H), 3.01-3.30 (m, 1.5H), 2.47-2.77 (m, 2H), 1.64-1.79 (m, 1H), 1.42 (d, J=6.5 Hz, 1.5H), 1.32 (d, J=6.5 Hz, 1.5H), 1.11-1.24 (m, 2H), 0.90 (d, J=5.8 Hz, 2H)
LC-MS: m/z 469.2 (M+H)$^+$

Compound 334 (General Procedure 1, Step H)

(R)-6-cyclopropyl-5-(2-ethyl-phenyl)-2-[4-(3-methoxy-propionyl)-3-methyl-piperazin-1-yl]-nicotinonitrile $^1$H NMR (METHANOL-d) δ 7.59 (s, 1H), 7.33-7.36 (d, J=4.4 Hz, 2H), 7.24-7.27 (m, 1H), 7.12-7.13 (d, J=7.6 Hz, 1H), 4.40-4.46 (m, 1H), 4.14-4.23 (m, 2H), 3.92-3.96 (d, J=14.4 Hz, 0.5H), 3.34 (s, 3H), 3.14-3.19 (m, 2H), 3.34 (s, 4H), 2.99-3.14 (m, 0.5H), 2.60-2.81 (m, 2H), 2.46-2.50 (m, 2H), 1.64-1.69 (m, 1H), 1.37-1.41 (q, J=7.2 Hz, 1.3H), 1.26-1.30 (t, J=6.4 Hz, 1.7H), 1.02-1.11 (m, 5H), 0.82-0.91 (m, 2H); LC-MS: m/z 433.6 (M+H)

Compound 357 (General Procedure 1, Step H)

(R)-6-cyclopropyl-5-(2,6-dimethyl-phenyl)-2-[4-(3-methoxy-propionyl)-3-methyl-piperazin-1-yl]-nicotinonitrile $^1$HNMR (METHANOL-d) δ 7.48 (s, 1H), 7.11-7.18 (m, 3H), 4.79 (s, 1H), 4.39-4.45 (m, 1H), 4.21-4.24 (d, J=12.8

Hz, 1.5H), 4.13-4.17 (d, J=13.2 Hz, 0.5H), 3.91-3.95 (d, J=13.6 Hz, 0.5H), 3.66-3.69 (t, J=5.2 Hz, 2H), 3.55-3.61 (t, J=7.2 Hz, 0.5H), 3.34 (s, 4H), 3.10-3.21 (m, 1H), 2.96-3.01 (m, 0.5H), 2.69-2.80 (m, 1H), 2.60-2.65 (m, 1H), 2.01-2.02 (d, J=2.8 Hz, 6H), 1.51-1.57 (m, 1H), 1.38-1.39 (d, J=6.4 Hz, 1.3H), 1.26-1.28 (d, J=6.8 Hz, 1.7H), 1.08-1.11 (m, 1H), 0.75-0.91 (m, 2H) LC-MS: m/z 433.2 (M+H)

Compound 344 (General Procedure 1, Step H)

(R)-6-cyclopropyl-5-(2-hydroxymethyl-phenyl)-2-[4-(3-methoxy-propionyl)-3-methyl-piperazin-1-yl]-nicotinonitrile 1HNMR (METHANOL-d) δ 7.63 (s, 1H), 7.58-7.60 (d, J=7.6 Hz, 1H), 7.40-7.44 (t, J=7.6 Hz, 1H), 7.33-7.36 (t, J=7.6 Hz, 1H), 7.16-7.18 (d, J=7.6 Hz, 1H), 4.78 (s, 1H), 4.36-4.49 (m, 3H), 4.13-4.24 (m, 2H), 3.91-3.95 (d, J=13.2 Hz, 0.5H), 3.66-6.69 (m, 2H), 3.54-3.61 (m, 0.5H), 3.33-3.34 (m, 4H), 3.25-3.28 (m, 0.5H), 3.13-3.15 (m, 1H), 2.96-3.02 (m, 0.5H), 2.69-2.81 (m, 1H), 2.60-2.65 (m, 1H), 1.62-1.68 (m, 1H), 1.37-1.39 (m, 1.5H), 1.25-1.28 (m, 1.5H), 1.11-1.12 (m, 2H), 0.83-0.92 (m, 2H); LC-MS: m/z 435.2 (M+H)

Compound 328 (General Procedure 1, Step H)

(R)-2-cyclopropyl-2'-methoxy-6-[4-(3-methoxy-propionyl)-3-methyl-piperazin-1-yl]-[3,3]bipyridinyl-5-carbonitrile $^1$HNMR (METHANOL-d) δ 8.17-8.18 (dd, J=4.8 Hz, 1H), 7.65 (s, 1H), 7.61-7.63 (dd, J=7.2 Hz, 1H), 7.04-7.07 (dd, J=7.2 Hz, 1H), 4.76-4.78 (m, 0.5H), 4.38-4.44 (m, 1H), 4.13-4.25 (m, 2H), 3.90 (s, 3H), 3.66-3.69 (t, J=5.6 Hz, 2H), 3.54-6.60 (m, 0.5H), 3.33 (s, 3H), 3.15-3.19 (m, 0.5H), 3.12-3.13 (m, 1H), 2.97-3.03 (m, 0.5H), 2.69-2.80 (m, 1H), 2.59-2.65 (m, 1H), 1.67-1.73 (m, 1H), 1.37-1.38 (d, J=6.4 Hz, 1H), 1.25-1.27 (d, J=6.8 Hz, 2H), 1.10-1.11 (m, 2H), 0.85-0.92 (m, 2H) LC-MS: m/z 436.2 (M+H)

Compound 338 (General Procedure 1, Step H)

(R)-6-cyclopropyl-5-[2-(2-methoxy-ethyl)-phenyl]-2-[4-(3-methoxy-propionyl)-3-methyl-piperazin-1-yl]-nicotinonitrile 1HNMR (METHANOL-d) δ 7.63 (s, 1H), 7.51-7.53 (d, J=6.4 Hz, 1H), 7.39-7.42 (m, 2H), 7.22-7.23 (dd, J=6.8 Hz, 1H), 4.15-4.45 (m, 4H), 3.93-3.96 (m, 0.5H), 3.66-3.69 (m, 2H), 3.34 (s, 4H), 3.16-3.17 (d, J=4.0 Hz, 3H), 3.13-3.14 (m, 0.5H), 3.00-3.04 (m, 0.5H), 2.70-2.81 (m, 1H), 2.61-2.64 (m, 1H), 1.63-1.67 (m, 1H), 1.38-1.40 (m, 1H), 1.26-1.29 (m, 2H), 1.12-1.25 (m, 2H), 0.83-0.94 (m, 2H) LC-MS: m/z 449.2 (M+H)

Compound 360 (General Procedure 1, Step H)

(R)-5-(2-chloro-quinolin-3-yl)-6-cyclopropyl-2-[4-(3-methoxy-propionyl)-3-methyl-piperazin-1-yl]-nicotinonitrile 1H NMR (METHANOL-d) δ 8.38 (S, 1H), 8.00-8.02 (m, 2H), 7.85 (t, J=7.2 Hz, 2H), 7.81 (S, 1H), 7.68 (t, J=8.0 Hz, 1H), 4.8 (m, 1H), 4.4-4.5 (m, 1H), 4.2-4.4 (m, 1H), 3.95 (d, J=14.0 Hz, 0.5H), 3.67 (t, J=18.0 Hz, 2h), 3.54-3.60 (m, 0.5H), 3.32-3.45 (m, 4.5H), 3.22-3.25 (m, 1H), 3.09-3.22 (m, 0.5H), 2.71-2.79 (m, 1H), 2.60-2.65 (m, 1H), 1.63-1.69 (m, 1H), 1.39-1.41 (m, 1H), 1.30 (t, J=6.8 Hz, 2H), 1.18-1.24 (m, 1H), 1.12-1.17 (m, 1H), 0.95-1.15 (m, 1H), 0.85-0.95 (m, 1H).

LC-MS: m/z 490.1 (M+H)+.

Compound 371 (General Procedure 1, Step H)

(R)-6-cyclopropyl-2-[4-(3-methoxy-propionyl)-3-methyl-piperazin-1-yl]-5-(2-methyl-2H-pyrazol-3-yl)-nicotinonitrile 1H NMR (METHANOL-d) δ 7.77 (s, 1H), 7.55 (d, J=2.0 Hz, 1H), 6.36 (d, J=2.0 Hz, 1H), 4.78 (m, 0.5H), 4.21-4.44 (m, 3H), 3.94 (d, J=12.6 Hz, 0.5H), 3.66-3.69 (m, 4.5H), 3.54-3.62 (m, 0.5H), 3.33 (m, 3.5H), 2.70-2.82 (m, 1H), 2.59-2.65 (m, 1H), 1.68-1.74 (m, 1H), 1.36 (d, J=6.8 Hz, 1H), 1.27 (d, J=11.2 Hz, 2H), 1.14-1.24 (m, 2H), 0.97-1.02 (m, 2H). LC-MS: m/z 409.2 (M+H)+.

Compound 345 (General Procedure 1, Step H)

(R)-6-cyclopropyl-5-(3,5-dimethyl-isoxazol-4-yl)-2-[4-(3-methoxy-propionyl)-3-methyl-piperazin-1-yl]-nicotinonitrile 1H NMR (METHANOL-d) δ 7.70 (s, 1H), 4.77-4.80 (m, 0.5H), 4.42 (d, J=13.2 Hz, 1H), 4.17-4.28 (m, 2H), 3.94 (d, J=13.2 Hz, 0.5H), 3.68 (t, J=5.2 Hz, 2H), 3.51-3.62 (m, 1H), 3.31-3.33 (m, 3H), 3.14-3.24 (m, 1H), 3.01-3.08 (m, 0.5H), 2.71-2.80 (m, 1H), 2.59-2.70 (m, 1H), 2.30 (s, 3H), 2.14 (s, 3H), 1.75-1.82 (m, 1H), 1.38 (d, J=6.8 Hz, 1H), 1.25 (d, J=11.2 Hz, 2H), 1.15-1.20 (m, 2H), 0.98-1.02 (m, 2H). LC-MS: m/z 424.2 (M+H)+.

Compound 394 (General Procedure 1, Step H)

(R)-6-cyclopropyl-5-(1H-indol-2-yl)-2-[4-(3-methoxy-propionyl)-3-methyl-piperazin-1-yl]-nicotinonitrile $^1$H NMR (CHLOROFORM-d) δ 8.27 (s, 1H), 7.79 (s, 1H0, 7.64 (d, J=8.0 Hz, 1H), 7.23 (t, J=8.0 Hz, 1H), 7.16 (t, J=7.6 Hz, 1H), 6.65 (t, J=1.2 Hz, 1H), 4.89 (s, 0.5H), 4.52 (d, J=13.2 Hz, 0.5H), 4.23-4.35 (m, 2.5H), 3.72-3.77 (m, 2.5H), 3.54-3.60 (m, 0.5H), 3.37 (s, 3H), 3.26-3.32 (m, 1H), 3.04-3.17 (m, 1H), 2.55-2.72 (m, 2H), 2.36-2.43 (m, 1H), 1.37 (d, J=5.6 Hz, 1H), 1.26 (d, J=6.8 Hz, 2H), 1.18-1.20 (m, 2H), 1.03-1.04 (m, 2H). LC-MS: m/z 444.2 (M+H)+.

Compound 361 (General Procedure 1, Step I)

(R)-5-(1H-benzoimidazol-5-yl)-6-cyclopropyl-2-[4-(3-methoxy-propionyl)-3-methyl-piperazin-1-yl]-nicotinonitrile $^1$H NMR (METHANOL-d) 8.226 (s, 1H), 7.764 (s, 1H), 7.697-7.614 (m, 2H), 7.333-7.313 (d, J=8 Hz, 2H), 4.775-4.856 (m, 0.5H), 4.459-4.389 (m, 1H), 4.268-4.147 (m, 2H), 3.968-3.929 (m, 0.5H), 3.688-3.567 (m, 3H), 3.342 (s, 3H), 3.193-3.022 (m, 2H), 2.814-2.626 (m, 2H), 2.125-2.076 (m, 1H), 1.402-1.274 (m, 3H), 1.175 (s, 2H), 1.54-0.928 (m, 2H). LC-MS: m/z 445.1 (M+H)+.

Compound 352 (General Procedure 1, Step I)

(R)-5-benzothiazol-5-yl-6-cyclopropyl-2-[4-(3-methoxy-propionyl)-3-methyl-piperazin-1-yl]-nicotinonitrile 1H NMR (METHANOL-d) 9.301 (s, 1H), 8.163-8.142 (d, J=8.4 Hz, 1H), 8.102-8.099 (d, J=1.2, 1H), 7.807 (s, 1H), 7.559-7.535 (dd, J1=9.6 Hz, J2=1.6 Hz, 1H), 4.792 (m, 0.5H), 4.453-4.418 (m, 1H), 4.282-4.170 (m, 2H), 3.959-3.926 (m, 0.5H), 3.682-3.667 (m, 2H), 3.616-3.561 (m, 0.5H), 3.338 (s, 3H), 3.212-3.004 (m, 2H), 2.806-2.594 (m, 2H), 2.085-2.022 (m, 1H), 1.392-1.262 (m, 3H), 1.211-1.176 (m, 2H), 1.000-0.900 (m, 2H). LC-MS: m/z 462.1 (M+H)+.

Compound 364 (General Procedure 1, Step I)

(R)-5-benzothiazol-6-yl-6-cyclopropyl-2-[4-(3-methoxy-propionyl)-3-methyl-piperazin-1-yl]-nicotinonitrile 1H NMR (METHANOL-d) 9.292 (s, 1H), 8.131 (s, 2H), 7.806 (s, 1H), 7.624-7.606 (d, J=7.2 Hz, 1H), 4.775-4.856 (m, 0.5H), 4.412-4.172 (m, 3H), 3.960-3.931 (m, 0.5H), 3.555-3.688 (m, 3H), 3.345 (s, 3H), 3.188-3.038 (m, 2H), 2.762-2.640 (m, 2H), 2.047-2.035 (m, 1H), 1.379-1.266 (m, 3H), 1.192 (s, 2H), 0.965 (s, 2H). LC-MS: m/z 462.0 (M+H)+.

Compound 417 (General Procedure 1, Step I)

(R)-5-(2-amino-benzothiazol-6-yl)-6-cyclopropyl-2-[4-(3-methoxy-propionyl)-3-methyl-piperazin-1-yl]-nicotinonitrile 1H NMR (CHLOROFORM-d) 7.844 (s, 1H), 7.719-7.715 (d, J=1.6 Hz, 1H), 7.547 (s, 2H), 7.402-7.381 (d, J=8.4 Hz, 1H), 7.266-7.242 (d, J=9.6, 1H), 4.631-4.664 (m, 0.5H), 4.297-4.017 (m, 3H), 3.869-3.838 (m, 0.5H), 3.564-3.453 (m, 3H), 3.349-3.228 (m, 3H), 3.109-2.929 (m, 2H), 2.669-2.500 (m, 2H), 2.081-2.058 (m, 1H), 1.236 (s, 1H), 1.135-1.079 (m, 4H), 0.964-0.936 (m, 2H). LC-MS: m/z 477.1 (M+H)+.

Compound 370 (General Procedure 1, Step I)

(R)-6-cyclopropyl-2-[4-(3-methoxy-propionyl)-3-methyl-piperazin-1-yl]-5-tetrazolo[1,5-a]pyridin-6-yl-nicotinonitrile 1H NMR (METHANOL-d) 9.213-9.215 (d, J=0.8 Hz, 1H), 8.131-8.154 (d, J=9.2 Hz, 1H), 7.917-7.947 (m, 2H), 4.784 (s, 0.5H), 4.220-4.782 (m, 3H), 3.973-3.939 (d, J=13.6 Hz, 0.5H), 3.680 (s, 0.5H), 3.051-3.40 (m, 6H), 2.595-2.821 (m, 2H), 1.973-2.033 (m, 1H), 1.231-1.369 (m, 5H), 0.90-1.120 (s, 2H). LC-MS: m/z 447.1 (M+H)+.

Compound 367 (General Procedure 1, Step I)

(R)-6-cyclopropyl-5-isoquinolin-8-yl-2-[4-(3-methoxy-propionyl)-3-methyl-piperazin-1-yl]-nicotinonitrile 1H NMR (METHANOL-d) 9.342-9.356 (d, J=5.6 Hz, 1H), 8.626-8.642 (d, J=6.4 Hz, 1H), 8.530-8.546 (d, J=6.4 Hz 1H), 8.347-8.368 (d, J=8.4 Hz 1H), 8.263-8.284 (d, J=8.4 Hz 1H), 7.976-7.994 (d, J=7.2 Hz, 1H), 7.912 (s, 1H), 4.814 (s, 0.5H), 4.265-4.808 (m, 3H), 3.968-4.002 (m, 2.5H), 3.151-3.441 (m, 5H), 2.622-2.804 (m, 2H), 1.182-1.496 (m, 5H), 0.801-0.981 (m, 2H). LC-MS: m/z 456.1 (M+H)+.

Compound 373 (General Procedure 1, Step I)

(R)-6-cyclopropyl-5-(1H-indol-7-yl)-2-[4-(3-methoxy-propionyl)-3-methyl-piperazin-1-yl]-nicotinonitrile 1H NMR (METHANOL-d) 7.759 (s, 1H), 7.579-7.599 (d, J=8 Hz, 1H), 7.218 (s, 1H), 7.080-7.099 (d, J=7.6 Hz 1H), 7.000-7.018 (d, J=7.2 Hz 1H), 6.506-6.513 (d, J=7.2 Hz, 1H), 4.417-4.466 (dd, J=8 Hz, 1H), 4.191-4.261 (m, 3H), 3.940-3.976 (d, J=1.44 Hz, 0.5H), 3.603-3.642 (m, 3H), 2.617-3.346 (m, 7H), 1.717-1.828 (m, 1H), 1.155-1.421 (m, 5H), 0.832-0.851 (dd, J=4.4 HZ, 2H). LC-MS: m/z 444.2 (M+H)+.

Compound 353 (General Procedure 1, Step I)

(R)-6-cyclopropyl-2-[4-(3-methoxy-propionyl)-3-methyl-piperazin-1-yl]-5-quinolin-6-yl-nicotinonitrile $^1$H NMR (METHANOL-d) 9.170-9.183 (d, J=5.2 Hz, 1H), 9.076-9.097 (d, J=8.4 Hz, 1H), 8.304-8.333 (t, 2H), 8.194-8.216 (d, J=8.8 Hz 1H), 8017-8.050 (m, 1H), 7.918 (s, 1H), 4.787 (s, 0.5H), 4.214-4.447 (m, 3H), 3.974-4.214 (d, J=96 Hz, 0.5H), 3.336-3.397 (m, 3H), 3.076-3.3.250 (m, 5H), 2.599-2.811 (m, 2H), 2.023-2.043 (m, 1H), 1.363-1.379 (d, J=6.4 Hz 1H), 1.244-1.263 (d, J=7.6 Hz 4H), 0.99-1.026 (m, 2H). LC-MS: m/z 456.1 (M+H)+.

Compound 374 (General Procedure 1, Step I)

(R)-6-cyclopropyl-2-[4-(3-methoxy-propionyl)-3-methyl-piperazin-1-yl]-5-(1H-pyrrolo[2,3-b]pyridin-5-yl)-nicotinonitrile $^1$H NMR (METHANOL-d) 8.313 (s, 1H), 8.280 (s, 1H), 7.831 (s, 1H), 7.563-7.572 (d, J=3.6 Hz 1H), 6.682-6.690 (d, J=3.2 Hz 1H), 4.795 (s, 0.5H), 4.183-4.455 (m, 3H), 3.929-3.969 (m, 0.5H), 3.568-3.687 (m, 3H), 3.179-3.342 (m, 4H), 3.046-3.078 (m, 1H), 2.609-2.810 (m, 2H), 2.020 (s, 1H), 1.194-1.392 (m, 5H), 0.964-0.991 (m, 2H). LC-MS: m/z 445.2 (M+H)+.

Compound 395 (General Procedure 1, Step I)

(R)-(4-{5-cyano-2-cyclopropyl-6-[4-(3-methoxy-propionyl)-3-methyl-piperazin-1-yl]-pyridin-3-yl}-thiazol-2-yl)-carbamic acid tert-butyl ester $^1$H NMR (CHLOROFORM-d) 8.282 (s, 1H), 7.884-7.889 (d, J=2 Hz, 1H), 6.947-6.951 (d, J=1.6 Hz, 1H), 4.888 (s, 0.5H), 4.493-4.524 (d, J=12.4 Hz, 0.5H), 4.205-4.371 (m, J=44.8 Hz, 2.5H), 3.719-3.790 (m, J=28.4 Hz, 2.5H), 3.499-3.550 (m, J=20.4, 0.5H), 3.367-3.372 (d, J=2 Hz, 3H), 3.218-3.246 (t, J=11.2 Hz, 1H), 3.006-3.118 (m, J=44.8 Hz, 1.5H), 2.544-2.745 (m, J=80.4 Hz, 2H), 2.404-2.465 (m, J=24.4 Hz, 1H), 1.532 (s, 9H), 1.243-1.355 (q, J=44.8 Hz, 3H), 1.153-1.158 (d, J=2 Hz, 2H), 0.969-0.985 (t, J=6.4 Hz, 2H). LC-MS: m/z 527.2 (M+H)+.

Compound 418 (General Procedure 1, Step I)

(R)-6-cyclopropyl-2-[4-(3-methoxy-propionyl)-3-methyl-piperazin-1-yl]-5-(2-methyl-1-oxo-1,2-dihydro-isoquinolin-4-yl)-nicotinonitrile 1H NMR (CHLOROFORM-d) 8.506-8.526 (d, J=8.0 Hz, 1H), 7.617-7.658 (t, J=16.4 Hz, 1H), 7.596 (s, 1H), 7.529-7.569 (t, J=16 Hz, 1H), 7.209-7.240 (t, J=12.4 Hz, 1H), 7.036 (s, 1H), 4.916 (s, 0.5H), 4.534-4.642 (m, J=43.2 Hz, 3H), 4.208-4.351 (m, J=57.2 Hz, 3H), 3.836-3.869 (m, J=13.2 Jz, 0.5H), 3.681-3.739 (t, J=23.2 Hz, 2H), 3.589 (s, 3H), 3.287-3.371 (m, J=33.6 Hz, 1H), 3.155-3.192 (m, 1.5H), 2.594-2.773 (m, 2H), 1.678-1.740 (m, J=24.8 Hz, 1H), 1.301-1.423 (d, J=48.8 Hz, 3H), 1.089-1.143 (m, 2H), 0.809-0.909 (m, 2H). LC-MS: m/z 486.2 (M+H)+.

Compound 354 (General Procedure 1, Step I)

(R)-6-cyclopropyl-2-[4-(3-methoxy-propionyl)-3-methyl-piperazin-1-yl]-5-(4-morpholin-4-yl-phenyl)-nicotinonitrile 1H NMR (CHLOROFORM-d) 7.665 (s, 1H), 7.348-7.327 (d, J=8.4 Hz, 2H), 7.129-7.107 (d, J=8.8 Hz, 2H), 4.824-4.780 (m, 1H), 4.440-4.408 (m, 1H), 4.220-4.109 (m, 2H), 3.884-3.860 (m, 4H), 3.693-3.520 (m, 3H), 3.361-3.4 (s, 3H), 3.230-3.298 (m, 4.5H), 3.183-2.988 (m, 1.5H), 2.798-2.600 (m, 2H), 2.115-2.076 (m, 1H), 1.382-1.253 (m, 3H), 1.162-1.128 (m, 2H), 0.986-0.957 (m, 2H). LC-MS: m/z 490.2 (M+H)+.

Compound 396 (General Procedure 1, Step I)

(R)-2-cyclopropyl-6-[4-(3-methoxy-propionyl)-3-methyl-piperazin-1-yl]-6'-piperazin-1-yl-[3,3']bipyridinyl-5-carbonitrile 1H NMR (CHLOROFORM-d) 8.201-8.207 (d, J=2.4 Hz, 1H), 7.531 (s, 2H), 6.718-6.739 (d, J=8.4 Hz, 1H), 4.867 (m, 1H), 4.477-4.507 (m, 4H), 4.149-4.302 (m, 3H), 4.17-4.39 (m, 3H), 3.601-3.807 (m, 6H), 3.494-3.549 (m, 1H), 3.349 (s, 3H), 2.992-3.213 (m, 6H), 2.531-2.734 (m, 2H), 1.974-2.030 (m, 1H), 1.352-1.367 (d, J=6 Hz, 1H), 1.235-1.265 (t, 2H), 0.967-0.992 (m, 2H). LC-MS: m/z 490.2 (M+H)+.

Compound 406 (General Procedure 1, Step I)

(R)-6-cyclopropyl-2-[4-(3-methoxy-propionyl)-3-methyl-piperazin-1-yl]-5-[3-(1H-pyrazol-4-yl)-phenyl]-nicotinonitrile 1H NMR (CHLOROFORM-d) 8.030 (s, 2H), 7.735 (s, 1H), 7.589-7.613 (m, 2H), 7.423-7.462 (m, 1H), 7.242-7.269 (m, 1H), 4.781 (m, 0.5H), 4.376-4.441 (m, 1H), 4.131-4.243 (m, 2H), 3.908-3.940 (d, J=12.8 Hz, 1H), 3.660-3.675 (m, 2H), 3.540-3.602 (m, 0.5H), 3.334 (s, 3H), 3.253-3.262 (d, J=3.6 Hz, 0.5H), 3.122-3.183 (t, 1H), 2.966-3.022 (t, 0.5H), 2.631-2.810 (m, 1H), 2.586-2.615 (m, 1H), 2.061-2.124 (m, 1H), 1.362-1.379 (d, J=6.8 Hz, 1H), 1.249-1.266 (d, J=6.8 Hz, 1H), 1.165-1.182 (m, 2H), 0.900-0.970 (m, 2H) 137. LC-MS: m/z 471.2 (M+H)+.

Compound 363 (General Procedure 1, Step I)

(R)-6-cyclopropyl-2-[4-(3-methoxy-propionyl)-3-methyl-piperazin-1-yl]-5-[3-(1H-pyrazol-3-yl)-phenyl]-nicotinonitrile ¹H NMR (CHLOROFORM-d) 7.820-7.824 (d, J=1.6 Hz, 1H), 7.767-7.795 (t, 2H), 7.686-7.692 (d, J=2.4 Hz, 1H), 7.490-7.528 (t, 1H), 7.374-7.393 (d, J=7.6 Hz, 1H), 6.720-6.725 (d, J=2 Hz, 1H), 4.790 (m, 0.5H), 4.396-4.452 (m, 1H), 4.153-4.264 (m, 2H), 3.920-3.953 (d, J=13.2 Hz, 0.5H), 3.608-3.680 (m, 2H), 3.554-3.582 (t, 0.5H), 3.337 (s, 3H), 3.220 (m, 0.5H), 3.140-3.197 (t, 1H), 2.986-3.043 (t, 0.5H), 2.751-2.803 (m, 1H), 2.591-2.729 (m, 1H), 2.069-2.120 (m, 1H), 1.372-1.388 (d, J=6.4 Hz, 1H), 1.259-1.276 (d, J=6.8 Hz, 2H), 1.156-1.191 (m, 2H), 0.982 (m, 2H). LC-MS: m/z 471.4 (M+H)+.

Compound 436 (General Procedure 1, Step I)

(R)-6-cyclopropyl-5-imidazo[1,2-a]pyridin-6-yl-2-[4-(3-methoxy-propionyl)-3-methyl-piperazin-1-yl]-nicotinonitrile ¹H NMR (CHLOROFORM-d) 8.126 (s, 1H), 7.952 (bs, 1H), 7.681-7.684 (d, J=1.2 Hz, 1H), 7.621 (s, 1H), 7.547 (s, 1H), 7.257-7.280 (d, J=13.6 Hz, 1H), 4.823 (br, 0.5H), 4.436-4.467 (d, J=12.4 Hz, 0.5H), 4.149-4.278 (m, 3H)), 3.649-3.717 (m, 2.5H), 3.446-3.501 (m, 0.5H), 3.299 (s, 3H), 3.219-3.254 (m, 1H), 3.019-3.121 (m, 2H), 2.628-2.646 (m, 1H), 2.501-2.531 (m, 1H), 1.842-1.897 (m, 1H), 1.293-1.308 (d, J=6 Hz, 1.5H), 1.183-1.204 (d, J=8.4 Hz, 1.5H), 1.097-1.115 (m, 2H), 0.902-0.933 (m, 2H). LC-MS: m/z 445.1 (M+H)+.

Compound 437 (General Procedure 1, Step I)

(R)-5-benzo[1,2,5]oxadiazol-4-yl-6-cyclopropyl-2-[4-(3-methoxy-propionyl)-3-methyl-piperazin-1-yl]-nicotinonitrile 1H NMR (CHLOROFORM-d) 7.785-7.808 (d, J=9.2 Hz, 1H), 7.646 (s, 1H), 7.433-7.473 (d, J=16 Hz, 1H), 7.335-7.353 (dd, J=7.2 Hz, 1H), 4.835 (m, 0.5H), 4.441 (m, 0.5H), 4.201-4.320 (m, 3H)), 3.669-3.725 (m, 2.5H), 3.478-3.487 (m, 0.5H), 3.312 (s, 3H), 3.103-3.106 (m, 1H), 3.402-3.705 (m, 2H), 2.596-2.654 (m, 1H), 2.484-2.537 (m, 1H), 1.769-1.800 (m, 1H), 1.308 (m, 1.5H), 1.204-1.219 (d, J=6 Hz, 1.5H), 1.127-1.145 (m, 2H), 0.870-0.889 (m, 2H). LC-MS: m/z 447.1 (M+H)+.

Compound 438 (General Procedure 1, Step I)

(R)-6-cyclopropyl-5-(1H-indazol-4-yl)-2-[4-(3-methoxy-propionyl)-3-methyl-piperazin-1-yl]-nicotinonitrile ¹H NMR (CHLOROFORM-d) 7.887 (bs, 1H), 7.646 (s, 1H), 7.462-7.483 (d, J=8.4 Hz, 1H), 7.391-7.429 (t, J=15.2 Hz, 1H), 7.055-7.071 (d, J=6.4 Hz, 1H), 4.859 (m, 0.5H), 4.465-4.500 (d, J=14 Hz, 0.5H), 4.166-4.281 (m, 3H)), 3.671-3.733 (m, 2.5H), 3.486-3.510 (m, 0.5H), 3.312 (s, 3H), 3.200-3.252 (m, 1H), 2.992-3.103 (m, 2H), 2.614-2.670 (m, 1H), 2.527-2.557 (m, 1H), 1.819-1.840 (m, 1H), 1.340-1.355 (d, J=6 Hz, 1.5H), 1.238-1.253 (d, J=6 Hz, 1.5H), 1.101-1.117 (m, 2H), 0.819-0.846 (m, 2H). LC-MS: m/z 445.1 (M+H)+.

Compound 473 (General Procedure 1, Step I)

(R)-6-cyclopropyl-2-[4-(3-methoxy-propionyl)-3-methyl-piperazin-1-yl]-5-(2-oxo-2,3-dihydro-benzo-oxazol-5-yl)-nicotinonitrile 1H NMR (CHLOROFORM-d) 8.492 (s, 1H), 7.568-7.569 (d, J=0.4 Hz, 1H), 7.277 (s, 1H), 7.121-7.125 (t, 1H), 7.064-7.068 (d, J=1.6 Hz, 1H), 6.720-6.725 (d, J=2 Hz, 1H), 4.897 (m, 0.5H), 4.510-4.549 (m, 0.5H), 4.175 (m, 2.5H), 3.780 (m, 2.5H), 3.543 (t, 0.5H), 3.369 (s, 3H), 3.246-3.273 (m, 1H), 3.113-3.119 (m, 1H), 3.019-3.048 (t, 0.5H), 2.649-2.759 (m, 1H), 2.556-2.609 (m, 1H), 1.998-2.006 (m, 1H), 1.268-1.387 (m, 3H), 1.129-1.155 (m, 2H), 0.928-0.955 (m, 2H). LC-MS: m/z 462.1 (M+H)+.

Compound 474 (General Procedure 1, Step I)

(R)-6-cyclopropyl-5-(1-methoxy-isoquinolin-4-yl)-2-[4-(3-methoxy-propionyl)-3-methyl-piperazin-1-yl]-nicotinonitrile $^1$H NMR (CHLOROFORM-d) 8.350-8.325 (d, J=10 Hz, 1H), 7.913 (s, 1H), 7.660-7.415 (m, 4H), 4.915 (s, 0.5H), 4.562-4.530 (m, 0.5H), 4.278-4.228 (m, 2.5H), 4.261 (s, 3H), 3.797-3.553 (m, 3H), 3.797 (s, 3H), 3.577-3.044 (m, 2.5H), 2.750-2.568 (m, 2H), 1.633-1.625 (m, 1H), 1.429-1.322 (m, 3H), 1.137-1.093 (m, 2H), 0.842-0.765 (m, 2H). LC-MS: m/z 486.1 (M+H)+.

Compound 299

(R)-6-cyclopropyl-2-(3-cyclopropyl-4-(3-methoxy-propanoyl)piperazin-1-yl)-5-(4-fluorophenyl)-4-methylnicotinonitrile $^1$H NMR (CHLOROFORM-d) δ 7.10-7.16 (m, 4H), 4.62-4.65 (m, 0.5H), 4.23 (d, J=12.8 Hz, 1H), 4.15 (d, J=12.5 Hz, 1H), 4.04 (d, J=8.3 Hz, 0.5H), 3.61-3.88 (m, 3.5H), 3.31-3.38 (m, 3H), 3.25 (br. s., 0.5H), 3.02-3.17 (m, 1H), 2.89-3.02 (m, 1H), 2.51-2.73 (m, 2H), 2.09-2.18 (m, 3H), 1.53-1.59 (m, 1H), 1.33-1.44 (m, 1H), 0.99-1.08 (m, 2H), 0.75-0.86 (m, 2H), 0.29-0.63 (m, 4H)
LC-MS: m/z 463.4 (M+H)+

Compound 300

(R)-6-cyclopropyl-2-(3-cyclopropyl-4-(3,3,3-trifluoropropanoyl)piperazin-1-yl)-5-(4-fluorophenyl)-4-methylnicotinonitrile $^1$H NMR (CHLOROFORM-d) δ 7.19 (d, J=7.3 Hz, 4H), 4.70 (br. s., 0.5H), 4.30 (d, J=13.1 Hz, 1H), 4.18-4.27 (m, 1H), 4.12 (d, J=8.3 Hz, 0.5H), 3.81-3.94 (m, 1H), 3.66-3.78 (m, 1H), 3.32 (q, J=9.8 Hz, 2H), 3.08-3.21 (m, 1H), 2.97-3.08 (m, 1H), 2.14-2.25 (m, 3H), 1.58-1.67 (m, 1H), 1.50 (br. s., 1H), 1.04-1.14 (m, 2H), 0.81-0.89 (m, 2H), 0.65 (br. s., 1H), 0.56 (br. s., 1H), 0.37-0.52 (m, 2H)
LC-MS: m/z 487.2 (M+H)$^{30}$

Compound 627

(R)-6-cyclopropyl-2-(4-(3-methoxypropanoyl)-3-methylpiperazin-1-yl)-4-methyl-5-(6-vinylpyrimidin-4-yl)nicotinonitrile 1H NMR (CHLOROFORM-d) δ 9.30 (d, J=1.1 Hz, 1H), 9.30 (d, J=1.1 Hz, 1H), 7.32 (t, J=4.5 Hz, 1H), 6.82 (dd, J=17.4, 10.7 Hz, 1H), 6.64-6.49 (m, 1H), 5.81 (dd, J=14.9, 4.1 Hz, 1H), 4.93 (d, J=17.7 Hz, 1H), 4.53 (d, J=13.3 Hz, 1H), 4.20 (dd, J=33.1, 13.9 Hz, 2H), 3.77 (dd, J=18.0, 11.5 Hz, 2H), 3.57 (dd, J=12.8, 9.6 Hz, 1H), 3.39 (s, 3H), 3.34-2.95 (m, 3H), 2.82-2.49 (m, 2H), 2.26 (s, 3H), 2.88-1.49 (m, 8H), 1.57 (ddd, J=12.5, 8.0, 4.5 Hz, 1H), 1.45-1.37 (m, 2H), 1.33-1.28 (m, 2H), 1.14 (dt, J=7.4, 3.5 Hz, 2H), 0.96-0.81 (m, 3H).
LC-MS: m/z 447.2 (M+H)$^+$

Compound 628

(R)-2-cyclopropyl-6-(4-(3-methoxypropanoyl)-3-methylpiperazin-1-yl)-4-methyl-2'-vinyl-[3,4'-bipyridine]-5-carbonitrile 1H NMR (CHLOROFORM-d) δ 8.70 (d, J=4.9 Hz, 1H), 7.23 (s, 1H), 7.08 (d, J=4.1 Hz, 1H), 6.88 (dd, J=17.4, 10.8 Hz, 1H), 6.30 (d, J=17.4 Hz, 1H), 5.58 (d, J=10.9 Hz, 1H), 4.92 (s, 1H), 4.53 (t, J=14.2 Hz, 1H), 4.29-4.08 (m, 3H), 3.76 (t, J=6.3 Hz, 2H), 3.57 (dd, J=23.8, 17.1 Hz, 1H), 3.40 (s, 3H), 3.31-2.95 (m, 3H), 2.68 (ddd, J=33.7, 17.4, 11.1 Hz, 2H), 2.20 (d, J=8.0 Hz, 3H), 1.57 (ddd, J=12.5, 8.1, 4.6 Hz, 1H), 1.41 (d, J=6.3 Hz, 2H), 1.36-1.25 (m, 4H), 1.10 (s, 2H), 0.94-0.74 (m, 3H).
LC-MS: m/z 446.2 (M+H)$^+$

Compound 411

(R)-5-(4-aminophenyl)-6-cyclopropyl-2-(4-(3-methoxypropanoyl)-3-methylpiperazin-1-yl)-4-methylnicotinonitrile 1H NMR (CHLOROFORM-d) δ: 6.97-7.10 (m, 2H), 6.87-6.97 (m, J=8.0 Hz, 2H), 4.92 (br. s., 0.5H), 4.54 (d, J=13.3 Hz, 0.5H), 4.23 (br. s., 0.5H), 3.95-4.18 (m, 2H), 3.71-3.83 (m, 2.5H), 3.58 (m, 0.5H) 3.40 (s, 3H), 3.11-3.27 (m, 1.5H), 2.88-3.10 (m, 1H), 2.53-2.82 (m, 2H), 2.16-2.28 (m, 3H), 1.68-1.78 (m, 1H), 1.38-1.47 (m, 1.5H), 1.33 (d, J=6.5 Hz, 1.5H), 0.98-1.13 (m, 2H), 0.75-0.93 (m, 2H)
LC-MS: m/z 433.5 (M+H)$^+$

Compound 278

(R)-6-cyclopropyl-5-(6-methoxynaphthalen-2-yl)-2-(4-(3-methoxypropanoyl)-3-methylpiperazin-1-yl)-4-methylnicotinonitrile $^1$H NMR (CHLOROFORM-d) δ 7.83 (d, J=8.3 Hz, 1H), 7.71-7.78 (m, 1H), 7.60 (s, 1H), 7.25-7.32 (m, 1H), 7.17-7.24 (m, 2H), 4.92 (br. s., 0.5H), 4.55 (d, J=13.3 Hz, 0.5H), 4.05-4.21 (m, 2.5H), 3.91-4.00 (m, 3H), 3.69-3.87 (m, 2.5H), 3.52-3.69 (m, 0.5H), 3.33-3.46 (m, 3H), 3.13-3.29 (m, 1.5H), 2.97-3.11 (m, 1H), 2.65-2.83 (m, 1H), 2.60 (dd, J=13.1, 6.5 Hz, 1H), 2.17-2.28 (m, 3H), 1.61-1.74 (m, 1H), 1.39-1.49 (m, 1.5H), 1.33 (d, J=6.5 Hz, 1.5H), 0.99-1.17 (m, 2H), 0.69-0.84 (m, 2H)
LC-MS: m/z 499.1 (M+H)$^+$

Compound 282

(R)-6-cyclopropyl-5-(2-fluorobiphenyl-4-yl)-2-(4-(3-methoxypropanoyl)-3-methylpiperazin-1-yl)-4-methylnicotinonitrile $^1$H NMR (CHLOROFORM-d) δ 7.61 (d, J=8.0 Hz, 2H), 7.44-7.57 (m, 3H), 7.37-7.44 (m, 1H), 7.00-7.10 (m, 2H), 4.91 (br. s., 0.5H), 4.54 (d, J=13.1 Hz, 0.5H), 4.04-4.32 (m, 2.5H), 3.69-3.89 (m, 2.5H), 3.58 (t, J=10.8 Hz, 0.5H), 3.34-3.42 (m, 3H), 3.12-3.30 (m, 1.5H), 2.93-3.12 (m, 1H), 2.64-2.82 (m, 1H), 2.59 (dd, J=13.3, 6.5 Hz, 1H), 2.25 (s, 3H), 1.66-1.76 (m, 1H), 1.41 (d, J=6.3 Hz, 1.5H), 1.32 (d, J=6.8 Hz, 1.5H), 1.04-1.15 (m, 2H), 0.87 (dt, J=7.5, 3.7 Hz, 2H)

LC-MS: m/z 513.1 (M+H)$^+$

Compound 318 (General Procedure 6, Step G')

(R)-6-cyclopropyl-5-(3-methyl-pyridyl-5-yl)-2-[4-(3-methoxy-propionyl)-3-methyl-piperazin-1-yl]-nicotinonitrile 1H NMR (METHANOL-d) δ 8.79 (s, 1H), 8.70 (s, 1H), 8.40 (d, J=0.4 Hz, 1H), 4.77-4.79 (m, 0.5H), 4.42 (d, J=14.4 Hz, 1H), 4.22-4.24 (m, 1.5H), 4.14 (d, J=13.2 Hz, 0.5H), 3.94 (d, J=13.2 Hz, 0.5H), 3.68 (t, J=6.0 Hz, 2H), 3.55-3.62 (m, 0.5H), 3.31-3.33 (m, 3H), 3.13-3.22 (m, 1H), 3.00-3.06 (m, 0.5H), 2.68-2.82 (m, 1H), 2.58-2.63 (m, 4H), 2.22 (s, 3H), 1.47-1.54 (m, 1H), 1.37 (d, J=6.8 Hz, 1H), 1.26 (d, J=11.2 Hz, 2H), 1.13-1.17 (m, 2H), 0.91-0.94 (m, 2H)

LC-MS: m/z 434.2 (M+H)+.

Compound 319 (General Procedure 6, Step G')

(R)-6-cyclopropyl-5-(4-methanesulfonyl-phenyl)-2-[4-(3-methoxy-propionyl)-3-methyl-piperazin-1-yl]-4-methyl-nicotinonitrile $^1$H NMR (METHANOL-d) d 8.07 (d, J=8.4 Hz, 2H), 7.52 (d, J=8.4 Hz, 2H), 4.75-4.85 (m, 0.5H), 4.35-4.48 (m, 3H), 4.05-4.12 (m, 2H), 3.88-3.97 (m, 0.5H), 3.65-3.72 (m, 2H), 3.52-3.62 (m, 0.5H), 3.43 (s, 3H), 3.34 (s, 3H), 3.03-3.25 (m, 2H), 2.87-2.98 (m, 0.5H), 2.68-2.85 (m, 1H), 2.57-2.63 (m, 1H), 2.18 (s, 3H), 1.62-1.69 (m, 1H), 1.34-1.41 (m, 3H), 1.05-1.09 (m, 2H), 0.78-0.85 (m, 2H)

LC-MS: m/z 497.2 (M+H)$^+$

Compound 320 (General Procedure 6, Step G')

(R)-2-cyclopropyl-2'-methoxy-6-[4-(3-methoxy-propionyl)-3-methyl-piperazin-1-yl]-4-methyl-[3,3']bipyridinyl-5-carbonitrile 1H NMR (METHANOL-d) δ 8.22 (dd, J1=2.0 Hz, J2=4.8 Hz, 1H), 7.54 (dd, J1=2.0 Hz, J2=7.2 Hz, 1H), 7.07-7.10 (m, 1H), 4.78 (s, 0.5H), 4.38-4.45 (m, 1H), 4.01-4.13 (m, 2H), 3.88-3.94 (m, 3.5H), 3.66-3.69 (m, 2H), 3.55-3.61 (m, 0.5H), 3.33 (s, 3H), 3.09-3.25 (m, 2H), 2.91-2.97 (m, 0.5H), 2.69-2.78 (m, 1H), 2.60-2.64 (m, 1H), 2.12 (s, 3H), 1.49-1.52 (m, 1H), 1.40 (d, J=6.4 Hz, 1.3H), 1.28 (dd, J1=2.4 Hz, J2=6.4 Hz, 1.7H), 0.99-1.10 (m, 2H), 0.80-0.83 (m, 2H)

LC-MS: m/z 450.2 (M+H)$^+$

Compound 321 (General Procedure 6, Step G')

(R)-5-(3-cyano-4-fluoro-phenyl)-6-cyclopropyl-2-[4-(3-methoxy-propionyl)-3-methyl-piperazin-1-yl]-4-methyl-nicotinonitrile 1H NMR (METHANOL-d) δ 7.71 (dd, J1=2.0 Hz, J2=6.4 Hz, 1H), 7.60-7.64 (m, 1H), 7.50 (t, J=9.2 Hz, 1H), 4.77-4.79 (m, 0.5H), 4.38-4.44 (m, 1H), 4.05-4.16 (m, 2H), 3.93 (d, J=13.6 Hz, 0.5H), 3.67-369 (m, 2H), 3.57-3.58 (m, 0.5H), 3.33 (s, 3H), 3.21-3.28 (m, 1H), 3.11-3.15 (m, 1H), 2.96-2.97 (m, 0.5H), 2.69-2.77 (m, 1H), 2.59-2.65 (m, 1H), 2.17 (s, 3H), 1.50-1.54 (m, 1H), 1.38 (d, J=6.4 Hz, 1.3H), 1.26 (d, J=6.8 Hz, 1.7H), 1.09-1.10 (m, 2H), 0.84-0.89 (m, 2H)

LC-MS: m/z 462.1 (M+H)$^+$

Compound 322 (General Procedure 6, Step G')

(R)-6-cyclopropyl-5-(3-methoxymethyl-phenyl)-2-[4-(3-methoxy-propionyl)-3-methyl-piperazin-1-yl]-4-methyl-nicotinonitrile 1H NMR (METHANOL-d) δ 7.47 (t, J=7.6 Hz, 1H), 7.38 (d, J=8.0 Hz, 1H), 7.20 (s, 1H), 7.15 (d, J=7.6 Hz, 1H), 4.79 (s, 0.5H), 4.50 (s, 2H), 4.37-4.45 (m, 1H), 4.01-4.12 (m, 2H), 3.93 (d, J=13.6 Hz, 0.5H), 3.66-3.69 (m, 2H), 3.55-3.62 (m, 0.6H), 3.39 (s, 3H), 3.33 (s, 3H), 3.04-3.29 (m, 2H), 2.90-2.97 (m, 0.5H), 2.59-2.81 (m, 2H), 2.15 (s, 3H), 1.62-1.66 (m, 1H), 1.42 (d, J=6.4 Hz, 1.4H), 1.31 (d, J=6.4 Hz, 1.6H), 1.02-1.09 (m, 2H), 0.77-0.84 (m, 2H)

LC-MS: m/z 463.2 (M+H)$^+$

Compound 323 (General Procedure 6, Step G')

(R)-6-cyclopropyl-5-(3-fluoro-4-methoxy-phenyl)-2-[4-(3-methoxy-propionyl)-3-methyl-piperazin-1-yl]-4-methyl-nicotinonitrile 1H NMR (METHANOL-d) δ 7.19 (t, J=8.4 Hz, 1H), 6.95-6.99 (m, 2H), 4.75-4.85 (m, 0.5H), 4.35-4.48 (m, 1H), 4.05-4.12 (m, 2H), 3.88-3.97 (m, 3.5H), 3.65-3.72 (m, 2H), 3.52-3.62 (m, 0.5H), 3.34 (s, 3H), 3.03-3.25 (m, 2H), 2.87-2.98 (m, 0.5H), 2.68-2.85 (m, 1H), 2.57-2.63 (m, 1H), 2.18 (s, 3H), 1.62-1.69 (m, 1H), 1.34-1.41 (m, 3H), 1.05-1.09 (m, 2H), 0.78-0.85 (m, 2H)

LC-MS: m/z 467.2 (M+H)$^+$

Compound 324 (General Procedure 6, Step G')

(R)-6-cyclopropyl-5-(2-fluoro-3-methoxy-phenyl)-2-[4-(3-methoxy-propionyl)-3-methyl-piperazin-1-yl]-4-methyl-nicotinonitrile 1H NMR (METHANOL-d) δ 7.25-7.34 (m, 2H), 6.75-6.79 (m, 1H), 4.75-4.85 (m, 0.5H), 4.35-4.48 (m, 1H), 4.05-4.12 (m, 2H), 3.88-3.97 (m, 3.5H), 3.65-3.72 (m, 2H), 3.52-3.62 (m, 0.5H), 3.34 (s, 3H), 3.03-3.25 (m, 2H), 2.87-2.98 (m, 0.5H), 2.68-2.85 (m, 1H), 2.57-2.63 (m, 1H), 2.18 (s, 3H), 1.62-1.69 (m, 1H), 1.34-1.41 (m, 3H), 1.05-1.09 (m, 2H), 0.78-0.85 (m, 2H)

LC-MS: m/z 467.2 (M+H)+.

Compound 325 (General Procedure 6, Step G')

(R)-6-cyclopropyl-2-[4-(3-methoxy-propionyl)-3-methyl-piperazin-1-yl]-4-methyl-5-(4-methyl-1H-indol-5-yl)-nicotinonitrile 1H NMR (METHANOL-d) δ 7.45 (d, J=8.4 Hz, 1H), 7.35 (s, 1H), 7.21 (s, 1H), 6.96 (d, J=8.4 Hz, 1H), 4.75-4.85 (m, 0.5H), 4.35-4.48 (m, 1H), 4.05-4.12 (m, 2H), 3.88-3.97 (m, 3.5H), 3.65-3.72 (m, 2H), 3.52-3.62 (m, 0.5H), 3.34 (s, 3H), 3.03-3.25 (m, 2H), 2.87-2.98 (m, 0.5H), 2.68-2.85 (m, 1H), 2.57-2.63 (m, 1H), 2.18 (s, 3H), 1.62-1.69 (m, 1H), 1.34-1.41 (m, 3H), 1.05-1.09 (m, 2H), 0.78-0.85 (m, 2H).

LC-MS: m/z 472.2 (M+H)+.

Compound 326 (General Procedure 6, Step G')

(R)—N-(4-{5-cyano-2-cyclopropyl-6-[4-(3-methoxy-propionyl)-3-methyl-piperazin-1-yl]-4-methyl-pyridin-3-yl}-phenyl)-acetamide 1H NMR (METHANOL-d) δ 7.66 (d, J=8.8 Hz, 2H), 7.16 (d, J=8.8 Hz, 2H), 4.75-4.85 (m, 0.5H), 4.35-4.48 (m, 1H), 4.05-4.12 (m, 2H), 3.88-3.97 (m, 0.5H), 3.65-3.72 (m, 2H), 3.52-3.62 (m, 0.5H), 3.34 (s, 3H), 3.03-3.25 (m, 2H), 2.87-2.98 (m, 0.5H), 2.68-2.85 (m, 1H), 2.57-2.63 (m, 1H), 2.18 (s, 3H), 2.15 (s, 3H), 1.62-1.69 (m, 1H), 1.34-1.41 (m, 3H), 1.05-1.09 (m, 2H), 0.78-0.85 (m, 2H).
LC-MS: m/z 476.2 (M+H)+.

Compound 327 (General Procedure 6, Step G')

(R)-3-{5-cyano-2-cyclopropyl-6-[4-(3-methoxy-propionyl)-3-methyl-piperazin-1-yl]-4-methyl-pyridin-3-yl}-N-methyl-benzamide 1H NMR (METHANOL-d) δ 7.87 (d, J=8.0 Hz, 1H), 7.69 (s, 1H), 7.56-7.62 (m, 1H), 7.41 (d, J=8.0 Hz, 1H) 4.75-4.85 (m, 0.5H), 4.35-4.48 (m, 1H), 4.05-4.12 (m, 2H), 3.88-3.97 (m, 0.5H), 3.65-3.72 (m, 2H), 3.52-3.62 (m, 0.5H), 3.34 (s, 3H), 3.03-3.25 (m, 2H), 2.87-2.98 (m, 3.5H), 2.68-2.85 (m, 1H), 2.57-2.63 (m, 1H), 2.16 (s, 3H), 1.62-1.69 (m, 1H), 1.34-1.41 (m, 3H), 1.05-1.09 (m, 2H), 0.78-0.85 (m, 2H).
LC-MS: m/z 476.2 (M+H)+.

Compound 329 (General Procedure 6, Step G')

(R)-6-cyclopropyl-5-(3-methanesulfonyl-phenyl)-2-[4-(3-methoxy-propionyl)-3-methyl-piperazin-1-yl]-4-methyl-nicotinonitrile 1H NMR (METHANOL-d) δ 8.02 (d, J=7.6 Hz, 1H), 7.85 (s, 1H), 7.75-7.79 (m, 1H), 7.61 (d, J=7.6 Hz, 1H) 4.75-4.85 (m, 0.5H), 4.35-4.48 (m, 1H), 4.05-4.12 (m, 2H), 3.88-3.97 (m, 0.5H), 3.65-3.72 (m, 2H), 3.52-3.62 (m, 0.5H), 3.34 (s, 3H), 3.03-3.25 (m, 5H), 2.87-2.98 (m, 0.5H), 2.68-2.85 (m, 1H), 2.57-2.63 (m, 1H), 2.16 (s, 3H), 1.62-1.69 (m, 1H), 1.34-1.41 (m, 3H), 1.05-1.09 (m, 2H), 0.78-0.85 (m, 2H).
LC-MS: m/z 497.1 (M+H)+.

Compound 330 (General Procedure 6, Step G')

(R)—N-(4-{5-cyano-2-cyclopropyl-6-[4-(3-methoxy-propionyl)-3-methyl-piperazin-1-yl]-4-methyl-pyridin-3-yl}-benzyl)-methanesulfonamide ¹H NMR (METHANOL-d) δ 7.51 (d, J=8.0 Hz, 2H), 7.22 (d, J=8.0 Hz, 2H), 4.75-4.85 (m, 0.5H), 4.35-4.48 (m, 3H), 4.05-4.12 (m, 2H), 3.88-3.97 (m, 0.5H), 3.65-3.72 (m, 2H), 3.52-3.62 (m, 0.5H), 3.34 (s, 3H), 3.03-3.25 (m, 2H), 2.87-2.98 (m, 3.5H), 2.68-2.85 (m, 1H), 2.57-2.63 (m, 1H), 2.18 (s, 3H), 1.62-1.69 (m, 1H), 1.34-1.41 (m, 3H), 1.05-1.09 (m, 2H), 0.78-0.85 (m, 2H).
LC-MS: m/z 526.2 (M+H)+.

Compound 331 (General Procedure 6, Step G')

(R)-4-{5-cyano-2-cyclopropyl-6-[4-(3-methoxy-propionyl)-3-methyl-piperazin-1-yl]-4-methyl-pyridin-3-yl}-N-methyl-benzenesulfonamide ¹H NMR (METHANOL-d) δ 7.95 (d, J=8.4 Hz, 2H), 7.47 (d, J=8.4 Hz, 2H), 4.75-4.85 (m, 0.5H), 4.35-4.48 (m, 1H), 4.05-4.12 (m, 2H), 3.88-3.97 (m, 0.5H), 3.65-3.72 (m, 2H), 3.52-3.62 (m, 0.5H), 3.43 (s, 3H), 3.16-3.25 (m, 1.5H), 2.87-2.98 (m, 0.5H), 2.68-2.85 (m, 1H), 2.57-2.63 (m, 4H), 2.18 (s, 3H), 1.62-1.69 (m, 1H), 1.34-1.41 (m, 3H), 1.05-1.09 (m, 2H), 0.78-0.85 (m, 2H).
LC-MS: m/z 512.2 (M+H)+.

Compound 332 (General Procedure 6, Step G')

(R)-6-cyclopropyl-2-[4-(3-methoxy-propionyl)-3-methyl-piperazin-1-yl]-4-methyl-5-[3-(pyrrolidine-1-carbonyl)-phenyl]-nicotinonitrile 1H NMR (METHANOL-d) δ 7.57-7.59 (m, 2H), 7.40 (s, 1H), 7.34-7.37 (m, 2H), 4.75-4.85 (m, 0.5H), 4.35-4.48 (m, 1H), 4.05-4.12 (m, 2H), 3.88-3.97 (m, 0.5H), 3.65-3.72 (m, 2H), 3.45-3.62 (m, 4.5H), 3.34 (s, 3H), 3.03-3.25 (m, 2H), 2.87-2.98 (m, 0.5H), 2.68-2.85 (m, 1H), 2.57-2.63 (m, 1H), 2.18 (s, 3H), 1.88-1.99 (m, 4H), 1.62-1.69 (m, 1H), 1.34-1.41 (m, 3H), 1.05-1.09 (m, 2H), 0.78-0.85 (m, 2H). LC-MS: m/z 516.2 (M+H)+.

Compound 333 (General Procedure 6, Step G')

(R)-6-cyclopropyl-2-[4-(3-methoxy-propionyl)-3-methyl-piperazin-1-yl]-4-methyl-5-[4-(pyrrolidine-1-carbonyl)-phenyl]-nicotinonitrile 1H NMR (METHANOL-d) δ 7.65 (d, J=8.4 Hz, 2H), 7.33 (d, J=8.4 Hz, 2H), 4.75-4.85 (m, 0.5H), 4.35-4.48 (m, 1H), 4.05-4.12 (m, 2H), 3.88-3.97 (m, 0.5H), 3.65-3.72 (m, 2H), 3.52-3.62 (m, 4.5H), 3.34 (s, 3H), 3.03-3.25 (m, 2H), 2.87-2.98 (m, 0.5H), 2.68-2.85 (m, 1H), 2.57-2.63 (m, 1H), 2.18 (s, 3H), 1.88-1.99 (m, 4H), 1.62-1.69 (m, 1H), 1.34-1.41 (m, 3H), 1.05-1.09 (m, 2H), 0.78-0.85 (m, 2H).
LC-MS: m/z 516.2 (M+H)+.

Compound 335 (General Procedure 6, Step G')

(R)—N-(3-{5-cyano-2-cyclopropyl-6-[4-(3-methoxy-propionyl)-3-methyl-piperazin-1-yl]-4-methyl-pyridin-3-yl}-benzyl)-methanesulfonamide ¹H NMR (METHANOL-d) δ 7.42-7.50 (m, 2H), 7.26 (s, 1H), 7.22 (d, J=7.2 Hz, 1H), 4.75-4.85 (m, 0.5H), 4.35-4.48 (m, 1H), 4.31 (s, 2H), 4.05-4.12 (m, 2H), 3.88-3.97 (m, 0.5H), 3.65-3.72 (m, 2H), 3.52-3.62 (m, 0.5H), 3.34 (s, 3H), 3.03-3.25 (m, 2H), 2.87-2.98 (m, 0.5H), 2.87 (s, 3H), 2.68-2.85 (m, 1H), 2.57-2.63 (m, 1H), 2.18 (s, 3H), 1.62-1.69 (m, 1H), 1.34-1.41 (m, 3H), 1.05-1.09 (m, 2H), 0.78-0.85 (m, 2H). LC-MS: m/z 526.2 (M+H)+.

Compound 336 (General Procedure 6, Step G')

(R)-6-cyclopropyl-5-(4-cyclopropylmethoxy-phenyl)-2-[4-(3-methoxy-propionyl)-3-methyl-piperazin-1-yl]-4-methyl-nicotinonitrile ¹H NMR (METHANOL-d) δ 7.11 (d, J=8.4 Hz, 2H), 7.01 (d, J=8.4 Hz, 2H), 4.75-4.85 (m, 0.5H), 4.35-4.48 (m, 1H), 3.88-4.12 (m, 5H), 3.65-3.72 (m, 2H), 3.52-3.62 (m, 0.5H), 3.34 (s, 3H), 3.03-3.25 (m, 2H), 2.87-2.98 (m, 0.5H), 2.68-2.85 (m, 1H), 2.57-2.63 (m, 1H), 2.18 (s, 3H), 1.62-1.69 (m, 1H), 1.21-1.41 (m, 4H), 1.05-1.09 (m, 2H), 0.78-0.85 (m, 2H), 0.61-0.69 (m, 2H), 0.35-0.41 (m, 2H).
LC-MS: m/z 489.2 (M+H)+.

Compound 337 (General Procedure 6, Step G')

(R)-6-cyclopropyl-2-[4-(3-methoxy-propionyl)-3-methyl-piperazin-1-yl]-4-methyl-5-(4-propoxy-phenyl)-nicotinonitrile 1H NMR (METHANOL-d) δ 7.10 (d, J=8.8 Hz, 2H), 7.01 (d, J=8.8 Hz, 2H), 4.75-4.85 (m, 0.5H), 4.35-4.48 (m, 1H), 3.98-4.12 (m, 4H), 3.88-3.97 (m, 0.5H), 3.65-3.72 (m, 2H), 3.52-3.62 (m, 0.5H), 3.34 (s, 3H), 3.03-3.25 (m, 2H), 2.87-2.98 (m, 0.5H), 2.68-2.85 (m, 1H), 2.57-2.63 (m, 1H), 2.18 (s, 3H), 1.78-1.89 (m, 2H), 1.62-1.69 (m, 1H), 1.34-1.41 (m, 3H), 1.05-1.09 (m, 5H), 0.78-0.85 (m, 2H).

LC-MS: m/z 477.2 (M+H)+.

Compound 340 (General Procedure 6, Step G')

(R)—N-(4-{5-cyano-2-cyclopropyl-6-[4-(3-methoxy-propionyl)-3-methyl-piperazin-1-yl]-4-methyl-pyridin-3-yl}-benzyl)-acetamide 1H NMR (METHANOL-d) δ 7.41 (d, J=8.0 Hz, 2H), 7.19 (d, J=8.0 Hz, 2H), 4.75-4.85 (m, 0.5H), 4.35-4.48 (m, 3H), 4.05-4.12 (m, 2H), 3.88-3.97 (m, 0.5H), 3.65-3.72 (m, 2H), 3.52-3.62 (m, 0.5H), 3.34 (s, 3H), 3.03-3.25 (m, 2H), 2.87-2.98 (m, 0.5H), 2.68-2.85 (m, 1H), 2.57-2.63 (m, 1H), 2.18 (s, 3H), 2.01 (s, 3H), 1.62-1.69 (m, 1H), 1.34-1.41 (m, 3H), 1.05-1.09 (m, 2H), 0.78-0.85 (m, 2H).

LC-MS: m/z 490.1 (M+H)+.

Compound 346 (General Procedure 6, Step G')

(R)-5-(4-fluoro-pyridyl-3-yl)-6-cyclopropyl-2-[4-(3-methoxy-propionyl)-3-methyl-piperazin-1-yl]-4-methyl-nicotinonitrile 1H NMR (METHANOL-d) δ 8.10-8.09 (d, J=2.4 Hz, 1H), 7.89-7.85 (m, 1H), 7.23-7.20 (m, 1H), 4.79-4.78 (d, J=1.2 Hz, 0.5H), 4.44-4.41 (d, J=14 Hz, 1H), 4.18-4.01 (m, 2H), 3.95-3.92 (d, J=13.6 Hz, 0.5H), 3.68-3.67 (d, J=5.6 Hz, 2H), 3.62-3.56 (t, J=11.6 Hz, 0.5H), 3.33 (s, 3H), 3.26-3.24 (m, 1H), 3.20-3.11 (m, 1H), 3.01-2.98 (m, 0.5H), 2.80-2.69 (m, 1H), 2.64-2.59 (m, 1H), 2.19 (s, 3H), 1.56-1.54 (m, 1H), 1.39-1.37 (d, J=6.4 Hz, 1H), 1.27-1.26 (d, J=6.8 Hz, 1H), 1.11-1.09 (t, J=3.6 Hz, 2H), 0.89-0.87 (m, 2H). LC-MS: m/z 438.1 (M+H)+.

Compound 347 (General Procedure 6, Step G')

(R)-5-(4-cyano-phenyl)-6-cyclopropyl-2-[4-(3-methoxy-propionyl)-3-methyl-piperazin-1-yl]-4-methyl-nicotinonitrile 1H NMR (METHANOL-d) δ 7.87-7.85 (d, J=8.4 Hz, 2H), 7.47-7.45 (d, J=8 Hz, 2H), 4.79 (s, 1H), 4.45-4.39 (m, 1H), 4.16-4.05 (m, 2H), 3.95-3.92 (d, J=13.2 Hz, 0.5H), 3.69-3.66 (t, J=11.6 Hz, 2H), 3.62-3.55 (m, 0.5H), 3.33 (s, 3H), 3.27-3.08 (m, 2H), 2.99-2.94 (m, 0.5H), 2.81-2.69 (m, 1H), 2.64-2.59 (m, 1H), 2.16 (s, 3H), 1.55-1.49 (m, 1H), 1.39-1.28 (m, 3H), 1.12-1.09 (m, 1H), 0.89-0.86 (m, 2H). LC-MS: m/z 444.1 (M+H)+.

Compound 348 (General Procedure 6, Step G')

(R)-6-cyclopropyl-5-(2-methoxymethyl-phenyl)-2-[4-(3-methoxy-propionyl)-3-methyl-piperazin-1-yl]-4-methyl-nicotinonitrile 1H NMR (METHANOL-d) δ 7.53-7.55 (m, 1H), 7.40-7.45 (m, 2H), 7.11-7.14 (m, 1H), 4.79 (s, 0.5H), 4.42 (t, J=14.4 Hz, 1H), 4.04-4.15 (m, 4H), 3.93 (d, J=12.8 Hz, 0.5H), 3.59-3.69 (m, 2.5H), 3.33 (s, 3H), 3.20 (d, J=4.8 Hz, 4H), 2.95-3.18 (m, 1H), 2.71-2.76 (m, 1H), 2.60-2.65 (m, 1H), 2.08 (s, 3H), 1.40-1.5 (m, 2.3H), 1.27-1.38 (m, 1.7H), 1.02-1.09 (m, 2H), 0.75-0.82 (m, 2H).

LC-MS: m/z 463.2 (M+H)+.

Compound 349 (General Procedure 6, Step G')

(R)-6-cyclopropyl-2-[4-(3-methoxy-propionyl)-3-methyl-piperazin-1-yl]-4-methyl-5-(2-methyl-2H-pyrazol-3-yl)-nicotinonitrile 1H NMR (METHANOL-d) d 7.60 (s, 1H), 6.33 (s, 1H), 4.75-4.85 (m, 0.5H), 4.35-4.48 (m, 1H), 4.21-4.38 (m, 2H), 3.88-3.95 (m, 0.5H), 3.65-3.72 (m, 2H), 3.63 (s, 3H), 3.52-3.62 (m, 0.5H), 3.34 (s, 3H), 3.03-3.25 (m, 1H), 2.97-3.08 (m, 0.5H), 2.68-2.85 (m, 1H), 2.57-2.63 (m, 1H), 2.18 (s, 3H), 1.62-1.69 (m, 1H), 1.34-1.41 (m, 3H), 1.05-1.19 (m, 2H), 0.78-0.95 (m, 2H). LC-MS: m/z 423.2 (M+H)+.

Compound 350 (General Procedure 6, Step G')

(R)—N-(3-{5-cyano-2-cyclopropyl-6-[4-(3-methoxy-propionyl)-3-methyl-piperazin-1-yl]-4-methyl-pyridin-3-yl}-phenyl)-methane sulfonamide 1H NMR (METHANOL-d) d 7.45-7.48 (m, 1H), 7.30 (d, J=7.6 Hz, 1H), 7.11 (s, 1H), 7.02 (d, J=7.6 Hz, 1H), 4.75-4.85 (m, 0.5H), 4.35-4.48 (m, 1H), 4.05-4.12 (m, 2H), 3.88-3.97 (m, 0.5H), 3.65-3.72 (m, 2H), 3.52-3.62 (m, 0.5H), 3.34 (s, 3H), 3.03-3.25 (m, 2H), 2.98 (s, 3H), 2.87-2.98 (m, 0.5H), 2.68-2.85 (m, 1H), 2.57-2.63 (m, 1H), 2.16 (s, 3H), 1.62-1.69 (m, 1H), 1.34-1.41 (m, 3H), 1.05-1.09 (m, 2H), 0.78-0.85 (m, 2H). LC-MS: m/z 512.1 (M+H)+.

Compound 351 (General Procedure 6, Step G')

(R)-6-cyclopropyl-5-(3,5-dimethyl-isoxazol-4-yl)-2-[4-(3-methoxy-propionyl)-3-methyl-piperazin-1-yl]-4-methyl-nicotinonitrile 1H NMR (METHANOL-d) d 4.75-4.85 (m, 0.5H), 4.35-4.48 (m, 1H), 4.05-4.12 (m, 2H), 3.88-3.97 (m, 0.5H), 3.65-3.72 (m, 2H), 3.52-3.62 (m, 0.5H), 3.34 (s, 3H), 3.03-3.25 (m, 2H), 2.87-2.98 (m, 0.5H), 2.68-2.85 (m, 1H), 2.57-2.63 (m, 1H), 2.24 (s, 3H), 2.21 (s, 3H), 2.08 (s, 3H), 1.62-1.69 (m, 1H), 1.34-1.41 (m, 3H), 1.05-1.12 (m, 2H), 0.85-0.95 (m, 2H).

LC-MS: m/z 438.2 (M+H)+.

Compound 358 (General Procedure 6, Step G')

(R)-5-(1-benzyl-1H-pyrazol-4-yl)-6-cyclopropyl-2-[4-(3-methoxy-propionyl)-3-methyl-piperazin-1-yl]-4-methyl-nicotinonitrile 1H NMR (METHANOL-d) 7.742 (s, 1H), 7.499 (s, 1H), 4.365-7.255 (m, 5H), 5.410 (s, 2H), 4.773 (s, 0.5H), 4.429-

4.359 (m, 1H), 4.109-4.004 (m, 2H), 3.924-3.891 (m, 0.5H), 3.683-3.655 (m, 2H), 3.592-3.535 (m, 0.5H), 3.328 (s, 3H), 3.255-3.041 (m, 2H), 2.954-2.898 (m, 0.5H), 2.801-2.588 (m, 2H), 2.260 (s, 3H), 1.909-1.869 (m, 1H), 1.375-1.246 (m, 3H), 1.071 (s, 2H), 0.90-0.80 (m, 2H). LC-MS: m/z 499.2 (M+H)+.

Compound 359 (General Procedure 6, Step G')

(R)-6-cyclopropyl-5-(2-ethyl-phenyl)-2-[4-(3-methoxy-propionyl)-3-methyl-piperazin-1-yl]-4-methyl-nicotinonitrile 1H NMR (METHANOL-d) δ 7.40-7.37 (m, 2H), 7.35-7.27 (m, 1H), 7.07-7.04 (m, 1H), 4.80-4.79 (d, J=2.4 Hz, 0.5H), 4.46-4.38 (m, 1H), 4.14-4.04 (m, 2H), 3.95-3.92 (d, J=12.8 Hz, 0.5H), 3.68-3.63 (m, 2H), 3.60 (m, 0.5H), 3.34 (s, 3H), 3.26-3.06 (m, 2H), 2.97-2.94 (d, J=12 Hz, 0.5H), 2.80-2.60 (m, 2H), 2.42-2.30 (m, 2H), 2.09 (s, 3H), 1.55-1.50 (m, 1H), 1.43-1.39 (m, 1H), 1.32-1.27 (m, 1H), 1.08-1.03 (m, 5.5H) 0.82-0.80 (m, 2H). LC-MS: m/z 447.2 (M+H)+.

Compound 362 (General Procedure 6, Step G')

(R)-6-cyclopropyl-5-(3-dimethylamino-phenyl)-2-[4-(3-methoxy-propionyl)-3-methyl-piperazin-1-yl]-4-methyl-nicotinonitrile 1H NMR (METHANOL-d) δ 7.53 (t, J=8.0 Hz, 1H), 7.27 (d, J=8.4 Hz, 1H), 7.09 (s, 1H), 7.02 (d, J=7.2 Hz, 1H), 4.78 (s, 1H), 4.38-4.45 (m, 1H), 4.03-4.14 (m, 2H), 3.91-3.95 (m, 0.5H), 3.65-3.70 (m, 2H), 3.53-3.62 (m, 0.5H), 3.34 (s, 4H), 3.21-3.31 (m, 1.5H), 3.16 (s, 7H), 2.96-2.98 (m, 0.5H), 2.71-2.79 (m, 1H), 2.62-2.65 (m, 1H), 2.19 (s, 3H), 1.61-1.67 (m, 1H), 1.38-1.40 (d, J=6.4 Hz, 1.3H), 1.27-1.28 (d, J=6.4 Hz, 1.7H), 1.07-1.09 (m, 2H), 0.81-0.84 (m, 2H). LC-MS: m/z 462.1 (M+H)+.

Compound 365 (General Procedure 6, Step G')

(R)-6-cyclopropyl-2-[4-(3-methoxy-propionyl)-3-methyl-piperazin-1-yl]-4-methyl-5-(1-methyl-1H-pyrazol-4-yl)-nicotinonitrile ¹H NMR (METHANOL-d) d 7.64 (s, 1H), 7.44 (s, 1H), 4.75-4.85 (m, 0.5H), 4.35-4.48 (m, 1H), 3.88-4.12 (m, 5.5H), 3.65-3.72 (m, 2H), 3.52-3.62 (m, 0.5H), 3.34 (s, 3H), 3.03-3.25 (m, 2H), 2.87-2.98 (m, 0.5H), 2.68-2.85 (m, 1H), 2.57-2.63 (m, 1H), 2.18 (s, 3H), 1.62-1.69 (m, 1H), 1.34-1.41 (m, 3H), 1.05-1.09 (m, 2H), 0.78-0.85 (m, 2H). LC-MS: m/z 423.1 (M+H)+.

Compound 366 (General Procedure 6, Step G')

(R)-3-{5-cyano-2-cyclopropyl-6-[4-(3-methoxy-propionyl)-3-methyl-piperazin-1-yl]-4-methyl-pyridin-3-yl}-benzoic acid methyl ester ¹H NMR (METHANOL-d) d 8.06 (d, J=8.0 Hz, 1H), 7.87 (s, 1H), 7.58-7.63 (m, 1H), 7.48 (d, J=8.0 Hz, 1H), 4.75-4.85 (m, 0.5H), 4.35-4.48 (m, 1H), 4.05-4.12 (m, 2H), 3.88-3.97 (m, 3.5H), 3.65-3.72 (m, 2H), 3.52-3.62 (m, 0.5H), 3.34 (s, 3H), 3.03-3.25 (m, 2H), 2.87-2.98 (m, 0.5H), 2.68-2.85 (m, 1H), 2.57-2.63 (m, 1H), 2.16 (s, 3H), 1.62-1.69 (m, 1H), 1.34-1.41 (m, 3H), 1.05-1.09 (m, 2H), 0.78-0.85 (m, 2H). LC-MS: m/z 477.1 (M+H)+.

Compound 369 (General Procedure 6, Step G')

(R)-2-cyclopropyl-2'-fluoro-6-[4-(3-methoxy-propionyl)-3-methyl-piperazin-1-yl]-4-methyl-[3,3']bipyridinyl-5-carbonitrile 1H NMR (METHANOL-d) δ 8.31-8.30 (d, J=4.4 Hz, 1H), 7.90-7.86 (t, J=8.4 Hz, 1H), 7.48-7.45 (m, 1H), 4.82-4.79 (m, 0.5H), 4.45-4.37 (m, 0.5H), 4.20-4.10 (m, 2H), 3.95-3.92 (d, J=12.8 Hz, 0.5H), 3.68-3.67 (m, 2H), 3.62-3.56 (t, J=12 Hz, 0.5H), 3.34-3.33 (m, 3.5H), 3.18-3.16 (d, J=10.8 Hz, 1H), 3.01 (m, 1H), 2.80-2.71 (m, 1H), 2.65-2.61 (m, 1H), 2.2 (s, 3H), 1.52-1.49 (m, 1H), 1.39-1.38 (d, J=2.8 Hz, 1H), 1.28-1.27 (d, J=6.4 Hz, 1H), 1.13-0.90 (m, 1H), 0.90-0.88 (m, 1H). LC-MS: m/z 438.2 (M+H)+.

Compound 372 (General Procedure 6, Step G')

(R)-6-cyclopropyl-5-(2-hydroxymethyl-phenyl)-2-[4-(3-methoxy-propionyl)-3-methyl-piperazin-1-yl]-4-methyl-nicotinonitrile 1H NMR (CHLOROFORM-d) δ 7.61-7.59 (d, J=7.6 Hz, 1H), 7.46-7.37 (m, 2H), 7.10-7.08 (d, J=7.2 Hz, 1H), 4.90 (s, 0.5H), 4.53-4.34 (M, 2.5H), 4.22-4.05 (m, 2.5H), 3.79-3.71 (m, 2.5H), 3.60-3.54 (M, 0.5H), 3.48 (S, 1H), 3.37 (S, 3H), 3.19-3.14 (M, 1.5H), 3.03-2.98 (m, 1H), 2.75-2.66 (M, 1H), 2.60-2.55 (m, 1H), 2.11 (s, 3H), 1.48-1.44 (m, 2H), 1.31-1.30 (d, J=4.8 Hz, 1.5H), 1.10-1.07 (m, 2H). LC-MS: m/z 449.1 (M+H)+.

Compound 380 (General Procedure 6, Step G')

(R)—N-(4-{5-cyano-2-cyclopropyl-6-[4-(3-methoxy-propionyl)-3-methyl-piperazin-1-yl]-4-methyl-pyridin-3-yl}-phenyl)-methane sulfonamide 1H NMR (METHANOL-d) d 7.36 (d, J=8.4 Hz, 2H), 7.21 (d, J=8.4 Hz, 2H), 4.75-4.85 (m, 0.5H), 4.35-4.48 (m, 1H), 4.05-4.12 (m, 2H), 3.88-3.97 (m, 0.5H), 3.65-3.72 (m, 2H), 3.52-3.62 (m, 0.5H), 3.43 (s, 3H), 3.16-3.25 (m, 1.5H), 3.03 (s, 3H), 2.87-2.98 (m, 0.5H), 2.68-2.85 (m, 1H), 2.57-2.63 (m, 1H), 2.18 (s, 3H), 1.62-1.69 (m, 1H), 1.34-1.41 (m, 3H), 1.05-1.09 (m, 2H), 0.78-0.85 (m, 2H). LC-MS: m/z 512.2 (M+H)+.

Compound 393 (General Procedure 6, Step G')

(R)-4-{5-cyano-2-cyclopropyl-6-[4-(3-methoxy-propionyl)-3-methyl-piperazin-1-yl]-4-methyl-pyridin-3-yl}-benzenesulfonamide 1H NMR (METHANOL-d) d 8.02 (d, J=8.4 Hz, 2H), 7.43 (d, J=8.4 Hz, 2H), 4.75-4.85 (m, 0.5H), 4.35-4.48 (m, 3H), 4.05-4.12 (m, 2H), 3.88-3.97 (m, 0.5H), 3.65-3.72 (m, 2H), 3.52-3.62 (m, 0.5H), 3.34 (s, 3H), 3.03-3.25 (m, 2H), 2.87-2.98 (m, 0.5H), 2.68-2.85 (m, 1H), 2.57-2.63 (m, 1H), 2.18 (s, 3H), 1.62-1.69 (m, 1H), 1.34-1.41 (m, 3H), 1.05-1.09 (m, 2H), 0.78-0.85 (m, 2H). LC-MS: m/z 498.1 (M+H)+.

Compound 405 (General Procedure 6, Step G')

(R)-6-cyclopropyl-5-(2,3-difluoro-phenyl)-2-[4-(3-methoxy-propionyl)-3-methyl-piperazin-1-yl]-4-methyl-nicotinonitrile 1H NMR (METHANOL-d) δ 7.26-7.39 (m, 2H), 7.07 (t, J=6.8 Hz, 1H), 4.72 (s, 0.5H), 4.41-4.45 (m, 1H), 4.07-4.19

(m, 2H), 3.93 (d, J=13.6 Hz, 0.5H), 3.66-3.69 (m, 2H), 3.56-3.62 (m, 0.5H), 3.33 (s, 3H), 3.20-3.28 (m, 1H), 3.14-3.17 (m, 1H), 2.96-3.02 (m, 0.5H), 2.60-2.81 (m, 2H), 2.18 (s, 3H), 1.55-1.61 (m, 1H), 1.38 (d, J=6.4 Hz, 1.3H), 1.27 (d, J=6.8 Hz, 1.7H), 1.06-1.1 (m, 2H), 0.82-0.89 (m, 2H). LC-MS: m/z 455.1 (M+H)+.

Compound 589

(R)-2-cyclopropyl-6-(3-cyclopropyl-4-(3-hydroxypropanoyl)piperazin-1-yl)-4-methyl-2'-vinyl-3,4'-bipyridine-5-carbonitrile It was obtained by the same procedure of Compound 527.

¹H NMR (CHLOROFORM-d) δ 8.70 (d, J=5.0 Hz, 1H), 7.26 (s, 1H), 7.10 (d, J=3.8 Hz, 1H), 6.90 (dd, J=17.4, 10.9 Hz, 1H), 6.32 (d, J=17.3 Hz, 1H), 5.61 (d, J=11.3 Hz, 1H), 4.60-4.76 (m, 0.5H), 4.34 (d, J=12.8 Hz, 1H), 4.26 (d, J=12.8 Hz, 1H), 4.08 (d, J=9.0 Hz, 0.5H), 3.92 (br. s., 2H), 3.78 (br. s., 1H), 3.39-3.56 (m, 1H), 3.23 (br. s., 1H), 3.15 (d, J=11.8 Hz, 1H), 3.05 (br. s., 1H), 2.61 (br. s., 2H), 2.17-2.29 (m, 3H), 1.55-1.60 (m, 1H), 1.38-1.47 (m, 1H), 1.27-1.33 (br. s., 1H), 1.12 (br. s., 2H), 0.64 (br. s., 2H), 0.33-0.54 (m, 2H)

LC-MS: m/z 458.3 (M+H)+

Compound 674

(R)-6-cyclopropyl-2-(3-cyclopropyl-4-(3-methoxypropanoyl)piperazin-1-yl)-5-(6-vinylpyridazin-4-yl)nicotinonitrile

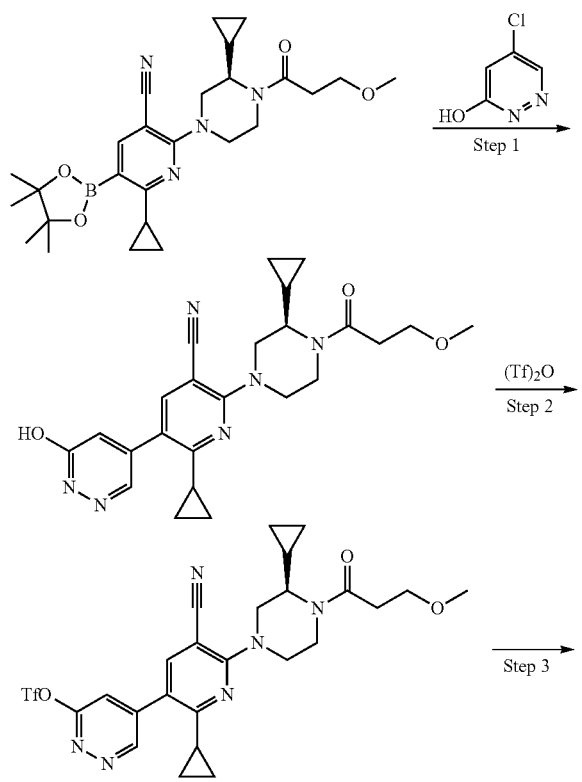

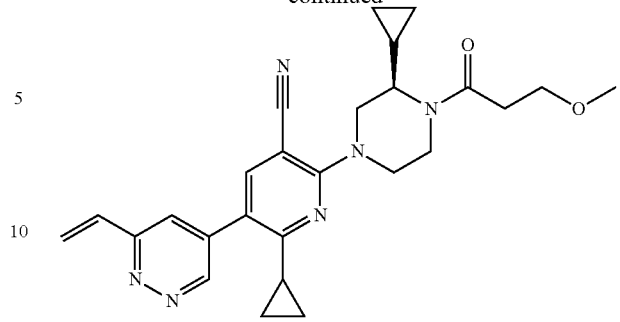

Step 1 (R)-6-cyclopropyl-2-(3-cyclopropyl-4-(3-methoxypropanoyl)piperazin-1-yl)-5-(6-hydroxypyridazin-4-yl)nicotinonitrile A mixture of (R)-6-cyclopropyl-2-(3-cyclopropyl-4-(3-methoxypropanoyl)piperazin-1-yl)-5-(4,4,5,5-tetramethyl-1,3,2-dioxaborolan-2-yl)nicotinonitrile (200 mg, 0.42 mmol), 5-chloropyridazin-3-ol (109 mg, 0.625 mmol), CsF (127 mg, 0.84 mmol) and Pd(dppf)Cl₂ (17 mg) in dioxane and water was heated at 100° C. for 2 hrs. The reaction mixture was concentrated and the residue was purified by pre-TLC to afford 120 mg of title compound.

LC-MS: m/z 449.2 (M+H)+

Step 2 (R)-5-(5-cyano-2-cyclopropyl-6-(3-cyclopropyl-4-(3-methoxypropanoyl) piperazin-1-yl)pyridin-3-yl)pyridazin-3-yltrifluoromethanesulfonate A solution of (R)-6-cyclopropyl-2-(3-cyclopropyl-4-(3-methoxypropanoyl)piperazin-1-yl)-5-(6-hydroxypyridazin-4-yl)nicotinonitrile (120 mg, 0.27 mmol), Tf₂O (100 mg, 0.48 mmol) and TEA (0.1 mL) in DCM was stirred for 1 hr. The reaction mixture was washed with water, dried and concentrated. The residue was purified by pre-TLC to afford 60 mg of title compound.

¹H NMR (CHLOROFORM-d) δ: 9.41 (d, J=1.5 Hz, 1H), 7.71 (s, 1H), 7.51 (d, J=1.8 Hz, 1H), 4.71 (d, J=12.8 Hz, 1.5H), 4.58 (d, J=11.5 Hz, 1H), 4.14 (brs, 0.5H), 3.93 (br. s., 0.5H), 3.75 (br. s., 2.5H), 3.39 (s, 3H), 3.21-3.36 (m, 3H), 2.54-2.83 (m, 2H), 1.86-1.96 (m, 1H), 1.08-1.28 (m, 5H), 0.48-0.63 (m, 4H).

LC-MS: m/z 580.7 (M+H)+

Step 3 (R)-6-cyclopropyl-2-(3-cyclopropyl-4-(3-methoxypropanoyl)piperazin-1-yl)-5-(6-vinylpyridazin-4-yl)nicotinonitrile (Compound 674)

A mixture of (R)-5-(5-cyano-2-cyclopropyl-6-(3-cyclopropyl-4-(3-methoxypropanoyl)piperazin-1-yl)pyridin-3-yl) pyridazin-3-yl trifluoromethanesulfonate (25 mg, 0.043 mmol), Potassium vinyltrifluoroborate (12 mg, 0.083 mmol), TEA (20 mg, 0.215 mmol) and Pd(dppf)Cl₂ (3.5 mg) in i-PrOH and water was heated at 100° C. for 2 hrs. The reaction mixture was concentrated and the residue was purified by pre-TLC to afford 11 mg of title compound.

¹H NMR (CHLOROFORM-d) δ9.21 (br. s., 1H), 7.68 (s, 1H), 7.61 (s, 1H), 7.13 (dd, J=17.6, 11.0 Hz, 1H), 6.37 (d, J=17.6 Hz, 1H), 5.79 (d, J=11.0 Hz, 1H), 4.63 (d, J=12.8 Hz, 1.5H), 4.50 (d, J=12.3 Hz, 1H), 4.05-4.18 (m, 0.5H), 3.90 (d, J=11.0 Hz, 0.5H), 3.63-3.83 (m, 2.5H), 3.38 (s, 3H), 3.18-

3.33 (m, 2H), 3.15 (br. s., 1H), 2.71-2.64 (m, 2H), 1.89-1.99 (m, 1H), 1.29-1.40 (m, 3H), 1.07 (dd, J=7.4, 2.9 Hz, 2H), 0.61-0.44 (m, 4H).
LC-MS: m/z 459.0 (M+H)+

Compound 675

(R)-5-(5-cyano-2-cyclopropyl-6-(3-cyclopropyl-4-(3-methoxypropanoyl)piperazin-1-yl)pyridin-3-yl)pyridazin-3-yl trifluoromethanesulfonate ¹H NMR (CHLOROFORM-d) δ: 9.41 (d, J=1.5 Hz, 1H), 7.71 (s, 1H), 7.51 (d, J=1.8 Hz, 1H), 4.71 (d, J=12.8 Hz, 1.5H), 4.58 (d, J=11.5 Hz, 1H), 4.14 (brs, 0.5H), 3.93 (br. s., 0.5H), 3.75 (br. s., 2.5H), 3.39 (s, 3H), 3.21-3.36 (m, 3H), 2.54-2.83 (m, 2H), 1.86-1.96 (m, 1H), 1.08-1.28 (m, 5H), 0.48-0.63 (m, 4H).
LC-MS: m/z 580.7 (M+H)+

Compound 687

(R)-5-(5-cyano-6-(4-(cyclopropanecarbonyl)-3-cyclopropylpiperazin-1-yl)-2-cyclopropylpyridin-3-yl)pyridazin-3-yl trifluoromethanesulfonate ¹H NMR (CHLOROFORM-d) δ: 9.42 (br. s., 1H), 7.72 (s, 1H), 7.52 (s, 1H), 4.73 (d, J=12.8 Hz, 1.5H), 4.60 (d, J=12.0 Hz, 1H), 4.33 (brs, 0.5H), 4.05 (brs, 0.5H), 3.76 (br. s., 1H), 3.24-3.40 (m, 2.5H), 1.89-1.97 (m, 1H), 1.72 (br. s., 1H), 1.29-1.34 (m, 3H), 0.99-1.20 (m, 4H), 0.78-0.90 (m, 2H), 0.41-0.66 (m, 4H).
LC-MS: m/z 563.0 (M+H)+

Compound 766

6-cyclopropyl-2-((R)-3-cyclopropyl-4-(2-((R)-oxetan-2-yl)acetyl)piperazin-1-yl)-5-(5-vinylpyridazin-3-yl)nicotinonitrile

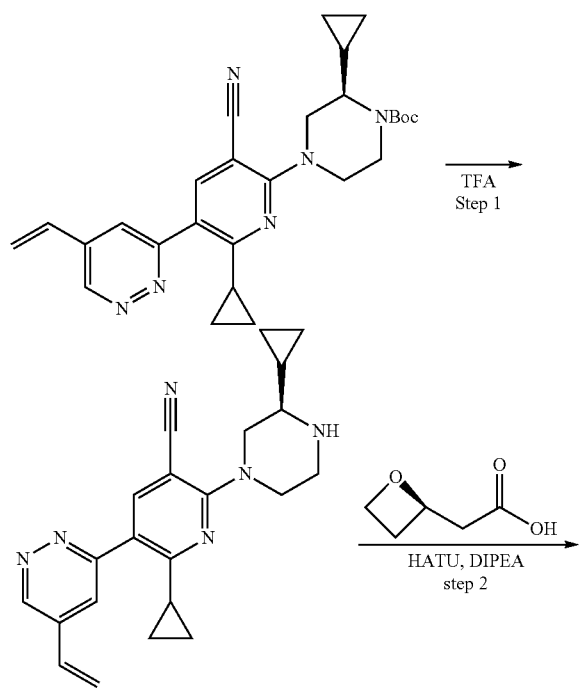

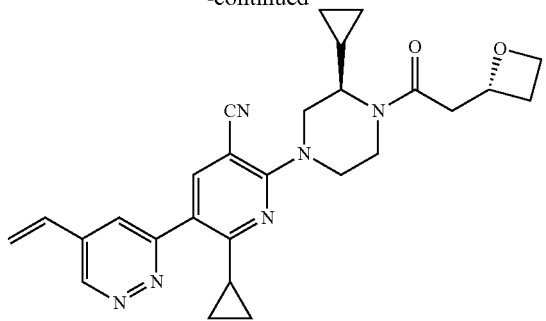

Step 1 (R)-6-cyclopropyl-2-(3-cyclopropylpiperazin-1-yl)-5-(5-vinylpyridazin-3-yl) nicotinonitrile A stirred solution of (R)-tert-butyl 4-(3-cyano-6-cyclopropyl-5-(5-vinylpyridazin-3-yl) pyridin-2-yl)-2-cyclopropylPiperazine-1-carboxylate (100 mg, 0.2 mmol) in TFA (2 mL) was stirred at room temperature overnight. When LC-MS showed completion of the reaction, the mixture was evaporated under reduced pressure and the residue was dissolved in DCM, washed with Sat. NaHCO3, and brine. The organic layer was evaporated under reduced pressure to give crude product which was used without further purification (70 mg)

Step 2. Compound 766

To a stirred 2-(oxetan-2-yl)acetic acid (20 mg) in CH₂Cl₂ was added HATU (72 mg, 0.19 mmol) followed by DIPEA, the mixture was stirred at room temperature for 1 hr, then (R)-6-cyclopropyl-2-(3-cyclopropylpiperazin-1-yl)-5-(5-vinylpyridazin-3-yl)nicotinonitrile (70 mg) was added. The mixture was stirred at room temperature overnight. It was quenched with water, extracted with CH₂Cl₂. The organic layer was washed with Sat. NaHCO3, brine and dried over Na2SO4, evaporated and purified by prepTLC to give product.

¹H NMR (CHLOROFORM-d) δ: 9.23 (br. s., 1H), 7.97 (s, 1H), 7.61 (d, J=1.8 Hz, 1H), 6.74 (dd, J=17.8, 11.0 Hz, 1H), 6.20 (d, J=17.6 Hz, 1H), 5.76 (d, J=10.9 Hz, 1H), 5.11-5.36 (m, 1H), 4.48-4.77 (m, 4H), 4.08 (d, J=8.5 Hz, 0.5H), 3.95 (d, J=13.2 Hz, 0.5H), 3.75 (d, J=11.2 Hz, 0.5H), 3.32 (br. s., 1H), 3.05-3.27 (m, 2H), 2.98 (dd, J=14.8, 6.0 Hz, 1.5H), 2.79-2.90 (m, 2H), 2.54 (d, J=7.9 Hz, 1H), 2.12-2.26 (m, 1H), 1.25 (dd, J=6.6, 3.7 Hz, 3H), 0.94-1.12 (m, 2H), 0.51-0.72 (m, 2H), 0.35-0.49 (m, 2H)
LC-MS: m/z 471.6 (M+H)+

Compound 769

(R,E)-6-cyclopropyl-2-(3-cyclopropyl-4-(5-hydroxypent-2-enoyl)piperazin-1-yl)-4-methyl-5-(5-vinylpyridazin-3-yl)nicotinonitrile ¹H NMR (CHLOROFORM-d) δ: 9.27 (d, J=2.1 Hz, 1H), 7.43 (d, J=2.1 Hz, 1H), 6.87 (dt, J=14.8, 7.3 Hz, 1H), 6.73 (dd, J=17.8, 11.0 Hz, 1H), 6.26-6.48 (m, 1H), 6.21 (d, J=17.6 Hz, 1H), 5.77 (d, J=10.9 Hz, 1H), 4.42 (d, J=12.9 Hz, 1H), 4.33 (d, J=12.6 Hz, 1H), 3.89-4.21 (m, 1H), 3.79 (t, J=6.0 Hz, 2H), 3.38 (br. s., 1H), 3.23 (d, J=10.0 Hz, 1H), 3.08 (td, J=12.5, 2.9 Hz, 1H), 2.50 (q, J=6.2 Hz, 2H), 2.18-2.29 (m, 3H), 1.36-1.50 (m, 2H), 1.15 (br. s., 2H), 0.88 (dd, J=7.6, 3.2 Hz, 2H), 0.65 (br. s., 1H), 0.51 (br. s., 1H), 0.44 (br. s., 2H)
LC-MS: m/z 485.6 (M+H)+

Compound 768

6-cyclopropyl-2-((R)-3-cyclopropyl-4-(2-((R)-oxetan-2-yl)acetyl)piperazin-1-yl)-4-methyl-5-(5-vinylpyridazin-3-yl)nicotinonitrile $^1$H NMR (CHLOROFORM-d) δ: 9.28 (d, J=2.1 Hz, 1H), 7.43 (d, J=2.1 Hz, 1H), 6.74 (dd, J=17.6, 10.9 Hz, 1H), 6.21 (d, J=17.9 Hz, 1H), 5.71-5.86 (m, 1H), 5.27 (quin, J=6.7 Hz, 1H), 4.64-4.76 (m, 1H), 4.49-4.63 (m, 1H), 4.41 (d, J=12.6 Hz, 1H), 4.23-4.37 (m, 1H), 4.07 (d, J=8.2 Hz, 1H), 3.92 (d, J=12.6 Hz, 1H), 3.69-3.86 (m, 1H), 3.20-3.36 (m, 1H), 2.93-3.20 (m, 3H), 2.74-2.93 (m, 2H), 2.46-2.66 (m, 1H), 2.18-2.30 (m, 3H), 1.78 (br. s., 1H), 1.41-1.51 (m, 2H), 1.33-1.41 (m, 1H), 1.10-1.20 (m, 2H), 0.89 (dd, J=7.8, 3.1 Hz, 2H), 0.58-0.72 (m, 1H), 0.53 (br. s., 1H), 0.45 (d, J=5.6 Hz, 2H)
LC-MS: m/z 485.6 (M+H)+

Compound 767

(R)-6-cyclopropyl-2-(3-cyclopropyl-4-(3-hydroxypropanoyl)piperazin-1-yl)-4-methyl-5-(5-vinylpyridazin-3-yl)nicotinonitrile $^1$H NMR (CHLOROFORM-d) δ: 9.28 (s, 1H), 7.44 (d, J=2.1 Hz, 1H), 7.28 (s, 1H), 6.74 (dd, J=17.6, 10.9 Hz, 1H), 6.21 (d, J=17.6 Hz, 1H), 5.78 (d, J=10.9 Hz, 1H), 4.37-4.47 (m, 1H), 4.26-4.36 (m, 1H), 4.01-4.13 (m, 1H), 3.83-3.98 (m, 2H), 3.65-3.83 (m, 1H), 3.13-3.29 (m, 2H), 2.98-3.13 (m, 1H), 2.46-2.68 (m, 2H), 2.19-2.29 (m, 3H), 1.84-2.10 (m, 1H), 1.42-1.55 (m, 1H), 1.15 (br. s., 1H), 0.81-0.95 (m, 3H), 0.63 (br. s., 1H), 0.53 (br. s., 1H), 0.32-0.48 (m, 2H)
LC-MS: m/z 459.6 (M+H)+

Compound 749

(R)-6-cyclopropyl-2-(3-cyclopropyl-4-(3-methoxypropanoyl)piperazin-1-yl)-4-methyl-5-(6-vinylpyridazin-4-yl)nicotinonitrile $^1$H NMR (CHLOROFORM-d) δ: 9.21 (d, J=2.1 Hz, 1H), 7.70 (s, 1H), 7.64 (d, J=2.1 Hz, 1H), 7.15 (dd, J=17.8, 11.0 Hz, 1H), 6.39 (d, J=17.9 Hz, 1H), 5.81 (d, J=10.9 Hz, 1H), 4.64 (d, J=13.2 Hz, 1H), 4.52 (d, J=12.9 Hz, 1H), 4.10 (d, J=9.7 Hz, 1H), 3.85-3.99 (m, 2H), 3.71-3.83 (m, 1H), 3.07-3.36 (m, 3H), 2.42-2.71 (m, 2H), 1.88-2.02 (m, 1H), 1.20-1.40 (m, 3H), 1.01-1.12 (m, 2H), 0.45-0.78 (m, 4H)
LC-MS: m/z 473.3 (M+H)+

Compound 724

(R)-6-cyclopropyl-2-(3-cyclopropyl-4-(2-methoxyacetyl)piperazin-1-yl)-5-(5-vinylpyridazin-3-yl)nicotinonitrile $^1$H NMR (CHLOROFORM-d) δ: 9.22 (s, 1H), 7.93-8.03 (m, 1H), 7.61 (d, J=1.8 Hz, 1H), 6.74 (dd, J=17.8, 11.0 Hz, 1H), 6.20 (d, J=17.6 Hz, 1H), 5.76 (d, J=10.9 Hz, 1H), 4.65 (d, J=13.2 Hz, 1H), 4.52 (d, J=12.6 Hz, 1H), 4.16 (m, 1H), 3.80-4.02 (m, 2H), 3.58-3.74 (m, 1H), 3.45 (s, 3H), 3.26 (d, J=10.3 Hz, 2H), 3.12 (t, J=10.6 Hz, 1H), 2.11-2.32 (m, 1H), 1.23-1.30 (m, 3H), 0.98-1.08 (m, 2H), 0.41-0.72 (m, 4H)
LC-MS: m/z 445.2 (M+H)+

Compound 723

(R)-tert-butyl(6-(5-cyano-2-cyclopropyl-6-(3-cyclopropyl-4-(3-hydroxypropanoyl)piperazin-1-yl)pyridin-3-yl)pyridazin-4-yl)carbamate The mixture of ((R)-6-cyclopropyl-2-(3-cyclopropyl-4-(3-hydroxypropanoyl)piperazin-1-yl)-5-(4,4,5,5-tetramethyl-1,3,2-dioxaborolan-2-yl)nicotinonitrile (67 mg, 0.157 mmol), tert-butyl (6-chloropyridazin-4-yl)carbamate (30 mg, 0.131 mmol), Pd(dppf)Cl$_2$ (5 mg, 0.007 mmol) and CsF (40 mg, 0.216 mmol) in dioxane/H$_2$O was stirred at 100° C. for 16 hours. The mixture was diluted with EtOAc (30 mL) and filtered. The filtrated was partitioned between EtOAc (30 mL) and water (10 mL), the organic layer was washed with water (10 mL), brine and dried over Na$_2$SO$_4$ and concentrated to give the crude which was purified by prep-TLC to give 20 mg of the product.

$^1$H NMR (CHLOROFORM-d) δ: 9.08 (s, 1H), 8.29 (s, 1H), 7.98 (s, 1H), 7.60 (br. s., 1H), 4.64 (d, J=12.9 Hz, 1H), 4.52 (d, J=12.3 Hz, 1H), 4.08 (d, J=8.5 Hz, 1H), 3.93 (s, 2H), 3.66-3.84 (m, 1H), 3.25 (m, 3H), 2.50-2.61 (m, 2H), 1.56 (s, 9H), 1.21-1.28 (m, 3H), 1.07 (s, 2H), 0.41-0.80 (m, 4H)
LC-MS: m/z 534.3 (M+H)+

Compound 716

(R)-6-cyclopropyl-2-(3-cyclopropyl-4-(3-hydroxypropanoyl)piperazin-1-yl)-5-(5-vinylpyridazin-3-yl)nicotinonitrile $^1$H NMR (CHLOROFORM-d) δ9.23 (s, 1H), 7.98 (s, 1H), 7.61 (d, J=2.1 Hz, 1H), 6.74 (dd, J=17.8, 11.0 Hz, 1H), 6.20 (d, J=17.6 Hz, 1H), 5.71-5.84 (m, 1H), 4.64 (d, J=12.9 Hz, 1H), 4.51 (d, J=12.6 Hz, 1H), 4.01-4.16 (m, 1H), 3.92 (s, 2H), 3.65-3.83 (m, 1H), 3.05-3.25 (d, J=11.2 Hz, 2H), 2.50-2.68 (m, 2H), 2.12-2.30 (m, 1H), 1.19-1.27 (m, 3H), 1.00-1.11 (m, 2H), 0.39-0.62 (m, 1H)
LC-MS: m/z 445.2 (M+H)+

Compound 715

(R)-6-cyclopropyl-2-(3-cyclopropyl-4-(2-methoxyacetyl)piperazin-1-yl)-5-(6-vinylpyridazin-4-yl)nicotinonitrile $^1$H NMR (CHLOROFORM-d) δ9.20 (s, 1H), 7.68 (s, 1H), 7.61 (s, 1H), 7.11 (dd, J=17.8, 11.0 Hz, 1H), 6.36 (d, J=17.9 Hz, 1H), 5.77 (d, J=11.2 Hz, 1H), 4.64 (d, J=12.9 Hz, 1H), 4.50 (d, J=12.6 Hz, 1H), 4.15 (s, 2H), 3.80-4.12 (m, 1H), 3.60-3.66 (m, 1H), 3.44 (s, 3H), 3.26 (dd, J=13.2, 3.5 Hz, 1H), 3.07-3.18 (m, 1H), 1.87-2.04 (m, 1H), 1.19-1.29 (m, 3H), 1.06 (dd, J=7.9, 2.9 Hz, 2H), 0.47-0.65 (m, 4H)
LC-MS: m/z 445.2 (M+H)+

Compound 696

(R)-2-(4-(cyclopropanecarbonyl)-3-cyclopropylpiperazin-1-yl)-6-cyclopropyl-5-(5-vinylpyridazin-3-yl)nicotinonitrile $^1$H NMR (CHLOROFORM-d) δ: 9.23 (d, J=2.1 Hz, 1H), 7.98 (s, 1H), 7.63 (d, J=2.1 Hz, 1H), 6.75 (dd, J=17.6, 10.9 Hz, 1H), 6.21 (d, J=17.6 Hz, 1H), 5.78 (d, J=10.9 Hz, 1H), 4.66 (d, J=12.9 Hz, 2.5H), 3.98-4.54 (m, 1H), 3.51-3.88 (m, 1H), 3.00-3.45 (m, 1H), 2.16-2.28 (m, 1H), 1.72 (s, 1H), 1.17-1.30 (m, 3H), 0.95-1.11 (m, 4H), 0.77-0.87 (m, 2H), 0.39-0.64 (m, 1H)

LC-MS: m/z 441.2 (M+H)+

Compound 686

(R)-6-cyclopropyl-2-(3-cyclopropyl-4-(3-hydroxypropanoyl)piperazin-1-yl)-5-(6-vinylpyridazin-4-yl)nicotinonitrile The mixture of (R)-6-cyclopropyl-2-(3-cyclopropyl-4-(3-hydroxypropanoyl)piperazin-1-yl)-5-(4,4,5,5-tetramethyl-1,3,2-dioxaborolan-2-yl)nicotinonitrile (100 mg, 0.235 mmol), 5-chloro-3-vinylpyridazine (30 mg, 0.213 mmol), Pd(dppf)Cl$_2$ (8 mg, 0.011 mmol) and CsF (98 mg, 0.640 mmol) in dioxane/H$_2$O was stirred at 100° C. for 16 hours. The mixture was diluted with EtOAc (30 mL) and filtered. The filtrate was partitioned between EtOAc (30 mL) and water (10 mL), the organic layer was washed with water (10 mL), brine, dried over Na$_2$SO$_4$ and concentrated to give the crude which was purified by prep-TLC to give 25 mg of the product.

$^1$H NMR (CHLOROFORM-d) δ: 9.21 (d, J=2.1 Hz, 1H), 7.70 (s, 1H), 7.64 (d, J=2.1 Hz, 1H), 7.15 (dd, J=17.8, 11.0 Hz, 1H), 6.39 (d, J=17.9 Hz, 1H), 5.81 (d, J=10.9 Hz, 1H), 4.64 (d, J=13.2 Hz, 1H), 4.52 (d, J=12.9 Hz, 1H), 4.10 (d, J=9.7 Hz, 1H), 3.87-4.01 (m, 2H), 3.71-3.87 (m, 1H), 3.07-3.36 (m, 3H), 2.46-2.70 (m, 2H), 1.81-2.03 (m, 1H), 1.20-1.34 (m, 3H), 1.03-1.13 (m, 2H), 0.60-0.69 (m, 1H), 0.46-0.57 (m, 4H)

LC-MS: m/z 445.2 (M+H)+

Compound 671

(R)-6-cyclopropyl-2-(3-cyclopropyl-4-(3-hydroxypropanoyl)piperazin-1-yl)-5-(6-hydroxypyridazin-4-yl)nicotinonitrile $^1$H NMR (CHLOROFORM-d) δ: 12.36 (br. s., 1H), 7.95 (d, J=2.0 Hz, 1H), 7.65 (s, 1H), 7.00 (d, J=2.0 Hz, 1H), 4.63 (d, J=13.1 Hz, 1H), 4.50 (d, J=12.8 Hz, 1H), 4.01-4.19 (m, 1H), 3.89-3.98 (m, 2H), 3.60-3.85 (m, 1H), 3.01-3.29 (m, 3H), 2.60 (dd, J=11.8, 6.0 Hz, 2H), 1.87-2.05 (m, 1H), 1.14-1.26 (m, 3H), 0.31-1.14 (m, 4H).

LC-MS: m/z 435.2 (M+H)+

Compound 673

(R)-6'-chloro-2-cyclopropyl-6-(4-(3-methoxypropanoyl)-3-methylpiperazin-1-yl)-[3,4'-bipyridine]-2',5-dicarbonitrile

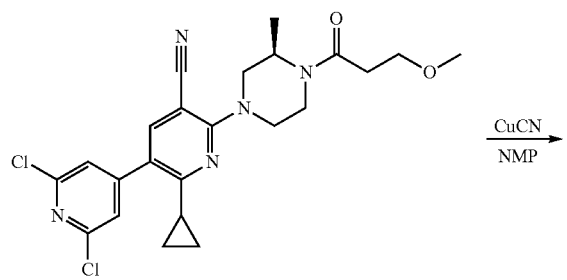

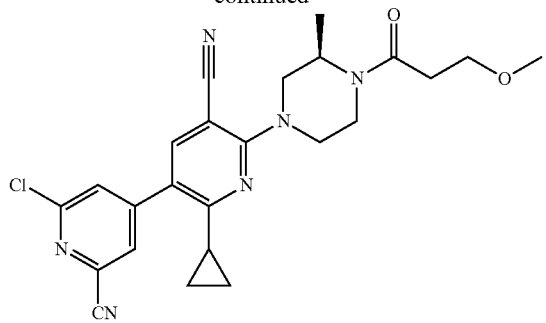

The mixture of (R)-2',6'-dichloro-2-cyclopropyl-6-(4-(3-methoxypropanoyl)-3-methylpiperazin-1-yl)-[3,4'-bipyridine]-5-carbonitrile (40 mg, 0.084 mmol), CuCN (15 mg, 0.169 mmol), CuI (1 mg) in NMP (2 mL) was stirred at 230° C. for 2 hours. After cooling to room temperature, the mixture was partitioned between EtOAc (30 mL) and water (10 mL), the organic layer was washed with water (10 mL), brine and dried over Na2SO4, concentrated to give the crude which was purified by prep-TLC to give 20 mg of the product.

$^1$H NMR (CHLOROFORM-d) δ: 7.72 (d, J=1.0 Hz, 1H), 7.59-7.66 (m, 2H), 4.91 (s, 0.5H), 4.54 (d, J=10.3 Hz, 0.5H), 4.24-4.48 (m, 2.5H), 3.69-3.79 (m, 2H), 3.51-3.62 (m, 0.5H), 3.33-3.44 (m, 4H), 3.18-3.29 (m, 1.5H), 3.10-3.25 (m, 1.5H), 2.63-2.82 (m, 1H), 2.52-2.63 (m, 1H), 1.82-1.95 (m, 1H), 1.36 (d, J=6.5 Hz, 1H), 1.23-1.28 (m, 4H), 1.04-1.15 (m, 2H)

LC-MS: m/z 465.2 (M+H)+

Compound 672

(R)-2-cyclopropyl-6-(4-(3-methoxypropanoyl)-3-methylpiperazin-1-yl)-6'-vinyl-[3,4'-bipyridine]-2',5-dicarbonitrile

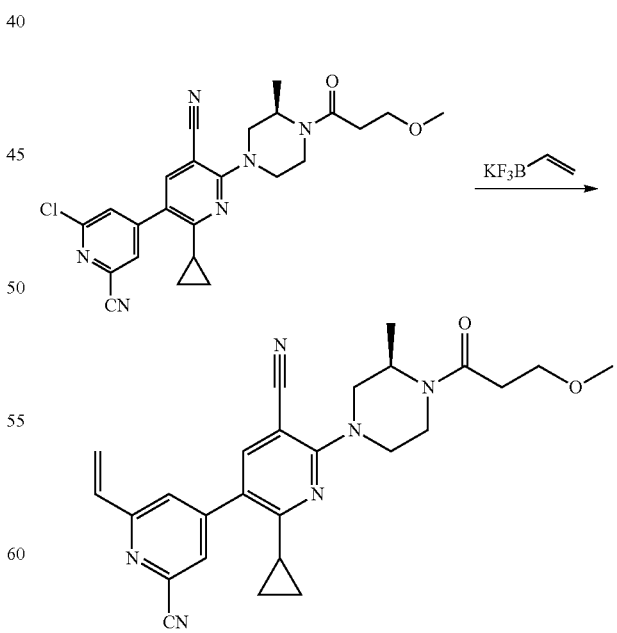

The mixture of (R)-6'-chloro-2-cyclopropyl-6-(4-(3-methoxypropanoyl)-3-methylpiperazin-1-yl)-[3,4'-bipyridine]-2',5-dicarbonitrile (10 mg, 0.0215 mmol), Potassium vinyltrifluoroborate (5 mg, 0.032 mmol), Pd(dppf)Cl$_2$ (1 mg, 0.001 mmol) and CsF (10 mg, 0.064 mmol) in dioxane/H$_2$O was stirred at 100° C. for 16 hours. The mixture was diluted with EtOAc (30 mL) and filtered. The filtrated was partitioned between EtOAc (30 mL) and water (10 mL), the organic layer was washed with water (10 mL), brine and dried over Na$_2$SO$_4$ and concentrated to give the crude which was purified by prep-TLC to give 5 mg of the product.

$^1$H NMR (CHLOROFORM-d) δ: 7.63 (s, 2H), 7.52-7.59 (m, 1H), 6.86 (dd, J=17.4, 10.7 Hz, 1H), 6.42 (d, J=17.6 Hz, 1H), 5.71 (d, J=10.8 Hz, 1H), 4.92 (s, 0.5H), 4.54 (d, J=9.5 Hz, 0.5H), 4.25-4.46 (m, 2.5H), 3.71-3.86 (m, 3.5H), 3.35-3.42 (m, 3.5H), 3.03-3.29 (m, 1.5H), 2.63-2.82 (m, 1H), 2.53-2.62 (m, 1H), 1.83-1.96 (m, 1H), 1.34-1.40 (m, 2H), 1.20-1.26 (m, 3H), 1.00-1.11 (m, 2H).

LC-MS: m/z 457.2 (M+H)$^+$

Compound 653

(R)-2-cyclopropyl-2'-(3-hydroxyprop-1-en-2-yl)-6-(4-(3-methoxypropanoyl)-3-methylpiperazin-1-yl)-[3,4'-bipyridine]-5-carbonitrile

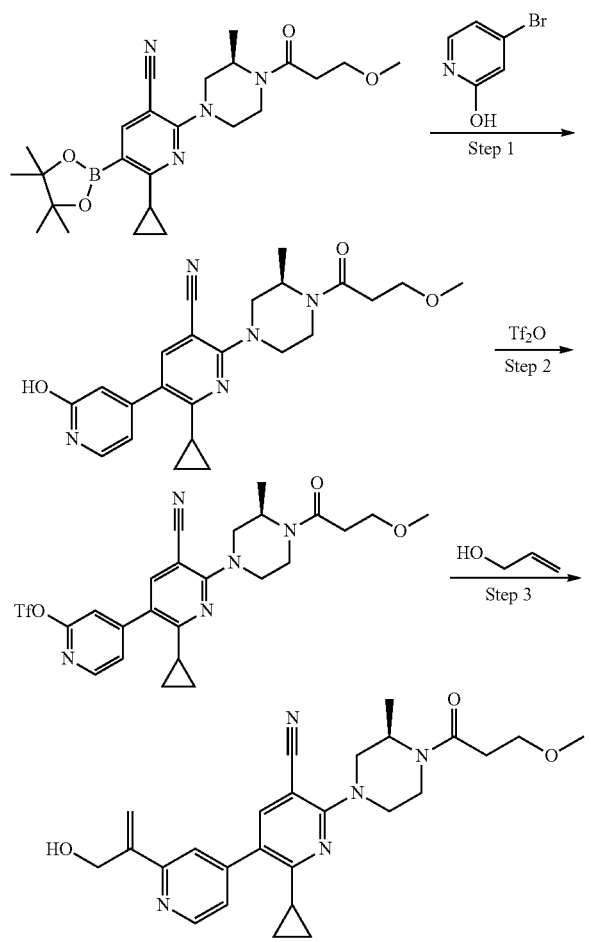

Step 1 (R)-2-cyclopropyl-2'-hydroxy-6-(4-(3-methoxypropanoyl)-3-methylpiperazin-1-yl)-[3,4'-bipyridine]-5-carbonitrile A mixture of (R)-6-cyclopropyl-2-(4-(3-methoxypropanoyl)-3-methylpiperazin-1-yl)-5-(4,4,5,5-tetramethyl-1,3,2-dioxaborolan-2-yl)nicotinonitrile (100 mg, 0.22 mmol), 4-bromopyridin-2-ol (38 mg, 0.22 mmol), CsF (66 mg, 0.44 mmol) and Pd(dppf)Cl$_2$ (5 mg) in dioxane and water was heated at 100° C. for 0.5 hr. The reaction mixture was concentrated and the residue was purified by pre-TLC to afford 52 mg of title compound.

LC-MS: m/z 422.1 (M+H)$^+$

Step 2 (R)-5-cyano-2-cyclopropyl-6-(4-(3-methoxypropanoyl)-3-methylpiperazin-1-yl)-[3,4'-bipyridin]-2'-yl trifluoromethanesulfonate A solution of (R)-2-cyclopropyl-2'-hydroxy-6-(4-(3-methoxypropanoyl)-3-methylpiperazin-1-yl)-[3,4'-bipyridine]-5-carbonitrile (100 mg, 0.24 mmol), Tf$_2$O (40 mg) and TEA (1 drop) in DCM (5 ml) was stirred for 1 hr. The reaction mixture was washed with water, dried and concentrated. The residue was purified by pre-TLC to afford 60 mg of title compound.

LC-MS: m/z 554.1 (M+H)$^+$

Step 3 (R)-2-cyclopropyl-2'-(3-hydroxyprop-1-en-2-yl)-6-(4-(3-methoxypropanoyl)-3-methylpiperazin-1-yl)-[3,4'-bipyridine]-5-carbonitrile Compound 653

A mixture of (R)-5-cyano-2-cyclopropyl-6-(4-(3-methoxypropanoyl)-3-methylpiperazin-1-yl)-[3,4'-bipyridin]-2'-yltrifluoromethanesulfonate (150 mg, 0.27 mmol), prop-2-en-1-ol (31 mg, 0.54 mmol), TEA (30 mg, 0.30 mmol), Pd(OAc)$_2$ (15 mg, 0.0675 mmol), and Dppf (72 mg, 0.13 mmol) in DMF (10 mL) was heated at 100° C. for 2 hrs. The reaction mixture was diluted with DCM and washed with water and brine, dried and concentrated and the residue was purified by prep-TLC and prep-HPLC to afford 16 mg of title compound.

$^1$H NMR (CHLOROFORM-d) δ8.62 (d, J=5.3 Hz, 1H), 7.69 (s, 1H), 7.65 (s, 1H), 7.31 (dd, J=5.0, 1.3 Hz, 1H), 5.87 (s, 1H), 5.60 (s, 1H), 4.92 (brs, 0.5H), 4.65 (s, 2H), 4.54 (d, J=12.5 Hz, 0.5H), 4.20-4.46 (m, 2.5H), 3.68-3.88 (m, 2.5H), 3.49-3.65 (m, 0.5H), 3.39 (s, 3H), 3.33 (d, J=13.3 Hz, 1H), 3.01-3.27 (m, 1.5H), 2.64-2.85 (m, 1H), 2.51-2.64 (m, 1H), 1.96-2.08 (m, 1H), 1.39 (d, J=6.5 Hz, 1.5H), 1.25-1.36 (m, 1.5H), 1.17-1.25 (m, 2H), 0.95-1.09 (m, 2H).

LC-MS: m/z 462.1 (M+H)$^+$

Compound 765

6-cyclopropyl-2-((R)-3-isopropyl-4-(3-methoxypropanoyl)piperazin-1-yl)-4-methyl-5-(2-vinylquinoxalin-5-yl)nicotinonitrile $^1$H NMR (CHLOROFORM-d) δ: 9.00 (s, 1H), 8.09-8.21 (m, 1H), 7.80-7.91 (m, 1H), 7.53-7.66 (m, 1H), 7.00-7.13 (m, 1H), 6.51 (d, J=17.6 Hz, 1H), 5.85 (d, J=11.2 Hz, 1H), 4.71 (d, J=10.0 Hz, 0.5H), 4.47 (d, J=10.3 Hz, 0.5H), 4.40 (d, J=13.5 Hz, 1H), 4.23-4.35 (m, 1H), 3.85 (d, J=13.5 Hz, 0.5H), 3.71-3.81 (m, 2H), 3.59 (d, J=10.3 Hz, 0.5H), 3.46-3.55 (m, 0.5H), 3.40 (d, J=5.0 Hz, 3H), 3.05-3.14 (m, 2H), 3.02 (d, J=9.7 Hz, 1H), 2.55-2.83 (m, 3H), 2.28-2.44 (m, 1H), 2.15-2.28 (m, 1H), 2.04-2.10 (m, 3H), 1.02-1.12 (m, 6H), 0.84-0.95 (m, 2H), 0.72-0.81 (m, 1H), 0.59-0.70 (m, 1H)

LC-MS: m/z 525.6 (M+H)$^+$

Compound 760

2-cyclopropyl-6-((R)-3-cyclopropyl-4-(2-((R)-oxetan-2-yl)acetyl)piperazin-1-yl)-4-methyl-2'-vinyl-3,4'-bipyridine-5-carbonitrile $^1$H NMR (CHLOROFORM-d) δ: 8.70 (d, J=4.4 Hz, 1H), 7.25 (s, 1H), 7.09 (d, J=3.5 Hz, 1H), 6.90 (dd, J=17.5, 10.7 Hz, 1H), 6.32 (d, J=17.3 Hz, 1H), 5.60 (d, J=10.9 Hz, 1H), 5.22-5.34 (m, 1H), 4.65-4.77 (m, 1H), 4.52-4.63 (m, 1H), 4.22-4.41 (m, 2H), 4.09 (d, J=8.2 Hz, 1H), 3.91 (br. s., 1H), 3.38 (s, 1H), 3.14 (br. s., 1H), 2.94-3.09 (m, 2H), 2.68-2.94 (m, 3H), 2.49-2.63 (m, 1H), 2.14-2.28 (m, 3H), 1.27 (s, 1H), 1.12 (br. s., 2H), 0.88 (dd, J=7.6, 2.9 Hz, 2H), 0.62 (br. s., 1H), 0.55 (br. s., 1H), 0.34-0.51 (m, 2H)

LC-MS: m/z 484.7 (M+H)$^+$

Compound 761

2-cyclopropyl-6-((R)-3-cyclopropyl-4-(2-((S)-oxetan-2-yl)acetyl)piperazin-1-yl)-4-methyl-2'-vinyl-3,4'-bipyridine-5-carbonitrile $^1$H NMR (CHLOROFORM-d) δ: 8.70 (d, J=4.4 Hz, 1H), 7.25 (s, 1H), 7.09 (d, J=3.5 Hz, 1H), 6.90 (dd, J=17.5, 10.7 Hz, 1H), 6.32 (d, J=17.3 Hz, 1H), 5.60 (d, J=10.9 Hz, 1H), 5.22-5.34 (m, 1H), 4.65-4.77 (m, 1H), 4.52-4.63 (m, 1H), 4.22-4.41 (m, 2H), 4.09 (d, J=8.2 Hz, 1H), 3.91 (br. s., 1H), 3.38 (s, 1H), 3.14 (br. s., 1H), 2.94-3.09 (m, 2H), 2.68-2.94 (m, 3H), 2.49-2.63 (m, 1H), 2.14-2.28 (m, 3H), 1.27 (s, 1H), 1.12 (br. s., 2H), 0.88 (dd, J=7.6, 2.9 Hz, 2H), 0.62 (br. s., 1H), 0.55 (br. s., 1H), 0.34-0.51 (m, 2H)

LC-MS: m/z 484.7 (M+H)$^+$

Compound 664

(R)-2-cyclopropyl-6-(4-(1-hydroxycyclopropanecarbonyl)-3-methylpiperazin-1-yl)-2'-vinyl-3,4'-bipyridine-5-carbonitrile $^1$H NMR (CHLOROFORM-d) δ: 8.64 (d, J=5.0 Hz, 1H), 7.64 (s, 1H), 7.40 (s, 1H), 7.24 (dd, J=5.0, 1.5 Hz, 1H), 6.88 (dd, J=17.6, 10.8 Hz, 1H), 6.27 (d, J=17.6 Hz, 1H), 5.57 (d, J=11.3 Hz, 1H), 4.87 (br. s., 1H), 4.50 (d, J=11.8 Hz, 1H), 4.39 (d, J=12.8 Hz, 1H), 4.32 (d, J=11.5 Hz, 1H), 3.32 (dd, J=13.1, 2.8 Hz, 1H), 3.21-3.66 (m, 2H), 1.99-2.07 (m, 1H), 1.30-1.50 (m, 3H), 1.21 (dt, J=7.2, 3.5 Hz, 2H), 1.11-1.17 (m, 1H), 0.91-1.09 (m, 5H).

LC-MS: m/z 430.2 (M+H)$^+$

Compound 739

(R)-methyl 4-(4-(2'-chloro-5-cyano-2-cyclopropyl-3,4'-bipyridin-6-yl)-2-cyclopropylpiperazin-1-yl)-4-oxobutanoate $^1$H NMR (CHLOROFORM-d) δ: 8.48 (d, J=5.0 Hz, 1H), 7.63 (s, 1H), 7.41 (s, 1H), 7.30 (d, J=4.4 Hz, 1H), 4.59 (d, J=12.3 Hz, 1H), 4.46 (d, J=12.0 Hz, 1H), 4.06 (br. s., 1H), 3.81-3.94 (m, 1H), 3.72 (s, 3H), 3.06-3.36 (m, 1.5H), 2.84 (br. s., 1.5H), 2.71 (d, J=7.9 Hz, 3H), 2.50-2.66 (m, 1H), 1.91-2.07 (m, 1H), 1.33 (br. s., 1H), 1.27 (br. s., 1H), 1.14-1.25 (m, 2H), 1.05 (dd, J=7.5, 3.4 Hz, 2H), 0.61 (br. s., 1H), 0.54 (br. s., 1H), 0.45 (d, J=4.1 Hz, 2H).

LC-MS: m/z 494.2 (M+H)$^+$

Compound 738

(R)-2-cyclopropyl-6-(3-cyclopropyl-4-(2-hydroxyacetyl)piperazin-1-yl)-2'-vinyl-3,4'-bipyridine-5-carbonitrile $^1$H NMR (CHLOROFORM-d) δ: 8.55-8.78 (m, 1H), 7.66 (s, 1H), 7.39 (br. s., 1H), 7.17-7.26 (m, 1H), 6.88 (dd, J=17.3, 10.9 Hz, 1H), 6.29 (d, J=17.3 Hz, 1H), 5.57 (d, J=10.9 Hz, 1H), 4.56 (d, J=12.9 Hz, 1H), 4.43 (d, J=12.9 Hz, 1H), 4.22 (br. s., 1H), 4.18 (br. s., 1H), 4.01 (br. s., 0.5H), 3.68 (br. s., 1.5H), 3.34-3.53 (m, 1H), 3.24 (d, J=10.9 Hz, 1H), 3.09 (t, J=11.3 Hz, 1H), 2.00-2.07 (m, 1H), 1.32 (br. s., 1H), 1.27 (br. s., 1H), 1.21 (br. s., 2H), 1.02 (br. s., 2H), 0.66 (br. s., 1H), 0.57 (br. s., 1H), 0.48 (br. s., 1H).

LC-MS: m/z 430.2 (M+H)$^+$

Compound 747

(R)-2-cyclopropyl-6-(3-cyclopropyl-4-(4-methoxybutanoyl)piperazin-1-yl)-2'-vinyl-3,4'-bipyridine-5-carbonitrile $^1$H NMR (CHLOROFORM-d) δ: 8.67 (d, J=4.7 Hz, 1H), 7.66 (s, 1H), 7.46 (br. s., 1H), 7.31 (br. s., 1H), 6.95 (dd, J=17.3, 10.9 Hz, 1H), 6.38 (d, J=17.3 Hz, 1H), 5.66 (d, J=10.6 Hz, 1H), 4.58 (d, J=12.9 Hz, 1H), 4.46 (d, J=12.3 Hz, 1H), 3.70-4.12 (br. s., 2H), 3.46 (br. s., 2H), 3.36 (s, 3H), 3.23 (br. s., 1H), 3.11 (br. s., 1H), 2.49 (br. s., 2H), 1.89-2.14 (m, 4H), 1.27-1.31 (m, 1H), 1.18-1.25 (m, 2H), 1.00-1.08 (m, 2H), 0.59 (d, J=15.6 Hz, 2H), 0.47 (d, J=5.0 Hz, 2H).

LC-MS: m/z 472.5 (M+H)$^+$

Compound 753

(R)-2-cyclopropyl-6-(3-cyclopropyl-4-(4-hydroxybutanoyl)piperazin-1-yl)-2'-vinyl-3,4'-bipyridine-5-carbonitrile $^1$H NMR (CHLOROFORM-d) δ: 8.64 (d, J=5.0 Hz, 1H), 7.64 (s, 1H), 7.39 (s, 1H), 7.18-7.27 (m, 1H), 6.87 (dd, J=17.3, 10.9 Hz, 1H), 6.28 (d, J=17.6 Hz, 1H), 5.57 (d, J=10.9 Hz, 1H), 4.55 (d, J=12.9 Hz, 1H), 4.42 (d, J=12.6 Hz, 1H), 4.09 (d, J=7.9 Hz, 0.5H), 3.86 (d, J=13.2 Hz, 0.5H), 3.73 (br. s., 2H), 3.05-3.32 (m, 2H), 2.97 (s, 1H), 2.89 (s, 1H), 2.57 (br. s., 3H), 2.00-2.08 (m, 1H), 1.91-1.98 (m, 2H), 1.28 (d, J=17.3 Hz, 1H), 1.21 (br. s., 2H), 1.01 (dd, J=7.6, 3.2 Hz, 2H), 0.61 (br. s., 1H), 0.54 (br. s., 1H), 0.30-0.50 (m, 2H).

LC-MS: m/z 458.6 (M+H)$^+$

Compound 726

(R)-2-cyclopropyl-6-(3-isopropyl-4-(2-methoxyacetyl)piperazin-1-yl)-2'-vinyl-3,4'-bipyridine-5-carbonitrile $^1$H NMR (CHLOROFORM-d) δ: 8.64 (d, J=5.0 Hz, 1H), 7.58-7.66 (m, 1H), 7.37 (s, 1H), 7.22 (dd, J=5.0, 1.5 Hz, 1H), 6.87 (dd, J=17.5, 10.7 Hz, 1H), 6.21-6.33 (m, 1H), 5.50-5.60 (m, 1H), 4.54-4.71 (m, 1H), 4.33-4.49 (m, 1.5H), 4.02-4.22 (m, 2H), 3.87 (d, J=13.8 Hz, 0.5H), 3.33-3.50 (m, 4H), 3.03-3.23 (m, 2.5H), 2.21 (d, J=7.6 Hz, 0.5H), 1.96-2.16 (m, 2H), 1.11-1.24 (m, 2H), 0.94-1.11 (m, 5H), 0.84-0.92 (m, 3H).

LC-MS: m/z 446.1 (M+H)$^+$

Compound 721

(R)-2-cyclopropyl-6-(4-(3-hydroxypropanoyl)-3-isopropylpiperazin-1-yl)-2'-vinyl-3,4'-bipyridine-5-carbonitrile $^1$H NMR (CHLOROFORM-d) δ: 8.66 (d, J=5.0 Hz, 1H), 7.64 (d, J=2.3 Hz, 1H), 7.40 (s, 1H), 7.25 (dd, J=5.1, 1.6 Hz, 1H), 6.89 (dd, J=17.5, 10.7 Hz, 1H), 6.23-6.35 (m, 1H), 5.55-5.63 (m, 1H), 4.58-4.74 (m, 1.5H), 4.38-4.50 (m, 1.5H), 3.87-4.00 (m, 2H), 3.78 (d, J=13.8 Hz, 1H), 3.39-3.55 (m, 1H), 3.05-3.24 (m, 2H), 2.56-2.66 (m, 2H), 2.20-2.30 (m, 1H), 1.98-2.06 (m, 2H), 1.25-1.33 (m, 6H), 0.84-0.95 (m, 4H)

LC-MS: m/z 446.1 (M+H)$^+$

Compound 719

(R)-5-(2-amino-6-vinylpyrimidin-4-yl)-6-cyclopropyl-2-(3-cyclopropyl-4-(3-hydroxypropanoyl)piperazin-1-yl)nicotinonitrile

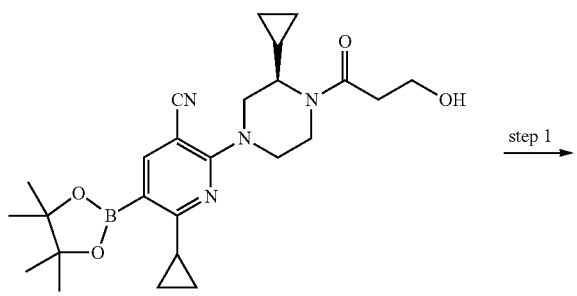

step 1 →

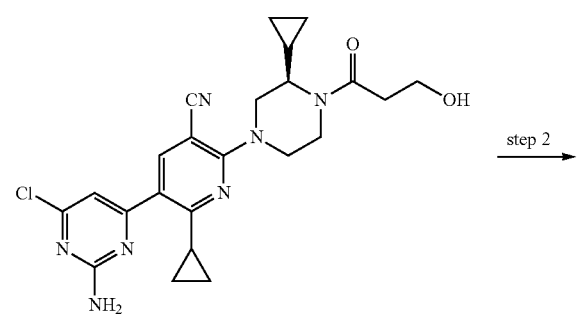

step 2 →

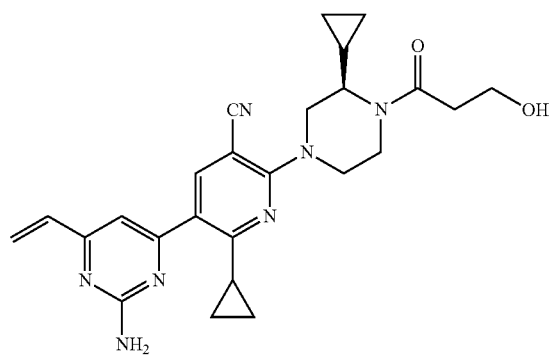

Step 1 (R)-5-(2-amino-6-chloropyrimidin-4-yl)-6-cyclopropyl-2-(3-cyclopropyl-4-(3-hydroxypropanoyl)piperazin-1-yl)nicotinonitrile

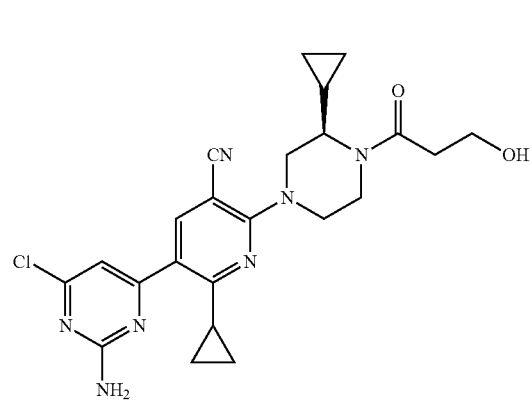 [SMILES: N#Cc1cc(-c2cc(Cl)nc(N)n2)c(C2CC2)nc1N1CCN(C(=O)CCO)[C@H](C2CC2)C1]

To a solution of 4,6-dichloropyrimidin-2-amine (270 mg, 0.58 mmol) in a mixture of dimethoxyethane (5 mL) and a 2M aqueous sodium carbonate solution (0.8 mL) were added (R)-6-cyclopropyl-2-(3-cyclopropyl-4-(3-hydroxypropanoyl)piperazin-1-yl)-5-(4,4,5,5-tetramethyl-1,3,2-dioxaborolan-2-yl)nicotinonitrile (100 mg, 0.22 mmol) and tetrakis(triphenylphosphine)palladium(0) (20 mg, 0.1 eq) under nitrogen atmosphere, and the mixture was heated for 2 hours at 100° C. After cooling to ambient temperature, the separated organic layer was evaporated under reduced pressure. The residue was taken up into ethyl acetate, washed in turn with a 10% aqueous potassium carbonate solution and brine, and dried over sodium sulfate. After evaporation, the residue was chromatographed on silica gel eluding with 5%-20% ethyl acetate in petroleum ether to give (R)-5-(2-amino-6-chloropyrimidin-4-yl)-6-cyclopropyl-2-(3-cyclopropyl-4-(3-hydroxypropanoyl) piperazin-1-yl)nicotinonitrile (140 mg crude).

LC-MS: m/z 468.2 (M+H)$^+$

Step 2: Compound 719

(R)-5-(2-amino-6-vinylpyrimidin-4-yl)-6-cyclopropyl-2-(3-cyclopropyl-4-(3-hydroxypropanoyl)piperazin-1-yl)nicotinonitrile A mixture of above (R)-5-(2-amino-6-chloropyrimidin-4-yl)-6-cyclopropyl-2-(3-cyclopropyl-4-(3-hydroxypropanoyl)piperazin-1-yl)nicotinonitrile (60 mg, 0.13 mmol), potassium vinylfluoborate (25 mg, 0.2 mmol), Pd(PPh$_3$)$_4$ (3 mg, 0.1 eq), and CsF (40 mg, 0.26 mmol) were suspended in 5 mL of dioxane and 1 mL of water, the resulting mixture was refluxed for 1 h. After the reaction was complete, the reaction mixture was concentrated in vacuo, and the residue was purified by column chromatography to afford 40 mg of title compound as yellow solid. (70% yield)

LC-MS: m/z 460.2 (M+H)$^+$ $^1$H NMR (CHLOROFORM-d) δ: 7.92 (s, 1H), 6.87 (s, 1H), 6.65 (dd, J=17.3, 10.6 Hz, 1H), 6.39 (d, J=17.5 Hz, 1H), 5.69 (d, J=10.7 Hz, 1H), 5.44 (br. s., 2H), 4.61 (d, J=13.2 Hz, 1H), 4.48 (d, J=12.1 Hz, 1H), 4.07 (d, J=7.5 Hz, 1H), 3.87-3.98 (m, 2H), 3.63-3.84 (m, 2H), 3.17-3.31 (m, 2H), 3.00-3.17 (m, 1H), 2.50-2.66 (m, 2H), 2.30-2.45 (m, 1H), 1.17-1.28 (m, 3H), 0.97-1.13 (m, 2H), 0.61 (br. s., 1H), 0.54 (br. s., 1H), 0.46 (br. s., 2H).

LC-MS: m/z 460.2 (M+H)$^+$

Compound 663

(R)-6-cyclopropyl-2-(3-cyclopropyl-4-(3-hydroxy-propanoyl)piperazin-1-yl)-5-(6-vinylpyrimidin-4-yl)nicotinonitrile ¹H NMR (CHLOROFORM-d) δ: 9.19-9.32 (m, 1H), 8.01 (s, 1H), 7.46-7.59 (m, 1H), 6.82 (dd, J=17.3, 10.8 Hz, 1H), 6.51-6.63 (m, 1H), 5.80 (d, J=11.3 Hz, 1H), 5.32 (s, 1H), 4.66 (d, J=13.1 Hz, 1H), 4.53 (d, J=12.8 Hz, 1H), 4.08 (d, J=9.8 Hz, 1H), 3.88-3.97 (m, 2H), 3.67-3.82 (m, 2H), 3.32 (br. s., 1H), 3.20-3.29 (m, 2H), 3.02-3.20 (m, 2H), 2.49-2.66 (m, 2H), 2.34-2.45 (m, 1H), 1.22-1.29 (m, 3H), 1.02-1.10 (m, 2H), 0.63 (d, J=7.8 Hz, 1H), 0.55 (br. s., 1H), 0.47 (br. s., 2H).

LC-MS: m/z 445.2 (M+H)⁺

Compound 701

(R)-5-(2-amino-6-(2-aminoethyl)pyrimidin-4-yl)-2-(4-(cyclopropanecarbonyl)-3-cyclopropylpiperazin-1-yl)-6-cyclopropylnicotinonitrile ¹H NMR (CHLOROFORM-d) δ 7.97-8.12 (m, 1H), 7.51 (br. s., 1H), 6.21 (br. s., 2H), 4.71 (d, J=12.8 Hz, 1H), 4.57 (d, J=11.0 Hz, 1H), 4.06 (s, 1H), 3.52 (br. s., 3H), 3.31 (br. s., 3H), 3.22 (br. s., 2H), 2.38 (br. s., 1H), 1.71 (br. s., 1H), 1.19-1.28 (m, 3H), 0.96-1.14 (m, 4H), 0.75-0.87 (m, 2H), 0.62 (br. s., 1H), 0.51 (br. s., 2H), 0.38-0.48 (m, 1H).

LC-MS: m/z 473.3 (M+H)⁺

Compound 759

(R)-5-(2-amino-6-vinylpyrimidin-4-yl)-6-cyclopropyl-2-(3-cyclopropyl-4-(2-methoxyacetyl)piperazin-1-yl)nicotinonitrile ¹H NMR (CHLOROFORM-d) δ: 7.95 (s, 1H), 6.88 (s, 1H), 6.66 (dd, J=17.5, 10.7 Hz, 1H), 6.47 (d, J=17.6 Hz, 1H), 5.71 (d, J=11.2 Hz, 1H), 5.27 (br. s., 2H), 4.64 (d, J=13.2 Hz, 2H), 4.50 (d, J=12.6 Hz, 2H), 4.16 (br. s., 3H), 4.01 (br. s., 1H), 3.90 (br. s., 1H), 3.65 (d, J=17.0 Hz, 1H), 3.46 (s, 3H), 3.18-3.32 (m, 2H), 3.02-3.18 (m, 1H), 2.32-2.47 (m, 1H), 1.18-1.32 (m, 3H), 1.00-1.11 (m, 2H), 0.63 (br. s., 2H), 0.46 (br. s., 2H)

LC-MS: m/z 460.2 (M+H)⁺

Compound 727

(R)-5-(1-acryloyl-1,2,5,6-tetrahydropyridin-3-yl)-6-cyclopropyl-2-(3-cyclopropyl-4-(3-hydroxypropanoyl)piperazin-1-yl)nicotinonitrile ¹H NMR (CHLOROFORM-d) δ: 7.51 (br. s., 1H), 6.66 (dd, J=16.7, 10.6 Hz, 1H), 6.35 (d, J=16.7 Hz, 1H), 5.88 (br. s., 1H), 5.66-5.83 (m, 1H), 4.44 (d, J=12.6 Hz, 1H), 4.25-4.38 (m, 2H), 4.19 (br. s., 1H), 3.98-4.10 (m, 1H), 3.91 (br. s., 2H), 3.84 (br. s., 1H), 3.60-3.79 (m, 3H), 3.08-3.25 (m, 2H), 2.89-3.08 (m, 1H), 2.47-2.65 (m, 2H), 2.40 (br. s., 2H), 2.01-2.08 (m, 1H), 1.27 (br. s., 1H), 1.14 (br. s., 2H), 0.98-1.10 (m, 2H), 0.62 (br. s., 1H), 0.53 (br. s., 1H), 0.34-0.50 (m, 2H).

LC-MS: m/z 476.6 (M+H)⁺

Compound 728

(R)-5-(1-acryloyl-1,2,5,6-tetrahydropyridin-3-yl)-6-cyclopropyl-2-(3-cyclopropyl-4-(2-methoxyacetyl)piperazin-1-yl)nicotinonitrile ¹H NMR (CHLOROFORM-d) δ: 7.44-7.56 (m, 1H), 6.49-6.74 (m, 1H), 6.35 (d, J=16.7 Hz, 1H), 5.88 (br. s., 1H), 5.67-5.82 (m, 1H), 4.46 (d, J=12.9 Hz, 1H), 4.25-4.39 (m, 2H), 4.07-4.23 (m, 3H), 3.98 (d, J=8.5 Hz, 1H), 3.84 (t, J=5.1 Hz, 1H), 3.73 (t, J=5.4 Hz, 1H), 3.45 (s, 3H), 3.10-3.21 (m, 1H), 3.02 (t, J=11.9 Hz, 1H), 2.39 (br. s., 2H), 2.00-2.16 (m, 1H), 1.69 (br. s., 1H), 1.30-1.37 (m, 1H), 1.14 (br. s., 2H), 0.97-1.09 (m, 2H), 0.64 (br. s., 1H), 0.51 (br. s., 1H), 0.45 (br. s., 1H).

LC-MS: m/z 476.6 (M+H)⁺

Compound 680

(R)-5-(1-acryloyl-1,2,5,6-tetrahydropyridin-3-yl)-6-cyclopropyl-2-(4-(3-methoxypropanoyl)-3-methyl-piperazin-1-yl)-4-methylnicotinonitrile ¹H NMR (CHLOROFORM-d) δ: 6.65 (d, J=10.0 Hz, 1H), 6.36 (d, J=16.8 Hz, 1H), 5.65-5.84 (m, 2H), 4.90 (br. s., 0.5H), 4.52 (d, J=13.1 Hz, 0.5H), 4.25-4.38 (m, 0.5H), 4.01-4.25 (m, 4H), 3.87-4.01 (m, 1H), 3.67-3.86 (m, 4H), 3.39 (s, 3H), 3.09-3.22 (m, 1H), 2.95-3.09 (m, 1H), 2.54-2.71 (m, 2H), 2.36-2.48 (m, 5H), 2.03 (br. s., 1H), 1.20-1.35 (m, 4H), 0.84-1.08 (m, 4H).

LC-MS: m/z 478.6 (M+H)⁺

Compound 745

(R)-5-(1-acryloyl-1,2,5,6-tetrahydropyridin-3-yl)-6-cyclopropyl-2-(3-cyclopropyl-4-(3-methoxypropanoyl)piperazin-1-yl)-4-methylnicotinonitrile ¹H NMR (CHLOROFORM-d) δ: 6.67 (dd, J=16.3, 10.4 Hz, 1H), 6.36 (d, J=16.1 Hz, 1H), 5.65-5.85 (m, 2H), 4.13-4.34 (m, 3H), 4.03-4.11 (m, 1H), 3.95 (d, J=18.8 Hz, 1H), 3.78-3.89 (m, 1H), 3.62-3.78 (m, 4H), 3.38 (s, 3H), 3.27 (br. s., 1H), 3.10 (br. s., 1H), 2.98 (br. s., 1H), 2.36-2.47 (m, 5H), 1.96-2.08 (m, 1H), 1.23-1.39 (m, 3H), 0.81-1.07 (m, 4H), 0.60 (br. s., 1H), 0.52 (br. s., 1H), 0.43 (br. s., 2H).

LC-MS: m/z 504.6 (M+H)⁺

Compound 755

(R)-5-(1-acryloyl-1,2,5,6-tetrahydropyridin-3-yl)-6-cyclopropyl-2-(3-cyclopropyl-4-(3-hydroxypropanoyl)piperazin-1-yl)-4-methylnicotinonitrile

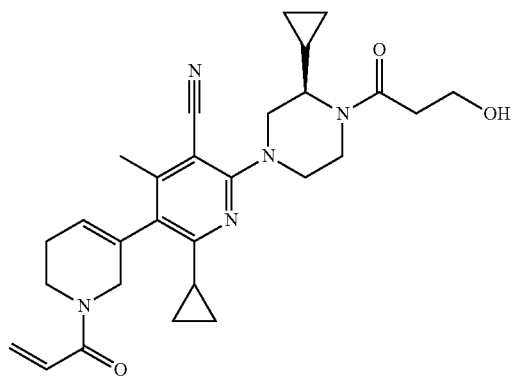 [SMILES: C=CC(=O)N1CCC=C(c2c(C3CC3)nc(N3CCN(C(=O)CCO)[C@H](C4CC4)C3)c(C#N)c2C)C1]

¹H NMR (CHLOROFORM-d) δ: 6.67 (dd, J=16.7, 10.9 Hz, 1H), 6.36 (d, J=16.7 Hz, 1H), 5.64-5.85 (m, 1H), 4.10-4.38 (m, 3H), 4.04 (br. s., 1H), 3.98 (br. s., 1H), 3.91 (br. s., 2H), 3.61-3.83 (m, 3H), 3.04-3.34 (m, 2H), 2.59 (br. s., 1H), 2.52 (d, J=10.3 Hz, 1H), 2.37-2.48 (m, 5H), 2.06 (br. s., 1H), 1.34-1.50 (m, 1H), 1.16 (br. s., 1H), 0.93-1.10 (m, 3H), 0.62 (br. s., 1H), 0.27-0.56 (m, 3H)

LC-MS: m/z 490.6 (M+H)⁺

Compound 762

(R)-1'-acryloyl-2-cyclopropyl-6-(4-(3-hydroxypropanoyl)-3-isopropylpiperazin-1-yl)-4-methyl-1',2',5',6'-tetrahydro-[3,3'-bipyridine]-5-carbonitrile ¹H NMR (CHLOROFORM-d) δ: 6.36 (d, J=16.7 Hz, 1H), 5.68-5.98 (m, 2H), 4.33 (d, J=11.7 Hz, 1H), 4.22 (d, J=13.2 Hz, 2H), 4.04 (br. s., 1H), 3.92 (t, J=5.0 Hz, 3H), 3.64-3.78 (m, 2H), 3.47 (d, J=7.9 Hz, 1H), 2.96-3.09 (m, 2H), 2.52-2.65 (m, 2H), 2.38-2.48 (m, 5H), 2.04 (br. s., 2H), 0.95-1.07 (m, 6H), 0.83-0.95 (m, 4H)

LC-MS: m/z 492.6 (M+H)⁺

Compound 649

2-cyclopropyl-6-((3R)-3-methyl-4-(2-(oxetan-2-yl)acetyl)piperazin-1-yl)-2'-vinyl-[3,4'-bipyridine]-5-carbonitrile ¹H NMR (CHLOROFORM-d) δ: 8.60 (m, 1H), 7.64 (s, 1H), 7.37 (s, 1H), 7.19-7.27 (m, 1H), 6.88 (dd, J=17.4, 10.9 Hz, 1H), 6.28 (d, J=17.6 Hz, 1H), 5.57 (d, J=11.0 Hz, 1H), 5.17-5.42 (m, 1H), 4.89 (m, 0.5H), 4.73 (q, J=7.0 Hz, 1H), 4.46-4.62 (m, 1.5H), 4.34 (m, 2H), 4.28 (d, J=13.3 Hz, 0.5H), 3.85 (t, J=13.3 Hz, 0.5H), 3.50-3.67 (m, 0.5H), 3.21-3.32 (m, 1H), 2.99-3.20 (m, 1.5H), 2.76-2.94 (m, 3H), 2.46-2.60 (m, 1H), 1.87-2.09 (m, 1H), 1.24-1.32 (m, 3H), 1.14-1.23 (m, 2H), 0.93-1.10 (m, 3H).

LC-MS: m/z 444.0 (M+H)⁺

Compound 648

2-cyclopropyl-6-((R)-3-methyl-4-(2-((R)-oxetan-2-yl)acetyl)piperazin-1-yl)-2'-vinyl-[3,4'-bipyridine]-5-carbonitrile ¹H NMR (CHLOROFORM-d) δ: 8.65 (d, J=5.0 Hz, 1H), 7.63 (s, 1H), 7.38 (s, 1H), 7.13-7.27 (m, 1H), 6.88 (dd, J=17.4, 10.9 Hz, 1H), 6.13-6.40 (m, 1H), 5.56 (d, J=11.5 Hz, 1H), 5.18-5.34 (m, 1H), 4.81-5.03 (m, 0.5H), 4.65-4.79 (m, 1H), 4.48-4.65 (m, 1.5H), 4.30-4.42 (m, 2H), 4.26 (d, J=12.8 Hz, 0.5H), 3.86 (d, J=13.3 Hz, 0.5H), 3.49-3.66 (m, 0.5H), 3.23-3.40 (m, 1H), 3.01-3.20 (m, 1.5H), 2.71-3.01 (m, 3H), 2.37-2.64 (m, 1H), 1.90-2.10 (m, 1H), 1.24-1.34 (m, 3H), 1.13-1.24 (m, 2H), 0.93-1.09 (m, 2H)

LC-MS: m/z 444.0 (M+H)⁺

Compound 654

(R)-2-cyclopropyl-6-(4-(3-hydroxypropanoyl)-3-methylpiperazin-1-yl)-4-methyl-2'-vinyl-[3,4'-bipyridine]-5-carbonitrile ¹H NMR (CHLOROFORM-d) δ: 8.70 (d, J=4.8 Hz, 1H), 7.23 (s, 1H), 7.07 (d, J=4.8 Hz, 1H), 6.88 (dd, J=17.4, 10.9 Hz, 1H), 6.30 (d, J=17.3 Hz, 1H), 5.58 (d, J=11.3 Hz, 1H), 4.90 (br. s., 0.5H), 4.54 (d, J=13.6 Hz, 0.5H), 4.07-4.26 (m, 2.5H), 3.93 (br. s., 2H), 3.66-3.79 (m, 0.5H), 3.58 (t, J=11.0 Hz, 0.5H), 3.46 (br. s., 1H), 3.13-3.29 (m, 1.5H), 2.95-3.13 (m, 1H), 2.47-2.75 (m, 2H), 2.22 (s, 3H), 1.74 (br. s., 1H), 1.50-1.63 (m, 1H), 1.37-1.46 (m, 1.5H), 1.33 (d, J=6.8 Hz, 1.5H), 1.01-1.14 (m, 2H), 0.79-0.95 (m, 2H).

LC-MS: m/z 431.5 (M+H)⁺

Compound 655

(R)-6-cyclopropyl-2-(3-cyclopropyl-4-(3-hydroxypropanoyl)piperazin-1-yl)-5-(2-vinyl-1,8-naphthyridin-4-yl)nicotinonitrile ¹H NMR (CHLOROFORM-d) δ: 7.94-8.05 (m, 1H), 7.69 (d, J=1.3 Hz, 1H), 7.60 (d, J=3.5 Hz, 1H), 7.43-7.48 (m, 1H), 7.14 (dd, J=17.6, 10.8 Hz, 1H), 6.55 (dd, J=17.6, 1.8 Hz, 1H), 5.81 (d, J=11.0 Hz, 1H), 4.60 (d, J=13.1 Hz, 1.5H), 4.48 (d, J=13.1 Hz, 1H), 4.13 (d, J=6.0 Hz, 0.5H), 3.86-3.99 (m, 2H), 3.82 (br. s., 1.5H), 3.28 (br. s., 1.5H), 3.15 (dd, J=15.7, 8.2 Hz, 2H), 2.56-2.68 (m, 2H), 1.13-1.23 (m, 2H), 0.80-0.97 (m, 3H), 0.68 (br. s., 1H), 0.59 (br. s., 1H), 0.51 (br. s., 2H).

LC-MS: m/z 495.1 (M+H)⁺

Compound 650

(R)-6-cyclopropyl-2-(4-(3-hydroxypropanoyl)-3-isopropylpiperazin-1-yl)-5-(2-vinylquinazolin-5-yl)nicotinonitrile ¹H NMR (CHLOROFORM-d) δ 9.20 (d, J=11.0 Hz, 1H), 8.14 (d, J=8.5 Hz, 1H), 7.96-8.04 (m, 1H), 7.68 (dd, J=4.4, 2.9 Hz, 1H), 7.49-7.59 (m, 1H), 7.06-7.23 (m, 1H), 6.86 (d, J=17.1 Hz, 1H), 5.94 (d, J=10.5 Hz, 1H), 4.62-4.80 (m, 1.5H), 4.43-4.54 (m, 1.5H), 3.87-4.03 (m, 2H), 3.73-3.86 (m, 1H), 2.91-3.31 (m, 3H), 2.54-2.67 (m, 2H), 2.09-2.25 (m, 1H), 1.54 (td, J=8.0, 4.1 Hz, 1H), 1.11 (dd, J=13.7, 6.4 Hz, 4H), 0.79-0.94 (m, 6H).

LC-MS: m/z 497.3 (M+H)⁺

Compound 652

(R)-6-cyclopropyl-2-(4-(3-hydroxypropanoyl)-3-methylpiperazin-1-yl)-5-(2-vinylquinazolin-5-yl)nicotinonitrile ¹H NMR (CHLOROFORM-d) δ 9.17 (d, J=3.3 Hz, 1H), 8.08 (d, J=8.5 Hz, 1H), 7.97 (dd, J=8.4, 7.2 Hz, 1H), 7.68 (s, 1H), 7.52 (d, J=7.0 Hz, 1H), 7.08 (dd, J=17.3, 10.5 Hz, 1H), 6.74-6.90 (m, 1H), 5.89 (dd, J=10.5, 1.5 Hz, 1H), 4.93 (br. s., 0.5H), 4.57 (d, J=12.5 Hz, 0.5H), 4.28-4.47 (m, 2H), 4.21 (br. s., 0.5H), 3.94 (s, 2H), 3.71-3.84 (m, 0.5H), 3.50-3.68 (m, 0.5H), 3.29-3.44 (m, 1H), 3.06-3.26 (m, 2H), 2.49-2.78 (m, 2H), 1.50-1.62 (m, 1H), 1.45 (t, J=7.2 Hz, 1H), 1.35 (t, J=6.4 Hz, 2H), 1.14-1.22 (m, 2H), 0.83-0.98 (m, 2H)

LC-MS: m/z 469.2 (M+H)⁺

Compound 651

(R)-6-cyclopropyl-2-(3-cyclopropyl-4-(3-hydroxypropanoyl)piperazin-1-yl)-5-(2-vinylquinazolin-5-yl)nicotinonitrile ¹H NMR (CHLOROFORM-d) δ: 8.08 (d, J=8.3 Hz, 1H), 7.97 (td, J=7.8, 1.3 Hz, 1H), 7.69 (d, J=1.5 Hz, 1H), 7.47-7.56 (m, 1H), 7.09 (dd, J=17.1, 10.5 Hz, 1H), 6.82 (d, J=17.1 Hz, 1H), 5.90 (dd, J=10.7, 1.6 Hz, 1H), 4.61 (dd, J=13.1, 7.3 Hz, 1H), 4.41-4.55 (m, 1H), 4.12 (d, J=6.5 Hz, 1H), 3.94 (s, 2H), 3.67-3.82 (m, 1H), 3.10-3.40 (m, 3H), 2.49-2.68 (m, 2H), 1.56 (td, J=8.1, 4.1 Hz, 1H), 1.32-1.41 (m, 1H), 1.14-1.24 (m, 2H), 0.84-0.95 (m, 2H), 0.51-0.69 (m, 4H)

LC-MS: m/z 495.2 (M+H)$^+$

Compound 657

(R)-6-cyclopropyl-2-(3-cyclopropyl-4-(3-hydroxypropanoyl)piperazin-1-yl)-5-(2-vinylquinoxalin-5-yl)nicotinonitrile $^1$H NMR (CHLOROFORM-d) δ: 9.00 (s, 1H), 8.08-8.18 (m, 1H), 7.79-7.90 (m, 1H), 7.65-7.76 (m, 2H), 7.07 (dd, J=17.8, 11.0 Hz, 1H), 6.51 (d, J=17.6 Hz, 1H), 5.84 (d, J=11.0 Hz, 1H), 4.51 (d, J=13.1 Hz, 1H), 4.40 (d, J=12.8 Hz, 1H), 4.13 (q, J=7.0 Hz, 1.5H), 3.86-3.99 (m, 2.5H), 3.76 (d, J=19.8 Hz, 2H), 3.37 (d, J=7.8 Hz, 1H), 3.22-3.33 (m, 1H), 3.17 (d, J=12.3 Hz, 1H), 3.09 (br. s., 1H), 2.55-2.69 (m, 2H), 1.58-1.69 (m, 1H), 1.17-1.37 (m, 3H), 1.08 (br. s., 2H), 0.83 (br. s., 2H), 0.66 (br. s., 1H), 0.55 (br. s., 1H), 0.48 (d, J=5.8 Hz, 3H).

LC-MS: m/z 495.1 (M+H)$^+$

Compound 740

(R)-6-cyclopropyl-2-(3-cyclopropyl-4-(3-hydroxypropanoyl)piperazin-1-yl)-5-(6-vinyl-1H-pyrrolo[2,3-b]pyridin-4-yl)nicotinonitrile $^1$H NMR (CHLOROFORM-d) δ: 10.15 (br. s., 1H), 7.69-7.87 (m, 1H), 7.36-7.45 (m, 1H), 7.23 (s, 1H), 6.97 (dd, J=17.3, 11.2 Hz, 1H), 6.43 (d, J=3.2 Hz, 1H), 6.28 (d, J=17.3 Hz, 1H), 5.56 (d, J=10.9 Hz, 1H), 4.58 (d, J=12.9 Hz, 1H), 4.45 (d, J=12.6 Hz, 1H), 4.12 (d, J=8.5 Hz, 1H), 3.94 (br. s., 2H), 3.63-3.87 (m, 2H), 3.13-3.27 (m, 2H), 2.54-2.69 (m, 2H), 1.95-2.02 (m, 1H), 1.54-1.74 (m, 1H), 1.22 (br. s., 2H), 0.97 (dd, J=7.6, 3.5 Hz, 2H), 0.67 (br. s., 1H), 0.57 (br. s., 1H), 0.50 (br. s., 2H)

LC-MS: m/z 483.6 (M+H)$^+$

Compound 735

(R)-6-cyclopropyl-2-(3-cyclopropyl-4-(3-hydroxypropanoyl)piperazin-1-yl)-5-(2-vinyl-1,7-naphthyridin-5-yl)nicotinonitrile $^1$H NMR (CHLOROFORM-d) δ9.53 (s, 1H), 8.54 (d, J=3.2 Hz, 1H), 7.88-8.00 (m, 1H), 7.79 (d, J=8.8 Hz, 1H), 7.69 (s, 1H), 7.09 (dd, J=17.8, 11.0 Hz, 1H), 6.41 (d, J=17.6 Hz, 1H), 5.81 (d, J=11.2 Hz, 1H), 4.59 (d, J=13.2 Hz, 1H), 4.47 (d, J=12.6 Hz, 1H), 4.1-4.2 (m, 0.5H), 3.93 (br. s., 2H), 3.82 (m, 1.5H), 3.44 (m, 1H), 3.05-3.35 (m, 3H), 2.54-2.70 (m, 2H), 1.47-1.64 (m, 2H), 1.13-1.23 (m, 2H), 0.90-0.96 (m, 2H), 0.68 (br. s., 1H), 0.58 (br. s., 1H), 0.51 (br. s., 2H)

LC-MS: m/z 495.2 (M+H)$^+$

Compound 744

(R)-6-cyclopropyl-2-(3-cyclopropyl-4-(3-hydroxypropanoyl)piperazin-1-yl)-5-(1-methyl-6-vinyl-1H-pyrazolo[3,4-b]pyridin-4-yl)nicotinonitrile $^1$H NMR (CHLOROFORM-d) δ7.90 (s, 1H), 7.77 (s, 1H), 7.21 (s, 1H), 6.99 (dd, J=17.5, 10.7 Hz, 1H), 6.41 (d, J=17.3 Hz, 1H), 5.58-5.73 (m, 1H), 4.60 (d, J=13.2 Hz, 1H), 4.48 (d, J=12.6 Hz, 1H), 4.20 (s, 3H), 4.11 (d, J=8.8 Hz, 1H), 3.93 (br. s., 2H), 3.65-3.85 (m, 1H), 3.44 (br. s., 1H), 3.18-3.36 (m, 2H), 3.13 (d, J=10.0 Hz, 1H), 2.46-2.70 (m, 2H), 1.88-2.01 (m, 1H), 1.31-1.42 (m, 1H), 1.24 (dt, J=7.0, 3.5 Hz, 2H), 0.93-1.04 (m, 2H), 0.66 (br. s., 1H), 0.57 (br. s., 1H), 0.32-0.53 (m, 2H)

LC-MS: m/z 498.2 (M+H)$^+$

Compound 670

(R)-6-cyclopropyl-2-(3-cyclopropyl-4-(3-hydroxypropanoyl)piperazin-1-yl)-5-(2-vinylquinazolin-4-yl)nicotinonitrile $^1$H NMR (CHLOROFORM-d) δ 8.09 (d, J=8.3 Hz, 1H), 7.86-7.97 (m, 2H), 7.82 (d, J=8.0 Hz, 1H), 7.58 (td, J=7.7, 1.0 Hz, 1H), 7.09 (dd, J=17.2, 10.4 Hz, 1H), 6.82 (dd, J=17.3, 1.8 Hz, 1H), 5.76-5.93 (m, 1H), 4.65 (d, J=13.1 Hz, 1H), 4.52 (d, J=12.8 Hz, 1H), 4.11 (d, J=9.3 Hz, 0.5H), 3.93 (br. s., 2H), 3.7-3.85 (m, 1.5H), 3.48 (br. s., 1H), 3.26 (d, J=13.1 Hz, 2H), 3.17 (m, 1H), 2.52-2.68 (m, 2H), 1.88 (br. s., 1H), 1.66-1.80 (m, 1H), 0.81-0.99 (m, 4H), 0.62-0.79 (m, 1H), 0.57 (br. s., 1H), 0.50 (d, J=5.8 Hz, 2H)

LC-MS: m/z 495.2 (M+H)$^+$

Compound 669

(R)-2-(4-(cyclopropanecarbonyl)-3-cyclopropylpiperazin-1-yl)-6-cyclopropyl-5-(2-vinylquinazolin-4-yl)nicotinonitrile $^1$H NMR (CHLOROFORM-d) δ8.08 (d, J=8.5 Hz, 1H), 7.87-7.97 (m, 2H), 7.83 (d, J=8.3 Hz, 1H), 7.54-7.66 (m, 1H), 7.08 (dd, J=17.2, 10.4 Hz, 1H), 6.74-6.90 (m, 1H), 5.78-5.94 (m, 1H), 4.66 (d, J=11.3 Hz, 1H), 4.46-4.62 (m, 1H), 4.15-4.35 (m, 1H), 3.53-3.77 (m, 1H), 3.48 (d, J=4.5 Hz, 1H), 3.30 (m, 1H), 3.19 (m, 1H), 1.60-1.83 (m, 2H), 1.43 (br. s., 1H), 1.16-1.29 (m, 2H), 1.04 (d, J=18.8 Hz, 2H), 0.77-0.97 (m, 4H), 0.59-0.77 (m, 1H), 0.37-0.59 (m, 3H)

LC-MS: m/z 491.2 (M+H)$^+$

Compound 720

(R)-6-cyclopropyl-2-(3-cyclopropyl-4-(3-hydroxypropanoyl) piperazin-1-yl)-5-(2-vinylquinolin-7-yl)nicotinonitrile $^1$H NMR (CHLOROFORM-d) δ: 8.15-8.23 (m, 1H), 8.08-8.15 (m, 1H), 7.88 (d, J=8.3 Hz, 1H), 7.72-7.79 (m, 1H), 7.66 (d, J=8.6 Hz, 1H), 7.56 (dd, J=8.1, 1.6 Hz, 1H), 7.07 (dd, J=17.6, 10.9 Hz, 1H), 6.34 (d, J=17.7 Hz, 1H), 5.73 (d, J=11.0 Hz, 1H), 4.69 (d, J=9.4 Hz, 0.5H), 4.54 (d, J=13.2 Hz, 1H), 4.42 (d, J=12.6 Hz, 1H), 4.10 (d, J=8.3 Hz, 0.5H), 3.93 (br. s., 2H), 3.69-3.86 (m, 1H), 3.16-3.36 (m, 2H), 2.99-3.16 (m, 1H), 2.48-2.69 (m, 2H), 2.11-2.20 (m, 1H), 1.16-1.31 (m, 3H), 0.93-1.05 (m, 2H), 0.66 (br. s., 1H), 0.56 (br. s., 1H), 0.39-0.52 (m, 2H)

LC-MS: m/z 494.9 (M+H)$^+$

Compound 709

(R)-2-(4-(cyclopropanecarbonyl)-3-cyclopropylpiperazin-1-yl)-6-cyclopropyl-5-(2-vinylquinolin-7-yl)nicotinonitrile (Exemplified by procedure COMPOUND 720)

$^1$H NMR (CHLOROFORM-d) δ: 8.17 (d, J=8.5 Hz, 1H), 8.11 (s, 1H), 7.86 (d, J=8.3 Hz, 1H), 7.74 (s, 1H), 7.65 (d,

J=8.5 Hz, 1H), 7.56 (dd, J=8.3, 1.5 Hz, 1H), 7.06 (dd, J=17.7, 10.9 Hz, 1H), 6.33 (d, J=17.8 Hz, 1H), 5.71 (d, J=10.8 Hz, 1H), 4.56 (d, J=12.8 Hz, 1H), 4.43 (d, J=12.3 Hz, 1H), 4.09 (m, 1H), 3.72 (m, 1H), 3.29 (br. s., 2H), 3.12 (br. s., 1H), 2.10-2.20 (m, 1H), 1.73 (br. s., 1H), 1.44 (br. s., 1H), 1.18-1.25 (m, 2H), 1.06 (t, J=4.4 Hz, 1H), 0.94-1.04 (m, 3H), 0.81 (dd, J=7.8, 2.3 Hz, 2H), 0.67 (br. s., 1H), 0.41-0.58 (m, 3H).

LC-MS: m/z 490.9 (M+H)+

Compound 746

6-cyclopropyl-2-((R)-3-cyclopropyl-4-(3-methoxypropanoyl)piperazin-1-yl)-4-methyl-5-(2-vinyl-1,7-naphthyridin-4-yl)nicotinonitrile ¹H NMR (CHLOROFORM-d) δ: 9.58 (br. s., 1H), 8.57 (br. s., 1H), 7.67 (d, J=7.3 Hz, 1H), 7.21-7.34 (m, 2H), 7.10 (dd, J=17.6, 10.9 Hz, 1H), 6.42 (dd, J=17.6, 2.6 Hz, 1H), 5.82 (d, J=10.9 Hz, 1H), 4.38-4.49 (m, 1H), 4.34 (d, J=12.6 Hz, 1H), 4.14 (d, J=7.0 Hz, 1H), 3.89 (br. s., 1H), 3.69-3.82 (m, 2H), 3.40 (s, 3H), 3.23 (d, J=13.8 Hz, 2H), 3.02-3.17 (m, 1H), 2.72 (br. s., 1H), 2.67 (br. s., 1H), 2.11 (d, J=1.8 Hz, 3H), 1.45 (br. s., 1H), 1.06-1.18 (m, 2H), 0.79-0.90 (m, 1H), 0.69-0.79 (m, 2H), 0.64 (br. s., 1H), 0.57 (br. s., 1H), 0.41-0.55 (m, 2H).

LC-MS: m/z 522.3 (M+H)+

Compound 741

(R)-6-cyclopropyl-2-(3-isopropyl-4-(2-methoxyacetyl)piperazin-1-yl)-5-(2-vinyl-1,7-naphthyridin-4-yl)nicotinonitrile ¹H NMR (CHLOROFORM-d) δ: 9.58 (s, 1H), 8.60 (br. s., 1H), 7.79 (d, J=10.9 Hz, 1H), 7.63-7.71 (m, 1H), 7.50-7.63 (m, 1H), 7.12 (dd, J=17.6, 10.9 Hz, 1H), 6.47 (d, J=17.6 Hz, 1H), 5.83-5.94 (m, 1H), 4.63-4.80 (m, 1.5H), 4.37-4.58 (m, 2H), 4.04-4.26 (m, 2H), 3.93 (d, J=13.5 Hz, 1H), 3.10-3.33 (m, 2H), 2.09-2.30 (m, 0.5H), 1.92-2.08 (m, 1H), 1.11 (dd, J=16.3, 6.6 Hz, 4H), 0.85-0.98 (m, 6H).

LC-MS: m/z 496.3 (M+H)+

Compound 717

(R)-6-cyclopropyl-2-(3-cyclopropyl-4-(2-methoxyacetyl)piperazin-1-yl)-5-(2-vinyl-1,7-naphthyridin-4-yl)nicotinonitrile ¹H NMR (CHLOROFORM-d) δ: 9.56 (s, 1H), 8.59 (d, J=5.6 Hz, 1H), 7.72 (d, J=3.2 Hz, 1H), 7.68 (s, 1H), 7.45 (dd, J=9.5, 5.7 Hz, 1H), 7.10 (dd, J=17.8, 11.0 Hz, 1H), 6.42 (dd, J=17.6, 2.1 Hz, 1H), 5.72-5.90 (m, 1H), 4.63 (d, J=13.2 Hz, 1H), 4.45-4.55 (m, 1H), 4.18 (br. s., 2H), 4.06 (br. s., 1H), 3.96 (br. s., 1H), 3.60-3.85 (m, 1H), 3.44-3.49 (m, 3H), 3.23-3.34 (m, 1H), 3.16 (br. s., 1H), 1.97 (br. s., 1H), 1.48-1.56 (m, 1H), 1.22 (dd, J=7.9, 3.8 Hz, 2H), 0.86-0.94 (m, 2H), 0.70 (br. s., 1H), 0.57 (br. s., 1.5H), 0.51 (br. s., 1.5H).

LC-MS: m/z 494.6 (M+H)+

Compound 689

(R)-2-(4-(cyclopropanecarbonyl)-3-cyclopropylpiperazin-1-yl)-6-cyclopropyl-5-(2-vinyl-1,7-naphthyridin-4-yl)nicotinonitrile ¹H NMR (CHLOROFORM-d) δ: 9.58 (br. s., 1H), 8.61 (br. s., 1H), 7.77 (d, J=3.0 Hz, 1H), 7.64-7.73 (m, 1H), 7.54 (br. s., 1H), 7.12 (dd, J=17.6, 10.8 Hz, 1H), 6.45 (dd, J=17.7, 2.1 Hz, 1H), 5.85 (d, J=11.0 Hz, 1H), 4.64 (d, J=10.0 Hz, 1H), 4.52 (d, J=12.0 Hz, 1H), 4.25 (br. s., 1H), 3.69-3.81 (br. s., 1H), 3.38 (d, J=15.3 Hz, 1.5H), 3.21 (br. s., 1.5H), 1.75 (br. s., 1H), 1.50 (br. s., 1H), 1.26-1.37 (m, 1H), 1.23 (br. s., 2H), 0.99-1.14 (m, 2H), 0.87-0.96 (m, 2H), 0.84 (dd, J=7.8, 2.3 Hz, 2H), 0.71 (br. s., 1H), 0.52-0.62 (m, 2H), 0.43-0.52 (m, 1H).

LC-MS: m/z 490.6 (M+H)+

Compound 688

(R)-6-cyclopropyl-2-(3-cyclopropyl-4-(3-hydroxypropanoyl)piperazin-1-yl)-5-(2-vinyl-1,7-naphthyridin-4-yl)nicotinonitrile ¹H NMR (CHLOROFORM-d) δ: 9.59 (s, 1H), 8.60 (d, J=5.5 Hz, 1H), 7.80 (d, J=2.8 Hz, 1H), 7.69 (d, J=1.3 Hz, 1H), 7.54-7.63 (m, 1H), 7.12 (dd, J=17.6, 10.8 Hz, 1H), 6.48 (dd, J=17.7, 2.1 Hz, 1H), 5.88 (d, J=11.0 Hz, 1H), 4.63 (d, J=12.5 Hz, 1H), 4.52 (d, J=7.5 Hz, 1H), 4.13 (d, J=9.3 Hz, 1H), 3.87-3.99 (m, 2H), 3.67-3.87 (m, 1H), 3.30 (br. s., 2H), 3.18 (br. s., 1H), 2.57-2.68 (m, 2H), 1.43-1.54 (m, 1H), 1.32-1.41 (m, 1H), 1.19-1.26 (m, 2H), 0.87-0.97 (m, 2H), 0.67 (br. s., 1H), 0.60 (br. s., 1H), 0.40-0.55 (m, 2H).

LC-MS: m/z 494.6 (M+H)+

Compound 658

(R)-6-cyclopropyl-2-(3-cyclopropyl-4-(3-methoxypropanoyl)piperazin-1-yl)-5-(2-vinyl-1,7-naphthyridin-4-yl)nicotinonitrile ¹H NMR (CHLOROFORM-d) δ: 9.57 (s, 1H), 8.59 (d, J=5.5 Hz, 1H), 7.76 (d, J=3.5 Hz, 1H), 7.68 (d, J=1.3 Hz, 1H), 7.49-7.60 (m, 1H), 7.11 (dd, J=17.6, 11.0 Hz, 1H), 6.45 (dd, J=17.6, 1.8 Hz, 1H), 5.85 (d, J=11.3 Hz, 1H), 4.55-4.68 (m, 1H), 4.50 (dd, J=12.8, 2.3 Hz, 1H), 4.15 (br. s., 0.5H), 3.92 (br. s., 0.5H), 3.66-3.84 (m, 3H), 3.40 (s, 3H), 3.30 (br. s., 1H), 3.22 (br. s., 1H), 3.15 (d, J=7.5 Hz, 1H), 2.66 (br. s., 1H), 2.56 (br. s., 1H), 1.46-1.54 (m, 1H), 1.32 (d, J=16.1 Hz, 1H), 1.19-1.24 (m, 2H), 0.84-0.99 (m, 2H), 0.66 (br. s., 1H), 0.60 (br. s., 1H), 0.49 (br. s., 2H).

LC-MS: m/z 508.6 (M+H)+

Compound 681

(R)-6-cyclopropyl-2-(4-(3-hydroxypropanoyl)-3-isopropylpiperazin-1-yl)-5-(2-vinyl-1,7-naphthyridin-4-yl)nicotinonitrile ¹H NMR (CHLOROFORM-d) δ: 9.55 (s, 1H), 8.59 (dd, J=5.3, 3.0 Hz, 1H), 7.73 (d, J=11.5 Hz, 1H), 7.67 (dd, J=4.5, 2.8 Hz, 1H), 7.45 (dd, J=12.5, 5.5 Hz, 1H), 7.10 (ddd, J=17.6, 10.9, 1.1 Hz, 1H), 6.42 (d, J=17.6 Hz, 1H), 5.82 (d, J=10.8 Hz, 1H), 4.61-4.79 (m, 1H), 4.41-4.60 (m, 2H), 3.86-4.01 (m, 2H), 3.82 (d, J=13.6 Hz, 0.5H), 3.53-3.60 (m, 0.5H), 3.10-3.30 (m, 2H), 3.01 (d, J=12.8 Hz, 0.5H), 2.73-2.84 (m, 0.5H), 2.56-2.68 (m, 2H), 2.09-2.37 (m, 1H), 1.47-1.55 (m, 1H), 1.05-1.17 (m, 4H), 0.80-1.01 (m, 6H).

LC-MS: m/z 496.6 (M+H)+

Compound 710

(R)-2-(4-(cyclopropanecarbonyl)-3-cyclopropylpiperazin-1-yl)-6-cyclopropyl-5-(1-vinylisoquinolin-7-yl)nicotinonitrile 1H NMR (CHLOROFORM-d) δ 8.61 (d, J=5.8 Hz, 1H), 8.30 (s, 1H), 7.95 (d, J=8.3 Hz, 1H), 7.80 (d, J=8.0 Hz, 1H), 7.74 (s, 1H), 7.65-7.72 (m, 1H), 7.58-7.65 (m, 1H), 6.64 (d, J=16.1 Hz, 1H), 5.84 (d, J=10.3 Hz, 1H), 4.58 (d, J=11.5 Hz, 1H), 4.46 (d, J=11.8 Hz, 1H), 4.01-4.31 (m, 1H), 3.61-3.89 (m, 1H), 3.33 (d, J=17.3 Hz, 1.5H), 3.15 (br. s., 1.5H), 2.02-2.09 (m, 1H), 1.42-1.47 (m, 1H), 1.34 (d, J=8.5 Hz, 1H), 1.25-1.30 (m, 3H), 1.06-1.11 (m, 1H), 0.98-1.02 (m, 2H), 0.90 (t, J=6.7 Hz, 1H), 0.80-0.84 (m, 2H), 0.68 (br. s., 1H), 0.52-0.56 (m, 1H), 0.46-0.49 (m, 1H)

LC-MS: m/z 492.0 (M+H)$^+$

Compound 685

(R)-5-((2-chloropyridin-4-yl)methyl)-2-(4-(cyclopropanecarbonyl)-3-cyclopropylpiperazin-1-yl)-6-cyclopropylnicotinonitrile $^1$H NMR (CHLOROFORM-d) δ: 8.33 (d, J=5.0 Hz, 1H), 7.49 (s, 1H), 7.12 (s, 1H), 6.98-7.06 (m, 1H), 4.47 (d, J=12.5 Hz, 1H), 4.30-4.50 (m, 2.5H), 4.20-4.30 (m, 1H), 4.04 (s, 1H), 3.60-3.90 (s, 1H), 2.90-3.45 (m, 1H), 2.01 (s, 1H), 1.80-1.91 (m, 1H), 1.72 (s, 1H), 1.09-1.17 (m, 2H), 0.93-1.09 (m, 4H), 0.74-0.86 (m, 2H), 0.37-0.65 (m, 4H)

LC-MS: m/z 462.2 (M+H)$^+$

Compound 684

(R)-2-(4-(cyclopropanecarbonyl)-3-cyclopropylpiperazin-1-yl)-6-cyclopropyl-5-((2-vinylpyridin-4-yl)methyl)nicotinonitrile $^1$H NMR (CHLOROFORM-d) □: 8.50 (d, J=5.0 Hz, 1H), 7.47 (s, 1H), 7.12 (s, 1H), 6.89-6.99 (m, 1H), 6.80 (dd, J=17.6, 10.8 Hz, 1H), 6.16-6.29 (m, 1H), 5.44-5.57 (m, 1H), 4.25-4.60 (m, 2.5H), 4.12-4.20 (m, 1H), 4.03 (s, 2H), 3.49-3.90 (m, 1H), 2.95-3.29 (m, 2.5H), 1.85-1.98 (m, 1H), 1.71 (s, 1H), 1.35-1.45 (m, 1H), 1.07-1.17 (m, 2H), 0.92-1.07 (m, 4H), 0.76-0.82 (m, 2H), 0.30-0.63 (m, 4H)

LC-MS: m/z 454.2 (M+H)$^+$

Compound 708

(R)-5-((2-chloropyridin-4-yl)methyl)-6-cyclopropyl-2-(3-cyclopropyl-4-(3-hydroxypropanoyl)piperazin-1-yl)nicotinonitrile $^1$H NMR (CHLOROFORM-d) δ: 8.34 (d, J=5.3 Hz, 1H), 7.49 (s, 1H), 7.11 (s, 1H), 7.03 (d, J=5.0 Hz, 1H), 4.39-4.52 (m, 2H), 4.33 (d, J=12.3 Hz, 1H), 4.04 (s, 2H), 3.85-3.97 (m, 2H), 3.66-3.81 (m, 1H), 3.01-3.22 (m, 3H), 2.51-2.65 (m, 2H), 1.79-1.92 (m, 1H), 1.31-1.39 (m, 1H), 1.08-1.15 (m, 2H), 0.93-1.03 (m, 2H), 0.46-0.63 (m, 4H)

LC-MS: m/z 466.2 (M+H)$^+$

Compound 697

(R)-6-cyclopropyl-2-(3-cyclopropyl-4-(3-hydroxypropanoyl)piperazin-1-yl)-5-((2-vinylpyridin-4-yl)methyl)nicotinonitrile A mixture of (R)-5-((2-chloropyridin-4-yl)methyl)-6-cyclopropyl-2-(3-cyclopropyl-4-(3-hydroxypropanoyl)piperazin-1-yl)nicotinonitrile (80 mg, 0.172 mmol), potassium vinyltrifluoroborate (46 mg, 0.343 mmol), Pd(dppf)Cl$_2$ (7 mg, 0.009 mmol) and CsF (79 mg, 0.515 mmol) in dioxane/H$_2$O was stirred at 100° C. for 16 hours. The mixture was diluted with EtOAc (30 mL) and filtered. The filtrated was partitioned between EtOAc (30 mL) and water (10 mL), the organic layer was washed with water (10 mL), brine and dried over Na$_2$SO$_4$ and concentrated to give the crude which was purified by prep-TLC to give 25 mg of the product.

$^1$H NMR (CHLOROFORM-d) □□: 8.47 (d, J=5.0 Hz, 1H), 7.46 (s, 1H), 7.10 (s, 1H), 6.87-6.97 (m, 1H), 6.76 (dd, J=17.3, 10.8 Hz, 1H), 6.18 (dd, J=17.6, 1.0 Hz, 1H), 5.41-5.53 (m, 1H), 4.39 (d, J=12.8 Hz, 1H), 4.27 (d, J=12.5 Hz, 1H), 4.01 (m, 2H), 3.80-3.92 (m, 2H), 3.51-3.79 (m, 2H), 2.99-3.18 (m, 3H), 2.42-2.66 (m, 2H), 1.85-1.97 (m, 1H), 1.30-1.40 (m, 1H), 1.03-1.12 (m, 2H), 0.88-1.00 (m, 2H), 0.30-0.59 (m, 4H)

LC-MS: m/z 458.3 (M+H)$^+$

Compound 698 (General Procedure 7)

(R)-6-cyclopropyl-2-(4-(3-hydroxypropanoyl)-3-methylpiperazin-1-yl)-5-((2-vinyl-1,7-naphthyridin-4-yl)amino)nicotinonitrile $^1$H NMR (CHLOROFORM-d) δ: 9.48 (s, 1H), 8.59 (d, J=5.8 Hz, 1H), 7.90 (br. s., 1H), 7.68-7.77 (m, 1H), 7.35-7.48 (m, 1H), 6.91 (dd, J=17.4, 10.9 Hz, 1H), 6.56 (s, 1H), 6.26 (d, J=17.6 Hz, 1H), 5.67 (d, J=11.0 Hz, 1H), 4.86-4.98 (m, 0.5H), 4.51-4.62 (d, 0.5H) 4.14-4.38 (m, 3H), 3.94 (br. s., 2H), 3.70-3.81 (m, 0.5H), 3.59 (t, J=10.8 Hz, 0.5H), 3.27-3.41 (m, 1H), 3.01-3.24 (m, 2H), 2.48-2.78 (m, 2H), 1.97-2.09 (m, 1H), 1.44 (d, J=6.5 Hz, 1.5H), 1.34 (d, J=6.8 Hz, 1.5H), 1.10-1.20 (m, 2H), 0.94-1.06 (m, 2H).

LC-MS: m/z 483.2 (M+H)$^+$

Compound 679 (General Procedure 7)

(R)-5-((2-chloropyridin-4-yl)amino)-6-cyclopropyl-2-(3-cyclopropyl-4-(3-methoxypropanoyl)piperazin-1-yl)nicotinonitrile $^1$H NMR (CHLOROFORM-d) δ: 8.06 (d, J=5.4 Hz, 1H), 7.60 (s, 1H), 6.57-6.47 (m, 2H), 6.08 (s, 1H), 4.75-4.64 (m, 0.5H), 4.49 (t, J=11.8 Hz, 1H), 4.37 (t, J=10.9 Hz, 1H), 4.14-4.09 (m, 0.5H), 3.89 (ddd, J=7.5, 3.5, 2.5 Hz, 0.5H), 3.81-3.64 (m, 2.5H), 3.39 (s, 3H), 3.31-3.17 (m, 1.5H), 3.10 (td, J=12.8, 3.4 Hz, 1H), 2.69 (ddd, J=22.8, 14.8, 9.9 Hz, 2H), 2.52 (dd, J=20.7, 9.1 Hz, 0.5H), 2.06 (ddd, J=7.5, 4.5, 1.6 Hz, 1H), 1.28 (m, J=4.7 Hz, 1H), 1.15 (m, 2H), 1.08-0.99 (m, 2H), 0.72-0.52 (m, 2H), 0.52-0.39 (m, 2H).

LC-MS: m/z NB250-076-2 481.1 (M+H)$^+$

Compound 678 (General Procedure 7)

(R)-6-cyclopropyl-2-(3-cyclopropyl-4-(3-methoxypropanoyl)piperazin-1-yl)-5-((2-vinylpyridin-4-yl)amino)nicotinonitrile $^1$H NMR (CHLOROFORM-d) δ: 8.26 (d, J=5.7 Hz, 1H), 7.62 (s, 1H), 6.72 (dd, J=17.4, 10.8 Hz, 1H), 6.58 (s, 1H), 6.46 (d, J=4.1 Hz, 1H), 6.20 (d, J=17.4 Hz, 1H), 5.94 (s, 1H), 5.49 (d, J=10.8 Hz, 1H), 4.70 (dd, J=14.5, 4.5 Hz, 0.5H), 4.46 (t, J=11.4 Hz, 1H), 4.33 (d, J=10.6 Hz, 1H), 4.13-4.07 (m, 0.5H), 3.92-3.85 (m, 0.5H), 3.83-3.62 (m, 2.5H), 3.39 (s, 3H), 3.31-3.16 (m, 1.5H), 3.09 (td, J=13.2, 3.7 Hz, 1H), 2.82-2.58 (m, 2H), 2.58-2.45 (m, 0.5H), 2.10 (dt, J=4.5, 3.0 Hz, 1H), 1.28 (s, 1H), 1.18-1.10 (m, 2H), 1.02 (ddd, J=9.9, 6.4, 3.2 Hz, 2H), 0.73-0.53 (m, 2H), 0.53-0.39 (m, 2H).

LC-MS: m/z 473.2 (M+H)$^+$

Compound 661 (General Procedure 7)

(R)-5-((2-chloropyridin-4-yl)amino)-6-cyclopropyl-2-(4-(3-hydroxypropanoyl)-3-methylpiperazin-1-yl)nicotinonitrile $^1$H NMR (CHLOROFORM-d) δ: 8.06 (d, J=5.8 Hz, 1H), 7.60 (s, 1H), 6.54 (s, 1H), 6.51 (dd, J=5.8, 2.0 Hz, 1H), 6.15 (s, 1H), 4.90 (s, 0.5H), 4.54 (d, J=13.4 Hz, 0.5H), 4.35-4.16 (m, 2.5H), 3.93 (s, 2H), 3.74 (d, J=13.4 Hz, 0.5H), 3.58 (d, J=11.0 Hz, 0.5H), 3.30 (dd, J=10.8, 6.4 Hz, 1H), 3.15 (t, J=12.2 Hz, 1H), 3.08-3.01 (m, 0.5H), 2.74-2.51 (m, 2H), 2.07 (ddd, J=12.6, 8.0, 4.7 Hz, 1H), 1.42 (d, J=6.6 Hz, 1.5H), 1.32 (d, J=6.7 Hz, 1.5H), 1.13 (dt, J=7.2, 3.6 Hz, 2H), 1.05 (ddd, J=10.3, 6.6, 3.5 Hz, 2H).

LC-MS: m/z 441.0 (M+H)$^+$

Compound 677 (General Procedure 7)

(R)-5-((2-chloropyridin-4-yl)amino)-6-cyclopropyl-2-(3-cyclopropyl-4-(3-hydroxypropanoyl)piperazin-1-yl)nicotinonitrile $^1$H NMR (CHLOROFORM-d) δ: 8.01 (d, J=5.7 Hz, 1H), 7.59 (s, 1H), 6.49 (d, J=1.8 Hz, 1H), 6.46 (dd, J=5.7, 2.0 Hz, 1H), 6.41 (s, 1H), 4.66 (d, J=13.6 Hz, 0.5H), 4.45 (d, J=12.9 Hz, 1H), 4.33 (d, J=12.7 Hz, 1H), 4.06 (d, J=9.3 Hz, 0.5H), 3.91 (s, 2H), 3.80 (d, J=13.2 Hz, 0.5H), 3.72 (d, J=11.6 Hz, 0.5H), 3.56 (m, 0.5H), 3.27-3.01 (m, 2.5H), 2.59 (dd, J=17.2, 5.2 Hz, 1.5H), 2.11-2.04 (m, 1H), 1.98 (m, 0.5H), 1.43-1.27 (m, 1H), 1.18-1.09 (m, 2H), 1.07-0.98 (m, 2H), 0.63 (m, J=7.2, 4.7 Hz, 1H), 0.58-0.28 (m, 3H).

LC-MS: m/z 467.0 (M+H)$^+$

Compound 676 (General Procedure 6)

(R)-6-cyclopropyl-2-(3-cyclopropyl-4-(3-hydroxypropanoyl)piperazin-1-yl)-5-((2-vinylpyridin-4-yl)amino)nicotinonitrile $^1$H NMR (CHLOROFORM-d) δ: 8.20 (d, J=6.1 Hz, 1H), 7.63 (s, 1H), 6.73 (dd, J=17.5, 10.9 Hz, 1H), 6.69 (d, J=3.2 Hz, 1H), 6.63 (d, J=3.1 Hz, 1H), 6.29 (d, J=17.5 Hz, 1H), 5.57 (d, J=10.9 Hz, 1H), 4.69 (d, J=11.0 Hz, 0.5H), 4.46 (d, J=13.0 Hz, 1H), 4.35 (d, J=13.1 Hz, 1H), 4.10 (d, J=7.7 Hz, 0.5H), 3.92 (d, J=3.9 Hz, 2H), 3.74 (ddd, J=21.2, 17.7, 8.0 Hz, 1.5H), 3.30-3.17 (m, 1.5H), 3.13-3.03 (m, 1H), 2.69-2.48 (m, 2H), 2.15-2.06 (m, 1H), 1.28 (d, J=5.0 Hz, 1H), 1.14 (dt, J=7.3, 3.6 Hz, 2H), 1.08-0.98 (m, 2H), 0.76-0.62 (m, 1H), 0.62-0.32 (m, 3H).

LC-MS: m/z 459.0 (M+H)$^+$

Compound 718 (General Procedure 7)

(R)-5-((2-chloropyridin-4-yl)amino)-6-cyclopropyl-2-(3-cyclopropyl-4-(2-methoxyacetyl)piperazin-1-yl)nicotinonitrile $^1$H NMR (CHLOROFORM-d) δ: 8.06 (d, J=5.7 Hz, 1H), 7.60 (s, 1H), 6.50 (d, J=2.1 Hz, 1H), 6.46 (dd, J=5.7, 2.2 Hz, 1H), 5.79 (s, 1H), 4.43 (dd, J=52.6, 11.8 Hz, 2.5H), 4.16 (s, 2H), 4.00 (s, 1.5H), 3.67 (d, J=24.8 Hz, 1H), 3.46 (s, 3H), 3.21 (dd, J=13.0, 3.4 Hz, 1H), 3.09 (t, J=11.3 Hz, 1H), 2.07 (ddd, J=12.7, 8.0, 4.7 Hz, 1H), 1.38 (s, 1H), 1.15 (dt, J=7.5, 3.7 Hz, 2H), 1.08-1.00 (m, 2H), 0.67 (s, 1H), 0.63-0.39 (m, 3H).

LC-MS: m/z 467.2 (M+H)$^+$

Compound 711 (General Procedure 7)

(R)-6-cyclopropyl-2-(3-cyclopropyl-4-(2-methoxyacetyl)piperazin-1-yl)-5-((2-vinylpyridin-4-yl)amino)nicotinonitrile $^1$H NMR (CHLOROFORM-d) δ: 8.26 (d, J=5.7 Hz, 1H), 7.62 (s, 1H), 6.71 (dd, J=17.4, 10.8 Hz, 1H), 6.59 (d, J=2.2 Hz, 1H), 6.45 (dd, J=5.7, 2.3 Hz, 1H), 6.18 (dd, J=17.4, 1.0 Hz, 1H), 6.01 (s, 1H), 5.47 (dd, J=10.8, 0.9 Hz, 1H), 4.81-4.26 (m, 2.6H), 4.16 (s, 2H), 3.95 (d, J=43.6 Hz, 1.5H), 3.70 (s, 1H), 3.46 (s, 3H), 3.20 (dd, J=13.0, 3.4 Hz, 1H), 3.07 (t, J=11.4 Hz, 1H), 2.15-2.07 (m, 1H), 1.41 (s, 1H), 1.19-1.10 (m, 2H), 1.02 (ddd, J=10.2, 6.6, 3.4 Hz, 2H), 0.67 (s, 1H), 0.61-0.37 (m, 3H).

LC-MS: m/z NB295-002-01 459.1 (M+H)$^+$

Compound 743

(R)-6-cyclopropyl-2-(3-isopropyl-4-(2-methoxyacetyl)piperazin-1-yl)-5-((2-vinylpyridin-4-yl)amino)nicotinonitrile $^1$H NMR (CHLOROFORM-d) δ: 8.24 (d, J=5.8 Hz, 1H), 7.60 (d, J=3.1 Hz, 1H), 6.72 (dd, J=17.4, 10.8 Hz, 1H), 6.61 (s, 1H), 6.51 (d, J=4.3 Hz, 1H), 6.37 (s, 1H), 6.23 (d, J=17.5 Hz, 1H), 5.52 (d, J=10.9 Hz, 1H), 4.68-4.47 (m, 1.5H), 4.37 (t, J=12.7 Hz, 1.5H), 4.28 (d, J=13.4 Hz, 0.5H), 4.22-4.13 (m, 1H), 4.08 (d, J=13.5 Hz, 0.5H), 3.88 (d, J=13.6 Hz, 0.5H), 3.56 (d, J=10.6 Hz, 0.5H), 3.47 (d, J=2.5 Hz, 3H), 3.42 (dd, J=13.3, 2.9 Hz, 0.5H), 3.24-2.95 (m, 2.5H), 2.19-2.04 (m, 2H), 1.28 (d, J=4.7 Hz, 1H), 1.19-1.11 (m, 1H), 1.07 (d, J=6.5 Hz, 3H), 1.05-0.97 (m, 2H), 0.91 (dd, J=15.7, 6.8 Hz, 3H).

LC-MS: m/z NB295-018-01 461.4 (M+H)$^+$

Compound 731

(R)-5-((2-chloropyridin-4-yl)(methyl)amino)-6-cyclopropyl-2-(3-cyclopropyl-4-(3-hydroxypropanoyl)piperazin-1-yl)nicotinonitrile

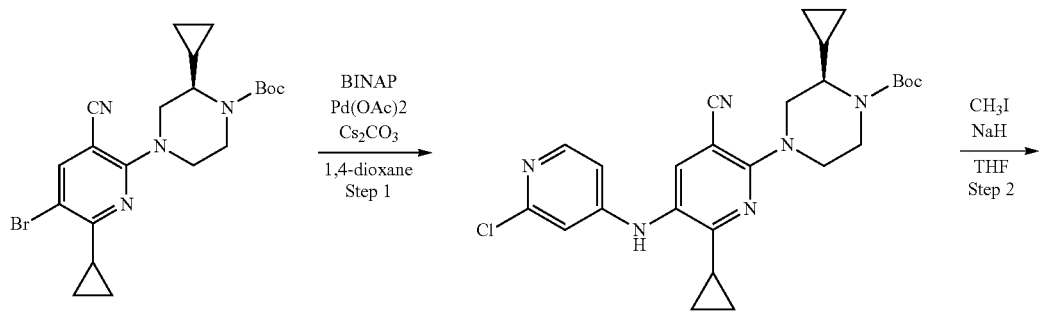

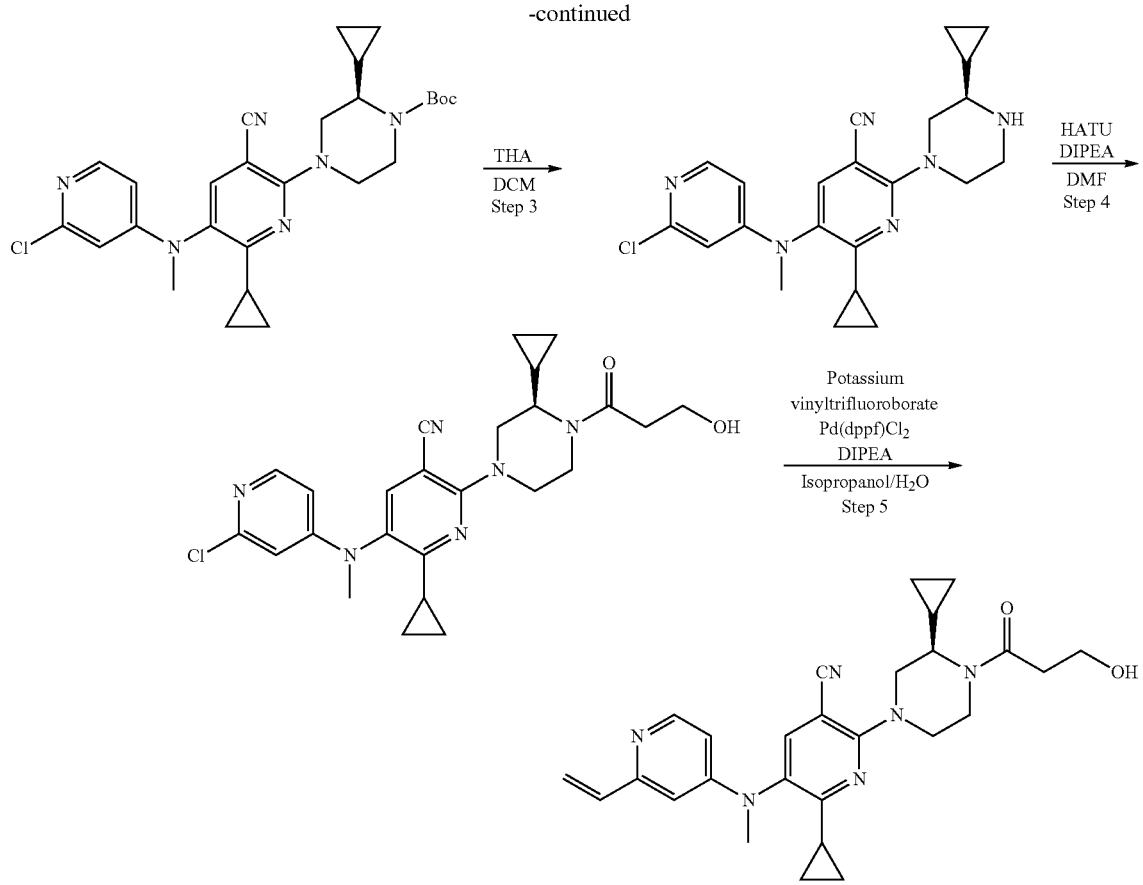

Step 1: (R)-tert-butyl 4-(5-(2-chloropyridin-4-ylamino)-3-cyano-6-cyclopropylpyridin-2-yl)-2-cyclopropylpiperazine-1-carboxylate To a solution of (R)-tert-butyl 4-(5-bromo-3-cyano-6-cyclopropylpyridin-2-yl)-2-cyclopropylpiperazine-1-carboxylate (1.5 g, 3.363 mmol) and 2-chloropyridin-4-amine (518.6 mg, 4.036 mmol) in 1,4-dioxane (20 mL) was added Pd(OAc)$_2$ (76 mg, 0.34 mmol), BINAP (314.3 mg, 0.505 mmol) and Cs$_2$CO$_3$ (2.2 g, 6.726 mmol) at r.t. under N$_2$. The resulting mixture was heated and stirred at 155° C. under N$_2$ in microwave for 1 h. The solvent was removed in vacuum and the residue was purified via column chromatography (petroleum ether: EtOAc) to afford the title compound (1.1 g, 66.2%) as a yellow solid.

LC-MS: m/z 495.0 (M+H)$^+$

Step 2: (R)-tert-butyl 4-(5-((2-chloropyridin-4-yl)(methyl)amino)-3-cyano-6-cyclopropylpyridin-2-yl)-2-cyclopropylpiperazine-1-carboxylate To a solution of (R)-tert-butyl 4-(5-(2-chloropyridin-4-ylamino)-3-cyano-6-cyclopropylpyridin-2-yl)-2-cyclopropylpiperazine-1-carboxylate (550 mg, 1.1 mmol) in anhydrous THF (10 mL) was added NaH (89 mg, 2.22 mmol) and iodomethane (2 drops) at r.t. The reaction mixture was stirred at r.t. for 3 hrs. The reaction mixture was quenched by water at 0° C. The mixture was extracted with EtOAc (15 mL×2). The combined organic layer was washed with brine, dried over Na$_2$SO$_4$. The organic phase was filtered and the filtrate was concentrated in vacuum to give out the title compound (crude, 567 mg) as a yellow solid.

LC-MS: m/z 509.1 (M+H)$^+$

Step 3: (R)-5-((2-chloropyridin-4-yl)(methyl)amino)-6-cyclopropyl-2-(3-cyclopropylpiperazin-1-yl)nicotinonitrile To a solution of (R)-tert-butyl 4-(5-((2-chloropyridin-4-yl)(methyl)amino)-3-cyano-6-cyclopropylpyridin-2-yl)-2-cyclopropylpiperazine-1-carboxylate (567 mg, 1.1 mmol) in anhydrous DCM (5 mL) was added TFA (5 mL) at r.t. The reaction mixture was stirred at r.t. for 2 hrs. The solvent was removed in vacuum and the residue was adjusted to pH>7.0. The residue mixture was extracted with EtOAc (15 mL×2). The combined organic layer was washed with brine, dried over Na$_2$SO$_4$. The organic phase was filtered and the filtrate was concentrated in vacuum to give out the title compound (crude, 432 mg) as a yellow solid.

LC-MS: m/z 409.1 (M+H)$^+$

Step 4: (R)-5-((2-chloropyridin-4-yl)(methyl)amino)-6-cyclopropyl-2-(3-cyclopropyl-4-(3-hydroxypropanoyl)piperazin-1-yl)nicotinonitrile To a solution of (R)-5-((2-chloropyridin-4-yl)(methyl)amino)-6-cyclopropyl-2-(3-cyclopropylpiperazin-1-yl)nicotinonitrile (410 mg, 1.0 mmol) in DMF (8 mL) was added sodium 3-hydroxypropanoate (203.5 mg, 1.5 mmol), HATU (572.3 mg, 1.5 mmol) and DIPEA (194 mg, 1.5 mmol) at r.t. The reaction mixture was stirred at r.t. for 3 hrs. The solvent was removed in vacuum and the residue was purified via silica gel column chromatography (DCM: MeOH) to afford the title compound (270 mg, 56.3%) as a pale yellow solid.

¹H NMR (CHLOROFORM-d) δ: 8.03 (d, J=5.8 Hz, 1H), 7.56 (s, 1H), 6.45 (s, 1H), 6.35 (d, J=3.5 Hz, 1H), 4.70 (d, J=11.2 Hz, 0.5H), 4.51 (d, J=13.0 Hz, 1H), 4.39 (d, J=13.4 Hz, 1H), 4.10 (d, J=9.2 Hz, 0.5H), 3.93 (d, J=4.5 Hz, 2H), 3.86-3.65 (m, 1.5H), 3.40 (s, 1H), 3.30 (s, 3H), 3.28-3.15 (m, 1.5H), 3.15-3.01 (m, 1H), 2.69-2.44 (m, 2H), 1.89-1.78 (m, 1H), 1.28 (d, J=5.0 Hz, 1H), 1.13 (s, 2H), 1.01 (d, J=11.8 Hz, 2H), 0.82-0.65 (m, 1H), 0.64-0.32 (m, 3H)

LC-MS: m/z 481.0 (M+H)⁺

Step 5: Compound 731

(R)-6-cyclopropyl-2-(3-cyclopropyl-4-(3-hydroxypropanoyl)piperazin-1-yl)-5-(methyl(2-vinylpyridin-4-yl)amino)nicotinonitrile To a solution of (R)-5-((2-chloropyridin-4-yl)(methyl)amino)-6-cyclopropyl-2-(3-cyclopropyl-4-(3-hydroxypropanoyl)piperazin-1-yl)nicotinonitrile (270 mg, 0.563 mmol) in isopropanol (10 mL) and H₂O (3 mL) was added Vinyltrifluoroboric acid potassium salt (113.1 mg, 0.844 mmol), Pd(dppf)Cl₂ (49.0 mg, 0.06 mmol) and DIPEA (145.3 mg, 1.126 mmol) at r.t. under N₂. The reaction mixture was heated and stirred at reflux under N₂ overnight. The solvent was removed in vacuum and the residue was purified via silica gel column chromatography (DCM: MeOH) to afford the title compound (121 mg, 45.5%) as a pale yellow solid.

¹H NMR (CHLOROFORM-d) δ: 8.25 (d, J=5.9 Hz, 1H), 7.58 (s, 1H), 6.71 (dd, J=17.4, 10.7 Hz, 1H), 6.46 (s, 1H), 6.33 (s, 1H), 6.20 (d, J=17.3 Hz, 1H), 5.45 (d, J=11.2 Hz, 1H), 4.69 (d, J=13.4 Hz, 0.4H), 4.49 (d, J=13.0 Hz, 1H), 4.37 (d, J=12.7 Hz, 1H), 4.10 (d, J=8.6 Hz, 0.6H), 3.92 (s, 2H), 3.86-3.65 (m, 1.5H), 3.42 (s, 1H), 3.31 (s, 3H), 3.22 (m, 1.5H), 3.15-3.00 (m, 1H), 2.69-2.45 (m, 2H), 1.88 (ddd, J=12.7, 8.1, 4.7 Hz, 1H), 1.40-1.31 (m, 1H), 1.12 (s, 2H), 0.99 (s, 2H), 0.81-0.34 (m, 4H).

LC-MS: m/z 473.4 (M+H)⁺

Compound 699

(R)-5-((2-chloropyridin-4-yl)(methyl)amino)-6-cyclopropyl-2-(4-(3-methoxypropanoyl)-3-methylpiperazin-1-yl)nicotinonitrile

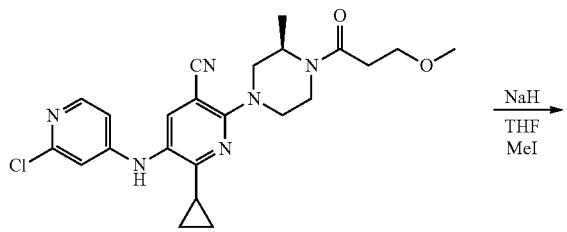

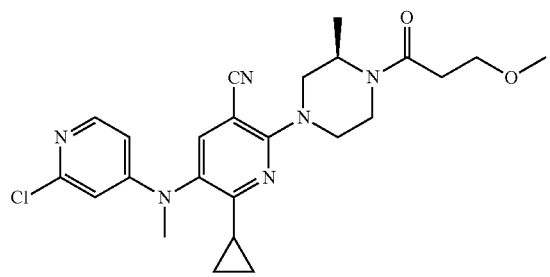

To a solution of (R)-5-(2-chloropyridin-4-ylamino)-6-cyclopropyl-2-(4-(3-methoxypropanoyl)-3-methylpiperazin-1-yl)nicotinonitrile (675 mg, 1.487 mmol) in anhydrous THF (15 mL) was added iodomethane (0.5 mL) and NaH (119 mg, 2.974 mmol) at r.t. The reaction mixture was stirred at r.t. for 3 hrs. The reaction mixture was quenched by water at 0° C. The mixture was extracted with EtOAc (15 mL×2). The combined organic layer was washed with brine, dried over Na₂SO₄. The organic phase was filtered and the filtrate was concentrated in vacuum. The residue was purified via silica gel column chromatography (DCM: MeOH) to afford the title compound (350 mg, 50.3%) as a white solid.

¹H NMR (CHLOROFORM-d) δ: 8.04 (d, J=5.7 Hz, 1H), 7.54 (s, 1H), 6.42 (d, J=44.6 Hz, 2H), 4.92 (s, 0.5H), 4.55 (d, J=13.0 Hz, 0.5H), 4.40-4.25 (m, 2H), 4.22 (d, J=13.9 Hz, 0.5H), 3.83 (d, J=13.7 Hz, 0.5H), 3.76 (t, J=6.3 Hz, 2H), 3.57 (t, J=11.5 Hz, 0.5H), 3.39 (s, 3H), 3.37-3.33 (m, 0.5H), 3.31 (s, 3H), 3.28-2.97 (m, 2H), 2.85-2.65 (m, 1H), 2.64-2.51 (m, 1H), 1.80 (ddd, J=12.5, 8.0, 4.6 Hz, 1H), 1.36 (dd, J=41.2, 6.2 Hz, 3H), 1.12 (s, 2H), 1.07-0.93 (m, 2H).

LC-MS: m/z 469.2 (M+H)⁺

Compound 690 (General Procedure 6)

(R)-6-cyclopropyl-2-(4-(3-methoxypropanoyl)-3-methylpiperazin-1-yl)-5-(methyl(2-vinylpyridin-4-yl)amino)nicotinonitrile

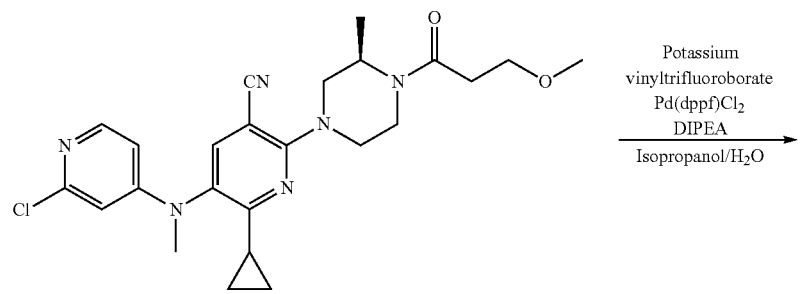

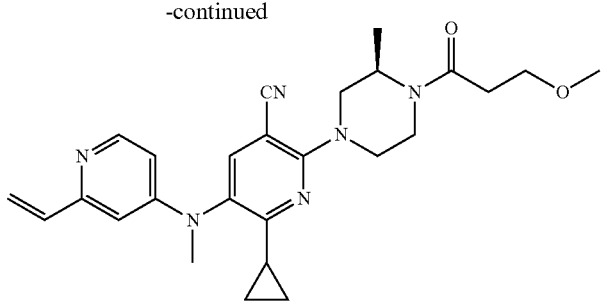

To a solution of (R)-5-((2-chloropyridin-4-yl)(methyl)amino)-6-cyclopropyl-2-(4-(3-methoxypropanoyl)-3-methylpiperazin-1-yl)nicotinonitrile (330 mg, 0.71 mmol) in isopropanol (30 mL) and H₂O (3 mL) was added Vinyltrifluoroboric acid potassium salt (142.1 mg, 1.06 mmol), Pd(dppf)Cl₂ (58.0 mg, 0.071 mmol) and DIPEA (182 mg, 1.41 mmol) at r.t. under N₂. The reaction mixture was heated and stirred at reflux under N₂ overnight. The solvent was removed in vacuum and the residue was purified via silica gel column chromatography (DCM:MeOH) to afford the title compound (89 mg, 27.5%) as a white solid.

¹H NMR (CHLOROFORM-d) δ: 8.24 (d, J=5.9 Hz, 1H), 7.55 (s, 1H), 6.71 (dd, J=17.4, 10.8 Hz, 1H), 6.46 (s, 1H), 6.33 (s, 1H), 6.20 (d, J=17.3 Hz, 1H), 5.46 (d, J=11.0 Hz, 1H), 4.91 (s, 0.5H), 4.54 (d, J=13.1 Hz, 0.5H), 4.34-4.16 (m, 2.5H), 3.89-3.68 (m, 2.5H), 3.56 (t, J=11.5 Hz, 0.5H), 3.39 (s, 3H), 3.31 (s, 3H), 3.29 (s, 1H), 3.10 (m, 1.5H), 2.80-2.52 (m, 2H), 1.88-1.83 (m, 1H), 1.41 (d, J=6.3 Hz, 1.5H), 1.30 (d, J=6.6 Hz, 1.5H), 1.10 (m, 2H), 0.97 (m, 2H).

LC-MS: m/z 461.2 (M+H)⁺

Compound 660 (General Procedure 6)

(R)-4-(5-cyano-2-cyclopropyl-6-(4-(3-methoxypropanoyl)-3-methylpiperazin-1-yl)pyridin-3-ylamino)picolinonitrile ¹H NMR (CHLOROFORM-d) δ: 8.32 (d, J=5.8 Hz, 1H), 7.59 (s, 1H), 7.01 (s, 1H), 6.72 (d, J=3.8 Hz, 1H), 6.62 (s, 1H), 4.92 (s, 0.5H), 4.55 (d, J=12.7 Hz, 0.5H), 4.30 (t, J=11.2 Hz, 2H), 4.22 (d, J=12.7 Hz, 0.5H), 3.83 (d, J=13.8 Hz, 0.5H), 3.76 (t, J=6.3 Hz, 2H), 3.57 (t, J=11.5 Hz, 0.5H), 3.39 (s, 3H), 3.33 (d, J=12.5 Hz, 1H), 3.21-3.04 (m, 1.5H), 2.73 (ddd, J=22.1, 14.2, 6.5 Hz, 1H), 2.64-2.53 (m, 1H), 2.05-1.99 (m, 1H), 1.40 (d, J=6.3 Hz, 1.5H), 1.30 (d, J=6.7 Hz, 1.5H), 1.18-1.10 (m, 2H), 1.09-0.98 (m, 2H).

LC-MS: m/z 446.0 (M+H)⁺

Compound 659 (General Procedure 6)

(R)-4,4'-(5-cyano-2-cyclopropyl-6-(4-(3-methoxypropanoyl)-3-methylpiperazin-1-yl)pyridin-3-ylazanediyl)dipicolinonitrile ¹H NMR (CHLOROFORM-d) δ: 8.62 (d, J=5.5 Hz, 2H), 7.53 (s, 1H), 7.28-7.20 (m, 4H), 4.95 (s, 0.5H), 4.58 (d, J=10.0 Hz, 0.5H), 4.37 (dd, J=42.6, 13.4 Hz, 2.5H), 3.89 (d, J=13.8 Hz, 0.5H), 3.77 (t, J=6.3 Hz, 2H), 3.66-3.57 (m, 0.5H), 3.44 (s, 0.5H), 3.40 (s, 3H), 3.35-3.13 (m, 1.5H), 2.87-2.67 (m, 1H), 2.62 (m, J=13.7, 7.4 Hz, 1H), 1.68 (d, J=4.3 Hz, 1H), 1.44 (d, J=6.6 Hz, 1.5H), 1.34 (d, J=6.3 Hz, 1.5H), 1.11 (dt, J=6.9, 3.5 Hz, 2H), 0.97-0.88 (m, 2H).

LC-MS: m/z 548.1 (M+H)⁺

Compound 729 (General Procedure 6)

(R)-4-(5-cyano-2-cyclopropyl-6-(4-(3-methoxypropanoyl)-3-methylpiperazin-1-yl)pyridin-3-ylamino)picolinamide ¹H NMR (CHLOROFORM-d) δ: 8.24 (d, J=5.7 Hz, 1H), 7.98 (s, 1H), 7.61 (s, 1H), 7.53 (s, 1H), 6.62 (dd, J=5.6, 2.3 Hz, 1H), 6.03 (s, 1H), 5.65 (s, 1H), 4.92 (s, 0.5H), 4.55 (d, J=13.9 Hz, 0.5H), 4.27 (t, J=11.1 Hz, 2H), 4.19 (d, J=13.0 Hz, 0.5H), 3.82 (d, J=13.0 Hz, 0.5H), 3.76 (t, J=6.2 Hz, 2H), 3.57 (t, J=11.5 Hz, 0.5H), 3.40 (s, 3H), 3.34-3.23 (m, 1H), 3.15 (t, J=12.1 Hz, 1H), 3.10-3.00 (m, 0.5H), 2.84-2.65 (m, 1H), 2.60 (m, 1H), 2.07 (ddd, J=12.6, 8.0, 4.6 Hz, 1H), 1.41 (d, J=6.2 Hz, 1.5H), 1.31 (d, J=6.7 Hz, 1.5H), 1.13 (dt, J=7.4, 3.6 Hz, 2H), 1.00 (td, J=6.6, 3.4 Hz, 2H).

LC-MS: m/z 464.1 (M+H)⁺

Compound 742 (General Procedure 6)

(R)-6-cyclopropyl-2-(3-cyclopropyl-4-(3-hydroxypropanoyl)piperazin-1-yl)-4-methyl-5-(2-vinylpyridin-4-ylamino)nicotinonitrile ¹H NMR (CHLOROFORM-d) δ: 8.24 (d, J=5.7 Hz, 1H), 6.70 (dd, J=17.4, 10.8 Hz, 1H), 6.49 (s, 1H), 6.35 (s, 1H), 6.19 (d, J=17.4 Hz, 1H), 5.79 (s, 1H), 5.48 (d, J=10.9 Hz, 1H), 4.68 (d, J=12.8 Hz, 0.5H), 4.51-4.38 (m, 0.5H), 4.34 (d, J=12.9 Hz, 1H), 4.26 (d, J=12.6 Hz, 1H), 4.08 (d, J=9.0 Hz, 0.5H), 3.93 (s, 2H), 3.82-3.70 (m, 1H), 3.31 (dd, J=19.9, 7.5 Hz, 0.5H), 3.24-3.12 (m, 1H), 3.11-2.97 (m, 1H), 2.56 (m, 2H), 2.39 (s, 3H), 2.11 (ddd, J=12.6, 8.0, 4.7 Hz, 1H), 1.35-1.25 (m, 1H), 1.10 (s, 2H), 0.97 (dd, J=7.9, 3.2 Hz, 2H), 0.78-0.34 (m, 4H).

LC-MS: m/z 473.4 (M+H)⁺

Compound 748 (General Procedure 6)

5-(2-chloropyridin-4-ylamino)-6-cyclopropyl-2-((R)-3-cyclopropyl-4-(2-((R)-oxetan-2-yl)acetyl)piperazin-1-yl)nicotinonitrile To a solution of (R)-5-(2-chloropyridin-4-ylamino)-6-cyclopropyl-2-(3-cyclopropylpiperazin-1-yl)nicotinonitrile (300 mg, 0.761 mmol) in DMF (3 mL) was added (R)-2-(oxetan-2-yl)acetic acid (115 mg, 0.99 mmol), HATU (436.0 mg, 1.142 mmol) and DIPEA (196.4 mg, 1.53 mmol) at r.t. The reaction mixture was stirred at r.t. for 3 hs. The solvent was removed in vacuum and the residue was purified via silica gel column chromatography (DCM:MeOH) to afford the title compound (182 mg, 48.5%) as a pale yellow solid.

¹H NMR (CHLOROFORM-d) δ: 8.06 (d, J=5.7 Hz, 1H), 7.60 (s, 1H), 6.50 (d, J=1.8 Hz, 1H), 6.47 (dd, J=5.7, 2.0 Hz, 1H), 5.80 (s, 1H), 5.27 (dt, J=13.0, 6.5 Hz, 1H), 4.72 (dd, J=14.0, 8.0 Hz, 1H), 4.65-4.43 (m, 2H), 4.37 (d, J=13.2 Hz, 1H), 4.09 (d, J=7.2 Hz, 0.5H), 3.95 (d, J=15.5 Hz, 0.5H), 3.80-3.67 (m, 1H), 3.28 (ddd, J=9.8, 9.1, 5.3 Hz, 1H), 3.16 (d, J=11.2 Hz, 0.5H), 3.13-3.03 (m, 1H), 2.98 (dd, J=15.2, 6.8 Hz, 1H), 2.93-2.78 (m, 2H), 2.78-2.66 (m, 0.5H), 2.66-2.47 (m, 1H), 2.10-2.02 (m, 1H), 1.28 (d, J=4.9 Hz, 1H), 1.15 (dt, J=7.3, 3.5 Hz, 2H), 1.04 (dt, J=7.0, 3.2 Hz, 2H), 0.77-0.38 (m, 4H).
LC-MS: m/z 494.0 (M+H)⁺

Compound 662

(R)—N-(5-cyano-2-cyclopropyl-6-(4-(3-methoxy-propanoyl)-3-methylpiperazin-1-yl)pyridin-3-yl)-N-(2-vinylpyridin-4-yl)acetamide

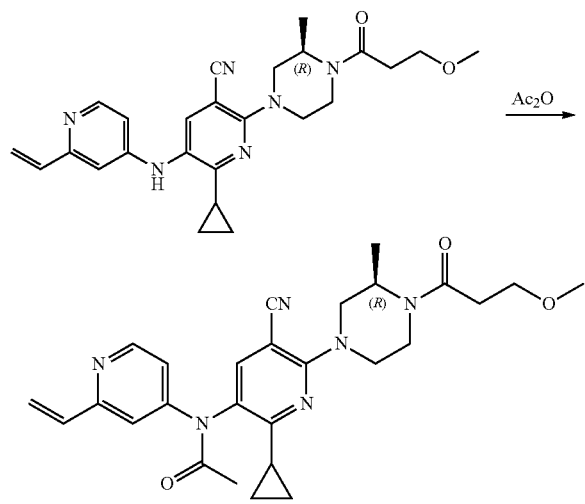

A solution of (R)-6-cyclopropyl-2-(4-(3-methoxypropanoyl)-3-methylpiperazin-1-yl)-5-(2-vinylpyridin-4-ylamino)nicotinonitrile (200 mg, 0.448 mmol) in acetic anhydride (5 mL) was heated and stirred at 135° C. overnight. The solvent was removed in vacuum and the residue was purified via reverse phase silica gel column chromatography (MeOH:H₂O) to afford the title compound (16 mg, 7.3%) as a pale yellow solid.
¹H NMR (CHLOROFORM-d) δ: 8.52 (d, J=5.5 Hz, 1H), 7.57 (s, 1H), 7.36 (d, J=5.3 Hz, 1H), 7.03 (d, J=5.2 Hz, 1H), 6.78 (dd, J=17.4, 10.8 Hz, 1H), 6.23 (d, J=17.3 Hz, 1H), 5.52 (d, J=10.9 Hz, 1H), 4.92 (s, 1H), 4.55 (d, J=11.4 Hz, 1H), 4.40-4.23 (m, 3H), 3.84 (d, J=12.8 Hz, 1H), 3.76 (t, J=6.3 Hz, 2H), 3.57 (t, J=11.0 Hz, 1H), 3.39 (s, 3H), 3.35 (s, 1H), 3.17 (dt, J=24.0, 11.2 Hz, 2H), 2.73 (ddd, J=23.2, 13.8, 6.3 Hz, 1H), 2.59 (dd, J=13.3, 7.2 Hz, 1H), 2.20-2.06 (m, 3H), 2.01 (dt, J=12.8, 6.2 Hz, 1H), 1.40 (d, J=5.9 Hz, 2H), 1.29 (d, J=6.7 Hz, 2H), 1.16 (d, J=4.3 Hz, 3H), 1.03 (d, J=7.5 Hz, 1H).
LC-MS: m/z 489.3 (M+H)⁺

Compound 758 (General Procedure 7)

(R)-6-cyclopropyl-2-(3-isopropyl-4-(3-methoxypropanoyl)piperazin-1-yl)-5-((4-vinylpyridin-2-yl)amino)nicotinonitrile ¹H NMR (CHLOROFORM-d) δ: 8.12 (d, J=5.4 Hz, 1H), 7.82 (d, J=5.7 Hz, 1H), 6.83 (d, J=5.4 Hz, 1H), 6.59 (dd, J=17.6, 10.8 Hz, 1H), 6.40 (s, 2H), 5.90 (d, J=17.5 Hz, 1H), 5.47 (d, J=10.9 Hz, 1H), 4.71 (d, J=12.5 Hz, 0.5H), 4.45 (dd, J=16.5, 9.9 Hz, 1.5H), 4.33-4.22 (m, 1H), 3.85 (d, J=13.3 Hz, 0.5H), 3.82-3.70 (m, 2H), 3.57 (d, J=10.5 Hz, 0.5H), 3.49-3.41 (m, 0.5H), 3.39 (d, J=3.3 Hz, 3H), 3.05 (dddd, J=21.0, 19.1, 13.7, 2.9 Hz, 2H), 2.82-2.54 (m, 2H), 2.27 (dd, J=16.7, 6.8 Hz, 0.5H), 2.18 (ddd, J=12.8, 8.2, 4.8 Hz, 1H), 1.35-1.27 (m, 1H), 1.18-0.97 (m, 7H), 0.91 (d, J=6.8 Hz, 1.5H), 0.86 (d, J=6.8 Hz, 1.5H).
LC-MS: m/z 475.6 (M+H)⁺

Compound 764 (General Procedure 7)

6-cyclopropyl-2-((R)-3-isopropyl-4-(2-((R)-oxetan-2-yl)acetyl)piperazin-1-yl)-5-((4-vinylpyridin-2-yl)amino)nicotinonitrile ¹H NMR (CHLOROFORM-d) δ: 8.10 (d, J=5.3 Hz, 1H), 7.81 (d, J=8.1 Hz, 1H), 6.82 (d, J=5.4 Hz, 1H), 6.69 (s, 1H), 6.58 (dd, J=17.6, 10.8 Hz, 1H), 6.39 (s, 1H), 5.89 (d, J=17.5 Hz, 1H), 5.46 (d, J=10.9 Hz, 1H), 5.32-5.24 (m, 1H), 4.83-4.61 (m, 1.5H), 4.56 (dtd, J=7.7, 5.8, 1.8 Hz, 1H), 4.48 (d, J=13.5 Hz, 0.5H), 4.46-4.39 (m, 1H), 4.27 (d, J=11.9 Hz, 1H), 3.88 (d, J=13.4 Hz, 0.5H), 3.56 (d, J=10.0 Hz, 0.5H), 3.45 (dd, J=13.4, 3.2 Hz, 0.5H), 3.13-2.92 (m, 3H), 2.92-2.75 (m, 2H), 2.65-2.44 (m, 1H), 2.31-2.24 (m, 0.5H), 2.21-2.10 (m, 2H), 1.16-1.07 (m, 2H), 1.05 (dd, J=6.5, 3.0 Hz, 3H), 1.04-0.98 (m, 2H), 0.92 (d, J=6.8 Hz, 1H), 0.86 (d, J=6.8 Hz, 2H).
LC-MS: m/z 487.6 (M+H)⁺

Compound 763 (General Procedure 7)

¹H NMR (CHLOROFORM-d) δ: 8.08 (d, J=5.6 Hz, 1H), 7.81 (s, 1H), 6.87 (d, J=5.6 Hz, 1H), 6.59 (dd, J=17.5, 10.9 Hz, 1H), 6.43 (s, 1H), 5.94 (d, J=17.6 Hz, 1H), 5.53 (d, J=10.9 Hz, 1H), 5.31-5.22 (m, 1H), 4.77-4.68 (m, 1H), 4.59-4.51 (m, 1H), 4.41 (s, 1H), 4.29-4.31 (m, 1H), 4.10-4.03 (m, 1H), 3.96-3.89 (m, 0.5H), 3.74-3.76 (m, 1H), 3.10-3.41 (m, 3H), 2.83-2.90 (m, 2.5H), 2.54-2.55 (m, 1H), 2.18-2.20 (m, 1H), 1.35-1.36 (m, 1H), 1.14-1.16 (m, 2H), 1.04-1.06 (m, 2H), 0.38-0.49 (m, 4H).
LC-MS: m/z 485.6 (M+H)⁺

Compound 756 (General Procedure 7)

(R)-6-cyclopropyl-2-(3-cyclopropyl-4-(3-hydroxy-propanoyl)piperazin-1-yl)-5-((4-vinylpyridin-2-yl)amino)nicotinonitrile To a solution of (R)-6-cyclopropyl-2-(3-cyclopropyl-4-(3-hydroxypropanoyl)piperazin-1-yl)-5-((4-vinylpyridin-2-yl)amino)nicotinonitrile (180 mg, 0.46 mmol) in 10 mL DMF was added sodium 3-hydroxypropanoate (104 mg, 0.92 mmol), and triethylamine (1 mL), HATU (350 mg, 0.92 mmol). The resulting reaction mixture was stirred at r.t. for overnight. After TLC showed the complete conversion of starting material to product, the reaction mixture was concentrated and purified by Prep-HPLC (50% EtOAc/petroleum ether) to get 100 mg title compound.
¹H NMR (CHLOROFORM-d) δ8.11 (d, 1H), 7.86 (s, 1H), 7.65 (s, 1H), 6.82 (dd, 1H), 6.53-6.62 (m, 1H), 6.40 (s, 1H), 5.89 (d., 1H), 5.45 (s, 1H), 4.75 (m, 0.5H), 4.37-4.32 (dd, 2H), 3.92 (m, 0.5H), 3.39-3.05 (m, 3H), 2.61-2.60 (m, 2H), 2.20-1.69 (m, 1H), 1.28-1.26 (m, 1H), 1.40-1.00 (m, 4H), 0.47-0.45 (m, 4H).
LC-MS: m/z 4 459 (M+H)⁺

Compound 656

(R)-4-(5-cyano-2-cyclopropyl-6-(4-(3-methoxypropanoyl)-3-methylpiperazin-1-yl)pyridin-3-yl)-N-methoxy-N-methylbenzamide

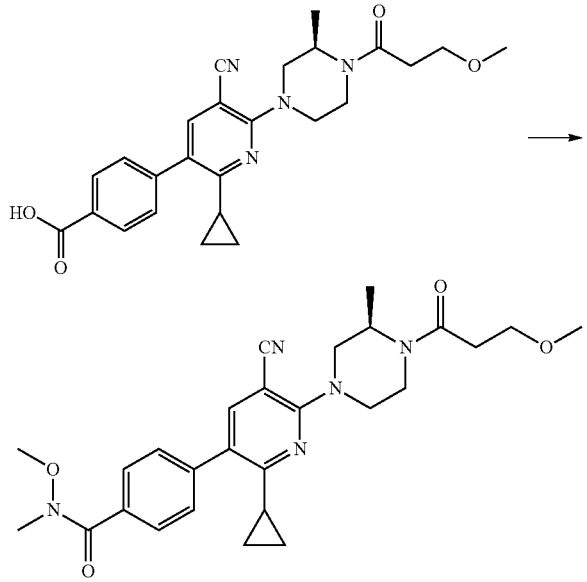

To a solution of (R)-4-(5-cyano-2-cyclopropyl-6-(4-(3-methoxypropanoyl)-3-methylpiperazin-1-yl)pyridin-3-yl) benzoic acid (450 mg, 1 mmol) and N,O-dimethylhydroxylammonium chloride (146 mg, 1.5 mmol) in DCM (10 mL) was added HATU (570 mg, 1.5 mmol) and DIPEA (516 mg, 4 mmol). The resulting mixture was stirred at r.t. for 2 h. The organic phase was washed with 1N HCl (10 mL×3), sat. NaHCO$_3$ (20 mL×1) and brine, dried over Na$_2$SO$_4$ and concentrated under vacuum to give 390 mg of the title compound as a white solid.

$^1$H NMR (CHLOROFORM-d) δ: 7.71-7.85 (m, J=8.3 Hz, 2H), 7.64 (s, 1H), 7.39-7.50 (m, J=8.3 Hz, 2H), 4.92 (br. s., 0.5H), 4.54 (d, J=12.3 Hz, 0.5H), 4.13-4.39 (m, 2.5H), 3.78-3.87 (m, 0.5H), 3.76 (br. s., 2H), 3.63 (s, 3H), 3.58 (d, J=10.3 Hz, 0.5H), 3.35-3.46 (m, 6H), 3.23-3.34 (m, 1H), 3.13 (br. s., 1H), 3.06 (d, J=12.5 Hz, 0.5H), 2.73 (br. s., 1H), 2.61 (br. s., 1H), 2.00-2.12 (m, 1H), 1.35-1.47 (m, 1.5H), 1.24-1.35 (m, 1.5H), 1.12-1.24 (m, 2H), 0.87-1.02 (m, 2H)

LC-MS: m/z 492.6 (M+H)$^+$

Compound 714 (General Procedure 7)

(R)-5-(bis(4-ethynylpyridin-2-yl)amino)-6-cyclopropyl-2-(4-(3-methoxypropanoyl)-3-methylpiperazin-1-yl)nicotinonitrile $^1$H NMR (CHLOROFORM-d) δ: 8.29 (d, J=5.1 Hz, 2H), 7.59 (s, 1H), 7.12 (br. s., 2H), 7.03 (dd, J=5.1, 1.1 Hz, 2H), 4.92 (br. s., 0.5H), 4.54 (d, J=13.2 Hz, 0.5H), 4.14-4.36 (m, 2.5H), 3.76 (t, J=6.2 Hz, 2.5H), 3.49-3.66 (m, 0.5H), 3.39 (s, 3H), 3.20-3.35 (m, 3H), 3.14 (d, J=11.3 Hz, 1H), 3.06 (d, J=11.3 Hz, 0.5H), 2.65-2.84 (m, 1H), 2.52-2.65 (m, 1H), 1.86-1.99 (m, 1H), 1.22-1.38 (m, 3H), 0.95-1.08 (m, 2H), 0.68-0.82 (m, 2H)

LC-MS: m/z 546.6 (M+H)$^+$

Compound 713 (General Procedure 7)

(R)-6-cyclopropyl-5-(4-ethynylpyridin-2-ylamino)-2-(4-(3-methoxypropanoyl)-3-methylpiperazin-1-yl) nicotinonitrile $^1$H NMR (CHLOROFORM-d) δ: 8.12 (d, J=5.4 Hz, 1H), 7.78 (s, 1H), 6.82 (dd, J=5.4, 1.1 Hz, 1H), 6.61 (br. s., 1H), 6.52 (s, 1H), 4.92 (br. s., 0.5H), 4.54 (d, J=13.4 Hz, 0.5H), 4.07-4.32 (m, 2.5H), 3.68-3.87 (m, 2.5H), 3.49-3.65 (m, 0.5H), 3.39 (s, 3H), 3.18-3.33 (m, 2H), 2.92-3.17 (m, 1.5H), 2.64-2.83 (m, 1H), 2.53-2.64 (m, 1H), 2.08-2.22 (m, 1H), 1.41 (d, J=6.2 Hz, 1.5H), 1.31 (d, J=6.4 Hz, 1.5H), 1.07-1.18 (m, 2H), 0.96-1.07 (m, 2H)

LC-MS: m/z 445.5 (M+H)$^+$

Compound 750 (General Procedure 7)

(R)-6-cyclopropyl-2-(3-cyclopropyl-4-(2-methoxyacetyl)piperazin-1-yl)-5-(4-ethynylpyridin-2-ylamino)nicotinonitrile $^1$H NMR (CHLOROFORM-d) δ: 8.00 (d, J=5.9 Hz, 1H), 7.71 (s, 1H), 6.88 (dd, J=5.9, 1.2 Hz, 1H), 6.64 (s, 1H), 4.51 (d, J=13.2 Hz, 1H), 4.37 (d, J=12.9 Hz, 1H), 4.17 (br. s., 2H), 4.01 (br. s., 0.5H), 3.89 (br. s., 0.5H), 3.71 (br. s., 0.5H), 3.40-3.52 (m, 4.5H), 3.22 (d, J=9.7 Hz, 1H), 3.02-3.16 (m, 1H), 2.09-2.20 (m, 1H), 1.03-1.22 (m, 4H), 0.67 (br. s., 2H), 0.47 (br. s., 4H)

LC-MS: m/z 457.5 (M+H)$^+$

Compound 647 (General Procedure 7)

(R)-6-cyclopropyl-2-(4-(3-methoxypropanoyl)-3-methylpiperazin-1-yl)-5-((4-vinylpyridin-2-yl)amino)nicotinonitrile To a solution of (R)-5-amino-6-cyclopropyl-2-(4-(3-methoxypropanoyl)-3-methylpiperazin-1-yl) nicotinonitrile (140 mg, 0.41 mmol) and 2-chloro-4-vinylpyridine (57 mg, 0.41 mmol) in 1,4-dioxane (15 mL) was added Pd2(dba)3 (56 mg, 0.061 mmol) and Xantphos (59 mg, 0.1 mmol) and Cs2CO3 (267 mg, 0.82 mmol) and the mixture was heated at 110° C. under N2. for 16 h. After TLC showed the complete conversion of starting material to product, the reaction mixture was concentrated and purified by column chromatography (DCM:MeOH=20:1) to afford 25 mg of title compound COMPOUND 647 and 20 mg compound COMPOUND 646.

$^1$H NMR (CHLOROFORM-d) δ: 7.94-7.93 (d, 1H), 7.68 (s, 1H), 6.84-6.82 (d, 1H), 6.58-6.51 (q, 1H), 6.38 (s, 1H), 5.95-5.90 (d, 1H), 5.55-5.52 (d, 1H), 4.87 (s, 0.5H), 4.54-4.51 (d, 0.5H); 4.48-4.13 (m, 3H) 3.79-3.70 (m, 2H) 3.44-3.35 (m, 1H) 3.25 (s, 3H) 3.11-2.98 (m, 3H), 2.77-2.56 (m, 2H), 2.17-2.12 (m, 1H), 1.38-1.13 (m, 3H), 1.09-1.00 (m, 2H), 0.99-0.98 (m, 2H).

LC-MS: m/z 447 (M+H)$^+$

Compound 646 (General Procedure 7)

(R)-5-(bis(4-vinylpyridin-2-yl)amino)-6-cyclopropyl-2-(4-(3-methoxypropanoyl)-3-methylpiperazin-1-yl)nicotinonitrile $^1$H NMR (CHLOROFORM-d) δ: 8.15-8.14 (d, 1H), 7.58 (s, 1H), 7.26-7.23 (d, 1H), 6.97-6.94 (dd, 1H), 6.79-6.72 (q, 1H), 6.03-5.98 (dd, 1H), 5.58 (s, 1H), 5.36-5.33 (dd, 1H), 4.88 (s, 0.5H), 4.54-4.51 (d, 0.5H); 4.20-4.09 (dd, 2H) 3.93 (s, 2H) 3.75-3.52 (m, 2H) 3.25-2.98 (m, 3H), 2.71-2.50 (m, 2H), 2.18-2.10 (m, 1H), 1.41-1.26 (m, 3H), 1.43-1.30 (m, 2H), 1.13-1.11 (m, 2H), 1.03-1.09 (m, 2H).

LC-MS: m/z 433 (M+H)$^+$

Compound 706 (General Procedure 7)

(R)-6-cyclopropyl-2-(3-cyclopropyl-4-(3-methoxypropanoyl)piperazin-1-yl)-5-((4-vinylpyridin-2-yl)amino)nicotinonitrile $^1$H NMR (CHLOROFORM-d) δ: 8.13 (d, 1H), 7.85 (s, 1H), 6.83 (dd, 1.2 Hz, 1H), 6.58 (dd, 10.7 Hz, 1H), 6.41 (s, 1H), 6.33 (br. s., 1H), 5.90 (d, 1H), 5.46 (d, 0.5H), 4.36 (d, 1H), 4.26 (d, Hz, 1H), 4.00-4.15 (m, 0.5H), 3.87 (d, 0.5H), 3.74 (t, 3H), 3.39 (s, 3H), 3.74-3.04 (m, 3H), 2.48-2.77 (m, 2H), 2.14-2.25 (m, 1H), 1.39 (br. s., 1H), 1.14 (t, 2H), 0.98-1.06 (m, 2H), 0.62-0.46 (d, 4H).

LC-MS: m/z 473 (M+H)$^+$

Compound 754 (General Procedure 7)

(R)-6-cyclopropyl-2-(4-(3-hydroxypropanoyl)-3-isopropylpiperazin-1-yl)-5-(2-vinylpyridin-4-ylamino)nicotinonitrile $^1$H NMR (DMSO-d$_6$) δ: 8.08-8.20 (m, 1H), 7.92 (d, J=5.3 Hz, 1H), 6.67-6.84 (m, 2H), 6.64 (br. s., 1H), 6.25 (d, J=16.7 Hz, 1H), 5.63 (br. s., 1H), 4.56 (t, J=5.3 Hz, 1.5H), 4.08-4.52 (m, 4.5H), 3.94 (d, J=13.5 Hz, 1H), 3.59-3.72 (m, 3.5H), 3.07-3.20 (m, 2H), 1.91-2.11 (m, 3H), 0.91-1.06 (m, 8H), 0.74 (d, J=6.7 Hz, 3H)

LC-MS: m/z 461.6 (M+H)$^+$

Compound 707 (General Procedure 7)

(R)-6-cyclopropyl-2-(4-(3-hydroxypropanoyl)-3-methylpiperazin-1-yl)-5-((4-vinylpyridin-2-yl)amino)nicotinonitrile $^1$H NMR (CHLOROFORM-d) δ: 8.11 (d, 1H), 7.84 (s, 1H), 7.28 (s, 1H), 6.74-6.92 (m, 1H), 6.67 (br. s., 1H), 6.58 (dd, 10.8 Hz, 1H), 6.41 (s, 1H), 5.90 (d, 1H), 5.47 (d, 1H), 4.89 (br. s., 0.5H), 4.53 (d, 0.5H), 4.07-4.36 (m, 2H), 3.93 (br. s., 2H), 3.72-3.65 (m, 1H), 2.98-3.27 (m, 2.5H), 2.44-2.74 (m, 2.5H), 2.14-2.44 (m, 1H), 1.83-2.11 (m, 1.5H), 1.21-1.50 (m, 1.5H), 0.96-1.20 (m, 2H), 0.90 (t, 2H).

LC-MS: m/z 433 (M+H)$^+$

Compound 725 (General Procedure 7)

(R)-6-cyclopropyl-2-(3-cyclopropyl-4-(3-hydroxypropanoyl)piperazin-1-yl)-4-methyl-5-((4-vinylpyridin-2-yl)amino)nicotinonitrile $^1$H NMR (CHLOROFORM-d) δ: 8.07 (d, J=5.3 Hz, 1H), 6.88 (br. s., 1H), 6.79 (dd, J=5.3, 1.2 Hz, 1H), 6.41-6.57 (m, 1H), 6.10 (s, 1H), 5.86 (d, J=17.6 Hz, 1H), 5.43 (d, J=10.9 Hz, 1H), 4.71-4.62 (m, 2-0.5H), 4.16-4.34 (m, 2H), 4.07 (d, J=8.8 Hz, 0.5H), 3.92 (br. s., 3H), 3.77 (br. s., 1H), 3.21-3.12 (d, 2H), 2.54-2.68 (m, 2H), 2.41 (s, 3H), 2.14-2.31 (m, 1H), 1.03-1.13 (m, 2H), 0.89-1.01 (m, 2H), 0.32-0.57 (m, 4H).

LC-MS: m/z 473 (M+H)$^+$

Compound 682 (General Procedure 7)

(R)-6-cyclopropyl-2-(4-(3-methoxypropanoyl)-3-methylpiperazin-1-yl)-5-((2-methoxypyridin-4-yl)amino)nicotinonitrile $^1$H NMR (CHLOROFORM-d) δ: 8.33 (s, 1H), 7.82 (s, 1H), 7.57 (s, 1H), 6.41-6.41 (d, 1H), 6.06 (s, 1H), 5.05 (m, 0.5H), 4.51-4.58 (m, 0.5H), 4.14 (s, 3H), 4.12 (m, 0.5H), 3.85 (m, 2H), 3.54-3.52 (m, 0.5H); 3.28 (s, 3H) 3.12-3.03 (m, 2H), 2.72-2.70 (m, 2H), 2.57-2.55 (m, 1H), 1.38-1.36 (m, 1.5H), 1.32 (m, 1.5H), 1.26-1.25 (m, 2H), 1.09-1.05 (m, 2H).

LC-MS: m/z 451 (M+H)$^+$

Compound 683 (General Procedure 7)

(R)-methyl 4-((5-cyano-2-cyclopropyl-6-(4-(3-methoxypropanoyl)-3-methylpiperazin-1-yl)pyridin-3-yl)amino)picolinate $^1$H NMR (CHLOROFORM-d) δ: 8.35 (s, 1H), 7.60 (s, 1H), 7.44 (s, 1H), 6.82 (s, 1H), 5.32-5.31 (m, 0.5H), 4.28-4.26 (m, 0.5H), 4.25-4.22 (m, 3H), 3.96 (s, 3H), 4.12 (m, 3H), 3.37 (s, 3H), 3.03-3.28 (m, 2H), 2.61-2.58 (m, 2H) 2.05-2.03 (m, 1H), 1.40-1.38 (m, 1.5H), 1.33-1.29 (m, 1.5H), 1.27-1.25 (m, 2H), 1.11-0.99 (m, 2H).

LC-MS: m/z 479 (M+H)$^+$

Compound 736 (General Procedure 7)

(R)-6-cyclopropyl-2-(4-(3-methoxypropanoyl)-3-methylpiperazin-1-yl)-5-((4-vinylpyrimidin-2-yl)amino)nicotinonitrile $^1$H NMR (CHLOROFORM-d) δ: 8.36 (d, 1H), 8.30 (s, 1H), 7.02-7.13 (m, 1H), 6.75 (d, 1H), 6.63 (dd, 10.6 Hz, 1H), 6.40 (d, 1H), 5.67 (d, 1H), 4.91 (br. s., 0.5H), 4.54 (d, 0.5H), 4.23 (br. s., 0.5H), 4.00-4.17 (m, 2H), 3.66-3.82 (m, 2H), 3.37-3.42 (m, 4H), 2.93-3.23 (m, 2H), 2.53-2.79 (m, 2H), 2.08-2.20 (m, 1H), 1.38-1.45 (m, 1.5H), 1.31 (d, 1.5H), 1.09-1.17 (m, 2H), 1.03 (dd, 2H).

LC-MS: m/z 448 (M+H)$^+$

Compound 705 (General Procedure 7)

(R)-6-cyclopropyl-2-(4-(3-methoxypropanoyl)-3-methylpiperazin-1-yl)-5-(2-vinyl-1,8-naphthyridin-4-ylamino)nicotinonitrile $^1$H NMR (CHLOROFORM-d) δ: 8.99 (br. s., 1H), 8.55 (d, J=7.8 Hz, 1H), 7.64 (s, 1H), 7.39 (dd, J=8.3, 4.3 Hz, 1H), 6.82 (dd, J=17.1, 10.8 Hz, 1H), 6.38 (br. s., 1H), 6.30 (d, J=17.6 Hz, 1H), 5.59 (d, J=10.8 Hz, 1H), 4.91 (br. s., 0.5H), 4.54 (d, J=13.6 Hz, 0.5H), 4.26 (d, J=11.3 Hz, 2H), 4.16 (d, J=13.3 Hz, 1H), 3.70-3.89 (m, 3H), 3.50-3.09 (m, 7H), 3.04 (d, J=12.3 Hz, 1H), 2.52-2.82 (m, 2.5H), 1.98-2.13 (m, 1.5H), 1.28-1.44 (m, 5H), 0.93-1.02 (m, 2H)

LC-MS: m/z 498.1 (M+H)$^+$

Compound 702

(R)—N-(5-cyano-2-cyclopropyl-6-(4-(3-methoxy-propanoyl)-3-methylpiperazin-1-yl) pyridin-3-yl)-N-(pyridin-4-yl) acryl amide

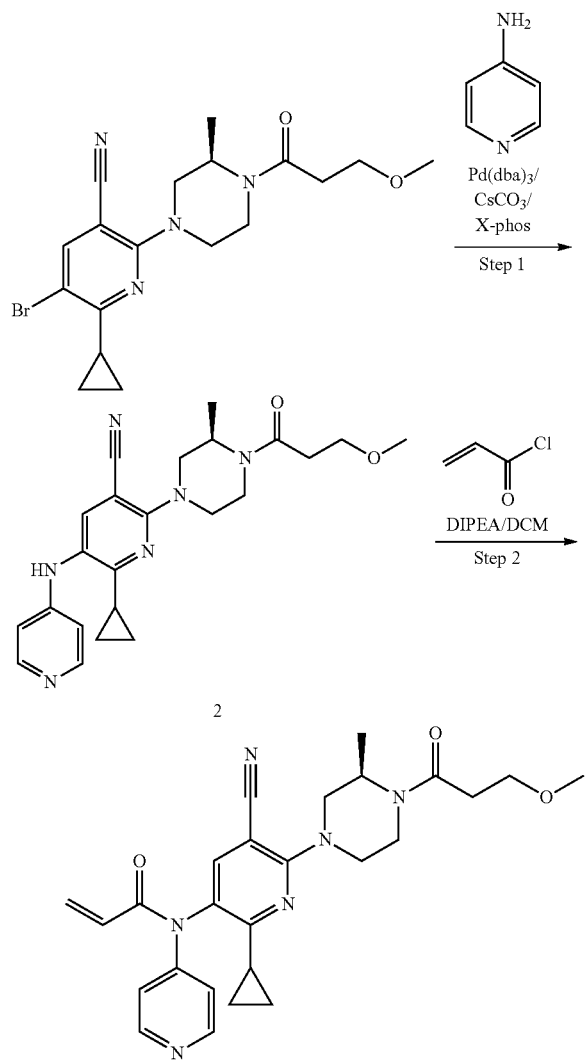

Step 1: (R)-6-cyclopropyl-2-(4-(3-methoxypropanoyl)-3-methylpiperazin-1-yl)-5-(pyridin-4-ylamino) nicotinonitrile To a solution of (R)-5-bromo-6-cyclopropyl-2-(4-(3-methoxypropanoyl)-3-methylpiperazin-1-yl)nicotinonitrile (406 mg, 1 mmol) and pyridin-4-amine (94 mg, 1 mmol) in 1,4-dioxane (5 mL) was added Pd(dba)$_3$ (136 mg, 0.15 mmol) and X-phos (72 mg, 0.15 mmol) and Cs$_2$CO$_3$ (752 mg, 2 mmol) at room temperature under N$_2$. The resulting mixture was heated and stirred at 120° C. under N$_2$ in microwave for 1.5 h. The solvent was removed in vacuum and the residue was purified by column chromatography (MeOH/DCM=1/15) afforded 168 mg of title compound as a yellow solid.

LC-MS: m/z 471.4 (M+H)$^+$

Step 2: Compound 702

(R)—N-(5-cyano-2-cyclopropyl-6-(4-(3-methoxy-propanoyl)-3-methylpiperazin-1-yl) pyridin-3-yl)-N-(pyridin-4-yl) acryl amide To a solution of (R)-6-cyclopropyl-2-(4-(3-methoxypropanoyl)-3-methylpiperazin-1-yl)-5-(pyridin-4-ylamino) nicotinonitrile (41 mg, 0.1 mmol) and N,N-Diisopropylethylamine (26 mg, 0.2 mmol) in 5 mL of DCM was added Acryloyl chloride (10 mg, 0.1 mmol) at room temperature. The reaction mixture was then stirred at room temperature for 3 h. After LC-MS showed the completion of reaction, the mixture was poured into water and extracted with methylene chloride. The combined organic layer was dried over anhy. Na$_2$SO$_4$ and concentrated in vacuo. Column chromatography (MeOH/DCM=1/15) afforded 12.6 mg of title compound as a colorless oil.

$^1$H NMR (CHLOROFORM-d) δ: 8.60 (d, J=4.8 Hz, 2H), 7.53 (s, 1H), 7.28 (s, 2H), 6.58 (d, J=16.7 Hz, 1H), 6.16 (d, J=5.1 Hz, 1H), 5.82 (d, J=10.5 Hz, 1H), 4.92 (m, 0.5H), 4.56 (m, 0.5H), 4.20-4.42 (m, 2H), 3.69-3.91 (m, 2H), 3.58 (m, 1H), 3.37-3.41 (m, 3H), 3.36 (br. s., 1H), 3.14 (br. s., 2H), 2.59 (d, J=5.9 Hz, 2H), 1.82-1.94 (m, 1H), 1.37-1.44 (m, 2H), 1.20-1.36 (m, 5H).

LC-MS: m/z 475.5 (M+H)$^+$

Compound 712

(R)—N-(5-cyano-2-cyclopropyl-6-(4-(3-methoxy-propanoyl)-3-methylpiperazin-1-yl)pyridin-3-yl)-N-(quinolin-4-yl)acryl amide $^1$H NMR (CHLOROFORM-d) δ: 8.96 (d, J=4.5 Hz, 1H), 8.26 (d, J=8.5 Hz, 1H), 7.93-8.03 (m, 1H), 7.84 (t, J=7.5 Hz, 1H), 7.70 (d, J=7.3 Hz, 1H), 7.44 (br. s., 1H), 7.30 (br. s., 1H), 6.61 (d, J=16.8 Hz, 1H), 6.16 (d, J=5.10 Hz, 1H), 5.82 (d, J=10.48 Hz, 1H), 4.88 (m, J=10.48 Hz, 0.5H), 4.52 (m, J=6.48 Hz, 0.5H), 4.27 (t, J=12.9 Hz, 2H), 3.74 (t, J=6.1 Hz, 2H), 3.52 (m, J=9.1 Hz, 1H), 3.37 (s, 3H), 3.29 (d, J=10.8 Hz, 1H), 3.12 (br. s., 2H), 2.72 (t, J=9.8 Hz, 1H), 2.58 (t, J=5.8 Hz, 1H), 2.23 (t, J=7.7 Hz, 1H), 1.31-1.40 (m, 2H), 1.21-1.31 (m, 3H), 1.14 (br. s., 2H).

LC-MS: m/z 525.5 (M+H)$^+$

Compound 732 (General Procedure 7)

(R)-6-cyclopropyl-2-(4-(3-methoxypropanoyl)-3-methylpiperazin-1-yl)-5-(2-vinylquinolin-7-ylamino) nicotinonitrile To a solution of (R)-5-amino-6-cyclopropyl-2-(4-(3-methoxypropanoyl)-3-methylpiperazin-1-yl)nicotinonitrile (34 mg, 0.1 mmol) and 7-bromo-2-vinylquinoline (23 mg, 0.1 mmol) in 1,4-dioxane (1 mL) was added Pd(dba)$_3$ (13.6 mg, 0.015 mmol) and X-phos (7.2 mg, 0.15 mmol) and Cs$_2$CO$_3$ (75.2 mg, 0.2 mmol) at room temperature under N$_2$. The resulting mixture was heated and stirred at 120° C. under N$_2$ in microwave for 1.5 h. The solvent was removed in vacuum and the residue was purified by column chromatography (MeOH/DCM=1/15) afforded 17.2 mg of title compound as a colorless oil.

$^1$H NMR (CHLOROFORM-d) δ: 8.08 (d, J=8.2 Hz, 1H), 7.68 (d, J=8.8 Hz, 1H), 7.64 (s, 1H), 7.44 (d, J=8.5 Hz, 1H), 7.31 (br. s., 1H), 7.03-7.18 (m, 2H), 6.32 (d, J=17.6 Hz, 1H), 6.18 (br. s., 1H), 5.74 (d, J=10.9 Hz, 1H), 4.92 (m, 0.5H), 4.54 (m, 0.5H), 4.09-4.33 (m, 2H), 3.71-3.86 (m, 2H), 3.57

(br. s., 1H), 3.40 (s, 3H), 3.25 (t, J=11.4 Hz, 1H), 3.13 (br. s., 2H), 2.75 (br. s., 1H), 2.53-2.64 (m, 1H), 2.14-2.27 (m, 1H), 1.40-1.47 (m, 1H), 1.24-1.35 (m, 2H), 1.12 (t, J=3.7 Hz, 2H), 0.97 (dd, J=7.9, 3.5 Hz, 2H).

LC-MS: m/z 497.4 (M+H)$^+$

Compound 665

(R)-methyl-4-(5-cyano-2-cyclopropyl-6-(4-(3-methoxypropanoyl)-3-methylpiperazin-1-yl)pyridin-3-yl)benzoate 1H NMR (CHLOROFORM-d) δ 8.12 (d, J=7.5 Hz, 2H), 7.63 (br. s., 1H), 7.48 (d, J=7.5 Hz, 2H), 4.47-4.61 (d, J=12.5 Hz, 0.5H), 4.19-4.37 (m, 2.5H), 3.96 (br. s., 3H), 3.75 (br. s., 2H), 3.47-3.61 (m, 1H), 3.38 (br. s., 3H), 3.28 (br. s., 1H), 3.01-3.18 (m, 1H), 2.65-2.79 (m, 1H), 2.60 (br. s., 1H), 1.96-2.10 (m, 1H), 1.72-1.91 (m, 1H), 1.38 (br. s., 1H), 1.28 (br. s., 2H), 1.18 (br. s., 2H), 0.97 (br. s., 2H)

LC-MS: m/z 463.2 (M+H)$^+$

Compound 704 (General Procedure 8)

(R)-5-((2-chloropyridin-4-yl)oxy)-6-cyclopropyl-2-(4-(3-hydroxypropanoyl)-3-methylpiperazin-1-yl) nicotinonitrile $^1$H NMR (CHLOROFORM-d) δ: 8.29 (d, J=5.7 Hz, 1H), 7.47 (s, 1H), 6.83-6.77 (m, 2H), 4.90-4.91 (m, 1H), 4.53-4.55 (m, 1H), 4.20 (t, J=12.8 Hz, 3H), 3.92 (s, 2H), 3.79-3.70 (m, 1H), 3.55 (d, J=10.9 Hz, 1H), 3.31-3.20 (m, 1H), 3.14-2.99 (m, 1H), 2.55 (s, 2H), 2.01 (t, J=4.6 Hz, 1H), 1.87 (d, J=3.4 Hz, 1H), 1.43 (d, J=6.4 Hz, 1H), 1.32 (d, J=6.4 Hz, 2H), 1.12 (dd, J=7.9, 3.1 Hz, 2H), 1.03 (dt, J=7.9, 3.1 Hz, 2H).

LC-MS: m/z 442.1 (M+H)$^+$

Compound 695 (General Procedure 8)

(R)-5-((2-chloropyridin-4-yl)oxy)-6-cyclopropyl-2-(3-cyclopropyl-4-(3-methoxypropanoyl)piperazin-1-yl)nicotinonitrile $^1$H NMR (CHLOROFORM-d) δ: 8.29 (d, J=5.6 Hz, 1H), 7.46 (s, 1H), 6.83-6.76 (m, 2H), 4.69-4.72 (m, 0.5H), 4.40 (d, J=12.6 Hz, 1H), 4.28 (d, J=12.7 Hz, 1H), 4.13 (dd, J=14.3, 7.2 Hz, 1H), 3.88 (d, J=12.0 Hz, 1H), 3.78-3.64 (m, 3H), 3.38 (s, 3H), 3.18 (d, J=13.1 Hz, 1H), 3.04 (d, J=26.4 Hz, 1H), 2.74-2.57 (m, 2H), 2.48-2.50 (m, 0.5H), 1.98-2.04 (m, 1H), 1.35 (t, J=10.7 Hz, 1H), 1.13 (dd, J=7.4, 3.1 Hz, 2H), 1.02 (dt, J=7.9, 3.1 Hz, 2H), 0.59 (d, J=30.2 Hz, 2H), 0.45-0.48 (m, 2H).

LC-MS: m/z 482.1 (M+H)$^+$

Compound 694 (General Procedure 8)

(R)-5-(2-chloropyridin-4-yloxy)-6-cyclopropyl-2-(3-cyclopropyl-4-(3-hydroxypropanoyl) piperazin-1-yl) nicotinonitrile A mixture of (R)-5-(2-chloropyridin-4-yloxy)-6-cyclopropyl-2-(3-cyclopropylpiperazin-1-yl) nicotinonitrile (3, general procedure 8 scheme) (0.35 g, 0.88 mol), sodium 3-hydroxypropanoate (0.10 g, 0.88 mol), HATU (0.5 g, 1.32 mmol) and 0.23 g DIEA (1.76 mmol) was stirred in 8 mL DMF for 4 hrs. Then the mixture was quenched by adding 6 mL water and extracted with EtOAc (15 mL×2), the organic phase was combined and concentrated to give a yellow oil, which was further purified by silica gel chromatography (DCM:MeOH=20:1) to give 0.10 g of product as yellow solid (52% yield).

$^1$H NMR (CHLOROFORM-d) δ: 8.30 (d, J=5.6 Hz, 1H), 7.48-7.49 (m, 0.5H), 6.81 (dt, J=5.6, 2.0 Hz, 2H), 4.70 (s, 1H), 4.41 (d, J=13.0 Hz, 1H), 4.29 (d, J=13.0 Hz, 1H), 4.12 (dd, J=18.6, 7.4 Hz, 1H), 3.93 (s, 2H), 3.84-3.67 (m, 1H), 3.18 (d, J=12.8 Hz, 1H), 3.13-2.99 (m, 1H), 2.61 (s, 2H), 2.32-2.22 (m, 0.5H), 2.02 (t, J=4.6 Hz, 1H), 1.35 (s, 1H), 1.29 (d, J=9.4 Hz, 3H), 1.14 (dd, J=7.4, 3.0 Hz, 2H), 1.04 (dt, J=7.9, 3.1 Hz, 2H), 0.66-0.67 (m, 2H), 0.46-0.51 (m, 2H).

LC-MS: m/z 468.1 (M+H)$^+$

Compound 692 (General Procedure 7)

(R)-6-cyclopropyl-2-(3-cyclopropyl-4-(3-hydroxypropanoyl)piperazin-1-yl)-5-(2-vinylpyridin-4-yloxy)nicotinonitrile A mixture of (R)-5-(2-chloropyridin-4-yloxy)-6-cyclopropyl-2-(3-cyclopropyl-4-(3-hydroxy propanoyl) piperazin-1-yl)nicotinonitrile (4) 0.35 g, (0.75 mmol), potassium trifluoro(vinyl)borate (0.15 g, 1.1 mmol), PdCl$_2$dppf (80 mg, 0.075 mmol) and DIEA (0.24 mL, 1.5 mmol) was heated in isopropanol at reflux at 85° C. under nitrogen for 5 hrs. The mixture was then concentrated under reduced pressure to give a yellow solid which was further purified by silica chromatography (PE/EA/MeOH=150/120/8) to give 0.19 g of product as a white solid (55% yield).

$^1$H NMR (CHLOROFORM-d) δ: 8.47 (d, J=5.6 Hz, 1H), 7.48-7.49 (m, 0.5H), 6.86 (d, J=2.3 Hz, 1H), 6.77 (dd, J=17.4, 10.8 Hz, 1H), 6.66 (dd, J=5.6, 2.4 Hz, 1H), 6.22 (dd, J=17.4, 0.9 Hz, 1H), 5.53 (dd, J=10.8, 0.8 Hz, 1H), 4.68 (d, J=11.7 Hz, 1H), 4.38 (d, J=12.9 Hz, 1H), 4.30-4.22 (m, 1H), 4.15-4.04 (m, 1H), 3.92 (s, 2H), 3.75 (d, J=20.7 Hz, 1H), 3.47 (d, J=21.7 Hz, 1H), 3.25-3.12 (m, 1H), 3.09-2.95 (m, 1H), 2.60 (s, 2H), 2.32-2.22 (m, 0.5H), 2.11-2.05 (m, 1H), 1.37 (d, J=20.5 Hz, 1H), 1.27 (d, J=2.0 Hz, 1H), 1.16-1.10 (m, 2H), 1.01 (ddd, J=10.1, 6.7, 3.3 Hz, 2H), 0.65 (t, J=33.7 Hz, 2H), 0.45-0.48 (m, 2H).

LC-MS: m/z 460.1 (M+H)$^+$

Compound 693 (General Procedure 8)

(R)-6-cyclopropyl-2-(3-cyclopropyl-4-(3-methoxypropanoyl)piperazin-1-yl)-5-(2-vinylpyridin-4-yloxy)nicotinonitrile $^1$H NMR (CHLOROFORM-d) δ: 8.46 (d, J=5.6 Hz, 1H), 7.46 (s, 1H), 6.86 (d, J=2.3 Hz, 1H), 6.77 (dd, J=17.4, 10.8 Hz, 1H), 6.66 (dd, J=5.6, 2.4 Hz, 1H), 6.22 (d, J=17.4 Hz, 1H), 5.53 (d, J=10.9 Hz, 1H), 4.54-4.71 (m, 0.5H), 4.37 (d, J=12.4 Hz, 1H), 4.26 (d, J=12.6 Hz, 1H), 4.11 (s, 1H), 3.88 (d, J=11.9 Hz, 1H), 3.80-3.68 (m, 3H), 3.38 (s, 3H), 3.20 (t, J=23.2 Hz, 1H), 3.05 (s, 1H), 2.68 (dd, J=15.1, 12.2 Hz, 2H), 2.47-2.53 (m, 0.5H), 2.06 (dd, J=8.6, 3.9 Hz, 1H), 1.38-1.28 (m, 1H), 1.13 (dd, J=7.4, 3.1 Hz, 2H), 1.01 (dt, J=7.9, 3.2 Hz, 2H), 0.73-0.51 (m, 2H), 0.43-0.46 (m, 2H).

LC-MS: m/z 476.1 (M+H)$^+$

Compound 668 (General Procedure 8)

(R)-5-((2-chloropyridin-4-yl)oxy)-6-cyclopropyl-2-(4-(3-methoxypropanoyl)-3-methylpiperazin-1-yl)nicotinonitrile $^1$H NMR (CHLOROFORM-d) δ: 8.33 (s, 1H), 7.47 (s, 1H), 6.85 (s, 2H), 4.93-5.05 (m, 0.5H), 4.56-4.58 (m, 0.5H), 4.33-4.09 (m, 3H), 3.88-3.68 (m, 3H), 3.57 (s, 1H), 3.40 (s, 3H), 3.30 (s, 1H), 3.10 (dd, J=36.0, 11.2 Hz, 1H), 2.82-2.48 (m, 1H), 1.42 (d, J=6.5 Hz, 2H), 1.36-1.29 (m, 2H), 1.14 (s, 2H), 1.03-1.05 (m, 2H).
LC-MS: m/z 456.0 (M+H)$^+$ Compound 666 (General Procedure 8)

(R)-5-((6-chloropyrimidin-4-yl)oxy)-6-cyclopropyl-2-(4-(3-methoxypropanoyl)-3-methylpiperazin-1-yl)nicotinonitrile $^1$H NMR (CHLOROFORM-d) δ: 8.33 (s, 1H), 7.47 (s, 1H), 6.85 (s, 2H), 4.92-4.96 (m, 0.5H), 4.55-4.58 (m, 0.5H), 4.33-4.09 (m, 3H), 3.88-3.68 (m, 2H), 3.57 (s, 1H), 3.40 (s, 3H), 3.30 (s, 1H), 3.10 (dd, J=36.0, 11.2 Hz, 1H), 2.82-2.48 (m, 1H), 1.42 (d, J=6.5 Hz, 2H), 1.36-1.29 (m, 2H), 1.14 (s, 2H), 1.03 (d, J=4.1 Hz, 2H).
LC-MS: m/z 449.0 (M+H)$^+$ Compound 734 (General Procedure 8)

(R)-5-((4-chloropyridin-2-yl)oxy)-6-cyclopropyl-2-(3-cyclopropyl-4-(3-hydroxypropanoyl)piperazin-1-yl)nicotinonitrile $^1$H NMR (CHLOROFORM-d) δ: 8.07 (d, J=6.0 Hz, 1H), 7.54 (s, 1H), 7.09-7.05 (m, 2H), 4.60-4.68 (m, 1H), 4.31-4.35 (m, 1H), 4.21 (d, J=13.0 Hz, 1H), 4.07 (d, J=9.8 Hz, 1H), 3.92 (s, 2H), 3.74 (d, J=11.5 Hz, 1H), 3.48 (d, J=24.4 Hz, 1H), 3.21-3.07 (m, 1H), 3.03 (d, J=10.9 Hz, 1H), 2.58 (d, J=17.5 Hz, 2H), 2.15-2.00 (m, 1H), 1.44 (s, 1H), 1.13 (dd, J=7.3, 3.6 Hz, 2H), 0.98 (dt, J=6.8, 2.7 Hz, 2H), 0.65 (s, 2H), 0.45-0.48 (m, 2H).
LC-MS: m/z 469.2 (M+H)$^+$ Compound 733 (General Procedure 8)

(R)-5-((4-chloropyridin-2-yl)oxy)-6-cyclopropyl-2-(3-cyclopropyl-4-(3-hydroxypropanoyl)piperazin-1-yl)nicotinonitrile $^1$H NMR (CHLOROFORM-d) δ: 8.10 (d, J=5.3 Hz, 1H), 7.53 (s, 1H), 7.07 (dd, J=5.3, 1.1 Hz, 1H), 6.97 (s, 1H), 6.70 (dd, J=17.6, 10.9 Hz, 1H), 6.01 (d, J=17.6 Hz, 1H), 5.56 (d, J=10.9 Hz, 1H), 4.69-4.71 (m, 0.5H), 4.28 (d, J=12.4 Hz, 1H), 4.18 (d, J=12.5 Hz, 1H), 4.09 (d, J=8.0 Hz, 1H), 3.80-3.90 (m, 0.5H), 3.72 (dd, J=13.7, 7.8 Hz, 3H), 3.39 (d, J=5.9 Hz, 3H), 3.27 (s, 1H), 3.09 (d, J=12.5 Hz, 1H), 2.97 (s, 1H), 2.73-2.59 (m, 2H), 2.18-2.10 (m, 1H), 1.12 (d, J=4.0 Hz, 2H), 0.96 (ddd, J=9.2, 8.5, 5.1 Hz, 3H), 0.89 (dd, J=13.9, 6.8 Hz, 2H), 0.62 (s, 2H), 0.45-0.47 (m, 2H).
LC-MS: m/z 474.2 (M+H)$^+$ Compound 832 (General Procedure 8)

(R)-6-cyclopropyl-2-(4-(3-methoxypropanoyl)-3-methylpiperazin-1-yl)-5-((2-vinylpyridin-4-yl)oxy)nicotinonitrile

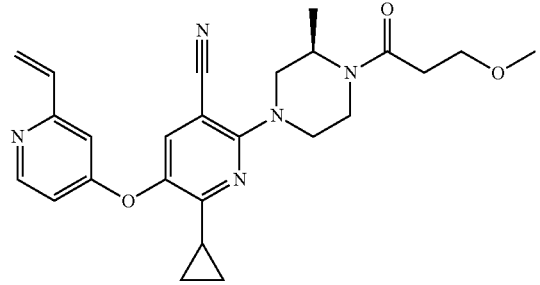 [SMILES: C=Cc1cc(Oc2cc(C#N)c(N3CCN(C(=O)CCOC)[C@H](C)C3)nc2C2CC2)ccn1]

$^1$H NMR (CHLOROFORM-d) δ: 8.47 (d, J=5.6 Hz, 1H), 7.44 (d, J=3.5 Hz, 1H), 6.88 (s, 1H), 6.84-6.74 (m, 1H), 6.69 (d, J=3.5 Hz, 1H), 6.28 (d, J=17.4 Hz, 1H), 5.58 (d, J=10.7 Hz, 1H), 4.89-4.91 (m, 0.5H), 4.50-4.54 (m, 0.5H), 4.23-4.06 (m, 2H), 3.82-3.68 (m, 2H), 3.50-3.53 (m, 0.5H), 3.37 (s, 3H), 3.26 (d, J=12.7 Hz, 1H), 3.05-3.10 (m, 1.5H), 2.78-2.52 (m, 2H), 2.05-1.93 (m, 1H), 1.39 (d, J=6.0 Hz, 1H), 1.32-1.25 (m, 3H), 1.14-1.08 (m, 2H), 0.99 (dt, J=11.5, 3.3 Hz, 2H).
LC-MS: m/z 448.0 (M+H)$^+$

Compound 703 (General Procedure 8)

(R)-6-cyclopropyl-2-(4-(3-methoxypropanoyl)-3-methylpiperazin-1-yl)-5-((2-vinylpyridin-4-yl)methoxy)nicotinonitrile $^1$H NMR (CHLOROFORM-d) δ: 8.61 (d, J=5.0 Hz, 1H), 7.39 (s, 1H), 7.21-7.26 (m, 1H), 7.18 (s, 1H), 6.85 (dd, J=17.4, 10.9 Hz, 1H), 6.26 (dd, J=17.4, 1.1 Hz, 1H), 5.47-5.61 (m, 1H), 5.06 (s, 2H), 4.88 (br. s., 0.5H), 4.52 (d, J=13.6 Hz, 0.5H), 4.21 (d, J=6.8 Hz, 0.5H), 3.85-4.05 (m, 2H), 3.67-3.81 (m, 2.5H), 3.54 (d, J=6.8 Hz, 0.5H), 3.37 (s, 3H), 3.04-3.18 (m, 1.5H), 2.84-3.04 (m, 1H), 2.63-2.80 (m, 1H), 2.44-2.63 (m, 2H), 1.22-1.36 (m, 3H), 1.03-1.17 (m, 4H)
LC-MS: m/z 461.6 (M+H)$^+$ Compound 789

5-(1-acryloyl-1,2,5,6-tetrahydropyridin-3-yl)-6-cyclopropyl-2-((R)-3-cyclopropyl-4-(2-((R)-oxetan-2-yl)acetyl)piperazin-1-yl)-4-methylnicotinonitrile 1H NMR (CHLOROFORM-d) □ 6.67 (dd, J=16.7, 10.6 Hz, 1H), 6.35 (dd, J=16.7, 7.0 Hz, 1H), 5.64-5.85 (m, 2H), 5.26 (m, 6.6 Hz, 1H), 4.66-4.79 (m, 1H), 4.56 (br. s., 1H), 4.23-4.39 (m, 2H), 4.18 (d, J=12.6 Hz, 1H), 3.95-4.11 (m, 2H), 3.90 (d, J=17.9 Hz, 1H), 3.63-3.83 (m, 2H), 3.27 (br. s., 1H), 3.08 (br. s., 1H), 2.96 (d, J=10.3 Hz, 2H), 2.79-2.92 (m, 2H), 2.53 (d, J=7.9 Hz, 1H), 2.31-2.48 (m, 5H), 2.04 (dd, J=13.4, 6.0 Hz, 1H), 1.44 (d, J=8.2 Hz, 1H), 1.15 (br. s., 1H), 0.85-1.07 (m, 3H), 0.60 (br. s., 1H), 0.52 (br. s., 1H), 0.44 (br. s., 2H)
LC-MS: m/z 516.6 (M+H)

Compound 778

6-cyclopropyl-2-((R)-3-cyclopropyl-4-(2-((R)-oxetan-2-yl)acetyl)piperazin-1-yl)-5-(1-methyl-6-vinyl-1H-pyrazolo[3,4-b]pyridin-4-yl)nicotinonitrile $^1$H NMR (CHLOROFORM-d) □ 7.86-7.94 (s, 1H), 7.71-7.81 (s, 1H), 7.22 (s, 1H), 6.99 (dd, J=17.6, 10.9 Hz, 1H), 6.28-6.48 (m, 1H), 5.66 (dd, J=10.9, 0.9 Hz, 1H), 5.28 (t, J=6.7 Hz, 1H), 4.68-4.78 (m, 1H), 4.54-4.68 (m, 2H), 4.48 (d, J=14.1 Hz, 1H), 4.21 (s, 3H), 3.75-4.17 (m, 2H), 2.77-3.35 (m, 6H), 2.45-2.65 (m, 1H), 1.85-2.01 (m, 2H), 1.18-1.25 (m, 2H), 0.95-1.05 (m, 2H), 0.61-0.81 (m, 1H), 0.57 (br. s., 1H), 0.48 (br. s., 2H)

LC-MS: m/z 524.2 (M+H)$^+$

Compound 777

(R)-6-cyclopropyl-2-(3-cyclopropyl-4-(3-hydroxypropanoyl)piperazin-1-yl)-4-methyl-5-((2-vinylpyridin-4-yl)oxy)nicotinonitrile $^1$H NMR (400 MHz, CDCl$_3$) δ 8.48 (d, J=5.7 Hz, 1H), 6.93-6.75 (m, 2H), 6.65 (d, J=3.7 Hz, 1H), 6.30 (d, J=17.4 Hz, 1H), 5.60 (d, J=10.7 Hz, 1H), 4.60-4.71 (m, 0.5H), 4.27-4.28 (m, 1H), 4.23-4.14 (m, 1H), 4.10-4.15 (m, 0.5H), 3.92-3.93 (m, 2H), 3.78-3.79 (m, 1H), 3.44-3.45 (m, 1H), 3.26-3.10 (m, 1H), 3.04-3.05 (m, 1H), 2.61-2.62 (m, 2H), 2.31 (s, 3H), 2.01-1.94 (m, 1H), 1.44-1.45 (m, 1H), 1.13-1.07 (m, 2H), 1.01-0.94 (m, 2H), 0.91-0.86 (m, 1H), 0.65-0.66 (m, 1H), 0.46-0.52 (m, 2H). MS (ES) M+H expected 474.0. found 474.6

Compound 833

(R)-6-cyclopropyl-2-(3-cyclopropyl-4-(3-methoxypropanoyl)piperazin-1-yl)-5-((5-vinylpyridazin-3-yl)amino)nicotinonitrile

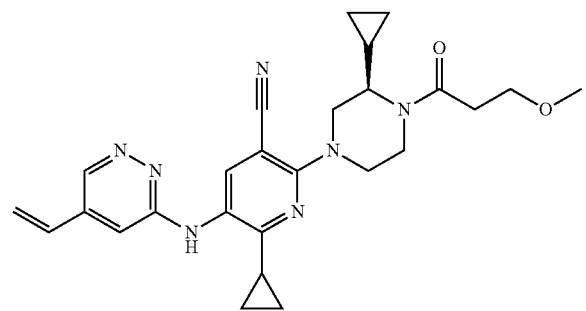 [SMILES: C=Cc1cnnc(Nc2cc(C#N)c(N3CCN(C(=O)CCOC)[C@H](C4CC4)C3)nc2C2CC2)c1]

$^1$H NMR (400 MHz, CDCl$_3$) δ 8.76 (s, 1H), 7.76 (s, 1H), 6.58 (dd, J=17.6, 11.0 Hz, 2H), 6.05 (d, J=17.6 Hz, 1H), 5.66 (d, J=11.0 Hz, 1H), 4.65-4.70 (m, 0.5H), 4.43-4.46 (m, 1H), 4.33 (d, J=12.4 Hz, 1H), 4.16-4.07 (m, 1H), 3.87-3.88 (m, 0.5H), 3.71-3.74 (m, 3H), 3.39 (s, 3H), 3.20 (s, 1H), 3.07-3.09 (m, 1H), 2.65-2.66 (m, 2H), 2.55-2.47 (m, 1H), 2.18 (d, J=10.1 Hz, 1H), 1.30-1.25 (m, 1H), 1.15 (s, 2H), 1.07-0.98 (m, 2H), 0.50-0.60 (m, 2H), 0.45-0.47 (m, 2H). MS (ES) M+H expected 474.0. found 474.6

Compound 792

(R)-5-(4-cyanopyridin-2-ylamino)-6-cyclopropyl-2-(3-cyclopropyl-4-(3-methoxypropanoyl)piperazin-1-yl)nicotinonitrile $^1$H NMR (400 MHz, CHLOROFORM-d) δ: 8.31 (d, J=5.0 Hz, 1H), 7.80-7.69 (m, 1H), 6.94 (dd, J=1.3, 5.1 Hz, 1H), 6.59 (s, 1H), 6.51 (s, 1H), 4.34 (d, J=12.6 Hz, 2H), 4.14-3.65 (m, 4H), 3.39 (s, 3H), 2.61-3.23 (m, 5H), 2.15-2.05 (m, 1H), 1.20-1.11 (m, 2H), 1.04 (td, J=3.0, 7.8 Hz, 2H), 0.45 (d, J=5.3 Hz, 5H)

LC_MS (M+1)$^+$ 472.5

Compound 783

4-(5-cyano-2-cyclopropyl-6-((R)-3-cyclopropyl-4-(2-((R)-oxetan-2-yl)acetyl)piperazin-1-yl)pyridin-3-ylamino)picolinonitrile $^1$H NMR (400 MHz, CHLOROFORM-d) δ: 8.30 (d, J=5.9 Hz, 1H), 7.59 (s, 1H), 6.92 (d, J=2.3 Hz, 1H), 6.77-6.62 (m, 2H), 5.27 (t, J=6.7 Hz, 1H), 4.75-4.65 (m, 1H), 4.62-4.51 (m, 1H), 4.47 (d, J=12.6 Hz, 1H), 4.37 (d, J=12.6 Hz, 1H), 4.07 (d, J=7.9 Hz, 1H), 3.65-3.75 (m, 1H), 3.30-3.04 (m, 2H), 2.98 (s, 1H), 2.92-2.72 (m, 3H), 2.62-2.44 (m, 1H), 2.05-1.98 (m, 1H), 1.08-0.99 (m, 2H), 0.93-0.80 (m, 4H), 0.63 (br. s., 1H), 0.52 (br. s., 1H), 0.48-0.36 (m, 1H)

LC_MS (M+1)$^+$ 484.6

Compound 774

6-cyclopropyl-2-((R)-3-cyclopropyl-4-(2-((S)-oxetan-2-yl)acetyl)piperazin-1-yl)-5-((2-vinylpyridin-4-yl)amino)nicotinonitrile $^1$H NMR (CHLOROFORM-d) δ 8.23 (d, J=5.9 Hz, 1H), 7.62 (s, 1H), 6.72 (dd, J=17.4, 10.9 Hz, 1H), 6.63 (s, 1H), 6.55 (s, 1H), 6.26 (d, J=17.6 Hz, 1H), 5.54 (d, J=10.7 Hz, 1H), 5.34-5.22 (m, 1H), 4.73 (dd, J=14.6, 8.2 Hz, 1H), 4.56 (dt, J=9.1, 5.8 Hz, 1H), 4.47 (d, J=12.9 Hz, 1H), 4.34 (d, J=13.2 Hz, 1H), 4.09 (d, J=10.0 Hz, 0.5H), 3.89 (d, J=13.3 Hz, 0.5H), 3.80-3.64 (m, 1H), 3.42-3.15 (m, 2H), 3.15-2.78 (m, 3H), 2.75-2.34 (m, 2H), 2.10 (ddd, J=12.7, 8.1, 4.7 Hz, 1H), 1.29 (dd, J=6.7, 4.8 Hz, 1H), 1.18-1.10 (m, 2H), 1.03 (dd, J=7.7, 3.2 Hz, 2H), 0.81-0.53 (m, 2H), 0.52-0.38 (m, 2H).

LC-MS: m/z NB295-063-01 485.1 (M+H)$^+$

Compound 791

(R,E)-6-cyclopropyl-2-(4-(5-hydroxypent-2-enoyl)-3-isopropylpiperazin-1-yl)-5-((4-vinylpyridin-2-yl)amino)nicotinonitrile $^1$H NMR (CHLOROFORM-d) δ 8.10 (d, J=5.3 Hz, 1H), 7.81 (s, 1H), 6.90 (tt, J=14.6, 7.3 Hz, 1H), 6.82 (d, J=5.3 Hz, 1H), 6.79-6.63 (m, 1H), 6.58 (dd, J=17.6, 10.8 Hz, 1H), 6.41 (d, J=14.1 Hz, 2H), 5.89 (d, J=17.5 Hz, 1H), 5.46 (d, J=10.8 Hz, 1H), 4.76-4.64 (m, 0.5H), 4.55-4.37 (m, 1.5H), 4.26 (t, J=11.6 Hz, 1H), 4.18 (d, J=5.2 Hz, 0.5H), 3.95 (d, J=13.7 Hz, 0.5H), 3.81 (t, J=6.0 Hz, 2H), 3.67 (d, J=9.3 Hz, 0.5H), 3.54-3.42 (m, 0.5H), 3.29-3.16 (m, 0.5H), 3.16-2.96 (m, 2.5H), 2.52 (dd, J=13.0, 6.4 Hz, 2H), 2.36-2.24 (m, 0.5H), 2.24-2.11 (m, 1.5H), 1.18-1.08 (m, 2H), 1.07 (d, J=6.5 Hz, 3H), 1.04-0.98 (m, 2H), 0.93-0.84 (m, 3H).
LC-MS: m/z NB295-055-02 487.7 (M+H)$^+$

Compound 790

(R)-6-cyclopropyl-2-(4-(5-hydroxypent-2-enoyl)-3-isopropylpiperazin-1-yl)-5-(2-vinylquinoxalin-5-yl)nicotinonitrile $^1$H NMR (400 MHz, CHLOROFORM-d) δ: 9.02 (s, 1H), 8.19-8.09 (m, 1H), 7.91-7.80 (m, 1H), 7.76-7.67 (m, 2H), 7.08 (dd, J=11.2, 17.6 Hz, 1H), 6.98-6.82 (m, 0.5H), 6.57-6.37 (m, 1.5H), 5.97-5.73 (m, 2H), 4.70-4.35 (m, 3.5H), 4.23-4.16 (m, 1H), 3.86-3.75 (m, 1.5H), 3.60-3.42 (m, 1H), 3.32-3.05 (m, 4H), 2.58-2.48 (m, 1H), 2.37-2.18 (m, 1H), 1.32-1.23 (m, 2H), 1.16-1.05 (m, 3H), 0.98-0.72 (m, 6H)
LC_MS (M+1)$^+$ 523.7

Compound 794

2-cyclopropyl-6-((R)-3-cyclopropyl-4-(3-((R)-oxetan-2-yl)propanoyl)piperazin-1-yl)-2'-vinyl-[3,4'-bipyridine]-5-carbonitrile $^1$H NMR (CHLOROFORM-d) δ 8.63 (d, J=5.3 Hz, 1H), 7.63 (s, 1H), 7.38 (s, 1H), 7.22 (d, J=5.0, 1.5 Hz, 1H), 6.86 (dd, J=17.3, 10.9 Hz, 1H), 6.26 (d, J=17.3 Hz, 1H), 5.55 (d, J=10.9 Hz, 1H), 4.86 (s, 1H), 4.60-4.74 (m, 1H), 4.46-4.60 (m, 2H), 4.40 (d, J=12.9 Hz, 1H), 4.07 (s, 1H), 3.82 (s, 1H), 3.69 (s, 1H), 3.12-3.42 (m, 2H), 2.99-3.10 (m, 1H), 2.48-2.63 (m, 3H), 1.96-2.24 (m, 3H), 1.19 (m, 2H), 0.93-1.02 (m, 2H), 0.33-0.54 (m, 4H)
LC-MS: m/z 484.3 (M+H)$^+$

Compound 785

6-cyclopropyl-2-((R)-3-cyclopropyl-4-(2-((R)-oxetan-2-yl)acetyl)piperazin-1-yl)-4-methyl-5-(6-vinylpyridazin-4-yl)nicotinonitrile $^1$H NMR (CHLOROFORM-d) δ 9.01 (d, J=1.8 Hz, 1H), 7.50 (d, J=2.1 Hz, 1H), 7.13 (dd, J=17.8, 11.0 Hz, 1H), 6.36 (d, J=17.9 Hz, 1H), 5.79 (d, J=11.2 Hz, 1H), 5.27 (t, J=6.7 Hz, 1H), 4.66-4.79 (m, 1H), 4.51-4.63 (m, 1H), 4.41 (d, J=12.6 Hz, 1H), 4.09 (d, J=7.6 Hz, 1H), 3.95 (d, J=12.6 Hz, 1H), 3.79 (d, J=10.9 Hz, 1H), 2.92-3.32 (m, 4H), 2.84-2.92 (m, 1H), 2.46-2.61 (m, 1H), 2.24 (s, 3H), 2.04 (dd, J=15.1, 7.5 Hz, 1H), 1.43-1.50 (m, 1H), 1.09-1.19 (m, 2H), 0.83-0.91 (m, 2H), 0.35-0.62 (m, 4H)
LC-MS: m/z 485.3 (M+H)$^+$

Compound 786

6-cyclopropyl-2-((R)-3-cyclopropyl-4-(2-((R)-oxetan-2-yl)acetyl)piperazin-1-yl)-4-methyl-5-(6-vinylpyridazin-4-yl)nicotinonitrile $^1$H NMR (CHLOROFORM-d) δ 9.01 (s, 1H), 7.50 (s, 1H), 7.12 (dd, J=17.9, 11.2 Hz, 1H), 6.36 (d, J=17.9 Hz, 1H), 5.78 (d, J=11.2 Hz, 1H), 5.23-5.31 (m, 1H), 4.64-4.78 (m, 1H), 4.39-4.63 (m, 3H), 4.34 (d, J=12.6 Hz, 1H), 3.91 (d, J=13.5 Hz, 1H), 3.43-3.65 (m, 1H), 2.92-3.17 (m, 4H), 2.82-2.91 (m, 1H), 2.44-2.66 (m, 1H), 2.22 (s, 3H), 2.07-2.17 (m, 1H), 1.91-2.04 (m, 1H), 1.38-1.58 (m, 1H), 1.00-1.15 (m, 3H), 0.85-0.94 (m, 6H)
LC-MS: m/z 487.3 (M+H)$^+$

Compound 776

(R)-6-cyclopropyl-2-(3-cyclopropyl-4-(3-hydroxypropanoyl)piperazin-1-yl)-4-methyl-5-(6-vinylpyridazin-4-yl)nicotinonitrile $^1$H NMR (CHLOROFORM-d) δ 9.01 (d, J=1.8 Hz, 1H), 7.50 (d, J=1.8 Hz, 1H), 7.13 (dd, J=17.8, 11.0 Hz, 1H), 6.37 (d, J=17.6 Hz, 1H), 5.80 (d, J=11.2 Hz, 1H), 4.41 (d, J=13.2 Hz, 1H), 4.32 (d, J=12.9 Hz, 1H), 4.09 (d, J=7.0 Hz, 1H), 3.93 (s, 2H), 3.68-3.84 (m, 2H), 3.13-3.37 (m, 2H), 3.09 (d, J=8.5 Hz, 1H), 2.54-2.67 (m, 2H), 2.24 (s, 3H), 1.45-1.49 (m, 1H), 1.07-1.19 (m, 2H), 0.92 (dd, J=12.5, 6.3 Hz, 2H), 0.47-0.67 (m, 4H)
LC-MS: m/z 459.2 (M+H)$^+$

Compound 793

6-cyclopropyl-2-((R)-3-isopropyl-4-(2-((R)-oxetan-2-yl)acetyl)piperazin-1-yl)-4-methyl-5-(5-vinylpyridazin-3-yl)nicotinonitrile $^1$H NMR (CHLOROFORM-d) δ 9.27 (br. s., 1H), 7.43 (br. s., 1H), 6.73 (dd, J=17.6, 11.2 Hz, 1H), 6.20 (d, J=17.6 Hz, 1H), 5.77 (d, J=10.9 Hz, 1H), 5.28 (m, 1H), 4.63-4.78 (m, 1H), 4.30-4.60 (m, 3.5H), 3.87 (d, J=13.2 Hz, 0.5H), 3.41-3.61 (m, 1H), 2.88-3.18 (m, 4H), 2.72-2.88 (m, 2H), 2.41-2.65 (m, 1H), 2.22 (s, 3H), 2.01-2.16 (m, 1H), 1.38-1.51 (m, 1H), 1.12 (d, J=16.4 Hz, 2H), 0.98-1.05 (m, 3H), 0.75-0.98 (m, 6H)
LC-MS: m/z 487.1 (M+H)

Compound 784

(R)-6-cyclopropyl-2-(4-(3-hydroxypropanoyl)-3-isopropylpiperazin-1-yl)-4-methyl-5-(5-vinylpyridazin-3-yl)nicotinonitrile $^1$H NMR (CHLOROFORM-d) δ 9.28 (d, J=2.1 Hz, 1H), 7.44 (d, J=2.1 Hz, 1H), 6.75 (dd, J=17.6, 10.9 Hz, 1H), 6.21 (d, J=17.6 Hz, 1H), 5.79 (d, J=11.2 Hz, 1H), 4.40-4.55 (m, 1.5H), 4.35 (d, J=11.2 Hz, 1H), 3.94 (t, J=4.8 Hz, 2H), 3.67-3.81 (m, 0.5H), 3.41-3.57 (m, 1H), 3.01-3.21 (m, 3H), 2.57-2.66 (m, 2H), 2.28 (s, 3H), 1.63-1.67 (m, 1H), 1.12-1.16 (m, 2H), 1.01-1.09 (m, 3H), 0.79-0.98 (m, 6H)
LC-MS: m/z 461.1 (M+H)

Compound 780

6-cyclopropyl-2-((R)-3-cyclopropyl-4-(2-((S)-oxetan-2-yl)acetyl)piperazin-1-yl)-4-methyl-5-(5-vinylpyridazin-3-yl)nicotinonitrile $^1$H NMR (CHLOROFORM-d) δ 9.27 (d, J=2.1 Hz, 1H), 7.43 (d, J=2.3 Hz, 1H), 6.74 (dd, J=17.8, 11.0 Hz, 1H), 6.20 (d, J=17.6 Hz, 1H), 5.77 (d, J=10.9 Hz, 1H), 5.20-5.29 (m, 1H), 4.68-4.78 (m, 1H), 4.51-4.68 (m, 1H), 4.43 (d, J=12.9 Hz, 1H), 4.33 (d, J=12.0 Hz, 1H), 4.07 (d, J=9.1 Hz, 0.5H), 3.81-3.93 (m, 0.5H), 3.69-3.81 (m, 0.5H), 3.09-3.28 (m, 3.5H), 2.81-3.01 (m, 3H), 2.55 (m, 1H), 2.30 (s, 3H), 1.82 (br. s., 1H), 1.41-1.54 (m, 1H), 1.15 (br. s., 2H), 0.88 (m, 2H), 0.43-0.72 (m, 4H)
LC-MS: m/z 485.1 (M+H)

Compound 779

(R)-5-cyano-2-cyclopropyl-6-(4-(3-methoxypropanoyl)-3-methylpiperazin-1-yl)-[3,4'-bipyridin]-2'-yl trifluoromethanesulfonate $^1$H NMR (CHLOROFORM-d) δ 8.49 (d, J=5.0 Hz, 1H), 7.65 (s, 1H), 7.46 (dd, J=5.1, 1.3 Hz, 1H), 7.23-7.28 (m, 1H), 4.92 (br. s., 0.5H), 4.55 (d, J=10.3 Hz, 0.5H), 4.23-4.47 (m, 2.5H), 3.68-3.88 (m, 2.5H), 3.49-3.65 (m, 0.5H), 3.31-3.45 (m, 4H), 3.05-3.29 (m, 1.5H), 2.64-2.80 (m, 1H), 2.53-2.64 (m, 1H), 1.90-2.03 (m, 1H), 1.38 (d, J=6.2 Hz, 1.5H), 1.18-1.33 (m, 3.5H), 1.02-1.13 (m, 2H)

LC-MS: m/z 554.1 (M+H)

Compound 773

(R)-6-cyclopropyl-2-(4-(3-hydroxypropanoyl)-3-isopropylpiperazin-1-yl)-4-methyl-5-(6-vinylpyridazin-4-yl)nicotinonitrile $^1$H NMR (CHLOROFORM-d) δ 9.02 (s, 1H), 7.52 (s, 1H), 7.14 (dd, J=17.6, 11.2 Hz, 1H), 6.37 (d, J=17.9 Hz, 1H), 5.80 (d, J=11.2 Hz, 1H), 4.65-4.76 (m, 0.5H), 4.40-4.55 (m, 1.5H), 4.34 (t, J=10.4 Hz, 1H), 3.86-4.01 (m, 2H), 3.77 (d, J=13.5 Hz, 0.5H), 3.42-3.57 (m, 1H), 2.96-3.21 (m, 3H), 2.53-2.69 (m, 2H), 2.20 (s, 3H), 1.42-1.50 (m, 1H), 1.10-1.16 (m, 2H), 1.00-1.08 (m, 3H), 0.83-1.00 (m, 6H)

LC-MS: m/z 461.1 (M+H)

Compound 771

(R)-tert-butyl 4-(3-cyano-6-cyclopropyl-4-methyl-5-(5-vinylpyridazin-3-yl)pyridin-2-yl)-2-cyclopropylpiperazine-1-carboxylate $^1$H NMR (CHLOROFORM-d) δ 9.28 (d, J=2.1 Hz, 1H), 7.44 (d, J=2.1 Hz, 1H), 6.75 (dd, J=17.8, 11.0 Hz, 1H), 6.15-6.26 (m, 1H), 5.79 (d, J=10.9 Hz, 1H), 4.41 (d, J=12.9 Hz, 1H), 4.31 (d, J=12.6 Hz, 1H), 4.08 (d, J=14.4 Hz, 1H), 3.36-3.55 (m, 2H), 3.24 (dd, J=12.9, 3.5 Hz, 1H), 3.07 (td, J=12.5, 3.5 Hz, 1H), 2.24 (s, 3H), 1.54 (s, 9H), 1.41-1.47 (m, 1H), 1.31-1.39 (m, 1H), 1.16 (br. s., 2H), 0.79-0.96 (m, 2H), 0.42-0.66 (m, 3H), 0.28-0.42 (m, 1H)

LC-MS: m/z 487.1 (M+H)

Compound 772

(R)-tert-butyl 4-(3-cyano-6-cyclopropyl-4-methyl-5-(6-vinylpyridazin-4-yl)pyridin-2-yl)-2-cyclopropylpiperazine-1-carboxylate $^1$H NMR (CHLOROFORM-d) δ $^1$H NMR (CHLOROFORM-d) □: 9.27 (d, J=2.1 Hz, 1H), 7.44 (d, J=2.1 Hz, 1H), 6.74 (dd, J=17.8, 11.0 Hz, 1H), 6.21 (d, J=17.6 Hz, 1H), 5.77 (d, J=10.9 Hz, 1H), 4.41 (d, J=12.9 Hz, 1H), 4.30 (d, J=12.6 Hz, 1H), 4.02-4.22 (m, 1H), 3.36-3.53 (m, 2H), 3.18-3.30 (m, 1H), 3.07 (td, J=12.4, 3.4 Hz, 1H), 2.23 (s, 3H), 1.49 (s, 9H), 1.42-1.48 (m, 1H), 1.31-1.38 (m, 1H), 1.09-1.21 (m, 2H), 0.87 (dd, J=7.8, 3.1 Hz, 2H), 0.42-0.65 (m, 3H), 0.30-0.42 (m, 1H)

LC-MS: m/z 487.1 (M+H)

Compound 769

(R,E)-6-cyclopropyl-2-(3-cyclopropyl-4-(5-hydroxypent-2-enoyl)piperazin-1-yl)-4-methyl-5-(5-vinylpyridazin-3-yl)nicotinonitrile $^1$H NMR (CHLOROFORM-d) δ 9.27 (d, J=2.1 Hz, 1H), 7.43 (d, J=2.1 Hz, 1H), 6.87 (dt, J=14.8, 7.3 Hz, 1H), 6.73 (dd, J=17.8, 11.0 Hz, 1H), 6.26-6.49 (m, 1H), 6.21 (d, J=17.6 Hz, 1H), 5.77 (d, J=10.9 Hz, 1H), 4.42 (d, J=12.9 Hz, 1H), 4.33 (d, J=12.6 Hz, 1H), 4.04-4.21 (m, 1H), 3.79 (t, J=6.0 Hz, 3H), 3.38 (br. s., 1H), 3.23 (d, J=10.0 Hz, 1H), 3.08 (td, J=12.5, 2.9 Hz, 1H), 2.50 (q, J=6.2 Hz, 2H), 2.27 (s, 3H), 1.35-1.52 (m, 2H), 1.15 (br. s., 2H), 0.88 (dd, J=7.6, 3.2 Hz, 2H), 0.65 (br. s., 1H), 0.51 (br. s., 1H), 0.44 (br. s., 2H)

LC-MS: m/z 485.1 (M+H)

Compound 770

(R)-2-cyclopropyl-6-(3-cyclopropyl-4-(4-hydroxybutanoyl)piperazin-1-yl)-4-methyl-2'-vinyl-3,4'-bipyridine-5-carbonitrile 1H NMR (CHLOROFORM-d) 8.69 (d, J=5.0 Hz, 1H), 7.23 (s, 1H), 7.07 (d, J=5.0 Hz, 1H), 6.87 (dd, J=17.5, 10.7 Hz, 1H), 6.29 (d, J=17.3 Hz, 1H), 5.57 (dd, J=10.7, 1.0 Hz, 1H), 4.33 (d, J=12.9 Hz, 1H), 4.25 (d, J=12.6 Hz, 1H), 4.09 (d, J=7.6 Hz, 0.5H), 3.79-3.92 (m, 1H), 3.65-3.79 (m, 2.5H), 3.31 (br. s., 0.5H), 3.14 (d, J=12.0 Hz, 1H), 2.99-3.11 (m, 1.5H), 2.58 (br. s., 2H), 2.17-2.26 (m, 3H), 1.90-2.00 (m, 2H), 1.51-1.62 (m, 1H), 1.43 (d, J=10.3 Hz, 1H), 1.02-1.16 (m, 2H), 0.87 (dd, J=7.9, 2.9 Hz, 2H), 0.62 (br. s., 1H), 0.54 (br. s., 1H), 0.31-0.50 (m, 2H)

LC-MS: m/z 472.5 (M+H)$^+$

Compound 781

2-cyclopropyl-6-((R)-3-isopropyl-4-(2-((R)-oxetan-2-yl)acetyl)piperazin-1-yl)-4-methyl-2'-vinyl-3,4'-bipyridine-5-carbonitrile 1H NMR (CHLOROFORM-d) 8.70 (d, J=5.0 Hz, 1H), 7.21-7.28 (m, 1H), 7.09 (br. s., 1H), 6.89 (dd, J=17.3, 10.9 Hz, 1H), 6.30 (d, J=17.3 Hz, 1H), 5.59 (d, J=10.9 Hz, 1H), 5.26-5.33 (m, 1H), 4.67-4.78 (m, 1.5H), 4.56 (dt, J=9.1, 5.9 Hz, 1H), 4.38-4.48 (m, 1.5H), 4.29 (d, J=12.3 Hz, 1H), 3.89 (d, J=13.5 Hz, 0.5H), 3.45-3.61 (m, 1H), 2.92-3.15 (m, 3.5H), 2.78-2.91 (m, 2H), 2.44-2.65 (m, 1H), 2.26 (br. s., 0.5H), 2.19-2.23 (m, 3H), 2.11-2.18 (m, 0.5H), 1.56 (td, J=8.0, 4.5 Hz, 1H), 1.12 (br. s., 1H), 1.04 (d, J=6.5 Hz, 4H), 0.93 (d, J=6.7 Hz, 1H), 0.83-0.90 (m, 4H)

LC-MS: m/z 486.6 (M+H)$^+$

Compound 795

(R,E)-2-cyclopropyl-6-(4-(5-hydroxypent-2-enoyl)-3-isopropylpiperazin-1-yl)-4-methyl-2'-vinyl-3,4'-bipyridine-5-carbonitrile 1H NMR (CHLOROFORM-d) 8.68 (d, J=5.0 Hz, 1H), 7.23 (d, J=9.7 Hz, 1H), 7.07 (br. s., 1H), 6.81-6.94 (m, 2H), 6.40 (d, J=15.3 Hz, 1H), 6.28 (d, J=17.6 Hz, 1H), 5.57 (d, J=10.9 Hz, 1H), 4.35-4.52 (m, 1.5H), 4.28 (d, J=9.4 Hz, 1H), 3.94 (d, J=12.9 Hz, 0.5H), 3.80 (t, J=5.9 Hz, 2H), 3.68 (d, J=9.7 Hz, 0.5H), 3.52 (t, J=11.9 Hz, 0.5H), 3.05-3.18 (m, 2H), 2.51 (q, J=6.4 Hz, 2H), 2.25-2.32 (m, 1H), 2.20 (s, 3H), 2.05 (d, J=7.3 Hz, 1H), 1.51-1.61 (m, 1H), 1.10 (br. s., 1H), 1.04 (d, J=6.5 Hz, 4H), 0.93 (d, J=6.7 Hz, 1H), 0.76-0.95 (m, 4H)

LC-MS: m/z 486.6 (M+H)+

Compound 782

(R)-6-(4-(2-cyclopentylacetyl)-3-cyclopropylpiperazin-1-yl)-2-cyclopropyl-4-methyl-2'-vinyl-3,4'-bipyridine-5-carbonitrile 1H NMR (CHLOROFORM-d) 8.69 (d, J=5.0 Hz, 1H), 7.24 (s, 1H), 7.08 (d, J=4.4 Hz, 1H), 6.88 (dd, J=17.3, 10.9 Hz, 1H), 6.29 (d, J=17.6 Hz, 1H), 5.57 (d, J=10.9 Hz, 1H), 4.34 (d, J=12.9 Hz, 1H), 4.26 (d, J=12.0 Hz, 1H), 4.13 (q, J=7.2 Hz, 1H), 3.70-3.91 (br. s., 1.5H), 3.23-3.39 (m, 0.5H), 3.09-3.21 (m, 1H), 3.03 (t, J=10.7 Hz, 1H), 2.33-2.51 (m, 2H), 2.24-2.32 (m, 1H), 2.17-2.24 (m, 3H), 1.80-1.95 (m, 2H), 1.61-1.72 (m, 2H), 1.50-1.61 (m, 3H), 1.43 (d, J=12.6 Hz, 1H), 1.14-1.24 (m, 2H), 1.11 (br. s., 2H), 0.82-0.91 (m, 2H), 0.51-0.75 (m, 2H), 0.44 (d, J=5.0 Hz, 2H)

LC-MS: m/z 496.7 (M+H)+

Compound 788

(R)-2-cyclopropyl-6-(3-isopropyl-4-(4-methoxybutanoyl)piperazin-1-yl)-4-methyl-2'-vinyl-3,4'-bipyridine-5-carbonitrile 1H NMR (CHLOROFORM-d) 8.68 (d, J=5.0 Hz, 1H), 7.23 (d, J=8.8 Hz, 1H), 7.07 (br. s., 1H), 6.87 (dd, J=17.3, 10.9 Hz, 1H), 6.23-6.33 (m, 1H), 5.48-5.66 (m, 1H), 4.69 (d, J=10.9 Hz, 0.5H), 4.37-4.48 (m, 1.5H), 4.23-4.31 (m, 1H), 3.82 (d, J=13.8 Hz, 0.5H), 3.41-3.53 (m, 3H), 3.22-3.38 (m, 3H), 2.92-3.15 (m, 3H), 2.39-2.56 (m, 2H), 2.25-2.33 (m, 0.5H), 2.17-2.24 (m, 3H), 2.09-2.17 (m, 0.5H), 1.90-2.00 (m, 2H), 1.52-1.60 (m, 1H), 1.09-1.15 (m, 1H), 1.03 (dd, J=6.5, 2.6 Hz, 4H), 0.91 (d, J=6.7 Hz, 1H), 0.80-0.89 (m, 4H)

LC-MS: m/z 488.7 (M+H)+

Compound 787

(R)-2-cyclopropyl-6-(3-cyclopropyl-4-(2-cyclopropylacetyl)piperazin-1-yl)-4-methyl-2'-vinyl-3,4'-bipyridine-5-carbonitrile 1H NMR (CHLOROFORM-d) 8.71 (d, J=5.0 Hz, 1H), 7.26 (br. s., 1H), 7.09 (d, J=4.7 Hz, 1H), 6.88 (dd, J=17.6, 10.9 Hz, 1H), 6.25 (d, J=17.6 Hz, 1H), 5.57 (d, J=11.2 Hz, 1H), 4.34 (d, J=12.9 Hz, 1H), 4.25 (d, J=12.6 Hz, 1H), 4.04-4.16 (m, 0.5H), 3.68-3.86 (m, 1.5H), 3.16 (br. s., 1.5H), 3.03 (br. s., 1H), 2.36 (br. s., 1.5H), 2.26 (d, J=7.3 Hz, 2H), 2.20 (s, 3H), 1.50-1.59 (m, 1H), 1.05-1.11 (m, 3H), 0.86 (dd, J=7.9, 3.2 Hz, 2H), 0.55-0.61 (m, 4H), 0.44 (br. s., 1H), 0.16-0.23 (m, 3H)

LC-MS: m/z 468.6 (M+H)+

Compound 408

6-cyclopropyl-5-(isoquinolin-4-yl)-2-((R)-4-(3-methoxypropanoyl)-3-methylpiperazin-1-yl)-4-methylnicotinonitrile $^1$H NMR (CHLOROFORM-d) δ 9.36 (s, 1H), 8.41 (br. s., 1H), 8.07-8.19 (m, 1H), 7.65-7.76 (m, 2H), 7.46 (t, J=9.0 Hz, 1H), 4.96 (br. s., 0.5H), 4.58 (br. s., 0.5H), 4.11-4.38 (m, 2.5H), 3.73-3.89 (m, 2.5H), 3.58-3.64 (m, 0.5H), 3.41 (s, 3H), 3.04-3.32 (m, 2.5H), 2.56-2.84 (m, 2H), 2.10 (s, 3H), 1.42-1.51 (m, 1H), 1.31-1.41 (m, 3H), 1.03-1.14 (m, 2H), 0.63-0.83 (m, 2H)

LC-MS: m/z 470.4 (M+H)+

Compound 410

6-cyclopropyl-5-(isoquinolin-5-yl)-2-((R)-4-(3-methoxypropanoyl)-3-methylpiperazin-1-yl)-4-methylnicotinonitrile $^1$H NMR (CHLOROFORM-d) δ 9.48 (br. s., 1H), 8.58 (br. s., 1H), 8.13 (d, J=8.3 Hz, 1H), 7.78 (t, J=7.7 Hz, 1H), 7.64 (d, J=7.0 Hz, 1H), 7.32 (d, J=10.3 Hz, 1H), 4.96 (br. s., 0.5H), 4.58 (d, J=12.3 Hz, 0.5H), 4.08-4.36 (m, 2.5H), 3.71-3.93 (m, 2.5H), 3.56-3.70 (m, 0.5H), 3.41 (s, 3H), 3.19-3.36 (m, 1.5H), 3.01-3.14 (m, 1H), 2.56-2.78 (m, 2H), 2.02-2.10 (m, 3H), 1.81 (br. s., 1H), 1.42-1.50 (m, 3H), 1.05-1.15 (m, 2H), 0.61-0.81 (m, 2H)

LC-MS: m/z 470.6 (M+H)+

Compound 470

(R)—N-(3-(5-cyano-6-(4-(cyclopropanecarbonyl)-3-cyclopropylpiperazin-1-yl)-2-cyclopropyl-4-methylpyridin-3-yl)phenyl)ethenesulfonamide 1H NMR (CHLOROFORM-d) δ 7.44 (t, J=7.8 Hz, 1H), 7.13-7.23 (m, 1H), 6.96-7.12 (m, 2H), 6.48-6.67 (m, 2H), 6.32 (d, J=16.3 Hz, 1H), 6.02 (d, J=10.0 Hz, 1H), 4.58 (br. s., H), 4.34 (d, J=12.5 Hz, 1H), 4.26 (d, J=12.3 Hz, 1H), 3.76 (br. s., 2H), 3.23 (br. s., 1H), 3.07 (br. s., 1H), 2.19 (s, 3H), 1.73 (br. s., 1H), 1.32 (d, J=11.5 Hz, 2H), 0.96-1.15 (m, 4H), 0.74-0.88 (m, 4H), 0.67 (br. s., 1H), 0.37-0.60 (m, 3H)

LC-MS: m/z 532.7 (M+H)+

Compound 271

(R)-5-(3-chloro-4-fluorophenyl)-6-cyclopropyl-2-(4-(3-methoxypropanoyl)-3-methylpiperazin-1-yl)-4-methylnicotinonitrile $^1$H NMR (CHLOROFORM-d) δ 7.22-7.30 (m, 2H), 7.08 (ddd, J=8.2, 4.6, 2.0 Hz, 1H), 4.90 (br. s., 0.5H), 4.53 (d, J=13.6 Hz, 0.5H), 4.00-4.29 (m, 2.5H), 3.66-3.85 (m, 2.5H), 3.49-3.65 (m, 0.5H), 3.38 (s, 3H), 3.01-3.25 (m, 2.5H), 2.63-2.84 (m, 1H), 2.48-2.63 (m, 1H), 2.18 (s, 3H), 1.51-1.61 (m, 1H), 1.31-1.40 (m, 2H), 1.01-1.14 (m, 2H), 0.80-0.90 (m, 2H)

LC-MS: m/z 471.2 (M+H)+

Compound 568

2-cyclopropyl-6-((3R)-3-cyclopropyl-4-(3-hydroxybutanoyl)piperazin-1-yl)-2'-vinyl-3,4'-bipyridine-5-carbonitrile 1H NMR (CHLOROFORM-d) δ 8.65 (d, J=4.8 Hz, 1H), 7.65 (s, 1H), 7.39 (s, 1H), 7.24 (d, J=4.3 Hz, 1H), 6.88 (dd, J=17.4, 10.9 Hz, 1H), 6.28 (d, J=17.3 Hz, 1H), 5.57 (d, J=10.8 Hz, 1H), 4.49-4.79 (m, 2H), 4.43 (d, J=12.5 Hz, 1H), 4.17-4.33 (m, 2H), 3.96-4.17 (m, 1H), 3.79 (br. s., 1H), 3.71 (d, J=11.8 Hz, 1H), 3.02-3.31 (m, 2H), 2.53 (d, J=9.8 Hz, 1H), 2.48 (m, 1H), 2.04 (m, 1H), 1.32 (br. s., 3H), 0.82-1.12 (m, 3H), 0.72 (br. s., 1H), 0.63 (br. s., 1H), 0.55 (br. s., 1H), 0.22-0.51 (m, 2H)

LC-MS: m/z 458.2 (M+H)$^+$

Compound 558

(R)-2-cyclopropyl-6-(3-cyclopropyl-4-(3-methoxypropanoyl)piperazin-1-yl)-4-methyl-2'-vinyl-3,4'-bipyridine-5-carbonitrile 1H NMR (CHLOROFORM-d) δ 8.59 (d, J=4.8 Hz, 1H), 7.16 (s, 1H), 7.00 (d, J=4.8 Hz, 1H), 6.78 (dd, J=17.3, 10.8 Hz, 1H), 6.19 (d, J=17.6 Hz, 1H), 5.46 (dd, J=10.8, 1.0 Hz, 1H), 4.60 (d, J=10.5 Hz, 0.5H), 4.26 (d, J=12.8 Hz, 1H), 4.17 (d, J=12.5 Hz, 1H), 3.96-4.06 (m, 0.5H), 3.80 (d, J=12.3 Hz, 1H), 3.59-3.74 (m, 3H), 3.18-3.37 (m, 4H), 3.04-3.14 (m, 1H), 2.90-3.01 (m, 1H), 2.37-2.67 (m, 2H), 2.08-2.18 (m, 3H), 1.39-1.56 (m, 1H), 0.98-1.10 (m, 2H), 0.78 (dd, J=7.9, 3.1 Hz, 2H), 0.51 (br. s., 1H), 0.44 (br. s., 1H), 0.29-0.40 (m, 2H)

LC-MS: m/z 472.4 (M+H)$^+$

Compound 598

(R)-6-cyclopropyl-2-(4-(3-methoxypropanoyl)-3-methylpiperazin-1-yl)-5-(6-(prop-1-en-2-yl)pyrimidin-4-yl)nicotinonitrile 1H NMR (CHLOROFORM-d) δ 9.22 (s, 1H), 7.98 (s, 1H), 7.61-7.76 (m, 1H), 6.18 (s, 1H), 5.54 (s, 1H), 4.88 (br. s., 1H), 4.51 (d, J=9.8 Hz, 1H), 4.18-4.47 (m, 3H), 3.63-3.93 (m, 3H), 3.41-3.63 (m, 1H), 3.36 (s, 4H), 2.97-3.24 (m, 2H), 2.49-2.79 (m, 2H), 2.28-2.47 (m, 1H), 2.22 (s, 3H), 1.34 (d, J=6.3 Hz, 2H), 1.14-1.30 (m, 4H), 1.04 (dd, J=7.9, 2.9 Hz, 2H)

LC-MS: m/z 447.2 (M+H)$^+$

Compound 478

(R)-2-(4-(cyclopropanecarbonyl)-3-cyclopropylpiperazin-1-yl)-6-cyclopropyl-4-methyl-5-(1H-pyrazol-4-yl)nicotinonitrile $^1$H NMR (CHLOROFORM-d) δ 7.61 (s, 2H), 4.59 (s, 1H), 4.33 (d, J=12.5 Hz, 1H), 4.24 (d, J=12.5 Hz, 1H), 3.98-4.15 (m, 1H), 3.84 (s, 1H), 3.22 (d, J=15.1 Hz, 1H), 3.05 (s, 1H), 2.31 (s, 3H), 1.83-1.98 (m, 1H), 1.73 (s, 1H), 1.37-1.60 (m, 1H), 0.98-1.15 (m, 4H), 0.74-0.92 (m, 4H), 0.34-0.65 (m, 4H).

LC-MS: m/z 416.2 (M+H)$^+$

Compound 463

(R)—N-(3-(5-cyano-6-(4-(cyclopropanecarbonyl)-3-cyclopropylpiperazin-1-yl)-2-cyclopropyl-4-methylpyridin-3-yl)phenyl)-N-(vinylsulfonyl)ethenesulfonamide $^1$H NMR (CHLOROFORM-d) δ 7.47-7.60 (m, 1H), 7.31-7.40 (m, 2H), 7.00-7.14 (m, 2H), 6.28 (s, 1H), 6.32 (s, 1H), 6.17 (d, J=9.8 Hz, 2H), 4.34 (d, J=12.8 Hz, 1H), 4.26 (d, J=12.5 Hz, 2H), 3.85 (s, 1H), 3.06 (br. s., 2H), 1.85 (br. s., 1H), 1.72 (br. s., 1H), 1.58 (td, J=8.2, 4.1 Hz, 2H), 0.95-1.18 (m, 4H), 0.72-0.95 (m, 5H), 0.65 (br. s., 1H), 0.32-0.59 (m, 3H)

LC-MS: m/z 622.2 (M+H)$^+$

Compound 535

(R)-5-(5-cyano-2-cyclopropyl-6-(3-cyclopropyl-4-(3,3,3-trifluoropropanoyl)piperazin-1-yl)pyridin-3-yl)quinoline-2-carbonitrile $^1$H NMR (CHLOROFORM-d) δ 8.27 (d, J=8.5 Hz, 1H), 8.11 (dd, J=11.5, 8.8 Hz, 1H), 7.94 (t, J=7.8 Hz, 1H), 7.53-7.78 (m, 3H), 4.59 (dt, J=13.1, 2.3 Hz, 1H), 4.48 (d, J=11.8 Hz, 1H), 4.04-4.34 (m, 1H), 3.81 (br. s., 1H), 3.21-3.51 (m, 3H), 3.15 (d, J=11.5 Hz, 2H), 1.68 (br. s., 2H), 1.37-1.48 (m, 3H), 1.14-1.36 (m, 13H), 0.77-1.04 (m, 4H), 0.71 (br. s., 1H), 0.60 (br. s., 1H), 0.31-0.57 (m, 2H)

LC-MS: m/z 513.2 (M+H)$^+$

Compound 563

(R)-5-(5-cyano-6-(4-(cyclopropanecarbonyl)-3-cyclopropylpiperazin-1-yl)-2-cyclopropylpyridin-3-yl)quinoline-2-carbonitrile $^1$H NMR (CHLOROFORM-d) δ 8.25 (d, J=8.8 Hz, 1H), 8.13 (dd, J=10.3, 9.0 Hz, 1H), 7.85-8.04 (m, 1H), 7.56-7.76 (m, 3H), 4.59 (d, J=12.0 Hz, 1H), 4.47 (d, J=12.5 Hz, 2H), 4.13 (q, J=7.0 Hz, 1H), 3.72 (br. s., 1H), 3.42 (d, J=10.0 Hz, 1H), 3.09-3.36 (m, 2H), 1.66-1.86 (m, 1H), 1.52-1.66 (m, 1H), 1.36-1.52 (m, 2H), 1.00-1.30 (m, 8H), 0.75-1.00 (m, 6H), 0.71 (d, J=7.8 Hz, 1H), 0.34-0.63 (m, 4H)

LC-MS: m/z 489.2 (M+H)$^+$

Compound 610

(R)-2-(4-(cyclopropanecarbonyl)-3-methylpiperazin-1-yl)-6-cyclopropyl-5-(1-propioloyl-2,5-dihydro-1H-pyrrol-3-yl)nicotinonitrile $^1$H NMR (CHLOROFORM-d) δ: 7.53 (d, J=1.0 Hz, 1H), 6.00 (dt, J=19.1, 2.0 Hz, 1H), 4.61-4.91 (m, 2H), 4.52-4.61 (m, 1H), 4.40-4.52 (m, 2H), 4.19-4.40 (m, 2H), 3.50 (s, 1H), 3.43 (d, J=6.0 Hz, 1H), 3.02-3.32 (m, 3H), 2.09-2.31 (m, 2H), 1.75 (br. s., 2H), 1.37-1.48 (m, 1H), 1.11-1.37 (m, 7H), 0.95-1.11 (m, 2H), 0.66-0.95 (m, 2H).

LC-MS: m/z 430.2 (M+H)$^+$

Compound 450

(R)—N-(3-(5-cyano-6-(4-(cyclopropanecarbonyl)-3-cyclopropylpiperazin-1-yl)-2-cyclopropylpyridin-3-yl)phenyl)propionamide $^1$H NMR (CHLOROFORM-d) δ: 7.70 (d, J=6.0 Hz, 2H), 7.61 (s, 1H), 7.48 (d, J=8.0 Hz, 1H), 7.38 (t, J=7.8 Hz, 1H), 7.13 (d, J=7.5 Hz, 1H), 4.50 (d, J=11.8 Hz, 1H), 4.38 (d, J=12.3 Hz, 1H), 3.73 (d, J=7.0 Hz, 1H), 3.25 (br. s., 1H), 3.07 (br. s., 1H), 2.38-2.51 (m, 2H), 1.98-2.22 (m, 1H), 1.73 (br. s., 1H), 1.21-1.45 (m, 6H), 1.16 (dt, J=7.8, 3.6 Hz, 3H), 0.87-1.11 (m, 5H), 0.76-0.86 (m, 2H), 0.65 (br. s., 1H), 0.29-0.59 (m, 3H).

LC-MS: m/z 484.3 (M+H)$^+$

Compound 834 (General Procedure 2, Step M)

6-cyclopropyl-2-((R)-3-cyclopropyl-4-((1S,2S)-2-ethoxycyclopropanecarbonyl)piperazin-1-yl)-5-(isoquinolin-5-yl)nicotinonitrile

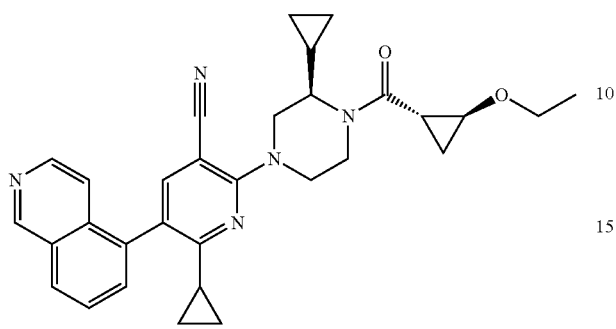

$^1$H NMR (DEUTERIUM OXIDE) □ 9.35 (s, 1H), 8.54 (dd, J=5.9, 1.9 Hz, 1H), 8.07 (d, J=8.0 Hz, 1H), 7.69-7.75 (m, 1H), 7.64-7.68 (m, 2H), 7.44 (dd, J=12.5, 6.0 Hz, 1H), 4.46-4.59 (m, 2.5H), 4.08-4.18 (m, 1H), 3.86 (br. s., 0.5H), 3.53-3.74 (m, 3H), 3.21-3.32 (m, 2H), 1.87-2.06 (m, 2H), 1.49-1.58 (m, 1H), 1.33 (d, J=5.8 Hz, 1H), 1.14-1.28 (m, 7H), 0.81-0.90 (m, 2H), 0.65 (br. s., 1H), 0.36-0.59 (m, 3H).
LC-MS: m/z 508.2 (M+H)$^+$

Compound 730

(R)-6-cyclopropyl-2-(3-cyclopropyl-4-(3-hydroxypropanoyl)piperazin-1-yl)-5-(methyl(2-vinylpyridin-4-yl)amino)nicotinonitrile $^1$H NMR (CHLOROFORM-d) δ 8.25 (d, J=5.9 Hz, 1H), 7.58 (s, 1H), 6.71 (dd, J=17.4, 10.7 Hz, 1H), 6.46 (s, 1H), 6.33 (s, 1H), 6.20 (d, J=17.3 Hz, 1H), 5.45 (d, J=11.2 Hz, 1H), 4.69 (d, J=13.4 Hz, 0.4H), 4.49 (d, J=13.0 Hz, 1H), 4.37 (d, J=12.7 Hz, 1H), 4.10 (d, J=8.6 Hz, 0.6H), 3.92 (s, 2H), 3.86-3.65 (m, 1.5H), 3.42 (s, 1H), 3.31 (s, 3H), 3.22 (m, 1.5H), 3.15-3.00 (m, 1H), 2.69-2.45 (m, 2H), 1.88 (ddd, J=12.7, 8.1, 4.7 Hz, 1H), 1.40-1.31 (m, 1H), 1.12 (s, 2H), 0.99 (s, 2H), 0.81-0.34 (m, 4H).
LC-MS: m/z 473.4 (M+H)$^+$

Compound 835

(R)-4-cyclopropyl-2-(3-cyclopropyl-4-(4-methoxybutanoyl)piperazin-1-yl)-5-(2-vinylpyridin-4-yl)benzonitrile

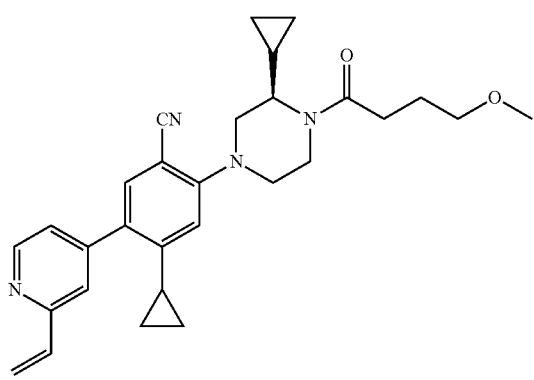

$^1$H NMR (CHLOROFORM-d) □ 8.64 (d, J=5.0 Hz, 1H), 7.46 (s, 1H), 7.34-7.42 (m, 1H), 7.21 (dd, J=5.0, 1.5 Hz, 1H), 6.87 (dd, J=17.6, 10.9 Hz, 1H), 6.54 (s, 1H), 6.21-6.33 (m, 1H), 5.55 (dd, J=10.9, 0.9 Hz, 1H), 4.63-4.77 (m, 0.3H), 4.01-4.18 (m, 0.7H), 3.80-3.94 (m, 1H), 3.41-3.82 (m, 4H), 3.35 (s, 3H), 3.18-3.35 (m, 1H), 2.97-3.05 (m, 1H), 2.79-2.93 (m, 1H), 2.46 (d, J=7.3 Hz, 2H), 1.81-1.99 (m, 4H), 0.94-1.07 (m, 2H), 0.72-0.83 (m, 2H), 0.36-0.56 (m, 4H).
LC-MS: m/z 471.2 (M+H)$^+$

Compound 775

(R)-6-cyclopropyl-2-(3-cyclopropyl-4-(3-methoxypropanoyl)piperazin-1-yl)-5-((5-vinylpyridazin-3-yl)amino)nicotinonitrile $^1$H NMR (400 MHz, CDCl3) δ 8.76 (s, 1H), 7.76 (s, 1H), 6.58 (dd, J=17.6, 11.0 Hz, 2H), 6.05 (d, J=17.6 Hz, 1H), 5.66 (d, J=11.0 Hz, 1H), 4.65-4.70 (m, 0.5H), 4.43-4.46 (m, 1H), 4.33 (d, J=12.4 Hz, 1H), 4.16-4.07 (m, 1H), 3.87-3.88 (m, 0.5H), 3.71-3.74 (m, 3H), 3.39 (s, 3H), 3.20 (s, 1H), 3.07-3.09 (m, 1H), 2.65-2.66 (m, 2H), 2.55-2.47 (m, 1H), 2.18 (d, J=10.1 Hz, 1H), 1.30-1.25 (m, 1H), 1.15 (s, 2H), 1.07-0.98 (m, 2H), 0.50-0.60 (m, 2H), 0.45-0.47 (m, 2H).
LC-MS: m/z 474.6 (M+H)$^+$

Compound 836

(R)-tert-butyl(5-(5-cyano-2-cyclopropyl-6-(3-cyclopropyl-4-(3-hydroxypropanoyl)piperazin-1-yl)pyridin-3-yl)pyridazin-3-yl)carbamate

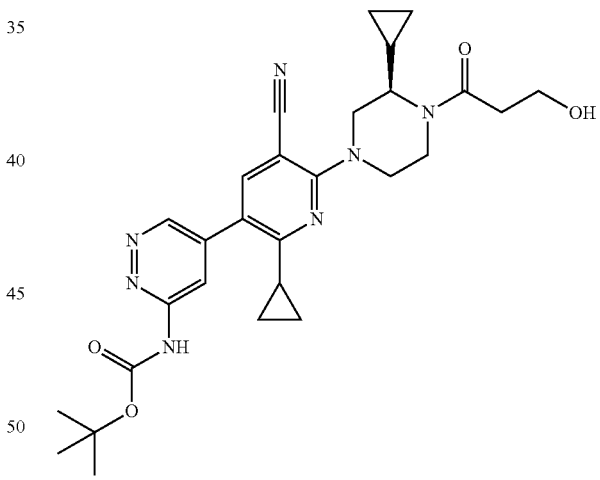

The mixture of (R)-6-cyclopropyl-2-(3-cyclopropyl-4-(3-hydroxypropanoyl)piperazin-1-yl)-5-(4,4,5,5-tetramethyl-1,3,2-dioxaborolan-2-yl)nicotinonitrile (268 mg, 0.627 mmol), tert-butyl (5-chloropyridazin-3-yl)carbamate (120 mg, 0.523 mmol), Pd(dppf)Cl$_2$ (20 mg, 0.026 mmol) and CsF (159 mg, 1.045 mmol) in dioxane/H$_2$O (8 mL/2 mL) was stirred at 100° C. for 16 hours. The mixture was diluted with EtOAc (50 mL) and filtered. The filtrated was partitioned between EtOAc (50 mL) and water (30 mL), the organic layer was washed with water (30 mL), brine and dried over Na$_2$SO$_4$ and concentrated to give the crude which was purified by prep-TLC to give 150 mg of the product.
1H NMR (CHLOROFORM-d) □: 8.97 (d, J=2.1 Hz, 1H), 8.33 (d, J=1.8 Hz, 1H), 8.24 (br. s., 1H), 7.70 (s, 1H), 4.62

(d, J=13.2 Hz, 1H), 4.49 (d, J=12.9 Hz, 1H), 4.08 (d, J=8.8 Hz, 1H), 3.92 (t, J=4.5 Hz, 2H), 3.63-3.85 (m, 1H), 3.02-3.23 (m, 1H), 2.41-2.67 (m, 2H), 1.91-2.06 (m, 1H), 1.48-1.63 (m, 9H), 1.15-1.25 (m, 3H), 1.02-1.13 (m, 2H), 0.46-0.72 (m, 4H)

LC-MS: m/z 534.3 (M+H)+

Compound 339 (General Procedure 9)

(R)-6-cyclopropyl-2-(4-(3-methoxypropanoyl)-3-methylpiperazin-1-yl)-5-(quinolin-3-ylamino)nicotinonitrile 1H NMR (MeOD): δ 8.797-8.790 (d, J=2.8 Hz, 1H), 8.059-8.037 (d, J=8.8 Hz, 1H), 7.985-7.962 (d, J=9.2 Hz, 1H), 7.926-7.920 (d, J=2.4 Hz, 1H), 7.861 (s, 1H), 7.795-7.710 (m, 2H), 4.797-4.783 (m, 0.5H), 4.451-4.416 (m, 1H), 4.227-4.112 (m, 2H), 3.972-3.932 (m, 0.5H), 3.694-3.613 (m, 2H), 3.608-3.577 (m, 0.5H), 3.334 (s, 3H), 3.284 (m, 0.5H), 3.211-3.137 (m, 1H), 3.045-3.007 (m, 0.5H), 2.852-2.704 (m, 1H), 2.700-2.578 (m, 1.5H), 2.240-2.177 (m, 1H), 1.401-1.384 (d, J=6.8 Hz, 1.5H), 1.284-1.267 (d, J=6.8 Hz, 1.5H), 1.188-1.170 (m, 2H), 0.992-0.965 (m, 2H);

LC-MS: m/z 471.5 (M+H)+

Compound 355 (General Procedure 9)

(R)-6-cyclopropyl-5-((4-fluorophenyl)amino)-2-(4-(3-methoxypropanoyl)-3-methylpiperazin-1-yl)nicotinonitrile 1H NMR (MeOD): δ 7.543 (s, 1H), 6.936-6.893 (t, J=8.6 Hz, 2H), 6.723-6.690 (q, J=4.4 Hz, 2H), 4.798-4.781 (m, 0.5H), 4.443-4.361 (m, 1H), 4.050-3.898 (m, 2.5H), 3.675-3.509 (m, 2.5H), 3.336 (s, 3H), 3.254-2.877 (m, 2.5H), 2.792-2.588 (m, 2H), 2.260-2.196 (m, 1H), 1.402-1.255 (m, 3H), 1.115-1.097 (m, 2H), 0.992-0.968 (m, 2H);

LC-MS: m/z 438.5 (M+H)+

Compound 356 (General Procedure 9)

(R)-6-cyclopropyl-2-(4-(3-methoxypropanoyl)-3-methylpiperazin-1-yl)-5-(quinolin-4-ylamino)nicotinonitrile 1H NMR (MeOD): δ 8.593-8.572 (d, J=8.4 Hz, 1H), 8.440-8.422 (d, J=7.2 Hz, 1H), 8.065-8.026 (m, 1H), 7.983-7.962 (d, J=8.4 Hz, 1H), 7.931 (s, 1H), 7.854-7.813 (m, 2H), 6.552-6.535 (d, J=6.8 Hz, 1H), 4.792-4.783 (m, 0.5H), 4.451-4.420 (m, 1H), 4.329-4.207 (m, 2H), 3.982-3.948 (m, 0.5H), 3.414-3.338 (m, 4H), 3.257-3.068 (m, 1.5H), 2.829-2.610 (m, 2H), 2.091-2.026 (m, 1H), 1.389-1.256 (m, 3H), 1.199-1.181 (m, 2H), 1.050-0.988 (m, 2H);

LC-MS: m/z 471.5 (M+H)+

Compound 368 (General Procedure 9)

(R)-5-(4-acetylpiperazin-1-yl)-6-cyclopropyl-2-(4-(3-methoxypropanoyl)-3-methylpiperazin-1-yl)nicotinonitrile 1H NMR (MeOD): δ 7.558 (s, 1H), 4.763-4.752 (m, 0.5H), 4.429-4.346 (m, 1H), 4.052-3.883 (m, 3H), 3.747-3.668 (m, 6H), 3.328 (s, 3H), 3.182-3.119 (m, 2H), 3.061-2.886 (m, 4.5H), 2.781-2.677 (m, 1H), 2.623-2.562 (m, 2H), 2.142 (s, 3H), 1.375-1.358 (m, 1.5H), 1.261-1.244 (m, 1.5H), 1.109-1.036 (m, 4H);

LC-MS: m/z 455.5 (M+H)+

Compound 375 (General Procedure 9)

(R)-6-cyclopropyl-2-(4-(3-methoxypropanoyl)-3-methylpiperazin-1-yl)-5-morpholinonicotinonitrile 1H NMR (MeOD): δ 7.551 (s, 1H), 4.762-4.748 (m, 0.5H), 4.428-4.352 (m, 1H), 4.039-3.975 (m, 2H), 3.941-3.827 (m, 5H), 3.681-3.667 (m, 2H), 3.574-3.501 (m, 1H), 3.327 (s, 3H), 3.173-3.116 (m, 2H), 3.046-2.991 (m, 1H), 2.940-2.882 (m, 4H), 2.744-2.522 (m, 2.5H), 1.378-1.361 (m, 1.5H), 1.264-1.247 (m, 1.5H), 1.097-1.012 (m, 4H);

LC-MS: m/z 414.5 (M+H)+

Compound 376 (General Procedure 9)

(R)-ethyl 4-(5-cyano-2-cyclopropyl-6-(4-(3-methoxypropanoyl)-3-methylpiperazin-1-yl)pyridin-3-yl)piperazine-1-carboxylate 1H NMR (MeOD): δ 7.549 (s, 1H), 4.763-4.747 (m, 0.5H), 4.426-4.343 (m, 1H), 4.171-4.118 (m, 2H), 4.044-3.882 (m, 1.5H), 3.666-3.639 (m, 6H), 3.573-3.501 (m, 1H), 3.327 (s, 3H), 3.176-2.988 (m, 2H), 2.911-2.886 (m, 4.5H), 2.781-2.546 (m, 3H), 1.374-1.358 (m, 1.5H), 1.289-1.253 (m, 4.5H), 1.101-1.026 (m, 4H);

LC-MS: m/z 485.6 (M+H)+

Compound 377 (General Procedure 9)

(R)-6-cyclopropyl-5-(4-(ethylsulfonyl)piperazin-1-yl)-2-(4-(3-methoxypropanoyl)-3-methylpiperazin-1-yl)nicotinonitrile 1H NMR (MeOD): δ 7.587 (s, 1H), 4.765-4.749 (m, 0.5H), 4.426-4.348 (m, 1H), 4.055-3.882 (m, 1.5H), 3.669-3.457 (m, 7H), 3.329 (s, 3H), 3.152-3.066 (m, 4H), 3.004-2.888 (m, 4.5H), 2.742-2.538 (m, 3H), 1.373-1.335 (m, 4.5H), 1.261-1.245 (m, 1.5H), 1.094-1.036 (m, 4H);

LC-MS: m/z 505.6 (M+H)+

Compound 378 (General Procedure 9)

(R)-6-cyclopropyl-5-(4-(cyclopropylmethyl)piperazin-1-yl)-2-(4-(3-methoxypropanoyl)-3-methylpiperazin-1-yl)nicotinonitrile 1H NMR (MeOD): δ 7.598 (s, 1H), 4.768-4.752 (m, 0.5H), 4.431-4.355 (m, 1H), 4.068-3.892 (m, 2.5H), 3.688-3.660 (m, 2H), 3.572-3.507 (m, 1H), 3.333 (s, 3H), 3.101-2.930 (m, 9H), 2.903-2.871 (m, 1H), 2.787-2.586 (m, 4H), 2.544-2.493 (m, 1H), 1.378-1.362 (m, 1.5H), 1.264-1.248 (m, 1.5H), 1.124-1.044 (m, 5H), 0.698-0.652 (m, 2H), 0.357-0.268 (m, 2H);

LC-MS: m/z 467.6 (M+H)+

Compound 379 (General Procedure 9)

(R)-5-(4-benzoylpiperazin-1-yl)-6-cyclopropyl-2-(4-(3-methoxypropanoyl)-3-methylpiperazin-1-yl)nicotinonitrile 1H NMR (MeOD): δ 7.588 (s, 1H), 7.492-7.451 (m, 5H), 4.780-4.768 (m, 0.5H), 4.430-4.346 (m, 1H), 4.053-3.881 (m, 4.5H), 3.667-3.630 (m, 2.5H), 3.536-3.477 (m, 2H), 3.326 (m, 4H), 3.180-3.085 (m, 1.5H), 3.023-2.923 (m, 5H), 2.756-2.709 (m, 1H), 2.619-2.567 (m, 2H), 1.373-1.357 (m, 1.5H), 1.259-1.243 (m, 1.5H), 1.113-1.033 (m, 4H);
LC-MS: m/z 517.6 (M+H)+

Compound 265 (General Procedure 6)

(R)-6-cyclopropyl-5-(3-fluorophenyl)-2-(4-(3-methoxypropanoyl)-3-methylpiperazin-1-yl)-4-methylnicotinonitrile ¹H NMR (CHLOROFORM-d) δ 7.41-7.51 (m, 1H), 7.12 (td, J=8.5, 2.5 Hz, 1H), 7.01 (d, J=7.5 Hz, 1H), 6.95 (d, J=9.0 Hz, 1H), 4.92 (br. s., 0.5H), 4.55 (d, J=12.8 Hz, 0.5H), 4.02-4.22 (m, 2.5H), 3.70-3.92 (m, 2.5H), 3.53-3.67 (m, 0.5H), 3.40 (s, 3H), 2.92-3.31 (m, 2.5H), 2.61-2.84 (m, 21H), 2.16-2.25 (m, 3H), 1.57-1.65 (m, 1H), 1.43 (d, J=6.5 Hz, 1.5H), 1.33 (d, J=6.8 Hz, 1.5H), 1.08 (t, J=4.6 Hz, 2H), 0.79-0.90 (m, 2H)
LC-MS: m/z 437.4 (M+H)+

Compound 264 (General Procedure 6)

6-cyclopropyl-5-(2,4-difluorophenyl)-2-((R)-4-(3-methoxypropanoyl)-3-methylpiperazin-1-yl)-4-methylnicotinonitrile ¹H NMR (CHLOROFORM-d) δ 7.15-7.25 (m, 1H), 6.94-7.06 (m, 2H), 4.92 (br. s., 0.5H), 4.55 (d, J=13.3 Hz, 0.5H), 4.05-4.34 (m, 2.5H), 3.70-3.85 (m, 2.5H), 3.52-3.67 (m, 0.5H), 3.40 (s, 3H), 2.93-3.31 (m, 2.5H), 2.73 (td, J=15.3, 7.3 Hz, 1H), 2.54-2.64 (m, 1H), 2.21 (s, 3H), 1.54-1.61 (m, 1H), 1.39-1.45 (m, 1.5H), 1.32 (t, J=5.8 Hz, 1.5H), 1.01-1.18 (m, 2H), 0.83-0.93 (m, 2H)
LC-MS: m/z 455.4 (M+H)+

Compound 263 (General Procedure 6)

(R)-6-cyclopropyl-2-(4-(3-methoxypropanoyl)-3-methylpiperazin-1-yl)-4-methyl-5-(4-(trifluoromethoxy)phenyl)nicotinonitrile ¹H NMR (CHLOROFORM-d) δ 7.31-7.36 (m, J=8.0 Hz, 2H), 7.23-7.28 (m, J=8.3 Hz, 2H), 4.92 (br. s., 0.5H), 4.55 (d, J=13.8 Hz, 0.5H), 4.00-4.22 (m, 2.5H), 3.68-3.87 (m, 2.5H), 3.53-3.67 (m, 0.5H), 3.36-3.44 (m, 3H), 3.12-3.31 (m, 1.5H), 2.94-3.12 (m, 1H), 2.64-2.83 (m, 1H), 2.61 (br. s., 1H), 2.16-2.22 (m, 3H), 1.52-1.63 (m, 1H), 1.39-1.47 (m, 1.5H), 1.32 (d, J=6.3 Hz, 1.5H), 1.03-1.15 (m, 2H), 0.78-0.90 (m, 2H)
LC-MS: m/z 503.3 (M+H)+

Compound 272 (General Procedure 8)

(R)-benzyl 2-(5-cyano-2-isopropyl-6-(4-(3-methoxypropanoyl)-3-methylpiperazin-1-yl)pyridin-3-yloxy)ethylcarbamate ¹H NMR (CHLOROFORM-d) δ 7.32-7.40 (m, 5H), 7.18 (s, 1H), 4.90 (br. s., 0.5H), 4.53 (d, J=12.5 Hz, 0.5H), 4.21 (br. s., 0.5H), 4.06 (d, J=14.1 Hz, 1H), 3.95-4.01 (m, 2.5H), 3.68-3.79 (m, 3H), 3.53-3.67 (m, 2.5H), 3.30-3.44 (m, 5H), 3.07-3.25 (m, 2H), 2.89-3.07 (m, 1H), 2.51-2.79 (m, 2.5H), 1.40 (d, J=6.5 Hz, 1.5H), 1.30 (d, J=6.8 Hz, 1.5H), 1.11-1.20 (m, 7H)
LC-MS: m/z 524.3 (M+H)+

Compound 270 (General Procedure 6)

(R)-6-cyclopropyl-2-(4-(3-methoxypropanoyl)-3-methylpiperazin-1-yl)-4-methyl-5-(thiophen-3-yl)nicotinonitrile ¹H NMR (CHLOROFORM-d) δ 7.47 (dd, J=5.0, 3.0 Hz, 1H), 7.17 (dd, J=2.8, 1.3 Hz, 1H), 7.00 (dd, J=5.0, 1.3 Hz, 1H), 4.91 (br. s., 0.5H), 4.55 (d, J=10.8 Hz, 0.5H), 3.98-4.28 (m, 2.5H), 3.75 (q, J=6.0 Hz, 2.5H), 3.50-3.67 (m, 0.5H), 3.36-3.46 (m, 3H), 3.10-3.30 (m, 1.5H), 2.89-3.10 (m, 1H), 2.65-2.81 (m, 2H), 2.25 (s, 3H), 1.71-1.79 (m, 1H), 1.42 (d, J=6.5 Hz, 1.5H), 1.32 (d, J=6.8 Hz, 1.5H), 1.05-1.12 (m, 2H), 0.81-0.90 (m, 2H)
LC-MS: m/z 425.3 (M+H)+

Compound 269 (General Procedure 6)

(R)-5-(benzo[d][1,3]dioxol-5-yl)-6-cyclopropyl-2-(4-(3-methoxypropanoyl)-3-methylpiperazin-1-yl)-4-methylnicotinonitrile ¹H NMR (CHLOROFORM-d) δ 6.91 (d, J=8.0 Hz, 1H), 6.60-6.74 (m, 2H), 6.01-6.11 (m, 2H), 4.92 (br. s., 0.5H), 4.55 (d, J=13.6 Hz, 0.5H), 4.24 (br. s., 0.5H), 4.02-4.20 (m, 2H), 3.70-3.85 (m, 2.5H), 3.59 (t, J=11.7 Hz, 0.5H), 3.39 (s, 3H), 3.19 (t, J=13.7 Hz, 1.5H), 2.92-3.08 (m, 1H), 2.65-2.83 (m, 1H), 2.55-2.64 (m, 1H), 2.19-2.27 (m, 3H), 1.67-1.76 (m, 1H), 1.42 (d, J=6.5 Hz, 1.5H), 1.31-1.38 (m, 1.5H), 1.06 (t, J=5.3 Hz, 2H), 0.79-0.91 (m, 2H)
LC-MS: m/z 463.3 (M+H)+

Compound 268 (General Procedure 6)

(R)-2-cyclopropyl-6-(4-(3-methoxypropanoyl)-3-methylpiperazin-1-yl)-4-methyl-3,4'-bipyridine-5-carbonitrile ¹H NMR (CHLOROFORM-d) δ 8.87 (br. s., 2H), 7.86 (br. s., 2H), 4.90-5.00 (m, 0.5H), 4.57 (br. s., 0.5H), 4.33 (d, J=12.5 Hz, 2.5H), 3.71-3.82 (m, 2.5H), 3.58 (br. s., 0.5H), 3.40 (s, 3H), 3.09-3.28 (m, 2.5H), 2.68 (br. s., 1H), 2.61 (br. s., 1H), 2.23-2.28 (m, 3H), 1.62-1.66 (m, 1H), 1.32-1.38 (m, 3H), 1.20 (br. s., 2H), 0.98 (br. s., 2H)
LC-MS: m/z 420.5 (M+H)+

Compound 267 (General Procedure 6)

(R)-6-cyclopropyl-2-(4-(3-methoxypropanoyl)-3-methylpiperazin-1-yl)-4-methyl-5-(naphthalen-2-yl)nicotinonitrile ¹H NMR (CHLOROFORM-d) δ 7.84-8.00 (m, 3H), 7.71 (s, 1H), 7.53-7.60 (m, 2H), 7.34 (dd, J=8.4, 1.4 Hz, 1H), 4.94 (br. s., 0.5H), 4.57 (d, J=13.3 Hz, 0.5H), 4.06-4.34 (m, 2.5H), 3.71-3.85 (m, 2.5H), 3.52-3.69 (m, 0.5H), 3.37-3.45 (m, 3H), 3.14-3.30 (m, 1.5H), 2.94-3.12 (m, 1H), 2.67-2.85 (m, 1H), 2.54-2.66 (m, 1H), 2.19-2.28 (m, 3H), 1.62-1.70 (m, 1H), 1.45 (d, J=5.8 Hz, 1.5H), 1.35 (d, J=5.5 Hz, 1.5H), 1.03-1.16 (m, 2H), 0.74-0.84 (m, 2H)
LC-MS: m/z 469.4 (M+H)+

Compound 559 (General Procedure 9)

(R)-6-cyclopropyl-5-(4-(ethylsulfonyl)piperazin-1-yl)-2-(3-methyl-4-(3,3,3-trifluoropropanoyl)piperazin-1-yl)nicotinonitrile ¹H NMR (CHLOROFORM-d) δ 7.38 (s, 1H), 4.29 (d, J=12.8 Hz, 1H), 4.18 (d, J=12.5 Hz, 1H), 4.09 (d, J=7.5 Hz, 0.5H), 3.70-3.81 (m, 1.5H), 3.46-3.55 (m, 4.5H), 3.30 (q, J=9.8 Hz, 2H), 2.92-3.14 (m, 8.5H), 2.38-2.53 (m, 1H), 1.38-1.49 (m, 3H), 1.29-1.36 (m, 1H), 1.02-1.17 (m, 4H), 0.42-0.67 (m, 4H)

LC-MS: m/z 555.2 (M+H)$^+$

Compound 529 (General Procedure 9)

(R)-2-(4-(cyclopropanecarbonyl)-3-cyclopropylpiperazin-1-yl)-6-cyclopropyl-5-(4-(ethylsulfonyl)piperazin-1-yl)nicotinonitrile $^1$H NMR (CHLOROFORM-d) δ 7.37 (s, 1H), 3.42-4.57 (m, 9H), 2.90-3.22 (m, 8H), 2.40-2.52 (m, 1H), 1.73 (br. s., 1H), 1.39-1.50 (m, 4H), 1.10-1.17 (m, 2H), 0.95-1.09 (m, 4H), 0.76-0.85 (m, 2H), 0.35-0.58 (m, 4H)

LC-MS: m/z 513.2 (M+H)$^+$

Compound 528 (General Procedure 9)

(R)-2-(4-(cyclopropanecarbonyl)-3-cyclopropylpiperazin-1-yl)-6-cyclopropyl-5-(quinolin-4-ylamino)nicotinonitrile $^1$H NMR (CHLOROFORM-d) δ 8.55 (d, J=5.5 Hz, 1H), 8.05 (d, J=8.0 Hz, 1H), 8.10 (d, J=8.3 Hz, 1H), 7.67-7.78 (m, 2H), 7.51-7.63 (m, 1H), 6.32 (d, J=5.3 Hz, 1H), 4.50 (d, J=12.3 Hz, 1H), 4.38 (d, J=12.3 Hz, 1H), 3.12-4.18 (m, 5H), 2.05-2.13 (m, 1H), 1.03-1.22 (m, 5H), 0.95-1.01 (m, 3H), 0.83 (dd, J=7.9, 2.4 Hz, 2H), 0.39-0.62 (m, 4H)

LC-MS: m/z 479.3 (M+H)$^+$

Compound 722 (General Procedure 7)

(R)-6-cyclopropyl-2-(3-cyclopropyl-4-(3-hydroxypropanoyl)piperazin-1-yl)-5-((2-vinyl-1,7-naphthyridin-4-yl)amino)nicotinonitrile $^1$H NMR (CHLOROFORM-d) δ 9.48 (s, 1H), 8.58 (d, J=5.9 Hz, 1H), 7.87 (br. s., 1H), 7.74 (s, 1H), 6.91 (dd, J=17.6, 10.9 Hz, 1H), 6.57 (s, 1H), 6.27 (d, J=17.6 Hz, 1H), 5.69 (d, J=10.9 Hz, 1H), 4.52 (d, J=12.9 Hz, 1H), 4.40 (d, J=12.3 Hz, 1H), 4.11 (d, J=7.9 Hz, 1H), 3.94 (br. s., 2H), 3.64-3.88 (m, 1H), 3.33 (br. s., 1H), 3.24 (d, J=13.5 Hz, 1H), 3.03-3.19 (m, 1H), 2.48-2.69 (m, 2H), 1.98-2.09 (m, 1H), 1.37 (d, J=16.1 Hz, 1H), 1.10-1.22 (m, 2H), 0.95-1.08 (m, 2H), 0.66 (br. s., 1H), 0.57 (br. s., 1H), 0.49 (br. s., 2H)

LC-MS: m/z 430.2 (M+H)$^+$

Compound 819 (General Procedure 6)

(R)-6-(4-(2-cyclobutylacetyl)-3-cyclopropylpiperazin-1-yl)-2-cyclopropyl-4-methyl-2'-vinyl-3,4'-bipyridine-5-carbonitrile 1H NMR (CHLOROFORM-d) δ 8.69 (d, J=4.7 Hz, 1H), 7.23 (br. s., 1H), 7.07 (d, J=4.4 Hz, 1H), 6.87 (dd, J=17.3, 10.9 Hz, 1H), 6.29 (d, J=17.3 Hz, 1H), 5.57 (d, J=11.7 Hz, 1H), 4.34 (d, J=12.9 Hz, 1H), 4.25 (d, J=12.0 Hz, 1H), 4.09 (br. s., 1H), 3.80 (br. s., 1H), 3.13 (br. s., 2H), 3.02 (br. s., 1H), 2.73 (dt, J=15.6, 7.8 Hz, 1H), 2.51 (br. s., 2H), 2.21 (s, 3H), 2.10-2.20 (m, 1H), 1.67-1.97 (m, 5H), 1.50-1.66 (m, 1H), 1.43 (d, J=15.8 Hz, 1H), 1.11 (br. s., 1H), 0.83-0.93 (m, 2H), 0.61 (br. s., 1H), 0.52 (br. s., 1H), 0.31-0.48 (m, 2H)

LC-MS: m/z 482.6 (M+H)$^+$

Compound 820 (General Procedure 6)

(R)-6-(4-(2-cyclobutylideneacetyl)-3-cyclopropylpiperazin-1-yl)-2-cyclopropyl-4-methyl-2'-vinyl-3,4'-bipyridine-5-carbonitrile 1H NMR (CHLOROFORM-d) δ 8.70 (d, J=5.0 Hz, 1H), 7.25 (s, 1H), 7.09 (d, J=3.8 Hz, 1H), 6.89 (dd, J=17.6, 10.9 Hz, 1H), 6.31 (d, J=17.3 Hz, 1H), 5.92 (br. s., 1H), 5.59 (d, J=11.2 Hz, 1H), 4.35 (d, J=12.9 Hz, 1H), 4.27 (d, J=12.6 Hz, 1H), 3.91-4.19 (m, 1H), 3.78 (br. s., 1H), 3.10-3.31 (m, 3H), 3.04 (td, J=12.4, 3.4 Hz, 1H), 2.84 (t, J=8.4 Hz, 2H), 2.43-2.55 (m, 1H), 2.22 (s, 3H), 1.98-2.17 (m, 2H), 1.53-1.63 (m, 1H), 1.45 (br. s., 1H), 1.04-1.18 (m, 2H), 0.82-0.96 (m, 2H), 0.64 (br. s., 1H), 0.50 (br. s., 1H), 0.31-0.48 (m, 2H)

LC-MS: m/z 480.6 (M+H)$^+$

Compound 266 (General Procedure 6)

(R)-6-cyclopropyl-5-(3-fluoro-4-methylphenyl)-2-(4-(3-methoxypropanoyl)-3-methylpiperazin-1-yl)-4-methylnicotinonitrile $^1$H NMR (CHLOROFORM-d) δ 7.25-7.31 (m, 1H), 6.85-6.92 (m, 2H), 4.91 (br. s., 0.5H), 4.54 (d, J=13.3 Hz, 0.5H), 4.00-4.23 (m, 2.5H), 3.68-3.87 (m, 2.5H), 3.51-3.63 (m, 0.5H), 3.39 (s, 3H), 3.10-3.27 (m, 1.5H), 2.94-3.09 (m, 1H), 2.64-2.82 (m, 1H), 2.55-2.64 (m, 1H), 2.32-2.39 (m, 3H), 2.20 (s, 3H), 1.60-1.70 (m, 1H), 1.39-1.47 (m, 1.5H), 1.30-1.35 (m, 1.5H), 1.07 (t, J=4.6 Hz, 2H), 0.83 (dt, J=7.5, 3.5 Hz, 2H)

LC-MS: m/z 451.4 (M+H)$^+$

Compound 277 (General Procedure 8)

6-cyclopropyl-2-((R)-4-(3-methoxypropanoyl)-3-methylpiperazin-1-yl)-5-(1-phenylethoxy)nicotinonitrile $^1$H NMR (CHLOROFORM-d) δ 7.28-7.42 (m, 5H), 6.97 (d, J=3.3 Hz, 1H), 5.15 (q, J=6.3 Hz, 1H), 4.85 (br. s., 0.5H), 4.48 (d, J=13.1 Hz, 0.5H), 4.15 (br. s., 0.5H), 3.76-3.94 (m, 2H), 3.64-3.76 (m, 2.5H), 3.41-3.57 (m, 0.5H), 3.36 (s, 3H), 2.96-3.13 (m, 1.5H), 2.77-2.96 (m, 1H), 2.61-2.77 (m, 1H), 2.48-2.61 (m, 2H), 1.67 (d, J=6.3 Hz, 3H), 1.26 (d, J=5.3 Hz, 3H), 0.97-1.15 (m, 4H)

LC-MS: m/z 449.2 (M+H)$^+$

Compound 279 (General Procedure 8)

(R)-6-cyclopropyl-2-(4-(3-methoxypropanoyl)-3-methylpiperazin-1-yl)-5-(pyridin-2-ylmethoxy)nicotinonitrile $^1$H NMR (CHLOROFORM-d) δ 8.64 (d, J=4.5 Hz, 1H), 7.82 (t, J=7.3 Hz, 1H), 7.51-7.62 (m, 1H), 7.29-7.39 (m, 1H), 7.23 (s, 1H), 5.22 (s, 2H), 4.88 (br. s., 0.5H), 4.51 (d, J=12.8 Hz, 0.5H), 4.18 (br. s., 0.5H), 3.82-4.03 (m, 2H), 3.63-3.81 (m, 2.5H), 3.44-3.61 (m, 0.5H), 3.37 (s, 3H), 3.09 (t, J=13.2 Hz, 1.5H), 2.82-3.01 (m, 1H), 2.62-2.79 (m, 1H), 2.45-2.61 (m, 2H), 1.26 (d, J=5.3 Hz, 3H), 0.99-1.16 (m, 4H)

LC-MS: m/z 436.2 (M+H)$^+$

Compound 280 (General Procedure 8)

(R)-6-cyclopropyl-5-(3-methoxybenzyloxy)-2-(4-(3-methoxypropanoyl)-3-methylpiperazin-1-yl)nicotinonitrile $^1$H NMR (CHLOROFORM-d) δ 7.32 (t, J=7.9 Hz, 1H), 7.18 (s, 1H), 6.93-7.05 (m, 2H), 6.89 (dd, J=8.0, 2.3 Hz, 1H), 5.02 (s, 2H), 4.87 (br. s., 0.5H), 4.51 (d, J=13.3 Hz, 0.5H), 4.18 (br. s., 0.5H), 3.92 (t, J=12.7 Hz, 2H), 3.83 (s, 3H), 3.73 (t, J=6.1 Hz, 2.5H), 3.53 (d, J=8.0 Hz, 0.5H), 3.37 (s, 3H), 3.01-3.18 (m, 1.5H), 2.81-3.00 (m, 1H), 2.62-2.78 (m, 1H), 2.45-2.62 (m, 2H), 1.27-1.44 (m, 3H), 0.97-1.15 (m, 4H)
LC-MS: m/z 465.2 (M+H)$^+$ Compound 281 (General Procedure 8)

(R)-6-cyclopropyl-5-(4-methoxybenzyloxy)-2-(4-(3-methoxypropanoyl)-3-methylpiperazin-1-yl)nicotinonitrile $^1$H NMR (CHLOROFORM-d) δ 7.28-7.39 (m, J=8.8 Hz, 2H), 7.20 (s, 1H), 6.88-6.97 (m, J=8.8 Hz, 2H), 4.96 (s, 2H), 4.88 (d, J=7.8 Hz, 0.5H), 4.51 (d, J=13.3 Hz, 0.5H), 4.18 (br. s., 1H), 3.92 (t, J=12.5 Hz, 2H), 3.83 (s, 3H), 3.67-3.78 (m, 2.5H), 3.46-3.60 (m, 0.5H), 3.37 (s, 3H), 3.00-3.16 (m, 1.5H), 2.80-2.99 (m, 1H), 2.61-2.80 (m, 1H), 2.42-2.61 (m, 2H), 1.39 (d, J=6.5 Hz, 1.5H), 1.29 (d, J=6.8 Hz, 1.5H), 0.92-1.14 (m, 4H)
LC-MS: m/z 465.2 (M+H)$^+$ Compound 292 (General Procedure 8)

(R)-methyl 3-((5-cyano-2-cyclopropyl-6-(4-(3-methoxypropanoyl)-3-methylpiperazin-1-yl)pyridin-3-yloxy)methyl)benzoate $^1$H NMR (CHLOROFORM-d) δ 8.11 (s, 1H), 8.04 (d, J=7.8 Hz, 1H), 7.63 (d, J=7.5 Hz, 1H), 7.50 (t, J=7.7 Hz, 1H), 7.19 (s, 1H), 5.07 (s, 2H), 4.88 (br. s., 0.5H), 4.51 (d, J=13.6 Hz, 0.5H), 4.18 (br. s., 0.5H), 3.94 (s, 3H), 3.83-4.02 (m, 2H), 3.64-3.80 (m, 2.5H), 3.52 (br. s., 0.5H), 3.37 (s, 3H), 3.09 (t, J=13.6 Hz, 1.5H), 2.82-3.01 (m, 1H), 2.62-2.80 (m, 1H), 2.41-2.62 (m, 2H), 1.39 (d, J=6.5 Hz, 1.5H), 1.29 (d, J=6.8 Hz, 1.5H), 0.98-1.15 (m, 4H)
LC-MS: m/z 493.2 (M+H)$^+$ Compound 293 (General Procedure 8)

(R)-methyl 4-((5-cyano-2-cyclopropyl-6-(4-(3-methoxypropanoyl)-3-methylpiperazin-1-yl)pyridin-3-yloxy)methyl)benzoate $^1$H NMR (CHLOROFORM-d) δ 8.01-8.14 (m, 2H), 7.44-7.56 (m, J=8.5 Hz, 2H), 7.18 (s, 1H), 5.10 (s, 2H), 4.88 (br. s., 0.5H), 4.51 (d, J=13.6 Hz, 0.5H), 4.19 (br. s., 0.5H), 3.93 (s, 3H), 3.82-4.02 (m, 2H), 3.66-3.81 (m, 2.5H), 3.46-3.60 (m, 0.5H), 3.37 (s, 3H), 3.10 (t, J=13.7 Hz, 1.5H), 2.82-3.01 (m, 1H), 2.62-2.79 (m, 1H), 2.43-2.62 (m, 2H), 1.39 (d, J=6.5 Hz, 1.5H), 1.27-1.34 (m, 1.5H), 0.96-1.17 (m, 4H)
LC-MS: m/z 493.2 (M+H)$^+$ Compound 294 (General Procedure 8)

(R)-5-(3-cyanobenzyloxy)-6-cyclopropyl-2-(4-(3-methoxypropanoyl)-3-methylpiperazin-1-yl)nicotinonitrile $^1$H NMR (CHLOROFORM-d) δ 7.75 (s, 1H), 7.61-7.71 (m, 2H), 7.54 (t, J=7.9 Hz, 1H), 7.17 (s, 1H), 5.06 (s, 2H), 4.88 (br. s., 0.5H), 4.52 (d, J=13.6 Hz, 0.5H), 4.21 (br. s., 0.5H), 3.85-4.06 (m, 2H), 3.74 (br. s., 2.5H), 3.54 (br. s., 0.5H), 3.37 (s, 3H), 3.04-3.21 (m, 1.5H), 2.84-3.04 (m, 1H), 2.55-2.81 (m, 2H), 2.40-2.51 (m, 1H), 1.39 (d, J=5.5 Hz, 1.5H), 1.30 (d, J=6.3 Hz, 1.5H), 0.98-1.16 (m, 4H)
LC-MS: m/z 460.2 (M+H)$^+$ Compound 301 (General Procedure 8)

(R)-6-cyclopropyl-5-(4-(hydroxymethyl)benzyloxy)-2-(4-(3-methoxypropanoyl)-3-methylpiperazin-1-yl) nicotinonitrile $^1$H NMR (CHLOROFORM-d) δ 7.35-7.49 (m, 4H), 7.18 (s, 1H), 5.04 (s, 2H), 4.81-4.91 (m, 0.5H), 4.73 (s, 2H), 4.50 (d, J=13.3 Hz, 0.5H), 4.18 (br. s., 0.5H), 3.81-4.00 (m, 2H), 3.64-3.81 (m, 2.5H), 3.45-3.60 (m, 0.5H), 3.37 (s, 3H), 3.00-3.17 (m, 1.5H), 2.81-2.99 (m, 1H), 2.61-2.79 (m, 1H), 2.43-2.61 (m, 2H), 1.92-2.08 (m, 1H), 1.31-1.41 (m, 3H), 0.97-1.14 (m, 4H)
LC-MS: m/z 465.2 (M+H)$^+$ Compound 302 (General Procedure 8)

6-cyclopropyl-2-((R)-4-(3-methoxypropanoyl)-3-methylpiperazin-1-yl)-5-(2-methyl-1-phenyl-propoxy)nicotinonitrile $^1$H NMR (CHLOROFORM-d) δ 7.27-7.39 (m, 5H), 6.87 (d, J=1.5 Hz, 1H), 4.84 (br. s., 0.5H), 4.66-4.74 (m, 1H), 4.47 (d, J=13.3 Hz, 0.5H), 4.14 (br. s., 0.5H), 3.63-3.90 (m, 4.5H), 3.40-3.57 (m, 0.5H), 3.35 (s, 3H), 2.93-3.12 (m, 1.5H), 2.76-2.93 (m, 1H), 2.47-2.75 (m, 3H), 2.18 (dq, J=13.3, 6.6 Hz, 1H), 1.19-1.39 (m, 3H), 1.00-1.11 (m, 7H), 0.87-0.97 (m, 3H)
LC-MS: m/z 477.2 (M+H)$^+$ Compound 303 (General Procedure 8)

6-cyclopropyl-2-((R)-4-(3-methoxypropanoyl)-3-methylpiperazin-1-yl)-5-((S)-1-phenylethoxy)nicotinonitrile $^1$H NMR (CHLOROFORM-d) δ 7.27-7.42 (m, 5H), 6.91-7.00 (m, 1H), 5.15 (q, J=6.5 Hz, 1H), 4.85 (br. s., 0.5H), 4.48 (d, J=13.6 Hz, 0.5H), 4.15 (br. s., 0.5H), 3.78-3.95 (m, 2H), 3.61-3.77 (m, 2.5H), 3.43-3.57 (m, 0.5H), 3.36 (s, 3H), 2.96-3.13 (m, 1.5H), 2.85 (td, J=12.4, 2.8 Hz, 1H), 2.48-2.76 (m, 3H), 1.67 (d, J=6.5 Hz, 3H), 1.36 (d, J=6.5 Hz, 1.5H), 1.21-1.28 (m, 1.5H), 0.97-1.13 (m, 4H)
LC-MS: m/z 449.2 (M+H)$^+$ Compound 304 (General Procedure 8)

(R)-6-cyclopropyl-2-(4-(3-methoxypropanoyl)-3-methylpiperazin-1-yl)-5-(pyridin-3-ylmethoxy)nicotinonitrile $^1$H NMR (CHLOROFORM-d) δ 8.70 (s, 1H), 8.63 (d, J=3.8 Hz, 1H), 7.79 (dt, J=7.8, 1.9 Hz, 1H), 7.37 (dd, J=7.8, 4.8 Hz, 1H), 7.24 (s, 1H), 5.06 (s, 2H), 4.88 (br. s., 0.5H), 4.51 (d, J=12.5 Hz, 0.5H), 4.20 (br. s., 0.5H), 3.83-4.04 (m, 2H), 3.63-3.83 (m, 2.5H), 3.53 (br. s., 0.5H), 3.37 (s, 3H), 3.03-3.17 (m, 1.5H), 2.84-3.02 (m, 1H), 2.62-2.78 (m, 1H), 2.51-2.62 (m, 1H), 2.39-2.51 (m, 1H), 1.36-1.43 (m, 2H), 1.27-1.34 (m, 2H), 0.91-1.15 (m, 4H)
LC-MS: m/z 436.2 (M+H)$^+$

Compound 307 (General Procedure 8)

6-cyclopropyl-2-((R)-4-(3-methoxypropanoyl)-3-methylpiperazin-1-yl)-5-((R)-1-phenylethoxy)nicotinonitrile $^1$H NMR (CHLOROFORM-d) δ 7.27-7.42 (m, 5H), 6.92-6.98 (m, 1H), 5.15 (q, J=6.4 Hz, 1H), 4.84 (br. s., 0.5H), 4.49 (d, J=13.6 Hz, 0.5H), 4.15 (br. s., 0.5H), 3.77-3.95 (m, 2H), 3.72 (t, J=6.3 Hz, 2.5H), 3.43-3.56 (m, 0.5H), 3.36 (s, 3H), 2.97-3.13 (m, 1.5H), 2.78-2.95 (m, 1H), 2.48-2.78 (m, 3H), 1.67 (d, J=6.3 Hz, 3H), 1.36 (d, J=6.8 Hz, 1.5H), 1.26 (d, J=5.5 Hz, 1.5H), 0.97-1.14 (m, 4H)

LC-MS: m/z 449.2 (M+H)$^+$

Compound 308 (General Procedure 8)

6-cyclopropyl-2-((R)-4-(3-methoxypropanoyl)-3-methylpiperazin-1-yl)-5-(1-phenylpropoxy)nicotinonitrile $^1$H NMR (CHLOROFORM-d) δ 7.28-7.42 (m, 5H), 6.92 (d, J=2.3 Hz, 1H), 4.78-4.95 (m, 1.5H), 4.48 (d, J=13.3 Hz, 0.5H), 4.14 (br. s., 0.5H), 3.77-3.93 (m, 2H), 3.65-3.77 (m, 2.5H), 3.48 (br. s., 0.5H), 3.36 (s, 3H), 2.95-3.12 (m, 1.5H), 2.76-2.95 (m, 1H), 2.46-2.76 (m, 3H), 2.00-2.13 (m, 1H), 1.84-1.98 (m, 1H), 1.36 (d, J=6.8 Hz, 1.5H), 1.25-1.29 (m, 1.5H), 0.92-1.12 (m, 7H)

LC-MS: m/z 463.2 (M+H)$^+$

Compound 309 (General Procedure 8)

(R)-6-cyclopropyl-2-(4-(3-methoxypropanoyl)-3-methylpiperazin-1-yl)-5-(pyridin-4-ylmethoxy)nicotinonitrile $^1$H NMR (CHLOROFORM-d) δ 8.67 (d, J=5.8 Hz, 2H), 7.39 (d, J=5.8 Hz, 2H), 7.17 (s, 1H), 5.07 (s, 2H), 4.79-4.95 (m, 0.5H), 4.51 (d, J=13.6 Hz, 0.5H), 4.19 (br. s., 0.5H), 3.86-4.04 (m, 2H), 3.62-3.81 (m, 2.5H), 3.45-3.59 (m, 0.5H), 3.37 (s, 3H), 3.03-3.18 (m, 1.5H), 2.83-3.02 (m, 1H), 2.62-2.79 (m, 1H), 2.43-2.61 (m, 2H), 1.39 (d, J=6.8 Hz, 1.5H), 1.27-1.31 (m, 1.5H), 0.99-1.15 (m, 4H)

LC-MS: m/z 436.2 (M+H)$^+$

Compound 310 (General Procedure 8)

5-(1-(3-chlorophenyl)ethoxy)-6-cyclopropyl-2-((R)-4-(3-methoxypropanoyl)-3-methylpiperazin-1-yl)nicotinonitrile $^1$H NMR (CHLOROFORM-d) δ 7.33-7.38 (m, 1H), 7.27-7.33 (m, 3H), 7.19-7.25 (m, 1H), 6.96 (d, J=4.5 Hz, 1H), 5.11 (q, J=6.3 Hz, 1H), 4.85 (br. s., 0.5H), 4.49 (d, J=13.6 Hz, 0.5H), 4.16 (br. s., 0.5H), 3.78-3.97 (m, 2H), 3.63-3.78 (m, 2.5H), 3.49 (br. s., 0.5H), 3.36 (s, 3H), 2.98-3.14 (m, 1.5H), 2.79-2.97 (m, 1H), 2.60-2.77 (m, 1H), 2.46-2.60 (m, 2H), 1.65 (d, J=6.3 Hz, 3H), 1.36 (d, J=6.5 Hz, 1.5H), 1.26 (d, J=7.8 Hz, 1.5H), 0.98-1.15 (m, 4H)

LC-MS: m/z 483.2 (M+H)$^+$

Compound 311 (General Procedure 8)

5-(1-(4-chlorophenyl)ethoxy)-6-cyclopropyl-2-((R)-4-(3-methoxypropanoyl)-3-methylpiperazin-1-yl)nicotinonitrile $^1$H NMR (CHLOROFORM-d) δ 7.23-7.40 (m, 4H), 6.95 (d, J=3.8 Hz, 1H), 5.13 (q, J=6.1 Hz, 1H), 4.85 (br. s., 0.5H), 4.49 (d, J=13.1 Hz, 0.5H), 4.16 (br. s., 0.5H), 3.79-3.98 (m, 2H), 3.63-3.78 (m, 2.5H), 3.42-3.57 (m, 0.5H), 3.36 (s, 3H), 2.98-3.13 (m, 1.5H), 2.77-2.97 (m, 1H), 2.60-2.76 (m, 1H), 2.43-2.60 (m, 2H), 1.65 (d, J=6.3 Hz, 3H), 1.33-1.39 (m, 1.5H), 1.22-1.29 (m, 1.5H), 0.97-1.13 (m, 4H)

LC-MS: m/z 483.2 (M+H)$^+$

Compound 312 (General Procedure 8)

(R)-6-cyclopropyl-2-(4-(3-methoxypropanoyl)-3-methylpiperazin-1-yl)-5-(3-nitrobenzyloxy)nicotinonitrile $^1$H NMR (CHLOROFORM-d) δ 8.33 (s, 1H), 8.24 (dd, J=8.2, 1.2 Hz, 1H), 7.72-7.84 (m, 1H), 7.54-7.67 (m, 1H), 7.21 (s, 1H), 5.13 (s, 2H), 4.88 (br. s., 0.5H), 4.51 (d, J=13.7 Hz, 0.5H), 4.19 (br. s., 0.5H), 3.86-4.03 (m, 2H), 3.63-3.84 (m, 2.5H), 3.53 (br. s., 0.5H), 3.37 (s, 3H), 3.04-3.18 (m, 1.5H), 2.84-3.04 (m, 1H), 2.62-2.78 (m, 1H), 2.42-2.61 (m, 2H), 1.39 (d, J=6.7 Hz, 1.5H), 1.29 (d, J=6.7 Hz, 1.5H), 0.97-1.19 (m, 4H)

LC-MS: m/z 480.2 (M+H)$^+$

Compound 341 (General Procedure 8)

(R)-5-(3-aminobenzoyloxy)-6-cyclopropyl-2-(4-(3-methoxypropanoyl)-3-methylpiperazin-1-yl)nicotinonitrile $^1$H NMR (CHLOROFORM-d) δ 7.13-7.24 (m, 2H), 6.79 (d, J=7.8 Hz, 1H), 6.74 (s, 1H), 6.67 (dd, J=8.0, 1.5 Hz, 1H), 4.95 (s, 2H), 4.87 (br. s., 0.5H), 4.50 (d, J=13.6 Hz, 0.5H), 4.17 (br. s., 0.5H), 3.81-3.98 (m, 2H), 3.73 (t, J=6.1 Hz, 2.5H), 3.53 (d, J=8.8 Hz, 0.5H), 3.37 (s, 3H), 3.01-3.16 (m, 1.5H), 2.81-3.00 (m, 1H), 2.61-2.79 (m, 1H), 2.46-2.61 (m, 2H), 1.39 (d, J=6.5 Hz, 1.5H), 1.29 (d, J=6.5 Hz, 1.5H), 0.95-1.14 (m, 4H)

LC-MS: m/z 450.2 (M+H)$^+$

Compound 381 (General Procedure 8)

(R)—N-(3-((5-cyano-2-cyclopropyl-6-(4-(3-methoxypropanoyl)-3-methylpiperazin-1-yl)pyridin-3-yloxy)methyl)phenyl)acrylamide $^1$H NMR (CHLOROFORM-d) δ 8.11 (br. s., 1H), 7.82 (br. s., 1H), 7.52 (d, J=8.3 Hz, 1H), 7.35 (t, J=7.8 Hz, 1H), 7.13-7.23 (m, 2H), 6.45 (dd, J=16.8, 1.3 Hz, 1H), 6.31 (dd, J=16.8, 10.0 Hz, 1H), 5.76 (dd, J=10.2, 1.4 Hz, 1H), 4.99 (s, 2H), 4.86 (br. s., 0.5H), 4.50 (d, J=13.6 Hz, 0.5H), 4.18 (br. s., 0.5H), 3.81-3.99 (m, 2H), 3.72 (t, J=6.0 Hz, 2.5H), 3.45-3.59 (m, 0.5H), 3.35 (s, 3H), 3.00-3.16 (m, 1.5H), 2.81-2.99 (m, 1H), 2.62-2.79 (m, 1H), 2.41-2.62 (m, 2H), 1.39 (d, J=6.8 Hz, 1.5H), 1.25-1.32 (m, 1.5H), 0.94-1.15 (m, 4H)

LC-MS: m/z 504.2 (M+H)$^+$

Compound 382 (General Procedure 8)

(R)-2-bromo-N-(3-((5-cyano-2-cyclopropyl-6-(4-(3-methoxypropanoyl)-3-methylpiperazin-1-yl)pyridin-3-yloxy)methyl)phenyl)acetamide $^1$H NMR (CHLOROFORM-d) δ 8.52 (s, 1H), 7.73 (s, 1H), 7.48 (d, J=8.0 Hz, 1H), 7.38 (t, J=7.8 Hz, 1H), 7.12-7.26 (m, 2H), 5.02 (s, 2H), 4.87 (br. s., 0.5H), 4.50 (d, J=13.3 Hz, 0.5H), 4.19 (d, J=8.5 Hz, 0.5H), 4.03 (s, 2H), 3.81-3.99 (m, 2H), 3.64-3.81 (m, 2.5H), 3.45-3.61 (m, 0.5H), 3.36 (s, 3H), 3.02-3.18 (m, 1.5H), 2.82-3.02 (m, 1H), 2.62-2.80 (m, 1H), 2.42-2.62 (m, 2H), 1.39 (d, J=6.5 Hz, 1.5H), 1.22-1.33 (m, 1.5H), 0.95-1.14 (m, 4H)

LC-MS: m/z 570.1 (M+H)$^+$

Compound 388 (General Procedure 8)

6-cyclopropyl-2-((R)-4-(3-methoxypropanoyl)-3-methylpiperazin-1-yl)-5-(1-(pyridin-4-yl)ethoxy)nicotinonitrile $^1$H NMR (CHLOROFORM-d) δ 8.57-8.70 (m, 2H), 7.33 (d, J=6.0 Hz, 2H), 6.96 (d, J=3.3 Hz, 1H), 5.17 (q, J=6.4 Hz, 1H), 4.86 (br. s., 0.5H), 4.49 (d, J=12.8 Hz, 0.5H), 4.17 (br. s., 0.5H), 3.81-4.05 (m, 2H), 3.63-3.81 (m, 2.5H), 3.51 (d, J=15.3 Hz, 0.5H), 3.36 (s, 3H), 3.07 (t, J=12.9 Hz, 1.5H), 2.81-3.00 (m, 1H), 2.60-2.78 (m, 1H), 2.46-2.60 (m, 2H), 1.67 (d, J=6.5 Hz, 3H), 1.36 (d, J=5.0 Hz, 1.5H), 1.24-1.28 (m, 1.5H), 0.99-1.16 (m, 4H)

LC-MS: m/z 450.2 (M+H)$^+$

Compound 389 (General Procedure 8)

N-(4-(1-(5-cyano-2-cyclopropyl-6-((R)-4-(3-methoxypropanoyl)-3-methylpiperazin-1-yl)pyridin-3-yloxy)ethyl)phenyl)acrylamide $^1$H NMR (CHLOROFORM-d) δ 8.03 (br. s., 1H), 7.56-7.64 (m, 2H), 7.30 (d, J=8.3 Hz, 2H), 6.90-7.05 (m, 1H), 6.43 (dd, J=16.8, 1.3 Hz, 1H), 6.29 (dd, J=16.8, 10.0 Hz, 1H), 5.74 (dd, J=10.0, 1.3 Hz, 1H), 5.05-5.19 (m, 1H), 4.85 (br. s., 0.5H), 4.48 (d, J=12.5 Hz, 0.5H), 4.16 (br. s., 0.5H), 3.65-3.95 (m, 5.5H), 3.50 (d, J=11.3 Hz, 0.5H), 3.34 (s, 3H), 2.97-3.14 (m, 1.5H), 2.77-2.95 (m, 1H), 2.61-2.77 (m, 1H), 2.47-2.61 (m, 2H), 1.65 (d, J=6.3 Hz, 3H), 1.36 (d, J=6.5 Hz, 1.5H), 1.26 (d, J=5.0 Hz, 1.5H), 0.97-1.15 (m, 4H)

LC-MS: m/z 518.2 (M+H)$^+$

Compound 400 (General Procedure 8)

(R,E)-N-(3-((5-cyano-2-cyclopropyl-6-(4-(3-methoxypropanoyl)-3-methylpiperazin-1-yl)pyridin-3-yloxy)methyl)phenyl)but-2-enamide $^1$H NMR (CHLOROFORM-d) δ 7.75 (br. s., 1H), 7.47 (d, J=8.0 Hz, 1H), 7.30-7.40 (m, 2H), 7.10-7.23 (m, 2H), 6.88-7.09 (m, 1H), 5.96 (dd, J=15.1, 1.5 Hz, 1H), 5.01 (s, 2H), 4.87 (br. s., 0.5H), 4.50 (d, J=13.6 Hz, 0.5H), 4.18 (br. s., 0.5H), 3.82-4.00 (m, 2H), 3.64-3.80 (m, 2.5H), 3.46-3.62 (m, 0.5H), 3.36 (s, 3H), 3.01-3.16 (m, 1.5H), 2.83-3.01 (m, 1H), 2.62-2.77 (m, 1H), 2.44-2.61 (m, 2H), 1.93 (dd, J=6.9, 1.6 Hz, 3H), 1.39 (d, J=6.5 Hz, 1.5H), 1.29 (d, J=7.0 Hz, 1.5H), 0.95-1.13 (m, 4H)

LC-MS: m/z 518.2 (M+H)$^+$

Compound 407 (General Procedure 8)

N-(3-(1-(5-cyano-2-cyclopropyl-6-((R)-4-(3-methoxypropanoyl)-3-methylpiperazin-1-yl)pyridin-3-yloxy)ethyl)phenyl)acrylamide $^1$H NMR (CHLOROFORM-d) δ 7.75 (br. s., 1H), 7.63 (br. s., 1H), 7.46 (br. s., 1H), 7.34 (t, J=7.8 Hz, 1H), 7.13 (d, J=7.5 Hz, 1H), 6.94-7.01 (m, 1H), 6.46 (dd, J=16.8, 1.3 Hz, 1H), 6.28 (dd, J=16.9, 10.2 Hz, 1H), 5.79 (dd, J=10.3, 1.0 Hz, 1H), 5.13 (q, J=6.1 Hz, 1H), 4.86 (br. s., 0.5H), 4.49 (d, J=13.3 Hz, 0.5H), 4.17 (br. s., 0.5H), 3.78-3.95 (m, 2H), 3.63-3.78 (m, 2.5H), 3.52 (d, J=14.6 Hz, 0.5H), 3.37 (s, 3H), 2.98-3.14 (m, 1.5H), 2.79-2.97 (m, 1H), 2.63-2.78 (m, 1H), 2.48-2.63 (m, 2H), 1.68 (d, J=6.3 Hz, 3H), 1.38 (d, J=6.3 Hz, 1.5H), 1.24-1.30 (m, 1.5H), 1.00-1.14 (m, 4H)

LC-MS: m/z 518.2 (M+H)$^+$

Compound 827 (General Procedure 6)

(R)-2-cyclopropyl-6-(3-cyclopropyl-4-hexanoylpiperazin-1-yl)-4-methyl-2'-vinyl-3,4'-bipyridine-5-carbonitrile $^1$H NMR (CHLOROFORM-d) δ 8.69 (d, J=4.7 Hz, 1H), 7.23 (s, 1H), 7.07 (d, J=4.7 Hz, 1H), 6.87 (dd, J=17.6, 10.9 Hz, 1H), 6.19-6.36 (m, 1H), 5.47-5.63 (m, 1H), 4.34 (d, J=12.9 Hz, 1H), 4.26 (d, J=12.6 Hz, 1H), 4.10 (br. s., 0.65H), 3.64-3.91 (m, 1.35H), 2.88-3.38 (m, 2H), 2.37 (br. s., 2H), 2.21 (s, 3H), 1.61-1.73 (m, 2H), 1.51-1.61 (m, 1H), 1.44 (br. s., 1H), 1.35 (br. s., 4H), 1.04-1.17 (m, 2H), 0.90-0.98 (m, 3H), 0.87 (dd, J=8.1, 3.1 Hz, 2H), 0.60 (br. s., 1H), 0.55 (br. s., 1H), 0.23-0.50 (m, 2H)

LC-MS: m/z 484.3 (M+H)$^+$

Compound 826 (General Procedure 6)

(R)-6-(4-(3-cyclobutylpropanoyl)-3-cyclopropylpiperazin-1-yl)-2-cyclopropyl-4-methyl-2'-vinyl-3,4'-bipyridine-5-carbonitrile $^1$H NMR (CHLOROFORM-d) δ 8.70 (d, J=5.0 Hz, 1H), 7.25 (s, 1H), 7.09 (d, J=4.7 Hz, 1H), 6.88 (dd, J=17.6, 10.9 Hz, 1H), 6.28 (d, J=17.6 Hz, 1H), 5.51-5.64 (m, 1H), 4.34 (d, J=12.9 Hz, 1H), 4.26 (d, J=12.0 Hz, 1H), 4.09 (br. s., 0.6H), 3.63-3.92 (m, 1.4H), 3.01-3.13 (m, 2H), 2.25-2.38 (m, 2H), 2.22 (s, 3H), 2.00-2.13 (m, 4H), 1.82-1.90 (m, 2H), 1.75 (q, J=7.4 Hz, 2H), 1.61-1.69 (m, 2H), 1.56 (td, J=8.3, 4.0 Hz, 1H), 1.12 (br. s., 2H), 0.80-0.94 (m, 2H), 0.61 (br. s., 1H), 0.55 (br. s., 1H), 0.44 (br. s., 2H)

LC-MS: m/z 496.3 (M+H)$^+$

Compound 825 (General Procedure 6)

(R)-2-cyclopropyl-6-(3-cyclopropyl-4-(3-cyclopropylpropanoyl)piperazin-1-yl)-4-methyl-2'-vinyl-3,4'-bipyridine-5-carbonitrile $^1$H NMR (CHLOROFORM-d) δ 8.72 (d, J=5.0 Hz, 1H), 7.26 (s, 1H), 7.09 (d, J=4.7 Hz, 1H), 6.89 (dd, J=17.6, 10.9 Hz, 1H), 6.27 (d, J=17.6 Hz, 1H), 5.52-5.65 (m, 1H), 4.34 (d, J=12.6 Hz, 1H), 4.26 (d, J=12.6 Hz, 1H), 4.02-4.17 (m, 0.6H), 3.71-3.95 (m, 1.4H), 2.95-3.4 (m, 2H), 2.45-2.56 (m, 1H), 2.36 (t, J=7.5 Hz, 3H), 2.22 (s, 3H), 1.63-1.70 (m, 2H), 1.11 (br. s., 2H), 0.75-0.89 (m, 3H), 0.51-0.74 (m, 3H), 0.34-0.50 (m, 4H), 0.10 (d, J=4.1 Hz, 2H)

LC-MS: m/z 482.2 (M+H)+

Compound 582 (General Procedure 7)

(R)-5-((5-cyano-2-cyclopropyl-6-(4-(3-hydroxypropanoyl)-3-methylpiperazin-1-yl)pyridin-3-yl)amino)picolinonitrile ¹H NMR (400 MHz, CDCl3) δ 8.18-8.17 (d, 1H), 7.61 (s, 1H), 7.51-7.49 (d, 1H), 6.89-6.86 (dd, 1H), 6.38 (s, 1H), 4.87 (s, 0.5H), 4.53-4.50 (d, 0.5H); 4.27-4.16 (dd, 2H) 3.92 (s, 2H) 3.75-3.10 (m, 4H) 2.69-2.51 (m, 2H), 2.07-2.02 (m, 1H), 1.41-1.26 (m, 3H), 1.43-1.10 (m, 2H), 1.04-1.01 (m, 2H).

LC-MS: m/z 432.2 (M+H)+

Compound 577 (General Procedure 7)

(R)-6-cyclopropyl-2-(4-(3-hydroxypropanoyl)-3-methylpiperazin-1-yl)-5-((6-vinylpyridin-3-yl)amino)nicotinonitrile ¹H NMR (400 MHz, CDCl₃) δ 8.15-8.14 (d, 1H), 7.58 (s, 1H), 7.26-7.23 (d, 1H), 6.97-6.94 (dd, 1H), 6.79-6.72 (q, 1H), 6.03-5.98 (dd, 1H), 5.58 (s, 1H), 5.36-5.33 (dd, 1H), 4.88 (s, 0.5H), 4.54-4.51 (d, 0.5H); 4.20-4.09 (dd, 2H) 3.93 (s, 2H) 3.75-3.52 (m, 2H) 3.25-2.98 (m, 3H), 2.71-2.50 (m, 2H), 2.18-2.10 (m, 1H), 1.41-1.26 (m, 3H), 1.43-1.30 (m, 2H), 1.13-1.11 (m, 2H), 1.03-1.09 (m, 2H).

LC-MS: m/z 433.2 (M+H)+

Compound 298 (General Procedure 6)

(R)-6-cyclopropyl-5-(4-fluorophenyl)-4-(methoxymethyl)-2-(4-(3-methoxypropanoyl)-3-methylpiperazin-1-yl)nicotinonitrile 1H NMR (CHLOROFORM-d) δ t: 7.21-7.27 (m, 2H), 7.11-7.19 (m, 2H), 4.85-4.95 (s, 0.5H), 4.45-4.57 (m, 0.5H), 4.05-4.27 (m, 4H), 3.74 (t, J=6.4 Hz, 2.5H), 3.57-3.63 (m, 0.5H), 3.35-3.40 (m, 3H), 3.29 (s, 3H), 3.09-3.26 (m, 2H), 2.59 (br. s., 1H), 1.60-1.70 (m, 1H), 1.38-1.44 (m, 1H), 1.30 (d, J=6.8 Hz, 2H), 1.25 (s, 1H), 1.04-1.10 (m, 2H), 0.81-0.88 (m, 2H).

LC-MS: m/z 487.2 (M+H)+

Compound 823 (General Procedure 6)

2-cyclopropyl-6-((R)-3-cyclopropyl-4-(2-((R)-oxetan-2-yl)acetyl)piperazin-1-yl)-4-ethyl-2'-vinyl-[3,4'-bipyridine]-5-carbonitrile ¹H NMR (CHLOROFORM-d) δ 8.57-8.87 (m, 1H), 7.25 (s, 1H), 7.02-7.16 (m, 1H), 6.89 (dd, J=17.5, 10.7 Hz, 1H), 6.30 (d, J=17.3 Hz, 1H), 5.59 (d, J=10.9 Hz, 1H), 5.27 (t, J=6.6 Hz, 1H), 4.51-4.78 (m, 1H), 4.30-4.42 (m, 1H), 4.26 (d, J=11.4 Hz, 1H), 4.09 (d, J=9.1 Hz, 1H), 3.84-3.98 (m, 1H), 3.56-3.84 (m, 1H), 2.95-3.45 (m, 3H), 2.68-2.92 (m, 2H), 2.41-2.63 (m, 3H), 1.49-1.55 (m, 1H), 1.34 (d, J=8.2 Hz, 1H), 1.10 (t, J=7.6 Hz, 5H), 0.80-0.94 (m, 3H), 0.35-0.75 (m, 4H)

LC-MS: m/z 498.3 (M+H)+

Compound 805 (General Procedure 6)

2-cyclopropyl-6-((3R)-3-cyclopropyl-4-(2-(tetrahydrofuran-2-yl)acetyl)piperazin-1-yl)-4-methyl-2'-vinyl-[3,4'-bipyridine]-5-carbonitrile ¹H NMR (CHLOROFORM-d) δ 8.69 (d, J=5.0 Hz, 1H), 7.23 (s, 1H), 7.07 (d, J=5.0 Hz, 1H), 6.87 (dd, J=17.3, 10.9 Hz, 1H), 6.22-6.40 (m, 1H), 5.57 (dd, J=10.9, 0.9 Hz, 1H), 4.60-4.70 (m, 0.5H), 4.18-4.41 (m, 3H), 4.02-4.15 (m, 0.5H), 3.89 (d, J=7.3 Hz, 1.5H), 3.63-3.82 (m, 1.5H), 2.90-3.45 (m, 3H), 2.64-2.85 (m, 1H), 2.53 (dd, J=14.8, 6.0 Hz, 1H), 2.08-2.32 (m, 4H), 1.88-2.00 (m, 2H), 1.51-1.69 (m, 2H), 1.43 (d, J=13.8 Hz, 1H), 1.11 (s, 2H), 0.87 (dd, J=7.9, 2.9 Hz, 2H), 0.35-0.66 (m, 4H)

LC-MS: m/z 498.3 (M+H)+

Compound 806 (General Procedure 6)

2-cyclopropyl-6-((3R)-3-cyclopropyl-4-(2-(5-oxotetrahydrofuran-2-yl)acetyl)piperazin-1-yl)-4-methyl-2'-vinyl-[3,4'-bipyridine]-5-carbonitrile ¹H NMR (CHLOROFORM-d) δ 8.71 (d, J=4.7 Hz, 1H), 7.25 (s, 1H), 7.09 (d, J=4.7 Hz, 1H), 6.90 (dd, J=17.3, 10.9 Hz, 1H), 6.31 (d, J=17.3 Hz, 1H), 5.60 (d, J=11.2 Hz, 1H), 4.94-5.08 (m, 1H), 4.17-4.45 (m, 2H), 4.08 (s, 1H), 3.79 (s, 2H), 2.80-3.45 (m, 4H), 2.51-2.73 (m, 4H), 2.19-2.28 (m, 3H), 1.57 (td, J=8.1, 4.0 Hz, 1H), 1.12 (s, 3H), 0.88 (dd, J=7.9, 3.2 Hz, 3H), 0.25-0.74 (m, 4H)

LC-MS: m/z 512.3 (M+H)+

Compound 808 (General Procedure 7)

2-(5-cyano-2-cyclopropyl-6-((R)-3-cyclopropyl-4-(2-((R)-oxetan-2-yl)acetyl)piperazin-1-yl)pyridin-3-ylamino)pyrimidine-4-carbonitrile ¹H NMR (CHLOROFORM-d) δ: 8.59 (d, J=4.7 Hz, 1H), 7.87-8.13 (m, 1H), 7.00-7.17 (m, 2H), 5.10-5.32 (m, 2H), 4.67-4.83 (m, 1H), 4.47-4.63 (m, 1H), 4.39 (d, J=11.7 Hz, 1H), 4.30 (d, J=12.3 Hz, 1H), 4.08 (d, J=7.3 Hz, 1H), 3.92 (d, J=12.9 Hz, 1H), 3.64-3.84 (m, 1H), 3.18-3.45 (m, 1H), 2.93-3.18 (m, 3H), 2.54 (d, J=6.7 Hz, 1H), 1.94-2.14 (m, 2H), 1.86 (br. s., 2H), 1.46 (d, J=8.2 Hz, 1H), 1.39 (br. s., 1H), 1.33 (br. s., 1H), 1.27 (s, 1H), 0.97-1.23 (m, 4H), 0.63 (br. s., 1H), 0.54 (br. s., 1H), 0.27-0.50 (m, 2H).

LC-MS: m/z 485.2 (M+H)+

Compound 809 (General Procedure 7)

5-(4-cyanopyridin-2-ylamino)-6-cyclopropyl-2-((R)-3-cyclopropyl-4-(2-((R)-oxetan-2-yl)acetyl)piperazin-1-yl)nicotinonitrile ¹H NMR (CHLOROFORM-d) δ: 8.65 (d, J=5.3 Hz, 1H), 7.65 (s, 1H), 7.39 (s, 1H), 7.24 (dd, J=5.0, 1.5 Hz, 1H), 6.88 (dd, J=17.3, 10.9 Hz, 1H), 6.20-6.35 (m, 1H), 5.51-5.65 (m, 1H), 4.55 (d, J=12.9 Hz, 1H), 4.29-4.48 (m, 1H), 4.05-4.29 (m, 1H), 4.00 (br. s., 1H), 3.80 (br. s., 1H), 3.62-3.77 (m, 1H), 3.54 (br. s., 2H), 3.22 (d, J=12.6 Hz, 2H), 3.09 (t, J=10.9 Hz, 1H), 2.40-2.54 (m, 3H), 2.01-2.17 (m, 4H), 1.15-1.45 (m, 11H), 0.94-1.10 (m, 3H), 0.74-0.94 (m, 2H), 0.65 (br. s., 2H), 0.47 (br. s., 3H).
LC-MS: m/z 484.2 (M+H)+

Compound 803 (General Procedure 6)

2-cyclopropyl-6-((3R)-3-cyclopropyl-4-(3-(oxetan-2-yl)propanoyl)piperazin-1-yl)-4-methyl-2'-vinyl-[3,4'-bipyridine]-5-carbonitrile $^1$H NMR (CHLOROFORM-d) δ 8.69 (d, J=5.0 Hz, 1H), 7.23 (s, 1H), 7.07 (d, J=3.8 Hz, 1H), 6.87 (dd, J=17.3, 10.9 Hz, 1H), 6.29 (d, J=17.3 Hz, 1H), 5.45-5.62 (m, 1H), 4.88 (s, 1H), 4.64-4.74 (m, 1H), 4.54 (dt, J=8.8, 5.9 Hz, 1H), 4.33 (d, J=12.6 Hz, 1H), 4.18-4.29 (m, 1H), 4.03-4.15 (m, 1H), 3.60-3.90 (m, 1H), 3.09-3.39 (m, 2H), 2.94-3.09 (m, 1H), 2.66-2.78 (m, 1H), 2.25-2.60 (m, 3H), 2.21 (s, 3H), 2.01-2.14 (m, 2H), 1.51-1.68 (m, 1H), 1.43 (d, J=12.9 Hz, 1H), 1.00-1.16 (m, 2H), 0.87 (dd, J=7.9, 2.9 Hz, 2H), 0.25-0.65 (m, 4H)
LC-MS: m/z 498.3 (M+H)+

Compound 802 (General Procedure 5)

2-cyclopropyl-6-((3R)-3-cyclopropyl-4-(2-(5-oxotetrahydrofuran-2-yl)acetyl)piperazin-1-yl)-2'-vinyl-[3,4'-bipyridine]-5-carbonitrile $^1$H NMR (CHLOROFORM-d) δ 8.67 (d, J=5.0 Hz, 1H), 7.60-7.71 (m, 1H), 7.40 (s, 1H), 7.21-7.27 (m, 1H), 6.89 (dd, J=17.5, 10.7 Hz, 1H), 6.29 (d, J=17.3 Hz, 1H), 5.58 (d, J=10.9 Hz, 1H), 4.94-5.06 (m, 1H), 4.35-4.75 (m, 2.5H), 4.01-4.09 (m, 0.5H), 3.70-3.81 (m, 1.5H), 2.90-3.40 (m, 3.5H), 2.50-2.79 (m, 4H), 1.98-2.04 (m, 1H), 1.29-1.37 (m, 2H), 1.22 (dt, J=7.0, 3.5 Hz, 2H), 0.97-1.06 (m, 2H), 0.26-0.70 (m, 4H)
LC-MS: m/z 498.2 (M+H)+

Compound 801 (General Procedure 5)

2-cyclopropyl-6-((3R)-3-cyclopropyl-4-(2-(tetrahydrofuran-2-yl)acetyl)piperazin-1-yl)-2'-vinyl-[3,4'-bipyridine]-5-carbonitrile $^1$H NMR (CHLOROFORM-d) δ 8.65 (d, J=5.0 Hz, 1H), 7.64 (s, 1H), 7.39 (s, 1H), 7.23 (d, J=4.7 Hz, 1H), 6.88 (dd, J=17.6, 10.9 Hz, 1H), 6.28 (d, J=17.6 Hz, 1H), 5.56 (d, J=10.9 Hz, 1H), 4.50-4.62 (m, 1H), 4.43 (d, J=12.9 Hz, 1H), 4.21-4.35 (m, 1H), 4.05-4.11 (m, 1H), 3.80-3.92 (m, 1.5H), 3.62-3.80 (m, 1.5H), 3.07-3.41 (m, 3H), 2.45-2.97 (m, 2H), 2.15-2.20 (m, 1H), 1.98-2.05 (m, 2H), 1.92 (dt, J=14.2, 6.9 Hz, 2H), 1.62 (d, J=7.3 Hz, 1H), 1.16-1.24 (m, 2H), 1.00 (dd, J=7.5, 3.4 Hz, 2H), 0.34-0.71 (m, 4H)
LC-MS: m/z 484.3 (M+H)+

Compound 824 (General Procedure 7)

6-cyclopropyl-2-((R)-3-cyclopropyl-4-(2-((R)-oxetan-2-yl)acetyl)piperazin-1-yl)-5-((2-(hydroxymethyl)pyridin-4-yl)amino)nicotinonitrile $^1$H NMR (400 MHz, MeOD) δ 8.08 (d, J=6.5 Hz, 1H), 7.80 (d, J=2.2 Hz, 1H), 6.81 (d, J=2.0 Hz, 1H), 6.71 (dd, J=6.4, 2.3 Hz, 1H), 6.18-6.11 (m, 1H), 5.62 (dd, J=6.8, 5.5 Hz, 1H), 5.24 (s, 1H), 4.66 (d, J=7.0 Hz, 3H), 4.51 (d, J=13.1 Hz, 1H), 4.37 (s, 1H), 4.14-3.97 (m, 1H), 3.71 (dd, J=10.8, 4.4 Hz, 2H), 3.62 (s, 1H), 3.18-3.04 (m, 1H), 2.84 (s, 1H), 2.49 (d, J=6.5 Hz, 1H), 2.17-2.09 (m, 1H), 1.96 (s, 1H), 1.53-1.25 (m, 3H), 1.21-1.13 (m, 2H), 1.04 (dd, J=7.7, 3.4 Hz, 2H), 0.71-0.36 (m, 4H).
LC-MS: m/z 489.2 (M+H)+

Compound 810 (General Procedure 5)

Sodium (R)-3-(4-(5-cyano-2-cyclopropyl-2'-vinyl-[3,4'-bipyridin]-6-yl)-2-cyclopropylpiperazin-1-yl)-3-oxopropyl phosphate $^1$H NMR (400 MHz, D$_2$O) δ 8.37 (d, J=5.0 Hz, 1H), 7.61 (s, 1H), 7.40 (s, 1H), 7.26 (s, 1H), 6.74 (dd, J=17.5, 11.3 Hz, 1H), 6.04 (d, J=17.8 Hz, 1H), 5.51 (d, J=11.2 Hz, 1H), 4.47 (s, 1H), 4.35 (s, 2H), 3.91 (d, J=6.7 Hz, 3H), 3.82 (s, 1H), 3.56 (q, J=7.1 Hz, 2H), 3.20 (s, 1H), 2.78 (s, 1H), 2.71-2.63 (m, 1H), 1.92 (s, 1H), 1.55 (s, 4H), 1.18 (s, 2H), 0.89 (s, 1H), 0.45-0.46 (m, 2H), 0.37-0.22 (m, 2H).
LC-MS: m/z 568.2 (M+H)+

Compound 828 (General Procedure 7)

1H NMR (CHLOROFORM-d) δ 8.07 (d, J=5.3 Hz, 1H), 7.81 (s, 1H), 7.02 (br. s., 1H), 6.71-6.84 (m, 1H), 6.55 (dd, J=17.6, 10.9 Hz, 1H), 6.38 (s, 1H), 5.86 (d, J=17.6 Hz, 1H), 5.42 (d, J=11.2 Hz, 1H), 4.18-4.44 (m, 3H), 4.11 (q, J=7.0 Hz, 1H), 3.81-3.99 (m, 2H), 3.62-3.81 (m, 2H), 3.11 (d, J=12.9 Hz, 2H), 3.04 (m, 1H), 2.73 (d, J=6.5 Hz, 1H), 2.08-2.28 (m, 2H), 1.82-1.97 (m, 2H), 1.59 (dd, J=12.0, 7.9 Hz, 1H), 1.25 (t, J=7.0 Hz, 1H), 1.04-1.18 (m, 2H), 0.88-1.02 (m, 2H), 0.51-0.59 (m, 2H), 0.42-0.49 (m, 2H)
LC-MS: m/z 499.2 (M+H)+

Compound 829 (General Procedure 7)

1H NMR (CHLOROFORM-d) δ 7.56 (s, 1H), 7.14 (d, J=7.3 Hz, 1H), 6.11 (br, s, 1H), 5.79 (dd, J=7.3, 2.3 Hz, 1H), 5.58 (br. s., 1H), 5.26 (t, J=6.6 Hz, 1H), 4.71 (td, J=7.9, 6.2 Hz, 1H), 4.56 (m, 1H), 4.43 (d, J=12.3 Hz, 1H), 4.32 (d, J=12.6 Hz, 1H), 4.06 (d, J=9.1 Hz, 0.5H), 3.92 (d, J=12.3 Hz, 0.5H), 3.69-3.82 (m, 1H), 3.47 (s, 3H), 3.08-3.34 (m, 2H), 2.92-3.08 (m, 2.5H), 2.78-2.90 (m, 1.5H), 2.54 (d, J=7.3 Hz, 1H), 2.06-2.17 (m, 1H), 1.27 (s, 1H), 1.06-1.16 (m, 2H), 0.98-1.05 (m, 2H), 0.53-0.63 (m, 2H), 0.30-0.49 (m, 2H)
LC-MS: m/z 489.2 (M+H)+

Compound 830 (General Procedure 7)

(R)-6-cyclopropyl-2-(3-cyclopropyl-4-hexanoylpiperazin-1-yl)-5-(4-vinylpyridin-2-ylamino)nicotinonitrile $^1$H NMR (CHLOROFORM-d) δ 8.02 (d, J=4.4 Hz, 1H), 7.72 (s, 1H), 6.82 (d, J=5.3 Hz, 1H), 6.56 (dd, J=17.3, 10.9 Hz, 1H), 6.34 (s, 1H), 5.90 (d, J=17.6 Hz, 1H), 5.49 (d, J=10.9 Hz, 1H), 4.40 (d, J=12.9 Hz, 1H), 4.29 (d, J=12.0 Hz, 1H), 4.11 (br. s., 1H), 3.80 (br. s., 2H), 3.16 (br. s., 2H), 2.90-3.11 (m, 1H), 2.25-2.45 (m, 5H), 1.56-1.73 (m, 4H), 1.20-1.48 (m, 4H), 1.07-1.20 (m, 2H), 0.82-1.07 (m, 2H).
LC-MS: m/z 485.2 (M+H)+

Compound 818 (General Procedure 5)

$^1$H NMR (CHLOROFORM-d) δ 8.66 (d, J=4.7 Hz, 1H), 7.66 (s, 1H), 7.41 (s, 1H), 7.22-7.28 (m, 1H), 6.90 (dd, J=17.3, 10.9 Hz, 1H), 6.31 (d, J=17.3 Hz, 1H), 5.60 (d,

J=10.9 Hz, 1H), 4.55 (d, J=12.9 Hz, 1H), 4.43 (dd, J=12.9, 2.1 Hz, 1H), 4.14 (m, 2H), 3.72 (m, 1H), 3.43-3.63 (m, 2H), 3.22 (d, J=11.4 Hz, 2H), 3.01-3.16 (m, 2H), 2.06-2.11 (m, 1H), 1.79-2.09 (m, 1H), 1.65 (br. s., 1H), 1.40-1.53 (m, 1H), 1.17-1.25 (m, 2H), 0.96-1.08 (m, 2H), 0.66-0.75 (m, 2H), 0.39-0.61 (m, 2H)

LC-MS: m/z 483.7 (M+H)$^+$

Compound 821 (General Procedure 5)

1H NMR (CHLOROFORM-d) δ 8.66 (d, J=5.3 Hz, 1H), 7.65 (s, 1H), 7.33-7.46 (m, 1H), 7.24 (dd, J=5.0, 1.5 Hz, 1H), 6.88 (dd, J=17.5, 10.7 Hz, 1H), 6.24-6.39 (m, 1H), 5.57 (dd, J=10.9, 1.2 Hz, 1H), 5.01 (t, J=6.3 Hz, 1H), 4.56 (m, 1.5H), 4.44 (d, J=14.1 Hz, 1H), 3.79 (m, 1H), 3.22 (m, 1.5H), 2.70 (d, J=6.7 Hz, 1H), 2.49-2.65 (m, 3H), 1.90-2.14 (m, 4H), 1.35 (m, 1H), 1.21 (m, 3H), 0.92-1.08 (m, 2H), 0.48 (m, 4H)

LC-MS: m/z 498.7 (M+H)$^+$

Compound 822 (General Procedure 5)

$^1$H NMR (CHLOROFORM-d) δ 8.64 (d, J=4.7 Hz, 1H), 7.53 (s, 1H), 7.38 (s, 1H), 7.22 (dd, J=5.0, 1.5 Hz, 1H), 6.87 (dd, J=17.6, 10.9 Hz, 1H), 6.18-6.36 (m, 1H), 5.49-5.62 (m, 1H), 4.67-4.71 (m, 0.5H), 4.54 (d, J=12.6 Hz, 1H), 4.36-4.46 (m, 1H), 4.28 (quin, J=6.5 Hz, 1H), 4.11 (d, J=7.9 Hz, 0.5H), 3.81-4.00 (m, 1.5H), 3.63-3.79 (m, 1.5H), 3.08-3.20 (m, 1H), 2.64-2.85 (m, 2H), 2.46-2.60 (m, 1H), 2.08-2.24 (m, 1H), 1.97-2.08 (m, 1H), 1.82-1.97 (m, 2H), 1.52-1.70 (m, 1H), 1.26-1.30 (m, 2H), 1.12-1.24 (m, 2H), 0.92-1.05 (m, 2H), 0.49-0.73 (m, 2H), 0.45 (m, 2H)

LC-MS: m/z 484.7 (M+H)$^+$

Compound 811 (General Procedure 6)

$^1$H NMR (CHLOROFORM-d) δ 7.23 (s, 1H), 7.07 (dd, J=5.0, 1.2 Hz, 1H), 6.87 (dd, J=17.5, 10.7 Hz, 1H), 6.29 (d, J=17.3 Hz, 1H), 5.57 (d, J=10.9, 1.2 Hz, 1H), 4.32 (d, J=12.9 Hz, 1H), 4.23 (dd, J=12.6, 2.1 Hz, 1H), 4.14 (m, 1H), 3.99 (br. s., 1H), 3.72 (br. s., 1.5H), 3.42-3.57 (m, 2.5H), 3.10-3.25 (m, 2H), 2.98-3.10 (m, 3H), 2.10-2.38 (m, 4H), 1.51-1.62 (m, 1H), 1.45 (dq, J=14.7, 7.3 Hz, 1H), 1.07-1.17 (m, 2H), 0.88 (dd, J=7.9, 3.2 Hz, 1H), 0.66 (br. s., 1H), 0.30-0.59 (m, 3H)

LC-MS: m/z 497.7 (M+H)$^+$

Compound 814 (General Procedure 5)

(R)-2-cyclopropyl-6-(3-cyclopropyl-4-(2-(2-oxopyrrolidin-1-yl)acetyl)piperazin-1-yl)-2'-vinyl-3,4'-bipyridine-5-carbonitrile $^1$H NMR (CHLOROFORM-d) δ 8.65 (d, J=5.3 Hz, 1H), 7.65 (s, 1H), 7.39 (s, 1H), 7.24 (dd, J=5.0, 1.5 Hz, 1H), 6.88 (dd, J=17.3, 10.9 Hz, 1H), 6.20-6.35 (m, 1H), 5.51-5.65 (m, 1H), 4.55 (d, J=12.9 Hz, 1H), 4.29-4.48 (m, 1H), 4.05-4.29 (m, 2H), 4.00 (br. s., 1H), 3.80 (br. s., 1H), 3.62-3.77 (m, 1H), 3.54 (br. s., 2H), 3.22 (d, J=12.6 Hz, 2H), 3.09 (t, J=10.9 Hz, 1H), 2.40-2.54 (m, 3H), 2.01-2.17 (m, 4H), 1.15-1.45 (m, 4H), 0.94-1.10 (m, 3H), 0.74-0.94 (m, 2H), 0.65 (br. s., 2H), 0.47 (br. s., 3H).

LC-MS: m/z 497.2 (M+H)$^+$

Compound 815 (General Procedure 7)

(R)-6-cyclopropyl-2-(3-cyclopropyl-4-(4-hydroxybutanoyl)piperazin-1-yl)-5-((4-vinylpyridin-2-yl)amino)nicotinonitrile $^1$H NMR (400 MHz, CDCl$_3$) δ 8.10 (d, J=5.5 Hz, 1H), 7.84 (s, 1H), 6.86 (dd, J=5.5, 1.1 Hz, 1H), 6.80 (s, 1H), 6.59 (dd, J=17.6, 10.9 Hz, 1H), 6.44 (s, 1H), 5.93 (d, J=17.5 Hz, 1H), 5.51 (d, J=10.9 Hz, 1H), 4.75-4.61 (m, 0.5H), 4.37 (d, J=12.8 Hz, 1H), 4.27 (d, J=12.6 Hz, 1H), 4.10 (d, J=7.2 Hz, 0.5H), 3.85 (d, J=10.0 Hz, 0.5H), 3.81-3.65 (m, 2.5H), 3.30 (dd, J=9.3, 5.7 Hz, 1H), 3.22-3.12 (m, 1H), 3.12-2.97 (m, 1H), 2.66-2.43 (m, 2H), 2.21-2.14 (m, 1H), 1.97 (dd, J=12.0, 6.2 Hz, 2H), 1.46 (dd, J=8.5, 6.8 Hz, 1H), 1.14 (dd, J=7.1, 4.0 Hz, 2H), 1.04 (ddd, J=9.5, 6.4, 3.0 Hz, 2H), 0.77-0.38 (m, 4H).

LC-MS: m/z 473.2 (M+H)$^+$

Compound 816 (General Procedure 7)

(R)-6-cyclopropyl-2-(3-cyclopropyl-4-(2-(2-oxopyrrolidin-1-yl)acetyl)piperazin-1-yl)-5-((4-vinylpyridin-2-yl)amino)nicotinonitrile $^1$H NMR (400 MHz, CDCl$_3$) δ 8.07 (d, J=5.6 Hz, 1H), 7.83 (s, 1H), 7.19 (s, 1H), 6.87 (dd, J=5.7, 1.3 Hz, 1H), 6.60 (dd, J=17.5, 10.9 Hz, 1H), 6.44 (s, 1H), 5.95 (d, J=17.5 Hz, 1H), 5.54 (d, J=10.9 Hz, 1H), 4.55 (s, 0.5H), 4.39 (d, J=12.9 Hz, 1H), 4.28 (dd, J=12.7, 2.1 Hz, 1H), 4.19 (s, 1H), 4.00 (s, 0.5H), 3.75 (dd, J=30.5, 3.9 Hz, 2H), 3.55 (s, 2H), 3.33 (s, 1H), 3.18 (d, J=11.9 Hz, 1H), 3.05 (t, J=13.2 Hz, 1H), 2.47 (t, J=8.0 Hz, 2H), 2.21-2.16 (m, 1H), 2.12 (dt, J=15.4, 7.6 Hz, 2H), 1.28 (d, J=5.1 Hz, 1H), 1.19-1.10 (m, 2H), 1.05 (ddd, J=9.0, 6.6, 2.5 Hz, 2H), 0.78-0.41 (m, 4H).

LC-MS: m/z 513.6 (M+H)$^+$

Compound 817 (General Procedure 7)

(R)-2-(4-(2-cyclobutylacetyl)-3-cyclopropylpiperazin-1-yl)-6-cyclopropyl-5-((4-vinylpyridin-2-yl)amino)nicotinonitrile $^1$H NMR (400 MHz, CDCl$_3$) δ 8.07 (d, J=5.6 Hz, 1H), 7.80 (s, 1H), 6.87 (dd, J=5.7, 1.2 Hz, 1H), 6.59 (dd, J=17.6, 10.8 Hz, 1H), 6.43 (s, 1H), 5.95 (d, J=17.5 Hz, 1H), 5.54 (d, J=10.8 Hz, 1H), 4.65 (d, J=11.7 Hz, 0.4H), 4.41 (d, J=12.6 Hz, 1H), 4.30 (d, J=12.3 Hz, 1H), 4.09 (d, J=5.2 Hz, 0.6H), 3.91-3.59 (m, 1.5H), 3.34-3.10 (m, 1.5H), 3.09-2.94 (m, 1H), 2.74 (dt, J=15.5, 7.8 Hz, 1H), 2.52 (s, 2H), 2.25-2.12 (m, 3H), 1.98-1.82 (m, 2H), 1.82-1.63 (m, 2H), 1.28 (s, 1H), 1.19-1.09 (m, 2H), 1.04 (dt, J=6.9, 3.0 Hz, 2H), 0.78-0.34 (m, 4H).

LC-MS: m/z 483.6 (M+H)$^+$

Compound 812 (General Procedure 7)

6-cyclopropyl-2-((3R)-3-cyclopropyl-4-(3-(oxetan-2-yl)propanoyl)piperazin-1-yl)-5-((4-vinylpyridin-2-yl)amino)nicotinonitrile $^1$H NMR (400 MHz, CDCl$_3$) δ 8.13 (d, J=5.4 Hz, 1H), 7.85 (s, 1H), 6.83 (dd, J=5.4, 1.3 Hz, 1H), 6.59 (dd, J=17.6, 10.8 Hz, 1H), 6.41 (s, 1H), 6.39 (s, 1H), 5.90 (d, J=17.6 Hz, 1H), 5.47 (d, J=11.0 Hz, 1H), 4.89 (d, J=14.1, 7.8 Hz, 1H), 4.55 (d, J=14.7, 5.8 Hz, 1H), 4.36 (d, J=12.8 Hz, 1H), 4.25 (dd, J=12.5, 1.8 Hz, 1H), 4.09 (dd, J=7.2, 2.6

Hz, 1H), 3.78 (ddd, J=23.5, 14.1, 6.1 Hz, 1.5H), 3.28 (s, 0.5H), 3.13 (d, J=12.4 Hz, 1H), 3.02 (dd, J=21.5, 9.8 Hz, 1H), 2.74 (ddd, J=14.2, 11.1, 8.0 Hz, 1H), 2.62-2.47 (m, 1H), 2.46-2.32 (m, 2H), 2.23-1.98 (m, 3H), 1.28 (d, J=4.8 Hz, 1H), 1.19-1.09 (m, 2H), 1.02 (ddd, J=9.4, 6.4, 3.0 Hz, 2H), 0.75-0.35 (m, 4H).

LC-MS: m/z 499.6 (M+H)+

Compound 813 (General Procedure 7)

6-cyclopropyl-2-((3R)-3-cyclopropyl-4-(2-(tetrahydrofuran-2-yl)acetyl)piperazin-1-yl)-5-((4-vinylpyridin-2-yl)amino)nicotinonitrile $^1$H NMR (400 MHz, CDCl$_3$) δ 8.12 (d, J=5.4 Hz, 1H), 7.84 (s, 1H), 6.84 (dd, J=5.4, 1.2 Hz, 1H), 6.59 (dd, J=17.5, 10.8 Hz, 1H), 6.46 (s, 1H), 6.41 (s, 1H), 5.91 (d, J=17.6 Hz, 1H), 5.47 (d, J=10.9 Hz, 1H), 4.69 (d, J=13.9 Hz, 0.5H), 4.46-4.33 (m, 1H), 4.28 (dd, J=15.4, 9.1 Hz, 2H), 4.11 (d, J=5.3 Hz, 0.5H), 3.98-3.83 (m, 1.5H), 3.75 (dt, J=22.2, 11.1 Hz, 1.5H), 3.40-3.09 (m, 2H), 3.09-2.93 (m, 1H), 2.83-2.47 (m, 2H), 2.47-2.29 (m, 0.5H), 2.26-2.12 (m, 2H), 2.11-1.99 (m, 0.5H), 1.93 (dt, J=13.7, 7.0 Hz, 2H), 1.28 (d, J=5.3 Hz, 1H), 1.19-1.09 (m, 2H), 1.02 (ddd, J=9.8, 6.6, 2.9 Hz, 2H), 0.77-0.32 (m, 4H).

LC-MS: m/z 499.3 (M+H)+

Compound 807 (General Procedure 7)

(R)-6-cyclopropyl-2-(3-isopropyl-4-(3-methoxypropanoyl)piperazin-1-yl)-4-methyl-5-((2-vinylpyridin-4-yl)amino)nicotinonitrile $^1$H NMR (400 MHz, CDCl$_3$) δ 8.19 (d, J=6.1 Hz, 1H), 6.69 (dd, J=17.4, 10.9 Hz, 1H), 6.57 (s, 1H), 6.45 (s, 1H), 6.21 (d, J=17.6 Hz, 1H), 6.18-6.10 (m, 1H), 5.60 (d, J=11.1 Hz, 1H), 4.71 (d, J=13.2 Hz, 0.5H), 4.50-4.37 (m, 1.5H), 4.33-4.25 (m, 1H), 3.87 (d, J=13.1 Hz, 0.5H), 3.82-3.67 (m, 2H), 3.60 (d, J=10.2 Hz, 0.5H), 3.47 (dd, J=18.2, 7.7 Hz, 0.5H), 3.38 (d, J=4.2 Hz, 3H), 3.14 (ddd, J=13.3, 9.5, 5.2 Hz, 1.5H), 3.09-2.94 (m, 1H), 2.81-2.56 (m, 2H), 2.38 (s, 3H), 2.25 (dd, J=13.6, 6.4 Hz, 0.5H), 2.07 (ddd, J=15.8, 11.1, 6.8 Hz, 1.5H), 1.15-1.09 (m, 1H), 1.04 (dd, J=6.5, 2.9 Hz, 4H), 0.97 (dd, J=7.5, 5.0 Hz, 2H), 0.93 (d, J=6.8 Hz, 1.5H), 0.86 (d, J=6.8 Hz, 1.5H).

LC-MS: m/z 489.6 (M+H)+

Compound 799 (General Procedure 7)

(R)-6-cyclopropyl-2-(4-(3-hydroxypropanoyl)-3-isopropylpiperazin-1-yl)-4-methyl-5-((2-vinylpyridin-4-yl)amino)nicotinonitrile $^1$H NMR (400 MHz, CDCl$_3$) δ 8.23 (d, J=5.7 Hz, 1H), 6.70 (dd, J=17.4, 10.8 Hz, 1H), 6.50 (s, 1H), 6.33 (s, 1H), 6.16 (d, J=17.4 Hz, 1H), 5.74 (s, 1H), 5.48 (dd, J=10.8, 0.9 Hz, 1H), 4.69 (d, J=9.7 Hz, 0.5H), 4.41 (ddd, J=6.7, 6.1, 4.4 Hz, 1.5H), 4.27 (t, J=10.2 Hz, 1H), 4.00-3.86 (m, 2H), 3.76 (d, J=13.5 Hz, 0.5H), 3.60-3.52 (m, 1H), 3.50-3.44 (m, 1H), 3.17-3.05 (m, 2H), 3.01 (dd, J=11.6, 9.4 Hz, 0.5H), 2.61 (pd, J=11.7, 5.1 Hz, 2H), 2.38 (s, 3H), 2.33-2.22 (m, 0.5H), 2.11 (ddd, J=12.7, 9.3, 5.2 Hz, 1.5H), 1.11 (ddd, J=8.9, 6.6, 4.7 Hz, 1H), 1.05 (d, J=6.5 Hz, 4H), 0.97 (dt, J=7.8, 6.6 Hz, 2H), 0.93 (d, J=6.9 Hz, 1.5H), 0.86 (d, J=6.8 Hz, 1.5H).

LC-MS: m/z 475.2 (M+H)+

Compound 798 (General Procedure 7)

(R,E)-6-cyclopropyl-2-(3-cyclopropyl-4-(5-hydroxypent-2-enoyl)piperazin-1-yl)-5-((4-vinylpyridin-2-yl)amino)nicotinonitrile $^1$H NMR (400 MHz, CDCl$_3$) δ 8.10 (d, J=5.3 Hz, 1H), 7.83 (s, 1H), 6.89-6.77 (m, 2H), 6.57 (dd, J=17.6, 10.8 Hz, 1H), 6.53-6.43 (m, 1H), 6.40 (s, 1H), 6.39-6.26 (m, 1H), 5.88 (d, J=17.5 Hz, 1H), 5.44 (d, J=10.9 Hz, 1H), 4.74-4.43 (m, 0.3H), 4.35 (t, J=11.7 Hz, 1H), 4.26 (d, J=12.5 Hz, 1H), 4.11-3.87 (m, 0.8H), 3.78 (dd, J=11.6, 5.5 Hz, 2H), 3.75-3.68 (m, 1H), 3.53 (m 0.5H), 3.45 (m 0.5H), 3.42-3.28 (m, 0.5H), 3.24-3.11 (m, 1.5H), 3.03 (td, J=12.6, 3.3 Hz, 1H), 2.49 (dd, J=12.5, 6.2 Hz, 2H), 2.22-2.15 (m, 1H), 1.45 (d, J=6.5 Hz, 1H), 1.17-1.08 (m, 2H), 1.00 (ddd, J=9.4, 6.5, 3.0 Hz, 2H), 0.73-0.32 (m, 4H).

LC-MS: m/z 485.6 (M+H)+

Compound 581 (General Procedure 7)

(R)-6-cyclopropyl-2-(4-(3-hydroxypropanoyl)-3-methylpiperazin-1-yl)-5-((2-vinylpyridin-4-yl)amino)nicotinonitrile $^1$H NMR (400 MHz, CDCl$_3$) δ 8.27 (d, J=5.7 Hz, 1H), 7.62 (s, 1H), 6.71 (dd, J=17.4, 10.8 Hz, 1H), 6.58 (d, J=2.0 Hz, 1H), 6.45 (dd, J=5.7, 2.2 Hz, 1H), 6.19 (d, J=17.2 Hz, 1H), 5.90 (s, 1H), 5.48 (d, J=11.2 Hz, 1H), 4.90 (s, 0.5H), 4.54 (d, J=13.6 Hz, 0.5H), 4.23 (dd, J=31.3, 14.0 Hz, 2.5H), 3.94 (s, 2H), 3.74 (d, J=13.6 Hz, 0.5H), 3.57 (t, J=11.0 Hz, 0.5H), 3.29 (dd, J=10.5, 6.5 Hz, 1H), 3.15 (dd, J=23.7, 11.6 Hz, 1H), 3.09-2.99 (m, 0.5H), 2.62 (m, J=34.8, 15.8 Hz, 2H), 2.12 (td, J=8.1, 4.1 Hz, 1H), 1.43 (d, J=6.4 Hz, 1.5H), 1.32 (d, J=6.8 Hz, 1.5H), 1.13 (dd, J=7.2, 4.2 Hz, 2H), 1.03 (ddd, J=10.0, 6.4, 3.3 Hz, 2H).

LC-MS: m/z 447.6 (M+H)+

Compound 642 (General Procedure 7)

(R)-6-cyclopropyl-2-(4-(3-methoxypropanoyl)-3-methylpiperazin-1-yl)-5-((2-vinylpyridin-4-yl)amino)nicotinonitrile $^1$H NMR (400 MHz, CDCl$_3$) δ 8.23 (d, J=5.9 Hz, 1H), 7.61 (s, 1H), 6.72 (dd, J=17.5, 10.9 Hz, 1H), 6.62 (s, 1H), 6.53 (d, J=4.4 Hz, 1H), 6.24 (d, J=17.4 Hz, 1H), 5.53 (d, J=10.9 Hz, 1H), 4.92 (s, 1H), 4.55 (d, J=16.6 Hz, 1H), 4.25 (t, J=11.9 Hz, 2H), 4.17 (d, J=13.8 Hz, 1H), 3.82 (d, J=8.4 Hz, 1H), 3.76 (t, J=6.2 Hz, 2H), 3.58 (d, J=12.3 Hz, 1H), 3.39 (s, 3H), 3.30 (d, J=13.0 Hz, 1H), 3.15 (t, J=11.7 Hz, 1H), 3.06 (d, J=12.2 Hz, 1H), 2.73 (ddd, J=22.9, 14.3, 6.7 Hz, 1H), 2.64-2.53 (m, 1H), 2.09 (td, J=7.9, 4.1 Hz, 1H), 1.40 (d, J=5.7 Hz, 2H), 1.30 (d, J=7.1 Hz, 2H), 1.13 (dd, J=6.8, 4.1 Hz, 2H), 1.02 (dd, J=7.6, 3.3 Hz, 2H).

LC-MS: m/z 447.2 (M+H)+

Compound 643 (General Procedure 7)

(R)-5-((2-chloropyridin-4-yl)amino)-6-cyclopropyl-2-(4-(3-methoxypropanoyl)-3-methylpiperazin-1-yl)nicotinonitrile $^1$H NMR (400 MHz, CDCl$_3$) δ 8.06 (d, J=4.9 Hz, 1H), 7.59 (s, 1H), 6.53 (s, 1H), 6.50 (s, 1H), 6.00 (s, 1H), 4.91 (s, 1H), 4.55 (d, J=10.6 Hz, 1H), 4.29 (d, J=11.2 Hz, 2H), 4.20 (d, J=12.9 Hz, 1H), 3.82 (d, J=13.8 Hz, 1H), 3.73 (dt, J=9.5, 5.8 Hz, 2H), 3.57 (t, J=11.0 Hz, 1H), 3.39 (s, 3H), 3.30 (d, J=12.0 Hz, 1H), 3.15 (t, J=11.8 Hz, 1H), 3.07 (d, J=12.0 Hz, 1H), 2.83-2.65 (m, 1H), 2.60 (dd, J=13.4, 7.5 Hz, 1H), 2.07 (ddd, J=12.6, 7.0, 4.8 Hz, 1H), 1.40 (d, J=6.4 Hz, 2H), 1.34-1.27 (m, 1H), 1.13 (s, 2H), 1.09-0.99 (m, 2H).

LC-MS: m/z 455.3 (M+H)$^+$

Compound 796 (General Procedure 6)

(R)-2-cyclopropyl-6-(3-cyclopropyl-4-(3-(furan-2-yl)propano yl)piperazin-1-yl)-4-methyl-2'-vinyl-3,4'-bipyridine-5-carbonitrile $^1$H NMR (CHLOROFORM-d) δ 8.69 (d, J=5.0 Hz, 1H), 7.31-7.38 (m, 1H), 7.23 (s, 1H), 7.07 (d, J=4.1 Hz, 1H), 6.88 (dd, J=17.6, 10.9 Hz, 1H), 6.21-6.40 (m, 2H), 6.06 (d, J=2.9 Hz, 1H), 5.57 (d, J=11.4 Hz, 1H), 4.22 (d, J=12.6 Hz, 2H), 2.93-3.18 (m, 4H), 2.72 (br. s., 2H), 2.21 (s, 3H), 1.33-1.62 (m, 2H), 1.03-1.33 (m, 3H), 0.87 (dd, J=7.9, 3.2 Hz, 2H), 0.44 (br. s., 4H).

LC-MS: m/z 508.6 (M+H)$^+$

Compound 797 (General Procedure 6)

(R)-6-(4-(3-cyclopentylpropanoyl)-3-cyclopropylpiperazin-1-yl)-2-cyclopropyl-4-methyl-2'-vinyl-3,4'-bipyridine-5-carbonitrile $^1$H NMR (CHLOROFORM-d) δ 8.69 (d, J=4.7 Hz, 1H), 7.23 (s, 1H), 7.07 (d, J=4.4 Hz, 1H), 6.87 (dd, J=17.5, 10.7 Hz, 1H), 6.12-6.41 (m, 1H), 5.41-5.69 (m, 1H), 4.19-4.48 (m, 2H), 3.96-4.19 (m, 1H), 3.80 (br. s., 1H), 3.15 (br. s., 2H), 3.04 (br. s., 1H), 2.28-2.49 (m, 2H), 2.21 (s, 3H), 1.86 (br. s., 1H), 1.80 (br. s., 3H), 1.47-1.72 (m, 8H), 1.11 (br. s., 4H), 0.73-1.00 (m, 3H), 0.60 (br. s., 1H), 0.55 (br. s., 1H), 0.23-0.50 (m, 2H).

LC-MS: m/z 510.7 (M+H)$^+$

Compound 804 (General Procedure 5)

(R)-di-tert-butyl 4-(4-(5-cyano-2-cyclopropyl-2'-vinyl-3,4'-bipyridin-6-yl)-2-cyclopropylpiperazin-1-yl)-4-oxobutyl phosphate $^1$H NMR (CHLOROFORM-d) δ 8.66 (d, J=5.0 Hz, 1H), 7.65 (s, 1H), 7.40 (s, 1H), 7.25 (dd, J=5.1, 1.6 Hz, 1H), 6.89 (dd, J=17.6, 10.9 Hz, 1H), 6.30 (d, J=16.7 Hz, 1H), 5.58 (d, J=11.2 Hz, 1H), 4.56 (d, J=12.9 Hz, 1H), 4.35-4.49 (m, 1H), 3.99-4.20 (m, 3H), 3.71-3.84 (m, 1H), 2.99-3.22 (m, 2H), 2.53 (d, J=5.9 Hz, 1H), 2.00-2.07 (m, 3H), 1.66 (d, J=12.3 Hz, 3H), 1.52 (s, 18H), 1.18-1.25 (m, 2H), 0.98-1.06 (m, 2H), 0.62 (br. s., 1H), 0.56 (br. s., 1H), 0.47 (d, J=5.0 Hz, 2H)

LC-MS: m/z 650.3 (M+H)$^+$

Compound 560 (General Procedure 7)

(R)-6-cyclopropyl-2-(3-cyclopropyl-4-(3,3,3-trifluoropropanoyl)piperazin-1-yl)-5-(quinolin-4-ylamino)nicotinonitrile $^1$H NMR (CHLOROFORM-d) δ 8.55 (d, J=5.5 Hz, 1H), 8.11 (d, J=8.3 Hz, 1H), 8.03 (d, J=8.3 Hz, 1H), 7.80 (t, J=7.3 Hz, 1H), 7.71 (s, 1H), 7.63 (t, J=7.7 Hz, 1H), 6.36 (d, J=5.5 Hz, 1H), 4.52 (d, J=13.3 Hz, 1H), 4.41 (d, J=13.8 Hz, 1H), 4.15 (br. s., 1H), 3.69-3.86 (m, 2H), 3.12-3.35 (m, 4H), 2.01-2.13 (m, 1H), 1.33-1.35 (m, 1H), 1.12-1.21 (m, 2H), 0.95-1.07 (m, 2H), 0.45-0.73 (m, 4H)

LC-MS: m/z 521.2 (M+H)$^+$

Compound 617 (General Procedure 7)

(R)-6-cyclopropyl-2-(4-(3-hydroxypropanoyl)-3-methylpiperazin-1-yl)-5-(6-vinylpyrimidin-4-ylamino)nicotinonitrile $^1$H NMR (CHLOROFORM-d) δ 8.58-8.68 (m, 1H), 7.72-7.80 (m, 1H), 6.90-7.01 (m, 1H), 6.53-6.66 (m, 1H), 6.35-6.48 (m, 1H), 6.27 (s, 1H), 5.62 (dd, J=10.5, 1.3 Hz, 1H), 4.90 (br. s., 0.5H), 4.54 (d, J=13.6 Hz, 0.5H), 4.11-4.34 (m, 2.5H), 3.93 (br. s., 2H), 3.74 (d, J=13.6 Hz, 0.5H), 3.50-3.65 (m, 0.5H), 3.45 (br. s., 0.5H), 3.23-3.32 (m, 1H), 3.10-3.20 (m, 0.5H), 2.98-3.09 (m, 0.5H), 2.48-2.76 (m, 2H), 2.08-2.16 (m, 1H), 1.42 (d, J=6.5 Hz, 1.5H), 1.32 (d, J=6.8 Hz, 1.5H), 1.10-1.20 (m, 2H), 0.97-1.09 (m, 2H)

LC-MS: m/z 434.3 (M+H)$^+$

Compound 700 (General Procedure 5)

(R)-5-(2-amino-6-vinylpyrimidin-4-yl)-2-(4-(cyclopropanecarbonyl)-3-cyclopropylpiperazin-1-yl)-6-cyclopropylnicotinonitrile $^1$H NMR (CHLOROFORM-d) δ 7.97 (s, 1H), 6.89 (s, 1H), 6.66 (dd, J=17.3, 10.5 Hz, 1H), 6.52 (d, J=17.8 Hz, 1H), 5.74 (d, J=10.5 Hz, 1H), 5.41 (br. s., 2H), 4.66 (d, J=12.5 Hz, 1H), 4.52 (d, J=12.5 Hz, 1H), 3.16-4.28 (m, 5H), 2.33-2.49 (m, 1H), 1.72 (br. s., 2H), 1.21-1.26 (m, 2H), 0.98-1.15 (m, 4H), 0.82 (dd, J=7.8, 2.3 Hz, 2H), 0.63 (br. s., 1H), 0.36-0.58 (m, 3H)

LC-MS: m/z 456.4 (M+H)$^+$

Compound 751 (General Procedure 7)

6-cyclopropyl-2-((R)-3-cyclopropyl-4-(2-((R)-oxetan-2-yl)acetyl)piperazin-1-yl)-5-(2-vinylpyridin-4-ylamino)nicotinonitrile $^1$H NMR (CHLOROFORM-d) δ 8.24 (d, J=5.9 Hz, 1H), 7.62 (s, 1H), 6.70 (dd, J=17.3, 10.9 Hz, 1H), 6.61 (d, J=2.1 Hz, 1H), 6.49 (d, J=5.9 Hz, 1H), 6.19 (d, J=17.6 Hz, 1H), 6.04 (br. s., 1H), 5.53 (d, J=10.9 Hz, 1H), 5.27 (quin, J=6.7 Hz, 1H), 4.69-4.79 (m, 1H), 4.42-4.58 (m, 2H), 4.35 (d, J=12.9 Hz, 1H), 4.09 (d, J=8.8 Hz, 1H), 3.95 (d, J=13.8 Hz, 1H), 3.67-3.82 (m, 1H), 2.75-3.34 (m, 5H), 2.55 (d, J=9.1 Hz, 1H), 2.08 (td, J=8.1, 4.0 Hz, 1H), 1.33 (br. s., 1H), 1.10-1.18 (m, 2H), 1.03 (dd, J=7.8, 3.4 Hz, 2H), 0.63 (br. s., 1H), 0.55 (br. s., 1H), 0.47 (d, J=5.9 Hz, 2H)

LC-MS: m/z 485.6 (M+H)$^+$

Compound 752 (General Procedure 5)

2-cyclopropyl-6-((R)-3-cyclopropyl-4-(2-((R)-oxetan-2-yl)acetyl)piperazin-1-yl)-2'-vinyl-3,4'-bipyridine-5-carbonitrile $^1$H NMR (CHLOROFORM-d) δ 8.66 (d, J=5.0 Hz, 1H), 7.65 (s, 1H), 7.35-7.46 (m, 1H), 7.23 (dd, J=5.1, 1.6 Hz, 1H), 6.88 (dd, J=17.5, 10.7 Hz, 1H), 6.21-6.36 (m, 1H), 5.49-5.61 (m, 1H), 5.27 (quin, J=6.6 Hz, 1H), 4.72 (td, J=7.9, 6.2 Hz, 1H), 4.50-4.65 (m, 2H), 4.44 (d, J=12.9 Hz, 1H), 4.09 (d, J=8.2 Hz, 0.6H), 3.84-4.02 (m, 0.7H), 3.74 (t, J=12.0 Hz, 0.7H), 3.25 (br. s., 1H), 2.91-3.23 (m, 3.5H), 2.55-2.9 (m, 2.5H), 2.55 (d, J=8.8 Hz, 1H), 1.97-2.11 (m, 1H), 1.33 (br. s., 1H), 1.18-1.26 (m, 2H), 0.94-1.07 (m, 2H), 0.63 (br. s., 1H), 0.56 (br. s., 1H), 0.47 (br. s., 2H)

LC-MS: m/z 470.2 (M+H)$^+$

Compound 800 (General Procedure 5)

2-cyclopropyl-6-((3R)-3-cyclopropyl-4-(3-(tetrahydrofuran-2-yl)propanoyl)piperazin-1-yl)-2'-vinyl-3,4'-bipyridine-5-carbonitrile $^1$H NMR (CHLOROFORM-d) δ: 8.63 (d, J=5.3 Hz, 1H), 7.62 (s, 1H), 7.37 (s, 1H), 7.21 (dd, J=5.0, 1.5 Hz, 1H), 6.86 (dd, J=17.5, 10.7 Hz, 1H), 6.26 (d, J=17.6 Hz, 1H), 5.54 (d, J=10.9 Hz, 1H), 4.53 (d, J=12.9 Hz, 1H), 4.41 (d, J=12.6 Hz, 1H), 4.00-4.22 (m, 1H), 3.85 (d, J=6.5 Hz, 3H), 3.62-3.77 (m, 2H), 3.08-3.29 (m, 3H), 2.31-2.60 (m, 2H), 1.83-2.11 (m, 5H), 1.68-1.83 (m, 1H), 1.46-1.58 (m, 1H), 1.20 (dt, J=7.3, 3.6 Hz, 2H), 0.93-1.07 (m, 2H), 0.49-0.76 (m, 2H), 0.43 (br. s., 2H)

LC-MS: m/z 498.7 (M+H)$^+$

Having thus described several aspects of several embodiments, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

The invention claimed is:
1. A compound of Structural Formula (I):

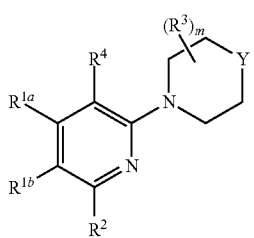

(I)

or a pharmaceutically acceptable salt thereof, wherein:
Y is —N(R$^5$);
R$^{1a}$ is hydrogen, —C$_1$-C$_4$ alkyl, —N(R$^7$)(C$_1$-C$_4$ alkylene)-N(R$^7$)(C$_1$-C$_4$ alkyl), aryl, heterocyclyl, —C(O)N(R$^7$)-aryl, —N(R$^7$)C(O)-aryl, —(C$_1$-C$_4$ alkylene)-aryl, —(C$_1$-C$_4$ alkylene)-heteroaryl, —O—(C$_0$-C$_4$ alkylene)-aryl, —O—(C$_0$-C$_4$ alkylene)-heteroaryl, —O—(C$_0$-C$_4$ alkylene)-heterocyclyl, —O—(C$_0$-C$_4$ alkylene)-carbocyclyl, —N(R$^7$)-aryl, N(R$^7$)-heteroaryl, —N(R$^9$)-aryl, —N(R$^9$)-heteroaryl, —O—(C$_1$-C$_4$ alkeylene)-N(R$^7$)C(O)O—(C$_1$-C$_4$ alkylene)-aryl, or —N(R$^9$)—C(O)—(C$_2$-C$_4$ alkenyl);
R$^{1b}$ is hydrogen, —C$_1$-C$_4$ alkyl, —N(R$^7$)(C$_1$-C$_4$ alkylene)-N(R$^7$)(C$_1$-C$_4$ alkyl), aryl, heteroaryl, heterocyclyl, —C(O)N(R$^7$)-aryl, —N(R$^7$)C(O)-aryl, —(C$_1$-C$_4$ alkylene)-aryl, —(C$_1$-C$_4$ alkylene)-heteroaryl, —O—(C$_0$-C$_4$ alkylene)-aryl, —O—(C$_0$-C$_4$ alkylene)-heteroaryl, —O—(C$_0$-C$_4$ alkylene)-heterocyclyl, —O—(C$_0$-C$_4$ alkylene)-carbocyclyl, —N(R$^7$)-aryl, N(R$^7$)-heteroaryl, —N(R$^9$)-aryl, —N(R$^9$)-heteroaryl, —O—(C$_1$-C$_4$ alkylene)-N(R$^7$)C(O)O—(C$_1$-C$_4$ alkylene)-aryl, or —N(R$^9$)—C(O)—(C$_2$-C$_4$ alkenyl), wherein:
at least one of R$^{1a}$ and R$^{1b}$ is not hydrogen or methyl;
any alkylene moiety present in R$^{1a}$ or R$^{1b}$ is optionally substituted with OH or F;
each R$^7$ is independently selected from hydrogen and C$_1$-C$_4$ alkyl; and
any aryl, heteroaryl, or heterocyclyl of R$^{1a}$ or R$^{1b}$ is optionally substituted with one or more substituents selected from -G-L-M, halo, —NO$_2$, C$_1$-C$_6$ alkyl, —C≡N, =O, —CF$_3$ and —OCF$_3$;
G is a bond or a bivalent C$_1$-C$_6$ saturated or unsaturated, straight or branched hydrocarbon chain wherein optionally one, two or three methylene units of the hydrocarbon chain are independently replaced by —NR$^8$—, —O—, —C(O)—, —OC(O)—, —C(O)O—, —S—, —SO—, —SO$_2$—, —C(=S)—, —C(=NR$^8$)—, —N=N—, or —C(=N$_2$)—;
L is a covalent bond or a bivalent C$_{1-8}$ saturated or unsaturated, straight or branched, hydrocarbon chain, wherein one, two, or three methylene units of L are optionally and independently replaced by cyclopropylene, —NR$^8$—, —N(R$^8$)C(O)—, —C(O)N(R$^8$)—, —N(R$^8$)SO$_2$—, SO$_2$N(R$^8$)—, —O—, —C(O)—, —OC(O)—, —C(O)O—, —S—, —SO—, —SO$_2$—, —C(=S)—, —C(=NR$^8$)—, —N=N—, or —C(=N$_2$)—;
M is E, or a 3-10 membered monocyclic or bicyclic, saturated, partially unsaturated, or aromatic ring having 0-3 heteroatoms independently selected from nitrogen, oxygen, or sulfur, and wherein said ring is substituted with at 1-4 groups independently selected from -D-E, oxo, NO$_2$, halogen, CN, C$_1$-C$_6$ alkyl, C$_2$-C$_6$ alkenyl, or C$_2$-C$_6$ alkynyl;
D is a covalent bond or a bivalent C$_1$-C$_6$ saturated or unsaturated, straight or branched, hydrocarbon chain, wherein one or two methylene units of D are optionally and independently replaced by —NR$^8$—, —S—, —O—, —C(O)—, —SO—, or —SO$_2$—;
E is hydrogen, C$_1$-C$_6$ alkyl, C$_2$-C$_6$ alkenyl, or C$_2$-C$_6$ alkynyl, wherein said alkyl, alkenyl or alkynyl is optionally substituted with oxo, halogen, or CN; and
each R$^8$ is independently hydrogen, C$_1$-C$_6$ alkyl, C$_2$-C$_6$ alkenyl, C$_2$-C$_6$ alkynyl, —C$_1$-C$_6$ alkoxy, —S(O)$_2$—C$_2$-C$_4$ alkenyl, or an optionally substituted group selected from phenyl, a 4-7 membered heterocyclyl having 1-2 heteroatoms independently selected from nitrogen, oxygen, or sulfur, or a 5-6 membered monocyclic heteroaryl ring having 1-4 heteroatoms independently selected from nitrogen, oxygen, or sulfur;
R$^2$ is selected from phenyl, a 3-7 membered cycloalkyl, C$_2$-C$_4$ alkyl, and CF$_3$, wherein the phenyl or cycloalkyl is optionally substituted with a substituent selected from methyl or fluoro;
each R$^3$ is independently selected from halo, —(C$_1$-C$_4$ alkylene)-O—(C$_1$-C$_4$ alkyl), —C$_1$-C$_4$ fluoroalkyl, —C(O)—O—(C$_1$-C$_4$ alkyl), -phenyl, -heteroaryl, C$_3$-C$_7$ cycloalkyl, —CH$_2$—N(C$_1$-C$_4$ alkyl)$_2$, C(O)—N—(C$_1$-C$_4$ alkyl)$_2$, —C(O)—NH—(C$_1$-C$_4$ alkyl), and —C$_1$-C$_4$ alkyl optionally substituted with one or more halo or —OH;
R$^4$ is selected from hydrogen, —CN, halo, C$_1$-C$_4$ alkoxy, —CH$_2$NH(C$_1$-C$_4$ alkyl), C$_2$-C$_4$ alkenyl, C$_2$-C$_4$ alkynyl, —(C$_1$-C$_4$ alkyl)-O—(C$_1$-C$_4$ alkyl), C$_1$-C$_4$ fluoroalkyl, C(O)—N—(C$_1$-C$_4$ alkyl)$_2$, —C(O)—NH—(C$_1$-C$_4$ alkyl), —C(O)—O—(C$_1$-C$_4$ alkyl), —C(O)—OH, —S(O)$_2$—(C$_1$-C$_4$ alkyl), and a 5-membered heteroaryl;
R$^5$ is selected from: —C(O)—(C$_1$-C$_5$ alkyl), —C(O)—(C$_2$-C$_6$ alkenyl), —C(O)—(C$_0$-C$_2$ alkylene)-Q, —C(O)—(C$_1$-C$_4$ alkenylene)-Q, —C(O)—O—(C$_0$-C$_2$ alkylene)-Q, —C(O)—(C$_1$-C$_2$ alkylene)-O—(C$_0$-C$_2$ alkylene)-Q, —C(O)—C(O)-Q, —S(O)$_2$-Q, —C(O)—(C$_1$-C$_4$ alkylene)-O—C(O)—(C$_1$-C$_4$ alkyl), —C(O)—(C$_1$-C$_4$ alkylene)-C(O)—O—(C$_1$-C$_4$ alkyl), —C(O)—(C$_1$-C$_2$ alkylene)-C(O)—(C$_1$-C$_4$ alkyl), —C(O)—(C$_1$-C$_2$ alkylene)-C(O)C(O)N(R)(C$_1$-C$_4$ alkyl), —C(O)—O—(C$_1$-C$_4$ alkylene)-O—(C$_1$-C$_4$ alkyl), —(C$_0$-C$_4$ alkylene)-O—C(O)—(C$_1$-C$_4$ alkyl), —(C$_0$-C$_4$ alkylene)-C(O)—O—(C$_1$-C$_4$ alkyl), —(C$_0$-C$_4$ alkylene)-O—(C$_1$-C$_4$ alkyl), —C(O)—(C$_1$-C$_2$ alkylene)-S(O)$_{0-2}$—(C$_1$-C$_4$ alkyl), —S(O)$_2$—(C$_1$-C$_4$ alkyl), —C(O)—(C$_1$-C$_4$ alkylene)-C(O)C(O)N(R$^6$) (C$_1$-C$_6$ alkyl), —C(O)—(C$_1$-C$_4$ alkylene)-N(R$^6$)S(O)$_2$—(C$_1$-C$_6$ alkyl), and —C(O)—(C$_1$-C$_4$ alkylene)-N(R$^6$)S(O)$_2$Q, wherein:

any alkylene moiety present in R$^5$ is optionally substituted with OCH$_3$, OH or F;

any terminal methyl moiety present in R$^5$ is optionally replaced with —CH$_2$OH, CF$_3$, —CH$_2$F, —CH$_2$Cl, C(O)CH$_3$, C(O)CF$_3$, CN, —OCH$_3$, —C(O)H, —OP(O)(OH)$_2$, —OP(O)(C$_1$-C$_4$ alkoxy)$_2$ or CO$_2$H;

each R$^6$ is independently selected from hydrogen and methyl;

Q is selected from aryl, heteroaryl, carbocyclyl and heterocyclyl, wherein Q is optionally substituted with up to 3 substituents independently selected from C$_1$-C$_4$ alkyl, C$_1$-C$_4$ alkoxy, —C(O)O—(C$_1$-C$_4$ alkyl)-, —(C$_1$-C$_4$ alkylene)-(C$_1$-C$_4$ alkoxy), —CN, —OH, fluoro, chloro, and bromo, wherein each C$_1$-C$_4$ alkyl is optionally substituted with OH;

R$^9$ is selected from aryl and heteroaryl, wherein each aryl or heteroaryl is optionally substituted with one or more substituents selected from -G-L-M, halo, C$_1$-C$_6$ alkyl, —C≡N, =O, —CF$_3$ and —OCF$_3$; and m is 0, 1, 2 or 3.

2. The compound of claim 1 or a pharmaceutically acceptable salt thereof, wherein:

Y is —N(R$^5$);

R$^{1a}$ is hydrogen, —C$_1$-C$_4$ alkyl, —N(R$^7$)(C$_1$-C$_4$ alkylene)-N(R$^7$)(C$_1$-C$_4$ alkyl), aryl, heterocyclyl, —C(O)N(R$^7$)-aryl, —N(R$^7$)C(O)-aryl, —(C$_1$-C$_4$ alkylene)-aryl, —(C$_1$-C$_4$ alkylene)-heteroaryl, —O—(C$_1$-C$_4$ alkylene)-aryl, —O—(C$_1$-C$_4$ alkylene)-heteroaryl, —O—(C$_1$-C$_4$ alkylene)-heterocyclyl, —N(R$^7$)-aryl, or —N(R$^7$)-heteroaryl;

R$^{1b}$ is hydrogen, —C$_1$-C$_4$ alkyl, —N(R$^7$)(C$_1$-C$_4$ alkylene)-N(R$^7$)(C$_1$-C$_4$ alkyl), aryl, heteroaryl, heterocyclyl, —C(O)N(R$^7$)-aryl, —N(R$^7$)C(O)-aryl, —(C$_1$-C$_4$ alkylene)-aryl, —(C$_1$-C$_4$ alkylene)-heteroaryl, —O—(C$_0$-C$_4$ alkylene)-aryl, —O—(C$_0$-C$_4$ alkylene)-heteroaryl, —O—(C$_0$-C$_4$ alkylene)-heterocyclyl, —O—(C$_0$-C$_4$ alkylene)-carbocyclyl, —N(R$^7$)-aryl, N(R$^7$)-heteroaryl, —N(R$^9$)-aryl, —N(R$^9$)-heteroaryl, —O—(C$_1$-C$_4$ alkeylene)-N(R$^7$)C(O)O—(C$_1$-C$_4$ alkylene)-aryl, or —N(R$^9$)—C(O)—(C$_2$-C$_4$ alkenyl), wherein:

at least one of R$^{1a}$ and R$^{1b}$ is not hydrogen or methyl;

any alkylene moiety present in R$^{1a}$ or R$^{1b}$ is optionally substituted with OH or F;

each R$^7$ is independently selected from hydrogen and C$_1$-C$_4$ alkyl; and any aryl, heteroaryl, or heterocylyl of R$^{1a}$ or R$^{1b}$ is optionally substituted with one or more substituents selected from -G-L-M, halo, C$_1$-C$_6$ alkyl, —C≡N, =O, —CF$_3$ and —OCF$_3$;

G is a bond or a bivalent C$_1$-C$_6$ saturated or unsaturated, straight or branched hydrocarbon chain wherein optionally one, two or three methylene units of the hydrocarbon chain are independently replaced by —NR$^8$—, —O—, —C(O)—, —OC(O)—, —C(O)O—, —S—, —SO—, —SO$_2$—, —C(=S)—, —C(=NR$^8$)—, —N=N—, or —C(=N$_2$)—;

L is a covalent bond or a bivalent C$_{1-8}$ saturated or unsaturated, straight or branched, hydrocarbon chain, wherein one, two, or three methylene units of L are optionally and independently replaced by cyclopropylene, —NR$^8$—, —N(R$^8$)C(O)—, —C(O)N(R$^8$)—, —N(R$^8$)SO$_2$—, SO$_2$N(R$^8$)—, —O—, —C(O)—, —OC(O)—, —C(O)O—, —S—, —SO—, —SO$_2$—, —C(=S)—, —C(=NR$^8$)—, —N=N—, or —C(=N$_2$)—;

M is E, or a 3-10 membered monocyclic or bicyclic, saturated, partially unsaturated, or aromatic ring having 0-3 heteroatoms independently selected from nitrogen, oxygen, or sulfur, and wherein said ring is substituted with at 1-4 groups independently selected from -D-E, oxo, NO$_2$, halogen, CN, C$_1$-C$_6$ alkyl, C$_2$-C$_6$ alkenyl, or C$_2$-C$_6$ alkynyl;

D is a covalent bond or a bivalent C$_1$-C$_6$ saturated or unsaturated, straight or branched, hydrocarbon chain, wherein one or two methylene units of D are optionally and independently replaced by —NR$^8$—, —S—, —O—, —C(O)—, —SO—, or —SO$_2$—;

E is hydrogen, C$_1$-C$_6$ alkyl, C$_2$-C$_6$ alkenyl, or C$_2$-C$_6$ alkynyl, wherein said alkyl, alkenyl or alkynyl is optionally substituted with oxo, halogen, or CN; and each R$^8$ is independently hydrogen, C$_1$-C$_6$ alkyl, C$_2$-C$_6$ alkenyl, C$_2$-C$_6$ alkynyl, or an optionally substituted group selected from phenyl, a 4-7 membered heterocyclyl having 1-2 heteroatoms independently selected from nitrogen, oxygen, or sulfur, or a 5-6 membered monocyclic heteroaryl ring having 1-4 heteroatoms independently selected from nitrogen, oxygen, or sulfur;

R$^2$ is selected from phenyl, a 3-7 membered cycloalkyl, and C$_2$-C$_4$ alkyl, wherein the phenyl or cycloalkyl is optionally substituted with a substituent selected from methyl or fluoro;

each R$^3$ is independently selected from —C$_1$-C$_4$ alkyl, —(C$_1$-C$_4$ alkyl)-O—(C$_1$-C$_4$ alkyl), —C$_1$-C$_4$ fluoroalkyl, —C(O)—O—(C$_1$-C$_4$ alkyl), -phenyl, -heteroaryl, C$_3$-C$_7$ cycloalkyl, —CH$_2$—N(C$_1$-C$_4$ alkyl)$_2$, C(O)—N—(C$_1$-C$_4$ alkyl)$_2$, and —C(O)—NH—(C$_1$-C$_4$ alkyl);

R$^4$ is selected from hydrogen, —CN, halo, C$_1$-C$_4$ alkoxy, —CH$_2$NH(C$_1$-C$_4$ alkyl), C$_2$-C$_4$ alkenyl, C$_2$-C$_4$ alkynyl, —(C$_1$-C$_4$ alkyl)-O—(C$_1$-C$_4$ alkyl), C$_1$-C$_4$ fluoroalkyl, C(O)—N—(C$_1$-C$_4$ alkyl)$_2$, —C(O)—NH—(C$_1$-C$_4$ alkyl), —C(O)—O—(C$_1$-C$_4$ alkyl), —C(O)—OH, —S(O)$_2$—(C$_1$-C$_4$ alkyl), and a 5-membered heteroaryl;

R$^5$ is selected from: —C(O)—(C$_1$-C$_4$alkyl), —C(O)—(CH$_2$)$_{0-2}$-Q, —C(O)—O—(CH$_2$)$_{1-2}$-Q, —C(O)—(CH$_2$)$_{1-2}$—O—(CH$_2$)$_{0-2}$-Q, —C(O)—C(O)-Q, —S(O)$_2$- Q, —C(O)—(C$_1$-C$_4$ alkylene)-O—C(O)—(C$_1$-C$_4$ alkyl), —C(O)—(C$_1$-C$_4$ alkylene)-C(O)—O—(C$_1$-C$_4$ alkyl), —C(O)—(CH$_2$)$_{1-2}$—O—(C$_1$-C$_4$ alkyl), —C(O)—O—(C$_1$-C$_4$ alkylene)-O—(C$_1$-C$_4$ alkyl), —(CH$_2$)$_{0-4}$—O—C(O)—(C$_1$-C$_4$ alkyl), —(CH$_2$)$_{0-4}$—C(O)—O—(C$_1$-C$_4$ alkyl), —(CH$_2$)$_{0-4}$—O—(C$_1$-C$_4$ alkyl), —C(O)—(CH$_2$)$_{1-2}$—S—(C$_1$-C$_4$ alkyl), —S(O)$_2$—(C$_1$-C$_4$ alkyl), —C(O)—(C$_1$-C$_4$ alkylene)-C(O)C(O)N(R$^6$) (C$_1$-C$_6$ alkyl), —C(O)—(C$_1$-C$_4$ alkylene)-N(R$^6$)S(O)$_2$—(C$_1$-C$_6$ alkyl), and —C(O)—(C$_1$-C$_4$ alkylene)-N(R$^6$)S(O)$_2$Q, wherein:

any alkylene moiety present in R$^5$ is optionally substituted with OH or F; any terminal methyl moiety present in R$^5$ is optionally replaced with —CH$_2$OH, CF$_3$, —CH$_2$F, —CH$_2$Cl, C(O)CH$_3$, or C(O)CF$_3$;

each R$^6$ is independently selected from hydrogen and methyl;

Q is selected from aryl, heteroaryl, carbocyclyl and heterocyclyl, wherein Q is optionally substituted with up to 3 substituents independently selected from C$_1$-C$_4$ alkyl, C$_1$-C$_4$ alkoxy, —CN, fluoro, chloro, and bromo, wherein each C$_1$-C$_4$ alkyl is optionally substituted with OH; and m is 0, 1, 2 or 3.

3. The compound of claim 1 or a pharmaceutically acceptable salt thereof, wherein R$^4$ is —CN or C(O)—O—C$_1$-C$_4$ alkyl.

4. The compound of claim 1 or a pharmaceutically acceptable salt thereof, wherein R$^4$ is

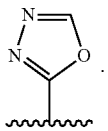

5. The compound of claim 1 or a pharmaceutically acceptable salt thereof, wherein R$^5$ is —C(O)—(C$_1$-C$_3$ alkyl)-O—(C$_1$-C$_2$ alkyl), —C(O)-Q, —C(O)—(C$_1$-C$_5$ alkyl), —C(O)—(C$_1$-C$_2$ alkylene)-Q, —C(O)—(C$_2$-C$_4$ alkenyl), —C(O)O—(C$_1$-C$_4$ alkyl), or —C(O)—(C$_1$-C$_4$ alkenylene)-Q; wherein: any alkylene moiety present in R$^5$ is optionally substituted with OH; any terminal methyl moiety present in R$^5$ is optionally replaced with —OH, CF$_3$, OCH$_3$, —C(O)H, OP(O)(C$_1$-C$_4$ alkoxy)$_2$, or —OP(O)(OH)$_2$ (or a salt of —OP(O)(OH)$_2$).

6. The compound of claim 5 or a pharmaceutically acceptable salt thereof, wherein Q is cyclopropyl, cyclobutyl, oxetanyl, furanyl, azetidinonyl, pyrrolidinonyl, tetrahydrofuranyl, dihydrofuranonyl, or cyclopentyl, wherein each member of Q is optionally substituted with one substituent independently selected from C$_1$-C$_4$ alkyl, C$_1$-C$_4$ alkoxy, —(C$_1$-C$_4$ alkylene)-(C$_1$-C$_4$ alkoxy), and —OH, wherein each C$_1$-C$_4$ alkyl is optionally substituted with OH.

7. The compound of claim 1 or a pharmaceutically acceptable salt thereof, wherein R$^{1a}$ is H and R$^{1b}$ is aryl, heteroaryl, heterocyclyl, —(C$_1$-C$_4$ alkylene)-aryl, —(C$_1$-C$_4$ alkylene)-heteroaryl, —O—(C$_0$-C$_4$ alkylene)-aryl, —O—(C$_0$-C$_4$ alkylene)-heteroaryl, —N(R$^7$)-aryl, —N(R$^7$)heteroaryl, —N(R$^9$)-aryl, or —N(R$^9$)-heteroaryl; wherein said aryl or heteroaryl is substituted with -G-L-M, CH$_3$, or CN.

8. The compound of claim 7 or a pharmaceutically acceptable salt thereof, wherein any aryl in R$^{1b}$ is phenyl.

9. The compound of claim 7 or a pharmaceutically acceptable salt thereof, wherein any heteroaryl in R$^{1b}$ is pyridyl, pyrimidinyl, naphthyridinyl, quinolyl, isoquinolyl, isoxazolyl, benzoxazolyl, imidazopyrazinyl, benzothiazolyl, benzimidazolyl, pyrollopyridinyl, pyrazolopyridinyl, indolyl, indazolyl, imidazopyridinyl, quinoxalinyl, quinazolinyl, pyridazinyl or pyrazolyl.

10. The compound of claim 7 or a pharmaceutically acceptable salt thereof, wherein any heterocyclyl in R$^{1b}$ is benzodioxole, pyridazinone, benzoxazolone, indolinone, N-methylindolinone, piperazinyl, N-methylisoquinolinone, tetrahydropyridinyl, dihydropyrrolyl and said phenyl, pyridyl, pyrimidinyl, naphthyridinyl, quinolyl, isoquinolyl, isoxazolyl, benzoxazolyl, imidazopyrazinyl, benzothiazolyl, benzimidazolyl, pyrollopyridinyl, pyrazolopyridinyl, indolyl, indazolyl, imidazopyridinyl, quinoxalinyl, quinazolinyl, pyridazinyl, pyrazolyl, benzodioxole, pyridazinone, benzoxazolone, indolinone, N-methylindolinone, piperazinyl, N-methylisoquinolinone, tetrahydropyridinyl, or dihydropyrrolyl.

11. The compound of claim 1 or a pharmaceutically acceptable salt thereof, wherein R$^{1a}$ is methyl and R$^{1b}$ is aryl, heteroaryl, heterocyclyl, —O—(C$_0$-C$_4$ alkylene)-aryl, or —O—(C$_0$-C$_4$ alkylene)-heteroaryl.

12. The compound of claim 11 or a pharmaceutically acceptable salt thereof, wherein R$^{1a}$ is methyl and R$^{1b}$ is aryl, heteroaryl, heterocyclyl, —O—(CH$_2$)-aryl, —O—CH(CH$_3$)-aryl, —O—(CH$_2$)-heteroaryl or —O—CH(CH$_3$)-heteroaryl.

13. The compound of claim 11 or a pharmaceutically acceptable salt thereof, wherein any aryl in R$^{1b}$ is phenyl or naphthyl.

14. The compound of claim 11 or a pharmaceutically acceptable salt thereof, wherein any heteroaryl in R$^{1b}$ is quinolinyl, pyrazolyl, isoquinolinyl, pyridyl, pyrimidinyl, indolyl, or pyrazolyl.

15. The compound of claim 11 or a pharmaceutically acceptable salt thereof, wherein any heterocyclyl in R$^{1b}$ is tetrahydropyridinyl.

16. The compound of claim 11 or a pharmaceutically acceptable salt thereof, wherein any aryl, heteroaryl or heterocyclyl in R$^{1b}$ is substituted with -G-L-M, halo, CH$_3$, or CN.

17. The compound of claim 7 or a pharmaceutically acceptable salt thereof, wherein -G-L-M is:

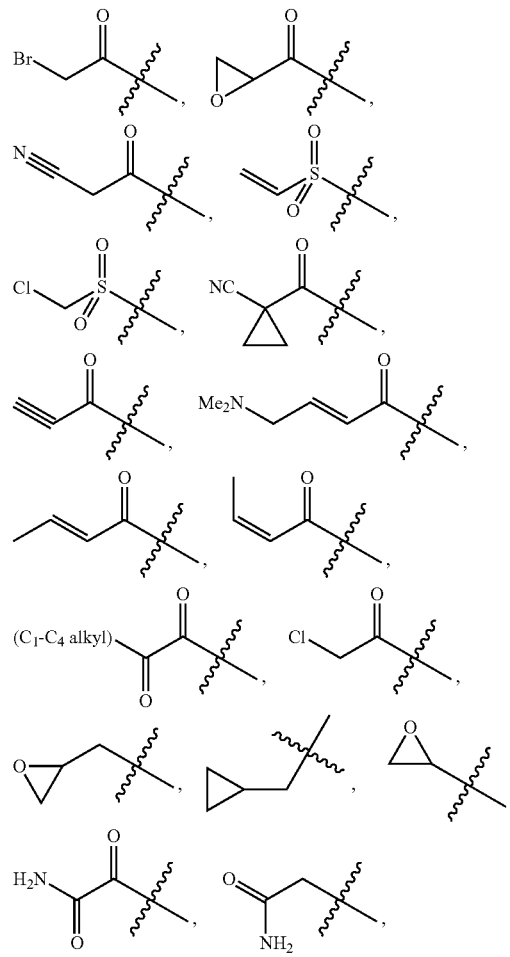

621
-continued

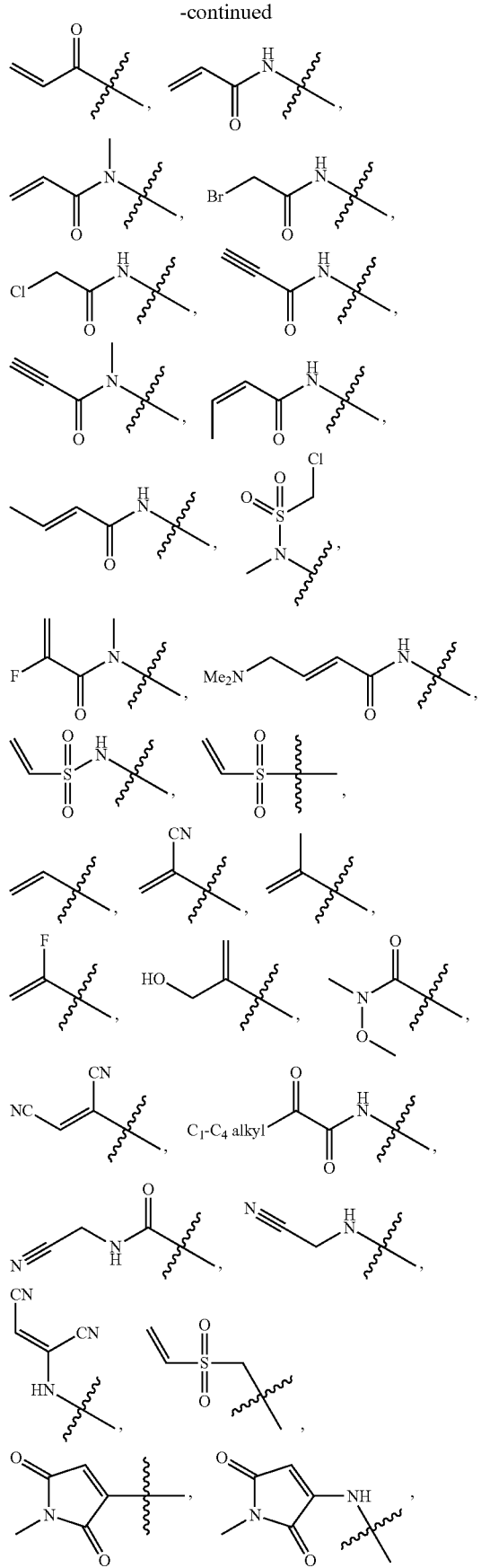

622
-continued

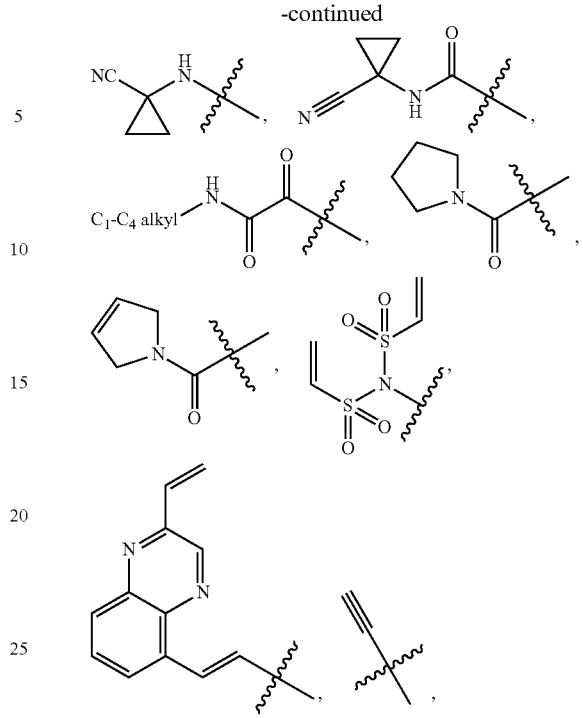

$C_1$-$C_4$ alkyl, $C_2$-$C_4$ alkenyl, $C_1$-$C_4$ alkoxy, tetrazolyl, morpholino, piperazinyl, pyrrolidinone, pyrazolyl, benzyl, —$(CH_2)_{1-4}$—SH, —$(CH_2)_{1-4}$—$NH_2$, —$NH_2$, —$(CH_2)_{1-4}$—OH, —N(H)C(O)OCH($CH_3$)$_3$, —$(CH_2)_{1-4}$—$OCH_3$, —NH—$(CH_2)_{1-4}$—OH, —C(O)—($C_1$-$C_4$ alkyl), —C(O)—($C_1$-$C_4$ alkenyl), —O—$(CH_2)_{1-4}$—C(O)—O—($C_1$-$C_4$ alkyl), —C(O)$NH_2$, —$(CH_2)_{1-4}$C(O)$CH_3$, —N($CH_3$)($CH_3$), —NHC(O)($C_2$-$C_4$ alkenyl), —NHC(O)($C_2$-$C_4$ alkyl), —$SO_2$($CH_2$)$_{1-4}$, —$(CH_2)_{1-4}$—$NHSO_2Me$, —$NHSO_2$($CH_2$)$_{1-4}$, —O—$SO_2CF_3$, —$SO_2NH$—($C_1$-$C_4$ alkyl), —$SO_2NH$—($C_2$-$C_4$ alkenyl), $SO_2$—$NH_2$ or —$NHSO_2Me$.

18. A pharmaceutical composition comprising a compound of claim 1 or a pharmaceutically acceptable salt thereof, and a pharmaceutically acceptable carrier.

19. The composition of claim 18, further comprising a second cancer therapeutic agent.

20. The compound according to claim 1 or a pharmaceutically acceptable salt thereof which is:

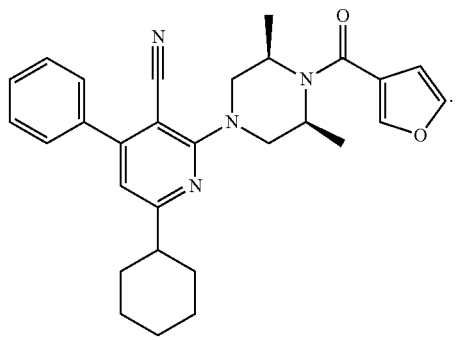 [SMILES: C[C@@H]1CN(c2nc(C3CCCCC3)cc(-c3ccccc3)c2C#N)C[C@H](C)N1C(=O)c1ccoc1]

21. The compound according to claim 1 or a pharmaceutically acceptable salt thereof which is:

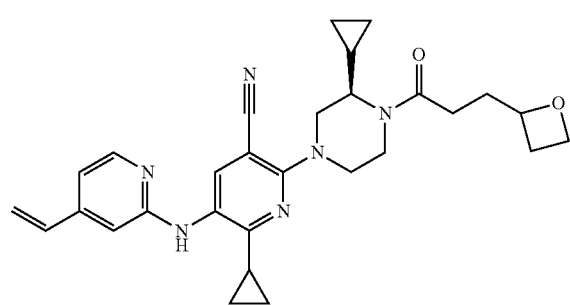

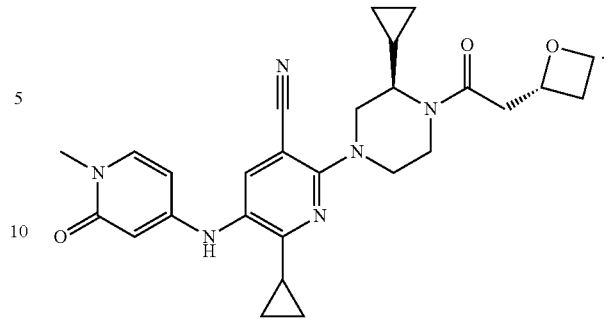

22. The compound according to claim 1 or a pharmaceutically acceptable salt thereof which is:

25. The compound according to claim 1 or a pharmaceutically acceptable salt thereof which is:

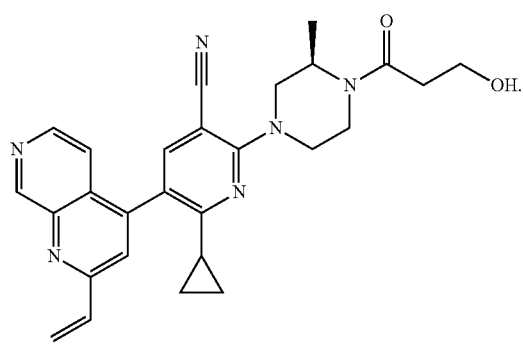 [SMILES: C=Cc1cc(-c2cc(C#N)c(N3CCN(C(=O)CCO)[C@H](C)C3)nc2C2CC2)c2ccncc2n1]

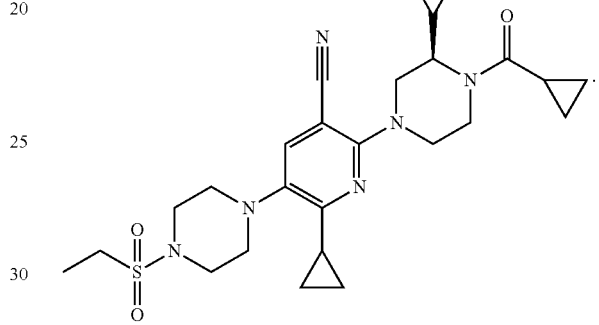

23. The compound according to claim 1 or a pharmaceutically acceptable salt thereof which is:

26. The compound according to claim 1 or a pharmaceutically acceptable salt thereof which is:

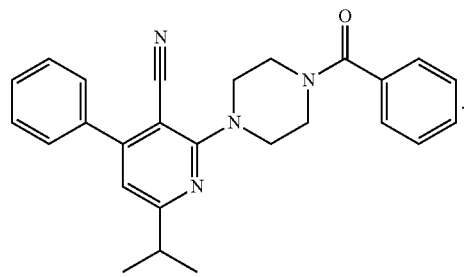 [SMILES: CC(C)c1cc(-c2ccccc2)c(C#N)c(N2CCN(C(=O)c3ccccc3)CC2)n1]

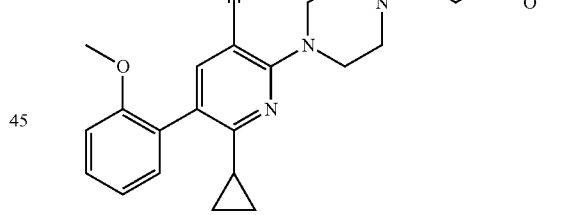

24. A compound or a pharmaceutically acceptable salt thereof which is:

* * * * *